US010543269B2

(12) United States Patent
Ciaramella et al.

(10) Patent No.: US 10,543,269 B2
(45) **Date of Patent: *Jan. 28, 2020**

(54) HMPV RNA VACCINES

(71) Applicant: ModernaTX, Inc., Cambridge, MA (US)

(72) Inventors: Giuseppe Ciaramella, Sudbury, MA (US); Sunny Himansu, Winchester, MA (US)

(73) Assignee: ModernaTX, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/368,099

(22) Filed: Mar. 28, 2019

(65) Prior Publication Data

US 2019/0216917 A1 Jul. 18, 2019

Related U.S. Application Data

(63) Continuation of application No. 16/040,981, filed on Jul. 20, 2018, now Pat. No. 10,272,150, which is a continuation of application No. 15/674,599, filed on Aug. 11, 2017, now Pat. No. 10,064,934, which is a continuation of application No. PCT/US2016/058327, filed on Oct. 21, 2016.

(60) Provisional application No. 62/247,362, filed on Oct. 28, 2015, provisional application No. 62/247,394, filed on Oct. 28, 2015, provisional application No. 62/247,483, filed on Oct. 28, 2015, provisional application No. 62/247,297, filed on Oct. 28, 2015, provisional application No. 62/244,802, filed on Oct. 22, 2015, provisional application No. 62/244,946, filed on Oct. 22, 2015, provisional application No. 62/244,813, filed on Oct. 22, 2015, provisional application No. 62/244,837, filed on Oct. 22, 2015, provisional application No. 62/245,031, filed on Oct. 22, 2015.

(51) Int. Cl.

| | |
|---|---|
| ***A61K 39/155*** | (2006.01) |
| ***A61K 39/12*** | (2006.01) |
| ***C07K 16/10*** | (2006.01) |
| *A61K 39/00* | (2006.01) |

(52) U.S. Cl.

CPC ............ *A61K 39/155* (2013.01); *A61K 39/12* (2013.01); *C07K 16/10* (2013.01); *C07K 16/1027* (2013.01); *A61K 2039/53* (2013.01); *A61K 2039/55511* (2013.01); *A61K 2039/55555* (2013.01); *A61K 2039/6018* (2013.01); *A61K 2039/70* (2013.01); *C07K 2317/76* (2013.01); *C12N 2760/18034* (2013.01); *C12N 2760/18334* (2013.01); *C12N 2760/18434* (2013.01); *C12N 2760/18534* (2013.01); *C12N 2760/18634* (2013.01); *C12N 2770/20034* (2013.01); *Y02A 50/39* (2018.01)

(58) Field of Classification Search

None

See application file for complete search history.

(56) References Cited

U.S. PATENT DOCUMENTS

| | | | |
|---|---|---|---|
| 3,906,092 | A | 9/1975 | Hilleman et al. |
| 4,790,987 | A | 12/1988 | Compans et al. |
| 5,169,628 | A | 12/1992 | Wathen |
| 5,427,782 | A | 6/1995 | Compans et al. |
| 6,225,091 | B1 | 5/2001 | Klein et al. |
| 6,500,419 | B1 | 12/2002 | Hone et al. |
| 6,514,948 | B1 | 2/2003 | Raz et al. |
| 7,001,890 | B1 | 2/2006 | Wagner et al. |
| 7,208,161 | B1 | 4/2007 | Murphy et al. |
| 7,449,324 | B2 | 11/2008 | Fouchier et al. |
| 7,531,342 | B2 | 5/2009 | Fouchier et al. |
| 7,671,186 | B2 | 3/2010 | Klein et al. |
| 7,704,720 | B2 | 4/2010 | Tang et al. |
| 8,217,016 | B2 | 7/2012 | Hoerr et al. |
| 8,252,289 | B2 | 8/2012 | Eleouët et al. |
| 8,710,200 | B2 | 4/2014 | Schrum et al. |
| 8,722,341 | B2 | 5/2014 | Fouchier et al. |
| 8,734,853 | B2 | 5/2014 | Sood et al. |
| 8,754,062 | B2 | 6/2014 | De Fougerolles et al. |
| 8,822,663 | B2 | 9/2014 | Schrum et al. |
| 8,841,433 | B2 | 9/2014 | Fouchier et al. |
| 8,889,146 | B2 | 11/2014 | Blais et al. |
| 8,927,206 | B2 | 1/2015 | De Jong et al. |
| 8,999,380 | B2 | 4/2015 | Bancel et al. |
| 9,192,661 | B2 | 11/2015 | Jain et al. |
| 9,221,891 | B2 | 12/2015 | Bancel et al. |
| 9,303,079 | B2 | 4/2016 | Bancel et al. |
| 9,376,726 | B2 | 6/2016 | Fouchier et al. |

(Continued)

FOREIGN PATENT DOCUMENTS

| | | |
|---|---|---|
| CA | 2473135 | 6/2003 |
| EP | 1026253 | 8/2000 |

(Continued)

OTHER PUBLICATIONS

Geall et al., PNAS, Sep. 2012, 109(36):14604-1460. (Year: 2012).*

(Continued)

*Primary Examiner* — Shanon A. Foley
*Assistant Examiner* — Myron G Hill
(74) *Attorney, Agent, or Firm* — Wolf, Greenfield & Sacks, P.C.

(57) ABSTRACT

The disclosure relates to respiratory virus ribonucleic acid (RNA) vaccines and combination vaccines, as well as methods of using the vaccines and compositions comprising the vaccines.

25 Claims, 24 Drawing Sheets

Specification includes a Sequence Listing.

(56) References Cited

U.S. PATENT DOCUMENTS

| | | | |
|---|---|---|---|
| 9,464,124 | B2 | 10/2016 | Bancel et al. |
| 9,512,456 | B2 | 12/2016 | Wang et al. |
| 9,567,653 | B2 | 2/2017 | Fouchier et al. |
| 9,597,380 | B2 | 3/2017 | Chakraborty et al. |
| 9,623,095 | B2 | 4/2017 | Kallen et al. |
| 9,669,089 | B2 | 6/2017 | Thess et al. |
| 9,790,531 | B2 | 10/2017 | Wang et al. |
| 9,868,691 | B2 | 1/2018 | Benenato et al. |
| 9,872,900 | B2 | 1/2018 | Ciaramella et al. |
| 9,937,196 | B2 | 4/2018 | Jain et al. |
| 10,064,934 | B2 | 9/2018 | Ciaramella et al. |
| 10,064,935 | B2 | 9/2018 | Ciaramella et al. |
| 10,124,055 | B2 | 11/2018 | Ciaramella et al. |
| 10,207,010 | B2 | 2/2019 | Besin et al. |
| 10,273,269 | B2 | 4/2019 | Ciaramella |
| 2003/0092653 | A1 | 5/2003 | Kisich et al. |
| 2003/0232061 | A1 | 12/2003 | Fouchier et al. |
| 2004/0005545 | A1 | 1/2004 | Fouchier et al. |
| 2004/0096451 | A1 | 5/2004 | Young et al. |
| 2005/0032730 | A1 | 2/2005 | Von Der Mulbe et al. |
| 2005/0059624 | A1 | 3/2005 | Hoerr et al. |
| 2005/0250723 | A1 | 11/2005 | Hoerr et al. |
| 2006/0002958 | A1 | 1/2006 | Naylor et al. |
| 2006/0172003 | A1 | 8/2006 | Meers et al. |
| 2006/0228367 | A1 | 10/2006 | Ulbrandt et al. |
| 2007/0280929 | A1 | 12/2007 | Hoerr et al. |
| 2008/0025944 | A1 | 1/2008 | Hoerr et al. |
| 2008/0171711 | A1 | 7/2008 | Hoerr et al. |
| 2009/0123529 | A1 | 5/2009 | Xiaomao |
| 2009/0162395 | A1 | 6/2009 | Crowe et al. |
| 2010/0203076 | A1 | 8/2010 | Fotin-Mleczek et al. |
| 2010/0239608 | A1 | 9/2010 | Von Der Mulbe et al. |
| 2010/0272747 | A1* | 10/2010 | Chow .................. A61K 39/155 424/199.1 |
| 2010/0291156 | A1 | 11/2010 | Barner et al. |
| 2010/0305196 | A1 | 12/2010 | Probst et al. |
| 2011/0135645 | A1 | 6/2011 | Williamson et al. |
| 2011/0250225 | A1 | 10/2011 | Fotin-Mleczek et al. |
| 2011/0269950 | A1 | 11/2011 | Von Der Mulbe et al. |
| 2012/0009221 | A1 | 1/2012 | Hoerr et al. |
| 2012/0045471 | A1 | 2/2012 | Haller et al. |
| 2012/0219573 | A1 | 8/2012 | Baumhof et al. |
| 2013/0022538 | A1 | 1/2013 | Rossi |
| 2013/0078281 | A1 | 3/2013 | He et al. |
| 2013/0102034 | A1 | 4/2013 | Schrum et al. |
| 2013/0121988 | A1 | 5/2013 | Hoerr et al. |
| 2013/0142818 | A1 | 6/2013 | Baumhof et al. |
| 2013/0183355 | A1 | 7/2013 | Jain et al. |
| 2013/0195867 | A1 | 8/2013 | Hoerr et al. |
| 2013/0195967 | A1 | 8/2013 | Guild et al. |
| 2013/0195969 | A1 | 8/2013 | Geall et al. |
| 2013/0202684 | A1 | 8/2013 | Geall et al. |
| 2013/0243848 | A1 | 9/2013 | Lobovkina et al. |
| 2013/0245103 | A1 | 9/2013 | de Fougerolles et al. |
| 2013/0259923 | A1 | 10/2013 | Bancel et al. |
| 2013/0266640 | A1 | 10/2013 | De Fougerolles et al. |
| 2013/0295043 | A1 | 11/2013 | Kallen et al. |
| 2013/0336998 | A1 | 12/2013 | Kallen et al. |
| 2014/0024076 | A1 | 1/2014 | Tang et al. |
| 2014/0037660 | A1 | 2/2014 | Folin-Mleczek et al. |
| 2014/0141042 | A1* | 5/2014 | Vitelli .................. A61K 39/155 424/210.1 |
| 2014/0147432 | A1 | 5/2014 | Bancel et al. |
| 2014/0148502 | A1 | 5/2014 | Bancel et al. |
| 2014/0193482 | A1* | 7/2014 | Bancel ................. A61K 48/005 424/450 |
| 2014/0206752 | A1 | 7/2014 | Afeyan et al. |
| 2014/0271829 | A1 | 9/2014 | Lilja et al. |
| 2014/0370497 | A1 | 12/2014 | Fouchier et al. |
| 2014/0378538 | A1 | 12/2014 | Bancel |
| 2015/0093413 | A1 | 4/2015 | Thess et al. |
| 2015/0126589 | A1 | 5/2015 | Geiger et al. |
| 2015/0141499 | A1 | 5/2015 | Bancel et al. |
| 2015/0307542 | A1 | 10/2015 | Roy et al. |
| 2015/0315541 | A1 | 11/2015 | Bancel et al. |
| 2015/0335728 | A1 | 11/2015 | Wong et al. |
| 2016/0024141 | A1 | 1/2016 | Issa et al. |
| 2016/0032273 | A1 | 2/2016 | Shahrokh et al. |
| 2016/0038612 | A1 | 2/2016 | Hoge et al. |
| 2016/0039884 | A1 | 2/2016 | Li et al. |
| 2016/0151474 | A1 | 6/2016 | Kallen et al. |
| 2016/0271272 | A1 | 9/2016 | Bancel et al. |
| 2016/0317647 | A1 | 11/2016 | Ciaramella et al. |
| 2016/0331828 | A1 | 11/2016 | Ciaramella et al. |
| 2017/0065675 | A1 | 3/2017 | Bancel et al. |
| 2017/0130255 | A1 | 5/2017 | Wang et al. |
| 2017/0202979 | A1 | 7/2017 | Chakraborty et al. |
| 2017/0340724 | A1 | 11/2017 | Ciaramella et al. |
| 2018/0000953 | A1 | 1/2018 | Almarsson et al. |
| 2018/0002393 | A1 | 1/2018 | Bancel et al. |
| 2018/0008694 | A1 | 1/2018 | Ciaramella et al. |
| 2018/0028645 | A1 | 2/2018 | Ciaramella et al. |
| 2018/0028664 | A1 | 2/2018 | Besin et al. |
| 2018/0237849 | A1 | 8/2018 | Thompson |
| 2018/0243225 | A1 | 8/2018 | Ciaramella |
| 2018/0243230 | A1 | 8/2018 | Smith |
| 2018/0271970 | A1 | 9/2018 | Ciaramella et al. |
| 2018/0273977 | A1 | 9/2018 | Mousavi et al. |
| 2018/0274009 | A1 | 9/2018 | Marquardt et al. |
| 2018/0280496 | A1 | 10/2018 | Ciaramella et al. |
| 2018/0289792 | A1 | 10/2018 | Ciaramella et al. |
| 2018/0303929 | A1 | 10/2018 | Ciaramella et al. |
| 2018/0311336 | A1 | 11/2018 | Ciaramella et al. |
| 2018/0318409 | A1 | 11/2018 | Valiante et al. |
| 2018/0363019 | A1 | 12/2018 | Hoge |
| 2019/0008938 | A1 | 1/2019 | Ciaramella et al. |
| 2019/0099481 | A1 | 4/2019 | Ciaramella et al. |
| 2019/0192646 | A1 | 6/2019 | Cohen et al. |

FOREIGN PATENT DOCUMENTS

| | | | | |
|---|---|---|---|---|
| EP | 1083232 | | | 2/2005 |
| EP | 1905844 | A2 | | 2/2008 |
| EP | 2548960 | A1 | | 1/2013 |
| WO | WO 1987/005326 | A1 | | 9/1987 |
| WO | WO 1990/11092 | | | 10/1990 |
| WO | WO 1993/14778 | | | 8/1993 |
| WO | WO 1995/24485 | | | 9/1995 |
| WO | WO 1995/26204 | | | 10/1995 |
| WO | WO 1995/33835 | | | 12/1995 |
| WO | WO 1998/058956 | | | 12/1998 |
| WO | WO 1999/33982 | | | 7/1999 |
| WO | WO 2003/072720 | A2 | | 9/2003 |
| WO | WO 2004/076645 | A1 | | 9/2004 |
| WO | WO 2005/009346 | | | 2/2005 |
| WO | WO 2006/056027 | A1 | | 6/2006 |
| WO | WO 2006/071903 | | | 7/2006 |
| WO | WO 2006/095259 | | | 9/2006 |
| WO | WO 2007/038862 | A1 | | 4/2007 |
| WO | WO 2007/095976 | A2 | | 8/2007 |
| WO | WO2008043052 | | * | 4/2008 |
| WO | WO 2008/052770 | A2 | | 5/2008 |
| WO | WO 2009/030254 | A1 | | 3/2009 |
| WO | WO 2009/030481 | A1 | | 3/2009 |
| WO | WO 2009/095226 | | | 8/2009 |
| WO | WO 2009/127230 | A1 | | 10/2009 |
| WO | WO 2010/037408 | A1 | | 4/2010 |
| WO | WO 2010/037539 | A1 | | 4/2010 |
| WO | WO 2010/042877 | A1 | | 4/2010 |
| WO | WO 2010/054406 | A1 | | 5/2010 |
| WO | WO 2010/088927 | A1 | | 8/2010 |
| WO | WO 2010/149743 | A2 | | 12/2010 |
| WO | WO 2011/005799 | A2 | | 1/2011 |
| WO | WO 2011/026641 | A9 | | 3/2011 |
| WO | WO 2011/068810 | A1 | | 6/2011 |
| WO | WO 2011/069529 | A1 | | 6/2011 |
| WO | WO 2011/069586 | A1 | | 6/2011 |
| WO | WO 2011/144358 | A1 | | 11/2011 |
| WO | WO 2012/019630 | A1 | | 2/2012 |
| WO | WO 2012/019780 | A1 | | 2/2012 |
| WO | WO 2012/116714 | A1 | | 9/2012 |
| WO | WO 2012/116715 | A1 | | 9/2012 |
| WO | WO 2012/116810 | A1 | | 9/2012 |
| WO | WO 2012/116811 | A1 | | 9/2012 |

(56) References Cited

FOREIGN PATENT DOCUMENTS

WO WO 2013/055905 A1 4/2013
WO WO 2013/090186 A1 6/2013
WO WO 2013/102203 A1 7/2013
WO WO 2013/120628 A1 8/2013
WO WO 2013/120629 A1 8/2013
WO WO 2013/185069 A1 12/2013
WO WO 2014/089486 A1 6/2014
WO WO 2014/152774 A1 9/2014
WO WO 2014/152940 A1 9/2014
WO WO 2014/160243 A1 10/2014
WO WO 2015/024668 A2 2/2015
WO WO 2015/101414 A2 7/2015
WO WO 2015/101415 A1 7/2015
WO WO 2015/130584 A2 9/2015
WO WO 2016/103238 6/2016
WO WO 2016/164762 A1 10/2016
WO WO 2016/201377 A1 12/2016
WO WO 2017/015457 A1 1/2017
WO WO 2017/015463 A1 1/2017
WO WO 2017/019935 A1 2/2017
WO WO 2017/020026 A1 2/2017
WO WO 2017/062513 A1 4/2017
WO WO 2017/066789 A1 4/2017
WO WO 2017/070601 A1 4/2017
WO WO 2017/070616 A1 4/2017
WO WO 2017/070618 A1 4/2017
WO WO 2017/070620 A1 4/2017
WO WO 2017/070622 A1 4/2017
WO WO 2017/070623 A1 4/2017
WO WO 2017/201340 A1 11/2017
WO WO 2017/201342 A1 11/2017
WO WO 2017/201347 A1 11/2017
WO WO 2018/053209 A1 3/2018
WO WO 2018/075980 A1 4/2018
WO WO 2018/081459 A1 5/2018
WO WO 2018/081462 A1 5/2018
WO WO 2018/089851 A1 5/2018
WO WO 2018/107088 A1 6/2018
WO WO 2018/111967 A1 6/2018
WO WO 2018/144082 A1 8/2018
WO WO 2018/144778 A1 8/2018
WO WO 2018/151816 A1 8/2018
WO WO 2018/170245 A1 9/2018
WO WO 2018/170256 A1 9/2018
WO WO 2018/170260 A1 9/2018
WO WO 2018/170270 A1 9/2018
WO WO 2018/170347 A1 9/2018
WO WO 2018/175783 A1 9/2018
WO WO 2018/187590 A2 10/2018
WO WO 2018/200737 A1 11/2018
WO WO 2018/232355 A1 12/2018
WO WO 2018/232357 A1 12/2018
WO WO 2019/036670 A1 2/2019
WO WO 2019/036682 A1 2/2019
WO WO 2019/036683 A1 2/2019
WO WO 2019/036685 A1 2/2019
WO WO 2019/103993 A1 5/2019
WO WO 2019/148101 A1 8/2019

OTHER PUBLICATIONS

Heyes et al., Journal of Controlled Release, 2005, 107:276-287. (Year: 2005).*

[No Author Listed], "Messenger RNA", Internet: Wikipedia. Jun. 19, 2013, XP002699196, Retrieved from the Internet: URL: http://en.wikipedia.org/wiki/Messenger RNA.

Archer, S.J., Induction of a T-cell specific antigen on bone marrow lymphocytes with thymus RNA. Immunology. Jan. 1978;34(1):123-9.

Ashley, D.M. et al., Bone marrow-generated dendritic cells pulsed with tumor extracts or tumor RNA induce antitumor immunity against central nervous system tumors. J Exp Med. Oct. 6, 1997; 186(7): 1177-82.

Bettinger, T. et al., Peptide-mediated RNA delivery: a novel approach for enhanced transfection of primary and post-mitotic cells. Nucleic Acids Res. Sep. 15, 2001;29(18):3882-91.

Bogers et al., Potent immune responses in rhesus macaques induced by nonviral delivery of a self-amplifying RNA vaccine expressing HIV type 1 envelope with a cationic nanoemulsion.J Infect Dis. Mar. 15, 2015;211(6):947-55. doi: 10.1093/infdis/jiu522. Epub Sep. 18, 2014.

Bonehill, A., et al., Single-step antigen loading and activation of dendritic cells by mRNA electroporation for the purpose of therapeutic vaccination in melanoma patients. Clin Cancer Res. May 2009; 15(10): 3366-3375.

Bose, S. et al., Role of nucleolin in human parainfluenza virus type 3 infection of human lung epithelial cells. J Viral. Aug. 2004;78(15):8146-58.

Conry, R.M. et al., Characterization of a messenger RNA polynucleotide vaccine vector. Cancer Res. Apr. 1, 1995 ;55 (7):1397-1400.

Dahlman, James E. et al., In vivo endothelial siRNA delivery using polymeric nanoparticles with low molecular weight, Nature Nanotechnology, 2014, No. vol.#, pp. 1-8.

Diken et al., Current Developments in Actively Personalized Cancer Vaccination with a Focus on RNA as the Drug Format. Prog Tumor Res. 2015;42:44-54. doi: 10.1159/000437184. Epub Sep. 4, 2015. Review.

Fleeton et al., Self-replicative RNA vaccines elicit protection against influenza A virus, respiratory syncytial virus, and a tickborne encephalitis virus. J Infect Dis. May 1, 2001;183(9):1395-8. Epub Mar. 30, 2001.

Geall et al., Nonviral delivery of self-amplifying RNA vaccines. Proc Natl Acad Sci U S A. Sep. 4, 2012;109(36):14604-9. doi:10.1073/pnas.1209367109. Epub Aug. 20, 2012.

Gilboa, E. et al., Cancer immunotherapy with mRNA-transfected dendritic cells. lmmunol Rev. Jun. 2004;199:251-63.

Greer et al., Long-term protection in hamsters against human parainfluenza virus type 3 following mucosal or combinations of mucosal and systemic immunizations with chimeric alphavirus-based replicon particles. Scand J Immunol. Dec. 2007;66(6):645-53. Epub Oct. 17, 2007.

Hecker, J.G. et al., Non-Viral DNA and mRNA Gene Delivery to the CNS Pre-Operatively for Neuroprotection and Following Neurotrauma. Molecular Therapy. 2004; 9, S258-S258.

Heiser, A. et al., Induction of polyclonal prostate cancer-specific CTL using dendritic cells transfected with amplified tumor RNA. J lmmunol. Mar. 1, 2001; 166(5):2953-60.

Hoerr, I. et al., In vivo application of RNA leads to induction of specific cytotoxic T lymphocytes and antibodies. EurJ Immunol. Jan. 2000;30(1):1-7.

Hoerr, I. et al., Stabilized Messenger RNA (RNActiveTM) as a Tool for Innovative Gene Delivery. Tissue Engineering. Apr. 2007; 13(4): 865-925.

Hoerr, More than a messenger: A new class of drugs-mRNA-based therapeutics. Genetic Engineering & Biotechnology News. Jun. 18, 2013. http://www.genengnews.com/gen-articles/more-than-a-messenger-a-new-class-of-drugs-mrna-based-therapeutics/4916/ [last accessed Mar. 25, 2016].

Holtkamp, S. et al., Modification of antigen-encoding RNA increases stability, translational efficacy, and T-cell stimulatory capacity of dendritic cells. Blood. Dec. 15, 2006;108(13):4009-17.

Jirikowski, G.F., et al., Reversal of diabetes insipidus in Brattleboro Rats: lntrahypothalamic injection of vasopressin mRNA. Science. Feb. 1992; 255(5047): 996-998.

Kallen et al., A development that may evolve into a revolution in medicine: mRNA as the basis for novel, nucleotide-based vaccines and drugs. Ther Adv Vaccines. Jan. 2014;2(1):10-31. doi: 10.1177/2051013613508729.

Kallen et al., A novel, disruptive vaccination technology: self-adjuvanted RNActive(®) vaccines. Hum Vaccin Immunother. Oct. 2013;9(10):2263-76. doi: 10.4161/hv.25181. Epub Jun. 4, 2013. Review.

Kalra et al., Virosomes: As a Drug Delivery Carrier. American Journal of Advanced Drug Delivery. 2013;1:29-35.

(56) References Cited

OTHER PUBLICATIONS

Kanapathipillai, et al., Nanoparticle targeting of anti-cancer drugs that alter intracellular signaling or influence the tumor microenvironment, Adv. Drug Deliv. Rev. (2014), , pp. 1-12.
Kariko, K., et al., Generating the optimal mRNA for therapy: HPLC purification eliminates immune activation and improves translation of nucleoside-modified, protein-encoding mRNA, Nucleic Acids Research, Oxford University Press, GB, vol. 39, No. 21, Sep. 2, 2011 (Sep. 2, 2011), e142. doi: 10.1093/nar/gkr695. Epub Sep. 2, 2011.
Kauffman et al., Optimization of Lipid Nanoparticle Formulations for mRNA Delivery in Vivo with Fractional Factorial and Definitive Screening Designs. Nano Lett. Nov. 11, 2015;15(11):7300-6. doi: 10.1021/acs.nanolett.5b02497. Epub Oct. 20, 2015.
Kisich et al., Antimycobacterial agent based on mRNA encoding human beta-defensin 2 enables primary macrophages to restrict growth of *Mycobacterium tuberculosis*.Infect Immun Apr. 2001;69(4):2692-9.
Kozielski et al., Bioreducible cationic polymer-based nanoparticles for efficient and environmentally triggered cytoplasmic siRNA delivery to primary human brain cancer cells. ACS Nano. Apr. 22, 2014;8(4):3232-41. doi: 10.1021/nn500704t. Epub Apr. 3, 2014.
Kreiter, S., et al., Intranodal vaccination with naked antigen-encoding RNA elicits potent prophylactic and therapeutic antitumoral immunity. Cancer Res. 2010; 70: 9031-9040.
Kreiter, S., et al., Tumor vaccination using messenger RNA: prospects of a future therapy. Curr Opinion in Immun. Jun. 2011; 23(3): 399-406.
Kuhn, A.N., et al., mRNA as a versatile tool for exogenous protein expression. Current Gene Therapy. Oct. 2012; 12 (5): 347-361.
Leitner, W.W. et al., DNA and RNA-based vaccines: principles, progress and prospects. Vaccine. Dec. 10, 1999;18 (9-10):765-77.
Li, L. et al., Overcoming obstacles to develop effective and safe siRNA therapeutics. Expert Opin Biol Ther. May 2009; 9(5): 609-19.
Lorenzi, J.C., et al., Intranasal vaccination with messenger RNA as a new approach in gene therapy: Use against tuberculosis. BMC Biotechnol. Oct. 2010; 10(77): 1-11.
Mackey et al., mRNA-based cancer vaccine: prevention of B16 melanoma progression and metastasis by systemic injection of MART1 mRNA histidylated lipopolyplexes, Cancer Gene Therapy, 2007, 14, pp. 802-814.
Magini et al., Self-Amplifying mRNA Vaccines Expressing Multiple Conserved Influenza Antigens Confer Protection against Homologous and Heterosubtypic Viral Challenge. PLoS One. Aug. 15, 2016;11(8):e0161193. doi: 10.1371/journal.pone.0161193. eCollection 2016.
Martinon, F. et al., Induction of virus-specific cytotoxic T lymphocytes in vivo by liposome-entrapped mRNA. EurJ Immunol. Jul. 1993;23(7):1719-22.
Midoux et al., Lipid-based mRNA vaccine delivery systems. Expert Rev Vaccines. Feb. 2015;14(2):221-34. doi: 10.1586/14760584.2015.986104. Epub Dec. 26, 2014. Review.
Mitchell, DA et al., RNA transfected dendritic cells as cancer vaccines. Curr Opin Mal Ther. Apr. 2000;2(2):176-81.
Mitchell, DA et al., RNA-transfected dendritic cells in cancer immunotherapy. J Clin Invest. Nov. 2000;106 (9):1065-9.
Muller, M.R. et al., Transfection of dendritic cells with RNA induces CD4- and COB-mediated T cell immunity against breast carcinomas and reveals the immunodominance of presented T cell epitopes. J lmmunol. Jun. 15, 2003;170 (12):5892-6.
Narayanan et al., Interplay between viruses and host mRNA degradation. Biochim Biophys Acta. Jun.-Jul. 2013;1829(6-7):732-41. doi: 10.1016/j.bbagrm.2012.12.003. Epub Dec. 26, 2012.
Petsch et al., Protective efficacy of in vitro synthesized, specific mRNA vaccines against influenza A virus infection. Nat Biotechnol. Dec. 2012;30(12):1210-6. doi: 10.1038/nbt.2436. Epub Nov. 25, 2012.
Phua et al., Messenger RNA (mRNA) nanoparticle tumour vaccination. Nanoscale. Jul. 21, 2014;6(14):7715-29. doi: 10.1039/c4nr01346h. Review.
Pulford, B., et al., Liposome-siRNA-peptide complexes cross the blood-brain barrier and significantly decrease PrP'C on neuronal cells and PrP'RES in infected cell cultures. PLoS ONE. 201 O; 5(6): e11085.
Rabinovich, P.M., et al., Synthetic messenger RNA as a tool for gene therapy. Hum. Gene Ther. Oct. 2006; 17: 1027-1035.
Rittig et al., Intradermal vaccinations with RNA coding for TAA generate CD8+ and CD4+ immune responses and induce clinical benefit in vaccinated patients. Mol Ther. May 2011;19(5):990-9. doi: 10.1038/mt.2010.289. Epub Dec. 28, 2010.
Sahin et al., mRNA-based therapeutics—developing a new class of drugs. Nat Rev Drug Discov. Oct. 2014;13(10):759-80. doi: 10.1038/nrd4278. Epub Sep. 19, 2014.
Schmitt, W.E. et al., In vitro induction of a bladder cancer-specific T-cell response by mRNA-transfected dendritic cells. J Cancer Res Clin Oncol. 2001 ;127(3):203-6.
Schott, J.W., et al., Viral and non-viral approaches for transient delivery of mRNA and proteins. Current Gene Ther. 2011; 11 (5): 382-398.
Segura, J., et al., Monitoring gene therapy by external imaging of mRNA: Pilot study on murine erythropoietin. Ther Drug Monit. Oct. 2007; 29(5): 612-8.
Smits, E., et al., RNA-based gene transfer for adult stem cells and T cells. Leukemia. 2004; 18: 1898-1902.
Sohn, R.L., et al., In-vivo particle mediated delivery of mRNA to mammalian tissues: ballistic and biological effects. Wound Rep and Regen. Jul.-Aug. 2001; 287-296.
Strong, V.T. et al., Incorporation of beta-globin untranslated regions into a Sindbis virus vector for augmentation of heterologous mRNA expression. Gene Ther. Jun. 1997;4(6):624-7.
Sullenger, BA et al., Emerging clinical applications of RNA. Nature. Jul. 11, 2002;418(6894):252-8.
Tavernier, G., et al., mRNA as gene therapeutic: How to control protein expression. J. of Controlled Release. Mar. 2011; 150(3): 238-247.
Teufel, R. et al., Human peripheral blood mononuclear cells transfected with messenger RNA stimulate antigen-specific cytotoxic T-lymphocytes in vitro. Cell Mol Life Sci. Aug. 2005;62(15):1755-62.
Thess et al., Sequence-engineered mRNA Without Chemical Nucleoside Modifications Enables an Effective Protein Therapy in Large Animals. Mol Ther. Sep. 2015;23(9):1456-64. doi: 10.1038/mt.2015.103. Epub Jun. 8, 2015.
Wang et al., Systemic delivery of modified mRNA encoding herpes simplex virus 1 thymidine kinase for targeted cancer gene therapy. Mol Ther. Feb. 2013;21(2):358-67. doi: 10.1038/mt.2012.250. Epub Dec. 11, 2012.
Wong et al., An mRNA vaccine for influenza. Nat Biotechnol. Dec. 2012;30(12):1202-4. doi: 10.1038/nbt.2439.
Yamamoto et al., Current prospects for mRNA gene delivery, European Journal of Pharmaceutics and Biopharmaceutics 71 (2009) 484-489.
Zhou, W.Z. et al., RNA melanoma vaccine: induction of antitumor immunity by human glycoprotein 100 mRNA immunization. Hum Gene Ther. Nov. 1, 1999;10(16):2719-24.

* cited by examiner

Mouse IgG2a - hMPV F specific
A450
2.0
1.5
1.0
0.5
0.0
Day 0
Day 14
Day 28
Day 35
2ug Dose
10ug Dose
PBS Mouse IgG1 - hMPV F specific
A450
2.0
1.5
1.0
0.5
0.0
Day 0
Day 14
Day 28
Day 35
2ug Dose
10ug Dose
PBS IgG2a/IgG1
IgG2a/Th1
IgG1/Th2
>1.0
0.0
0.5
1.0
1.5
2.0
10ug Dose
2ug Dose IL10
pg/mL
800
600
400
200
0
PBS
10ug Dose
2ug Dose TNF-α
pg/mL
500
400
300
200
100
0
PBS
10ug Dose
2ug Dose
Media only
HMPV F peptide pool
Con-A IL4
pg/mL
400
300
200
100
0
PBS
10ug Dose
2ug Dose IL5
pg/mL
500
400
300
200
100
0
PBS
10ug Dose
2ug Dose IL6
pg/mL
6000
4000
2000
0
PBS
10ug Dose
2ug Dose PIV3 serum neutralizing antibody titers
(day 42)

MERS-CoV RNA loads in lungs

Group 1a

Group 1b

Group 2 — dropped out

| Legend | PCR Range |
|---|---|
| | <3.5 |
| | 3.5 - 5 |
| | 5 - 6 |
| | 6 - 7 |
| | >7 |

Summary

SEQUENCE LISTING

```
<160> NUMBER OF SEQ ID NOS: 147

<210> SEQ ID NO 1
<211> LENGTH: 1620
<212> TYPE: DNA
<213> ORGANISM: Human metapneumovirus

<400> SEQUENCE: 1

atgagctgga aggtggtgat tatcttcagc ctgctgatta cacctcaaca cggcctgaag     60

gagagctacc tggaagagag ctgctccacc atcaccgagg gctacctgag cgtgctgcgg    120

accggctggt acaccaacgt gttcaccctg gaggtgggcg acgtggagaa cctgacctgc    180

agcgacggcc ctagcctgat caagaccgag ctggacctga ccaagagcgc tctgagagag    240

ctgaagaccg tgtccgccga ccagctggcc agagaggaac agatcgagaa ccctcggcag    300

agcagattcg tgctgggcgc catcgctctg ggagtcgccg ctgccgctgc agtgacagct    360

ggagtggcca ttgctaagac catcagactg gaaagcgagg tgacagccat caacaatgcc    420

ctgaagaaga ccaacgaggc cgtgagcacc ctgggcaatg gagtgagagt gctggccaca    480

gccgtgcggg agctgaagga cttcgtgagc aagaacctga ccagagccat caacaagaac    540

aagtgcgaca tcgatgacct gaagatggcc gtgagcttct cccagttcaa cagacggttc    600

ctgaacgtgg tgagacagtt ctccgacaac gctggaatca cacctgccat tagcctggac    660

ctgatgaccg acgccgagct ggctagagcc gtgcccaaca tgcccaccag cgctggccag    720

atcaagctga tgctggagaa cagagccatg gtgcggagaa agggcttcgg catcctgatt    780

ggggtgtatg gaagctccgt gatctacatg gtgcagctgc ccatcttcgg cgtgatcgac    840

acaccctgct ggatcgtgaa ggccgctcct agctgctccg agaagaaagg aaactatgcc    900

tgtctgctga gagaggacca gggctggtac tgccagaacg ccggaagcac agtgtactat    960

cccaacgaga aggactgcga gaccagaggc gaccacgtgt tctgcgacac cgctgccgga   1020

atcaacgtgg ccgagcagag caaggagtgc aacatcaaca tcagcacaac caactacccc   1080

tgcaaggtga gcaccggacg gcaccccatc agcatggtgg ctctgagccc tctgggcgct   1140

ctggtggcct gctataaggg cgtgtcctgt agcatcggca gcaatcgggt gggcatcatc   1200

aagcagctga acaagggatg ctcctacatc accaaccagg acgccgacac cgtgaccatc   1260

gacaacaccg tgtaccagct gagcaaggtg gagggcgagc agcacgtgat caagggcaga   1320
```

cccgtgagct ccagcttcga ccccatcaag ttccctgagg accagttcaa cgtggccctg 1380
gaccaggtgt ttgagaacat cgagaacagc caggccctgg tggaccagag caacagaatc 1440
ctgtccagcg ctgagaaggg caacaccggc ttcatcattg tgatcattct gatcgccgtg 1500
ctgggcagct ccatgatcct ggtgagcatc ttcatcatta tcaagaagac caagaaaccc 1560
accggagccc ctcctgagct gagcggcgtg accaacaatg gcttcattcc ccacaactga 1620

<210> SEQ ID NO 2
<211> LENGTH: 1620
<212> TYPE: DNA
<213> ORGANISM: Human metapneumovirus

<400> SEQUENCE: 2
atgtcttgga aagtgatgat catcatttcg ttactcataa caccccagca cgggctaaag 60
gagagttatt tggaagaatc atgtagtact ataactgagg gatacctcag tgttttaaga 120
acaggctggt acactaatgt cttcacatta gaagttggtg atgttgaaaa tcttacatgt 180
actgatggac ctagcttaat caaaacagaa cttgatctaa caaaaagtgc tttaagggaa 240
ctcaaaacag tctctgctga tcagttggcg agagaggagc aaattgaaaa tcccagacaa 300
tcaagatttg tcttaggtgc gatagctctc ggagttgcta cagcagcagc agtcacagca 360
ggcattgcaa tagccaaaac cataaggctt gagagtgagg tgaatgcaat taaaggtgct 420
ctcaaacaaa ctaatgaagc agtatccaca ttagggaatg gtgtgcgggt cctagccact 480
gcagtgagag agctaaaaga atttgtgagc aaaaacctga ctagtgcaat caacaggaac 540
aaatgtgaca ttgctgatct gaagatggct gtcagcttca gtcaattcaa cagaagattt 600
ctaaatgttg tgcggcagtt ttcagacaat gcagggataa caccagcaat atcattggac 660
ctgatgactg atgctgagtt ggccagagct gtatcataca tgccaacatc tgcagggcag 720
ataaaactga tgttggagaa ccgcgcaatg gtaaggagaa aaggatttgg aatcctgata 780
ggggtctacg gaagctctgt gatttacatg gttcaattgc cgatctttgg tgtcatagat 840
acaccttgtt ggatcatcaa ggcagctccc tcttgctcag aaaaaaacgg gaattatgct 900
tgcctcctaa gagaggatca agggtggtat tgtaaaaatg caggatctac tgtttactac 960
ccaaatgaaa aagactgcga aacaagaggt gatcatgttt tttgtgacac agcagcaggg 1020
atcaatgttg ctgagcaatc aagagaatgc aacatcaaca tatctactac caactaccca 1080
tgcaaagtca gcacaggaag acaccctata agcatggttg cactatcacc tctcggtgct 1140
ttggtggctt gctataaagg ggtaagctgc tcgattggca gcaattgggt tggaatcatc 1200
aaacaattac ccaaaggctg ctcatacata accaaccagg atgcagacac tgtaacaatt 1260
gacaataccg tgtatcaact aagcaaagtt gaaggtgaac agcatgtaat aaaagggaga 1320
ccagtttcaa gcagttttga tccaatcaag tttcctgagg atcagttcaa tgttgcgctt 1380
gatcaagtct tcgaaagcat tgagaacagt caggcactag tggaccagtc aaacaaaatt 1440
ctaaacagtg cagaaaaagg aaacactggt ttcattatcg tagtaatttt ggttgctgtt 1500
cttggtctaa ccatgatttc agtgagcatc atcatcataa tcaagaaaac aaggaagccc 1560
acaggagcac ctccagagct gaatggtgtc accaacggcg gtttcatacc acatagttag 1620

<210> SEQ ID NO 3
<211> LENGTH: 1620
<212> TYPE: DNA
<213> ORGANISM: Human metapneumovirus

<400> SEQUENCE: 3

```
atgtcttgga aagtgatgat tatcatttcg ttactcataa cacctcagca tggactaaaa      60
gaaagttatt tagaagaatc atgtagtact ataactgaag gatatctcag tgttttaaga     120
acaggttggt acaccaatgt ctttacatta gaagttggtg atgttgaaaa tcttacatgt     180
actgatggac ctagcttaat caaaacagaa cttgacctaa ccaaaagtgc tttaagagaa     240
ctcaaaacag tttctgctga tcagttagcg agagaagaac aaattgaaaa tcccagacaa     300
tcaaggtttg tcctaggtgc aatagctctt ggagttgcca cagcagcagc agtcacagca     360
ggcattgcaa tagccaaaac tataaggctt gagagtgaag tgaatgcaat caaaggtgct     420
ctcaaaacaa ccaatgaggc agtatcaaca ctaggaaatg gagtgcgggt cctagccact     480
gcagtaagag agctgaaaga atttgtgagc aaaaacctga ctagtgcgat caacaagaac     540
aagtgtgaca ttgctgattt gaagatggct gtcagcttca gtcagttcaa cagaagattc     600
ctaaatgttg tgcggcagtt ttcagacaat gcagggataa caccagcaat atcattggac     660
ctgatgaatg atgctgagct ggccagagct gtatcataca tgccaacatc tgcaggacag     720
ataaaactaa tgttagagaa ccgtgcaatg gtgaggagaa aaggatttgg aatcttgata     780
ggggtctacg gaagctctgt gatttacatg gtccagctgc cgatctttgg tgtcataaat     840
acaccttgtt ggataatcaa ggcagctccc tcttgttcag aaaaagatgg aaattatgct     900
tgcctcctaa gagaggatca agggtggtat tgtaaaaatg caggatccac tgtttactac     960
ccaaatgaaa aagactgcga aacaagaggt gatcatgttt tttgtgacac agcagcaggg    1020
atcaatgttg ctgagcaatc aagagaatgc aacatcaaca tatctaccac caactaccca    1080
tgcaaagtca gcacaggaag acaccctatc agcatggttg cactatcacc tctcggtgct    1140
ttggtagctt gctacaaagg ggttagctgc tcgactggca gtaatcaggt tggaataatc    1200
aaacaactac ctaaaggctg ctcatacata actaaccagg acgcagacac tgtaacaatt    1260
gacaacactg tgtatcaact aagcaaagtt gagggtgaac agcatgtaat aaaagggaga    1320
ccagtttcaa gcagttttga tccaatcagg tttcctgagg atcagttcaa tgttgcgctt    1380
gatcaagtct ttgaaagcat tgaaaacagt caagcactag tggaccagtc aaacaaaatt    1440
ctgaacagtg cagaaaaagg aaacactggt ttcattattg taataatttt gattgctgtt    1500
cttgggttaa ccatgatttc agtgagcatc atcatcataa tcaaaaaaac aaggaagccc    1560
acaggggcac ctccggagct gaatggtgtt accaacggcg gtttcatacc gcatagttag    1620
```

<210> SEQ ID NO 4
<211> LENGTH: 1725
<212> TYPE: DNA
<213> ORGANISM: Human respiratory syncytial virus

<400> SEQUENCE: 4

```
atggagttgc caatcctcaa aacaaatgca attaccacaa tccttgctgc agtcacactc      60
tgtttcgctt ccagtcaaaa catcactgaa gaattttatc aatcaacatg cagtgcagtt     120
agcaaaggct atcttagtgc tctaagaact ggttggtata ctagtgttat aactatagaa     180
ttaagtaata tcaaggaaaa taagtgtaat ggaacagatg ctaaggtaaa attgataaaa     240
caagaattag ataaatataa aaatgctgta acagaattgc agttgctcat gcaaagcaca     300
ccagcagcca acaatcgagc cagaagagaa ctaccaaggt ttatgaatta tacactcaat     360
aataccaaaa ataccaatgt aacattaagc aagaaaagga aaagaagatt tcttggcttt     420
ttgttaggtg ttggatctgc aatcgccagt ggcattgctg tatctaaggt cctgcaccta     480
```

```
gaaggggaag tgaacaaaat caaaagtgct ctactatcca caaacaaggc tgtagtcagc    540
ttatcaaatg gagttagtgt cttaaccagc aaagtgttag acctcaaaaa ctatatagat    600
aaacagttgt tacctattgt gaacaagcaa agctgcagca tatcaaacat tgaaactgtg    660
atagagttcc aacaaaagaa caacagacta ctagagatta ccagggaatt tagtgttaat    720
gcaggtgtaa ctacacctgt aagcacttat atgttaacta atagtgaatt attatcatta    780
atcaatgata tgcctataac aaatgatcag aaaaagttaa tgtccaacaa tgttcaaata    840
gttagacagc aaagttactc tatcatgtcc ataataaagg aggaagtctt agcatatgta    900
gtacaattac cactatatgg tgtaatagat acaccctgtt ggaaactgca cacatcccct    960
ctatgtacaa ccaacacaaa ggaagggtcc aacatctgct taacaagaac cgacagagga   1020
tggtattgtg acaatgcagg atcagtatct ttcttcccac aagctgaaac atgtaaagtt   1080
caatcgaatc gggtattttg tgacacaatg aacagtttaa cattaccaag tgaagtaaat   1140
ctctgcaaca ttgacatatt caaccccaaa tatgattgca aaattatgac ttcaaaaaca   1200
gatgtaagca gctccgttat cacatctcta ggagccattg tgtcatgcta tggcaaaact   1260
aaatgtacag catccaataa aaatcgtggg atcataaaga cattttctaa cgggtgtgat   1320
tatgtatcaa ataagggggt ggatactgtg tctgtaggta atacattata ttatgtaaat   1380
aagcaagaag gcaaaagtct ctatgtaaaa ggtgaaccaa taataaattt ctatgaccca   1440
ttagtgttcc cctctgatga atttgatgca tcaatatctc aagtcaatga gaagattaac   1500
cagagcctag catttattcg taaatccgat gaattattac ataatgtaaa tgctggtaaa   1560
tccaccacaa atatcatgat aactactata attatagtga ttatagtaat attgttatca   1620
ttaattgcag ttggactgct cctatactgc aaggccagaa gcacaccagt cacactaagt   1680
aaggatcaac tgagtggtat aaataatatt gcatttagta actga                   1725
```

<210> SEQ ID NO 5
<211> LENGTH: 539
<212> TYPE: PRT
<213> ORGANISM: Human metapneumovirus isolate

<400> SEQUENCE: 5

```
Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Ser Asp Gly Pro
    50                  55                  60

Ser Leu Ile Lys Thr Glu Leu Asp Leu Thr Lys Ser Ala Leu Arg Glu
65                  70                  75                  80

Leu Lys Thr Val Ser Ala Asp Gln Leu Ala Arg Glu Glu Gln Ile Glu
                85                  90                  95

Asn Pro Arg Gln Ser Arg Phe Val Leu Gly Ala Ile Ala Leu Gly Val
            100                 105                 110

Ala Ala Ala Ala Ala Val Thr Ala Gly Val Ala Ile Ala Lys Thr Ile
        115                 120                 125

Arg Leu Glu Ser Glu Val Thr Ala Ile Asn Asn Ala Leu Lys Lys Thr
    130                 135                 140

Asn Glu Ala Val Ser Thr Leu Gly Asn Gly Val Arg Val Leu Ala Thr
145                 150                 155                 160
```

```
Ala Val Arg Glu Leu Lys Asp Phe Val Ser Lys Asn Leu Thr Arg Ala
                165                 170                 175

Ile Asn Lys Asn Lys Cys Asp Ile Asp Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Pro Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
            260                 265                 270

Leu Pro Ile Phe Gly Val Ile Asp Thr Pro Cys Trp Ile Val Lys Ala
        275                 280                 285

Ala Pro Ser Cys Ser Glu Lys Lys Gly Asn Tyr Ala Cys Leu Leu Arg
    290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Ile Lys Phe Pro Glu Asp Gln Phe Asn Val Ala Leu Asp Gln Val Phe
    450                 455                 460

Glu Asn Ile Glu Asn Ser Gln Ala Leu Val Asp Gln Ser Asn Arg Ile
465                 470                 475                 480

Leu Ser Ser Ala Glu Lys Gly Asn Thr Gly Phe Ile Ile Val Ile Ile
                485                 490                 495

Leu Ile Ala Val Leu Gly Ser Ser Met Ile Leu Val Ser Ile Phe Ile
            500                 505                 510

Ile Ile Lys Lys Thr Lys Lys Pro Thr Gly Ala Pro Pro Glu Leu Ser
        515                 520                 525

Gly Val Thr Asn Asn Gly Phe Ile Pro His Asn
    530                 535
```

<210> SEQ ID NO 6
<211> LENGTH: 539
<212> TYPE: PRT
<213> ORGANISM: Human metapneumovirus

<400> SEQUENCE: 6

Met Ser Trp Lys Val Met Ile Ile Ile Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Thr Asp Gly Pro
    50                  55                  60

Ser Leu Ile Lys Thr Glu Leu Asp Leu Thr Lys Ser Ala Leu Arg Glu
65                  70                  75                  80

Leu Lys Thr Val Ser Ala Asp Gln Leu Ala Arg Glu Glu Gln Ile Glu
                85                  90                  95

Asn Pro Arg Gln Ser Arg Phe Val Leu Gly Ala Ile Ala Leu Gly Val
            100                 105                 110

Ala Thr Ala Ala Ala Val Thr Ala Gly Ile Ala Ile Ala Lys Thr Ile
        115                 120                 125

Arg Leu Glu Ser Glu Val Asn Ala Ile Lys Gly Ala Leu Lys Gln Thr
    130                 135                 140

Asn Glu Ala Val Ser Thr Leu Gly Asn Gly Val Arg Val Leu Ala Thr
145                 150                 155                 160

Ala Val Arg Glu Leu Lys Glu Phe Val Ser Lys Asn Leu Thr Ser Ala
                165                 170                 175

Ile Asn Arg Asn Lys Cys Asp Ile Ala Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Ser Tyr Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
            260                 265                 270

Leu Pro Ile Phe Gly Val Ile Asp Thr Pro Cys Trp Ile Ile Lys Ala
        275                 280                 285

Ala Pro Ser Cys Ser Glu Lys Asn Gly Asn Tyr Ala Cys Leu Leu Arg
    290                 295                 300

Glu Asp Gln Gly Trp Tyr Cys Lys Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Arg Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Trp Val Gly Ile Ile
385                 390                 395                 400

Lys Gln Leu Pro Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
420 425 430

Glu Gln His Val Ile Lys Gly Arg Pro Val Ser Ser Ser Phe Asp Pro
435 440 445

Ile Lys Phe Pro Glu Asp Gln Phe Asn Val Ala Leu Asp Gln Val Phe
450 455 460

Glu Ser Ile Glu Asn Ser Gln Ala Leu Val Asp Gln Ser Asn Lys Ile
465 470 475 480

Leu Asn Ser Ala Glu Lys Gly Asn Thr Gly Phe Ile Ile Val Val Ile
485 490 495

Leu Val Ala Val Leu Gly Leu Thr Met Ile Ser Val Ser Ile Ile Ile
500 505 510

Ile Ile Lys Lys Thr Arg Lys Pro Thr Gly Ala Pro Pro Glu Leu Asn
515 520 525

Gly Val Thr Asn Gly Gly Phe Ile Pro His Ser
530 535

<210> SEQ ID NO 7
<211> LENGTH: 539
<212> TYPE: PRT
<213> ORGANISM: Human metapneumovirus

<400> SEQUENCE: 7

Met Ser Trp Lys Val Met Ile Ile Ile Ser Leu Leu Ile Thr Pro Gln
1 5 10 15

His Gly Leu Lys Glu Ser Tyr Leu Glu Glu Ser Cys Ser Thr Ile Thr
20 25 30

Glu Gly Tyr Leu Ser Val Leu Arg Thr Gly Trp Tyr Thr Asn Val Phe
35 40 45

Thr Leu Glu Val Gly Asp Val Glu Asn Leu Thr Cys Thr Asp Gly Pro
50 55 60

Ser Leu Ile Lys Thr Glu Leu Asp Leu Thr Lys Ser Ala Leu Arg Glu
65 70 75 80

Leu Lys Thr Val Ser Ala Asp Gln Leu Ala Arg Glu Glu Gln Ile Glu
85 90 95

Asn Pro Arg Gln Ser Arg Phe Val Leu Gly Ala Ile Ala Leu Gly Val
100 105 110

Ala Thr Ala Ala Ala Val Thr Ala Gly Ile Ala Ile Ala Lys Thr Ile
115 120 125

Arg Leu Glu Ser Glu Val Asn Ala Ile Lys Gly Ala Leu Lys Thr Thr
130 135 140

Asn Glu Ala Val Ser Thr Leu Gly Asn Gly Val Arg Val Leu Ala Thr
145 150 155 160

Ala Val Arg Glu Leu Lys Glu Phe Val Ser Lys Asn Leu Thr Ser Ala
165 170 175

Ile Asn Lys Asn Lys Cys Asp Ile Ala Asp Leu Lys Met Ala Val Ser
180 185 190

Phe Ser Gln Phe Asn Arg Arg Phe Leu Asn Val Val Arg Gln Phe Ser
195 200 205

Asp Asn Ala Gly Ile Thr Pro Ala Ile Ser Leu Asp Leu Met Asn Asp
210 215 220

Ala Glu Leu Ala Arg Ala Val Ser Tyr Met Pro Thr Ser Ala Gly Gln
225 230 235 240

Ile Lys Leu Met Leu Glu Asn Arg Ala Met Val Arg Arg Lys Gly Phe

```
                245                 250                 255

Gly Ile Leu Ile Gly Val Tyr Gly Ser Ser Val Ile Tyr Met Val Gln
            260                 265                 270

Leu Pro Ile Phe Gly Val Ile Asn Thr Pro Cys Trp Ile Ile Lys Ala
        275                 280                 285

Ala Pro Ser Cys Ser Glu Lys Asp Gly Asn Tyr Ala Cys Leu Leu Arg
    290                 295                 300

Glu Asp Gln Gly Trp Tyr Cys Lys Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Arg Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Thr Gly Ser Asn Gln Val Gly Ile Ile
385                 390                 395                 400

Lys Gln Leu Pro Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Ile Arg Phe Pro Glu Asp Gln Phe Asn Val Ala Leu Asp Gln Val Phe
    450                 455                 460

Glu Ser Ile Glu Asn Ser Gln Ala Leu Val Asp Gln Ser Asn Lys Ile
465                 470                 475                 480

Leu Asn Ser Ala Glu Lys Gly Asn Thr Gly Phe Ile Ile Val Ile Ile
                485                 490                 495

Leu Ile Ala Val Leu Gly Leu Thr Met Ile Ser Val Ser Ile Ile Ile
            500                 505                 510

Ile Ile Lys Lys Thr Arg Lys Pro Thr Gly Ala Pro Pro Glu Leu Asn
        515                 520                 525

Gly Val Thr Asn Gly Gly Phe Ile Pro His Ser
    530                 535


<210> SEQ ID NO 8
<211> LENGTH: 574
<212> TYPE: PRT
<213> ORGANISM: Human respiratory syncytial virus

<400> SEQUENCE: 8

Met Glu Leu Pro Ile Leu Lys Thr Asn Ala Ile Thr Thr Ile Leu Ala
1               5                   10                  15

Ala Val Thr Leu Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80
```

```
Gln Glu Leu Asp Lys Tyr Lys Asn Ala Val Thr Glu Leu Gln Leu Leu
                85                  90                  95

Met Gln Ser Thr Pro Ala Ala Asn Asn Arg Ala Arg Arg Glu Leu Pro
            100                 105                 110

Arg Phe Met Asn Tyr Thr Leu Asn Asn Thr Lys Asn Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Ile
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
```

-continued

```
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570


<210> SEQ ID NO 9
<211> LENGTH: 1617
<212> TYPE: DNA
<213> ORGANISM: Human parainfluenza virus 3

<400> SEQUENCE: 9

atgccaattt caatactgtt aattattaca accatgatca tggcatcaca ctgccaaata     60

gacatcacaa aactacagca tgtaggtgta ttggtcaaca gtcccaaagg gatgaagata    120

tcacaaaact tcgaaacaag atatctaatc ctgagtctca taccaaaaat agaagattct    180

aactcttgtg gtgaccaaca gatcaagcaa tacaagaggt tattggatag actgatcatt    240

cctttatatg atggactaag attacagaag gatgtgatag tgactaatca agaatccaat    300

gaaaacactg atcccagaac agaacgattc tttggagggg taattggaac tattgctcta    360

ggagtagcaa cctcagcaca aattacagca gcagttgctc tggttgaagc caagcaggca    420

agatcagaca ttgaaaaact caaggaagca atcagggaca caaataaagc agtgcagtca    480

gttcagagct ctgtaggaaa tttgatagta gcaattaaat cagtccagga ttatgtcaac    540

aaagaaatcg tgccatcgat tgcgagacta ggttgtgaag cagcaggact tcagttaggg    600

attgcattaa cacagcatta ctcagaatta acaaatatat ttggtgataa cataggatcg    660

ttacaagaaa aaggaataaa attacaaggt atagcatcat tataccgtac aaatatcaca    720

gaaatattca caacatcaac agttgacaaa tatgatattt atgatctatt atttacagaa    780

tcaataaagg tgagagttat agatgttgat ttgaatgatt actcaataac cctccaagtc    840

agactccctt tattgaccag actgctgaac actcaaatct acaaagtaga ttccatatca    900

tacaatatcc aaaatagaga atggtatatc cctcttccca gccatatcat gacgaaaggg    960

gcatttctag gtggagcaga tgtcaaagaa tgcatagaag cattcagcag ttatatatgc   1020

ccttctgatc caggatttgt actaaaccat gaaatggaga gctgtctatc aggaaacata   1080

tcccaatgtc caagaaccac agtcacatca gacatagttc ctaggtatgc atttgtcaat   1140

ggaggagtgg ttgcgaattg tataacaact acatgtacat gcaatggtat cggtaataga   1200

atcaaccaac cacctgatca aggagtcaaa attataacac ataaagaatg taatacaata   1260

ggtatcaacg gaatgctatt caacacaaac aaagaaggaa ctcttgcatt ctacacacca   1320

gacgacataa cattaaacaa ttctgttgca cttgatccga ttgacatatc aatcgagctc   1380

aacaaggcca aatcagatct tgaggaatca aaagaatgga taagaaggtc aaatcaaaag   1440

ctagattcta ttggaagttg gcatcaatct agcactacaa tcatagttat tttgataatg   1500

atgattatat tgtttataat taatataaca ataattacaa ttgcaattaa gtattacaga   1560

attcaaaaga gaaatcgagt ggatcaaaat gataagccgt atgtattaac aaacaag      1617


<210> SEQ ID NO 10
<211> LENGTH: 1716
```

<212> TYPE: DNA
<213> ORGANISM: Human parainfluenza virus 3

<400> SEQUENCE: 10
atggaatact ggaagcacac caaccacgga aaggatgctg gtaatgagct ggagacatcc 60
acagccactc atggcaacaa gctcaccaac aagataacat atatattgtg gacgataacc 120
ctggtgttat tatcaatagt cttcatcata gtgctaacta attccatcaa aagtgaaaag 180
gcccgcgaat cattgctaca agacataaat aatgagttta tggaagttac agaaaagatc 240
caagtggcat cggataatac taatgatcta atacagtcag gagtgaatac aaggcttctt 300
acaattcaga gtcatgtcca gaattatata ccaatatcat tgacacaaca aatatcggat 360
cttaggaaat tcattagtga aattacaatt agaaatgata atcaagaagt gccaccacaa 420
agaataacac atgatgtggg tataaaacct ttaaatccag atgatttctg gagatgcacg 480
tctggtcttc catctttgat gaaaactcca aaaataagat taatgccggg accaggatta 540
ttagctatgc caacgactgt tgatggctgt gtcagaaccc cgtccttagt gataaatgat 600
ctgatttatg cttacacctc aaatctaatt actcgaggtt gccaggatat agggaaatca 660
tatcaagtat tacagatagg gataataact gtaaactcag acttggtacc tgacttaaat 720
cctaggatct ctcatacctt caacataaat gacaatagaa agtcatgttc tctagcactc 780
ctaaatacag atgtatatca actgtgttca accccaaaag ttgatgaaag atcagattat 840
gcatcatcag gcatagaaga tattgtactt gatattgtca attatgatgg ctcaatctcg 900
acaacaagat ttaagaataa taatataagt tttgatcaac catatgcggc attataccca 960
tctgttggac cagggatata ctacaaaggc aaaataatat ttctcgggta tggaggtctt 1020
gaacatccaa taaatgagaa tgcaatctgc aacacaactg ggtgtcctgg gaaaacacag 1080
agagactgta atcaagcatc tcatagtcca tggttttcag atagaaggat ggtcaactct 1140
ataattgttg ttgacaaggg cttgaactca gttccaaaat tgaaggtatg gacgatatct 1200
atgagacaaa attactgggg gtcagaagga agattacttc tactaggtaa caagatctac 1260
atatacacaa gatctacaag ttggcacagc aagttacaat taggaataat tgacattact 1320
gactacagtg atataaggat aaaatggaca tggcataatg tgctatcaag accaggaaac 1380
aatgaatgtc catggggaca ttcatgtccg gatggatgta taacgggagt atataccgat 1440
gcatatccac tcaatcccac aggaagcatt gtatcatctg tcatattgga ctcacaaaaa 1500
tcgagagtca acccagtcat aacttactca acagcaaccg aaagggtaaa cgagctggct 1560
atccgaaaca aaacactctc agctgggtac acaacaacaa gctgcattac acactataac 1620
aaagggtatt gttttcatat agtagaaata aatcataaaa gcttaaacac atttcaaccc 1680
atgttgttca aaacagagat tccaaaaagc tgcagt 1716

<210> SEQ ID NO 11
<211> LENGTH: 1716
<212> TYPE: DNA
<213> ORGANISM: Artificial Sequence
<220> FEATURE:
<223> OTHER INFORMATION: Synthetic Polynucleotide

<400> SEQUENCE: 11
atggaatact ggaagcacac caaccacggc aaggacgccg gcaacgagct ggaaaccagc 60
acagccacac acggcaacaa gctgaccaac aagatcacct acatcctgtg gaccatcacc 120
ctggtgctgc tgagcatcgt gttcatcatc gtgctgacca atagcatcaa gagcgagaag 180

-continued

```
gccagagaga gcctgctgca ggacatcaac aacgagttca tggaagtgac cgagaagatc    240

caggtggcca gcgacaacac caacgacctg atccagagcg gcgtgaacac ccggctgctg    300

accatccaga gccacgtgca gaactacatc cccatcagcc tgacccagca gatcagcgac    360

ctgcggaagt tcatcagcga gatcaccatc cggaacgaca accaggaagt gcccccccag    420

agaatcaccc acgacgtggg catcaagccc ctgaaccccg acgatttctg gcggtgtaca    480

agcggcctgc ccagcctgat gaagaccccc aagatccggc tgatgcctgg ccctggactg    540

ctggccatgc ctaccacagt ggatggctgt gtgcggaccc ccagcctcgt gatcaacgat    600

ctgatctacg cctacaccag caacctgatc acccggggct gccaggatat cggcaagagc    660

taccaggtgc tgcagatcgg catcatcacc gtgaactccg acctggtgcc cgacctgaac    720

cctcggatca gccacacctt caacatcaac gacaacagaa agagctgcag cctggctctg    780

ctgaacaccg acgtgtacca gctgtgcagc acccccaagg tggacgagag aagcgactac    840

gccagcagcg gcatcgagga tatcgtgctg gacatcgtga actacgacgg cagcatcagc    900

accacccggt tcaagaacaa caacatcagc ttcgaccagc cctacgccgc cctgtaccct    960

tctgtgggcc ctggcatcta ctacaagggc aagatcatct tcctgggcta cggcggcctg   1020

gaacacccca tcaacgagaa cgccatctgc aacaccaccg gctgccctgg caagacccag   1080

agagactgca atcaggccag ccacagcccc tggttcagcg accgcagaat ggtcaactct   1140

atcatcgtgg tggacaaggg cctgaacagc gtgcccaagc tgaaagtgtg gacaatcagc   1200

atgcgccaga actactgggg cagcgagggc agacttctgc tgctgggaaa caagatctac   1260

atctacaccc ggtccaccag ctggcacagc aaactgcagc tgggaatcat cgacatcacc   1320

gactacagcg acatccggat caagtggacc tggcacaacg tgctgagcag acccggcaac   1380

aatgagtgcc cttggggcca cagctgcccc gatggatgta tcaccggcgt gtacaccgac   1440

gcctaccccc tgaatcctac cggctccatc gtgtccagcg tgatcctgga cagccagaaa   1500

agcagagtga accccgtgat cacatacagc accgccaccg agagagtgaa cgaactggcc   1560

atcagaaaca agaccctgag cgccggctac accaccacaa gctgcatcac acactacaac   1620

aagggctact gcttccacat cgtggaaatc aaccacaagt ccctgaacac cttccagccc   1680

atgctgttca agaccgagat ccccaagagc tgctcc                              1716
```

```
<210> SEQ ID NO 12
<211> LENGTH: 1617
<212> TYPE: DNA
<213> ORGANISM: Artificial Sequence
<220> FEATURE:
<223> OTHER INFORMATION: Synthetic Polynucleotide

<400> SEQUENCE: 12

atgcccatca gcatcctgct gatcatcacc acaatgatca tggccagcca ctgccagatc     60

gacatcacca agctgcagca cgtgggcgtg ctcgtgaaca gccccaaggg catgaagatc    120

agccagaact tcgagacacg ctacctgatc ctgagcctga tccccaagat cgaggacagc    180

aacagctgcg gcgaccagca gatcaagcag tacaagcggc tgctggacag actgatcatc    240

cccctgtacg acggcctgcg gctgcagaaa gacgtgatcg tgaccaacca ggaaagcaac    300

gagaacaccg acccccggac cgagagattc ttcggcggcg tgatcggcac aatcgccctg    360

ggagtggcca caagcgccca gattacagcc gctgtggccc tggtggaagc caagcaggcc    420

agaagcgaca tcgagaagct gaaagaggcc atccgggaca ccaacaaggc cgtgcagagc    480

gtgcagtcca gcgtgggcaa tctgatcgtg gccatcaagt ccgtgcagga ctacgtgaac    540
```

aaagaaatcg tgccctctat cgcccggctg ggctgtgaag ctgccggact gcagctgggc 600
attgccctga cacagcacta cagcgagctg accaacatct tcggcgacaa catcggcagc 660
ctgcaggaaa agggcattaa gctgcaggga atcgccagcc tgtaccgcac caacatcacc 720
gagatcttca ccaccagcac cgtggataag tacgacatct acgacctgct gttcaccgag 780
agcatcaaag tgcgcgtgat cgacgtggac ctgaacgact acagcatcac cctgcaagtg 840
cggctgcccc tgctgaccag actgctgaac acccagatct acaaggtgga cagcatctcc 900
tacaacatcc agaaccgcga gtggtacatc cctctgccca gccacattat gaccaagggc 960
gcctttctgg gcggagccga cgtgaaagag tgcatcgagg ccttcagcag ctacatctgc 1020
cccagcgacc ctggcttcgt gctgaaccac gagatggaaa gctgcctgag cggcaacatc 1080
agccagtgcc ccagaaccac cgtgacctcc gacatcgtgc ccagatacgc cttcgtgaat 1140
ggcggcgtgg tggccaactg catcaccacc acctgtacct gcaacggcat cggcaaccgg 1200
atcaaccagc ctcccgatca gggcgtgaag attatcaccc acaaagagtg taacaccatc 1260
ggcatcaacg gcatgctgtt caataccaac aaagagggca ccctggcctt ctacaccccc 1320
gacgatatca ccctgaacaa ctccgtggct ctggacccca tcgacatctc catcgagctg 1380
aacaaggcca agagcgacct ggaagagtcc aaagagtgga tccggcggag caaccagaag 1440
ctggactcta tcggcagctg gcaccagagc agcaccacca tcatcgtgat cctgattatg 1500
atgattatcc tgttcatcat caacattacc atcatcacta tcgccattaa gtactaccgg 1560
atccagaaac ggaaccgggt ggaccagaat gacaagccct acgtgctgac aaacaag 1617

<210> SEQ ID NO 13
<211> LENGTH: 539
<212> TYPE: PRT
<213> ORGANISM: Human parainfluenza virus 3

<400> SEQUENCE: 13

Met Pro Ile Ser Ile Leu Leu Ile Ile Thr Thr Met Ile Met Ala Ser
1 5 10 15

His Cys Gln Ile Asp Ile Thr Lys Leu Gln His Val Gly Val Leu Val
20 25 30

Asn Ser Pro Lys Gly Met Lys Ile Ser Gln Asn Phe Glu Thr Arg Tyr
35 40 45

Leu Ile Leu Ser Leu Ile Pro Lys Ile Glu Asp Ser Asn Ser Cys Gly
50 55 60

Asp Gln Gln Ile Lys Gln Tyr Lys Arg Leu Leu Asp Arg Leu Ile Ile
65 70 75 80

Pro Leu Tyr Asp Gly Leu Arg Leu Gln Lys Asp Val Ile Val Thr Asn
85 90 95

Gln Glu Ser Asn Glu Asn Thr Asp Pro Arg Thr Glu Arg Phe Phe Gly
100 105 110

Gly Val Ile Gly Thr Ile Ala Leu Gly Val Ala Thr Ser Ala Gln Ile
115 120 125

Thr Ala Ala Val Ala Leu Val Glu Ala Lys Gln Ala Arg Ser Asp Ile
130 135 140

Glu Lys Leu Lys Glu Ala Ile Arg Asp Thr Asn Lys Ala Val Gln Ser
145 150 155 160

Val Gln Ser Ser Val Gly Asn Leu Ile Val Ala Ile Lys Ser Val Gln
165 170 175

Asp Tyr Val Asn Lys Glu Ile Val Pro Ser Ile Ala Arg Leu Gly Cys

-continued

```
            180                 185                 190

Glu Ala Ala Gly Leu Gln Leu Gly Ile Ala Leu Thr Gln His Tyr Ser
        195                 200                 205

Glu Leu Thr Asn Ile Phe Gly Asp Asn Ile Gly Ser Leu Gln Glu Lys
    210                 215                 220

Gly Ile Lys Leu Gln Gly Ile Ala Ser Leu Tyr Arg Thr Asn Ile Thr
225                 230                 235                 240

Glu Ile Phe Thr Thr Ser Thr Val Asp Lys Tyr Asp Ile Tyr Asp Leu
                245                 250                 255

Leu Phe Thr Glu Ser Ile Lys Val Arg Val Ile Asp Val Asp Leu Asn
            260                 265                 270

Asp Tyr Ser Ile Thr Leu Gln Val Arg Leu Pro Leu Leu Thr Arg Leu
        275                 280                 285

Leu Asn Thr Gln Ile Tyr Lys Val Asp Ser Ile Ser Tyr Asn Ile Gln
    290                 295                 300

Asn Arg Glu Trp Tyr Ile Pro Leu Pro Ser His Ile Met Thr Lys Gly
305                 310                 315                 320

Ala Phe Leu Gly Gly Ala Asp Val Lys Glu Cys Ile Glu Ala Phe Ser
                325                 330                 335

Ser Tyr Ile Cys Pro Ser Asp Pro Gly Phe Val Leu Asn His Glu Met
            340                 345                 350

Glu Ser Cys Leu Ser Gly Asn Ile Ser Gln Cys Pro Arg Thr Thr Val
        355                 360                 365

Thr Ser Asp Ile Val Pro Arg Tyr Ala Phe Val Asn Gly Gly Val Val
    370                 375                 380

Ala Asn Cys Ile Thr Thr Thr Cys Thr Cys Asn Gly Ile Gly Asn Arg
385                 390                 395                 400

Ile Asn Gln Pro Pro Asp Gln Gly Val Lys Ile Ile Thr His Lys Glu
                405                 410                 415

Cys Asn Thr Ile Gly Ile Asn Gly Met Leu Phe Asn Thr Asn Lys Glu
            420                 425                 430

Gly Thr Leu Ala Phe Tyr Thr Pro Asp Asp Ile Thr Leu Asn Asn Ser
        435                 440                 445

Val Ala Leu Asp Pro Ile Asp Ile Ser Ile Glu Leu Asn Lys Ala Lys
    450                 455                 460

Ser Asp Leu Glu Glu Ser Lys Glu Trp Ile Arg Arg Ser Asn Gln Lys
465                 470                 475                 480

Leu Asp Ser Ile Gly Ser Trp His Gln Ser Ser Thr Thr Ile Ile Val
                485                 490                 495

Ile Leu Ile Met Met Ile Ile Leu Phe Ile Ile Asn Ile Thr Ile Ile
            500                 505                 510

Thr Ile Ala Ile Lys Tyr Tyr Arg Ile Gln Lys Arg Asn Arg Val Asp
        515                 520                 525

Gln Asn Asp Lys Pro Tyr Val Leu Thr Asn Lys
    530                 535


<210> SEQ ID NO 14
<211> LENGTH: 572
<212> TYPE: PRT
<213> ORGANISM: Human parainfluenza virus 3

<400> SEQUENCE: 14

Met Glu Tyr Trp Lys His Thr Asn His Gly Lys Asp Ala Gly Asn Glu
1               5                   10                  15
```

-continued

```
Leu Glu Thr Ser Thr Ala Thr His Gly Asn Lys Leu Thr Asn Lys Ile
            20                  25                  30

Thr Tyr Ile Leu Trp Thr Ile Thr Leu Val Leu Leu Ser Ile Val Phe
        35                  40                  45

Ile Ile Val Leu Thr Asn Ser Ile Lys Ser Glu Lys Ala Arg Glu Ser
    50                  55                  60

Leu Leu Gln Asp Ile Asn Asn Glu Phe Met Glu Val Thr Glu Lys Ile
65                  70                  75                  80

Gln Val Ala Ser Asp Asn Thr Asn Asp Leu Ile Gln Ser Gly Val Asn
                85                  90                  95

Thr Arg Leu Leu Thr Ile Gln Ser His Val Gln Asn Tyr Ile Pro Ile
            100                 105                 110

Ser Leu Thr Gln Gln Ile Ser Asp Leu Arg Lys Phe Ile Ser Glu Ile
        115                 120                 125

Thr Ile Arg Asn Asp Asn Gln Glu Val Pro Pro Gln Arg Ile Thr His
    130                 135                 140

Asp Val Gly Ile Lys Pro Leu Asn Pro Asp Asp Phe Trp Arg Cys Thr
145                 150                 155                 160

Ser Gly Leu Pro Ser Leu Met Lys Thr Pro Lys Ile Arg Leu Met Pro
                165                 170                 175

Gly Pro Gly Leu Leu Ala Met Pro Thr Thr Val Asp Gly Cys Val Arg
            180                 185                 190

Thr Pro Ser Leu Val Ile Asn Asp Leu Ile Tyr Ala Tyr Thr Ser Asn
        195                 200                 205

Leu Ile Thr Arg Gly Cys Gln Asp Ile Gly Lys Ser Tyr Gln Val Leu
    210                 215                 220

Gln Ile Gly Ile Ile Thr Val Asn Ser Asp Leu Val Pro Asp Leu Asn
225                 230                 235                 240

Pro Arg Ile Ser His Thr Phe Asn Ile Asn Asp Asn Arg Lys Ser Cys
                245                 250                 255

Ser Leu Ala Leu Leu Asn Thr Asp Val Tyr Gln Leu Cys Ser Thr Pro
            260                 265                 270

Lys Val Asp Glu Arg Ser Asp Tyr Ala Ser Ser Gly Ile Glu Asp Ile
        275                 280                 285

Val Leu Asp Ile Val Asn Tyr Asp Gly Ser Ile Ser Thr Thr Arg Phe
    290                 295                 300

Lys Asn Asn Asn Ile Ser Phe Asp Gln Pro Tyr Ala Ala Leu Tyr Pro
305                 310                 315                 320

Ser Val Gly Pro Gly Ile Tyr Tyr Lys Gly Lys Ile Ile Phe Leu Gly
                325                 330                 335

Tyr Gly Gly Leu Glu His Pro Ile Asn Glu Asn Ala Ile Cys Asn Thr
            340                 345                 350

Thr Gly Cys Pro Gly Lys Thr Gln Arg Asp Cys Asn Gln Ala Ser His
        355                 360                 365

Ser Pro Trp Phe Ser Asp Arg Arg Met Val Asn Ser Ile Ile Val Val
    370                 375                 380

Asp Lys Gly Leu Asn Ser Val Pro Lys Leu Lys Val Trp Thr Ile Ser
385                 390                 395                 400

Met Arg Gln Asn Tyr Trp Gly Ser Glu Gly Arg Leu Leu Leu Leu Gly
                405                 410                 415

Asn Lys Ile Tyr Ile Tyr Thr Arg Ser Thr Ser Trp His Ser Lys Leu
            420                 425                 430

Gln Leu Gly Ile Ile Asp Ile Thr Asp Tyr Ser Asp Ile Arg Ile Lys
```

```
        435                 440                 445

Trp Thr Trp His Asn Val Leu Ser Arg Pro Gly Asn Asn Glu Cys Pro
    450                 455                 460

Trp Gly His Ser Cys Pro Asp Gly Cys Ile Thr Gly Val Tyr Thr Asp
465                 470                 475                 480

Ala Tyr Pro Leu Asn Pro Thr Gly Ser Ile Val Ser Ser Val Ile Leu
                485                 490                 495

Asp Ser Gln Lys Ser Arg Val Asn Pro Val Ile Thr Tyr Ser Thr Ala
            500                 505                 510

Thr Glu Arg Val Asn Glu Leu Ala Ile Arg Asn Lys Thr Leu Ser Ala
        515                 520                 525

Gly Tyr Thr Thr Thr Ser Cys Ile Thr His Tyr Asn Lys Gly Tyr Cys
    530                 535                 540

Phe His Ile Val Glu Ile Asn His Lys Ser Leu Asn Thr Phe Gln Pro
545                 550                 555                 560

Met Leu Phe Lys Thr Glu Ile Pro Lys Ser Cys Ser
                565                 570


<210> SEQ ID NO 15
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 15

Met Glu Thr Pro Ala Gln Leu Leu Phe Leu Leu Leu Leu Trp Leu Pro
1               5                   10                  15

Asp Thr Thr Gly
            20


<210> SEQ ID NO 16
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 16

Met Asp Trp Thr Trp Ile Leu Phe Leu Val Ala Ala Ala Thr Arg Val
1               5                   10                  15

His Ser


<210> SEQ ID NO 17
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 17

Met Leu Gly Ser Asn Ser Gly Gln Arg Val Val Phe Thr Ile Leu Leu
1               5                   10                  15

Leu Leu Val Ala Pro Ala Tyr Ser
            20


<210> SEQ ID NO 18
<211> LENGTH: 17
<212> TYPE: PRT
<213> ORGANISM: Artificial Sequence
<220> FEATURE:
```

<223> OTHER INFORMATION: Synthetic Polypeptide

<400> SEQUENCE: 18

Met Lys Cys Leu Leu Tyr Leu Ala Phe Leu Phe Ile Gly Val Asn Cys
1               5                   10                  15

Ala

<210> SEQ ID NO 19
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 19

Met Trp Leu Val Ser Leu Ala Ile Val Thr Ala Cys Ala Gly Ala
1               5                   10                  15

<210> SEQ ID NO 20
<211> LENGTH: 4062
<212> TYPE: DNA
<213> ORGANISM: Middle East respiratory syndrome coronavirus

<400> SEQUENCE: 20
atgatacact cagtgtttct actgatgttc ttgttaacac ctacagaaag ttacgttgat 60
gtagggccag attctgttaa gtctgcttgt attgaggttg atatacaaca gaccttcttt 120
gataaaactt ggcctaggcc aattgatgtt tctaaggctg acggtattat ataccctcaa 180
ggccgtacat attctaacat aactatcact tatcaaggtc tttttcccta tcagggagac 240
catggtgata tgtatgttta ctctgcagga catgctacag gcacaactcc acaaaagttg 300
tttgtagcta actattctca ggacgtcaaa cagtttgcta atgggtttgt cgtccgtata 360
ggagcagctg ccaattccac tggcactgtt attattagcc catctaccag cgctactata 420
cgaaaaattt accctgcttt tatgctgggt tcttcagttg gtaatttctc agatggtaaa 480
atgggccgct tcttcaatca tactctagtt cttttgcccg atggatgtgg cactttactt 540
agagcttttt attgtattct agagcctcgc tctggaaatc attgtcctgc tggcaattcc 600
tatacttctt ttgccactta tcacactcct gcaacagatt gttctgatgg caattacaat 660
cgtaatgcca gtctgaactc ttttaaggag tattttaatt tacgtaactg cacctttatg 720
tacacttata acattaccga agatgagatt ttagagtggt ttggcattac acaaactgct 780
caaggtgttc acctcttctc atctcggtat gttgatttgt acggcggcaa tatgtttcaa 840
tttgccacct tgcctgttta tgatactatt aagtattatt ctatcattcc tcacagtatt 900
cgttctatcc aaagtgatag aaaagcttgg gctgccttct acgtatataa acttcaaccg 960
ttaactttcc tgttggattt ttctgttgat ggttatatac gcagagctat agactgtggt 1020
tttaatgatt tgtcacaact ccactgctca tatgaatcct tcgatgttga atctggagtt 1080
tattcagttt cgtctttcga agcaaaacct tctggctcag ttgtggaaca ggctgaaggt 1140
gttgaatgtg atttttcacc tcttctgtct ggcacacctc ctcaggttta taatttcaag 1200
cgtttggttt ttaccaattg caattataat cttaccaaat tgctttcact tttttctgtg 1260
aatgatttta cttgtagtca aatatctcca gcagcaattg ctagcaactg ttattcttca 1320
ctgattttgg attatttttc atacccactt agtatgaaat ccgatctcag tgttagttct 1380
gctggtccaa tatcccagtt taattataaa cagtcctttt ctaatcccac atgtttgatc 1440
ttagcgactg ttcctcataa ccttactact attactaagc ctcttaagta cagctatatt 1500

```
aacaagtgct ctcgtcttct ttctgatgat cgtactgaag tacctcagtt agtgaacgct   1560
aatcaatact caccctgtgt atccattgtc ccatccactg tgtgggaaga cggtgattat   1620
tataggaaac aactatctcc acttgaaggt ggtggctggc ttgttgctag tggctcaact   1680
gttgccatga ctgagcaatt acagatgggc tttggtatta cagttcaata tggtacagac   1740
accaatagtg tttgccccaa gcttgaattt gctaatgaca caaaaattgc ctctcaatta   1800
ggcaattgcg tggaatattc cctctatggt gtttcgggcc gtggtgtttt tcagaattgc   1860
acagctgtag gtgttcgaca gcagcgcttt gtttatgatg cgtaccagaa tttagttggc   1920
tattattctg atgatggcaa ctactactgt ctgcgtgctt gtgttagtgt tcctgtttct   1980
gtcatctatg ataaagaaac taaaacccac gctactctat ttggtagtgt tgcatgtgaa   2040
cacatttctt ctaccatgtc tcaatactcc cgttctacgc gatcaatgct taaacggcga   2100
gattctacat atggccccct tcagacacct gttggttgtg tcctaggact tgttaattcc   2160
tctttgttcg tagaggactg caagttgcct ctcggtcaat ctctctgtgc tcttcctgac   2220
acacctagta ctctcacacc tcgcagtgtg cgctctgtgc caggtgaaat gcgcttggca   2280
tccattgctt ttaatcatcc cattcaggtt gatcaactta atagtagtta ttttaaatta   2340
agtataccca ctaatttttc ctttggtgtg actcaggagt acattcagac aaccattcag   2400
aaagttactg ttgattgtaa acagtacgtt tgcaatggtt tccagaagtg tgagcaatta   2460
ctgcgcgagt atggccagtt ttgttccaaa ataaaccagg ctctccatgg tgccaattta   2520
cgccaggatg attctgtacg taatttgttt gcgagcgtga aaagctctca atcatctcct   2580
atcataccag gttttggagg tgactttaat ttgacacttc tagaacctgt ttctatatct   2640
actggcagtc gtagtgcacg tagtgctatt gaggatttgc tatttgacaa agtcactata   2700
gctgatcctg gttatatgca aggttacgat gattgtatgc agcaaggtcc agcatcagct   2760
cgtgatctta tttgtgctca atatgtggct ggttataaag tattacctcc tcttatggat   2820
gttaatatgg aagccgcgta tacttcatct ttgcttggca gcatagcagg tgttggctgg   2880
actgctggct tatcctcctt tgctgctatt ccatttgcac agagtatytt ttataggtta   2940
aacggtgttg gcattactca acaggttctt tcagagaacc aaaagcttat tgccaataag   3000
tttaatcagg ctctgggagc tatgcaaaca ggcttcacta caactaatga agcttttcgg   3060
aaggttcagg atgctgtgaa caacaatgca caggctctat ccaaattagc tagcgagcta   3120
tctaatactt ttggtgctat ttccgcctct attggagaca tcatacaacg tcttgatgtt   3180
ctcgaacagg acgcccaaat agacagactt attaatggcc gtttgacaac actaaatgct   3240
tttgttgcac agcagcttgt tcgttccgaa tcagctgctc tttccgctca attggctaaa   3300
gataaagtca atgagtgtgt caaggcacaa tccaagcgtt ctggattttg cggtcaaggc   3360
acacatatag tgtcctttgt tgtaaatgcc cctaatggcc tttactttat gcatgttggt   3420
tattacccta gcaaccacat tgaggttgtt tctgcttatg gtctttgcga tgcagctaac   3480
cctactaatt gtatagcccc tgttaatggc tactttatta aaactaataa cactaggatt   3540
gttgatgagt ggtcatatac tggctcgtcc ttctatgcac ctgagcccat cacctctctt   3600
aatactaagt atgttgcacc acaggtgaca taccaaaaca tttctactaa cctccctcct   3660
cctcttctcg gcaattccac cgggattgac ttccaagatg agttggatga gtttttcaaa   3720
aatgttagca ccagtatacc taattttggt tctctaacac agattaatac tacattactc   3780
gatcttacct acgagatgtt gtctcttcaa caagttgtta aagcccttaa tgagtcttac   3840
```

atagacctta aagagcttgg caattatact tattacaaca aatggccgtg gtacatttgg 3900
cttggtttca ttgctgggct tgttgcctta gctctatgcg tcttcttcat actgtgctgc 3960
actggttgtg gcacaaactg tatgggaaaa cttaagtgta atcgttgttg tgatagatac 4020
gaggaatacg acctcgagcc gcataaggtt catgttcact aa 4062

<210> SEQ ID NO 21
<211> LENGTH: 4062
<212> TYPE: DNA
<213> ORGANISM: Artificial Sequence
<220> FEATURE:
<223> OTHER INFORMATION: Synthetic Polynucleotide

<400> SEQUENCE: 21
atgatacact cagtgtttct actgatgttc ttgttaacac ctacagaaag ttacgttgat 60
gtagggccag attctgttaa gtctgcttgt attgaggttg atatacaaca gactttcttt 120
gataaaactt ggcctaggcc aattgatgtt tctaaggctg acggtattat ataccctcaa 180
ggccgtacat attctaacat aactatcact tatcaaggtc tttttcccta tcagggagac 240
catggtgata tgtatgttta ctctgcagga catgctacag gcacaactcc acaaaagttg 300
tttgtagcta actattctca ggacgtcaaa cagtttgcta atgggtttgt cgtccgtata 360
ggagcagctg ccaattccac tggcactgtt attattagcc catctaccag cgctactata 420
cgaaaaattt accctgcttt tatgctgggt tcttcagttg gtaatttctc agatggtaaa 480
atgggccgct tcttcaatca tactctagtt cttttgcccg atggatgtgg cactttactt 540
agagcttttt attgtattct ggagcctcgc tctggaaatc attgtcctgc tggcaattcc 600
tatacttctt ttgccactta tcacactcct gcaacagatt gttctgatgg caattacaat 660
cgtaatgcca gtctgaactc ttttaaggag tattttaatt tacgtaactg cacctttatg 720
tacacttata acattaccga agatgagatt ttagagtggt ttggcattac acaaactgct 780
caaggtgttc acctcttctc atctcggtat gttgatttgt acggcggcaa tatgtttcaa 840
tttgccacct tgcctgttta tgatactatt aagtattatt ctatcattcc tcacagtatt 900
cgttctatcc aaagtgatag aaaagcttgg gctgccttct acgtatataa acttcaaccg 960
ttaactttcc tgttggattt ttctgttgat ggttatatac gcagagctat agactgtggt 1020
tttaatgatt tgtcacaact ccactgctca tatgaatcct tcgatgttga atctggagtt 1080
tattcagttt cgtctttcga agcaaaacct tctggctcag ttgtggaaca ggctgaaggt 1140
gttgaatgtg atttttcacc tcttctgtct ggcacacctc ctcaggttta taatttcaag 1200
cgtttggttt ttaccaattg caattataat cttaccaaat tgctttcact tttttctgtg 1260
aatgatttta cttgtagtca aatatctcca gcagcaattg ctagcaactg ttattcttca 1320
ctgattttgg attacttttc atacccactt agtatgaaat ccgatctcag tgttagttct 1380
gctggtccaa tatcccagtt taattataaa cagtcctttt ctaatcccac atgtttgatt 1440
ttagcgactg ttcctcataa ccttactact attactaagc ctcttaagta cagctatatt 1500
aacaagtgct ctcgtcttct ttctgatgat cgtactgaag tacctcagtt agtgaacgct 1560
aatcaatact caccctgtgt atccattgtc ccatccactg tgtgggaaga cggtgattat 1620
tataggaaac aactatctcc acttgaaggt ggtggctggc ttgttgctag tggctcaact 1680
gttgccatga ctgagcaatt acagatgggc tttggtatta cagttcaata tggtacagac 1740
accaatagtg tttgccccaa gcttgaattt gctaatgaca caaaaattgc ctctcaatta 1800
ggcaattgcg tggaatattc cctctatggt gtttcgggcc gtggtgtttt tcagaattgc 1860

```
acagctgtag gtgttcgaca gcagcgcttt gtttatgatg cgtaccagaa tttagttggc   1920
tattattctg atgatggcaa ctactactgt ttgcgtgctt gtgttagtgt tcctgtttct   1980
gtcatctatg ataaagaaac taaaacccac gctactctat ttggtagtgt tgcatgtgaa   2040
cacatttctt ctaccatgtc tcaatactcc cgttctacgc gatcaatgct taaacggcga   2100
gattctacat atggccccct tcagacacct gttggttgtg tcctaggact tgttaattcc   2160
tctttgttcg tagaggactg caagttgcct cttggtcaat ctctctgtgc tcttcctgac   2220
acacctagta ctctcacacc tcgcagtgtg cgctctgttc caggtgaaat gcgcttggca   2280
tccattgctt ttaatcatcc tattcaggtt gatcaactta atagtagtta ttttaaatta   2340
agtataccca ctaatttttc ctttggtgtg actcaggagt acattcagac aaccattcag   2400
aaagttactg ttgattgtaa acagtacgtt tgcaatggtt tccagaagtg tgagcaatta   2460
ctgcgcgagt atggccagtt ttgttccaaa ataaaccagg ctctccatgg tgccaattta   2520
cgccaggatg attctgtacg taatttgttt gcgagcgtga aaagctctca atcatctcct   2580
atcataccag gttttggagg tgactttaat ttgacacttc tggaacctgt ttctatatct   2640
actggcagtc gtagtgcacg tagtgctatt gaggatttgc tatttgacaa agtcactata   2700
gctgatcctg gttatatgca aggttacgat gattgcatgc agcaaggtcc agcatcagct   2760
cgtgatctta tttgtgctca atatgtggct ggttacaaag tattacctcc tcttatggat   2820
gttaatatgg aagccgcgta tacttcatct ttgcttggca gcatagcagg tgttggctgg   2880
actgctggct tatcctcctt tgctgctatt ccatttgcac agagtatctt ttataggtta   2940
aacggtgttg gcattactca acaggttctt tcagagaacc aaaagcttat tgccaataag   3000
tttaatcagg ctctgggagc tatgcaaaca ggcttcacta caactaatga agcttttcag   3060
aaggttcagg atgctgtgaa caacaatgca caggctctat ccaaattagc tagcgagcta   3120
tctaatactt ttggtgctat ttccgcctct attggagaca tcatacaacg tcttgatgtt   3180
ctcgaacagg acgcccaaat agacagactt attaatggcc gtttgacaac actaaatgct   3240
tttgttgcac agcagcttgt tcgttccgaa tcagctgctc tttccgctca attggctaaa   3300
gataaagtca atgagtgtgt caaggcacaa tccaagcgtt ctggattttg cggtcaaggc   3360
acacatatag tgtcctttgt tgtaaatgcc cctaatggcc tttacttcat gcatgttggt   3420
tattacccta gcaaccacat tgaggttgtt tctgcttatg gtctttgcga tgcagctaac   3480
cctactaatt gtatagcccc tgttaatggc tactttatta aaactaataa cactaggatt   3540
gttgatgagt ggtcatatac tggctcgtcc ttctatgcac ctgagcccat tacctccctt   3600
aatactaagt atgttgcacc acaggtgaca taccaaaaca tttctactaa cctccctcct   3660
cctcttctcg gcaattccac cgggattgac ttccaagatg agttggatga gtttttcaaa   3720
aatgttagca ccagtatacc taattttggt tccctaacac agattaatac tacattactc   3780
gatcttacct acgagatgtt gtctcttcaa caagttgtta aagcccttaa tgagtcttac   3840
atagacctta aagagcttgg caattatact tattacaaca aatggccgtg gtacatttgg   3900
cttggtttca ttgctgggct tgttgcctta gctctatgcg tcttcttcat actgtgctgc   3960
actggttgtg gcacaaactg tatgggaaaa cttaagtgta atcgttgttg tgatagatac   4020
gaggaatacg acctcgagcc gcataaggtt catgttcact aa                      4062
```

<210> SEQ ID NO 22
<211> LENGTH: 1845
<212> TYPE: DNA

<213> ORGANISM: Artificial Sequence
<220> FEATURE:
<223> OTHER INFORMATION: Synthetic Polynucleotide

<400> SEQUENCE: 22
atgatccact ccgtgttcct cctcatgttc ctgttgaccc ccactgagtc agactgcaag 60
ctcccgctgg gacagtccct gtgtgcgctg cctgacactc ctagcactct gaccccacgc 120
tccgtgcggt cggtgcctgg cgaaatgcgg ctggcctcca tcgccttcaa tcacccaatc 180
caagtggatc agctgaatag ctcgtatttc aagctgtcca tccccacgaa cttctcgttc 240
ggggtcaccc aggagtacat ccagaccaca attcagaagg tcaccgtcga ttgcaagcaa 300
tacgtgtgca acggcttcca gaagtgcgag cagctgctga gagaatacgg gcagttttgc 360
agcaagatca accaggcgct gcatggagct aacttgcgcc aggacgactc cgtgcgcaac 420
ctctttgcct ctgtgaagtc atcccagtcc tccccaatca tcccgggatt cggaggggac 480
ttcaacctga ccctcctgga gcccgtgtcg atcagcaccg gtagcagatc ggcgcgctca 540
gccattgaag atcttctgtt cgacaaggtc accatcgccg atccgggcta catgcaggga 600
tacgacgact gtatgcagca gggaccagcc tccgcgaggg acctcatctg cgcgcaatac 660
gtggccgggt acaaagtgct gcctcctctg atggatgtga acatggaggc cgcttatact 720
tcgtccctgc tcggctctat cgccggcgtg gggtggaccg ccggcctgtc ctccttcgcc 780
gctatcccct ttgcacaatc cattttctac cggctcaacg gcgtgggcat tactcaacaa 840
gtcctgtcgg agaaccagaa gttgatcgca aacaagttca atcaggccct gggggccatg 900
cagactggat tcactacgac taacgaagcg ttccagaagg tccaggacgc tgtgaacaac 960
aacgcccagg cgctctcaaa gctggcctcc gaactcagca acaccttcgg agccatcagc 1020
gcatcgatcg gtgacataat tcagcggctg gacgtgctgg agcaggacgc ccagatcgac 1080
cgcctcatca acggacggct gaccaccttg aatgccttcg tggcacaaca gctggtccgg 1140
agcgaatcag cggcactttc cgcccaactc gccaaggaca aagtcaacga atgcgtgaag 1200
gcccagtcca agaggtccgg tttctgcggt caaggaaccc atattgtgtc cttcgtcgtg 1260
aacgcgccca acggtctgta ctttatgcac gtcggctact acccgagcaa tcatatcgaa 1320
gtggtgtccg cctacggcct gtgcgatgcc gctaacccca ctaactgtat tgcccctgtg 1380
aacggatatt ttattaagac caacaacacc cgcattgtgg acgaatggtc atacaccggt 1440
tcgtccttct acgcgcccga gcccatcact tcactgaaca ccaaatacgt ggctccgcaa 1500
gtgacctacc agaacatctc caccaatttg ccgccgccgc tgctcggaaa cagcaccgga 1560
attgatttcc aagatgaact ggacgaattc ttcaagaacg tgtccacttc cattcccaac 1620
ttcggaagcc tgacacagat caacaccacc cttctcgacc tgacctacga gatgctgagc 1680
cttcaacaag tggtcaaggc cctgaacgag agctacatcg acctgaagga gctgggcaac 1740
tatacctact acaacaagtg gccggacaag attgaggaga ttctgtcgaa aatctaccac 1800
attgaaaacg agatcgccag aatcaagaag cttatcggcg aagcc 1845

<210> SEQ ID NO 23
<211> LENGTH: 4071
<212> TYPE: DNA
<213> ORGANISM: Artificial Sequence
<220> FEATURE:
<223> OTHER INFORMATION: Synthetic Polynucleotide

<400> SEQUENCE: 23
atggaaaccc ctgcccagct gctgttcctg ctgctgctgt ggctgcctga taccaccggc 60

-continued

```
agctatgtgg acgtgggccc cgatagcgtg aagtccgcct gtatcgaagt ggacatccag    120
cagacctttt tcgacaagac ctggcccaga cccatcgacg tgtccaaggc cgacggcatc    180
atctatccac aaggccggac ctacagcaac atcaccatta cctaccaggg cctgttccca    240
tatcaaggcg accacggcga tatgtacgtg tactctgccg gccacgccac cggcaccaca    300
ccccagaaac tgttcgtggc caactacagc caggacgtga agcagttcgc caacggcttc    360
gtcgtgcgga ttggcgccgc tgccaatagc accggcacag tgatcatcag ccccagcacc    420
agcgccacca tccggaagat ctaccccgcc ttcatgctgg gcagctccgt gggcaatttc    480
agcgacggca agatgggccg gttcttcaac cacaccctgg tgctgctgcc cgatggctgt    540
ggcacactgc tgagagcctt ctactgcatc ctggaaccca gaagcggcaa ccactgccct    600
gccggcaata gctacaccag cttcgccacc taccacacac ccgccaccga ttgctccgac    660
ggcaactaca accggaacgc cagcctgaac agcttcaaag agtacttcaa cctgcggaac    720
tgcaccttca tgtacaccta caatatcacc gaggacgaga tcctggaatg gttcggcatc    780
acccagaccg cccagggcgt gcacctgttc agcagcagat acgtggacct gtacggcggc    840
aacatgttcc agtttgccac cctgcccgtg tacgacacca tcaagtacta cagcatcatc    900
ccccacagca tccggtccat ccagagcgac agaaaagcct gggccgcctt ctacgtgtac    960
aagctgcagc ccctgacctt cctgctggac ttcagcgtgg acggctacat cagacgggcc   1020
atcgactgcg gcttcaacga cctgagccag ctgcactgct cctacgagag cttcgacgtg   1080
gaaagcggcg tgtacagcgt gtccagcttc gaggccaagc ctagcggcag cgtggtggaa   1140
caggctgagg gcgtggaatg cgacttcagc cctctgctga gcggcacccc tccccaggtg   1200
tacaacttca agcggctggt gttcaccaac tgcaattaca acctgaccaa gctgctgagc   1260
ctgttctccg tgaacgactt cacctgtagc cagatcagcc ctgccgccat tgccagcaac   1320
tgctacagca gcctgatcct ggactacttc agctaccccc tgagcatgaa gtccgatctg   1380
agcgtgtcct ccgccggacc catcagccag ttcaactaca agcagagctt cagcaaccct   1440
acctgcctga ttctggccac cgtgccccac aatctgacca ccatcaccaa gcccctgaag   1500
tacagctaca tcaacaagtg cagcagactg ctgtccgacg accggaccga agtgccccag   1560
ctcgtgaacg ccaaccagta cagcccctgc gtgtccatcg tgcccagcac cgtgtgggag   1620
gacggcgact actacagaaa gcagctgagc cccctggaag gcggcggatg gctggtggct   1680
tctggaagca cagtggccat gaccgagcag ctgcagatgg gctttggcat caccgtgcag   1740
tacggcaccg acaccaacag cgtgtgcccc aagctggaat tcgccaatga caccaagatc   1800
gccagccagc tgggaaactg cgtggaatac tccctgtatg gcgtgtccgg acggggcgtg   1860
ttccagaatt gcacagcagt gggagtgcgg cagcagagat tcgtgtacga tgcctaccag   1920
aacctcgtgg gctactacag cgacgacggc aattactact gcctgcgggc ctgtgtgtcc   1980
gtgcccgtgt ccgtgatcta cgacaaagag acaaagaccc acgccacact gttcggctcc   2040
gtggcctgcg agcacatcag ctccaccatg agccagtact cccgctccac ccggtccatg   2100
ctgaagcgga gagatagcac ctacggcccc ctgcagacac ctgtgggatg tgtgctgggc   2160
ctcgtgaaca gctccctgtt tgtggaagat tgcaagctgc ccctgggcca gagcctgtgt   2220
gccctgccag atacccctag caccctgacc cctagaagcg tgcgctctgt gcccggcgaa   2280
atgcggctgg cctctatcgc cttcaatcac cccatccagg tggaccagct gaactccagc   2340
tacttcaagc tgagcatccc caccaacttc agcttcggcg tgacccagga gtacatccag   2400
```

```
accacaatcc agaaagtgac cgtggactgc aagcagtacg tgtgcaacgg ctttcagaag   2460
tgcgaacagc tgctgcgcga gtacggccag ttctgcagca agatcaacca ggccctgcac   2520
ggcgccaacc tgagacagga tgacagcgtg cggaacctgt tcgccagcgt gaaaagcagc   2580
cagtccagcc ccatcatccc tggcttcggc ggcgacttta acctgaccct gctggaacct   2640
gtgtccatca gcaccggctc cagaagcgcc agatccgcca tcgaggacct gctgttcgac   2700
aaagtgacca ttgccgaccc cggctacatg cagggctacg acgattgcat gcagcagggc   2760
ccagccagcg ccagggatct gatctgtgcc cagtatgtgg ccggctacaa ggtgctgccc   2820
cccctgatgg acgtgaacat ggaagccgcc tacacctcca gcctgctggg ctctattgct   2880
ggcgtgggat ggacagccgg cctgtctagc tttgccgcca tccctttcgc ccagagcatc   2940
ttctaccggc tgaacggcgt gggcatcaca caacaggtgc tgagcgagaa ccagaagctg   3000
atcgccaaca agtttaacca ggcactgggc gccatgcaga ccggcttcac caccaccaac   3060
gaggccttca gaaaggtgca ggacgccgtg aacaacaacg cccaggctct gagcaagctg   3120
gcctccgagc tgagcaatac cttcggcgcc atcagcgcct ccatcggcga catcatccag   3180
cggctggacg tgctggaaca ggacgcccag atcgaccggc tgatcaacgg cagactgacc   3240
accctgaacg ccttcgtggc acagcagctc gtgcggagcg aatctgccgc tctgtctgct   3300
cagctggcca aggacaaagt gaacgagtgc gtgaaggccc agtccaagcg gagcggcttt   3360
tgtggccagg gcacccacat cgtgtccttc gtcgtgaatg cccccaacgg cctgtacttt   3420
atgcacgtgg gctattaccc cagcaaccac atcgaggtgg tgtccgccta tggcctgtgc   3480
gacgccgcca atcctaccaa ctgtatcgcc cccgtgaacg gctacttcat caagaccaac   3540
aacacccgga tcgtggacga gtggtcctac acaggcagca gcttctacgc ccccgagccc   3600
atcacctccc tgaacaccaa atacgtggcc ccccaagtga cataccagaa catctccacc   3660
aacctgcccc ctccactgct gggaaattcc accggcatcg acttccagga cgagctggac   3720
gagttcttca agaacgtgtc cacctccatc cccaacttcg gcagcctgac ccagatcaac   3780
accactctgc tggacctgac ctacgagatg ctgtccctgc aacaggtcgt gaaagccctg   3840
aacgagagct acatcgacct gaaagagctg ggaaactaca cctactacaa caagtggcct   3900
tggtacattt ggctgggctt tatcgccggc ctggtggccc tggccctgtg cgtgttcttc   3960
atcctgtgct gcaccggctg cggcaccaat tgcatgggca agctgaaatg caaccggtgc   4020
tgcgacagat acgaggaata cgacctggaa cctcacaaag tgcatgtgca c            4071
```

```
<210> SEQ ID NO 24
<211> LENGTH: 1353
<212> TYPE: PRT
<213> ORGANISM: Middle East respiratory syndrome coronavirus

<400> SEQUENCE: 24

Met Ile His Ser Val Phe Leu Leu Met Phe Leu Leu Thr Pro Thr Glu
1               5                   10                  15

Ser Tyr Val Asp Val Gly Pro Asp Ser Val Lys Ser Ala Cys Ile Glu
            20                  25                  30

Val Asp Ile Gln Gln Thr Phe Phe Asp Lys Thr Trp Pro Arg Pro Ile
        35                  40                  45

Asp Val Ser Lys Ala Asp Gly Ile Ile Tyr Pro Gln Gly Arg Thr Tyr
    50                  55                  60

Ser Asn Ile Thr Ile Thr Tyr Gln Gly Leu Phe Pro Tyr Gln Gly Asp
65                  70                  75                  80
```

```
His Gly Asp Met Tyr Val Tyr Ser Ala Gly His Ala Thr Gly Thr Thr
                85                  90                  95

Pro Gln Lys Leu Phe Val Ala Asn Tyr Ser Gln Asp Val Lys Gln Phe
            100                 105                 110

Ala Asn Gly Phe Val Val Arg Ile Gly Ala Ala Ala Asn Ser Thr Gly
        115                 120                 125

Thr Val Ile Ile Ser Pro Ser Thr Ser Ala Thr Ile Arg Lys Ile Tyr
    130                 135                 140

Pro Ala Phe Met Leu Gly Ser Ser Val Gly Asn Phe Ser Asp Gly Lys
145                 150                 155                 160

Met Gly Arg Phe Phe Asn His Thr Leu Val Leu Leu Pro Asp Gly Cys
                165                 170                 175

Gly Thr Leu Leu Arg Ala Phe Tyr Cys Ile Leu Glu Pro Arg Ser Gly
            180                 185                 190

Asn His Cys Pro Ala Gly Asn Ser Tyr Thr Ser Phe Ala Thr Tyr His
        195                 200                 205

Thr Pro Ala Thr Asp Cys Ser Asp Gly Asn Tyr Asn Arg Asn Ala Ser
    210                 215                 220

Leu Asn Ser Phe Lys Glu Tyr Phe Asn Leu Arg Asn Cys Thr Phe Met
225                 230                 235                 240

Tyr Thr Tyr Asn Ile Thr Glu Asp Glu Ile Leu Glu Trp Phe Gly Ile
                245                 250                 255

Thr Gln Thr Ala Gln Gly Val His Leu Phe Ser Ser Arg Tyr Val Asp
            260                 265                 270

Leu Tyr Gly Gly Asn Met Phe Gln Phe Ala Thr Leu Pro Val Tyr Asp
        275                 280                 285

Thr Ile Lys Tyr Tyr Ser Ile Ile Pro His Ser Ile Arg Ser Ile Gln
    290                 295                 300

Ser Asp Arg Lys Ala Trp Ala Ala Phe Tyr Val Tyr Lys Leu Gln Pro
305                 310                 315                 320

Leu Thr Phe Leu Leu Asp Phe Ser Val Asp Gly Tyr Ile Arg Arg Ala
                325                 330                 335

Ile Asp Cys Gly Phe Asn Asp Leu Ser Gln Leu His Cys Ser Tyr Glu
            340                 345                 350

Ser Phe Asp Val Glu Ser Gly Val Tyr Ser Val Ser Ser Phe Glu Ala
        355                 360                 365

Lys Pro Ser Gly Ser Val Val Glu Gln Ala Glu Gly Val Glu Cys Asp
    370                 375                 380

Phe Ser Pro Leu Leu Ser Gly Thr Pro Pro Gln Val Tyr Asn Phe Lys
385                 390                 395                 400

Arg Leu Val Phe Thr Asn Cys Asn Tyr Asn Leu Thr Lys Leu Leu Ser
                405                 410                 415

Leu Phe Ser Val Asn Asp Phe Thr Cys Ser Gln Ile Ser Pro Ala Ala
            420                 425                 430

Ile Ala Ser Asn Cys Tyr Ser Ser Leu Ile Leu Asp Tyr Phe Ser Tyr
        435                 440                 445

Pro Leu Ser Met Lys Ser Asp Leu Ser Val Ser Ser Ala Gly Pro Ile
    450                 455                 460

Ser Gln Phe Asn Tyr Lys Gln Ser Phe Ser Asn Pro Thr Cys Leu Ile
465                 470                 475                 480

Leu Ala Thr Val Pro His Asn Leu Thr Thr Ile Thr Lys Pro Leu Lys
                485                 490                 495

Tyr Ser Tyr Ile Asn Lys Cys Ser Arg Leu Leu Ser Asp Asp Arg Thr
```

```
            500                 505                 510

Glu Val Pro Gln Leu Val Asn Ala Asn Gln Tyr Ser Pro Cys Val Ser
        515                 520                 525

Ile Val Pro Ser Thr Val Trp Glu Asp Gly Asp Tyr Tyr Arg Lys Gln
    530                 535                 540

Leu Ser Pro Leu Glu Gly Gly Gly Trp Leu Val Ala Ser Gly Ser Thr
545                 550                 555                 560

Val Ala Met Thr Glu Gln Leu Gln Met Gly Phe Gly Ile Thr Val Gln
                565                 570                 575

Tyr Gly Thr Asp Thr Asn Ser Val Cys Pro Lys Leu Glu Phe Ala Asn
            580                 585                 590

Asp Thr Lys Ile Ala Ser Gln Leu Gly Asn Cys Val Glu Tyr Ser Leu
        595                 600                 605

Tyr Gly Val Ser Gly Arg Gly Val Phe Gln Asn Cys Thr Ala Val Gly
    610                 615                 620

Val Arg Gln Gln Arg Phe Val Tyr Asp Ala Tyr Gln Asn Leu Val Gly
625                 630                 635                 640

Tyr Tyr Ser Asp Asp Gly Asn Tyr Tyr Cys Leu Arg Ala Cys Val Ser
                645                 650                 655

Val Pro Val Ser Val Ile Tyr Asp Lys Glu Thr Lys Thr His Ala Thr
            660                 665                 670

Leu Phe Gly Ser Val Ala Cys Glu His Ile Ser Ser Thr Met Ser Gln
        675                 680                 685

Tyr Ser Arg Ser Thr Arg Ser Met Leu Lys Arg Arg Asp Ser Thr Tyr
    690                 695                 700

Gly Pro Leu Gln Thr Pro Val Gly Cys Val Leu Gly Leu Val Asn Ser
705                 710                 715                 720

Ser Leu Phe Val Glu Asp Cys Lys Leu Pro Leu Gly Gln Ser Leu Cys
                725                 730                 735

Ala Leu Pro Asp Thr Pro Ser Thr Leu Thr Pro Arg Ser Val Arg Ser
            740                 745                 750

Val Pro Gly Glu Met Arg Leu Ala Ser Ile Ala Phe Asn His Pro Ile
        755                 760                 765

Gln Val Asp Gln Leu Asn Ser Ser Tyr Phe Lys Leu Ser Ile Pro Thr
    770                 775                 780

Asn Phe Ser Phe Gly Val Thr Gln Glu Tyr Ile Gln Thr Thr Ile Gln
785                 790                 795                 800

Lys Val Thr Val Asp Cys Lys Gln Tyr Val Cys Asn Gly Phe Gln Lys
                805                 810                 815

Cys Glu Gln Leu Leu Arg Glu Tyr Gly Gln Phe Cys Ser Lys Ile Asn
            820                 825                 830

Gln Ala Leu His Gly Ala Asn Leu Arg Gln Asp Asp Ser Val Arg Asn
        835                 840                 845

Leu Phe Ala Ser Val Lys Ser Ser Gln Ser Ser Pro Ile Ile Pro Gly
    850                 855                 860

Phe Gly Gly Asp Phe Asn Leu Thr Leu Leu Glu Pro Val Ser Ile Ser
865                 870                 875                 880

Thr Gly Ser Arg Ser Ala Arg Ser Ala Ile Glu Asp Leu Leu Phe Asp
                885                 890                 895

Lys Val Thr Ile Ala Asp Pro Gly Tyr Met Gln Gly Tyr Asp Asp Cys
            900                 905                 910

Met Gln Gln Gly Pro Ala Ser Ala Arg Asp Leu Ile Cys Ala Gln Tyr
        915                 920                 925
```

```
Val Ala Gly Tyr Lys Val Leu Pro Pro Leu Met Asp Val Asn Met Glu
    930                 935                 940

Ala Ala Tyr Thr Ser Ser Leu Leu Gly Ser Ile Ala Gly Val Gly Trp
945                 950                 955                 960

Thr Ala Gly Leu Ser Ser Phe Ala Ala Ile Pro Phe Ala Gln Ser Ile
                965                 970                 975

Phe Tyr Arg Leu Asn Gly Val Gly Ile Thr Gln Gln Val Leu Ser Glu
            980                 985                 990

Asn Gln Lys Leu Ile Ala Asn Lys  Phe Asn Gln Ala Leu  Gly Ala Met
        995                 1000                 1005

Gln Thr  Gly Phe Thr Thr Thr  Asn Glu Ala Phe Arg  Lys Val Gln
    1010                 1015                 1020

Asp Ala  Val Asn Asn Asn Ala  Gln Ala Leu Ser Lys  Leu Ala Ser
    1025                 1030                 1035

Glu Leu  Ser Asn Thr Phe Gly  Ala Ile Ser Ala Ser  Ile Gly Asp
    1040                 1045                 1050

Ile Ile  Gln Arg Leu Asp Val  Leu Glu Gln Asp Ala  Gln Ile Asp
    1055                 1060                 1065

Arg Leu  Ile Asn Gly Arg Leu  Thr Thr Leu Asn Ala  Phe Val Ala
    1070                 1075                 1080

Gln Gln  Leu Val Arg Ser Glu  Ser Ala Ala Leu Ser  Ala Gln Leu
    1085                 1090                 1095

Ala Lys  Asp Lys Val Asn Glu  Cys Val Lys Ala Gln  Ser Lys Arg
    1100                 1105                 1110

Ser Gly  Phe Cys Gly Gln Gly  Thr His Ile Val Ser  Phe Val Val
    1115                 1120                 1125

Asn Ala  Pro Asn Gly Leu Tyr  Phe Met His Val Gly  Tyr Tyr Pro
    1130                 1135                 1140

Ser Asn  His Ile Glu Val Val  Ser Ala Tyr Gly Leu  Cys Asp Ala
    1145                 1150                 1155

Ala Asn  Pro Thr Asn Cys Ile  Ala Pro Val Asn Gly  Tyr Phe Ile
    1160                 1165                 1170

Lys Thr  Asn Asn Thr Arg Ile  Val Asp Glu Trp Ser  Tyr Thr Gly
    1175                 1180                 1185

Ser Ser  Phe Tyr Ala Pro Glu  Pro Ile Thr Ser Leu  Asn Thr Lys
    1190                 1195                 1200

Tyr Val  Ala Pro Gln Val Thr  Tyr Gln Asn Ile Ser  Thr Asn Leu
    1205                 1210                 1215

Pro Pro  Pro Leu Leu Gly Asn  Ser Thr Gly Ile Asp  Phe Gln Asp
    1220                 1225                 1230

Glu Leu  Asp Glu Phe Phe Lys  Asn Val Ser Thr Ser  Ile Pro Asn
    1235                 1240                 1245

Phe Gly  Ser Leu Thr Gln Ile  Asn Thr Thr Leu Leu  Asp Leu Thr
    1250                 1255                 1260

Tyr Glu  Met Leu Ser Leu Gln  Gln Val Val Lys Ala  Leu Asn Glu
    1265                 1270                 1275

Ser Tyr  Ile Asp Leu Lys Glu  Leu Gly Asn Tyr Thr  Tyr Tyr Asn
    1280                 1285                 1290

Lys Trp  Pro Trp Tyr Ile Trp  Leu Gly Phe Ile Ala  Gly Leu Val
    1295                 1300                 1305

Ala Leu  Ala Leu Cys Val Phe  Phe Ile Leu Cys Cys  Thr Gly Cys
    1310                 1315                 1320
```

-continued

Gly Thr Asn Cys Met Gly Lys Leu Lys Cys Asn Arg Cys Cys Asp
1325 1330 1335

Arg Tyr Glu Glu Tyr Asp Leu Glu Pro His Lys Val His Val His
1340 1345 1350

<210> SEQ ID NO 25
<211> LENGTH: 1353
<212> TYPE: PRT
<213> ORGANISM: Artificial Sequence
<220> FEATURE:
<223> OTHER INFORMATION: Synthetic Polypeptide

<400> SEQUENCE: 25

Met Ile His Ser Val Phe Leu Leu Met Phe Leu Leu Thr Pro Thr Glu
1 5 10 15

Ser Tyr Val Asp Val Gly Pro Asp Ser Val Lys Ser Ala Cys Ile Glu
20 25 30

Val Asp Ile Gln Gln Thr Phe Phe Asp Lys Thr Trp Pro Arg Pro Ile
35 40 45

Asp Val Ser Lys Ala Asp Gly Ile Ile Tyr Pro Gln Gly Arg Thr Tyr
50 55 60

Ser Asn Ile Thr Ile Thr Tyr Gln Gly Leu Phe Pro Tyr Gln Gly Asp
65 70 75 80

His Gly Asp Met Tyr Val Tyr Ser Ala Gly His Ala Thr Gly Thr Thr
85 90 95

Pro Gln Lys Leu Phe Val Ala Asn Tyr Ser Gln Asp Val Lys Gln Phe
100 105 110

Ala Asn Gly Phe Val Val Arg Ile Gly Ala Ala Ala Asn Ser Thr Gly
115 120 125

Thr Val Ile Ile Ser Pro Ser Thr Ser Ala Thr Ile Arg Lys Ile Tyr
130 135 140

Pro Ala Phe Met Leu Gly Ser Ser Val Gly Asn Phe Ser Asp Gly Lys
145 150 155 160

Met Gly Arg Phe Phe Asn His Thr Leu Val Leu Leu Pro Asp Gly Cys
165 170 175

Gly Thr Leu Leu Arg Ala Phe Tyr Cys Ile Leu Glu Pro Arg Ser Gly
180 185 190

Asn His Cys Pro Ala Gly Asn Ser Tyr Thr Ser Phe Ala Thr Tyr His
195 200 205

Thr Pro Ala Thr Asp Cys Ser Asp Gly Asn Tyr Asn Arg Asn Ala Ser
210 215 220

Leu Asn Ser Phe Lys Glu Tyr Phe Asn Leu Arg Asn Cys Thr Phe Met
225 230 235 240

Tyr Thr Tyr Asn Ile Thr Glu Asp Glu Ile Leu Glu Trp Phe Gly Ile
245 250 255

Thr Gln Thr Ala Gln Gly Val His Leu Phe Ser Ser Arg Tyr Val Asp
260 265 270

Leu Tyr Gly Gly Asn Met Phe Gln Phe Ala Thr Leu Pro Val Tyr Asp
275 280 285

Thr Ile Lys Tyr Tyr Ser Ile Ile Pro His Ser Ile Arg Ser Ile Gln
290 295 300

Ser Asp Arg Lys Ala Trp Ala Ala Phe Tyr Val Tyr Lys Leu Gln Pro
305 310 315 320

Leu Thr Phe Leu Leu Asp Phe Ser Val Asp Gly Tyr Ile Arg Arg Ala
325 330 335

```
Ile Asp Cys Gly Phe Asn Asp Leu Ser Gln Leu His Cys Ser Tyr Glu
            340                 345                 350

Ser Phe Asp Val Glu Ser Gly Val Tyr Ser Val Ser Ser Phe Glu Ala
        355                 360                 365

Lys Pro Ser Gly Ser Val Val Glu Gln Ala Glu Gly Val Glu Cys Asp
    370                 375                 380

Phe Ser Pro Leu Leu Ser Gly Thr Pro Pro Gln Val Tyr Asn Phe Lys
385                 390                 395                 400

Arg Leu Val Phe Thr Asn Cys Asn Tyr Asn Leu Thr Lys Leu Leu Ser
                405                 410                 415

Leu Phe Ser Val Asn Asp Phe Thr Cys Ser Gln Ile Ser Pro Ala Ala
            420                 425                 430

Ile Ala Ser Asn Cys Tyr Ser Ser Leu Ile Leu Asp Tyr Phe Ser Tyr
        435                 440                 445

Pro Leu Ser Met Lys Ser Asp Leu Ser Val Ser Ser Ala Gly Pro Ile
    450                 455                 460

Ser Gln Phe Asn Tyr Lys Gln Ser Phe Ser Asn Pro Thr Cys Leu Ile
465                 470                 475                 480

Leu Ala Thr Val Pro His Asn Leu Thr Thr Ile Thr Lys Pro Leu Lys
                485                 490                 495

Tyr Ser Tyr Ile Asn Lys Cys Ser Arg Leu Leu Ser Asp Asp Arg Thr
            500                 505                 510

Glu Val Pro Gln Leu Val Asn Ala Asn Gln Tyr Ser Pro Cys Val Ser
        515                 520                 525

Ile Val Pro Ser Thr Val Trp Glu Asp Gly Asp Tyr Tyr Arg Lys Gln
    530                 535                 540

Leu Ser Pro Leu Glu Gly Gly Gly Trp Leu Val Ala Ser Gly Ser Thr
545                 550                 555                 560

Val Ala Met Thr Glu Gln Leu Gln Met Gly Phe Gly Ile Thr Val Gln
                565                 570                 575

Tyr Gly Thr Asp Thr Asn Ser Val Cys Pro Lys Leu Glu Phe Ala Asn
            580                 585                 590

Asp Thr Lys Ile Ala Ser Gln Leu Gly Asn Cys Val Glu Tyr Ser Leu
        595                 600                 605

Tyr Gly Val Ser Gly Arg Gly Val Phe Gln Asn Cys Thr Ala Val Gly
    610                 615                 620

Val Arg Gln Gln Arg Phe Val Tyr Asp Ala Tyr Gln Asn Leu Val Gly
625                 630                 635                 640

Tyr Tyr Ser Asp Asp Gly Asn Tyr Tyr Cys Leu Arg Ala Cys Val Ser
                645                 650                 655

Val Pro Val Ser Val Ile Tyr Asp Lys Glu Thr Lys Thr His Ala Thr
            660                 665                 670

Leu Phe Gly Ser Val Ala Cys Glu His Ile Ser Ser Thr Met Ser Gln
        675                 680                 685

Tyr Ser Arg Ser Thr Arg Ser Met Leu Lys Arg Arg Asp Ser Thr Tyr
    690                 695                 700

Gly Pro Leu Gln Thr Pro Val Gly Cys Val Leu Gly Leu Val Asn Ser
705                 710                 715                 720

Ser Leu Phe Val Glu Asp Cys Lys Leu Pro Leu Gly Gln Ser Leu Cys
                725                 730                 735

Ala Leu Pro Asp Thr Pro Ser Thr Leu Thr Pro Arg Ser Val Arg Ser
            740                 745                 750

Val Pro Gly Glu Met Arg Leu Ala Ser Ile Ala Phe Asn His Pro Ile
```

-continued

```
        755                 760                 765

Gln Val Asp Gln Leu Asn Ser Ser Tyr Phe Lys Leu Ser Ile Pro Thr
    770                 775                 780

Asn Phe Ser Phe Gly Val Thr Gln Glu Tyr Ile Gln Thr Thr Ile Gln
785                 790                 795                 800

Lys Val Thr Val Asp Cys Lys Gln Tyr Val Cys Asn Gly Phe Gln Lys
                805                 810                 815

Cys Glu Gln Leu Leu Arg Glu Tyr Gly Gln Phe Cys Ser Lys Ile Asn
            820                 825                 830

Gln Ala Leu His Gly Ala Asn Leu Arg Gln Asp Asp Ser Val Arg Asn
        835                 840                 845

Leu Phe Ala Ser Val Lys Ser Ser Gln Ser Ser Pro Ile Ile Pro Gly
    850                 855                 860

Phe Gly Gly Asp Phe Asn Leu Thr Leu Leu Glu Pro Val Ser Ile Ser
865                 870                 875                 880

Thr Gly Ser Arg Ser Ala Arg Ser Ala Ile Glu Asp Leu Leu Phe Asp
                885                 890                 895

Lys Val Thr Ile Ala Asp Pro Gly Tyr Met Gln Gly Tyr Asp Asp Cys
            900                 905                 910

Met Gln Gln Gly Pro Ala Ser Ala Arg Asp Leu Ile Cys Ala Gln Tyr
        915                 920                 925

Val Ala Gly Tyr Lys Val Leu Pro Pro Leu Met Asp Val Asn Met Glu
    930                 935                 940

Ala Ala Tyr Thr Ser Ser Leu Leu Gly Ser Ile Ala Gly Val Gly Trp
945                 950                 955                 960

Thr Ala Gly Leu Ser Ser Phe Ala Ala Ile Pro Phe Ala Gln Ser Ile
                965                 970                 975

Phe Tyr Arg Leu Asn Gly Val Gly Ile Thr Gln Gln Val Leu Ser Glu
            980                 985                 990

Asn Gln Lys Leu Ile Ala Asn Lys  Phe Asn Gln Ala Leu  Gly Ala Met
        995                 1000                1005

Gln Thr  Gly Phe Thr Thr Thr  Asn Glu Ala Phe Gln  Lys Val Gln
    1010                1015                1020

Asp Ala  Val Asn Asn Asn Ala  Gln Ala Leu Ser Lys  Leu Ala Ser
    1025                1030                1035

Glu Leu  Ser Asn Thr Phe Gly  Ala Ile Ser Ala Ser  Ile Gly Asp
    1040                1045                1050

Ile Ile  Gln Arg Leu Asp Val  Leu Glu Gln Asp Ala  Gln Ile Asp
    1055                1060                1065

Arg Leu  Ile Asn Gly Arg Leu  Thr Thr Leu Asn Ala  Phe Val Ala
    1070                1075                1080

Gln Gln  Leu Val Arg Ser Glu  Ser Ala Ala Leu Ser  Ala Gln Leu
    1085                1090                1095

Ala Lys  Asp Lys Val Asn Glu  Cys Val Lys Ala Gln  Ser Lys Arg
    1100                1105                1110

Ser Gly  Phe Cys Gly Gln Gly  Thr His Ile Val Ser  Phe Val Val
    1115                1120                1125

Asn Ala  Pro Asn Gly Leu Tyr  Phe Met His Val Gly  Tyr Tyr Pro
    1130                1135                1140

Ser Asn  His Ile Glu Val Val  Ser Ala Tyr Gly Leu  Cys Asp Ala
    1145                1150                1155

Ala Asn  Pro Thr Asn Cys Ile  Ala Pro Val Asn Gly  Tyr Phe Ile
    1160                1165                1170
```

```
Lys Thr  Asn Asn Thr Arg Ile  Val Asp Glu Trp Ser  Tyr Thr Gly
    1175                 1180                 1185

Ser Ser  Phe Tyr Ala Pro Glu  Pro Ile Thr Ser Leu  Asn Thr Lys
    1190                 1195                 1200

Tyr Val  Ala Pro Gln Val Thr  Tyr Gln Asn Ile Ser  Thr Asn Leu
    1205                 1210                 1215

Pro Pro  Pro Leu Leu Gly Asn  Ser Thr Gly Ile Asp  Phe Gln Asp
    1220                 1225                 1230

Glu Leu  Asp Glu Phe Phe Lys  Asn Val Ser Thr Ser  Ile Pro Asn
    1235                 1240                 1245

Phe Gly  Ser Leu Thr Gln Ile  Asn Thr Thr Leu Leu  Asp Leu Thr
    1250                 1255                 1260

Tyr Glu  Met Leu Ser Leu Gln  Gln Val Val Lys Ala  Leu Asn Glu
    1265                 1270                 1275

Ser Tyr  Ile Asp Leu Lys Glu  Leu Gly Asn Tyr Thr  Tyr Tyr Asn
    1280                 1285                 1290

Lys Trp  Pro Trp Tyr Ile Trp  Leu Gly Phe Ile Ala  Gly Leu Val
    1295                 1300                 1305

Ala Leu  Ala Leu Cys Val Phe  Phe Ile Leu Cys Cys  Thr Gly Cys
    1310                 1315                 1320

Gly Thr  Asn Cys Met Gly Lys  Leu Lys Cys Asn Arg  Cys Cys Asp
    1325                 1330                 1335

Arg Tyr  Glu Glu Tyr Asp Leu  Glu Pro His Lys Val  His Val His
    1340                 1345                 1350


<210> SEQ ID NO 26
<211> LENGTH: 615
<212> TYPE: PRT
<213> ORGANISM: Artificial Sequence
<220> FEATURE:
<223> OTHER INFORMATION: Synthetic Polypeptide

<400> SEQUENCE: 26

Met Ile His Ser Val Phe Leu Leu Met Phe Leu Leu Thr Pro Thr Glu
1               5                   10                  15

Ser Asp Cys Lys Leu Pro Leu Gly Gln Ser Leu Cys Ala Leu Pro Asp
            20                  25                  30

Thr Pro Ser Thr Leu Thr Pro Arg Ser Val Arg Ser Val Pro Gly Glu
        35                  40                  45

Met Arg Leu Ala Ser Ile Ala Phe Asn His Pro Ile Gln Val Asp Gln
    50                  55                  60

Leu Asn Ser Ser Tyr Phe Lys Leu Ser Ile Pro Thr Asn Phe Ser Phe
65                  70                  75                  80

Gly Val Thr Gln Glu Tyr Ile Gln Thr Thr Ile Gln Lys Val Thr Val
                85                  90                  95

Asp Cys Lys Gln Tyr Val Cys Asn Gly Phe Gln Lys Cys Glu Gln Leu
            100                 105                 110

Leu Arg Glu Tyr Gly Gln Phe Cys Ser Lys Ile Asn Gln Ala Leu His
        115                 120                 125

Gly Ala Asn Leu Arg Gln Asp Asp Ser Val Arg Asn Leu Phe Ala Ser
    130                 135                 140

Val Lys Ser Ser Gln Ser Ser Pro Ile Ile Pro Gly Phe Gly Gly Asp
145                 150                 155                 160

Phe Asn Leu Thr Leu Leu Glu Pro Val Ser Ile Ser Thr Gly Ser Arg
                165                 170                 175
```

-continued

```
Ser Ala Arg Ser Ala Ile Glu Asp Leu Leu Phe Asp Lys Val Thr Ile
            180                 185                 190

Ala Asp Pro Gly Tyr Met Gln Gly Tyr Asp Asp Cys Met Gln Gln Gly
        195                 200                 205

Pro Ala Ser Ala Arg Asp Leu Ile Cys Ala Gln Tyr Val Ala Gly Tyr
    210                 215                 220

Lys Val Leu Pro Pro Leu Met Asp Val Asn Met Glu Ala Ala Tyr Thr
225                 230                 235                 240

Ser Ser Leu Leu Gly Ser Ile Ala Gly Val Gly Trp Thr Ala Gly Leu
                245                 250                 255

Ser Ser Phe Ala Ala Ile Pro Phe Ala Gln Ser Ile Phe Tyr Arg Leu
            260                 265                 270

Asn Gly Val Gly Ile Thr Gln Gln Val Leu Ser Glu Asn Gln Lys Leu
        275                 280                 285

Ile Ala Asn Lys Phe Asn Gln Ala Leu Gly Ala Met Gln Thr Gly Phe
    290                 295                 300

Thr Thr Thr Asn Glu Ala Phe Gln Lys Val Gln Asp Ala Val Asn Asn
305                 310                 315                 320

Asn Ala Gln Ala Leu Ser Lys Leu Ala Ser Glu Leu Ser Asn Thr Phe
                325                 330                 335

Gly Ala Ile Ser Ala Ser Ile Gly Asp Ile Ile Gln Arg Leu Asp Val
            340                 345                 350

Leu Glu Gln Asp Ala Gln Ile Asp Arg Leu Ile Asn Gly Arg Leu Thr
        355                 360                 365

Thr Leu Asn Ala Phe Val Ala Gln Gln Leu Val Arg Ser Glu Ser Ala
    370                 375                 380

Ala Leu Ser Ala Gln Leu Ala Lys Asp Lys Val Asn Glu Cys Val Lys
385                 390                 395                 400

Ala Gln Ser Lys Arg Ser Gly Phe Cys Gly Gln Gly Thr His Ile Val
                405                 410                 415

Ser Phe Val Val Asn Ala Pro Asn Gly Leu Tyr Phe Met His Val Gly
            420                 425                 430

Tyr Tyr Pro Ser Asn His Ile Glu Val Val Ser Ala Tyr Gly Leu Cys
        435                 440                 445

Asp Ala Ala Asn Pro Thr Asn Cys Ile Ala Pro Val Asn Gly Tyr Phe
    450                 455                 460

Ile Lys Thr Asn Asn Thr Arg Ile Val Asp Glu Trp Ser Tyr Thr Gly
465                 470                 475                 480

Ser Ser Phe Tyr Ala Pro Glu Pro Ile Thr Ser Leu Asn Thr Lys Tyr
                485                 490                 495

Val Ala Pro Gln Val Thr Tyr Gln Asn Ile Ser Thr Asn Leu Pro Pro
            500                 505                 510

Pro Leu Leu Gly Asn Ser Thr Gly Ile Asp Phe Gln Asp Glu Leu Asp
        515                 520                 525

Glu Phe Phe Lys Asn Val Ser Thr Ser Ile Pro Asn Phe Gly Ser Leu
    530                 535                 540

Thr Gln Ile Asn Thr Thr Leu Leu Asp Leu Thr Tyr Glu Met Leu Ser
545                 550                 555                 560

Leu Gln Gln Val Val Lys Ala Leu Asn Glu Ser Tyr Ile Asp Leu Lys
                565                 570                 575

Glu Leu Gly Asn Tyr Thr Tyr Tyr Asn Lys Trp Pro Asp Lys Ile Glu
            580                 585                 590
```

-continued

```
Glu Ile Leu Ser Lys Ile Tyr His Ile Glu Asn Glu Ile Ala Arg Ile
        595                 600                 605

Lys Lys Leu Ile Gly Glu Ala
    610                 615


<210> SEQ ID NO 27
<211> LENGTH: 1353
<212> TYPE: PRT
<213> ORGANISM: Middle East respiratory syndrome coronavirus

<400> SEQUENCE: 27

Met Ile His Ser Val Phe Leu Leu Met Phe Leu Leu Thr Pro Thr Glu
1               5                   10                  15

Ser Tyr Val Asp Val Gly Pro Asp Ser Val Lys Ser Ala Cys Ile Glu
            20                  25                  30

Val Asp Ile Gln Gln Thr Phe Phe Asp Lys Thr Trp Pro Arg Pro Ile
        35                  40                  45

Asp Val Ser Lys Ala Asp Gly Ile Ile Tyr Pro Gln Gly Arg Thr Tyr
    50                  55                  60

Ser Asn Ile Thr Ile Thr Tyr Gln Gly Leu Phe Pro Tyr Gln Gly Asp
65                  70                  75                  80

His Gly Asp Met Tyr Val Tyr Ser Ala Gly His Ala Thr Gly Thr Thr
                85                  90                  95

Pro Gln Lys Leu Phe Val Ala Asn Tyr Ser Gln Asp Val Lys Gln Phe
            100                 105                 110

Ala Asn Gly Phe Val Val Arg Ile Gly Ala Ala Ala Asn Ser Thr Gly
        115                 120                 125

Thr Val Ile Ile Ser Pro Ser Thr Ser Ala Thr Ile Arg Lys Ile Tyr
    130                 135                 140

Pro Ala Phe Met Leu Gly Ser Ser Val Gly Asn Phe Ser Asp Gly Lys
145                 150                 155                 160

Met Gly Arg Phe Phe Asn His Thr Leu Val Leu Leu Pro Asp Gly Cys
                165                 170                 175

Gly Thr Leu Leu Arg Ala Phe Tyr Cys Ile Leu Glu Pro Arg Ser Gly
            180                 185                 190

Asn His Cys Pro Ala Gly Asn Ser Tyr Thr Ser Phe Ala Thr Tyr His
        195                 200                 205

Thr Pro Ala Thr Asp Cys Ser Asp Gly Asn Tyr Asn Arg Asn Ala Ser
    210                 215                 220

Leu Asn Ser Phe Lys Glu Tyr Phe Asn Leu Arg Asn Cys Thr Phe Met
225                 230                 235                 240

Tyr Thr Tyr Asn Ile Thr Glu Asp Glu Ile Leu Glu Trp Phe Gly Ile
                245                 250                 255

Thr Gln Thr Ala Gln Gly Val His Leu Phe Ser Ser Arg Tyr Val Asp
            260                 265                 270

Leu Tyr Gly Gly Asn Met Phe Gln Phe Ala Thr Leu Pro Val Tyr Asp
        275                 280                 285

Thr Ile Lys Tyr Tyr Ser Ile Ile Pro His Ser Ile Arg Ser Ile Gln
    290                 295                 300

Ser Asp Arg Lys Ala Trp Ala Ala Phe Tyr Val Tyr Lys Leu Gln Pro
305                 310                 315                 320

Leu Thr Phe Leu Leu Asp Phe Ser Val Asp Gly Tyr Ile Arg Arg Ala
                325                 330                 335

Ile Asp Cys Gly Phe Asn Asp Leu Ser Gln Leu His Cys Ser Tyr Glu
            340                 345                 350
```

```
Ser Phe Asp Val Glu Ser Gly Val Tyr Ser Val Ser Ser Phe Glu Ala
        355                 360                 365

Lys Pro Ser Gly Ser Val Val Glu Gln Ala Glu Gly Val Glu Cys Asp
    370                 375                 380

Phe Ser Pro Leu Leu Ser Gly Thr Pro Pro Gln Val Tyr Asn Phe Lys
385                 390                 395                 400

Arg Leu Val Phe Thr Asn Cys Asn Tyr Asn Leu Thr Lys Leu Leu Ser
                405                 410                 415

Leu Phe Ser Val Asn Asp Phe Thr Cys Ser Gln Ile Ser Pro Ala Ala
            420                 425                 430

Ile Ala Ser Asn Cys Tyr Ser Ser Leu Ile Leu Asp Tyr Phe Ser Tyr
        435                 440                 445

Pro Leu Ser Met Lys Ser Asp Leu Ser Val Ser Ser Ala Gly Pro Ile
    450                 455                 460

Ser Gln Phe Asn Tyr Lys Gln Ser Phe Ser Asn Pro Thr Cys Leu Ile
465                 470                 475                 480

Leu Ala Thr Val Pro His Asn Leu Thr Thr Ile Thr Lys Pro Leu Lys
                485                 490                 495

Tyr Ser Tyr Ile Asn Lys Cys Ser Arg Leu Leu Ser Asp Asp Arg Thr
            500                 505                 510

Glu Val Pro Gln Leu Val Asn Ala Asn Gln Tyr Ser Pro Cys Val Ser
        515                 520                 525

Ile Val Pro Ser Thr Val Trp Glu Asp Gly Asp Tyr Tyr Arg Lys Gln
    530                 535                 540

Leu Ser Pro Leu Glu Gly Gly Gly Trp Leu Val Ala Ser Gly Ser Thr
545                 550                 555                 560

Val Ala Met Thr Glu Gln Leu Gln Met Gly Phe Gly Ile Thr Val Gln
                565                 570                 575

Tyr Gly Thr Asp Thr Asn Ser Val Cys Pro Lys Leu Glu Phe Ala Asn
            580                 585                 590

Asp Thr Lys Ile Ala Ser Gln Leu Gly Asn Cys Val Glu Tyr Ser Leu
        595                 600                 605

Tyr Gly Val Ser Gly Arg Gly Val Phe Gln Asn Cys Thr Ala Val Gly
    610                 615                 620

Val Arg Gln Gln Arg Phe Val Tyr Asp Ala Tyr Gln Asn Leu Val Gly
625                 630                 635                 640

Tyr Tyr Ser Asp Asp Gly Asn Tyr Tyr Cys Leu Arg Ala Cys Val Ser
                645                 650                 655

Val Pro Val Ser Val Ile Tyr Asp Lys Glu Thr Lys Thr His Ala Thr
            660                 665                 670

Leu Phe Gly Ser Val Ala Cys Glu His Ile Ser Ser Thr Met Ser Gln
        675                 680                 685

Tyr Ser Arg Ser Thr Arg Ser Met Leu Lys Arg Arg Asp Ser Thr Tyr
    690                 695                 700

Gly Pro Leu Gln Thr Pro Val Gly Cys Val Leu Gly Leu Val Asn Ser
705                 710                 715                 720

Ser Leu Phe Val Glu Asp Cys Lys Leu Pro Leu Gly Gln Ser Leu Cys
                725                 730                 735

Ala Leu Pro Asp Thr Pro Ser Thr Leu Thr Pro Arg Ser Val Arg Ser
            740                 745                 750

Val Pro Gly Glu Met Arg Leu Ala Ser Ile Ala Phe Asn His Pro Ile
        755                 760                 765
```

-continued

```
Gln Val Asp Gln Leu Asn Ser Ser Tyr Phe Lys Leu Ser Ile Pro Thr
    770                 775                 780

Asn Phe Ser Phe Gly Val Thr Gln Glu Tyr Ile Gln Thr Thr Ile Gln
785                 790                 795                 800

Lys Val Thr Val Asp Cys Lys Gln Tyr Val Cys Asn Gly Phe Gln Lys
                805                 810                 815

Cys Glu Gln Leu Leu Arg Glu Tyr Gly Gln Phe Cys Ser Lys Ile Asn
            820                 825                 830

Gln Ala Leu His Gly Ala Asn Leu Arg Gln Asp Asp Ser Val Arg Asn
        835                 840                 845

Leu Phe Ala Ser Val Lys Ser Ser Gln Ser Ser Pro Ile Ile Pro Gly
    850                 855                 860

Phe Gly Gly Asp Phe Asn Leu Thr Leu Leu Glu Pro Val Ser Ile Ser
865                 870                 875                 880

Thr Gly Ser Arg Ser Ala Arg Ser Ala Ile Glu Asp Leu Leu Phe Asp
                885                 890                 895

Lys Val Thr Ile Ala Asp Pro Gly Tyr Met Gln Gly Tyr Asp Asp Cys
            900                 905                 910

Met Gln Gln Gly Pro Ala Ser Ala Arg Asp Leu Ile Cys Ala Gln Tyr
        915                 920                 925

Val Ala Gly Tyr Lys Val Leu Pro Pro Leu Met Asp Val Asn Met Glu
    930                 935                 940

Ala Ala Tyr Thr Ser Ser Leu Leu Gly Ser Ile Ala Gly Val Gly Trp
945                 950                 955                 960

Thr Ala Gly Leu Ser Ser Phe Ala Ala Ile Pro Phe Ala Gln Ser Ile
                965                 970                 975

Phe Tyr Arg Leu Asn Gly Val Gly Ile Thr Gln Gln Val Leu Ser Glu
            980                 985                 990

Asn Gln Lys Leu Ile Ala Asn Lys  Phe Asn Gln Ala Leu  Gly Ala Met
        995                 1000                1005

Gln Thr  Gly Phe Thr Thr Thr  Asn Glu Ala Phe Arg  Lys Val Gln
    1010                1015                1020

Asp Ala  Val Asn Asn Asn Ala  Gln Ala Leu Ser Lys  Leu Ala Ser
    1025                1030                1035

Glu Leu  Ser Asn Thr Phe Gly  Ala Ile Ser Ala Ser  Ile Gly Asp
    1040                1045                1050

Ile Ile  Gln Arg Leu Asp Val  Leu Glu Gln Asp Ala  Gln Ile Asp
    1055                1060                1065

Arg Leu  Ile Asn Gly Arg Leu  Thr Thr Leu Asn Ala  Phe Val Ala
    1070                1075                1080

Gln Gln  Leu Val Arg Ser Glu  Ser Ala Ala Leu Ser  Ala Gln Leu
    1085                1090                1095

Ala Lys  Asp Lys Val Asn Glu  Cys Val Lys Ala Gln  Ser Lys Arg
    1100                1105                1110

Ser Gly  Phe Cys Gly Gln Gly  Thr His Ile Val Ser  Phe Val Val
    1115                1120                1125

Asn Ala  Pro Asn Gly Leu Tyr  Phe Met His Val Gly  Tyr Tyr Pro
    1130                1135                1140

Ser Asn  His Ile Glu Val Val  Ser Ala Tyr Gly Leu  Cys Asp Ala
    1145                1150                1155

Ala Asn  Pro Thr Asn Cys Ile  Ala Pro Val Asn Gly  Tyr Phe Ile
    1160                1165                1170

Lys Thr  Asn Asn Thr Arg Ile  Val Asp Glu Trp Ser  Tyr Thr Gly
```

```
    1175                1180                1185

Ser Ser  Phe Tyr Ala Pro Glu  Pro Ile Thr Ser Leu  Asn Thr Lys
    1190                1195                1200

Tyr Val  Ala Pro His Val Thr  Tyr Gln Asn Ile Ser  Thr Asn Leu
    1205                1210                1215

Pro Pro  Pro Leu Leu Gly Asn  Ser Thr Gly Ile Asp  Phe Gln Asp
    1220                1225                1230

Glu Leu  Asp Glu Phe Phe Lys  Asn Val Ser Thr Ser  Ile Pro Asn
    1235                1240                1245

Phe Gly  Ser Leu Thr Gln Ile  Asn Thr Thr Leu Leu  Asp Leu Thr
    1250                1255                1260

Tyr Glu  Met Leu Ser Leu Gln  Gln Val Val Lys Ala  Leu Asn Glu
    1265                1270                1275

Ser Tyr  Ile Asp Leu Lys Glu  Leu Gly Asn Tyr Thr  Tyr Tyr Asn
    1280                1285                1290

Lys Trp  Pro Trp Tyr Ile Trp  Leu Gly Phe Ile Ala  Gly Leu Val
    1295                1300                1305

Ala Leu  Ala Leu Cys Val Phe  Phe Ile Leu Cys Cys  Thr Gly Cys
    1310                1315                1320

Gly Thr  Asn Cys Met Gly Lys  Leu Lys Cys Asn Arg  Cys Cys Asp
    1325                1330                1335

Arg Tyr  Glu Glu Tyr Asp Leu  Glu Pro His Lys Val  His Val His
    1340                1345                1350


<210> SEQ ID NO 28
<211> LENGTH: 1353
<212> TYPE: PRT
<213> ORGANISM: Middle East respiratory syndrome coronavirus

<400> SEQUENCE: 28

Met Ile His Ser Val Phe Leu Leu Met Phe Leu Leu Thr Pro Thr Glu
1               5                   10                  15

Ser Tyr Val Asp Val Gly Pro Asp Ser Val Lys Ser Ala Cys Ile Glu
            20                  25                  30

Val Asp Ile Gln Gln Thr Phe Phe Asp Lys Thr Trp Pro Arg Pro Ile
        35                  40                  45

Asp Val Ser Lys Ala Asp Gly Ile Ile Tyr Pro Gln Gly Arg Thr Tyr
    50                  55                  60

Ser Asn Ile Thr Ile Thr Tyr Gln Gly Leu Phe Pro Tyr Gln Gly Asp
65                  70                  75                  80

His Gly Asp Met Tyr Val Tyr Ser Ala Gly His Ala Thr Gly Thr Thr
                85                  90                  95

Pro Gln Lys Leu Phe Val Ala Asn Tyr Ser Gln Asp Val Lys Gln Phe
            100                 105                 110

Ala Asn Gly Phe Val Val Arg Ile Gly Ala Ala Ala Asn Ser Thr Gly
        115                 120                 125

Thr Val Ile Ile Ser Pro Ser Thr Ser Ala Thr Ile Arg Lys Ile Tyr
    130                 135                 140

Pro Ala Phe Met Leu Gly Ser Ser Val Gly Asn Phe Ser Asp Gly Lys
145                 150                 155                 160

Met Gly Arg Phe Phe Asn His Thr Leu Val Leu Leu Pro Asp Gly Cys
                165                 170                 175

Gly Thr Leu Leu Arg Ala Phe Tyr Cys Ile Leu Glu Pro Arg Ser Gly
            180                 185                 190
```

```
Asn His Cys Pro Ala Gly Asn Ser Tyr Thr Ser Phe Ala Thr Tyr His
        195                 200                 205

Thr Pro Ala Thr Asp Cys Ser Asp Gly Asn Tyr Asn Arg Asn Ala Ser
    210                 215                 220

Leu Asn Ser Phe Lys Glu Tyr Phe Asn Leu Arg Asn Cys Thr Phe Met
225                 230                 235                 240

Tyr Thr Tyr Asn Ile Thr Glu Asp Glu Ile Leu Glu Trp Phe Gly Ile
                245                 250                 255

Thr Gln Thr Ala Gln Gly Val His Leu Phe Ser Ser Arg Tyr Val Asp
            260                 265                 270

Leu Tyr Gly Gly Asn Met Phe Gln Phe Ala Thr Leu Pro Val Tyr Asp
        275                 280                 285

Thr Ile Lys Tyr Tyr Ser Ile Ile Pro His Ser Ile Arg Ser Ile Gln
    290                 295                 300

Ser Asp Arg Lys Ala Trp Ala Ala Phe Tyr Val Tyr Lys Leu Gln Pro
305                 310                 315                 320

Leu Thr Phe Leu Leu Asp Phe Ser Val Asp Gly Tyr Ile Arg Arg Ala
                325                 330                 335

Ile Asp Cys Gly Phe Asn Asp Leu Ser Gln Leu His Cys Ser Tyr Glu
            340                 345                 350

Ser Phe Asp Val Glu Ser Gly Val Tyr Ser Val Ser Ser Phe Glu Ala
        355                 360                 365

Lys Pro Ser Gly Ser Val Val Glu Gln Ala Glu Gly Val Glu Cys Asp
    370                 375                 380

Phe Ser Pro Leu Leu Ser Gly Thr Pro Pro Gln Val Tyr Asn Phe Lys
385                 390                 395                 400

Arg Leu Val Phe Thr Asn Cys Asn Tyr Asn Leu Thr Lys Leu Leu Ser
                405                 410                 415

Leu Phe Ser Val Asn Asp Phe Thr Cys Ser Gln Ile Ser Pro Ala Ala
            420                 425                 430

Ile Ala Ser Asn Cys Tyr Ser Ser Leu Ile Leu Asp Tyr Phe Ser Tyr
        435                 440                 445

Pro Leu Ser Met Lys Ser Asp Leu Ser Val Ser Ser Ala Gly Pro Ile
    450                 455                 460

Ser Gln Phe Asn Tyr Lys Gln Ser Phe Ser Asn Pro Thr Cys Leu Ile
465                 470                 475                 480

Leu Ala Thr Val Pro His Asn Leu Thr Thr Ile Thr Lys Pro Leu Lys
                485                 490                 495

Tyr Ser Tyr Ile Asn Lys Cys Ser Arg Leu Leu Ser Asp Asp Arg Thr
            500                 505                 510

Glu Val Pro Gln Leu Val Asn Ala Asn Gln Tyr Ser Pro Cys Val Ser
        515                 520                 525

Ile Val Pro Ser Thr Val Trp Glu Asp Gly Asp Tyr Tyr Arg Lys Gln
    530                 535                 540

Leu Ser Pro Leu Glu Gly Gly Gly Trp Leu Val Ala Ser Gly Ser Thr
545                 550                 555                 560

Val Ala Met Thr Glu Gln Leu Gln Met Gly Phe Gly Ile Thr Val Gln
                565                 570                 575

Tyr Gly Thr Asp Thr Asn Ser Val Cys Pro Lys Leu Glu Phe Ala Asn
            580                 585                 590

Asp Thr Lys Ile Ala Ser Gln Leu Gly Asn Cys Val Glu Tyr Ser Leu
        595                 600                 605

Tyr Gly Val Ser Gly Arg Gly Val Phe Gln Asn Cys Thr Ala Val Gly
```

```
    610                 615                 620

Val Arg Gln Gln Arg Phe Val Tyr Asp Ala Tyr Gln Asn Leu Val Gly
625                 630                 635                 640

Tyr Tyr Ser Asp Asp Gly Asn Tyr Tyr Cys Leu Arg Ala Cys Val Ser
                645                 650                 655

Val Pro Val Ser Val Ile Tyr Asp Lys Glu Thr Lys Thr His Ala Thr
            660                 665                 670

Leu Phe Gly Ser Val Ala Cys Glu His Ile Ser Ser Thr Met Ser Gln
        675                 680                 685

Tyr Ser Arg Ser Thr Arg Ser Met Leu Lys Arg Arg Asp Ser Thr Tyr
    690                 695                 700

Gly Pro Leu Gln Thr Pro Val Gly Cys Val Leu Gly Leu Val Asn Ser
705                 710                 715                 720

Ser Leu Phe Val Glu Asp Cys Lys Leu Pro Leu Gly Gln Ser Leu Cys
                725                 730                 735

Ala Leu Pro Asp Thr Pro Ser Thr Leu Thr Pro Arg Ser Val Arg Ser
            740                 745                 750

Val Pro Gly Glu Met Arg Leu Ala Ser Ile Ala Phe Asn His Pro Ile
        755                 760                 765

Gln Val Asp Gln Leu Asn Ser Ser Tyr Phe Lys Leu Ser Ile Pro Thr
    770                 775                 780

Asn Phe Ser Phe Gly Val Thr Gln Glu Tyr Ile Gln Thr Thr Ile Gln
785                 790                 795                 800

Lys Val Thr Val Asp Cys Lys Gln Tyr Val Cys Asn Gly Phe Gln Lys
                805                 810                 815

Cys Glu Gln Leu Leu Arg Glu Tyr Gly Gln Phe Cys Ser Lys Ile Asn
            820                 825                 830

Gln Ala Leu His Gly Ala Asn Leu Arg Gln Asp Asp Ser Val Arg Asn
        835                 840                 845

Leu Phe Ala Ser Val Lys Ser Ser Gln Ser Ser Pro Ile Ile Pro Gly
    850                 855                 860

Phe Gly Gly Asp Phe Asn Leu Thr Leu Leu Glu Pro Val Ser Ile Ser
865                 870                 875                 880

Thr Gly Ser Arg Ser Ala Arg Ser Ala Ile Glu Asp Leu Leu Phe Asp
                885                 890                 895

Lys Val Thr Ile Ala Asp Pro Gly Tyr Met Gln Gly Tyr Asp Asp Cys
            900                 905                 910

Met Gln Gln Gly Pro Ala Ser Ala Arg Asp Leu Ile Cys Ala Gln Tyr
        915                 920                 925

Val Ala Gly Tyr Lys Val Leu Pro Pro Leu Met Asp Val Asn Met Glu
    930                 935                 940

Ala Ala Tyr Thr Ser Ser Leu Leu Gly Ser Ile Ala Gly Val Gly Trp
945                 950                 955                 960

Thr Ala Gly Leu Ser Ser Phe Ala Ala Ile Pro Phe Ala Gln Ser Ile
                965                 970                 975

Phe Tyr Arg Leu Asn Gly Val Gly Ile Thr Gln Gln Val Leu Ser Glu
            980                 985                 990

Asn Gln Lys Leu Ile Ala Asn Lys  Phe Asn Gln Ala Leu  Gly Ala Met
        995                 1000                1005

Gln Thr  Gly Phe Thr Thr Thr  Asn Glu Ala Phe Arg  Lys Val Gln
    1010                1015                1020

Asp Ala  Val Asn Asn Asn Ala  Gln Ala Leu Ser Lys  Leu Ala Ser
    1025                1030                1035
```

Glu Leu Ser Asn Thr Phe Gly Ala Ile Ser Ala Ser Ile Gly Asp
    1040                1045                1050

Ile Ile Gln Arg Leu Asp Val Leu Glu Gln Asp Ala Gln Ile Asp
    1055                1060                1065

Arg Leu Ile Asn Gly Arg Leu Thr Thr Leu Asn Ala Phe Val Ala
    1070                1075                1080

Gln Gln Leu Val Arg Ser Glu Ser Ala Ala Leu Ser Ala Gln Leu
    1085                1090                1095

Ala Lys Asp Lys Val Asn Glu Cys Val Lys Ala Gln Ser Lys Arg
    1100                1105                1110

Ser Gly Phe Cys Gly Gln Gly Thr His Ile Val Ser Phe Val Val
    1115                1120                1125

Asn Ala Pro Asn Gly Leu Tyr Phe Met His Val Gly Tyr Tyr Pro
    1130                1135                1140

Ser Asn His Ile Glu Val Val Ser Ala Tyr Gly Leu Cys Asp Ala
    1145                1150                1155

Ala Asn Pro Thr Asn Cys Ile Ala Pro Val Asn Gly Tyr Phe Ile
    1160                1165                1170

Lys Thr Asn Asn Thr Arg Ile Val Asp Glu Trp Ser Tyr Thr Gly
    1175                1180                1185

Ser Ser Phe Tyr Ala Pro Glu Pro Ile Thr Ser Leu Asn Thr Lys
    1190                1195                1200

Tyr Val Ala Pro His Val Thr Tyr Gln Asn Ile Ser Thr Asn Leu
    1205                1210                1215

Pro Pro Pro Leu Leu Gly Asn Ser Thr Gly Ile Asp Phe Gln Asp
    1220                1225                1230

Glu Leu Asp Glu Phe Phe Lys Asn Val Ser Thr Ser Ile Pro Asn
    1235                1240                1245

Phe Gly Ser Leu Thr Gln Ile Asn Thr Thr Leu Leu Asp Leu Thr
    1250                1255                1260

Tyr Glu Met Leu Ser Leu Gln Gln Val Val Lys Ala Leu Asn Glu
    1265                1270                1275

Ser Tyr Ile Asp Leu Lys Glu Leu Gly Asn Tyr Thr Tyr Tyr Asn
    1280                1285                1290

Lys Trp Pro Trp Tyr Ile Trp Leu Gly Phe Ile Ala Gly Leu Val
    1295                1300                1305

Ala Leu Ala Leu Cys Val Phe Phe Ile Leu Cys Cys Thr Gly Cys
    1310                1315                1320

Gly Thr Asn Cys Met Gly Lys Leu Lys Cys Asn Arg Cys Cys Asp
    1325                1330                1335

Arg Tyr Glu Glu Tyr Asp Leu Glu Pro His Lys Val His Val His
    1340                1345                1350

<210> SEQ ID NO 29
<211> LENGTH: 1255
<212> TYPE: PRT
<213> ORGANISM: Human SARS coronavirus

<400> SEQUENCE: 29

Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
            20                  25                  30

His Thr Ser Ser Met Arg Gly Val Tyr Tyr Pro Asp Glu Ile Phe Arg

-continued

```
        35                  40                  45

Ser Asp Thr Leu Tyr Leu Thr Gln Asp Leu Phe Leu Pro Phe Tyr Ser
    50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
    130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
        195                 200                 205

Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Ala Tyr Phe Val Gly Tyr
                245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
        275                 280                 285

Ser Val Lys Ser Phe Glu Ile Asp Lys Gly Ile Tyr Gln Thr Ser Asn
    290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
            340                 345                 350

Ser Val Leu Tyr Asn Ser Thr Phe Phe Ser Thr Phe Lys Cys Tyr Gly
        355                 360                 365

Val Ser Ala Thr Lys Leu Asn Asp Leu Cys Phe Ser Asn Val Tyr Ala
    370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
            420                 425                 430

Thr Gly Asn Tyr Asn Tyr Lys Tyr Arg Tyr Leu Arg His Gly Lys Leu
        435                 440                 445

Arg Pro Phe Glu Arg Asp Ile Ser Asn Val Pro Phe Ser Pro Asp Gly
    450                 455                 460
```

```
Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
            500                 505                 510

Pro Lys Leu Ser Thr Asp Leu Ile Lys Asn Gln Cys Val Asn Phe Asn
        515                 520                 525

Phe Asn Gly Leu Thr Gly Thr Gly Val Leu Thr Pro Ser Ser Lys Arg
    530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ser Phe Gly Gly Val Ser Val Ile Thr Pro Gly Thr Asn Ala Ser Ser
            580                 585                 590

Glu Val Ala Val Leu Tyr Gln Asp Val Asn Cys Thr Asp Val Ser Thr
        595                 600                 605

Ala Ile His Ala Asp Gln Leu Thr Pro Ala Trp Arg Ile Tyr Ser Thr
    610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
            660                 665                 670

Ser Ile Val Ala Tyr Thr Met Ser Leu Gly Ala Asp Ser Ser Ile Ala
        675                 680                 685

Tyr Ser Asn Asn Thr Ile Ala Ile Pro Thr Asn Phe Ser Ile Ser Ile
    690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
            740                 745                 750

Ala Ala Glu Gln Asp Arg Asn Thr Arg Glu Val Phe Ala Gln Val Lys
        755                 760                 765

Gln Met Tyr Lys Thr Pro Thr Leu Lys Tyr Phe Gly Gly Phe Asn Phe
    770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
            820                 825                 830

Cys Ala Gln Lys Phe Asn Gly Leu Thr Val Leu Pro Pro Leu Leu Thr
        835                 840                 845

Asp Asp Met Ile Ala Ala Tyr Thr Ala Ala Leu Val Ser Gly Thr Ala
    850                 855                 860

Thr Ala Gly Trp Thr Phe Gly Ala Gly Ala Ala Leu Gln Ile Pro Phe
865                 870                 875                 880
```

```
Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala
            900                 905                 910

Ile Ser Gln Ile Gln Glu Ser Leu Thr Thr Thr Ser Thr Ala Leu Gly
        915                 920                 925

Lys Leu Gln Asp Val Val Asn Gln Asn Ala Gln Ala Leu Asn Thr Leu
    930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
                965                 970                 975

Arg Leu Ile Thr Gly Arg Leu Gln Ser Leu Gln Thr Tyr Val Thr Gln
            980                 985                 990

Gln Leu Ile Arg Ala Ala Glu Ile  Arg Ala Ser Ala Asn  Leu Ala Ala
        995                 1000                1005

Thr Lys  Met Ser Glu Cys Val  Leu Gly Gln Ser Lys  Arg Val Asp
    1010                 1015                 1020

Phe Cys  Gly Lys Gly Tyr His  Leu Met Ser Phe Pro  Gln Ala Ala
    1025                 1030                 1035

Pro His  Gly Val Val Phe Leu  His Val Thr Tyr Val  Pro Ser Gln
    1040                 1045                 1050

Glu Arg  Asn Phe Thr Thr Ala  Pro Ala Ile Cys His  Glu Gly Lys
    1055                 1060                 1065

Ala Tyr  Phe Pro Arg Glu Gly  Val Phe Val Phe Asn  Gly Thr Ser
    1070                 1075                 1080

Trp Phe  Ile Thr Gln Arg Asn  Phe Phe Ser Pro Gln  Ile Ile Thr
    1085                 1090                 1095

Thr Asp  Asn Thr Phe Val Ser  Gly Asn Cys Asp Val  Val Ile Gly
    1100                 1105                 1110

Ile Ile  Asn Asn Thr Val Tyr  Asp Pro Leu Gln Pro  Glu Leu Asp
    1115                 1120                 1125

Ser Phe  Lys Glu Glu Leu Asp  Lys Tyr Phe Lys Asn  His Thr Ser
    1130                 1135                 1140

Pro Asp  Val Asp Leu Gly Asp  Ile Ser Gly Ile Asn  Ala Ser Val
    1145                 1150                 1155

Val Asn  Ile Gln Lys Glu Ile  Asp Arg Leu Asn Glu  Val Ala Lys
    1160                 1165                 1170

Asn Leu  Asn Glu Ser Leu Ile  Asp Leu Gln Glu Leu  Gly Lys Tyr
    1175                 1180                 1185

Glu Gln  Tyr Ile Lys Trp Pro  Trp Tyr Val Trp Leu  Gly Phe Ile
    1190                 1195                 1200

Ala Gly  Leu Ile Ala Ile Val  Met Val Thr Ile Leu  Leu Cys Cys
    1205                 1210                 1215

Met Thr  Ser Cys Cys Ser Cys  Leu Lys Gly Ala Cys  Ser Cys Gly
    1220                 1225                 1230

Ser Cys  Cys Lys Phe Asp Glu  Asp Asp Ser Glu Pro  Val Leu Lys
    1235                 1240                 1245

Gly Val  Lys Leu His Tyr Thr
    1250                 1255
```

<210> SEQ ID NO 30
<211> LENGTH: 1353
<212> TYPE: PRT

<213> ORGANISM: Human coronavirus

<400> SEQUENCE: 30

```
Met Phe Leu Ile Leu Leu Ile Ser Leu Pro Thr Ala Phe Ala Val Ile
1               5                   10                  15

Gly Asp Leu Lys Cys Thr Ser Asp Asn Ile Asn Asp Lys Asp Thr Gly
            20                  25                  30

Pro Pro Pro Ile Ser Thr Asp Thr Val Asp Val Thr Asn Gly Leu Gly
        35                  40                  45

Thr Tyr Tyr Val Leu Asp Arg Val Tyr Leu Asn Thr Thr Leu Phe Leu
    50                  55                  60

Asn Gly Tyr Tyr Pro Thr Ser Gly Ser Thr Tyr Arg Asn Met Ala Leu
65                  70                  75                  80

Lys Gly Ser Val Leu Leu Ser Arg Leu Trp Phe Lys Pro Pro Phe Leu
                85                  90                  95

Ser Asp Phe Ile Asn Gly Ile Phe Ala Lys Val Lys Asn Thr Lys Val
            100                 105                 110

Ile Lys Asp Arg Val Met Tyr Ser Glu Phe Pro Ala Ile Thr Ile Gly
        115                 120                 125

Ser Thr Phe Val Asn Thr Ser Tyr Ser Val Val Val Gln Pro Arg Thr
    130                 135                 140

Ile Asn Ser Thr Gln Asp Gly Asp Asn Lys Leu Gln Gly Leu Leu Glu
145                 150                 155                 160

Val Ser Val Cys Gln Tyr Asn Met Cys Glu Tyr Pro Gln Thr Ile Cys
                165                 170                 175

His Pro Asn Leu Gly Asn His Arg Lys Glu Leu Trp His Leu Asp Thr
            180                 185                 190

Gly Val Val Ser Cys Leu Tyr Lys Arg Asn Phe Thr Tyr Asp Val Asn
        195                 200                 205

Ala Asp Tyr Leu Tyr Phe His Phe Tyr Gln Glu Gly Gly Thr Phe Tyr
    210                 215                 220

Ala Tyr Phe Thr Asp Thr Gly Val Val Thr Lys Phe Leu Phe Asn Val
225                 230                 235                 240

Tyr Leu Gly Met Ala Leu Ser His Tyr Tyr Val Met Pro Leu Thr Cys
                245                 250                 255

Asn Ser Lys Leu Thr Leu Glu Tyr Trp Val Thr Pro Leu Thr Ser Arg
            260                 265                 270

Gln Tyr Leu Leu Ala Phe Asn Gln Asp Gly Ile Ile Phe Asn Ala Glu
        275                 280                 285

Asp Cys Met Ser Asp Phe Met Ser Glu Ile Lys Cys Lys Thr Gln Ser
    290                 295                 300

Ile Ala Pro Pro Thr Gly Val Tyr Glu Leu Asn Gly Tyr Thr Val Gln
305                 310                 315                 320

Pro Ile Ala Asp Val Tyr Arg Arg Lys Pro Asn Leu Pro Asn Cys Asn
                325                 330                 335

Ile Glu Ala Trp Leu Asn Asp Lys Ser Val Pro Ser Pro Leu Asn Trp
            340                 345                 350

Glu Arg Lys Thr Phe Ser Asn Cys Asn Phe Asn Met Ser Ser Leu Met
        355                 360                 365

Ser Phe Ile Gln Ala Asp Ser Phe Thr Cys Asn Asn Ile Asp Ala Ala
    370                 375                 380

Lys Ile Tyr Gly Met Cys Phe Ser Ser Ile Thr Ile Asp Lys Phe Ala
385                 390                 395                 400
```

-continued

```
Ile Pro Asn Gly Arg Lys Val Asp Leu Gln Leu Gly Asn Leu Gly Tyr
                405                 410                 415

Leu Gln Ser Phe Asn Tyr Arg Ile Asp Thr Thr Ala Thr Ser Cys Gln
            420                 425                 430

Leu Tyr Tyr Asn Leu Pro Ala Ala Asn Val Ser Val Ser Arg Phe Asn
        435                 440                 445

Pro Ser Thr Trp Asn Lys Arg Phe Gly Phe Ile Glu Asp Ser Val Phe
    450                 455                 460

Lys Pro Arg Pro Ala Gly Val Leu Thr Asn His Asp Val Val Tyr Ala
465                 470                 475                 480

Gln His Cys Phe Lys Ala Pro Lys Asn Phe Cys Pro Cys Lys Leu Asn
                485                 490                 495

Gly Ser Cys Val Gly Ser Gly Pro Gly Lys Asn Asn Gly Ile Gly Thr
            500                 505                 510

Cys Pro Ala Gly Thr Asn Tyr Leu Thr Cys Asp Asn Leu Cys Thr Pro
        515                 520                 525

Asp Pro Ile Thr Phe Thr Gly Thr Tyr Lys Cys Pro Gln Thr Lys Ser
    530                 535                 540

Leu Val Gly Ile Gly Glu His Cys Ser Gly Leu Ala Val Lys Ser Asp
545                 550                 555                 560

Tyr Cys Gly Gly Asn Ser Cys Thr Cys Arg Pro Gln Ala Phe Leu Gly
                565                 570                 575

Trp Ser Ala Asp Ser Cys Leu Gln Gly Asp Lys Cys Asn Ile Phe Ala
            580                 585                 590

Asn Phe Ile Leu His Asp Val Asn Ser Gly Leu Thr Cys Ser Thr Asp
        595                 600                 605

Leu Gln Lys Ala Asn Thr Asp Ile Ile Leu Gly Val Cys Val Asn Tyr
    610                 615                 620

Asp Leu Tyr Gly Ile Leu Gly Gln Gly Ile Phe Val Glu Val Asn Ala
625                 630                 635                 640

Thr Tyr Tyr Asn Ser Trp Gln Asn Leu Leu Tyr Asp Ser Asn Gly Asn
                645                 650                 655

Leu Tyr Gly Phe Arg Asp Tyr Ile Ile Asn Arg Thr Phe Met Ile Arg
            660                 665                 670

Ser Cys Tyr Ser Gly Arg Val Ser Ala Ala Phe His Ala Asn Ser Ser
        675                 680                 685

Glu Pro Ala Leu Leu Phe Arg Asn Ile Lys Cys Asn Tyr Val Phe Asn
    690                 695                 700

Asn Ser Leu Thr Arg Gln Leu Gln Pro Ile Asn Tyr Phe Asp Ser Tyr
705                 710                 715                 720

Leu Gly Cys Val Val Asn Ala Tyr Asn Ser Thr Ala Ile Ser Val Gln
                725                 730                 735

Thr Cys Asp Leu Thr Val Gly Ser Gly Tyr Cys Val Asp Tyr Ser Lys
            740                 745                 750

Asn Arg Arg Ser Arg Gly Ala Ile Thr Thr Gly Tyr Arg Phe Thr Asn
        755                 760                 765

Phe Glu Pro Phe Thr Val Asn Ser Val Asn Asp Ser Leu Glu Pro Val
    770                 775                 780

Gly Gly Leu Tyr Glu Ile Gln Ile Pro Ser Glu Phe Thr Ile Gly Asn
785                 790                 795                 800

Met Val Glu Phe Ile Gln Thr Ser Ser Pro Lys Val Thr Ile Asp Cys
                805                 810                 815

Ala Ala Phe Val Cys Gly Asp Tyr Ala Ala Cys Lys Ser Gln Leu Val
```

```
            820                 825                 830

Glu Tyr Gly Ser Phe Cys Asp Asn Ile Asn Ala Ile Leu Thr Glu Val
        835                 840                 845

Asn Glu Leu Leu Asp Thr Thr Gln Leu Gln Val Ala Asn Ser Leu Met
    850                 855                 860

Asn Gly Val Thr Leu Ser Thr Lys Leu Lys Asp Gly Val Asn Phe Asn
865                 870                 875                 880

Val Asp Asp Ile Asn Phe Ser Pro Val Leu Gly Cys Leu Gly Ser Glu
                885                 890                 895

Cys Ser Lys Ala Ser Ser Arg Ser Ala Ile Glu Asp Leu Leu Phe Asp
            900                 905                 910

Lys Val Lys Leu Ser Asp Val Gly Phe Val Glu Ala Tyr Asn Asn Cys
        915                 920                 925

Thr Gly Gly Ala Glu Ile Arg Asp Leu Ile Cys Val Gln Ser Tyr Lys
    930                 935                 940

Gly Ile Lys Val Leu Pro Pro Leu Leu Ser Glu Asn Gln Ile Ser Gly
945                 950                 955                 960

Tyr Thr Leu Ala Ala Thr Ser Ala Ser Leu Phe Pro Pro Trp Thr Ala
                965                 970                 975

Ala Ala Gly Val Pro Phe Tyr Leu Asn Val Gln Tyr Arg Ile Asn Gly
            980                 985                 990

Leu Gly Val Thr Met Asp Val Leu  Ser Gln Asn Gln Lys  Leu Ile Ala
        995                 1000                1005

Asn Ala  Phe Asn Asn Ala Leu  Tyr Ala Ile Gln Glu  Gly Phe Asp
    1010                1015                1020

Ala Thr  Asn Ser Ala Leu Val  Lys Ile Gln Ala Val  Val Asn Ala
    1025                1030                1035

Asn Ala  Glu Ala Leu Asn Asn  Leu Leu Gln Gln Leu  Ser Asn Arg
    1040                1045                1050

Phe Gly  Ala Ile Ser Ala Ser  Leu Gln Glu Ile Leu  Ser Arg Leu
    1055                1060                1065

Asp Ala  Leu Glu Ala Glu Ala  Gln Ile Asp Arg Leu  Ile Asn Gly
    1070                1075                1080

Arg Leu  Thr Ala Leu Asn Ala  Tyr Val Ser Gln Gln  Leu Ser Asp
    1085                1090                1095

Ser Thr  Leu Val Lys Phe Ser  Ala Ala Gln Ala Met  Glu Lys Val
    1100                1105                1110

Asn Glu  Cys Val Lys Ser Gln  Ser Ser Arg Ile Asn  Phe Cys Gly
    1115                1120                1125

Asn Gly  Asn His Ile Ile Ser  Leu Val Gln Asn Ala  Pro Tyr Gly
    1130                1135                1140

Leu Tyr  Phe Ile His Phe Ser  Tyr Val Pro Thr Lys  Tyr Val Thr
    1145                1150                1155

Ala Arg  Val Ser Pro Gly Leu  Cys Ile Ala Gly Asp  Arg Gly Ile
    1160                1165                1170

Ala Pro  Lys Ser Gly Tyr Phe  Val Asn Val Asn Asn  Thr Trp Met
    1175                1180                1185

Tyr Thr  Gly Ser Gly Tyr Tyr  Tyr Pro Glu Pro Ile  Thr Glu Asn
    1190                1195                1200

Asn Val  Val Val Met Ser Thr  Cys Ala Val Asn Tyr  Thr Lys Ala
    1205                1210                1215

Pro Tyr  Val Met Leu Asn Thr  Ser Ile Pro Asn Leu  Pro Asp Phe
    1220                1225                1230
```

```
Lys Glu  Glu Leu Asp Gln Trp  Phe Lys Asn Gln Thr  Ser Val Ala
    1235                1240                1245

Pro Asp  Leu Ser Leu Asp Tyr  Ile Asn Val Thr Phe  Leu Asp Leu
    1250                1255                1260

Gln Val  Glu Met Asn Arg Leu  Gln Glu Ala Ile Lys  Val Leu Asn
    1265                1270                1275

Gln Ser  Tyr Ile Asn Leu Lys  Asp Ile Gly Thr Tyr  Glu Tyr Tyr
    1280                1285                1290

Val Lys  Trp Pro Trp Tyr Val  Trp Leu Leu Ile Cys  Leu Ala Gly
    1295                1300                1305

Val Ala  Met Leu Val Leu Leu  Phe Phe Ile Cys Cys  Cys Thr Gly
    1310                1315                1320

Cys Gly  Thr Ser Cys Phe Lys  Lys Cys Gly Gly Cys  Cys Asp Asp
    1325                1330                1335

Tyr Thr  Gly Tyr Gln Glu Leu  Val Ile Lys Thr Ser  His Asp Asp
    1340                1345                1350


<210> SEQ ID NO 31
<211> LENGTH: 1351
<212> TYPE: PRT
<213> ORGANISM: Human coronavirus

<400> SEQUENCE: 31

Met Phe Leu Ile Ile Phe Ile Leu Pro Thr Thr Leu Ala Val Ile Gly
1               5                   10                  15

Asp Phe Asn Cys Thr Asn Ser Phe Ile Asn Asp Tyr Asn Lys Thr Ile
            20                  25                  30

Pro Arg Ile Ser Glu Asp Val Val Asp Val Ser Leu Gly Leu Gly Thr
        35                  40                  45

Tyr Tyr Val Leu Asn Arg Val Tyr Leu Asn Thr Thr Leu Leu Phe Thr
    50                  55                  60

Gly Tyr Phe Pro Lys Ser Gly Ala Asn Phe Arg Asp Leu Ala Leu Lys
65                  70                  75                  80

Gly Ser Ile Tyr Leu Ser Thr Leu Trp Tyr Lys Pro Pro Phe Leu Ser
                85                  90                  95

Asp Phe Asn Asn Gly Ile Phe Ser Lys Val Lys Asn Thr Lys Leu Tyr
            100                 105                 110

Val Asn Asn Thr Leu Tyr Ser Glu Phe Ser Thr Ile Val Ile Gly Ser
        115                 120                 125

Val Phe Val Asn Thr Ser Tyr Thr Ile Val Val Gln Pro His Asn Gly
    130                 135                 140

Ile Leu Glu Ile Thr Ala Cys Gln Tyr Thr Met Cys Glu Tyr Pro His
145                 150                 155                 160

Thr Val Cys Lys Ser Lys Gly Ser Ile Arg Asn Glu Ser Trp His Ile
                165                 170                 175

Asp Ser Ser Glu Pro Leu Cys Leu Phe Lys Lys Asn Phe Thr Tyr Asn
            180                 185                 190

Val Ser Ala Asp Trp Leu Tyr Phe His Phe Tyr Gln Glu Arg Gly Val
        195                 200                 205

Phe Tyr Ala Tyr Tyr Ala Asp Val Gly Met Pro Thr Thr Phe Leu Phe
    210                 215                 220

Ser Leu Tyr Leu Gly Thr Ile Leu Ser His Tyr Tyr Val Met Pro Leu
225                 230                 235                 240

Thr Cys Asn Ala Ile Ser Ser Asn Thr Asp Asn Glu Thr Leu Glu Tyr
```

-continued

```
                245                 250                 255

Trp Val Thr Pro Leu Ser Arg Arg Gln Tyr Leu Leu Asn Phe Asp Glu
            260                 265                 270

His Gly Val Ile Thr Asn Ala Val Asp Cys Ser Ser Ser Phe Leu Ser
        275                 280                 285

Glu Ile Gln Cys Lys Thr Gln Ser Phe Ala Pro Asn Thr Gly Val Tyr
    290                 295                 300

Asp Leu Ser Gly Phe Thr Val Lys Pro Val Ala Thr Val Tyr Arg Arg
305                 310                 315                 320

Ile Pro Asn Leu Pro Asp Cys Asp Ile Asp Asn Trp Leu Asn Asn Val
                325                 330                 335

Ser Val Pro Ser Pro Leu Asn Trp Glu Arg Arg Ile Phe Ser Asn Cys
            340                 345                 350

Asn Phe Asn Leu Ser Thr Leu Leu Arg Leu Val His Val Asp Ser Phe
        355                 360                 365

Ser Cys Asn Asn Leu Asp Lys Ser Lys Ile Phe Gly Ser Cys Phe Asn
    370                 375                 380

Ser Ile Thr Val Asp Lys Phe Ala Ile Pro Asn Arg Arg Arg Asp Asp
385                 390                 395                 400

Leu Gln Leu Gly Ser Ser Gly Phe Leu Gln Ser Ser Asn Tyr Lys Ile
                405                 410                 415

Asp Ile Ser Ser Ser Ser Cys Gln Leu Tyr Tyr Ser Leu Pro Leu Val
            420                 425                 430

Asn Val Thr Ile Asn Asn Phe Asn Pro Ser Ser Trp Asn Arg Arg Tyr
        435                 440                 445

Gly Phe Gly Ser Phe Asn Leu Ser Ser Tyr Asp Val Val Tyr Ser Asp
    450                 455                 460

His Cys Phe Ser Val Asn Ser Asp Phe Cys Pro Cys Ala Asp Pro Ser
465                 470                 475                 480

Val Val Asn Ser Cys Ala Lys Ser Lys Pro Pro Ser Ala Ile Cys Pro
                485                 490                 495

Ala Gly Thr Lys Tyr Arg His Cys Asp Leu Asp Thr Thr Leu Tyr Val
            500                 505                 510

Lys Asn Trp Cys Arg Cys Ser Cys Leu Pro Asp Pro Ile Ser Thr Tyr
        515                 520                 525

Ser Pro Asn Thr Cys Pro Gln Lys Lys Val Val Val Gly Ile Gly Glu
    530                 535                 540

His Cys Pro Gly Leu Gly Ile Asn Glu Glu Lys Cys Gly Thr Gln Leu
545                 550                 555                 560

Asn His Ser Ser Cys Phe Cys Ser Pro Asp Ala Phe Leu Gly Trp Ser
                565                 570                 575

Phe Asp Ser Cys Ile Ser Asn Asn Arg Cys Asn Ile Phe Ser Asn Phe
            580                 585                 590

Ile Phe Asn Gly Ile Asn Ser Gly Thr Thr Cys Ser Asn Asp Leu Leu
        595                 600                 605

Tyr Ser Asn Thr Glu Ile Ser Thr Gly Val Cys Val Asn Tyr Asp Leu
    610                 615                 620

Tyr Gly Ile Thr Gly Gln Gly Ile Phe Lys Glu Val Ser Ala Ala Tyr
625                 630                 635                 640

Tyr Asn Asn Trp Gln Asn Leu Leu Tyr Asp Ser Asn Gly Asn Ile Ile
                645                 650                 655

Gly Phe Lys Asp Phe Leu Thr Asn Lys Thr Tyr Thr Ile Leu Pro Cys
            660                 665                 670
```

-continued

```
Tyr Ser Gly Arg Val Ser Ala Ala Phe Tyr Gln Asn Ser Ser Ser Pro
        675                 680                 685

Ala Leu Leu Tyr Arg Asn Leu Lys Cys Ser Tyr Val Leu Asn Asn Ile
    690                 695                 700

Ser Phe Ile Ser Gln Pro Phe Tyr Phe Asp Ser Tyr Leu Gly Cys Val
705                 710                 715                 720

Leu Asn Ala Val Asn Leu Thr Ser Tyr Ser Val Ser Ser Cys Asp Leu
                725                 730                 735

Arg Met Gly Ser Gly Phe Cys Ile Asp Tyr Ala Leu Pro Ser Ser Arg
            740                 745                 750

Arg Lys Arg Arg Gly Ile Ser Ser Pro Tyr Arg Phe Val Thr Phe Glu
        755                 760                 765

Pro Phe Asn Val Ser Phe Val Asn Asp Ser Val Glu Thr Val Gly Gly
    770                 775                 780

Leu Phe Glu Ile Gln Ile Pro Thr Asn Phe Thr Ile Ala Gly His Glu
785                 790                 795                 800

Glu Phe Ile Gln Thr Ser Ser Pro Lys Val Thr Ile Asp Cys Ser Ala
                805                 810                 815

Phe Val Cys Ser Asn Tyr Ala Ala Cys His Asp Leu Leu Ser Glu Tyr
            820                 825                 830

Gly Thr Phe Cys Asp Asn Ile Asn Ser Ile Leu Asn Glu Val Asn Asp
        835                 840                 845

Leu Leu Asp Ile Thr Gln Leu Gln Val Ala Asn Ala Leu Met Gln Gly
    850                 855                 860

Val Thr Leu Ser Ser Asn Leu Asn Thr Asn Leu His Ser Asp Val Asp
865                 870                 875                 880

Asn Ile Asp Phe Lys Ser Leu Leu Gly Cys Leu Gly Ser Gln Cys Gly
                885                 890                 895

Ser Ser Ser Arg Ser Leu Leu Glu Asp Leu Leu Phe Asn Lys Val Lys
            900                 905                 910

Leu Ser Asp Val Gly Phe Val Glu Ala Tyr Asn Asn Cys Thr Gly Gly
        915                 920                 925

Ser Glu Ile Arg Asp Leu Leu Cys Val Gln Ser Phe Asn Gly Ile Lys
    930                 935                 940

Val Leu Pro Pro Ile Leu Ser Glu Thr Gln Ile Ser Gly Tyr Thr Thr
945                 950                 955                 960

Ala Ala Thr Val Ala Ala Met Phe Pro Pro Trp Ser Ala Ala Ala Gly
                965                 970                 975

Val Pro Phe Ser Leu Asn Val Gln Tyr Arg Ile Asn Gly Leu Gly Val
            980                 985                 990

Thr Met Asp Val Leu Asn Lys Asn  Gln Lys Leu Ile Ala  Asn Ala Phe
        995                 1000                1005

Asn Lys  Ala Leu Leu Ser Ile  Gln Asn Gly Phe Thr  Ala Thr Asn
    1010                1015                1020

Ser Ala  Leu Ala Lys Ile Gln  Ser Val Val Asn Ala  Asn Ala Gln
    1025                1030                1035

Ala Leu  Asn Ser Leu Leu Gln  Gln Leu Phe Asn Lys  Phe Gly Ala
    1040                1045                1050

Ile Ser  Ser Ser Leu Gln Glu  Ile Leu Ser Arg Leu  Asp Asn Leu
    1055                1060                1065

Glu Ala  Gln Val Gln Ile Asp  Arg Leu Ile Asn Gly  Arg Leu Thr
    1070                1075                1080
```

Ala Leu Asn Ala Tyr Val Ser Gln Gln Leu Ser Asp Ile Thr Leu
1085 1090 1095

Ile Lys Ala Gly Ala Ser Arg Ala Ile Glu Lys Val Asn Glu Cys
1100 1105 1110

Val Lys Ser Gln Ser Pro Arg Ile Asn Phe Cys Gly Asn Gly Asn
1115 1120 1125

His Ile Leu Ser Leu Val Gln Asn Ala Pro Tyr Gly Leu Leu Phe
1130 1135 1140

Ile His Phe Ser Tyr Lys Pro Thr Ser Phe Lys Thr Val Leu Val
1145 1150 1155

Ser Pro Gly Leu Cys Leu Ser Gly Asp Arg Gly Ile Ala Pro Lys
1160 1165 1170

Gln Gly Tyr Phe Ile Lys Gln Asn Asp Ser Trp Met Phe Thr Gly
1175 1180 1185

Ser Ser Tyr Tyr Tyr Pro Glu Pro Ile Ser Asp Lys Asn Val Val
1190 1195 1200

Phe Met Asn Ser Cys Ser Val Asn Phe Thr Lys Ala Pro Phe Ile
1205 1210 1215

Tyr Leu Asn Asn Ser Ile Pro Asn Leu Ser Asp Phe Glu Ala Glu
1220 1225 1230

Leu Ser Leu Trp Phe Lys Asn His Thr Ser Ile Ala Pro Asn Leu
1235 1240 1245

Thr Phe Asn Ser His Ile Asn Ala Thr Phe Leu Asp Leu Tyr Tyr
1250 1255 1260

Glu Met Asn Val Ile Gln Glu Ser Ile Lys Ser Leu Asn Ser Ser
1265 1270 1275

Phe Ile Asn Leu Lys Glu Ile Gly Thr Tyr Glu Met Tyr Val Lys
1280 1285 1290

Trp Pro Trp Tyr Ile Trp Leu Leu Ile Val Ile Leu Phe Ile Ile
1295 1300 1305

Phe Leu Met Ile Leu Phe Phe Ile Cys Cys Cys Thr Gly Cys Gly
1310 1315 1320

Ser Ala Cys Phe Ser Lys Cys His Asn Cys Cys Asp Glu Tyr Gly
1325 1330 1335

Gly His Asn Asp Phe Val Ile Lys Ala Ser His Asp Asp
1340 1345 1350

<210> SEQ ID NO 32
<211> LENGTH: 526
<212> TYPE: PRT
<213> ORGANISM: Artificial Sequence
<220> FEATURE:
<223> OTHER INFORMATION: Synthetic Polypeptide

<400> SEQUENCE: 32

Met Phe Ile Phe Leu Leu Phe Leu Thr Leu Thr Ser Gly Ser Asp Leu
1 5 10 15

Asp Arg Ala Leu Ser Gly Ile Ala Ala Glu Gln Asp Arg Asn Thr Arg
20 25 30

Glu Val Phe Ala Gln Val Lys Gln Met Tyr Lys Thr Pro Thr Leu Lys
35 40 45

Tyr Phe Gly Gly Phe Asn Phe Ser Gln Ile Leu Pro Asp Pro Leu Lys
50 55 60

Pro Thr Lys Arg Ser Phe Ile Glu Asp Leu Leu Phe Asn Lys Val Thr
65 70 75 80

-continued

```
Leu Ala Asp Ala Gly Phe Met Lys Gln Tyr Gly Glu Cys Leu Gly Asp
                85                  90                  95

Ile Asn Ala Arg Asp Leu Ile Cys Ala Gln Lys Phe Asn Gly Leu Thr
            100                 105                 110

Val Leu Pro Pro Leu Leu Thr Asp Asp Met Ile Ala Ala Tyr Thr Ala
        115                 120                 125

Ala Leu Val Ser Gly Thr Ala Thr Ala Gly Trp Thr Phe Gly Ala Gly
    130                 135                 140

Ala Ala Leu Gln Ile Pro Phe Ala Met Gln Met Ala Tyr Arg Phe Asn
145                 150                 155                 160

Gly Ile Gly Val Thr Gln Asn Val Leu Tyr Glu Asn Gln Lys Gln Ile
                165                 170                 175

Ala Asn Gln Phe Asn Lys Ala Ile Ser Gln Ile Gln Glu Ser Leu Thr
            180                 185                 190

Thr Thr Ser Thr Ala Leu Gly Lys Leu Gln Asp Val Val Asn Gln Asn
        195                 200                 205

Ala Gln Ala Leu Asn Thr Leu Val Lys Gln Leu Ser Ser Asn Phe Gly
    210                 215                 220

Ala Ile Ser Ser Val Leu Asn Asp Ile Leu Ser Arg Leu Asp Lys Val
225                 230                 235                 240

Glu Ala Glu Val Gln Ile Asp Arg Leu Ile Thr Gly Arg Leu Gln Ser
                245                 250                 255

Leu Gln Thr Tyr Val Thr Gln Gln Leu Ile Arg Ala Ala Glu Ile Arg
            260                 265                 270

Ala Ser Ala Asn Leu Ala Ala Thr Lys Met Ser Glu Cys Val Leu Gly
        275                 280                 285

Gln Ser Lys Arg Val Asp Phe Cys Gly Lys Gly Tyr His Leu Met Ser
    290                 295                 300

Phe Pro Gln Ala Ala Pro His Gly Val Val Phe Leu His Val Thr Tyr
305                 310                 315                 320

Val Pro Ser Gln Glu Arg Asn Phe Thr Thr Ala Pro Ala Ile Cys His
                325                 330                 335

Glu Gly Lys Ala Tyr Phe Pro Arg Glu Gly Val Phe Val Phe Asn Gly
            340                 345                 350

Thr Ser Trp Phe Ile Thr Gln Arg Asn Phe Phe Ser Pro Gln Ile Ile
        355                 360                 365

Thr Thr Asp Asn Thr Phe Val Ser Gly Asn Cys Asp Val Val Ile Gly
    370                 375                 380

Ile Ile Asn Asn Thr Val Tyr Asp Pro Leu Gln Pro Glu Leu Asp Ser
385                 390                 395                 400

Phe Lys Glu Glu Leu Asp Lys Tyr Phe Lys Asn His Thr Ser Pro Asp
                405                 410                 415

Val Asp Leu Gly Asp Ile Ser Gly Ile Asn Ala Ser Val Val Asn Ile
            420                 425                 430

Gln Lys Glu Ile Asp Arg Leu Asn Glu Val Ala Lys Asn Leu Asn Glu
        435                 440                 445

Ser Leu Ile Asp Leu Gln Glu Leu Gly Lys Tyr Glu Gln Tyr Ile Lys
    450                 455                 460

Trp Pro Trp Tyr Val Trp Leu Gly Phe Ile Ala Gly Leu Ile Ala Ile
465                 470                 475                 480

Val Met Val Thr Ile Leu Leu Cys Cys Met Thr Ser Cys Cys Ser Cys
                485                 490                 495

Leu Lys Gly Ala Cys Ser Cys Gly Ser Cys Cys Lys Phe Asp Glu Asp
```

500 505 510

Asp Ser Glu Pro Val Leu Lys Gly Val Lys Leu His Tyr Thr
515 520 525

<210> SEQ ID NO 33
<211> LENGTH: 588
<212> TYPE: PRT
<213> ORGANISM: Artificial Sequence
<220> FEATURE:
<223> OTHER INFORMATION: Synthetic Polypeptide

<400> SEQUENCE: 33

Met Ile His Ser Val Phe Leu Leu Met Phe Leu Leu Thr Pro Thr Glu
1 5 10 15

Ser Asp Cys Lys Leu Pro Leu Gly Gln Ser Leu Cys Ala Leu Pro Asp
20 25 30

Thr Pro Ser Thr Leu Thr Pro Arg Ser Val Arg Ser Val Pro Gly Glu
35 40 45

Met Arg Leu Ala Ser Ile Ala Phe Asn His Pro Ile Gln Val Asp Gln
50 55 60

Leu Asn Ser Ser Tyr Phe Lys Leu Ser Ile Pro Thr Asn Phe Ser Phe
65 70 75 80

Gly Val Thr Gln Glu Tyr Ile Gln Thr Thr Ile Gln Lys Val Thr Val
85 90 95

Asp Cys Lys Gln Tyr Val Cys Asn Gly Phe Gln Lys Cys Glu Gln Leu
100 105 110

Leu Arg Glu Tyr Gly Gln Phe Cys Ser Lys Ile Asn Gln Ala Leu His
115 120 125

Gly Ala Asn Leu Arg Gln Asp Asp Ser Val Arg Asn Leu Phe Ala Ser
130 135 140

Val Lys Ser Ser Gln Ser Ser Pro Ile Ile Pro Gly Phe Gly Gly Asp
145 150 155 160

Phe Asn Leu Thr Leu Leu Glu Pro Val Ser Ile Ser Thr Gly Ser Arg
165 170 175

Ser Ala Arg Ser Ala Ile Glu Asp Leu Leu Phe Asp Lys Val Thr Ile
180 185 190

Ala Asp Pro Gly Tyr Met Gln Gly Tyr Asp Asp Cys Met Gln Gln Gly
195 200 205

Pro Ala Ser Ala Arg Asp Leu Ile Cys Ala Gln Tyr Val Ala Gly Tyr
210 215 220

Lys Val Leu Pro Pro Leu Met Asp Val Asn Met Glu Ala Ala Tyr Thr
225 230 235 240

Ser Ser Leu Leu Gly Ser Ile Ala Gly Val Gly Trp Thr Ala Gly Leu
245 250 255

Ser Ser Phe Ala Ala Ile Pro Phe Ala Gln Ser Ile Phe Tyr Arg Leu
260 265 270

Asn Gly Val Gly Ile Thr Gln Gln Val Leu Ser Glu Asn Gln Lys Leu
275 280 285

Ile Ala Asn Lys Phe Asn Gln Ala Leu Gly Ala Met Gln Thr Gly Phe
290 295 300

Thr Thr Thr Asn Glu Ala Phe Gln Lys Val Gln Asp Ala Val Asn Asn
305 310 315 320

Asn Ala Gln Ala Leu Ser Lys Leu Ala Ser Glu Leu Ser Asn Thr Phe
325 330 335

Gly Ala Ile Ser Ala Ser Ile Gly Asp Ile Ile Gln Arg Leu Asp Val

```
            340                 345                 350

Leu Glu Gln Asp Ala Gln Ile Asp Arg Leu Ile Asn Gly Arg Leu Thr
        355                 360                 365

Thr Leu Asn Ala Phe Val Ala Gln Gln Leu Val Arg Ser Glu Ser Ala
    370                 375                 380

Ala Leu Ser Ala Gln Leu Ala Lys Asp Lys Val Asn Glu Cys Val Lys
385                 390                 395                 400

Ala Gln Ser Lys Arg Ser Gly Phe Cys Gly Gln Gly Thr His Ile Val
                405                 410                 415

Ser Phe Val Val Asn Ala Pro Asn Gly Leu Tyr Phe Met His Val Gly
            420                 425                 430

Tyr Tyr Pro Ser Asn His Ile Glu Val Val Ser Ala Tyr Gly Leu Cys
        435                 440                 445

Asp Ala Ala Asn Pro Thr Asn Cys Ile Ala Pro Val Asn Gly Tyr Phe
    450                 455                 460

Ile Lys Thr Asn Asn Thr Arg Ile Val Asp Glu Trp Ser Tyr Thr Gly
465                 470                 475                 480

Ser Ser Phe Tyr Ala Pro Glu Pro Ile Thr Ser Leu Asn Thr Lys Tyr
                485                 490                 495

Val Ala Pro Gln Val Thr Tyr Gln Asn Ile Ser Thr Asn Leu Pro Pro
            500                 505                 510

Pro Leu Leu Gly Asn Ser Thr Gly Ile Asp Phe Gln Asp Glu Leu Asp
        515                 520                 525

Glu Phe Phe Lys Asn Val Ser Thr Ser Ile Pro Asn Phe Gly Ser Leu
    530                 535                 540

Thr Gln Ile Asn Thr Thr Leu Leu Asp Leu Thr Tyr Glu Met Leu Ser
545                 550                 555                 560

Leu Gln Gln Val Val Lys Ala Leu Asn Glu Ser Tyr Ile Asp Leu Lys
                565                 570                 575

Glu Leu Gly Asn Tyr Thr Tyr Tyr Asn Lys Trp Pro
            580                 585


<210> SEQ ID NO 34
<211> LENGTH: 526
<212> TYPE: PRT
<213> ORGANISM: Artificial Sequence
<220> FEATURE:
<223> OTHER INFORMATION: Synthetic Polypeptide

<400> SEQUENCE: 34

Met Phe Ile Phe Leu Leu Phe Leu Thr Leu Thr Ser Gly Ser Asp Leu
1               5                   10                  15

Asp Arg Ala Leu Ser Gly Ile Ala Ala Glu Gln Asp Arg Asn Thr Arg
            20                  25                  30

Glu Val Phe Ala Gln Val Lys Gln Met Tyr Lys Thr Pro Thr Leu Lys
        35                  40                  45

Tyr Phe Gly Gly Phe Asn Phe Ser Gln Ile Leu Pro Asp Pro Leu Lys
    50                  55                  60

Pro Thr Lys Arg Ser Phe Ile Glu Asp Leu Leu Phe Asn Lys Val Thr
65                  70                  75                  80

Leu Ala Asp Ala Gly Phe Met Lys Gln Tyr Gly Glu Cys Leu Gly Asp
                85                  90                  95

Ile Asn Ala Arg Asp Leu Ile Cys Ala Gln Lys Phe Asn Gly Leu Thr
            100                 105                 110

Val Leu Pro Pro Leu Leu Thr Asp Asp Met Ile Ala Ala Tyr Thr Ala
```

```
        115                 120                 125

Ala Leu Val Ser Gly Thr Ala Thr Ala Gly Trp Thr Phe Gly Ala Gly
    130                 135                 140

Ala Ala Leu Gln Ile Pro Phe Ala Met Gln Met Ala Tyr Arg Phe Asn
145                 150                 155                 160

Gly Ile Gly Val Thr Gln Asn Val Leu Tyr Glu Asn Gln Lys Gln Ile
                165                 170                 175

Ala Asn Gln Phe Asn Lys Ala Ile Ser Gln Ile Gln Glu Ser Leu Thr
            180                 185                 190

Thr Thr Ser Thr Ala Leu Gly Lys Leu Gln Asp Val Val Asn Gln Asn
        195                 200                 205

Ala Gln Ala Leu Asn Thr Leu Val Lys Gln Leu Ser Ser Asn Phe Gly
    210                 215                 220

Ala Ile Ser Ser Val Leu Asn Asp Ile Leu Ser Arg Leu Asp Lys Val
225                 230                 235                 240

Glu Ala Glu Val Gln Ile Asp Arg Leu Ile Thr Gly Arg Leu Gln Ser
                245                 250                 255

Leu Gln Thr Tyr Val Thr Gln Gln Leu Ile Arg Ala Ala Glu Ile Arg
            260                 265                 270

Ala Ser Ala Asn Leu Ala Ala Thr Lys Met Ser Glu Cys Val Leu Gly
        275                 280                 285

Gln Ser Lys Arg Val Asp Phe Cys Gly Lys Gly Tyr His Leu Met Ser
    290                 295                 300

Phe Pro Gln Ala Ala Pro His Gly Val Val Phe Leu His Val Thr Tyr
305                 310                 315                 320

Val Pro Ser Gln Glu Arg Asn Phe Thr Thr Ala Pro Ala Ile Cys His
                325                 330                 335

Glu Gly Lys Ala Tyr Phe Pro Arg Glu Gly Val Phe Val Phe Asn Gly
            340                 345                 350

Thr Ser Trp Phe Ile Thr Gln Arg Asn Phe Phe Ser Pro Gln Ile Ile
        355                 360                 365

Thr Thr Asp Asn Thr Phe Val Ser Gly Asn Cys Asp Val Val Ile Gly
    370                 375                 380

Ile Ile Asn Asn Thr Val Tyr Asp Pro Leu Gln Pro Glu Leu Asp Ser
385                 390                 395                 400

Phe Lys Glu Glu Leu Asp Lys Tyr Phe Lys Asn His Thr Ser Pro Asp
                405                 410                 415

Val Asp Leu Gly Asp Ile Ser Gly Ile Asn Ala Ser Val Val Asn Ile
            420                 425                 430

Gln Lys Glu Ile Asp Arg Leu Asn Glu Val Ala Lys Asn Leu Asn Glu
        435                 440                 445

Ser Leu Ile Asp Leu Gln Glu Leu Gly Lys Tyr Glu Gln Tyr Ile Lys
    450                 455                 460

Trp Pro Trp Tyr Val Trp Leu Gly Phe Ile Ala Gly Leu Ile Ala Ile
465                 470                 475                 480

Val Met Val Thr Ile Leu Leu Cys Cys Met Thr Ser Cys Cys Ser Cys
                485                 490                 495

Leu Lys Gly Ala Cys Ser Cys Gly Ser Cys Cys Lys Phe Asp Glu Asp
            500                 505                 510

Asp Ser Glu Pro Val Leu Lys Gly Val Lys Leu His Tyr Thr
        515                 520                 525
```

<210> SEQ ID NO 35

<211> LENGTH: 1864
<212> TYPE: DNA
<213> ORGANISM: Artificial Sequence
<220> FEATURE:
<223> OTHER INFORMATION: Synthetic Polynucleotide

<400> SEQUENCE: 35
tcaagctttt ggaccctcgt acagaagcta atacgactca ctatagggaa ataagagaga 60
aaagaagagt aagaagaaat ataagagcca ccatgggtct caaggtgaac gtctctgccg 120
tattcatggc agtactgtta actctccaaa cacccgccgg tcaaattcat tggggcaatc 180
tctctaagat aggggtagta ggaataggaa gtgcaagcta caaagttatg actcgttcca 240
gccatcaatc attagtcata aaattaatgc ccaatataac tctcctcaat aactgcacga 300
gggtagagat tgcagaatac aggagactac taagaacagt tttggaacca attagggatg 360
cacttaatgc aatgacccag aacataaggc cggttcagag cgtagcttca agtaggagac 420
acaagagatt tgcgggagta gtcctggcag gtgcggccct aggtgttgcc acagctgctc 480
agataacagc cggcattgca cttcaccggt ccatgctgaa ctctcaggcc atcgacaatc 540
tgagagcgag cctggaaact actaatcagg caattgaggc aatcagacaa gcagggcagg 600
agatgatatt ggctgttcag ggtgtccaag actacatcaa taatgagctg ataccgtcta 660
tgaaccagct atcttgtgat ctaatcggtc agaagctcgg gctcaaattg cttagatact 720
atacagaaat cctgtcatta tttggcccca gcctacggga ccccatatct gcggagatat 780
ctatccaggc tttgagttat gcacttggag gagatatcaa taaggtgtta gaaaagctcg 840
gatacagtgg aggcgattta ctaggcatct tagagagcag aggaataaag gctcggataa 900
ctcacgtcga cacagagtcc tacttcatag tcctcagtat agcctatccg acgctgtccg 960
agattaaggg ggtgattgtc caccggctag agggggtctc gtacaacata ggctctcaag 1020
agtggtatac cactgtgccc aagtatgttg caacccaagg gtaccttatc tcgaattttg 1080
atgagtcatc atgtactttc atgccagagg ggactgtgtg cagccaaaat gccttgtacc 1140
cgatgagtcc tctgctccaa gaatgcctcc gggggtccac caagtcctgt gctcgtacac 1200
tcgtatccgg gtcttttggg aaccggttca ttttatcaca agggaaccta atagccaatt 1260
gtgcatcaat tctttgtaag tgttacacaa caggtacgat tattaatcaa gaccctgaca 1320
agatcctaac atacattgct gccgatcgct gcccggtagt cgaggtgaac ggcgtgacca 1380
tccaagtcgg gagcaggagg tatccagacg ctgtgtactt gcacagaatt gacctcggtc 1440
ctcccatatc attggagagg ttggacgtag ggacaaatct ggggaatgca attgccaaat 1500
tggaggatgc caaggaattg ttggaatcat cggaccagat attgagaagt atgaaaggtt 1560
tatcgagcac tagcatagtc tacatcctga ttgcagtgtg tcttggaggg ttgataggga 1620
tccccacttt aatatgttgc tgcagggggc gttgtaacaa aaagggagaa caagttggta 1680
tgtcaagacc aggcctaaag cctgacctta caggaacatc aaaatcctat gtaagatcgc 1740
tttgatgata ataggctgga gcctcggtgg ccaagcttct tgccccttgg gcctcccccc 1800
agcccctcct ccccttcctg cacccgtacc cccgtggtct ttgaataaag tctgagtggg 1860
cggc 1864

<210> SEQ ID NO 36
<211> LENGTH: 1653
<212> TYPE: DNA
<213> ORGANISM: Artificial Sequence
<220> FEATURE:
<223> OTHER INFORMATION: Synthetic Polynucleotide

<400> SEQUENCE: 36
atgggtctca aggtgaacgt ctctgccgta ttcatggcag tactgttaac tctccaaaca 60
cccgccggtc aaattcattg ggcaatctc tctaagatag ggtagtagg aataggaagt 120
gcaagctaca aagttatgac tcgttccagc catcaatcat tagtcataaa attaatgccc 180
aatataactc tcctcaataa ctgcacgagg gtagagattg cagaatacag gagactacta 240
agaacagttt tggaaccaat tagggatgca cttaatgcaa tgacccagaa cataaggccg 300
gttcagagcg tagcttcaag taggagacac aagagatttg cgggagtagt cctggcaggt 360
gcggccctag gtgttgccac agctgctcag ataacagccg gcattgcact tcaccggtcc 420
atgctgaact ctcaggccat cgacaatctg agagcgagcc tggaaactac taatcaggca 480
attgaggcaa tcagacaagc agggcaggag atgatattgg ctgttcaggg tgtccaagac 540
tacatcaata atgagctgat accgtctatg aaccagctat cttgtgatct aatcggtcag 600
aagctcgggc tcaaattgct tagatactat acagaaatcc tgtcattatt tggccccagc 660
ctacgggacc ccatatctgc ggagatatct atccaggctt tgagttatgc acttggagga 720
gatatcaata aggtgttaga aaagctcgga tacagtggag gcgatttact aggcatctta 780
gagagcagag gaataaaggc tcggataact cacgtcgaca cagagtccta cttcatagtc 840
ctcagtatag cctatccgac gctgtccgag attaaggggg tgattgtcca ccggctagag 900
ggggtctcgt acaacatagg ctctcaagag tggtatacca ctgtgcccaa gtatgttgca 960
acccaagggt accttatctc gaattttgat gagtcatcat gtactttcat gccagagggg 1020
actgtgtgca gccaaaatgc cttgtacccg atgagtcctc tgctccaaga atgcctccgg 1080
gggtccacca agtcctgtgc tcgtacactc gtatccgggt cttttgggaa ccggttcatt 1140
ttatcacaag ggaacctaat agccaattgt gcatcaattc tttgtaagtg ttacacaaca 1200
ggtacgatta ttaatcaaga ccctgacaag atcctaacat acattgctgc cgatcgctgc 1260
ccggtagtcg aggtgaacgg cgtgaccatc caagtcggga gcaggaggta tccagacgct 1320
gtgtacttgc acagaattga cctcggtcct cccatatcat tggagaggtt ggacgtaggg 1380
acaaatctgg ggaatgcaat tgccaaattg gaggatgcca aggaattgtt ggaatcatcg 1440
gaccagatat tgagaagtat gaaaggttta tcgagcacta gcatagtcta catcctgatt 1500
gcagtgtgtc ttggagggtt gatagggatc cccactttaa tatgttgctg caggggggcgt 1560
tgtaacaaaa agggagaaca agttggtatg tcaagaccag gcctaaagcc tgaccttaca 1620
ggaacatcaa aatcctatgt aagatcgctt tga 1653

<210> SEQ ID NO 37
<211> LENGTH: 1925
<212> TYPE: DNA
<213> ORGANISM: Artificial Sequence
<220> FEATURE:
<223> OTHER INFORMATION: Synthetic Polynucleotide

<400> SEQUENCE: 37
ggggaaataa gagagaaaag aagagtaaga agaaatataa gagccaccat gggtctcaag 60
gtgaacgtct ctgccgtatt catggcagta ctgttaactc tccaaacacc cgccggtcaa 120
attcattggg gcaatctctc taagataggg gtagtaggaa taggaagtgc aagctacaaa 180
gttatgactc gttccagcca tcaatcatta gtcataaaat taatgcccaa tataactctc 240
ctcaataact gcacgagggt agagattgca gaatacagga gactactaag aacagttttg 300

-continued

```
gaaccaatta gggatgcact taatgcaatg acccagaaca taaggccggt tcagagcgta    360
gcttcaagta ggagacacaa gagatttgcg ggagtagtcc tggcaggtgc ggccctaggt    420
gttgccacag ctgctcagat aacagccggc attgcacttc accggtccat gctgaactct    480
caggccatcg acaatctgag agcgagcctg gaaactacta atcaggcaat tgaggcaatc    540
agacaagcag ggcaggagat gatattggct gttcagggtg tccaagacta catcaataat    600
gagctgatac cgtctatgaa ccagctatct tgtgatctaa tcggtcagaa gctcgggctc    660
aaattgctta gatactatac agaaatcctg tcattatttg gccccagcct acgggacccc    720
atatctgcgg agatatctat ccaggctttg agttatgcac ttggaggaga tatcaataag    780
gtgttagaaa agctcggata cagtggaggc gatttactag gcatcttaga gagcagagga    840
ataaaggctc ggataactca cgtcgacaca gagtcctact tcatagtcct cagtatagcc    900
tatccgacgc tgtccgagat taagggggtg attgtccacc ggctagaggg ggtctcgtac    960
aacataggct ctcaagagtg gtataccact gtgcccaagt atgttgcaac ccaagggtac   1020
cttatctcga attttgatga gtcatcatgt actttcatgc cagaggggac tgtgtgcagc   1080
caaaatgcct tgtacccgat gagtcctctg ctccaagaat gcctccgggg gtccaccaag   1140
tcctgtgctc gtacactcgt atccgggtct tttgggaacc ggttcatttt atcacaaggg   1200
aacctaatag ccaattgtgc atcaattctt tgtaagtgtt acacaacagg tacgattatt   1260
aatcaagacc ctgacaagat cctaacatac attgctgccg atcgctgccc ggtagtcgag   1320
gtgaacggcg tgaccatcca agtcgggagc aggaggtatc cagacgctgt gtacttgcac   1380
agaattgacc tcggtcctcc catatcattg gagaggttgg acgtagggac aaatctgggg   1440
aatgcaattg ccaaattgga ggatgccaag gaattgttgg aatcatcgga ccagatattg   1500
agaagtatga aaggtttatc gagcactagc atagtctaca tcctgattgc agtgtgtctt   1560
ggagggttga tagggatccc cactttaata tgttgctgca gggggcgttg taacaaaaag   1620
ggagaacaag ttggtatgtc aagaccaggc ctaaagcctg accttacagg aacatcaaaa   1680
tcctatgtaa gatcgctttg atgataatag gctggagcct cggtggccaa gcttcttgcc   1740
ccttgggcct ccccccagcc cctcctcccc ttcctgcacc cgtacccccg tggtctttga   1800
ataaagtctg agtgggcggc aaaaaaaaaa aaaaaaaaaa aaaaaaaaaa aaaaaaaaaa   1860
aaaaaaaaaa aaaaaaaaaa aaaaaaaaaa aaaaaaaaaa aaaaaaaaaa aaaaaaaaaa   1920
tctag                                                               1925
```

<210> SEQ ID NO 38
<211> LENGTH: 1864
<212> TYPE: DNA
<213> ORGANISM: Artificial Sequence
<220> FEATURE:
<223> OTHER INFORMATION: Synthetic Polynucleotide

<400> SEQUENCE: 38

```
tcaagctttt ggaccctcgt acagaagcta atacgactca ctatagggaa ataagagaga     60
aaagaagagt aagaagaaat ataagagcca ccatgggtct caaggtgaac gtctctgtca    120
tattcatggc agtactgtta actcttcaaa cacccaccgg tcaaatccat tggggcaatc    180
tctctaagat aggggtggta ggggtaggaa gtgcaagcta caaagttatg actcgttcca    240
gccatcaatc attagtcata aagttaatgc ccaatataac tctcctcaac aattgcacga    300
gggtagggat tgcagaatac aggagactac tgagaacagt tctggaacca attagagatg    360
cacttaatgc aatgacccag aatataagac cggttcagag tgtagcttca agtaggagac    420
```

acaagagatt tgcgggagtt gtcctggcag gtgcggccct aggcgttgcc acagctgctc 480
aaataacagc cggtattgca cttcaccagt ccatgctgaa ctctcaagcc atcgacaatc 540
tgagagcgag cctagaaact actaatcagg caattgaggc aatcagacaa gcagggcagg 600
agatgatatt ggctgttcag ggtgtccaag actacatcaa taatgagctg ataccgtcta 660
tgaatcaact atcttgtgat ttaatcggcc agaagctagg gctcaaattg ctcagatact 720
atacagaaat cctgtcatta tttggcccca gcttacggga ccccatatct gcggagatat 780
ctatccaggc tttgagctat gcgcttggag gagatatcaa taaggtgttg gaaaagctcg 840
gatacagtgg aggtgatcta ctgggcatct tagagagcag aggaataaag gcccggataa 900
ctcacgtcga cacagagtcc tacttcattg tactcagtat agcctatccg acgctatccg 960
agattaaggg ggtgattgtc caccggctag agggggtctc gtacaacata ggctctcaag 1020
agtggtatac cactgtgccc aagtatgttg caacccaagg gtaccttatc tcgaattttg 1080
atgagtcatc atgcactttc atgccagagg ggactgtgtg cagccagaat gccttgtacc 1140
cgatgagtcc tctgctccaa gaatgcctcc gggggtccac taagtcctgt gctcgtacac 1200
tcgtatccgg gtctttcggg aaccggttca ttttatcaca ggggaaccta atagccaatt 1260
gtgcatcaat cctttgcaag tgttacacaa caggaacaat cattaatcaa gaccctgaca 1320
agatcctaac atacattgct gccgatcact gcccggtggt cgaggtgaat ggcgtgacca 1380
tccaagtcgg gagcaggagg tatccggacg ctgtgtactt gcacaggatt gacctcggtc 1440
ctcccatatc tttggagagg ttggacgtag ggacaaatct ggggaatgca attgctaagt 1500
tggaggatgc caaggaattg ttggagtcat cggaccagat attgaggagt atgaaaggtt 1560
tatcgagcac tagtatagtt tacatcctga ttgcagtgtg tcttggagga ttgataggga 1620
tccccgcttt aatatgttgc tgcagggggc gttgtaacaa gaagggagaa caagttggta 1680
tgtcaagacc aggcctaaag cctgatctta caggaacatc aaaatcctat gtaaggtcac 1740
tctgatgata ataggctgga gcctcggtgg ccaagcttct tgccccttgg gcctcccccc 1800
agcccctcct ccccttcctg cacccgtacc cccgtggtct ttgaataaag tctgagtggg 1860
cggc 1864

<210> SEQ ID NO 39
<211> LENGTH: 1653
<212> TYPE: DNA
<213> ORGANISM: Artificial Sequence
<220> FEATURE:
<223> OTHER INFORMATION: Synthetic Polynucleotide

<400> SEQUENCE: 39
atgggtctca aggtgaacgt ctctgtcata ttcatggcag tactgttaac tcttcaaaca 60
cccaccggtc aaatccattg gggcaatctc tctaagatag ggtggtaggg ggtaggaagt 120
gcaagctaca aagttatgac tcgttccagc catcaatcat tagtcataaa gttaatgccc 180
aatataactc tcctcaacaa ttgcacgagg gtagggattg cagaatacag gagactactg 240
agaacagttc tggaaccaat tagagatgca cttaatgcaa tgacccagaa tataagaccg 300
gttcagagtg tagcttcaag taggagacac aagagatttg cgggagttgt cctggcaggt 360
gcggccctag gcgttgccac agctgctcaa ataacagccg gtattgcact tcaccagtcc 420
atgctgaact ctcaagccat cgacaatctg agagcgagcc tagaaactac taatcaggca 480
attgaggcaa tcagacaagc agggcaggag atgatattgg ctgttcaggg tgtccaagac 540

-continued

```
tacatcaata atgagctgat accgtctatg aatcaactat cttgtgattt aatcggccag    600

aagctagggc tcaaattgct cagatactat acagaaatcc tgtcattatt tggccccagc    660

ttacgggacc ccatatctgc ggagatatct atccaggctt tgagctatgc gcttggagga    720

gatatcaata aggtgttgga aaagctcgga tacagtggag gtgatctact gggcatctta    780

gagagcagag gaataaaggc ccggataact cacgtcgaca cagagtccta cttcattgta    840

ctcagtatag cctatccgac gctatccgag attaaggggg tgattgtcca ccggctagag    900

ggggtctcgt acaacatagg ctctcaagag tggtatacca ctgtgcccaa gtatgttgca    960

acccaagggt accttatctc gaattttgat gagtcatcat gcactttcat gccagagggg   1020

actgtgtgca gccagaatgc cttgtacccg atgagtcctc tgctccaaga atgcctccgg   1080

gggtccacta agtcctgtgc tcgtacactc gtatccgggt ctttcgggaa ccggttcatt   1140

ttatcacagg ggaacctaat agccaattgt gcatcaatcc tttgcaagtg ttacacaaca   1200

ggaacaatca ttaatcaaga ccctgacaag atcctaacat acattgctgc cgatcactgc   1260

ccggtggtcg aggtgaatgg cgtgaccatc caagtcggga gcaggaggta tccggacgct   1320

gtgtacttgc acaggattga cctcggtcct cccatatctt tggagaggtt ggacgtaggg   1380

acaaatctgg ggaatgcaat tgctaagttg gaggatgcca aggaattgtt ggagtcatcg   1440

gaccagatat tgaggagtat gaaaggttta tcgagcacta gtatagttta catcctgatt   1500

gcagtgtgtc ttggaggatt gatagggatc cccgctttaa tatgttgctg caggggggcgt  1560

tgtaacaaga agggagaaca agttggtatg tcaagaccag gcctaaagcc tgatcttaca   1620

ggaacatcaa aatcctatgt aaggtcactc tga                                1653
```

```
<210> SEQ ID NO 40
<211> LENGTH: 1925
<212> TYPE: DNA
<213> ORGANISM: Artificial Sequence
<220> FEATURE:
<223> OTHER INFORMATION: Synthetic Polynucleotide

<400> SEQUENCE: 40

ggggaaataa gagagaaaag aagagtaaga agaaatataa gagccaccat gggtctcaag     60

gtgaacgtct ctgtcatatt catggcagta ctgttaactc ttcaaacacc caccggtcaa    120

atccattggg gcaatctctc taagataggg gtggtagggg taggaagtgc aagctacaaa    180

gttatgactc gttccagcca tcaatcatta gtcataaagt taatgcccaa tataactctc    240

ctcaacaatt gcacgagggt agggattgca gaatacagga gactactgag aacagttctg    300

gaaccaatta gagatgcact taatgcaatg acccagaata taagaccggt tcagagtgta    360

gcttcaagta ggagacacaa gagatttgcg ggagttgtcc tggcaggtgc ggccctaggc    420

gttgccacag ctgctcaaat aacagccggt attgcacttc accagtccat gctgaactct    480

caagccatcg acaatctgag agcgagccta gaaactacta atcaggcaat tgaggcaatc    540

agacaagcag ggcaggagat gatattggct gttcagggtg tccaagacta catcaataat    600

gagctgatac cgtctatgaa tcaactatct tgtgatttaa tcggccagaa gctagggctc    660

aaattgctca gatactatac agaaatcctg tcattatttg gccccagctt acgggacccc    720

atatctgcgg agatatctat ccaggctttg agctatgcgc ttggaggaga tatcaataag    780

gtgttggaaa agctcggata cagtggaggt gatctactgg gcatcttaga gagcagagga    840

ataaaggccc ggataactca cgtcgacaca gagtcctact tcattgtact cagtatagcc    900

tatccgacgc tatccgagat taagggggtg attgtccacc ggctagaggg ggtctcgtac    960
```

aacataggct ctcaagagtg gtataccact gtgcccaagt atgttgcaac ccaagggtac 1020
cttatctcga attttgatga gtcatcatgc actttcatgc cagaggggac tgtgtgcagc 1080
cagaatgcct tgtacccgat gagtcctctg ctccaagaat gcctccgggg gtccactaag 1140
tcctgtgctc gtacactcgt atccgggtct ttcgggaacc ggttcatttt atcacagggg 1200
aacctaatag ccaattgtgc atcaatcctt tgcaagtgtt acacaacagg aacaatcatt 1260
aatcaagacc ctgacaagat cctaacatac attgctgccg atcactgccc ggtggtcgag 1320
gtgaatggcg tgaccatcca agtcgggagc aggaggtatc cggacgctgt gtacttgcac 1380
aggattgacc tcggtcctcc catatctttg gagaggttgg acgtagggac aaatctgggg 1440
aatgcaattg ctaagttgga ggatgccaag gaattgttgg agtcatcgga ccagatattg 1500
aggagtatga aaggtttatc gagcactagt atagtttaca tcctgattgc agtgtgtctt 1560
ggaggattga tagggatccc cgctttaata tgttgctgca gggggcgttg taacaagaag 1620
ggagaacaag ttggtatgtc aagaccaggc ctaaagcctg atcttacagg aacatcaaaa 1680
tcctatgtaa ggtcactctg atgataatag gctggagcct cggtggccaa gcttcttgcc 1740
ccttgggcct ccccccagcc cctcctcccc ttcctgcacc cgtacccccg tggtctttga 1800
ataaagtctg agtgggcggc aaaaaaaaaa aaaaaaaaaa aaaaaaaaaa aaaaaaaaaa 1860
aaaaaaaaaa aaaaaaaaaa aaaaaaaaaa aaaaaaaaaa aaaaaaaaaa aaaaaaaaaa 1920
tctag 1925

<210> SEQ ID NO 41
<211> LENGTH: 2065
<212> TYPE: DNA
<213> ORGANISM: Artificial Sequence
<220> FEATURE:
<223> OTHER INFORMATION: Synthetic Polynucleotide

<400> SEQUENCE: 41
tcaagctttt ggaccctcgt acagaagcta atacgactca ctatagggaa ataagagaga 60
aaagaagagt aagaagaaat ataagagcca ccatgtcacc gcaacgagac cggataaatg 120
ccttctacaa agataaccct tatcccaagg gaagtaggat agttattaac agagaacatc 180
ttatgattga cagaccctat gttctgctgg ctgttctgtt cgtcatgttt ctgagcttga 240
tcggattgct ggcaattgca ggcattagac ttcatcgggc agccatctac accgcggaga 300
tccataaaag cctcagtacc aatctggatg tgactaactc catcgagcat caggtcaagg 360
acgtgctgac accactcttt aaaatcatcg gggatgaagt gggcctgaga acacctcaga 420
gattcactga cctagtgaaa ttcatctcgg acaagattaa attccttaat ccggataggg 480
agtacgactt cagagatctc acttggtgca tcaacccgcc agagaggatc aaactagatt 540
atgatcaata ctgtgcagat gtggctgctg aagagctcat gaatgcattg gtgaactcaa 600
ctctactgga gaccagaaca accactcagt tcctagctgt ctcaaaggga aactgctcag 660
ggcccactac aatcagaggt caattctcaa acatgtcgct gtccttgttg gacttgtact 720
taggtcgagg ttacaatgtg tcatctatag tcactatgac atcccaggga atgtatgggg 780
gaacctacct agttgaaaag cctaatctga acagcaaagg gtcagagttg tcacaactga 840
gcatgtaccg agtgtttgaa gtaggtgtga tcagaaaccc gggtttgggg gctccggtgt 900
tccatatgac aaactatttt gagcaaccag tcagtaatgg tctcggcaac tgtatggtgg 960
ctttggggga gctcaaactc gcagcccttt gtcacgggga cgattctatc ataattccct 1020
atcagggatc agggaaaggt gtcagcttcc agctcgtcaa gctgggtgtc tggaaatccc 1080
caaccgacat gcaatcctgg gtccccttat caacggatga tccagtggta gacaggcttt 1140
acctctcatc tcacagaggt gtcatcgctg acaatcaagc aaaatgggct gtcccgacaa 1200
cacgaacaga tgacaagttg cgaatggaga catgcttcca gcaggcgtgt aaaggtaaaa 1260
tccaagcact ctgcgagaat cccgagtggg taccattgaa ggataacagg attccttcat 1320
acggggtcct gtctgttgat ctgagtctga cggttgagct taaaatcaaa attgcttcgg 1380
gattcgggcc attgatcaca cacggctcag ggatggacct atacaaatcc aactgcaaca 1440
atgtgtattg gctgactatt ccgccaatga gaaatctagc cttaggcgta atcaacacat 1500
tggagtggat accgagattc aaggttagtc ccaacctctt cactgtccca attaaggaag 1560
caggcgaaga ctgccatgcc ccaacatacc tacctgcgga ggtggacggt gatgtcaaac 1620
tcagttccaa cctggtgatt ctacctggtc aagatctcca atatgttttg gcaacctacg 1680
atacctccag ggttgagcat gctgtggttt attacgttta cagcccaagc cgctcatttt 1740
cttactttta tccttttagg ttgcctataa agggggtccc aatcgaacta caagtggaat 1800
gcttcacatg ggatcaaaaa ctctggtgcc gtcacttctg tgtgcttgcg gactcagaat 1860
ccggtggact tatcactcac tctgggatgg tgggcatggg agtcagctgc acagctaccc 1920
gggaagatgg aaccaatcgc agataatgat aataggctgg agcctcggtg gccaagcttc 1980
ttgccccttg ggcctccccc cagcccctcc tccccttcct gcacccgtac cccgtggtc 2040 tttgaataaa gtctgagtgg gcggc 2065

<210> SEQ ID NO 42
<211> LENGTH: 1854
<212> TYPE: DNA
<213> ORGANISM: Artificial Sequence
<220> FEATURE:
<223> OTHER INFORMATION: Synthetic Polynucleotide

<400> SEQUENCE: 42
atgtcaccgc aacgagaccg gataaatgcc ttctacaaag ataacccttta tcccaaggga 60 agtaggatag ttattaacag agaacatctt atgattgaca gaccctatgt tctgctggct 120
gttctgttcg tcatgtttct gagcttgatc ggattgctgg caattgcagg cattagactt 180
catcgggcag ccatctacac cgcggagatc cataaaagcc tcagtaccaa tctggatgtg 240
actaactcca tcgagcatca ggtcaaggac gtgctgacac cactctttaa aatcatcggg 300
gatgaagtgg gcctgagaac acctcagaga ttcactgacc tagtgaaatt catctcggac 360
aagattaaat tccttaatcc ggatagggag tacgacttca gagatctcac ttggtgcatc 420
aacccgccag agaggatcaa actagattat gatcaatact gtgcagatgt ggctgctgaa 480
gagctcatga atgcattggt gaactcaact ctactggaga ccagaacaac cactcagttc 540
ctagctgtct caaagggaaa ctgctcaggg cccactacaa tcagaggtca attctcaaac 600
atgtcgctgt ccttgttgga cttgtactta ggtcgaggtt acaatgtgtc atctatagtc 660
actatgacat cccagggaat gtatgggggga acctacctag ttgaaaagcc taatctgaac 720
agcaaagggt cagagttgtc acaactgagc atgtaccgag tgtttgaagt aggtgtgatc 780
agaaacccgg gtttgggggc tccggtgttc catatgacaa actattttga gcaaccagtc 840
agtaatggtc tcggcaactg tatggtggct ttgggggagc tcaaactcgc agccctttgt 900
cacggggacg attctatcat aattccctat cagggatcag ggaaaggtgt cagcttccag 960
ctcgtcaagc tgggtgtctg gaaatcccca accgacatgc aatcctgggt ccccttatca 1020
acggatgatc cagtggtaga caggctttac ctctcatctc acagaggtgt catcgctgac 1080
aatcaagcaa aatgggctgt cccgacaaca cgaacagatg acaagttgcg aatggagaca 1140
tgcttccagc aggcgtgtaa aggtaaaatc caagcactct gcgagaatcc cgagtgggta 1200
ccattgaagg ataacaggat tccttcatac ggggtcctgt ctgttgatct gagtctgacg 1260
gttgagctta aaatcaaaat tgcttcggga ttcgggccat tgatcacaca cggctcaggg 1320
atggacctat acaaatccaa ctgcaacaat gtgtattggc tgactattcc gccaatgaga 1380
aatctagcct taggcgtaat caacacattg gagtggatac cgagattcaa ggttagtccc 1440
aacctcttca ctgtcccaat taaggaagca ggcgaagact gccatgcccc aacataccta 1500
cctgcggagg tggacggtga tgtcaaactc agttccaacc tggtgattct acctggtcaa 1560
gatctccaat atgttttggc aacctacgat acctccaggg ttgagcatgc tgtggtttat 1620
tacgtttaca gcccaagccg ctcattttct tacttttatc cttttaggtt gcctataaag 1680
ggggtcccaa tcgaactaca agtggaatgc ttcacatggg atcaaaaact ctggtgccgt 1740
cacttctgtg tgcttgcgga ctcagaatcc ggtggactta tcactcactc tgggatggtg 1800
ggcatgggag tcagctgcac agctacccgg gaagatggaa ccaatcgcag ataa 1854

<210> SEQ ID NO 43
<211> LENGTH: 2126
<212> TYPE: DNA
<213> ORGANISM: Artificial Sequence
<220> FEATURE:
<223> OTHER INFORMATION: Synthetic Polynucleotide

<400> SEQUENCE: 43
ggggaaataa gagagaaaag aagagtaaga agaaatataa gagccaccat gtcaccgcaa 60
cgagaccgga taaatgcctt ctacaaagat aacccttatc ccaagggaag taggatagtt 120
attaacagag aacatcttat gattgacaga ccctatgttc tgctggctgt tctgttcgtc 180
atgtttctga gcttgatcgg attgctggca attgcaggca ttagacttca tcgggcagcc 240
atctacaccg cggagatcca taaaagcctc agtaccaatc tggatgtgac taactccatc 300
gagcatcagg tcaaggacgt gctgacacca ctctttaaaa tcatcgggga tgaagtgggc 360
ctgagaacac ctcagagatt cactgaccta gtgaaattca tctcggacaa gattaaattc 420
cttaatccgg atagggagta cgacttcaga gatctcactt ggtgcatcaa cccgccagag 480
aggatcaaac tagattatga tcaatactgt gcagatgtgg ctgctgaaga gctcatgaat 540
gcattggtga actcaactct actggagacc agaacaacca ctcagttcct agctgtctca 600
aagggaaact gctcagggcc cactacaatc agaggtcaat tctcaaacat gtcgctgtcc 660
ttgttggact tgtacttagg tcgaggttac aatgtgtcat ctatagtcac tatgacatcc 720
cagggaatgt atgggggaac ctacctagtt gaaaagccta atctgaacag caaagggtca 780
gagttgtcac aactgagcat gtaccgagtg tttgaagtag gtgtgatcag aaacccgggt 840
ttgggggctc cggtgttcca tatgacaaac tattttgagc aaccagtcag taatggtctc 900
ggcaactgta tggtggcttt gggggagctc aaactcgcag ccctttgtca cggggacgat 960
tctatcataa ttccctatca gggatcaggg aaaggtgtca gcttccagct cgtcaagctg 1020
ggtgtctgga aatccccaac cgacatgcaa tcctgggtcc ccttatcaac ggatgatcca 1080
gtggtagaca ggctttacct ctcatctcac agaggtgtca tcgctgacaa tcaagcaaaa 1140
tgggctgtcc cgacaacacg aacagatgac aagttgcgaa tggagacatg cttccagcag 1200

-continued

```
gcgtgtaaag gtaaaatcca agcactctgc gagaatcccg agtgggtacc attgaaggat   1260

aacaggattc cttcatacgg ggtcctgtct gttgatctga gtctgacggt tgagcttaaa   1320

atcaaaattg cttcgggatt cggccattg atcacacacg gctcagggat ggacctatac   1380

aaatccaact gcaacaatgt gtattggctg actattccgc caatgagaaa tctagcctta   1440

ggcgtaatca acacattgga gtggataccg agattcaagg ttagtcccaa cctcttcact   1500

gtcccaatta aggaagcagg cgaagactgc catgccccaa catacctacc tgcggaggtg   1560

gacggtgatg tcaaactcag ttccaacctg gtgattctac ctggtcaaga tctccaatat   1620

gttttggcaa cctacgatac ctccagggtt gagcatgctg tggtttatta cgtttacagc   1680

ccaagccgct cattttctta cttttatcct tttaggttgc ctataaaggg ggtcccaatc   1740

gaactacaag tggaatgctt cacatgggat caaaaactct ggtgccgtca cttctgtgtg   1800

cttgcggact cagaatccgg tggacttatc actcactctg ggatggtggg catgggagtc   1860

agctgcacag ctacccggga agatggaacc aatcgcagat aatgataata ggctggagcc   1920

tcggtggcca agcttcttgc cccttgggcc tccccccagc ccctcctccc cttcctgcac   1980

ccgtaccccc gtggtctttg aataaagtct gagtgggcgg caaaaaaaaa aaaaaaaaaa   2040

aaaaaaaaaa aaaaaaaaaa aaaaaaaaaa aaaaaaaaaa aaaaaaaaaa aaaaaaaaaa   2100

aaaaaaaaaa aaaaaaaaaa atctag                                        2126
```

<210> SEQ ID NO 44
<211> LENGTH: 2065
<212> TYPE: DNA
<213> ORGANISM: Artificial Sequence
<220> FEATURE:
<223> OTHER INFORMATION: Synthetic Polynucleotide

<400> SEQUENCE: 44

```
tcaagctttt ggaccctcgt acagaagcta atacgactca ctatagggaa ataagagaga     60

aaagaagagt aagaagaaat ataagagcca ccatgtcacc acaacgagac cggataaatg    120

ccttctacaa agacaacccc catcctaagg gaagtaggat agttattaac agagaacatc    180

ttatgattga tagaccttat gttttgctgg ctgttctatt cgtcatgttt ctgagcttga    240

tcgggttgct agccattgca ggcattagac ttcatcgggc agccatctac accgcagaga    300

tccataaaag cctcagcacc aatctggatg taactaactc aatcgagcat caggttaagg    360

acgtgctgac accactcttc aagatcatcg gtgatgaagt gggcttgagg acacctcaga    420

gattcactga cctagtgaag ttcatctctg acaagattaa attccttaat ccggacaggg    480

aatacgactt cagagatctc acttggtgta tcaacccgcc agagagaatc aaattggatt    540

atgatcaata ctgtgcagat gtggctgctg aagaactcat gaatgcattg gtgaactcaa    600

ctctactgga gaccagggca accaatcagt tcctagctgt ctcaaaggga aactgctcag    660

ggcccactac aatcagaggc caattctcaa acatgtcgct gtccctgttg gacttgtatt    720

taagtcgagg ttacaatgtg tcatctatag tcactatgac atcccaggga atgtacgggg    780

gaacttacct agtggaaaag cctaatctga gcagcaaagg gtcagagttg tcacaactga    840

gcatgcaccg agtgtttgaa gtaggtgtta tcagaaatcc gggtttgggg gctccggtat    900

tccatatgac aaactatctt gagcaaccag tcagtaatga tttcagcaac tgcatggtgg    960

ctttggggga gctcaagttc gcagccctct gtcacaggga agattctatc acaattccct   1020

atcagggatc agggaaaggt gtcagcttcc agcttgtcaa gctaggtgtc tggaaatccc   1080

caaccgacat gcaatcctgg gtccccctat caacggatga tccagtgata gacaggcttt   1140
```

acctctcatc tcacagaggc gttatcgctg acaatcaagc aaaatgggct gtcccgacaa 1200
cacggacaga tgacaagttg cgaatggaga catgcttcca gcaggcgtgt aagggtaaaa 1260
tccaagcact ttgcgagaat cccgagtgga caccattgaa ggataacagg attccttcat 1320
acggggtctt gtctgttgat ctgagtctga cagttgagct taaaatcaaa attgtttcag 1380
gattcgggcc attgatcaca cacggttcag ggatggacct atacaaatcc aaccacaaca 1440
atatgtattg gctgactatc ccgccaatga agaacctggc cttaggtgta atcaacacat 1500
tggagtggat accgagattc aaggttagtc ccaacctctt cactgttcca attaaggaag 1560
caggcgagga ctgccatgcc ccaacatacc tacctgcgga ggtggatggt gatgtcaaac 1620
tcagttccaa tctggtgatt ctacctggtc aagatctcca atatgttctg gcaacctacg 1680
atacttccag agttgaacat gctgtagttt attacgttta cagcccaagc cgctcatttt 1740
cttactttta tccttttagg ttgcctgtaa ggggggtccc cattgaatta caagtggaat 1800
gcttcacatg ggaccaaaaa ctctggtgcc gtcacttctg tgtgcttgcg gactcagaat 1860
ctggtggaca tatcactcac tctgggatgg tgggcatggg agtcagctgc acagccactc 1920
gggaagatgg aaccagccgc agatagtgat aataggctgg agcctcggtg gccaagcttc 1980
ttgccccttg ggcctccccc cagcccctcc tccccttcct gcacccgtac ccccgtggtc 2040
tttgaataaa gtctgagtgg gcggc 2065

<210> SEQ ID NO 45
<211> LENGTH: 1854
<212> TYPE: DNA
<213> ORGANISM: Artificial Sequence
<220> FEATURE:
<223> OTHER INFORMATION: Synthetic Polynucleotide

<400> SEQUENCE: 45
atgtcaccac aacgagaccg gataaatgcc ttctacaaag acaacccccca tcctaaggga 60 agtaggatag ttattaacag agaacatctt atgattgata gaccttatgt tttgctggct 120
gttctattcg tcatgtttct gagcttgatc gggttgctag ccattgcagg cattagactt 180
catcgggcag ccatctacac cgcagagatc cataaaagcc tcagcaccaa tctggatgta 240
actaactcaa tcgagcatca ggttaaggac gtgctgacac cactcttcaa gatcatcggt 300
gatgaagtgg gcttgaggac acctcagaga ttcactgacc tagtgaagtt catctctgac 360
aagattaaat tccttaatcc ggacagggaa tacgacttca gagatctcac ttggtgtatc 420
aacccgccag agagaatcaa attggattat gatcaatact gtgcagatgt ggctgctgaa 480
gaactcatga atgcattggt gaactcaact ctactggaga ccagggcaac caatcagttc 540
ctagctgtct caaagggaaa ctgctcaggg cccactacaa tcagaggcca attctcaaac 600
atgtcgctgt ccctgttgga cttgtattta agtcgaggtt acaatgtgtc atctatagtc 660
actatgacat cccagggaat gtacgggggga acttacctag tggaaaagcc taatctgagc 720
agcaaagggt cagagttgtc acaactgagc atgcaccgag tgtttgaagt aggtgttatc 780
agaaatccgg gtttgggggc tccggtattc catatgacaa actatcttga gcaaccagtc 840
agtaatgatt tcagcaactg catggtggct ttgggggagc tcaagttcgc agccctctgt 900
cacagggaag attctatcac aattccctat cagggatcag ggaaaggtgt cagcttccag 960
cttgtcaagc taggtgtctg gaaatcccca accgacatgc aatcctgggt ccccctatca 1020
acggatgatc cagtgataga caggctttac ctctcatctc acagaggcgt tatcgctgac 1080

-continued aatcaagcaa aatgggctgt cccgacaaca cggacagatg acaagttgcg aatggagaca 1140
tgcttccagc aggcgtgtaa gggtaaaatc caagcacttt gcgagaatcc cgagtggaca 1200
ccattgaagg ataacaggat tccttcatac ggggtcttgt ctgttgatct gagtctgaca 1260
gttgagctta aaatcaaaat tgtttcagga ttcgggccat tgatcacaca cggttcaggg 1320
atggacctat acaaatccaa ccacaacaat atgtattggc tgactatccc gccaatgaag 1380
aacctggcct taggtgtaat caacacattg gagtggatac cgagattcaa ggttagtccc 1440
aacctcttca ctgttccaat taaggaagca ggcgaggact gccatgcccc aacataccta 1500
cctgcggagg tggatggtga tgtcaaactc agttccaatc tggtgattct acctggtcaa 1560
gatctccaat atgttctggc aacctacgat acttccagag ttgaacatgc tgtagtttat 1620
tacgtttaca gcccaagccg ctcattttct tacttttatc cttttaggtt gcctgtaagg 1680
ggggtcccca ttgaattaca agtggaatgc ttcacatggg accaaaaact ctggtgccgt 1740
cacttctgtg tgcttgcgga ctcagaatct ggtggacata tcactcactc tgggatggtg 1800
ggcatgggag tcagctgcac agccactcgg gaagatggaa ccagccgcag atag 1854

<210> SEQ ID NO 46
<211> LENGTH: 2126
<212> TYPE: DNA
<213> ORGANISM: Artificial Sequence
<220> FEATURE:
<223> OTHER INFORMATION: Synthetic Polynucleotide

<400> SEQUENCE: 46
ggggaaataa gagagaaaag aagagtaaga agaaatataa gagccaccat gtcaccacaa 60
cgagaccgga taaatgcctt ctacaaagac aaccccccatc ctaagggaag taggatagtt 120
attaacagag aacatcttat gattgataga ccttatgttt tgctggctgt tctattcgtc 180
atgtttctga gcttgatcgg gttgctagcc attgcaggca ttagacttca tcgggcagcc 240
atctacaccg cagagatcca taaaagcctc agcaccaatc tggatgtaac taactcaatc 300
gagcatcagg ttaaggacgt gctgacacca ctcttcaaga tcatcggtga tgaagtgggc 360
ttgaggacac ctcagagatt cactgaccta gtgaagttca tctctgacaa gattaaattc 420
cttaatccgg acagggaata cgacttcaga gatctcactt ggtgtatcaa cccgccagag 480
agaatcaaat tggattatga tcaatactgt gcagatgtgg ctgctgaaga actcatgaat 540
gcattggtga actcaactct actggagacc agggcaacca atcagttcct agctgtctca 600
aagggaaact gctcagggcc cactacaatc agaggccaat tctcaaacat gtcgctgtcc 660
ctgttggact tgtatttaag tcgaggttac aatgtgtcat ctatagtcac tatgacatcc 720
cagggaatgt acgggggaac ttacctagtg gaaaagccta atctgagcag caaagggtca 780
gagttgtcac aactgagcat gcaccgagtg tttgaagtag gtgttatcag aaatccgggt 840
ttgggggctc cggtattcca tatgacaaac tatcttgagc aaccagtcag taatgatttc 900
agcaactgca tggtggcttt gggggagctc aagttcgcag ccctctgtca cagggaagat 960
tctatcacaa ttccctatca gggatcaggg aaaggtgtca gcttccagct tgtcaagcta 1020
ggtgtctgga aatccccaac cgacatgcaa tcctgggtcc ccctatcaac ggatgatcca 1080
gtgatagaca ggctttacct ctcatctcac agaggcgtta tcgctgacaa tcaagcaaaa 1140
tgggctgtcc cgacaacacg gacagatgac aagttgcgaa tggagacatg cttccagcag 1200
gcgtgtaagg gtaaaatcca agcactttgc gagaatcccg agtggacacc attgaaggat 1260
aacaggattc cttcatacgg ggtcttgtct gttgatctga gtctgacagt tgagcttaaa 1320

```
atcaaaattg tttcaggatt cgggccattg atcacacacg gttcagggat ggacctatac   1380

aaatccaacc acaacaatat gtattggctg actatcccgc caatgaagaa cctggcctta   1440

ggtgtaatca acacattgga gtggataccg agattcaagg ttagtcccaa cctcttcact   1500

gttccaatta aggaagcagg cgaggactgc catgccccaa catacctacc tgcggaggtg   1560

gatggtgatg tcaaactcag ttccaatctg gtgattctac ctggtcaaga tctccaatat   1620

gttctggcaa cctacgatac ttccagagtt gaacatgctg tagtttatta cgtttacagc   1680

ccaagccgct catttcttta cttttatcct tttaggttgc ctgtaagggg ggtccccatt   1740

gaattacaag tggaatgctt cacatgggac caaaaactct ggtgccgtca cttctgtgtg   1800

cttgcggact cagaatctgg tggacatatc actcactctg ggatggtggg catgggagtc   1860

agctgcacag ccactcggga agatggaacc agccgcagat agtgataata ggctggagcc   1920

tcggtggcca agcttcttgc cccttgggcc tccccccagc ccctcctccc cttcctgcac   1980

ccgtaccccc gtggtctttg aataaagtct gagtgggcgg caaaaaaaaa aaaaaaaaaa   2040

aaaaaaaaaa aaaaaaaaaa aaaaaaaaaa aaaaaaaaaa aaaaaaaaaa aaaaaaaaaa   2100

aaaaaaaaaa aaaaaaaaaa atctag                                         2126
```

```
<210> SEQ ID NO 47
<211> LENGTH: 550
<212> TYPE: PRT
<213> ORGANISM: Artificial Sequence
<220> FEATURE:
<223> OTHER INFORMATION: Synthetic Polypeptide

<400> SEQUENCE: 47

Met Gly Leu Lys Val Asn Val Ser Ala Val Phe Met Ala Val Leu Leu
1               5                   10                  15

Thr Leu Gln Thr Pro Ala Gly Gln Ile His Trp Gly Asn Leu Ser Lys
            20                  25                  30

Ile Gly Val Val Gly Ile Gly Ser Ala Ser Tyr Lys Val Met Thr Arg
        35                  40                  45

Ser Ser His Gln Ser Leu Val Ile Lys Leu Met Pro Asn Ile Thr Leu
    50                  55                  60

Leu Asn Asn Cys Thr Arg Val Glu Ile Ala Glu Tyr Arg Arg Leu Leu
65                  70                  75                  80

Arg Thr Val Leu Glu Pro Ile Arg Asp Ala Leu Asn Ala Met Thr Gln
                85                  90                  95

Asn Ile Arg Pro Val Gln Ser Val Ala Ser Ser Arg Arg His Lys Arg
            100                 105                 110

Phe Ala Gly Val Val Leu Ala Gly Ala Ala Leu Gly Val Ala Thr Ala
        115                 120                 125

Ala Gln Ile Thr Ala Gly Ile Ala Leu His Arg Ser Met Leu Asn Ser
    130                 135                 140

Gln Ala Ile Asp Asn Leu Arg Ala Ser Leu Glu Thr Thr Asn Gln Ala
145                 150                 155                 160

Ile Glu Ala Ile Arg Gln Ala Gly Gln Glu Met Ile Leu Ala Val Gln
                165                 170                 175

Gly Val Gln Asp Tyr Ile Asn Asn Glu Leu Ile Pro Ser Met Asn Gln
            180                 185                 190

Leu Ser Cys Asp Leu Ile Gly Gln Lys Leu Gly Leu Lys Leu Leu Arg
        195                 200                 205

Tyr Tyr Thr Glu Ile Leu Ser Leu Phe Gly Pro Ser Leu Arg Asp Pro
```

-continued

```
    210                 215                 220

Ile Ser Ala Glu Ile Ser Ile Gln Ala Leu Ser Tyr Ala Leu Gly Gly
225                 230                 235                 240

Asp Ile Asn Lys Val Leu Glu Lys Leu Gly Tyr Ser Gly Gly Asp Leu
                245                 250                 255

Leu Gly Ile Leu Glu Ser Arg Gly Ile Lys Ala Arg Ile Thr His Val
            260                 265                 270

Asp Thr Glu Ser Tyr Phe Ile Val Leu Ser Ile Ala Tyr Pro Thr Leu
        275                 280                 285

Ser Glu Ile Lys Gly Val Ile Val His Arg Leu Glu Gly Val Ser Tyr
    290                 295                 300

Asn Ile Gly Ser Gln Glu Trp Tyr Thr Thr Val Pro Lys Tyr Val Ala
305                 310                 315                 320

Thr Gln Gly Tyr Leu Ile Ser Asn Phe Asp Glu Ser Ser Cys Thr Phe
                325                 330                 335

Met Pro Glu Gly Thr Val Cys Ser Gln Asn Ala Leu Tyr Pro Met Ser
            340                 345                 350

Pro Leu Leu Gln Glu Cys Leu Arg Gly Ser Thr Lys Ser Cys Ala Arg
        355                 360                 365

Thr Leu Val Ser Gly Ser Phe Gly Asn Arg Phe Ile Leu Ser Gln Gly
    370                 375                 380

Asn Leu Ile Ala Asn Cys Ala Ser Ile Leu Cys Lys Cys Tyr Thr Thr
385                 390                 395                 400

Gly Thr Ile Ile Asn Gln Asp Pro Asp Lys Ile Leu Thr Tyr Ile Ala
                405                 410                 415

Ala Asp Arg Cys Pro Val Val Glu Val Asn Gly Val Thr Ile Gln Val
            420                 425                 430

Gly Ser Arg Arg Tyr Pro Asp Ala Val Tyr Leu His Arg Ile Asp Leu
        435                 440                 445

Gly Pro Pro Ile Ser Leu Glu Arg Leu Asp Val Gly Thr Asn Leu Gly
    450                 455                 460

Asn Ala Ile Ala Lys Leu Glu Asp Ala Lys Glu Leu Leu Glu Ser Ser
465                 470                 475                 480

Asp Gln Ile Leu Arg Ser Met Lys Gly Leu Ser Ser Thr Ser Ile Val
                485                 490                 495

Tyr Ile Leu Ile Ala Val Cys Leu Gly Gly Leu Ile Gly Ile Pro Thr
            500                 505                 510

Leu Ile Cys Cys Cys Arg Gly Arg Cys Asn Lys Lys Gly Glu Gln Val
        515                 520                 525

Gly Met Ser Arg Pro Gly Leu Lys Pro Asp Leu Thr Gly Thr Ser Lys
    530                 535                 540

Ser Tyr Val Arg Ser Leu
545                 550


<210> SEQ ID NO 48
<211> LENGTH: 550
<212> TYPE: PRT
<213> ORGANISM: Artificial Sequence
<220> FEATURE:
<223> OTHER INFORMATION: Synthetic Polypeptide

<400> SEQUENCE: 48

Met Gly Leu Lys Val Asn Val Ser Val Ile Phe Met Ala Val Leu Leu
1               5                   10                  15

Thr Leu Gln Thr Pro Thr Gly Gln Ile His Trp Gly Asn Leu Ser Lys
```

```
            20                  25                  30

Ile Gly Val Val Gly Val Gly Ser Ala Ser Tyr Lys Val Met Thr Arg
        35                  40                  45

Ser Ser His Gln Ser Leu Val Ile Lys Leu Met Pro Asn Ile Thr Leu
    50                  55                  60

Leu Asn Asn Cys Thr Arg Val Gly Ile Ala Glu Tyr Arg Arg Leu Leu
65                  70                  75                  80

Arg Thr Val Leu Glu Pro Ile Arg Asp Ala Leu Asn Ala Met Thr Gln
                85                  90                  95

Asn Ile Arg Pro Val Gln Ser Val Ala Ser Ser Arg Arg His Lys Arg
            100                 105                 110

Phe Ala Gly Val Val Leu Ala Gly Ala Ala Leu Gly Val Ala Thr Ala
        115                 120                 125

Ala Gln Ile Thr Ala Gly Ile Ala Leu His Gln Ser Met Leu Asn Ser
    130                 135                 140

Gln Ala Ile Asp Asn Leu Arg Ala Ser Leu Glu Thr Thr Asn Gln Ala
145                 150                 155                 160

Ile Glu Ala Ile Arg Gln Ala Gly Gln Glu Met Ile Leu Ala Val Gln
                165                 170                 175

Gly Val Gln Asp Tyr Ile Asn Asn Glu Leu Ile Pro Ser Met Asn Gln
            180                 185                 190

Leu Ser Cys Asp Leu Ile Gly Gln Lys Leu Gly Leu Lys Leu Leu Arg
        195                 200                 205

Tyr Tyr Thr Glu Ile Leu Ser Leu Phe Gly Pro Ser Leu Arg Asp Pro
    210                 215                 220

Ile Ser Ala Glu Ile Ser Ile Gln Ala Leu Ser Tyr Ala Leu Gly Gly
225                 230                 235                 240

Asp Ile Asn Lys Val Leu Glu Lys Leu Gly Tyr Ser Gly Gly Asp Leu
                245                 250                 255

Leu Gly Ile Leu Glu Ser Arg Gly Ile Lys Ala Arg Ile Thr His Val
            260                 265                 270

Asp Thr Glu Ser Tyr Phe Ile Val Leu Ser Ile Ala Tyr Pro Thr Leu
        275                 280                 285

Ser Glu Ile Lys Gly Val Ile Val His Arg Leu Glu Gly Val Ser Tyr
    290                 295                 300

Asn Ile Gly Ser Gln Glu Trp Tyr Thr Thr Val Pro Lys Tyr Val Ala
305                 310                 315                 320

Thr Gln Gly Tyr Leu Ile Ser Asn Phe Asp Glu Ser Ser Cys Thr Phe
                325                 330                 335

Met Pro Glu Gly Thr Val Cys Ser Gln Asn Ala Leu Tyr Pro Met Ser
            340                 345                 350

Pro Leu Leu Gln Glu Cys Leu Arg Gly Ser Thr Lys Ser Cys Ala Arg
        355                 360                 365

Thr Leu Val Ser Gly Ser Phe Gly Asn Arg Phe Ile Leu Ser Gln Gly
    370                 375                 380

Asn Leu Ile Ala Asn Cys Ala Ser Ile Leu Cys Lys Cys Tyr Thr Thr
385                 390                 395                 400

Gly Thr Ile Ile Asn Gln Asp Pro Asp Lys Ile Leu Thr Tyr Ile Ala
                405                 410                 415

Ala Asp His Cys Pro Val Val Glu Val Asn Gly Val Thr Ile Gln Val
            420                 425                 430

Gly Ser Arg Arg Tyr Pro Asp Ala Val Tyr Leu His Arg Ile Asp Leu
        435                 440                 445
```

-continued

```
Gly Pro Pro Ile Ser Leu Glu Arg Leu Asp Val Gly Thr Asn Leu Gly
    450                 455                 460

Asn Ala Ile Ala Lys Leu Glu Asp Ala Lys Glu Leu Leu Glu Ser Ser
465                 470                 475                 480

Asp Gln Ile Leu Arg Ser Met Lys Gly Leu Ser Ser Thr Ser Ile Val
                485                 490                 495

Tyr Ile Leu Ile Ala Val Cys Leu Gly Gly Leu Ile Gly Ile Pro Ala
            500                 505                 510

Leu Ile Cys Cys Cys Arg Gly Arg Cys Asn Lys Lys Gly Glu Gln Val
        515                 520                 525

Gly Met Ser Arg Pro Gly Leu Lys Pro Asp Leu Thr Gly Thr Ser Lys
    530                 535                 540

Ser Tyr Val Arg Ser Leu
545                 550


<210> SEQ ID NO 49
<211> LENGTH: 617
<212> TYPE: PRT
<213> ORGANISM: Artificial Sequence
<220> FEATURE:
<223> OTHER INFORMATION: Synthetic Polypeptide

<400> SEQUENCE: 49

Met Ser Pro Gln Arg Asp Arg Ile Asn Ala Phe Tyr Lys Asp Asn Pro
1               5                   10                  15

Tyr Pro Lys Gly Ser Arg Ile Val Ile Asn Arg Glu His Leu Met Ile
            20                  25                  30

Asp Arg Pro Tyr Val Leu Leu Ala Val Leu Phe Val Met Phe Leu Ser
        35                  40                  45

Leu Ile Gly Leu Leu Ala Ile Ala Gly Ile Arg Leu His Arg Ala Ala
    50                  55                  60

Ile Tyr Thr Ala Glu Ile His Lys Ser Leu Ser Thr Asn Leu Asp Val
65                  70                  75                  80

Thr Asn Ser Ile Glu His Gln Val Lys Asp Val Leu Thr Pro Leu Phe
                85                  90                  95

Lys Ile Ile Gly Asp Glu Val Gly Leu Arg Thr Pro Gln Arg Phe Thr
            100                 105                 110

Asp Leu Val Lys Phe Ile Ser Asp Lys Ile Lys Phe Leu Asn Pro Asp
        115                 120                 125

Arg Glu Tyr Asp Phe Arg Asp Leu Thr Trp Cys Ile Asn Pro Pro Glu
    130                 135                 140

Arg Ile Lys Leu Asp Tyr Asp Gln Tyr Cys Ala Asp Val Ala Ala Glu
145                 150                 155                 160

Glu Leu Met Asn Ala Leu Val Asn Ser Thr Leu Leu Glu Thr Arg Thr
                165                 170                 175

Thr Thr Gln Phe Leu Ala Val Ser Lys Gly Asn Cys Ser Gly Pro Thr
            180                 185                 190

Thr Ile Arg Gly Gln Phe Ser Asn Met Ser Leu Ser Leu Leu Asp Leu
        195                 200                 205

Tyr Leu Gly Arg Gly Tyr Asn Val Ser Ser Ile Val Thr Met Thr Ser
    210                 215                 220

Gln Gly Met Tyr Gly Gly Thr Tyr Leu Val Glu Lys Pro Asn Leu Asn
225                 230                 235                 240

Ser Lys Gly Ser Glu Leu Ser Gln Leu Ser Met Tyr Arg Val Phe Glu
                245                 250                 255
```

Val Gly Val Ile Arg Asn Pro Gly Leu Gly Ala Pro Val Phe His Met
260 265 270

Thr Asn Tyr Phe Glu Gln Pro Val Ser Asn Gly Leu Gly Asn Cys Met
275 280 285

Val Ala Leu Gly Glu Leu Lys Leu Ala Ala Leu Cys His Gly Asp Asp
290 295 300

Ser Ile Ile Ile Pro Tyr Gln Gly Ser Gly Lys Gly Val Ser Phe Gln
305 310 315 320

Leu Val Lys Leu Gly Val Trp Lys Ser Pro Thr Asp Met Gln Ser Trp
325 330 335

Val Pro Leu Ser Thr Asp Asp Pro Val Val Asp Arg Leu Tyr Leu Ser
340 345 350

Ser His Arg Gly Val Ile Ala Asp Asn Gln Ala Lys Trp Ala Val Pro
355 360 365

Thr Thr Arg Thr Asp Asp Lys Leu Arg Met Glu Thr Cys Phe Gln Gln
370 375 380

Ala Cys Lys Gly Lys Ile Gln Ala Leu Cys Glu Asn Pro Glu Trp Val
385 390 395 400

Pro Leu Lys Asp Asn Arg Ile Pro Ser Tyr Gly Val Leu Ser Val Asp
405 410 415

Leu Ser Leu Thr Val Glu Leu Lys Ile Lys Ile Ala Ser Gly Phe Gly
420 425 430

Pro Leu Ile Thr His Gly Ser Gly Met Asp Leu Tyr Lys Ser Asn Cys
435 440 445

Asn Asn Val Tyr Trp Leu Thr Ile Pro Pro Met Arg Asn Leu Ala Leu
450 455 460

Gly Val Ile Asn Thr Leu Glu Trp Ile Pro Arg Phe Lys Val Ser Pro
465 470 475 480

Asn Leu Phe Thr Val Pro Ile Lys Glu Ala Gly Glu Asp Cys His Ala
485 490 495

Pro Thr Tyr Leu Pro Ala Glu Val Asp Gly Asp Val Lys Leu Ser Ser
500 505 510

Asn Leu Val Ile Leu Pro Gly Gln Asp Leu Gln Tyr Val Leu Ala Thr
515 520 525

Tyr Asp Thr Ser Arg Val Glu His Ala Val Val Tyr Tyr Val Tyr Ser
530 535 540

Pro Ser Arg Ser Phe Ser Tyr Phe Tyr Pro Phe Arg Leu Pro Ile Lys
545 550 555 560

Gly Val Pro Ile Glu Leu Gln Val Glu Cys Phe Thr Trp Asp Gln Lys
565 570 575

Leu Trp Cys Arg His Phe Cys Val Leu Ala Asp Ser Glu Ser Gly Gly
580 585 590

Leu Ile Thr His Ser Gly Met Val Gly Met Gly Val Ser Cys Thr Ala
595 600 605

Thr Arg Glu Asp Gly Thr Asn Arg Arg
610 615

<210> SEQ ID NO 50
<211> LENGTH: 617
<212> TYPE: PRT
<213> ORGANISM: Artificial Sequence
<220> FEATURE:
<223> OTHER INFORMATION: Synthetic Polypeptide

<400> SEQUENCE: 50

-continued

Met Ser Pro Gln Arg Asp Arg Ile Asn Ala Phe Tyr Lys Asp Asn Pro
1               5                   10                  15

His Pro Lys Gly Ser Arg Ile Val Ile Asn Arg Glu His Leu Met Ile
            20                  25                  30

Asp Arg Pro Tyr Val Leu Leu Ala Val Leu Phe Val Met Phe Leu Ser
        35                  40                  45

Leu Ile Gly Leu Leu Ala Ile Ala Gly Ile Arg Leu His Arg Ala Ala
    50                  55                  60

Ile Tyr Thr Ala Glu Ile His Lys Ser Leu Ser Thr Asn Leu Asp Val
65                  70                  75                  80

Thr Asn Ser Ile Glu His Gln Val Lys Asp Val Leu Thr Pro Leu Phe
                85                  90                  95

Lys Ile Ile Gly Asp Glu Val Gly Leu Arg Thr Pro Gln Arg Phe Thr
            100                 105                 110

Asp Leu Val Lys Phe Ile Ser Asp Lys Ile Lys Phe Leu Asn Pro Asp
        115                 120                 125

Arg Glu Tyr Asp Phe Arg Asp Leu Thr Trp Cys Ile Asn Pro Pro Glu
    130                 135                 140

Arg Ile Lys Leu Asp Tyr Asp Gln Tyr Cys Ala Asp Val Ala Ala Glu
145                 150                 155                 160

Glu Leu Met Asn Ala Leu Val Asn Ser Thr Leu Leu Glu Thr Arg Ala
                165                 170                 175

Thr Asn Gln Phe Leu Ala Val Ser Lys Gly Asn Cys Ser Gly Pro Thr
            180                 185                 190

Thr Ile Arg Gly Gln Phe Ser Asn Met Ser Leu Ser Leu Leu Asp Leu
        195                 200                 205

Tyr Leu Ser Arg Gly Tyr Asn Val Ser Ser Ile Val Thr Met Thr Ser
    210                 215                 220

Gln Gly Met Tyr Gly Gly Thr Tyr Leu Val Glu Lys Pro Asn Leu Ser
225                 230                 235                 240

Ser Lys Gly Ser Glu Leu Ser Gln Leu Ser Met His Arg Val Phe Glu
                245                 250                 255

Val Gly Val Ile Arg Asn Pro Gly Leu Gly Ala Pro Val Phe His Met
            260                 265                 270

Thr Asn Tyr Leu Glu Gln Pro Val Ser Asn Asp Phe Ser Asn Cys Met
        275                 280                 285

Val Ala Leu Gly Glu Leu Lys Phe Ala Ala Leu Cys His Arg Glu Asp
    290                 295                 300

Ser Ile Thr Ile Pro Tyr Gln Gly Ser Gly Lys Gly Val Ser Phe Gln
305                 310                 315                 320

Leu Val Lys Leu Gly Val Trp Lys Ser Pro Thr Asp Met Gln Ser Trp
                325                 330                 335

Val Pro Leu Ser Thr Asp Asp Pro Val Ile Asp Arg Leu Tyr Leu Ser
            340                 345                 350

Ser His Arg Gly Val Ile Ala Asp Asn Gln Ala Lys Trp Ala Val Pro
        355                 360                 365

Thr Thr Arg Thr Asp Asp Lys Leu Arg Met Glu Thr Cys Phe Gln Gln
    370                 375                 380

Ala Cys Lys Gly Lys Ile Gln Ala Leu Cys Glu Asn Pro Glu Trp Thr
385                 390                 395                 400

Pro Leu Lys Asp Asn Arg Ile Pro Ser Tyr Gly Val Leu Ser Val Asp
                405                 410                 415

```
Leu Ser Leu Thr Val Glu Leu Lys Ile Lys Ile Val Ser Gly Phe Gly
            420                 425                 430

Pro Leu Ile Thr His Gly Ser Gly Met Asp Leu Tyr Lys Ser Asn His
        435                 440                 445

Asn Asn Met Tyr Trp Leu Thr Ile Pro Pro Met Lys Asn Leu Ala Leu
    450                 455                 460

Gly Val Ile Asn Thr Leu Glu Trp Ile Pro Arg Phe Lys Val Ser Pro
465                 470                 475                 480

Asn Leu Phe Thr Val Pro Ile Lys Glu Ala Gly Glu Asp Cys His Ala
                485                 490                 495

Pro Thr Tyr Leu Pro Ala Glu Val Asp Gly Asp Val Lys Leu Ser Ser
            500                 505                 510

Asn Leu Val Ile Leu Pro Gly Gln Asp Leu Gln Tyr Val Leu Ala Thr
        515                 520                 525

Tyr Asp Thr Ser Arg Val Glu His Ala Val Val Tyr Tyr Val Tyr Ser
    530                 535                 540

Pro Ser Arg Ser Phe Ser Tyr Phe Tyr Pro Phe Arg Leu Pro Val Arg
545                 550                 555                 560

Gly Val Pro Ile Glu Leu Gln Val Glu Cys Phe Thr Trp Asp Gln Lys
                565                 570                 575

Leu Trp Cys Arg His Phe Cys Val Leu Ala Asp Ser Glu Ser Gly Gly
            580                 585                 590

His Ile Thr His Ser Gly Met Val Gly Met Gly Val Ser Cys Thr Ala
        595                 600                 605

Thr Arg Glu Asp Gly Thr Ser Arg Arg
    610                 615
```

<210> SEQ ID NO 51
<211> LENGTH: 1729
<212> TYPE: DNA
<213> ORGANISM: Artificial Sequence
<220> FEATURE:
<223> OTHER INFORMATION: Synthetic Polynucleotide

<400> SEQUENCE: 51

```
tcaagctttt ggaccctcgt acagaagcta atacgactca ctatagggaa ataagagaga      60

aaagaagagt aagaagaaat ataagagcca ccatggcaca agtcattaat acaaacagcc     120

tgtcgctgtt gacccagaat aacctgaaca aatcccagtc cgcactgggc actgctatcg     180

agcgtttgtc ttccggtctg cgtatcaaca gcgcgaaaga cgatgcggca ggacaggcga     240

ttgctaaccg ttttaccgcg aacatcaaag gtctgactca ggcttcccgt aacgctaacg     300

acggtatctc cattgcgcag accactgaag gcgcgctgaa cgaaatcaac aacaacctgc     360

agcgtgtgcg tgaactggcg gttcagtctg cgaatggtac taactcccag tctgacctcg     420

actccatcca ggctgaaatc acccagcgcc tgaacgaaat cgaccgtgta tccggccaga     480

ctcagttcaa cggcgtgaaa gtcctggcgc aggacaacac cctgaccatc caggttggtg     540

ccaacgacgg tgaaactatc gatattgatt taaaagaaat cagctctaaa acactgggac     600

ttgataagct taatgtccaa gatgcctaca ccccgaaaga aactgctgta accgttgata     660

aaactaccta taaaaatggt acagatccta ttacagccca gagcaatact gatatccaaa     720

ctgcaattgg cggtggtgca acgggggtta ctggggctga tatcaaattt aaagatggtc     780

aatactattt agatgttaaa ggcggtgctt ctgctggtgt ttataaagcc acttatgatg     840

aaactacaaa gaaagttaat attgatacga ctgataaaac tccgttggca actgcggaag     900
```

-continued

```
ctacagctat tcggggaacg gccactataa cccacaacca aattgctgaa gtaacaaaag     960

agggtgttga tacgaccaca gttgcggctc aacttgctgc agcaggggtt actggcgccg    1020

ataaggacaa tactagcctt gtaaaactat cgtttgagga taaaaacggt aaggttattg    1080

atggtggcta tgcagtgaaa atgggcgacg atttctatgc cgctacatat gatgagaaaa    1140

caggtgcaat tactgctaaa accactactt atacagatgg tactggcgtt gctcaaactg    1200

gagctgtgaa atttggtggc gcaaatggta aatctgaagt tgttactgct accgatggta    1260

agacttactt agcaagcgac cttgacaaac ataacttcag aacaggcggt gagcttaaag    1320

aggttaatac agataagact gaaaacccac tgcagaaaat tgatgctgcc ttggcacagg    1380

ttgatacact tcgttctgac ctgggtgcgg ttcagaaccg tttcaactcc gctatcacca    1440

acctgggcaa taccgtaaat aacctgtctt ctgcccgtag ccgtatcgaa gattccgact    1500

acgcaaccga agtctccaac atgtctcgcg cgcagattct gcagcaggcc ggtacctccg    1560

ttctggcgca ggcgaaccag gttccgcaaa acgtcctctc tttactgcgt tgataatagg    1620

ctggagcctc ggtggccatg cttcttgccc cttgggcctc cccccagccc ctcctcccct    1680

tcctgcaccc gtacccccgt ggtctttgaa taaagtctga gtgggcggc                1729
```

```
<210> SEQ ID NO 52
<211> LENGTH: 1518
<212> TYPE: DNA
<213> ORGANISM: Artificial Sequence
<220> FEATURE:
<223> OTHER INFORMATION: Synthetic Polynucleotide

<400> SEQUENCE: 52

atggcacaag tcattaatac aaacagcctg tcgctgttga cccagaataa cctgaacaaa      60

tcccagtccg cactgggcac tgctatcgag cgtttgtctt ccggtctgcg tatcaacagc     120

gcgaaagacg atgcggcagg acaggcgatt gctaaccgtt ttaccgcgaa catcaaaggt     180

ctgactcagg cttcccgtaa cgctaacgac ggtatctcca ttgcgcagac cactgaaggc     240

gcgctgaacg aaatcaacaa caacctgcag cgtgtgcgtg aactggcggt tcagtctgcg     300

aatggtacta actcccagtc tgacctcgac tccatccagg ctgaaatcac ccagcgcctg     360

aacgaaatcg accgtgtatc cggccagact cagttcaacg gcgtgaaagt cctggcgcag     420

gacaacaccc tgaccatcca ggttggtgcc aacgacggtg aaactatcga tattgattta     480

aaagaaatca gctctaaaac actgggactt gataagctta atgtccaaga tgcctacacc     540

ccgaaagaaa ctgctgtaac cgttgataaa actacctata aaaatggtac agatcctatt     600

acagcccaga gcaatactga tatccaaact gcaattggcg gtggtgcaac gggggttact     660

ggggctgata tcaaatttaa agatggtcaa tactatttag atgttaaagg cggtgcttct     720

gctggtgttt ataaagccac ttatgatgaa actacaaaga aagttaatat tgatacgact     780

gataaaactc cgttggcaac tgcggaagct acagctattc ggggaacggc cactataacc     840

cacaaccaaa ttgctgaagt aacaaaagag ggtgttgata cgaccacagt tgcggctcaa     900

cttgctgcag caggggttac tggcgccgat aaggacaata ctagccttgt aaaactatcg     960

tttgaggata aaaacggtaa ggttattgat ggtggctatg cagtgaaaat gggcgacgat    1020

ttctatgccg ctacatatga tgagaaaaca ggtgcaatta ctgctaaaac cactacttat    1080

acagatggta ctggcgttgc tcaaactgga gctgtgaaat ttggtggcgc aaatggtaaa    1140

tctgaagttg ttactgctac cgatggtaag acttacttag caagcgacct tgacaaacat    1200

aacttcagaa caggcggtga gcttaaagag gttaatacag ataagactga aaacccactg    1260
```

```
cagaaaattg atgctgcctt ggcacaggtt gatacacttc gttctgacct gggtgcggtt   1320

cagaaccgtt tcaactccgc tatcaccaac ctgggcaata ccgtaaataa cctgtcttct   1380

gcccgtagcc gtatcgaaga ttccgactac gcaaccgaag tctccaacat gtctcgcgcg   1440

cagattctgc agcaggccgg tacctccgtt ctggcgcagg cgaaccaggt tccgcaaaac   1500

gtcctctctt tactgcgt                                                 1518


<210> SEQ ID NO 53
<211> LENGTH: 1790
<212> TYPE: RNA
<213> ORGANISM: Artificial Sequence
<220> FEATURE:
<223> OTHER INFORMATION: Synthetic Polynucleotide

<400> SEQUENCE: 53

ggggaaauaa gagagaaaag aagaguaaga agaaauauaa gagccaccau ggcacaaguc     60

auuaauacaa acagccuguc gcuguugacc cagaauaacc ugaacaaauc ccaguccgca    120

cugggcacug cuaucgagcg uuugucuucc ggucugcgua ucaacagcgc gaaagacgau    180

gcggcaggac aggcgauugc uaaccguuuu accgcgaaca ucaaaggucu gacucaggcu    240

ucccguaacg cuaacgacgg uaucuccauu gcgcagacca cugaaggcgc gcugaacgaa    300

aucaacaaca accugcagcg ugugcgugaa cuggcgguuc agucugcgaa ugguacuaac    360

ucccagucug accucgacuc cauccaggcu gaaaucaccc agcgccugaa cgaaaucgac    420

cguguauccg gccagacuca guucaacggc gugaaagucc uggcgcagga caacacccug    480

accauccagg uuggugccaa cgacggugaa acuaucgaua uugauuuaaa agaaaucagc    540

ucuaaaacac ugggacuuga uaagcuuaau guccaagaug ccuacacccc gaaagaaacu    600

gcuguaaccg uugauaaaac uaccuauaaa aaugguacag auccuauuac agcccagagc    660

aauacugaua uccaaacugc aauuggcggu ggugcaacgg ggguuacugg ggcugauauc    720

aaauuuaaag augaucaaua cuauuuagau guuaaaggcg gugcuucugc ugguguuuau    780

aaagccacuu augaugaaac uacaaagaaa guuaauauug auacgacuga uaaaacuccg    840

uuggcaacug cggaagcuac agcuauucgg ggaacggcca cuauaaccca caaccaaauu    900

gcugaaguaa caaaagaggg uguugauacg accacaguug cggcucaacu ugcugcagca    960

gggguuacug gcgccgauaa ggacaauacu agccuuguaa aacuaucguu ugaggauaaa   1020

aacgguaagg uuauugaugg uggcuaugca gugaaaaugg gcgacgauuu cuaugccgcu   1080

acauaugaug agaaaacagg ugcaauuacu gcuaaaacca cuacuuauac agaugguacu   1140

ggcguugcuc aaacuggagc ugugaaauuu gguggcgcaa augguaaauc ugaaguuguu   1200

acugcuaccg augguaagac uuacuuagca agcgaccuug acaaacauaa cuucagaaca   1260

ggcggugagc uuaaagaggu uaauacagau aagacugaaa acccacugca gaaaauugau   1320

gcugccuugg cacagguuga uacacuucgu ucugaccugg gugcgguuca gaaccguuuc   1380

aacuccgcua ucaccaaccu gggcaauacc guaaauaacc ugucuucugc ccguagccgu   1440

aucgaagauu ccgacuacgc aaccgaaguc uccaacaugu cucgcgcgca gauucugcag   1500

caggccggua ccuccguucu ggcgcaggcg aaccagguuc cgcaaaacgu ccucucuuua   1560

cugcguugau aauaggcugg agccucggug gccaugcuuc uugccccuug ggccuccccc   1620

cagccccucc uccccuuccu gcacccguac cccgugguc uuugaauaaa gucugagugg    1680

gcggcaaaaa aaaaaaaaaa aaaaaaaaaa aaaaaaaaaa aaaaaaaaaa aaaaaaaaaa   1740
```

aaaaaaaaaa aaaaaaaaaa aaaaaaaaaa aaaaaaaaaa aaaaaucuag 1790

<210> SEQ ID NO 54
<211> LENGTH: 506
<212> TYPE: PRT
<213> ORGANISM: Artificial Sequence
<220> FEATURE:
<223> OTHER INFORMATION: Synthetic Polypeptide

<400> SEQUENCE: 54

Met Ala Gln Val Ile Asn Thr Asn Ser Leu Ser Leu Leu Thr Gln Asn
1 5 10 15

Asn Leu Asn Lys Ser Gln Ser Ala Leu Gly Thr Ala Ile Glu Arg Leu
20 25 30

Ser Ser Gly Leu Arg Ile Asn Ser Ala Lys Asp Asp Ala Ala Gly Gln
35 40 45

Ala Ile Ala Asn Arg Phe Thr Ala Asn Ile Lys Gly Leu Thr Gln Ala
50 55 60

Ser Arg Asn Ala Asn Asp Gly Ile Ser Ile Ala Gln Thr Thr Glu Gly
65 70 75 80

Ala Leu Asn Glu Ile Asn Asn Asn Leu Gln Arg Val Arg Glu Leu Ala
85 90 95

Val Gln Ser Ala Asn Gly Thr Asn Ser Gln Ser Asp Leu Asp Ser Ile
100 105 110

Gln Ala Glu Ile Thr Gln Arg Leu Asn Glu Ile Asp Arg Val Ser Gly
115 120 125

Gln Thr Gln Phe Asn Gly Val Lys Val Leu Ala Gln Asp Asn Thr Leu
130 135 140

Thr Ile Gln Val Gly Ala Asn Asp Gly Glu Thr Ile Asp Ile Asp Leu
145 150 155 160

Lys Glu Ile Ser Ser Lys Thr Leu Gly Leu Asp Lys Leu Asn Val Gln
165 170 175

Asp Ala Tyr Thr Pro Lys Glu Thr Ala Val Thr Val Asp Lys Thr Thr
180 185 190

Tyr Lys Asn Gly Thr Asp Pro Ile Thr Ala Gln Ser Asn Thr Asp Ile
195 200 205

Gln Thr Ala Ile Gly Gly Gly Ala Thr Gly Val Thr Gly Ala Asp Ile
210 215 220

Lys Phe Lys Asp Gly Gln Tyr Tyr Leu Asp Val Lys Gly Gly Ala Ser
225 230 235 240

Ala Gly Val Tyr Lys Ala Thr Tyr Asp Glu Thr Thr Lys Lys Val Asn
245 250 255

Ile Asp Thr Thr Asp Lys Thr Pro Leu Ala Thr Ala Glu Ala Thr Ala
260 265 270

Ile Arg Gly Thr Ala Thr Ile Thr His Asn Gln Ile Ala Glu Val Thr
275 280 285

Lys Glu Gly Val Asp Thr Thr Thr Val Ala Ala Gln Leu Ala Ala Ala
290 295 300

Gly Val Thr Gly Ala Asp Lys Asp Asn Thr Ser Leu Val Lys Leu Ser
305 310 315 320

Phe Glu Asp Lys Asn Gly Lys Val Ile Asp Gly Gly Tyr Ala Val Lys
325 330 335

Met Gly Asp Asp Phe Tyr Ala Ala Thr Tyr Asp Glu Lys Thr Gly Ala
340 345 350

Ile Thr Ala Lys Thr Thr Thr Tyr Thr Asp Gly Thr Gly Val Ala Gln

```
        355                 360                 365

Thr Gly Ala Val Lys Phe Gly Gly Ala Asn Gly Lys Ser Glu Val Val
    370                 375                 380

Thr Ala Thr Asp Gly Lys Thr Tyr Leu Ala Ser Asp Leu Asp Lys His
385                 390                 395                 400

Asn Phe Arg Thr Gly Gly Glu Leu Lys Glu Val Asn Thr Asp Lys Thr
                405                 410                 415

Glu Asn Pro Leu Gln Lys Ile Asp Ala Ala Leu Ala Gln Val Asp Thr
            420                 425                 430

Leu Arg Ser Asp Leu Gly Ala Val Gln Asn Arg Phe Asn Ser Ala Ile
        435                 440                 445

Thr Asn Leu Gly Asn Thr Val Asn Asn Leu Ser Ser Ala Arg Ser Arg
    450                 455                 460

Ile Glu Asp Ser Asp Tyr Ala Thr Glu Val Ser Asn Met Ser Arg Ala
465                 470                 475                 480

Gln Ile Leu Gln Gln Ala Gly Thr Ser Val Leu Ala Gln Ala Asn Gln
                485                 490                 495

Val Pro Gln Asn Val Leu Ser Leu Leu Arg
            500                 505


<210> SEQ ID NO 55
<211> LENGTH: 698
<212> TYPE: PRT
<213> ORGANISM: Artificial Sequence
<220> FEATURE:
<223> OTHER INFORMATION: Synthetic Polypeptide

<400> SEQUENCE: 55

Met Ala Gln Val Ile Asn Thr Asn Ser Leu Ser Leu Leu Thr Gln Asn
1               5                   10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ala
                85                  90                  95

Val Gln Ser Ala Asn Ser Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Thr Leu Asn Val Gln
                165                 170                 175

Gln Lys Tyr Lys Val Ser Asp Thr Ala Ala Thr Val Thr Gly Tyr Ala
            180                 185                 190

Asp Thr Thr Ile Ala Leu Asp Asn Ser Thr Phe Lys Ala Ser Ala Thr
        195                 200                 205

Gly Leu Gly Gly Thr Asp Gln Lys Ile Asp Gly Asp Leu Lys Phe Asp
```

```
    210                 215                 220

Asp Thr Thr Gly Lys Tyr Tyr Ala Lys Val Thr Val Thr Gly Gly Thr
225                 230                 235                 240

Gly Lys Asp Gly Tyr Tyr Glu Val Ser Val Asp Lys Thr Asn Gly Glu
                245                 250                 255

Val Thr Leu Ala Gly Gly Ala Thr Ser Pro Leu Thr Gly Gly Leu Pro
            260                 265                 270

Ala Thr Ala Thr Glu Asp Val Lys Asn Val Gln Val Ala Asn Ala Asp
        275                 280                 285

Leu Thr Glu Ala Lys Ala Ala Leu Thr Ala Ala Gly Val Thr Gly Thr
    290                 295                 300

Ala Ser Val Val Lys Met Ser Tyr Thr Asp Asn Asn Gly Lys Thr Ile
305                 310                 315                 320

Asp Gly Gly Leu Ala Val Lys Val Gly Asp Asp Tyr Tyr Ser Ala Thr
                325                 330                 335

Gln Asn Lys Asp Gly Ser Ile Ser Ile Asn Thr Thr Lys Tyr Thr Ala
            340                 345                 350

Asp Asp Gly Thr Ser Lys Thr Ala Leu Asn Lys Leu Gly Gly Ala Asp
        355                 360                 365

Gly Lys Thr Glu Val Val Ser Ile Gly Gly Lys Thr Tyr Ala Ala Ser
    370                 375                 380

Lys Ala Glu Gly His Asn Phe Lys Ala Gln Pro Asp Leu Ala Glu Ala
385                 390                 395                 400

Ala Ala Thr Thr Thr Glu Asn Pro Leu Gln Lys Ile Asp Ala Ala Leu
                405                 410                 415

Ala Gln Val Asp Thr Leu Arg Ser Asp Leu Gly Ala Val Gln Asn Arg
            420                 425                 430

Phe Asn Ser Ala Ile Thr Asn Leu Gly Asn Thr Val Asn Asn Leu Thr
        435                 440                 445

Ser Ala Arg Ser Arg Ile Glu Asp Ser Asp Tyr Ala Thr Glu Val Ser
    450                 455                 460

Asn Met Ser Arg Ala Gln Ile Leu Gln Gln Ala Gly Thr Ser Val Leu
465                 470                 475                 480

Ala Gln Ala Asn Gln Val Pro Gln Asn Val Leu Ser Leu Leu Arg Gly
                485                 490                 495

Gly Gly Gly Ser Gly Gly Gly Gly Ser Met Met Ala Pro Asp Pro Asn
            500                 505                 510

Ala Asn Pro Asn Ala Asn Pro Asn Ala Asn Pro Asn Ala Asn Pro Asn
        515                 520                 525

Ala Asn Pro Asn Ala Asn Pro Asn Ala Asn Pro Asn Ala Asn Pro Asn
    530                 535                 540

Ala Asn Pro Asn Ala Asn Pro Asn Ala Asn Pro Asn Ala Asn Pro Asn
545                 550                 555                 560

Ala Asn Pro Asn Ala Asn Pro Asn Ala Asn Pro Asn Ala Asn Pro Asn
                565                 570                 575

Ala Asn Pro Asn Ala Asn Pro Asn Ala Asn Pro Asn Lys Asn Asn Gln
            580                 585                 590

Gly Asn Gly Gln Gly His Asn Met Pro Asn Asp Pro Asn Arg Asn Val
        595                 600                 605

Asp Glu Asn Ala Asn Ala Asn Asn Ala Val Lys Asn Asn Asn Asn Glu
    610                 615                 620

Glu Pro Ser Asp Lys His Ile Glu Gln Tyr Leu Lys Lys Ile Lys Asn
625                 630                 635                 640
```

```
Ser Ile Ser Thr Glu Trp Ser Pro Cys Ser Val Thr Cys Gly Asn Gly
                645                 650                 655

Ile Gln Val Arg Ile Lys Pro Gly Ser Ala Asn Lys Pro Lys Asp Glu
            660                 665                 670

Leu Asp Tyr Glu Asn Asp Ile Glu Lys Lys Ile Cys Lys Met Glu Lys
        675                 680                 685

Cys Ser Ser Val Phe Asn Val Val Asn Ser
    690                 695


<210> SEQ ID NO 56
<211> LENGTH: 692
<212> TYPE: PRT
<213> ORGANISM: Artificial Sequence
<220> FEATURE:
<223> OTHER INFORMATION: Synthetic Polypeptide

<400> SEQUENCE: 56

Met Met Ala Pro Asp Pro Asn Ala Asn Pro Asn Ala Asn Pro Asn Ala
1               5                   10                  15

Asn Pro Asn Ala Asn Pro Asn Ala Asn Pro Asn Ala Asn Pro Asn Ala
            20                  25                  30

Asn Pro Asn Ala Asn Pro Asn Ala Asn Pro Asn Ala Asn Pro Asn Ala
        35                  40                  45

Asn Pro Asn Ala Asn Pro Asn Ala Asn Pro Asn Ala Asn Pro Asn Ala
    50                  55                  60

Asn Pro Asn Ala Asn Pro Asn Ala Asn Pro Asn Ala Asn Pro Asn Ala
65                  70                  75                  80

Asn Pro Asn Lys Asn Asn Gln Gly Asn Gly Gln Gly His Asn Met Pro
                85                  90                  95

Asn Asp Pro Asn Arg Asn Val Asp Glu Asn Ala Asn Ala Asn Asn Ala
            100                 105                 110

Val Lys Asn Asn Asn Asn Glu Glu Pro Ser Asp Lys His Ile Glu Gln
        115                 120                 125

Tyr Leu Lys Lys Ile Lys Asn Ser Ile Ser Thr Glu Trp Ser Pro Cys
    130                 135                 140

Ser Val Thr Cys Gly Asn Gly Ile Gln Val Arg Ile Lys Pro Gly Ser
145                 150                 155                 160

Ala Asn Lys Pro Lys Asp Glu Leu Asp Tyr Glu Asn Asp Ile Glu Lys
                165                 170                 175

Lys Ile Cys Lys Met Glu Lys Cys Ser Ser Val Phe Asn Val Val Asn
            180                 185                 190

Ser Arg Pro Val Thr Met Ala Gln Val Ile Asn Thr Asn Ser Leu Ser
        195                 200                 205

Leu Leu Thr Gln Asn Asn Leu Asn Lys Ser Gln Ser Ala Leu Gly Thr
    210                 215                 220

Ala Ile Glu Arg Leu Ser Ser Gly Leu Arg Ile Asn Ser Ala Lys Asp
225                 230                 235                 240

Asp Ala Ala Gly Gln Ala Ile Ala Asn Arg Phe Thr Ala Asn Ile Lys
                245                 250                 255

Gly Leu Thr Gln Ala Ser Arg Asn Ala Asn Asp Gly Ile Ser Ile Ala
            260                 265                 270

Gln Thr Thr Glu Gly Ala Leu Asn Glu Ile Asn Asn Asn Leu Gln Arg
        275                 280                 285

Val Arg Glu Leu Ala Val Gln Ser Ala Asn Ser Thr Asn Ser Gln Ser
    290                 295                 300
```

Asp Leu Asp Ser Ile Gln Ala Glu Ile Thr Gln Arg Leu Asn Glu Ile
305 310 315 320

Asp Arg Val Ser Gly Gln Thr Gln Phe Asn Gly Val Lys Val Leu Ala
325 330 335

Gln Asp Asn Thr Leu Thr Ile Gln Val Gly Ala Asn Asp Gly Glu Thr
340 345 350

Ile Asp Ile Asp Leu Lys Gln Ile Asn Ser Gln Thr Leu Gly Leu Asp
355 360 365

Thr Leu Asn Val Gln Gln Lys Tyr Lys Val Ser Asp Thr Ala Ala Thr
370 375 380

Val Thr Gly Tyr Ala Asp Thr Thr Ile Ala Leu Asp Asn Ser Thr Phe
385 390 395 400

Lys Ala Ser Ala Thr Gly Leu Gly Gly Thr Asp Gln Lys Ile Asp Gly
405 410 415

Asp Leu Lys Phe Asp Asp Thr Thr Gly Lys Tyr Tyr Ala Lys Val Thr
420 425 430

Val Thr Gly Gly Thr Gly Lys Asp Gly Tyr Tyr Glu Val Ser Val Asp
435 440 445

Lys Thr Asn Gly Glu Val Thr Leu Ala Gly Gly Ala Thr Ser Pro Leu
450 455 460

Thr Gly Gly Leu Pro Ala Thr Ala Thr Glu Asp Val Lys Asn Val Gln
465 470 475 480

Val Ala Asn Ala Asp Leu Thr Glu Ala Lys Ala Ala Leu Thr Ala Ala
485 490 495

Gly Val Thr Gly Thr Ala Ser Val Val Lys Met Ser Tyr Thr Asp Asn
500 505 510

Asn Gly Lys Thr Ile Asp Gly Gly Leu Ala Val Lys Val Gly Asp Asp
515 520 525

Tyr Tyr Ser Ala Thr Gln Asn Lys Asp Gly Ser Ile Ser Ile Asn Thr
530 535 540

Thr Lys Tyr Thr Ala Asp Asp Gly Thr Ser Lys Thr Ala Leu Asn Lys
545 550 555 560

Leu Gly Gly Ala Asp Gly Lys Thr Glu Val Val Ser Ile Gly Gly Lys
565 570 575

Thr Tyr Ala Ala Ser Lys Ala Glu Gly His Asn Phe Lys Ala Gln Pro
580 585 590

Asp Leu Ala Glu Ala Ala Ala Thr Thr Thr Glu Asn Pro Leu Gln Lys
595 600 605

Ile Asp Ala Ala Leu Ala Gln Val Asp Thr Leu Arg Ser Asp Leu Gly
610 615 620

Ala Val Gln Asn Arg Phe Asn Ser Ala Ile Thr Asn Leu Gly Asn Thr
625 630 635 640

Val Asn Asn Leu Thr Ser Ala Arg Ser Arg Ile Glu Asp Ser Asp Tyr
645 650 655

Ala Thr Glu Val Ser Asn Met Ser Arg Ala Gln Ile Leu Gln Gln Ala
660 665 670

Gly Thr Ser Val Leu Ala Gln Ala Asn Gln Val Pro Gln Asn Val Leu
675 680 685

Ser Leu Leu Arg
690

<210> SEQ ID NO 57
<211> LENGTH: 1620

<212> TYPE: RNA
<213> ORGANISM: Human metapneumovirus

<400> SEQUENCE: 57
augagcugga agguggugau uaucuucagc cugcugauua caccucaaca cggccugaag 60
gagagcuacc uggaagagag cugcuccacc aucaccgagg gcuaccugag cgugcugcgg 120
accggcuggu acaccaacgu guucacccug gaggugggcg acguggagaa ccugaccugc 180
agcgacggcc cuagccugau caagaccgag cuggaccuga ccaagagcgc ucugagagag 240
cugaagaccg uguccgccga ccagcuggcc agagaggaac agaucgagaa cccucggcag 300
agcagauucg ugcugggcgc caucgcucug ggagucgccg cugccgcugc agugacagcu 360
ggaguggcca uugcuaagac caucagacug gaaagcgagg ugacagccau caacaaugcc 420
cugaagaaga ccaacgaggc cgugagcacc cugggcaaug gagugagagu gcuggccaca 480
gccgugcggg agcugaagga cuucgugagc aagaaccuga ccagagccau caacaagaac 540
aagugcgaca ucgaugaccu gaagauggcc gugagcuucu cccaguucaa cagacgguuc 600
cugaacgugg ugagacaguu cuccgacaac gcuggaauca caccugccau uagccuggac 660
cugaugaccg acgccgagcu ggcuagagcc gugcccaaca ugcccaccag cgcuggccag 720
aucaagcuga ugcuggagaa cagagccaug gugcggagaa agggcuucgg cauccugauu 780
gggguguaug gaagcuccgu gaucuacaug gugcagcugc ccaucuucgg cgugaucgac 840
acacccugcu ggaucgugaa ggccgcuccu agcugcuccg agaagaaagg aaacuaugcc 900
ugucugcuga gagaggacca gggcugguac ugccagaacg ccggaagcac aguguacuau 960
cccaacgaga aggacugcga gaccagaggc gaccacgugu ucugcgacac cgcugccgga 1020
aucaacgugg ccgagcagag caaggagugc aacaucaaca ucagcacaac caacuacccc 1080
ugcaagguga gcaccggacg gcaccccauc agcauggugg cucugagccc ucugggcgcu 1140
cugguggccu gcuauaaggg cguguccugu agcaucggca gcaaucgggu gggcaucauc 1200
aagcagcuga acaagggaug cuccuacauc accaaccagg acgccgacac cgugaccauc 1260
gacaacaccg uguaccagcu gagcaaggug gagggcgagc agcacgugau caagggcaga 1320
cccgugagcu ccagcuucga ccccaucaag uucccugagg accaguucaa cguggcccug 1380
gaccaggugu uugagaacau cgagaacagc caggcccugg uggaccagag caacagaauc 1440
cuguccagcg cugagaaggg caacaccggc uucaucauug ugaucauucu gaucgccgug 1500
cugggcagcu ccaugauccu ggugagcauc uucaucauua ucaagaagac caagaaaccc 1560
accggagccc cuccugagcu gagcggcgug accaacaaug gcuucauucc ccacaacuga 1620

<210> SEQ ID NO 58
<211> LENGTH: 1620
<212> TYPE: RNA
<213> ORGANISM: Human metapneumovirus

<400> SEQUENCE: 58
augucuugga aagugaugau caucauuucg uuacucauaa caccccagca cgggcuaaag 60
gagaguuauu uggaagaauc auguaguacu auaacugagg gauaccucag uguuuuaaga 120
acaggcuggu acacuaaugu cuucacauua gaaguuggug auguugaaaa ucuuacaugu 180
acugauggac cuagcuuaau caaaacagaa cuugaucuaa caaaaagugc uuuaagggaa 240
cucaaaacag ucucugcuga ucaguuggcg agagaggagc aaauugaaaa ucccagacaa 300
ucaagauuug ucuuaggugc gauagcucuc ggaguugcua cagcagcagc agucacagca 360
ggcauugcaa uagccaaaac cauaaggcuu gagagugagg ugaaugcaau uaaaggugcu 420
cucaaacaaa cuaaugaagc aguauccaca uuagggaaug gugugcgggu ccuagccacu 480
gcagugagag agcuaaaaga auuugugagc aaaaaccuga cuagugcaau caacaggaac 540
aaaugugaca uugcugaucu gaagauggcu gucagcuuca gucaauucaa cagaagauuu 600
cuaaauguug ugcggcaguu uucagacaau gcagggauaa caccagcaau aucauuggac 660
cugaugacug augcugaguu ggccagagcu guaucauaca ugccaacauc ugcagggcag 720 auaaaaacuga uguuggagaa ccgcgcaaug guaaggagaa aaggauuugg aauccugaua 780
ggggucuacg gaagcucugu gauuuacaug guucaauugc cgaucuuugg ugucauagau 840
acaccuuguu ggaucaucaa ggcagcuccc ucuugcucag aaaaaaacgg gaauuaugcu 900
ugccuccuaa gagaggauca agggugguau uguaaaaaug caggaucuac uguuuacuac 960
ccaaaugaaa aagacugcga aacaagaggu gaucauguuu uuugugacac agcagcaggg 1020
aucaauguug cugagcaauc aagagaaugc aacaucaaca uaucuacuac caacuaccca 1080
ugcaaaguca gcacaggaag acacccuaua agcaugguug cacuaucacc ucucggugcu 1140
uugguggcuu gcuauaaagg gguaagcugc ucgauuggca gcaauugggu uggaaucauc 1200
aaacaauuac ccaaaggcug cucauacaua accaaccagg augcagacac uguaacaauu 1260
gacaauaccg uguaucaacu aagcaaaguu gaaggugaac agcauguaau aaaagggaga 1320
ccaguuucaa gcaguuuuga uccaaucaag uuuccugagg aucaguucaa uguugcgcuu 1380
gaucaagucu ucgaaagcau ugagaacagu caggcacuag uggaccaguc aaacaaaauu 1440
cuaaacagug cagaaaaagg aaacacuggu uucauuaucg uaguaauuuu gguugcuguu 1500
cuuggucuaa ccaugauuuc agugagcauc aucaucauaa ucaagaaaac aaggaagccc 1560
acaggagcac cuccagagcu gaaugguguc accaacggcg guuucauacc acauaguuag 1620

<210> SEQ ID NO 59
<211> LENGTH: 1620
<212> TYPE: RNA
<213> ORGANISM: Human metapneumovirus

<400> SEQUENCE: 59
augucuugga aagugaugau uaucauuucg uuacucauaa caccucagca uggacuaaaa 60
gaaaguuauu uagaagaauc auguaguacu auaacugaag gauaucucag uguuuuaaga 120
acagguuggu acaccaaugu cuuuacauua gaaguuggug auguugaaaa ucuuacaugu 180
acugauggac cuagcuuaau caaaacagaa cuugaccuaa ccaaaagugc uuuaagagaa 240
cucaaaacag uuucugcuga ucaguuagcg agagaagaac aaauugaaaa ucccagacaa 300
ucaagguuug uccuaggugc aauagcucuu ggaguugcca cagcagcagc agucacagca 360
ggcauugcaa uagccaaaac uauaaggcuu gagagugaag ugaaugcaau caaaggugcu 420
cucaaaacaa ccaaugaggc aguaucaaca cuaggaaaug gagugcgggu ccuagccacu 480
gcaguaagag agcugaaaga auuugugagc aaaaaccuga cuagugcgau caacaagaac 540
aagugugaca uugcugauuu gaagauggcu gucagcuuca gucaguucaa cagaagauuc 600
cuaaauguug ugcggcaguu uucagacaau gcagggauaa caccagcaau aucauuggac 660
cugaugaaug augcugagcu ggccagagcu guaucauaca ugccaacauc ugcaggacag 720
auaaaacuaa uguuagagaa ccgugcaaug gugaggagaa aaggauuugg aaucuugaua 780
ggggucuacg gaagcucugu gauuuacaug guccagcugc cgaucuuugg ugucauaaau 840
acaccuuguu ggauaaucaa ggcagcuccc ucuuguucag aaaaagaugg aaauuaugcu 900

```
ugccuccuaa gagaggauca agggugguau uguaaaaaug caggauccac uguuuacuac    960

ccaaaugaaa aagacugcga aacaagaggu gaucauguuu uuugugacac agcagcaggg   1020

aucaauguug cugagcaauc aagagaaugc aacaucaaca uaucuaccac caacuaccca   1080

ugcaaaguca gcacaggaag acacccuauc agcaugguug cacuaucacc ucucggugcu   1140

uugguagcuu gcuacaaagg gguuagcugc ucgacuggca guaaucaggu uggaauaaauc  1200

aaacaacuac cuaaaggcug cucauacaua acuaaccagg acgcagacac uguaacaauu   1260

gacaacacug uguaucaacu aagcaaaguu gaggggugaac agcauguaau aaaagggaga  1320

ccaguuucaa gcaguuuuga uccaaucagg uuuccugagg aucaguucaa uguugcgcuu   1380

gaucaagucu uugaaagcau ugaaaacagu caagcacuag uggaccaguc aaacaaaauu   1440

cugaacagug cagaaaaagg aaacacuggu uucauuauug uaauaauuuu gauugcuguu   1500

cuuggguuaa ccaugauuuc agugagcauc aucaucauaa ucaaaaaaac aaggaagccc   1560

acaggggcac cuccggagcu gaauggugu u accaacggcg guuucauacc gcauaguuag  1620
```

```
<210> SEQ ID NO 60
<211> LENGTH: 1725
<212> TYPE: RNA
<213> ORGANISM: Human respiratory syncytial virus

<400> SEQUENCE: 60

auggaguugc caauccucaa aacaaaugca auuaccacaa uccuugcugc agucacacuc     60

uguuucgcuu ccagucaaaa caucacugaa gaauuuuauc aaucaacaug cagugcaguu    120

agcaaaggcu aucuuagugc ucuaagaacu gguugguaua cuaguguuau aacuauagaa    180

uuaaguaaua ucaaggaaaa uaaguguaau ggaacagaug cuaagguaaa auugauaaaa    240

caagaauuag auaaaauaaa aaaugcugua acagaauugc aguugcucau gcaaagcaca    300

ccagcagcca acaaucgagc cagaagagaa cuaccaaggu uuaugaauua uacacucaau    360

aauaccaaaa auaccaaugu aacauuaagc aagaaaagga aaagaagauu ucuuggcuuu    420

uuguuaggug uuggaucugc aaucgccagu ggcauugcug uaucuaaggu ccugcaccua    480

gaaggggaag ugaacaaaau caaaagugcu cuacuaucca caaacaaggc uguagucagc    540

uuaucaaaug gaguuagugu cuuaaccagc aaaguguuag accucaaaaa cuauauagau    600

aaacaguugu uaccuauugu gaacaagcaa agcugcagca uaucaaacau ugaaacugug    660

auagaguucc aacaaaagaa caacagacua cuagagauua ccagggaauu uaguguuaau    720

gcagguguaa cuacaccugu aagcacuuau auguuaacua auagugaauu auuaucauua    780

aucaaugaua ugccuauaac aaaugaucag aaaaaguuaa uguccaacaa uguucaaaua    840

guuagacagc aaaguuacuc uaucaugucc auaauaaagg aggaagucuu agcauaugua    900

guacaauuac cacuauaugg uguaauagau acacccuguu ggaaacugca cacaucccu     960

cuauguacaa ccaacacaaa ggaagggucc aacaucugcu uaacaagaac cgacagagga   1020

ugguauugug acaaugcagg aucaguaucu uucuucccac aagcugaaac auguaaaguu   1080

caaucgaauc ggguauuuug ugacacaaug aacaguuuaa cauuaccaag ugaaguaaau   1140

cucugcaaca uugacauauu caaccccaaa uaugauugca aaauuaugac uucaaaaaca   1200

gauguaagca gcuccguuau cacaucucua ggagccauug ugucaugcua uggcaaaacu   1260

aaauguacag cauccaauaa aaaucguggg aucauaaaga cauuuucuaa cgggugugau   1320

uauguaucaa auaaaggggu ggauacugug ucuguaggua auacauuaua uuauguaaau   1380
```

```
aagcaagaag gcaaaagucu cuauguaaaa ggugaaccaa uaauaaauuu cuaugaccca   1440

uuaguguucc ccucugauga auuugaugca ucaauaucuc aagucaauga gaagauuaac   1500

cagagccuag cauuuauucg uaaauccgau gaauuauuac auaauguaaa ugcugguaaa   1560

uccaccacaa auaucaugau aacuacuaua auuauaguga uuauaguaau auuguuauca   1620

uuaauugcag uuggacugcu ccuauacugc aaggccagaa gcacaccagu cacacuaagu   1680

aaggaucaac ugagugguau aaauaauauu gcauuuagua acuga                    1725
```

<210> SEQ ID NO 61
<211> LENGTH: 1617
<212> TYPE: RNA
<213> ORGANISM: Human parainfluenza virus

<400> SEQUENCE: 61

```
augccaauuu caauacuguu aauuauuaca accaugauca uggcaucaca cugccaaaua     60

gacaucacaa aacuacagca uguaggugua uuggucaaca gucccaaagg gaugaagaua    120

ucacaaaacu ucgaaacaag auaucuaauc cugagucuca uaccaaaaau agaagauucu    180

aacucuugug gugaccaaca gaucaagcaa uacaagaggu uauuggauag acugaucauu    240

ccuuuauaug auggacuaag auuacagaag gaugugauag ugacuaauca agaauccaau    300

gaaaacacug aucccagaac agaacgauuc uuuggagggg uaauuggaac uauugcucua    360

ggaguagcaa ccucagcaca aauuacagca gcaguugcuc ugguugaagc caagcaggca    420

agaucagaca uugaaaaacu caaggaagca aucagggaca caaauaaagc agugcaguca    480

guucagagcu cuguaggaaa uuugauagua gcaauuaaau caguccagga uuaugucaac    540

aaagaaaucg ugccaucgau ugcgagacua gguugugaag cagcaggacu ucaguuaggg    600

auugcauuaa cacagcauua cucagaauua acaaauauau uuggugauaa cauaggaucg    660

uuacaagaaa aaggaauaaa auuacaaggu auagcaucau uauaccguac aaauaucaca    720

gaaauauuca caacaucaac aguugacaaa uaugauauuu augaucuauu auuuacagaa    780

ucaauaaagg ugagaguuau agauguugau uugaaugauu acucaauaac ccuccaaguc    840

agacucccuu uauugaccag acugcugaac acucaaaucu acaaaguaga uuccauauca    900

uacaauaucc aaaauagaga augguauauc ccucuuccca gccauaucau gacgaaaggg    960

gcauuucuag guggagcaga ugucaaagaa ugcauagaag cauucagcag uuauauaugc   1020

ccuucugauc caggauuugu acuaaaccau gaaauggaga gcugucuauc aggaaacaua   1080

ucccaauguc caagaaccac agucacauca gacauaguuc cuagguaugc auuugucaau   1140

ggaggagugg uugcgaauug uauaacaacu acauguacau gcaaugguau cgguaauaga   1200

aucaaccaac caccugauca aggagucaaa auuauaacac auaaagaaug uaauacaaua   1260

gguaucaacg gaaugcuauu caacacaaac aaagaaggaa cucuugcauu cuacacacca   1320

gacgacauaa cauuaaacaa uucuguugca cuugauccga uugacauauc aaucgagcuc   1380

aacaaggcca aaucagaucu ugaggaauca aaagaaugga uaagaagguc aaaucaaaag   1440

cuagauucua uuggaaguug gcaucaaucu agcacuacaa ucauaguuau uuugauaaug   1500

augauuauau uguuuauaau uaauauaaca auaauuacaa uugcaauuaa guauuacaga   1560

auucaaaaga gaaaucgagu ggaucaaaau gauaagccgu auguauuaac aaacaag      1617
```

<210> SEQ ID NO 62
<211> LENGTH: 1716
<212> TYPE: RNA
<213> ORGANISM: Human parainfluenza virus 3

<400> SEQUENCE: 62
auggaauacu ggaagcacac caaccacgga aaggaugcug guaaugagcu ggagacaucc 60
acagccacuc auggcaacaa gcucaccaac aagauaacau auauauugug gacgauaacc 120
cugguguuau uaucaauagu cuucaucaua gugcuaacua auuccaucaa aagugaaaag 180
gcccgcgaau cauugcuaca agacauaaau aaugaguuua uggaaguuac agaaaagauc 240
caaguggcau cggauaauac uaaugaucua auacagucag gagugaauac aaggcuucuu 300
acaauucaga gucaugucca gaauuauaua ccaauaucau ugacacaaca aauaucggau 360
cuuaggaaau ucauuaguga aauuacaauu agaaaugaua aucaagaagu gccaccacaa 420
agaauaacac augauguggg uauaaaaccu uuaaauccag augauuucug gagaugcacg 480
ucuggucuuc caucuuugau gaaaacucca aaaauaagau uaaugccggg accaggauua 540
uuagcuaugc caacgacugu ugauggcugu gucagaaccc cguccuuagu gauaaaugau 600
cugauuuaug cuuacaccuc aaaucuaauu acucgagguu gccaggauau agggaaauca 660
uaucaaguau uacagauagg gauaauaacu guaaacucag acuugguacc ugacuuaaau 720
ccuaggaucu cucauaccuu caacauaaau gacaauagaa agucauguuc ucuagcacuc 780
cuaaauacag auguauauca acuguguuca accccaaaag uugaugaaag aucagauuau 840
gcaucaucag gcauagaaga uauuguacuu gauauuguca auuaugaugg cucaaucucg 900
acaacaagau uuaagaauaa uaauauaagu uuugaucaac cauaugcggc auuauaccca 960
ucuguuggac cagggauaua cuacaaaggc aaaauaauau uucucgggua uggaggucuu 1020
gaacauccaa uaaaugagaa ugcaaucugc aacacaacug ggugucccgg gaaaacacag 1080
agagacugua aucaagcauc ucauagucca ugguuuucag auagaaggau ggucaacucu 1140
auaauuguug uugacaaggg cuugaacuca guuccaaaau ugaagguaug gacgauaucu 1200
augagacaaa auuacugggg gucagaagga agauuacuuc uacuagguaa caagaucuac 1260
auauacacaa gaucuacaag uuggcacagc aaguuacaau uaggaauaau ugacauuacu 1320
gacuacagug auauaaggau aaaauggaca uggcauaaug ugcuaucaag accaggaaac 1380
aaugaauguc cauggggaca uucauguccg gauggaugua uaacgggagu auauaccgau 1440
gcauauccac ucaaucccac aggaagcauu guaucaucug ucauauugga cucacaaaaa 1500
ucgagaguca acccagucau aacuuacuca acagcaaccg aaaggguaaa cgagcuggcu 1560
auccgaaaca aaacacucuc agcuggguac acaacaacaa gcugcauuac acacuauaac 1620
aaaggguauu guuuucauau aguagaaaua aaucauaaaa gcuuaaacac auuucaaccc 1680
auguuguuca aaacagagau uccaaaaagc ugcagu 1716

<210> SEQ ID NO 63
<211> LENGTH: 1716
<212> TYPE: RNA
<213> ORGANISM: Artificial Sequence
<220> FEATURE:
<223> OTHER INFORMATION: Synthetic Polynucleotide

<400> SEQUENCE: 63
auggaauacu ggaagcacac caaccacggc aaggacgccg gcaacgagcu ggaaaccagc 60
acagccacac acggcaacaa gcugaccaac aagaucaccu acauccugug gaccaucacc 120
cuggugcugc ugagcaucgu guucaucauc gugcugacca auagcaucaa gagcgagaag 180
gccagagaga gccugcugca ggacaucaac aacgaguuca uggaagugac cgagaagauc 240

-continued

```
caggugccca gcgacaacac caacgaccug auccagagcg gcgugaacac ccggcugcug    300

accauccaga gccacgugca gaacuacauc cccaucagcc ugacccagca gaucagcgac    360

cugcggaagu ucaucagcga gaucaccauc cggaacgaca accaggaagu gcccccccag    420

agaaucaccc acgacguggg caucaagccc cugaaccccg acgauuucug gcgguguaca    480

agcggccugc ccagccugau gaagaccccc aagauccggc ugaugccugg cccuggacug    540

cuggccaugc cuaccacagu ggauggcugu gugcggaccc ccagccucgu gaucaacgau    600

cugaucuacg ccuacaccag caaccugauc acccggggcu gccaggauau cggcaagagc    660

uaccaggugc ugcagaucgg caucaucacc gugaacuccg accuggugcc cgaccugaac    720

ccucggauca gccacaccuu caacaucaac gacaacagaa agagcugcag ccuggcucug    780

cugaacaccg acguguacca gcugugcagc accccccaagg uggacgagag aagcgacuac    840

gccagcagcg gcaucgagga uaucgugcug gacaucguga acuacgacgg cagcaucagc    900

accacccggu ucaagaacaa caacaucagc uucgaccagc ccuacgccgc ccuguacccu    960

ucugugggcc cuggcaucua cuacaagggc aagaucaucu uccugggcua cggcggccug   1020

gaacacccca ucaacgagaa cgccaucugc aacaccaccg gcugcccugg caagacccag   1080

agagacugca aucaggccag ccacagcccc ugguucagcg accgcagaau ggucaacucu   1140

aucaucgugg uggacaaggg ccugaacagc gugcccaagc ugaaagugug gacaaucagc   1200

augcgccaga acuacugggg cagcgagggc agacuucugc ugcugggaaa caagaucuac   1260

aucuacaccc gguccaccag cuggcacagc aaacugcagc ugggaaucau cgacaucacc   1320

gacuacagcg acauccggau caaguggacc uggcacaacg ugcugagcag acccggcaac   1380

aaugagugcc cuuggggcca cagcugcccc gauggaugua ucaccggcgu guacaccgac   1440

gccuaccccc ugaauccuac cggcuccauc guguccagcg ugauccugga cagccagaaa   1500

agcagaguga accccgugau cacauacagc accgccaccg agagagugaa cgaacuggcc   1560

aucagaaaca agacccugag cgccggcuac accaccacaa gcugcaucac acacuacaac   1620

aagggcuacu gcuuccacau cguggaaauc aaccacaagu cccugaacac cuuccagccc   1680

augcuguuca agaccgagau ccccaagagc ugcucc                             1716
```

<210> SEQ ID NO 64
<211> LENGTH: 1617
<212> TYPE: RNA
<213> ORGANISM: Artificial Sequence
<220> FEATURE:
<223> OTHER INFORMATION: Synthetic Polynucleotide

<400> SEQUENCE: 64

```
augcccauca gcauccugcu gaucaucacc acaaugauca uggccagcca cugccagauc     60

gacaucacca agcugcagca cgugggcgug cucgugaaca gccccaaggg caugaagauc    120

agccagaacu ucgagacacg cuaccugauc cugagccuga uccccaagau cgaggacagc    180

aacagcugcg gcgaccagca gaucaagcag uacaagcggc ugcuggacag acugaucauc    240

ccccuguacg acggccugcg gcugcagaaa gacgugaucg ugaccaacca ggaaagcaac    300

gagaacaccg accccccggac cgagagauuc uucggcggcg ugaucggcac aaucgcccug    360

ggaguggcca caagcgccca gauuacagcc gcuguggccc ugguggaagc caagcaggcc    420

agaagcgaca ucgagaagcu gaaagaggcc auccgggaca ccaacaaggc cgugcagagc    480

gugcagucca gcgugggcaa ucugaucgug gccaucaagu ccgugcagga cuacgugaac    540

aaagaaaucg ugcccucuau cgcccggcug ggcugugaag cugccggacu gcagcugggc    600
```

-continued auugcccuga cacagcacua cagcgagcug accaacaucu ucggcgacaa caucggcagc 660
cugcaggaaa agggcauuaa gcugcaggga aucgccagcc uguaccgcac caacaucacc 720
gagaucuuca ccaccagcac cguggauaag uacgacaucu acgaccugcu guucaccgag 780
agcaucaaag ugcgcgugau cgacguggac cugaacgacu acagcaucac ccugcaagug 840
cggcugcccc ugcugaccag acugcugaac acccagaucu acaaggugga cagcaucucc 900
uacaacaucc agaaccgcga gugguacauc ccucugccca gccacauuau gaccaagggc 960
gccuuucugg gcggagccga cgugaaagag ugcaucgagg ccuucagcag cuacaucugc 1020
cccagcgacc cuggcuucgu gcugaaccac gagauggaaa gcugccugag cggcaacauc 1080
agccagugcc ccagaaccac cgugaccucc gacaucgugc ccagauacgc cuucgugaau 1140
ggcggcgugg uggccaacug caucaccacc accuguaccu gcaacggcau cggcaaccgg 1200
aucaaccagc cucccgauca gggcgugaag auuaucaccc acaaagagug uaacaccauc 1260
ggcaucaacg gcaugcuguu caauaccaac aaagagggca cccuggccuu cuacaccccc 1320
gacgauauca cccugaacaa cuccguggcu cuggacccca ucgacaucuc caucgagcug 1380
aacaaggcca agagcgaccu ggaagagucc aaagagugga uccggcggag caaccagaag 1440
cuggacucua ucggcagcug gcaccagagc agcaccacca ucaucgugau ccugauuaug 1500
augauuaucc uguucaucau caacauuacc aucaucacua ucgccauuaa guacuaccgg 1560
auccagaaac ggaaccgggu ggaccagaau gacaagcccu acgugcugac aaacaag 1617

<210> SEQ ID NO 65
<211> LENGTH: 4062
<212> TYPE: RNA
<213> ORGANISM: Middle East respiratory syndrome coronavirus

<400> SEQUENCE: 65
augauacacu caguguuucu acugauguuc uuguuaacac cuacagaaag uuacguugau 60
guagggccag auucuguuaa gucugcuugu auugagguug auauacaaca gaccuucuuu 120
gauaaaacuu ggccuaggcc aauugauguu ucuaaggcug acgguauuau auacccucaa 180
ggccguacau auucuaacau aacuaucacu uaucaagguc uuuuucccua ucagggagac 240
cauggugaua uguauguuua cucugcagga caugcuacag gcacaacucc acaaaaguug 300
uuuguagcua acuauucuca ggacgucaaa caguuugcua augggguuugu cguccguaua 360 ggagcagcug ccaauuccac uggcacuguu auuauuagcc caucuaccag cgcuacuaua 420
cgaaaaauuu acccugcuuu uaugcugggu ucuucaguug guaauuucuc agaugguaaa 480
augggccgcu ucuucaauca uacucuaguu cuuuugcccg auggaugugg cacuuuacuu 540
agagcuuuuu auuguauucu agagccucgc ucuggaaauc auuguccugc uggcaauucc 600
uauacuucuu uugccacuua ucacacuccu gcaacagauu guucugaugg caauuacaau 660
cguaaugcca gucugaacuc uuuuaaggag uauuuuaauu uacguaacug caccuuuaug 720
uacacuuaua acauuaccga agaugagauu uuagaguggu uuggcauuac acaaacugcu 780
caagguguuc accucuucuc aucucgguau guugauuugu acggcggcaa uauguuucaa 840
uuugccaccu ugccuguuua ugauacuauu aaguauuauu cuaucauucc ucacaguauu 900
cguucuaucc aaagugauag aaaagcuugg gcugccuucu acguauauaa acuucaaccg 960
uuaacuuucc uguuggauuu uucuguugau gguuauauac gcagagcuau agacuguggu 1020
uuuaaugauu ugucacaacu ccacugcuca uaugaauccu ucgauguuga aucuggaguu 1080
uauucaguuu cgucuuucga agcaaaaccu ucuggcucag uuguggaaca ggcugaaggu 1140
guugaaugug auuuuucacc ucuucugucu ggcacaccuc cucagguuua uaauuucaag 1200
cguuugguuu uuaccaauug caauuauaau cuuaccaaau ugcuuucacu uuuuucugug 1260
aaugauuuua cuuguaguca aauaucucca gcagcaauug cuagcaacug uuauucuuca 1320
cugauuuugg auuauuuuuc auacccacuu aguaugaaau ccgaucucag uguuaguucu 1380
gcugguccaa uaucccaguu uaauuauaaa caguccuuuu cuaaucccac auguuugauc 1440
uuagcgacug uuccucauaa ccuuacuacu auuacuaagc cucuuaagua cagcuauauu 1500
aacaagugcu cucgucuucu uucugaugau cguacugaag uaccucaguu agugaacgcu 1560
aaucaauacu cacccugugu auccauuguc ccauccacug ugugggaaga cggugauuau 1620
uauaggaaac aacuaucucc acuugaaggu gguggcuggc uuguugcuag uggcucaacu 1680
guugccauga cugagcaauu acagaugggc uuugguauua caguucaaua ugguacagac 1740
accaauagug uuugccccaa gcuugaauuu gcuaaugaca caaaaauugc cucucaauua 1800
ggcaauugcg uggaauauuc ccucuauggu guuucgggcc guggugu uuu ucagaauugc 1860 acagcuguag guguucgaca gcagcgcuuu guuuaugaug cguaccagaa uuuaguuggc 1920
uauuauucug augauggcaa cuacuacugu cugcgugcuu guguuagugu uccuguuucu 1980
gucaucuaug auaaagaaac uaaaacccac gcuacucuau uugguagugu ugcaugugaa 2040
cacauuucuu cuaccauguc ucaauacucc cguucuacgc gaucaaugcu uaaacggcga 2100
gauucuacau auggcccccu ucagacaccu guugguugug uccuaggacu uguuaauucc 2160
ucuuuguucg uagaggacug caaguugccu cucggucaau cucucugugc ucuuccugac 2220
acaccuagua cucucacacc ucgcagugug cgcucugugc caggugaaau gcgcuuggca 2280
uccauugcuu uuaaucaucc cauucagguu gaucaacuua auaguaguua uuuuaaauua 2340
aguauaccca cuaauuuuuc cuuuggugug acucaggagu acauucagac aaccauucag 2400
aaaguuacug uugauuguaa acaguacguu ugcaaugguu uccagaagug ugagcaauua 2460
cugcgcgagu auggccaguu uuguuccaaa auaaaccagg cucuccaugg ugccaauuua 2520
cgccaggaug auucuguacg uaauuuguuu gcgagcguga aaagcucuca aucaucuccu 2580
aucauaccag guuuuggagg ugacuuuaau uugacacuuc uagaaccugu uucuauaucu 2640
acuggcaguc guagugcacg uagugcuauu gaggauuugc uauuugacaa agucacuaua 2700
gcugauccug guuauaugca agguuacgau gauuguaugc agcaaggucc agcaucagcu 2760
cgugaucuua uuugugcuca auauguggcu gguuauaaag uauuaccucc ucuuauggau 2820
guuaauaugg aagccgcgua uacuucaucu uugcuuggca gcauagcagg uguuggcugg 2880
acugcuggcu uauccuccuu ugcugcuauu ccauuugcac agaguauyuu uuauagguua 2940
aacgguguug gcauuacuca acagguucuu ucagagaacc aaaagcuuau ugccaauaag 3000
uuuaaucagg cucugggagc uaugcaaaca ggcuucacua caacuaauga agcuuuucgg 3060
aagguucagg augcugugaa caacaaugca caggcucuau ccaaauuagc uagcgagcua 3120
ucuaauacuu uuggugcuau uuccgccucu auuggagaca ucauacaacg ucuugauguu 3180
cucgaacagg acgcccaaau agacagacuu auuaauggcc guuugacaac acuaaaugcu 3240
uuuguugcac agcagcuugu ucguuccgaa ucagcugcuc uuuccgcuca auuggcuaaa 3300
gauaaaguca augagugugu caaggcacaa uccaagcguu cuggauuuug cggucaaggc 3360
acacauauag uguccuuugu uguaaaugcc ccuaauggcc uuuacuuuau gcauguuggu 3420
uauuacccua gcaaccacau ugagguuguu ucugcuuaug gucuuugcga ugcagcuaac 3480

-continued ccuacuaauu guauagcccc uguuaauggc uacuuuauua aaacuaauaa cacuaggauu 3540
guugaugagu ggucauauac uggcucgucc uucuaugcac cugagcccau caccucucuu 3600
aauacuaagu auguugcacc acaggugaca uaccaaaaca uuucuacuaa ccucccuccu 3660
ccucuucucg gcaauuccac cgggauugac uuccaagaug aguuggauga guuuuucaaa 3720
aauguuagca ccaguauacc uaauuuuggu ucucuaacac agauuaauac uacauuacuc 3780
gaucuuaccu acgagauguu gucucuucaa caaguuguua aagcccuuaa ugagucuuac 3840
auagaccuua aagagcuugg caauuauacu uauuacaaca aauggccgug guacauuugg 3900
cuugguuuca uugcugggcu uguugccuua gcucuaugcg ucuucuucau acugugcugc 3960
acugguugug gcacaaacug uaugggaaaa cuuaagugua aucguuguug ugauagauac 4020
gaggaauacg accucgagcc gcauaagguu cauguucacu aa 4062

<210> SEQ ID NO 66
<211> LENGTH: 4062
<212> TYPE: RNA
<213> ORGANISM: Artificial Sequence
<220> FEATURE:
<223> OTHER INFORMATION: Synthetic Polynucleotide

<400> SEQUENCE: 66
augauacacu caguguuucu acugauguuc uuguuaacac cuacagaaag uuacguugau 60
guagggccag auucuguuaa gucugcuugu auugagguug auauacaaca gacuuucuuu 120
gauaaaacuu ggccuaggcc aauugauguu ucuaaggcug acgguauuau auacccucaa 180
ggccguacau auucuaacau aacuaucacu uaucaagguc uuuuucccua ucagggagac 240
cauggugaua uguauguuua cucugcagga caugcuacag gcacaacucc acaaaaguug 300
uuuguagcua acuauucuca ggacgucaaa caguuugcua augguuugu cguccguaua 360 ggagcagcug ccaauuccac uggcacuguu auuauuagcc caucuaccag cgcuacuaua 420
cgaaaaauuu acccugcuuu uaugcugggu ucuucaguug guaauuucuc agaugguaaa 480
augggccgcu ucuucaauca uacucuaguu cuuuugcccg auggaugugg cacuuuacuu 540
agagcuuuuu auuguauucu ggagccucgc ucuggaaauc auuguccugc uggcaauucc 600
uauacuucuu uugccacuua ucacacuccu gcaacagauu guucugaugg caauuacaau 660
cguaaugcca gucugaacuc uuuuaaggag uauuuuaauu uacguaacug caccuuuaug 720
uacacuuaua acauuaccga agaugagauu uuagaguggu uuggcauuac acaaacugcu 780
caagguguuc accucuucuc aucucgguau guugauuugu acggcggcaa uauguuucaa 840
uuugccaccu ugccuguuua ugauacuauu aaguauuauu cuaucauucc ucacaguauu 900
cguucuaucc aaagugauag aaaagcuugg gcugccuucu acguauauaa acuucaaccg 960
uuaacuuucc uguuggauuu uucuguugau gguuauauac gcagagcuau agacuguggu 1020
uuuaaugauu ugucacaacu ccacugcuca uaugaauccu ucgauguuga aucuggaguu 1080
uauucaguuu cgucuuucga agcaaaaccu ucuggcucag uuguggaaca ggcugaaggu 1140
guugaaugug auuuuucacc ucuucugucu ggcacaccuc cucagguuua uaauuucaag 1200
cguuugguuu uuaccaauug caauuauaau cuuaccaaau ugcuuucacu uuuuucugug 1260
aaugauuuua cuuguaguca aauaucucca gcagcaauug cuagcaacug uuauucuuca 1320
cugauuuugg auuacuuuuc auacccacuu aguaugaaau ccgaucucag uguuaguucu 1380
gcugguccaa uaucccaguu uaauuauaaa caguccuuuu cuaaucccac auguuugauu 1440

-continued

```
uuagcgacug uuccucauaa ccuuacuacu auuacuaagc cucuuaagua cagcuauauu   1500
aacaagugcu cucgucuucu uucugaugau cguacugaag uaccucaguu agugaacgcu   1560
aaucaauacu cacccugugu auccauuguc ccauccacug ugugggaaga cggugauuau   1620
uauaggaaac aacuaucucc acuugaaggu gguggcuggc uuguugcuag uggcucaacu   1680
guugccauga cugagcaauu acagaugggc uuugguauua caguucaaua ugguacagac   1740
accaauagug uuugccccaa gcuugaauuu gcuaaugaca caaaaauugc cucucaauua   1800
ggcaauugcg uggaauauuc ccucuauggu guuucgggcc guggugcuuu ucagaauugc   1860
acagcuguag guguucgaca gcagcgcuuu guuuaugaug cguaccagaa uuuaguuggc   1920
uauuauucug augauggcaa cuacuacugu uugcgugcuu guguuagugu uccuguuucu   1980
gucaucuaug auaaagaaac uaaaacccac gcuacucuau uugguagugu ugcaugugaa   2040
cacauuucuu cuaccauguc ucaauacucc cguucuacgc gaucaaugcu uaaacggcga   2100
gauucuacau auggcccccu ucagacaccu guugguugug uccuaggacu uguuaauucc   2160
ucuuuguucg uagaggacug caaguugccu cuuggucaau cucucugugc ucuuccugac   2220
acaccuagua cucucacacc ucgcagugug cgcucuguuc caggugaaau gcgcuuggca   2280
uccauugcuu uuaaucaucc uauucagguu gaucaacuua auaguaguua uuuuaaauua   2340
aguauaccca cuaauuuuuc cuuuggugug acucaggagu acauucagac aaccauucag   2400
aaaguuacug uugauuguaa acaguacguu ugcaaugguu uccagaagug ugagcaauua   2460
cugcgcgagu auggccaguu uuguuccaaa auaaaccagg cucuccaugg ugccaauuua   2520
cgccaggaug auucuguacg uaauuuguuu gcgagcguga aaagcucuca aucaucuccu   2580
aucauaccag guuuuggagg ugacuuuaau uugacacuuc uggaaccugu uucuauaucu   2640
acuggcaguc guagugcacg uagugcuauu gaggauuugc uauuugacaa agucacuaua   2700
gcugauccug guuauaugca agguuacgau gauugcaugc agcaaggucc agcaucagcu   2760
cgugaucuua uuugugcuca auauguggcu gguuacaaag uauuaccucc ucuuauggau   2820
guuaauaugg aagccgcgua uacuucaucu uugcuuggca gcauagcagg uguuggcugg   2880
acugcuggcu uauccuccuu ugcugcuauu ccauuugcac agaguaucuu uuauagguua   2940
aacggguguug gcauuacuca acagguucuu ucagagaacc aaaagcuuau ugccaauaag   3000
uuuaaucagg cucugggagc uaugcaaaca ggcuucacua caacuaauga agcuuuucag   3060
aagguucagg augcugugaa caacaaugca caggcucuau ccaaauuagc uagcgagcua   3120
ucuaauacuu uuggugcuau uuccgccucu auuggagaca ucauacaacg ucuugauguu   3180
cucgaacagg acgcccaaau agacagacuu auuaauggcc guuugacaac acuaaaugcu   3240
uuuguugcac agcagcuugu ucguuccgaa ucagcugcuc uuuccgcuca auuggcuaaa   3300
gauaaaguca augagugugu caaggcacaa uccaagcguu cuggauuuug cggucaaggc   3360
acacauauag uguccuuugu uguaaaugcc ccuaauggcc uuuacuucau gcauguuggu   3420
uauuacccua gcaaccacau ugagguuguu ucugcuuaug gucuuugcga ugcagcuaac   3480
ccuacuaauu guauagcccc uguuaauggc uacuuuauua aaacuaauaa cacuaggauu   3540
guugaugagu ggucauauac uggcucgucc uucuaugcac cugagcccau uaccucccuu   3600
aauacuaagu auguugcacc acaggugaca uaccaaaaca uuucuacuaa ccucccuccu   3660
ccucuucucg gcaauuccac cgggauugac uuccaagaug aguuggauga guuuuucaaa   3720
aauguuagca ccaguauacc uaauuuuggu ucccuaacac agauuaauac uacauuacuc   3780
gaucuuaccu acgagauguu gucucuucaa caaguuguua aagcccuuaa ugagucuuac   3840
```

auagaccuua aagagcuugg caauuauacu uauuacaaca aauggccgug guacauuugg 3900
cuugguuuca uugcugggcu uguugccuua gcucuaugcg ucuucuucau acugugcugc 3960
acugguugug gcacaaacug uaugggaaaa cuuaagugua aucguuguug ugauagauac 4020
gaggaauacg accucgagcc gcauaagguu cauguucacu aa 4062

<210> SEQ ID NO 67
<211> LENGTH: 1845
<212> TYPE: RNA
<213> ORGANISM: Artificial Sequence
<220> FEATURE:
<223> OTHER INFORMATION: Synthetic Polynucleotide

<400> SEQUENCE: 67
augauccacu ccguguuccu ccucauguuc cuguugaccc ccacugaguc agacugcaag 60 cuccccgcugg gacaguccu gugugcgcug ccugacacuc cuagcacucu gaccccacgc 120
uccgugcggu cggugccugg cgaaaugcgg cuggccucca ucgccuucaa ucacccaauc 180
caaguggauc agcugaauag cucguauuuc aagcugucca uccccacgaa cuucucguuc 240
ggggucaccc aggaguacau ccagaccaca auucagaagg ucaccgucga uugcaagcaa 300
uacgugugca acggcuucca gaagugcgag cagcugcuga gagaauacgg gcaguuuugc 360
agcaagauca accaggcgcu gcauggagcu aacuugcgcc aggacgacuc cgugcgcaac 420
cucuuugccu cugugaaguc aucccagucc uccccaauca ucccgggauu cggaggggac 480
uucaaccuga cccuccugga gcccgugucg aucagcaccg guagcagauc ggcgcgcuca 540
gccauugaag aucuucuguu cgacaagguc accaucgccg auccgggcua caugcaggga 600
uacgacgacu guaugcagca gggaccagcc uccgcgaggg accucaucug cgcgcaauac 660
guggccgggu acaaagugcu gccuccucug auggauguga acauggaggc cgcuuauacu 720 ucguccugc ucggcucuau cgccggcgug ggguggaccg ccggccuguc cuccuucgcc 780 gcuaucccu uugcacaauc cauuuucuac cggcucaacg gcgugggcau uacucaacaa 840
guccugucgg agaaccagaa guugaucgca aacaaguuca aucaggcccu gggggccaug 900
cagacuggau ucacuacgac uaacgaagcg uuccagaagg uccaggacgc ugugaacaac 960
aacgcccagg cgcucucaaa gcuggccucc gaacucagca acaccuucgg agccaucagc 1020
gcaucgaucg gugacauaau ucagcggcug gacgugcugg agcaggacgc ccagaucgac 1080
cgccucauca acggacggcu gaccaccuug aaugccuucg uggcacaaca gcugguccgg 1140
agcgaaucag cggcacuuuc cgcccaacuc gccaaggaca aagucaacga augcgugaag 1200
gcccagucca agagguccgg uuucugcggu caaggaaccc auauuguguc cuucgucgug 1260
aacgcgccca acggucugua cuuuaugcac gucggcuacu acccgagcaa ucauaucgaa 1320 guggguccg ccuacggccu gugcgaugcc gcuaacccca cuaacuguau ugccccugug 1380
aacggauauu uuauuaagac caacaacacc cgcauugugg acgaaugguc auacaccggu 1440
ucguccuucu acgcgcccga gcccaucacu ucacugaaca ccaaauacgu ggcuccgcaa 1500
gugaccuacc agaacaucuc caccaauuug ccgccgccgc ugcucggaaa cagcaccgga 1560
auugauuucc aagaugaacu ggacgaauuc uucaagaacg uguccacuuc cauucccaac 1620
uucggaagcc ugacacagau caacaccacc cuucucgacc ugaccuacga gaugcugagc 1680
cuucaacaag uggucaaggc ccugaacgag agcuacaucg accugaagga gcugggcaac 1740
uauaccuacu acaacaagug gccggacaag auugaggaga uucugucgaa aaucuaccac 1800

-continued auugaaaacg agaucgccag aaucaagaag cuuaucggcg aagcc 1845

<210> SEQ ID NO 68
<211> LENGTH: 4071
<212> TYPE: RNA
<213> ORGANISM: Artificial Sequence
<220> FEATURE:
<223> OTHER INFORMATION: Synthetic Polynucleotide

<400> SEQUENCE: 68
auggaaaccc cugcccagcu gcuguuccug cugcugcugu ggcugccuga uaccaccggc 60
agcuaugugg acgugggccc cgauagcgug aaguccgccu guaucgaagu ggacauccag 120
cagaccuuuu ucgacaagac cuggcccaga cccaucgacg uguccaaggc cgacggcauc 180
aucuauccac aaggccggac cuacagcaac aucaccauua ccuaccaggg ccuguuccca 240
uaucaaggcg accacggcga uauguacgug uacucugccg gccacgccac cggcaccaca 300
ccccagaaac uguucguggc caacuacagc caggacguga agcaguucgc caacggcuuc 360
gucgugcgga uuggcgccgc ugccaauagc accggcacag ugaucaucag ccccagcacc 420
agcgccacca uccggaagau cuaccccgcc uucaugcugg gcagcuccgu gggcaauuuc 480
agcgacggca agaugggccg guucuucaac cacacccugg ugcugcugcc cgauggcugu 540
ggcacacugc ugagagccuu cuacugcauc cuggaaccca gaagcggcaa ccacugcccu 600
gccggcaaua gcuacaccag cuucgccacc uaccacacac ccgccaccga uugcuccgac 660
ggcaacuaca accggaacgc cagccugaac agcuucaaag aguacuucaa ccugcggaac 720
ugcaccuuca uguacaccua caauaucacc gaggacgaga uccuggaaug guucggcauc 780
acccagaccg cccagggcgu gcaccuguuc agcagcagau acguggaccu guacggcggc 840
aacauguucc aguuugccac ccugcccgug uacgacacca ucaaguacua cagcaucauc 900
ccccacagca uccgguccau ccagagcgac agaaaagccu gggccgccuu cuacguguac 960
aagcugcagc cccugaccuu ccugcuggac uucagcgugg acggcuacau cagacgggcc 1020
aucgacugcg gcuucaacga ccugagccag cugcacugcu ccuacgagag cuucgacgug 1080
gaaagcggcg uguacagcgu guccagcuuc gaggccaagc cuagcggcag cgugguggaa 1140
caggcugagg gcguggaaug cgacuucagc ccucugcuga gcggcacccc uccccaggug 1200
uacaacuuca agcggcuggu guucaccaac ugcaauuaca accugaccaa gcugcugagc 1260
cuguucuccg ugaacgacuu caccuguagc cagaucagcc cugccgccau ugccagcaac 1320
ugcuacagca gccugauccu ggacuacuuc agcuaccccc ugagcaugaa guccgaucug 1380
agcguguccu ccgccggacc caucagccag uucaacuaca agcagagcuu cagcaacccu 1440
accugccuga uucuggccac cgugccccac aaucugacca ccaucaccaa gccccugaag 1500
uacagcuaca ucaacaagug cagcagacug cuguccgacg accggaccga agugccccag 1560
cucgugaacg ccaaccagua cagccccugc guguccaucg ugcccagcac cgugugggag 1620
gacggcgacu acuacagaaa gcagcugagc cccccuggaag gcggcggaug gcugguggcu 1680
ucuggaagca caguggccau gaccgagcag cugcagaugg gcuuuggcau caccgugcag 1740
uacggcaccg acaccaacag cgugugcccc aagcuggaau ucgccaauga caccaagauc 1800
gccagccagc ugggaaacug cguggaauac ucccuguaug gcguguccgg acggggcgug 1860
uuccagaauu gcacagcagu gggagugcgg cagcagagau ucguguacga ugccuaccag 1920
aaccucgugg gcuacuacag cgacgacggc aauuacuacu gccugcgggc cugugugucc 1980
gugcccgugu ccgugaucua cgacaaagag acaaagaccc acgccacacu guucggcucc 2040
guggccugcg agcacaucag cuccaccaug agccaguacu cccgcuccac ccgguccaug 2100
cugaagcgga gagauagcac cuacggcccc cugcagacac cugugggaug ugugcugggc 2160
cucgugaaca gcucccuguu uguggaagau ugcaagcugc cccugggcca gagccugugu 2220
gcccugccag auaccccuag cacccugacc ccuagaagcg ugcgcucugu gcccggcgaa 2280
augcggcugg ccucuaucgc cuucaaucac cccauccagg uggaccagcu gaacuccagc 2340
uacuucaagc ugagcauccc caccaacuuc agcuucggcg ugacccagga guacauccag 2400
accacaaucc agaaagugac cguggacugc aagcaguacg ugugcaacgg cuuucagaag 2460
ugcgaacagc ugcugcgcga guacggccag uucugcagca agaucaacca ggcccugcac 2520
ggcgccaacc ugagacagga ugacagcgug cggaaccugu ucgccagcgu gaaaagcagc 2580
caguccagcc ccaucauccc uggcuucggc ggcgacuuua accugacccu gcuggaaccu 2640
guguccauca gcaccggcuc cagaagcgcc agauccgcca ucgaggaccu gcuguucgac 2700
aaagugacca uugccgaccc cggcuacaug cagggcuacg acgauugcau gcagcagggc 2760
ccagccagcg ccagggaucu gaucugugcc caguaugugg ccggcuacaa ggugcugccc 2820
ccccugaugg acgugaacau ggaagccgcc uacaccucca gccugcuggg cucuauugcu 2880
ggcgugggau ggacagccgg ccugucuagc uuugccgcca ucccuuucgc ccagagcauc 2940
uucuaccggc ugaacggcgu gggcaucaca caacaggugc ugagcgagaa ccagaagcug 3000
aucgccaaca aguuuaacca ggcacugggc gccaugcaga ccggcuucac caccaccaac 3060
gaggccuuca gaaaggugca ggacgccgug aacaacaacg cccaggcucu gagcaagcug 3120
gccuccgagc ugagcaauac cuucggcgcc aucagcgccu ccaucggcga caucauccag 3180
cggcuggacg ugcuggaaca ggacgcccag aucgaccggc ugaucaacgg cagacugacc 3240
acccugaacg ccuucguggc acagcagcuc gugcggagcg aaucugccgc ucugucugcu 3300
cagcuggcca aggacaaagu gaacgagugc gugaaggccc aguccaagcg gagcggcuuu 3360
uguggccagg gcacccacau cguguccuuc gucgugaaug cccccaacgg ccuguacuuu 3420
augcacgugg gcuauuaccc cagcaaccac aucgaggugg uguccgccua uggccugugc 3480
gacgccgcca auccuaccaa cuguaucgcc cccgugaacg gcuacuucau caagaccaac 3540
aacacccgga ucguggacga gugguccuac acaggcagca gcuucuacgc ccccgagccc 3600
aucaccuccc ugaacaccaa auacguggcc ccccaaguga cauaccagaa caucuccacc 3660
aaccugcccc cuccacugcu gggaaauucc accggcaucg acuuccagga cgagcuggac 3720
gaguucuuca agaacguguc caccuccauc cccaacuucg gcagccugac ccagaucaac 3780
accacucugc uggaccugac cuacgagaug cugucccugc aacaggucgu gaaagcccug 3840
aacgagagcu acaucgaccu gaaagagcug ggaacuaca ccuacuacaa caaguggccu 3900
ugguacauuu ggcugggcuu uaucgccggc cugguggccc uggcccugug cguguucuuc 3960
auccugugcu gcaccggcug cggcaccaau ugcaugggca agcugaaaug caaccggugc 4020
ugcgacagau acgaggaaua cgaccuggaa ccucacaaag ugcaugugca c 4071

<210> SEQ ID NO 69
<211> LENGTH: 1864
<212> TYPE: RNA
<213> ORGANISM: Artificial Sequence
<220> FEATURE:
<223> OTHER INFORMATION: Synthetic Polynucleotide

<400> SEQUENCE: 69

```
ucaagcuuuu ggacccucgu acagaagcua auacgacuca cuauagggaa auaagagaga     60
aaagaagagu aagaagaaau auaagagcca ccaugggucu caaggugaac gucucugccg    120
uauucauggc aguacuguua acucuccaaa cacccgccgg ucaaauucau uggggcaauc    180
ucucuaagau aggggguagua ggaauaggaa gugcaagcua caaaguuaug acucguucca    240
gccaucaauc auuagucaua aaauuaaugc ccaauauaac ucuccucaau aacugcacga    300
ggguagagau ugcagaauac aggagacuac uaagaacagu uuuggaacca auuagggaug    360
cacuuaaugc aaugacccag aacauaaggc cgguucagag cguagcuuca aguaggagac    420
acaagagauu ugcgggagua guccuggcag gugcggcccu agguguugcc acagcugcuc    480
agauaacagc cggcauugca cuucaccggu ccaugcugaa cucucaggcc aucgacaauc    540
ugagagcgag ccuggaaacu acuaaucagg caauugaggc aaucagacaa gcagggcagg    600
agaugauauu ggcuguucag gguguccaag acuacaucaa uaaugagcug auaccgucua    660
ugaaccagcu aucuugugau cuaaucgguc agaagcucgg gcucaaauug cuuagauacu    720
auacagaaau ccugucauua uuuggcccca gccuacggga ccccauaucu gcggagauau    780
cuauccaggc uuugaguuau gcacuuggag gagauaucaa uaaggugua gaaaagcucg    840
gauacagugg aggcgauuua cuaggcaucu uagagagcag aggaauaaag gcucggauaa    900
cucacgucga cacagagucc uacuucauag uccucaguau agccuauccg acgcuguccg    960
agauuaaggg ggugauuguc caccggcuag agggggucuc guacaacaua ggcucucaag   1020
agugguauac cacugugccc aaguauguug caacccaagg guaccuuauc ucgaauuuug   1080
augagucauc auguacuuuc augccagagg ggacugugug cagccaaaau gccuuguacc   1140
cgaugagucc ucugcuccaa gaaugccucc gggggucccac caaguccugu gcucguacac   1200
ucguauccgg gucuuuuggg aaccgguuca uuuuaucaca agggaaccua auagccaauu   1260
gugcaucaau ucuuuguaag uguuacacaa cagguacgau uauuaaucaa gacccugaca   1320
agauccuaac auacauugcu gccgaucgcu gcccgguagu cgaggugaac ggcgugacca   1380
uccaagucgg gagcaggagg uauccagacg cuguguacuu gcacagaauu gaccucgguc   1440
cucccauauc auuggagagg uuggacguag ggacaaaucu ggggaaugca auugccaaau   1500
uggaggaugc caaggaauug uuggaaucau cggaccagau auugagaagu augaaaggu   1560
uaucgagcac uagcauaguc uacauccuga uugcagugug ucuuggaggg uugauaggga   1620
uccccacuuu aauauguugc ugcagggggc guuguaacaa aaagggagaa caaguuggua   1680
ugucaagacc aggccuaaag ccugaccuua caggaacauc aaaauccuau guaagaucgc   1740
uuugaugaua auaggcugga gccucggugg ccaagcuucu ugccccuugg gccucccccc   1800
agccccuccu ccccuuccug cacccguacc cccguggucu uugaauaaag ucugaguggg   1860
cggc                                                                1864
```

```
<210> SEQ ID NO 70
<211> LENGTH: 1653
<212> TYPE: RNA
<213> ORGANISM: Artificial Sequence
<220> FEATURE:
<223> OTHER INFORMATION: Synthetic Polynucleotide

<400> SEQUENCE: 70

augggucuca aggugaacgu cucugccgua uucauggcag uacuguuaac ucuccaaaca     60
cccgccgguc aaauucauug gggcaaucuc ucuaagauag ggguaguagg aauaggaagu    120
gcaagcuaca aaguuaugac ucguuccagc caucaaucau uagucauaaa auuaaugccc    180
```

aauauaacuc uccucaauaa cugcacgagg guagagauug cagaauacag gagacuacua 240
agaacaguuu uggaaccaau uagggaugca cuuaaugcaa ugacccagaa cauaaggccg 300
guucagagcg uagcuucaag uaggagacac aagagauuug cgggaguagu ccuggcaggu 360
gcggcccuag guguugccac agcugcucag auaacagccg gcauugcacu ucaccggucc 420
augcugaacu cucaggccau cgacaaucug agagcgagcc uggaaacuac uaaucaggca 480
auugaggcaa ucagacaagc agggcaggag augauauugg cuguucaggg uguccaagac 540
uacaucaaua augagcugau accgucuaug aaccagcuau cuugugaucu aaucggucag 600
aagcucgggc ucaaauugcu uagauacuau acagaaaucc ugucauuauu uggccccagc 660
cuacgggacc ccauaucugc ggagauaucu auccaggcuu ugaguuaugc acuuggagga 720
gauaucaaua agguguuaga aaagcucgga uacaguggag gcgauuuacu aggcaucuua 780
gagagcagag gaauaaaggc ucggauaacu cacgucgaca cagaguccua cuucauaguc 840
cucaguauag ccuauccgac gcuguccgag auuaaggggg ugauugucca ccggcuagag 900
ggggucucgu acaacauagg cucucaagag ugguauacca cugugcccaa guauguugca 960
acccaagggu accuuaucuc gaauuuugau gagucaucau guacuuucau gccagagggg 1020
acugugugca gccaaaaugc cuuguacccg augaguccuc ugcuccaaga augccuccgg 1080
ggguccacca aguccugugc ucguacacuc guauccgggu cuuuugggaa ccgguucauu 1140
uuaucacaag ggaaccuaau agccaauugu gcaucaauuc uuuguaagug uuacacaaca 1200
gguacgauua uuaaucaaga cccugacaag auccuaacau acauugcugc cgaucgcugc 1260
ccgguagucg aggugaacgg cgugaccauc caagucggga gcaggaggua uccagacgcu 1320
guguacuugc acagaauuga ccucgguccu cccauaucau uggagagguu ggacguaggg 1380
acaaaucugg ggaaugcaau ugccaaauug gaggaugcca aggaauuguu ggaaucaucg 1440
gaccagauau ugagaaguau gaaagguuua ucgagcacua gcauagucua cauccugauu 1500 gcagugugu c uuggagggguu gauagggauc cccacuuuaa uauguugcug caggggggcgu 1560 uguaacaaaa agggagaaca aguugguaug ucaagaccag gccuaaagcc ugaccuuaca 1620
ggaacaucaa aauccuaugu aagaucgcuu uga 1653

<210> SEQ ID NO 71
<211> LENGTH: 1925
<212> TYPE: RNA
<213> ORGANISM: Artificial Sequence
<220> FEATURE:
<223> OTHER INFORMATION: Synthetic Polynucleotide

<400> SEQUENCE: 71
ggggaaauaa gagagaaaag aagaguaaga agaaauauaa gagccaccau gggucucaag 60
gugaacgucu cugccguauu cauggcagua cuguuaacuc uccaaacacc cgccggucaa 120
auucauuggg gcaaucucuc uaagauaggg guaguaggaa uaggaagugc aagcuacaaa 180
guuaugacuc guuccagcca ucaaucauua gucauaaaau uaaugcccaa uauaacucuc 240
cucaauaacu gcacgagggu agagauugca gaauacagga gacuacuaag aacaguuuug 300
gaaccaauua gggaugcacu uaaugcaaug acccagaaca uaaggccggu ucagagcgua 360
gcuucaagua ggagacacaa gagauuugcg ggaguagucc uggcaggugc ggcccuaggu 420
guugccacag cugcucagau aacagccggc auugcacuuc accgguccau gcugaacucu 480
caggccaucg acaaucugag agcgagccug gaaacuacua aucaggcaau ugaggcaauc 540
agacaagcag ggcaggagau gauauuggcu guucagggug uccaagacua caucaauaau 600
gagcugauac cgucuaugaa ccagcuaucu ugugaucuaa ucggucagaa gcucgggcuc 660
aaauugcuua gauacuauac agaaauccug ucauuauuug gccccagccu acgggacccc 720
auaucugcgg agauaucuau ccaggcuuug aguuaugcac uuggaggaga uaucaauaag 780
guguuagaaa agcucggaua caguggaggc gauuuacuag gcaucuuaga gagcagagga 840
auaaaggcuc ggauaacuca cgucgacaca gaguccuacu ucauaguccu caguauagcc 900
uauccgacgc uguccgagau uaagggggug auuguccacc ggcuagaggg ggucucguac 960
aacauaggcu cucaagagug guauaccacu gugcccaagu auguugcaac ccaaggguac 1020
cuuaucucga auuuugauga gucaucaugu acuuucaugc cagaggggac ugugugcagc 1080
caaaaugccu uguacccgau gaguccucug cuccaagaau gccuccgggg guccaccaag 1140
uccugugcuc guacacucgu auccgggucu uuugggaacc gguucauuuu aucacaaggg 1200
aaccuaauag ccaauugugc aucaauucuu uguaaguguu acacaacagg uacgauuauu 1260
aaucaagacc cugacaagau ccuaacauac auugcugccg aucgcugccc gguagucgag 1320
gugaacggcg ugaccaucca agucgggagc aggagguauc cagacgcugu guacuugcac 1380
agaauugacc ucgguccucc cauaucauug gagagguugg acguagggac aaaucugggg 1440
aaugcaauug ccaaauugga ggaugccaag gaauuguugg aaucaucgga ccagauauug 1500
agaaguauga aagguuuauc gagcacuagc auagucuaca uccugauugc agugugucuu 1560
ggaggguuga uagggauccc cacuuuaaua uguugcugca gggggcguug uaacaaaaag 1620
ggagaacaag uugguauguc aagaccaggc cuaaagccug accuuacagg aacaucaaaa 1680
uccuauguaa gaucgcuuug augauaauag gcuggagccu cgguggccaa gcuucuugcc 1740
ccuugggccu ccccccagcc ccuccucccc uuccugcacc cguacccccg uggucuuuga 1800
auaaagucug agugggcggc aaaaaaaaaa aaaaaaaaaa aaaaaaaaaa aaaaaaaaaa 1860
aaaaaaaaaa aaaaaaaaaa aaaaaaaaaa aaaaaaaaaa aaaaaaaaaa aaaaaaaaaa 1920
ucuag 1925

<210> SEQ ID NO 72
<211> LENGTH: 1864
<212> TYPE: RNA
<213> ORGANISM: Artificial Sequence
<220> FEATURE:
<223> OTHER INFORMATION: Synthetic Polynucleotide

<400> SEQUENCE: 72
ucaagcuuuu ggacccucgu acagaagcua auacgacuca cuauagggaa auaagagaga 60
aaagaagagu aagaagaaau auaagagcca ccaugggucu caaggugaac gucucuguca 120
uauucauggc aguacuguua acucuucaaa cacccaccgg ucaaauccau uggggcaauc 180
ucucuaagau aggggguggua ggggguaggaa gugcaagcua caaaguuaug acucguucca 240
gccaucaauc auuagucaua aaguuaaugc ccaauauaac ucuccucaac aauugcacga 300
ggguagggau ugcagaauac aggagacuac ugagaacagu ucuggaacca auuagagaug 360
cacuuaaugc aaugacccag aauauaagac cgguucagag uguagcuuca aguaggagac 420
acaagagauu ugcgggaguu guccuggcag gugcggcccu aggcguugcc acagcugcuc 480
aaauaacagc cgguauugca cuucaccagu ccaugcugaa cucucaagcc aucgacaauc 540
ugagagcgag ccuagaaacu acuaaucagg caauugaggc aaucagacaa gcagggcagg 600
agaugauauu ggcuguucag ggguguccaag acuacaucaa uaaugagcug auaccgucua 660

-continued ugaaucaacu aucuugugau uuaaucggcc agaagcuagg gcucaaauug cucagauacu 720
auacagaaau ccugucauua uuuggcccca gcuuacggga ccccauaucu gcggagauau 780
cuauccaggc uuugagcuau gcgcuuggag gagauaucaa uaaggugug gaaaagcucg 840 gauacagugg aggugaucua cugggcaucu uagagagcag aggaauaaag gcccggauaa 900
cucacgucga cacagagucc uacuucauug uacucaguau agccuauccg acgcuauccg 960
agauuaaggg ggugauuguc caccggcuag agggggucuc guacaacaua ggcucucaag 1020
agugguauac cacugugccc aaguauguug caacccaagg guaccuuauc ucgaauuuug 1080
augagucauc augcacuuuc augccagagg ggacugugug cagccagaau gccuuguacc 1140
cgaugagucc ucugcuccaa gaaugccucc gggguccac uaaguccugu gcucguacac 1200
ucguauccgg gucuuucggg aaccgguuca uuuuaucaca ggggaaccua auagccaauu 1260
gugcaucaau ccuuugcaag uguuacacaa caggaacaau cauuaaucaa gacccugaca 1320
agauccuaac auacauugcu gccgaucacu gcccgguggu cgaggugaau ggcgugacca 1380
uccaagucgg gagcaggagg uauccggacg cuguguacuu gcacaggauu gaccucgguc 1440
cucccauauc uuuggagagg uuggacguag ggacaaaucu ggggaaugca auugcuaagu 1500
uggaggaugc caaggaauug uuggagucau cggaccagau auugaggagu augaaaggu 1560 uaucgagcac uaguauaguu uacauccuga uugcagugug ucuuggagga uugauaggga 1620 ucccgcuuu aauauguugc ugcaggggc guuguaacaa gaagggagaa caaguuggua 1680
ugucaagacc aggccuaaag ccugaucuua caggaacauc aaaauccuau guaaggucac 1740
ucugaugaua auaggcugga gccucggugg ccaagcuucu ugccccuugg gccucccccc 1800
agccccuccu ccccuuccug cacccguacc cccguggucu uugaauaaag ucugaguggg 1860
cggc 1864

<210> SEQ ID NO 73
<211> LENGTH: 1653
<212> TYPE: RNA
<213> ORGANISM: Artificial Sequence
<220> FEATURE:
<223> OTHER INFORMATION: Synthetic Polynucleotide

<400> SEQUENCE: 73
augggucuca aggugaacgu cucugucaua uucauggcag uacuguuaac ucuucaaaca 60
cccaccgguc aaauccauug gggcaaucuc ucuaagauag gggugguagg gguaggaagu 120
gcaagcuaca aaguuaugac ucguuccagc caucaaucau uagucauaaa guuaaugccc 180
aauauaacuc uccucaacaa uugcacgagg guagggauug cagaauacag gagacuacug 240
agaacaguuc uggaaccaau uagagaugca cuuaaugcaa ugacccagaa uauaagaccg 300
guucagagug uagcuucaag uaggagacac aagagauuug cgggaguugu ccuggcaggu 360
gcggcccuag gcguugccac agcugcucaa auaacagccg guauugcacu ucaccagucc 420
augcugaacu cucaagccau cgacaaucug agagcgagcc uagaaacuac uaaucaggca 480
auugaggcaa ucagacaagc agggcaggag augauauugg cuguucaggg uguccaagac 540
uacaucaaua augagcugau accgucuaug aaucaacuau cuugugauuu aaucggccag 600
aagcuagggc ucaaauugcu cagauacuau acagaaaucc ugucauuauu uggccccagc 660
uuacgggacc ccauaucugc ggagauaucu auccaggcuu ugagcuaugc gcuuggagga 720
gauaucaaua agguguugga aaagcucgga uacaguggag gugaucuacu gggcaucuua 780

-continued gagagcagag gaauaaaggc ccggauaacu cacgucgaca cagaguccua cuucauugua 840
cucaguauag ccuauccgac gcuauccgag auuaaggggg ugauugucca ccggcuagag 900
ggggucucgu acaacauagg cucucaagag ugguauacca cugugcccaa guauguugca 960
acccaagggu accuuaucuc gaauuuugau gagucaucau gcacuuucau gccagagggg 1020
acugugugca gccagaaugc cuuguacccg augaguccuc ugcuccaaga augccuccgg 1080
ggguccacua aguccugugc ucguacacuc guaucccggu cuuucgggaa ccgguucauu 1140
uuaucacagg ggaaccuaau agccaauugu gcaucaaucc uuugcaagug uuacacaaca 1200
ggaacaauca uuaaucaaga cccugacaag auccuaacau acauugcugc cgaucacugc 1260
ccgguggucg aggugaaugg cgugaccauc caagucggga gcaggaggua uccggacgcu 1320
guguacuugc acaggauuga ccucgguccu cccauaucuu uggagagguu ggacguaggg 1380
acaaaucugg ggaaugcaau ugcuaaguug gaggaugcca aggaauuguu ggagucaucg 1440
gaccagauau ugaggaguau gaaagguuua ucgagcacua guauaguuua cauccugauu 1500
gcagugaguc uuggaggauu gauagggauc cccgcuuuaa uauguugcug caggggggcgu 1560 uguaacaaga agggagaaca aguugguaug ucaagaccag gccuaaagcc ugaucuuaca 1620
ggaacaucaa aauccuaugu aaggucacuc uga 1653

<210> SEQ ID NO 74
<211> LENGTH: 1925
<212> TYPE: RNA
<213> ORGANISM: Artificial Sequence
<220> FEATURE:
<223> OTHER INFORMATION: Synthetic Polynucleotide

<400> SEQUENCE: 74
ggggaaauaa gagagaaaag aagaguaaga agaaauauaa gagccaccau gggucucaag 60
gugaacgucu cugucauauu cauggcagua cuguuaacuc uucaaacacc caccggucaa 120
auccauuggg gcaaucucuc uaagauaggg gugguagggg uaggaagugc aagcuacaaa 180
guuaugacuc guuccagcca ucaaucauua gucauaaagu uaaugcccaa uauaacucuc 240
cucaacaauu gcacgagggu agggauugca gaauacagga gacuacugag aacaguucug 300
gaaccaauua gagaugcacu uaaugcaaug acccagaaua uaagaccggu ucagagugua 360
gcuucaagua ggagacacaa gagauuugcg ggaguugucc uggcaggugc ggcccuaggc 420
guugccacag cugcucaaau aacagccggu auugcacuuc accaguccau gcugaacucu 480
caagccaucg acaaucugag agcgagccua gaaacuacua aucaggcaau ugaggcaauc 540
agacaagcag ggcaggagau gauauuggcu guucagggug uccaagacua caucaauaau 600
gagcugauac cgucuaugaa ucaacuaucu ugugauuuaa ucggccagaa gcuagggcuc 660
aaauugcuca gauacuauac agaaauccug ucauuauuug gccccagcuu acgggacccc 720
auaucugcgg agauaucuau ccaggcuuug agcuaugcgc uuggaggaga uaucaauaag 780
guguuggaaa agcucggaua caguggaggu gaucuacugg gcaucuuaga gagcagagga 840
auaaaggccc ggauaacuca cgucgacaca gaguccuacu ucauuguacu caguauagcc 900
uauccgacgc uauccgagau uaaggggug auuguccacc ggcuagaggg ggucucguac 960
aacauaggcu cucaagagug guauaccacu gugcccaagu auguugcaac ccaaggguac 1020
cuuaucucga auuuugauga gucaucaugc acuuucaugc cagaggggac ugugugcagc 1080
cagaaugccu uguacccgau gaguccucug cuccaagaau gccuccgggg guccacuaag 1140
uccugugcuc guacacucgu aucccggucu uucgggaacc gguucauuuu aucacagggg 1200
aaccuaauag ccaauugugc aucaauccuu ugcaaguguu acacaacagg aacaaucauu 1260
aaucaagacc cugacaagau ccuaacauac auugcugccg aucacugccc gguggucgag 1320
gugaauggcg ugaccaucca agucgggagc aggagguauc cggacgcugu guacuugcac 1380
aggauugacc ucgguccucc cauaucuuug gagagguugg acguagggac aaaucugggg 1440
aaugcaauug cuaaguugga ggaugccaag gaauuguugg agucaucgga ccagauauug 1500
aggaguauga aagguuuauc gagcacuagu auaguuuaca uccugauugc agugugucuu 1560
ggaggauuga uagggauccc cgcuuuaaua uguugcugca gggggcguug uaacaagaag 1620
ggagaacaag uugguauguc aagaccaggc cuaaagccug aucuuacagg aacaucaaaa 1680
uccuauguaa ggucacucug augauaauag gcuggagccu cgguggccaa gcuucuugcc 1740
ccuugggccu ccccccagcc ccuccucccc uuccugcacc cguacccccg uggucuuuga 1800
auaaagucug agugggcggc aaaaaaaaaa aaaaaaaaaa aaaaaaaaaa aaaaaaaaaa 1860
aaaaaaaaaa aaaaaaaaaa aaaaaaaaaa aaaaaaaaaa aaaaaaaaaa aaaaaaaaaa 1920
ucuag 1925

<210> SEQ ID NO 75
<211> LENGTH: 2065
<212> TYPE: RNA
<213> ORGANISM: Artificial Sequence
<220> FEATURE:
<223> OTHER INFORMATION: Synthetic Polynucleotide

<400> SEQUENCE: 75
ucaagcuuuu ggacccucgu acagaagcua auacgacuca cuauagggaa auaagagaga 60
aaagaagagu aagaagaaau auaagagcca ccaugucacc gcaacgagac cggauaaaug 120
ccuucuacaa agauaacccu uaucccaagg gaaguaggau aguuauuaac agagaacauc 180
uuaugauuga cagacccuau guucugcugg cuguucuguu cgucauguuu cugagcuuga 240
ucggauugcu ggcaauugca ggcauuagac uucaucgggc agccaucuac accgcggaga 300
uccauaaaag ccucaguacc aaucuggaug ugacuaacuc caucgagcau cagguucaagg 360 acgugcugac accacucuuu aaaaucaucg gggaugaagu gggccugaga acaccucaga 420
gauucacuga ccuagugaaa uucaucucgg acaagauuaa auuccuuaau ccggauaggg 480
aguacgacuu cagagaucuc acuuggugca ucaacccgcc agagaggauc aaacuagauu 540
augaucaaua cugugcagau guggcugcug aagagcucau gaaugcauug gugaacucaa 600
cucuacugga gaccagaaca accacucagu uccuagcugu cucaaaggga aacugcucag 660
ggcccacuac aaucagaggu caauucucaa acaugucgcu guccuuguug gacuuguacu 720
uaggucgagg uuacaaugug ucaucuauag ucacuaugac aucccaggga auguaugggg 780
gaaccuaccu aguugaaaag ccuaaucuga acagcaaagg gucagaguug ucacaacuga 840
gcauguaccg aguguuugaa guaggugga ucagaaaccc ggguuugggg gcuccggugu 900
uccauaugac aaacuauuuu gagcaaccag ucaguaaugg ucucggcaac uguauggugg 960
cuuuggggga gcucaaacuc gcagcccuuu gucacgggga cgauucuauc auaaaucccu 1020
aucagggauc agggaaaggu gucagcuucc agcucgucaa gcuggguguc uggaaauccc 1080
caaccgacau gcaauccugg guccccuuau caacggauga uccaguggua gacaggcuuu 1140
accucucauc ucacagaggu gucaucgcug acaaucaagc aaaaugggcu gucccgacaa 1200
cacgaacaga ugacaaguug cgaauggaga caugcuucca gcaggcgugu aaagguaaaa 1260

-continued uccaagcacu cugcgagaau cccgaguggg uaccauugaa ggauaacagg auuccuucau 1320
acgggguccu gucuguugau cugagucuga cgguugagcu uaaaaucaaa auugcuucgg 1380
gauucgggcc auugaucaca cacggcucag ggauggaccu auacaaaucc aacugcaaca 1440
auguguauug gcugacuauu ccgccaauga gaaaucuagc cuuaggcgua aucaacacau 1500
uggaguggau accgagauuc aagguuaguc ccaaccucuu cacuguccca auuaaggaag 1560
caggcgaaga cugccaugcc ccaacauacc uaccugcgga gguggacggu gaugucaaac 1620
ucaguuccaa ccuggugauu cuaccugguc aagaucucca auauguuuug gcaaccuacg 1680
auaccuccag gguugagcau gcugugguuu auuacguuua cagcccaagc cgcucauuuu 1740
cuuacuuuua uccuuuuagg uugccuauaa agggggucce aaucgaacua caaguggaau 1800
gcuucacaug ggaucaaaaa cucuggugcc gucacuucug ugugcuugcg gacucagaau 1860
ccgguggacu uaucacucac ucugggaugg ugggcauggg agucagcugc acagcuaccc 1920
gggaagaugg aaccaaucgc agauaaugau aauaggcugg agccucggug gccaagcuuc 1980
uugccccuug ggccuccccc cagccccucc uccccuuccu gcacccguac ccccguggucu 2040 uuugaauaaa gucugagugg gcggc 2065

<210> SEQ ID NO 76
<211> LENGTH: 1854
<212> TYPE: RNA
<213> ORGANISM: Artificial Sequence
<220> FEATURE:
<223> OTHER INFORMATION: Synthetic Polynucleotide

<400> SEQUENCE: 76
augucaccgc aacgagaccg gauaaaugcc uucuacaaag auaacccuua ucccaaggga 60
aguaggauag uuauuaacag agaacaucuu augauugaca gacccuaugu ucugcuggcu 120
guucuguucg ucauguuucu gagcuugauc ggauugcugg caauugcagg cauuagacuu 180
caucgggcag ccaucuacac cgcggagauc cauaaaagcc ucaguaccaa ucuggaugug 240
acuaacucca ucgagcauca ggucaaggac gugcugacac cacucuuuaa aaucaucggg 300
gaugaagugg gccugagaac accucagaga uucacugacc uagugaaauu caucucggac 360
aagauuaaau uccuuaaucc ggauagggag uacgacuuca gagaucucac uuggugcauc 420
aacccgccag agaggaucaa acuagauuau gaucaauacu gugcagaugu ggcugcugaa 480
gagcucauga augcauuggu gaacucaacu cuacuggaga ccagaacaac cacucaguuc 540
cuagcugucu caaagggaaa cugcucaggg cccacuacaa ucagagguca auucucaaac 600
augucgcugu ccuuguugga cuuguacuua ggucgagguu acaauguguc aucuauaguc 660
acuaugacau cccagggaau guaugggga accuaccuag uugaaaagcc uaaucugaac 720
agcaaagggu cagaguuguc acaacugagc auguaccgag uguuugaagu aggugugauc 780
agaaacccgg guuuggggc uccggguguuc cauaugacaa acuauuuuga gcaaccaguc 840
aguaaugguc ucggcaacug uauggugggcu uugggggagc ucaaacucgc agcccuuugu 900
cacggggacg auucuaucau aauucccuau cagggaucag ggaaaggugu cagcuuccag 960
cucgucaagc ugggugucug gaaaucccca accgacaugc aauccugggu ccccuuauca 1020
acggaugauc caguggguaga caggcuuuac cucucaucuc acagaggugu caucgcugac 1080
aaucaagcaa aaugggcugu cccgacaaca cgaacagaug acaaguugcg aauggagaca 1140
ugcuuccagc aggcguguaa agguaaaauc caagcacucu gcgagaaucc cgaguggga 1200 ccauugaagg auaacaggau uccuucauac ggggguccugu cuguugaucu gagucugacg 1260

```
guugagcuua aaaucaaaau ugcuucggga uucgggccau ugaucacaca cggcucaggg   1320

auggaccuau acaaauccaa cugcaacaau guguauuggc ugacuauucc gccaaugaga   1380

aaucuagccu uaggcguaau caacacauug gaguggauac cgagauucaa gguuaguccc   1440

aaccucuuca cugucccaau uaaggaagca ggcgaagacu gccaugcccc aacauaccua   1500

ccugcggagg uggacggug a ugucaaacuc aguuccaacc uggugauucu accuggucaa   1560

gaucuccaau auguuuuggc aaccuacgau accuccaggg uugagcaugc uguggguuuau   1620

uacguuuaca gcccaagccg cucauuuucu uacuuuuauc cuuuuagguu gccuauaaag   1680

gggguoccaa ucgaacuaca aguggaaugc uucacauggg aucaaaaacu cuggugccgu   1740

cacuucugug ugcuugcgga cucagaaucc gguggacuua ucacucacuc ugggauggug   1800

ggcaugggag ucagcugcac agcuacccgg gaagauggaa ccaaucgcag auaa          1854
```

<210> SEQ ID NO 77
<211> LENGTH: 2126
<212> TYPE: RNA
<213> ORGANISM: Artificial Sequence
<220> FEATURE:
<223> OTHER INFORMATION: Synthetic Polynucleotide

<400> SEQUENCE: 77

```
ggggaaauaa gagagaaaag aagaguaaga agaaauauaa gagccaccau gucaccgcaa     60

cgagaccgga uaaaugccuu cuacaaagau aacccuuauc ccaagggaag uaggauaguu    120

auuaacagag aacaucuuau gauugacaga cccuauguuc ugcuggcugu ucuguucguc    180

auguuucuga gcuugaucgg auugcuggca auugcaggca uuagacuuca ucgggcagcc    240

aucuacaccg cggagaucca uaaaagccuc aguaccaauc uggaugugac uaacuccauc    300

gagcaucagg ucaaggacgu gcugacacca cucuuuaaaa ucaucgggga ugaagugggc    360

cugagaacac cucagagauu cacugaccua gugaaauuca ucucggacaa gauuaaauuc    420

cuuaauccgg auagggagua cgacuucaga gaucucacuu ggugcaucaa cccgccagag    480

aggaucaaac uagauuauga ucaauacugu gcagaugugg cugcugaaga gcucaugaau    540

gcauuggug a acucaacucu acuggagacc agaacaacca cucaguuccu agcugucuca    600

aagggaaacu gcucagggcc cacuacaauc agaggucaau ucucaaacau gucgcugucc    660

uuguuggacu uguacuuagg ucgagguuac aaugugucau cuauagucac uaugacaucc    720

cagggaaugu augggggaac cuaccuaguu gaaaagccua aucugaacag caaaggguca    780

gaguugucac aacugagcau guaccgagug uuugaaguag gugugaucag aaacccgggu    840

uugggggcuc cgguguucca uaugacaaac uauuuugagc aaccagucag uaauggucuc    900

ggcaacugua ugguggcuuu gggggagcuc aaacucgcag cccuuuguca cggggacgau    960

ucuaucauaa uucccuauca gggaucaggg aaaggugucca gcuuccagcu cgucaagcug   1020

ggugucugga aauccccaac cgacaugcaa uccugggucc ccuuaucaac ggaugaucca   1080

gugguagaca ggcuuuaccu cucaucucac agagguguca ucgcugacaa ucaagcaaaa   1140

ugggcugucc cgacaacacg aacagaugac aaguugcgaa uggagacaug cuuccagcag   1200

gcguguaaag guaaaaucca agcacucugc gagaaucccg agugggguacc auugaaggau   1260

aacaggauuc cuucauacgg gguccugucu guugaucuga gucugacggu ugagcuuaaa   1320

aucaaaauug cuucgggauu cgggccauug aucacacacg gcucagggau ggaccuauac   1380

aaauccaacu gcaacaaugu guauuggcug acuauuccgc caaugagaaa ucuagccuua   1440
```

-continued

```
ggcguaauca acacauugga guggauaccg agauucaagg uuagucccaa ccucuucacu   1500

gucccaauua aggaagcagg cgaagacugc caugccccaa cauaccuacc ugcggaggug   1560

gacggugaug ucaaacucag uuccaaccug gugauucuac cuggucaaga ucuccaauau   1620

guuuuggcaa ccuacgauac cuccaggguu gagcaugcug ugguuuauua cguuuacagc   1680

ccaagccgcu cauuuucuua cuuuuauccu uuuagguugc cuauaaaggg ggucccaauc   1740

gaacuacaag uggaaugcuu cacaugggau caaaaacucu ggugccguca cuucugugug   1800

cuugcggacu cagaauccgg uggacuuauc acucacucug ggaugguggg caugggaguc   1860

agcugcacag cuacccggga agauggaacc aaucgcagau aaugauaaua ggcuggagcc   1920

ucgguggcca agcuucuugc cccuugggcc uccccccagc cccuccuccc cuuccugcac   1980

ccguaccccc guggucuuug aauaaagucu gagugggcgg caaaaaaaaa aaaaaaaaaa   2040

aaaaaaaaaa aaaaaaaaaa aaaaaaaaaa aaaaaaaaaa aaaaaaaaaa aaaaaaaaaa   2100

aaaaaaaaaa aaaaaaaaaa aucuag                                        2126
```

<210> SEQ ID NO 78
<211> LENGTH: 2065
<212> TYPE: RNA
<213> ORGANISM: Artificial Sequence
<220> FEATURE:
<223> OTHER INFORMATION: Synthetic Polynucleotide

<400> SEQUENCE: 78

```
ucaagcuuuu ggacccucgu acagaagcua auacgacuca cuauagggaa auaagagaga     60

aaagaagagu aagaagaaau auaagagcca ccaugucacc acaacgagac cggauaaaug    120

ccuucuacaa agacaacccc cauccuaagg gaaguaggau aguuauuaac agagaacauc    180

uuaugauuga uagaccuuau guuuugcugg cuguucuauu cgucauguuu cugagcuuga    240

ucggguugcu agccauugca ggcauuagac uucaucgggc agccaucuac accgcagaga    300

uccauaaaag ccucagcacc aaucuggaug uaacuaacuc aaucgagcau cagguuaagg    360

acgugcugac accacucuuc aagaucaucg gugaugaagu gggcuugagg acaccucaga    420

gauucacuga ccuagugaag uucaucucug acaagauuaa auuccuuaau ccggacaggg    480

aauacgacuu cagagaucuc acuuggugua ucaaccegcc agagagaauc aaauuggauu    540

augaucaaua cugugcagau guggcugcug aagaacucau gaaugcauug gugaacucaa    600

cucuacugga gaccagggca accaaucagu uccuagcugu cucaaaggga aacugcucag    660

ggcccacuac aaucagaggc caauucucaa acaugucgcu gucccuguug gacuuguauu    720

uaagucgagg uuacaaugug ucaucuauag ucacuaugac aucccaggga auguacgggg    780

gaacuuaccu aguggaaaag ccuaaucuga gcagcaaagg gucagaguug ucacaacuga    840

gcaugcaccg aguguuugaa guagguguua ucagaaaucc ggguuugggg gcuccgguau    900

uccauaugac aaacuaucuu gagcaaccag ucaguaauga uuucagcaac ugcauggugg    960

cuuuggggga gcucaaguuc gcagcccucu gucacaggga agauucuauc acaauucccu   1020

aucagggauc agggaaaggu gucagcuucc agcuugucaa gcuaggugguc uggaaauccc   1080

caaccgacau gcaauccugg guccccuau caacggauga uccagugaua gacaggcuuu   1140

accucucauc ucacagaggc guuaucgcug acaaucaagc aaaaugggcu gucccgacaa   1200

cacggacaga ugacaaguug cgaauggaga caugcuucca gcaggcgugu aaggguaaaa   1260

uccaagcacu uugcgagaau cccgagugga caccauugaa ggauaacagg auuccuucau   1320

acggggucuu gucuguugau cugagucuga caguugagcu uaaaaucaaa auuguuucag   1380
```

```
gauucgggcc auugaucaca cacgguucag ggauggaccu auacaaaucc aaccacaaca   1440
auauguauug gcugacuauc ccgccaauga agaaccuggc cuuaggugua aucaacacau   1500
uggaguggau accgagauuc aagguuaguc ccaaccucuu cacuguucca auuaaggaag   1560
caggcgagga cugccaugcc ccaacauacc uaccugcgga gguggauggu gaugucaaac   1620
ucaguuccaa ucuggugauu cuaccugguc aagaucucca auauguucug gcaaccuacg   1680
auacuuccag aguugaacau gcuguaguuu auuacguuua cagcccaagc cgcucauuuu   1740
cuuacuuuua uccuuuuagg uugccuguaa ggggggcccc cauugaauua caaguggaau   1800
gcuucacaug ggaccaaaaa cucuggugcc gucacuucug ugugcuugcg gacucagaau   1860
cugguggaca uaucacucac ucugggaugg ugggcauggg agucagcugc acagccacuc   1920
gggaagaugg aaccagccgc agauagugau aauaggcugg agccucggug gccaagcuuc   1980
uugccccuug ggccuccccc cagccccucc uccccuuccu gcacccguac ccccgugguc   2040
uuugaauaaa gucugagugg gcggc                                         2065
```

<210> SEQ ID NO 79
<211> LENGTH: 1854
<212> TYPE: RNA
<213> ORGANISM: Artificial Sequence
<220> FEATURE:
<223> OTHER INFORMATION: Synthetic Polynucleotide

<400> SEQUENCE: 79

```
augucaccac aacgagaccg gauaaaugcc uucuacaaag acaaccccca uccuaaggga     60
aguaggauag uuauuaacag agaacaucuu augauugaua gaccuuaugu uuugcuggcu    120
guucuauucg ucauguuucu gagcuugauc ggguugcuag ccauugcagg cauuagacuu    180
caucgggcag ccaucuacac cgcagagauc cauaaaagcc ucagcaccaa ucuggaugua    240
acuaacucaa ucgagcauca gguuaaggac gugcugacac cacucuucaa gaucaucggu    300
gaugaagugg gcuugaggac accucagaga uucacugacc uagugaaguu caucucugac    360
aagauuaaau uccuuaaucc ggacagggaa uacgacuuca gagaucucac uugguguauc    420
aacccgccag agagaaucaa auuggauuau gaucaauacu gugcagaugu ggcugcugaa    480
gaacucauga augcauuggu gaacucaacu cuacuggaga ccagggcaac caaucaguuc    540
cuagcugucu caaagggaaa cugcucaggg cccacuacaa ucagaggcca auucucaaac    600
augucgcugu cccuguugga cuuguauuua agucgagguu acaaugugdc aucuauaguc    660
acuaugacau cccagggaau guacgggggga acuuaccuag uggaaaagcc uaaucugagc    720
agcaaagggu cagaguuguc acaacugagc augcaccgag uguuugaagu agguguuauc    780
agaaauccgg guuugggggc uccgguauuc cauaugacaa acuaucuuga gcaaccaguc    840
aguaaugauu ucagcaacug caugguggcu uugggggagc ucaaguucgc agcccucugu    900
cacagggaag auucuaucac aauucccuau cagggaucag ggaaaggugu cagcuuccag    960
cuugucaagc uaggugucug gaaaucccca accgacaugc aauccugggu cccccuauca   1020
acggaugauc cagugauaga caggcuuuac cucucaucuc acagaggcgu uaucgcugac   1080
aaucaagcaa aaugggcugu cccgacaaca cggacagaug acaaguugcg aauggagaca   1140
ugcuuccagc aggcguguaa ggguaaaauc caagcacuuu gcgagaaucc cgaguggaca   1200
ccauugaagg auaacaggau uccuucauac ggggucuugu cuguugaucu gagucugaca   1260
guugagcuua aaaucaaaau uguuucagga uucgggccau ugaucacaca cgguucaggg   1320
```

auggaccuau acaaauccaa ccacaacaau auguauuggc ugacuauccc gccaaugaag 1380
aaccuggccu uaggugu aau caacacauug gaguggauac cgagauucaa gguuaguccc 1440
aaccucuuca cuguuccaau uaaggaagca ggcgaggacu gccaugcccc aacauaccua 1500
ccugcggagg uggaugguga ugucaaacuc aguuccaauc uggugauucu accuggucaa 1560
gaucuccaau auguucuggc aaccuacgau acuuccagag uugaacaugc uguaguuuau 1620
uacguuuaca gcccaagccg cucauuuucu uacuuuuauc cuuuuagguu gccuguaagg 1680
ggggucccca uugaauuaca aguggaaugc uucacauggg accaaaaacu cuggugccgu 1740
cacuucugug ugcuugcgga cucagaaucu gguggacaua ucacucacuc ugggauggug 1800
ggcaugggag ucagcugcac agccacucgg gaagauggaa ccagccgcag auag 1854

<210> SEQ ID NO 80
<211> LENGTH: 2126
<212> TYPE: RNA
<213> ORGANISM: Artificial Sequence
<220> FEATURE:
<223> OTHER INFORMATION: Synthetic Polynucleotide

<400> SEQUENCE: 80
ggggaaauaa gagagaaaag aagaguaaga agaaauauaa gagccaccau gucaccacaa 60
cgagaccgga uaaaugccuu cuacaaagac aacccccauc cuaagggaag uaggauaguu 120
auuaacagag aacaucuuau gauugauaga ccuuauguuu ugcuggcugu ucuauucguc 180
auguuucuga gcuugaucgg guugcuagcc auugcaggca uuagacuuca ucgggcagcc 240
aucuacaccg cagagaucca uaaaagccuc agcaccaauc uggauguaac uaacucaauc 300
gagcaucagg uuaaggacgu gcugacacca cucuucaaga ucaucgguga ugaagugggc 360
uugaggacac cucagagauu cacugaccua gugaaguuca ucucugacaa gauuaaauuc 420
cuuaauccgg acagggaaua cgacuucaga gaucucacuu gguguaucaa cccgccagag 480
agaaucaaau uggauuauga ucaauacugu gcagaugugg cugcugaaga acucaugaau 540
gcauugguga acucaacucu acuggagacc agggcaacca aucaguuccu agcugucuca 600
aagggaaacu gcucagggcc cacuacaauc agaggccaau ucucaaacau gucgcugucc 660
cuguuggacu uguauuuaag ucgagguuac aaugugucau cuauagucac uaugacaucc 720
cagggaaugu acgggggaac uuaccuagug gaaaagccua aucugagcag caaaggguca 780
gaguugucac aacugagcau gcaccgagug uuugaaguag guguuaucag aaauccgggu 840
uugggggcuc cgguauucca uaugacaaac uaucuugagc aaccagucag uaaugauuuc 900
agcaacugca ugguggcuuu gggggagcuc aaguucgcag cccucuguca cagggaagau 960
ucuaucacaa uucccuauca gggaucaggg aaagguguca gcuuccagcu ugucaagcua 1020
ggugucugga aauccccaac cgacaugcaa uccugggucc cccuaucaac ggaugaucca 1080
gugauagaca ggcuuuaccu cucaucucac agaggcguua ucgcugacaa ucaagcaaaa 1140
ugggcugucc cgacaacacg gacagaugac aaguugcgaa uggagacaug cuuccagcag 1200
gcguguaagg guaaaaucca agcacuuugc gagaaucccg aguggacacc auugaaggau 1260
aacaggauuc cuucauacgg ggucuugucu guugaucuga gucugacagu ugagcuuaaa 1320
aucaaaauug uuucaggauu cgggccauug aucacacacg guucagggau ggaccuauac 1380
aaauccaacc acaacaauau guauuggcug acuaucccgc caaugaagaa ccuggccuua 1440
gguguaauca acacauugga guggauaccg agauucaagg uuagucccaa ccucuucacu 1500
guuccaauua aggaagcagg cgaggacugc caugccccaa cauaccuacc ugcggaggug 1560
gauggugaug ucaaacucag uuccaaucug gugauucuac cuggucaaga ucuccaauau 1620
guucuggcaa ccuacgauac uuccagaguu gaacaugcug uaguuuauua cguuuacagc 1680
ccaagccgcu cauuuucuua cuuuuauccu uuuagguugc cuguaagggg gguccccauu 1740
gaauuacaag uggaaugcuu cacaugggac caaaaacucu ggugccguca cuucugugug 1800
cuugcggacu cagaaucugg uggacauauc acucacucug ggaugguggg caugggaguc 1860
agcugcacag ccacucggga agauggaacc agccgcagau agugauaaua ggcuggagcc 1920
ucgguggcca agcuucuugc cccuugggcc uccccccagc cccuccuccc cuuccugcac 1980
ccguaccccc guggucuuug aauaaagucu gagugggcgg caaaaaaaaa aaaaaaaaaa 2040
aaaaaaaaaa aaaaaaaaaa aaaaaaaaaa aaaaaaaaaa aaaaaaaaaa aaaaaaaaaa 2100
aaaaaaaaaa aaaaaaaaaa aucuag 2126

<210> SEQ ID NO 81
<211> LENGTH: 1729
<212> TYPE: RNA
<213> ORGANISM: Artificial Sequence
<220> FEATURE:
<223> OTHER INFORMATION: Synthetic Polynucleotide

<400> SEQUENCE: 81
ucaagcuuuu ggacccucgu acagaagcua auacgacuca cuauagggaa auaagagaga 60
aaagaagagu aagaagaaau auaagagcca ccauggcaca agucauuaau acaaacagcc 120
ugucgcuguu gacccagaau aaccugaaca aaucccaguc cgcacugggc acugcuaucg 180
agcguuuguc uuccggucug cguaucaaca gcgcgaaaga cgaugcggca ggacaggcga 240
uugcuaaccg uuuuaccgcg aacaucaaag gucugacuca ggcuucccgu aacgcuaacg 300
acgguaucuc cauugcgcag accacugaag gcgcgcugaa cgaaaucaac aacaaccugc 360
agcgugugcg ugaacuggcg guucagucug cgaaugguac uaacucccag ucugaccucg 420
acuccaucca ggcugaaauc acccagcgcc ugaacgaaau cgaccgugua uccggccaga 480
cucaguucaa cggcgugaaa guccuggcgc aggacaacac ccugaccauc cagguuggug 540
ccaacgacgg ugaaacuauc gauauugauu uaaaagaaau cagcucuaaa acacugggac 600
uugauaagcu uaauguccaa gaugccuaca ccccgaaaga aacugcugua accguugaua 660
aaacuaccua uaaaaauggu acagauccua uuacagccca gagcaauacu gauauccaaa 720
cugcaauugg cgguggugca acgggggua cuggggcuga uaucaaauuu aaagaugguc 780
aauacuauuu agauguuaaa ggcggugcuu cugcuggugu uuauaaagcc acuuaugaug 840
aaacuacaaa gaaaguuaau auugauacga cugauaaaac uccguuggca acugcggaag 900
cuacagcuau ucggggaacg gccacuauaa cccacaacca aauugcugaa guaacaaaag 960 agggguguuga uacgaccaca guugcggcuc aacuugcugc agcagggguu acuggcgccg 1020
auaaggacaa uacuagccuu guaaaacuau cguuugagga uaaaaacggu aagguuauug 1080
augguggcua ugcagugaaa augggcgacg auuucuaugc cgcuacauau gaugagaaaa 1140
caggugcaau uacugcuaaa accacuacuu auacagaugg uacuggcguu gcucaaacug 1200
gagcugugaa auuuggugge gcaaauggua aaucugaagu uguuacugcu accgauggua 1260
agacuuacuu agcaagcgac cuugacaaac auaacuucag aacaggcggu gagcuuaaag 1320
agguuaauac agauaagacu gaaaacccac ugcagaaaau ugaugcugcc uuggcacagg 1380
uugauacacu ucguucugac cugggugcgg uucagaaccg uuucaacucc gcuaucacca 1440

-continued accugggcaa uaccguaaau aaccugucuu cugcccguag ccguaucgaa gauuccgacu 1500
acgcaaccga agucuccaac augucucgcg cgcagauucu gcagcaggcc gguaccuccg 1560
uucuggcgca ggcgaaccag guuccgcaaa acguccucuc uuuacugcgu ugauaauagg 1620
cuggagccuc gguggccaug cuucuugccc cuugggccuc cccccagccc cuccuccccu 1680
uccugcaccc guacccccgu ggucuuugaa uaaagucuga gugggcggc 1729

<210> SEQ ID NO 82
<211> LENGTH: 1518
<212> TYPE: RNA
<213> ORGANISM: Artificial Sequence
<220> FEATURE:
<223> OTHER INFORMATION: Synthetic Polynucleotide

<400> SEQUENCE: 82
auggcacaag ucauuaauac aaacagccug ucgcuguuga cccagaauaa ccugaacaaa 60
ucccaguccg cacugggcac ugcuaucgag cguuugucuu ccggucugcg uaucaacagc 120
gcgaaagacg augcggcagg acaggcgauu gcuaaccguu uuaccgcgaa caucaaaggu 180
cugacucagg cuucccguaa cgcuaacgac gguaucucca uugcgcagac cacugaaggc 240
gcgcugaacg aaaucaacaa caaccugcag cgugugcgug aacuggcggu ucagucugcg 300
aaugguacua acucccaguc ugaccucgac uccauccagg cugaaaucac ccagcgccug 360
aacgaaaucg accguguauc cggccagacu caguucaacg gcgugaaagu ccuggcgcag 420
gacaacaccc ugaccaucca gguuggugcc aacgacggug aaacuaucga uauugauuua 480
aaagaaauca gcucuaaaac acugggacuu gauaagcuua auguccaaga ugccuacacc 540
ccgaaagaaa cugcuguaac cguugauaaa acuaccuaua aaaaugguac agauccuauu 600
acagcccaga gcaauacuga uauccaaacu gcaauuggcg guggugcaac gggggguuacu 660 ggggcugaua ucaaauuuaa agauggucaa uacuauuuag auguuaaagg cggugcuucu 720
gcugguguuu auaaagccac uuaugaugaa acuacaaaga aaguuaauau ugauacgacu 780
gauaaaacuc cguuggcaac ugcggaagcu acagcuauuc ggggaacggc cacuauaacc 840
cacaaccaaa uugcugaagu aacaaaagag gguguugaua cgaccacagu ugcggcucaa 900
cuugcugcag cagggguuac uggcgccgau aaggacaaua cuagccuugu aaaacuaucg 960
uuugaggaua aaaacgguaa gguuauugau gguggcuaug cagugaaaau gggcgacgau 1020
uucuaugccg cuacauauga ugagaaaaca ggugcaauua cugcuaaaac cacuacuuau 1080
acagauggua cuggcguugc ucaaacugga gcugugaaau uugguggcgc aaaugguaaa 1140
ucugaaguug uuacugcuac cgaugguaag acuuacuuag caagcgaccu ugacaaacau 1200
aacuucagaa caggcgguga gcuuaaagag guuaauacag auaagacuga aaacccacug 1260
cagaaaauug augcugccuu ggcacagguu gauacacuuc guucugaccu gggugcgguu 1320
cagaaccguu ucaacuccgc uaucaccaac cugggcaaua ccguaaauaa ccugucuucu 1380
gcccguagcc guaucgaaga uuccgacuac gcaaccgaag ucuccaacau gucucgcgcg 1440
cagauucugc agcaggccgg uaccuccguu cuggcgcagg cgaaccaggu uccgcaaaac 1500
guccucucuu uacugcgu 1518

<210> SEQ ID NO 83
<211> LENGTH: 1790
<212> TYPE: RNA
<213> ORGANISM: Artificial Sequence
<220> FEATURE:
<223> OTHER INFORMATION: Synthetic Polynucleotide

<400> SEQUENCE: 83

```
ggggaaauaa gagagaaaag aagaguaaga agaaauauaa gagccaccau ggcacaaguc      60
auuaauacaa acagccuguc gcuguugacc cagaauaacc ugaacaaauc ccaguccgca     120
cugggcacug cuaucgagcg uuugucuucc ggucugcgua ucaacagcgc gaaagacgau     180
gcggcaggac aggcgauugc uaaccguuuu accgcgaaca ucaaaggucu gacucaggcu     240
ucccguaacg cuaacgacgg uaucuccauu gcgcagacca cugaaggcgc gcugaacgaa     300
aucaacaaca accugcagcg ugugcgugaa cuggcgguuc agucugcgaa ugguacuaac     360
ucccagucug accucgacuc cauccaggcu gaaaucaccc agcgccugaa cgaaaucgac     420
cguguauccg gccagacuca guucaacggc gugaaagucc uggcgcagga caacacccug     480
accauccagg uuggugccaa cgacggugaa acuaucgaua uugauuuaaa agaaaucagc     540
ucuaaaacac ugggacuuga uaagcuuaau guccaagaug ccuacacccc gaaagaaacu     600
gcuguaaccg uugauaaaac uaccuauaaa aaugguacag auccuauuac agcccagagc     660
aauacugaua uccaaacugc aauuggcggu ggugcaacgg ggguuacugg ggcugauauc     720
aaauuuaaag auggucaaua cuauuuagau guuaaaggcg gugcuucugc ugguguuuau     780
aaagccacuu augaugaaac uacaaagaaa guuaauauug auacgacuga uaaaacuccg     840
uuggcaacug cggaagcuac agcuauucgg ggaacggcca cuauaaccca caaccaaauu     900
gcugaaguaa caaaagaggg uguugauacg accacaguug cggcucaacu ugcugcagca     960
gggguuacug gcgccgauaa ggacaauacu agccuuguaa aacuaucguu ugaggauaaa    1020
aacgguaagg uuauugaugg uggcuaugca gugaaaaugg gcgacgauuu cuaugccgcu    1080
acauaugaug agaaaacagg ugcaauuacu gcuaaaacca cuacuuauac agaugguacu    1140
ggcguugcuc aaacuggagc ugugaaauuu gguggcgcaa augguaaauc ugaaguuguu    1200
acugcuaccg augguaagac uuacuuagca agcgaccuug acaaacauaa cuucagaaca    1260
ggcggugagc uuaaagaggu uaauacagau aagacugaaa acccacugca gaaaauugau    1320
gcugccuugg cacagguuga uacacuucgu ucugaccugg gugcgguuca gaaccguuuc    1380
aacuccgcua ucaccaaccu gggcaauacc guaaauaacc ugucuucugc ccguagccgu    1440
aucgaagauu ccgacuacgc aaccgaaguc uccaacaugu cucgcgcgca gauucugcag    1500
caggccggua ccuccguucu ggcgcaggcg aaccagguuc cgcaaaacgu ccucucuuua    1560
cugcguugau aauaggcugg agccucggug gccaugcuuc uugccccuug ggccuccccc    1620
cagccccucc uccccuuccu gcacccguac ccccgugguc uuugaauaaa gucugagugg    1680
gcggcaaaaa aaaaaaaaaa aaaaaaaaaa aaaaaaaaaa aaaaaaaaaa aaaaaaaaaa    1740
aaaaaaaaaa aaaaaaaaaa aaaaaaaaaa aaaaaaaaaa aaaaaucuag               1790
```

<210> SEQ ID NO 84
<211> LENGTH: 13
<212> TYPE: PRT
<213> ORGANISM: Salmonella typhimurium

<400> SEQUENCE: 84

```
Leu Gln Arg Val Arg Glu Leu Ala Val Gln Ser Ala Asn
1               5                   10
```

<210> SEQ ID NO 85
<211> LENGTH: 539
<212> TYPE: PRT
<213> ORGANISM: Artificial Sequence
<220> FEATURE:
<223> OTHER INFORMATION: Synthetic Polypeptide

<400> SEQUENCE: 85

Met Ser Trp Lys Val Val Ile Ile Phe Ser Leu Leu Ile Thr Pro Gln
1 5 10 15

His Gly Leu Lys Glu Ser Tyr Leu Glu Glu Ser Cys Ser Thr Ile Thr
20 25 30

Glu Gly Tyr Leu Ser Val Leu Arg Thr Gly Trp Tyr Thr Asn Val Phe
35 40 45

Thr Leu Glu Val Gly Asp Val Glu Asn Leu Thr Cys Ser Asp Gly Pro
50 55 60

Ser Leu Ile Lys Thr Glu Leu Asp Leu Thr Lys Ser Ala Leu Arg Glu
65 70 75 80

Leu Lys Thr Val Ser Ala Asp Gln Leu Ala Arg Glu Glu Gln Ile Glu
85 90 95

Asn Pro Gly Ser Gly Ser Phe Val Leu Gly Ala Ile Ala Leu Gly Val
100 105 110

Ala Ala Ala Ala Ala Val Thr Ala Gly Val Ala Ile Cys Lys Thr Ile
115 120 125

Arg Leu Glu Ser Glu Val Thr Ala Ile Asn Asn Ala Leu Lys Lys Thr
130 135 140

Asn Glu Ala Val Ser Thr Leu Gly Asn Gly Val Arg Val Leu Ala Phe
145 150 155 160

Ala Val Arg Glu Leu Lys Asp Phe Val Ser Lys Asn Leu Thr Arg Ala
165 170 175

Leu Asn Lys Asn Lys Cys Asp Ile Asp Asp Leu Lys Met Ala Val Ser
180 185 190

Phe Ser Gln Phe Asn Arg Arg Phe Leu Asn Val Val Arg Gln Phe Ser
195 200 205

Asp Asn Ala Gly Ile Thr Pro Ala Ile Ser Leu Asp Leu Met Thr Asp
210 215 220

Ala Glu Leu Ala Arg Ala Val Pro Asn Met Pro Thr Ser Ala Gly Gln
225 230 235 240

Ile Lys Leu Met Leu Glu Asn Arg Ala Met Val Arg Arg Lys Gly Phe
245 250 255

Gly Ile Leu Cys Gly Val Tyr Gly Ser Ser Val Ile Tyr Met Val Gln
260 265 270

Leu Pro Ile Phe Gly Val Ile Asp Thr Pro Cys Trp Ile Val Lys Ala
275 280 285

Ala Pro Ser Cys Ser Glu Lys Lys Gly Asn Tyr Ala Cys Leu Leu Arg
290 295 300

Glu Asp Gln Gly Trp Tyr Cys Gln Asn Ala Gly Ser Thr Val Tyr Tyr
305 310 315 320

Pro Asn Glu Lys Asp Cys Glu Thr Arg Gly Asp His Val Phe Cys Asp
325 330 335

Thr Ala Ala Gly Ile Asn Val Ala Glu Gln Ser Lys Glu Cys Asn Ile
340 345 350

Asn Ile Ser Thr Thr Asn Tyr Pro Cys Lys Val Ser Thr Gly Arg His
355 360 365

Pro Ile Ser Met Val Ala Leu Ser Pro Leu Gly Ala Leu Val Ala Cys
370 375 380

Tyr Lys Gly Val Ser Cys Ser Ile Gly Ser Asn Arg Val Gly Ile Ile
385 390 395 400

Lys Gln Leu Asn Lys Gly Cys Ser Tyr Ile Thr Asn Gln Asp Ala Asp
405 410 415

Thr Val Thr Ile Asp Asn Thr Val Tyr Gln Leu Ser Lys Val Glu Gly
420 425 430

Glu Gln His Val Ile Lys Gly Arg Pro Val Ser Ser Ser Phe Asp Pro
435 440 445

Ile Lys Phe Pro Glu Asp Gln Phe Asn Val Ala Leu Asp Gln Val Phe
450 455 460

Glu Asn Ile Glu Asn Ser Gln Ala Leu Val Asp Gln Ser Asn Arg Ile
465 470 475 480

Leu Ser Ser Ala Glu Lys Gly Asn Thr Gly Phe Ile Ile Val Ile Ile
485 490 495

Leu Ile Ala Val Leu Gly Ser Ser Met Ile Leu Val Ser Ile Phe Ile
500 505 510

Ile Ile Lys Lys Thr Lys Lys Pro Thr Gly Ala Pro Pro Glu Leu Ser
515 520 525

Gly Val Thr Asn Asn Gly Phe Ile Pro His Asn
530 535

<210> SEQ ID NO 86
<211> LENGTH: 539
<212> TYPE: PRT
<213> ORGANISM: Artificial Sequence
<220> FEATURE:
<223> OTHER INFORMATION: Synthetic Polypeptide

<400> SEQUENCE: 86

Met Ser Trp Lys Val Val Ile Ile Phe Ser Leu Leu Ile Thr Pro Gln
1 5 10 15

His Gly Leu Lys Glu Ser Tyr Leu Glu Glu Ser Cys Ser Thr Ile Thr
20 25 30

Glu Gly Tyr Leu Ser Val Leu Arg Thr Gly Trp Tyr Thr Asn Val Phe
35 40 45

Thr Leu Glu Val Gly Asp Val Glu Asn Leu Thr Cys Ser Asp Gly Pro
50 55 60

Ser Leu Ile Lys Thr Glu Leu Asp Leu Thr Lys Ser Ala Leu Arg Glu
65 70 75 80

Leu Lys Thr Val Ser Ala Asp Gln Leu Ala Arg Glu Glu Gln Ile Glu
85 90 95

Asn Pro Gly Ser Gly Ser Phe Val Leu Gly Ala Ile Ala Leu Gly Val
100 105 110

Ala Ala Ala Ala Ala Val Thr Ala Gly Val Ala Ile Cys Lys Thr Ile
115 120 125

Arg Leu Glu Ser Glu Val Thr Ala Ile Asn Asn Ala Leu Lys Lys Thr
130 135 140

Asn Glu Ala Val Ser Thr Leu Gly Asn Gly Val Arg Val Leu Ala Thr
145 150 155 160

Ala Val Arg Glu Leu Lys Asp Phe Val Ser Lys Asn Leu Thr Arg Ala
165 170 175

Ile Asn Lys Asn Lys Cys Asp Ile Asp Asp Leu Lys Met Ala Val Ser
180 185 190

Phe Ser Gln Phe Asn Arg Arg Phe Leu Asn Val Val Arg Gln Phe Ser
195 200 205

Asp Asn Ala Gly Ile Thr Pro Ala Ile Ser Leu Asp Leu Met Thr Asp
210 215 220

```
Ala Glu Leu Ala Arg Ala Val Pro Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Cys Gly Val Tyr Gly Ser Ser Val Ile Tyr Met Val Gln
            260                 265                 270

Leu Pro Ile Phe Gly Val Ile Asp Thr Pro Cys Trp Ile Val Lys Ala
        275                 280                 285

Ala Pro Ser Cys Ser Glu Lys Lys Gly Asn Tyr Ala Cys Leu Leu Arg
    290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Ile Lys Phe Pro Glu His Gln Trp His Val Ala Leu Asp Gln Val Phe
    450                 455                 460

Glu Asn Ile Glu Asn Ser Gln Ala Leu Val Asp Gln Ser Asn Arg Ile
465                 470                 475                 480

Leu Ser Ser Ala Glu Lys Gly Asn Thr Gly Phe Ile Ile Val Ile Ile
                485                 490                 495

Leu Ile Ala Val Leu Gly Ser Ser Met Ile Leu Val Ser Ile Phe Ile
            500                 505                 510

Ile Ile Lys Lys Thr Lys Lys Pro Thr Gly Ala Pro Pro Glu Leu Ser
        515                 520                 525

Gly Val Thr Asn Asn Gly Phe Ile Pro His Asn
    530                 535
```

<210> SEQ ID NO 87
<211> LENGTH: 539
<212> TYPE: PRT
<213> ORGANISM: Artificial Sequence
<220> FEATURE:
<223> OTHER INFORMATION: Synthetic Polypeptide

<400> SEQUENCE: 87

```
Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45
```

```
Thr Leu Glu Val Gly Asp Val Glu Asn Leu Thr Cys Ser Asp Gly Pro
    50                  55                  60

Ser Leu Ile Lys Thr Glu Leu Asp Leu Leu Lys Ser Ala Leu Arg Glu
65                  70                  75                  80

Leu Lys Thr Val Ser Ala Asp Gln Leu Ala Arg Glu Glu Gln Ile Glu
                85                  90                  95

Asn Pro Gly Ser Gly Ser Phe Val Leu Gly Ala Ile Ala Leu Gly Val
            100                 105                 110

Ala Ala Ala Ala Ala Val Thr Ala Gly Val Ala Ile Ala Lys Thr Ile
        115                 120                 125

Arg Leu Glu Ser Glu Val Thr Ala Ile Asn Asn Ala Leu Lys Lys Thr
    130                 135                 140

Asn Glu Ala Val Ser Thr Leu Gly Asn Gly Val Arg Val Leu Ala Thr
145                 150                 155                 160

Ala Val Arg Glu Leu Lys Asp Phe Val Ser Lys Asn Leu Thr Arg Ala
                165                 170                 175

Ile Asn Lys Asn Lys Cys Asp Ile Pro Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Pro Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
            260                 265                 270

Leu Pro Ile Phe Gly Val Ile Asp Thr Pro Cys Trp Ile Val Lys Ala
        275                 280                 285

Ala Pro Ser Cys Ser Glu Lys Lys Gly Asn Tyr Ala Cys Leu Leu Arg
    290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Ile Lys Phe Pro Glu Asp Gln Phe Gln Val Ala Leu Asp Gln Val Phe
    450                 455                 460
```

-continued

```
Glu Asn Ile Glu Asn Ser Gln Ala Leu Val Asp Gln Ser Asn Arg Ile
465                 470                 475                 480

Leu Ser Ser Ala Glu Lys Gly Asn Thr Gly Phe Ile Ile Val Ile Ile
                485                 490                 495

Leu Ile Ala Val Leu Gly Ser Ser Met Ile Leu Val Ser Ile Phe Ile
            500                 505                 510

Ile Ile Lys Lys Thr Lys Lys Pro Thr Gly Ala Pro Pro Glu Leu Ser
        515                 520                 525

Gly Val Thr Asn Asn Gly Phe Ile Pro His Asn
    530                 535


<210> SEQ ID NO 88
<211> LENGTH: 539
<212> TYPE: PRT
<213> ORGANISM: Artificial Sequence
<220> FEATURE:
<223> OTHER INFORMATION: Synthetic Polypeptide

<400> SEQUENCE: 88

Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Ser Asp Gly Pro
    50                  55                  60

Ser Leu Ile Lys Thr Glu Leu Asp Leu Leu Lys Ser Ala Leu Arg Glu
65                  70                  75                  80

Leu Lys Thr Val Ser Ala Asp Gln Leu Ala Arg Glu Glu Gln Ile Glu
                85                  90                  95

Asn Pro Gly Ser Gly Ser Phe Val Leu Gly Ala Ile Ala Leu Gly Val
            100                 105                 110

Ala Ala Ala Ala Ala Val Thr Ala Gly Val Ala Ile Ala Lys Thr Ile
        115                 120                 125

Arg Leu Glu Ser Glu Val Thr Ala Ile Asn Asn Ala Leu Lys Lys Thr
    130                 135                 140

Asn Glu Ala Val Ser Thr Leu Gly Asn Gly Val Arg Val Leu Ala Thr
145                 150                 155                 160

Ala Val Arg Glu Leu Lys Asp Phe Val Ser Lys Asn Leu Thr Arg Ala
                165                 170                 175

Ile Asn Lys Asn Lys Cys Asp Ile Pro Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Pro Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
            260                 265                 270

Leu Pro Ile Phe Gly Val Ile Asp Thr Pro Cys Trp Ile Val Lys Ala
        275                 280                 285
```

```
Ala Pro Ser Cys Ser Glu Lys Lys Gly Asn Tyr Ala Cys Leu Leu Arg
    290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Ile Lys Phe Pro Glu Asn Gln Phe Gln Val Ala Leu Asp Gln Val Phe
    450                 455                 460

Glu Asn Ile Glu Asn Ser Gln Ala Leu Val Asp Gln Ser Asn Arg Ile
465                 470                 475                 480

Leu Ser Ser Ala Glu Lys Gly Asn Thr Gly Phe Ile Ile Val Ile Ile
                485                 490                 495

Leu Ile Ala Val Leu Gly Ser Ser Met Ile Leu Val Ser Ile Phe Ile
            500                 505                 510

Ile Ile Lys Lys Thr Lys Lys Pro Thr Gly Ala Pro Pro Glu Leu Ser
        515                 520                 525

Gly Val Thr Asn Asn Gly Phe Ile Pro His Asn
    530                 535
```

<210> SEQ ID NO 89
<211> LENGTH: 539
<212> TYPE: PRT
<213> ORGANISM: Artificial Sequence
<220> FEATURE:
<223> OTHER INFORMATION: Synthetic Polypeptide

<400> SEQUENCE: 89

```
Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Ser Asp Gly Pro
    50                  55                  60

Ser Leu Ile Lys Thr Glu Leu Asp Leu Leu Lys Ser Ala Leu Arg Glu
65                  70                  75                  80

Leu Lys Thr Val Ser Ala Asp Gln Leu Ala Arg Glu Glu Gln Ile Glu
                85                  90                  95

Asn Pro Gly Ser Gly Ser Phe Val Leu Gly Ala Ile Ala Leu Gly Val
            100                 105                 110
```

```
Ala Ala Ala Ala Ala Val Thr Ala Gly Val Ala Ile Ala Lys Thr Ile
        115                 120                 125

Arg Leu Glu Ser Glu Val Thr Ala Ile Asn Asn Ala Leu Lys Lys Thr
    130                 135                 140

Asn Glu Ala Val Ser Thr Leu Gly Asn Gly Val Arg Val Leu Ala Thr
145                 150                 155                 160

Ala Val Arg Glu Leu Lys Asp Phe Val Leu Lys Asn Leu Thr Arg Ala
                165                 170                 175

Ile Asn Lys Asn Lys Cys Asp Ile Pro Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Pro Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
            260                 265                 270

Leu Pro Ile Phe Gly Val Ile Asp Thr Pro Cys Trp Ile Val Lys Ala
        275                 280                 285

Ala Pro Ser Cys Ser Glu Lys Lys Gly Asn Tyr Ala Cys Leu Leu Arg
    290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Ile Lys Phe Pro Glu Asp Gln Phe Gln Val Ala Leu Asp Gln Val Phe
    450                 455                 460

Glu Asn Ile Glu Asn Ser Gln Ala Leu Val Asp Gln Ser Asn Arg Ile
465                 470                 475                 480

Leu Ser Ser Ala Glu Lys Gly Asn Thr Gly Phe Ile Ile Val Ile Ile
                485                 490                 495

Leu Ile Ala Val Leu Gly Ser Ser Met Ile Leu Val Ser Ile Phe Ile
            500                 505                 510

Ile Ile Lys Lys Thr Lys Lys Pro Thr Gly Ala Pro Pro Glu Leu Ser
        515                 520                 525

Gly Val Thr Asn Asn Gly Phe Ile Pro His Asn
```

530 535

<210> SEQ ID NO 90
<211> LENGTH: 539
<212> TYPE: PRT
<213> ORGANISM: Artificial Sequence
<220> FEATURE:
<223> OTHER INFORMATION: Synthetic Polypeptide

<400> SEQUENCE: 90

Met Ser Trp Lys Val Val Ile Ile Phe Ser Leu Leu Ile Thr Pro Gln
1 5 10 15

His Gly Leu Lys Glu Ser Tyr Leu Glu Glu Ser Cys Ser Thr Ile Thr
20 25 30

Glu Gly Tyr Leu Ser Val Leu Arg Thr Gly Trp Tyr Thr Asn Val Phe
35 40 45

Thr Leu Glu Val Gly Asp Val Glu Asn Leu Thr Cys Ser Asp Gly Pro
50 55 60

Ser Leu Ile Lys Thr Glu Leu Asp Leu Leu Lys Ser Ala Leu Arg Glu
65 70 75 80

Leu Lys Thr Val Ser Ala Asp Gln Leu Ala Arg Glu Glu Gln Ile Glu
85 90 95

Asn Pro Gly Ser Gly Ser Phe Val Leu Gly Ala Ile Ala Leu Gly Val
100 105 110

Ala Ala Ala Ala Ala Val Thr Ala Gly Val Ala Ile Ala Lys Thr Ile
115 120 125

Arg Leu Glu Ser Glu Val Thr Ala Ile Asn Asn Ala Leu Lys Lys Thr
130 135 140

Asn Glu Ala Val Ser Thr Leu Gly Asn Gly Val Arg Val Leu Ala Thr
145 150 155 160

Ala Val Arg Glu Leu Lys Asp Phe Val Leu Lys Asn Leu Thr Arg Ala
165 170 175

Ile Asn Lys Asn Lys Cys Asp Ile Pro Asp Leu Lys Met Ala Val Ser
180 185 190

Phe Ser Gln Phe Asn Arg Arg Phe Leu Asn Val Val Arg Gln Phe Ser
195 200 205

Asp Asn Ala Gly Ile Thr Pro Ala Ile Ser Leu Asp Leu Met Thr Asp
210 215 220

Ala Glu Leu Ala Arg Ala Val Pro Asn Met Pro Thr Ser Ala Gly Gln
225 230 235 240

Ile Lys Leu Met Leu Glu Asn Arg Ala Met Val Arg Arg Lys Gly Phe
245 250 255

Gly Ile Leu Ile Gly Val Tyr Gly Ser Ser Val Ile Tyr Met Val Gln
260 265 270

Leu Pro Ile Phe Gly Val Ile Asp Thr Pro Cys Trp Ile Val Lys Ala
275 280 285

Ala Pro Ser Cys Ser Glu Lys Lys Gly Asn Tyr Ala Cys Leu Leu Arg
290 295 300

Glu Asp Gln Gly Trp Tyr Cys Gln Asn Ala Gly Ser Thr Val Tyr Tyr
305 310 315 320

Pro Asn Glu Lys Asp Cys Glu Thr Arg Gly Asp His Val Phe Cys Asp
325 330 335

Thr Ala Ala Gly Ile Asn Val Ala Glu Gln Ser Lys Glu Cys Asn Ile
340 345 350

Asn Ile Ser Thr Thr Asn Tyr Pro Cys Lys Val Ser Thr Gly Arg His

```
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Ile Lys Phe Pro Glu Asn Gln Phe Gln Val Ala Leu Asp Gln Val Phe
    450                 455                 460

Glu Asn Ile Glu Asn Ser Gln Ala Leu Val Asp Gln Ser Asn Arg Ile
465                 470                 475                 480

Leu Ser Ser Ala Glu Lys Gly Asn Thr Gly Phe Ile Ile Val Ile Ile
                485                 490                 495

Leu Ile Ala Val Leu Gly Ser Ser Met Ile Leu Val Ser Ile Phe Ile
            500                 505                 510

Ile Ile Lys Lys Thr Lys Lys Pro Thr Gly Ala Pro Pro Glu Leu Ser
        515                 520                 525

Gly Val Thr Asn Asn Gly Phe Ile Pro His Asn
    530                 535


<210> SEQ ID NO 91
<211> LENGTH: 539
<212> TYPE: PRT
<213> ORGANISM: Artificial Sequence
<220> FEATURE:
<223> OTHER INFORMATION: Synthetic Polypeptide

<400> SEQUENCE: 91

Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Pro Val Gly Asp Val Glu Asn Leu Thr Cys Ser Asp Gly Pro
    50                  55                  60

Ser Leu Ile Lys Thr Glu Leu Asp Leu Leu Lys Ser Ala Leu Arg Glu
65                  70                  75                  80

Leu Lys Thr Val Ser Ala Asp Gln Leu Ala Arg Glu Glu Gln Ile Glu
                85                  90                  95

Asn Pro Gly Ser Gly Ser Phe Val Leu Gly Ala Ile Ala Leu Gly Val
            100                 105                 110

Ala Ala Ala Ala Ala Val Thr Ala Gly Val Ala Ile Ala Lys Thr Ile
        115                 120                 125

Arg Leu Glu Ser Glu Val Thr Ala Ile Asn Asn Ala Leu Lys Lys Thr
    130                 135                 140

Asn Glu Ala Val Ser Thr Leu Gly Asn Gly Val Arg Val Leu Ala Thr
145                 150                 155                 160

Ala Val Arg Glu Leu Lys Asp Phe Val Ser Lys Asn Leu Thr Arg Ala
                165                 170                 175

Ile Asn Lys Asn Lys Cys Asp Ile Asp Asp Leu Lys Met Ala Val Ser
```

180 185 190

Phe Ser Gln Phe Asn Arg Arg Phe Leu Asn Val Val Arg Gln Phe Ser
195 200 205

Asp Asn Ala Gly Ile Thr Pro Ala Ile Ser Leu Asp Leu Met Thr Asp
210 215 220

Ala Glu Leu Ala Arg Ala Val Pro Asn Met Pro Thr Ser Ala Gly Gln
225 230 235 240

Ile Lys Leu Met Leu Glu Asn Arg Ala Met Val Arg Arg Lys Gly Phe
245 250 255

Gly Ile Leu Ile Gly Val Tyr Gly Ser Ser Val Ile Tyr Met Val Gln
260 265 270

Leu Pro Ile Phe Gly Val Ile Asp Thr Pro Cys Trp Ile Val Lys Ala
275 280 285

Ala Pro Ser Cys Ser Glu Lys Lys Gly Asn Tyr Ala Cys Leu Leu Arg
290 295 300

Glu Asp Gln Gly Trp Tyr Cys Gln Asn Ala Gly Ser Thr Val Tyr Tyr
305 310 315 320

Pro Asn Glu Lys Asp Cys Glu Thr Arg Gly Asp His Val Phe Cys Asp
325 330 335

Thr Ala Ala Gly Ile Asn Val Ala Glu Gln Ser Lys Glu Cys Asn Ile
340 345 350

Asn Ile Ser Thr Thr Asn Tyr Pro Cys Lys Val Ser Thr Gly Arg His
355 360 365

Pro Ile Ser Met Val Ala Leu Ser Pro Leu Gly Ala Leu Val Ala Cys
370 375 380

Tyr Lys Gly Val Ser Cys Ser Ile Gly Ser Asn Arg Val Gly Ile Ile
385 390 395 400

Lys Gln Leu Asn Lys Gly Cys Ser Tyr Ile Thr Asn Gln Asp Ala Asp
405 410 415

Thr Val Thr Ile Asp Asn Thr Val Tyr Gln Leu Ser Lys Val Glu Gly
420 425 430

Glu Gln His Val Ile Lys Gly Arg Pro Val Ser Ser Ser Phe Asp Pro
435 440 445

Ile Lys Phe Pro Glu Asp Gln Phe Gln Val Ala Leu Asp Gln Val Phe
450 455 460

Glu Asn Ile Glu Asn Ser Gln Ala Leu Val Asp Gln Ser Asn Arg Ile
465 470 475 480

Leu Ser Ser Ala Glu Lys Gly Asn Thr Gly Phe Ile Ile Val Ile Ile
485 490 495

Leu Ile Ala Val Leu Gly Ser Ser Met Ile Leu Val Ser Ile Phe Ile
500 505 510

Ile Ile Lys Lys Thr Lys Lys Pro Thr Gly Ala Pro Pro Glu Leu Ser
515 520 525

Gly Val Thr Asn Asn Gly Phe Ile Pro His Asn
530 535

<210> SEQ ID NO 92
<211> LENGTH: 539
<212> TYPE: PRT
<213> ORGANISM: Artificial Sequence
<220> FEATURE:
<223> OTHER INFORMATION: Synthetic Polypeptide

<400> SEQUENCE: 92

Met Ser Trp Lys Val Val Ile Ile Phe Ser Leu Leu Ile Thr Pro Gln

-continued

```
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Pro Val Gly Asp Val Glu Asn Leu Thr Cys Ser Asp Gly Pro
    50                  55                  60

Ser Leu Ile Lys Thr Glu Leu Asp Leu Leu Lys Ser Ala Leu Arg Glu
65                  70                  75                  80

Leu Lys Thr Val Ser Ala Asp Gln Leu Ala Arg Glu Glu Gln Ile Glu
                85                  90                  95

Asn Pro Gly Ser Gly Ser Phe Val Leu Gly Ala Ile Ala Leu Gly Val
            100                 105                 110

Ala Ala Ala Ala Ala Val Thr Ala Gly Val Ala Ile Ala Lys Thr Ile
        115                 120                 125

Arg Leu Glu Ser Glu Val Thr Ala Ile Asn Asn Ala Leu Lys Lys Thr
    130                 135                 140

Asn Glu Ala Val Ser Thr Leu Gly Asn Gly Val Arg Val Leu Ala Thr
145                 150                 155                 160

Ala Val Arg Glu Leu Lys Asp Phe Val Ser Lys Asn Leu Thr Arg Ala
                165                 170                 175

Ile Asn Lys Asn Lys Cys Asp Ile Asp Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Pro Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
            260                 265                 270

Leu Pro Ile Phe Gly Val Ile Asp Thr Pro Cys Trp Ile Val Lys Ala
        275                 280                 285

Ala Pro Ser Cys Ser Glu Lys Lys Gly Asn Tyr Ala Cys Leu Leu Arg
    290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430
```

Glu Gln His Val Ile Lys Gly Arg Pro Val Ser Ser Ser Phe Asp Pro
        435                 440                 445

Ile Lys Phe Pro Glu Asn Gln Phe Gln Val Ala Leu Asp Gln Val Phe
    450                 455                 460

Glu Asn Ile Glu Asn Ser Gln Ala Leu Val Asp Gln Ser Asn Arg Ile
465                 470                 475                 480

Leu Ser Ser Ala Glu Lys Gly Asn Thr Gly Phe Ile Ile Val Ile Ile
                485                 490                 495

Leu Ile Ala Val Leu Gly Ser Ser Met Ile Leu Val Ser Ile Phe Ile
            500                 505                 510

Ile Ile Lys Lys Thr Lys Lys Pro Thr Gly Ala Pro Pro Glu Leu Ser
        515                 520                 525

Gly Val Thr Asn Asn Gly Phe Ile Pro His Asn
    530                 535

<210> SEQ ID NO 93
<211> LENGTH: 539
<212> TYPE: PRT
<213> ORGANISM: Artificial Sequence
<220> FEATURE:
<223> OTHER INFORMATION: Synthetic Polypeptide

<400> SEQUENCE: 93

Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Ser Asp Gly Pro
    50                  55                  60

Ser Leu Ile Lys Thr Glu Leu Asp Leu Leu Lys Ser Ala Leu Arg Glu
65                  70                  75                  80

Leu Lys Thr Val Ser Ala Asp Gln Leu Ala Arg Glu Glu Gln Ile Glu
                85                  90                  95

Asn Pro Gly Ser Gly Ser Phe Val Leu Gly Ala Ile Ala Leu Gly Val
            100                 105                 110

Ala Ala Ala Ala Ala Val Thr Ala Gly Val Ala Ile Ala Lys Thr Ile
        115                 120                 125

Arg Leu Glu Ser Glu Val Thr Ala Ile Asn Asn Ala Leu Lys Lys Thr
    130                 135                 140

Asn Glu Ala Val Ser Thr Leu Gly Asn Gly Val Arg Val Leu Ala Thr
145                 150                 155                 160

Ala Val Arg Glu Leu Lys Asp Phe Val Ser Lys Asn Leu Thr Arg Ala
                165                 170                 175

Ile Asn Lys Asn Lys Cys Asp Ile Asp Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Pro Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

```
Gly Ile Leu Ile Gly Val Tyr Gly Ser Ser Val Ile Tyr Met Val Gln
            260                 265                 270

Leu Pro Ile Phe Gly Val Ile Asp Thr Pro Cys Trp Ile Val Lys Ala
        275                 280                 285

Ala Pro Ser Cys Ser Glu Lys Lys Gly Asn Tyr Ala Cys Leu Leu Arg
    290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Ile Lys Phe Pro Glu Asp Gln Phe Gln Val Ala Leu Asp Gln Val Phe
    450                 455                 460

Glu Asn Ile Glu Asn Ser Gln Ala Leu Val Asp Gln Ser Asn Arg Ile
465                 470                 475                 480

Leu Ser Ser Ala Glu Lys Gly Asn Thr Gly Phe Ile Ile Val Ile Ile
                485                 490                 495

Leu Ile Ala Val Leu Gly Ser Ser Met Ile Leu Val Ser Ile Phe Ile
            500                 505                 510

Ile Ile Lys Lys Thr Lys Lys Pro Thr Gly Ala Pro Pro Glu Leu Ser
        515                 520                 525

Gly Val Thr Asn Asn Gly Phe Ile Pro His Asn
    530                 535
```

<210> SEQ ID NO 94
<211> LENGTH: 539
<212> TYPE: PRT
<213> ORGANISM: Artificial Sequence
<220> FEATURE:
<223> OTHER INFORMATION: Synthetic Polypeptide

<400> SEQUENCE: 94

```
Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Leu Glu Asn Leu Thr Cys Ser Asp Gly Pro
    50                  55                  60

Ser Leu Ile Lys Thr Glu Leu Asp Leu Thr Lys Ser Ala Leu Arg Glu
65                  70                  75                  80
```

```
Leu Lys Thr Val Ser Ala Asp Gln Leu Ala Arg Glu Glu Gln Ile Glu
                85                  90                  95

Asn Pro Gly Ser Gly Ser Phe Val Leu Gly Ala Ile Ala Leu Gly Val
            100                 105                 110

Ala Ala Ala Ala Ala Val Thr Ala Gly Val Ala Ile Ala Lys Thr Ile
        115                 120                 125

Arg Leu Glu Ser Glu Val Thr Ala Ile Asn Asn Ala Leu Lys Lys Thr
    130                 135                 140

Asn Glu Ala Val Ser Thr Leu Gly Asn Gly Val Arg Val Leu Ala Thr
145                 150                 155                 160

Ala Val Arg Glu Leu Lys Asp Phe Val Ser Lys Asn Leu Thr Arg Ala
                165                 170                 175

Ile Asn Lys Asn Lys Cys Asp Ile Asp Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Pro Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
            260                 265                 270

Leu Pro Ile Phe Gly Val Ile Asp Thr Pro Cys Trp Ile Val Lys Ala
        275                 280                 285

Ala Pro Ser Cys Ser Glu Lys Lys Gly Asn Tyr Ala Cys Leu Leu Arg
    290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Ile Lys Phe Pro Glu Asp Gln Phe Gln Val Ala Leu Asp Gln Val Phe
    450                 455                 460

Glu Asn Ile Glu Asn Ser Gln Ala Leu Val Asp Gln Ser Asn Arg Ile
465                 470                 475                 480

Leu Ser Ser Ala Glu Lys Gly Asn Thr Gly Phe Ile Ile Val Ile Ile
                485                 490                 495
```

```
Leu Ile Ala Val Leu Gly Ser Ser Met Ile Leu Val Ser Ile Phe Ile
            500                 505                 510

Ile Ile Lys Lys Thr Lys Lys Pro Thr Gly Ala Pro Pro Glu Leu Ser
        515                 520                 525

Gly Val Thr Asn Asn Gly Phe Ile Pro His Asn
    530                 535


<210> SEQ ID NO 95
<211> LENGTH: 539
<212> TYPE: PRT
<213> ORGANISM: Artificial Sequence
<220> FEATURE:
<223> OTHER INFORMATION: Synthetic Polypeptide

<400> SEQUENCE: 95

Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Ser Asp Gly Pro
    50                  55                  60

Ser Leu Ile Lys Thr Glu Leu Asp Leu Thr Lys Ser Ala Leu Arg Glu
65                  70                  75                  80

Leu Lys Thr Val Ser Ala Asp Gln Leu Ala Arg Glu Glu Gln Ile Glu
                85                  90                  95

Asn Pro Gly Ser Gly Ser Phe Val Leu Gly Ala Ile Ala Leu Gly Val
            100                 105                 110

Ala Ala Ala Ala Ala Val Thr Ala Gly Val Ala Ile Ala Lys Thr Ile
        115                 120                 125

Arg Leu Glu Ser Glu Val Thr Ala Ile Asn Asn Ala Leu Lys Lys Thr
    130                 135                 140

Asn Glu Ala Val Ser Thr Leu Gly Asn Gly Val Arg Val Leu Ala Thr
145                 150                 155                 160

Ala Val Arg Glu Leu Lys Asp Phe Val Leu Lys Asn Leu Thr Arg Ala
                165                 170                 175

Ile Asn Lys Asn Lys Cys Asp Ile Asp Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Pro Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
            260                 265                 270

Leu Pro Ile Phe Gly Val Ile Asp Thr Pro Cys Trp Ile Val Lys Ala
        275                 280                 285

Ala Pro Ser Cys Ser Glu Lys Lys Gly Asn Tyr Ala Cys Leu Leu Arg
    290                 295                 300

Glu Asp Gln Gly Trp Tyr Cys Gln Asn Ala Gly Ser Thr Val Tyr Tyr
305                 310                 315                 320
```

```
Pro Asn Glu Lys Asp Cys Glu Thr Arg Gly Asp His Val Phe Cys Asp
                325                 330                 335

Thr Ala Ala Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Ile Lys Phe Pro Glu Asp Gln Phe Gln Val Ala Leu Asp Gln Val Phe
    450                 455                 460

Glu Asn Ile Glu Asn Ser Gln Ala Leu Val Asp Gln Ser Asn Arg Ile
465                 470                 475                 480

Leu Ser Ser Ala Glu Lys Gly Asn Thr Gly Phe Ile Ile Val Ile Ile
                485                 490                 495

Leu Ile Ala Val Leu Gly Ser Ser Met Ile Leu Val Ser Ile Phe Ile
            500                 505                 510

Ile Ile Lys Lys Thr Lys Lys Pro Thr Gly Ala Pro Pro Glu Leu Ser
        515                 520                 525

Gly Val Thr Asn Asn Gly Phe Ile Pro His Asn
    530                 535
```

<210> SEQ ID NO 96
<211> LENGTH: 539
<212> TYPE: PRT
<213> ORGANISM: Artificial Sequence
<220> FEATURE:
<223> OTHER INFORMATION: Synthetic Polypeptide

<400> SEQUENCE: 96

```
Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Ser Asp Gly Pro
    50                  55                  60

Ser Leu Ile Lys Thr Glu Leu Asp Leu Thr Lys Ser Ala Leu Arg Glu
65                  70                  75                  80

Leu Lys Thr Val Ser Ala Asp Gln Leu Ala Arg Glu Glu Gln Ile Glu
                85                  90                  95

Asn Pro Gly Ser Gly Ser Phe Val Leu Gly Ala Ile Ala Leu Gly Val
            100                 105                 110

Ala Ala Ala Ala Ala Val Thr Ala Gly Val Ala Ile Ala Lys Thr Ile
        115                 120                 125

Arg Leu Glu Ser Glu Val Thr Ala Ile Asn Asn Ala Leu Lys Lys Thr
    130                 135                 140
```

```
Asn Glu Ala Val Ser Thr Leu Gly Asn Gly Val Arg Val Leu Ala Thr
145                 150                 155                 160

Ala Val Arg Glu Leu Lys Asp Phe Val Ser Lys Asn Leu Trp Arg Ala
                165                 170                 175

Ile Asn Lys Asn Lys Cys Asp Ile Asp Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Pro Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
            260                 265                 270

Leu Pro Ile Phe Gly Val Ile Asp Thr Pro Cys Trp Ile Val Lys Ala
        275                 280                 285

Ala Pro Ser Cys Ser Glu Lys Lys Gly Asn Tyr Ala Cys Leu Leu Arg
    290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Ile Lys Phe Pro Glu Asp Gln Phe Gln Val Ala Leu Asp Gln Val Phe
    450                 455                 460

Glu Asn Ile Glu Asn Ser Gln Ala Leu Val Asp Gln Ser Asn Arg Ile
465                 470                 475                 480

Leu Ser Ser Ala Glu Lys Gly Asn Thr Gly Phe Ile Ile Val Ile Ile
                485                 490                 495

Leu Ile Ala Val Leu Gly Ser Ser Met Ile Leu Val Ser Ile Phe Ile
            500                 505                 510

Ile Ile Lys Lys Thr Lys Lys Pro Thr Gly Ala Pro Pro Glu Leu Ser
        515                 520                 525

Gly Val Thr Asn Asn Gly Phe Ile Pro His Asn
    530                 535
```

<210> SEQ ID NO 97
<211> LENGTH: 539
<212> TYPE: PRT

```
<213> ORGANISM: Artificial Sequence
<220> FEATURE:
<223> OTHER INFORMATION: Synthetic Polypeptide

<400> SEQUENCE: 97

Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Leu Glu Asn Leu Thr Cys Ser Asp Gly Pro
    50                  55                  60

Ser Leu Ile Lys Thr Glu Leu Asp Leu Leu Lys Ser Ala Leu Arg Glu
65                  70                  75                  80

Leu Lys Thr Val Ser Ala Asp Gln Leu Ala Arg Glu Glu Gln Ile Glu
                85                  90                  95

Asn Pro Gly Ser Gly Ser Phe Val Leu Gly Ala Ile Ala Leu Gly Val
            100                 105                 110

Ala Ala Ala Ala Ala Val Thr Ala Gly Val Ala Ile Ala Lys Thr Ile
        115                 120                 125

Arg Leu Glu Ser Glu Val Thr Ala Ile Asn Asn Ala Leu Lys Lys Thr
    130                 135                 140

Asn Glu Ala Val Ser Thr Leu Gly Asn Gly Val Arg Val Leu Ala Thr
145                 150                 155                 160

Ala Val Arg Glu Leu Lys Asp Phe Val Leu Lys Asn Leu Trp Arg Ala
                165                 170                 175

Ile Asn Lys Asn Lys Cys Asp Ile Asp Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Pro Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
            260                 265                 270

Leu Pro Ile Phe Gly Val Ile Asp Thr Pro Cys Trp Ile Val Lys Ala
        275                 280                 285

Ala Pro Ser Cys Ser Glu Lys Lys Gly Asn Tyr Ala Cys Leu Leu Arg
    290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
```

385 390 395 400

Lys Gln Leu Asn Lys Gly Cys Ser Tyr Ile Thr Asn Gln Asp Ala Asp
405 410 415

Thr Val Thr Ile Asp Asn Thr Val Tyr Gln Leu Ser Lys Val Glu Gly
420 425 430

Glu Gln His Val Ile Lys Gly Arg Pro Val Ser Ser Ser Phe Asp Pro
435 440 445

Ile Lys Phe Pro Glu Asp Gln Phe Gln Val Ala Leu Asp Gln Val Phe
450 455 460

Glu Asn Ile Glu Asn Ser Gln Ala Leu Val Asp Gln Ser Asn Arg Ile
465 470 475 480

Leu Ser Ser Ala Glu Lys Gly Asn Thr Gly Phe Ile Ile Val Ile Ile
485 490 495

Leu Ile Ala Val Leu Gly Ser Ser Met Ile Leu Val Ser Ile Phe Ile
500 505 510

Ile Ile Lys Lys Thr Lys Lys Pro Thr Gly Ala Pro Pro Glu Leu Ser
515 520 525

Gly Val Thr Asn Asn Gly Phe Ile Pro His Asn
530 535

<210> SEQ ID NO 98
<211> LENGTH: 539
<212> TYPE: PRT
<213> ORGANISM: Artificial Sequence
<220> FEATURE:
<223> OTHER INFORMATION: Synthetic Polypeptide

<400> SEQUENCE: 98

Met Ser Trp Lys Val Val Ile Ile Phe Ser Leu Leu Ile Thr Pro Gln
1 5 10 15

His Gly Leu Lys Glu Ser Tyr Leu Glu Glu Ser Cys Ser Thr Ile Thr
20 25 30

Glu Gly Tyr Leu Ser Val Leu Arg Thr Gly Trp Tyr Thr Asn Val Phe
35 40 45

Thr Leu Pro Val Gly Asp Val Glu Asn Leu Thr Cys Ser Asp Gly Pro
50 55 60

Ser Leu Ile Lys Thr Glu Leu Asp Leu Thr Lys Ser Ala Leu Arg Glu
65 70 75 80

Leu Lys Thr Val Ser Ala Asp Gln Leu Ala Arg Glu Glu Gln Ile Glu
85 90 95

Asn Pro Gly Ser Gly Ser Phe Val Leu Gly Ala Ile Ala Leu Gly Val
100 105 110

Ala Ala Ala Ala Ala Val Thr Ala Gly Val Ala Ile Ala Lys Thr Ile
115 120 125

Arg Leu Glu Ser Glu Val Thr Ala Ile Asn Asn Ala Leu Lys Lys Thr
130 135 140

Asn Glu Ala Val Ser Thr Leu Gly Asn Gly Val Arg Val Leu Ala Thr
145 150 155 160

Ala Val Arg Glu Leu Lys Asp Phe Val Ser Lys Asn Leu Thr Arg Ala
165 170 175

Ile Asn Lys Asn Lys Cys Asp Ile Asp Asp Leu Lys Met Ala Val Ser
180 185 190

Phe Ser Gln Phe Asn Arg Arg Phe Leu Asn Val Val Arg Gln Phe Ser
195 200 205

Asp Asn Ala Gly Ile Thr Pro Ala Ile Ser Leu Asp Leu Met Thr Asp

```
    210                 215                 220

Ala Glu Leu Ala Arg Ala Val Pro Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
            260                 265                 270

Leu Pro Ile Phe Gly Val Ile Asp Thr Pro Cys Trp Ile Val Lys Ala
        275                 280                 285

Ala Pro Ser Cys Ser Glu Lys Lys Gly Asn Tyr Ala Cys Leu Leu Arg
    290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Ile Lys Phe Pro Glu Asp Gln Phe Gln Val Ala Leu Asp Gln Val Phe
    450                 455                 460

Glu Asn Ile Glu Asn Ser Gln Ala Leu Val Asp Gln Ser Asn Arg Ile
465                 470                 475                 480

Leu Ser Ser Ala Glu Lys Gly Asn Thr Gly Phe Ile Ile Val Ile Ile
                485                 490                 495

Leu Ile Ala Val Leu Gly Ser Ser Met Ile Leu Val Ser Ile Phe Ile
            500                 505                 510

Ile Ile Lys Lys Thr Lys Lys Pro Thr Gly Ala Pro Pro Glu Leu Ser
        515                 520                 525

Gly Val Thr Asn Asn Gly Phe Ile Pro His Asn
    530                 535
```

<210> SEQ ID NO 99
<211> LENGTH: 539
<212> TYPE: PRT
<213> ORGANISM: Artificial Sequence
<220> FEATURE:
<223> OTHER INFORMATION: Synthetic Polypeptide

<400> SEQUENCE: 99

```
Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
```

-continued

```
        35                  40                  45

Thr Leu Glu Val Gly Asp Val Glu Asn Leu Thr Cys Ser Asp Gly Pro
    50                  55                  60

Ser Leu Ile Lys Thr Glu Leu Asp Leu Thr Lys Ser Ala Leu Arg Glu
65                  70                  75                  80

Leu Lys Thr Val Ser Ala Asp Gln Leu Ala Arg Glu Glu Gln Ile Glu
                85                  90                  95

Asn Pro Gly Ser Gly Ser Phe Val Leu Gly Ala Ile Ala Leu Gly Val
            100                 105                 110

Ala Ala Ala Ala Ala Val Thr Ala Gly Val Ala Ile Ala Lys Thr Ile
        115                 120                 125

Arg Leu Glu Ser Glu Val Thr Ala Ile Asn Asn Ala Leu Lys Lys Thr
    130                 135                 140

Asn Glu Ala Val Ser Thr Leu Gly Asn Gly Val Arg Val Leu Ala Thr
145                 150                 155                 160

Ala Val Arg Glu Leu Lys Asp Phe Val Ser Lys Asn Leu Thr Arg Ala
                165                 170                 175

Ile Asn Lys Asn Lys Cys Asp Ile Pro Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Pro Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
            260                 265                 270

Leu Pro Ile Phe Gly Val Ile Asp Thr Pro Cys Trp Ile Val Lys Ala
        275                 280                 285

Ala Pro Ser Cys Ser Glu Lys Lys Gly Asn Tyr Ala Cys Leu Leu Arg
    290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Ile Lys Phe Pro Glu Asp Gln Phe Gln Val Ala Leu Asp Gln Val Phe
    450                 455                 460
```

Glu Asn Ile Glu Asn Ser Gln Ala Leu Val Asp Gln Ser Asn Arg Ile
465 470 475 480

Leu Ser Ser Ala Glu Lys Gly Asn Thr Gly Phe Ile Ile Val Ile Ile
485 490 495

Leu Ile Ala Val Leu Gly Ser Ser Met Ile Leu Val Ser Ile Phe Ile
500 505 510

Ile Ile Lys Lys Thr Lys Lys Pro Thr Gly Ala Pro Pro Glu Leu Ser
515 520 525

Gly Val Thr Asn Asn Gly Phe Ile Pro His Asn
530 535

<210> SEQ ID NO 100
<211> LENGTH: 539
<212> TYPE: PRT
<213> ORGANISM: Artificial Sequence
<220> FEATURE:
<223> OTHER INFORMATION: Synthetic Polypeptide

<400> SEQUENCE: 100

Met Ser Trp Lys Val Val Ile Ile Phe Ser Leu Leu Ile Thr Pro Gln
1 5 10 15

His Gly Leu Lys Glu Ser Tyr Leu Glu Glu Ser Cys Ser Thr Ile Thr
20 25 30

Glu Gly Tyr Leu Ser Val Leu Arg Thr Gly Trp Tyr Thr Asn Val Phe
35 40 45

Thr Leu Glu Val Gly Asp Val Glu Asn Leu Thr Cys Ser Asp Gly Pro
50 55 60

Ser Leu Ile Lys Thr Glu Leu Asp Leu Thr Lys Ser Ala Leu Arg Glu
65 70 75 80

Leu Lys Thr Val Ser Ala Asp Gln Leu Ala Arg Glu Glu Gln Ile Glu
85 90 95

Asn Pro Gly Ser Gly Ser Phe Val Leu Gly Ala Ile Ala Leu Gly Val
100 105 110

Ala Ala Ala Ala Ala Val Thr Ala Gly Val Ala Ile Ala Lys Thr Ile
115 120 125

Arg Leu Glu Ser Glu Val Thr Ala Ile Asn Asn Ala Leu Lys Lys Thr
130 135 140

Asn Glu Ala Val Ser Thr Leu Gly Asn Gly Val Arg Val Leu Ala Thr
145 150 155 160

Ala Val Arg Glu Leu Lys Asp Phe Val Ser Lys Asn Leu Thr Arg Ala
165 170 175

Ile Asn Lys Asn Lys Cys Pro Ile Asp Asp Leu Lys Met Ala Val Ser
180 185 190

Phe Ser Gln Phe Asn Arg Arg Phe Leu Asn Val Val Arg Gln Phe Ser
195 200 205

Asp Asn Ala Gly Ile Thr Pro Ala Ile Ser Leu Asp Leu Met Thr Asp
210 215 220

Ala Glu Leu Ala Arg Ala Val Pro Asn Met Pro Thr Ser Ala Gly Gln
225 230 235 240

Ile Lys Leu Met Leu Glu Asn Arg Ala Met Val Arg Arg Lys Gly Phe
245 250 255

Gly Ile Leu Ile Gly Val Tyr Gly Ser Ser Val Ile Tyr Met Val Gln
260 265 270

Leu Pro Ile Phe Gly Val Ile Asp Thr Pro Cys Trp Ile Val Lys Ala
275 280 285

```
Ala Pro Ser Cys Ser Glu Lys Lys Gly Asn Tyr Ala Cys Leu Leu Arg
    290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Ile Lys Phe Pro Glu Asp Gln Phe Gln Val Ala Leu Asp Gln Val Phe
    450                 455                 460

Glu Asn Ile Glu Asn Ser Gln Ala Leu Val Asp Gln Ser Asn Arg Ile
465                 470                 475                 480

Leu Ser Ser Ala Glu Lys Gly Asn Thr Gly Phe Ile Ile Val Ile Ile
                485                 490                 495

Leu Ile Ala Val Leu Gly Ser Ser Met Ile Leu Val Ser Ile Phe Ile
            500                 505                 510

Ile Ile Lys Lys Thr Lys Lys Pro Thr Gly Ala Pro Pro Glu Leu Ser
        515                 520                 525

Gly Val Thr Asn Asn Gly Phe Ile Pro His Asn
    530                 535
```

<210> SEQ ID NO 101
<211> LENGTH: 539
<212> TYPE: PRT
<213> ORGANISM: Artificial Sequence
<220> FEATURE:
<223> OTHER INFORMATION: Synthetic Polypeptide

<400> SEQUENCE: 101

```
Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Ser Asp Gly Pro
    50                  55                  60

Ser Leu Ile Lys Thr Glu Leu Asp Leu Thr Lys Ser Ala Leu Arg Glu
65                  70                  75                  80

Leu Lys Thr Val Ser Ala Asp Gln Leu Ala Arg Glu Glu Gln Ile Glu
                85                  90                  95

Asn Pro Gly Ser Gly Ser Phe Val Leu Gly Ala Ile Ala Leu Gly Val
            100                 105                 110
```

-continued

```
Ala Ala Ala Ala Ala Val Thr Ala Gly Val Ala Ile Ala Lys Thr Ile
        115                 120                 125

Arg Leu Pro Ser Glu Val Thr Ala Ile Asn Asn Ala Leu Lys Lys Thr
    130                 135                 140

Asn Glu Ala Val Ser Thr Leu Gly Asn Gly Val Arg Val Leu Ala Thr
145                 150                 155                 160

Ala Val Arg Glu Leu Lys Asp Phe Val Ser Lys Asn Leu Thr Arg Ala
                165                 170                 175

Ile Asn Lys Asn Lys Cys Asp Ile Asp Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Pro Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
            260                 265                 270

Leu Pro Ile Phe Gly Val Ile Asp Thr Pro Cys Trp Ile Val Lys Ala
        275                 280                 285

Ala Pro Ser Cys Ser Glu Lys Lys Gly Asn Tyr Ala Cys Leu Leu Arg
    290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Ile Lys Phe Pro Glu Asp Gln Phe Gln Val Ala Leu Asp Gln Val Phe
    450                 455                 460

Glu Asn Ile Glu Asn Ser Gln Ala Leu Val Asp Gln Ser Asn Arg Ile
465                 470                 475                 480

Leu Ser Ser Ala Glu Lys Gly Asn Thr Gly Phe Ile Ile Val Ile Ile
                485                 490                 495

Leu Ile Ala Val Leu Gly Ser Ser Met Ile Leu Val Ser Ile Phe Ile
            500                 505                 510

Ile Ile Lys Lys Thr Lys Lys Pro Thr Gly Ala Pro Pro Glu Leu Ser
        515                 520                 525
```

Gly Val Thr Asn Asn Gly Phe Ile Pro His Asn
    530                 535

<210> SEQ ID NO 102
<211> LENGTH: 539
<212> TYPE: PRT
<213> ORGANISM: Artificial Sequence
<220> FEATURE:
<223> OTHER INFORMATION: Synthetic Polypeptide

<400> SEQUENCE: 102

Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Ser Asp Gly Pro
    50                  55                  60

Ser Leu Ile Lys Thr Glu Leu Asp Leu Thr Lys Ser Ala Leu Arg Glu
65                  70                  75                  80

Leu Lys Thr Val Ser Ala Asp Gln Leu Ala Arg Glu Glu Gln Ile Glu
                85                  90                  95

Asn Pro Gly Ser Gly Ser Phe Val Leu Gly Ala Ile Ala Leu Gly Val
            100                 105                 110

Ala Ala Ala Ala Ala Val Thr Ala Gly Val Ala Ile Ala Lys Thr Ile
        115                 120                 125

Arg Leu Glu Ser Glu Val Thr Ala Ile Asn Asn Ala Leu Lys Lys Thr
    130                 135                 140

Asn Glu Ala Val Ser Thr Leu Gly Asn Gly Val Arg Val Leu Ala Thr
145                 150                 155                 160

Ala Val Arg Glu Leu Lys Asp Phe Val Ser Lys Asn Leu Thr Arg Ala
                165                 170                 175

Ile Asn Lys Asn Lys Cys Asp Ile Asp Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Pro Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
            260                 265                 270

Leu Pro Ile Phe Gly Val Ile Asp Thr Pro Cys Trp Ile Val Lys Ala
        275                 280                 285

Ala Pro Ser Cys Ser Glu Lys Lys Gly Asn Tyr Ala Cys Leu Leu Arg
    290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Lys Glu Cys Asn Ile
            340                 345                 350

```
Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Pro Pro
        435                 440                 445

Ile Lys Phe Pro Glu Asp Gln Phe Gln Val Ala Leu Asp Gln Val Phe
    450                 455                 460

Glu Asn Ile Glu Asn Ser Gln Ala Leu Val Asp Gln Ser Asn Arg Ile
465                 470                 475                 480

Leu Ser Ser Ala Glu Lys Gly Asn Thr Gly Phe Ile Ile Val Ile Ile
                485                 490                 495

Leu Ile Ala Val Leu Gly Ser Ser Met Ile Leu Val Ser Ile Phe Ile
            500                 505                 510

Ile Ile Lys Lys Thr Lys Lys Pro Thr Gly Ala Pro Pro Glu Leu Ser
        515                 520                 525

Gly Val Thr Asn Asn Gly Phe Ile Pro His Asn
    530                 535


<210> SEQ ID NO 103
<211> LENGTH: 539
<212> TYPE: PRT
<213> ORGANISM: Artificial Sequence
<220> FEATURE:
<223> OTHER INFORMATION: Synthetic Polypeptide

<400> SEQUENCE: 103

Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Ser Asp Gly Pro
    50                  55                  60

Ser Leu Ile Lys Thr Glu Leu Asp Leu Thr Lys Ser Ala Leu Arg Glu
65                  70                  75                  80

Leu Lys Thr Val Ser Ala Asp Gln Leu Ala Arg Glu Glu Gln Ile Glu
                85                  90                  95

Asn Pro Gly Ser Gly Ser Phe Val Leu Gly Ala Ile Ala Leu Gly Val
            100                 105                 110

Ala Ala Ala Ala Ala Val Thr Ala Gly Val Ala Ile Ala Lys Thr Ile
        115                 120                 125

Arg Leu Glu Ser Glu Val Thr Ala Ile Asn Asn Ala Leu Lys Lys Thr
    130                 135                 140

Asn Glu Ala Val Ser Thr Leu Gly Asn Gly Val Arg Val Leu Ala Thr
145                 150                 155                 160

Ala Val Arg Glu Leu Lys Asp Phe Val Ser Lys Asn Leu Thr Arg Ala
                165                 170                 175
```

```
Ile Asn Lys Asn Lys Cys Asp Ile Asp Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Pro Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
            260                 265                 270

Leu Pro Ile Phe Gly Val Ile Asp Thr Pro Cys Trp Ile Val Lys Ala
        275                 280                 285

Ala Pro Ser Cys Ser Glu Lys Lys Gly Asn Tyr Ala Cys Leu Leu Arg
    290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Ile Lys Phe Pro Glu Asn Gln Phe Gln Val Ala Leu Asp Gln Val Phe
    450                 455                 460

Glu Asn Ile Glu Asn Ser Gln Ala Leu Val Asp Gln Ser Asn Arg Ile
465                 470                 475                 480

Leu Ser Ser Ala Glu Lys Gly Asn Thr Gly Phe Ile Ile Val Ile Ile
                485                 490                 495

Leu Ile Ala Val Leu Gly Ser Ser Met Ile Leu Val Ser Ile Phe Ile
            500                 505                 510

Ile Ile Lys Lys Thr Lys Lys Pro Thr Gly Ala Pro Pro Glu Leu Ser
        515                 520                 525

Gly Val Thr Asn Asn Gly Phe Ile Pro His Asn
    530                 535
```

```
<210> SEQ ID NO 104
<211> LENGTH: 539
<212> TYPE: PRT
<213> ORGANISM: Artificial Sequence
<220> FEATURE:
<223> OTHER INFORMATION: Synthetic Polypeptide

<400> SEQUENCE: 104
```

-continued

```
Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Ser Asp Gly Pro
    50                  55                  60

Ser Leu Ile Lys Thr Glu Leu Asp Leu Thr Lys Ser Ala Leu Arg Glu
65                  70                  75                  80

Leu Lys Thr Val Ser Ala Asp Gln Leu Ala Arg Glu Glu Gln Ile Glu
                85                  90                  95

Asn Pro Gly Ser Gly Ser Phe Val Leu Gly Ala Ile Ala Leu Gly Val
            100                 105                 110

Ala Ala Ala Ala Ala Val Thr Ala Gly Val Ala Ile Ala Lys Thr Ile
        115                 120                 125

Arg Leu Glu Ser Glu Val Thr Ala Ile Asn Asn Ala Leu Lys Lys Thr
    130                 135                 140

Asn Glu Ala Val Ser Thr Leu Gly Asn Gly Val Arg Val Leu Ala Thr
145                 150                 155                 160

Ala Val Arg Glu Leu Lys Asp Phe Val Ser Lys Asn Leu Thr Arg Ala
                165                 170                 175

Ile Asn Lys Asn Lys Cys Asp Ile Asp Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Pro Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
            260                 265                 270

Leu Pro Ile Phe Gly Val Ile Asp Thr Pro Cys Trp Ile Val Lys Ala
        275                 280                 285

Ala Pro Ser Cys Ser Glu Lys Lys Gly Asn Tyr Ala Cys Leu Leu Arg
    290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
```

```
            420                 425                 430

Glu Gln His Val Ile Lys Gly Arg Pro Val Ser Ser Ser Phe Asp Pro
        435                 440                 445

Ile Lys Phe Pro Gln Asp Gln Phe Gln Val Ala Leu Asp Gln Val Phe
    450                 455                 460

Glu Asn Ile Glu Asn Ser Gln Ala Leu Val Asp Gln Ser Asn Arg Ile
465                 470                 475                 480

Leu Ser Ser Ala Glu Lys Gly Asn Thr Gly Phe Ile Ile Val Ile Ile
                485                 490                 495

Leu Ile Ala Val Leu Gly Ser Ser Met Ile Leu Val Ser Ile Phe Ile
            500                 505                 510

Ile Ile Lys Lys Thr Lys Lys Pro Thr Gly Ala Pro Pro Glu Leu Ser
        515                 520                 525

Gly Val Thr Asn Asn Gly Phe Ile Pro His Asn
    530                 535


<210> SEQ ID NO 105
<211> LENGTH: 539
<212> TYPE: PRT
<213> ORGANISM: Artificial Sequence
<220> FEATURE:
<223> OTHER INFORMATION: Synthetic Polypeptide

<400> SEQUENCE: 105

Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Ser Asp Gly Pro
    50                  55                  60

Ser Leu Ile Lys Thr Glu Leu Asp Leu Thr Lys Ser Ala Leu Arg Glu
65                  70                  75                  80

Leu Lys Thr Val Ser Ala Asp Gln Leu Ala Arg Glu Glu Gln Ile Glu
                85                  90                  95

Asn Pro Gly Ser Gly Ser Phe Val Leu Gly Ala Ile Ala Leu Gly Val
            100                 105                 110

Ala Ala Ala Ala Ala Val Thr Ala Gly Val Ala Ile Ala Lys Thr Ile
        115                 120                 125

Arg Leu Glu Ser Glu Val Thr Ala Ile Asn Asn Ala Leu Lys Lys Thr
    130                 135                 140

Asn Glu Ala Val Ser Thr Leu Gly Asn Gly Val Arg Val Leu Ala Thr
145                 150                 155                 160

Ala Val Arg Glu Leu Lys Asp Phe Val Ser Lys Asn Leu Thr Arg Ala
                165                 170                 175

Ile Asn Lys Asn Lys Cys Asp Ile Asp Asp Leu Lys Met Ala Val Ser
            180                 185                 190

Phe Ser Gln Trp Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Pro Asn Met Pro Thr Ser Ala Gly Gln
225                 230                 235                 240

Ile Lys Leu Met Leu Glu Asn Arg Ala Met Val Arg Arg Lys Gly Phe
```

```
                245                 250                 255

Gly Ile Leu Ile Gly Val Tyr Gly Ser Ser Val Ile Tyr Met Val Gln
            260                 265                 270

Leu Pro Ile Phe Gly Val Ile Asp Thr Pro Cys Trp Ile Val Lys Ala
        275                 280                 285

Ala Pro Ser Cys Ser Glu Lys Lys Gly Asn Tyr Ala Cys Leu Leu Arg
    290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Ile Lys Phe Pro Glu Asp Gln Phe Gln Val Ala Leu Asp Gln Val Phe
    450                 455                 460

Glu Asn Ile Glu Asn Ser Gln Ala Leu Val Asp Gln Ser Asn Arg Ile
465                 470                 475                 480

Leu Ser Ser Ala Glu Lys Gly Asn Thr Gly Phe Ile Ile Val Ile Ile
                485                 490                 495

Leu Ile Ala Val Leu Gly Ser Ser Met Ile Leu Val Ser Ile Phe Ile
            500                 505                 510

Ile Ile Lys Lys Thr Lys Lys Pro Thr Gly Ala Pro Pro Glu Leu Ser
        515                 520                 525

Gly Val Thr Asn Asn Gly Phe Ile Pro His Asn
    530                 535
```

<210> SEQ ID NO 106
<211> LENGTH: 1617
<212> TYPE: DNA
<213> ORGANISM: Artificial Sequence
<220> FEATURE:
<223> OTHER INFORMATION: Synthetic Polynucleotide

<400> SEQUENCE: 106

```
atgagctgga aggtggtcat catcttcagc ctgctgatca cacctcagca cggcctgaaa      60

gagagctacc tggaagagtc ctgcagcacc atcacagagg gctacctgtc tgtgctgaga     120

accggctggt acaccaacgt gttcacactg gaagtgggcg acgtcgagaa tctgacatgc     180

tctgatggcc ctagcctgat caagaccgag ctggatctga ccaagagcgc cctgagagaa     240

ctcaagaccg tgtctgccga tcagctggcc agagaggaac agatcgagaa tcctggcagc     300

ggcagctttg tgctgggagc cattgctctt ggagtggctg ctgctgcagc tgttacagca     360

ggcgtggcca tctgcaagac catcagactg gaaagcgaag tgaccgccat caacaacgcc     420
```

ctgaagaaga caaacgaggc cgtcagcaca ctcggcaatg gcgttagagt gctggccttt 480
gccgtgcgcg agctgaagga cttcgtgtcc aagaacctga cacgggccct gaacaagaac 540
aagtgcgaca tcgacgacct gaagatggcc gtgtccttta gccagttcaa ccggcggttt 600
ctgaacgtcg tgcggcagtt tagcgacaac gccggaatca caccagccat cagcctggac 660
ctgatgacag atgctgagct ggctagagcc gtgcctaaca tgcctacatc tgccggccag 720
atcaagctga tgctcgagaa tagagccatg gtccgacgga aaggcttcgg cattctgtgt 780
ggcgtgtacg gcagcagcgt gatctatatg gtgcagctgc ctatcttcgg cgtgatcgac 840
acaccctgct ggattgtgaa ggccgctcct agctgtagcg agaagaaggg caattacgcc 900
tgcctgctga gagaggacca aggctggtat tgtcagaacg ccggcagcac cgtgtactac 960
cctaacgaga aggactgcga gacaagaggc gaccacgtgt tctgtgatac cgccgctgga 1020
atcaatgtgg ccgagcagag caaagagtgc aacatcaaca tcagcaccac caactatccc 1080
tgcaaggtgt ccaccggcag gcaccctatt tctatggtgg ctctgtctcc tctgggagcc 1140
ctggtggctt gttataaggg cgtgtcctgt agcatcggca gcaacagagt gggcatcatc 1200
aagcagctga acaagggctg cagctacatc accaaccagg acgccgatac cgtgaccatc 1260
gacaacaccg tgtatcagct gagcaaggtg gaaggcgaac agcacgtgat caagggcaga 1320
cctgtgtcca gcagcttcga ccctatcaag ttccctgagg atcagttcaa cgtggccctg 1380
gaccaggtgt tcgagaacat cgagaattcc caggctctgg tggaccagtc caacagaatc 1440
ctgtctagcg ccgagaaggg aaacaccggc ttcatcatcg tgatcatcct gatcgccgtg 1500
ctgggcagct ccatgatcct ggtgtccatc ttcatcatta tcaagaagac caagaagccc 1560
accggcgctc ctccagaact gagcggagtg accaacaatg gcttcatccc tcacaac 1617

<210> SEQ ID NO 107
<211> LENGTH: 1617
<212> TYPE: DNA
<213> ORGANISM: Artificial Sequence
<220> FEATURE:
<223> OTHER INFORMATION: Synthetic Polynucleotide

<400> SEQUENCE: 107
atgagctgga aggtggtcat catcttcagc ctgctgatca cacctcagca cggcctgaaa 60
gagagctacc tggaagagtc ctgcagcacc atcacagagg gctacctgtc tgtgctgaga 120
accggctggt acaccaacgt gttcacactg gaagtgggcg acgtcgagaa tctgacatgc 180
tctgatggcc ctagcctgat caagaccgag ctggatctga ccaagagcgc cctgagagaa 240
ctcaagaccg tgtctgccga tcagctggcc agagaggaac agatcgagaa tcctggcagc 300
ggcagctttg tgctgggagc cattgctctt ggagtggctg ctgctgcagc tgttacagca 360
ggcgtggcca tctgcaagac catcagactg gaaagcgaag tgaccgccat caacaacgcc 420
ctgaagaaga caaacgaggc cgtcagcaca ctcggcaatg gcgttagagt gctggccaca 480
gccgtgcgcg agctgaagga cttcgtgtcc aagaacctga cacgggccat taacaagaac 540
aagtgcgaca tcgacgacct gaagatggcc gtgtccttta gccagttcaa ccggcggttt 600
ctgaacgtcg tgcggcagtt tagcgacaac gccggaatca caccagccat cagcctggac 660
ctgatgacag atgctgagct ggctagagcc gtgcctaaca tgcctacatc tgccggccag 720
atcaagctga tgctcgagaa tagagccatg gtccgacgga aaggcttcgg cattctgtgt 780
ggcgtgtacg gcagcagcgt gatctatatg gtgcagctgc ctatcttcgg cgtgatcgac 840

-continued

```
acaccctgct ggattgtgaa ggccgctcct agctgtagcg agaagaaggg caattacgcc    900

tgcctgctga gagaggacca aggctggtat tgtcagaacg ccggcagcac cgtgtactac    960

cctaacgaga aggactgcga gacaagaggc gaccacgtgt tctgtgatac cgccgctgga   1020

atcaatgtgg ccgagcagag caaagagtgc aacatcaaca tcagcaccac caactatccc   1080

tgcaaggtgt ccaccggcag gcaccctatt tctatggtgg ctctgtctcc tctgggagcc   1140

ctggtggctt gttataaggg cgtgtcctgt agcatcggca gcaacagagt gggcatcatc   1200

aagcagctga acaagggctg cagctacatc accaaccagg acgccgatac cgtgaccatc   1260

gacaacaccg tgtatcagct gagcaaggtg gaaggcgaac agcacgtgat caagggcaga   1320

cctgtgtcca gcagcttcga ccctatcaag ttccctgagc accagtggca tgtggccctg   1380

gaccaggtgt tcgagaacat cgagaattcc caggctctgg tggaccagtc caacagaatc   1440

ctgtctagcg ccgagaaggg aaacaccggc ttcatcatcg tgatcatcct gatcgccgtg   1500

ctgggcagct ccatgatcct ggtgtccatc ttcatcatta tcaagaagac caagaagccc   1560

accggcgctc ctccagaact gagcggagtg accaacaatg gcttcatccc tcacaac      1617
```

<210> SEQ ID NO 108
<211> LENGTH: 1617
<212> TYPE: DNA
<213> ORGANISM: Artificial Sequence
<220> FEATURE:
<223> OTHER INFORMATION: Synthetic Polynucleotide

<400> SEQUENCE: 108

```
atgagctgga aggtggtcat catcttcagc ctgctgatca cacctcagca cggcctgaaa     60

gagagctacc tggaagagtc ctgcagcacc atcacagagg gctacctgtc tgtgctgaga    120

accggctggt acaccaacgt gttcacactg gaagtgggcg acgtcgagaa tctgacatgc    180

tctgatggcc ctagcctgat caagaccgag ctggatctgc tcaagagcgc cctgagagaa    240

ctcaagaccg tgtctgccga tcagctggcc agagaggaac agatcgagaa tcctggcagc    300

ggcagctttg tgctgggagc cattgctctt ggagtggctg ctgctgcagc tgttacagca    360

ggcgtggcca tcgctaagac catcagactg gaaagcgaag tgaccgccat caacaacgcc    420

ctgaagaaga caaacgaggc cgtcagcaca ctcggcaatg gcgttagagt gctggccaca    480

gccgtgcgcg agctgaagga cttcgtgtcc aagaacctga cacgggccat taacaagaac    540

aagtgcgaca tccctgacct gaagatggcc gtgtccttta gccagttcaa ccggcggttt    600

ctgaacgtcg tgcggcagtt tagcgacaac gccggaatca caccagccat cagcctggac    660

ctgatgacag atgctgagct ggctagagcc gtgcctaaca tgcctacatc tgccggccag    720

atcaagctga tgctcgagaa tagagccatg gtccgacgga aaggcttcgg cattctgatt    780

ggcgtgtacg gcagcagcgt gatctatatg gtgcagctgc ctatcttcgg cgtgatcgac    840

acaccctgct ggattgtgaa ggccgctcct agctgtagcg agaagaaggg caattacgcc    900

tgcctgctga gagaggacca aggctggtat tgtcagaacg ccggcagcac cgtgtactac    960

cctaacgaga aggactgcga gacaagaggc gaccacgtgt tctgtgatac cgccgctgga   1020

atcaatgtgg ccgagcagag caaagagtgc aacatcaaca tcagcaccac caactatccc   1080

tgcaaggtgt ccaccggcag gcaccctatt tctatggtgg ctctgtctcc tctgggagcc   1140

ctggtggctt gttataaggg cgtgtcctgt agcatcggca gcaacagagt gggcatcatc   1200

aagcagctga acaagggctg cagctacatc accaaccagg acgccgatac cgtgaccatc   1260

gacaacaccg tgtatcagct gagcaaggtg gaaggcgaac agcacgtgat caagggcaga   1320
```

cctgtgtcca gcagcttcga ccctatcaag ttccctgagg atcagttcca ggtggccctg 1380
gaccaggtgt tcgagaacat cgagaattcc caggctctgg tggaccagtc caacagaatc 1440
ctgtctagcg ccgagaaggg aaacaccggc ttcatcatcg tgatcatcct gatcgccgtg 1500
ctgggcagct ccatgatcct ggtgtccatc ttcatcatta tcaagaagac caagaagccc 1560
accggcgctc ctccagaact gagcggagtg accaacaatg gcttcatccc tcacaac 1617

<210> SEQ ID NO 109
<211> LENGTH: 1617
<212> TYPE: DNA
<213> ORGANISM: Artificial Sequence
<220> FEATURE:
<223> OTHER INFORMATION: Synthetic Polynucleotide

<400> SEQUENCE: 109
atgagctgga aggtggtcat catcttcagc ctgctgatca cacctcagca cggcctgaaa 60
gagagctacc tggaagagtc ctgcagcacc atcacagagg gctacctgtc tgtgctgaga 120
accggctggt acaccaacgt gttcacactg gaagtgggcg acgtcgagaa tctgacatgc 180
tctgatggcc ctagcctgat caagaccgag ctggatctgc tcaagagcgc cctgagagaa 240
ctcaagaccg tgtctgccga tcagctggcc agagaggaac agatcgagaa tcctggcagc 300
ggcagctttg tgctgggagc cattgctctt ggagtggctg ctgctgcagc tgttacagca 360
ggcgtggcca tcgctaagac catcagactg gaaagcgaag tgaccgccat caacaacgcc 420
ctgaagaaga caaacgaggc cgtcagcaca ctcggcaatg gcgttagagt gctggccaca 480
gccgtgcgcg agctgaagga cttcgtgtcc aagaacctga cacgggccat taacaagaac 540
aagtgcgaca tccctgacct gaagatggcc gtgtccttta gccagttcaa ccggcggttt 600
ctgaacgtcg tgcggcagtt tagcgacaac gccggaatca caccagccat cagcctggac 660
ctgatgacag atgctgagct ggctagagcc gtgcctaaca tgcctacatc tgccggccag 720
atcaagctga tgctcgagaa tagagccatg gtccgacgga aaggcttcgg cattctgatt 780
ggcgtgtacg gcagcagcgt gatctatatg gtgcagctgc ctatcttcgg cgtgatcgac 840
acaccctgct ggattgtgaa ggccgctcct agctgtagcg agaagaaggg caattacgcc 900
tgcctgctga gagaggacca aggctggtat tgtcagaacg ccggcagcac cgtgtactac 960
cctaacgaga aggactgcga gacaagaggc gaccacgtgt tctgtgatac cgccgctgga 1020
atcaatgtgg ccgagcagag caaagagtgc aacatcaaca tcagcaccac caactatccc 1080
tgcaaggtgt ccaccggcag gcaccctatt tctatggtgg ctctgtctcc tctgggagcc 1140
ctggtggctt gttataaggg cgtgtcctgt agcatcggca gcaacagagt gggcatcatc 1200
aagcagctga acaagggctg cagctacatc accaaccagg acgccgatac cgtgaccatc 1260
gacaacaccg tgtatcagct gagcaaggtg gaaggcgaac agcacgtgat caagggcaga 1320
cctgtgtcca gcagcttcga ccctatcaag ttccctgaga accagttcca ggtggccctg 1380
gaccaggtgt tcgagaacat cgagaattcc caggctctgg tggaccagtc caacagaatc 1440
ctgtctagcg ccgagaaggg aaacaccggc ttcatcatcg tgatcatcct gatcgccgtg 1500
ctgggcagct ccatgatcct ggtgtccatc ttcatcatta tcaagaagac caagaagccc 1560
accggcgctc ctccagaact gagcggagtg accaacaatg gcttcatccc tcacaac 1617

<210> SEQ ID NO 110
<211> LENGTH: 1617
<212> TYPE: DNA

<213> ORGANISM: Artificial Sequence
<220> FEATURE:
<223> OTHER INFORMATION: Synthetic Polynucleotide

<400> SEQUENCE: 110
atgagctgga aggtggtcat catcttcagc ctgctgatca cacctcagca cggcctgaaa 60
gagagctacc tggaagagtc ctgcagcacc atcacagagg gctacctgtc tgtgctgaga 120
accggctggt acaccaacgt gttcacactg gaagtgggcg acgtcgagaa tctgacatgc 180
tctgatggcc ctagcctgat caagaccgag ctggatctgc tcaagagcgc cctgagagaa 240
ctcaagaccg tgtctgccga tcagctggcc agagaggaac agatcgagaa tcctggcagc 300
ggcagctttg tgctgggagc cattgctctt ggagtggctg ctgctgcagc tgttacagca 360
ggcgtggcca tcgctaagac catcagactg gaaagcgaag tgaccgccat caacaacgcc 420
ctgaagaaga caaacgaggc cgtcagcaca ctcggcaatg gcgttagagt gctggccaca 480
gccgtgcgcg agctgaagga cttcgtgctt aagaacctga cacgggccat taacaagaac 540
aagtgcgaca tccctgacct gaagatggcc gtgtccttta gccagttcaa ccggcggttt 600
ctgaacgtcg tgcggcagtt tagcgacaac gccggaatca caccagccat cagcctggac 660
ctgatgacag atgctgagct ggctagagcc gtgcctaaca tgcctacatc tgccggccag 720
atcaagctga tgctcgagaa tagagccatg gtccgacgga aaggcttcgg cattctgatt 780
ggcgtgtacg gcagcagcgt gatctatatg gtgcagctgc ctatcttcgg cgtgatcgac 840
acaccctgct ggattgtgaa ggccgctcct agctgtagcg agaagaaggg caattacgcc 900
tgcctgctga gagaggacca aggctggtat tgtcagaacg ccggcagcac cgtgtactac 960
cctaacgaga aggactgcga gacaagaggc gaccacgtgt tctgtgatac cgccgctgga 1020
atcaatgtgg ccgagcagag caaagagtgc aacatcaaca tcagcaccac caactatccc 1080
tgcaaggtgt ccaccggcag gcaccctatt tctatggtgg ctctgtctcc tctgggagcc 1140
ctggtggctt gttataaggg cgtgtcctgt agcatcggca gcaacagagt gggcatcatc 1200
aagcagctga acaagggctg cagctacatc accaaccagg acgccgatac cgtgaccatc 1260
gacaacaccg tgtatcagct gagcaaggtg gaaggcgaac agcacgtgat caagggcaga 1320
cctgtgtcca gcagcttcga ccctatcaag ttccctgagg atcagttcca ggtggccctg 1380
gaccaggtgt tcgagaacat cgagaattcc caggctctgg tggaccagtc caacagaatc 1440
ctgtctagcg ccgagaaggg aaacaccggc ttcatcatcg tgatcatcct gatcgccgtg 1500
ctgggcagct ccatgatcct ggtgtccatc ttcatcatta tcaagaagac caagaagccc 1560
accggcgctc ctccagaact gagcggagtg accaacaatg gcttcatccc tcacaac 1617

<210> SEQ ID NO 111
<211> LENGTH: 1617
<212> TYPE: DNA
<213> ORGANISM: Artificial Sequence
<220> FEATURE:
<223> OTHER INFORMATION: Synthetic Polynucleotide

<400> SEQUENCE: 111
atgagctgga aggtggtcat catcttcagc ctgctgatca cacctcagca cggcctgaaa 60
gagagctacc tggaagagtc ctgcagcacc atcacagagg gctacctgtc tgtgctgaga 120
accggctggt acaccaacgt gttcacactg gaagtgggcg acgtcgagaa tctgacatgc 180
tctgatggcc ctagcctgat caagaccgag ctggatctgc tcaagagcgc cctgagagaa 240
ctcaagaccg tgtctgccga tcagctggcc agagaggaac agatcgagaa tcctggcagc 300
ggcagctttg tgctgggagc cattgctctt ggagtggctg ctgctgcagc tgttacagca 360
ggcgtggcca tcgctaagac catcagactg gaaagcgaag tgaccgccat caacaacgcc 420
ctgaagaaga caaacgaggc cgtcagcaca ctcggcaatg gcgttagagt gctggccaca 480
gccgtgcgcg agctgaagga cttcgtgctt aagaacctga cacgggccat taacaagaac 540
aagtgcgaca tccctgacct gaagatggcc gtgtccttta gccagttcaa ccggcggttt 600
ctgaacgtcg tgcggcagtt tagcgacaac gccggaatca caccagccat cagcctggac 660
ctgatgacag atgctgagct ggctagagcc gtgcctaaca tgcctacatc tgccggccag 720
atcaagctga tgctcgagaa tagagccatg gtccgacgga aaggcttcgg cattctgatt 780
ggcgtgtacg gcagcagcgt gatctatatg gtgcagctgc ctatcttcgg cgtgatcgac 840
acaccctgct ggattgtgaa ggccgctcct agctgtagcg agaagaaggg caattacgcc 900
tgcctgctga gagaggacca aggctggtat tgtcagaacg ccggcagcac cgtgtactac 960
cctaacgaga aggactgcga gacaagaggc gaccacgtgt tctgtgatac cgccgctgga 1020
atcaatgtgg ccgagcagag caaagagtgc aacatcaaca tcagcaccac caactatccc 1080
tgcaaggtgt ccaccggcag gcaccctatt tctatggtgg ctctgtctcc tctgggagcc 1140
ctggtggctt gttataaggg cgtgtcctgt agcatcggca gcaacagagt gggcatcatc 1200
aagcagctga acaagggctg cagctacatc accaaccagg acgccgatac cgtgaccatc 1260
gacaacaccg tgtatcagct gagcaaggtg gaaggcgaac agcacgtgat caagggcaga 1320
cctgtgtcca gcagcttcga ccctatcaag ttccctgaga accagttcca ggtggccctg 1380
gaccaggtgt tcgagaacat cgagaattcc caggctctgg tggaccagtc caacagaatc 1440
ctgtctagcg ccgagaaggg aaacaccggc ttcatcatcg tgatcatcct gatcgccgtg 1500
ctgggcagct ccatgatcct ggtgtccatc ttcatcatta tcaagaagac caagaagccc 1560
accggcgctc ctccagaact gagcggagtg accaacaatg gcttcatccc tcacaac 1617

<210> SEQ ID NO 112
<211> LENGTH: 1617
<212> TYPE: DNA
<213> ORGANISM: Artificial Sequence
<220> FEATURE:
<223> OTHER INFORMATION: Synthetic Polynucleotide

<400> SEQUENCE: 112
atgagctgga aggtggtcat catcttcagc ctgctgatca cacctcagca cggcctgaaa 60
gagagctacc tggaagagtc ctgcagcacc atcacagagg gctacctgtc tgtgctgaga 120
accggctggt acaccaacgt gttcacactg cctgtgggcg acgtcgagaa tctgacatgc 180
tctgatggcc ctagcctgat caagaccgag ctggatctgc tcaagagcgc cctgagagaa 240
ctcaagaccg tgtctgccga tcagctggcc agagaggaac agatcgagaa tcctggcagc 300
ggcagctttg tgctgggagc cattgctctt ggagtggctg ctgctgcagc tgttacagca 360
ggcgtggcca tcgctaagac catcagactg gaaagcgaag tgaccgccat caacaacgcc 420
ctgaagaaga caaacgaggc cgtcagcaca ctcggcaatg gcgttagagt gctggccaca 480
gccgtgcgcg agctgaagga cttcgtgtcc aagaacctga cacgggccat taacaagaac 540
aagtgcgaca tcgacgacct gaagatggcc gtgtccttta gccagttcaa ccggcggttt 600
ctgaacgtcg tgcggcagtt tagcgacaac gccggaatca caccagccat cagcctggac 660
ctgatgacag atgctgagct ggctagagcc gtgcctaaca tgcctacatc tgccggccag 720
atcaagctga tgctcgagaa tagagccatg gtccgacgga aaggcttcgg cattctgatt 780
ggcgtgtacg gcagcagcgt gatctatatg gtgcagctgc ctatcttcgg cgtgatcgac 840
acaccctgct ggattgtgaa ggccgctcct agctgtagcg agaagaaggg caattacgcc 900
tgcctgctga gagaggacca aggctggtat tgtcagaacg ccggcagcac cgtgtactac 960
cctaacgaga aggactgcga gacaagaggc gaccacgtgt tctgtgatac cgccgctgga 1020
atcaatgtgg ccgagcagag caaagagtgc aacatcaaca tcagcaccac caactatccc 1080
tgcaaggtgt ccaccggcag gcaccctatt tctatggtgg ctctgtctcc tctgggagcc 1140
ctggtggctt gttataaggg cgtgtcctgt agcatcggca gcaacagagt gggcatcatc 1200
aagcagctga acaagggctg cagctacatc accaaccagg acgccgatac cgtgaccatc 1260
gacaacaccg tgtatcagct gagcaaggtg gaaggcgaac agcacgtgat caagggcaga 1320
cctgtgtcca gcagcttcga ccctatcaag ttccctgagg atcagttcca ggtggccctg 1380
gaccaggtgt tcgagaacat cgagaattcc caggctctgg tggaccagtc caacagaatc 1440
ctgtctagcg ccgagaaggg aaacaccggc ttcatcatcg tgatcatcct gatcgccgtg 1500
ctgggcagct ccatgatcct ggtgtccatc ttcatcatta tcaagaagac caagaagccc 1560
accggcgctc ctccagaact gagcggagtg accaacaatg gcttcatccc tcacaac 1617

<210> SEQ ID NO 113
<211> LENGTH: 1617
<212> TYPE: DNA
<213> ORGANISM: Artificial Sequence
<220> FEATURE:
<223> OTHER INFORMATION: Synthetic Polynucleotide

<400> SEQUENCE: 113
atgagctgga aggtggtcat catcttcagc ctgctgatca cacctcagca cggcctgaaa 60
gagagctacc tggaagagtc ctgcagcacc atcacagagg gctacctgtc tgtgctgaga 120
accggctggt acaccaacgt gttcacactg cctgtgggcg acgtcgagaa tctgacatgc 180
tctgatggcc ctagcctgat caagaccgag ctggatctgc tcaagagcgc cctgagagaa 240
ctcaagaccg tgtctgccga tcagctggcc agagaggaac agatcgagaa tcctggcagc 300
ggcagctttg tgctgggagc cattgctctt ggagtggctg ctgctgcagc tgttacagca 360
ggcgtggcca tcgctaagac catcagactg gaaagcgaag tgaccgccat caacaacgcc 420
ctgaagaaga caaacgaggc cgtcagcaca ctcggcaatg gcgttagagt gctggccaca 480
gccgtgcgcg agctgaagga cttcgtgtcc aagaacctga cacgggccat taacaagaac 540
aagtgcgaca tcgacgacct gaagatggcc gtgtccttta gccagttcaa ccggcggttt 600
ctgaacgtcg tgcggcagtt tagcgacaac gccggaatca caccagccat cagcctggac 660
ctgatgacag atgctgagct ggctagagcc gtgcctaaca tgcctacatc tgccggccag 720
atcaagctga tgctcgagaa tagagccatg gtccgacgga aaggcttcgg cattctgatt 780
ggcgtgtacg gcagcagcgt gatctatatg gtgcagctgc ctatcttcgg cgtgatcgac 840
acaccctgct ggattgtgaa ggccgctcct agctgtagcg agaagaaggg caattacgcc 900
tgcctgctga gagaggacca aggctggtat tgtcagaacg ccggcagcac cgtgtactac 960
cctaacgaga aggactgcga gacaagaggc gaccacgtgt tctgtgatac cgccgctgga 1020
atcaatgtgg ccgagcagag caaagagtgc aacatcaaca tcagcaccac caactatccc 1080
tgcaaggtgt ccaccggcag gcaccctatt tctatggtgg ctctgtctcc tctgggagcc 1140
ctggtggctt gttataaggg cgtgtcctgt agcatcggca gcaacagagt gggcatcatc 1200
aagcagctga acaagggctg cagctacatc accaaccagg acgccgatac cgtgaccatc 1260
gacaacaccg tgtatcagct gagcaaggtg gaaggcgaac agcacgtgat caagggcaga 1320
cctgtgtcca gcagcttcga ccctatcaag ttccctgaga accagttcca ggtggccctg 1380
gaccaggtgt tcgagaacat cgagaattcc caggctctgg tggaccagtc caacagaatc 1440
ctgtctagcg ccgagaaggg aaacaccggc ttcatcatcg tgatcatcct gatcgccgtg 1500
ctgggcagct ccatgatcct ggtgtccatc ttcatcatta tcaagaagac caagaagccc 1560
accggcgctc ctccagaact gagcggagtg accaacaatg gcttcatccc tcacaac 1617

<210> SEQ ID NO 114
<211> LENGTH: 1617
<212> TYPE: DNA
<213> ORGANISM: Artificial Sequence
<220> FEATURE:
<223> OTHER INFORMATION: Synthetic Polynucleotide

<400> SEQUENCE: 114
atgagctgga aggtggtcat catcttcagc ctgctgatca cacctcagca cggcctgaaa 60
gagagctacc tggaagagtc ctgcagcacc atcacagagg gctacctgtc tgtgctgaga 120
accggctggt acaccaacgt gttcacactg gaagtgggcg acgtcgagaa tctgacatgc 180
tctgatggcc ctagcctgat caagaccgag ctggatctgc tcaagagcgc cctgagagaa 240
ctcaagaccg tgtctgccga tcagctggcc agagaggaac agatcgagaa tcctggcagc 300
ggcagctttg tgctgggagc cattgctctt ggagtggctg ctgctgcagc tgttacagca 360
ggcgtggcca tcgctaagac catcagactg gaaagcgaag tgaccgccat caacaacgcc 420
ctgaagaaga caaacgaggc cgtcagcaca ctcggcaatg gcgttagagt gctggccaca 480
gccgtgcgcg agctgaagga cttcgtgtcc aagaacctga cacgggccat taacaagaac 540
aagtgcgaca tcgacgacct gaagatggcc gtgtccttta gccagttcaa ccggcggttt 600
ctgaacgtcg tgcggcagtt tagcgacaac gccggaatca caccagccat cagcctggac 660
ctgatgacag atgctgagct ggctagagcc gtgcctaaca tgcctacatc tgccggccag 720
atcaagctga tgctcgagaa tagagccatg gtccgacgga aaggcttcgg cattctgatt 780
ggcgtgtacg gcagcagcgt gatctatatg gtgcagctgc ctatcttcgg cgtgatcgac 840
acaccctgct ggattgtgaa ggccgctcct agctgtagcg agaagaaggg caattacgcc 900
tgcctgctga gagaggacca aggctggtat tgtcagaacg ccggcagcac cgtgtactac 960
cctaacgaga aggactgcga gacaagaggc gaccacgtgt tctgtgatac cgccgctgga 1020
atcaatgtgg ccgagcagag caaagagtgc aacatcaaca tcagcaccac caactatccc 1080
tgcaaggtgt ccaccggcag gcaccctatt tctatggtgg ctctgtctcc tctgggagcc 1140
ctggtggctt gttataaggg cgtgtcctgt agcatcggca gcaacagagt gggcatcatc 1200
aagcagctga acaagggctg cagctacatc accaaccagg acgccgatac cgtgaccatc 1260
gacaacaccg tgtatcagct gagcaaggtg gaaggcgaac agcacgtgat caagggcaga 1320
cctgtgtcca gcagcttcga ccctatcaag ttccctgagg atcagttcca ggtggccctg 1380
gaccaggtgt tcgagaacat cgagaattcc caggctctgg tggaccagtc caacagaatc 1440
ctgtctagcg ccgagaaggg aaacaccggc ttcatcatcg tgatcatcct gatcgccgtg 1500
ctgggcagct ccatgatcct ggtgtccatc ttcatcatta tcaagaagac caagaagccc 1560
accggcgctc ctccagaact gagcggagtg accaacaatg gcttcatccc tcacaac 1617

<210> SEQ ID NO 115
<211> LENGTH: 1617
<212> TYPE: DNA
<213> ORGANISM: Artificial Sequence
<220> FEATURE:
<223> OTHER INFORMATION: Synthetic Polynucleotide

<400> SEQUENCE: 115
atgagctgga aggtggtcat catcttcagc ctgctgatca cacctcagca cggcctgaaa 60
gagagctacc tggaagagtc ctgcagcacc atcacagagg gctacctgtc tgtgctgaga 120
accggctggt acaccaacgt gttcacactg gaagtgggcg acctcgagaa tctgacatgc 180
tctgatggcc ctagcctgat caagaccgag ctggatctga ccaagagcgc cctgagagaa 240
ctcaagaccg tgtctgccga tcagctggcc agagaggaac agatcgagaa tcctggcagc 300
ggcagctttg tgctgggagc cattgctctt ggagtggctg ctgctgcagc tgttacagca 360
ggcgtggcca tcgctaagac catcagactg gaaagcgaag tgaccgccat caacaacgcc 420
ctgaagaaga caaacgaggc cgtcagcaca ctcggcaatg gcgttagagt gctggccaca 480
gccgtgcgcg agctgaagga cttcgtgtcc aagaacctga cacgggccat taacaagaac 540
aagtgcgaca tcgacgacct gaagatggcc gtgtccttta gccagttcaa ccggcggttt 600
ctgaacgtcg tgcggcagtt tagcgacaac gccggaatca caccagccat cagcctggac 660
ctgatgacag atgctgagct ggctagagcc gtgcctaaca tgcctacatc tgccggccag 720
atcaagctga tgctcgagaa tagagccatg gtccgacgga aaggcttcgg cattctgatt 780
ggcgtgtacg gcagcagcgt gatctatatg gtgcagctgc ctatcttcgg cgtgatcgac 840
acaccctgct ggattgtgaa ggccgctcct agctgtagcg agaagaaggg caattacgcc 900
tgcctgctga gagaggacca aggctggtat tgtcagaacg ccggcagcac cgtgtactac 960
cctaacgaga aggactgcga gacaagaggc gaccacgtgt tctgtgatac cgccgctgga 1020
atcaatgtgg ccgagcagag caaagagtgc aacatcaaca tcagcaccac caactatccc 1080
tgcaaggtgt ccaccggcag gcaccctatt tctatggtgg ctctgtctcc tctgggagcc 1140
ctggtggctt gttataaggg cgtgtcctgt agcatcggca gcaacagagt gggcatcatc 1200
aagcagctga acaagggctg cagctacatc accaaccagg acgccgatac cgtgaccatc 1260
gacaacaccg tgtatcagct gagcaaggtg gaaggcgaac agcacgtgat caagggcaga 1320
cctgtgtcca gcagcttcga ccctatcaag ttccctgagg atcagttcca ggtggccctg 1380
gaccaggtgt tcgagaacat cgagaattcc caggctctgg tggaccagtc caacagaatc 1440
ctgtctagcg ccgagaaggg aaacaccggc ttcatcatcg tgatcatcct gatcgccgtg 1500
ctgggcagct ccatgatcct ggtgtccatc ttcatcatta tcaagaagac caagaagccc 1560
accggcgctc ctccagaact gagcggagtg accaacaatg gcttcatccc tcacaac 1617

<210> SEQ ID NO 116
<211> LENGTH: 1617
<212> TYPE: DNA
<213> ORGANISM: Artificial Sequence
<220> FEATURE:
<223> OTHER INFORMATION: Synthetic Polynucleotide

<400> SEQUENCE: 116
atgagctgga aggtggtcat catcttcagc ctgctgatca cacctcagca cggcctgaaa 60
gagagctacc tggaagagtc ctgcagcacc atcacagagg gctacctgtc tgtgctgaga 120
accggctggt acaccaacgt gttcacactg gaagtgggcg acgtcgagaa tctgacatgc 180

```
tctgatggcc ctagcctgat caagaccgag ctggatctga ccaagagcgc cctgagagaa    240
ctcaagaccg tgtctgccga tcagctggcc agagaggaac agatcgagaa tcctggcagc    300
ggcagctttg tgctgggagc cattgctctt ggagtggctg ctgctgcagc tgttacagca    360
ggcgtggcca tcgctaagac catcagactg gaaagcgaag tgaccgccat caacaacgcc    420
ctgaagaaga caaacgaggc cgtcagcaca ctcggcaatg gcgttagagt gctggccaca    480
gccgtgcgcg agctgaagga cttcgtgctt aagaacctga cacgggccat taacaagaac    540
aagtgcgaca tcgacgacct gaagatggcc gtgtccttta gccagttcaa ccggcggttt    600
ctgaacgtcg tgcggcagtt tagcgacaac gccggaatca caccagccat cagcctggac    660
ctgatgacag atgctgagct ggctagagcc gtgcctaaca tgcctacatc tgccggccag    720
atcaagctga tgctcgagaa tagagccatg gtccgacgga aaggcttcgg cattctgatt    780
ggcgtgtacg gcagcagcgt gatctatatg gtgcagctgc ctatcttcgg cgtgatcgac    840
acaccctgct ggattgtgaa ggccgctcct agctgtagcg agaagaaggg caattacgcc    900
tgcctgctga gagaggacca aggctggtat tgtcagaacg ccggcagcac cgtgtactac    960
cctaacgaga aggactgcga gacaagaggc gaccacgtgt tctgtgatac cgccgctgga   1020
atcaatgtgg ccgagcagag caaagagtgc aacatcaaca tcagcaccac caactatccc   1080
tgcaaggtgt ccaccggcag gcaccctatt tctatggtgg ctctgtctcc tctgggagcc   1140
ctggtggctt gttataaggg cgtgtcctgt agcatcggca gcaacagagt gggcatcatc   1200
aagcagctga acaagggctg cagctacatc accaaccagg acgccgatac cgtgaccatc   1260
gacaacaccg tgtatcagct gagcaaggtg gaaggcgaac agcacgtgat caagggcaga   1320
cctgtgtcca gcagcttcga ccctatcaag ttccctgagg atcagttcca ggtggccctg   1380
gaccaggtgt tcgagaacat cgagaattcc caggctctgg tggaccagtc caacagaatc   1440
ctgtctagcg ccgagaaggg aaacaccggc ttcatcatcg tgatcatcct gatcgccgtg   1500
ctgggcagct ccatgatcct ggtgtccatc ttcatcatta tcaagaagac caagaagccc   1560
accggcgctc ctccagaact gagcggagtg accaacaatg gcttcatccc tcacaac      1617
```

<210> SEQ ID NO 117
<211> LENGTH: 1617
<212> TYPE: DNA
<213> ORGANISM: Artificial Sequence
<220> FEATURE:
<223> OTHER INFORMATION: Synthetic Polynucleotide

<400> SEQUENCE: 117

```
atgagctgga aggtggtcat catcttcagc ctgctgatca cacctcagca cggcctgaaa     60
gagagctacc tggaagagtc ctgcagcacc atcacagagg gctacctgtc tgtgctgaga    120
accggctggt acaccaacgt gttcacactg gaagtgggcg acgtcgagaa tctgacatgc    180
tctgatggcc ctagcctgat caagaccgag ctggatctga ccaagagcgc cctgagagaa    240
ctcaagaccg tgtctgccga tcagctggcc agagaggaac agatcgagaa tcctggcagc    300
ggcagctttg tgctgggagc cattgctctt ggagtggctg ctgctgcagc tgttacagca    360
ggcgtggcca tcgctaagac catcagactg gaaagcgaag tgaccgccat caacaacgcc    420
ctgaagaaga caaacgaggc cgtcagcaca ctcggcaatg gcgttagagt gctggccaca    480
gccgtgcgcg agctgaagga cttcgtgtcc aagaacctgt ggcgggccat taacaagaac    540
aagtgcgaca tcgacgacct gaagatggcc gtgtccttta gccagttcaa ccggcggttt    600
```

-continued ctgaacgtcg tgcggcagtt tagcgacaac gccggaatca caccagccat cagcctggac 660
ctgatgacag atgctgagct ggctagagcc gtgcctaaca tgcctacatc tgccggccag 720
atcaagctga tgctcgagaa tagagccatg gtccgacgga aaggcttcgg cattctgatt 780
ggcgtgtacg gcagcagcgt gatctatatg gtgcagctgc ctatcttcgg cgtgatcgac 840
acaccctgct ggattgtgaa ggccgctcct agctgtagcg agaagaaggg caattacgcc 900
tgcctgctga gagaggacca aggctggtat tgtcagaacg ccggcagcac cgtgtactac 960
cctaacgaga aggactgcga gacaagaggc gaccacgtgt tctgtgatac cgccgctgga 1020
atcaatgtgg ccgagcagag caaagagtgc aacatcaaca tcagcaccac caactatccc 1080
tgcaaggtgt ccaccggcag gcaccctatt tctatggtgg ctctgtctcc tctgggagcc 1140
ctggtggctt gttataaggg cgtgtcctgt agcatcggca gcaacagagt gggcatcatc 1200
aagcagctga acaagggctg cagctacatc accaaccagg acgccgatac cgtgaccatc 1260
gacaacaccg tgtatcagct gagcaaggtg gaaggcgaac agcacgtgat caagggcaga 1320
cctgtgtcca gcagcttcga ccctatcaag ttccctgagg atcagttcca ggtggccctg 1380
gaccaggtgt tcgagaacat cgagaattcc caggctctgg tggaccagtc caacagaatc 1440
ctgtctagcg ccgagaaggg aaacaccggc ttcatcatcg tgatcatcct gatcgccgtg 1500
ctgggcagct ccatgatcct ggtgtccatc ttcatcatta tcaagaagac caagaagccc 1560
accggcgctc ctccagaact gagcggagtg accaacaatg gcttcatccc tcacaac 1617

<210> SEQ ID NO 118
<211> LENGTH: 1617
<212> TYPE: DNA
<213> ORGANISM: Artificial Sequence
<220> FEATURE:
<223> OTHER INFORMATION: Synthetic Polynucleotide

<400> SEQUENCE: 118
atgagctgga aggtggtcat catcttcagc ctgctgatca cacctcagca cggcctgaaa 60
gagagctacc tggaagagtc ctgcagcacc atcacagagg gctacctgtc tgtgctgaga 120
accggctggt acaccaacgt gttcacactg gaagtgggcg acctcgagaa tctgacatgc 180
tctgatggcc ctagcctgat caagaccgag ctggatctgc tcaagagcgc cctgagagaa 240
ctcaagaccg tgtctgccga tcagctggcc agagaggaac agatcgagaa tcctggcagc 300
ggcagctttg tgctgggagc cattgctctt ggagtggctg ctgctgcagc tgttacagca 360
ggcgtggcca tcgctaagac catcagactg gaaagcgaag tgaccgccat caacaacgcc 420
ctgaagaaga caaacgaggc cgtcagcaca ctcggcaatg gcgttagagt gctggccaca 480
gccgtgcgcg agctgaagga cttcgtgctt aagaacctgt ggcgggccat taacaagaac 540
aagtgcgaca tcgacgacct gaagatggcc gtgtccttta gccagttcaa ccggcggttt 600
ctgaacgtcg tgcggcagtt tagcgacaac gccggaatca caccagccat cagcctggac 660
ctgatgacag atgctgagct ggctagagcc gtgcctaaca tgcctacatc tgccggccag 720
atcaagctga tgctcgagaa tagagccatg gtccgacgga aaggcttcgg cattctgatt 780
ggcgtgtacg gcagcagcgt gatctatatg gtgcagctgc ctatcttcgg cgtgatcgac 840
acaccctgct ggattgtgaa ggccgctcct agctgtagcg agaagaaggg caattacgcc 900
tgcctgctga gagaggacca aggctggtat tgtcagaacg ccggcagcac cgtgtactac 960
cctaacgaga aggactgcga gacaagaggc gaccacgtgt tctgtgatac cgccgctgga 1020
atcaatgtgg ccgagcagag caaagagtgc aacatcaaca tcagcaccac caactatccc 1080

```
tgcaaggtgt ccaccggcag gcaccctatt tctatggtgg ctctgtctcc tctgggagcc   1140

ctggtggctt gttataaggg cgtgtcctgt agcatcggca gcaacagagt gggcatcatc   1200

aagcagctga acaagggctg cagctacatc accaaccagg acgccgatac cgtgaccatc   1260

gacaacaccg tgtatcagct gagcaaggtg gaaggcgaac agcacgtgat caagggcaga   1320

cctgtgtcca gcagcttcga ccctatcaag ttccctgagg atcagttcca ggtggccctg   1380

gaccaggtgt tcgagaacat cgagaattcc caggctctgg tggaccagtc caacagaatc   1440

ctgtctagcg ccgagaaggg aaacaccggc ttcatcatcg tgatcatcct gatcgccgtg   1500

ctgggcagct ccatgatcct ggtgtccatc ttcatcatta tcaagaagac caagaagccc   1560

accggcgctc ctccagaact gagcggagtg accaacaatg gcttcatccc tcacaac      1617
```

<210> SEQ ID NO 119
<211> LENGTH: 1617
<212> TYPE: DNA
<213> ORGANISM: Artificial Sequence
<220> FEATURE:
<223> OTHER INFORMATION: Synthetic Polynucleotide

<400> SEQUENCE: 119

```
atgagctgga aggtggtcat catcttcagc ctgctgatca cacctcagca cggcctgaaa     60

gagagctacc tggaagagtc ctgcagcacc atcacagagg gctacctgtc tgtgctgaga    120

accggctggt acaccaacgt gttcacactg cctgtgggcg acgtcgagaa tctgacatgc    180

tctgatggcc ctagcctgat caagaccgag ctggatctga ccaagagcgc cctgagagaa    240

ctcaagaccg tgtctgccga tcagctggcc agagaggaac agatcgagaa tcctggcagc    300

ggcagctttg tgctgggagc cattgctctt ggagtggctg ctgctgcagc tgttacagca    360

ggcgtggcca tcgctaagac catcagactg gaaagcgaag tgaccgccat caacaacgcc    420

ctgaagaaga caaacgaggc cgtcagcaca ctcggcaatg gcgttagagt gctggccaca    480

gccgtgcgcg agctgaagga cttcgtgtcc aagaacctga cacgggccat taacaagaac    540

aagtgcgaca tcgacgacct gaagatggcc gtgtccttta gccagttcaa ccggcggttt    600

ctgaacgtcg tgcggcagtt tagcgacaac gccggaatca caccagccat cagcctggac    660

ctgatgacag atgctgagct ggctagagcc gtgcctaaca tgcctacatc tgccggccag    720

atcaagctga tgctcgagaa tagagccatg gtccgacgga aaggcttcgg cattctgatt    780

ggcgtgtacg gcagcagcgt gatctatatg gtgcagctgc ctatcttcgg cgtgatcgac    840

acaccctgct ggattgtgaa ggccgctcct agctgtagcg agaagaaggg caattacgcc    900

tgcctgctga gagaggacca aggctggtat tgtcagaacg ccggcagcac cgtgtactac    960

cctaacgaga aggactgcga gacaagaggc gaccacgtgt tctgtgatac cgccgctgga   1020

atcaatgtgg ccgagcagag caaagagtgc aacatcaaca tcagcaccac caactatccc   1080

tgcaaggtgt ccaccggcag gcaccctatt tctatggtgg ctctgtctcc tctgggagcc   1140

ctggtggctt gttataaggg cgtgtcctgt agcatcggca gcaacagagt gggcatcatc   1200

aagcagctga acaagggctg cagctacatc accaaccagg acgccgatac cgtgaccatc   1260

gacaacaccg tgtatcagct gagcaaggtg gaaggcgaac agcacgtgat caagggcaga   1320

cctgtgtcca gcagcttcga ccctatcaag ttccctgagg atcagttcca ggtggccctg   1380

gaccaggtgt tcgagaacat cgagaattcc caggctctgg tggaccagtc caacagaatc   1440

ctgtctagcg ccgagaaggg aaacaccggc ttcatcatcg tgatcatcct gatcgccgtg   1500
```

-continued

```
ctgggcagct ccatgatcct ggtgtccatc ttcatcatta tcaagaagac caagaagccc   1560

accggcgctc ctccagaact gagcggagtg accaacaatg gcttcatccc tcacaac      1617


<210> SEQ ID NO 120
<211> LENGTH: 1617
<212> TYPE: DNA
<213> ORGANISM: Artificial Sequence
<220> FEATURE:
<223> OTHER INFORMATION: Synthetic Polynucleotide

<400> SEQUENCE: 120

atgagctgga aggtggtcat catcttcagc ctgctgatca cacctcagca cggcctgaaa     60

gagagctacc tggaagagtc ctgcagcacc atcacagagg gctacctgtc tgtgctgaga    120

accggctggt acaccaacgt gttcacactg gaagtgggcg acgtcgagaa tctgacatgc    180

tctgatggcc ctagcctgat caagaccgag ctggatctga ccaagagcgc cctgagagaa    240

ctcaagaccg tgtctgccga tcagctggcc agagaggaac agatcgagaa tcctggcagc    300

ggcagctttg tgctgggagc cattgctctt ggagtggctg ctgctgcagc tgttacagca    360

ggcgtggcca tcgctaagac catcagactg gaaagcgaag tgaccgccat caacaacgcc    420

ctgaagaaga caaacgaggc cgtcagcaca ctcggcaatg gcgttagagt gctggccaca    480

gccgtgcgcg agctgaagga cttcgtgtcc aagaacctga cacgggccat taacaagaac    540

aagtgcgaca tccctgacct gaagatggcc gtgtccttta gccagttcaa ccggcggttt    600

ctgaacgtcg tgcggcagtt tagcgacaac gccggaatca caccagccat cagcctggac    660

ctgatgacag atgctgagct ggctagagcc gtgcctaaca tgcctacatc tgccggccag    720

atcaagctga tgctcgagaa tagagccatg gtccgacgga aaggcttcgg cattctgatt    780

ggcgtgtacg gcagcagcgt gatctatatg gtgcagctgc ctatcttcgg cgtgatcgac    840

acaccctgct ggattgtgaa ggccgctcct agctgtagcg agaagaaggg caattacgcc    900

tgcctgctga gagaggacca aggctggtat tgtcagaacg ccggcagcac cgtgtactac    960

cctaacgaga aggactgcga gacaagaggc gaccacgtgt tctgtgatac cgccgctgga   1020

atcaatgtgg ccgagcagag caaagagtgc aacatcaaca tcagcaccac caactatccc   1080

tgcaaggtgt ccaccggcag gcaccctatt tctatggtgg ctctgtctcc tctgggagcc   1140

ctggtggctt gttataaggg cgtgtcctgt agcatcggca gcaacagagt gggcatcatc   1200

aagcagctga acaagggctg cagctacatc accaaccagg acgccgatac cgtgaccatc   1260

gacaacaccg tgtatcagct gagcaaggtg gaaggcgaac agcacgtgat caagggcaga   1320

cctgtgtcca gcagcttcga ccctatcaag ttccctgagg atcagttcca ggtggccctg   1380

gaccaggtgt tcgagaacat cgagaattcc caggctctgg tggaccagtc caacagaatc   1440

ctgtctagcg ccgagaaggg aaacaccggc ttcatcatcg tgatcatcct gatcgccgtg   1500

ctgggcagct ccatgatcct ggtgtccatc ttcatcatta tcaagaagac caagaagccc   1560

accggcgctc ctccagaact gagcggagtg accaacaatg gcttcatccc tcacaac      1617


<210> SEQ ID NO 121
<211> LENGTH: 1617
<212> TYPE: DNA
<213> ORGANISM: Artificial Sequence
<220> FEATURE:
<223> OTHER INFORMATION: Synthetic Polynucleotide

<400> SEQUENCE: 121

atgagctgga aggtggtcat catcttcagc ctgctgatca cacctcagca cggcctgaaa     60
```

gagagctacc tggaagagtc ctgcagcacc atcacagagg gctacctgtc tgtgctgaga 120
accggctggt acaccaacgt gttcacactg gaagtgggcg acgtcgagaa tctgacatgc 180
tctgatggcc ctagcctgat caagaccgag ctggatctga ccaagagcgc cctgagagaa 240
ctcaagaccg tgtctgccga tcagctggcc agagaggaac agatcgagaa tcctggcagc 300
ggcagctttg tgctgggagc cattgctctt ggagtggctg ctgctgcagc tgttacagca 360
ggcgtggcca tcgctaagac catcagactg gaaagcgaag tgaccgccat caacaacgcc 420
ctgaagaaga caaacgaggc cgtcagcaca ctcggcaatg gcgttagagt gctggccaca 480
gccgtgcgcg agctgaagga cttcgtgtcc aagaacctga cacgggccat taacaagaac 540
aagtgcccta tcgacgacct gaagatggcc gtgtccttta gccagttcaa ccggcggttt 600
ctgaacgtcg tgcggcagtt tagcgacaac gccggaatca caccagccat cagcctggac 660
ctgatgacag atgctgagct ggctagagcc gtgcctaaca tgcctacatc tgccggccag 720
atcaagctga tgctcgagaa tagagccatg gtccgacgga aaggcttcgg cattctgatt 780
ggcgtgtacg gcagcagcgt gatctatatg gtgcagctgc ctatcttcgg cgtgatcgac 840
acaccctgct ggattgtgaa ggccgctcct agctgtagcg agaagaaggg caattacgcc 900
tgcctgctga gagaggacca aggctggtat tgtcagaacg ccggcagcac cgtgtactac 960
cctaacgaga aggactgcga gacaagaggc gaccacgtgt tctgtgatac cgccgctgga 1020
atcaatgtgg ccgagcagag caaagagtgc aacatcaaca tcagcaccac caactatccc 1080
tgcaaggtgt ccaccggcag gcaccctatt tctatggtgg ctctgtctcc tctgggagcc 1140
ctggtggctt gttataaggg cgtgtcctgt agcatcggca gcaacagagt gggcatcatc 1200
aagcagctga acaagggctg cagctacatc accaaccagg acgccgatac cgtgaccatc 1260
gacaacaccg tgtatcagct gagcaaggtg gaaggcgaac agcacgtgat caagggcaga 1320
cctgtgtcca gcagcttcga ccctatcaag ttccctgagg atcagttcca ggtggccctg 1380
gaccaggtgt tcgagaacat cgagaattcc caggctctgg tggaccagtc caacagaatc 1440
ctgtctagcg ccgagaaggg aaacaccggc ttcatcatcg tgatcatcct gatcgccgtg 1500
ctgggcagct ccatgatcct ggtgtccatc ttcatcatta tcaagaagac caagaagccc 1560
accggcgctc ctccagaact gagcggagtg accaacaatg gcttcatccc tcacaac 1617

<210> SEQ ID NO 122
<211> LENGTH: 1617
<212> TYPE: DNA
<213> ORGANISM: Artificial Sequence
<220> FEATURE:
<223> OTHER INFORMATION: Synthetic Polynucleotide

<400> SEQUENCE: 122
atgagctgga aggtggtcat catcttcagc ctgctgatca cacctcagca cggcctgaaa 60
gagagctacc tggaagagtc ctgcagcacc atcacagagg gctacctgtc tgtgctgaga 120
accggctggt acaccaacgt gttcacactg gaagtgggcg acgtcgagaa tctgacatgc 180
tctgatggcc ctagcctgat caagaccgag ctggatctga ccaagagcgc cctgagagaa 240
ctcaagaccg tgtctgccga tcagctggcc agagaggaac agatcgagaa tcctggcagc 300
ggcagctttg tgctgggagc cattgctctt ggagtggctg ctgctgcagc tgttacagca 360
ggcgtggcca tcgctaagac catcagactg cctagcgaag tgaccgccat caacaacgcc 420
ctgaagaaga caaacgaggc cgtcagcaca ctcggcaatg gcgttagagt gctggccaca 480

```
gccgtgcgcg agctgaagga cttcgtgtcc aagaacctga cacgggccat taacaagaac    540

aagtgcgaca tcgacgacct gaagatggcc gtgtccttta gccagttcaa ccggcggttt    600

ctgaacgtcg tgcggcagtt tagcgacaac gccggaatca caccagccat cagcctggac    660

ctgatgacag atgctgagct ggctagagcc gtgcctaaca tgcctacatc tgccggccag    720

atcaagctga tgctcgagaa tagagccatg gtccgacgga aaggcttcgg cattctgatt    780

ggcgtgtacg gcagcagcgt gatctatatg gtgcagctgc ctatcttcgg cgtgatcgac    840

acaccctgct ggattgtgaa ggccgctcct agctgtagcg agaagaaggg caattacgcc    900

tgcctgctga gagaggacca aggctggtat tgtcagaacg ccggcagcac cgtgtactac    960

cctaacgaga aggactgcga gacaagaggc gaccacgtgt tctgtgatac cgccgctgga   1020

atcaatgtgg ccgagcagag caaagagtgc aacatcaaca tcagcaccac caactatccc   1080

tgcaaggtgt ccaccggcag gcaccctatt tctatggtgg ctctgtctcc tctgggagcc   1140

ctggtggctt gttataaggg cgtgtcctgt agcatcggca gcaacagagt gggcatcatc   1200

aagcagctga acaagggctg cagctacatc accaaccagg acgccgatac cgtgaccatc   1260

gacaacaccg tgtatcagct gagcaaggtg gaaggcgaac agcacgtgat caagggcaga   1320

cctgtgtcca gcagcttcga ccctatcaag ttccctgagg atcagttcca ggtggccctg   1380

gaccaggtgt tcgagaacat cgagaattcc caggctctgg tggaccagtc caacagaatc   1440

ctgtctagcg ccgagaaggg aaacaccggc ttcatcatcg tgatcatcct gatcgccgtg   1500

ctgggcagct ccatgatcct ggtgtccatc ttcatcatta tcaagaagac caagaagccc   1560

accggcgctc ctccagaact gagcggagtg accaacaatg gcttcatccc tcacaac      1617
```

<210> SEQ ID NO 123
<211> LENGTH: 1617
<212> TYPE: DNA
<213> ORGANISM: Artificial Sequence
<220> FEATURE:
<223> OTHER INFORMATION: Synthetic Polynucleotide

<400> SEQUENCE: 123

```
atgagctgga aggtggtcat catcttcagc ctgctgatca cacctcagca cggcctgaaa     60

gagagctacc tggaagagtc ctgcagcacc atcacagagg gctacctgtc tgtgctgaga    120

accggctggt acaccaacgt gttcacactg gaagtgggcg acgtcgagaa tctgacatgc    180

tctgatggcc ctagcctgat caagaccgag ctggatctga ccaagagcgc cctgagagaa    240

ctcaagaccg tgtctgccga tcagctggcc agagaggaac agatcgagaa tcctggcagc    300

ggcagctttg tgctgggagc cattgctctt ggagtggctg ctgctgcagc tgttacagca    360

ggcgtggcca tcgctaagac catcagactg gaaagcgaag tgaccgccat caacaacgcc    420

ctgaagaaga caaacgaggc cgtcagcaca ctcggcaatg gcgttagagt gctggccaca    480

gccgtgcgcg agctgaagga cttcgtgtcc aagaacctga cacgggccat taacaagaac    540

aagtgcgaca tcgacgacct gaagatggcc gtgtccttta gccagttcaa ccggcggttt    600

ctgaacgtcg tgcggcagtt tagcgacaac gccggaatca caccagccat cagcctggac    660

ctgatgacag atgctgagct ggctagagcc gtgcctaaca tgcctacatc tgccggccag    720

atcaagctga tgctcgagaa tagagccatg gtccgacgga aaggcttcgg cattctgatt    780

ggcgtgtacg gcagcagcgt gatctatatg gtgcagctgc ctatcttcgg cgtgatcgac    840

acaccctgct ggattgtgaa ggccgctcct agctgtagcg agaagaaggg caattacgcc    900

tgcctgctga gagaggacca aggctggtat tgtcagaacg ccggcagcac cgtgtactac    960
```

cctaacgaga aggactgcga gacaagaggc gaccacgtgt tctgtgatac cgccgctgga 1020
atcaatgtgg ccgagcagag caaagagtgc aacatcaaca tcagcaccac caactatccc 1080
tgcaaggtgt ccaccggcag gcaccctatt tctatggtgg ctctgtctcc tctgggagcc 1140
ctggtggctt gttataaggg cgtgtcctgt agcatcggca gcaacagagt gggcatcatc 1200
aagcagctga acaagggctg cagctacatc accaaccagg acgccgatac cgtgaccatc 1260
gacaacaccg tgtatcagct gagcaaggtg gaaggcgaac agcacgtgat caagggcaga 1320
cctgtgtcca gcagcttccc acctatcaag ttccctgagg atcagttcca ggtggccctg 1380
gaccaggtgt tcgagaacat cgagaattcc caggctctgg tggaccagtc caacagaatc 1440
ctgtctagcg ccgagaaggg aaacaccggc ttcatcatcg tgatcatcct gatcgccgtg 1500
ctgggcagct ccatgatcct ggtgtccatc ttcatcatta tcaagaagac caagaagccc 1560
accggcgctc ctccagaact gagcggagtg accaacaatg gcttcatccc tcacaac 1617

<210> SEQ ID NO 124
<211> LENGTH: 1617
<212> TYPE: DNA
<213> ORGANISM: Artificial Sequence
<220> FEATURE:
<223> OTHER INFORMATION: Synthetic Polynucleotide

<400> SEQUENCE: 124
atgagctgga aggtggtcat catcttcagc ctgctgatca cacctcagca cggcctgaaa 60
gagagctacc tggaagagtc ctgcagcacc atcacagagg gctacctgtc tgtgctgaga 120
accggctggt acaccaacgt gttcacactg gaagtgggcg acgtcgagaa tctgacatgc 180
tctgatggcc ctagcctgat caagaccgag ctggatctga ccaagagcgc cctgagagaa 240
ctcaagaccg tgtctgccga tcagctggcc agagaggaac agatcgagaa tcctggcagc 300
ggcagctttg tgctgggagc cattgctctt ggagtggctg ctgctgcagc tgttacagca 360
ggcgtggcca tcgctaagac catcagactg gaaagcgaag tgaccgccat caacaacgcc 420
ctgaagaaga caaacgaggc cgtcagcaca ctcggcaatg gcgttagagt gctggccaca 480
gccgtgcgcg agctgaagga cttcgtgtcc aagaacctga cacgggccat taacaagaac 540
aagtgcgaca tcgacgacct gaagatggcc gtgtccttta gccagttcaa ccggcggttt 600
ctgaacgtcg tgcggcagtt tagcgacaac gccggaatca caccagccat cagcctggac 660
ctgatgacag atgctgagct ggctagagcc gtgcctaaca tgcctacatc tgccggccag 720
atcaagctga tgctcgagaa tagagccatg gtccgacgga aaggcttcgg cattctgatt 780
ggcgtgtacg gcagcagcgt gatctatatg gtgcagctgc ctatcttcgg cgtgatcgac 840
acaccctgct ggattgtgaa ggccgctcct agctgtagcg agaagaaggg caattacgcc 900
tgcctgctga gagaggacca aggctggtat tgtcagaacg ccggcagcac cgtgtactac 960
cctaacgaga aggactgcga gacaagaggc gaccacgtgt tctgtgatac cgccgctgga 1020
atcaatgtgg ccgagcagag caaagagtgc aacatcaaca tcagcaccac caactatccc 1080
tgcaaggtgt ccaccggcag gcaccctatt tctatggtgg ctctgtctcc tctgggagcc 1140
ctggtggctt gttataaggg cgtgtcctgt agcatcggca gcaacagagt gggcatcatc 1200
aagcagctga acaagggctg cagctacatc accaaccagg acgccgatac cgtgaccatc 1260
gacaacaccg tgtatcagct gagcaaggtg gaaggcgaac agcacgtgat caagggcaga 1320
cctgtgtcca gcagcttcga ccctatcaag ttccctgaga accagttcca ggtggccctg 1380

-continued

```
gaccaggtgt tcgagaacat cgagaattcc caggctctgg tggaccagtc caacagaatc   1440

ctgtctagcg ccgagaaggg aaacaccggc ttcatcatcg tgatcatcct gatcgccgtg   1500

ctgggcagct ccatgatcct ggtgtccatc ttcatcatta tcaagaagac caagaagccc   1560

accggcgctc ctccagaact gagcggagtg accaacaatg gcttcatccc tcacaac      1617
```

<210> SEQ ID NO 125
<211> LENGTH: 1617
<212> TYPE: DNA
<213> ORGANISM: Artificial Sequence
<220> FEATURE:
<223> OTHER INFORMATION: Synthetic Polynucleotide

<400> SEQUENCE: 125

```
atgagctgga aggtggtcat catcttcagc ctgctgatca cacctcagca cggcctgaaa     60

gagagctacc tggaagagtc ctgcagcacc atcacagagg gctacctgtc tgtgctgaga    120

accggctggt acaccaacgt gttcacactg gaagtgggcg acgtcgagaa tctgacatgc    180

tctgatggcc ctagcctgat caagaccgag ctggatctga ccaagagcgc cctgagagaa    240

ctcaagaccg tgtctgccga tcagctggcc agagaggaac agatcgagaa tcctggcagc    300

ggcagctttg tgctgggagc cattgctctt ggagtggctg ctgctgcagc tgttacagca    360

ggcgtggcca tcgctaagac catcagactg gaaagcgaag tgaccgccat caacaacgcc    420

ctgaagaaga caaacgaggc cgtcagcaca ctcggcaatg gcgttagagt gctggccaca    480

gccgtgcgcg agctgaagga cttcgtgtcc aagaacctga cacgggccat taacaagaac    540

aagtgcgaca tcgacgacct gaagatggcc gtgtccttta gccagttcaa ccggcggttt    600

ctgaacgtcg tgcggcagtt tagcgacaac gccggaatca caccagccat cagcctggac    660

ctgatgacag atgctgagct ggctagagcc gtgcctaaca tgcctacatc tgccggccag    720

atcaagctga tgctcgagaa tagagccatg gtccgacgga aaggcttcgg cattctgatt    780

ggcgtgtacg gcagcagcgt gatctatatg gtgcagctgc ctatcttcgg cgtgatcgac    840

acaccctgct ggattgtgaa ggccgctcct agctgtagcg agaagaaggg caattacgcc    900

tgcctgctga gagaggacca aggctggtat tgtcagaacg ccggcagcac cgtgtactac    960

cctaacgaga aggactgcga gacaagaggc gaccacgtgt tctgtgatac cgccgctgga   1020

atcaatgtgg ccgagcagag caaagagtgc aacatcaaca tcagcaccac caactatccc   1080

tgcaaggtgt ccaccggcag gcaccctatt tctatggtgg ctctgtctcc tctgggagcc   1140

ctggtggctt gttataaggg cgtgtcctgt agcatcggca gcaacagagt gggcatcatc   1200

aagcagctga acaagggctg cagctacatc accaaccagg acgccgatac cgtgaccatc   1260

gacaacaccg tgtatcagct gagcaaggtg gaaggcgaac agcacgtgat caagggcaga   1320

cctgtgtcca gcagcttcga ccctatcaag ttccctcagg atcagttcca ggtggccctg   1380

gaccaggtgt tcgagaacat cgagaattcc caggctctgg tggaccagtc caacagaatc   1440

ctgtctagcg ccgagaaggg aaacaccggc ttcatcatcg tgatcatcct gatcgccgtg   1500

ctgggcagct ccatgatcct ggtgtccatc ttcatcatta tcaagaagac caagaagccc   1560

accggcgctc ctccagaact gagcggagtg accaacaatg gcttcatccc tcacaac      1617
```

<210> SEQ ID NO 126
<211> LENGTH: 1617
<212> TYPE: DNA
<213> ORGANISM: Artificial Sequence
<220> FEATURE:
<223> OTHER INFORMATION: Synthetic Polynucleotide

<400> SEQUENCE: 126
atgagctgga aggtggtcat catcttcagc ctgctgatca cacctcagca cggcctgaaa 60
gagagctacc tggaagagtc ctgcagcacc atcacagagg gctacctgtc tgtgctgaga 120
accggctggt acaccaacgt gttcacactg gaagtgggcg acgtcgagaa tctgacatgc 180
tctgatggcc ctagcctgat caagaccgag ctggatctga ccaagagcgc cctgagagaa 240
ctcaagaccg tgtctgccga tcagctggcc agagaggaac agatcgagaa tcctggcagc 300
ggcagctttg tgctgggagc cattgctctt ggagtggctg ctgctgcagc tgttacagca 360
ggcgtggcca tcgctaagac catcagactg gaaagcgaag tgaccgccat caacaacgcc 420
ctgaagaaga caaacgaggc cgtcagcaca ctcggcaatg gcgttagagt gctggccaca 480
gccgtgcgcg agctgaagga cttcgtgtcc aagaacctga cacgggccat taacaagaac 540
aagtgcgaca tcgacgacct gaagatggcc gtgtccttta gccagtggaa ccggcggttt 600
ctgaacgtcg tgcggcagtt tagcgacaac gccggaatca caccagccat cagcctggac 660
ctgatgacag atgctgagct ggctagagcc gtgcctaaca tgcctacatc tgccggccag 720
atcaagctga tgctcgagaa tagagccatg gtccgacgga aaggcttcgg cattctgatt 780
ggcgtgtacg gcagcagcgt gatctatatg gtgcagctgc ctatcttcgg cgtgatcgac 840
acaccctgct ggattgtgaa ggccgctcct agctgtagcg agaagaaggg caattacgcc 900
tgcctgctga gagaggacca aggctggtat tgtcagaacg ccggcagcac cgtgtactac 960
cctaacgaga aggactgcga gacaagaggc gaccacgtgt tctgtgatac cgccgctgga 1020
atcaatgtgg ccgagcagag caaagagtgc aacatcaaca tcagcaccac caactatccc 1080
tgcaaggtgt ccaccggcag gcaccctatt tctatggtgg ctctgtctcc tctgggagcc 1140
ctggtggctt gttataaggg cgtgtcctgt agcatcggca gcaacagagt gggcatcatc 1200
aagcagctga acaagggctg cagctacatc accaaccagg acgccgatac cgtgaccatc 1260
gacaacaccg tgtatcagct gagcaaggtg gaaggcgaac agcacgtgat caagggcaga 1320
cctgtgtcca gcagcttcga ccctatcaag ttccctgagg atcagttcca ggtggccctg 1380
gaccaggtgt tcgagaacat cgagaattcc caggctctgg tggaccagtc caacagaatc 1440
ctgtctagcg ccgagaaggg aaacaccggc ttcatcatcg tgatcatcct gatcgccgtg 1500
ctgggcagct ccatgatcct ggtgtccatc ttcatcatta tcaagaagac caagaagccc 1560
accggcgctc ctccagaact gagcggagtg accaacaatg gcttcatccc tcacaac 1617

<210> SEQ ID NO 127
<211> LENGTH: 1617
<212> TYPE: RNA
<213> ORGANISM: Artificial Sequence
<220> FEATURE:
<223> OTHER INFORMATION: Synthetic Polynucleotide

<400> SEQUENCE: 127
augagcugga agguggucau caucuucagc cugcugauca caccucagca cggccugaaa 60
gagagcuacc uggaagaguc cugcagcacc aucacagagg gcuaccuguc ugugcugaga 120
accggcuggu acaccaacgu guucacacug gaagugggcg acgucgagaa ucugacaugc 180
ucugauggcc cuagccugau caagaccgag cuggaucuga ccaagagcgc ccugagagaa 240
cucaagaccg ugucugccga ucagcuggcc agagaggaac agaucgagaa uccuggcagc 300
ggcagcuuug ugcugggagc cauugcucuu ggaguggcug cugcugcagc uguuacagca 360
ggcguggcca ucugcaagac caucagacug gaaagcgaag ugaccgccau caacaacgcc 420
cugaagaaga caaacgaggc cgucagcaca cucggcaaug gcguuagagu gcuggccuuu 480
gccgugcgcg agcugaagga cuucgugucc aagaaccuga cacgggcccu gaacaagaac 540
aagugcgaca ucgacgaccu gaagauggcc guguccuuua gccaguucaa ccggcgguuu 600
cugaacgucg ugcggcaguu uagcgacaac gccggaauca caccagccau cagccuggac 660
cugaugacag augcugagcu ggcuagagcc gugccuaaca ugccuacauc ugccggccag 720
aucaagcuga ugcucgagaa uagagccaug guccgacgga aaggcuucgg cauucugugu 780
ggcguguacg gcagcagcgu gaucuauaug gugcagcugc cuaucuucgg cgugaucgac 840
acacccugcu ggauugugaa ggccgcuccu agcuguagcg agaagaaggg caauuacgcc 900
ugccugcuga gagaggacca aggcugguau ugucagaacg ccggcagcac cguguacuac 960
ccuaacgaga aggacugcga gacaagaggc gaccacgugu ucugugauac cgccgcugga 1020
aucaaugugg ccgagcagag caaagagugc aacaucaaca ucagcaccac caacuauccc 1080
ugcaaggugu ccaccggcag gcacccuauu ucuauggugg cucugucucc ucugggagcc 1140
cugguggcuu guuauaaggg cguguccugu agcaucggca gcaacagagu gggcaucauc 1200
aagcagcuga acaagggcug cagcuacauc accaaccagg acgccgauac cgugaccauc 1260
gacaacaccg uguaucagcu gagcaaggug gaaggcgaac agcacgugau caagggcaga 1320
ccugugucca gcagcuucga cccuaucaag uucccugagg aucaguucaa cguggcccug 1380
gaccaggugu ucgagaacau cgagaauucc caggcucugg uggaccaguc caacagaauc 1440
cugucuagcg ccgagaaggg aaacaccggc uucaucaucg ugaucauccu gaucgccgug 1500
cugggcagcu ccaugauccu ggugguccauc uucaucauua ucaagaagac caagaagccc 1560
accggcgcuc cuccagaacu gagcggagug accaacaaug gcuucauccc ucacaac 1617

<210> SEQ ID NO 128
<211> LENGTH: 1617
<212> TYPE: RNA
<213> ORGANISM: Artificial Sequence
<220> FEATURE:
<223> OTHER INFORMATION: Synthetic Polynucleotide

<400> SEQUENCE: 128
augagcugga aggugguaau caucuucagc cugcugauca caccucagca cggccugaaa 60
gagagcuacc uggaagaguc cugcagcacc aucacagagg gcuaccuguc ugugcugaga 120
accggcuggu acaccaacgu guucacacug gaagugggcg acgucgagaa ucugacaugc 180
ucugauggcc cuagccugau caagaccgag cuggaucuga ccaagagcgc ccugagagaa 240
cucaagaccg ugucugccga ucagcuggcc agagaggaac agaucgagaa uccuggcagc 300
ggcagcuuug ugcugggagc cauugcucuu ggaguggcug cugcugcagc uguuacagca 360
ggcguggcca ucugcaagac caucagacug gaaagcgaag ugaccgccau caacaacgcc 420
cugaagaaga caaacgaggc cgucagcaca cucggcaaug gcguuagagu gcuggccaca 480
gccgugcgcg agcugaagga cuucgugucc aagaaccuga cacgggccau uaacaagaac 540
aagugcgaca ucgacgaccu gaagauggcc guguccuuua gccaguucaa ccggcgguuu 600
cugaacgucg ugcggcaguu uagcgacaac gccggaauca caccagccau cagccuggac 660
cugaugacag augcugagcu ggcuagagcc gugccuaaca ugccuacauc ugccggccag 720
aucaagcuga ugcucgagaa uagagccaug guccgacgga aaggcuucgg cauucugugu 780
ggcguguacg gcagcagcgu gaucuauaug gugcagcugc cuaucuucgg cgugaucgac 840
acacccugcu ggauugugaa ggccgcuccu agcuguagcg agaagaaggg caauuacgcc 900
ugccugcuga gagaggacca aggcugguau ugucagaacg ccggcagcac cguguacuac 960
ccuaacgaga aggacugcga gacaagaggc gaccacgugu ucugugauac cgccgcugga 1020
aucaaugugg ccgagcagag caaagagugc aacaucaaca ucagcaccac caacuauccc 1080
ugcaaggugu ccaccggcag gcacccuauu ucuauggugg cucugucucc ucugggagcc 1140
cugguggcuu guuauaaggg cguguccugu agcaucggca gcaacagagu gggcaucauc 1200
aagcagcuga acaagggcug cagcuacauc accaaccagg acgccgauac cgugaccauc 1260
gacaacaccg uguaucagcu gagcaaggug gaaggcgaac agcacgugau caagggcaga 1320
ccugugucca gcagcuucga cccuaucaag uucccugagc accaguggca uguggcccug 1380
gaccaggugu ucgagaacau cgagaauucc caggcucugg uggaccaguc caacagaauc 1440
cugucuagcg ccgagaaggg aaacaccggc uucaucaucg ugaucauccu gaucgccgug 1500
cugggcagcu ccaugauccu gguguccauc uucaucauua ucaagaagac caagaagccc 1560
accggcgcuc cuccagaacu gagcggagug accaacaaug gcuucauccc ucacaac 1617

<210> SEQ ID NO 129
<211> LENGTH: 1617
<212> TYPE: RNA
<213> ORGANISM: Artificial Sequence
<220> FEATURE:
<223> OTHER INFORMATION: Synthetic Polynucleotide

<400> SEQUENCE: 129
augagcugga agguggucau caucuucagc cugcugauca caccucagca cggccugaaa 60
gagagcuacc uggaagaguc cugcagcacc aucacagagg gcuaccuguc ugugcugaga 120
accggcuggu acaccaacgu guucacacug gaagugggcg acgucgagaa ucugacaugc 180
ucugauggcc cuagccugau caagaccgag cuggaucugc ucaagagcgc ccugagagaa 240
cucaagaccg ugucugccga ucagcuggcc agagaggaac agaucgagaa uccuggcagc 300
ggcagcuuug ugcugggagc cauugcucuu ggaguggcug cugcugcagc uguuacagca 360
ggcguggcca ucgcuaagac caucagacug gaaagcgaag ugaccgccau caacaacgcc 420
cugaagaaga caaacgaggc cgucagcaca cucggcaaug gcguuagagu gcuggccaca 480
gccgugcgcg agcugaagga cuucgugucc aagaaccuga cacgggccau uaacaagaac 540
aagugcgaca ucccugaccu gaagauggcc guguccuuua gccaguucaa ccggcgguuu 600
cugaacgucg ugcggcaguu uagcgacaac gccggaauca caccagccau cagccuggac 660
cugaugacag augcugagcu ggcuagagcc gugccuaaca ugccuacauc ugccggccag 720
aucaagcuga ugcucgagaa uagagccaug guccgacgga aaggcuucgg cauucugauu 780
ggcguguacg gcagcagcgu gaucuauaug gugcagcugc cuaucuucgg cgugaucgac 840
acacccugcu ggauugugaa ggccgcuccu agcuguagcg agaagaaggg caauuacgcc 900
ugccugcuga gagaggacca aggcugguau ugucagaacg ccggcagcac cguguacuac 960
ccuaacgaga aggacugcga gacaagaggc gaccacgugu ucugugauac cgccgcugga 1020
aucaaugugg ccgagcagag caaagagugc aacaucaaca ucagcaccac caacuauccc 1080
ugcaaggugu ccaccggcag gcacccuauu ucuauggugg cucugucucc ucugggagcc 1140
cugguggcuu guuauaaggg cguguccugu agcaucggca gcaacagagu gggcaucauc 1200
aagcagcuga acaagggcug cagcuacauc accaaccagg acgccgauac cgugaccauc 1260

-continued

```
gacaacaccg uguaucagcu gagcaaggug gaaggcgaac agcacgugau caagggcaga   1320

ccugugucca gcagcuucga cccuaucaag uucccugagg aucaguucca gguggcccug   1380

gaccaggugu ucgagaacau cgagaauucc caggcucugg uggaccaguc caacagaauc   1440

cugucuagcg ccgagaaggg aaacaccggc uucaucaucg ugaucauccu gaucgccgug   1500

cugggcagcu ccaugauccu ggugucc auc uucaucauua ucaagaagac caagaagccc   1560

accggcgcuc cuccagaacu gagcggagug accaacaaug gcuucauccc ucacaac      1617
```

<210> SEQ ID NO 130
<211> LENGTH: 1617
<212> TYPE: RNA
<213> ORGANISM: Artificial Sequence
<220> FEATURE:
<223> OTHER INFORMATION: Synthetic Polynucleotide

<400> SEQUENCE: 130

```
augagcugga agguggucau caucuucagc cugcugauca caccucagca cggccugaaa     60

gagagcuacc uggaagaguc cugcagcacc aucacagagg gcuaccuguc ugugcugaga    120

accggcuggu acaccaacgu guucacacug gaagugggcg acgucgagaa ucugacaugc    180

ucugauggcc cuagccugau caagaccgag cuggaucugc ucaagagcgc ccugagagaa    240

cucaagaccg ugucugccga ucagcuggcc agagaggaac agaucgagaa uccuggcagc    300

ggcagcuuug ugcugggagc cauugcucuu ggaguggcug cugcugcagc uguuacagca    360

ggcguggcca ucgcuaagac caucagacug gaaagcgaag ugaccgccau caacaacgcc    420

cugaagaaga caaacgaggc cgucagcaca cucggcaaug gcguuagagu gcuggccaca    480

gccgugcgcg agcugaagga cuucgugucc aagaaccuga cacgggccau uaacaagaac    540

aagugcgaca ucccugaccu gaagauggcc guguccuuua gccaguucaa ccggcgguuu    600

cugaacgucg ugcggcaguu uagcgacaac gccggaauca caccagccau cagccuggac    660

cugaugacag augcugagcu ggcuagagcc gugccuaaca ugccuacauc ugccggccag    720

aucaagcuga ugcucgagaa uagagccaug guccgacgga aaggcuucgg cauucugauu    780

ggcguguacg gcagcagcgu gaucuauaug gugcagcugc cuaucuucgg cgugaucgac    840

acacccugcu ggauugugaa ggccgcuccu agcuguagcg agaagaaggg caauuacgcc    900

ugccugcuga gagaggacca aggcugguau ugucagaacg ccggcagcac cguguacuac    960

ccuaacgaga aggacugcga gacaagaggc gaccacgugu ucugugauac cgccgcugga   1020

aucaaugugg ccgagcagag caaagagugc aacaucaaca ucagcaccac caacuauccc   1080

ugcaaggugu ccaccggcag gcacccuauu ucuauggugg cucugucucc ucugggagcc   1140

cugguggcuu guuauaaggg cguguccugu agcaucggca gcaacagagu gggcaucauc   1200

aagcagcuga acaagggcug cagcuacauc accaaccagg acgccgauac cgugaccauc   1260

gacaacaccg uguaucagcu gagcaaggug gaaggcgaac agcacgugau caagggcaga   1320

ccugugucca gcagcuucga cccuaucaag uucccugaga accaguucca gguggcccug   1380

gaccaggugu ucgagaacau cgagaauucc caggcucugg uggaccaguc caacagaauc   1440

cugucuagcg ccgagaaggg aaacaccggc uucaucaucg ugaucauccu gaucgccgug   1500

cugggcagcu ccaugauccu gguguccauc uucaucauua ucaagaagac caagaagccc   1560

accggcgcuc cuccagaacu gagcggagug accaacaaug gcuucauccc ucacaac      1617
```

<210> SEQ ID NO 131
<211> LENGTH: 1617

-continued

<212> TYPE: RNA
<213> ORGANISM: Artificial Sequence
<220> FEATURE:
<223> OTHER INFORMATION: Synthetic Polynucleotide

<400> SEQUENCE: 131
augagcugga agguggucau caucuucagc cugcugauca caccucagca cggccugaaa 60
gagagcuacc uggaagaguc cugcagcacc aucacagagg gcuaccuguc ugugcugaga 120
accggcuggu acaccaacgu guucacacug gaagugggcg acgucgagaa ucugacaugc 180
ucugauggcc cuagccugau caagaccgag cuggaucugc ucaagagcgc ccugagagaa 240
cucaagaccg ugucugccga ucagcuggcc agagaggaac agaucgagaa uccuggcagc 300
ggcagcuuug ugcugggagc cauugcucuu ggaguggcug cugcugcagc uguuacagca 360
ggcguggcca ucgcuaagac caucagacug gaaagcgaag ugaccgccau caacaacgcc 420
cugaagaaga caaacgaggc cgucagcaca cucggcaaug gcguuagagu gcuggccaca 480
gccgugcgcg agcugaagga cuucgugcuu aagaaccuga cacgggccau uaacaagaac 540
aagugcgaca ucccugaccu gaagauggcc guguccuuua gccaguucaa ccggcgguuu 600
cugaacgucg ugcggcaguu uagcgacaac gccggaauca caccagccau cagccuggac 660
cugaugacag augcugagcu ggcuagagcc gugccuaaca ugccuacauc ugccggccag 720
aucaagcuga ugcucgagaa uagagccaug guccgacgga aaggcuucgg cauucugauu 780
ggcguguacg gcagcagcgu gaucuauaug gugcagcugc cuaucuucgg cgugaucgac 840
acacccugcu ggauugugaa ggccgcuccu agcuguagcg agaagaaggg caauuacgcc 900
ugccugcuga gagaggacca aggcugguau ugucagaacg ccggcagcac cguguacuac 960
ccuaacgaga aggacugcga gacaagaggc gaccacgugu ucugugauac cgccgcugga 1020
aucaaugugg ccgagcagag caaagagugc aacaucaaca ucagcaccac caacuauccc 1080
ugcaaggugu ccaccggcag gcacccuauu ucuauggugg cucugucucc ucugggagcc 1140
cugguggcuu guuauaaggg cguguccugu agcaucggca gcaacagagu gggcaucauc 1200
aagcagcuga acaagggcug cagcuacauc accaaccagg acgccgauac cgugaccauc 1260
gacaacaccg uguaucagcu gagcaaggug gaaggcgaac agcacgugau caagggcaga 1320
ccugugucca gcagcuucga cccuaucaag uucccugagg aucaguucca gguggcccug 1380
gaccaggugu ucgagaacau cgagaauucc caggcucugg uggaccaguc caacagaauc 1440
cugucuagcg ccgagaaggg aaacaccggc uucaucaucg ugaucauccu gaucgccgug 1500
cugggcagcu ccaugauccu gguguccauc uucaucauua ucaagaagac caagaagccc 1560
accggcgcuc cuccagaacu gagcggagug accaacaaug gcuucauccc ucacaac 1617

<210> SEQ ID NO 132
<211> LENGTH: 1617
<212> TYPE: RNA
<213> ORGANISM: Artificial Sequence
<220> FEATURE:
<223> OTHER INFORMATION: Synthetic Polynucleotide

<400> SEQUENCE: 132
augagcugga agguggucau caucuucagc cugcugauca caccucagca cggccugaaa 60
gagagcuacc uggaagaguc cugcagcacc aucacagagg gcuaccuguc ugugcugaga 120
accggcuggu acaccaacgu guucacacug gaagugggcg acgucgagaa ucugacaugc 180
ucugauggcc cuagccugau caagaccgag cuggaucugc ucaagagcgc ccugagagaa 240

-continued

```
cucaagaccg ugucugccga ucagcuggcc agagaggaac agaucgagaa uccuggcagc    300
ggcagcuuug ugcugggagc cauugcucuu ggaguggcug cugcugcagc uguuacagca    360
ggcguggcca ucgcuaagac caucagacug gaaagcgaag ugaccgccau caacaacgcc    420
cugaagaaga caaacgaggc cgucagcaca cucggcaaug gcguuagagu gcuggccaca    480
gccgugcgcg agcugaagga cuucgugcuu aagaaccuga cacgggccau uaacaagaac    540
aagugcgaca ucccugaccu gaagauggcc guguccuuua gccaguucaa ccggcgguuu    600
cugaacgucg ugcggcaguu uagcgacaac gccggaauca caccagccau cagccuggac    660
cugaugacag augcugagcu ggcuagagcc gugccuaaca ugccuacauc ugccggccag    720
aucaagcuga ugcucgagaa uagagccaug guccgacgga aaggcuucgg cauucugauu    780
ggcguguacg gcagcagcgu gaucuauaug gugcagcugc cuaucuucgg cgugaucgac    840
acacccugcu ggauugugaa ggccgcuccu agcuguagcg agaagaaggg caauuacgcc    900
ugccugcuga gagaggacca aggcugguau ugucagaacg ccggcagcac cguguacuac    960
ccuaacgaga aggacugcga gacaagaggc gaccacgugu ucugugauac cgccgcugga   1020
aucaaugugg ccgagcagag caaagagugc aacaucaaca ucagcaccac caacuauccc   1080
ugcaaggugu ccaccggcag gcacccuauu ucuauggugg cucugucucc ucugggagcc   1140
cugguggcuu guuauaaggg cguguccugu agcaucggca gcaacagagu gggcaucauc   1200
aagcagcuga acaagggcug cagcuacauc accaaccagg acgccgauac cgugaccauc   1260
gacaacaccg uguaucagcu gagcaaggug gaaggcgaac agcacgugau caagggcaga   1320
ccugugucca gcagcuucga cccuaucaag uucccugaga accaguucca gguggcccug   1380
gaccaggugu ucgagaacau cgagaauucc caggcucugg uggaccaguc caacagaauc   1440
cugucuagcg ccgagaaggg aaacaccggc uucaucaucg ugaucauccu gaucgccgug   1500
cugggcagcu ccaugauccu gguguccauc uucaucauua ucaagaagac caagaagccc   1560
accggcgcuc cuccagaacu gagcggagug accaacaaug gcuucauccc ucacaac      1617
```

<210> SEQ ID NO 133
<211> LENGTH: 1617
<212> TYPE: RNA
<213> ORGANISM: Artificial Sequence
<220> FEATURE:
<223> OTHER INFORMATION: Synthetic Polynucleotide

<400> SEQUENCE: 133

```
augagcugga agguggucau caucuucagc cugcugauca caccucagca cggccugaaa     60
gagagcuacc uggaagaguc cugcagcacc aucacagagg gcuaccuguc ugugcugaga    120
accggcuggu acaccaacgu guucacacug ccugugggcg acgucgagaa ucugacaugc    180
ucugauggcc cuagccugau caagaccgag cuggaucugc ucaagagcgc ccugagagaa    240
cucaagaccg ugucugccga ucagcuggcc agagaggaac agaucgagaa uccuggcagc    300
ggcagcuuug ugcugggagc cauugcucuu ggaguggcug cugcugcagc uguuacagca    360
ggcguggcca ucgcuaagac caucagacug gaaagcgaag ugaccgccau caacaacgcc    420
cugaagaaga caaacgaggc cgucagcaca cucggcaaug gcguuagagu gcuggccaca    480
gccgugcgcg agcugaagga cuucgugucc aagaaccuga cacgggccau uaacaagaac    540
aagugcgaca ucgacgaccu gaagauggcc guguccuuua gccaguucaa ccggcgguuu    600
cugaacgucg ugcggcaguu uagcgacaac gccggaauca caccagccau cagccuggac    660
cugaugacag augcugagcu ggcuagagcc gugccuaaca ugccuacauc ugccggccag    720
```

aucaagcuga ugcucgagaa uagagccaug guccgacgga aaggcuucgg cauucugauu 780
ggcguguacg gcagcagcgu gaucuauaug gugcagcugc cuaucuucgg cgugaucgac 840
acacccugcu ggauugugaa ggccgcuccu agcuguagcg agaagaaggg caauuacgcc 900
ugccugcuga gagaggacca aggcugguau ugucagaacg ccggcagcac cguguacuac 960
ccuaacgaga aggacugcga gacaagaggc gaccacgugu ucugugauac cgccgcugga 1020
aucaaugugg ccgagcagag caaagagugc aacaucaaca ucagcaccac caacuauccc 1080
ugcaaggugu ccaccggcag gcacccuauu ucuauggugg cucugucucc ucugggagcc 1140
cugguggcuu guuauaaggg cguguccugu agcaucggca gcaacagagu gggcaucauc 1200
aagcagcuga acaagggcug cagcuacauc accaaccagg acgccgauac cgugaccauc 1260
gacaacaccg uguaucagcu gagcaaggug gaaggcgaac agcacgugau caagggcaga 1320
ccugugucca gcagcuucga cccuaucaag uucccugagg aucaguucca gguggcccug 1380
gaccaggugu ucgagaacau cgagaauucc caggcucugg uggaccaguc caacagaauc 1440
cugucuagcg ccgagaaggg aaacaccggc uucaucaucg ugaucauccu gaucgccgug 1500
cugggcagcu ccaugauccu gguguccauc uucaucauua ucaagaagac caagaagccc 1560
accggcgcuc cuccagaacu gagcggagug accaacaaug gcuucauccc ucacaac 1617

<210> SEQ ID NO 134
<211> LENGTH: 1617
<212> TYPE: RNA
<213> ORGANISM: Artificial Sequence
<220> FEATURE:
<223> OTHER INFORMATION: Synthetic Polynucleotide

<400> SEQUENCE: 134
augagcugga agguggucau caucuucagc cugcugauca caccucagca cggccugaaa 60
gagagcuacc uggaagaguc cugcagcacc aucacagagg gcuaccuguc ugugcugaga 120
accggcuggu acaccaacgu guucacacug ccugugggcg acgucgagaa ucugacaugc 180
ucugauggcc cuagccugau caagaccgag cuggaucugc ucaagagcgc ccugagagaa 240
cucaagaccg ugucugccga ucagcuggcc agagaggaac agaucgagaa uccuggcagc 300
ggcagcuuug ugcugggagc cauugcucuu ggaguggcug cugcugcagc uguuacagca 360
ggcguggcca ucgcuaagac caucagacug gaaagcgaag ugaccgccau caacaacgcc 420
cugaagaaga caaacgaggc cgucagcaca cucggcaaug gcguuagagu gcuggccaca 480
gccgugcgcg agcugaagga cuucgugucc aagaaccuga cacgggccau uaacaagaac 540
aagugcgaca ucgacgaccu gaagauggcc guguccuuua gccaguucaa ccggcgguuu 600
cugaacgucg ugcggcaguu uagcgacaac gccggaauca caccagccau cagccuggac 660
cugaugacag augcugagcu ggcuagagcc gugccuaaca ugccuacauc ugccggccag 720
aucaagcuga ugcucgagaa uagagccaug guccgacgga aaggcuucgg cauucugauu 780
ggcguguacg gcagcagcgu gaucuauaug gugcagcugc cuaucuucgg cgugaucgac 840
acacccugcu ggauugugaa ggccgcuccu agcuguagcg agaagaaggg caauuacgcc 900
ugccugcuga gagaggacca aggcugguau ugucagaacg ccggcagcac cguguacuac 960
ccuaacgaga aggacugcga gacaagaggc gaccacgugu ucugugauac cgccgcugga 1020
aucaaugugg ccgagcagag caaagagugc aacaucaaca ucagcaccac caacuauccc 1080
ugcaaggugu ccaccggcag gcacccuauu ucuauggugg cucugucucc ucugggagcc 1140

-continued cugguggcuu guuauaaggg cguguccugu agcaucggca gcaacagagu gggcaucauc 1200
aagcagcuga acaagggcug cagcuacauc accaaccagg acgccgauac cgugaccauc 1260
gacaacaccg uguaucagcu gagcaaggug gaaggcgaac agcacgugau caagggcaga 1320
ccugugucca gcagcuucga cccuaucaag uucccugaga accaguucca gguggcccug 1380
gaccaggugu ucgagaacau cgagaauucc caggcucugg uggaccaguc caacagaauc 1440
cugucuagcg ccgagaaggg aaacaccggc uucaucaucg ugaucauccu gaucgccgug 1500
cugggcagcu ccaugauccu gguguccauc uucaucauua ucaagaagac caagaagccc 1560
accggcgcuc cuccagaacu gagcggagug accaacaaug gcuucauccc ucacaac 1617

<210> SEQ ID NO 135
<211> LENGTH: 1617
<212> TYPE: RNA
<213> ORGANISM: Artificial Sequence
<220> FEATURE:
<223> OTHER INFORMATION: Synthetic Polynucleotide

<400> SEQUENCE: 135
augagcugga agguggucau caucuucagc cugcugauca caccucagca cggccugaaa 60
gagagcuacc uggaagaguc cugcagcacc aucacagagg gcuaccuguc ugugcugaga 120
accggcuggu acaccaacgu guucacacug gaagugggcg acgucgagaa ucugacaugc 180
ucugauggcc cuagccugau caagaccgag cuggaucugc ucaagagcgc ccugagagaa 240
cucaagaccg ugucugccga ucagcuggcc agagaggaac agaucgagaa uccuggcagc 300
ggcagcuuug ugcugggagc cauugcucuu ggaguggcug cugcugcagc uguuacagca 360
ggcguggcca ucgcuaagac caucagacug gaaagcgaag ugaccgccau caacaacgcc 420
cugaagaaga caaacgaggc cgucagcaca cucggcaaug gcguuagagu gcuggccaca 480
gccgugcgcg agcugaagga cuucgugucc aagaaccuga cacgggccau uaacaagaac 540
aagugcgaca ucgacgaccu gaagauggcc guguccuuua gccaguucaa ccggcgguuu 600
cugaacgucg ugcggcaguu uagcgacaac gccggaauca caccagccau cagccuggac 660
cugaugacag augcugagcu ggcuagagcc gugccuaaca ugccuacauc ugccggccag 720
aucaagcuga ugcucgagaa uagagccaug guccgacgga aaggcuucgg cauucugauu 780
ggcguguacg gcagcagcgu gaucuauaug gugcagcugc cuaucuucgg cgugaucgac 840
acacccugcu ggauugugaa ggccgcuccu agcuguagcg agaagaaggg caauuacgcc 900
ugccugcuga gagaggacca aggcugguau ugucagaacg ccggcagcac cguguacuac 960
ccuaacgaga aggacugcga gacaagaggc gaccacgugu ucugugauac cgccgcugga 1020
aucaaugugg ccgagcagag caaagagugc aacaucaaca ucagcaccac caacuauccc 1080
ugcaaggugu ccaccggcag gcacccuauu ucuauggugg cucugucucc ucugggagcc 1140
cugguggcuu guuauaaggg cguguccugu agcaucggca gcaacagagu gggcaucauc 1200
aagcagcuga acaagggcug cagcuacauc accaaccagg acgccgauac cgugaccauc 1260
gacaacaccg uguaucagcu gagcaaggug gaaggcgaac agcacgugau caagggcaga 1320
ccugugucca gcagcuucga cccuaucaag uucccugagg aucaguucca gguggcccug 1380
gaccaggugu ucgagaacau cgagaauucc caggcucugg uggaccaguc caacagaauc 1440
cugucuagcg ccgagaaggg aaacaccggc uucaucaucg ugaucauccu gaucgccgug 1500
cugggcagcu ccaugauccu gguguccauc uucaucauua ucaagaagac caagaagccc 1560
accggcgcuc cuccagaacu gagcggagug accaacaaug gcuucauccc ucacaac 1617

<210> SEQ ID NO 136
<211> LENGTH: 1617
<212> TYPE: RNA
<213> ORGANISM: Artificial Sequence
<220> FEATURE:
<223> OTHER INFORMATION: Synthetic Polynucleotide

<400> SEQUENCE: 136
augagcugga agguggucau caucuucagc cugcugauca caccucagca cggccugaaa 60
gagagcuacc uggaagaguc cugcagcacc aucacagagg gcuaccuguc ugugcugaga 120
accggcuggu acaccaacgu guucacacug gaagugggcg accucgagaa ucugacaugc 180
ucugauggcc cuagccugau caagaccgag cuggaucuga ccaagagcgc ccugagagaa 240
cucaagaccg ugucugccga ucagcuggcc agagaggaac agaucgagaa uccuggcagc 300
ggcagcuuug ugcugggagc cauugcucuu ggaguggcug cugcugcagc uguuacagca 360
ggcguggcca ucgcuaagac caucagacug gaaagcgaag ugaccgccau caacaacgcc 420
cugaagaaga caaacgaggc cgucagcaca cucggcaaug gcguuagagu gcuggccaca 480
gccgugcgcg agcugaagga cuucgugucc aagaaccuga cacgggccau uaacaagaac 540
aagugcgaca ucgacgaccu gaagauggcc guguccuuua gccaguucaa ccggcgguuu 600
cugaacgucg ugcggcaguu uagcgacaac gccggaauca caccagccau cagccuggac 660
cugaugacag augcugagcu ggcuagagcc gugccuaaca ugccuacauc ugccggccag 720
aucaagcuga ugcucgagaa uagagccaug guccgacgga aaggcuucgg cauucugauu 780
ggcguguacg gcagcagcgu gaucuauaug gugcagcugc cuaucuucgg cgugaucgac 840
acacccugcu ggauugugaa ggccgcuccu agcuguagcg agaagaaggg caauuacgcc 900
ugccugcuga gagaggacca aggcugguau ugucagaacg ccggcagcac cguguacuac 960
ccuaacgaga aggacugcga gacaagaggc gaccacgugu ucugugauac cgccgcugga 1020
aucaaugugg ccgagcagag caaagagugc aacaucaaca ucagcaccac caacuauccc 1080
ugcaaggugu ccaccggcag gcacccuauu ucuauggugg cucugucucc ucugggagcc 1140
cugguggcuu guuauaaggg cguguccugu agcaucggca gcaacagagu gggcaucauc 1200
aagcagcuga acaagggcug cagcuacauc accaaccagg acgccgauac cgugaccauc 1260
gacaacaccg uguaucagcu gagcaaggug gaaggcgaac agcacgugau caagggcaga 1320
ccugugucca gcagcuucga cccuaucaag uucccugagg aucaguucca gguggcccug 1380
gaccaggugu ucgagaacau cgagaauucc caggcucugg uggaccaguc caacagaauc 1440
cugucuagcg ccgagaaggg aaacaccggc uucaucaucg ugaucauccu gaucgccgug 1500
cugggcagcu ccaugauccu gguguccauc uucaucauua ucaagaagac caagaagccc 1560
accggcgcuc cuccagaacu gagcggagug accaacaaug gcuucauccc ucacaac 1617

<210> SEQ ID NO 137
<211> LENGTH: 1617
<212> TYPE: RNA
<213> ORGANISM: Artificial Sequence
<220> FEATURE:
<223> OTHER INFORMATION: Synthetic Polynucleotide

<400> SEQUENCE: 137
augagcugga agguggucau caucuucagc cugcugauca caccucagca cggccugaaa 60
gagagcuacc uggaagaguc cugcagcacc aucacagagg gcuaccuguc ugugcugaga 120
accggcuggu acaccaacgu guucacacug gaagugggcg acgucgagaa ucugacaugc 180
ucugauggcc cuagccugau caagaccgag cuggaucuga ccaagagcgc ccugagagaa 240
cucaagaccg ugucugccga ucagcuggcc agagaggaac agaucgagaa uccuggcagc 300
ggcagcuuug ugcugggagc cauugcucuu ggaguggcug cugcugcagc uguuacagca 360
ggcguggcca ucgcuaagac caucagacug gaaagcgaag ugaccgccau caacaacgcc 420
cugaagaaga caaacgaggc cgucagcaca cucggcaaug gcguuagagu gcuggccaca 480
gccgugcgcg agcugaagga cuucgugcuu aagaaccuga cacgggccau uaacaagaac 540
aagugcgaca ucgacgaccu gaagauggcc guguccuuua gccaguucaa ccggcgguuu 600
cugaacgucg ugcggcaguu uagcgacaac gccggaauca caccagccau cagccuggac 660
cugaugacag augcugagcu ggcuagagcc gugccuaaca ugccuacauc ugccggccag 720
aucaagcuga ugcucgagaa uagagccaug guccgacgga aaggcuucgg cauucugauu 780
ggcguguacg gcagcagcgu gaucuauaug gugcagcugc cuaucuucgg cgugaucgac 840
acacccugcu ggauugugaa ggccgcuccu agcuguagcg agaagaaggg caauuacgcc 900
ugccugcuga gagaggacca aggcugguau ugucagaacg ccggcagcac cguguacuac 960
ccuaacgaga aggacugcga gacaagaggc gaccacgugu ucugugauac cgccgcugga 1020
aucaaugugg ccgagcagag caaagagugc aacaucaaca ucagcaccac caacuauccc 1080
ugcaaggugu ccaccggcag gcacccuauu ucuauggugg cucugucucc ucugggagcc 1140
cugguggcuu guuauaaggg cguguccugu agcaucggca gcaacagagu gggcaucauc 1200
aagcagcuga acaagggcug cagcuacauc accaaccagg acgccgauac cgugaccauc 1260
gacaacaccg uguaucagcu gagcaaggug gaaggcgaac agcacgugau caagggcaga 1320
ccugugucca gcagcuucga cccuaucaag uucccugagg aucaguucca gguggcccug 1380
gaccaggugu ucgagaacau cgagaauucc caggcucugg uggaccaguc caacagaauc 1440
cugucuagcg ccgagaaggg aaacaccggc uucaucaucg ugaucauccu gaucgccgug 1500
cugggcagcu ccaugauccu gguguccauc uucaucauua ucaagaagac caagaagccc 1560
accggcgcuc cuccagaacu gagcggagug accaacaaug gcuucauccc ucacaac 1617

<210> SEQ ID NO 138
<211> LENGTH: 1617
<212> TYPE: RNA
<213> ORGANISM: Artificial Sequence
<220> FEATURE:
<223> OTHER INFORMATION: Synthetic Polynucleotide

<400> SEQUENCE: 138
augagcugga agguggucau caucuucagc cugcugauca caccucagca cggccugaaa 60
gagagcuacc uggaagaguc cugcagcacc aucacagagg gcuaccuguc ugugcugaga 120
accggcuggu acaccaacgu guucacacug gaagugggcg acgucgagaa ucugacaugc 180
ucugauggcc cuagccugau caagaccgag cuggaucuga ccaagagcgc ccugagagaa 240
cucaagaccg ugucugccga ucagcuggcc agagaggaac agaucgagaa uccuggcagc 300
ggcagcuuug ugcugggagc cauugcucuu ggaguggcug cugcugcagc uguuacagca 360
ggcguggcca ucgcuaagac caucagacug gaaagcgaag ugaccgccau caacaacgcc 420
cugaagaaga caaacgaggc cgucagcaca cucggcaaug gcguuagagu gcuggccaca 480
gccgugcgcg agcugaagga cuucgugucc aagaaccugu ggcgggccau uaacaagaac 540
aagugcgaca ucgacgaccu gaagauggcc guguccuuua gccaguucaa ccggcgguuu 600

-continued

```
cugaacgucg ugcggcaguu uagcgacaac gccggaauca caccagccau cagccuggac    660

cugaugacag augcugagcu ggcuagagcc gugccuaaca ugccuacauc ugccggccag    720

aucaagcuga ugcucgagaa uagagccaug guccgacgga aaggcuucgg cauucugauu    780

ggcguguacg gcagcagcgu gaucuauaug gugcagcugc cuaucuucgg cgugaucgac    840

acacccugcu ggauugugaa ggccgcuccu agcuguagcg agaagaaggg caauuacgcc    900

ugccugcuga gagaggacca aggcugguau ugucagaacg ccggcagcac cguguacuac    960

ccuaacgaga aggacugcga gacaagaggc gaccacgugu ucugugauac cgccgcugga   1020

aucaaugugg ccgagcagag caaagagugc aacaucaaca ucagcaccac caacuauccc   1080

ugcaaggugu ccaccggcag gcacccuauu ucuauggugg cucugucucc ucugggagcc   1140

cugguggcuu guuauaaggg cguguccugu agcaucggca gcaacagagu gggcaucauc   1200

aagcagcuga acaagggcug cagcuacauc accaaccagg acgccgauac cgugaccauc   1260

gacaacaccg uguaucagcu gagcaaggug gaaggcgaac agcacgugau caagggcaga   1320

ccugugucca gcagcuucga cccuaucaag uucccugagg aucaguucca gguggcccug   1380

gaccaggugu ucgagaacau cgagaauucc caggcucugg uggaccaguc caacagaauc   1440

cugucuagcg ccgagaaggg aaacaccggc uucaucaucg ugaucauccu gaucgccgug   1500

cugggcagcu ccaugauccu gguguccauc uucaucauua ucaagaagac caagaagccc   1560

accggcgcuc cuccagaacu gagcggagug accaacaaug gcuucauccc ucacaac      1617
```

<210> SEQ ID NO 139
<211> LENGTH: 1617
<212> TYPE: RNA
<213> ORGANISM: Artificial Sequence
<220> FEATURE:
<223> OTHER INFORMATION: Synthetic Polynucleotide

<400> SEQUENCE: 139

```
augagcugga agguggucau caucuucagc cugcugauca caccucagca cggccugaaa     60

gagagcuacc uggaagaguc cugcagcacc aucacagagg gcuaccuguc ugugcugaga    120

accggcuggu acaccaacgu guucacacug gaagugggcg accucgagaa ucugacaugc    180

ucugauggcc cuagccugau caagaccgag cuggaucugc ucaagagcgc ccugagagaa    240

cucaagaccg ugucugccga ucagcuggcc agagaggaac agaucgagaa uccuggcagc    300

ggcagcuuug ugcugggagc cauugcucuu ggaguggcug cugcugcagc uguuacagca    360

ggcguggcca ucgcuaagac caucagacug gaaagcgaag ugaccgccau caacaacgcc    420

cugaagaaga caaacgaggc cgucagcaca cucggcaaug gcguuagagu gcuggccaca    480

gccgugcgcg agcugaagga cuucgugcuu aagaaccugu ggcgggccau uaacaagaac    540

aagugcgaca ucgacgaccu gaagauggcc guguccuuua gccaguucaa ccggcgguuu    600

cugaacgucg ugcggcaguu uagcgacaac gccggaauca caccagccau cagccuggac    660

cugaugacag augcugagcu ggcuagagcc gugccuaaca ugccuacauc ugccggccag    720

aucaagcuga ugcucgagaa uagagccaug guccgacgga aaggcuucgg cauucugauu    780

ggcguguacg gcagcagcgu gaucuauaug gugcagcugc cuaucuucgg cgugaucgac    840

acacccugcu ggauugugaa ggccgcuccu agcuguagcg agaagaaggg caauuacgcc    900

ugccugcuga gagaggacca aggcugguau ugucagaacg ccggcagcac cguguacuac    960

ccuaacgaga aggacugcga gacaagaggc gaccacgugu ucugugauac cgccgcugga   1020
```

```
aucaaugugg ccgagcagag caaagagugc aacaucaaca ucagcaccac caacuauccc   1080
ugcaaggugu ccaccggcag gcacccuauu ucuauggugg cucugucucc ucugggagcc   1140
cugguggcuu guuauaaggg cguguccugu agcaucggca gcaacagagu gggcaucauc   1200
aagcagcuga acaagggcug cagcuacauc accaaccagg acgccgauac cgugaccauc   1260
gacaacaccg uguaucagcu gagcaaggug gaaggcgaac agcacgugau caagggcaga   1320
ccugugucca gcagcuucga cccuaucaag uucccugagg aucaguucca gguggcccug   1380
gaccaggugu ucgagaacau cgagaauucc caggcucugg uggaccaguc caacagaauc   1440
cugucuagcg ccgagaaggg aaacaccggc uucaucaucg ugaucauccu gaucgccgug   1500
cugggcagcu ccaugauccu gguguccauc uucaucauua ucaagaagac caagaagccc   1560
accggcgcuc cuccagaacu gagcggagug accaacaaug gcuucauccc ucacaac      1617
```

```
<210> SEQ ID NO 140
<211> LENGTH: 1617
<212> TYPE: RNA
<213> ORGANISM: Artificial Sequence
<220> FEATURE:
<223> OTHER INFORMATION: Synthetic Polynucleotide

<400> SEQUENCE: 140

augagcugga agguggucau caucuucagc cugcugauca caccucagca cggccugaaa     60
gagagcuacc uggaagaguc cugcagcacc aucacagagg gcuaccuguc ugugcugaga    120
accggcuggu acaccaacgu guucacacug ccugugggcg acgucgagaa ucugacaugc    180
ucugauggcc cuagccugau caagaccgag cuggaucuga ccaagagcgc ccugagagaa    240
cucaagaccg ugucugccga ucagcuggcc agagaggaac agaucgagaa uccuggcagc    300
ggcagcuuug ugcugggagc cauugcucuu ggaguggcug cugcugcagc uguuacagca    360
ggcguggcca ucgcuaagac caucagacug gaaagcgaag ugaccgccau caacaacgcc    420
cugaagaaga caaacgaggc cgucagcaca cucggcaaug gcguuagagu gcuggccaca    480
gccgugcgcg agcugaagga cuucgugucc aagaaccuga cacgggccau uaacaagaac    540
aagugcgaca ucgacgaccu gaagauggcc guguccuuua gccaguucaa ccggcgguuu    600
cugaacgucg ugcggcaguu uagcgacaac gccggaauca caccagccau cagccuggac    660
cugaugacag augcugagcu ggcuagagcc gugccuaaca ugccuacauc ugccggccag    720
aucaagcuga ugcucgagaa uagagccaug guccgacgga aaggcuucgg cauucugauu    780
ggcguguacg gcagcagcgu gaucuauaug gugcagcugc cuaucuucgg cgugaucgac    840
acacccugcu ggauugugaa ggccgcuccu agcuguagcg agaagaaggg caauuacgcc    900
ugccugcuga gagaggacca aggcugguau ugucagaacg ccggcagcac cguguacuac    960
ccuaacgaga aggacugcga gacaagaggc gaccacgugu ucugugauac cgccgcugga   1020
aucaaugugg ccgagcagag caaagagugc aacaucaaca ucagcaccac caacuauccc   1080
ugcaaggugu ccaccggcag gcacccuauu ucuauggugg cucugucucc ucugggagcc   1140
cugguggcuu guuauaaggg cguguccugu agcaucggca gcaacagagu gggcaucauc   1200
aagcagcuga acaagggcug cagcuacauc accaaccagg acgccgauac cgugaccauc   1260
gacaacaccg uguaucagcu gagcaaggug gaaggcgaac agcacgugau caagggcaga   1320
ccugugucca gcagcuucga cccuaucaag uucccugagg aucaguucca gguggcccug   1380
gaccaggugu ucgagaacau cgagaauucc caggcucugg uggaccaguc caacagaauc   1440
cugucuagcg ccgagaaggg aaacaccggc uucaucaucg ugaucauccu gaucgccgug   1500
```

cugggcagcu ccaugauccu ggugguccauc uucaucauua ucaagaagac caagaagccc 1560
accggcgcuc cuccagaacu gagcggagug accaacaaug gcuucauccc ucacaac 1617

<210> SEQ ID NO 141
<211> LENGTH: 1617
<212> TYPE: RNA
<213> ORGANISM: Artificial Sequence
<220> FEATURE:
<223> OTHER INFORMATION: Synthetic Polynucleotide

<400> SEQUENCE: 141
augagcugga agguggucau caucuucagc cugcugauca caccucagca cggccugaaa 60
gagagcuacc uggaagaguc cugcagcacc aucacagagg gcuaccuguc ugugcugaga 120
accggcuggu acaccaacgu guucacacug gaagugggcg acgucgagaa ucugacaugc 180
ucugauggcc cuagccugau caagaccgag cuggaucuga ccaagagcgc ccugagagaa 240
cucaagaccg ugucugccga ucagcuggcc agagaggaac agaucgagaa uccuggcagc 300
ggcagcuuug ugcugggagc cauugcucuu ggaguggcug cugcugcagc uguuacagca 360
ggcguggcca ucgcuaagac caucagacug gaaagcgaag ugaccgccau caacaacgcc 420
cugaagaaga caaacgaggc cgucagcaca cucggcaaug gcguuagagu gcuggccaca 480
gccgugcgcg agcugaagga cuucgugucc aagaaccuga cacgggccau uaacaagaac 540
aagugcgaca ucccugaccu gaagauggcc guguccuuua gccaguucaa ccggcgguuu 600
cugaacgucg ugcggcaguu uagcgacaac gccggaauca caccagccau cagccuggac 660
cugaugacag augcugagcu ggcuagagcc gugccuaaca ugccuacauc ugccggccag 720
aucaagcuga ugcucgagaa uagagccaug guccgacgga aaggcuucgg cauucugauu 780
ggcguguacg gcagcagcgu gaucuauaug gugcagcugc cuaucuucgg cgugaucgac 840
acacccugcu ggauugugaa ggccgcuccu agcuguagcg agaagaaggg caauuacgcc 900
ugccugcuga gagaggacca aggcugguau ugucagaacg ccggcagcac cguguacuac 960
ccuaacgaga aggacugcga gacaagaggc gaccacgugu ucugugauac cgccgcugga 1020
aucaaugugg ccgagcagag caaagagugc aacaucaaca ucagcaccac caacuauccc 1080
ugcaaggugu ccaccggcag gcacccuauu ucuauggugg cucugucucc ucugggagcc 1140
cugguggcuu guuauaaggg cguguccugu agcaucggca gcaacagagu gggcaucauc 1200
aagcagcuga acaagggcug cagcuacauc accaaccagg acgccgauac cgugaccauc 1260
gacaacaccg uguaucagcu gagcaaggug gaaggcgaac agcacgugau caagggcaga 1320
ccugugucca gcagcuucga cccuaucaag uucccugagg aucaguucca gguggcccug 1380
gaccaggugu ucgagaacau cgagaauucc caggcucugg uggaccaguc caacagaauc 1440
cugucuagcg ccgagaaggg aaacaccggc uucaucaucg ugaucauccu gaucgccgug 1500
cugggcagcu ccaugauccu ggugguccauc uucaucauua ucaagaagac caagaagccc 1560
accggcgcuc cuccagaacu gagcggagug accaacaaug gcuucauccc ucacaac 1617

<210> SEQ ID NO 142
<211> LENGTH: 1617
<212> TYPE: RNA
<213> ORGANISM: Artificial Sequence
<220> FEATURE:
<223> OTHER INFORMATION: Synthetic Polynucleotide

<400> SEQUENCE: 142

-continued augagcugga agguggucau caucuucagc cugcugauca caccucagca cggccugaaa 60
gagagcuacc uggaagaguc cugcagcacc aucacagagg gcuaccuguc ugugcugaga 120
accggcuggu acaccaacgu guucacacug gaagugggcg acgucgagaa ucugacaugc 180
ucugauggcc cuagccugau caagaccgag cuggaucuga ccaagagcgc ccugagagaa 240
cucaagaccg ugucugccga ucagcuggcc agagaggaac agaucgagaa uccuggcagc 300
ggcagcuuug ugcugggagc cauugcucuu ggaguggcug cugcugcagc uguuacagca 360
ggcguggcca ucgcuaagac caucagacug gaaagcgaag ugaccgccau caacaacgcc 420
cugaagaaga caaacgaggc cgucagcaca cucggcaaug gcguuagagu gcuggccaca 480
gccgugcgcg agcugaagga cuucgugucc aagaaccuga cacgggccau uaacaagaac 540
aagugcccua ucgacgaccu gaagauggcc guguccuuua gccaguucaa ccggcgguuu 600
cugaacgucg ugcggcaguu uagcgacaac gccggaauca caccagccau cagccuggac 660
cugaugacag augcugagcu ggcuagagcc gugccuaaca ugccuacauc ugccggccag 720
aucaagcuga ugcucgagaa uagagccaug guccgacgga aaggcuucgg cauucugauu 780
ggcguguacg gcagcagcgu gaucuauaug gugcagcugc cuaucuucgg cgugaucgac 840
acacccugcu ggauugugaa ggccgcuccu agcuguagcg agaagaaggg caauuacgcc 900
ugccugcuga gagaggacca aggcugguau ugucagaacg ccggcagcac cguguacuac 960
ccuaacgaga aggacugcga gacaagaggc gaccacgugu ucugugauac cgccgcugga 1020
aucaaugugg ccgagcagag caaagagugc aacaucaaca ucagcaccac caacuauccc 1080
ugcaaggugu ccaccggcag gcacccuauu ucuauggugg cucugucucc ucugggagcc 1140
cugguggcuu guuauaaggg cguguccugu agcaucggca gcaacagagu gggcaucauc 1200
aagcagcuga acaagggcug cagcuacauc accaaccagg acgccgauac cgugaccauc 1260
gacaacaccg uguaucagcu gagcaaggug gaaggcgaac agcacgugau caagggcaga 1320
ccugugucca gcagcuucga cccuaucaag uucccugagg aucaguucca gguggcccug 1380
gaccaggugu ucgagaacau cgagaauucc caggcucugg uggaccaguc caacagaauc 1440
cugucuagcg ccgagaaggg aaacaccggc uucaucaucg ugaucauccu gaucgccgug 1500
cugggcagcu ccaugauccu gguguccauc uucaucauua ucaagaagac caagaagccc 1560
accggcgcuc cuccagaacu gagcggagug accaacaaug gcuucauccc ucacaac 1617

<210> SEQ ID NO 143
<211> LENGTH: 1617
<212> TYPE: RNA
<213> ORGANISM: Artificial Sequence
<220> FEATURE:
<223> OTHER INFORMATION: Synthetic Polynucleotide

<400> SEQUENCE: 143
augagcugga agguggucau caucuucagc cugcugauca caccucagca cggccugaaa 60
gagagcuacc uggaagaguc cugcagcacc aucacagagg gcuaccuguc ugugcugaga 120
accggcuggu acaccaacgu guucacacug gaagugggcg acgucgagaa ucugacaugc 180
ucugauggcc cuagccugau caagaccgag cuggaucuga ccaagagcgc ccugagagaa 240
cucaagaccg ugucugccga ucagcuggcc agagaggaac agaucgagaa uccuggcagc 300
ggcagcuuug ugcugggagc cauugcucuu ggaguggcug cugcugcagc uguuacagca 360
ggcguggcca ucgcuaagac caucagacug ccuagcgaag ugaccgccau caacaacgcc 420
cugaagaaga caaacgaggc cgucagcaca cucggcaaug gcguuagagu gcuggccaca 480
gccgugcgcg agcugaagga cuucgugucc aagaaccuga cacgggccau uaacaagaac 540
aagugcgaca ucgacgaccu gaagauggcc guguccuuua gccaguucaa ccggcgguuu 600
cugaacgucg ugcggcaguu uagcgacaac gccggaauca caccagccau cagccuggac 660
cugaugacag augcugagcu ggcuagagcc gugccuaaca ugccuacauc ugccggccag 720
aucaagcuga ugcucgagaa uagagccaug guccgacgga aaggcuucgg cauucugauu 780
ggcguguacg gcagcagcgu gaucuauaug gugcagcugc cuaucuucgg cgugaucgac 840
acacccugcu ggauugugaa ggccgcuccu agcuguagcg agaagaaggg caauuacgcc 900
ugccugcuga gagaggacca aggcugguau ugucagaacg ccggcagcac cguguacuac 960
ccuaacgaga aggacugcga gacaagaggc gaccacgugu ucugugauac cgccgcugga 1020
aucaaugugg ccgagcagag caaagagugc aacaucaaca ucagcaccac caacuauccc 1080
ugcaaggugu ccaccggcag gcacccuauu ucuauggugg cucugucucc ucugggagcc 1140
cugguggcuu guuauaaggg cguguccugu agcaucggca gcaacagagu gggcaucauc 1200
aagcagcuga acaagggcug cagcuacauc accaaccagg acgccgauac cgugaccauc 1260
gacaacaccg uguaucagcu gagcaaggug gaaggcgaac agcacgugau caagggcaga 1320 ccuguguucca gcagcuucga cccuaucaag uucccugagg aucaguucca gguggcccug 1380
gaccaggugu ucgagaacau cgagaauucc caggcucugg uggaccaguc caacagaauc 1440
cugucuagcg ccgagaaggg aaacaccggc uucaucaucg ugaucaccu gaucgccgug 1500 cugggcagcu ccaugauccu ggugguccauc uucaucauua ucaagaagac caagaagccc 1560
accggcgcuc cuccagaacu gagcggagug accaacaaug gcuucauccc ucacaac 1617

<210> SEQ ID NO 144
<211> LENGTH: 1617
<212> TYPE: RNA
<213> ORGANISM: Artificial Sequence
<220> FEATURE:
<223> OTHER INFORMATION: Synthetic Polynucleotide

<400> SEQUENCE: 144
augagcugga agguggucau caucuucagc cugcugauca caccucagca cggccugaaa 60
gagagcuacc uggaagaguc cugcagcacc aucacagagg gcuaccuguc ugugcugaga 120
accggcuggu acaccaacgu guucacacug gaagugggcg acgucgagaa ucugacaugc 180
ucugauggcc cuagccugau caagaccgag cuggaucuga ccaagagcgc ccugagagaa 240
cucaagaccg ugucugccga ucagcuggcc agagaggaac agaucgagaa uccuggcagc 300
ggcagcuuug ugcugggagc cauugcucuu ggaguggcug cugcugcagc uguuacagca 360
ggcguggcca ucgcuaagac caucagacug gaaagcgaag ugaccgccau caacaacgcc 420
cugaagaaga caaacgaggc cgucagcaca cucggcaaug gcguuagagu gcuggccaca 480
gccgugcgcg agcugaagga cuucgugucc aagaaccuga cacgggccau uaacaagaac 540
aagugcgaca ucgacgaccu gaagauggcc guguccuuua gccaguucaa ccggcgguuu 600
cugaacgucg ugcggcaguu uagcgacaac gccggaauca caccagccau cagccuggac 660
cugaugacag augcugagcu ggcuagagcc gugccuaaca ugccuacauc ugccggccag 720
aucaagcuga ugcucgagaa uagagccaug guccgacgga aaggcuucgg cauucugauu 780
ggcguguacg gcagcagcgu gaucuauaug gugcagcugc cuaucuucgg cgugaucgac 840
acacccugcu ggauugugaa ggccgcuccu agcuguagcg agaagaaggg caauuacgcc 900

-continued

```
ugccugcuga gagaggacca aggcugguau ugucagaacg ccggcagcac cguguacuac    960
ccuaacgaga aggacugcga gacaagaggc gaccacgugu ucugugauac cgccgcugga   1020
aucaaugugg ccgagcagag caaagagugc aacaucaaca ucagcaccac caacuauccc   1080
ugcaaggugu ccaccggcag gcacccuauu ucuauggugg cucugucucc ucugggagcc   1140
cugguggcuu guuauaaggg cguguccugu agcaucggca gcaacagagu gggcaucauc   1200
aagcagcuga acaagggcug cagcuacauc accaaccagg acgccgauac cgugaccauc   1260
gacaacaccg uguaucagcu gagcaaggug gaaggcgaac agcacgugau caagggcaga   1320
ccugugucca gcagcuuccc accuaucaag uucccugagg aucaguucca gguggcccug   1380
gaccaggugu ucgagaacau cgagaauucc caggcucugg uggaccaguc caacagaauc   1440
cugucuagcg ccgagaaggg aaacaccggc uucaucaucg ugaucauccu gaucgccgug   1500
cugggcagcu ccaugauccu ggugucca uc uucaucauua ucaagaagac caagaagccc   1560
accggcgcuc cuccagaacu gagcggagug accaacaaug gcuucauccc ucacaac      1617
```

```
<210> SEQ ID NO 145
<211> LENGTH: 1617
<212> TYPE: RNA
<213> ORGANISM: Artificial Sequence
<220> FEATURE:
<223> OTHER INFORMATION: Synthetic Polynucleotide

<400> SEQUENCE: 145

augagcugga agguggucau caucuucagc cugcugauca caccucagca cggccugaaa     60
gagagcuacc uggaagaguc cugcagcacc aucacagagg gcuaccuguc ugugcugaga    120
accggcuggu acaccaacgu guucacacug gaagugggcg acgucgagaa ucugacaugc    180
ucugauggcc cuagccugau caagaccgag cuggaucuga ccaagagcgc ccugagagaa    240
cucaagaccg ugucugccga ucagcuggcc agagaggaac agaucgagaa uccuggcagc    300
ggcagcuuug ugcugggagc cauugcucuu ggaguggcug cugcugcagc uguuacagca    360
ggcguggcca ucgcuaagac caucagacug gaaagcgaag ugaccgccau caacaacgcc    420
cugaagaaga caaacgaggc cgucagcaca cucggcaaug gcguuagagu gcuggccaca    480
gccgugcgcg agcugaagga cuucgugucc aagaaccuga cacgggccau uaacaagaac    540
aagugcgaca ucgacgaccu gaagauggcc guguccuuua gccaguucaa ccggcgguuu    600
cugaacgucg ugcggcaguu uagcgacaac gccggaauca caccagccau cagccuggac    660
cugaugacag augcugagcu ggcuagagcc gugccuaaca ugccuacauc ugccggccag    720
aucaagcuga ugcucgagaa uagagccaug guccgacgga aaggcuucgg cauucugauu    780
ggcguguacg gcagcagcgu gaucuauaug gugcagcugc cuaucuucgg cgugaucgac    840
acacccugcu ggauugugaa ggccgcuccu agcuguagcg agaagaaggg caauuacgcc    900
ugccugcuga gagaggacca aggcugguau ugucagaacg ccggcagcac cguguacuac    960
ccuaacgaga aggacugcga gacaagaggc gaccacgugu ucugugauac cgccgcugga   1020
aucaaugugg ccgagcagag caaagagugc aacaucaaca ucagcaccac caacuauccc   1080
ugcaaggugu ccaccggcag gcacccuauu ucuauggugg cucugucucc ucugggagcc   1140
cugguggcuu guuauaaggg cguguccugu agcaucggca gcaacagagu gggcaucauc   1200
aagcagcuga acaagggcug cagcuacauc accaaccagg acgccgauac cgugaccauc   1260
gacaacaccg uguaucagcu gagcaaggug gaaggcgaac agcacgugau caagggcaga   1320
ccugugucca gcagcuucga cccuaucaag uucccugaga accaguucca gguggcccug   1380
```

gaccaggugu ucgagaacau cgagaauucc caggcucugg uggaccaguc caacagaauc 1440
cugucuagcg ccgagaaggg aaacaccggc uucaucaucg ugaucauccu gaucgccgug 1500
cugggcagcu ccaugauccu ggguguccauc uucaucauua ucaagaagac caagaagccc 1560
accggcgcuc cuccagaacu gagcggagug accaacaaug gcuucauccc ucacaac 1617

<210> SEQ ID NO 146
<211> LENGTH: 1617
<212> TYPE: RNA
<213> ORGANISM: Artificial Sequence
<220> FEATURE:
<223> OTHER INFORMATION: Synthetic Polynucleotide

<400> SEQUENCE: 146
augagcugga agguggucau caucuucagc cugcugauca caccucagca cggccugaaa 60
gagagcuacc uggaagaguc cugcagcacc aucacagagg gcuaccuguc ugugcugaga 120
accggcuggu acaccaacgu guucacacug gaagugggcg acgucgagaa ucugacaugc 180
ucugauggcc cuagccugau caagaccgag cuggaucuga ccaagagcgc ccugagagaa 240
cucaagaccg ugucugccga ucagcuggcc agagaggaac agaucgagaa uccuggcagc 300
ggcagcuuug ugcugggagc cauugcucuu ggaguggcug cugcugcagc uguuacagca 360
ggcguggcca ucgcuaagac caucagacug gaaagcgaag ugaccgccau caacaacgcc 420
cugaagaaga caaacgaggc cgucagcaca cucggcaaug gcguuagagu gcuggccaca 480
gccgugcgcg agcugaagga cuucgugucc aagaaccuga cacgggccau uaacaagaac 540
aagugcgaca ucgacgaccu gaagauggcc guguccuuua gccaguucaa ccggcgguuu 600
cugaacgucg ugcggcaguu uagcgacaac gccggaauca caccagccau cagccuggac 660
cugaugacag augcugagcu ggcuagagcc gugccuaaca ugccuacauc ugccggccag 720
aucaagcuga ugcucgagaa uagagccaug guccgacgga aaggcuucgg cauucugauu 780
ggcguguacg gcagcagcgu gaucuauaug gugcagcugc cuaucuucgg cgugaucgac 840
acacccugcu ggauugugaa ggccgcuccu agcuguagcg agaagaaggg caauuacgcc 900
ugccugcuga gagaggacca aggcugguau ugucagaacg ccggcagcac cguguacuac 960
ccuaacgaga aggacugcga gacaagaggc gaccacgugu ucugugauac cgccgcugga 1020
aucaaugugg ccgagcagag caaagagugc aacaucaaca ucagcaccac caacuauccc 1080
ugcaaggugu ccaccggcag gcacccuauu ucuauggugg cucugucucc ucugggagcc 1140
cugguggcuu guuauaaggg cguguccugu agcaucggca gcaacagagu gggcaucauc 1200
aagcagcuga acaagggcug cagcuacauc accaaccagg acgccgauac cgugaccauc 1260
gacaacaccg uguaucagcu gagcaaggug gaaggcgaac agcacgugau caagggcaga 1320
ccugugucca gcagcuucga cccuaucaag uucccucagg aucaguucca gguggcccug 1380
gaccaggugu ucgagaacau cgagaauucc caggcucugg uggaccaguc caacagaauc 1440
cugucuagcg ccgagaaggg aaacaccggc uucaucaucg ugaucauccu gaucgccgug 1500
cugggcagcu ccaugauccu ggguguccauc uucaucauua ucaagaagac caagaagccc 1560
accggcgcuc cuccagaacu gagcggagug accaacaaug gcuucauccc ucacaac 1617

<210> SEQ ID NO 147
<211> LENGTH: 1617
<212> TYPE: RNA
<213> ORGANISM: Artificial Sequence
<220> FEATURE:

<223> OTHER INFORMATION: Synthetic Polynucleotide

<400> SEQUENCE: 147

```
augagcugga agguggucau caucuucagc cugcugauca caccucagca cggccugaaa      60
gagagcuacc uggaagaguc cugcagcacc aucacagagg gcuaccuguc ugugcugaga     120
accggcuggu acaccaacgu guucacacug gaagugggcg acgucgagaa ucugacaugc     180
ucugauggcc cuagccugau caagaccgag cuggaucuga ccaagagcgc ccugagagaa     240
cucaagaccg ugucugccga ucagcuggcc agagaggaac agaucgagaa uccuggcagc     300
ggcagcuuug ugcugggagc cauugcucuu ggaguggcug cugcugcagc uguuacagca     360
ggcguggcca ucgcuaagac caucagacug gaaagcgaag ugaccgccau caacaacgcc     420
cugaagaaga caaacgaggc cgucagcaca cucggcaaug gcguuagagu gcuggccaca     480
gccgugcgcg agcugaagga cuucgugucc aagaaccuga cacgggccau uaacaagaac     540
aagugcgaca ucgacgaccu gaagauggcc guguccuuua gccaguggaa ccggcgguuu     600
cugaacgucg ugcggcaguu uagcgacaac gccggaauca caccagccau cagccuggac     660
cugaugacag augcugagcu ggcuagagcc gugccuaaca ugccuacauc ugccggccag     720
aucaagcuga ugcucgagaa uagagccaug guccgacgga aaggcuucgg cauucugauu     780
ggcguguacg gcagcagcgu gaucuauaug gugcagcugc cuaucuucgg cgugaucgac     840
acacccugcu ggauugugaa ggccgcuccu agcuguagcg agaagaaggg caauuacgcc     900
ugccugcuga gagaggacca aggcugguau ugucagaacg ccggcagcac cguguacuac     960
ccuaacgaga aggacugcga gacaagaggc gaccacgugu ucugugauac cgccgcugga    1020
aucaauguggg ccgagcagag caaagagugc aacaucaaca ucagcaccac caacuauccc    1080
ugcaaggugu ccaccggcag gcacccuauu ucuauggugg cucugucucc ucugggagcc    1140
cugguggcuu guuauaaggg cguguccugu agcaucggca gcaacagagu gggcaucauc    1200
aagcagcuga acaagggcug cagcuacauc accaaccagg acgccgauac cgugaccauc    1260
gacaacaccg uguaucagcu gagcaaggug gaaggcgaac agcacgugau caagggcaga    1320
ccugugucca gcagcuucga cccuaucaag uucccugagg aucaguucca gguggcccug    1380
gaccaggugu ucgagaacau cgagaauucc caggcucugg uggaccaguc caacagaauc    1440
cugucuagcg ccgagaaggg aaacaccggc uucaucaucg ugaucauccu gaucgccgug    1500
cugggcagcu ccaugauccu gguguccauc uucaucauua ucaagaagac caagaagccc    1560
accggcgcuc cuccagaacu gagcggagug accaacaaug gcuucauccc ucacaac       1617
```

HMPV RNA VACCINES

RELATED APPLICATIONS

This application is a continuation of U.S. application Ser. No. 16/040,981, filed Jul. 20, 2018, which is a continuation of U.S. application Ser. No. 15/674,599, now U.S. Pat. No. 10,064,934, filed Aug. 11, 2017, which is a continuation of international application number PCT/US2016/058327, which claims the benefit under 35 U.S.C. § 119(e) of U.S. provisional application No. 62/244,802, filed Oct. 22, 2015, U.S. provisional application No. 62/247,297, filed Oct. 28, 2015, U.S. provisional application No. 62/244,946, filed Oct. 22, 2015, U.S. provisional application No. 62/247,362, filed Oct. 28, 2015, U.S. provisional application No. 62/244,813, filed Oct. 22, 2015, U.S. provisional application No. 62/247,394, filed Oct. 28, 2015, U.S. provisional application No. 62/244,837, filed Oct. 22, 2015, U.S. provisional application No. 62/247,483, filed Oct. 28, 2015, and U.S. provisional application No. 62/245,031, filed Oct. 22, 2015, each of which is incorporated by reference herein in its entirety.

BACKGROUND

Respiratory disease is a medical term that encompasses pathological conditions affecting the organs and tissues that make gas exchange possible in higher organisms, and includes conditions of the upper respiratory tract, trachea, bronchi, bronchioles, alveoli, pleura and pleural cavity, and the nerves and muscles of breathing. Respiratory diseases range from mild and self-limiting, such as the common cold, to life-threatening entities like bacterial pneumonia, pulmonary embolism, acute asthma and lung cancer. Respiratory disease is a common and significant cause of illness and death around the world. In the US, approximately 1 billion "common colds" occur each year. Respiratory conditions are among the most frequent reasons for hospital stays among children.

The human metapneumovirus (hMPV) is a negative-sense, single-stranded RNA virus of the genus Pneumovirinae and of the family Paramyxoviridae and is closely related to the avian metapneumovirus (AMPV) subgroup C. It was isolated for the first time in 2001 in the Netherlands by using the RAP-PCR (RNA arbitrarily primed PCR) technique for identification of unknown viruses growing in cultured cells. hPMV is second only to RSV as an important cause of viral lower respiratory tract illness (LRI) in young children. The seasonal epidemiology of hMPV appears to be similar to that of RSV, but the incidence of infection and illness appears to be substantially lower.

Parainfluenza virus type 3 (PIV3), like hMPV, is also a negative-sense, single-stranded sense RNA virus of the genus Pneumovirinae and of the family Paramyxoviridae and is a major cause of ubiquitous acute respiratory infections of infancy and early childhood. Its incidence peaks around 4-12 months of age, and the virus is responsible for 3-10% of hospitalizations, mainly for bronchiolitis and pneumonia. PIV3 can be fatal, and in some instances is associated with neurologic diseases, such as febrile seizures. It can also result in airway remodeling, a significant cause of morbidity. In developing regions of the world, infants and young children are at the highest risk of mortality, either from primary PIV3 viral infection or a secondary consequences, such as bacterial infections. Human parainfluenza viruses (hPIV) types 1, 2 and 3 (hPIV1, hPIV2 and hPIV3, respectively), also like hMPV, are second only to RSV as important causes of viral LRI in young children.

RSV, too, is a negative-sense, single-stranded RNA virus of the genus Pneumovirinae and of the family Paramyxoviridae. Symptoms in adults typically resemble a sinus infection or the common cold, although the infection may be asymptomatic. In older adults (e.g., >60 years), RSV infection may progress to bronchiolitis or pneumonia. Symptoms in children are often more severe, including bronchiolitis and pneumonia. It is estimated that in the United States, most children are infected with RSV by the age of three. The RSV virion consists of an internal nucleocapsid comprised of the viral RNA bound to nucleoprotein (N), phosphoprotein (P), and large polymerase protein (L). The nucleocapsid is surrounded by matrix protein (M) and is encapsulated by a lipid bilayer into which the viral fusion (F) and attachment (G) proteins as well as the small hydrophobic protein (SH) are incorporated. The viral genome also encodes two nonstructural proteins (NS1 and NS2), which inhibit type I interferon activity as well as the M-2 protein.

The continuing health problems associated with hMPV, PIV3 and RSV are of concern internationally, reinforcing the importance of developing effective and safe vaccine candidates against these virus.

Despite decades of research, no vaccines currently exist (Sato and Wright, *Pediatr. Infect. Dis. J.* 2008; 27(10 Suppl): S123-5). Recombinant technology, however, has been used to target the formation of vaccines for hPIV-1, 2 and 3 serotypes, for example, and has taken the form of several live-attenuated intranasal vaccines. Two vaccines in particular were found to be immunogenic and well tolerated against hPIV-3 in phase I trials. hPIV1 and hPIV2 vaccine candidates remain less advanced (Durbin and Karron, Clinical infectious diseases: an official publication of the Infectious Diseases Society of America 2003; 37(12):1668-77).

Measles virus (MeV), like hMPV, PIV3 and RSV, is a negative-sense, single-stranded RNA virus that is the cause of measles, an infection of the respiratory system. MeV is of the genus Morbillivirus within the family Paramyxoviridae. Humans are the natural hosts of the virus; no animal reservoirs are known to exist. Symptoms of measles include fever, cough, runny nose, red eyes and a generalized, maculopapular, erythematous rash. The virus is highly contagious and is spread by coughing In additional to hMPV, PIV, RSV and MeV, betacoronaviruses are known to cause respiratory illnesses. Betacoronaviruses (BetaCoVs) are one of four genera of coronaviruses of the subfamily Coronavirinae in the family Coronaviridae, of the order Nidovirales. They are enveloped, positive-sense, single-stranded RNA viruses of zoonotic origin. The coronavirus genera are each composed of varying viral lineages, with the betacoronavirus genus containing four such lineages. The BetaCoVs of the greatest clinical importance concerning humans are OC43 and HKU1 of the A lineage, SARS-CoV of the B lineage, and MERS-CoV of the C lineage. MERS-CoV is the first betacoronavirus belonging to lineage C that is known to infect humans.

The Middle East respiratory syndrome coronavirus (MERS-CoV), or EMC/2012 (HCoV-EMC/2012), initially referred to as novel coronavirus 2012 or simply novel coronavirus, was first reported in 2012 after genome sequencing of a virus isolated from sputum samples from a person who fell ill during a 2012 outbreak of a new flu. As of July 2015, MERS-CoV cases have been reported in over 21 countries. The outbreaks of MERS-CoV have raised serious concerns world-wide, reinforcing the importance of developing effective and safe vaccine candidates against MERS-CoV.

Severe acute respiratory syndrome (SARS) emerged in China in 2002 and spread to other countries before brought under control. Because of a concern for reemergence or a deliberate release of the SARS coronavirus, vaccine development was initiated.

Deoxyribonucleic acid (DNA) vaccination is one technique used to stimulate humoral and cellular immune responses to foreign antigens, such as hMPV antigens and/or PIV antigens and/or RSV antigens. The direct injection of genetically engineered DNA (e.g., naked plasmid DNA) into a living host results in a small number of its cells directly producing an antigen, resulting in a protective immunological response. With this technique, however, comes potential problems, including the possibility of insertional mutagenesis, which could lead to the activation of oncogenes or the inhibition of tumor suppressor genes.

SUMMARY

Provided herein are ribonucleic acid (RNA) vaccines that build on the knowledge that RNA (e.g., messenger RNA (mRNA)) can safely direct the body's cellular machinery to produce nearly any protein of interest, from native proteins to antibodies and other entirely novel protein constructs that can have therapeutic activity inside and outside of cells. The RNA (e.g., mRNA) vaccines of the present disclosure may be used to induce a balanced immune response against hMPV, PIV, RSV, MeV, and/or BetaCoV (e.g., MERS-CoV, SARS-CoV, HCoV-OC43, HCoV-229E, HCoV-NL63, HCoV-NL, HCoV-NH and/or HCoV-HKU1), or any combination of two or more of the foregoing viruses, comprising both cellular and humoral immunity, without risking the possibility of insertional mutagenesis, for example. hMPV, PIV, RSV, MeV, BetaCoV (e.g., MERS-CoV, SARS-CoV, HCoV-OC43, HCoV-229E, HCoV-NL63, HCoV-NL, HCoV-NH and HCoV-HKU1) and combinations thereof are referred to herein as "respiratory viruses." Thus, the term "respiratory virus RNA vaccines" encompasses hMPV RNA vaccines, PIV RNA vaccines, RSV RNA vaccines, MeV RNA vaccines, BetaCoV RNA vaccines, and any combination of two or more of hMPV RNA vaccines, PIV RNA vaccines, RSV RNA vaccines, MeV RNA vaccines, and BetaCoV RNA vaccines.

The RNA (e.g., mRNA) vaccines may be utilized in various settings depending on the prevalence of the infection or the degree or level of unmet medical need. The RNA (e.g. mRNA) vaccines may be utilized to treat and/or prevent a hMPV, PIV, RSV, MeV, a BetaCoV (e.g., MERS-CoV, SARS-CoV, HCoV-OC43, HCoV-229E, HCoV-NL63, HCoV-NL, HCoV-NH, HCoV-HKU1), or any combination of two or more of the foregoing viruses, of various genotypes, strains, and isolates. The RNA (e.g., mRNA) vaccines have superior properties in that they produce much larger antibody titers and produce responses earlier than commercially available anti-viral therapeutic treatments. While not wishing to be bound by theory, it is believed that the RNA (e.g., mRNA) vaccines, as mRNA polynucleotides, are better designed to produce the appropriate protein conformation upon translation as the RNA (e.g., mRNA) vaccines co-opt natural cellular machinery. Unlike traditional vaccines, which are manufactured ex vivo and may trigger unwanted cellular responses, RNA (e.g., mRNA) vaccines are presented to the cellular system in a more native fashion.

In some aspects the invention is a respiratory virus vaccine, comprising at least one RNA polynucleotide having an open reading frame encoding at least one respiratory virus antigenic polypeptide, formulated in a cationic lipid nanoparticle.

Surprisingly, in some aspects, it has also been shown that efficacy of mRNA vaccines can be significantly enhanced when combined with a flagellin adjuvant, in particular, when one or more antigen-encoding mRNAs is combined with an mRNA encoding flagellin.

RNA (e.g., mRNA) vaccines combined with the flagellin adjuvant (e.g., mRNA-encoded flagellin adjuvant) have superior properties in that they may produce much larger antibody titers and produce responses earlier than commercially available vaccine formulations. While not wishing to be bound by theory, it is believed that the RNA (e.g., mRNA) vaccines, for example, as mRNA polynucleotides, are better designed to produce the appropriate protein conformation upon translation, for both the antigen and the adjuvant, as the RNA (e.g., mRNA) vaccines co-opt natural cellular machinery. Unlike traditional vaccines, which are manufactured ex vivo and may trigger unwanted cellular responses, RNA (e.g., mRNA) vaccines are presented to the cellular system in a more native fashion.

Some embodiments of the present disclosure provide RNA (e.g., mRNA) vaccines that include at least one RNA (e.g., mRNA) polynucleotide having an open reading frame encoding at least one antigenic polypeptide or an immunogenic fragment thereof (e.g., an immunogenic fragment capable of inducing an immune response to the antigenic polypeptide) and at least one RNA (e.g., mRNA polynucleotide) having an open reading frame encoding a flagellin adjuvant.

In some embodiments, at least one flagellin polypeptide (e.g., encoded flagellin polypeptide) is a flagellin protein. In some embodiments, at least one flagellin polypeptide (e.g., encoded flagellin polypeptide) is an immunogenic flagellin fragment. In some embodiments, at least one flagellin polypeptide and at least one antigenic polypeptide are encoded by a single RNA (e.g., mRNA) polynucleotide. In other embodiments, at least one flagellin polypeptide and at least one antigenic polypeptide are each encoded by a different RNA polynucleotide.

In some embodiments at least one flagellin polypeptide has at least 80%, at least 85%, at least 90%, or at least 95% identity to a flagellin polypeptide having a sequence identified by any one of SEQ ID NO: 54-56.

Provided herein, in some embodiments, is a ribonucleic acid (RNA) (e.g., mRNA) vaccine, comprising at least one (e.g., at least 2, 3, 4 or 5) RNA (e.g., mRNA) polynucleotide having an open reading frame encoding at least one (e.g., at least 2, 3, 4 or 5) hMPV, PIV, RSV, MeV, or a BetaCoV (e.g., MERS-CoV, SARS-CoV, HCoV-OC43, HCoV-229E, HCoV-NL63, HCoV-NL, HCoV-NH, HCoV-HKU1) antigenic polypeptide, or any combination of two or more of the foregoing antigenic polypeptides. Herein, use of the term "antigenic polypeptide" encompasses immunogenic fragments of the antigenic polypeptide (an immunogenic fragment that is induces (or is capable of inducing) an immune response to hMPV, PIV, RSV, MeV, or a BetaCoV), unless otherwise stated.

Also provided herein, in some embodiments, is a RNA (e.g., mRNA) vaccine comprising at least one (e.g., at least 2, 3, 4 or 5) RNA polynucleotide having an open reading frame encoding at least one (e.g., at least 2, 3, 4 or 5) hMPV, PIV, RSV, MeV, and/or a BetaCoV (e.g., MERS-CoV, SARS-CoV, HCoV-OC43, HCoV-229E, HCoV-NL63, HCoV-NL, HCoV-NH, HCoV-HKU1) antigenic polypeptide or an immunogenic fragment thereof, linked to a signal peptide.

Further provided herein, in some embodiments, is a nucleic acid (e.g., DNA) encoding at least one (e.g., at least 2, 3, 4 or 5) hMPV, PIV, RSV, MeV, and/or a BetaCoV (e.g., MERS-CoV, SARS-CoV, HCoV-OC43, HCoV-229E, HCoV-NL63, HCoV-NL, HCoV-NH, HCoV-HKU1) RNA (e.g., mRNA) polynucleotide.

Further still, provided herein, in some embodiments, is a method of inducing an immune response in a subject, the method comprising administering to the subject a vaccine comprising at least one (e.g., at least 2, 3, 4 or 5) RNA (e.g., mRNA) polynucleotide having an open reading frame encoding at least one (e.g., at least 2, 3, 4 or 5) hMPV, PIV, RSV, MeV, and/or a BetaCoV (e.g., MERS-CoV, SARS-CoV, HCoV-OC43, HCoV-229E, HCoV-NL63, HCoV-NL, HCoV-NH, HCoV-HKU1) antigenic polypeptide, or any combination of two or more of the foregoing antigenic polypeptides.

hMPV/PIV3/RSV

In some embodiments, a RNA (e.g., mRNA) vaccine comprises at least one RNA (e.g., mRNA) polynucleotide having an open reading frame encoding at least one hMPV, PIV3 or RSV antigenic polypeptide. In some embodiments, at least one antigenic polypeptide is a hMPV, PIV3 or RSV polyprotein. In some embodiments, at least one antigenic polypeptide is major surface glycoprotein G or an immunogenic fragment thereof. In some embodiments, at least one antigenic polypeptide is Fusion (F) glycoprotein (e.g., Fusion glycoprotein F0, F1 or F2) or an immunogenic fragment thereof. In some embodiments, at least one antigenic polypeptide is major surface glycoprotein G or an immunogenic fragment thereof and F glycoprotein or an immunogenic fragment thereof. In some embodiments, the antigenic polypeptide is nucleoprotein (N) or an immunogenic fragment thereof, phosphoprotein (P) or an immunogenic fragment thereof, large polymerase protein (L) or an immunogenic fragment thereof, matrix protein (M) or an immunogenic fragment thereof, small hydrophobic protein (SH) or an immunogenic fragment thereof nonstructural protein1 (NS1) or an immunogenic fragment thereof, or nonstructural protein 2 (NS2) and an immunogenic fragment thereof.

In some embodiments, at least one hMPV antigenic polypeptide comprises an amino acid sequence identified by any one of SEQ ID NO: 5-8 (Table 3; see also amino acid sequences of Table 4). In some embodiments, the amino acid sequence of the hMPV antigenic polypeptide is, or is a fragment of, or is a homolog or variant having at least 80% (e.g., 85%, 90%, 95%, 98%, 99%) identity to, the amino acid sequence identified by any one of SEQ ID NO: 5-8 (Table 3; see also amino acid sequences of Table 4).

In some embodiments, at least one hMPV antigenic polypeptide is encoded by a nucleic acid sequence identified by any one of SEQ ID NO: 1-4 (Table 2).

In some embodiments, at least one hMPV RNA (e.g., mRNA) polynucleotide is encoded by a nucleic acid sequence, or a fragment of a nucleotide sequence, identified by any one of SEQ ID NO: 1-4 (Table 2). In some embodiments, at least one hMPV RNA (e.g., mRNA) polynucleotide comprises a nucleic acid sequence, or a fragment of a nucleotide sequence, identified by any one of SEQ ID NO: 57-60 (Table 2).

In some embodiments, at least one antigenic polypeptide is obtained from hMPV strain CAN98-75 (CAN75) or the hMPV strain CAN97-83 (CAN83).

In some embodiments, at least one PIV3 antigenic polypeptide comprises hemagglutinin-neuraminidase, Fusion (F) glycoprotein, matrix protein (M), nucleocapsid protein (N), viral replicase (L), non-structural V protein, or an immunogenic fragment thereof.

In some embodiments, at least one PIV3 antigenic polypeptide comprises an amino acid sequence identified by any one of SEQ ID NO: 12-13 (Table 6; see also amino acid sequences of Table 7). In some embodiments, the amino acid sequence of the PIV3 antigenic polypeptide is, or is a fragment of, or is a homolog or variant having at least 80% (e.g., 85%, 90%, 95%, 98%, 99%) identity to, the amino acid sequence identified by any one of SEQ ID NO: 12-13 (Table 6; see also amino acid sequences of Table 7).

In some embodiments, at least one PIV3 antigenic polypeptide is encoded by a nucleic acid sequence identified by any one of SEQ ID NO: 9-12 (Table 5; see also nucleic acid sequences of Table 7).

In some embodiments, at least one PIV3 RNA (e.g., mRNA) polynucleotide is encoded by a nucleic acid sequence, or a fragment of a nucleotide sequence, identified by any one of SEQ ID NO: 9-12 (Table 5; see also nucleic acid sequences of Table 7). In some embodiments, at least one PIV3 RNA (e.g., mRNA) polynucleotide comprises a nucleic acid sequence, or a fragment of a nucleotide sequence, identified by any one of SEQ ID NO: 61-64 (Table 5).

In some embodiments, at least one antigenic polypeptide is obtained from PIV3 strain HPIV3/*Homo sapiens*/PER/FLA4815/2008.

In some embodiments, at least one RSV antigenic polypeptide comprises at least one antigenic polypeptide that comprises glycoprotein G, glycoprotein F, or an immunogenic fragment thereof. In some embodiments, at least one RSV antigenic polypeptide comprises at least one antigenic polypeptide that comprises glycoprotein F and at least one or at least two antigenic polypeptide selected from G, M, N, P, L, SH, M2, NS1 and NS2.

MeV

In some embodiments, a RNA (e.g., mRNA) vaccine comprises at least one RNA (e.g., mRNA) polynucleotide having an open reading frame encoding at least one MeV antigenic polypeptide. In some embodiments, at least one antigenic polypeptide is a hemagglutinin (HA) protein or an immunogenic fragment thereof. The HA protein may be from MeV strain D3 or B8, for example. In some embodiments, at least one antigenic polypeptide is a Fusion (F) protein or an immunogenic fragment thereof. The F protein may be from MeV strain D3 or B8, for example. In some embodiments, a MeV RNA (e.g., mRNA) vaccines comprises a least one RNA polynucleotide encoding a HA protein and a F protein. The HA and F proteins may be from MeV strain D3 or B8, for example.

In some embodiments, at least one MeV antigenic polypeptide comprises an amino acid sequence identified by any one of SEQ ID NO: 47-50 (Table 14). In some embodiments, the amino acid sequence of the MeV antigenic polypeptide is, or is a fragment of, or is a homolog or variant having at least 80% (e.g., 85%, 90%, 95%, 98%, 99%) identity to, the amino acid sequence identified by any one of SEQ ID NO: 47-50 (Table 14).

In some embodiments, at least one MeV antigenic polypeptide is encoded by a nucleic acid sequence of SEQ ID NO: 35-46 (Table 13).

In some embodiments, at least one MeV RNA (e.g., mRNA) polynucleotide is encoded by a nucleic acid sequence, or a fragment of a nucleotide sequence, identified by any one of SEQ ID NO: 35-46 (Table 13). In some embodiments, at least one MeV RNA (e.g., mRNA) polynucleotide comprises a nucleic acid sequence, or a fragment of a nucleotide sequence, identified by any one of SEQ ID NO: 69-80 (Table 13).

In some embodiments, at least one antigenic polypeptide is obtained from MeV strain B3/B3.1, C2, D4, D6, D7, D8, G3, H1, Moraten, Rubeovax, MVi/New Jersey.USA/45.05, MVi/Texas.USA/4.07, AIK-C, MVi/New York.USA/26.09/3, MVi/California.USA/16.03, MVi/Virginia.USA/15.09, MVi/California.USA/8.04, or MVi/Pennsylvania.USA/20.09.

BetaCoV

In some embodiments, a RNA (e.g., mRNA) vaccine comprises at least one RNA (e.g., mRNA) polynucleotide having an open reading frame encoding at least one BetaCoV antigenic polypeptide. In some embodiments, the BetaCoV is MERS-CoV. In some embodiments, the BetaCoV is SARS-CoV. In some embodiments, the BetaCoV is HCoV-OC43. In some embodiments, the BetaCoV is HCoV-229E. In some embodiments, the BetaCoV is HCoV-NL63. In some embodiments, the BetaCoV is HCoV-HKU1. In some embodiments, at least one antigenic polypeptide is a betacoronavirus structural protein. For example, a betacoronavirus structural protein may be spike protein (S), envelope protein (E), nucleocapsid protein (N), membrane protein (M) or an immunogenic fragment thereof. In some embodiments, a betacoronavirus structural protein is a spike protein (S). In some embodiments, a betacoronavirus structural protein is a S1 subunit or a S2 subunit of spike protein (S) or an immunogenic fragment thereof.

BetaCoV RNA (e.g., mRNA) polynucleotides of the vaccines provided herein may encode viral protein components of betacoronaviruses, for example, accessory proteins, replicase proteins and the like are encompassed by the present disclosure. RNA (e.g., mRNA) vaccines may include RNA polynucleotides encoding at least one accessory protein (e.g., protein 3, protein 4a, protein 4b, protein 5), at least one replicase protein (e.g., protein 1a, protein 1b), or a combination of at least one accessory protein and at least one replicase protein. The present disclosure also encompasses RNA (e.g., mRNA) vaccines comprising RNA (e.g., mRNA) polynucleotides encoding an accessory protein and/or a replicase protein in combination with at least one structural protein. Due to their surface expression properties, vaccines featuring RNA polynucleotides encoding structural proteins are believed to have preferred immunogenic activity and, hence, may be most suitable for use in the vaccines of the present disclosure.

Some embodiments of the present disclosure provide betacoronavirus (e.g., MERS-CoV, SARS-CoV, HCoV-OC43, HCoV-229E, HCoV-NL63, HCoV-NL, HCoV-NH, HCoV-HKU1 or a combination thereof) vaccines that include at least one RNA (e.g., mRNA) polynucleotide having an open reading frame encoding at least one betacoronavirus (e.g., MERS-CoV, SARS-CoV, HCoV-OC43, HCoV-229E, HCoV-NL63, HCoV-NL, HCoV-NH, HCoV-HKU1) antigenic polypeptide. Also provided herein are pan-betacoronavirus vaccines. Thus, a betacoronavirus vaccine comprising a RNA (e.g., mRNA) polynucleotide having an open reading frame encoding any one, two, three or four of MERS-CoV, SARS-CoV, HCoV-OC43, HCoV-229E, HCoV-NL63, and HCoV-HKU1, for example, may be effective against any one of, any combination of, or all of, MERS-CoV, SARS-CoV, HCoV-OC43, HCoV-229E, HCoV-NL63, HCoV-NL, HCoV-NH and HCoV-HKU1. Other betacoronaviruses are encompassed by the present disclosure.

In some embodiments, at least one antigenic polypeptide is a MERS-CoV structural protein. For example, a MERS-CoV structural protein may be spike protein (S), envelope protein (E), nucleocapsid protein (N), membrane protein (M) or an immunogenic fragment thereof. In some embodiments, the MERS-CoV structural protein is a spike protein (S) (see, e.g., Coleman C M et al. Vaccine 2014; 32:3169-74, incorporated herein by reference). In some embodiments, the MERS-CoV structural protein is a 51 subunit or a S2 subunit of spike protein (S) or an immunogenic fragment thereof (Li J et al. *Viral Immunol* 2013; 26(2):126-32; He Y et al. *Biochem Biophys Res Commun* 2004; 324(2):773-81, each of which is incorporated herein by reference).

In some embodiments, at least one MERS-CoV antigenic polypeptide comprises an amino acid sequence identified by any one of SEQ ID NO: 24-28 or 33 (Table 11). In some embodiments, the amino acid sequence of the MERS-CoV antigenic polypeptide is, or is a fragment of, or is a homolog or variant having at least 80% (e.g., 85%, 90%, 95%, 98%, 99%) identity to, the amino acid sequence identified by any one of SEQ ID NO: 24-28 or 33 (Table 11).

In some embodiments, at least one MERS-CoV antigenic polypeptide is encoded by a nucleic acid sequence identified by any one of SEQ ID NO: 20-23 (Table 10).

In some embodiments, at least one MERS-CoV RNA (e.g., mRNA) polynucleotide is encoded by a nucleic acid sequence, or a fragment of a nucleotide sequence, identified by any one of SEQ ID NO: 20-23 (Table 10). In some embodiments, at least one MERS-CoV RNA (e.g., mRNA) polynucleotide comprises a nucleic acid sequence, or a fragment of a nucleotide sequence, identified by any one of SEQ ID NO: 65-68 (Table 10).

In some embodiments, at least one antigenic polypeptide is obtained from MERS-CoV strain Riyadh_14_2013, 2cEMC/2012, or Hasa_1_2013.

In some embodiments, at least one antigenic polypeptide is a SARS-CoV structural protein. For example, a SARS-CoV structural protein may be spike protein (S), envelope protein (E), nucleocapsid protein (N), membrane protein (M) or an immunogenic fragment thereof. In some embodiments, the SARS-CoV structural protein is a spike protein (S). In some embodiments, the SARS-CoV structural protein is a 51 subunit or a S2 subunit of spike protein (S) or an immunogenic fragment thereof.

In some embodiments, at least one SARS-CoV antigenic polypeptide comprises an amino acid sequence identified by any one of SEQ ID NO: 29, 32 or 34 (Table 11). In some embodiments, the amino acid sequence of the SARS-CoV antigenic polypeptide is, or is a fragment of, or is a homolog or variant having at least 80% (e.g., 85%, 90%, 95%, 98%, 99%) identity to, the amino acid sequence identified by any one of SEQ ID NO: 29, 32 or 34 (Table 11).

In some embodiments, at least one antigenic polypeptide is a HCoV-OC43 structural protein. For example, a HCoV-OC43 structural protein may be spike protein (S), envelope protein (E), nucleocapsid protein (N), membrane protein (M) or an immunogenic fragment thereof. In some embodiments, the HCoV-OC43 structural protein is a spike protein (S). In some embodiments, the HCoV-OC43 structural protein is a 51 subunit or a S2 subunit of spike protein (S) or an immunogenic fragment thereof.

In some embodiments, at least one HCoV-OC43 antigenic polypeptide comprises an amino acid sequence identified by any one of SEQ ID NO: 30 (Table 11). In some embodiments, the amino acid sequence of the HCoV-OC43 antigenic polypeptide is, or is a fragment of, or is a homolog or variant having at least 80% (e.g., 85%, 90%, 95%, 98%, 99%) identity to, the amino acid sequence identified by any one of SEQ ID NO: 30 (Table 11).

In some embodiments, an antigenic polypeptide is a HCoV-HKU1 structural protein. For example, a HCoV-HKU1 structural protein may be spike protein (S), envelope protein (E), nucleocapsid protein (N), membrane protein (M) or an immunogenic fragment thereof. In some embodiments, the HCoV-HKU1 structural protein is a spike protein (S). In some embodiments, the HCoV-HKU1 structural protein is a 51 subunit or a S2 subunit of spike protein (S) or an immunogenic fragment thereof.

In some embodiments, at least one HCoV-HKU1 antigenic polypeptide comprises an amino acid sequence identified by any one of SEQ ID NO: 31 (Table 11). In some embodiments, the amino acid sequence of the HCoV-HKU1 antigenic polypeptide is, or is a fragment of, or is a homolog or variant having at least 80% (e.g., 85%, 90%, 95%, 98%, 99%) identity to, the amino acid sequence identified by any one of SEQ ID NO: 31 (Table 11).

In some embodiments, an open reading frame of a RNA (e.g., mRNA) vaccine is codon-optimized. In some embodiments, at least one RNA polynucleotide encodes at least one antigenic polypeptide having an amino acid sequence identified by any one of SEQ ID NO: 5-8, 12-13, 24-34, or 47-50 (Tables 3, 6, 11 and 14; see also amino acid sequences of Tables 4, 7, 12 and 15) and is codon optimized mRNA.

In some embodiments, a RNA (e.g., mRNA) vaccine further comprising an adjuvant.

Tables 4, 7, 12 and 15 provide National Center for Biotechnology Information (NCBI) accession numbers of interest. It should be understood that the phrase "an amino acid sequence of Tables 4, 7, 12 and 15" refers to an amino acid sequence identified by one or more NCBI accession numbers listed in Tables 4, 7, 12 and 15. Each of the amino acid sequences, and variants having greater than 95% identity or greater than 98% identity to each of the amino acid sequences encompassed by the accession numbers of Tables 4, 7, 12 and 15 are included within the constructs (polynucleotides/polypeptides) of the present disclosure.

In some embodiments, at least one mRNA polynucleotide is encoded by a nucleic acid having a sequence identified by any one of SEQ ID NO: 1-4, 9-12, 20-23, or 35-46 (Tables 2, 5, 10 and 13; see also nucleic acid sequences of Table 7) and having less than 80% identity to wild-type mRNA sequence. In some embodiments, at least one mRNA polynucleotide is encoded by a nucleic acid having a sequence identified by any one of SEQ ID NO: 1-4, 9-12, 20-23, or 35-46 (Tables 2, 5, 10 and 13; see also nucleic acid sequences of Table 7) and having less than 75%, 85% or 95% identity to a wild-type mRNA sequence. In some embodiments, at least one mRNA polynucleotide is encoded by a nucleic acid having a sequence identified by any one of SEQ ID NO: 1-4, 9-12, 20-23, or 35-46 (Tables 2, 5, 10 and 13; see also nucleic acid sequences of Table 7) and having less than 50-80%, 60-80%, 40-80%, 30-80%, 70-80%, 75-80% or 78-80% identity to wild-type mRNA sequence. In some embodiments, at least one mRNA polynucleotide is encoded by a nucleic acid having a sequence identified by any one of SEQ ID NO: 1-4, 9-12, 20-23, or 35-46 (Tables 2, 5, 10 and 13; see also nucleic acid sequences of Table 7) and having less than 40-85%, 50-85%, 60-85%, 30-85%, 70-85%, 75-85% or 80-85% identity to wild-type mRNA sequence. In some embodiments, at least one mRNA polynucleotide is encoded by a nucleic acid having a sequence identified by any one of SEQ ID NO: 1-4, 9-12, 20-23, or 35-46 (Tables 2, 5, 10 and 13; see also nucleic acid sequences of Table 7) and having less than 40-90%, 50-90%, 60-90%, 30-90%, 70-90%, 75-90%, 80-90%, or 85-90% identity to wild-type mRNA sequence.

In some embodiments, at least one RNA polynucleotide encodes at least one antigenic polypeptide having an amino acid sequence identified by any one of SEQ ID NO: 5-8, 12-13, 24-34, or 47-50 (Tables 3, 6, 11 and 14; see also amino acid sequences of Tables 4, 7, 12 and 15) and having at least 80% (e.g., 85%, 90%, 95%, 98%, 99%) identity to wild-type mRNA sequence, but does not include wild-type mRNA sequence.

In some embodiments, at least one RNA polynucleotide encodes at least one antigenic polypeptide having an amino acid sequence identified by any one of SEQ ID NO: 5-8, 12-13, 24-34, or 47-50 (Tables 3, 6, 11 and 14; see also amino acid sequences of Tables 4, 7, 12 and 15) and has less than 95%, 90%, 85%, 80% or 75% identity to wild-type mRNA sequence.

In some embodiments, at least one RNA polynucleotide encodes at least one antigenic polypeptide having an amino acid sequence identified by any one of SEQ ID NO: 5-8, 12-13, 24-34, or 47-50 (Tables 3, 6, 11 and 14; see also amino acid sequences of Tables 4, 7, 12 and 15) and has 30-80%, 40-80%, 50-80%, 60-80%, 70-80%, 75-80% or 78-80%, 30-85%, 40-85%, 50-805%, 60-85%, 70-85%, 75-85% or 78-85%, 30-90%, 40-90%, 50-90%, 60-90%, 70-90%, 75-90%, 80-90% or 85-90% identity to wild-type mRNA sequence.

In some embodiments, at least one RNA polynucleotide encodes at least one antigenic polypeptide having at least 90%, at least 95%, at least 96%, at least 97%, at least 98%, or at least 99% identity to an amino acid sequence identified by any one of SEQ ID NO: 5-8, 12-13, 24-34, or 47-50 (Tables 3, 6, 11 and 14; see also amino acid sequences of Tables 4, 7, 12 and 15). In some embodiments, at least one RNA polynucleotide encodes at least one antigenic polypeptide having 95%-99% identity to an amino acid sequence identified by any one of SEQ ID NO: 5-8, 12-13, 24-34, or 47-50 (Tables 3, 6, 11 and 14; see also amino acid sequences of Tables 4, 7, 12 and 15).

In some embodiments, at least one RNA polynucleotide encodes at least one antigenic polypeptide having at least 90%, at least 95%, at least 96%, at least 97%, at least 98%, or at least 99% identity to an amino acid sequence identified by any one of SEQ ID NO: 5-8, 12-13, 24-34, or 47-50 (Tables 3, 6, 11 and 14; see also amino acid sequences of Tables 4, 7, 12 and 15) and having membrane fusion activity. In some embodiments, at least one RNA polynucleotide encodes at least one antigenic polypeptide having 95%-99% identity to an amino acid sequence identified by any one of SEQ ID NO: 5-8, 12-13, 24-34, or 47-50 (Tables 3, 6, 11 and 14; see also amino acid sequences of Tables 4, 7, 12 and 15) and having membrane fusion activity.

In some embodiments, at least one RNA polynucleotide encodes at least one antigenic polypeptide (e.g., at least one hMPV antigenic polypeptide, at least one PIV3 antigenic polypeptide, at least one RSV antigenic polypeptide, at least one MeV antigenic polypeptide, or at least one BetaCoV antigenic polypeptide, e.g., selected from MERS-CoV, SARS-CoV, HCoV-OC43, HCoV-229E, HCoV-NL63, HCoV-NL, HCoV-NH and HCoV-HKU1, or any combination of two or more of the foregoing antigenic polypeptides) that attaches to cell receptors.

In some embodiments, at least one RNA polynucleotide encodes at least one antigenic polypeptide (e.g., at least one hMPV antigenic polypeptide, at least one PIV3 antigenic polypeptide, at least one RSV antigenic polypeptide, at least one MeV antigenic polypeptide, or at least one BetaCoV antigenic polypeptide, e.g., selected from MERS-CoV, SARS-CoV, HCoV-OC43, HCoV-229E, HCoV-NL63, HCoV-NL, HCoV-NH and HCoV-HKU1, or any combination of two or more of the foregoing antigenic polypeptides) that causes fusion of viral and cellular membranes.

In some embodiments, at least one RNA polynucleotide encodes at least one antigenic polypeptide (e.g., at least one hMPV antigenic polypeptide, at least one PIV3 antigenic polypeptide, at least one RSV antigenic polypeptide, at least one MeV antigenic polypeptide, or at least one BetaCoV antigenic polypeptide, e.g., selected from MERS-CoV, SARS-CoV, HCoV-OC43, HCoV-229E, HCoV-NL63, HCoV-NL, HCoV-NH and HCoV-HKU1, or any combination of two or more of the foregoing antigenic polypeptides) that is responsible for binding of the virus to a cell being infected.

Some embodiments of the present disclosure provide a vaccine that includes at least one ribonucleic acid (RNA) (e.g., mRNA) polynucleotide having an open reading frame encoding at least one antigenic polypeptide (e.g., at least one hMPV antigenic polypeptide, at least one PIV3 antigenic polypeptide, at least one RSV antigenic polypeptide, at least one MeV antigenic polypeptide, or at least one BetaCoV antigenic polypeptide, e.g., selected from MERS-CoV, SARS-CoV, HCoV-OC43, HCoV-229E, HCoV-NL63, HCoV-NL, HCoV-NH and HCoV-HKU1, or any combination of two or more of the foregoing antigenic polypeptides), at least one 5' terminal cap and at least one chemical modification, formulated within a lipid nanoparticle.

In some embodiments, a 5' terminal cap is 7mG(5')ppp (5')NlmpNp.

In some embodiments, at least one chemical modification is selected from pseudouridine, N1-methylpseudouridine, N1-ethylpseudouridine, 2-thiouridine, 4'-thiouridine, 5-methylcytosine, 5-methyluridine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine and 2'-O-methyl uridine. In some embodiments, the chemical modification is in the 5-position of the uracil. In some embodiments, the chemical modification is a N1-methylpseudouridine. In some embodiments, the chemical modification is a N1-ethylpseudouridine.

In some embodiments, a lipid nanoparticle comprises a cationic lipid, a PEG-modified lipid, a sterol and a non-cationic lipid. In some embodiments, a cationic lipid is an ionizable cationic lipid and the non-cationic lipid is a neutral lipid, and the sterol is a cholesterol. In some embodiments, a cationic lipid is selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino)butanoyl)oxy)heptadecanedioate (L319), (12Z,15Z)—N,N-dimethyl-2-nonylhenicosa-12,15-dien-1-amine (L608), and N,N-dimethyl-1-[(1S,2R)-2-octylcyclopropyl]heptadecan-8-amine (L530).

In some embodiments, the lipid is (L608)

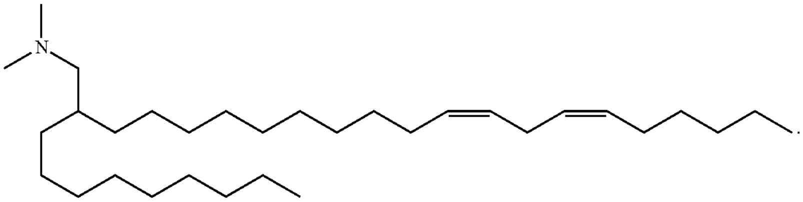

In some embodiments, the lipid is (L530)

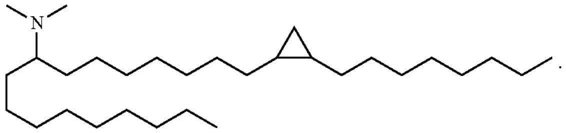

In some embodiments, a lipid nanoparticle comprises compounds of Formula (I) and/or Formula (II), discussed below.

In some embodiments, a repiratory virus RNA (e.g., mRNA) vaccine is formulated in a lipid nanoparticle that comprises a compound selected from Compounds 3, 18, 20, 25, 26, 29, 30, 60, 108-112 and 122, described below.

Some embodiments of the present disclosure provide a vaccine that includes at least one RNA (e.g., mRNA) polynucleotide having an open reading frame encoding at least one antigenic polypeptide (e.g., at least one hMPV antigenic polypeptide, at least one PIV3 antigenic polypeptide, at least one RSV antigenic polypeptide, at least one MeV antigenic polypeptide, or at least one BetaCoV antigenic polypeptide, e.g., selected from MERS-CoV, SARS-CoV, HCoV-OC43, HCoV-229E, HCoV-NL63, HCoV-NL, HCoV-NH and HCoV-HKU1, or any combination of two or more of the foregoing antigenic polypeptides), wherein at least 80% (e.g., 85%, 90%, 95%, 98%, 99%) of the uracil in the open reading frame have a chemical modification, optionally wherein the vaccine is formulated in a lipid nanoparticle (e.g., a lipid nanoparticle comprises a cationic lipid, a PEG-modified lipid, a sterol and a non-cationic lipid).

In some embodiments, 100% of the uracil in the open reading frame have a chemical modification. In some embodiments, a chemical modification is in the 5-position of the uracil. In some embodiments, a chemical modification is a N1-methyl pseudouridine. In some embodiments, 100% of the uracil in the open reading frame have a N1-methyl pseudouridine in the 5-position of the uracil.

In some embodiments, an open reading frame of a RNA (e.g., mRNA) polynucleotide encodes at least two antigenic polypeptides (e.g., at least two hMPV antigenic polypeptides, at least two PIV3 antigenic polypeptides, at least two RSV antigenic polypeptides, at least two MeV antigenic polypeptides, or at least two BetaCoV antigenic polypeptides, e.g., selected from MERS-CoV, SARS-CoV, HCoV-OC43, HCoV-229E, HCoV-NL63, HCoV-NL, HCoV-NH and HCoV-HKU1, or any combination of two or more of the foregoing antigenic polypeptides). In some embodiments, the open reading frame encodes at least five or at least ten antigenic polypeptides. In some embodiments, the open reading frame encodes at least 100 antigenic polypeptides. In some embodiments, the open reading frame encodes 2-100 antigenic polypeptides.

In some embodiments, a vaccine comprises at least two RNA (e.g., mRNA) polynucleotides, each having an open reading frame encoding at least one antigenic polypeptide (e.g., at least one hMPV antigenic polypeptide, at least one PIV3 antigenic polypeptide, at least one RSV antigenic polypeptide, at least one MeV antigenic polypeptide, or at least one BetaCoV antigenic polypeptide, e.g., selected from MERS-CoV, SARS-CoV, HCoV-OC43, HCoV-229E, HCoV-NL63, HCoV-NL, HCoV-NH and HCoV-HKU1, or any combination of two or more of the foregoing antigenic polypeptides). In some embodiments, the vaccine comprises at least five or at least ten RNA (e.g., mRNA) polynucleotides, each having an open reading frame encoding at least one antigenic polypeptide or an immunogenic fragment thereof. In some embodiments, the vaccine comprises at least 100 RNA (e.g., mRNA) polynucleotides, each having an open reading frame encoding at least one antigenic polypeptide. In some embodiments, the vaccine comprises 2-100 RNA (e.g., mRNA) polynucleotides, each having an open reading frame encoding at least one antigenic polypeptide.

In some embodiments, at least one antigenic polypeptide (e.g., at least one hMPV antigenic polypeptide, at least one PIV3 antigenic polypeptide, at least one RSV antigenic polypeptide, at least one MeV antigenic polypeptide, or at least one BetaCoV antigenic polypeptide, e.g., selected from MERS-CoV, SARS-CoV, HCoV-OC43, HCoV-229E, HCoV-NL63, HCoV-NL, HCoV-NH and HCoV-HKU1, or any combination of two or more of the foregoing antigenic polypeptides) is fused to a signal peptide. In some embodiments, the signal peptide is selected from: a HuIgGk signal peptide (METPAQLLFLLLLWLPDTTG; SEQ ID NO: 15); IgE heavy chain epsilon-1 signal peptide (MDWTWILFLVAAATRVHS; SEQ ID NO: 16); Japanese encephalitis PRM signal sequence (MLGSNSGQRVVFTILLLLVAPAYS; SEQ ID NO: 17), VSVg protein signal sequence (MKCLLYLAFLFIGVNCA; SEQ ID NO: 18) and Japanese encephalitis JEV signal sequence (MWLVSLAIVTACAGA; SEQ ID NO: 19).

In some embodiments, the signal peptide is fused to the N-terminus of at least one antigenic polypeptide. In some embodiments, a signal peptide is fused to the C-terminus of at least one antigenic polypeptide.

In some embodiments, at least one antigenic polypeptide (e.g., at least one hMPV antigenic polypeptide, at least one PIV3 antigenic polypeptide, at least one RSV antigenic polypeptide, at least one MeV antigenic polypeptide, or at least one BetaCoV antigenic polypeptide, e.g., selected from MERS-CoV, SARS-CoV, HCoV-OC43, HCoV-229E, HCoV-NL63, HCoV-NL, HCoV-NH and HCoV-HKU1, or any combination of two or more of the foregoing antigenic polypeptides) comprises a mutated N-linked glycosylation site.

Also provided herein is a RNA (e.g., mRNA) vaccine of any one of the foregoing paragraphs (e.g., a hMPV vaccine, a PIV3 vaccine, a RSV vaccine, a MeV vaccine, or a BetaCoV vaccine, e.g., selected from MERS-CoV, SARS-CoV, HCoV-OC43, HCoV-229E, HCoV-NL63, HCoV-NL, HCoV-NH and HCoV-HKU1, or any combination of two or more of the foregoing vaccines), formulated in a nanoparticle (e.g., a lipid nanoparticle).

In some embodiments, the nanoparticle has a mean diameter of 50-200 nm. In some embodiments, the nanoparticle is a lipid nanoparticle. In some embodiments, the lipid nanoparticle comprises a cationic lipid, a PEG-modified lipid, a sterol and a non-cationic lipid. In some embodiments, the lipid nanoparticle comprises a molar ratio of about 20-60% cationic lipid, 0.5-15% PEG-modified lipid, 25-55% sterol, and 25% non-cationic lipid. In some embodiments, the cationic lipid is an ionizable cationic lipid and the non-cationic lipid is a neutral lipid, and the sterol is a cholesterol. In some embodiments, the cationic lipid is selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319).

In some embodiments, a lipid nanoparticle comprises compounds of Formula (I) and/or Formula (II), as discussed below.

In some embodiments, a lipid nanoparticle comprises Compounds 3, 18, 20, 25, 26, 29, 30, 60, 108-112, or 122, as discussed below.

In some embodiments, the nanoparticle has a polydispersity value of less than 0.4 (e.g., less than 0.3, 0.2 or 0.1).

In some embodiments, the nanoparticle has a net neutral charge at a neutral pH value.

In some embodiments, the respiratory virus vaccine is multivalent.

Some embodiments of the present disclosure provide methods of inducing an antigen specific immune response in a subject, comprising administering to the subject any of the RNA (e.g., mRNA) vaccine as provided herein in an amount effective to produce an antigen-specific immune response. In some embodiments, the RNA (e.g., mRNA) vaccine is a hMPV vaccine, a PIV3 vaccine, a RSV vaccine, a MeV vaccine, or a BetaCoV vaccine, e.g., selected from MERS-CoV, SARS-CoV, HCoV-OC43, HCoV-229E, HCoV-NL63, HCoV-NL, HCoV-NH and HCoV-HKU1 vaccines. In some embodiments, the RNA (e.g., mRNA) vaccine is a combination vaccine comprising a combination of any two or more of the foregoing vaccines.

In some embodiments, an antigen-specific immune response comprises a T cell response or a B cell response.

In some embodiments, a method of producing an antigen-specific immune response comprises administering to a subject a single dose (no booster dose) of a RNA (e.g., mRNA) vaccine of the present disclosure. In some embodiments, the RNA (e.g., mRNA) vaccine is a hMPV vaccine, a PIV3 vaccine, a RSV vaccine, a MeV vaccine, or a BetaCoV vaccine, e.g., selected from MERS-CoV, SARS-CoV, HCoV-OC43, HCoV-229E, HCoV-NL63, HCoV-NL, HCoV-NH and HCoV-HKU1 vaccines. In some embodiments, the RNA (e.g., mRNA) vaccine is a combination vaccine comprising a combination of any two or more of the foregoing vaccines.

In some embodiments, a method further comprises administering to the subject a second (booster) dose of a RNA (e.g., mRNA) vaccine. Additional doses of a RNA (e.g., mRNA) vaccine may be administered.

In some embodiments, the subjects exhibit a seroconversion rate of at least 80% (e.g., at least 85%, at least 90%, or at least 95%) following the first dose or the second (booster) dose of the vaccine. Seroconversion is the time period during which a specific antibody develops and becomes detectable in the blood. After seroconversion has occurred, a virus can be detected in blood tests for the antibody. During an infection or immunization, antigens enter the blood, and the immune system begins to produce antibodies in response. Before seroconversion, the antigen itself may or may not be detectable, but antibodies are considered absent. During seroconversion, antibodies are present but not yet detectable. Any time after seroconversion, the antibodies can be detected in the blood, indicating a prior or current infection.

In some embodiments, a RNA (e.g., mRNA) vaccine is administered to a subject by intradermal or intramuscular injection.

Some embodiments, of the present disclosure provide methods of inducing an antigen specific immune response in a subject, including administering to a subject a RNA (e.g., mRNA) vaccine in an effective amount to produce an antigen specific immune response in a subject. Antigen-specific immune responses in a subject may be determined, in some embodiments, by assaying for antibody titer (for titer of an antibody that binds to a hMPV, PIV3, RSV, MeV and/or BetaCoV antigenic polypeptide) following administration to the subject of any of the RNA (e.g., mRNA) vaccines of the present disclosure. In some embodiments, the anti-antigenic polypeptide antibody titer produced in the subject is increased by at least 1 log relative to a control. In some embodiments, the anti-antigenic polypeptide antibody titer produced in the subject is increased by 1-3 log relative to a control.

In some embodiments, the anti-antigenic polypeptide antibody titer produced in a subject is increased at least 2 times relative to a control. In some embodiments, the anti-antigenic polypeptide antibody titer produced in the subject is increased at least 5 times relative to a control. In some embodiments, the anti-antigenic polypeptide antibody titer produced in the subject is increased at least 10 times relative to a control. In some embodiments, the anti-antigenic polypeptide antibody titer produced in the subject is increased 2-10 times relative to a control.

In some embodiments, the control is an anti-antigenic polypeptide antibody titer produced in a subject who has not been administered a RNA (e.g., mRNA) vaccine of the present disclosure. In some embodiments, the control is an anti-antigenic polypeptide antibody titer produced in a subject who has been administered a live attenuated or inactivated hMPV, PIV3, RSV, MeV and/or BetaCoV vaccine (see, e.g., Ren J. et al. *J of Gen. Virol.* 2015; 96: 1515-1520), or wherein the control is an anti-antigenic polypeptide antibody titer produced in a subject who has been administered a recombinant or purified hMPV, PIV3, RSV, MeV and/or BetaCoV protein vaccine. In some embodiments, the control is an anti-antigenic polypeptide antibody titer produced in a subject who has been administered a hMPV, PIV3, RSV, MeV and/or BetaCoV virus-like particle (VLP) vaccine (see, e.g., Cox R G et al., *J Virol.* 2014 June; 88(11): 6368-6379).

A RNA (e.g., mRNA) vaccine of the present disclosure is administered to a subject in an effective amount (an amount effective to induce an immune response). In some embodiments, the effective amount is a dose equivalent to an at least 2-fold, at least 4-fold, at least 10-fold, at least 100-fold, at least 1000-fold reduction in the standard of care dose of a recombinant hMPV, PIV3, RSV, MeV and/or BetaCoV protein vaccine, wherein the anti-antigenic polypeptide antibody titer produced in the subject is equivalent to an anti-antigenic polypeptide antibody titer produced in a control subject administered the standard of care dose of a recombinant hMPV, PIV3, RSV, MeV and/or BetaCoV protein vaccine, a purified hMPV, PIV3, RSV, MeV and/or BetaCoV protein vaccine, a live attenuated hMPV, PIV3, RSV, MeV and/or BetaCoV vaccine, an inactivated hMPV, PIV3, RSV, MeV and/or BetaCoV vaccine, or a hMPV, PIV3, RSV, MeV and/or BetaCoV VLP vaccine. In some embodiments, the effective amount is a dose equivalent to 2-1000-fold reduction in the standard of care dose of a recombinant hMPV, PIV3, RSV, MeV and/or BetaCoV protein vaccine, wherein the anti-antigenic polypeptide antibody titer produced in the subject is equivalent to an anti-antigenic polypeptide antibody titer produced in a control subject administered the standard of care dose of a recombinant hMPV, PIV3, RSV, MeV and/or BetaCoV protein vaccine, a purified hMPV, PIV3, RSV, MeV and/or BetaCoV protein vaccine, a live attenuated hMPV, PIV3, RSV, MeV and/or BetaCoV vaccine, an inactivated hMPV, PIV3, RSV, MeV and/or BetaCoV vaccine, or a hMPV, PIV3, RSV, MeV and/or BetaCoV VLP vaccine.

In some embodiments, the control is an anti-antigenic polypeptide antibody titer produced in a subject who has been administered a virus-like particle (VLP) vaccine comprising structural proteins of hMPV, PIV3, RSV, MeV and/or BetaCoV.

In some embodiments, the RNA (e.g., mRNA) vaccine is formulated in an effective amount to produce an antigen specific immune response in a subject.

In some embodiments, the effective amount is a total dose of 25 μg to 1000 μg, or 50 μg to 1000 μg. In some embodiments, the effective amount is a total dose of 100 μg. In some embodiments, the effective amount is a dose of 25 μg administered to the subject a total of two times. In some embodiments, the effective amount is a dose of 100 μg administered to the subject a total of two times. In some embodiments, the effective amount is a dose of 400 μg administered to the subject a total of two times. In some embodiments, the effective amount is a dose of 500 μg administered to the subject a total of two times.

In some embodiments, the efficacy (or effectiveness) of a RNA (e.g., mRNA) vaccine is greater than 60%. In some embodiments, the RNA (e.g., mRNA) polynucleotide of the vaccine at least one hMPV antigenic polypeptide, at least one PIV3 antigenic polypeptide, at least one RSV antigenic polypeptide, at least one MeV antigenic polypeptide, at least one BetaCoV antigenic polypeptide, e.g., selected from MERS-CoV, SARS-CoV, HCoV-OC43, HCoV-229E, HCoV-NL63, HCoV-NL, HCoV-NH and HCoV-HKU1, or any combination of two or more of the foregoing antigenic polypeptides.

Vaccine efficacy may be assessed using standard analyses (see, e.g., Weinberg et al., *J Infect Dis.* 2010 Jun. 1; 201(11):1607-10). For example, vaccine efficacy may be measured by double-blind, randomized, clinical controlled trials. Vaccine efficacy may be expressed as a proportionate reduction in disease attack rate (AR) between the unvaccinated (ARU) and vaccinated (ARV) study cohorts and can be calculated from the relative risk (RR) of disease among the vaccinated group with use of the following formulas:

$$\text{Efficacy}=(\text{ARU}-\text{ARV})/\text{ARU}\times 100; \text{ and}$$

$$\text{Efficacy}=(1-\text{RR})\times 100.$$

Likewise, vaccine effectiveness may be assessed using standard analyses (see, e.g., Weinberg et al., *J Infect Dis.* 2010 Jun. 1; 201(11):1607-10). Vaccine effectiveness is an assessment of how a vaccine (which may have already proven to have high vaccine efficacy) reduces disease in a population. This measure can assess the net balance of benefits and adverse effects of a vaccination program, not just the vaccine itself, under natural field conditions rather than in a controlled clinical trial. Vaccine effectiveness is proportional to vaccine efficacy (potency) but is also affected by how well target groups in the population are immunized, as well as by other non-vaccine-related factors that influence the 'real-world' outcomes of hospitalizations, ambulatory visits, or costs. For example, a retrospective case control analysis may be used, in which the rates of vaccination among a set of infected cases and appropriate controls are compared. Vaccine effectiveness may be expressed as a rate difference, with use of the odds ratio (OR) for developing infection despite vaccination:

$$\text{Effectiveness}=(1-\text{OR})\times 100.$$

In some embodiments, the efficacy (or effectiveness) of a RNA (e.g., mRNA) vaccine is at least 65%, at least 70%, at least 75%, at least 80%, at least 85%, or at least 90%.

In some embodiments, the vaccine immunizes the subject against hMPV, PIV3, RSV, MeV, BetaCoV (e.g., selected from MERS-CoV, SARS-CoV, HCoV-OC43, HCoV-229E, HCoV-NL63, HCoV-NL, HCoV-NH and HCoV-HKU1), or any combination of two or more of the foregoing viruses for up to 2 years. In some embodiments, the vaccine immunizes the subject against hMPV, PIV3, RSV, MeV, BetaCoV (e.g., selected from MERS-CoV, SARS-CoV, HCoV-OC43, HCoV-229E, HCoV-NL63, HCoV-NL, HCoV-NH and HCoV-HKU1), or any combination of two or more of the foregoing viruses for more than 2 years, more than 3 years, more than 4 years, or for 5-10 years.

In some embodiments, the subject is about 5 years old or younger. For example, the subject may be between the ages of about 1 year and about 5 years (e.g., about 1, 2, 3, 5 or 5 years), or between the ages of about 6 months and about 1 year (e.g., about 6, 7, 8, 9, 10, 11 or 12 months). In some embodiments, the subject is about 12 months or younger (e.g., 12, 11, 10, 9, 8, 7, 6, 5, 4, 3, 2 months or 1 month). In some embodiments, the subject is about 6 months or younger.

In some embodiments, the subject was born full term (e.g., about 37-42 weeks). In some embodiments, the subject was born prematurely, for example, at about 36 weeks of gestation or earlier (e.g., about 36, 35, 34, 33, 32, 31, 30, 29, 28, 27, 26 or 25 weeks). For example, the subject may have been born at about 32 weeks of gestation or earlier. In some embodiments, the subject was born prematurely between about 32 weeks and about 36 weeks of gestation. In such subjects, a RNA (e.g., mRNA) vaccine may be administered later in life, for example, at the age of about 6 months to about 5 years, or older.

In some embodiments, the subject is pregnant (e.g., in the first, second or third trimester) when administered an RNA (e.g., mRNA) vaccine. Viruses such as hMPV, PIV3 and RSV causes infections of the lower respiratory tract, mainly in infants and young children. One-third of RSV related deaths, for example, occur in the first year of life, with 99 percent of these deaths occurring in low-resource countries. It's so widespread in the United States that nearly all children become infected with the virus before their second birthdays. Thus, the present disclosure provides RNA (e.g., mRNA) vaccines for maternal immunization to improve mother-to-child transmission of protection against the virus.

In some embodiments, the subject is a young adult between the ages of about 20 years and about 50 years (e.g., about 20, 25, 30, 35, 40, 45 or 50 years old).

In some embodiments, the subject is an elderly subject about 60 years old, about 70 years old, or older (e.g., about 60, 65, 70, 75, 80, 85 or 90 years old).

In some embodiments, the subject is has a chronic pulmonary disease (e.g., chronic obstructive pulmonary disease (COPD) or asthma). Two forms of COPD include chronic bronchitis, which involves a long-term cough with mucus, and emphysema, which involves damage to the lungs over time. Thus, a subject administered a RNA (e.g., mRNA) vaccine may have chronic bronchitis or emphysema.

In some embodiments, the subject has been exposed to hMPV, PIV3, RSV, MeV, BetaCoV (e.g., selected from MERS-CoV, SARS-CoV, HCoV-OC43, HCoV-229E, HCoV-NL63, HCoV-NL, HCoV-NH and HCoV-HKU1), or any combination of two or more of the foregoing viruses; the subject is infected with hMPV, PIV3, RSV, MeV, BetaCoV (e.g., selected from MERS-CoV, SARS-CoV, HCoV-OC43, HCoV-229E, HCoV-NL63, HCoV-NL, HCoV-NH and HCoV-HKU1), or any combination of two or more of the foregoing viruses; or subject is at risk of infection by hMPV, PIV3, RSV, MeV, BetaCoV (e.g., selected from MERS-CoV, SARS-CoV, HCoV-OC43, HCoV-229E, HCoV-NL63, HCoV-NL, HCoV-NH and HCoV-HKU1), or any combination of two or more of the foregoing viruses.

In some embodiments, the subject is immunocompromised (has an impaired immune system, e.g., has an immune disorder or autoimmune disorder).

In some embodiments the nucleic acid vaccines described herein are chemically modified. In other embodiments the nucleic acid vaccines are unmodified.

Yet other aspects provide compositions for and methods of vaccinating a subject comprising administering to the subject a nucleic acid vaccine comprising one or more RNA polynucleotides having an open reading frame encoding a first respiratory virus antigenic polypeptide, wherein the RNA polynucleotide does not include a stabilization element, and wherein an adjuvant is not coformulated or co-administered with the vaccine.

In other aspects the invention is a composition for or method of vaccinating a subject comprising administering to the subject a nucleic acid vaccine comprising one or more RNA polynucleotides having an open reading frame encoding a first antigenic polypeptide wherein a dosage of between 10 μg/kg and 400 μg/kg of the nucleic acid vaccine is administered to the subject. In some embodiments the dosage of the RNA polynucleotide is 1-5 μg, 5-10 μg, 10-15 μg, 15-20 μg, 10-25 μg, 20-25 μg, 20-50 μg, 30-50 μg, 40-50 μg, 40-60 μg, 60-80 μg, 60-100 μg, 50-100 μg, 80-120 μg, 40-120 μg, 40-150 μg, 50-150 μg, 50-200 μg, 80-200 μg, 100-200 μg, 120-250 μg, 150-250 μg, 180-280 μg, 200-300 μg, 50-300 μg, 80-300 μg, 100-300 μg, 40-300 μg, 50-350 μg, 100-350 μg, 200-350 μg, 300-350 μg, 320-400 μg, 40-380 μg, 40-100 μg, 100-400 μg, 200-400 μg, or 300-400 μg per dose. In some embodiments, the nucleic acid vaccine is administered to the subject by intradermal or intramuscular injection. In some embodiments, the nucleic acid vaccine is administered to the subject on day zero. In some embodiments, a second dose of the nucleic acid vaccine is administered to the subject on day twenty one.

In some embodiments, a dosage of 25 micrograms of the RNA polynucleotide is included in the nucleic acid vaccine administered to the subject. In some embodiments, a dosage of 100 micrograms of the RNA polynucleotide is included in the nucleic acid vaccine administered to the subject. In some embodiments, a dosage of 50 micrograms of the RNA polynucleotide is included in the nucleic acid vaccine administered to the subject. In some embodiments, a dosage of 75 micrograms of the RNA polynucleotide is included in the nucleic acid vaccine administered to the subject. In some embodiments, a dosage of 150 micrograms of the RNA polynucleotide is included in the nucleic acid vaccine administered to the subject. In some embodiments, a dosage of 400 micrograms of the RNA polynucleotide is included in the nucleic acid vaccine administered to the subject. In some embodiments, a dosage of 200 micrograms of the RNA polynucleotide is included in the nucleic acid vaccine administered to the subject. In some embodiments, the RNA polynucleotide accumulates at a 100 fold higher level in the local lymph node in comparison with the distal lymph node. In other embodiments the nucleic acid vaccine is chemically modified and in other embodiments the nucleic acid vaccine is not chemically modified.

Aspects of the invention provide a nucleic acid vaccine comprising one or more RNA polynucleotides having an open reading frame encoding a first antigenic polypeptide, wherein the RNA polynucleotide does not include a stabilization element, and a pharmaceutically acceptable carrier or excipient, wherein an adjuvant is not included in the vaccine. In some embodiments, the stabilization element is a histone stem-loop. In some embodiments, the stabilization element is a nucleic acid sequence having increased GC content relative to wild type sequence.

Aspects of the invention provide nucleic acid vaccines comprising one or more RNA polynucleotides having an open reading frame encoding a first antigenic polypeptide, wherein the RNA polynucleotide is present in the formulation for in vivo administration to a host, which confers an antibody titer superior to the criterion for seroprotection for the first antigen for an acceptable percentage of human subjects. In some embodiments, the antibody titer produced by the mRNA vaccines of the invention is a neutralizing antibody titer. In some embodiments the neutralizing antibody titer is greater than a protein vaccine. In other embodiments the neutralizing antibody titer produced by the mRNA vaccines of the invention is greater than an adjuvanted protein vaccine. In yet other embodiments the neutralizing antibody titer produced by the mRNA vaccines of the invention is 1,000-10,000, 1,200-10,000, 1,400-10,000, 1,500-10,000, 1,000-5,000, 1,000-4,000, 1,800-10,000, 2000-10,000, 2,000-5,000, 2,000-3,000, 2,000-4,000, 3,000-5,000, 3,000-4,000, or 2,000-2,500. A neutralization titer is typically expressed as the highest serum dilution required to achieve a 50% reduction in the number of plaques.

Also provided are nucleic acid vaccines comprising one or more RNA polynucleotides having an open reading frame encoding a first antigenic polypeptide, wherein the RNA polynucleotide is present in a formulation for in vivo administration to a host for eliciting a longer lasting high antibody titer than an antibody titer elicited by an mRNA vaccine having a stabilizing element or formulated with an adjuvant and encoding the first antigenic polypeptide. In some embodiments, the RNA polynucleotide is formulated to produce a neutralizing antibodies within one week of a single administration. In some embodiments, the adjuvant is selected from a cationic peptide and an immunostimulatory nucleic acid. In some embodiments, the cationic peptide is protamine.

Aspects provide nucleic acid vaccines comprising one or more RNA polynucleotides having an open reading frame comprising at least one chemical modification or optionally no nucleotide modification, the open reading frame encoding a first antigenic polypeptide, wherein the RNA polynucleotide is present in the formulation for in vivo administration to a host such that the level of antigen expression in the host significantly exceeds a level of antigen expression produced by an mRNA vaccine having a stabilizing element or formulated with an adjuvant and encoding the first antigenic polypeptide.

Other aspects provide nucleic acid vaccines comprising one or more RNA polynucleotides having an open reading frame comprising at least one chemical modification or optionally no nucleotide modification, the open reading frame encoding a first antigenic polypeptide, wherein the vaccine has at least 10 fold less RNA polynucleotide than is required for an unmodified mRNA vaccine to produce an equivalent antibody titer. In some embodiments, the RNA polynucleotide is present in a dosage of 25-100 micrograms.

Aspects of the invention also provide a unit of use vaccine, comprising between 10 ug and 400 ug of one or more RNA polynucleotides having an open reading frame comprising at least one chemical modification or optionally no nucleotide modification, the open reading frame encoding a first antigenic polypeptide, and a pharmaceutically acceptable carrier or excipient, formulated for delivery to a human subject. In some embodiments, the vaccine further comprises a cationic lipid nanoparticle.

Aspects of the invention provide methods of creating, maintaining or restoring antigenic memory to a respiratory virus strain in an individual or population of individuals comprising administering to said individual or population an antigenic memory booster nucleic acid vaccine comprising (a) at least one RNA polynucleotide, said polynucleotide comprising at least one chemical modification or optionally no nucleotide modification and two or more codon-optimized open reading frames, said open reading frames encoding a set of reference antigenic polypeptides, and (b) optionally a pharmaceutically acceptable carrier or excipient. In some embodiments, the vaccine is administered to the individual via a route selected from the group consisting of intramuscular administration, intradermal administration and subcutaneous administration. In some embodiments, the administering step comprises contacting a muscle tissue of the subject with a device suitable for injection of the composition. In some embodiments, the administering step comprises contacting a muscle tissue of the subject with a device suitable for injection of the composition in combination with electroporation.

Aspects of the invention provide methods of vaccinating a subject comprising administering to the subject a single dosage of between 25 ug/kg and 400 ug/kg of a nucleic acid vaccine comprising one or more RNA polynucleotides having an open reading frame encoding a first antigenic polypeptide in an effective amount to vaccinate the subject.

Other aspects provide nucleic acid vaccines comprising one or more RNA polynucleotides having an open reading frame comprising at least one chemical modification, the open reading frame encoding a first antigenic polypeptide, wherein the vaccine has at least 10 fold less RNA polynucleotide than is required for an unmodified mRNA vaccine to produce an equivalent antibody titer. In some embodiments, the RNA polynucleotide is present in a dosage of 25-100 micrograms.

Other aspects provide nucleic acid vaccines comprising an LNP formulated RNA polynucleotide having an open reading frame comprising no nucleotide modifications (unmodified), the open reading frame encoding a first antigenic polypeptide, wherein the vaccine has at least 10 fold less RNA polynucleotide than is required for an unmodified mRNA vaccine not formulated in a LNP to produce an equivalent antibody titer. In some embodiments, the RNA polynucleotide is present in a dosage of 25-100 micrograms.

The data presented in the Examples demonstrate significant enhanced immune responses using the formulations of the invention. Both chemically modified and unmodified RNA vaccines are useful according to the invention. Surprisingly, in contrast to prior art reports that it was preferable to use chemically unmodified mRNA formulated in a carrier for the production of vaccines, it is described herein that chemically modified mRNA-LNP vaccines required a much lower effective mRNA dose than unmodified mRNA, i.e., tenfold less than unmodified mRNA when formulated in carriers other than LNP. Both the chemically modified and unmodified RNA vaccines of the invention produce better immune responses than mRNA vaccines formulated in a different lipid carrier.

In other aspects the invention encompasses a method of treating an elderly subject age 60 years or older comprising administering to the subject a nucleic acid vaccine comprising one or more RNA polynucleotides having an open reading frame encoding a respiratory virus antigenic polypeptide in an effective amount to vaccinate the subject.

In other aspects the invention encompasses a method of treating a young subject age 17 years or younger comprising administering to the subject a nucleic acid vaccine comprising one or more RNA polynucleotides having an open reading frame encoding a respiratory virus antigenic polypeptide in an effective amount to vaccinate the subject.

In other aspects the invention encompasses a method of treating an adult subject comprising administering to the subject a nucleic acid vaccine comprising one or more RNA polynucleotides having an open reading frame encoding a respiratory virus antigenic polypeptide in an effective amount to vaccinate the subject.

In some aspects the invention is a method of vaccinating a subject with a combination vaccine including at least two nucleic acid sequences encoding respiratory antigens wherein the dosage for the vaccine is a combined therapeutic dosage wherein the dosage of each individual nucleic acid encoding an antigen is a sub therapeutic dosage. In some embodiments, the combined dosage is 25 micrograms of the RNA polynucleotide in the nucleic acid vaccine administered to the subject. In some embodiments, the combined dosage is 100 micrograms of the RNA polynucleotide in the nucleic acid vaccine administered to the subject. In some embodiments the combined dosage is 50 micrograms of the RNA polynucleotide in the nucleic acid vaccine administered to the subject. In some embodiments, the combined dosage is 75 micrograms of the RNA polynucleotide in the nucleic acid vaccine administered to the subject. In some embodiments, the combined dosage is 150 micrograms of the RNA polynucleotide in the nucleic acid vaccine administered to the subject. In some embodiments, the combined dosage is 400 micrograms of the RNA polynucleotide in the nucleic acid vaccine administered to the subject. In some embodiments, the sub therapeutic dosage of each individual nucleic acid encoding an antigen is 1, 2, 3, 4, 5, 6, 7, 8, 9, 10, 11, 12, 13, 14, 15, 16, 17, 18, 19, or 20 micrograms. In other embodiments the nucleic acid vaccine is chemically modified and in other embodiments the nucleic acid vaccine is not chemically modified.

The RNA polynucleotide is one of SEQ ID NO: 1-4, 9-12, 20-23, 35-46, 57-61, and 64-80 and includes at least one chemical modification. In other embodiments the RNA polynucleotide is one of SEQ ID NO: 1-4, 9-12, 20-23, 35-46, 57-61, and 64-80 and does not include any nucleotide modifications, or is unmodified. In yet other embodiments the at least one RNA polynucleotide encodes an antigenic protein of any of SEQ ID NO: 5-8, 12-13, 24-34, and 47-50 and includes at least one chemical modification. In other embodiments the RNA polynucleotide encodes an antigenic protein of any of SEQ ID NO: 5-8, 12-13, 24-34, and 47-50 and does not include any nucleotide modifications, or is unmodified.

In preferred aspects, vaccines of the invention (e.g., LNP-encapsulated mRNA vaccines) produce prophylactically- and/or therapeutically-efficacious levels, concentrations and/or titers of antigen-specific antibodies in the blood or serum of a vaccinated subject. As defined herein, the term antibody titer refers to the amount of antigen-specific antibody produces in s subject, e.g., a human subject. In exemplary embodiments, antibody titer is expressed as the inverse of the greatest dilution (in a serial dilution) that still gives a positive result. In exemplary embodiments, antibody titer is determined or measured by enzyme-linked immunosorbent assay (ELISA). In exemplary embodiments, antibody titer is determined or measured by neutralization assay, e.g., by microneutralization assay. In certain aspects, antibody titer measurement is expressed as a ratio, such as 1:40, 1:100, etc.

In exemplary embodiments of the invention, an efficacious vaccine produces an antibody titer of greater than 1:40, greater that 1:100, greater than 1:400, greater than 1:1000, greater than 1:2000, greater than 1:3000, greater than 1:4000, greater than 1:500, greater than 1:6000, greater than 1:7500, greater than 1:10000. In exemplary embodiments, the antibody titer is produced or reached by 10 days following vaccination, by 20 days following vaccination, by 30 days following vaccination, by 40 days following vaccination, or by 50 or more days following vaccination. In exemplary embodiments, the titer is produced or reached following a single dose of vaccine administered to the subject. In other embodiments, the titer is produced or reached following multiple doses, e.g., following a first and a second dose (e.g., a booster dose.)

In exemplary aspects of the invention, antigen-specific antibodies are measured in units of μg/ml or are measured in units of IU/L (International Units per liter) or mIU/ml (milli International Units per ml). In exemplary embodiments of the invention, an efficacious vaccine produces >0.5 μg/ml, >0.1 μg/ml, >0.2 μg/ml, >0.35 μg/ml, >0.5 μg/ml, >1 μg/ml, >2 μg/ml, >5 μg/ml or >10 μg/ml. In exemplary embodiments of the invention, an efficacious vaccine produces >10 mIU/ml, >20 mIU/ml, >50 mIU/ml, >100 mIU/ml, >200 mIU/ml, >500 mIU/ml or >1000 mIU/ml. In exemplary embodiments, the antibody level or concentration is produced or reached by 10 days following vaccination, by 20 days following vaccination, by 30 days following vaccination, by 40 days following vaccination, or by 50 or more days following vaccination. In exemplary embodiments, the level or concentration is produced or reached following a single dose of vaccine administered to the subject. In other embodiments, the level or concentration is produced or reached following multiple doses, e.g., following a first and a second dose (e.g., a booster dose.) In exemplary embodiments, antibody level or concentration is determined or measured by enzyme-linked immunosorbent assay (ELISA). In exemplary embodiments, antibody level or concentration is determined or measured by neutralization assay, e.g., by microneutralization assay.

The details of various embodiments of the disclosure are set forth in the description below. Other features, objects, and advantages of the disclosure will be apparent from the description and from the claims.

BRIEF DESCRIPTION OF THE DRAWINGS

The foregoing and other objects, features and advantages will be apparent from the following description of particular embodiments of the disclosure, as illustrated in the accompanying drawings in which like reference characters refer to the same parts throughout the different views. The drawings are not necessarily to scale, emphasis instead being placed upon illustrating the principles of various embodiments of the disclosure.

FIG. 3C shows that hMPV fusion protein mRNA vaccine induced a mixed Th1/Th2 cytokine response with a Th1 bias.

µg-doses (on day 0 and 21) of MERS-CoV mRNA vaccine encoding the full-length Spike protein before challenge. FIG. 19A shows that two doses of MERS-CoV mRNA vaccine resulted in a 3 log reduction of viral load in the nose and led to complete protection in the throat of the New Zealand white rabbits. FIG. 19B shows that two doses of MERS-CoV mRNA vaccine resulted in a 4 log reduction of viral load in the BAL of the New Zealand white rabbits. FIG. 19C show one dose of MERS-CoV mRNA vaccine resulted in a 2 log reduction of viral load, while two doses of MERS-CoV mRNA vaccine resulted in an over 4 log reduction of viral load in the lungs of the New Zealand white rabbits.

FIG. 20A shows that two doses of 20 µg a MERS-CoV mRNA vaccine reduced over 99% (2 log) of viruses in the lungs of New Zealand white rabbits. FIG. 20B shows that the group of New Zealand white rabbits that received 2 doses of 20 µg MERS-CoV mRNA vaccine did not have any detectable replicating MERS-CoV virus in their lungs.

DETAILED DESCRIPTION

Figure 1:
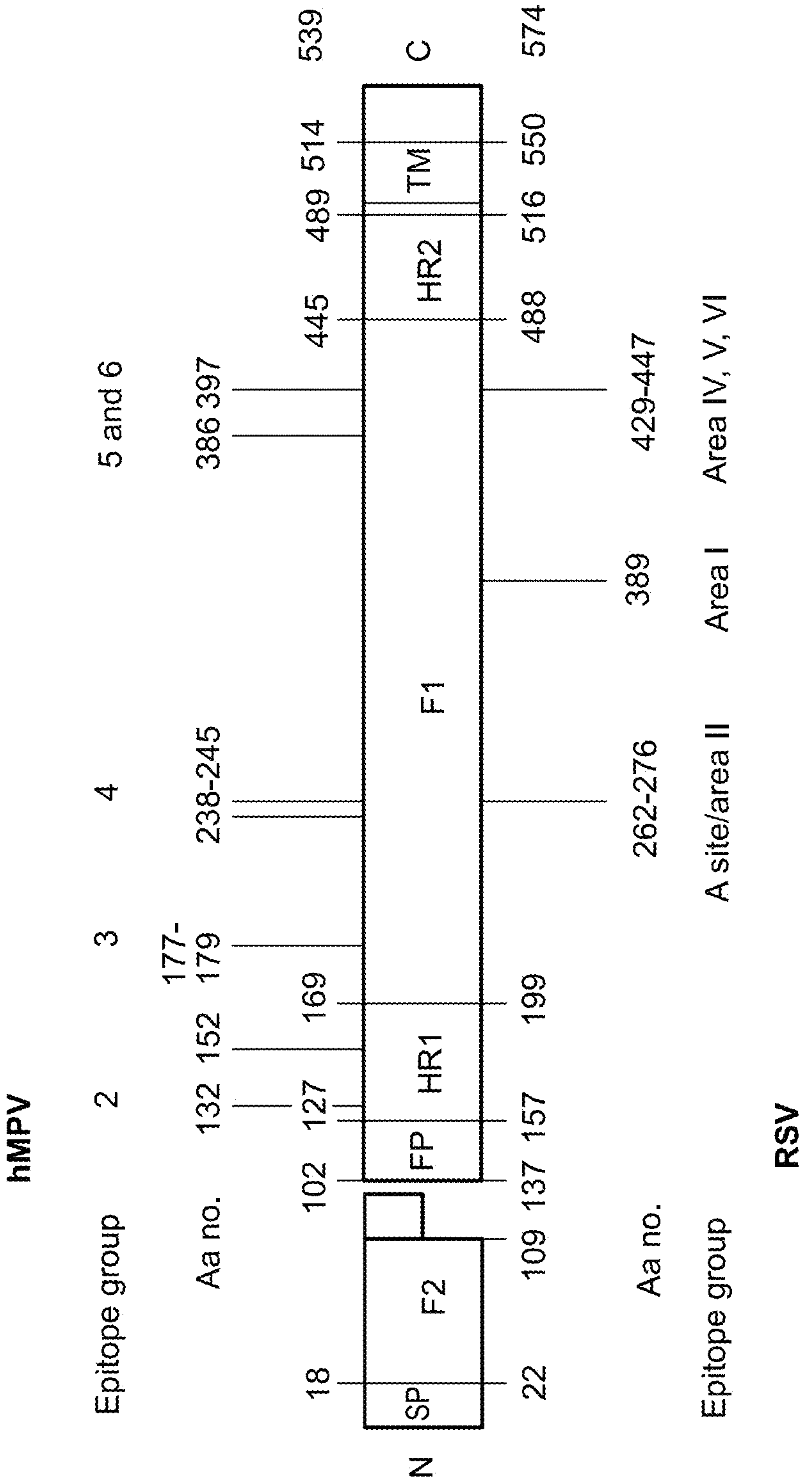
FIG. 1 shows a schematic of one example of a RNA (e.g. mRNA) vaccine construct of the present disclosure. The construct depicts a human metapneumovirus and human respiratory syncytial virus full length fusion protein obtained from wild-type strains (*The Journal of General Virology.* 2008; 89(Pt 12):3113-3118, incorporated herein by reference).

The present disclosure provides, in some embodiments, vaccines that comprise RNA (e.g., mRNA) polynucleotides encoding a human metapneumovirus (hMPV) antigenic polypeptide, a parainfluenza virus type 3 (PIV3) antigenic polypeptide, a respiratory syncytial virus (RSV) antigenic polypeptide, a measles virus (MeV) antigenic polypeptide, or a betacoronavirus antigenic polypeptide (e.g., Middle East respiratory syndrome coronavirus (MERS-CoV), SARS-CoV, human coronavirus (HCoV)-OC43, HCoV-229E, HCoV-NL63, HCoV-NL, HCoV-NH (New Haven) and HCoV-HKU1) (see, e.g., Esper F. et al. *Emerging Infectious Diseases,* 12(5), 2006; and Pyrc K. et al. *Journal of Virology,* 81(7):3051-57, 2007, the contents of each of which is here incorporated by reference in their entirety). The present disclosure also provides, in some embodiments, combination vaccines that comprise at least one RNA (e.g., mRNA) polynucleotide encoding at least two antigenic polypeptides selected from hMPV antigenic polypeptides, PIV3 antigenic polypeptides, RSV antigenic polypeptides, MeV antigenic polypeptides and BetaCoV antigenic polypeptides. Also provided herein are methods of administering the RNA (e.g., mRNA) vaccines, methods of producing the RNA (e.g., mRNA) vaccines, compositions (e.g., pharmaceutical compositions) comprising the RNA (e.g., mRNA) vaccines, and nucleic acids (e.g., DNA) encoding the RNA (e.g., mRNA) vaccines. In some embodiments, a RNA (e.g., mRNA) vaccine comprises an adjuvant, such as a flagellin adjuvant, as provided herein.

The RNA (e.g., mRNA) vaccines (e.g., hMPV, PIV3, RSV, MeV, BetaCoV RNA vaccines and combinations thereof), in some embodiments, may be used to induce a balanced immune response, comprising both cellular and humoral immunity, without many of the risks associated with DNA vaccination.

The entire contents of International Application No. PCT/US2015/02740 is incorporated herein by reference.

Human Metapneumovirus (hMPV)

hMPV shares substantial homology with respiratory syncytial virus (RSV) in its surface glycoproteins. hMPV fusion protein (F) is related to other paramyxovirus fusion proteins and appears to have homologous regions that may have similar functions. The hMPV fusion protein amino acid sequence contains features characteristic of other paramyxovirus F proteins, including a putative cleavage site and potential N-linked glycosylation sites. Paramyxovirus fusion proteins are synthesized as inactive precursors (F0) that are cleaved by host cell proteases into the biologically fusion-active F1 and F2 domains (see, e.g., Cseke G. et al. *Journal of Virology* 2007; 81(2):698-707, incorporated herein by reference). hMPV has one putative cleavage site, in contrast to the two sites established for RSV F, and only shares 34% amino acid sequence identity with RSV F. F2 is extracellular and disulfide linked to F1. Fusion proteins are type I glycoproteins existing as trimers, with two 4-3 heptad repeat domains at the N- and C-terminal regions of the protein (HR1 and HR2), which form coiled-coil alpha-helices. These coiled coils become apposed in an antiparallel fashion when the protein undergoes a conformational change into the fusogenic state. There is a hydrophobic fusion peptide N proximal to the N-terminal heptad repeat, which is thought to insert into the target cell membrane, while the association of the heptad repeats brings the transmembrane domain into close proximity, inducing membrane fusion (see, e.g., Baker, K A et al. *Mol. Cell* 1999; 3:309-319). This mechanism has been proposed for a number of different viruses, including RSV, influenza virus, and human immunodeficiency virus. Fusion proteins are major antigenic determinants for all known paramyxoviruses and for other viruses that possess similar fusion proteins such as human immunodeficiency virus, influenza virus, and Ebola virus.

In some embodiments, a hMPV vaccine of the present disclosure comprises a RNA (e.g., mRNA) polynucleotide encoding hMPV fusion protein (F). In some embodiments, a hMPV vaccine of the present disclosure comprises a RNA (e.g., mRNA) polynucleotide encoding a F1 or F2 subunit of a hMPV F protein. In some embodiments, a hMPV vaccine of the present disclosure comprises a RNA (e.g., mRNA) polynucleotide encoding hMPV glycoprotein (G). In some embodiments, a hMPV vaccine of the present disclosure comprises a RNA (e.g., mRNA) polynucleotide encoding hMPV matrix protein (M). In some embodiments, a hMPV vaccine of the present disclosure comprises a RNA (e.g., mRNA) polynucleotide encoding hMPV phosphoprotein (P). In some embodiments, a hMPV vaccine of the present disclosure comprises a RNA (e.g., mRNA) polynucleotide encoding hMPV nucleoprotein (N). In some embodiments, a hMPV vaccine of the present disclosure comprises a RNA (e.g., mRNA) polynucleotide encoding hMPV SH protein (SH).

In some embodiments, a hMPV vaccine of the present disclosure comprises a RNA (e.g., mRNA) polynucleotide encoding F protein, G protein, M protein, P protein, N protein and SH protein.

In some embodiments, a hMPV vaccine of the present disclosure comprises a RNA (e.g., mRNA) polynucleotide encoding F protein and G protein. In some embodiments, a hMPV vaccine of the present disclosure comprises a RNA (e.g., mRNA) polynucleotide encoding F protein and M protein. In some embodiments, a hMPV vaccine of the present disclosure comprises a RNA (e.g., mRNA) polynucleotide encoding F protein and P protein. In some embodiments, a hMPV vaccine of the present disclosure comprises a RNA (e.g., mRNA) polynucleotide encoding F protein and N protein. In some embodiments, a hMPV vaccine of the present disclosure comprises a RNA (e.g., mRNA) polynucleotide encoding F protein and SH protein.

In some embodiments, a hMPV vaccine of the present disclosure comprises a RNA (e.g., mRNA) polynucleotide encoding G protein and M protein. In some embodiments, a hMPV vaccine of the present disclosure comprises a RNA (e.g., mRNA) polynucleotide encoding G protein and P protein. In some embodiments, a hMPV vaccine of the present disclosure comprises a RNA (e.g., mRNA) polynucleotide encoding G protein and N protein. In some embodiments, a hMPV vaccine of the present disclosure comprises a RNA (e.g., mRNA) polynucleotide encoding G protein and SH protein.

In some embodiments, a hMPV vaccine of the present disclosure comprises a RNA (e.g., mRNA) polynucleotide encoding F protein, G protein and M protein. In some embodiments, a hMPV vaccine of the present disclosure comprises a RNA (e.g., mRNA) polynucleotide encoding F protein, G protein and P protein. In some embodiments, a hMPV vaccine of the present disclosure comprises a RNA (e.g., mRNA) polynucleotide encoding F protein, G protein and N protein. In some embodiments, a hMPV vaccine of the present disclosure comprises a RNA (e.g., mRNA) polynucleotide encoding F protein, G protein and SH protein.

A hMPV vaccine may comprise, for example, at least one RNA (e.g., mRNA) polynucleotide having an open reading frame encoding at least one hMPV antigenic polypeptide identified by any one of SEQ ID NO: 5-8 (Table 3; see also amino acid sequences of Table 4).

A hMPV vaccine may comprise, for example, at least one RNA (e.g., mRNA) polynucleotide encoded by a nucleic acid (e.g., DNA) identified by any one of SEQ ID NO: 1-4 (Table 2).

The present disclosure is not limited by a particular strain of hMPV. The strain of hMPV used in a vaccine may be any strain of hMPV. Non-limiting examples of strains of hMPV for use as provide herein include the CAN98-75 (CAN75) and the CAN97-83 (CAN83) hMPV strains (Skiadopoulos M H et al. *J Virol.* 20014; 78(13)6927-37, incorporated herein by reference), a hMPV A1, A2, B1 or B2 strain (see, e.g., de Graaf M et al. *The Journal of General Virology* 2008; 89:975-83; Peret T C T et al. *The Journal of Infectious Disease* 2002; 185:1660-63, incorporated herein by reference), a hMPV isolate TN/92-4 (e.g., SEQ ID NO: 1 and 5), a hMPV isolate NL/1/99 (e.g., SEQ ID NO: 2 and 6), or a hMPV isolate PER/CFI0497/2010/B (e.g., SEQ ID NO: 3 and 7).

In some embodiments, at least one hMPV antigenic polypeptide is obtained from a hMPV A1, A2, B1 or B2 strain (see, e.g., de Graaf M et al. *The Journal of General Virology* 2008; 89:975-83; Peret T C T et al. *The Journal of Infectious Disease* 2002; 185:1660-63, incorporated herein by reference). In some embodiments, at least one antigenic polypeptide is obtained from the CAN98-75 (CAN75) hMPV strain. In some embodiments, at least one antigenic polypeptide is obtained from the CAN97-83 (CAN83) hMPV strain. In some embodiments, at least one antigenic polypeptide is obtained from hMPV isolate TN/92-4 (e.g., SEQ ID NO: 1 and 5). In some embodiments, at least one antigenic polypeptide is obtained from hMPV isolate NL/1/99 (e.g., SEQ ID NO: 2 and 6). In some embodiments, at least one antigenic polypeptide is obtained from hMPV isolate PER/CFI0497/2010/B (e.g., SEQ ID NO: 3 and 7).

In some embodiments, hMPV vaccines comprise RNA (e.g., mRNA) polynucleotides encoding a hMPV antigenic polypeptides having at least 95%, at least 96%, at least 97%, at least 98% or at least 99% identity with hMPV F protein and having F protein activity.

A protein is considered to have F protein activity if, for example, the protein acts to fuse the viral envelope and host cell plasma membrane, mediates viral entry into a host cell via an interaction with arginine-glycine-aspartate RGD-binding integrins, or a combination thereof (see, e.g., Cox R G et al. *J Virol.* 2012; 88(22):12148-60, incorporated herein by reference).

In some embodiments, hMPV vaccines comprise RNA (e.g., mRNA) polynucleotides encoding hMPV antigenic polypeptides having at least 95%, at least 96%, at least 97%, at least 98% or at least 99% identity with hMPV G protein and having G protein activity.

A protein is considered to have G protein activity if, for example, the protein acts to modulate (e.g., inhibit) hMPV-induced cellular (immune) responses (see, e.g., Bao X et al. *PLoS Pathog.* 2008; 4(5):e1000077, incorporated herein by reference).

Human Parainfluenza Virus Type 3 (PIV3)

Parainfluenza viruses belong to the family Paramyxoviridae. These are enveloped viruses with a negative-sense single-stranded RNA genome. Parainfluenza viruses belong to the subfamily Paramyxoviridae, which is subdivided into three genera: Respirovirus (PIV-1, PIV-3, and Sendai virus (SeV)), Rubulavirus (PIV-2, PIV-4 and mumps virus) and Morbillivirus (measles virus, rinderpest virus and canine distemper virus (CDV)). Their genome, a ~15 500 nucleotide-long negative-sense RNA molecule, encodes two envelope glycoproteins, the hemagglutinin-neuraminidase (HN), the fusion protein (F or F0), which is cleaved into F1 and F2 subunits, a matrix protein (M), a nucleocapsid protein (N) and several nonstructural proteins including the viral replicase (L). All parainfluenza viruses, except for PIV-1, express a non-structural V protein that blocks IFN signaling in the infected cell and acts therefore as a virulence factor (see, e.g., Nishio M et al. *J Virol.* 2008; 82(13):6130-38).

PIV3 hemagglutinin-neuraminidase (HN), a structural protein, is found on the viral envelope, where it is necessary for attachment and cell entry. It recognizes and binds to sialic acid-containing receptors on the host cell's surface. As a neuroaminidase, HN removes sialic acid from virus particles, preventing self-aggregation of the virus, and promoting the efficient spread of the virus. Furthermore, HN promotes the activity of the fusion (F or F0) protein, contributing to the penetration of the host cell's surface.

PIV3 fusion protein (PIV3 F) is located on the viral envelope, where it facilitates the viral fusion and cell entry. The F protein is initially inactive, but proteolytic cleavage leads to its active forms, F1 and F2, which are linked by disulfide bonds. This occurs when the HN protein binds its receptor on the host cell's surface. During early phases of infection, the F glycoprotein mediates penetration of the host cell by fusion of the viral envelope to the plasma membrane. In later stages of the infection, the F protein facilitates the fusion of the infected cells with neighboring uninfected cells, which leads to the formation of a syncytium and spread of the infection.

PIV3 matrix protein (M) is found within the viral envelope and assists with viral assembly. It interacts with the nucleocapsid and envelope glycoproteins, where it facilitates the budding of progeny viruses through its interactions with specific sites on the cytoplasmic tail of the viral glycoproteins and nucleocapsid. It also plays a role in transporting viral components to the budding site.

PIV3 phosphoprotein (P) and PIV3 large polymerase protein (L) are found in the nucleocapsid where they form part of the RNA polymerase complex. The L protein, a viral RNA-dependent RNA polymerase, facilitates genomic transcription, while the host cell's ribosomes translate the viral mRNA into viral proteins.

PIV3 V is a non-structural protein that blocks IFN signaling in the infected cell, therefore acting as a virulence factor.

PIV3 nucleoprotein (N) encapsidates the genome in a ratio of 1 N per 6 ribonucleotides, protecting it from nucleases. The nucleocapsid (NC) has a helical structure. The encapsidated genomic RNA is termed the NC and serves as template for transcription and replication. During replication, encapsidation by PIV3 N is coupled to RNA synthesis and all replicative products are resistant to nucleases. PIV3 N homo-multimerizes to form the nucleocapsid and binds to viral genomic RNA. PIV3 N binds the P protein and thereby positions the polymerase on the template.

In some embodiments, a PIV3 vaccine of the present disclosure comprises a RNA (e.g., mRNA) polynucleotide encoding PIV3 fusion protein (F). In some embodiments, a PIV3 vaccine of the present disclosure comprises a RNA (e.g., mRNA) polynucleotide encoding a F1 or F2 subunit of a PIV3 F protein. In some embodiments, a PIV3 vaccine of the present disclosure comprises a RNA (e.g., mRNA) polynucleotide encoding PIV3 hemagglutinin-neuraminidase (HN) (see, e.g., van Wyke Coelingh K L et al. *J Virol.* 1987; 61(5):1473-77, incorporated herein by reference). In some embodiments, a PIV3 vaccine of the present disclosure comprises a RNA (e.g., mRNA) polynucleotide encoding PIV3 matrix protein (M). In some embodiments, a PIV3 vaccine of the present disclosure comprises a RNA (e.g., mRNA) polynucleotide encoding PIV3 phosphoprotein (P). In some embodiments, a PIV3 vaccine of the present disclosure comprises a RNA (e.g., mRNA) polynucleotide encoding PIV3 nucleoprotein (N).

In some embodiments, a PIV3 vaccine of the present disclosure comprises a RNA (e.g., mRNA) polynucleotide encoding F protein, HN protein, M protein, P protein, and N protein.

In some embodiments, a PIV3 vaccine of the present disclosure comprises a RNA (e.g., mRNA) polynucleotide encoding F protein and HN protein. In some embodiments, a PIV3 vaccine of the present disclosure comprises a RNA (e.g., mRNA) polynucleotide encoding F protein and M protein. In some embodiments, a PIV3 vaccine of the present disclosure comprises a RNA (e.g., mRNA) polynucleotide encoding F protein and P protein. In some embodiments, a PIV3 vaccine of the present disclosure comprises a RNA (e.g., mRNA) polynucleotide encoding F protein and N protein.

In some embodiments, a PIV3 vaccine of the present disclosure comprises a RNA (e.g., mRNA) polynucleotide encoding HN protein and M protein. In some embodiments, a PIV3 vaccine of the present disclosure comprises a RNA (e.g., mRNA) polynucleotide encoding HN protein and P protein. In some embodiments, a PIV3 vaccine of the present disclosure comprises a RNA (e.g., mRNA) polynucleotide encoding HN protein and N protein.

In some embodiments, a PIV3 vaccine of the present disclosure comprises a RNA (e.g., mRNA) polynucleotide encoding F protein, HN protein and M protein. In some embodiments, a PIV3 vaccine of the present disclosure comprises a RNA (e.g., mRNA) polynucleotide encoding F protein, HN protein and P protein. In some embodiments, a PIV3 vaccine of the present disclosure comprises a RNA (e.g., mRNA) polynucleotide encoding F protein, HN protein and N protein.

A PIV3 vaccine may comprise, for example, at least one RNA (e.g., mRNA) polynucleotide having an open reading frame encoding at least one PIV3 antigenic polypeptide identified by any one of SEQ ID NO: 12-13 (Table 6; see also amino acid sequences of Table 7).

A PIV3 vaccine may comprise, for example, at least one RNA (e.g., mRNA) polynucleotide encoded by a nucleic acid (e.g., DNA) identified by any one of SEQ ID NO: 9-12 (Table 5; see also nucleic acid sequences of Table 7).

The present disclosure is not limited by a particular strain of PIV3. The strain of PIV3 used in a vaccine may be any strain of PIV3. A non-limiting example of a strain of PIV3 for use as provide herein includes HPIV3/*Homo sapiens*/PER/FLA4815/2008.

In some embodiments, PIV3 vaccines comprise RNA (e.g., mRNA) polynucleotides encoding a PIV3 antigenic polypeptides having at least 95%, at least 96%, at least 97%, at least 98% or at least 99% identity with PIV3 F protein and having F protein activity.

In some embodiments, PIV3 vaccines comprise RNA (e.g., mRNA) polynucleotides encoding PIV3 antigenic polypeptides having at least 95%, at least 96%, at least 97%, at least 98% or at least 99% identity with PIV3 hemagglutinin-neuraminidase (HN) and having hemagglutinin-neuraminidase activity.

A protein is considered to have hemagglutinin-neuraminidase activity if, for example, it is capable of both receptor binding and receptor cleaving. Such proteins are major surface glycoproteins that have functional sites for cell attachment and for neuraminidase activity. They are able to cause red blood cells to agglutinate and to cleave the glycosidic linkages of neuraminic acids, so they have the potential to both bind a potential host cell and then release the cell if necessary, for example, to prevent self-aggregation of the virus.

In some embodiments, PIV3 vaccines comprise RNA (e.g., mRNA) polynucleotides encoding PIV3 antigenic polypeptides having at least 95%, at least 96%, at least 97%, at least 98% or at least 99% identity with PIV3 HN, F (e.g., F, F1 or F2), M, N, L or V and having HN, F (e.g., F, F1 or F2), M, N, L or V activity, respectively.

Respiratory Syncytial Virus (RSV)

RSV is a negative-sense, single-stranded RNA virus of the genus Pneumovirinae. The virus is present in at least two antigenic subgroups, known as Group A and Group B, primarily resulting from differences in the surface G glycoproteins. Two RSV surface glycoproteins—G and F—mediate attachment with and attachment to cells of the respiratory epithelium. F surface glycoproteins mediate coalescence of neighboring cells. This results in the formation of syncytial cells. RSV is the most common cause of bronchiolitis. Most infected adults develop mild cold-like symptoms such as congestion, low-grade fever, and wheezing. Infants and small children may suffer more severe symptoms such as bronchiolitis and pneumonia. The disease may be transmitted among humans via contact with respiratory secretions.

The genome of RSV encodes at least three surface glycoproteins, including F, G, and SH, four nucleocapsid proteins, including L, P, N, and M2, and one matrix protein, M. Glycoprotein F directs viral penetration by fusion between the virion and the host membrane. Glycoprotein G is a type II transmembrane glycoprotein and is the major attachment protein. SH is a short integral membrane protein. Matrix protein M is found in the inner layer of the lipid bilayer and assists virion formation. Nucleocapsid proteins L, P, N, and M2 modulate replication and transcription of the RSV genome. It is thought that glycoprotein G tethers and stabilizes the virus particle at the surface of bronchial epithelial cells, while glycoprotein F interacts with cellular glycosaminoglycans to mediate fusion and delivery of the RSV virion contents into the host cell (Krzyzaniak M A et al. *PLoS Pathog* 2013; 9(4)).

In some embodiments, a RSV vaccine of the present disclosure comprises a RNA (e.g., mRNA) polynucleotide encoding F protein. In some embodiments, a PIV3 vaccine of the present disclosure comprises a RNA (e.g., mRNA) polynucleotide encoding G protein. In some embodiments, a PIV3 vaccine of the present disclosure comprises a RNA (e.g., mRNA) polynucleotide encoding L protein. In some embodiments, a PIV3 vaccine of the present disclosure comprises a RNA (e.g., mRNA) polynucleotide encoding P protein. In some embodiments, a PIV3 vaccine of the present disclosure comprises a RNA (e.g., mRNA) polynucleotide encoding N protein. In some embodiments, a PIV3 vaccine of the present disclosure comprises a RNA (e.g., mRNA) polynucleotide encoding M2 protein. In some embodiments, a PIV3 vaccine of the present disclosure comprises a RNA (e.g., mRNA) polynucleotide encoding M protein.

In some embodiments, a RSV vaccine of the present disclosure comprises a RNA (e.g., mRNA) polynucleotide encoding F protein, G protein, L protein, P protein, N protein, M2 protein and M protein.

In some embodiments, a RSV vaccine of the present disclosure comprises a RNA (e.g., mRNA) polynucleotide encoding F protein and G protein. In some embodiments, a RSV vaccine of the present disclosure comprises a RNA (e.g., mRNA) polynucleotide encoding F protein and L protein. In some embodiments, a RSV vaccine of the present disclosure comprises a RNA (e.g., mRNA) polynucleotide encoding F protein and P protein. In some embodiments, a RSV vaccine of the present disclosure comprises a RNA (e.g., mRNA) polynucleotide encoding F protein and N protein. In some embodiments, a RSV vaccine of the present disclosure comprises a RNA (e.g., mRNA) polynucleotide encoding F protein and M2 protein. In some embodiments, a RSV vaccine of the present disclosure comprises a RNA (e.g., mRNA) polynucleotide encoding F protein and M protein.

In some embodiments, a RSV vaccine of the present disclosure comprises a RNA (e.g., mRNA) polynucleotide encoding G protein and L protein. In some embodiments, a RSV vaccine of the present disclosure comprises a RNA (e.g., mRNA) polynucleotide encoding G protein and P protein. In some embodiments, a RSV vaccine of the present disclosure comprises a RNA (e.g., mRNA) polynucleotide encoding G protein and N protein. In some embodiments, a RSV vaccine of the present disclosure comprises a RNA (e.g., mRNA) polynucleotide encoding G protein and M2 protein. In some embodiments, a RSV vaccine of the present disclosure comprises a RNA (e.g., mRNA) polynucleotide encoding G protein and M protein.

In some embodiments, a RSV vaccine of the present disclosure comprises a RNA (e.g., mRNA) polynucleotide encoding F protein, G protein and L protein. In some embodiments, a RSV vaccine of the present disclosure comprises a RNA (e.g., mRNA) polynucleotide encoding F protein, G protein and P protein. In some embodiments, a RSV vaccine of the present disclosure comprises a RNA (e.g., mRNA) polynucleotide encoding F protein, G protein and N protein. In some embodiments, a RSV vaccine of the present disclosure comprises a RNA (e.g., mRNA) polynucleotide encoding F protein, G protein and M2 protein. In some embodiments, a RSV vaccine of the present disclosure comprises a RNA (e.g., mRNA) polynucleotide encoding F protein, G protein and M protein.

The present disclosure is not limited by a particular strain of RSV. The strain of RSV used in a vaccine may be any strain of RSV.

In some embodiments, RSV vaccines comprise RNA (e.g., mRNA) polynucleotides encoding a RSV antigenic polypeptides having at least 95%, at least 96%, at least 97%, at least 98% or at least 99% identity with RSV F protein and having F protein activity.

In some embodiments, RSV vaccines comprise RNA (e.g., mRNA) polynucleotides encoding RSV antigenic polypeptides having at least 95%, at least 96%, at least 97%, at least 98% or at least 99% identity with RSV G protein and having G protein activity.

A protein is considered to have G protein activity if, for example, the protein acts to modulate (e.g., inhibit) hMPV-induced cellular (immune) responses (see, e.g., Bao X et al. *PLoS Pathog.* 2008; 4(5):e1000077, incorporated herein by reference).

Measles Virus (MeV)

Molecular epidemiologic investigations and virologic surveillance contribute notably to the control and prevention of measles. Nearly half of measles-related deaths worldwide occur in India, yet virologic surveillance data are incomplete for many regions of the country. Previous studies have documented the presence of measles virus genotypes D4, D7, and D8 in India, and genotypes D5, D9, D11, H1, and G3 have been detected in neighboring countries. Recently, MeV genotype B3 was detected in India (Kuttiatt V S et al. *Emerg Infect Dis.* 2014; 20(10): 1764-66).

The glycoprotein complex of paramyxoviruses mediates receptor binding and membrane fusion. In particular, the MeV fusion (F) protein executes membrane fusion, after receptor binding by the hemagglutinin (HA) protein (Muhlebach M D et al. *Journal of Virology* 2008; 82(22):11437-45). The MeV P gene codes for three proteins: P, an essential polymerase cofactor, and V and C, which have multiple functions but are not strictly required for viral propagation in cultured cells. V shares the amino-terminal domain with P but has a zinc-binding carboxyl-terminal domain, whereas C is translated from an overlapping reading frame. The MeV C protein is an infectivity factor. During replication, the P protein binds incoming monomeric nucleocapsid (N) proteins with its amino-terminal domain and positions them for assembly into the nascent ribonucleocapsid. The P protein amino-terminal domain is natively unfolded (Deveaux P et al. *Journal of Virology* 2004; 78(21):11632-40).

In some embodiments, a MeV vaccine of the present disclosure comprises a RNA (e.g., mRNA) polynucleotide encoding HA protein. In some embodiments, a MeV vaccine of the present disclosure comprises a RNA (e.g., mRNA) polynucleotide encoding F protein. In some embodiments, a MeV vaccine of the present disclosure comprises a RNA (e.g., mRNA) polynucleotide encoding P protein. In some embodiments, a MeV vaccine of the present disclosure comprises a RNA (e.g., mRNA) polynucleotide encoding V protein. In some embodiments, a MeV vaccine of the present disclosure comprises a RNA (e.g., mRNA) polynucleotide encoding C protein.

In some embodiments, a MeV vaccine of the present disclosure comprises a RNA (e.g., mRNA) polynucleotide encoding HA protein, F protein, P protein, V protein and C protein.

In some embodiments, a MeV vaccine of the present disclosure comprises a RNA (e.g., mRNA) polynucleotide encoding HA protein and F protein. In some embodiments, a MeV vaccine of the present disclosure comprises a RNA (e.g., mRNA) polynucleotide encoding HA protein and P protein. In some embodiments, a MeV vaccine of the present disclosure comprises a RNA (e.g., mRNA) polynucleotide encoding HA protein and V protein. In some embodiments, a MeV vaccine of the present disclosure comprises a RNA (e.g., mRNA) polynucleotide encoding HA protein and C protein.

some embodiments, a MeV vaccine of the present disclosure comprises a RNA (e.g., mRNA) polynucleotide encoding F protein and P protein. In some embodiments, a MeV vaccine of the present disclosure comprises a RNA (e.g., mRNA) polynucleotide encoding F protein and V protein. In some embodiments, a MeV vaccine of the present disclosure comprises a RNA (e.g., mRNA) polynucleotide encoding F protein and C protein.

In some embodiments, a MeV vaccine of the present disclosure comprises a RNA (e.g., mRNA) polynucleotide encoding HA protein, F protein and P protein. In some embodiments, a MeV vaccine of the present disclosure comprises a RNA (e.g., mRNA) polynucleotide encoding HA protein, F protein and V protein. In some embodiments, a MeV vaccine of the present disclosure comprises a RNA (e.g., mRNA) polynucleotide encoding HA protein, F protein and C protein.

In some embodiments, MeV vaccines comprise RNA (e.g., mRNA) encoding a MeV antigenic polypeptide having at least 95%, at least 96%, at least 97%, at least 98% or at least 99% identity with MeV HA protein and having MeV HA protein activity.

In some embodiments, MeV vaccines comprise RNA (e.g., mRNA) encoding a MeV antigenic polypeptide having at least 95%, at least 96%, at least 97%, at least 98% or at least 99% identity with MeV F protein and having MeV F protein activity.

A protein is considered to have HA protein activity if the protein mediates receptor binding and/or membrane fusion. MeV F protein executes membrane fusion, after receptor binding by the MeV HA protein.

A MeV vaccine may comprise, for example, at least one RNA (e.g., mRNA) polynucleotide having an open reading frame encoding at least one MeV antigenic polypeptide identified by any one of SEQ ID NO: 47-50 (Table 14; see also amino acid sequences of Table 15).

A MeV vaccine may comprise, for example, at least one RNA (e.g., mRNA) polynucleotide identified by any one of SEQ ID NO: 37, 40, 43, 46 (Table 13).

A MeV vaccine may comprise, for example, at least one RNA (e.g., mRNA) polynucleotide encoded by a nucleic acid (e.g., DNA) identified by any one of SEQ ID NO: 35, 36, 38, 39, 41, 42, 44 and 45 (Table 13).

The present disclosure is not limited by a particular strain of MeV. The strain of MeV used in a vaccine may be any strain of MeV. Non-limiting examples of strains of MeV for use as provide herein include B3/B3.1, C2, D4, D6, D7, D8, G3, H1, Moraten, Rubeovax, MVi/New Jersey.USA/45.05, MVi/Texas.USA/4.07, AIK-C, MVi/New York.USA/26.09/3, MVi/California.USA/16.03, MVi/Virginia.USA/15.09, MVi/California.USA/8.04, and MVi/Pennsylvania.USA/20.09.

MeV proteins may be from MeV genotype D4, D5, D7, D8, D9, D11, H1, G3 or B3. In some embodiments, a MeV HA protein or a MeV F protein is from MeV genotype D8. In some embodiments, a MeV HA protein or a MeV F protein is from MeV genotype B3.

Betacoronaviruses (BetaCoV)

MERS-Co V.

MERS-CoV is a positive-sense, single-stranded RNA virus of the genus Betacoronavirus. The genomes are phylogenetically classified into two clades, Glade A and Glade B. It has a strong tropism for non-ciliated bronchial epithelial cells, evades the innate immune response and antagonizes interferon (IFN) production in infected cells. Dipeptyl peptidase 4 (DDP4, also known as CD26) has been identified as a functional cellular receptor for MERS-CoV. Its enzymatic activity is not required for infection, although its amino acid sequence is highly conserved across species and is expressed in the human bronchial epithelium and kidneys. Most infected individuals develop severe acute respiratory illnesses, including fever, cough, and shortness of breath, and the virus can be fatal. The disease may be transmitted among humans, generally among those in close contact.

The genome of MERS-CoV encodes at least four unique accessory proteins, such as 3, 4a, 4b and 5, two replicase proteins (open reading frame 1a and 1b), and four major structural proteins, including spike (S), envelope (E), nucleocapsid (N), and membrane (M) proteins (Almazan F et al. *M Bio* 2013; 4(5):e00650-13). The accessory proteins play nonessential roles in MERS-CoV replication, but they are likely structural proteins or interferon antagonists, modulating in vivo replication efficiency and/or pathogenesis, as in the case of SARS-CoV (Almazan F et al. *M Bio* 2013; 4(5):e00650-13; Totura A L et al. *Curr Opin Virol* 2012; 2(3):264-75; Scobey T et al. *Proc Natl Acad Sci USA* 2013; 110(40):16157-62). The other proteins of MERS-CoV maintain different functions in virus replication. The E protein, for example, involves in virulence, and deleting the E-coding gene results in replication-competent and propagation-defective viruses or attenuated viruses (Almazan F et al. *M Bio* 2013; 4(5):e00650-13). The S protein is particularly essential in mediating virus binding to cells expressing receptor dipeptidyl peptidase-4 (DPP4) through receptor-binding domain (RBD) in the 51 subunit, whereas the S2 subunit subsequently mediates virus entry via fusion of the virus and target cell membranes (Li F. *J Virol* 2015; 89(4):1954-64; Raj V S et al. *Nature* 2013; 495(7440):251-4).

In some embodiments, a MERS-CoV vaccine of the present disclosure comprises a RNA (e.g., mRNA) polynucleotide encoding S protein. In some embodiments, a MERS-CoV vaccine of the present disclosure comprises a RNA (e.g., mRNA) polynucleotide encoding the S1 subunit of the S protein. In some embodiments, a MERS-CoV vaccine of the present disclosure comprises a RNA (e.g., mRNA) polynucleotide encoding the S2 subunit of the S protein. In some embodiments, a MERS-CoV vaccine of the present disclosure comprises a RNA (e.g., mRNA) polynucleotide encoding E protein. In some embodiments, a MERS-CoV vaccine of the present disclosure comprises a RNA (e.g., mRNA) polynucleotide encoding N protein. In some embodiments, a MERS-CoV vaccine of the present disclosure comprises a RNA (e.g., mRNA) polynucleotide encoding M protein.

In some embodiments, a MERS-CoV vaccine of the present disclosure comprises a RNA (e.g., mRNA) polynucleotide encoding S protein (S, S1 and/or S2), E protein, N protein and M protein.

In some embodiments, a MERS-CoV vaccine of the present disclosure comprises a RNA (e.g., mRNA) polynucleotide encoding S protein (S, S1 and/or S2) and E protein. In some embodiments, a MERS-CoV vaccine of the present disclosure comprises a RNA (e.g., mRNA) polynucleotide encoding S protein (S, S1 and/or S2) and N protein. In some embodiments, a MERS-CoV vaccine of the present disclosure comprises a RNA (e.g., mRNA) polynucleotide encoding S protein (S, S1 and/or S2) and M protein.

In some embodiments, a MERS-CoV vaccine of the present disclosure comprises a RNA (e.g., mRNA) polynucleotide encoding S protein (S, S1 and/or S2), E protein and M protein. In some embodiments, a MERS-CoV vaccine of the present disclosure comprises a RNA (e.g., mRNA) polynucleotide encoding S protein (S, S1 and/or S2), E protein and N protein. In some embodiments, a MERS-CoV vaccine of the present disclosure comprises a RNA (e.g., mRNA) polynucleotide encoding S protein (S, S1 and/or S2), M protein and N protein. In some embodiments, a MERS-CoV vaccine of the present disclosure comprises a RNA (e.g., mRNA) polynucleotide encoding E protein, M protein and N protein.

A MERS-CoV vaccine may comprise, for example, at least one RNA (e.g., mRNA) polynucleotide having an open reading frame encoding at least one MERS-CoV antigenic polypeptide identified by any one of SEQ ID NO: 24-38 or 33 (Table 11; see also amino acid sequences of Table 12).

A MERS-CoV vaccine may comprise, for example, at least one RNA (e.g., mRNA) polynucleotide encoded by a nucleic acid (e.g., DNA) identified by any one of SEQ ID NO: 20-23 (Table 10).

The present disclosure is not limited by a particular strain of MERS-CoV. The strain of MERS-CoV used in a vaccine may be any strain of MERS-CoV. Non-limiting examples of strains of MERS-CoV for use as provide herein include Riyadh_14_2013, and 2cEMC/2012, Hasa_1_2013.

SARS-CoV.

The genome of SARS-CoV includes of a single, positive-strand RNA that is approximately 29,700 nucleotides long. The overall genome organization of SARS-CoV is similar to that of other coronaviruses. The reference genome includes 13 genes, which encode at least 14 proteins. Two large overlapping reading frames (ORFs) encompass 71% of the genome. The remainder has 12 potential ORFs, including genes for structural proteins S (spike), E (small envelope), M (membrane), and N (nucleocapsid). Other potential ORFs code for unique putative SARS-CoV-specific polypeptides that lack obvious sequence similarity to known proteins. A detailed analysis of the SARS-CoV genome has been published in *J Mol Biol* 2003; 331: 991-1004.

In some embodiments, a SARS-CoV vaccine of the present disclosure comprises a RNA (e.g., mRNA) polynucleotide encoding S protein (S, S1 and/or S2), E protein, N protein and M protein.

In some embodiments, a SARS-CoV vaccine of the present disclosure comprises a RNA (e.g., mRNA) polynucleotide encoding S protein (S, S1 and/or S2) and E protein. In some embodiments, a SARS-CoV vaccine of the present disclosure comprises a RNA (e.g., mRNA) polynucleotide encoding S protein (S, S1 and/or S2) and N protein. In some embodiments, a SARS-CoV vaccine of the present disclosure comprises a RNA (e.g., mRNA) polynucleotide encoding S protein (S, S1 and/or S2) and M protein.

In some embodiments, a SARS-CoV vaccine of the present disclosure comprises a RNA (e.g., mRNA) polynucleotide encoding S protein (S, S1 and/or S2), E protein and M protein. In some embodiments, a SARS-CoV vaccine of the present disclosure comprises a RNA (e.g., mRNA) polynucleotide encoding S protein (S, S1 and/or S2), E protein and N protein. In some embodiments, a SARS-CoV vaccine of the present disclosure comprises a RNA (e.g., mRNA) polynucleotide encoding S protein (S, S1 and/or S2), M protein and N protein. In some embodiments, a SARS-CoV vaccine of the present disclosure comprises a RNA (e.g., mRNA) polynucleotide encoding E protein, M protein and N protein.

A SARS-CoV vaccine may comprise, for example, at least one RNA (e.g., mRNA) polynucleotide having an open reading frame encoding at least one SARS-CoV antigenic polypeptide identified by any one of SEQ ID NO: 29, 32 or 34 (Table 11; see also amino acid sequences of Table 12).

The present disclosure is not limited by a particular strain of SARS-CoV. The strain of SARS-CoV used in a vaccine may be any strain of SARS-CoV.

HCoV-OC43.

Human coronavirus OC43 is an enveloped, positive-sense, single-stranded RNA virus in the species Betacoronavirus-1 (genus Betacoronavirus, subfamily Coronavirinae, family Coronaviridae, order Nidovirales). Four HCoV-OC43 genotypes (A to D), have been identified with genotype D most likely arising from recombination. The complete genome sequencing of two genotype C and D strains and bootscan analysis shows recombination events between genotypes B and C in the generation of genotype D. Of 29 strains identified, none belong to the more ancient genotype A. Along with HCoV-229E, a species in the Alphacoronavirus genus, HCoV-OC43 are among the known viruses that cause the common cold. Both viruses can cause severe lower respiratory tract infections, including pneumonia in infants, the elderly, and immunocompromised individuals such as those undergoing chemotherapy and those with HIV-AIDS.

HCoV-HKU1.

Human coronavirus HKU1 (HCoV-HKU1) is a positive-sense, single-stranded RNA virus with the HE gene, which distinguishes it as a group 2, or betacoronavirus. It was discovered in January 2005 in two patients in Hong Kong. The genome of HCoV-HKU1 is a 29,926-nucleotide, polyadenylated RNA. The GC content is 32%, the lowest among all known coronaviruses. The genome organization is the same as that of other group II coronaviruses, with the characteristic gene order 1a, 1b, HE, S, E, M, and N. Furthermore, accessory protein genes are present between the S and E genes (ORF4) and at the position of the N gene (ORF8). The TRS is presumably located within the AAUCUAAAC sequence, which precedes each ORF except E. As in sialodacryoadenitis virus and mouse hepatitis virus (MHV), translation of the E protein possibly occurs via an internal ribosomal entry site. The 3' untranslated region contains a predicted stem-loop structure immediately downstream of the N ORF (nucleotide position 29647 to 29711). Further downstream, a pseudoknot structure is present at nucleotide position 29708 to 29760. Both RNA structures are conserved in group II coronaviruses and are critical for virus replication.

HCoV-NL63.

The RNA genome of human coronavirus NL63 (HCoV-NL63) is 27,553 nucleotides, with a poly(A) tail (FIG. 1). With a GC content of 34%, HCoV-NL63 has one of the lowest GC contents of the coronaviruses, for which GC content ranges from 32 to 42%. Untranslated regions of 286 and 287 nucleotides are present at the 5' and 3' termini, respectively. Genes predicted to encode the S, E, M, and N proteins are found in the 3' part of the HCoV-NL63 genome. The HE gene, which is present in some group II coronaviruses, is absent, and there is only a single, monocistronic accessory protein ORF (ORF3) located between the S and E genes. Subgenomic mRNAs are generated for all ORFs (S, ORF3, E, M, and N), and the core sequence of the TRS of HCoV-NL63 is defined as AACUAAA. This sequence is situated upstream of every ORF except for the E ORF, which contains the suboptimal core sequence AACUAUA. Interestingly, a 13-nucleotide sequence with perfect homology to the leader sequence is situated upstream of the suboptimal E TRS. Annealing of this 13-nucleotide sequence to the leader sequence may act as a compensatory mechanism for the disturbed leader-TRS/body-TRS interaction.

HCoV-229E.

Human coronavirus 229E (HCoV-229E) is a single-stranded, positive-sense, RNA virus species in the Alphacoronavirus genus of the subfamily Coronavirinae, in the family Coronaviridae, of the order Nidovirales. Along with Human coronavirus OC43, it is responsible for the common cold. HCoV-NL63 and HCoV-229E are two of the four human coronaviruses that circulate worldwide. These two viruses are unique in their relationship towards each other. Phylogenetically, the viruses are more closely related to each other than to any other human coronavirus, yet they only share 65% sequence identity. Moreover, the viruses use different receptors to enter their target cell. HCoV-NL63 is associated with croup in children, whereas all signs suggest that the virus probably causes the common cold in healthy adults. HCoV-229E is a proven common cold virus in healthy adults, so it is probable that both viruses induce comparable symptoms in adults, even though their mode of infection differs (HCoV-NL63 and HCoV-229E are two of the four human coronaviruses that circulate worldwide. These two viruses are unique in their relationship towards each other. Phylogenetically, the viruses are more closely related to each other than to any other human coronavirus, yet they only share 65% sequence identity. Moreover, the viruses use different receptors to enter their target cell. HCoV-NL63 is associated with croup in children, whereas all signs suggest that the virus probably causes the common cold in healthy adults. HCoV-229E is a proven common cold virus in healthy adults, so it is probable that both viruses induce comparable symptoms in adults, even though their mode of infection differs (Dijkman R. et al. *J Formos Med Assoc.* 2009 April; 108(4):270-9, the contents of which is incorporated herein by reference in their entirety).

Combination Vaccines

Embodiments of the present disclosure also provide combination RNA (e.g., mRNA) vaccines. A "combination RNA (e.g., mRNA) vaccine" of the present disclosure refers to a vaccine comprising at least one (e.g., at least 2, 3, 4, or 5) RNA (e.g., mRNA) polynucleotide having an open reading frame encoding a combination of any two or more (or all of) antigenic polypeptides selected from hMPV antigenic polypeptides, PIV3 antigenic polypeptides, RSV antigenic polypeptides, MeV antigenic polypeptides, and BetaCoV antigenic polypeptides (e.g., selected from MERS-CoV, SARS-CoV, HCoV-OC43, HCoV-229E, HCoV-NL63, HCoV-NL, HCoV-NH and HCoV-HKU1).

In some embodiments, a combination RNA (e.g., mRNA) vaccine comprises a RNA (e.g., mRNA) polynucleotide encoding a hMPV antigenic polypeptide, a PIV3 antigenic polypeptide, a RSV antigenic polypeptide, a MeV antigenic polypeptide, and a BetaCoV antigenic polypeptide (e.g., selected from MERS-CoV, SARS-CoV, HCoV-OC43, HCoV-229E, HCoV-NL63, HCoV-NL, HCoV-NH and HCoV-HKU1).

In some embodiments, a combination RNA (e.g., mRNA) vaccine comprises a RNA (e.g., mRNA) polynucleotide encoding a hMPV antigenic polypeptide and a PIV3 antigenic polypeptide.

In some embodiments, a combination RNA (e.g., mRNA) vaccine comprises a RNA (e.g., mRNA) polynucleotide encoding a hMPV antigenic polypeptide and a RSV antigenic polypeptide.

In some embodiments, a combination RNA (e.g., mRNA) vaccine comprises a RNA (e.g., mRNA) polynucleotide encoding a hMPV antigenic polypeptide and a MeV antigenic polypeptide.

In some embodiments, a combination RNA (e.g., mRNA) vaccine comprises a RNA (e.g., mRNA) polynucleotide encoding a hMPV antigenic polypeptide and a BetaCoV antigenic polypeptide.

In some embodiments, a combination RNA (e.g., mRNA) vaccine comprises a RNA (e.g., mRNA) polynucleotide encoding a PIV3 antigenic polypeptide and a RSV antigenic polypeptide.

In some embodiments, a combination RNA (e.g., mRNA) vaccine comprises a RNA (e.g., mRNA) polynucleotide encoding a PIV3 antigenic polypeptide and a MeV antigenic polypeptide.

In some embodiments, a combination RNA (e.g., mRNA) vaccine comprises a RNA (e.g., mRNA) polynucleotide encoding a PIV3 antigenic polypeptide and a BetaCoV antigenic polypeptide (e.g., selected from MERS-CoV, SARS-CoV, HCoV-OC43, HCoV-229E, HCoV-NL63, HCoV-NL, HCoV-NH and HCoV-HKU1).

In some embodiments, a combination RNA (e.g., mRNA) vaccine comprises a RNA (e.g., mRNA) polynucleotide encoding a RSV antigenic polypeptide and a MeV antigenic polypeptide.

In some embodiments, a combination RNA (e.g., mRNA) vaccine comprises a RNA (e.g., mRNA) polynucleotide encoding a RSV antigenic polypeptide and a BetaCoV antigenic polypeptide (e.g., selected from MERS-CoV, SARS-CoV, HCoV-OC43, HCoV-229E, HCoV-NL63, HCoV-NL, HCoV-NH and HCoV-HKU1).

In some embodiments, a combination RNA (e.g., mRNA) vaccine comprises a RNA (e.g., mRNA) polynucleotide encoding a MeV antigenic polypeptide and a BetaCoV antigenic polypeptide (e.g., selected from MERS-CoV, SARS-CoV, HCoV-OC43, HCoV-229E, HCoV-NL63, HCoV-NL, HCoV-NH and HCoV-HKU1).

In some embodiments, a combination RNA (e.g., mRNA) vaccine comprises a RNA (e.g., mRNA) polynucleotide encoding a hMPV antigenic polypeptide, a PIV3 antigenic polypeptide, a RSV antigenic polypeptide and a MeV antigenic polypeptide.

In some embodiments, a combination RNA (e.g., mRNA) vaccine comprises a RNA (e.g., mRNA) polynucleotide encoding a hMPV antigenic polypeptide, a PIV3 antigenic polypeptide, a RSV antigenic polypeptide and a BetaCoV antigenic polypeptide (e.g., selected from MERS-CoV, SARS-CoV, HCoV-OC43, HCoV-229E, HCoV-NL63, HCoV-NL, HCoV-NH and HCoV-HKU1).

In some embodiments, a combination RNA (e.g., mRNA) vaccine comprises a RNA (e.g., mRNA) polynucleotide encoding a hMPV antigenic polypeptide, a PIV3 antigenic polypeptide, a MeV antigenic polypeptide and a BetaCoV antigenic polypeptide (e.g., selected from MERS-CoV, SARS-CoV, HCoV-OC43, HCoV-229E, HCoV-NL63, HCoV-NL, HCoV-NH and HCoV-HKU1).

In some embodiments, a combination RNA (e.g., mRNA) vaccine comprises a RNA (e.g., mRNA) polynucleotide encoding a hMPV antigenic polypeptide, a RSV antigenic polypeptide, a MeV antigenic polypeptide and a BetaCoV antigenic polypeptide (e.g., selected from MERS-CoV, SARS-CoV, HCoV-OC43, HCoV-229E, HCoV-NL63, HCoV-NL, HCoV-NH and HCoV-HKU1).

In some embodiments, a combination RNA (e.g., mRNA) vaccine comprises a RNA (e.g., mRNA) polynucleotide encoding a PIV3 antigenic polypeptide, a RSV antigenic polypeptide, a MeV antigenic polypeptide and a BetaCoV antigenic polypeptide (e.g., selected from MERS-CoV, SARS-CoV, HCoV-OC43, HCoV-229E, HCoV-NL63, HCoV-NL, HCoV-NH and HCoV-HKU1).

In some embodiments, a combination RNA (e.g., mRNA) vaccine comprises a RNA (e.g., mRNA) polynucleotide encoding a hMPV antigenic polypeptide, a PIV3 antigenic polypeptide and a RSV antigenic polypeptide.

In some embodiments, a combination RNA (e.g., mRNA) vaccine comprises a RNA (e.g., mRNA) polynucleotide encoding a hMPV antigenic polypeptide, a PIV3 antigenic polypeptide and a MeV antigenic polypeptide.

In some embodiments, a combination RNA (e.g., mRNA) vaccine comprises a RNA (e.g., mRNA) polynucleotide encoding a hMPV antigenic polypeptide, a PIV3 antigenic polypeptide and a BetaCoV antigenic polypeptide (e.g., selected from MERS-CoV, SARS-CoV, HCoV-OC43, HCoV-229E, HCoV-NL63, HCoV-NL, HCoV-NH and HCoV-HKU1).

In some embodiments, a combination RNA (e.g., mRNA) vaccine comprises a RNA (e.g., mRNA) polynucleotide encoding a hMPV antigenic polypeptide, a RSV antigenic polypeptide and a MeV antigenic polypeptide.

In some embodiments, a combination RNA (e.g., mRNA) vaccine comprises a RNA (e.g., mRNA) polynucleotide encoding a hMPV antigenic polypeptide, a RSV antigenic polypeptide and a BetaCoV antigenic polypeptide (e.g., selected from MERS-CoV, SARS-CoV, HCoV-OC43, HCoV-229E, HCoV-NL63, HCoV-NL, HCoV-NH and HCoV-HKU1).

In some embodiments, a combination RNA (e.g., mRNA) vaccine comprises a RNA (e.g., mRNA) polynucleotide encoding a hMPV antigenic polypeptide, a MeV antigenic polypeptide and a BetaCoV antigenic polypeptide (e.g., selected from MERS-CoV, SARS-CoV, HCoV-OC43, HCoV-229E, HCoV-NL63, HCoV-NL, HCoV-NH and HCoV-HKU1).

In some embodiments, a combination RNA (e.g., mRNA) vaccine comprises a RNA (e.g., mRNA) polynucleotide encoding a PIV3 antigenic polypeptide, a RSV antigenic polypeptide and a MeV antigenic polypeptide.

In some embodiments, a combination RNA (e.g., mRNA) vaccine comprises a RNA (e.g., mRNA) polynucleotide encoding a PIV3 antigenic polypeptide, a RSV antigenic polypeptide and a BetaCoV antigenic polypeptide (e.g., selected from MERS-CoV, SARS-CoV, HCoV-OC43, HCoV-229E, HCoV-NL63, HCoV-NL, HCoV-NH and HCoV-HKU1).

In some embodiments, a combination RNA (e.g., mRNA) vaccine comprises a RNA (e.g., mRNA) polynucleotide encoding a RSV antigenic polypeptide, a MeV antigenic polypeptide and a BetaCoV antigenic polypeptide (e.g., selected from MERS-CoV, SARS-CoV, HCoV-OC43, HCoV-229E, HCoV-NL63, HCoV-NL, HCoV-NH and HCoV-HKU1).

Other combination respiratory virus RNA (e.g., mRNA) vaccines are encompassed by the present disclosure.

It has been discovered that the mRNA vaccines described herein are superior to current vaccines in several ways. First, the lipid nanoparticle (LNP) delivery is superior to other formulations including a protamine base approach described in the literature and no additional adjuvants are to be necessary. The use of LNPs enables the effective delivery of chemically modified or unmodified mRNA vaccines. Additionally it has been demonstrated herein that both modified and unmodified LNP formulated mRNA vaccines were superior to conventional vaccines by a significant degree. In some embodiments the mRNA vaccines of the invention are superior to conventional vaccines by a factor of at least 10 fold, 20 fold, 40 fold, 50 fold, 100 fold, 500 fold or 1,000 fold.

Although attempts have been made to produce functional RNA vaccines, including mRNA vaccines and self-replicating RNA vaccines, the therapeutic efficacy of these RNA vaccines have not yet been fully established. Quite surprisingly, the inventors have discovered, according to aspects of the invention a class of formulations for delivering mRNA vaccines in vivo that results in significantly enhanced, and in many respects synergistic, immune responses including enhanced antigen generation and functional antibody production with neutralization capability. These results can be achieved even when significantly lower doses of the mRNA are administered in comparison with mRNA doses used in other classes of lipid based formulations. The formulations of the invention have demonstrated significant unexpected in vivo immune responses sufficient to establish the efficacy of functional mRNA vaccines as prophylactic and therapeutic agents. Additionally, self-replicating RNA vaccines rely on viral replication pathways to deliver enough RNA to a cell to produce an immunogenic response. The formulations of the invention do not require viral replication to produce enough protein to result in a strong immune response. Thus, the mRNA of the invention are not self-replicating RNA and do not include components necessary for viral replication.

The invention involves, in some aspects, the surprising finding that lipid nanoparticle (LNP) formulations significantly enhance the effectiveness of mRNA vaccines, including chemically modified and unmodified mRNA vaccines. The efficacy of mRNA vaccines formulated in LNP was examined in vivo using several distinct antigens. The results presented herein demonstrate the unexpected superior efficacy of the mRNA vaccines formulated in LNP over other commercially available vaccines.

In addition to providing an enhanced immune response, the formulations of the invention generate a more rapid immune response with fewer doses of antigen than other vaccines tested. The mRNA-LNP formulations of the invention also produce quantitatively and qualitatively better immune responses than vaccines formulated in a different carriers.

The data described herein demonstrate that the formulations of the invention produced significant unexpected improvements over existing antigen vaccines. Additionally, the mRNA-LNP formulations of the invention are superior to other vaccines even when the dose of mRNA is lower than other vaccines. Mice immunized with either 10 μg or 2 μg doses of an hMPV fusion protein mRNA LNP vaccine or a PIV3 mRNA LNP vaccine produced neutralizing antibodies which for instance, successfully neutralized the hMPV B2 virus. A 10 μg dose of mRNA vaccine protected 100% of mice from lethal challenge and drastically reduced the viral titer after challenge (~2 log reduction).

Two 20 μg doses of MERS-CoV mRNA LNP vaccine significantly reduced viral load and induced significant amount of neutralizing antibodies against MERS-CoV ($EC_{50}$ between 500-1000). The MERS-CoV mRNA vaccine induced antibody titer was 3-5 fold better than any other vaccines tested in the same model.

The LNP used in the studies described herein has been used previously to deliver siRNA in various animal models as well as in humans. In view of the observations made in association with the siRNA delivery of LNP formulations, the fact that LNP is useful in vaccines is quite surprising. It has been observed that therapeutic delivery of siRNA formulated in LNP causes an undesirable inflammatory response associated with a transient IgM response, typically leading to a reduction in antigen production and a compromised immune response. In contrast to the findings observed with siRNA, the LNP-mRNA formulations of the invention are demonstrated herein to generate enhanced IgG levels, sufficient for prophylactic and therapeutic methods rather than transient IgM responses.

Nucleic Acids/Polynucleotides

Respiratory virus vaccines, as provided herein, comprise at least one (one or more) ribonucleic acid (RNA) (e.g., mRNA) polynucleotide having an open reading frame encoding at least one antigenic polypeptide selected from hMPV, PIV3, RSV, MeV and BetaCoV (e.g., selected from MERS-CoV, SARS-CoV, HCoV-OC43, HCoV-229E, HCoV-NL63, HCoV-NL, HCoV-NH and HCoV-HKU1) antigenic polypeptides. The term “nucleic acid” includes any compound and/or substance that comprises a polymer of nucleotides (nucleotide monomer). These polymers are referred to as polynucleotides. Thus, the terms “nucleic acid” and “polynucleotide” are used interchangeably.

Nucleic acids may be or may include, for example, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization), ethylene nucleic acids (ENA), cyclohexenyl nucleic acids (CeNA) or chimeras or combinations thereof.

In some embodiments, polynucleotides of the present disclosure function as messenger RNA (mRNA). “Messenger RNA” (mRNA) refers to any polynucleotide that encodes a (at least one) polypeptide (a naturally-occurring, non-naturally-occurring, or modified polymer of amino acids) and can be translated to produce the encoded polypeptide in vitro, in vivo, in situ or ex vivo. The skilled artisan will appreciate that, except where otherwise noted, polynucleotide sequences set forth in the instant application will recite “T”s in a representative DNA sequence but where the sequence represents RNA (e.g., mRNA), the “T”s would be substituted for “U”s. Thus, any of the RNA polynucleotides encoded by a DNA identified by a particular sequence identification number may also comprise the corresponding RNA (e.g., mRNA) sequence encoded by the DNA, where each “T” of the DNA sequence is substituted with “U.”

The basic components of an mRNA molecule typically include at least one coding region, a 5' untranslated region (UTR), a 3' UTR, a 5' cap and a poly-A tail. Polynucleotides of the present disclosure may function as mRNA but can be distinguished from wild-type mRNA in their functional and/or structural design features, which serve to overcome existing problems of effective polypeptide expression using nucleic-acid based therapeutics.

In some embodiments, a RNA polynucleotide of an RNA (e.g., mRNA) vaccine encodes 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9 or 9-10 antigenic polypeptides. In some embodiments, a RNA (e.g., mRNA) polynucleotide of a respiratory virus vaccine encodes at least 10, 20, 30, 40, 50, 60, 70, 80, 90 or 100 antigenic polypeptides. In some embodiments, a RNA (e.g., mRNA) polynucleotide of a respiratory virus vaccine encodes at least 100 or at least 200 antigenic polypeptides. In some embodiments, a RNA polynucleotide of an respiratory virus vaccine encodes 1-10, 5-15, 10-20, 15-25, 20-30, 25-35, 30-40, 35-45, 40-50, 1-50, 1-100, 2-50 or 2-100 antigenic polypeptides.

Polynucleotides of the present disclosure, in some embodiments, are codon optimized. Codon optimization methods are known in the art and may be used as provided herein. Codon optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions; insert or remove protein trafficking sequences; remove/add post translation modification sites in encoded protein (e.g. glycosylation sites); add, remove or shuffle protein domains; insert or delete restriction sites; modify ribosome binding sites and mRNA degradation sites; adjust translational rates to allow the various domains of the protein to fold properly; or to reduce or eliminate problem secondary structures within the polynucleotide. Codon optimization tools, algorithms and services are known in the art—non-limiting examples include services from GeneArt (Life Technologies), DNA2.0 (Menlo Park Calif.) and/or proprietary methods. In some embodiments, the open reading frame (ORF) sequence is optimized using optimization algorithms.

In some embodiments, a codon optimized sequence shares less than 95% sequence identity, less than 90% sequence identity, less than 85% sequence identity, less than 80% sequence identity, or less than 75% sequence identity to a naturally-occurring or wild-type sequence (e.g., a naturally-occurring or wild-type mRNA sequence encoding a polypeptide or protein of interest (e.g., an antigenic protein or antigenic polypeptide)).

In some embodiments, a codon-optimized sequence shares between 65% and 85% (e.g., between about 67% and about 85%, or between about 67% and about 80%) sequence identity to a naturally-occurring sequence or a wild-type sequence (e.g., a naturally-occurring or wild-type mRNA sequence encoding a polypeptide or protein of interest (e.g., an antigenic protein or polypeptide)). In some embodiments, a codon-optimized sequence shares between 65% and 75%, or about 80% sequence identity to a naturally-occurring sequence or wild-type sequence (e.g., a naturally-occurring or wild-type mRNA sequence encoding a polypeptide or protein of interest (e.g., an antigenic protein or polypeptide)).

In some embodiments a codon-optimized RNA (e.g., mRNA) may, for instance, be one in which the levels of G/C are enhanced. The G/C-content of nucleic acid molecules may influence the stability of the RNA. RNA having an increased amount of guanine (G) and/or cytosine (C) residues may be functionally more stable than nucleic acids containing a large amount of adenine (A) and thymine (T) or uracil (U) nucleotides. WO02/098443 discloses a pharmaceutical composition containing an mRNA stabilized by sequence modifications in the translated region. Due to the degeneracy of the genetic code, the modifications work by substituting existing codons for those that promote greater RNA stability without changing the resulting amino acid. The approach is limited to coding regions of the RNA.

Antigens/Antigenic Polypeptides

In some embodiments, an antigenic polypeptide (e.g., a hMPV, PIV3, RSV, MeV or BetaCoV antigenic polypeptide) is longer than 25 amino acids and shorter than 50 amino acids. Polypeptides include gene products, naturally occurring polypeptides, synthetic polypeptides, homologs, orthologs, paralogs, fragments and other equivalents, variants, and analogs of the foregoing. A polypeptide may be a single molecule or may be a multi-molecular complex such as a dimer, trimer or tetramer. Polypeptides may also comprise single chain polypeptides or multichain polypeptides, such as antibodies or insulin, and may be associated or linked to each other. Most commonly, disulfide linkages are found in multichain polypeptides. The term "polypeptide" may also apply to amino acid polymers in which at least one amino acid residue is an artificial chemical analogue of a corresponding naturally-occurring amino acid.

A "polypeptide variant" is a molecule that differs in its amino acid sequence relative to a native sequence or a reference sequence. Amino acid sequence variants may possess substitutions, deletions, insertions, or a combination of any two or three of the foregoing, at certain positions within the amino acid sequence, as compared to a native sequence or a reference sequence. Ordinarily, variants possess at least 50% identity to a native sequence or a reference sequence. In some embodiments, variants share at least 80% identity or at least 90% identity with a native sequence or a reference sequence.

In some embodiments "variant mimics" are provided. A "variant mimic" contains at least one amino acid that would mimic an activated sequence. For example, glutamate may serve as a mimic for phosphoro-threonine and/or phosphoro-serine. Alternatively, variant mimics may result in deactivation or in an inactivated product containing the mimic. For example, phenylalanine may act as an inactivating substitution for tyrosine, or alanine may act as an inactivating substitution for serine.

"Orthologs" refers to genes in different species that evolved from a common ancestral gene by speciation. Normally, orthologs retain the same function in the course of evolution. Identification of orthologs is important for reliable prediction of gene function in newly sequenced genomes.

"Analogs" is meant to include polypeptide variants that differ by one or more amino acid alterations, for example, substitutions, additions or deletions of amino acid residues that still maintain one or more of the properties of the parent or starting polypeptide.

The present disclosure provides several types of compositions that are polynucleotide or polypeptide based, including variants and derivatives. These include, for example, substitutional, insertional, deletion and covalent variants and derivatives. The term "derivative" is synonymous with the term "variant" and generally refers to a molecule that has been modified and/or changed in any way relative to a reference molecule or a starting molecule.

As such, polynucleotides encoding peptides or polypeptides containing substitutions, insertions and/or additions, deletions and covalent modifications with respect to reference sequences, in particular the polypeptide sequences disclosed herein, are included within the scope of this disclosure. For example, sequence tags or amino acids, such as one or more lysines, can be added to peptide sequences (e.g., at the N-terminal or C-terminal ends). Sequence tags can be used for peptide detection, purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal residues or N-terminal residues) alternatively may be deleted depending on the use of the sequence, as for example, expression of the sequence as part of a larger sequence that is soluble, or linked to a solid support.

"Substitutional variants" when referring to polypeptides are those that have at least one amino acid residue in a native or starting sequence removed and a different amino acid inserted in its place at the same position. Substitutions may be single, where only one amino acid in the molecule has been substituted, or they may be multiple, where two or more (e.g., 3, 4 or 5) amino acids have been substituted in the same molecule.

As used herein the term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue such as lysine, arginine or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

"Features" when referring to polypeptide or polynucleotide are defined as distinct amino acid sequence-based or nucleotide-based components of a molecule respectively. Features of the polypeptides encoded by the polynucleotides include surface manifestations, local conformational shape, folds, loops, half-loops, domains, half-domains, sites, termini and any combination(s) thereof.

As used herein when referring to polypeptides the term "domain" refers to a motif of a polypeptide having one or more identifiable structural or functional characteristics or properties (e.g., binding capacity, serving as a site for protein-protein interactions).

As used herein when referring to polypeptides the terms "site" as it pertains to amino acid based embodiments is used synonymously with "amino acid residue" and "amino acid side chain." As used herein when referring to polynucleotides the terms "site" as it pertains to nucleotide based embodiments is used synonymously with "nucleotide." A site represents a position within a peptide or polypeptide or polynucleotide that may be modified, manipulated, altered, derivatized or varied within the polypeptide-based or polynucleotide-based molecules.

As used herein the terms "termini" or "terminus" when referring to polypeptides or polynucleotides refers to an extremity of a polypeptide or polynucleotide respectively. Such extremity is not limited only to the first or final site of the polypeptide or polynucleotide but may include additional amino acids or nucleotides in the terminal regions. Polypeptide-based molecules may be characterized as having both an N-terminus (terminated by an amino acid with a free amino group (NH2)) and a C-terminus (terminated by an amino acid with a free carboxyl group (COOH)). Proteins are in some cases made up of multiple polypeptide chains brought together by disulfide bonds or by non-covalent forces (multimers, oligomers). These proteins have multiple N- and C-termini. Alternatively, the termini of the polypeptides may be modified such that they begin or end, as the case may be, with a non-polypeptide based moiety such as an organic conjugate.

As recognized by those skilled in the art, protein fragments, functional protein domains, and homologous proteins are also considered to be within the scope of polypeptides of interest. For example, provided herein is any protein fragment (meaning a polypeptide sequence at least one amino acid residue shorter than a reference polypeptide sequence but otherwise identical) of a reference protein having a length of 10, 20, 30, 40, 50, 60, 70, 80, 90, 100 or longer than 100 amino acids. In another example, any protein that includes a stretch of 20, 30, 40, 50, or 100 (contiguous) amino acids that are 40%, 50%, 60%, 70%, 80%, 90%, 95%, or 100% identical to any of the sequences described herein can be utilized in accordance with the disclosure. In some embodiments, a polypeptide includes 2, 3, 4, 5, 6, 7, 8, 9, 10, or more mutations as shown in any of the sequences provided herein or referenced herein. In another example, any protein that includes a stretch of 20, 30, 40, 50, or 100 amino acids that are greater than 80%, 90%, 95%, or 100% identical to any of the sequences described herein, wherein the protein has a stretch of 5, 10, 15, 20, 25, or 30 amino acids that are less than 80%, 75%, 70%, 65% to 60% identical to any of the sequences described herein can be utilized in accordance with the disclosure.

Polypeptide or polynucleotide molecules of the present disclosure may share a certain degree of sequence similarity or identity with the reference molecules (e.g., reference polypeptides or reference polynucleotides), for example, with art-described molecules (e.g., engineered or designed molecules or wild-type molecules). The term "identity," as known in the art, refers to a relationship between the sequences of two or more polypeptides or polynucleotides, as determined by comparing the sequences. In the art, identity also means the degree of sequence relatedness between two sequences as determined by the number of matches between strings of two or more amino acid residues or nucleic acid residues. Identity measures the percent of identical matches between the smaller of two or more sequences with gap alignments (if any) addressed by a particular mathematical model or computer program (e.g., "algorithms"). Identity of related peptides can be readily calculated by known methods. "% identity" as it applies to polypeptide or polynucleotide sequences is defined as the percentage of residues (amino acid residues or nucleic acid residues) in the candidate amino acid or nucleic acid sequence that are identical with the residues in the amino acid sequence or nucleic acid sequence of a second sequence after aligning the sequences and introducing gaps, if necessary, to achieve the maximum percent identity. Methods and computer programs for the alignment are well known in the art. Identity depends on a calculation of percent identity but may differ in value due to gaps and penalties introduced in the calculation. Generally, variants of a particular polynucleotide or polypeptide have at least 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. Such tools for alignment include those of the BLAST suite (Stephen F. Altschul, et al. (1997). "Gapped BLAST and PSI-BLAST: a new generation of protein database search programs," *Nucleic Acids Res.* 25:3389-3402). Another popular local alignment technique is based on the Smith-Waterman algorithm (Smith, T. F. & Waterman, M. S. (1981) "Identification of common molecular subsequences." *J. Mol. Biol.* 147:195-197). A general global alignment technique based on dynamic programming is the Needleman-Wunsch algorithm (Needleman, S. B. & Wunsch, C. D. (1970) "A general method applicable to the search for similarities in the amino acid sequences of two proteins." *J. Mol. Biol.* 48:443-453). More recently, a Fast Optimal Global Sequence Alignment Algorithm (FOGSAA) was developed that purportedly produces global alignment of nucleotide and protein sequences faster than other optimal global alignment methods, including the Needleman-Wunsch algorithm. Other tools are described herein, specifically in the definition of "identity" below.

As used herein, the term "homology" refers to the overall relatedness between polymeric molecules, e.g. between nucleic acid molecules (e.g. DNA molecules and/or RNA molecules) and/or between polypeptide molecules. Polymeric molecules (e.g. nucleic acid molecules (e.g. DNA molecules and/or RNA molecules) and/or polypeptide molecules) that share a threshold level of similarity or identity determined by alignment of matching residues are termed homologous. Homology is a qualitative term that describes a relationship between molecules and can be based upon the quantitative similarity or identity. Similarity or identity is a quantitative term that defines the degree of sequence match between two compared sequences. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). Two polynucleotide sequences are considered homologous if the polypeptides they encode are at least 50%, 60%, 70%, 80%, 90%, 95%, or even 99% for at least one stretch of at least 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. Two protein sequences are considered homologous if the proteins are at least 50%, 60%, 70%, 80%, or 90% identical for at least one stretch of at least 20 amino acids.

Homology implies that the compared sequences diverged in evolution from a common origin. The term "homolog" refers to a first amino acid sequence or nucleic acid sequence (e.g., gene (DNA or RNA) or protein sequence) that is related to a second amino acid sequence or nucleic acid sequence by descent from a common ancestral sequence. The term "homolog" may apply to the relationship between genes and/or proteins separated by the event of speciation or to the relationship between genes and/or proteins separated by the event of genetic duplication. "Orthologs" are genes (or proteins) in different species that evolved from a common ancestral gene (or protein) by speciation. Typically, orthologs retain the same function in the course of evolution. "Paralogs" are genes (or proteins) related by duplication within a genome. Orthologs retain the same function in the course of evolution, whereas paralogs evolve new functions, even if these are related to the original one.

The term "identity" refers to the overall relatedness between polymeric molecules, for example, between polynucleotide molecules (e.g. DNA molecules and/or RNA molecules) and/or between polypeptide molecules. Calculation of the percent identity of two polynucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleic acid sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleic acid sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleic acid sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM *J Applied Math.,* 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research,* 12(1), 387 (1984)), BLASTP, BLASTN, and FASTA Altschul, S. F. et al., *J. Molec. Biol.,* 215, 403 (1990)).

Multiprotein and Multicomponent Vaccines

The present disclosure encompasses respiratory virus vaccines comprising multiple RNA (e.g., mRNA) polynucleotides, each encoding a single antigenic polypeptide, as well as respiratory virus vaccines comprising a single RNA polynucleotide encoding more than one antigenic polypeptide (e.g., as a fusion polypeptide). Thus, a vaccine composition comprising a RNA (e.g., mRNA) polynucleotide having an open reading frame encoding a first antigenic polypeptide and a RNA (e.g., mRNA) polynucleotide having an open reading frame encoding a second antigenic polypeptide encompasses (a) vaccines that comprise a first RNA polynucleotide encoding a first antigenic polypeptide and a second RNA polynucleotide encoding a second antigenic polypeptide, and (b) vaccines that comprise a single RNA polynucleotide encoding a first and second antigenic polypeptide (e.g., as a fusion polypeptide). RNA (e.g., mRNA) vaccines of the present disclosure, in some embodiments, comprise 2-10 (e.g., 2, 3, 4, 5, 6, 7, 8, 9 or 10), or more, RNA polynucleotides having an open reading frame, each of which encodes a different antigenic polypeptide (or a single RNA polynucleotide encoding 2-10, or more, different antigenic polypeptides). The antigenic polypeptides may be selected from hMPV, PIV3, RSV, MEV and BetaCoV (e.g., selected from MERS-CoV, SARS-CoV, HCoV-OC43, HCoV-229E, HCoV-NL63, HCoV-NL, HCoV-NH and HCoV-HKU1) antigenic polypeptides.

In some embodiments, a respiratory virus vaccine comprises a RNA (e.g., mRNA) polynucleotide having an open reading frame encoding a viral capsid protein, a RNA (e.g., mRNA) polynucleotide having an open reading frame encoding a viral premembrane/membrane protein, and a RNA (e.g., mRNA) polynucleotide having an open reading frame encoding a viral envelope protein. In some embodiments, a respiratory virus vaccine comprises a RNA (e.g., mRNA) polynucleotide having an open reading frame encoding a viral fusion (F) protein and a RNA polynucleotide having an open reading frame encoding a viral major surface glycoprotein (G protein). In some embodiments, a vaccine comprises a RNA (e.g., mRNA) polynucleotide having an open reading frame encoding a viral F protein. In some embodiments, a vaccine comprises a RNA (e.g., mRNA) polynucleotide having an open reading frame encoding a viral G protein. In some embodiments, a vaccine comprises a RNA (e.g., mRNA) polynucleotide having an open reading frame encoding a HN protein.

In some embodiments, a multicomponent vaccine comprises at least one RNA (e.g., mRNA) polynucleotide encoding at least one antigenic polypeptide fused to a signal peptide (e.g., any one of SEQ ID NO: 15-19). The signal peptide may be fused at the N-terminus or the C-terminus of an antigenic polypeptide. An antigenic polypeptide fused to a signal peptide may be selected from hMPV, PIV3, RSV, MEV and BetaCoV (e.g., selected from MERS-CoV, SARS-CoV, HCoV-OC43, HCoV-229E, HCoV-NL63, HCoV-NL, HCoV-NH and HCoV-HKU1) antigenic polypeptides.

Signal Peptides

In some embodiments, antigenic polypeptides encoded by respiratory virus RNA (e.g., mRNA) polynucleotides comprise a signal peptide. Signal peptides, comprising the N-terminal 15-60 amino acids of proteins, are typically needed for the translocation across the membrane on the secretory pathway and, thus, universally control the entry of most proteins both in eukaryotes and prokaryotes to the secretory pathway. Signal peptides generally include three regions: an N-terminal region of differing length, which usually comprises positively charged amino acids; a hydrophobic region; and a short carboxy-terminal peptide region. In eukaryotes, the signal peptide of a nascent precursor protein (pre-protein) directs the ribosome to the rough endoplasmic reticulum (ER) membrane and initiates the transport of the growing peptide chain across it for processing. ER processing produces mature proteins, wherein the signal peptide is cleaved from precursor proteins, typically by a ER-resident signal peptidase of the host cell, or they remain uncleaved and function as a membrane anchor. A signal peptide may also facilitate the targeting of the protein to the cell membrane. The signal peptide, however, is not responsible for the final destination of the mature protein. Secretory proteins devoid of additional address tags in their sequence are by default secreted to the external environment. During recent years, a more advanced view of signal peptides has evolved, showing that the functions and immunodominance of certain signal peptides are much more versatile than previously anticipated.

Respiratory virus vaccines of the present disclosure may comprise, for example, RNA (e.g., mRNA) polynucleotides encoding an artificial signal peptide, wherein the signal peptide coding sequence is operably linked to and is in frame with the coding sequence of the antigenic polypeptide. Thus, respiratory virus vaccines of the present disclosure, in some embodiments, produce an antigenic polypeptide comprising an antigenic polypeptide (e.g., hMPV, PIV3, RSV, MeV or BetaCoV) fused to a signal peptide. In some embodiments, a signal peptide is fused to the N-terminus of the antigenic polypeptide. In some embodiments, a signal peptide is fused to the C-terminus of the antigenic polypeptide.

In some embodiments, the signal peptide fused to the antigenic polypeptide is an artificial signal peptide. In some embodiments, an artificial signal peptide fused to the antigenic polypeptide encoded by the RNA (e.g., mRNA) vaccine is obtained from an immunoglobulin protein, e.g., an IgE signal peptide or an IgG signal peptide. In some embodiments, a signal peptide fused to the antigenic polypeptide encoded by a RNA (e.g., mRNA) vaccine is an Ig heavy chain epsilon-1 signal peptide (IgE HC SP) having the sequence of: MDWTWILFLVAAATRVHS (SEQ ID NO: 16). In some embodiments, a signal peptide fused to the antigenic polypeptide encoded by the (e.g., mRNA) RNA (e.g., mRNA) vaccine is an IgGk chain V-III region HAH signal peptide (IgGk SP) having the sequence of METPAQLLFLLLLWLPDTTG (SEQ ID NO: 15). In some embodiments, the signal peptide is selected from: Japanese encephalitis PRM signal sequence (MLGSNSGQRVVFTILLLLVAPAYS; SEQ ID NO: 17), VSVg protein signal sequence (MKCLLYLAFLFIGVNCA; SEQ ID NO: 18) and Japanese encephalitis JEV signal sequence (MWLVSLAIVTACAGA; SEQ ID NO: 19).

In some embodiments, the antigenic polypeptide encoded by a RNA (e.g., mRNA) vaccine comprises an amino acid sequence identified by any one of SEQ ID NO: 5-8, 12-13, 24-34, 47-50 or 54-56 (Tables 3, 6, 11, 14 or 17; see also amino acid sequences of Tables 4, 7, 12 or 15) fused to a signal peptide identified by any one of SEQ ID NO: 15-19 (Table 8). The examples disclosed herein are not meant to be limiting and any signal peptide that is known in the art to facilitate targeting of a protein to ER for processing and/or targeting of a protein to the cell membrane may be used in accordance with the present disclosure.

A signal peptide may have a length of 15-60 amino acids. For example, a signal peptide may have a length of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids. In some embodiments, a signal peptide has a length of 20-60, 25-60, 30-60, 35-60, 40-60, 45-60, 50-60, 55-60, 15-55, 20-55, 25-55, 30-55, 35-55, 40-55, 45-55, 50-55, 15-50, 20-50, 25-50, 30-50, 35-50, 40-50, 45-50, 15-45, 20-45, 25-45, 30-45, 35-45, 40-45, 15-40, 20-40, 25-40, 30-40, 35-40, 15-35, 20-35, 25-35, 30-35, 15-30, 20-30, 25-30, 15-25, 20-25, or 15-20 amino acids.

A signal peptide is typically cleaved from the nascent polypeptide at the cleavage junction during ER processing. The mature antigenic polypeptide produce by a respiratory virus RNA (e.g., mRNA) vaccine of the present disclosure typically does not comprise a signal peptide.

Chemical Modifications

Respiratory virus vaccines of the present disclosure, in some embodiments, comprise at least RNA (e.g. mRNA) polynucleotide having an open reading frame encoding at least one antigenic polypeptide that comprises at least one chemical modification.

The terms "chemical modification" and "chemically modified" refer to modification with respect to adenosine (A), guanosine (G), uridine (U), thymidine (T) or cytidine (C) ribonucleosides or deoxyribnucleosides in at least one of their position, pattern, percent or population. Generally, these terms do not refer to the ribonucleotide modifications in naturally occurring 5'-terminal mRNA cap moieties. With respect to a polypeptide, the term "modification" refers to a modification relative to the canonical set 20 amino acids. Polypeptides, as provided herein, are also considered "modified" of they contain amino acid substitutions, insertions or a combination of substitutions and insertions.

Polynucleotides (e.g., RNA polynucleotides, such as mRNA polynucleotides), in some embodiments, comprise various (more than one) different modifications. In some embodiments, a particular region of a polynucleotide contains one, two or more (optionally different) nucleoside or nucleotide modifications. In some embodiments, a modified RNA polynucleotide (e.g., a modified mRNA polynucleotide), introduced to a cell or organism, exhibits reduced degradation in the cell or organism, respectively, relative to an unmodified polynucleotide. In some embodiments, a modified RNA polynucleotide (e.g., a modified mRNA polynucleotide), introduced into a cell or organism, may exhibit reduced immunogenicity in the cell or organism, respectively (e.g., a reduced innate response).

Modifications of polynucleotides include, without limitation, those described herein. Polynucleotides (e.g., RNA polynucleotides, such as mRNA polynucleotides) may comprise modifications that are naturally-occurring, non-naturally-occurring or the polynucleotide may comprise a combination of naturally-occurring and non-naturally-occurring modifications. Polynucleotides may include any useful modification, for example, of a sugar, a nucleobase, or an internucleoside linkage (e.g., to a linking phosphate, to a phosphodiester linkage or to the phosphodiester backbone).

Polynucleotides (e.g., RNA polynucleotides, such as mRNA polynucleotides), in some embodiments, comprise non-natural modified nucleotides that are introduced during synthesis or post-synthesis of the polynucleotides to achieve desired functions or properties. The modifications may be present on an internucleotide linkages, purine or pyrimidine bases, or sugars. The modification may be introduced with chemical synthesis or with a polymerase enzyme at the terminal of a chain or anywhere else in the chain. Any of the regions of a polynucleotide may be chemically modified.

The present disclosure provides for modified nucleosides and nucleotides of a polynucleotide (e.g., RNA polynucleotides, such as mRNA polynucleotides). A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A nucleotide" refers to a nucleoside, including a phosphate group. Modified nucleotides may by synthesized by any useful method, such as, for example, chemically, enzymatically, or recombinantly, to include one or more modified or non-natural nucleosides. Polynucleotides may comprise a region or regions of linked nucleosides. Such regions may have variable backbone linkages. The linkages may be standard phosphdioester linkages, in which case the polynucleotides would comprise regions of nucleotides.

Modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures. One example of such non-standard base pairing is the base pairing between the modified nucleotide inosine and adenine, cytosine or uracil. Any combination of base/sugar or linker may be incorporated into polynucleotides of the present disclosure.

Modifications of polynucleotides (e.g., RNA polynucleotides, such as mRNA polynucleotides) that are useful in the vaccines of the present disclosure include, but are not limited to the following: 2-methylthio-N6-(cis-hydroxyisopentenyl)adenosine; 2-methylthio-N6-methyladenosine; 2-methylthio-N6-threonyl carbamoyladenosine; N6-glycinylcarbamoyladenosine; N6-isopentenyladenosine; N6-methyladenosine; N6-threonylcarbamoyladenosine; 1,2'-O-dimethyladenosine; 1-methyladenosine; 2'-O-methyladenosine; 2'-O-ribosyladenosine (phosphate); 2-methyladenosine; 2-methylthio-N6 isopentenyladenosine; 2-methylthio-N6-hydroxynorvalyl carbamoyladenosine; 2'-O-methyladenosine; 2'-O-ribosyladenosine (phosphate); Isopentenyladenosine; N6-(cis-hydroxyisopentenyl)adenosine; N6,2'-O-dimethyladenosine; N6,2'-O-dimethyladenosine; N6,N6,2'-O-trimethyladenosine; N6,N6-dimethyladenosine; N6-acetyladenosine; N6-hydroxynorvalylcarbamoyladenosine; N6-methyl-N6-threonylcarbamoyladenosine; 2-methyladenosine; 2-methylthio-N6-isopentenyladenosine; 7-deaza-adenosine; N1-methyl-adenosine; N6, N6 (dimethyl)adenine; N6-cis-hydroxy-isopentenyl-adenosine; α-thio-adenosine; 2 (amino)adenine; 2 (aminopropyl)adenine; 2 (methylthio) N6 (isopentenyl)adenine; 2-(alkyl)adenine; 2-(aminoalkyl)adenine; 2-(aminopropyl)adenine; 2-(halo)adenine; 2-(halo) adenine; 2-(propyl)adenine; 2'-Amino-2'-deoxy-ATP; 2'-Azido-2'-deoxy-ATP; 2'-Deoxy-2'-α-aminoadenosine TP; 2'-Deoxy-2'-α-azidoadenosine TP; 6 (alkyl)adenine; 6 (methyl)adenine; 6-(alkyl)adenine; 6-(methyl)adenine; 7 (deaza)adenine; 8 (alkenyl)adenine; 8 (alkynyl)adenine; 8 (amino)adenine; 8 (thioalkyl)adenine; 8-(alkenyl)adenine; 8-(alkyl)adenine; 8-(alkynyl)adenine; 8-(amino)adenine; 8-(halo)adenine; 8-(hydroxyl)adenine; 8-(thioalkyl)adenine; 8-(thiol)adenine; 8-azido-adeno sine; aza adenine; deaza adenine; N6 (methyl)adenine; N6-(isopentyl)adenine; 7-deaza-8-aza-adenosine; 7-methyladenine; 1-Deazaadenosine TP; 2'Fluoro-N6-Bz-deoxyadenosine TP; 2'-OMe-2-Amino-ATP; 2'O-methyl-N6-Bz-deoxyadenosine TP; 2'-α-Ethynyladenosine TP; 2-aminoadenine; 2-Aminoadenosine TP; 2-Amino-ATP; 2'-α-Trifluoromethyladenosine TP; 2-Azidoadenosine TP; 2'-b-Ethynyladenosine TP; 2-Bromoadenosine TP; 2'-b-Trifluoromethyladenosine TP; 2-Chloroadenosine TP; 2'-Deoxy-2',2'-difluoroadenosine TP; 2'-Deoxy-2'-a-mercaptoadenosine TP; 2'-Deoxy-2'-a-thiomethoxyadenosine TP; 2'-Deoxy-2'-b-aminoadenosine TP; 2'-Deoxy-2'-b-azidoadenosine TP; 2'-Deoxy-2'-b-bromoadenosine TP; 2'-Deoxy-2'-b-chloroadenosine TP; 2'-Deoxy-2'-b-fluoroadenosine TP; 2'-Deoxy-2'-b-iodoadenosine TP; 2'-Deoxy-2'-b-mercaptoadenosine TP; 2'-Deoxy-2'-b-thiomethoxyadenosine TP; 2-Fluoroadenosine TP; 2-Iodoadenosine TP; 2-Mercaptoadenosine TP; 2-methoxy-adenine; 2-methylthio-adenine; 2-Trifluoromethyladenosine TP; 3-Deaza-3-bromoadenosine TP; 3-Deaza-3-chloroadenosine TP; 3-Deaza-3-fluoroadenosine TP; 3-Deaza-3-iodoadenosine TP; 3-Deazaadenosine TP; 4'-Azidoadenosine TP; 4'-Carbocyclic adenosine TP; 4'-Ethynyladenosine TP; 5'-Homo-adenosine TP; 8-Aza-ATP; 8-bromo-adenosine TP; 8-Trifluoromethyladenosine TP; 9-Deazaadenosine TP; 2-aminopurine; 7-deaza-2,6-diaminopurine; 7-deaza-8-aza-2,6-diaminopurine; 7-deaza-8-aza-2-aminopurine; 2,6-diaminopurine; 7-deaza-8-aza-adenine, 7-deaza-2-aminopurine; 2-thiocytidine; 3-methylcytidine; 5-formylcytidine; 5-hydroxymethylcytidine; 5-methylcytidine; N4-acetylcytidine; 2'-O-methylcytidine; 2'-O-methylcytidine; 5,2'-O-dimethylcytidine; 5-formyl-2'-O-methylcytidine; Lysidine; N4,2'-O-dimethylcytidine; N4-acetyl-2'-O-methylcytidine; N4-methylcytidine; N4,N4-Dimethyl-2'-OMe-Cytidine TP; 4-methylcytidine; 5-aza-cytidine; Pseudo-iso-cytidine; pyrrolo-cytidine; α-thio-cytidine; 2-(thio)cytosine; 2'-Amino-2'-deoxy-CTP; 2'-Azido-2'-deoxy-CTP; 2'-Deoxy-2'-a-aminocytidine TP; 2'-Deoxy-2'-a-azidocytidine TP; 3 (deaza) 5 (aza)cytosine; 3 (methyl)cytosine; 3-(alkyl)cytosine; 3-(deaza) 5 (aza)cytosine; 3-(methyl)cytidine; 4,2'-O-dimethylcytidine; 5 (halo)cytosine; 5 (methyl)cytosine; 5 (propynyl)cytosine; 5 (trifluoromethyl)cytosine; 5-(alkyl) cytosine; 5-(alkynyl)cytosine; 5-(halo)cytosine; 5-(propynyl)cytosine; 5-(trifluoromethyl)cytosine; 5-bromo-cytidine; 5-iodo-cytidine; 5-propynyl cytosine; 6-(azo)cytosine; 6-aza-cytidine; aza cytosine; deaza cytosine; N4 (acetyl) cytosine; 1-methyl-1-deaza-pseudoisocytidine; 1-methyl-pseudoisocytidine; 2-methoxy-5-methyl-cytidine; 2-methoxy-cytidine; 2-thio-5-methyl-cytidine; 4-methoxy-1-methyl-pseudoisocytidine; 4-methoxy-pseudoisocytidine; 4-thio-1-methyl-1-deaza-pseudoisocytidine; 4-thio-1-methyl-pseudoisocytidine; 4-thio-pseudoisocytidine; 5-aza-zebularine; 5-methyl-zebularine; pyrrolo-pseudoisocytidine; Zebularine; (E)-5-(2-Bromo-vinyl)cytidine TP; 2,2'-anhydro-cytidine TP hydrochloride; 2'Fluor-N4-Bz-cytidine TP; 2'Fluoro-N4-Acetyl-cytidine TP; 2'-O-Methyl-N4-Acetyl-cytidine TP; 2'O-methyl-N4-Bz-cytidine TP; 2'-a-Ethynylcytidine TP; 2'-a-Trifluoromethylcytidine TP; 2'-b-Ethynylcytidine TP; 2'-b-Trifluoromethylcytidine TP; 2'-Deoxy-2',2'-difluorocytidine TP; 2'-Deoxy-2'-a-mercaptocytidine TP; 2'-Deoxy-2'-a-thiomethoxycytidine TP; 2'-Deoxy-2'-b-aminocytidine TP; 2'-Deoxy-2'-b-azidocytidine TP; 2'-Deoxy-2'-b-bromocytidine TP; 2'-Deoxy-2'-b-chlorocytidine TP; 2'-Deoxy-2'-b-fluorocytidine TP; 2'-Deoxy-2'-b-iodocytidine TP; 2'-Deoxy-2'-b-mercaptocytidine TP; 2'-Deoxy-2'-b-thiomethoxycytidine TP; 2'-O-Methyl-5-(1-propynyl)cytidine TP; 3'-Ethynylcytidine TP; 4'-Azidocytidine TP; 4'-Carbocyclic cytidine TP; 4'-Ethynylcytidine TP; 5-(1-Propynyl)ara-cytidine TP; 5-(2-Chloro-phenyl)-2-thiocytidine TP; 5-(4-Amino-phenyl)-2-thiocytidine TP; 5-Aminoallyl-CTP; 5-Cyanocytidine TP; 5-Ethynylara-cytidine TP; 5-Ethynylcytidine TP; 5'-Homo-cytidine TP; 5-Methoxycytidine TP; 5-Trifluoromethyl-Cytidine TP; N4-Amino-cytidine TP; N4-Benzoyl-cytidine TP; Pseudoisocytidine; 7-methylguanosine; N2,2'-O-dimethylguanosine; N2-methylguanosine; Wyosine; 1,2'-O-dimethylguanosine; 1-methylguanosine; 2'-O-methylguanosine; 2'-O-ribosylguanosine (phosphate); 2'-O-methylguanosine; 2'-O-ribosylguanosine (phosphate); 7-aminomethyl-7-deazaguanosine; 7-cyano-7-deazaguanosine; Archaeosine; Methylwyosine; N2,7-dimethylguanosine; N2,N2,2'-O-trimethylguanosine; N2,N2,7-trimethylguanosine; N2,N2-dimethylguanosine; N2,7,2'-O-trimethylguanosine; 6-thio-guanosine; 7-deaza-guanosine; 8-oxo-guanosine; N1-methyl-guanosine; α-thio-guanosine; 2 (propyl)guanine; 2-(alkyl)guanine; 2'-Amino-2'-deoxy-GTP; 2'-Azido-2'-deoxy-GTP; 2'-Deoxy-2'-a-aminoguanosine TP; 2'-Deoxy-2'-a-azidoguanosine TP; 6 (methyl)guanine; 6-(alkyl)guanine; 6-(methyl)guanine; 6-methyl-guanosine; 7 (alkyl)guanine; 7 (deaza)guanine; 7 (methyl)guanine; 7-(alkyl)guanine; 7-(deaza)guanine; 7-(methyl)guanine; 8 (alkyl)guanine; 8 (alkynyl)guanine; 8 (halo)guanine; 8 (thioalkyl)guanine; 8-(alkenyl)guanine; 8-(alkyl)guanine; 8-(alkynyl)guanine; 8-(amino)guanine; 8-(halo)guanine; 8-(hydroxyl)guanine; 8-(thioalkyl)guanine; 8-(thiol)guanine; aza guanine; deaza guanine; N (methyl)guanine; N-(methyl)guanine; 1-methyl-6-thio-guanosine; 6-methoxy-guanosine; 6-thio-7-deaza-8-aza-guanosine; 6-thio-7-deaza-guanosine; 6-thio-7-methyl-guanosine; 7-deaza-8-aza-guanosine; 7-methyl-8-oxo-guanosine; N2,N2-dimethyl-6-thio-guanosine; N2-methyl-6-thio-guanosine; 1-Me-GTP; 2'Fluoro-N2-isobutyl-guanosine TP; 2'O-methyl-N2-isobutyl-guanosine TP; 2'-a-Ethynylguanosine TP; 2'-a-Trifluoromethylguanosine TP; 2'-b-Ethynylguanosine TP; 2'-b-Trifluoromethylguanosine TP; 2'-Deoxy-2',2'-difluoroguanosine TP; 2'-Deoxy-2'-a-mercaptoguanosine TP; 2'-Deoxy-2'-a-thiomethoxyguanosine TP; 2'-Deoxy-2'-b-aminoguanosine TP; 2'-Deoxy-2'-b-azidoguanosine TP; 2'-Deoxy-2'-b-bromoguanosine TP; 2'-Deoxy-2'-b-chloroguanosine TP; 2'-Deoxy-2'-b-fluoroguanosine TP; 2'-Deoxy-2'-b-iodoguanosine TP; 2'-Deoxy-2'-b-mercaptoguanosine TP; 2'-Deoxy-2'-b-thiomethoxyguanosine TP; 4'-Azidoguanosine TP; 4'-Carbocyclic guanosine TP; 4'-Ethynylguanosine TP; 5'-Homo-guanosine TP; 8-bromo-guanosine TP; 9-Deazaguanosine TP; N2-isobutyl-guanosine TP; 1-methylinosine; Inosine; 1,2'-O-dimethylinosine; 2'-O-methylinosine; 7-methylinosine; 2'-O-methylinosine; Epoxyqueuosine; galactosyl-queuosine; Mannosylqueuosine; Queuosine; allyamino-thymidine; aza thymidine; deaza thymidine; deoxy-thymidine; 2'-O-methyluridine; 2-thiouridine; 3-methyluridine; 5-carboxymethyluridine; 5-hydroxyuridine; 5-methyluridine; 5-taurinomethyl-2-thiouridine; 5-taurinomethyluridine; Dihydrouridine; Pseudouridine; (3-(3-amino-3-carboxypropyl)uridine; 1-methyl-3-(3-amino-5-carboxypropyl)pseudouridine; 1-methylpseduouridine; 1-methyl-pseudouridine; 2'-O-methyluridine; 2'-O-methylpseudouridine; 2'-O-methyluridine; 2-thio-2'-O-methyluridine; 3-(3-amino-3-carboxypropyl)uridine; 3,2'-O-dimethyluridine; 3-Methyl-pseudo-Uridine TP; 4-thiouridine; 5-(carboxyhydroxymethyl)uridine; 5-(carboxyhydroxymethyl)uridine methyl ester; 5,2'-O-dimethyluridine; 5,6-dihydro-uridine; 5-aminomethyl-2-thiouridine; 5-carbamoylmethyl-2'-O-methyluridine; 5-carbamoylmethyluridine; 5-carboxyhydroxymethyluridine; 5-carboxyhydroxymethyluridine methyl ester; 5-carboxymethylaminomethyl-2'-O-methyluridine; 5-carboxymethylaminomethyl-2-thiouridine; 5-carboxymethylaminomethyl-2-thiouridine; 5-carboxymethylaminomethyluridine; 5-carboxymethylaminomethyluridine; 5-Carbamoylmethyluridine TP; 5-methoxycarbonylmethyl-2'-O-methyluridine; 5-methoxycarbonylmethyl-2-thiouridine; 5-methoxycarbonylmethyluridine; 5-methoxyuridine; 5-methyl-2-thiouridine; 5-methylaminomethyl-2-selenouridine; 5-methylaminomethyl-2-thiouridine; 5-methylaminomethyluridine; 5-Methyldihydrouridine; 5-Oxyacetic acid-Uridine TP; 5-Oxyacetic acid-methyl ester-Uridine TP; N1-methyl-pseudo-uridine; uridine 5-oxyacetic acid; uridine 5-oxyacetic acid methyl ester; 3-(3-Amino-3-carboxypropyl)-Uridine TP; 5-(iso-Pentenylaminomethyl)-2-thiouridine TP; 5-(iso-Pentenylaminomethyl)-2'-O-methyluridine TP; 5-(iso-Pentenylaminomethyl)uridine TP; 5-propynyl uracil; α-thio-uridine; 1 (aminoalkylamino-carbonylethylenyl)-2 (thio)-pseudouracil; 1 (aminoalkylaminocarbonylethylenyl)-2,4-(dithio)pseudouracil; 1 (aminoalkylaminocarbonylethylenyl)-4 (thio)pseudouracil; 1 (aminoalkylaminocarbonylethylenyl)-pseudouracil; 1 (aminocarbonylethylenyl)-2(thio)-pseudouracil; 1 (aminocarbonylethylenyl)-2,4-(dithio)pseudouracil; 1 (aminocarbonylethylenyl)-4 (thio)pseudouracil; 1 (aminocarbonylethylenyl)-pseudouracil; 1 substituted 2(thio)-pseudouracil; 1 substituted 2,4-(dithio)pseudouracil; 1 substituted 4 (thio) pseudouracil; 1 substituted pseudouracil; 1-(aminoalkylamino-carbonylethylenyl)-2-(thio)-pseudouracil; 1-Methyl-3-(3-amino-3-carboxypropyl) pseudouridine TP; 1-Methyl-3-(3-amino-3-carboxypropyl)pseudo-UTP; 1-Methyl-pseudo-UTP; 2 (thio)pseudouracil; 2' deoxy uridine; 2' fluorouridine; 2-(thio)uracil; 2,4-(dithio)psuedouracil; 2' methyl, 2'amino, 2'azido, 2'fluro-guanosine; 2'-Amino-2'-deoxy-UTP; 2'-Azido-2'-deoxy-UTP; 2'-Azido-deoxyuridine TP; 2'-O-methylpseudouridine; 2' deoxy uridine; 2' fluorouridine; 2'-Deoxy-2'-a-aminouridine TP; 2'-Deoxy-2'-a-azidouridine TP; 2-methylpseudouridine; 3 (3 amino-3 carboxypropyl)uracil; 4 (thio)pseudouracil; 4-(thio)pseudouracil; 4-(thio)uracil; 4-thiouracil; 5 (1,3-diazole-1-alkyl)uracil; 5 (2-aminopropyl)uracil; 5 (aminoalkyl)uracil; 5 (dimethylaminoalkyl)uracil; 5 (guanidiniumalkyl)uracil; 5 (methoxycarbonylmethyl)-2-(thio)uracil; 5 (methoxycarbonyl-methyl)uracil; 5 (methyl) 2 (thio)uracil; 5 (methyl) 2,4 (dithio)uracil; 5 (methyl) 4 (thio)uracil; 5 (methylaminomethyl)-2 (thio)uracil; 5 (methylaminomethyl)-2,4 (dithio)uracil; 5 (methylaminomethyl)-4 (thio) uracil; 5 (propynyl)uracil; 5 (trifluoromethyl)uracil; 5-(2-aminopropyl)uracil; 5-(alkyl)-2-(thio)pseudouracil; 5-(alkyl)-2,4 (dithio)pseudouracil; 5-(alkyl)-4 (thio) pseudouracil; 5-(alkyl)pseudouracil; 5-(alkyl)uracil; 5-(alkynyl)uracil; 5-(allylamino)uracil; 5-(cyanoalkyl)uracil; 5-(dialkylaminoalkyl)uracil; 5-(dimethylaminoalkyl) uracil; 5-(guanidiniumalkyl)uracil; 5-(halo)uracil; 5-(1,3-diazole-1-alkyl)uracil; 5-(methoxy)uracil; 5-(methoxycarbonylmethyl)-2-(thio)uracil; 5-(methoxycarbonyl-methyl)uracil; 5-(methyl) 2(thio)uracil; 5-(methyl) 2,4 (dithio)uracil; 5-(methyl) 4 (thio)uracil; 5-(methyl)-2-(thio)pseudouracil; 5-(methyl)-2,4 (dithio)pseudouracil; 5-(methyl)-4 (thio)pseudouracil; 5-(methyl)pseudouracil; 5-(methylaminomethyl)-2 (thio)uracil; 5-(methylaminomethyl)-2,4(dithio)uracil; 5-(methylaminomethyl)-4-(thio) uracil; 5-(propynyl)uracil; 5-(trifluoromethyl)uracil; 5-aminoallyl-uridine; 5-bromo-uridine; 5-iodo-uridine; 5-uracil; 6 (azo)uracil; 6-(azo)uracil; 6-aza-uridine; allyamino-uracil; aza uracil; deaza uracil; N3 (methyl)uracil; Pseudo-UTP-1-2-ethanoic acid; Pseudouracil; 4-Thio-pseudo-UTP; 1-carboxymethyl-pseudouridine; 1-methyl-1- deaza-pseudouridine; 1-propynyl-uridine; 1-taurinomethyl-1-methyl-uridine; 1-taurinomethyl-4-thio-uridine; 1-taurinomethyl-pseudouridine; 2-methoxy-4-thio-pseudouridine; 2-thio-1-methyl-1-deaza-pseudouridine; 2-thio-1-methyl-pseudouridine; 2-thio-5-aza-uridine; 2-thio-dihydropseudouridine; 2-thio-dihydrouridine; 2-thio-pseudouridine; 4-methoxy-2-thio-pseudouridine; 4-methoxy-pseudouridine; 4-thio-1-methyl-pseudouridine; 4-thio-pseudouridine; 5-aza-uridine; Dihydropseudouridine; (±)1-(2-Hydroxypropyl)pseudouridine TP; (2R)-1-(2-Hydroxypropyl)pseudouridine TP; (2S)-1-(2-Hydroxypropyl) pseudouridine TP; (E)-5-(2-Bromo-vinyl)ara-uridine TP; (E)-5-(2-Bromo-vinyl)uridine TP; (Z)-5-(2-Bromo-vinyl) ara-uridine TP; (Z)-5-(2-Bromo-vinyl)uridine TP; 1-(2,2,2-Trifluoroethyl)-pseudo-UTP; 1-(2,2,3,3,3-Pentafluoropropyl)pseudouridine TP; 1-(2,2-Diethoxyethyl)pseudouridine TP; 1-(2,4,6-Trimethylbenzyl)pseudouridine TP; 1-(2,4,6-Trimethyl-benzyl)pseudo-UTP; 1-(2,4,6-Trimethyl-phenyl) pseudo-UTP; 1-(2-Amino-2-carboxyethyl)pseudo-UTP; 1-(2-Amino-ethyl)pseudo-UTP; 1-(2-Hydroxyethyl) pseudouridine TP; 1-(2-Methoxyethyl)pseudouridine TP; 1-(3,4-Bis-trifluoromethoxybenzyl)pseudouridine TP; 1-(3,4-Dimethoxybenzyl)pseudouridine TP; 1-(3-Amino-3-carboxypropyl)pseudo-UTP; 1-(3-Amino-propyl)pseudo-UTP; 1-(3-Cyclopropyl-prop-2-ynyl)pseudouridine TP; 1-(4-Amino-4-carboxybutyl)pseudo-UTP; 1-(4-Amino-benzyl) pseudo-UTP; 1-(4-Amino-butyl)pseudo-UTP; 1-(4-Amino-phenyl)pseudo-UTP; 1-(4-Azidobenzyl)pseudouridine TP; 1-(4-Bromobenzyl)pseudouridine TP; 1-(4-Chlorobenzyl) pseudouridine TP; 1-(4-Fluorobenzyl)pseudouridine TP; 1-(4-Iodobenzyl)pseudouridine TP; 1-(4-Methanesulfonylbenzyl)pseudouridine TP; 1-(4-Methoxybenzyl)pseudouridine TP; 1-(4-Methoxy-benzyl)pseudo-UTP; 1-(4-Methoxy-phenyl)pseudo-UTP; 1-(4-Methylbenzyl)pseudouridine TP; 1-(4-Methyl-benzyl)pseudo-UTP; 1-(4-Nitrobenzyl) pseudouridine TP; 1-(4-Nitro-benzyl)pseudo-UTP; 1(4-Nitro-phenyl)pseudo-UTP; 1-(4-Thiomethoxybenzyl) pseudouridine TP; 1-(4-Trifluoromethoxybenzyl) pseudouridine TP; 1-(4-Trifluoromethylbenzyl) pseudouridine TP; 1-(5-Amino-pentyl)pseudo-UTP; 1-(6-Amino-hexyl)pseudo-UTP; 1,6-Dimethyl-pseudo-UTP; 1-[3-(2-{2-[2-(2-Aminoethoxy)-ethoxy]-ethoxy}-ethoxy)-propionyl]pseudouridine TP; 1-{3-[2-(2-Aminoethoxy)-ethoxy]-propionyl} pseudouridine TP; 1-Acetylpseudouridine TP; 1-Alkyl-6-(1-propynyl)-pseudo-UTP; 1-Alkyl-6-(2-propynyl)-pseudo-UTP; 1-Alkyl-6-allyl-pseudo-UTP; 1-Alkyl-6-ethynyl-pseudo-UTP; 1-Alkyl-6-homoallyl-pseudo-UTP; 1-Alkyl-6-vinyl-pseudo-UTP; 1-Allylpseudouridine TP; 1-Aminomethyl-pseudo-UTP; 1-Benzoylpseudouridine TP; 1-Benzyloxymethylpseudouridine TP; 1-Benzyl-pseudo-UTP; 1-Biotinyl-PEG2-pseudouridine TP; 1-Biotinylpseudouridine TP; 1-Butyl-pseudo-UTP; 1-Cyanomethylpseudouridine TP; 1-Cyclobutylmethyl-pseudo-UTP; 1-Cyclobutyl-pseudo-UTP; 1-Cycloheptylmethyl-pseudo-UTP; 1-Cycloheptyl-pseudo-UTP; 1-Cyclohexylmethyl-pseudo-UTP; 1-Cyclohexyl-pseudo-UTP; 1-Cyclooctylmethyl-pseudo-UTP; 1-Cyclooctyl-pseudo-UTP; 1-Cyclopentylmethyl-pseudo-UTP; 1-Cyclopentyl-pseudo-UTP; 1-Cyclopropylmethyl-pseudo-UTP; 1-Cyclopropyl-pseudo-UTP; 1-Ethyl-pseudo-UTP; 1-Hexyl-pseudo-UTP; 1-Homoallylpseudouridine TP; 1-Hydroxymethylpseudouridine TP; 1-iso-propyl-pseudo-UTP; 1-Me-2-thio-pseudo-UTP; 1-Me-4-thio-pseudo-UTP; 1-Me-alpha-thio-pseudo-UTP; 1-Methanesulfonylmethylpseudouridine TP; 1-Methoxymethylpseudouridine TP; 1-Methyl-6-(2,2,2-Trifluoroethyl)pseudo-UTP; 1-Methyl-6-(4-morpholino)-pseudo-UTP; 1-Methyl-6-(4-thiomorpholino)-pseudo-UTP; 1-Methyl-6-(substituted phenyl) pseudo-UTP; 1-Methyl-6-amino-pseudo-UTP; 1-Methyl-6-azido-pseudo-UTP; 1-Methyl-6-bromo-pseudo-UTP; 1-Methyl-6-butyl-pseudo-UTP; 1-Methyl-6-chloro-pseudo-UTP; 1-Methyl-6-cyano-pseudo-UTP; 1-Methyl-6-dimethylamino-pseudo-UTP; 1-Methyl-6-ethoxy-pseudo-UTP; 1-Methyl-6-ethylcarboxylate-pseudo-UTP; 1-Methyl-6-ethyl-pseudo-UTP; 1-Methyl-6-fluoro-pseudo-UTP; 1-Methyl-6-formyl-pseudo-UTP; 1-Methyl-6-hydroxyamino-pseudo-UTP; 1-Methyl-6-hydroxy-pseudo-UTP; 1-Methyl-6-iodo-pseudo-UTP; 1-Methyl-6-iso-propyl-pseudo-UTP; 1-Methyl-6-methoxy-pseudo-UTP; 1-Methyl-6-methylamino-pseudo-UTP; 1-Methyl-6-phenyl-pseudo-UTP; 1-Methyl-6-propyl-pseudo-UTP; 1-Methyl-6-tert-butyl-pseudo-UTP; 1-Methyl-6-trifluoromethoxy-pseudo-UTP; 1-Methyl-6-trifluoromethyl-pseudo-UTP; 1-Morpholinomethylpseudouridine TP; 1-Pentyl-pseudo-UTP; 1-Phenyl-pseudo-UTP; 1-Pivaloylpseudouridine TP; 1-Propargylpseudouridine TP; 1-Propyl-pseudo-UTP; 1-propynyl-pseudouridine; 1-p-tolyl-pseudo-UTP; 1-tert-Butyl-pseudo-UTP; 1-Thiomethoxymethylpseudouridine TP; 1-Thiomorpholinomethylpseudouridine TP; 1-Trifluoroacetylpseudouridine TP; 1-Trifluoromethyl-pseudo-UTP; 1-Vinylpseudouridine TP; 2,2'-anhydro-uridine TP; 2'-bromo-deoxyuridine TP; 2'-F-5-Methyl-2'-deoxy-UTP; 2'-OMe-5-Me-UTP; 2'-OMe-pseudo-UTP; 2'-a-Ethynyluridine TP; 2'-a-Trifluoromethyluridine TP; 2'-b-Ethynyluridine TP; 2'-b-Trifluoromethyluridine TP; 2'-Deoxy-2',2'-difluorouridine TP; 2'-Deoxy-2'-a-mercaptouridine TP; 2'-Deoxy-2'-a-thiomethoxyuridine TP; 2'-Deoxy-2'-b-aminouridine TP; 2'-Deoxy-2'-b-azidouridine TP; 2'-Deoxy-2'-b-bromouridine TP; 2'-Deoxy-2'-b-chlorouridine TP; 2'-Deoxy-2'-b-fluorouridine TP; 2'-Deoxy-2'-b-iodouridine TP; 2'-Deoxy-2'-b-mercaptouridine TP; 2'-Deoxy-2'-b-thiomethoxyuridine TP; 2-methoxy-4-thio-uridine; 2-methoxyuridine; 2'-O-Methyl-5-(1-propynyl)uridine TP; 3-Alkyl-pseudo-UTP; 4'-Azidouridine TP; 4'-Carbocyclic uridine TP; 4'-Ethynyluridine TP; 5-(1-Propynyl)ara-uridine TP; 5-(2-Furanyl)uridine TP; 5-Cyanouridine TP; 5-Dimethylaminouridine TP; 5'-Homo-uridine TP; 5-iodo-2'-fluoro-deoxyuridine TP; 5-Phenylethynyluridine TP; 5-Trideuteromethyl-6-deuterouridine TP; 5-Trifluoromethyl-Uridine TP; 5-Vinylarauridine TP; 6-(2,2,2-Trifluoroethyl)-pseudo-UTP; 6-(4-Morpholino)-pseudo-UTP; 6-(4-Thiomorpholino)-pseudo-UTP; 6-(Substituted-Phenyl)-pseudo-UTP; 6-Amino-pseudo-UTP; 6-Azido-pseudo-UTP; 6-Bromo-pseudo-UTP; 6-Butyl-pseudo-UTP; 6-Chloro-pseudo-UTP; 6-Cyano-pseudo-UTP; 6-Dimethylamino-pseudo-UTP; 6-Ethoxy-pseudo-UTP; 6-Ethylcarboxylate-pseudo-UTP; 6-Ethyl-pseudo-UTP; 6-Fluoro-pseudo-UTP; 6-Formyl-pseudo-UTP; 6-Hydroxyamino-pseudo-UTP; 6-Hydroxy-pseudo-UTP; 6-Iodo-pseudo-UTP; 6-iso-Propyl-pseudo-UTP; 6-Methoxy-pseudo-UTP; 6-Methylamino-pseudo-UTP; 6-Methyl-pseudo-UTP; 6-Phenyl-pseudo-UTP; 6-Phenyl-pseudo-UTP; 6-Propyl-pseudo-UTP; 6-tert-Butyl-pseudo-UTP; 6-Trifluoromethoxy-pseudo-UTP; 6-Trifluoromethyl-pseudo-UTP; Alpha-thio-pseudo-UTP; Pseudouridine 1-(4-methylbenzenesulfonic acid) TP; Pseudouridine 1-(4-methylbenzoic acid) TP; Pseudouridine TP 1-[3-(2-ethoxy)]propionic acid; Pseudouridine TP 1-[3-{2-(2-[2-(2-ethoxy)-ethoxy]-ethoxy)-ethoxy}]propionic acid; Pseudouridine TP 1-[3-{2-(2-[2-{2 (2-ethoxy)-ethoxy}-ethoxy]-ethoxy)-ethoxy}]propionic acid; Pseudouridine TP 1-[3-{2-(2-[2-ethoxy]-ethoxy)-ethoxy}]propionic acid; Pseudouridine TP 1-[3-{2-(2-ethoxy)-ethoxy}] propionic acid; Pseudouridine TP 1-methylphosphonic acid; Pseudouridine TP 1-methylphosphonic acid diethyl ester; Pseudo-UTP-N1-3-propionic acid; Pseudo-UTP-N1-4-butanoic acid; Pseudo-UTP-N1-5-pentanoic acid; Pseudo-UTP-N1-6-hexanoic acid; Pseudo-UTP-N1-7-heptanoic acid; Pseudo-UTP-N1-methyl-p-benzoic acid; Pseudo-UTP-N1-p-benzoic acid; Wybutosine; Hydroxywybutosine; Isowyosine; Peroxywybutosine; undermodified hydroxywybutosine; 4-demethylwyosine; 2,6-(diamino)purine; 1-(aza)-2-(thio)-3-(aza)-phenoxazin-1-yl: 1,3-(diaza)-2-(oxo)-phenthiazin-1-yl; 1,3-(diaza)-2-(oxo)-phenoxazin-1-yl; 1,3,5-(triaza)-2,6-(dioxa)-naphthalene; 2 (amino)purine; 2,4,5-(trimethyl)phenyl; 2' methyl, 2'amino, 2'azido, 2'fluro-cytidine; 2' methyl, 2'amino, 2'azido, 2'fluro-adenine; 2'methyl, 2'amino, 2'azido, 2'fluro-uridine; 2'-amino-2'-deoxyribose; 2-amino-6-Chloro-purine; 2-aza-inosinyl; 2'-azido-2'-deoxyribose; 2'fluoro-2'-deoxyribose; 2'-fluoro-modified bases; 2'-O-methyl-ribose; 2-oxo-7-aminopyridopyrimidin-3-yl; 2-oxo-pyridopyrimidine-3-yl; 2-pyridinone; 3 nitropyrrole; 3-(methyl)-7-(propynyl) isocarbostyrilyl; 3-(methyl)isocarbostyrilyl; 4-(fluoro)-6-(methyl)benzimidazole; 4-(methyl)benzimidazole; 4-(methyl)indolyl; 4,6-(dimethyl)indolyl; 5 nitroindole; 5 substituted pyrimidines; 5-(methyl)isocarbostyrilyl; 5-nitroindole; 6-(aza)pyrimidine; 6-(azo)thymine; 6-(methyl)-7-(aza)indolyl; 6-chloro-purine; 6-phenyl-pyrrolo-pyrimidin-2-on-3-yl; 7-(aminoalkylhydroxy)-1-(aza)-2-(thio)-3-(aza)-phenthiazin-1-yl; 7-(aminoalkylhydroxy)-1-(aza)-2-(thio)-3-(aza)-phenoxazin-1-yl; 7-(aminoalkylhydroxy)-1,3-(diaza)-2-(oxo)-phenoxazin-1-yl; 7-(aminoalkylhydroxy)-1,3-(diaza)-2-(oxo)-phenthiazin-1-yl; 7-(aminoalkylhydroxy)-1,3-(diaza)-2-(oxo)-phenoxazin-1-yl; 7-(aza)indolyl; 7-(guanidiniumalkylhydroxy)-1-(aza)-2-(thio)-3-(aza)-phenoxazinl-yl; 7-(guanidiniumalkylhydroxy)-1-(aza)-2-(thio)-3-(aza)-phenthiazin-1-yl; 7-(guanidiniumalkylhydroxy)-1-(aza)-2-(thio)-3-(aza)-phenoxazin-1-yl; 7-(guanidiniumalkylhydroxy)-1,3-(diaza)-2-(oxo)-phenoxazin-1-yl; 7-(guanidiniumalkylhydroxy)-1,3-(diaza)-2-(oxo)-phenthiazin-1-yl; 7-(guanidiniumalkylhydroxy)-1,3-(diaza)-2-(oxo)-phenoxazin-1-yl; 7-(propynyl)isocarbostyrilyl; 7-(propynyl)isocarbostyrilyl, propynyl-7-(aza)indolyl; 7-deaza-inosinyl; 7-substituted 1-(aza)-2-(thio)-3-(aza)-phenoxazin-1-yl; 7-substituted 1,3-(diaza)-2-(oxo)-phenoxazin-1-yl; 9-(methyl)-imidizopyridinyl; Aminoindolyl; Anthracenyl; bis-ortho-(aminoalkylhydroxy)-6-phenyl-pyrrolo-pyrimidin-2-on-3-yl; bis-ortho-substituted-6-phenyl-pyrrolo-pyrimidin-2-on-3-yl; Difluorotolyl; Hypoxanthine; Imidizopyridinyl; Inosinyl; Isocarbostyrilyl; Isoguanisine; N2-substituted purines; N6-methyl-2-amino-purine; N6-substituted purines; N-alkylated derivative; Napthalenyl; Nitrobenzimidazolyl; Nitroimidazolyl; Nitroindazolyl; Nitropyrazolyl; Nubularine; 06-substituted purines; O-alkylated derivative; ortho-(aminoalkylhydroxy)-6-phenyl-pyrrolo-pyrimidin-2-on-3-yl; ortho-substituted-6-phenyl-pyrrolo-pyrimidin-2-on-3-yl; Oxoformycin TP; para-(aminoalkylhydroxy)-6-phenyl-pyrrolo-pyrimidin-2-on-3-yl; para-substituted-6-phenyl-pyrrolo-pyrimidin-2-on-3-yl; Pentacenyl; Phenanthracenyl; Phenyl; propynyl-7-(aza)indolyl; Pyrenyl; pyridopyrimidin-3-yl; pyridopyrimidin-3-yl, 2-oxo-7-aminopyridopyrimidin-3-yl; pyrrolo-pyrimidin-2-on-3-yl; Pyrrolopyrimidinyl; Pyrrolopyrizinyl; Stilbenzyl; substituted 1,2,4-triazoles; Tetracenyl; Tubercidine; Xanthine; Xanthosine-5'-TP; 2-thio-zebularine; 5-aza-2-thio-zebularine; 7-deaza-2-amino-purine; pyridin-4-one ribonucleoside; 2-Amino-riboside-TP; Formycin A TP; Formycin B TP; Pyrrolosine TP; 2'-OH-ara-adenosine TP; 2'-OH-ara-cytidine TP; 2'-OH-ara-uridine TP; 2'-OH-ara-guanosine TP; 5-(2-carbomethoxyvinyl)uridine TP; and N6-(19-Amino-pentaoxanonadecyl)adenosine TP.

In some embodiments, polynucleotides (e.g., RNA polynucleotides, such as mRNA polynucleotides) include a combination of at least two (e.g., 2, 3, 4 or more) of the aforementioned modified nucleobases.

In some embodiments, modified nucleobases in polynucleotides (e.g., RNA polynucleotides, such as mRNA polynucleotides) are selected from the group consisting of pseudouridine (ψ), N1-methylpseudouridine ($m^1$ψ), N1-ethylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine and 2'-O-methyl uridine. In some embodiments, polynucleotides (e.g., RNA polynucleotides, such as mRNA polynucleotides) include a combination of at least two (e.g., 2, 3, 4 or more) of the aforementioned modified nucleobases.

In some embodiments, modified nucleobases in polynucleotides (e.g., RNA polynucleotides, such as mRNA polynucleotides) are selected from the group consisting of 1-methyl-pseudouridine ($m^1$ψ), 5-methoxy-uridine ($mo^5$U), 5-methyl-cytidine ($m^5$C), pseudouridine (ψ), α-thio-guanosine and α-thio-adenosine. In some embodiments, polynucleotides includes a combination of at least two (e.g., 2, 3, 4 or more) of the aforementioned modified nucleobases.

In some embodiments, polynucleotides (e.g., RNA polynucleotides, such as mRNA polynucleotides) comprise pseudouridine (ψ) and 5-methyl-cytidine ($m^5$C). In some embodiments, polynucleotides (e.g., RNA polynucleotides, such as mRNA polynucleotides) comprise 1-methyl-pseudouridine ($m^1$ψ). In some embodiments, polynucleotides (e.g., RNA polynucleotides, such as mRNA polynucleotides) comprise 1-methyl-pseudouridine ($m^1$ψ) and 5-methyl-cytidine ($m^5$C). In some embodiments, polynucleotides (e.g., RNA polynucleotides, such as mRNA polynucleotides) comprise 2-thiouridine ($s^2$U). In some embodiments, polynucleotides (e.g., RNA polynucleotides, such as mRNA polynucleotides) comprise 2-thiouridine and 5-methyl-cytidine ($m^5$C). In some embodiments, polynucleotides (e.g., RNA polynucleotides, such as mRNA polynucleotides) comprise methoxy-uridine ($mo^5$U). In some embodiments, polynucleotides (e.g., RNA polynucleotides, such as mRNA polynucleotides) comprise 5-methoxy-uridine ($mo^5$U) and 5-methyl-cytidine ($m^5$C). In some embodiments, polynucleotides (e.g., RNA polynucleotides, such as mRNA polynucleotides) comprise 2'-O-methyl uridine. In some embodiments polynucleotides (e.g., RNA polynucleotides, such as mRNA polynucleotides) comprise 2'-O-methyl uridine and 5-methyl-cytidine ($m^5$C). In some embodiments, polynucleotides (e.g., RNA polynucleotides, such as mRNA polynucleotides) comprise N6-methyl-adenosine ($m^6$A). In some embodiments, polynucleotides (e.g., RNA polynucleotides, such as mRNA polynucleotides) comprise N6-methyl-adenosine ($m^6$A) and 5-methyl-cytidine ($m^5$C).

In some embodiments, polynucleotides (e.g., RNA polynucleotides, such as mRNA polynucleotides) are uniformly modified (e.g., fully modified, modified throughout the entire sequence) for a particular modification. For example, a polynucleotide can be uniformly modified with 5-methyl-cytidine ($m^5$C), meaning that all cytosine residues in the mRNA sequence are replaced with 5-methyl-cytidine ($m^5$C).

Similarly, a polynucleotide can be uniformly modified for any type of nucleoside residue present in the sequence by replacement with a modified residue such as those set forth above.

Exemplary nucleobases and nucleosides having a modified cytosine include N4-acetyl-cytidine (ac4C), 5-methyl-cytidine (m5C), 5-halo-cytidine (e.g., 5-iodo-cytidine), 5-hydroxymethyl-cytidine (hm5C), 1-methyl-pseudoisocytidine, 2-thio-cytidine (s2C), and 2-thio-5-methyl-cytidine.

In some embodiments, a modified nucleobase is a modified uridine. Exemplary nucleobases and In some embodiments, a modified nucleobase is a modified cytosine. nucleosides having a modified uridine include 5-cyano uridine, and 4'-thio uridine.

In some embodiments, a modified nucleobase is a modified adenine. Exemplary nucleobases and nucleosides having a modified adenine include 7-deaza-adenine, 1-methyl-adenosine (m1A), 2-methyl-adenine (m2A), and N6-methyl-adenosine (m6A).

In some embodiments, a modified nucleobase is a modified guanine. Exemplary nucleobases and nucleosides having a modified guanine include inosine (I), 1-methyl-inosine (m1I), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, 7-methyl-8-oxo-guanosine.

The polynucleotides of the present disclosure may be partially or fully modified along the entire length of the molecule. For example, one or more or all or a given type of nucleotide (e.g., purine or pyrimidine, or any one or more or all of A, G, U, C) may be uniformly modified in a polynucleotide of the disclosure, or in a given predetermined sequence region thereof (e.g., in the mRNA including or excluding the polyA tail). In some embodiments, all nucleotides X in a polynucleotide of the present disclosure (or in a given sequence region thereof) are modified nucleotides, wherein X may any one of nucleotides A, G, U, C, or any one of the combinations A+G, A+U, A+C, G+U, G+C, U+C, A+G+U, A+G+C, G+U+C or A+G+C.

The polynucleotide may contain from about 1% to about 100% modified nucleotides (either in relation to overall nucleotide content, or in relation to one or more types of nucleotide, i.e., any one or more of A, G, U or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%). Any remaining percentage is accounted for by the presence of unmodified A, G, U, or C.

The polynucleotides may contain at a minimum 1% and at maximum 100% modified nucleotides, or any intervening percentage, such as at least 5% modified nucleotides, at least 10% modified nucleotides, at least 25% modified nucleotides, at least 50% modified nucleotides, at least 80% modified nucleotides, or at least 90% modified nucleotides. For example, the polynucleotides may contain a modified pyrimidine such as a modified uracil or cytosine. In some embodiments, at least 5%, at least 10%, at least 25%, at least 50%, at least 80%, at least 90% or 100% of the uracil in the polynucleotide is replaced with a modified uracil (e.g., a 5-substituted uracil). The modified uracil can be replaced by a compound having a single unique structure, or can be replaced by a plurality of compounds having different structures (e.g., 2, 3, 4 or more unique structures). n some embodiments, at least 5%, at least 10%, at least 25%, at least 50%, at least 80%, at least 90% or 100% of the cytosine in the polynucleotide is replaced with a modified cytosine (e.g., a 5-substituted cytosine). The modified cytosine can be replaced by a compound having a single unique structure, or can be replaced by a plurality of compounds having different structures (e.g., 2, 3, 4 or more unique structures).

Thus, in some embodiments, the RNA (e.g., mRNA) vaccines comprise a 5'UTR element, an optionally codon optimized open reading frame, and a 3'UTR element, a poly(A) sequence and/or a polyadenylation signal wherein the RNA is not chemically modified.

In some embodiments, the modified nucleobase is a modified uracil. Exemplary nucleobases and nucleosides having a modified uracil include pseudouridine (w), pyridin-4-one ribonucleoside, 5-aza-uridine, 6-aza-uridine, 2-thio-5-aza-uridine, 2-thio-uridine ($s^2U$), 4-thio-uridine ($s^4U$), 4-thio-pseudouridine, 2-thio-pseudouridine, 5-hydroxy-uridine (ho$^5$U), 5-aminoallyl-uridine, 5-halo-uridine (e.g., 5-iodo-uridineor 5-bromo-uridine), 3-methyl-uridine (m$^3$U), 5-methoxy-uridine (mo$^5$U), uridine 5-oxyacetic acid (cmo$^5$U), uridine 5-oxyacetic acid methyl ester (mcmo$^5$U), 5-carboxymethyl-uridine (cm$^5$U), 1-carboxymethyl-pseudouridine, 5-carboxyhydroxymethyl-uridine (chm$^5$U), 5-carboxyhydroxymethyl-uridine methyl ester (mchm$^5$U), 5-methoxycarbonylmethyl-uridine (mcm$^5$U), 5-methoxycarbonylmethyl-2-thio-uridine (mcm$^5$s$^2$U), 5-aminomethyl-2-thio-uridine (nm$^5$s$^2$U), 5-methylaminomethyl-uridine (mnm$^5$U), 5-methylaminomethyl-2-thio-uridine (mnm$^5$s$^2$U), 5-methylaminomethyl-2-seleno-uridine (mnm$^5$se$^2$U), 5-carbamoylmethyl-uridine (ncm$^5$U), 5-carboxymethylaminomethyl-uridine (cmnm$^5$U), 5-carboxymethylaminomethyl-2-thio-uridine (cmnm$^5$s$^2$U), 5-propynyl-uridine, 1-propynyl-pseudouridine, 5-taurinomethyl-uridine (τm$^5$U), 1-taurinomethyl-pseudouridine, 5-taurinomethyl-2-thio-uridine(τ$^5$s$^2$U), 1-taurinomethyl-4-thio-pseudouridine, 5-methyl-uridine (m$^5$U, i.e., having the nucleobase deoxythymine), 1-methyl-pseudouridine (m$^1$ψ), 5-methyl-2-thio-uridine (m$^5$s$^2$U), 1-methyl-4-thio-pseudouridine (m$^1$s$^4$ψ), 4-thio-1-methyl-pseudouridine, 3-methyl-pseudouridine (m$^3$ψ), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyldihydrouridine (m$^5$D), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl)uridine (acp$^3$U), 1-methyl-3-(3-amino-3-carboxypropyl)pseudouridine (acp$^3$ψ), 5-(isopentenylaminomethyl)uridine (inm$^5$U), 5-(isopentenylaminomethyl)-2-thio-uridine (inm$^5$s$^2$U), α-thio-uridine, 2'-O-methyl-uridine (Um), 5,2'-O-dimethyl-uridine (m$^5$Um), 2'-O-methyl-pseudouridine (ψm), 2-thio-2'-O-methyl-uridine (s$^2$Um), 5-methoxycarbonylmethyl-2'-O-methyl-uridine (mcm$^5$Um), 5-carbamoylmethyl-2'-O-methyl-uridine (ncm$^5$Um), 5-carboxymethylaminomethyl-2'-O-methyl-uridine (cmnm$^5$Um), 3,2'-O-dimethyl-uridine (m$^3$Um), and 5-(isopentenylaminomethyl)-2'-O-methyl-uridine (inm$^5$Um), 1-thio-uridine, deoxythymidine, 2'-F-arauridine, 2'-F-uridine, 2'-OH-ara-uridine, 5-(2-carbomethoxyvinyl) uridine, and 5-[3-(1-E-propenylamino)] uridine.

In some embodiments, the modified nucleobase is a modified cytosine. Exemplary nucleobases and nucleosides having a modified cytosine include 5-aza-cytidine, 6-aza-cytidine, pseudoisocytidine, 3-methyl-cytidine ($m^3C$), N4-acetyl-cytidine ($ac^4C$), 5-formylcytidine ($f^5C$), N4-methyl-cytidine ($m^4C$), 5-methyl-cytidine ($m^5C$), 5-halo-cytidine (e.g., 5-iodo-cytidine), 5-hydroxymethyl-cytidine ($hm^5C$), 1-methyl-pseudoisocytidine, pyrrolo-cytidine, pyrrolo-pseudoisocytidine, 2-thio-cytidine ($s^2C$), 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, lysidine ($k_2C$), α-thio-cytidine, 2'-O-methyl-cytidine (Cm), 5,2'-O-dimethyl-cytidine ($m^5Cm$), N4-acetyl-2'-O-methyl-cytidine ($ac^4Cm$), N4,2'-O-dimethyl-cytidine ($m^4Cm$), 5-formyl-2'-O-methyl-cytidine ($f^5Cm$), N4,N4,2'-O-trimethyl-cytidine ($m^4_2Cm$), 1-thio-cytidine, 2'-F-ara-cytidine, 2'-F-cytidine, and 2'-0H-ara-cytidine.

In some embodiments, the modified nucleobase is a modified adenine. Exemplary nucleobases and nucleosides having a modified adenine include 2-amino-purine, 2, 6-diaminopurine, 2-amino-6-halo-purine (e.g., 2-amino-6-chloro-purine), 6-halo-purine (e.g., 6-chloro-purine), 2-amino-6-methyl-purine, 8-azido-adenosine, 7-deaza-adenine, 7-deaza-8-aza-adenine, 7-deaza-2-amino-purine, 7-deaza-8-aza-2-amino-purine, 7-deaza-2,6-diaminopurine, 7-deaza-8-aza-2,6-diaminopurine, 1-methyl-adenosine ($m^1A$), 2-methyl-adenine ($m^2A$), N6-methyl-adenosine ($m^6A$), 2-methylthio-N6-methyl-adenosine ($ms^2$ $m^6A$), N6-isopentenyl-adenosine ($i^6A$), 2-methylthio-N6-isopentenyl-adenosine ($ms^2i^6A$), N6-(cis-hydroxyisopentenyl)adenosine ($io^6A$), 2-methylthio-N6-(cis-hydroxyisopentenyl) adenosine ($ms^2io^6A$), N6-glycinylcarbamoyl-adenosine ($g^6A$), N6-threonylcarbamoyl-adenosine ($t^6A$), N6-methyl-N6-threonylcarbamoyl-adenosine ($m^6t^6A$), 2-methylthio-N6-threonylcarbamoyl-adenosine ($ms^2g^6A$), N6,N6-dimethyl-adenosine ($m^6_2A$), N6-hydroxynorvalylcarbamoyl-adenosine ($hn^6A$), 2-methylthio-N6-hydroxynorvalylcarbamoyl-adenosine ($ms^2hn^6A$), N6-acetyl-adenosine ($ac^6A$), 7-methyl-adenine, 2-methyl-thio-adenine, 2-methoxy-adenine, α-thio-adenosine, 2'-O-methyl-adenosine (Am), N6,2'-O-dimethyl-adenosine ($m^6Am$), N6,N6,2'-O-trimethyl-adenosine ($m^6_2Am$), 1,2'-O-dimethyl-adenosine ($m^1Am$), 2'-O-ribosyladenosine (phosphate) (Ar(p)), 2-amino-N6-methyl-purine, 1-thio-adenosine, 8-azido-adenosine, 2'-F-ara-adenosine, 2'-F-adenosine, 2'-0H-ara-adenosine, and N6-(19-amino-pentaoxanonadecyl)-adenosine.

In some embodiments, the modified nucleobase is a modified guanine. Exemplary nucleobases and nucleosides having a modified guanine include inosine (I), 1-methyl-inosine ($m^1I$), wyosine (imG), methylwyosine (mimG), 4-demethyl-wyosine (imG-14), isowyosine (imG2), wybutosine (yW), peroxywybutosine ($o_2yW$), hydroxywybutosine (OhyW), undermodified hydroxywybutosine (OhyW*), 7-deaza-guanosine, queuosine (Q), epoxyqueuosine (oQ), galactosyl-queuosine (galQ), mannosyl-queuosine (manQ), 7-cyano-7-deaza-guanosine ($preQ_0$), 7-aminomethyl-7-deaza-guanosine ($preQ_1$), archaeosine ($G^+$), 7-deaza-8-aza-guanosine, 6-thio-guanosine, 6-thio-7-deaza-guanosine, 6-thio-7-deaza-8-aza-guanosine, 7-methyl-guanosine ($m^7G$), 6-thio-7-methyl-guanosine, 7-methyl-inosine, 6-methoxy-guanosine, 1-methyl-guanosine ($m^1G$), N2-methyl-guanosine ($m^2G$), N2,N2-dimethyl-guanosine ($m^2_2G$), N2,7-dimethyl-guano sine ($m^{2,7}G$), N2, N2,7-dimethyl-guanosine ($m^{2,2,7}G$), 8-oxo-guanosine, 7-methyl-8-oxo-guanosine, 1-methyl-6-thio-guanosine, N2-methyl-6-thio-guanosine, N2,N2-dimethyl-6-thio-guanosine, α-thio-guanosine, 2'-O-methyl-guanosine (Gm), N2-methyl-2'-O-methyl-guanosine ($m^2Gm$), N2,N2-dimethyl-2'-O-methyl-guanosine ($m^2_2Gm$), 1-methyl-2'-O-methyl-guanosine ($m^1Gm$), N2,7-dimethyl-2'-O-methyl-guanosine ($m^{2,7}Gm$), 2'-O-methyl-inosine (Im), 1,2'-O-dimethyl-inosine ($m^1Im$), 2'-O-ribosylguanosine (phosphate) (Gr(p)), 1-thio-guanosine, O6-methyl-guanosine, 2'-F-ara-guanosine, and 2'-F-guanosine.

N-Linked Glycosylation Site Mutants

N-linked glycans of viral proteins play important roles in modulating the immune response. Glycans can be important for maintaining the appropriate antigenic conformations, shielding potential neutralization epitopes, and may alter the proteolytic susceptibility of proteins. Some viruses have putative N-linked glycosylation sites. Deletion or modification of an N-linked glycosylation site may enhance the immune response. Thus, the present disclosure provides, in some embodiments, RNA (e.g., mRNA) vaccines comprising nucleic acids (e.g., mRNA) encoding antigenic polypeptides that comprise a deletion or modification at one or more N-linked glycosylation sites.

In Vitro Transcription of RNA (e.g., mRNA)

Respiratory virus vaccines of the present disclosure comprise at least one RNA polynucleotide, such as a mRNA (e.g., modified mRNA). mRNA, for example, is transcribed in vitro from template DNA, referred to as an "in vitro transcription template." In some embodiments, an in vitro transcription template encodes a 5' untranslated (UTR) region, contains an open reading frame, and encodes a 3' UTR and a polyA tail. The particular nucleic acid sequence composition and length of an in vitro transcription template will depend on the mRNA encoded by the template.

A "5' untranslated region" (5'UTR) refers to a region of an mRNA that is directly upstream (i.e., 5') from the start codon (i.e., the first codon of an mRNA transcript translated by a ribosome) that does not encode a polypeptide.

A "3' untranslated region" (3'UTR) refers to a region of an mRNA that is directly downstream (i.e., 3') from the stop codon (i.e., the codon of an mRNA transcript that signals a termination of translation) that does not encode a polypeptide.

An "open reading frame" is a continuous stretch of DNA beginning with a start codon (e.g., methionine (ATG)), and ending with a stop codon (e.g., TAA, TAG or TGA) and encodes a polypeptide.

A "polyA tail" is a region of mRNA that is downstream, e.g., directly downstream (i.e., 3'), from the 3' UTR that contains multiple, consecutive adenosine monophosphates. A polyA tail may contain 10 to 300 adenosine monophosphates. For example, a polyA tail may contain 10, 20, 30, 40, 50, 60, 70, 80, 90, 100, 110, 120, 130, 140, 150, 160, 170, 180, 190, 200, 210, 220, 230, 240, 250, 260, 270, 280, 290 or 300 adenosine monophosphates. In some embodiments, a polyA tail contains 50 to 250 adenosine monophosphates. In a relevant biological setting (e.g., in cells, in vivo) the poly(A) tail functions to protect mRNA from enzymatic degradation, e.g., in the cytoplasm, and aids in transcription termination, export of the mRNA from the nucleus and translation.

In some embodiments, a polynucleotide includes 200 to 3,000 nucleotides. For example, a polynucleotide may include 200 to 500, 200 to 1000, 200 to 1500, 200 to 3000, 500 to 1000, 500 to 1500, 500 to 2000, 500 to 3000, 1000 to 1500, 1000 to 2000, 1000 to 3000, 1500 to 3000, or 2000 to 3000 nucleotides.

Flagellin Adjuvants

Flagellin is an approximately 500 amino acid monomeric protein that polymerizes to form the flagella associated with bacterial motion. Flagellin is expressed by a variety of flagellated bacteria (*Salmonella typhimurium* for example) as well as non-flagellated bacteria (such as *Escherichia coli*). Sensing of flagellin by cells of the innate immune system (dendritic cells, macrophages, etc.) is mediated by the Toll-like receptor 5 (TLR5) as well as by Nod-like receptors (NLRs) Ipaf and Naip5. TLRs and NLRs have been identified as playing a role in the activation of innate immune response and adaptive immune response. As such, flagellin provides an adjuvant effect in a vaccine.

The nucleotide and amino acid sequences encoding known flagellin polypeptides are publicly available in the NCBI GenBank database. The flagellin sequences from *S. Typhimurium, H. Pylori, V. Cholera, S. marcesens, S. flexneri, T. Pallidum, L. pneumophila, B. burgdorferei, C. difficile, R. meliloti, A. tumefaciens, R. lupini, B. clarridgeiae, P. Mirabilis, B. subtilus, L. monocytogenes, P. aeruginosa*, and *E. coli*, among others are known.

A flagellin polypeptide, as used herein, refers to a full length flagellin protein, immunogenic fragments thereof, and peptides having at least 50% sequence identify to a flagellin protein or immunogenic fragments thereof. Exemplary flagellin proteins include flagellin from *Salmonella typhi* (UniPro Entry number: Q56086), *Salmonella typhimurium* (A0A0C9DG09), *Salmonella enteritidis* (A0A0C9BAB7), and *Salmonella choleraesuis* (Q6V2X8), and SEQ ID NO: 54-56 (Table 17). In some embodiments, the flagellin polypeptide has at least 60%, 70%, 75%, 80%, 90%, 95%, 97%, 98%, or 99% sequence identify to a flagellin protein or immunogenic fragments thereof.

In some embodiments, the flagellin polypeptide is an immunogenic fragment. An immunogenic fragment is a portion of a flagellin protein that provokes an immune response. In some embodiments, the immune response is a TLR5 immune response. An example of an immunogenic fragment is a flagellin protein in which all or a portion of a hinge region has been deleted or replaced with other amino acids. For example, an antigenic polypeptide may be inserted in the hinge region. Hinge regions are the hypervariable regions of a flagellin. Hinge regions of a flagellin are also referred to as "D3 domain or region, "propeller domain or region," "hypervariable domain or region" and "variable domain or region." "At least a portion of a hinge region," as used herein, refers to any part of the hinge region of the flagellin, or the entirety of the hinge region. In other embodiments an immunogenic fragment of flagellin is a 20, 25, 30, 35, or 40 amino acid C-terminal fragment of flagellin.

The flagellin monomer is formed by domains D0 through D3. D0 and D1, which form the stem, are composed of tandem long alpha helices and are highly conserved among different bacteria. The D1 domain includes several stretches of amino acids that are useful for TLR5 activation. The entire D1 domain or one or more of the active regions within the domain are immunogenic fragments of flagellin. Examples of immunogenic regions within the D1 domain include residues 88-114 and residues 411-431 (in *Salmonella typhimurium* FliC flagellin. Within the 13 amino acids in the 88-100 region, at least 6 substitutions are permitted between *Salmonella* flagellin and other flagellins that still preserve TLR5 activation. Thus, immunogenic fragments of flagellin include flagellin like sequences that activate TLR5 and contain a 13 amino acid motif that is 53% or more identical to the *Salmonella* sequence in 88-100 of FliC (LQRVRELAVQSAN; SEQ ID NO: 84).

In some embodiments, the RNA (e.g., mRNA) vaccine includes an RNA that encodes a fusion protein of flagellin and one or more antigenic polypeptides. A "fusion protein" as used herein, refers to a linking of two components of the construct. In some embodiments, a carboxy-terminus of the antigenic polypeptide is fused or linked to an amino terminus of the flagellin polypeptide. In other embodiments, an amino-terminus of the antigenic polypeptide is fused or linked to a carboxy-terminus of the flagellin polypeptide. The fusion protein may include, for example, one, two, three, four, five, six or more flagellin polypeptides linked to one, two, three, four, five, six or more antigenic polypeptides. When two or more flagellin polypeptides and/or two or more antigenic polypeptides are linked such a construct may be referred to as a "multimer."

Each of the components of a fusion protein may be directly linked to one another or they may be connected through a linker. For instance, the linker may be an amino acid linker. The amino acid linker encoded for by the RNA (e.g., mRNA) vaccine to link the components of the fusion protein may include, for instance, at least one member selected from the group consisting of a lysine residue, a glutamic acid residue, a serine residue and an arginine residue. In some embodiments the linker is 1-30, 1-25, 1-25, 5-10, 5, 15, or 5-20 amino acids in length.

In other embodiments the RNA (e.g., mRNA) vaccine includes at least two separate RNA polynucleotides, one encoding one or more antigenic polypeptides and the other encoding the flagellin polypeptide. The at least two RNA polynucleotides may be co-formulated in a carrier such as a lipid nanoparticle.

Broad Spectrum RNA (e.g., mRNA) Vaccines

There may be situations where persons are at risk for infection with more than one strain of hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1). RNA (e.g., mRNA) therapeutic vaccines are particularly amenable to combination vaccination approaches due to a number of factors including, but not limited to, speed of manufacture, ability to rapidly tailor vaccines to accommodate perceived geographical threat, and the like. Moreover, because the vaccines utilize the human body to produce the antigenic protein, the vaccines are amenable to the production of larger, more complex antigenic proteins, allowing for proper folding, surface expression, antigen presentation, etc. in the human subject. To protect against more than one strain of hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1), a combination vaccine can be administered that includes RNA (e.g., mRNA) encoding at least one antigenic polypeptide protein (or antigenic portion thereof) of a first respiratory virus and further includes RNA encoding at least one antigenic polypeptide protein (or antigenic portion thereof) of a second respiratory virus. RNA (e.g., mRNA) can be co-formulated, for example, in a single lipid nanoparticle (LNP) or can be formulated in separate LNPs for co-administration.

Methods of Treatment

Provided herein are compositions (e.g., pharmaceutical compositions), methods, kits and reagents for prevention and/or treatment of respiratory diseases/infections in humans and other mammals. Respiratory virus RNA (e.g. mRNA) vaccines can be used as therapeutic or prophylactic agents, alone or in combination with other vaccine(s). They may be used in medicine to prevent and/or treat respiratory disease/infection. In exemplary aspects, the RNA (e.g., mRNA) vaccines of the present disclosure are used to provide prophylactic protection from hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1). Prophylactic protection from hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1) can be achieved following administration of a RNA (e.g., mRNA) vaccine of the present disclosure. Respiratory virus RNA (e.g., mRNA) vaccines of the present disclosure may be used to treat or prevent viral "co-infections" containing two or more respiratory infections. Vaccines can be administered once, twice, three times, four times or more, but it is likely sufficient to administer the vaccine once (optionally followed by a single booster). It is possible, although less desirable, to administer the vaccine to an infected individual to achieve a therapeutic response. Dosing may need to be adjusted accordingly.

A method of eliciting an immune response in a subject against hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1) is provided in aspects of the present disclosure. The method involves administering to the subject a respiratory virus RNA (e.g., mRNA) vaccine comprising at least one RNA (e.g., mRNA) polynucleotide having an open reading frame encoding at least one hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1) antigenic polypeptide thereof, thereby inducing in the subject an immune response specific to hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1) antigenic polypeptide or an immunogenic fragment thereof, wherein anti-antigenic polypeptide antibody titer in the subject is increased following vaccination relative to anti-antigenic polypeptide antibody titer in a subject vaccinated with a prophylactically effective dose of a traditional vaccine against hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1). An "anti-antigenic polypeptide antibody" is a serum antibody the binds specifically to the antigenic polypeptide.

In some embodiments, a RNA (e.g., mRNA) vaccine (e.g., a hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1 RNA vaccine) capable of eliciting an immune response is administered intramuscularly via a composition including a compound according to Formula (I), (IA), (II), (IIa), (IIb), (IIc), (IId) or (IIe) (e.g., Compound 3, 18, 20, 25, 26, 29, 30, 60, 108-112, or 122).

A prophylactically effective dose is a therapeutically effective dose that prevents infection with the virus at a clinically acceptable level. In some embodiments the therapeutically effective dose is a dose listed in a package insert for the vaccine. A traditional vaccine, as used herein, refers to a vaccine other than the RNA (e.g., mRNA) vaccines of the present disclosure. For instance, a traditional vaccine includes but is not limited to live/attenuated microorganism vaccines, killed/inactivated microorganism vaccines, subunit vaccines, protein antigen vaccines, DNA vaccines, VLP vaccines, etc. In exemplary embodiments, a traditional vaccine is a vaccine that has achieved regulatory approval and/or is registered by a national drug regulatory body, for example the Food and Drug Administration (FDA) in the United States or the European Medicines Agency (EMA).

In some embodiments the anti-antigenic polypeptide antibody titer in the subject is increased 1 log to 10 log following vaccination relative to anti-antigenic polypeptide antibody titer in a subject vaccinated with a prophylactically effective dose of a traditional vaccine against hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1).

In some embodiments the anti-antigenic polypeptide antibody titer in the subject is increased 1 log, 2 log, 3 log, 5 log or 10 log following vaccination relative to anti-antigenic polypeptide antibody titer in a subject vaccinated with a prophylactically effective dose of a traditional vaccine against hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1).

A method of eliciting an immune response in a subject against hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1) is provided in other aspects of the disclosure. The method involves administering to the subject a respiratory virus RNA (e.g., mRNA) vaccine comprising at least one RNA (e.g., mRNA) polynucleotide having an open reading frame encoding at least one hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1) antigenic polypeptide or an immunogenic fragment thereof, thereby inducing in the subject an immune response specific to hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1) antigenic polypeptide or an immunogenic fragment thereof, wherein the immune response in the subject is equivalent to an immune response in a subject vaccinated with a traditional vaccine against the hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1) at 2 times to 100 times the dosage level relative to the RNA (e.g., mRNA) vaccine.

In some embodiments, the immune response in the subject is equivalent to an immune response in a subject vaccinated with a traditional vaccine at 2, 3, 4, 5, 10, 50, 100 times the dosage level relative to the hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1) RNA (e.g., mRNA) vaccine.

In some embodiments the immune response in the subject is equivalent to an immune response in a subject vaccinated with a traditional vaccine at 10-100 times, or 100-1000 times, the dosage level relative to the hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1) RNA (e.g., mRNA) vaccine.

In some embodiments the immune response is assessed by determining [protein] antibody titer in the subject.

Some aspects of the present disclosure provide a method of eliciting an immune response in a subject against a In some embodiments the immune response in the subject is equivalent to an immune response in a subject vaccinated with a traditional vaccine at 2, 3, 4, 5, 10, 50, 100 times the dosage level relative to the hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1) RNA (e.g., mRNA) vaccine by administering to the subject a respiratory virus RNA (e.g., mRNA) vaccine comprising at least one RNA (e.g., mRNA) polynucleotide having an open reading frame encoding at least one hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1) antigenic polypeptide, thereby inducing in the subject an immune response specific to the antigenic polypeptide or an immunogenic fragment thereof, wherein the immune response in the subject is induced 2 days to 10 weeks earlier relative to an immune response induced in a subject vaccinated with a prophylactically effective dose of a traditional vaccine against the hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1). In some embodiments, the immune response in the subject is induced in a subject vaccinated with a prophylactically effective dose of a traditional vaccine at 2 times to 100 times the dosage level relative to the RNA (e.g., mRNA) vaccine.

In some embodiments, the immune response in the subject is induced 2 days earlier, or 3 days earlier, relative to an immune response induced in a subject vaccinated with a prophylactically effective dose of a traditional vaccine.

In some embodiments the immune response in the subject is induced 1 week, 2 weeks, 3 weeks, 5 weeks, or 10 weeks earlier relative to an immune response induced in a subject vaccinated with a prophylactically effective dose of a traditional vaccine.

Also provided herein is a method of eliciting an immune response in a subject against hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1) by administering to the subject a respiratory virus RNA (e.g., mRNA) vaccine having an open reading frame encoding a first antigenic polypeptide, wherein the RNA polynucleotide does not include a stabilization element, and wherein an adjuvant is not co-formulated or co-administered with the vaccine.

Therapeutic and Prophylactic Compositions

Provided herein are compositions (e.g., pharmaceutical compositions), methods, kits and reagents for prevention, treatment or diagnosis of hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1) in humans and other mammals, for example. Respiratory virus RNA (e.g. mRNA) vaccines can be used as therapeutic or prophylactic agents. They may be used in medicine to prevent and/or treat infectious disease. In some embodiments, the respiratory RNA (e.g., mRNA) vaccines of the present disclosure are used fin the priming of immune effector cells, for example, to activate peripheral blood mononuclear cells (PBMCs) ex vivo, which are then infused (re-infused) into a subject.

In some embodiments, respiratory virus vaccine containing RNA (e.g., mRNA) polynucleotides as described herein can be administered to a subject (e.g., a mammalian subject, such as a human subject), and the RNA (e.g., mRNA) polynucleotides are translated in vivo to produce an antigenic polypeptide.

The respiratory virus RNA (e.g., mRNA) vaccines may be induced for translation of a polypeptide (e.g., antigen or immunogen) in a cell, tissue or organism. In some embodiments, such translation occurs in vivo, although such translation may occur ex vivo, in culture or in vitro. In some embodiments, the cell, tissue or organism is contacted with an effective amount of a composition containing a respiratory virus RNA (e.g., mRNA) vaccine that contains a polynucleotide that has at least one a translatable region encoding an antigenic polypeptide.

An "effective amount" of an respiratory virus RNA (e.g. mRNA) vaccine is provided based, at least in part, on the target tissue, target cell type, means of administration, physical characteristics of the polynucleotide (e.g., size, and extent of modified nucleosides) and other components of the vaccine, and other determinants. In general, an effective amount of the respiratory virus RNA (e.g., mRNA) vaccine composition provides an induced or boosted immune response as a function of antigen production in the cell, preferably more efficient than a composition containing a corresponding unmodified polynucleotide encoding the same antigen or a peptide antigen. Increased antigen production may be demonstrated by increased cell transfection (the percentage of cells transfected with the RNA, e.g., mRNA, vaccine), increased protein translation from the polynucleotide, decreased nucleic acid degradation (as demonstrated, for example, by increased duration of protein translation from a modified polynucleotide), or altered antigen specific immune response of the host cell.

In some embodiments, RNA (e.g. mRNA) vaccines (including polynucleotides their encoded polypeptides) in accordance with the present disclosure may be used for treatment of hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1).

Respiratory RNA (e.g. mRNA) vaccines may be administered prophylactically or therapeutically as part of an active immunization scheme to healthy individuals or early in infection during the incubation phase or during active infection after onset of symptoms. In some embodiments, the amount of RNA (e.g., mRNA) vaccine of the present disclosure provided to a cell, a tissue or a subject may be an amount effective for immune prophylaxis.

Respiratory virus RNA (e.g. mRNA) vaccines may be administrated with other prophylactic or therapeutic compounds. As a non-limiting example, a prophylactic or therapeutic compound may be an adjuvant or a booster. As used herein, when referring to a prophylactic composition, such as a vaccine, the term "booster" refers to an extra administration of the prophylactic (vaccine) composition. A booster (or booster vaccine) may be given after an earlier administration of the prophylactic composition. The time of administration between the initial administration of the prophylactic composition and the booster may be, but is not limited to, 1 minute, 2 minutes, 3 minutes, 4 minutes, 5 minutes, 6 minutes, 7 minutes, 8 minutes, 9 minutes, 10 minutes, 15 minutes, 20 minutes 35 minutes, 40 minutes, 45 minutes, 50 minutes, 55 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 36 hours, 2 days, 3 days, 4 days, 5 days, 6 days, 1 week, 10 days, 2 weeks, 3 weeks, 1 month, 2 months, 3 months, 4 months, 5 months, 6 months, 7 months, 8 months, 9 months, 10 months, 11 months, 1 year, 18 months, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 25 years, 30 years, 35 years, 40 years, 45 years, 50 years, 55 years, 60 years, 65 years, 70 years, 75 years, 80 years, 85 years, 90 years, 95 years or more than 99 years. In some embodiments, the time of administration between the initial administration of the prophylactic composition and the booster may be, but is not limited to, 1 week, 2 weeks, 3 weeks, 1 month, 2 months, 3 months, 6 months or 1 year.

In some embodiments, respiratory virus RNA (e.g. mRNA) vaccines may be administered intramuscularly or intradermally, similarly to the administration of inactivated vaccines known in the art.

Respiratory virus RNA (e.g. mRNA) vaccines may be utilized in various settings depending on the prevalence of the infection or the degree or level of unmet medical need. As a non-limiting example, the RNA (e.g., mRNA) vaccines may be utilized to treat and/or prevent a variety of respiratory infections. RNA (e.g., mRNA) vaccines have superior properties in that they produce much larger antibody titers and produce responses early than commercially available anti-viral agents/compositions.

Provided herein are pharmaceutical compositions including respiratory virus RNA (e.g. mRNA) vaccines and RNA (e.g. mRNA) vaccine compositions and/or complexes optionally in combination with one or more pharmaceutically acceptable excipients.

Respiratory virus RNA (e.g. mRNA) vaccines may be formulated or administered alone or in conjunction with one or more other components. For instance, hMPV/PIV3/RSV RNA (e.g., mRNA) vaccines (vaccine compositions) may comprise other components including, but not limited to, adjuvants.

In some embodiments, respiratory virus (e.g. mRNA) vaccines do not include an adjuvant (they are adjuvant free).

Respiratory virus RNA (e.g. mRNA) vaccines may be formulated or administered in combination with one or more pharmaceutically-acceptable excipients. In some embodiments, vaccine compositions comprise at least one additional active substances, such as, for example, a therapeutically-active substance, a prophylactically-active substance, or a combination of both. Vaccine compositions may be sterile, pyrogen-free or both sterile and pyrogen-free. General considerations in the formulation and/or manufacture of pharmaceutical agents, such as vaccine compositions, may be found, for example, in Remington: The Science and Practice of Pharmacy 21st ed., Lippincott Williams & Wilkins, 2005 (incorporated herein by reference in its entirety).

In some embodiments, respiratory virus RNA (e.g. mRNA) vaccines are administered to humans, human patients or subjects. For the purposes of the present disclosure, the phrase "active ingredient" generally refers to the RNA (e.g., mRNA) vaccines or the polynucleotides contained therein, for example, RNA polynucleotides (e.g., mRNA polynucleotides) encoding antigenic polypeptides.

Formulations of the respiratory virus vaccine compositions described herein may be prepared by any method known or hereafter developed in the art of pharmacology. In general, such preparatory methods include the step of bringing the active ingredient (e.g., mRNA polynucleotide) into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the disclosure will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

Respiratory virus RNA (e.g. mRNA) vaccines can be formulated using one or more excipients to: (1) increase stability; (2) increase cell transfection; (3) permit the sustained or delayed release (e.g., from a depot formulation); (4) alter the biodistribution (e.g., target to specific tissues or cell types); (5) increase the translation of encoded protein in vivo; and/or (6) alter the release profile of encoded protein (antigen) in vivo. In addition to traditional excipients such as any and all solvents, dispersion media, diluents, or other liquid vehicles, dispersion or suspension aids, surface active agents, isotonic agents, thickening or emulsifying agents, preservatives, excipients can include, without limitation, lipidoids, liposomes, lipid nanoparticles, polymers, lipoplexes, core-shell nanoparticles, peptides, proteins, cells transfected with respiratory virus RNA (e.g. mRNA) vaccines (e.g., for transplantation into a subject), hyaluronidase, nanoparticle mimics and combinations thereof.

Stabilizing Elements

Naturally-occurring eukaryotic mRNA molecules have been found to contain stabilizing elements, including, but not limited to untranslated regions (UTR) at their 5'-end (5'UTR) and/or at their 3'-end (3'UTR), in addition to other structural features, such as a 5'-cap structure or a 3'-poly(A) tail. Both the 5'UTR and the 3'UTR are typically transcribed from the genomic DNA and are elements of the premature mRNA. Characteristic structural features of mature mRNA, such as the 5'-cap and the 3'-poly(A) tail are usually added to the transcribed (premature) mRNA during mRNA processing. The 3'-poly(A) tail is typically a stretch of adenine nucleotides added to the 3'-end of the transcribed mRNA. It can comprise up to about 400 adenine nucleotides. In some embodiments the length of the 3'-poly(A) tail may be an essential element with respect to the stability of the individual mRNA.

In some embodiments the RNA (e.g., mRNA) vaccine may include one or more stabilizing elements. Stabilizing elements may include for instance a histone stem-loop. A stem-loop binding protein (SLBP), a 32 kDa protein has been identified. It is associated with the histone stem-loop at the 3'-end of the histone messages in both the nucleus and the cytoplasm. Its expression level is regulated by the cell cycle; it peaks during the S-phase, when histone mRNA levels are also elevated. The protein has been shown to be essential for efficient 3'-end processing of histone pre-mRNA by the U7 snRNP. SLBP continues to be associated with the stem-loop after processing, and then stimulates the translation of mature histone mRNAs into histone proteins in the cytoplasm. The RNA binding domain of SLBP is conserved through metazoa and protozoa; its binding to the histone stem-loop depends on the structure of the loop. The minimum binding site includes at least three nucleotides 5' and two nucleotides 3' relative to the stem-loop.

In some embodiments, the RNA (e.g., mRNA) vaccines include a coding region, at least one histone stem-loop, and optionally, a poly(A) sequence or polyadenylation signal. The poly(A) sequence or polyadenylation signal generally should enhance the expression level of the encoded protein. The encoded protein, in some embodiments, is not a histone protein, a reporter protein (e.g. Luciferase, GFP, EGFP, β-Galactosidase, EGFP), or a marker or selection protein (e.g. alpha-Globin, Galactokinase and Xanthine:guanine phosphoribosyl transferase (GPT)).

In some embodiments, the combination of a poly(A) sequence or polyadenylation signal and at least one histone stem-loop, even though both represent alternative mechanisms in nature, acts synergistically to increase the protein expression beyond the level observed with either of the individual elements. It has been found that the synergistic effect of the combination of poly(A) and at least one histone stem-loop does not depend on the order of the elements or the length of the poly(A) sequence.

In some embodiments, the RNA (e.g., mRNA) vaccine does not comprise a histone downstream element (HDE). "Histone downstream element" (HDE) includes a purine-rich polynucleotide stretch of approximately 15 to 20 nucleotides 3' of naturally occurring stem-loops, representing the binding site for the U7 snRNA, which is involved in processing of histone pre-mRNA into mature histone mRNA. Ideally, the inventive nucleic acid does not include an intron.

In some embodiments, the RNA (e.g., mRNA) vaccine may or may not contain a enhancer and/or promoter sequence, which may be modified or unmodified or which may be activated or inactivated. In some embodiments, the histone stem-loop is generally derived from histone genes, and includes an intramolecular base pairing of two neighbored partially or entirely reverse complementary sequences separated by a spacer, including (e.g., consisting of) a short sequence, which forms the loop of the structure. The unpaired loop region is typically unable to base pair with either of the stem loop elements. It occurs more often in RNA, as is a key component of many RNA secondary structures, but may be present in single-stranded DNA as well. Stability of the stem-loop structure generally depends on the length, number of mismatches or bulges, and base composition of the paired region. In some embodiments, wobble base pairing (non-Watson-Crick base pairing) may result. In some embodiments, the at least one histone stem-loop sequence comprises a length of 15 to 45 nucleotides.

In other embodiments the RNA (e.g., mRNA) vaccine may have one or more AU-rich sequences removed. These sequences, sometimes referred to as AURES are destabilizing sequences found in the 3'UTR. The AURES may be removed from the RNA (e.g., mRNA) vaccines. Alternatively the AURES may remain in the RNA (e.g., mRNA) vaccine.

Nanoparticle Formulations

In some embodiments, respiratory virus RNA (e.g. mRNA) vaccines are formulated in a nanoparticle. In some embodiments, respiratory virus RNA (e.g. mRNA) vaccines are formulated in a lipid nanoparticle. In some embodiments, respiratory virus RNA (e.g. mRNA) vaccines are formulated in a lipid-polycation complex, referred to as a cationic lipid nanoparticle. As a non-limiting example, the polycation may include a cationic peptide or a polypeptide such as, but not limited to, polylysine, polyornithine and/or polyarginine. In some embodiments, respiratory virus RNA (e.g., mRNA) vaccines are formulated in a lipid nanoparticle that includes a non-cationic lipid such as, but not limited to, cholesterol or dioleoyl phosphatidylethanolamine (DOPE).

A lipid nanoparticle formulation may be influenced by, but not limited to, the selection of the cationic lipid component, the degree of cationic lipid saturation, the nature of the PEGylation, ratio of all components and biophysical parameters such as size. In one example by Semple et al. (*Nature Biotech.* 2010 28:172-176), the lipid nanoparticle formulation is composed of 57.1% cationic lipid, 7.1% dipalmitoylphosphatidylcholine, 34.3% cholesterol, and 1.4% PEG-c-DMA. As another example, changing the composition of the cationic lipid can more effectively deliver siRNA to various antigen presenting cells (Basha et al. *Mol Ther.* 2011 19:2186-2200).

In some embodiments, lipid nanoparticle formulations may comprise 35 to 45% cationic lipid, 40% to 50% cationic lipid, 50% to 60% cationic lipid and/or 55% to 65% cationic lipid. In some embodiments, the ratio of lipid to RNA (e.g., mRNA) in lipid nanoparticles may be 5:1 to 20:1, 10:1 to 25:1, 15:1 to 30:1 and/or at least 30:1.

In some embodiments, the ratio of PEG in the lipid nanoparticle formulations may be increased or decreased and/or the carbon chain length of the PEG lipid may be modified from C14 to C18 to alter the pharmacokinetics and/or biodistribution of the lipid nanoparticle formulations. As a non-limiting example, lipid nanoparticle formulations may contain 0.5% to 3.0%, 1.0% to 3.5%, 1.5% to 4.0%, 2.0% to 4.5%, 2.5% to 5.0% and/or 3.0% to 6.0% of the lipid molar ratio of PEG-c-DOMG (R-3-[(ω-methoxy-poly(ethyleneglycol)2000)carbamoyl)]-1,2-dimyristyloxypropyl-3-amine) (also referred to herein as PEG-DOMG) as compared to the cationic lipid, DSPC and cholesterol. In some embodiments, the PEG-c-DOMG may be replaced with a PEG lipid such as, but not limited to, PEG-DSG (1,2-Distearoyl-sn-glycerol, methoxypolyethylene glycol), PEG-DMG (1,2-Dimyristoyl-sn-glycerol) and/or PEG-DPG (1,2-Dipalmitoyl-sn-glycerol, methoxypolyethylene glycol). The cationic lipid may be selected from any lipid known in the art such as, but not limited to, DLin-MC3-DMA, DLin-DMA, C12-200 and DLin-KC2-DMA.

In some embodiments, an respiratory virus RNA (e.g. mRNA) vaccine formulation is a nanoparticle that comprises at least one lipid. The lipid may be selected from, but is not limited to, DLin-DMA, DLin-K-DMA, 98N12-5, C12-200, DLin-MC3-DMA, DLin-KC2-DMA, DODMA, PLGA, PEG, PEG-DMG, PEGylated lipids and amino alcohol lipids. In some embodiments, the lipid may be a cationic lipid such as, but not limited to, DLin-DMA, DLin-D-DMA, DLin-MC3-DMA, DLin-KC2-DMA, DODMA and amino alcohol lipids. The amino alcohol cationic lipid may be the lipids described in and/or made by the methods described in U.S. Patent Publication No. US20130150625, herein incorporated by reference in its entirety. As a non-limiting example, the cationic lipid may be 2-amino-3-[(9Z,12Z)-octadeca-9,12-dien-1-yloxy]-2-{[(9Z,2Z)-octadeca-9,12-dien-1-yloxy]methyl}propan-1-ol (Compound 1 in US20130150625); 2-amino-3-[(9Z)-octadec-9-en-1-yloxy]-2-{[(9Z)-octadec-9-en-1-yloxy]methyl}propan-1-ol (Compound 2 in US20130150625); 2-amino-3-[(9Z,12Z)-octadeca-9,12-dien-1-yloxy]-2-[(octyloxy)methyl]propan-1-ol (Compound 3 in US20130150625); and 2-(dimethylamino)-3-[(9Z,12Z)-octadeca-9,12-dien-1-yloxy]-2-{[(9Z,12Z)-octadeca-9,12-dien-1-yloxy]methyl}propan-1-ol (Compound 4 in US20130150625); or any pharmaceutically acceptable salt or stereoisomer thereof.

Lipid nanoparticle formulations typically comprise a lipid, in particular, an ionizable cationic lipid, for example, 2,2-dilinoleyl-4-dimethylaminoethyl-[1,3]-dioxolane (DLin-KC2-DMA), dilinoleyl-methyl-4-dimethylaminobutyrate (DLin-MC3-DMA), or di((Z)-non-2-en-1-yl) 9-((4-(dimethylamino)butanoyl)oxy)heptadecanedioate (L319), and further comprise a neutral lipid, a sterol and a molecule capable of reducing particle aggregation, for example a PEG or PEG-modified lipid.

In some embodiments, a lipid nanoparticle formulation consists essentially of (i) at least one lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy) heptadecanedioate (L319); (ii) a neutral lipid selected from DSPC, DPPC, POPC, DOPE and SM; (iii) a sterol, e.g., cholesterol; and (iv) a PEG-lipid, e.g., PEG-DMG or PEG-cDMA, in a molar ratio of 20-60% cationic lipid:5-25% neutral lipid:25-55% sterol; 0.5-15% PEG-lipid.

In some embodiments, a lipid nanoparticle formulation includes 25% to 75% on a molar basis of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), e.g., 35 to 65%, 45 to 65%, 60%, 57.5%, 50% or 40% on a molar basis.

In some embodiments, a lipid nanoparticle formulation includes 0.5% to 15% on a molar basis of the neutral lipid, e.g., 3 to 12%, 5 to 10% or 15%, 10%, or 7.5% on a molar basis. Examples of neutral lipids include, without limitation, DSPC, POPC, DPPC, DOPE and SM. In some embodiments, the formulation includes 5% to 50% on a molar basis of the sterol (e.g., 15 to 45%, 20 to 40%, 40%, 38.5%, 35%, or 31% on a molar basis. A non-limiting example of a sterol is cholesterol. In some embodiments, a lipid nanoparticle formulation includes 0.5% to 20% on a molar basis of the PEG or PEG-modified lipid (e.g., 0.5 to 10%, 0.5 to 5%, 1.5%, 0.5%, 1.5%, 3.5%, or 5% on a molar basis. In some embodiments, a PEG or PEG modified lipid comprises a PEG molecule of an average molecular weight of 2,000 Da. In some embodiments, a PEG or PEG modified lipid comprises a PEG molecule of an average molecular weight of less than 2,000, for example around 1,500 Da, around 1,000 Da, or around 500 Da. Non-limiting examples of PEG-modified lipids include PEG-distearoyl glycerol (PEG-DMG) (also referred herein as PEG-C14 or C14-PEG), PEG-cDMA (further discussed in Reyes et al. J. Controlled Release, 107, 276-287 (2005) the contents of which are herein incorporated by reference in their entirety).

In some embodiments, lipid nanoparticle formulations include 25-75% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 0.5-15% of the neutral lipid, 5-50% of the sterol, and 0.5-20% of the PEG or PEG-modified lipid on a molar basis.

In some embodiments, lipid nanoparticle formulations include 35-65% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 3-12% of the neutral lipid, 15-45% of the sterol, and 0.5-10% of the PEG or PEG-modified lipid on a molar basis.

In some embodiments, lipid nanoparticle formulations include 45-65% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 5-10% of the neutral lipid, 25-40% of the sterol, and 0.5-10% of the PEG or PEG-modified lipid on a molar basis.

In some embodiments, lipid nanoparticle formulations include 60% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 7.5% of the neutral lipid, 31% of the sterol, and 1.5% of the PEG or PEG-modified lipid on a molar basis.

In some embodiments, lipid nanoparticle formulations include 50% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 10% of the neutral lipid, 38.5% of the sterol, and 1.5% of the PEG or PEG-modified lipid on a molar basis.

In some embodiments, lipid nanoparticle formulations include 50% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 10% of the neutral lipid, 35% of the sterol, 4.5% or 5% of the PEG or PEG-modified lipid, and 0.5% of the targeting lipid on a molar basis.

In some embodiments, lipid nanoparticle formulations include 40% of a cationic lipid selected from 2,2-dilinoleyl-4-dimethylaminoethyl[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 15% of the neutral lipid, 40% of the sterol, and 5% of the PEG or PEG-modified lipid on a molar basis.

In some embodiments, lipid nanoparticle formulations include 57.2% of a cationic lipid selected from 2,2-dilinoleyl-4-dimethylaminoethyl[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 7.1% of the neutral lipid, 34.3% of the sterol, and 1.4% of the PEG or PEG-modified lipid on a molar basis.

In some embodiments, lipid nanoparticle formulations include 57.5% of a cationic lipid selected from the PEG lipid is PEG-cDMA (PEG-cDMA is further discussed in Reyes et al. (J. Controlled Release, 107, 276-287 (2005), the contents of which are herein incorporated by reference in their entirety), 7.5% of the neutral lipid, 31.5% of the sterol, and 3.5% of the PEG or PEG-modified lipid on a molar basis.

In some embodiments, lipid nanoparticle formulations consists essentially of a lipid mixture in molar ratios of 20-70% cationic lipid: 5-45% neutral lipid: 20-55% cholesterol: 0.5-15% PEG-modified lipid. In some embodiments, lipid nanoparticle formulations consists essentially of a lipid mixture in a molar ratio of 20-60% cationic lipid:5-25% neutral lipid:25-55% cholesterol:0.5-15% PEG-modified lipid.

In some embodiments, the molar lipid ratio is 50/10/38.5/1.5 (mol % cationic lipid/neutral lipid, e.g., DSPC/Chol/PEG-modified lipid, e.g., PEG-DMG, PEG-DSG or PEG- DPG), 57.2/7.1134.3/1.4 (mol % cationic lipid/neutral lipid, e.g., DPPC/Chol/PEG-modified lipid, e.g., PEG-cDMA), 40/15/40/5 (mol % cationic lipid/neutral lipid, e.g., DSPC/Chol/PEG-modified lipid, e.g., PEG-DMG), 50/10/35/4.5/0.5 (mol % cationic lipid/neutral lipid, e.g., DSPC/Chol/PEG-modified lipid, e.g., PEG-DSG), 50/10/35/5 (cationic lipid/neutral lipid, e.g., DSPC/Chol/PEG-modified lipid, e.g., PEG-DMG), 40/10/40/10 (mol % cationic lipid/neutral lipid, e.g., DSPC/Chol/PEG-modified lipid, e.g., PEG-DMG or PEG-cDMA), 35/15/40/10 (mol % cationic lipid/neutral lipid, e.g., DSPC/Chol/PEG-modified lipid, e.g., PEG-DMG or PEG-cDMA) or 52/13/30/5 (mol % cationic lipid/neutral lipid, e.g., DSPC/Chol/PEG-modified lipid, e.g., PEG-DMG or PEG-cDMA).

Non-limiting examples of lipid nanoparticle compositions and methods of making them are described, for example, in Semple et al. (2010) *Nat. Biotechnol.* 28:172-176; Jayarama et al. (2012), *Angew. Chem. Int. Ed.,* 51: 8529-8533; and Maier et al. (2013) *Molecular Therapy* 21, 1570-1578 (the contents of each of which are incorporated herein by reference in their entirety).

In some embodiments, lipid nanoparticle formulations may comprise a cationic lipid, a PEG lipid and a structural lipid and optionally comprise a non-cationic lipid. As a non-limiting example, a lipid nanoparticle may comprise 40-60% of cationic lipid, 5-15% of a non-cationic lipid, 1-2% of a PEG lipid and 30-50% of a structural lipid. As another non-limiting example, the lipid nanoparticle may comprise 50% cationic lipid, 10% non-cationic lipid, 1.5% PEG lipid and 38.5% structural lipid. As yet another non-limiting example, a lipid nanoparticle may comprise 55% cationic lipid, 10% non-cationic lipid, 2.5% PEG lipid and 32.5% structural lipid. In some embodiments, the cationic lipid may be any cationic lipid described herein such as, but not limited to, DLin-KC2-DMA, DLin-MC3-DMA and L319.

In some embodiments, the lipid nanoparticle formulations described herein may be 4 component lipid nanoparticles. The lipid nanoparticle may comprise a cationic lipid, a non-cationic lipid, a PEG lipid and a structural lipid. As a non-limiting example, the lipid nanoparticle may comprise 40-60% of cationic lipid, 5-15% of a non-cationic lipid, 1-2% of a PEG lipid and 30-50% of a structural lipid. As another non-limiting example, the lipid nanoparticle may comprise 50% cationic lipid, 10% non-cationic lipid, 1.5% PEG lipid and 38.5% structural lipid. As yet another non-limiting example, the lipid nanoparticle may comprise 55% cationic lipid, 10% non-cationic lipid, 2.5% PEG lipid and 32.5% structural lipid. In some embodiments, the cationic lipid may be any cationic lipid described herein such as, but not limited to, DLin-KC2-DMA, DLin-MC3-DMA and L319.

In some embodiments, the lipid nanoparticle formulations described herein may comprise a cationic lipid, a non-cationic lipid, a PEG lipid and a structural lipid. As a non-limiting example, the lipid nanoparticle comprise 50% of the cationic lipid DLin-KC2-DMA, 10% of the non-cationic lipid DSPC, 1.5% of the PEG lipid PEG-DOMG and 38.5% of the structural lipid cholesterol. As a non-limiting example, the lipid nanoparticle comprise 50% of the cationic lipid DLin-MC3-DMA, 10% of the non-cationic lipid DSPC, 1.5% of the PEG lipid PEG-DOMG and 38.5% of the structural lipid cholesterol. As a non-limiting example, the lipid nanoparticle comprise 50% of the cationic lipid DLin-MC3-DMA, 10% of the non-cationic lipid DSPC, 1.5% of the PEG lipid PEG-DMG and 38.5% of the structural lipid cholesterol. As yet another non-limiting example, the lipid nanoparticle comprise 55% of the cationic lipid L319, 10% of the non-cationic lipid DSPC, 2.5% of the PEG lipid PEG-DMG and 32.5% of the structural lipid cholesterol.

Relative amounts of the active ingredient, the pharmaceutically acceptable excipient, and/or any additional ingredients in a vaccine composition may vary, depending upon the identity, size, and/or condition of the subject being treated and further depending upon the route by which the composition is to be administered. For example, the composition may comprise between 0.1% and 99% (w/w) of the active ingredient. By way of example, the composition may comprise between 0.1% and 100%, e.g., between 0.5 and 50%, between 1-30%, between 5-80%, at least 80% (w/w) active ingredient.

In some embodiments, the respiratory virus RNA (e.g. mRNA) vaccine composition may comprise the polynucleotide described herein, formulated in a lipid nanoparticle comprising MC3, Cholesterol, DSPC and PEG2000-DMG, the buffer trisodium citrate, sucrose and water for injection. As a non-limiting example, the composition comprises: 2.0 mg/mL of drug substance (e.g., polynucleotides encoding H10N8 hMPV), 21.8 mg/mL of MC3, 10.1 mg/mL of cholesterol, 5.4 mg/mL of DSPC, 2.7 mg/mL of PEG2000-DMG, 5.16 mg/mL of trisodium citrate, 71 mg/mL of sucrose and 1.0 mL of water for injection.

In some embodiments, a nanoparticle (e.g., a lipid nanoparticle) has a mean diameter of 10-500 nm, 20-400 nm, 30-300 nm, 40-200 nm. In some embodiments, a nanoparticle (e.g., a lipid nanoparticle) has a mean diameter of 50-150 nm, 50-200 nm, 80-100 nm or 80-200 nm.

Liposomes, Lipoplexes, and Lipid Nanoparticles

The RNA (e.g., mRNA) vaccines of the disclosure can be formulated using one or more liposomes, lipoplexes, or lipid nanoparticles. In some embodiments, pharmaceutical compositions of RNA (e.g., mRNA) vaccines include liposomes. Liposomes are artificially-prepared vesicles which may primarily be composed of a lipid bilayer and may be used as a delivery vehicle for the administration of nutrients and pharmaceutical formulations. Liposomes can be of different sizes such as, but not limited to, a multilamellar vesicle (MLV) which may be hundreds of nanometers in diameter and may contain a series of concentric bilayers separated by narrow aqueous compartments, a small unicellular vesicle (SUV) which may be smaller than 50 nm in diameter, and a large unilamellar vesicle (LUV) which may be between 50 and 500 nm in diameter. Liposome design may include, but is not limited to, opsonins or ligands in order to improve the attachment of liposomes to unhealthy tissue or to activate events such as, but not limited to, endocytosis. Liposomes may contain a low or a high pH in order to improve the delivery of the pharmaceutical formulations.

The formation of liposomes may depend on the physicochemical characteristics such as, but not limited to, the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimization size, polydispersity and the shelf-life of the vesicles for the intended application, and the batch-to-batch reproducibility and possibility of large-scale production of safe and efficient liposomal products.

In some embodiments, pharmaceutical compositions described herein may include, without limitation, liposomes such as those formed from 1,2-dioleyloxy-N,N-dimethylaminopropane (DODMA) liposomes, DiLa2 liposomes from Marina Biotech (Bothell, Wash.), 1,2-dilinoleyloxy-3-dimethylaminopropane (DLin-DMA), 2,2-dilinoleyl-4-(2-dimethylaminoethyl)-[1,3]-dioxolane (DLin-KC2-DMA), and MC3 (US20100324120; herein incorporated by reference in its entirety) and liposomes which may deliver small molecule drugs such as, but not limited to, DOXIL® from Janssen Biotech, Inc. (Horsham, Pa.).

In some embodiments, pharmaceutical compositions described herein may include, without limitation, liposomes such as those formed from the synthesis of stabilized plasmid-lipid particles (SPLP) or stabilized nucleic acid lipid particle (SNALP) that have been previously described and shown to be suitable for oligonucleotide delivery in vitro and in vivo (see Wheeler et al. Gene Therapy. 1999 6:271-281; Zhang et al. Gene Therapy. 1999 6:1438-1447; Jeffs et al. Pharm Res. 2005 22:362-372; Morrissey et al., Nat Biotechnol. 2005 2:1002-1007; Zimmermann et al., Nature. 2006 441:111-114; Heyes et al. J Contr Rel. 2005 107:276-287; Semple et al. Nature Biotech. 2010 28:172-176; Judge et al. J Clin Invest. 2009 119:661-673; deFougerolles Hum Gene Ther. 2008 19:125-132; U.S. Patent Publication No US20130122104; all of which are incorporated herein in their entireties). The original manufacture method by Wheeler et al. was a detergent dialysis method, which was later improved by Jeffs et al. and is referred to as the spontaneous vesicle formation method. The liposome formulations are composed of 3 to 4 lipid components in addition to the polynucleotide. As an example a liposome can contain, but is not limited to, 55% cholesterol, 20% disteroylphosphatidyl choline (DSPC), 10% PEG-S-DSG, and 15% 1,2-dioleyloxy-N,N-dimethylaminopropane (DODMA), as described by Jeffs et al. As another example, certain liposome formulations may contain, but are not limited to, 48% cholesterol, 20% DSPC, 2% PEG-c-DMA, and 30% cationic lipid, where the cationic lipid can be 1,2-distearloxy-N,N-dimethylaminopropane (DSDMA), DODMA, DLin-DMA, or 1,2-dilinolenyloxy-3-dimethylaminopropane (DLenDMA), as described by Heyes et al.

In some embodiments, liposome formulations may comprise from about 25.0% cholesterol to about 40.0% cholesterol, from about 30.0% cholesterol to about 45.0% cholesterol, from about 35.0% cholesterol to about 50.0% cholesterol and/or from about 48.5% cholesterol to about 60% cholesterol. In some embodiments, formulations may comprise a percentage of cholesterol selected from the group consisting of 28.5%, 31.5%, 33.5%, 36.5%, 37.0%, 38.5%, 39.0% and 43.5%. In some embodiments, formulations may comprise from about 5.0% to about 10.0% DSPC and/or from about 7.0% to about 15.0% DSPC.

In some embodiments, the RNA (e.g., mRNA) vaccine pharmaceutical compositions may be formulated in liposomes such as, but not limited to, DiLa2 liposomes (Marina Biotech, Bothell, Wash.), SMARTICLES® (Marina Biotech, Bothell, Wash.), neutral DOPC (1,2-dioleoyl-sn-glycero-3-phosphocholine) based liposomes (e.g., siRNA delivery for ovarian cancer (Landen et al. Cancer Biology & Therapy 2006 5(12)1708-1713); herein incorporated by reference in its entirety) and hyaluronan-coated liposomes (Quiet Therapeutics, Israel).

In some embodiments, the cationic lipid may be a low molecular weight cationic lipid such as those described in U.S. Patent Application No. 20130090372, the contents of which are herein incorporated by reference in their entirety.

In some embodiments, the RNA (e.g., mRNA) vaccines may be formulated in a lipid vesicle, which may have crosslinks between functionalized lipid bilayers.

In some embodiments, the RNA (e.g., mRNA) vaccines may be formulated in a lipid-polycation complex. The formation of the lipid-polycation complex may be accomplished by methods known in the art and/or as described in U.S. Pub. No. 20120178702, herein incorporated by reference in its entirety. As a non-limiting example, the polycation may include a cationic peptide or a polypeptide such as, but not limited to, polylysine, polyornithine and/or polyarginine. In some embodiments, the RNA (e.g., mRNA) vaccines may be formulated in a lipid-polycation complex, which may further include a non-cationic lipid such as, but not limited to, cholesterol or dioleoyl phosphatidylethanolamine (DOPE).

In some embodiments, the ratio of PEG in the lipid nanoparticle (LNP) formulations may be increased or decreased and/or the carbon chain length of the PEG lipid may be modified from C14 to C18 to alter the pharmacokinetics and/or biodistribution of the LNP formulations. As a non-limiting example, LNP formulations may contain from about 0.5% to about 3.0%, from about 1.0% to about 3.5%, from about 1.5% to about 4.0%, from about 2.0% to about 4.5%, from about 2.5% to about 5.0% and/or from about 3.0% to about 6.0% of the lipid molar ratio of PEG-c-DOMG (R-3-[(ω-methoxy-poly(ethyleneglycol)2000)carbamoyl)]-1,2-dimyristyloxypropyl-3-amine) (also referred to herein as PEG-DOMG) as compared to the cationic lipid, DSPC and cholesterol. In some embodiments, the PEG-c-DOMG may be replaced with a PEG lipid such as, but not limited to, PEG-DSG (1,2-Distearoyl-sn-glycerol, methoxypolyethylene glycol), PEG-DMG (1,2-Dimyristoyl-sn-glycerol) and/or PEG-DPG (1,2-Dipalmitoyl-sn-glycerol, methoxypolyethylene glycol). The cationic lipid may be selected from any lipid known in the art such as, but not limited to, DLin-MC3-DMA, DLin-DMA, C12-200 and DLin-KC2-DMA.

In some embodiments, the RNA (e.g., mRNA) vaccines may be formulated in a lipid nanoparticle.

In some embodiments, the RNA (e.g., mRNA) vaccine formulation comprising the polynucleotide is a nanoparticle which may comprise at least one lipid. The lipid may be selected from, but is not limited to, DLin-DMA, DLin-K-DMA, 98N12-5, C12-200, DLin-MC3-DMA, DLin-KC2-DMA, DODMA, PLGA, PEG, PEG-DMG, PEGylated lipids and amino alcohol lipids. In another aspect, the lipid may be a cationic lipid such as, but not limited to, DLin-DMA, DLin-D-DMA, DLin-MC3-DMA, DLin-KC2-DMA, DODMA and amino alcohol lipids. The amino alcohol cationic lipid may be the lipids described in and/or made by the methods described in U.S. Patent Publication No. US20130150625, herein incorporated by reference in its entirety. As a non-limiting example, the cationic lipid may be 2-amino-3-[(9Z,12Z)-octadeca-9,12-dien-1-yloxy]-2-{[(9Z,2Z)-octadeca-9,12-dien-1-yloxy]methyl}propan-1-ol (Compound 1 in US20130150625); 2-amino-3-[(9Z)-octadec-9-en-1-yloxy]-2-{[(9Z)-octadec-9-en-1-yloxy]methyl}propan-1-ol (Compound 2 in US20130150625); 2-amino-3-[(9Z,12Z)-octadeca-9,12-dien-1-yloxy]-2-[(octyloxy)methyl]propan-1-ol (Compound 3 in US20130150625); and 2-(dimethylamino)-3-[(9Z,12Z)-octadeca-9,12-dien-1-yloxy]-2-{[(9Z,12Z)-octadeca-9,12-dien-1-yloxy]methyl}propan-1-ol (Compound 4 in US20130150625); or any pharmaceutically acceptable salt or stereoisomer thereof.

Lipid nanoparticle formulations typically comprise a lipid, in particular, an ionizable cationic lipid, for example, 2,2-dilinoleyl-4-dimethylaminoethyl-[1,3]-dioxolane (DLin-KC2-DMA), dilinoleyl-methyl-4-dimethylaminobutyrate (DLin-MC3-DMA), or di((Z)-non-2-en-1-yl) 9-((4-(dimethylamino)butanoyl)oxy)heptadecanedioate (L319), and further comprise a neutral lipid, a sterol and a molecule capable of reducing particle aggregation, for example a PEG or PEG-modified lipid.

In some embodiments, the lipid nanoparticle formulation consists essentially of (i) at least one lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy) heptadecanedioate (L319); (ii) a neutral lipid selected from DSPC, DPPC, POPC, DOPE and SM; (iii) a sterol, e.g., cholesterol; and (iv) a PEG-lipid, e.g., PEG-DMG or PEG-cDMA, in a molar ratio of about 20-60% cationic lipid:5-25% neutral lipid:25-55% sterol; 0.5-15% PEG-lipid.

In some embodiments, the formulation includes from about 25% to about 75% on a molar basis of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), e.g., from about 35 to about 65%, from about 45 to about 65%, about 60%, about 57.5%, about 50% or about 40% on a molar basis.

In some embodiments, the formulation includes from about 0.5% to about 15% on a molar basis of the neutral lipid e.g., from about 3 to about 12%, from about 5 to about 10% or about 15%, about 10%, or about 7.5% on a molar basis. Examples of neutral lipids include, but are not limited to, DSPC, POPC, DPPC, DOPE and SM. In some embodiments, the formulation includes from about 5% to about 50% on a molar basis of the sterol (e.g., about 15 to about 45%, about 20 to about 40%, about 40%, about 38.5%, about 35%, or about 31% on a molar basis. An exemplary sterol is cholesterol. In some embodiments, the formulation includes from about 0.5% to about 20% on a molar basis of the PEG or PEG-modified lipid (e.g., about 0.5 to about 10%, about 0.5 to about 5%, about 1.5%, about 0.5%, about 1.5%, about 3.5%, or about 5% on a molar basis. In some embodiments, the PEG or PEG modified lipid comprises a PEG molecule of an average molecular weight of 2,000 Da. In other embodiments, the PEG or PEG modified lipid comprises a PEG molecule of an average molecular weight of less than 2,000, for example around 1,500 Da, around 1,000 Da, or around 500 Da. Examples of PEG-modified lipids include, but are not limited to, PEG-distearoyl glycerol (PEG-DMG) (also referred herein as PEG-C14 or C14-PEG), PEG-cDMA (further discussed in Reyes et al. *J. Controlled Release,* 107, 276-287 (2005) the contents of which are herein incorporated by reference in their entirety)

In some embodiments, the formulations of the present disclosure include 25-75% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 0.5-15% of the neutral lipid, 5-50% of the sterol, and 0.5-20% of the PEG or PEG-modified lipid on a molar basis.

In some embodiments, the formulations of the present disclosure include 35-65% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 3-12% of the neutral lipid, 15-45% of the sterol, and 0.5-10% of the PEG or PEG-modified lipid on a molar basis.

In some embodiments, the formulations of the present disclosure include 45-65% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 5-10% of the neutral lipid, 25-40% of the sterol, and 0.5-10% of the PEG or PEG-modified lipid on a molar basis.

In some embodiments, the formulations of the present disclosure include about 60% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 7.5% of the neutral lipid, about 31% of the sterol, and about 1.5% of the PEG or PEG-modified lipid on a molar basis.

In some embodiments, the formulations of the present disclosure include about 50% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 10% of the neutral lipid, about 38.5% of the sterol, and about 1.5% of the PEG or PEG-modified lipid on a molar basis.

In some embodiments, the formulations of the present disclosure include about 50% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 10% of the neutral lipid, about 35% of the sterol, about 4.5% or about 5% of the PEG or PEG-modified lipid, and about 0.5% of the targeting lipid on a molar basis.

In some embodiments, the formulations of the present disclosure include about 40% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 15% of the neutral lipid, about 40% of the sterol, and about 5% of the PEG or PEG-modified lipid on a molar basis.

In some embodiments, the formulations of the present disclosure include about 57.2% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 7.1% of the neutral lipid, about 34.3% of the sterol, and about 1.4% of the PEG or PEG-modified lipid on a molar basis.

In some embodiments, the formulations of the present disclosure include about 57.5% of a cationic lipid selected from the PEG lipid is PEG-cDMA (PEG-cDMA is further discussed in Reyes et al. (J. Controlled Release, 107, 276-287 (2005), the contents of which are herein incorporated by reference in their entirety), about 7.5% of the neutral lipid, about 31.5% of the sterol, and about 3.5% of the PEG or PEG-modified lipid on a molar basis.

In some embodiments, lipid nanoparticle formulation consists essentially of a lipid mixture in molar ratios of about 20-70% cationic lipid: 5-45% neutral lipid: 20-55% cholesterol: 0.5-15% PEG-modified lipid; more preferably in a molar ratio of about 20-60% cationic lipid:5-25% neutral lipid:25-55% cholesterol:0.5-15% PEG-modified lipid.

In some embodiments, the molar lipid ratio is approximately 50/10/38.5/1.5 (mol % cationic lipid/neutral lipid, e.g., DSPC/Chol/PEG-modified lipid, e.g., PEG-DMG, PEG-DSG or PEG-DPG), 57.2/7.1134.3/1.4 (mol % cationic lipid/neutral lipid, e.g., DPPC/Chol/PEG-modified lipid, e.g., PEG-cDMA), 40/15/40/5 (mol % cationic lipid/neutral lipid, e.g., DSPC/Chol/PEG-modified lipid, e.g., PEG-DMG), 50/10/35/4.5/0.5 (mol % cationic lipid/neutral lipid, e.g., DSPC/Chol/PEG-modified lipid, e.g., PEG-DSG), 50/10/35/5 (cationic lipid/neutral lipid, e.g., DSPC/Chol/PEG-modified lipid, e.g., PEG-DMG), 40/10/40/10 (mol % cationic lipid/neutral lipid, e.g., DSPC/Chol/PEG-modified lipid, e.g., PEG-DMG or PEG-cDMA), 35/15/40/10 (mol % cationic lipid/neutral lipid, e.g., DSPC/Chol/PEG-modified lipid, e.g., PEG-DMG or PEG-cDMA) or 52/13/30/5 (mol % cationic lipid/neutral lipid, e.g., DSPC/Chol/PEG-modified lipid, e.g., PEG-DMG or PEG-cDMA).

Examples of lipid nanoparticle compositions and methods of making same are described, for example, in Semple et al. (2010) *Nat. Biotechnol.* 28:172-176; Jayarama et al. (2012), *Angew. Chem. Int. Ed.,* 51: 8529-8533; and Maier et al. (2013) *Molecular Therapy* 21, 1570-1578 (the contents of each of which are incorporated herein by reference in their entirety).

In some embodiments, the lipid nanoparticle formulations described herein may comprise a cationic lipid, a PEG lipid and a structural lipid and optionally comprise a non-cationic lipid. As a non-limiting example, the lipid nanoparticle may comprise about 40-60% of cationic lipid, about 5-15% of a non-cationic lipid, about 1-2% of a PEG lipid and about 30-50% of a structural lipid. As another non-limiting example, the lipid nanoparticle may comprise about 50% cationic lipid, about 10% non-cationic lipid, about 1.5% PEG lipid and about 38.5% structural lipid. As yet another non-limiting example, the lipid nanoparticle may comprise about 55% cationic lipid, about 10% non-cationic lipid, about 2.5% PEG lipid and about 32.5% structural lipid. In some embodiments, the cationic lipid may be any cationic lipid described herein such as, but not limited to, DLin-KC2-DMA, DLin-MC3-DMA and L319.

In some embodiments, the lipid nanoparticle formulations described herein may be 4 component lipid nanoparticles. The lipid nanoparticle may comprise a cationic lipid, a non-cationic lipid, a PEG lipid and a structural lipid. As a non-limiting example, the lipid nanoparticle may comprise about 40-60% of cationic lipid, about 5-15% of a non-cationic lipid, about 1-2% of a PEG lipid and about 30-50% of a structural lipid. As another non-limiting example, the lipid nanoparticle may comprise about 50% cationic lipid, about 10% non-cationic lipid, about 1.5% PEG lipid and about 38.5% structural lipid. As yet another non-limiting example, the lipid nanoparticle may comprise about 55% cationic lipid, about 10% non-cationic lipid, about 2.5% PEG lipid and about 32.5% structural lipid. In some embodiments, the cationic lipid may be any cationic lipid described herein such as, but not limited to, DLin-KC2-DMA, DLin-MC3-DMA and L319.

In some embodiments, the lipid nanoparticle formulations described herein may comprise a cationic lipid, a non-cationic lipid, a PEG lipid and a structural lipid. As a non-limiting example, the lipid nanoparticle comprise about 50% of the cationic lipid DLin-KC2-DMA, about 10% of the non-cationic lipid DSPC, about 1.5% of the PEG lipid PEG-DOMG and about 38.5% of the structural lipid cholesterol. As a non-limiting example, the lipid nanoparticle comprise about 50% of the cationic lipid DLin-MC3-DMA, about 10% of the non-cationic lipid DSPC, about 1.5% of the PEG lipid PEG-DOMG and about 38.5% of the structural lipid cholesterol. As a non-limiting example, the lipid nanoparticle comprise about 50% of the cationic lipid DLin-MC3-DMA, about 10% of the non-cationic lipid DSPC, about 1.5% of the PEG lipid PEG-DMG and about 38.5% of the structural lipid cholesterol. As yet another non-limiting example, the lipid nanoparticle comprise about 55% of the cationic lipid L319, about 10% of the non-cationic lipid DSPC, about 2.5% of the PEG lipid PEG-DMG and about 32.5% of the structural lipid cholesterol.

As a non-limiting example, the cationic lipid may be selected from (20Z,23Z)—N,N-dimethylnonacosa-20,23-dien-10-amine, (17Z,20Z)—N,N-dimemylhexacosa-17,20-dien-9-amine, (1Z,19Z)—N5N-dimethylpentacosa-1 6, 19-dien-8-amine, (13Z,16Z)—N,N-dimethyldocosa-13,16-dien-5-amine, (12Z,15Z)—N,N-dimethylhenicosa-12,15-dien-4-amine, (14Z,17Z)—N,N-dimethyltricosa-14,17-dien-6-amine, (15Z,18Z)—N,N-dimethyltetracosa-15,18-dien-7-amine, (18Z,21Z)—N,N-dimethylheptacosa-18,21-dien-10-amine, (15Z,18Z)—N,N-dimethyltetracosa-15,18-dien-5-amine, (14Z,17Z)—N,N-dimethyltricosa-14,17-dien-4-amine, (19Z,22Z)—N,N-dimeihyloctacosa-19,22-dien-9-amine, (18Z,21 Z)—N,N-dimethylheptacosa-18,21-dien-8-amine, (17Z,20Z)—N,N-dimethylhexacosa-17,20-dien-7-amine, (16Z,19Z)—N,N-dimethylpentacosa-16,19-dien-6-amine, (22Z,25Z)—N,N-dimethylhentriaconta-22,25-dien-10-amine, (21 Z,24Z)—N,N-dimethyltriaconta-21,24-dien-9-amine, (18Z)—N,N-dimetylheptacos-18-en-10-amine, (17Z)—N,N-dimethylhexacos-17-en-9-amine, (19Z,22Z)—N,N-dimethyloctacosa-19,22-dien-7-amine, N,N-dimethylheptacosan-10-amine, (20Z,23Z)—N-ethyl-N-methylnonacosa-20,23-dien-10-amine, 1-[(11Z,14Z)-1-nonylicosa-11,14-dien-1-yl]pyrrolidine, (20Z)—N,N-dimethylheptacos-20-en-10-amine, (15Z)—N,N-dimethyleptacos-15-en-10-amine, (14Z)—N,N-dimethylnonacos-14-en-10-amine, (17Z)—N,N-dimethylnonacos-17-en-10-amine, (24Z)—N,N-dimethyltritriacont-24-en-10-amine, (20Z)—N,N-dimethylnonacos-20-en-10-amine, (22Z)—N,N-dimethylhentriacont-22-en-10-amine, (16Z)—N,N-dimethylpentacos-16-en-8-amine, (12Z,15Z)—N,N-dimethyl-2-nonylhenicosa-12,15-dien-1-amine, (13Z,16Z)—N,N-dimethyl-3-nonyldocosa-13,16-dien-1-amine, N,N-dimethyl-1-[(1S,2R)-2-octylcyclopropyl]eptadecan-8-amine, 1-[(1S,2R)-2-hexylcyclopropyl]-N,N-dimethylnonadecan-10-amine, N,N-dimethyl-1-[(1R,2R)-2-octylcyclopropyl]nonadecan-10-amine, N,N-dimethyl-21-[(1S,2R)-2-octylcyclopropyl]henicosan-10-amine,N,N-dimethyl-1-[(1S,2S)-2-{[(1R,2R)-2-pentylcyclopropyl] methyl}cyclopropyl]nonadecan-10-amine,N,N-dimethyl-1-[(1S,2R)-2-octylcyclopropyl]hexadecan-8-amine, N,N-dimethyl-[(1R,2S)-2-undecylcyclopropyl]tetradecan-5-amine, N,N-dimethyl-3-{7-[(1S,2R)-2-octylcyclopropyl] heptyl} dodecan-1-amine, 1-[(1R,2S)-2-heptylcyclopropyl]-N,N-dimethyloctadecan-9-amine, 1-[(1S,2R)-2-decylcyclopropyl]-N,N-dimethylpentadecane-6-amine, N,N-dimethyl-1-[(1S,2R)-2-octylcyclopropyl]pentadecan-8-amine, R—N,N-dimethyl-1-[(9Z,12Z)-octadeca-9,12-dien-1-yloxy]-3-(octyloxy)propan-2-amine, S—N,N-dimethyl-1-[(9Z,12Z)-octadeca-9,12-dien-1-yloxy]-3-(octyloxy)propan-2-amine, 1-{2-[(9Z,12Z)-octadeca-9,12-dien-1-yloxy]-1-[(octyloxy)methyl]ethyl}pyrrolidine, (2S)—N,N-dimethyl-1-[(9Z,12Z)-octadeca-9,12-dien-1-yloxy]-3-[(5Z)-oct-5-en-1-yloxy]propan-2-amine, 1-{2-[(9Z,12Z)-octadeca-9,12-dien-1-yloxy]-1-[(octyloxy) methyl]ethyl}azetidine, (2S)-1-(hexyloxy)-N,N-dimethyl-3-[(9Z,12Z)-octadeca-9,12-dien-1-yloxy]propan-2-amine, (2S)-1-(heptyloxy)-N,N-dimethyl-3-[(9Z,12Z)-octadeca-9,12-dien-1-yloxy]propan-2-amine, N,N-dimethyl-1-(nonyloxy)-3-[(9Z,12Z)-octadeca-9,12-dien-1-yloxy]propan-2-amine, N,N-dimethyl-1-[(9Z)-octadec-9-en-1-yloxy]-3-(octyloxy)propan-2-amine; (2S)—N,N-dimethyl-1-[(6Z,9Z,12Z)-octadeca-6,9,12-trien-1-yloxy]-3-(octyloxy)propan-2-amine, (2S)-1-[(11Z,14Z)-icosa-11,14-dien-1-yloxy]-N,N-dimethyl-3-(pentyloxy)propan-2-amine, (2S)-1-(hexyloxy)-3-[(11Z,14Z)-icosa-11,14-dien-1-yloxy]-N,N-dimethylpropan-2-amine, 1-[(11Z,14Z)-icosa-11,14-dien-1-yloxy]-N,N-dimethyl-3-(octyloxy)propan-2-amine, 1-[(13Z,16Z)-docosa-13,16-dien-1-yloxy]-N,N-dimethyl-3-(octyloxy)propan-2-amine, (2S)-1-[(13Z,16Z)-docosa-13,16-dien-1-yloxy]-3-(hexyloxy)-N,N-dimethylpropan-2-amine, (2S)-1-[(13Z)-docos-13-en-1-yloxy]-3-(hexyloxy)-N,N-dimethylpropan-2-amine, 1-[(13Z)-docos-13-en-1-yloxy]-N,N-dimethyl-3-(octyloxy)propan-2-amine, 1-[(9Z)-hexadec-9-en-1-yloxy]-N,N-dimethyl-3-(octyloxy)propan-2-amine, (2R)—N,N-dimethyl-H(1-metoyloctyl)oxyl-3-[(9Z,12Z)-octadeca-9,12-dien-1-yloxy]propan-2-amine, (2R)-1-[(3,7-dimethyloctyl)oxy]-N,N-dimethyl-3[(9Z,12Z)-octadeca-9,12-dien-1-yloxy]propan-2-amine, N,N-dimethyl-1-(octyloxy)-3-({8-[(1S,2S)-2-{[(1R,2R)-2-pentylcyclopropyl]methyl}cyclopropyl]octyl}oxy)propan-2-amine, N,N-dimethyl-1-{[8-(2-oclylcyclopropyl)octyl]oxyl}-3-(octyloxy)propan-2-amine and (11E,20Z,23Z)—N,N-dimethylnonacosa-11,20,2-trien-10-amine or a pharmaceutically acceptable salt or stereoisomer thereof.

In some embodiments, the LNP formulations of the RNA (e.g., mRNA) vaccines may contain PEG-c-DOMG at 3% lipid molar ratio. In some embodiments, the LNP formulations of the RNA (e.g., mRNA) vaccines may contain PEG-c-DOMG at 1.5% lipid molar ratio.

In some embodiments, the pharmaceutical compositions of the RNA (e.g., mRNA) vaccines may include at least one of the PEGylated lipids described in International Publication No. WO2012099755, the contents of which are herein incorporated by reference in their entirety.

In some embodiments, the LNP formulation may contain PEG-DMG 2000 (1,2-dimyristoyl-sn-glycero-3-phophoethanolamine-N-[methoxy(polyethylene glycol)-2000). In some embodiments, the LNP formulation may contain PEG-DMG 2000, a cationic lipid known in the art and at least one other component. In some embodiments, the LNP formulation may contain PEG-DMG 2000, a cationic lipid known in the art, DSPC and cholesterol. As a non-limiting example, the LNP formulation may contain PEG-DMG 2000, DLin-DMA, DSPC and cholesterol. As another non-limiting example the LNP formulation may contain PEG-DMG 2000, DLin-DMA, DSPC and cholesterol in a molar ratio of 2:40:10:48 (see e.g., Geall et al., Nonviral delivery of self-amplifying RNA (e.g., mRNA) vaccines, PNAS 2012; PMID: 22908294, the contents of each of which are herein incorporated by reference in their entirety).

The lipid nanoparticles described herein may be made in a sterile environment.

In some embodiments, the LNP formulation may be formulated in a nanoparticle such as a nucleic acid-lipid particle. As a non-limiting example, the lipid particle may comprise one or more active agents or therapeutic agents; one or more cationic lipids comprising from about 50 mol % to about 85 mol % of the total lipid present in the particle; one or more non-cationic lipids comprising from about 13 mol % to about 49.5 mol % of the total lipid present in the particle; and one or more conjugated lipids that inhibit aggregation of particles comprising from about 0.5 mol % to about 2 mol % of the total lipid present in the particle.

The nanoparticle formulations may comprise a phosphate conjugate. The phosphate conjugate may increase in vivo circulation times and/or increase the targeted delivery of the nanoparticle. As a non-limiting example, the phosphate conjugates may include a compound of any one of the formulas described in International Application No. WO2013033438, the contents of which are herein incorporated by reference in its entirety.

The nanoparticle formulation may comprise a polymer conjugate. The polymer conjugate may be a water soluble conjugate. The polymer conjugate may have a structure as described in U.S. Patent Application No. 20130059360, the contents of which are herein incorporated by reference in its entirety. In some embodiments, polymer conjugates with the polynucleotides of the present disclosure may be made using the methods and/or segmented polymeric reagents described in U.S. Patent Application No. 20130072709, the contents of which are herein incorporated by reference in its entirety. In some embodiments, the polymer conjugate may have pendant side groups comprising ring moieties such as, but not limited to, the polymer conjugates described in U.S. Patent Publication No. US20130196948, the contents which are herein incorporated by reference in its entirety.

The nanoparticle formulations may comprise a conjugate to enhance the delivery of nanoparticles of the present disclosure in a subject. Further, the conjugate may inhibit phagocytic clearance of the nanoparticles in a subject. In one aspect, the conjugate may be a "self" peptide designed from the human membrane protein CD47 (e.g., the "self" particles described by Rodriguez et al. (*Science* 2013 339, 971-975), herein incorporated by reference in its entirety). As shown by Rodriguez et al., the self peptides delayed macrophage-mediated clearance of nanoparticles which enhanced delivery of the nanoparticles. In another aspect, the conjugate may be the membrane protein CD47 (e.g., see Rodriguez et al. *Science* 2013 339, 971-975, herein incorporated by reference in its entirety). Rodriguez et al. showed that, similarly to "self" peptides, CD47 can increase the circulating particle ratio in a subject as compared to scrambled peptides and PEG coated nanoparticles.

In some embodiments, the RNA (e.g., mRNA) vaccines of the present disclosure are formulated in nanoparticles which comprise a conjugate to enhance the delivery of the nanoparticles of the present disclosure in a subject. The conjugate may be the CD47 membrane or the conjugate may be derived from the CD47 membrane protein, such as the "self" peptide described previously. In some embodiments, the nanoparticle may comprise PEG and a conjugate of CD47 or a derivative thereof. In some embodiments, the nanoparticle may comprise both the "self" peptide described above and the membrane protein CD47.

In some embodiments, a "self" peptide and/or CD47 protein may be conjugated to a virus-like particle or pseudovirion, as described herein for delivery of the RNA (e.g., mRNA) vaccines of the present disclosure.

In some embodiments, RNA (e.g., mRNA) vaccine pharmaceutical compositions comprising the polynucleotides of the present disclosure and a conjugate that may have a degradable linkage. Non-limiting examples of conjugates include an aromatic moiety comprising an ionizable hydrogen atom, a spacer moiety, and a water-soluble polymer. As a non-limiting example, pharmaceutical compositions comprising a conjugate with a degradable linkage and methods for delivering such pharmaceutical compositions are described in U.S. Patent Publication No. US20130184443, the contents of which are herein incorporated by reference in their entirety.

The nanoparticle formulations may be a carbohydrate nanoparticle comprising a carbohydrate carrier and a RNA (e.g., mRNA) vaccine. As a non-limiting example, the carbohydrate carrier may include, but is not limited to, an anhydride-modified phytoglycogen or glycogen-type material, phtoglycogen octenyl succinate, phytoglycogen beta-dextrin, anhydride-modified phytoglycogen beta-dextrin. (See e.g., International Publication No. WO2012109121; the contents of which are herein incorporated by reference in their entirety).

Nanoparticle formulations of the present disclosure may be coated with a surfactant or polymer in order to improve the delivery of the particle. In some embodiments, the nanoparticle may be coated with a hydrophilic coating such as, but not limited to, PEG coatings and/or coatings that have a neutral surface charge. The hydrophilic coatings may help to deliver nanoparticles with larger payloads such as, but not limited to, RNA (e.g., mRNA) vaccines within the central nervous system. As a non-limiting example nanoparticles comprising a hydrophilic coating and methods of making such nanoparticles are described in U.S. Patent Publication No. US20130183244, the contents of which are herein incorporated by reference in their entirety.

In some embodiments, the lipid nanoparticles of the present disclosure may be hydrophilic polymer particles. Non-limiting examples of hydrophilic polymer particles and methods of making hydrophilic polymer particles are described in U.S. Patent Publication No. US20130210991, the contents of which are herein incorporated by reference in their entirety.

In some embodiments, the lipid nanoparticles of the present disclosure may be hydrophobic polymer particles.

Lipid nanoparticle formulations may be improved by replacing the cationic lipid with a biodegradable cationic lipid which is known as a rapidly eliminated lipid nanoparticle (reLNP). Ionizable cationic lipids, such as, but not limited to, DLinDMA, DLin-KC2-DMA, and DLin-MC3-DMA, have been shown to accumulate in plasma and tissues over time and may be a potential source of toxicity. The rapid metabolism of the rapidly eliminated lipids can improve the tolerability and therapeutic index of the lipid nanoparticles by an order of magnitude from a 1 mg/kg dose to a 10 mg/kg dose in rat. Inclusion of an enzymatically degraded ester linkage can improve the degradation and metabolism profile of the cationic component, while still maintaining the activity of the reLNP formulation. The ester linkage can be internally located within the lipid chain or it may be terminally located at the terminal end of the lipid chain. The internal ester linkage may replace any carbon in the lipid chain.

In some embodiments, the internal ester linkage may be located on either side of the saturated carbon.

In some embodiments, an immune response may be elicited by delivering a lipid nanoparticle which may include a nanospecies, a polymer and an immunogen. (U.S. Publication No. 20120189700 and International Publication No. WO2012099805; each of which is herein incorporated by reference in their entirety). The polymer may encapsulate the nanospecies or partially encapsulate the nanospecies. The immunogen may be a recombinant protein, a modified RNA and/or a polynucleotide described herein. In some embodiments, the lipid nanoparticle may be formulated for use in a vaccine such as, but not limited to, against a pathogen.

Lipid nanoparticles may be engineered to alter the surface properties of particles so the lipid nanoparticles may penetrate the mucosal barrier. Mucus is located on mucosal tissue such as, but not limited to, oral (e.g., the buccal and esophageal membranes and tonsil tissue), ophthalmic, gastrointestinal (e.g., stomach, small intestine, large intestine, colon, rectum), nasal, respiratory (e.g., nasal, pharyngeal, tracheal and bronchial membranes), genital (e.g., vaginal, cervical and urethral membranes). Nanoparticles larger than 10-200 nm which are preferred for higher drug encapsulation efficiency and the ability to provide the sustained delivery of a wide array of drugs have been thought to be too large to rapidly diffuse through mucosal barriers. Mucus is continuously secreted, shed, discarded or digested and recycled so most of the trapped particles may be removed from the mucosa tissue within seconds or within a few hours. Large polymeric nanoparticles (200 nm-500 nm in diameter) which have been coated densely with a low molecular weight polyethylene glycol (PEG) diffused through mucus only 4 to 6-fold lower than the same particles diffusing in water (Lai et al. PNAS 2007 104(5):1482-487; Lai et al. *Adv Drug Deliv Rev.* 2009 61(2): 158-171; each of which is herein incorporated by reference in their entirety). The transport of nanoparticles may be determined using rates of permeation and/or fluorescent microscopy techniques including, but not limited to, fluorescence recovery after photobleaching (FRAP) and high resolution multiple particle tracking (MPT). As a non-limiting example, compositions which can penetrate a mucosal barrier may be made as described in U.S. Pat. No. 8,241,670 or International Patent Publication No. WO2013110028, the contents of each of which are herein incorporated by reference in its entirety.

The lipid nanoparticle engineered to penetrate mucus may comprise a polymeric material (i.e. a polymeric core) and/or a polymer-vitamin conjugate and/or a tri-block co-polymer. The polymeric material may include, but is not limited to, polyamines, polyethers, polyamides, polyesters, polycarbamates, polyureas, polycarbonates, poly(styrenes), polyimides, polysulfones, polyurethanes, polyacetylenes, polyethylenes, polyethyeneimines, polyisocyanates, polyacrylates, polymethacrylates, polyacrylonitriles, and polyarylates. The polymeric material may be biodegradable and/or biocompatible. Non-limiting examples of biocompatible polymers are described in International Patent Publication No. WO2013116804, the contents of which are herein incorporated by reference in their entirety. The polymeric material may additionally be irradiated. As a non-limiting example, the polymeric material may be gamma irradiated (see e.g., International App. No. WO201282165, herein incorporated by reference in its entirety). Non-limiting examples of specific polymers include poly(caprolactone) (PCL), ethylene vinyl acetate polymer (EVA), poly(lactic acid) (PLA), poly(L-lactic acid) (PLLA), poly(glycolic acid) (PGA), poly (lactic acid-co-glycolic acid) (PLGA), poly(L-lactic acid-co-glycolic acid) (PLLGA), poly(D,L-lactide) (PDLA), poly (L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacralate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly (ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth) acrylate) (PMMA), poly(ethyl(meth)acrylate), poly(butyl (meth)acrylate), poly(isobutyl(meth)acrylate), poly(hexyl (meth)acrylate), poly(isodecyl(meth)acrylate), poly(lauryl (meth)acrylate), poly(phenyl(meth)acrylate), poly(methyl acrylate), poly(isopropyl acrylate), poly(isobutyl acrylate), poly(octadecyl acrylate) and copolymers and mixtures thereof, polydioxanone and its copolymers, polyhydroxyalkanoates, polypropylene fumarate, polyoxymethylene, poloxamers, poly(ortho)esters, poly(butyric acid), poly(valeric acid), poly(lactide-co-caprolactone), PEG-PLGA-PEG and trimethylene carbonate, polyvinylpyrrolidone. The lipid nanoparticle may be coated or associated with a co-polymer such as, but not limited to, a block co-polymer (such as a branched polyether-polyamide block copolymer described in International Publication No. WO2013012476, herein incorporated by reference in its entirety), and (poly(ethylene glycol))-(poly(propylene oxide))-(poly(ethylene glycol)) triblock copolymer (see e.g., U.S. Publication 20120121718 and U.S. Publication 20100003337 and U.S. Pat. No. 8,263,665, the contents of each of which is herein incorporated by reference in their entirety). The co-polymer may be a polymer that is generally regarded as safe (GRAS) and the formation of the lipid nanoparticle may be in such a way that no new chemical entities are created. For example, the lipid nanoparticle may comprise poloxamers coating PLGA nanoparticles without forming new chemical entities which are still able to rapidly penetrate human mucus (Yang et al. Angew. Chem. Int. Ed. 2011 50:2597-2600; the contents of which are herein incorporated by reference in their entirety). A non-limiting scalable method to produce nanoparticles which can penetrate human mucus is described by Xu et al. (see, e.g., J Control Release 2013, 170(2):279-86; the contents of which are herein incorporated by reference in their entirety).

The vitamin of the polymer-vitamin conjugate may be vitamin E. The vitamin portion of the conjugate may be substituted with other suitable components such as, but not limited to, vitamin A, vitamin E, other vitamins, cholesterol, a hydrophobic moiety, or a hydrophobic component of other surfactants (e.g., sterol chains, fatty acids, hydrocarbon chains and alkylene oxide chains).

The lipid nanoparticle engineered to penetrate mucus may include surface altering agents such as, but not limited to, polynucleotides, anionic proteins (e.g., bovine serum albumin), surfactants (e.g., cationic surfactants such as for example dimethyldioctadecylammonium bromide), sugars or sugar derivatives (e.g., cyclodextrin), nucleic acids, polymers (e.g., heparin, polyethylene glycol and poloxamer), mucolytic agents (e.g., N-acetylcysteine, mugwort, bromelain, papain, clerodendrum, acetylcysteine, bromhexine, carbocisteine, eprazinone, mesna, ambroxol, sobrerol, domiodol, letosteine, stepronin, tiopronin, gelsolin, thymosin (34 dornase alfa, neltenexine, erdosteine) and various DNases including rhDNase. The surface altering agent may be embedded or enmeshed in the particle's surface or disposed (e.g., by coating, adsorption, covalent linkage, or other process) on the surface of the lipid nanoparticle. (see e.g., U.S. Publication 20100215580 and U.S. Publication 20080166414 and US20130164343; the contents of each of which are herein incorporated by reference in their entirety).

In some embodiments, the mucus penetrating lipid nanoparticles may comprise at least one polynucleotide described herein. The polynucleotide may be encapsulated in the lipid nanoparticle and/or disposed on the surface of the particle. The polynucleotide may be covalently coupled to the lipid nanoparticle. Formulations of mucus penetrating lipid nanoparticles may comprise a plurality of nanoparticles. Further, the formulations may contain particles which may interact with the mucus and alter the structural and/or adhesive properties of the surrounding mucus to decrease mucoadhesion, which may increase the delivery of the mucus penetrating lipid nanoparticles to the mucosal tissue.

In some embodiments, the mucus penetrating lipid nanoparticles may be a hypotonic formulation comprising a mucosal penetration enhancing coating. The formulation may be hypotonice for the epithelium to which it is being delivered. Non-limiting examples of hypotonic formulations may be found in International Patent Publication No. WO2013110028, the contents of which are herein incorporated by reference in their entirety.

In some embodiments, in order to enhance the delivery through the mucosal barrier the RNA (e.g., mRNA) vaccine formulation may comprise or be a hypotonic solution. Hypotonic solutions were found to increase the rate at which mucoinert particles such as, but not limited to, mucus-penetrating particles, were able to reach the vaginal epithelial surface (see e.g., Ensign et al. Biomaterials 2013 34(28): 6922-9, the contents of which are herein incorporated by reference in their entirety).

In some embodiments, the RNA (e.g., mRNA) vaccine is formulated as a lipoplex, such as, without limitation, the ATUPLEX™ system, the DACC system, the DBTC system and other siRNA-lipoplex technology from Silence Therapeutics (London, United Kingdom), STEMFECT™ from STEMGENT® (Cambridge, Mass.), and polyethylenimine (PEI) or protamine-based targeted and non-targeted delivery of nucleic acids acids (Aleku et al. Cancer Res. 2008 68:9788-9798; Strumberg et al. Int J Clin Pharmacol Ther 2012 50:76-78; Santel et al., Gene Ther 2006 13:1222-1234; Santel et al., Gene Ther 2006 13:1360-1370; Gutbier et al., Pulm Pharmacol. Ther. 2010 23:334-344; Kaufmann et al. Microvasc Res 2010 80:286-293Weide et al. J Immunother. 2009 32:498-507; Weide et al. J Immunother. 2008 31:180-188; Pascolo Expert Opin. Biol. Ther. 4:1285-1294; Fotin-Mleczek et al., 2011 J. Immunother. 34:1-15; Song et al., Nature Biotechnol. 2005, 23:709-717; Peer et al., Proc Natl Acad Sci USA. 2007 6; 104:4095-4100; deFougerolles Hum Gene Ther. 2008 19:125-132, the contents of each of which are incorporated herein by reference in their entirety).

In some embodiments, such formulations may also be constructed or compositions altered such that they passively or actively are directed to different cell types in vivo, including but not limited to hepatocytes, immune cells, tumor cells, endothelial cells, antigen presenting cells, and leukocytes (Akinc et al. Mol Ther. 2010 18:1357-1364; Song et al., Nat Biotechnol. 2005 23:709-717; Judge et al., J Clin Invest. 2009 119:661-673; Kaufmann et al., Microvasc Res 2010 80:286-293; Santel et al., Gene Ther 2006 13:1222-1234; Santel et al., Gene Ther 2006 13:1360-1370; Gutbier et al., Pulm Pharmacol. Ther. 2010 23:334-344; Basha et al., Mol. Ther. 2011 19:2186-2200; Fenske and Cullis, Expert Opin Drug Deliv. 2008 5:25-44; Peer et al., Science. 2008 319:627-630; Peer and Lieberman, Gene Ther. 2011 18:1127-1133, the contents of each of which are incorporated herein by reference in their entirety). One example of passive targeting of formulations to liver cells includes the DLin-DMA, DLin-KC2-DMA and DLin-MC3-DMA-based lipid nanoparticle formulations, which have been shown to bind to apolipoprotein E and promote binding and uptake of these formulations into hepatocytes in vivo (Akinc et al. Mol Ther. 2010 18:1357-1364, the contents of which are incorporated herein by reference in their entirety). Formulations can also be selectively targeted through expression of different ligands on their surface as exemplified by, but not limited by, folate, transferrin, N-acetylgalactosamine (GalNAc), and antibody targeted approaches (Kolhatkar et al., Curr Drug Discov Technol. 2011 8:197-206; Musacchio and Torchilin, Front Biosci. 2011 16:1388-1412; Yu et al., Mol Membr Biol. 2010 27:286-298; Patil et al., Crit Rev Ther Drug Carrier Syst. 2008 25:1-61; Benoit et al., Biomacromolecules. 2011 12:2708-2714; Zhao et al., Expert Opin Drug Deliv. 2008 5:309-319; Akinc et al., Mol Ther. 2010 18:1357-1364; Srinivasan et al., Methods Mol Biol. 2012 820:105-116; Ben-Arie et al., Methods Mol Biol. 2012 757:497-507; Peer 2010 J Control Release. 20:63-68; Peer et al., Proc Natl Acad Sci USA. 2007 104:4095-4100; Kim et al., Methods Mol Biol. 2011 721:339-353; Subramanya et al., Mol Ther. 2010 18:2028-2037; Song et al., Nat Biotechnol. 2005 23:709-717; Peer et al., Science. 2008 319:627-630; Peer and Lieberman, Gene Ther. 2011 18:1127-1133, the contents of each of which are incorporated herein by reference in their entirety).

In some embodiments, the RNA (e.g., mRNA) vaccine is formulated as a solid lipid nanoparticle. A solid lipid nanoparticle (SLN) may be spherical with an average diameter between 10 to 1000 nm. SLN possess a solid lipid core matrix that can solubilize lipophilic molecules and may be stabilized with surfactants and/or emulsifiers. In some embodiments, the lipid nanoparticle may be a self-assembly lipid-polymer nanoparticle (see Zhang et al., ACS Nano, 2008, 2 (8), pp 1696-1702; the contents of which are herein incorporated by reference in their entirety). As a non-limiting example, the SLN may be the SLN described in International Patent Publication No. WO2013105101, the contents of which are herein incorporated by reference in their entirety. As another non-limiting example, the SLN may be made by the methods or processes described in International Patent Publication No. WO2013105101, the contents of which are herein incorporated by reference in their entirety.

Liposomes, lipoplexes, or lipid nanoparticles may be used to improve the efficacy of polynucleotides directed protein production as these formulations may be able to increase cell transfection by the RNA (e.g., mRNA) vaccine; and/or increase the translation of encoded protein. One such example involves the use of lipid encapsulation to enable the effective systemic delivery of polyplex plasmid DNA (Heyes et al., Mol Ther. 2007 15:713-720; the contents of which are incorporated herein by reference in their entirety). The liposomes, lipoplexes, or lipid nanoparticles may also be used to increase the stability of the polynucleotide.

In some embodiments, the RNA (e.g., mRNA) vaccines of the present disclosure can be formulated for controlled release and/or targeted delivery. As used herein, "controlled release" refers to a pharmaceutical composition or compound release profile that conforms to a particular pattern of release to effect a therapeutic outcome. In some embodiments, the RNA (e.g., mRNA) vaccines may be encapsulated into a delivery agent described herein and/or known in the art for controlled release and/or targeted delivery. As used herein, the term "encapsulate" means to enclose, surround or encase. As it relates to the formulation of the compounds of the disclosure, encapsulation may be substantial, complete or partial. The term "substantially encapsulated" means that at least greater than 50, 60, 70, 80, 85, 90, 95, 96, 97, 98, 99, 99.9, 99.9 or greater than 99.999% of the pharmaceutical composition or compound of the disclosure may be enclosed, surrounded or encased within the delivery agent. "Partially encapsulation" means that less than 10, 10, 20, 30, 40 50 or less of the pharmaceutical composition or compound of the disclosure may be enclosed, surrounded or encased within the delivery agent. Advantageously, encapsulation may be determined by measuring the escape or the activity of the pharmaceutical composition or compound of the disclosure using fluorescence and/or electron micrograph. For example, at least 1, 5, 10, 20, 30, 40, 50, 60, 70, 80, 85, 90, 95, 96, 97, 98, 99, 99.9, 99.99 or greater than 99.99% of the pharmaceutical composition or compound of the disclosure are encapsulated in the delivery agent.

In some embodiments, the controlled release formulation may include, but is not limited to, tri-block co-polymers. As a non-limiting example, the formulation may include two different types of tri-block co-polymers (International Pub. No. WO2012131104 and WO2012131106, the contents of each of which are incorporated herein by reference in their entirety).

In some embodiments, the RNA (e.g., mRNA) vaccines may be encapsulated into a lipid nanoparticle or a rapidly eliminated lipid nanoparticle and the lipid nanoparticles or a rapidly eliminated lipid nanoparticle may then be encapsulated into a polymer, hydrogel and/or surgical sealant described herein and/or known in the art. As a non-limiting example, the polymer, hydrogel or surgical sealant may be PLGA, ethylene vinyl acetate (EVAc), poloxamer, GELSITE® (Nanotherapeutics, Inc. Alachua, Fla.), HYLENEX® (Halozyme Therapeutics, San Diego Calif.), surgical sealants such as fibrinogen polymers (Ethicon Inc. Cornelia, Ga.), TISSELL® (Baxter International, Inc Deerfield, Ill.), PEG-based sealants, and COSEAL® (Baxter International, Inc Deerfield, Ill.).

In some embodiments, the lipid nanoparticle may be encapsulated into any polymer known in the art which may form a gel when injected into a subject. As another non-limiting example, the lipid nanoparticle may be encapsulated into a polymer matrix which may be biodegradable.

In some embodiments, the RNA (e.g., mRNA) vaccine formulation for controlled release and/or targeted delivery may also include at least one controlled release coating. Controlled release coatings include, but are not limited to, OPADRY®, polyvinylpyrrolidone/vinyl acetate copolymer, polyvinylpyrrolidone, hydroxypropyl methylcellulose, hydroxypropyl cellulose, hydroxyethyl cellulose, EUDRAGIT RL®, EUDRAGIT RS® and cellulose derivatives such as ethylcellulose aqueous dispersions (AQUACOAT® and SURELEASE®).

In some embodiments, the RNA (e.g., mRNA) vaccine controlled release and/or targeted delivery formulation may comprise at least one degradable polyester which may contain polycationic side chains. Degradeable polyesters include, but are not limited to, poly(serine ester), poly(L-lactide-co-L-lysine), poly(4-hydroxy-L-proline ester), and combinations thereof. In some embodiments, the degradable polyesters may include a PEG conjugation to form a PEGylated polymer.

In some embodiments, the RNA (e.g., mRNA) vaccine controlled release and/or targeted delivery formulation comprising at least one polynucleotide may comprise at least one PEG and/or PEG related polymer derivatives as described in U.S. Pat. No. 8,404,222, the contents of which are incorporated herein by reference in their entirety.

In some embodiments, the RNA (e.g., mRNA) vaccine controlled release delivery formulation comprising at least one polynucleotide may be the controlled release polymer system described in US20130130348, the contents of which are incorporated herein by reference in their entirety.

In some embodiments, the RNA (e.g., mRNA) vaccines of the present disclosure may be encapsulated in a therapeutic nanoparticle, referred to herein as "therapeutic nanoparticle RNA (e.g., mRNA) vaccines." Therapeutic nanoparticles may be formulated by methods described herein and known in the art such as, but not limited to, International Pub Nos. WO2010005740, WO2010030763, WO2010005721, WO2010005723, WO2012054923, U.S. Publication Nos. US20110262491, US20100104645, US20100087337, US20100068285, US20110274759, US20100068286, US20120288541, US20130123351 and US20130230567 and U.S. Pat. Nos. 8,206,747, 8,293,276, 8,318,208 and 8,318,211; the contents of each of which are herein incorporated by reference in their entirety. In some embodiments, therapeutic polymer nanoparticles may be identified by the methods described in US Pub No. US20120140790, the contents of which are herein incorporated by reference in their entirety.

In some embodiments, the therapeutic nanoparticle RNA (e.g., mRNA) vaccine may be formulated for sustained release. As used herein, "sustained release" refers to a pharmaceutical composition or compound that conforms to a release rate over a specific period of time. The period of time may include, but is not limited to, hours, days, weeks, months and years. As a non-limiting example, the sustained release nanoparticle may comprise a polymer and a therapeutic agent such as, but not limited to, the polynucleotides of the present disclosure (see International Pub No. 2010075072 and US Pub No. US20100216804, US20110217377 and US20120201859, the contents of each of which are incorporated herein by reference in their entirety). In another non-limiting example, the sustained release formulation may comprise agents which permit persistent bioavailability such as, but not limited to, crystals, macromolecular gels and/or particulate suspensions (see U.S. Patent Publication No US20130150295, the contents of each of which are incorporated herein by reference in their entirety).

In some embodiments, the therapeutic nanoparticle RNA (e.g., mRNA) vaccines may be formulated to be target specific. As a non-limiting example, the therapeutic nanoparticles may include a corticosteroid (see International Pub. No. WO2011084518, the contents of which are incorporated herein by reference in their entirety). As a non-limiting example, the therapeutic nanoparticles may be formulated in nanoparticles described in International Pub No. WO2008121949, WO2010005726, WO2010005725, WO2011084521 and US Pub No. US20100069426, US20120004293 and US20100104655, the contents of each of which are incorporated herein by reference in their entirety.

In some embodiments, the nanoparticles of the present disclosure may comprise a polymeric matrix. As a non-limiting example, the nanoparticle may comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester) or combinations thereof.

In some embodiments, the therapeutic nanoparticle comprises a diblock copolymer. In some embodiments, the diblock copolymer may include PEG in combination with a polymer such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester) or combinations thereof. In yet another embodiment, the diblock copolymer may be a high-X diblock copolymer such as those described in International Patent Publication No. WO2013120052, the contents of which are incorporated herein by reference in their entirety.

As a non-limiting example the therapeutic nanoparticle comprises a PLGA-PEG block copolymer (see U.S. Publication No. US20120004293 and U.S. Pat. No. 8,236,330, each of which is herein incorporated by reference in their entirety). In another non-limiting example, the therapeutic nanoparticle is a stealth nanoparticle comprising a diblock copolymer of PEG and PLA or PEG and PLGA (see U.S. Pat. No. 8,246,968 and International Publication No. WO2012166923, the contents of each of which are herein incorporated by reference in their entirety). In yet another non-limiting example, the therapeutic nanoparticle is a stealth nanoparticle or a target-specific stealth nanoparticle as described in U.S. Patent Publication No. US20130172406, the contents of which are herein incorporated by reference in their entirety.

In some embodiments, the therapeutic nanoparticle may comprise a multiblock copolymer (see e.g., U.S. Pat. Nos. 8,263,665 and 8,287,910 and U.S. Patent Pub. No. US20130195987, the contents of each of which are herein incorporated by reference in their entirety).

In yet another non-limiting example, the lipid nanoparticle comprises the block copolymer PEG-PLGA-PEG (see e.g., the thermosensitive hydrogel (PEG-PLGA-PEG) was used as a TGF-beta1 gene delivery vehicle in Lee et al. Thermosensitive Hydrogel as a Tgf-β1 Gene Delivery Vehicle Enhances Diabetic Wound Healing. Pharmaceutical Research, 2003 20(12): 1995-2000; as a controlled gene delivery system in Li et al. Controlled Gene Delivery System Based on Thermosensitive Biodegradable Hydrogel. Pharmaceutical Research 2003 20(6):884-888; and Chang et al., Non-ionic amphiphilic biodegradable PEG-PLGA-PEG copolymer enhances gene delivery efficiency in rat skeletal muscle. J Controlled Release. 2007 118:245-253, the contents of each of which are herein incorporated by reference in their entirety). The RNA (e.g., mRNA) vaccines of the present disclosure may be formulated in lipid nanoparticles comprising the PEG-PLGA-PEG block copolymer.

In some embodiments, the therapeutic nanoparticle may comprise a multiblock copolymer (see e.g., U.S. Pat. Nos. 8,263,665 and 8,287,910 and U.S. Patent Pub. No. US20130195987, the contents of each of which are herein incorporated by reference in their entirety).

In some embodiments, the block copolymers described herein may be included in a polyion complex comprising a non-polymeric micelle and the block copolymer. (see e.g., U.S. Publication No. 20120076836, the contents of which are herein incorporated by reference in their entirety).

In some embodiments, the therapeutic nanoparticle may comprise at least one acrylic polymer. Acrylic polymers include but are not limited to, acrylic acid, methacrylic acid, acrylic acid and methacrylic acid copolymers, methyl methacrylate copolymers, ethoxyethyl methacrylates, cyanoethyl methacrylate, amino alkyl methacrylate copolymer, poly (acrylic acid), poly(methacrylic acid), polycyanoacrylates and combinations thereof.

In some embodiments, the therapeutic nanoparticles may comprise at least one poly(vinyl ester) polymer. The poly (vinyl ester) polymer may be a copolymer such as a random copolymer. As a non-limiting example, the random copolymer may have a structure such as those described in International Application No. WO2013032829 or U.S. Patent Publication No US20130121954, the contents of each of which are herein incorporated by reference in their entirety. In some embodiments, the poly(vinyl ester) polymers may be conjugated to the polynucleotides described herein.

In some embodiments, the therapeutic nanoparticle may comprise at least one diblock copolymer. The diblock copolymer may be, but it not limited to, a poly(lactic) acid-poly (ethylene)glycol copolymer (see, e.g., International Patent Publication No. WO2013044219, the contents of which are herein incorporated by reference in their entirety). As a non-limiting example, the therapeutic nanoparticle may be used to treat cancer (see International publication No. WO2013044219, the contents of which are herein incorporated by reference in their entirety).

In some embodiments, the therapeutic nanoparticles may comprise at least one cationic polymer described herein and/or known in the art.

In some embodiments, the therapeutic nanoparticles may comprise at least one amine-containing polymer such as, but not limited to polylysine, polyethylene imine, poly(amidoamine) dendrimers, poly(beta-amino esters) (see, e.g., U.S. Pat. No. 8,287,849, the contents of which are herein incorporated by reference in their entirety) and combinations thereof.

In some embodiments, the nanoparticles described herein may comprise an amine cationic lipid such as those described in International Patent Application No. WO2013059496, the contents of which are herein incorporated by reference in their entirety. In some embodiments, the cationic lipids may have an amino-amine or an amino-amide moiety.

In some embodiments, the therapeutic nanoparticles may comprise at least one degradable polyester which may contain polycationic side chains. Degradeable polyesters include, but are not limited to, poly(serine ester), poly(L-lactide-co-L-lysine), poly(4-hydroxy-L-proline ester), and combinations thereof. In some embodiments, the degradable polyesters may include a PEG conjugation to form a PEGylated polymer.

In some embodiments, the synthetic nanocarriers may contain an immunostimulatory agent to enhance the immune response from delivery of the synthetic nanocarrier. As a non-limiting example, the synthetic nanocarrier may comprise a Th1 immunostimulatory agent, which may enhance a Th1-based response of the immune system (see International Pub No. WO2010123569 and U.S. Publication No. US20110223201, the contents of each of which are herein incorporated by reference in their entirety).

In some embodiments, the synthetic nanocarriers may be formulated for targeted release. In some embodiments, the synthetic nanocarrier is formulated to release the polynucleotides at a specified pH and/or after a desired time interval. As a non-limiting example, the synthetic nanoparticle may be formulated to release the RNA (e.g., mRNA) vaccines after 24 hours and/or at a pH of 4.5 (see International Publication Nos. WO2010138193 and WO2010138194 and US Pub Nos. US20110020388 and US20110027217, each of which is herein incorporated by reference in their entireties).

In some embodiments, the synthetic nanocarriers may be formulated for controlled and/or sustained release of the polynucleotides described herein. As a non-limiting example, the synthetic nanocarriers for sustained release may be formulated by methods known in the art, described herein and/or as described in International Pub No. WO2010138192 and US Pub No. 20100303850, each of which is herein incorporated by reference in their entirety.

In some embodiments, the RNA (e.g., mRNA) vaccine may be formulated for controlled and/or sustained release wherein the formulation comprises at least one polymer that is a crystalline side chain (CYSC) polymer. CYSC polymers are described in U.S. Pat. No. 8,399,007, herein incorporated by reference in its entirety.

In some embodiments, the synthetic nanocarrier may be formulated for use as a vaccine. In some embodiments, the synthetic nanocarrier may encapsulate at least one polynucleotide which encode at least one antigen. As a non-limiting example, the synthetic nanocarrier may include at least one antigen and an excipient for a vaccine dosage form (see International Publication No. WO2011150264 and U.S. Publication No. US20110293723, the contents of each of which are herein incorporated by reference in their entirety). As another non-limiting example, a vaccine dosage form may include at least two synthetic nanocarriers with the same or different antigens and an excipient (see International Publication No. WO2011150249 and U.S. Publication No. US20110293701, the contents of each of which are herein incorporated by reference in their entirety). The vaccine dosage form may be selected by methods described herein, known in the art and/or described in International Publication No. WO2011150258 and U.S. Publication No. US20120027806, the contents of each of which are herein incorporated by reference in their entirety).

In some embodiments, the synthetic nanocarrier may comprise at least one polynucleotide which encodes at least one adjuvant. As non-limiting example, the adjuvant may comprise dimethyldioctadecylammonium-bromide, dimethyldioctadecylammonium-chloride, dimethyldioctadecylammonium-phosphate or dimethyldioctadecylammonium-acetate (DDA) and an apolar fraction or part of said apolar fraction of a total lipid extract of a *mycobacterium* (see, e.g., U.S. Pat. No. 8,241,610, the content of which is herein incorporated by reference in its entirety). In some embodiments, the synthetic nanocarrier may comprise at least one polynucleotide and an adjuvant. As a non-limiting example, the synthetic nanocarrier comprising and adjuvant may be formulated by the methods described in International Publication No. WO2011150240 and U.S. Publication No. US20110293700, the contents of each of which are herein incorporated by reference in their entirety.

In some embodiments, the synthetic nanocarrier may encapsulate at least one polynucleotide that encodes a peptide, fragment or region from a virus. As a non-limiting example, the synthetic nanocarrier may include, but is not limited to, any of the nanocarriers described in International Publication No. WO2012024621, WO201202629, WO2012024632 and U.S. Publication No. US20120064110, US20120058153 and US20120058154, the contents of each of which are herein incorporated by reference in their entirety.

In some embodiments, the synthetic nanocarrier may be coupled to a polynucleotide which may be able to trigger a humoral and/or cytotoxic T lymphocyte (CTL) response (see, e.g., International Publication No. WO2013019669, the contents of which are herein incorporated by reference in their entirety).

In some embodiments, the RNA (e.g., mRNA) vaccine may be encapsulated in, linked to and/or associated with zwitterionic lipids. Non-limiting examples of zwitterionic lipids and methods of using zwitterionic lipids are described in U.S. Patent Publication No. US20130216607, the contents of which are herein incorporated by reference in their entirety. In some aspects, the zwitterionic lipids may be used in the liposomes and lipid nanoparticles described herein.

In some embodiments, the RNA (e.g., mRNA) vaccine may be formulated in colloid nanocarriers as described in U.S. Patent Publication No. US20130197100, the contents of which are herein incorporated by reference in their entirety.

In some embodiments, the nanoparticle may be optimized for oral administration. The nanoparticle may comprise at least one cationic biopolymer such as, but not limited to, chitosan or a derivative thereof. As a non-limiting example, the nanoparticle may be formulated by the methods described in U.S. Publication No. 20120282343, the contents of which are herein incorporated by reference in their entirety.

In some embodiments, LNPs comprise the lipid KL52 (an amino-lipid disclosed in U.S. Application Publication No. 2012/0295832, the contents of which are herein incorporated by reference in their entirety. Activity and/or safety (as measured by examining one or more of ALT/AST, white blood cell count and cytokine induction, for example) of LNP administration may be improved by incorporation of such lipids. LNPs comprising KL52 may be administered intravenously and/or in one or more doses. In some embodiments, administration of LNPs comprising KL52 results in equal or improved mRNA and/or protein expression as compared to LNPs comprising MC3.

In some embodiments, RNA (e.g., mRNA) vaccine may be delivered using smaller LNPs. Such particles may comprise a diameter from below 0.1 um up to 100 nm such as, but not limited to, less than 0.1 um, less than 1.0 um, less than 5 um, less than 10 um, less than 15 um, less than 20 um, less than 25 um, less than 30 um, less than 35 um, less than 40 um, less than 50 um, less than 55 um, less than 60 um, less than 65 um, less than 70 um, less than 75 um, less than 80 um, less than 85 um, less than 90 um, less than 95 um, less than 100 um, less than 125 um, less than 150 um, less than 175 um, less than 200 um, less than 225 um, less than 250 um, less than 275 um, less than 300 um, less than 325 um, less than 350 um, less than 375 um, less than 400 um, less than 425 um, less than 450 um, less than 475 um, less than 500 um, less than 525 um, less than 550 um, less than 575 um, less than 600 um, less than 625 um, less than 650 um, less than 675 um, less than 700 um, less than 725 um, less than 750 um, less than 775 um, less than 800 um, less than 825 um, less than 850 um, less than 875 um, less than 900 um, less than 925 um, less than 950 um, less than 975 um, or less than 1000 um.

In some embodiments, RNA (e.g., mRNA) vaccines may be delivered using smaller LNPs, which may comprise a diameter from about 1 nm to about 100 nm, from about 1 nm to about 10 nm, about 1 nm to about 20 nm, from about 1 nm to about 30 nm, from about 1 nm to about 40 nm, from about 1 nm to about 50 nm, from about 1 nm to about 60 nm, from about 1 nm to about 70 nm, from about 1 nm to about 80 nm, from about 1 nm to about 90 nm, from about 5 nm to about from 100 nm, from about 5 nm to about 10 nm, about 5 nm to about 20 nm, from about 5 nm to about 30 nm, from about 5 nm to about 40 nm, from about 5 nm to about 50 nm, from about 5 nm to about 60 nm, from about 5 nm to about 70 nm, from about 5 nm to about 80 nm, from about 5 nm to about 90 nm, about 10 to about 50 nm, from about 20 to about 50 nm, from about 30 to about 50 nm, from about 40 to about 50 nm, from about 20 to about 60 nm, from about 30 to about 60 nm, from about 40 to about 60 nm, from about 20 to about 70 nm, from about 30 to about 70 nm, from about 40 to about 70 nm, from about 50 to about 70 nm, from about 60 to about 70 nm, from about 20 to about 80 nm, from about 30 to about 80 nm, from about 40 to about 80 nm, from about 50 to about 80 nm, from about 60 to about 80 nm, from about 20 to about 90 nm, from about 30 to about 90 nm, from about 40 to about 90 nm, from about 50 to about 90 nm, from about 60 to about 90 nm and/or from about 70 to about 90 nm.

In some embodiments, such LNPs are synthesized using methods comprising microfluidic mixers. Examples of microfluidic mixers may include, but are not limited to, a slit interdigital micromixer including, but not limited to those manufactured by Microinnova (Allerheiligen bei Wildon, Austria) and/or a staggered herringbone micromixer (SHM) (Zhigaltsev, I. V. et al., Bottom-up design and synthesis of limit size lipid nanoparticle systems with aqueous and triglyceride cores using millisecond microfluidic mixing have been published (Langmuir. 2012. 28:3633-40; Belliveau, N. M. et al., Microfluidic synthesis of highly potent limit-size lipid nanoparticles for in vivo delivery of siRNA. Molecular Therapy-Nucleic Acids. 2012. 1:e37; Chen, D. et al., Rapid discovery of potent siRNA-containing lipid nanoparticles enabled by controlled microfluidic formulation. J Am Chem Soc. 2012. 134(16):6948-51, the contents of each of which are herein incorporated by reference in their entirety). In some embodiments, methods of LNP generation comprising SHM, further comprise the mixing of at least two input streams wherein mixing occurs by microstructure-induced chaotic advection (MICA). According to this method, fluid streams flow through channels present in a herringbone pattern causing rotational flow and folding the fluids around each other. This method may also comprise a surface for fluid mixing wherein the surface changes orientations during fluid cycling. Methods of generating LNPs using SHM include those disclosed in U.S. Application Publication Nos. 2004/0262223 and 2012/0276209, the contents of each of which are herein incorporated by reference in their entirety.

In some embodiments, the RNA (e.g., mRNA) vaccine of the present disclosure may be formulated in lipid nanoparticles created using a micromixer such as, but not limited to, a Slit Interdigital Microstructured Mixer (SIMM-V2) or a Standard Slit Interdigital Micro Mixer (SSIMM) or Caterpillar (CPMM) or Impinging-jet (IJMM) from the Institut für Mikrotechnik Mainz GmbH, Mainz Germany).

In some embodiments, the RNA (e.g., mRNA) vaccines of the present disclosure may be formulated in lipid nanoparticles created using microfluidic technology (see, e.g., Whitesides, George M. The Origins and the Future of Microfluidics. Nature, 2006 442: 368-373; and Abraham et al. Chaotic Mixer for Microchannels. Science, 2002 295: 647-651; each of which is herein incorporated by reference in its entirety). As a non-limiting example, controlled microfluidic formulation includes a passive method for mixing streams of steady pressure-driven flows in micro channels at a low Reynolds number (see, e.g., Abraham et al. Chaotic Mixer for Microchannels. Science, 2002 295: 647-651, the contents of which are herein incorporated by reference in their entirety).

In some embodiments, the RNA (e.g., mRNA) vaccines of the present disclosure may be formulated in lipid nanoparticles created using a micromixer chip such as, but not limited to, those from Harvard Apparatus (Holliston, Mass.) or Dolomite Microfluidics (Royston, UK). A micromixer chip can be used for rapid mixing of two or more fluid streams with a split and recombine mechanism.

In some embodiments, the RNA (e.g., mRNA) vaccines of the disclosure may be formulated for delivery using the drug encapsulating microspheres described in International Patent Publication No. WO2013063468 or U.S. Pat. No. 8,440,614, the contents of each of which are herein incorporated by reference in their entirety. The microspheres may comprise a compound of the formula (I), (II), (III), (IV), (V) or (VI) as described in International Patent Publication No. WO2013063468, the contents of which are herein incorporated by reference in their entirety. In some embodiments, the amino acid, peptide, polypeptide, lipids (APPL) are useful in delivering the RNA (e.g., mRNA) vaccines of the disclosure to cells (see International Patent Publication No. WO2013063468, the contents of which are herein incorporated by reference in their entirety).

In some embodiments, the RNA (e.g., mRNA) vaccines of the disclosure may be formulated in lipid nanoparticles having a diameter from about 10 to about 100 nm such as, but not limited to, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In some embodiments, the lipid nanoparticles may have a diameter from about 10 to 500 nm.

In some embodiments, the lipid nanoparticle may have a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In some embodiments, the lipid nanoparticle may be a limit size lipid nanoparticle described in International Patent Publication No. WO2013059922, the contents of which are herein incorporated by reference in their entirety. The limit size lipid nanoparticle may comprise a lipid bilayer surrounding an aqueous core or a hydrophobic core; where the lipid bilayer may comprise a phospholipid such as, but not limited to, diacylphosphatidylcholine, a diacylphosphatidylethanolamine, a ceramide, a sphingomyelin, a dihydrosphingomyelin, a cephalin, a cerebroside, a C8-C20 fatty acid diacylphophatidylcholine, and 1-palmitoyl-2-oleoyl phosphatidylcholine (POPC). In some embodiments, the limit size lipid nanoparticle may comprise a polyethylene glycol-lipid such as, but not limited to, DLPE-PEG, DMPE-PEG, DPPC-PEG and DSPE-PEG.

In some embodiments, the RNA (e.g., mRNA) vaccines may be delivered, localized and/or concentrated in a specific location using the delivery methods described in International Patent Publication No. WO2013063530, the contents of which are herein incorporated by reference in their entirety. As a non-limiting example, a subject may be administered an empty polymeric particle prior to, simultaneously with or after delivering the RNA (e.g., mRNA) vaccines to the subject. The empty polymeric particle undergoes a change in volume once in contact with the subject and becomes lodged, embedded, immobilized or entrapped at a specific location in the subject.

In some embodiments, the RNA (e.g., mRNA) vaccines may be formulated in an active substance release system (see, e.g., U.S. Patent Publication No. US20130102545, the contents of which are herein incorporated by reference in their entirety). The active substance release system may comprise 1) at least one nanoparticle bonded to an oligonucleotide inhibitor strand which is hybridized with a catalytically active nucleic acid and 2) a compound bonded to at least one substrate molecule bonded to a therapeutically active substance (e.g., polynucleotides described herein), where the therapeutically active substance is released by the cleavage of the substrate molecule by the catalytically active nucleic acid.

In some embodiments, the RNA (e.g., mRNA) vaccines may be formulated in a nanoparticle comprising an inner core comprising a non-cellular material and an outer surface comprising a cellular membrane. The cellular membrane may be derived from a cell or a membrane derived from a virus. As a non-limiting example, the nanoparticle may be made by the methods described in International Patent Publication No. WO2013052167, the contents of which are herein incorporated by reference in their entirety. As another non-limiting example, the nanoparticle described in International Patent Publication No. WO2013052167, the contents of which are herein incorporated by reference in their entirety, may be used to deliver the RNA (e.g., mRNA) vaccines described herein.

In some embodiments, the RNA (e.g., mRNA) vaccines may be formulated in porous nanoparticle-supported lipid bilayers (protocells). Protocells are described in International Patent Publication No. WO2013056132, the contents of which are herein incorporated by reference in their entirety.

In some embodiments, the RNA (e.g., mRNA) vaccines described herein may be formulated in polymeric nanoparticles as described in or made by the methods described in U.S. Pat. Nos. 8,420,123 and 8,518,963 and European Patent No. EP2073848B1, the contents of each of which are herein incorporated by reference in their entirety. As a non-limiting example, the polymeric nanoparticle may have a high glass transition temperature such as the nanoparticles described in or nanoparticles made by the methods described in U.S. Pat. No. 8,518,963, the contents of which are herein incorporated by reference in their entirety. As another non-limiting example, the polymer nanoparticle for oral and parenteral formulations may be made by the methods described in European Patent No. EP2073848B1, the contents of which are herein incorporated by reference in their entirety.

In some embodiments, the RNA (e.g., mRNA) vaccines described herein may be formulated in nanoparticles used in imaging. The nanoparticles may be liposome nanoparticles such as those described in U.S. Patent Publication No US20130129636, herein incorporated by reference in its entirety. As a non-limiting example, the liposome may comprise gadolinium(III)2-{4,7-bis-carboxymethyl-10-[(N, N-distearylamidomethyl-N'-amido-methyl]-1,4,7,10-tetra-azacyclododec-1-yl}-acetic acid and a neutral, fully saturated phospholipid component (see, e.g., U.S. Patent Publication No US20130129636, the contents of which are herein incorporated by reference in their entirety).

In some embodiments, the nanoparticles which may be used in the present disclosure are formed by the methods described in U.S. Patent Application No. US20130130348, the contents of which are herein incorporated by reference in their entirety.

The nanoparticles of the present disclosure may further include nutrients such as, but not limited to, those which deficiencies can lead to health hazards from anemia to neural tube defects (see, e.g., the nanoparticles described in International Patent Publication No WO2013072929, the contents of which are herein incorporated by reference in their entirety). As a non-limiting example, the nutrient may be iron in the form of ferrous, ferric salts or elemental iron, iodine, folic acid, vitamins or micronutrients.

In some embodiments, the RNA (e.g., mRNA) vaccines of the present disclosure may be formulated in a swellable nanoparticle. The swellable nanoparticle may be, but is not limited to, those described in U.S. Pat. No. 8,440,231, the contents of which are herein incorporated by reference in their entirety. As a non-limiting embodiment, the swellable nanoparticle may be used for delivery of the RNA (e.g., mRNA) vaccines of the present disclosure to the pulmonary system (see, e.g., U.S. Pat. No. 8,440,231, the contents of which are herein incorporated by reference in their entirety).

The RNA (e.g., mRNA) vaccines of the present disclosure may be formulated in polyanhydride nanoparticles such as, but not limited to, those described in U.S. Pat. No. 8,449,916, the contents of which are herein incorporated by reference in their entirety.

The nanoparticles and microparticles of the present disclosure may be geometrically engineered to modulate macrophage and/or the immune response. In some embodiments, the geometrically engineered particles may have varied shapes, sizes and/or surface charges in order to incorporated the polynucleotides of the present disclosure for targeted delivery such as, but not limited to, pulmonary delivery (see, e.g., International Publication No WO2013082111, the contents of which are herein incorporated by reference in their entirety). Other physical features the geometrically engineering particles may have include, but are not limited to, fenestrations, angled arms, asymmetry and surface roughness, charge which can alter the interactions with cells and tissues. As a non-limiting example, nanoparticles of the present disclosure may be made by the methods described in International Publication No WO2013082111, the contents of which are herein incorporated by reference in their entirety.

In some embodiments, the nanoparticles of the present disclosure may be water soluble nanoparticles such as, but not limited to, those described in International Publication No. WO2013090601, the contents of which are herein incorporated by reference in their entirety. The nanoparticles may be inorganic nanoparticles which have a compact and zwitterionic ligand in order to exhibit good water solubility. The nanoparticles may also have small hydrodynamic diameters (HD), stability with respect to time, pH, and salinity and a low level of non-specific protein binding.

In some embodiments the nanoparticles of the present disclosure may be developed by the methods described in U.S. Patent Publication No. US20130172406, the contents of which are herein incorporated by reference in their entirety.

In some embodiments, the nanoparticles of the present disclosure are stealth nanoparticles or target-specific stealth nanoparticles such as, but not limited to, those described in U.S. Patent Publication No. US20130172406, the contents of which are herein incorporated by reference in their entirety. The nanoparticles of the present disclosure may be made by the methods described in U.S. Patent Publication No. US20130172406, the contents of which are herein incorporated by reference in their entirety.

In some embodiments, the stealth or target-specific stealth nanoparticles may comprise a polymeric matrix. The polymeric matrix may comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polyesters, polyanhydrides, polyethers, polyurethanes, polymethacrylates, polyacrylates, polycyanoacrylates or combinations thereof.

In some embodiments, the nanoparticle may be a nanoparticle-nucleic acid hybrid structure having a high density nucleic acid layer. As a non-limiting example, the nanoparticle-nucleic acid hybrid structure may made by the methods described in U.S. Patent Publication No. US20130171646, the contents of which are herein incorporated by reference in their entirety. The nanoparticle may comprise a nucleic acid such as, but not limited to, polynucleotides described herein and/or known in the art.

At least one of the nanoparticles of the present disclosure may be embedded in in the core a nanostructure or coated with a low density porous 3-D structure or coating which is capable of carrying or associating with at least one payload within or on the surface of the nanostructure. Non-limiting examples of the nanostructures comprising at least one nanoparticle are described in International Patent Publication No. WO2013123523, the contents of which are herein incorporated by reference in their entirety.

In some embodiments the RNA (e.g., mRNA) vaccine may be associated with a cationic or polycationic compounds, including protamine, nucleoline, spermine or spermidine, or other cationic peptides or proteins, such as poly-L-lysine (PLL), polyarginine, basic polypeptides, cell penetrating peptides (CPPs), including HIV-binding peptides, HIV-1 Tat (HIV), Tat-derived peptides, Penetratin, $VP^{22}$ derived or analog peptides, Pestivirus Ems, HSV, $VP^{22}$ (Herpes simplex), MAP, KALA or protein transduction domains (PTDs), PpT620, prolin-rich peptides, arginine-rich peptides, lysine-rich peptides, MPG-peptide(s), Pep-1, L-oligomers, Calcitonin peptide(s), Antennapedia-derived peptides (particularly from *Drosophila antennapedia*), pAntp, pIsl, FGF, Lactoferrin, Transportan, Buforin-2, Bac715-24, SynB, SynB(1), pVEC, hCT-derived peptides, SAP, histones, cationic polysaccharides, for example chitosan, polybrene, cationic polymers, e.g. polyethyleneimine (PEI), cationic lipids, e.g. DOTMA: [1-(2,3-sioleyloxy) propyl)]-N,N,N-trimethylammonium chloride, DMRIE, di-C14-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecylamidoglicylspermin, DIMRI: Dimyristooxypropyl dimethyl hydroxyethyl ammonium bromide, DOTAP: dioleoyloxy-3-(trimethylammonio)propane, DC-6-14: O,O-ditetradecanoyl-N-.alpha.-trimethylammonioacetyl)diethanolamine chloride, CLIP 1: rac-[(2,3-dioctadecyloxypropyl)(2-hydroxyethyl)]-dimethylammonium chloride, CLIP6: rac-[2(2,3-dihexadecyloxypropyloxymethyloxy)ethyl]-trimethylammonium, CLIP9: rac-[2(2,3-dihexadecyloxypropyloxysuccinyloxy)ethyl]-trimethylammo-nium, oligofectamine, or cationic or polycationic polymers, e.g. modified polyaminoacids, such as beta-aminoacid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified amidoamines such as pAMAM (poly(amidoamine)), etc., modified polybetaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly(ethyleneimine), poly(propyleneimine), etc., polyallylamine, sugar backbone based polymers, such as cyclodextrin based polymers, dextran based polymers, chitosan, etc., silan backbone based polymers, such as PMOXA-PDMS copolymers, etc., blockpolymers consisting of a combination of one or more cationic blocks (e.g. selected from a cationic polymer as mentioned above) and of one or more hydrophilic or hydrophobic blocks (e.g. polyethyleneglycole), etc.

In other embodiments the RNA (e.g., mRNA) vaccine is not associated with a cationic or polycationic compounds.

In some embodiments, a nanoparticle comprises compounds of Formula (I):

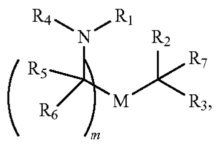

(I)

or a salt or isomer thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —$CQ(R)_2$, and unsubstituted $C_{1-6}$ alkyl, where Q is selected from a carbocycle, heterocycle, —OR, —$O(CH_2)_nN(R)_2$, —C(O)OR, —OC(O)R, —$CX_3$, —$CX_2H$, —$CXH_2$, —CN, —$N(R)_2$, —$C(O)N(R)_2$, —N(R)C(O)R, —$N(R)S(O)_2R$, —$N(R)C(O)N(R)_2$, —$N(R)C(S)N(R)_2$, —$N(R)R_8$, —$O(CH_2)_nOR$, —$N(R)C(=NR_9)N(R)_2$, —$N(R)C(=CHR_9)N(R)_2$, —$OC(O)N(R)_2$, —N(R)C(O)OR, —N(OR)C(O)R, —$N(OR)S(O)_2R$, —N(OR)C(O)OR, —$N(OR)C(O)N(R)_2$, —$N(OR)C(S)N(R)_2$, —$N(OR)C(=NR_9)N(R)_2$, —$N(OR)C(=CHR_9)N(R)_2$, —$C(=NR_9)N(R)_2$, —$C(=NR_9)R$, —C(O)N(R)OR, and —$C(R)N(R)_2C(O)OR$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—,

—N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of C1-12 alkyl and $C_{2-12}$ alkenyl;

each Y is independently a C3-6 carbocycle;

each X is independently selected from the group consisting of F, Cl, Br, and I; and m is selected from 5, 6, 7, 8, 9, 10, 11, 12, and 13.

In some embodiments, a subset of compounds of Formula (I) includes those in which when $R_4$ is —$(CH_2)_n$Q, —$(CH_2)_n$CHQR, —CHQR, or —$CQ(R)_2$, then (i) Q is not —$N(R)_2$ when n is 1, 2, 3, 4 or 5, or (ii) Q is not 5, 6, or 7-membered heterocycloalkyl when n is 1 or 2.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —$CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —$C(O)N(R)_2$, —N(R)C(O)R, —$N(R)S(O)_2R$, —$N(R)C(O)N(R)_2$, —$N(R)C(S)N(R)_2$, —$CRN(R)_2C(O)OR$, —$N(R)R_8$, —$O(CH_2)_nOR$, —$N(R)C(=NR_9)N(R)_2$, —$N(R)C(=CHR_9)N(R)_2$, —$OC(O)N(R)_2$, —N(R)C(O)OR, —N(OR)C(O)R, —$N(OR)S(O)_2R$, —N(OR)C(O)OR, —$N(OR)C(O)N(R)_2$, —$N(OR)C(S)N(R)_2$, —$N(OR)C(=NR_9)N(R)_2$, —$N(OR)C(=CHR_9)N(R)_2$, —$C(=NR_9)N(R)_2$, —$C(=NR_9)R$, —C(O)N(R)OR, and a 5- to 14-membered heterocycloalkyl having one or more heteroatoms selected from N, O, and S which is substituted with one or more substituents selected from oxo (=O), OH, amino, mono- or di-alkylamino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_nCHQR$, —CHQR, —$CQ(R)_2$, and unsubstituted $C_{1-6}$ alkyl, where Q is selected from a $C_{3-6}$ carbocycle, a 5- to 14-membered heterocycle having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —$C(O)N(R)_2$, —N(R)C(O)R, —$N(R)S(O)_2R$, —$N(R)C(O)N(R)_2$, —$N(R)C(S)N(R)_2$, —$CRN(R)_2C(O)OR$, —$N(R)R_8$, —$O(CH_2)_nOR$, —N(R)C(=$NR_9$)$N(R)_2$, —N(R)C(=$CHR_9$)$N(R)_2$, —$OC(O)N(R)_2$, —N(R)C(O)OR, —N(OR)C(O)R, —$N(OR)S(O)_2R$, —N(OR)C(O)OR, —$N(OR)C(O)N(R)_2$, —$N(OR)C(S)N(R)_2$, —N(OR)C(=$NR_9$)$N(R)_2$, —N(OR)C(=$CHR_9$)$N(R)_2$, —C(=$NR_9$)R, —C(O)N(R)OR, and —C(=$NR_9$)$N(R)_2$, and each n is independently selected from 1, 2, 3, 4, and 5; and when Q is a 5- to 14-membered heterocycle and (i) $R_4$ is —$(CH_2)_nQ$ in which n is 1 or 2, or (ii) $R_4$ is —$(CH_2)_nCHQR$ in which n is 1, or (iii) $R_4$ is —CHQR, and —$CQ(R)_2$, then Q is either a 5- to 14-membered heteroaryl or 8- to 14-membered heterocycloalkyl;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_nCHQR$, —CHQR, —$CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —$C(O)N(R)_2$, —N(R)C(O)R, —$N(R)S(O)_2R$, —$N(R)C(O)N(R)_2$, —$N(R)C(S)N(R)_2$, —$CRN(R)_2C(O)OR$, —$N(R)R_8$, —$O(CH_2)_nOR$, —N(R)C(=$NR_9$)$N(R)_2$, —N(R)C(=$CHR_9$)$N(R)_2$, —$OC(O)N(R)_2$, —N(R)C(O)OR, —N(OR)C(O)R, —$N(OR)S(O)_2R$, —N(OR)C(O)OR, —$N(OR)C(O)N(R)_2$, —$N(OR)C(S)N(R)_2$, —N(OR)C(=$NR_9$)$N(R)_2$, —N(OR)C(=$CHR_9$)$N(R)_2$, —C(=$NR_9$)R, —C(O)N(R)OR, and —C(=$NR_9$)$N(R)_2$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is —$(CH_2)_n$Q or —$(CH_2)_n$CHQR, where Q is —$N(R)_2$, and n is selected from 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of —$(CH_2)_n$Q, —$(CH_2)_n$CHQR, —CHQR, and —$CQ(R)_2$, where Q is —$N(R)_2$, and n is selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those of Formula (IA):

(IA)

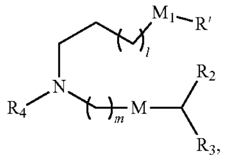

or a salt or isomer thereof, wherein 1 is selected from 1, 2, 3, 4, and 5; m is selected from 5, 6, 7, 8, and 9; $M_1$ is a bond or M'; $R_4$ is unsubstituted $C_{1-3}$ alkyl, or —$(CH_2)_n$Q, in which Q is OH, —NHC(S)$N(R)_2$, —NHC(O)$N(R)_2$, —N(R)C(O)R, —N(R)$S(O)_2$R, —N(R)$R_8$, —NHC(=$NR_9$)$N(R)_2$, —NHC(=$CHR_9$)$N(R)_2$, —OC(O)$N(R)_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (II):

(II)

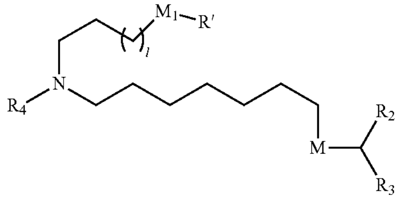

or a salt or isomer thereof, wherein 1 is selected from 1, 2, 3, 4, and 5; $M_1$ is a bond or M'; $R_4$ is unsubstituted $C_{1-3}$ alkyl, or —$(CH_2)_n$Q, in which n is 2, 3, or 4, and Q is OH, —NHC(S)$N(R)_2$, —NHC(O)$N(R)_2$, —N(R)C(O)R, —N(R)$S(O)_2$R, —N(R)$R_8$, —NHC(=$NR_9$)$N(R)_2$, —NHC(=$CHR_9$)$N(R)_2$, —OC(O)$N(R)_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (IIa), (IIb), (IIc), or (IIe):

(IIa)

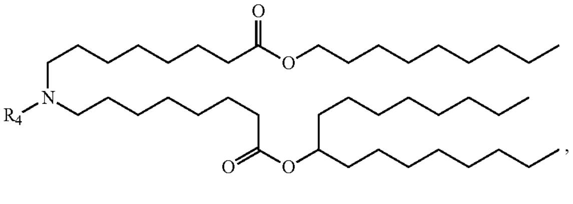

-continued (IIb)

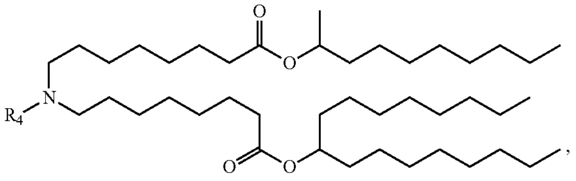

(IIc)

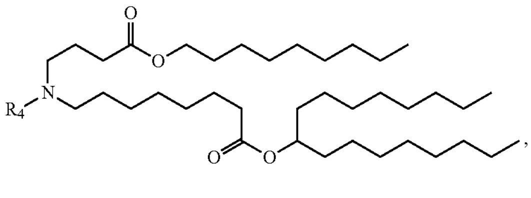

, or (IIe)

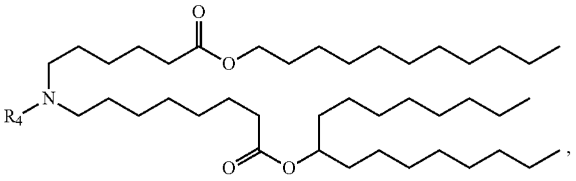

or a salt or isomer thereof, wherein $R_4$ is as described herein.

In some embodiments, a subset of compounds of Formula (I) includes those of Formula (IId):

(IId)

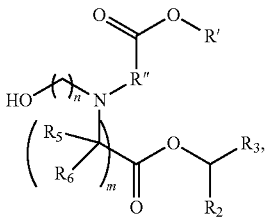

or a salt or isomer thereof, wherein n is 2, 3, or 4; and m, R', R", and $R_2$ through $R_6$ are as described herein. For example, each of $R_2$ and $R_3$ may be independently selected from the group consisting of $C_{5-14}$ alkyl and $C_{5-14}$ alkenyl.

In some embodiments, a subset of compounds of Formula (I) includes those of Formula (IIa), (IIb), (IIc), or (IIe):

(IIa)

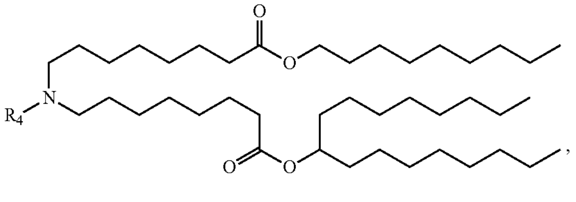

-continued (IIb)

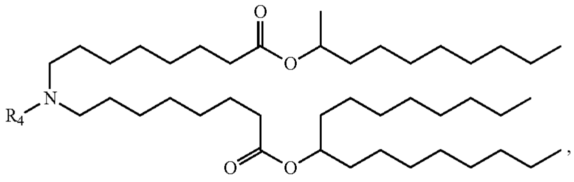

(IIc)

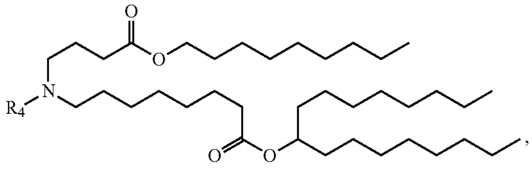

, or (IIe)

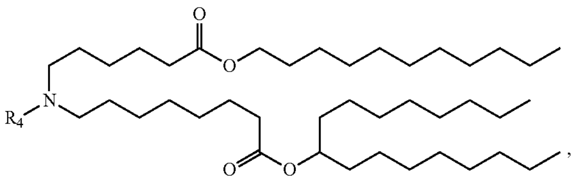

or a salt or isomer thereof, wherein $R_4$ is as described herein.

In some embodiments, a subset of compounds of Formula (I) includes those of Formula (IId):

(IId)

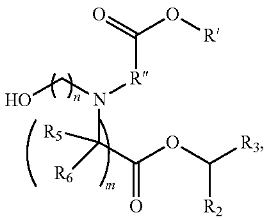

or a salt or isomer thereof, wherein n is 2, 3, or 4; and m, R', R", and $R_2$ through $R_6$ are as described herein. For example, each of $R_2$ and $R_3$ may be independently selected from the group consisting of $C_{5-14}$ alkyl and $C_{5-14}$ alkenyl.

In some embodiments, the compound of Formula (I) is selected from the group consisting of:
(Compound 1)
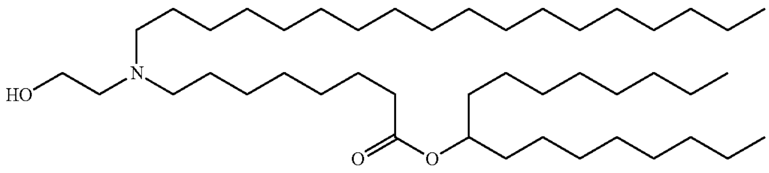
(Compound 2)
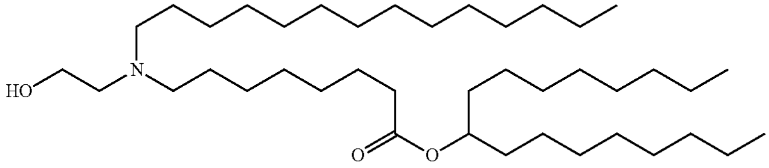
(Compound 3)
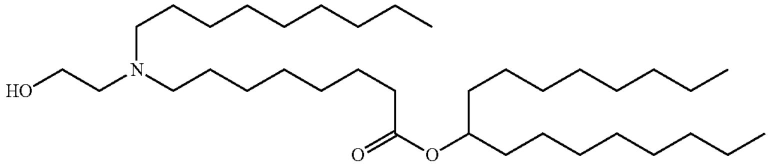
(Compound 4)
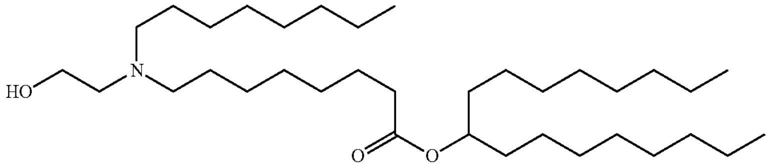
(Compound 5)
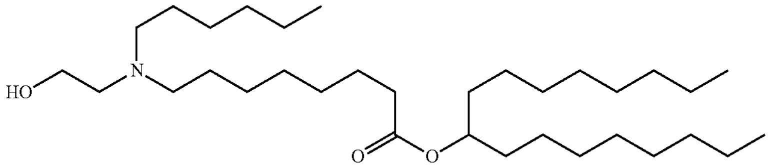
(Compound 6)
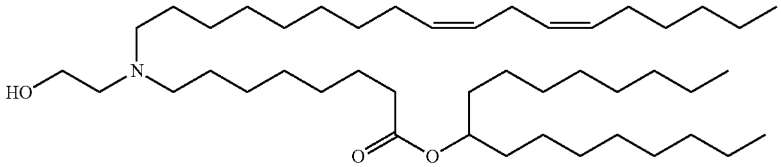
(Compound 7)
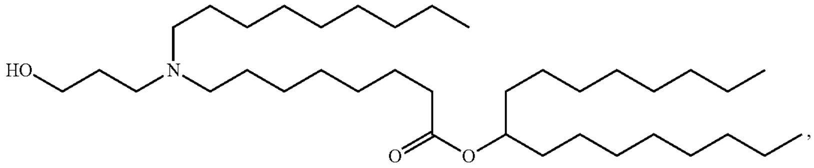
(Compound 8)
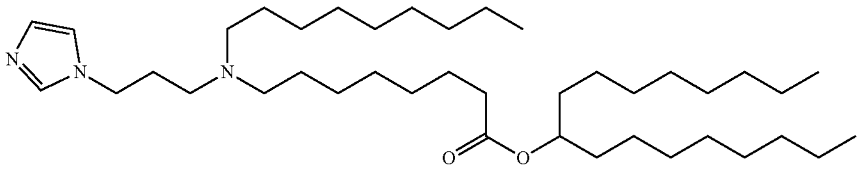

-continued
(Compound 9)
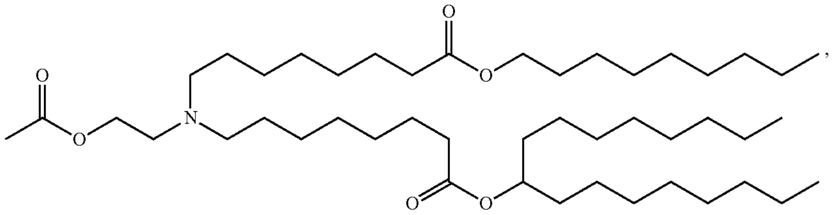
(Compound 10)
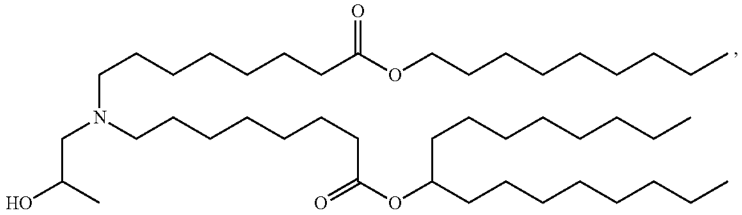
(Compound 11)
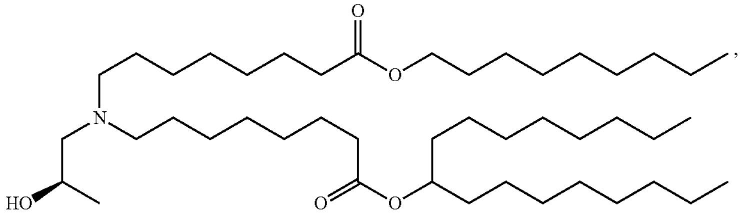
(Compound 12)
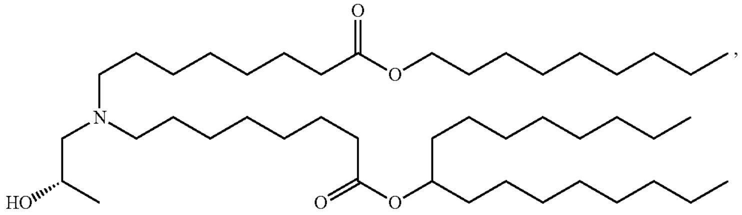
(Compound 13)
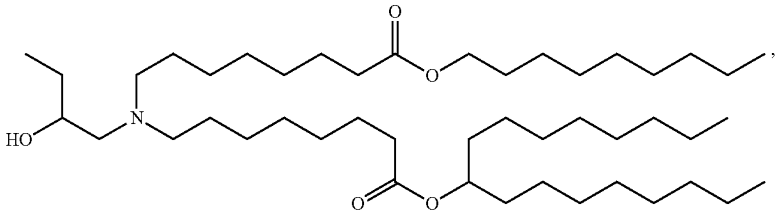
(Compound 14)
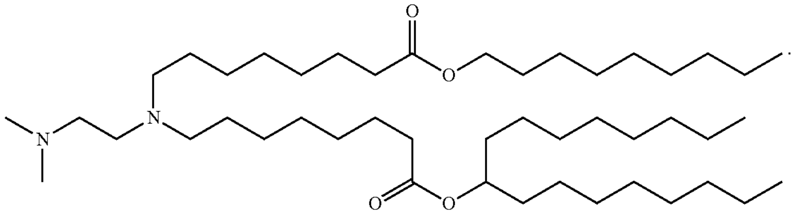
(Compound 15)
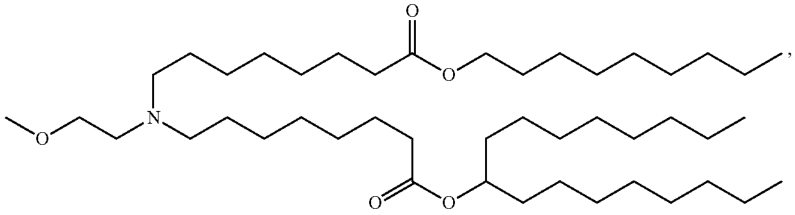

-continued
(Compound 16)
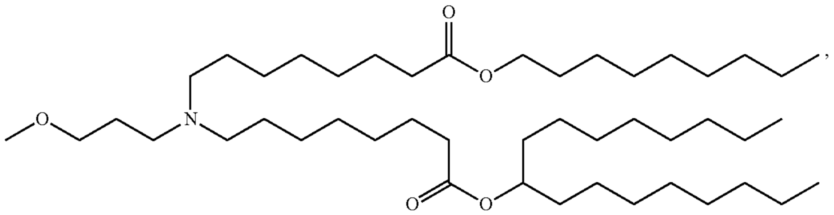
(Compound 17)
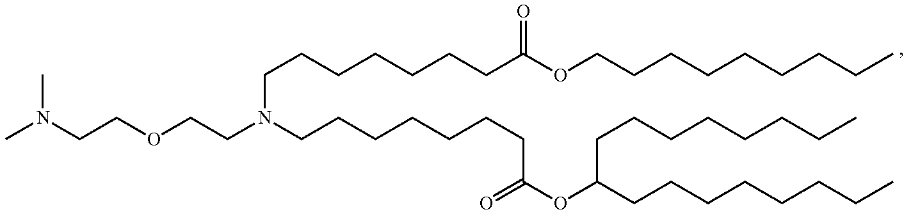
(Compound 18)
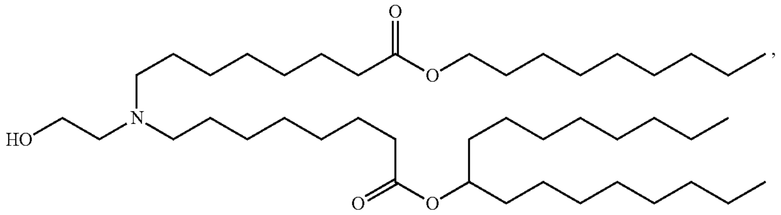
(Compound 19)
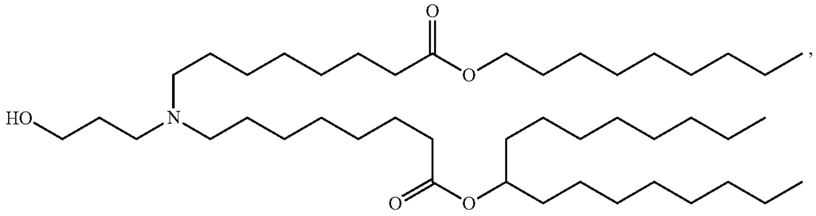
(Compound 20)
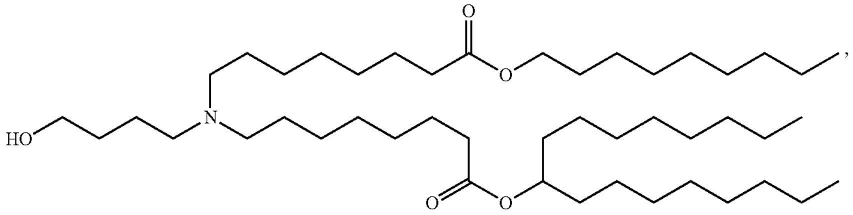
(Compound 21)
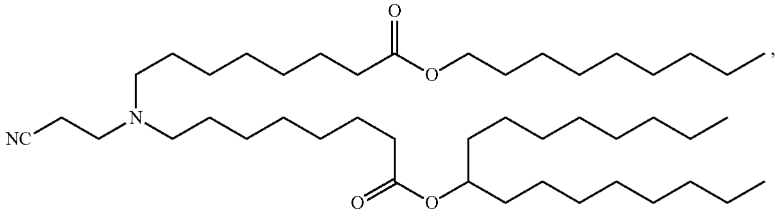
(Compound 22)
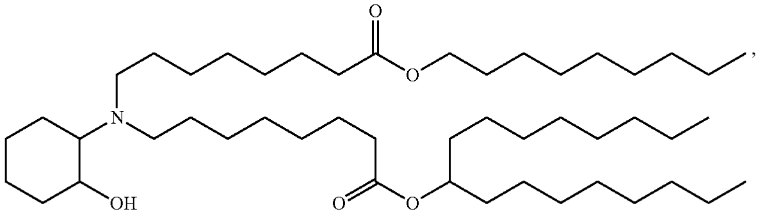

-continued
(Compound 23)
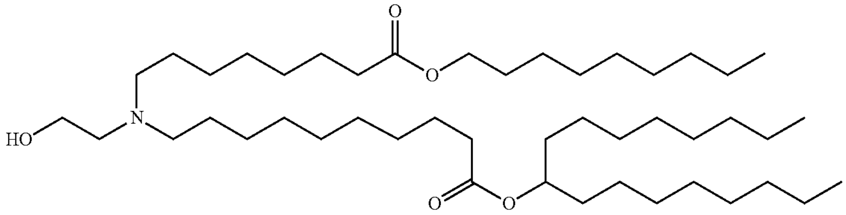
,
(Compound 24)
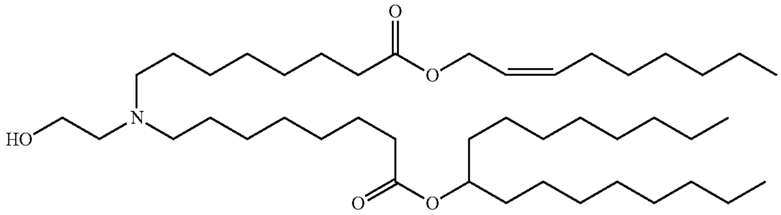
,
(Compound 25)
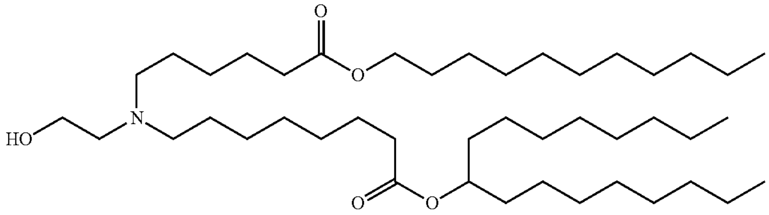
,
(Compound 26)
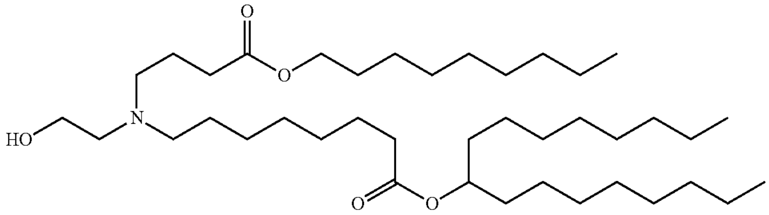
,
(Compound 27)
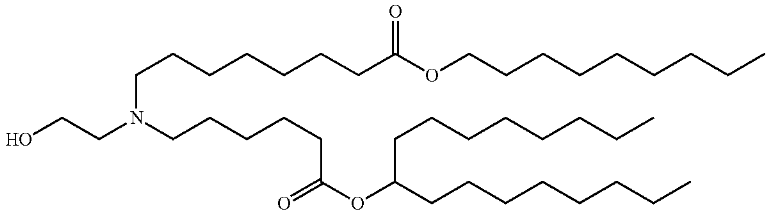
,
(Compound 28)
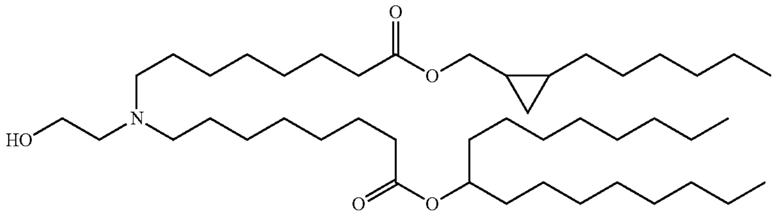
,
(Compound 29)
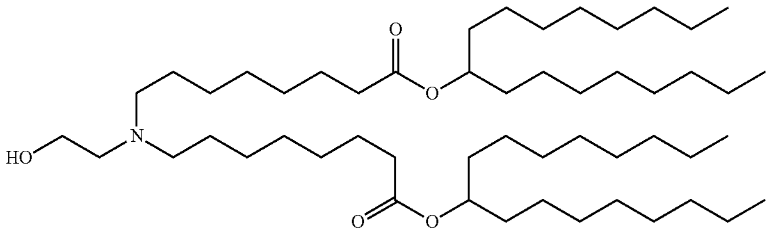
, -continued
(Compound 30)
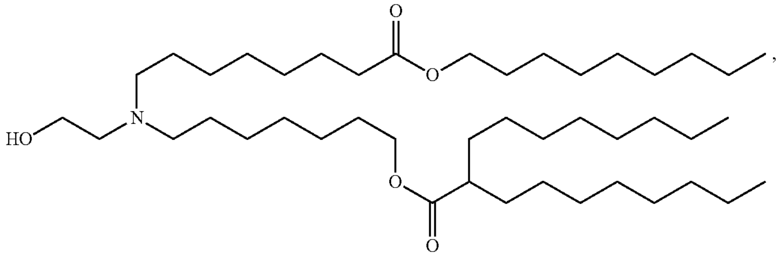
(Compound 31)
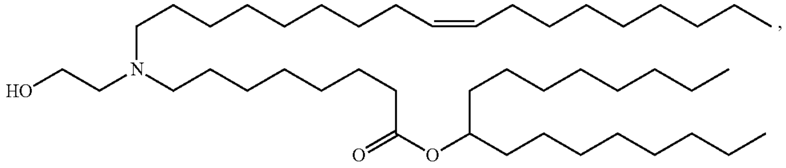
(Compound 32)
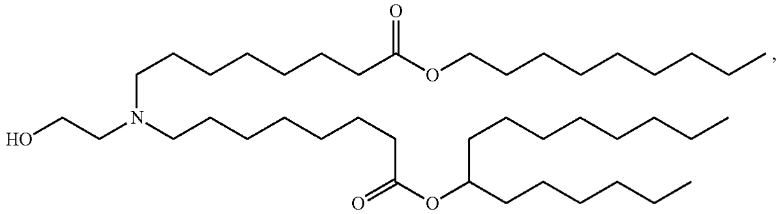
(Compound 33)
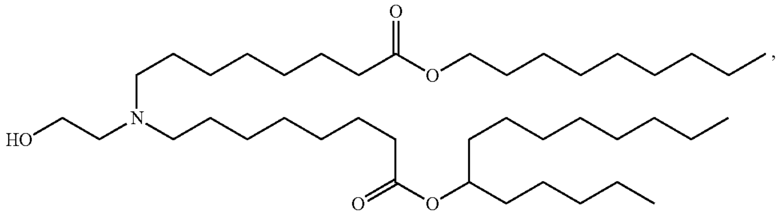
(Compound 34)
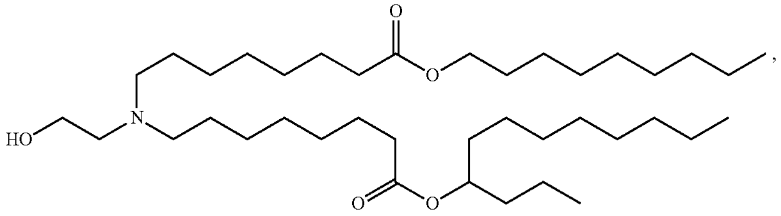
(Compound 35)
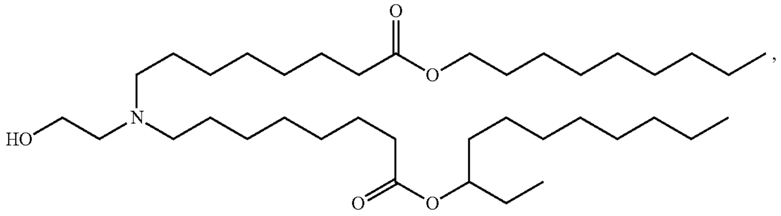
(Compound 36)
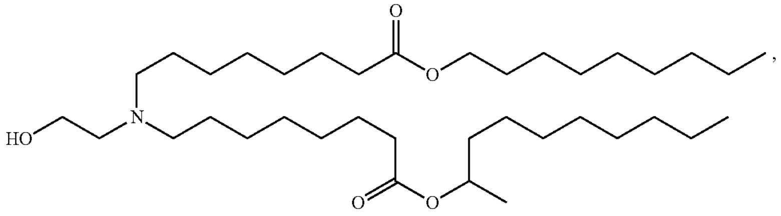

-continued
(Compound 37)
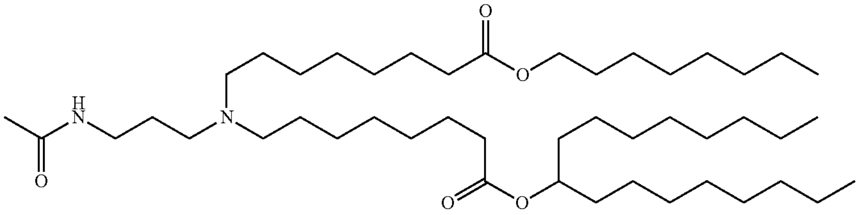,
(Compound 38)
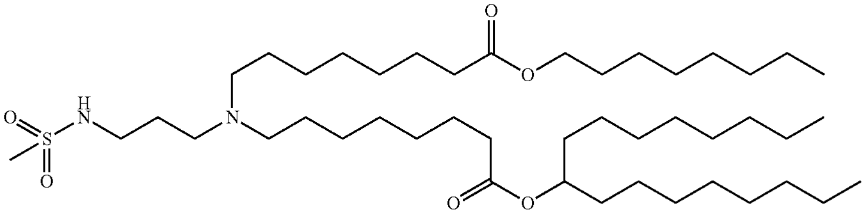,
(Compound 39)
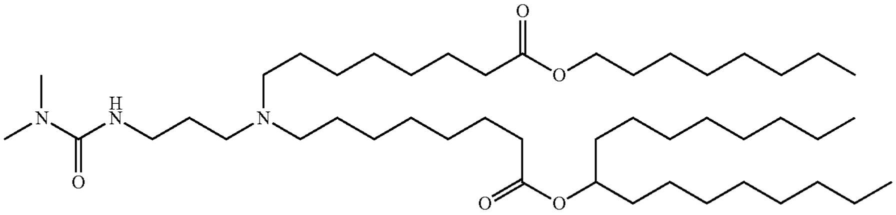,
(Compound 40)
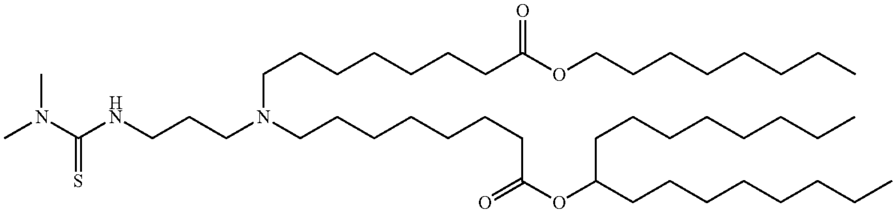,
(Compound 41)
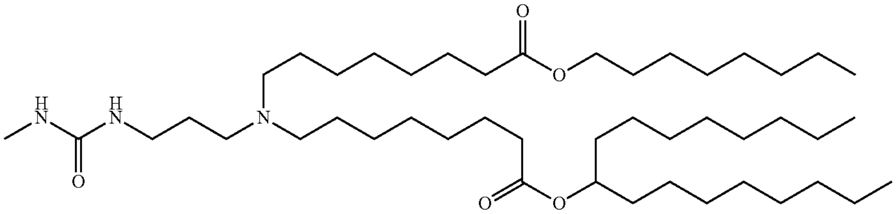,
(Compound 42)
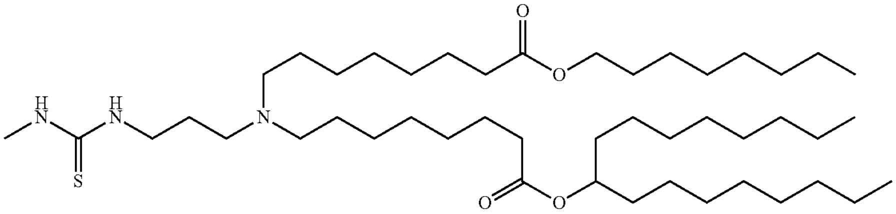,
(Compound 43)
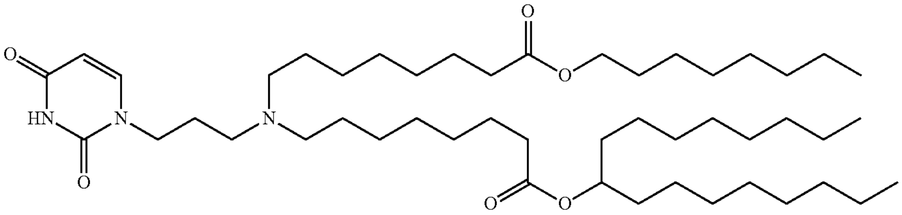, -continued
(Compound 44)
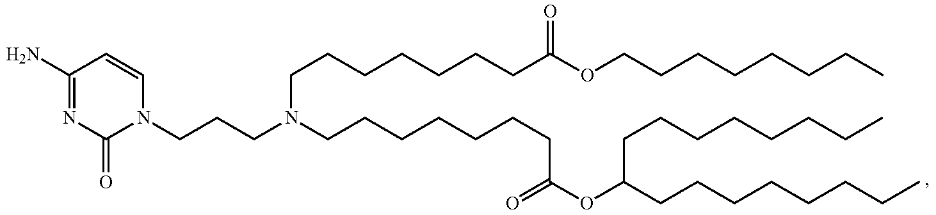
(Compound 45)
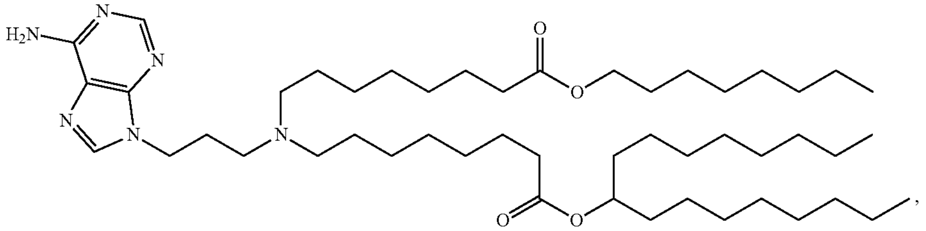
(Compound 46)
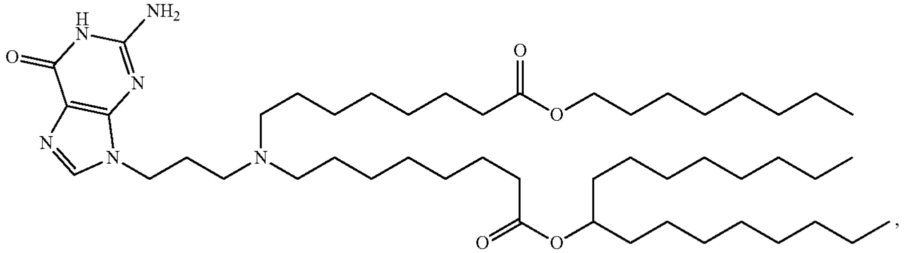
(Compound 47)
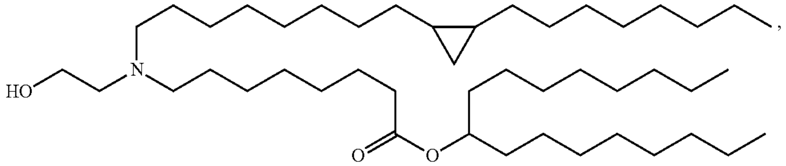
(Compound 48)
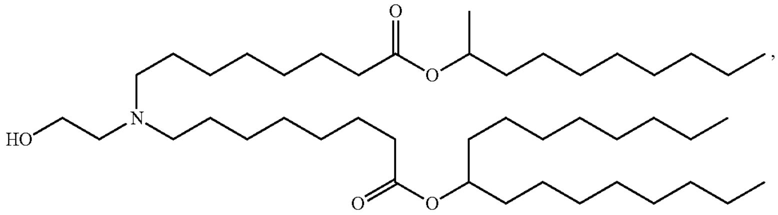
(Compound 49)
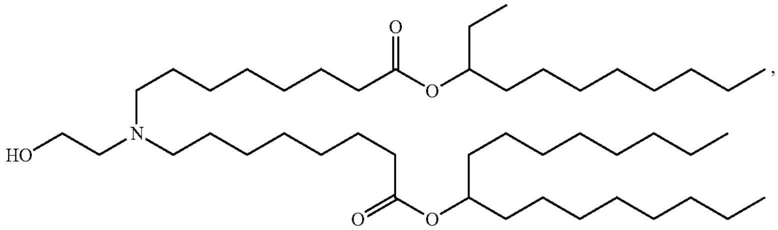
(Compound 50)
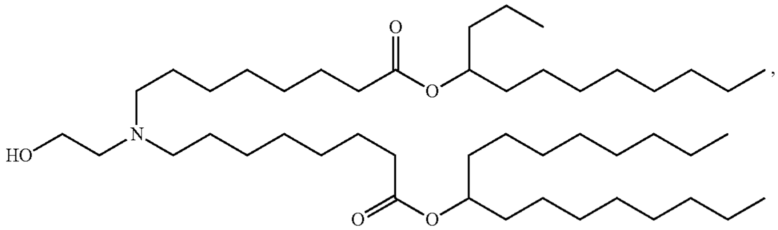

-continued
(Compound 51)
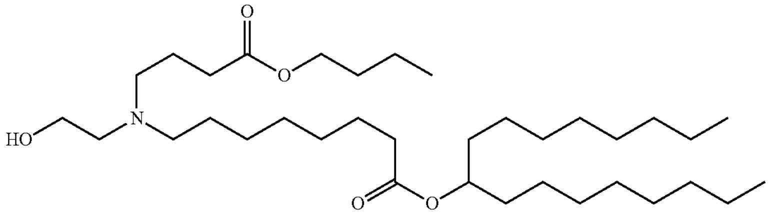,
(Compound 52)
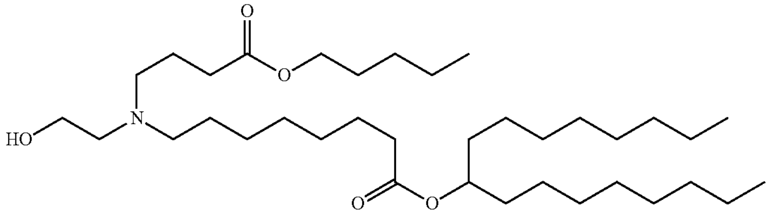,
(Compound 53)
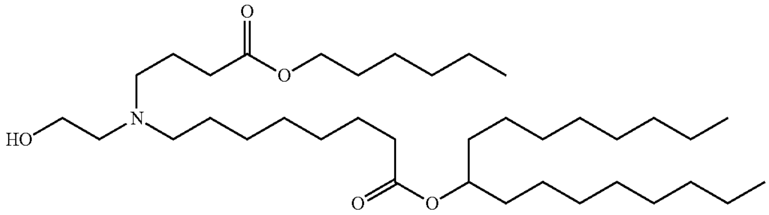,
(Compound 54)
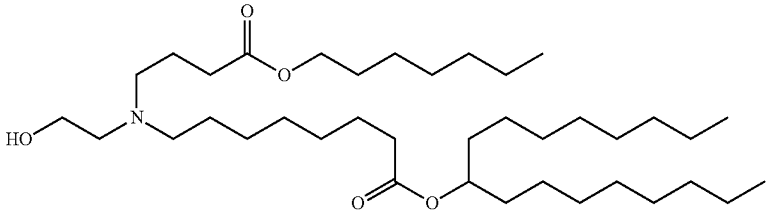,
(Compound 55)
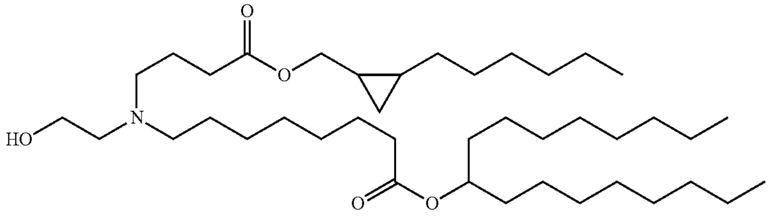,
(Compound 56)
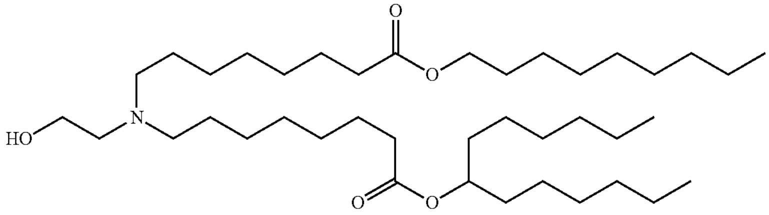,
(Compound 57)
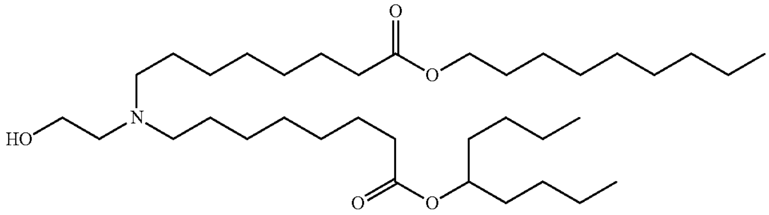, -continued
(Compound 58)
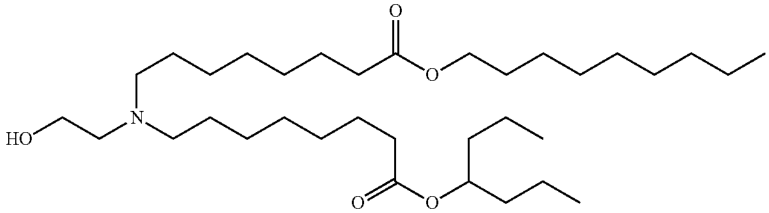
,
(Compound 59)
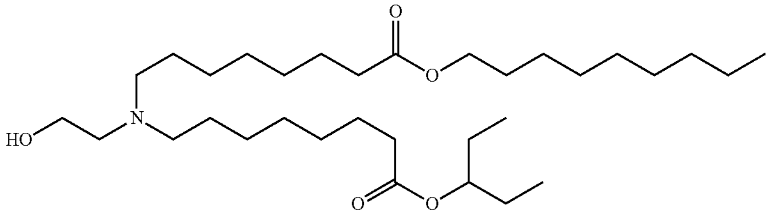
,
(Compound 60)
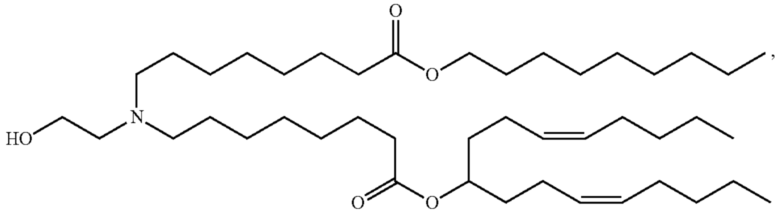
, and
(Compound 61)
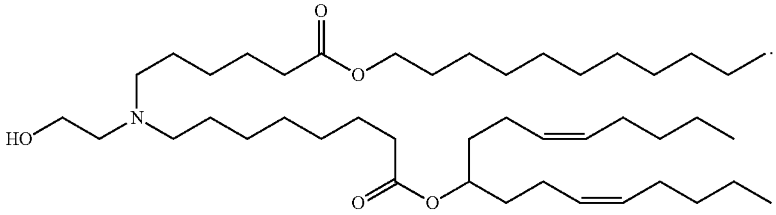
.
In further embodiments, the compound of Formula (I) is selected from the group consisting of:
(Compound 62)
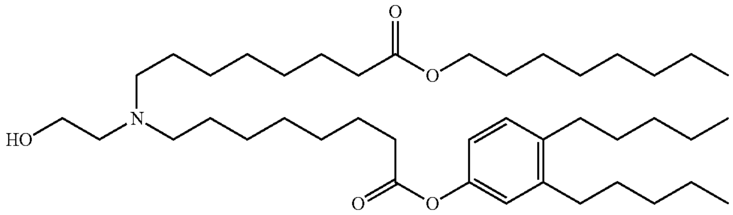
,
(Compound 63)
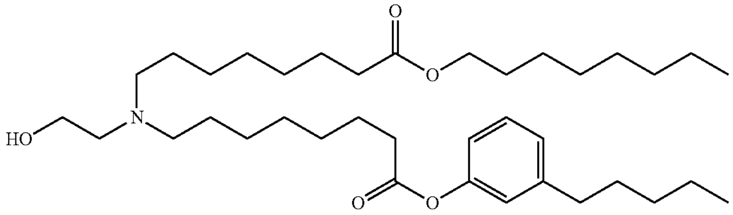
, and -continued
(Compound 64)
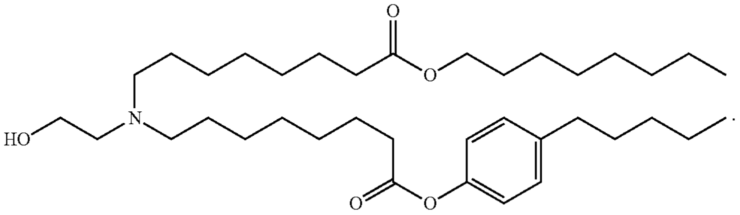
In some embodiments, the compound of Formula (I) is selected from the group consisting of:
(Compound 65)
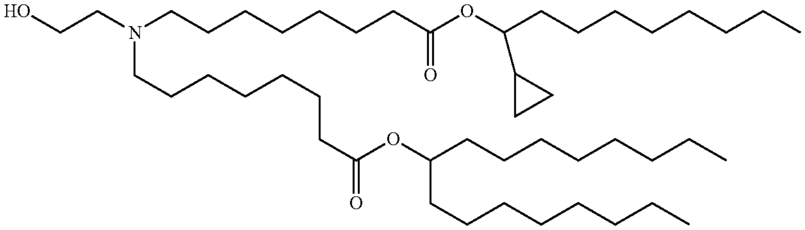
,
(Compound 66)
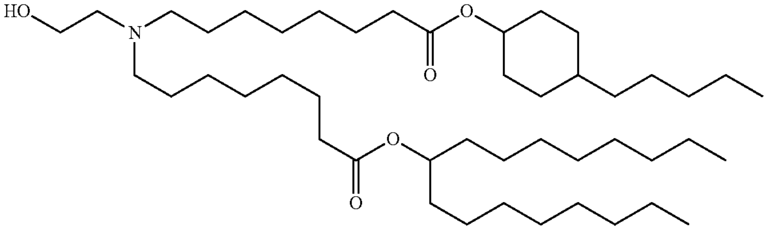
,
(Compound 67)
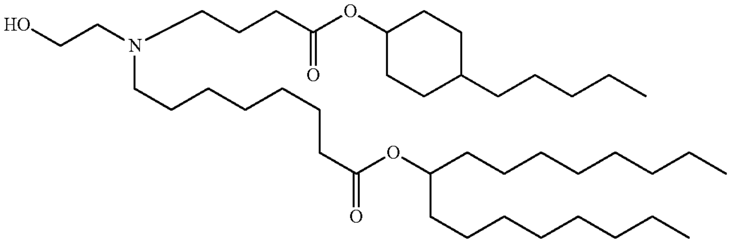
,
(Compound 68)
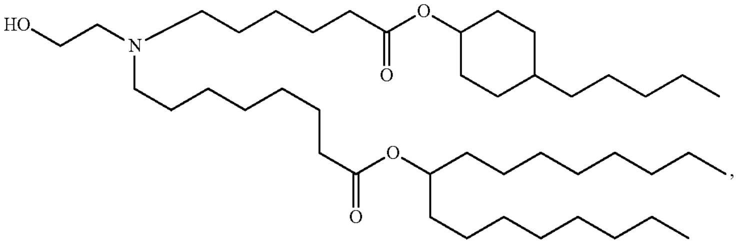
,
(Compound 69)
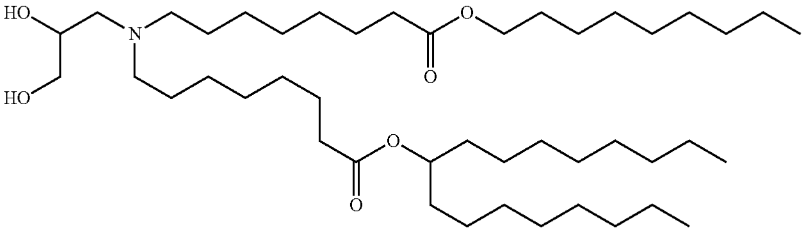
, -continued
(Compound 70)
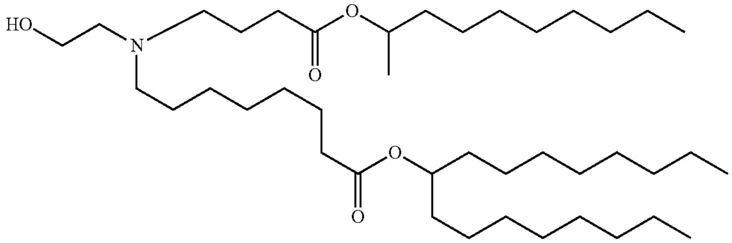
,
(Compound 71)
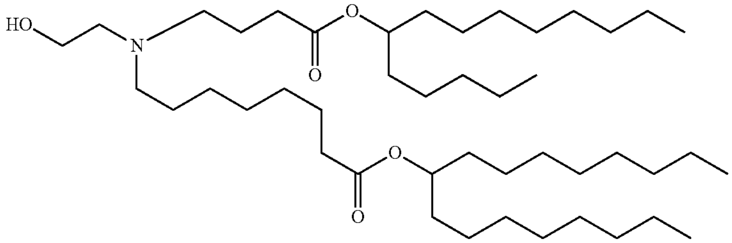
,
(Compound 72)
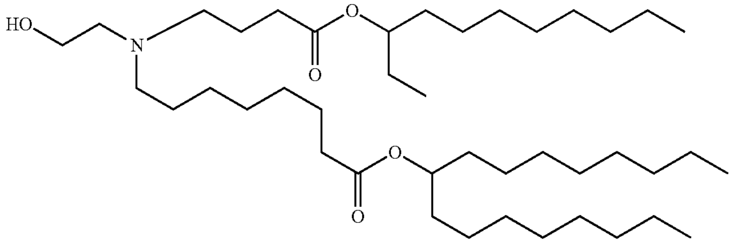
,
(Compound 73)
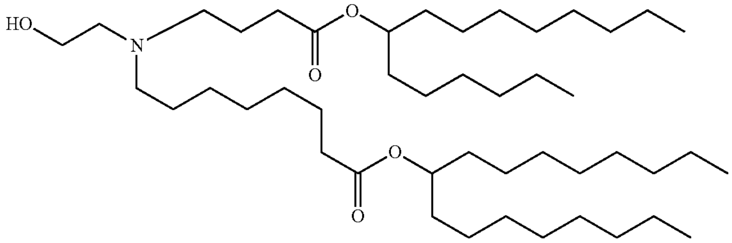
,
(Compound 74)
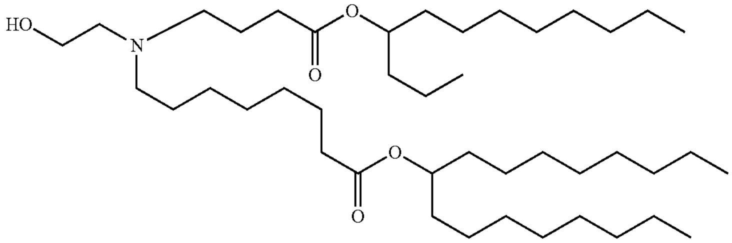
,
(Compound 75)
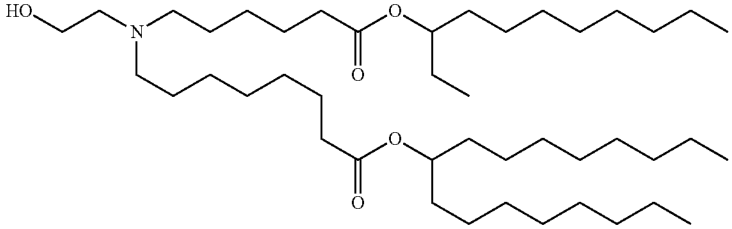
, -continued
(Compound 76)
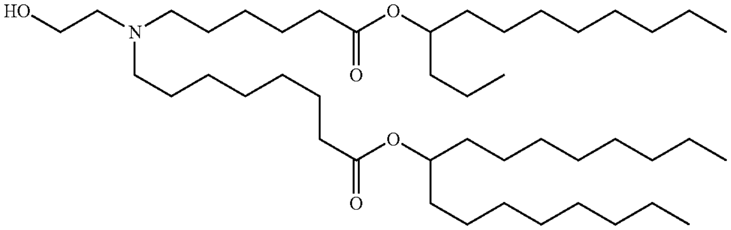
,
(Compound 77)
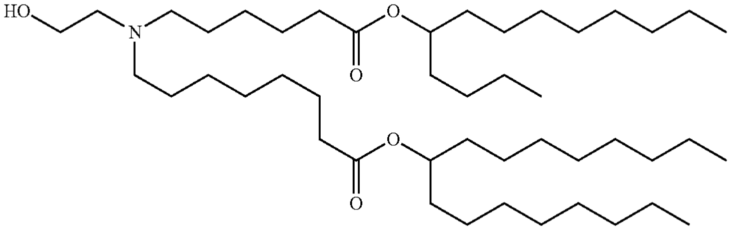
,
(Compound 78)
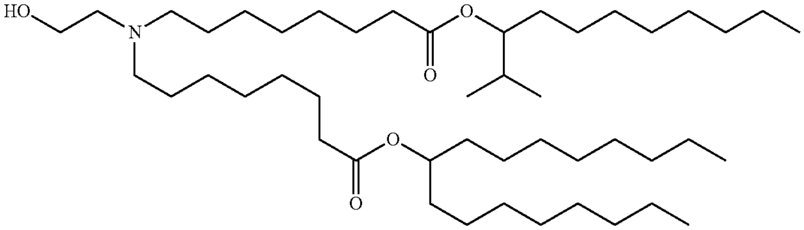
,
(Compound 79)
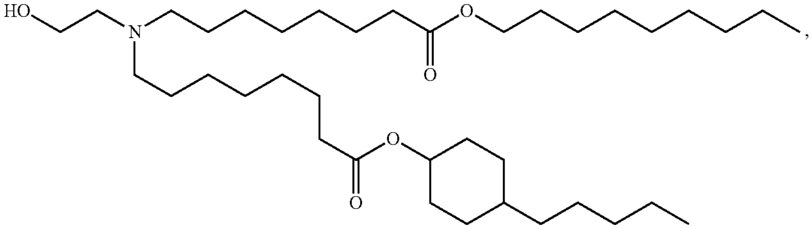
,
(Compound 80)
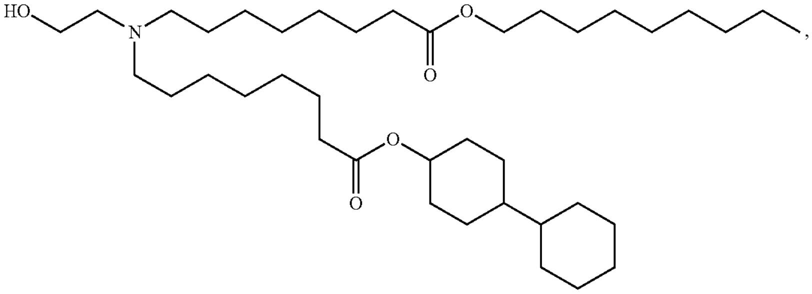
,
(Compound 81)
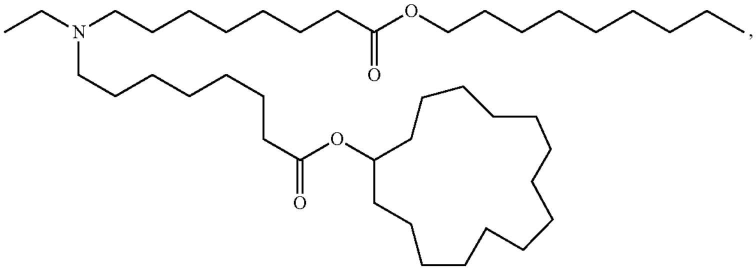
, -continued
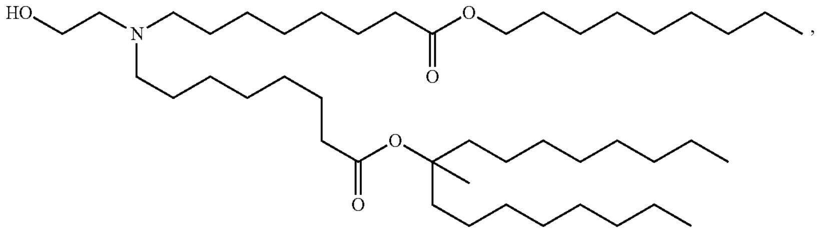
(Compound 82)
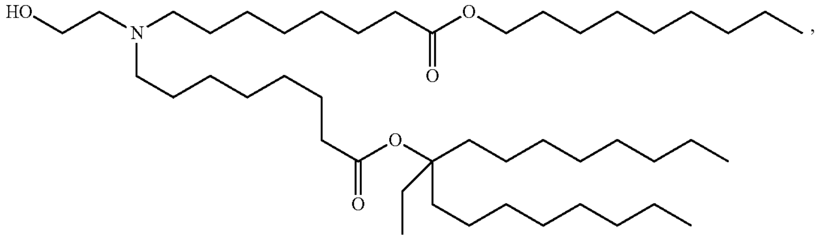
(Compound 83)
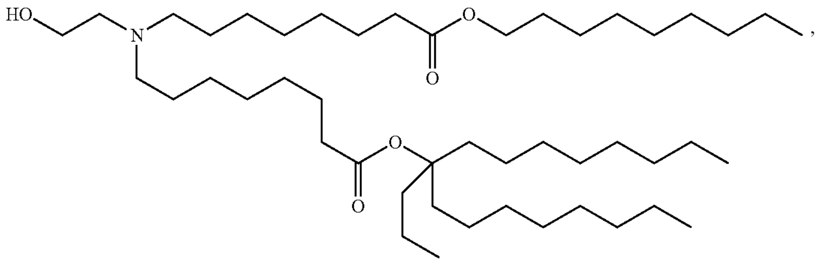
(Compound 84)
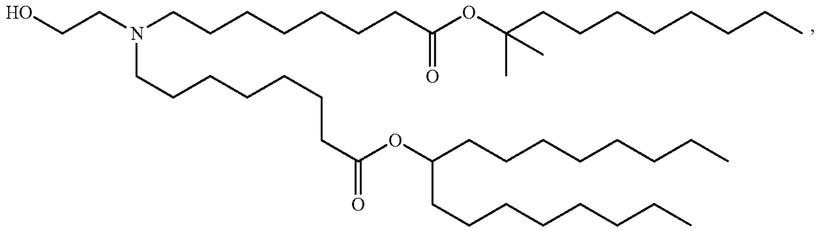
(Compound 85)
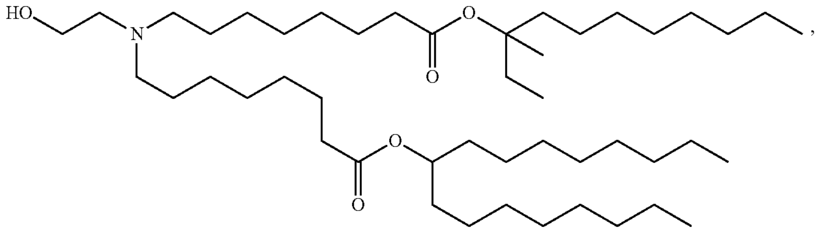
(Compound 86)
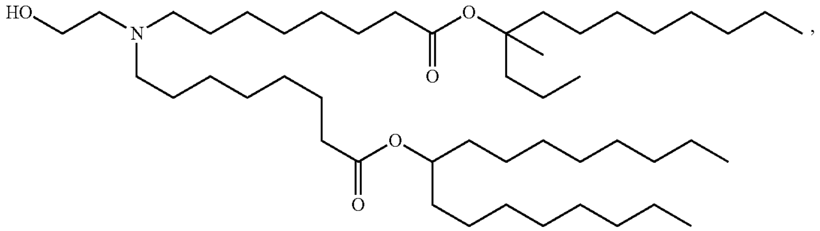
(Compound 87)

-continued
(Compound 88)
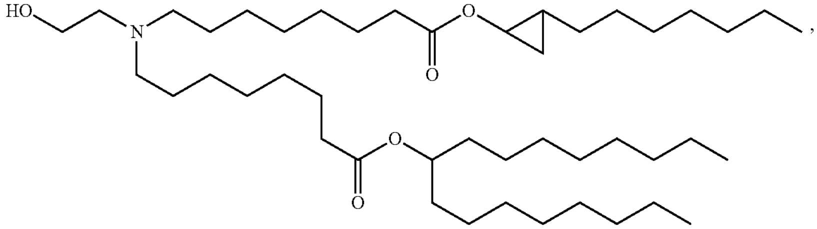
(Compound 89)
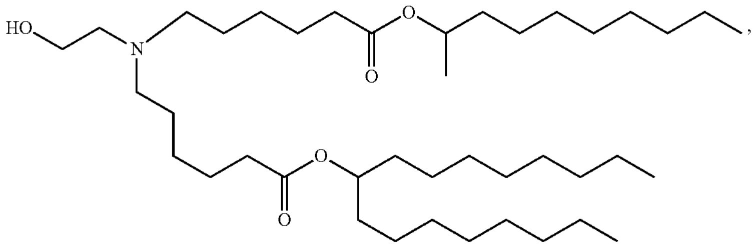
(Compound 90)
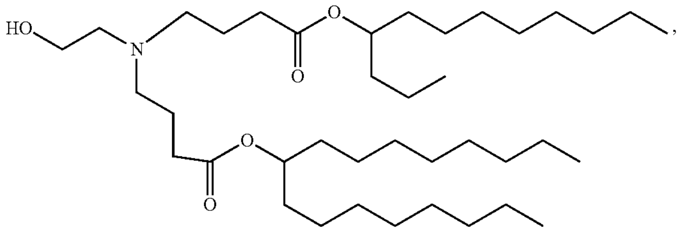
(Compound 91)
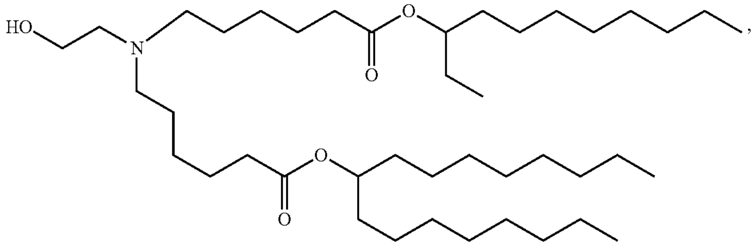
(Compound 92)
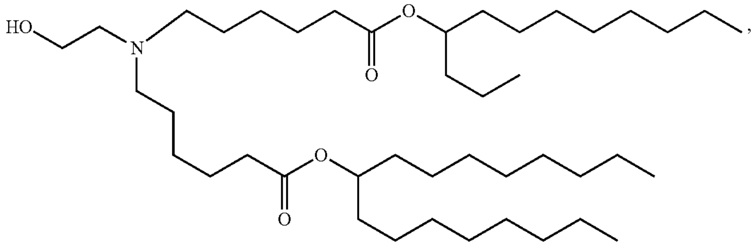
(Compound 93)
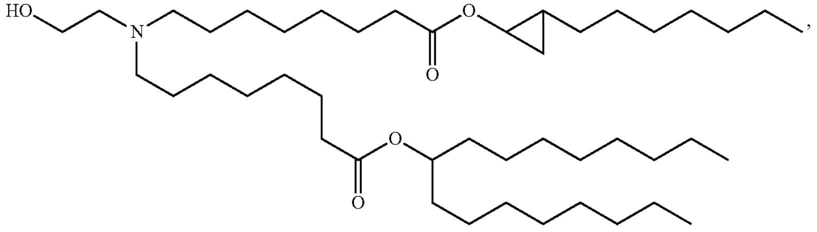

-continued
(Compound 94)
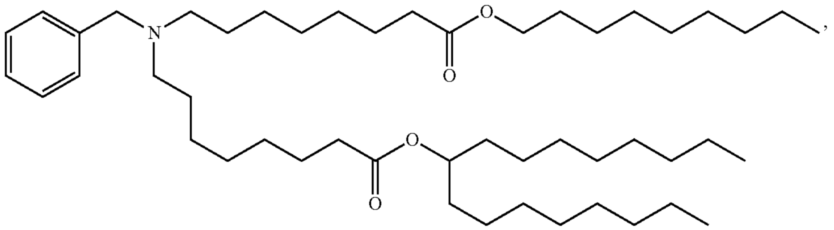
(Compound 95)
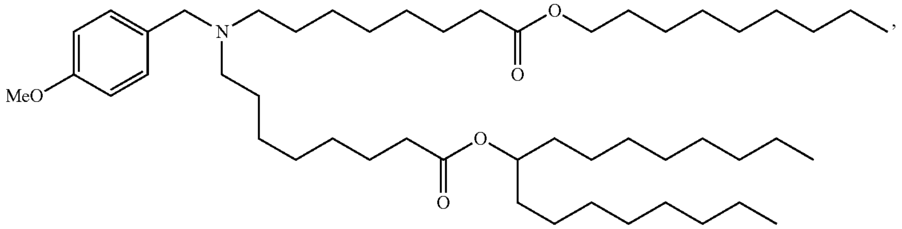
(Compound 96)
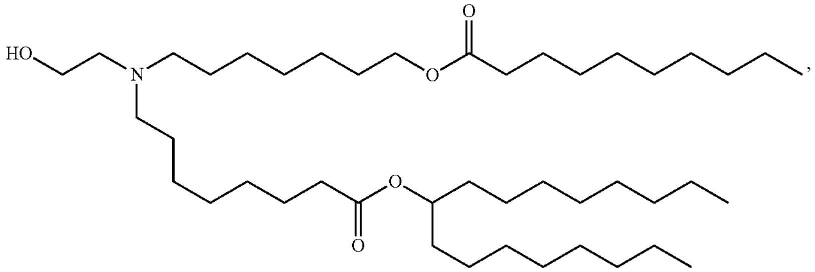
(Compound 97)
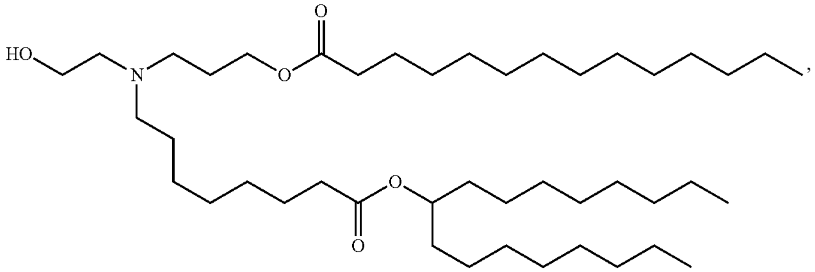
(Compound 98)
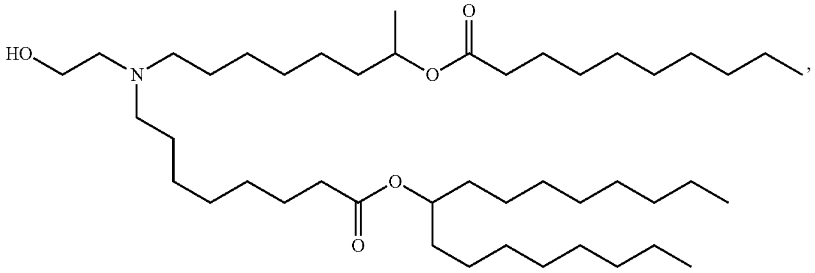
(Compound 99)
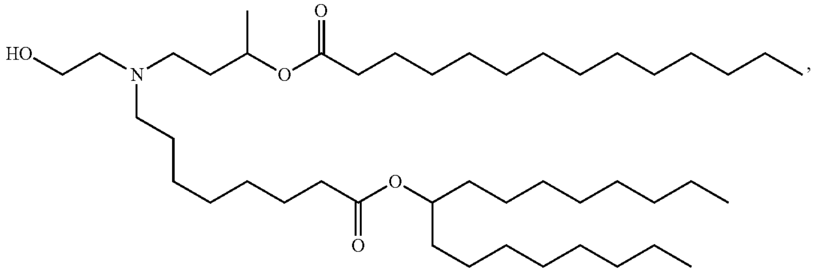

-continued
(Compound 100)
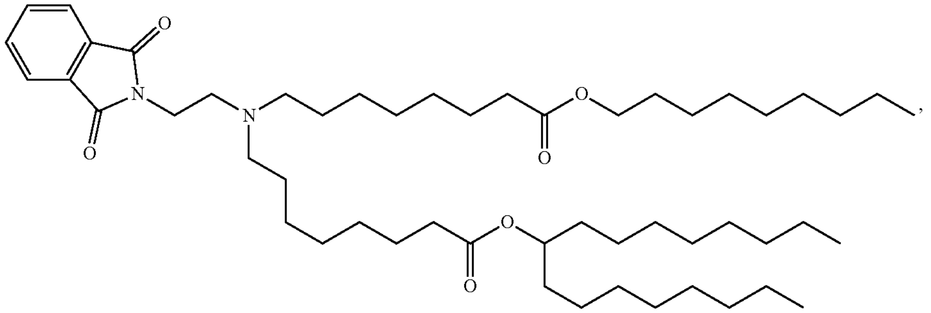
(Compound 101)
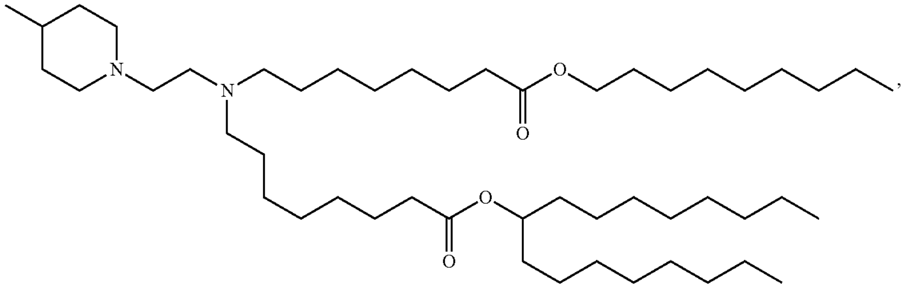
(Compound 102)
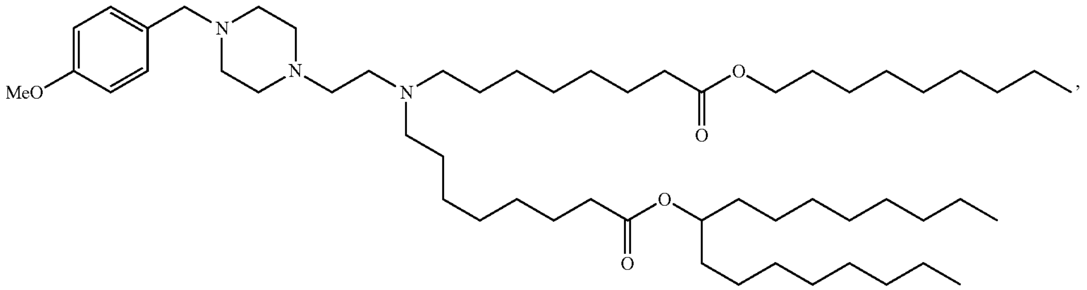
(Compound 103)
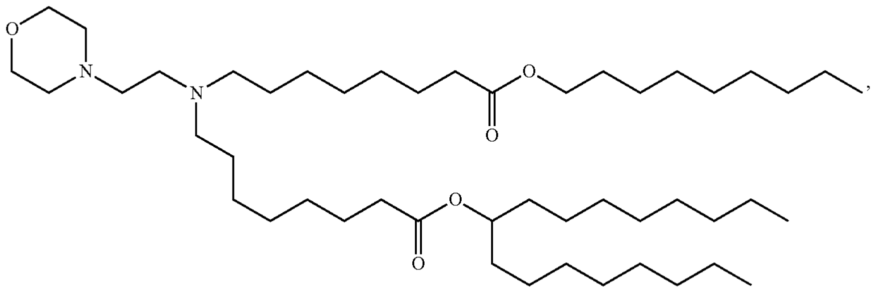
(Compound 104)
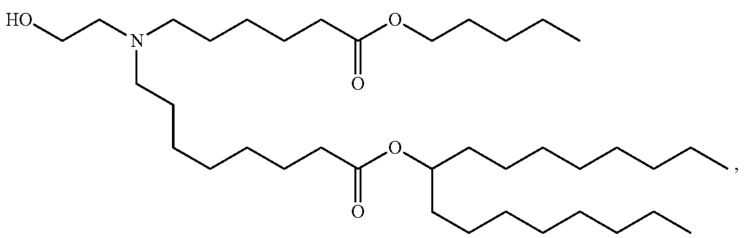

-continued
(Compound 105)
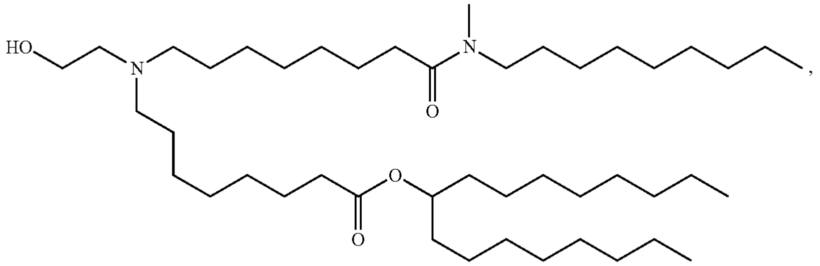
(Compound 106)
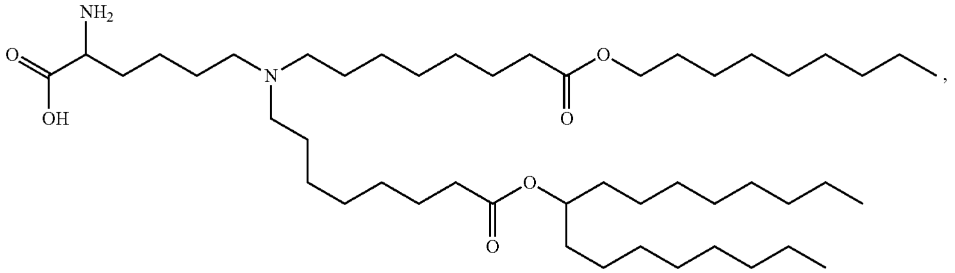
(Compound 107)
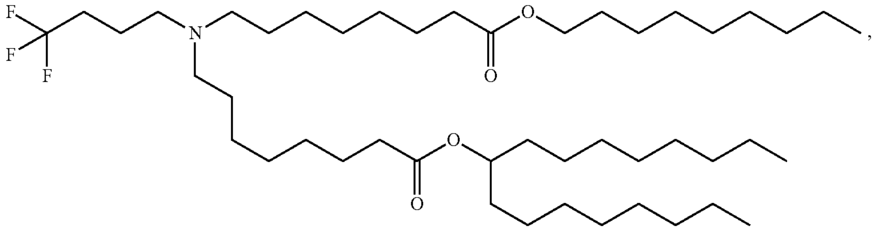
(Compound 108)
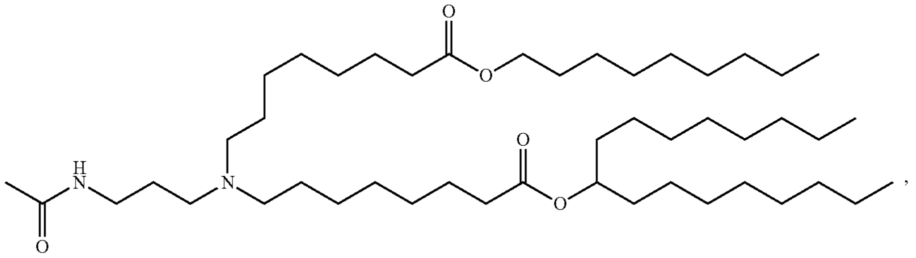
(Compound 109)
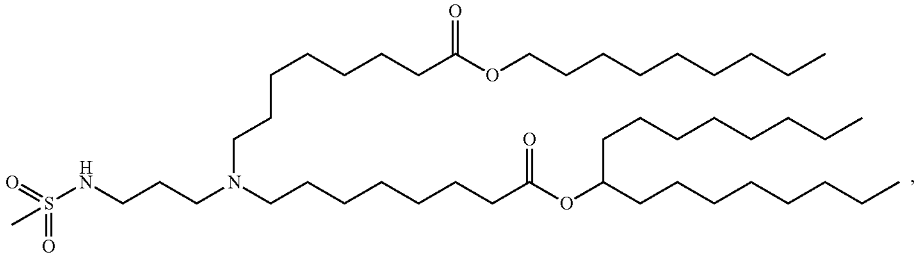
(Compound 110)
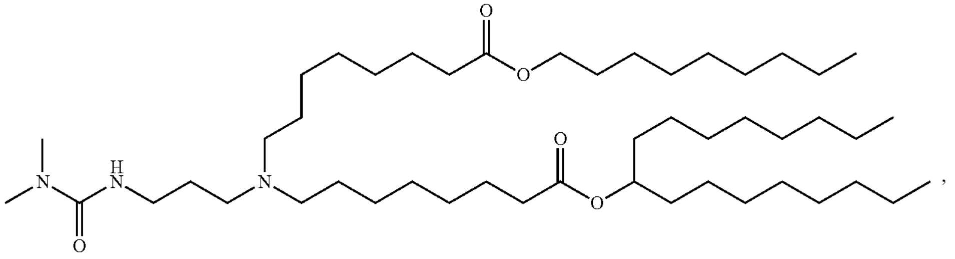

-continued
(Compound 111)
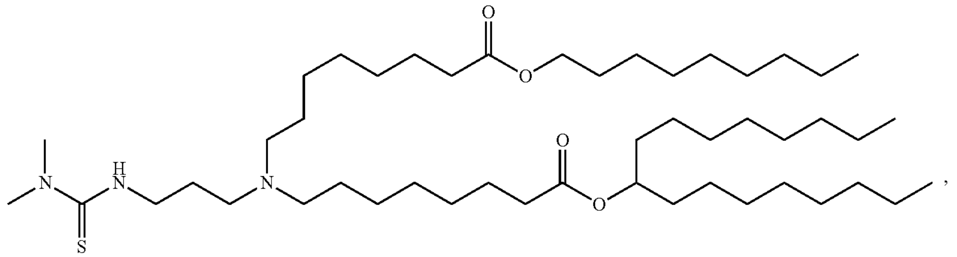
(Compound 112)
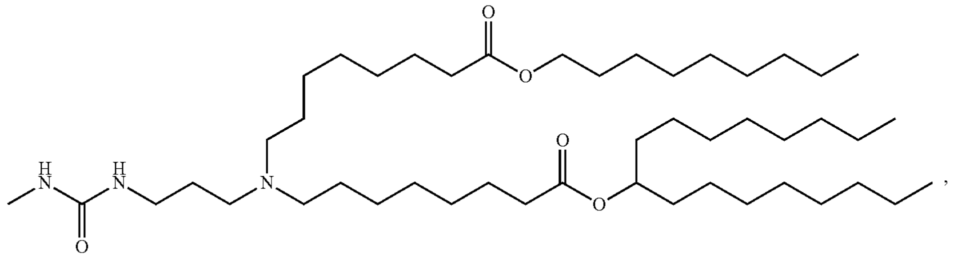
(Compound 113)
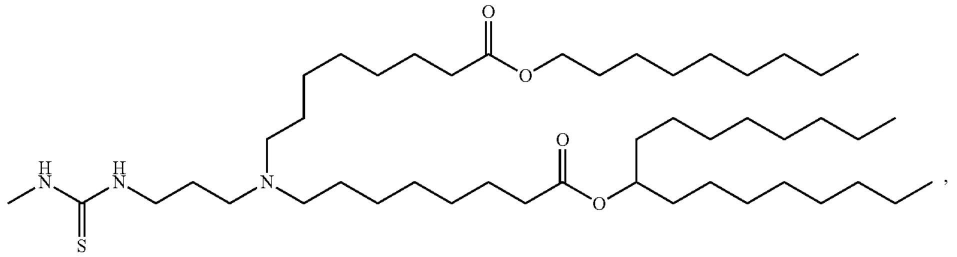
(Compound 114)
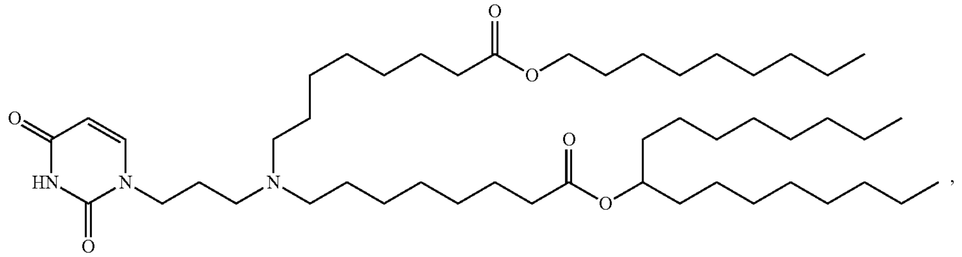
(Compound 115)
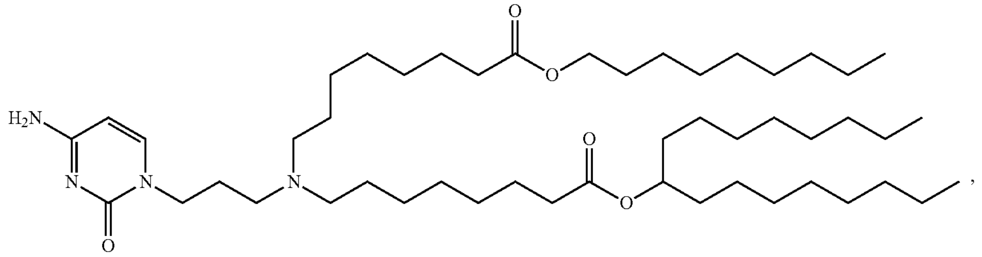
(Compound 116)
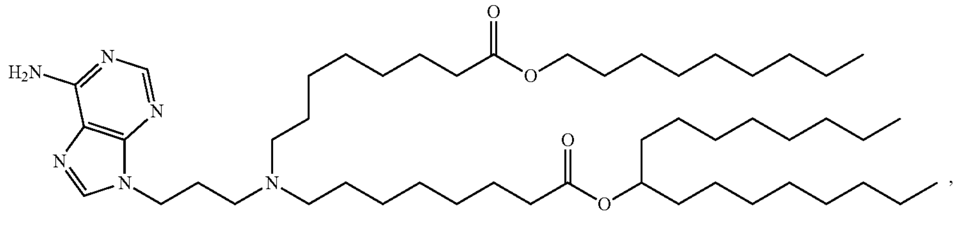

-continued
(Compound 117)
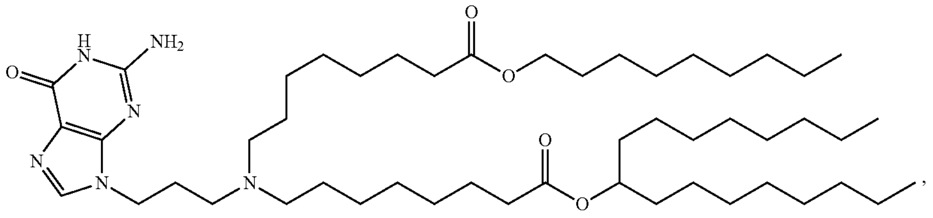
,
(Compound 118)
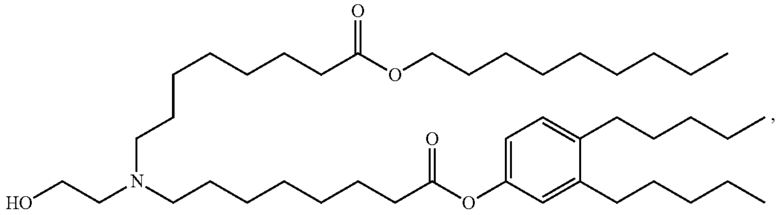
,
(Compound 119)
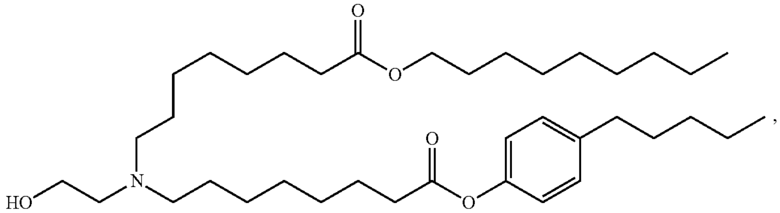
,
(Compound 120)
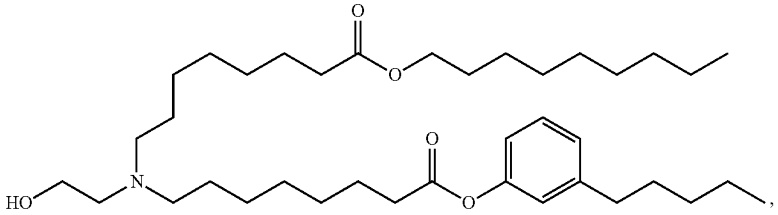
,
(Compound 121)
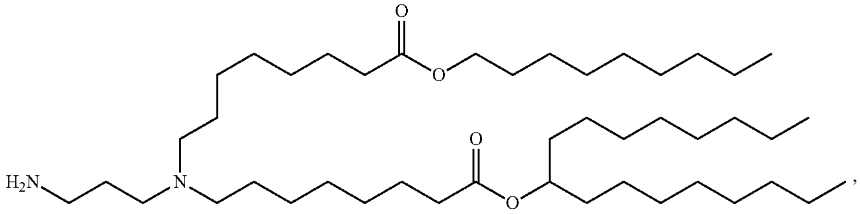
,
(Compound 122)
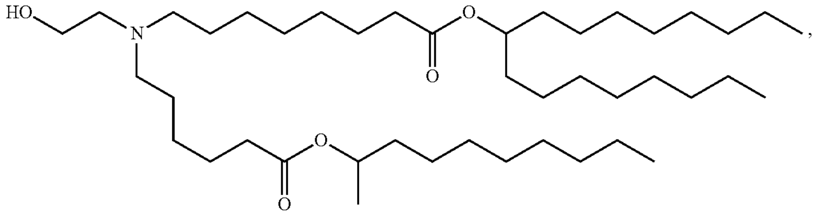
,
(Compound 123)
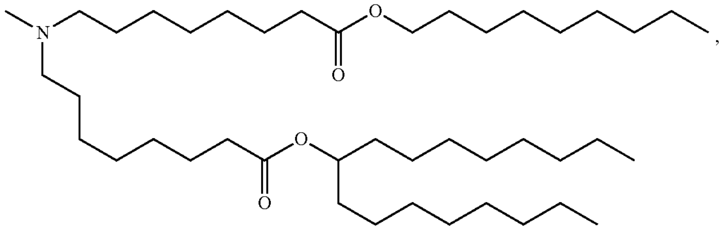
, -continued
(Compound 124)
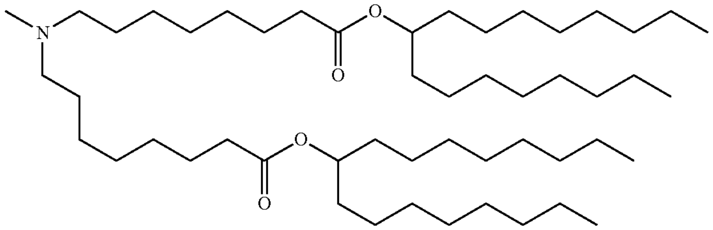
,
(Compound 125)
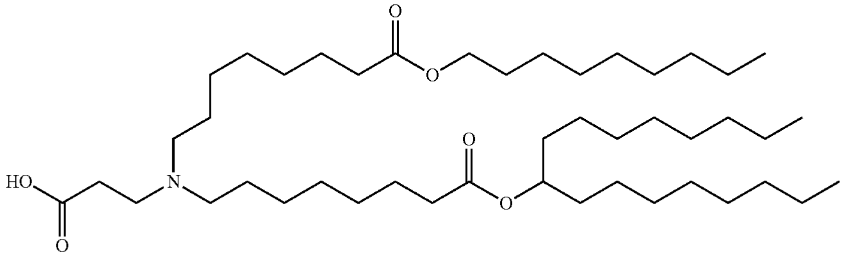
,
(Compound 126)
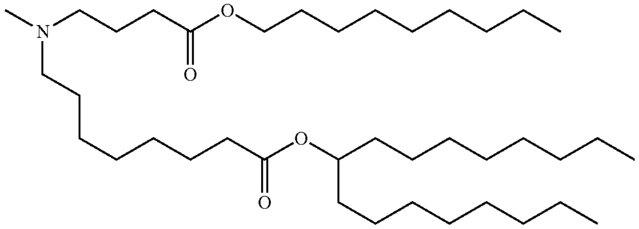
,
(Compound 127)
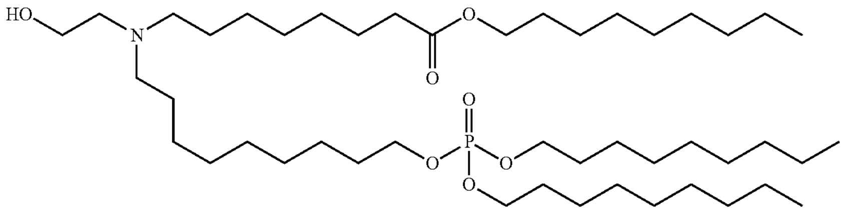
,
(Compound 128)
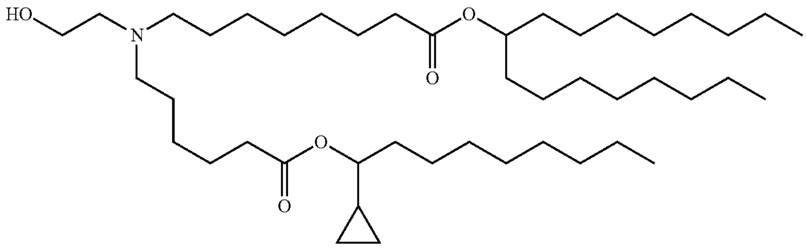
,
(Compound 129)
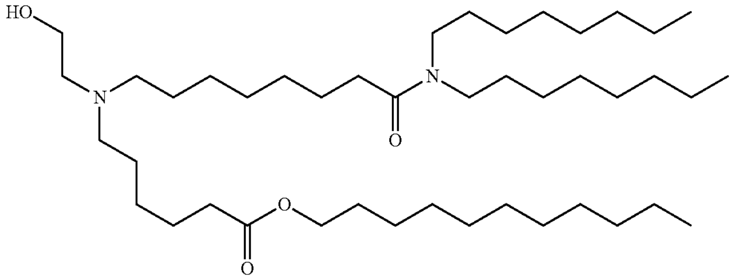
, -continued
(Compound 130)
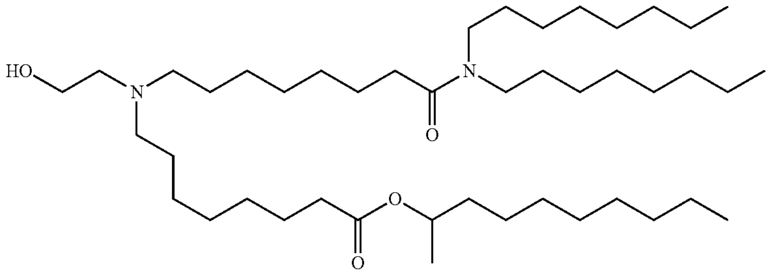
,
(Compound 131)
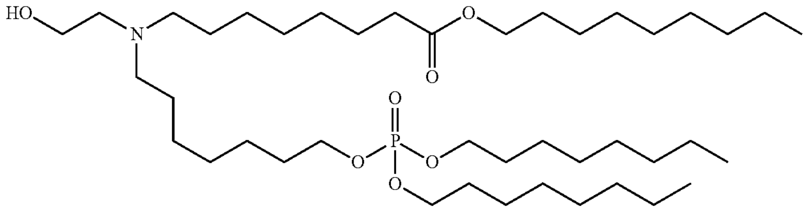
,
(Compound 132)
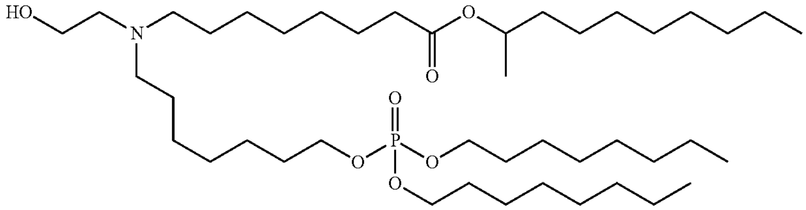
,
(Compound 133)
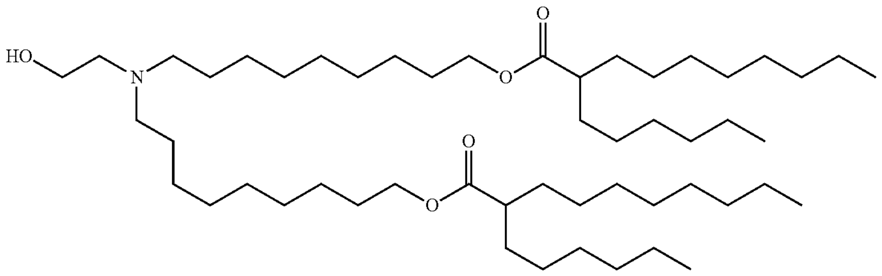
,
(Compound 134)
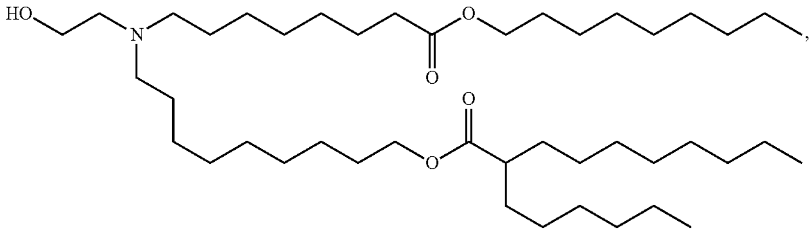
,
(Compound 135)
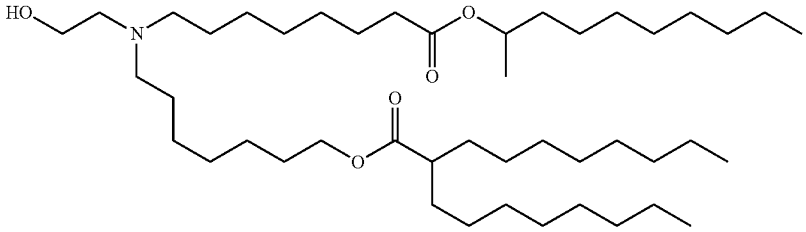
, -continued
(Compound 136)
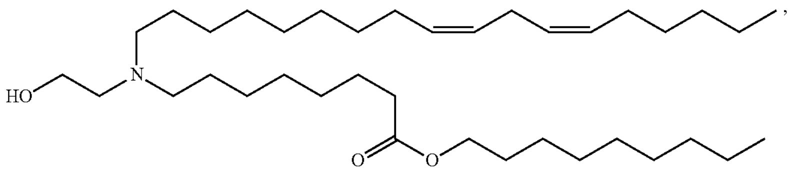
(Compound 137)
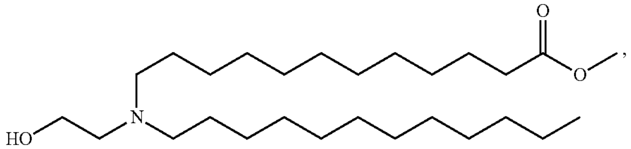
(Compound 138)
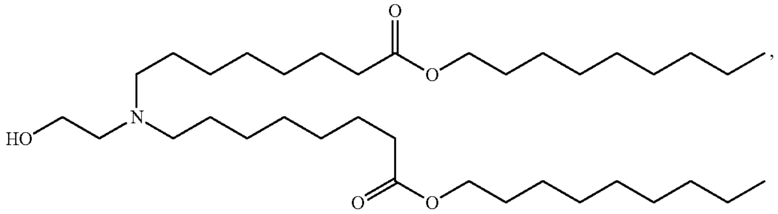
(Compound 139)
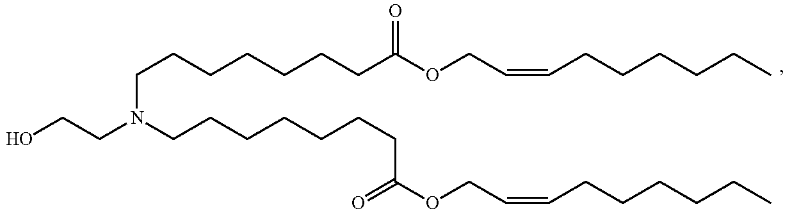
(Compound 140)
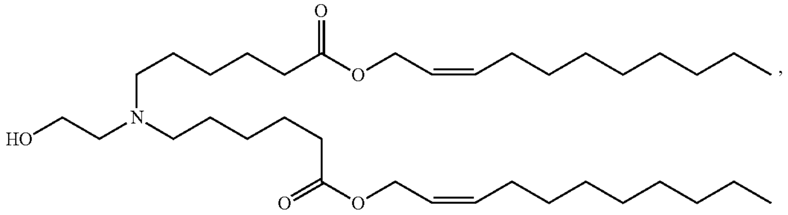
(Compound 141)
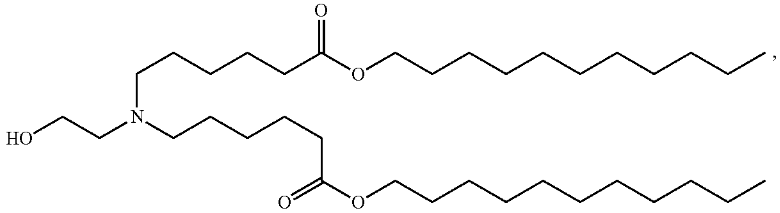
(Compound 142)
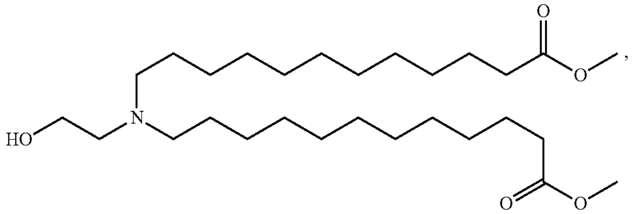

-continued
(Compound 143)
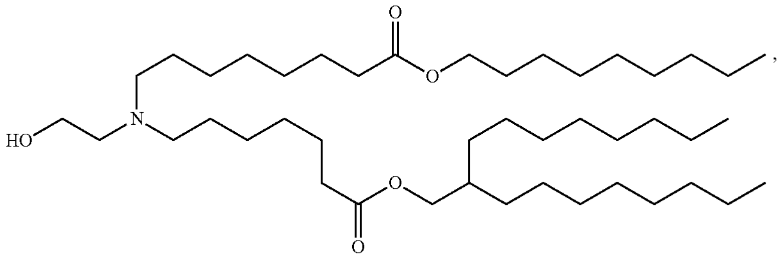
(Compound 144)
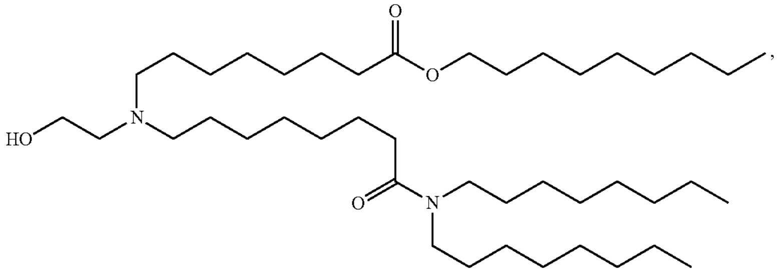
(Compound 145)
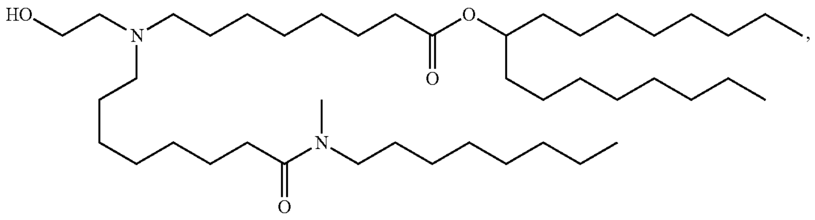
(Compound 146)
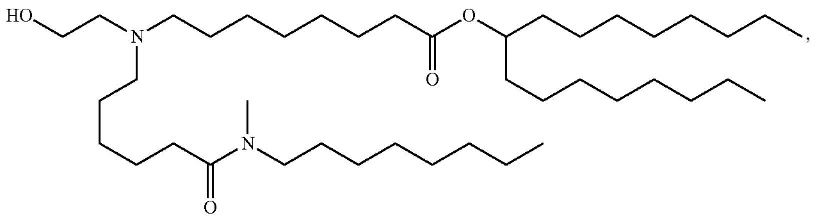
(Compound 147)
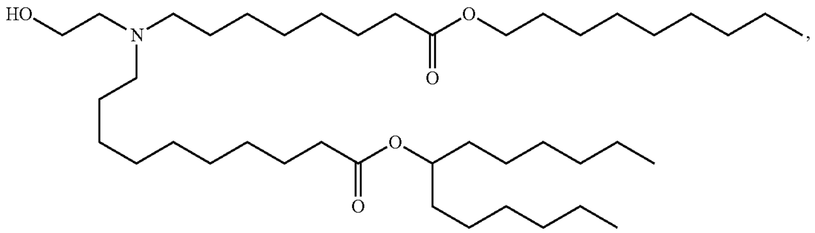
(Compound 148)
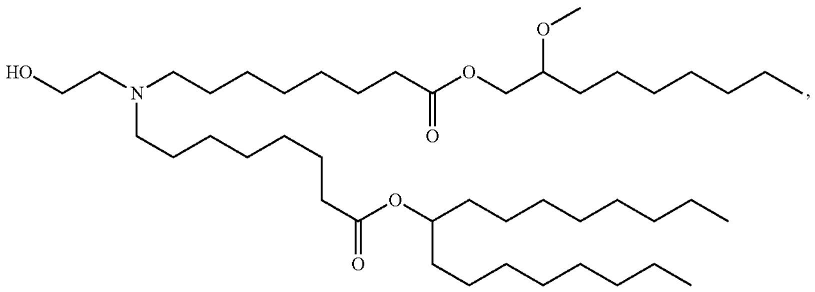

-continued
(Compound 149)
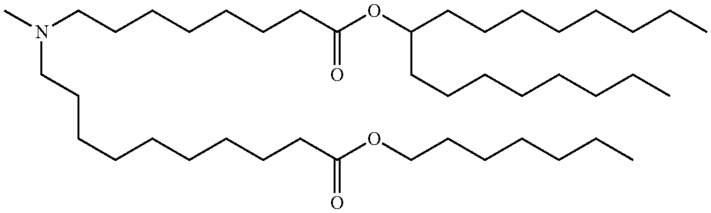
,
(Compound 150)
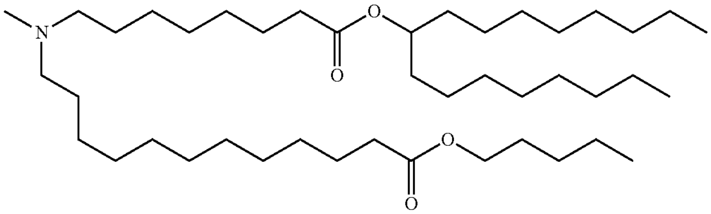
,
(Compound 151)
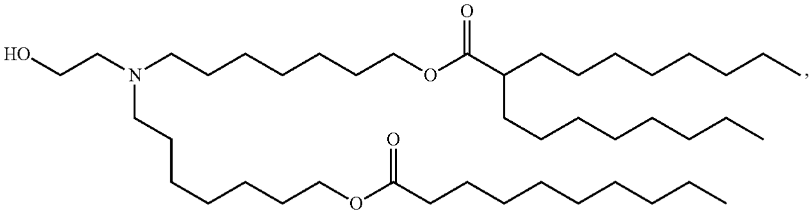
,
(Compound 152)
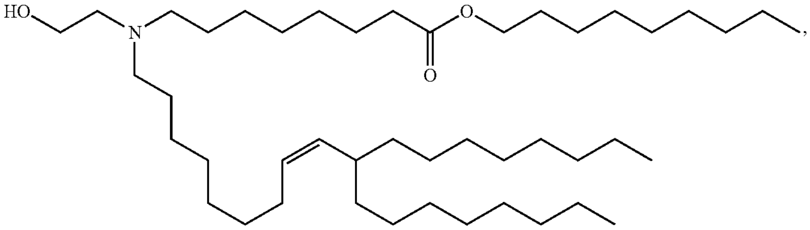
,
(Compound 153)
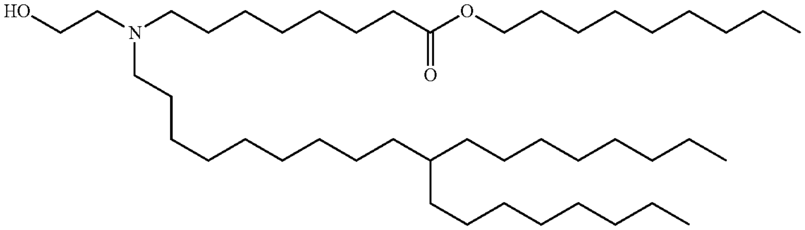
,
(Compound 154)
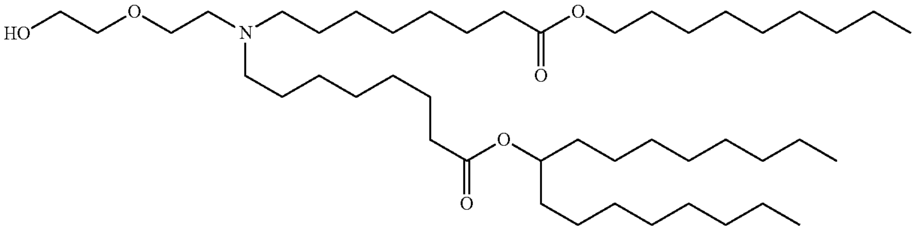
,
(Compound 155)
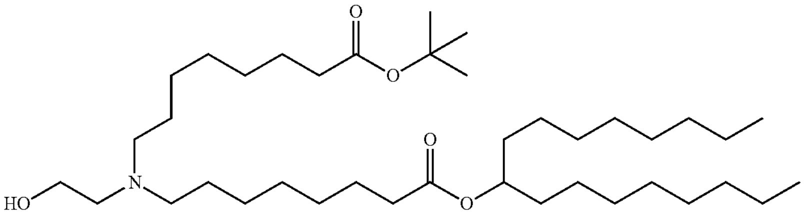
, -continued
(Compound 156)
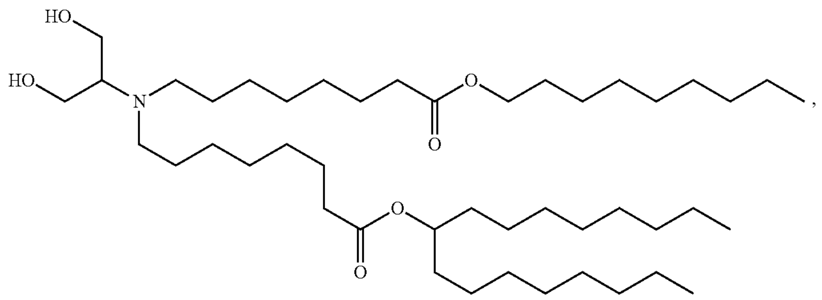
(Compound 157)
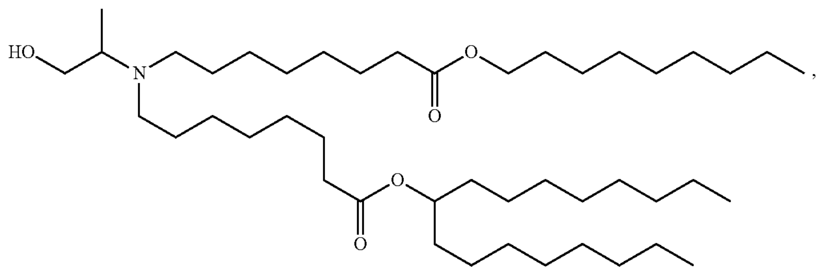
(Compound 158)
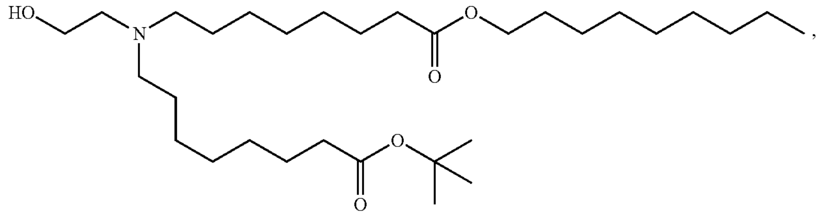
(Compound 159)
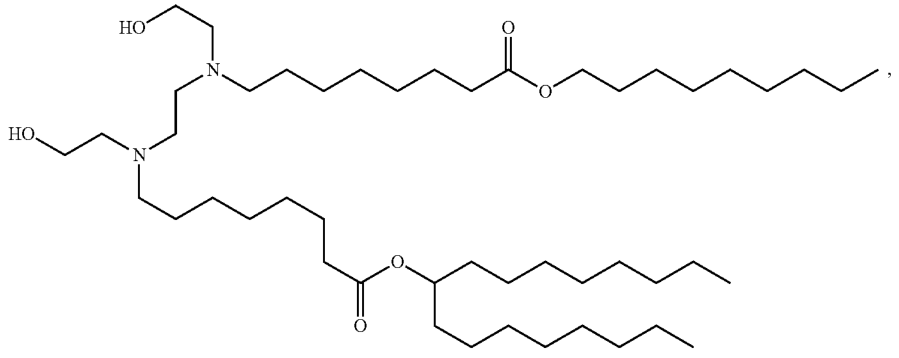

-continued
(Compound 160)
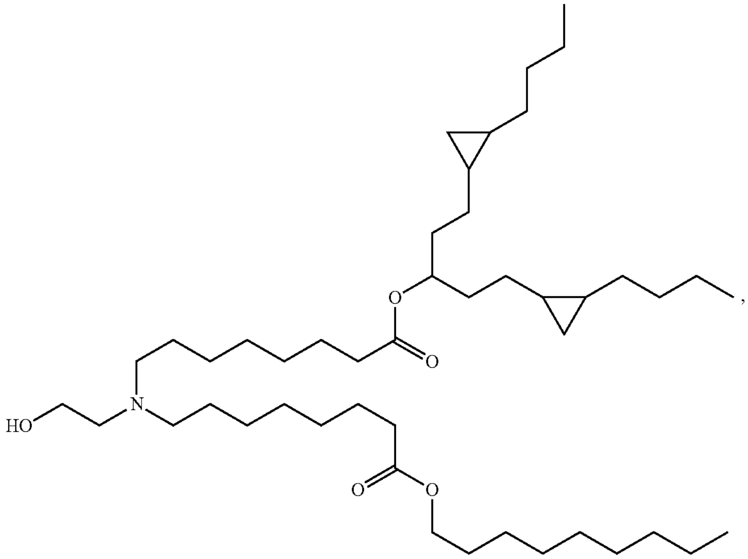
,
(Compound 161)
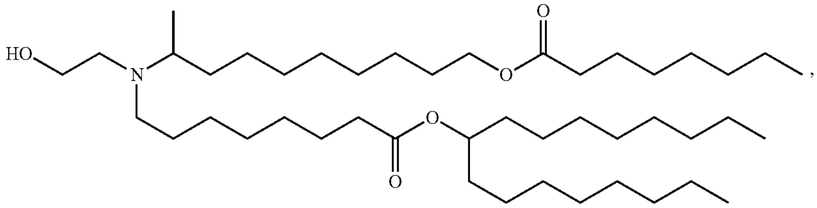
,
(Compound 162)
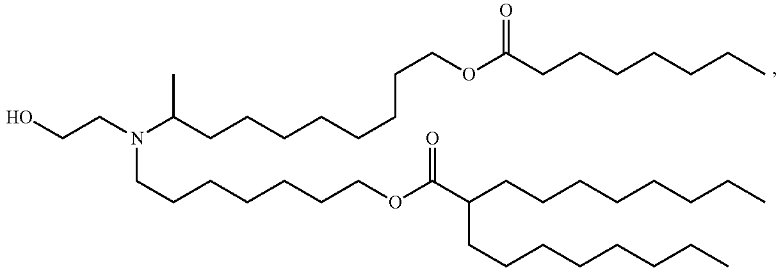
,
(Compound 163)
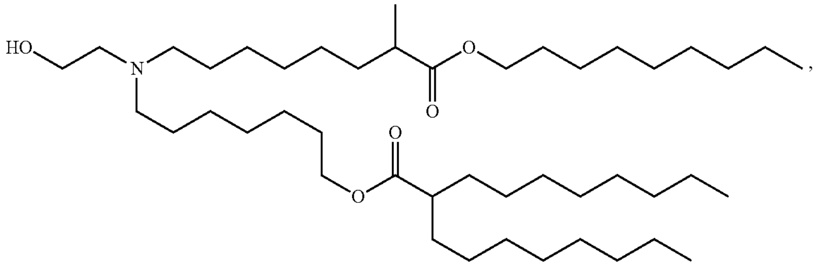
,
(Compound 164)
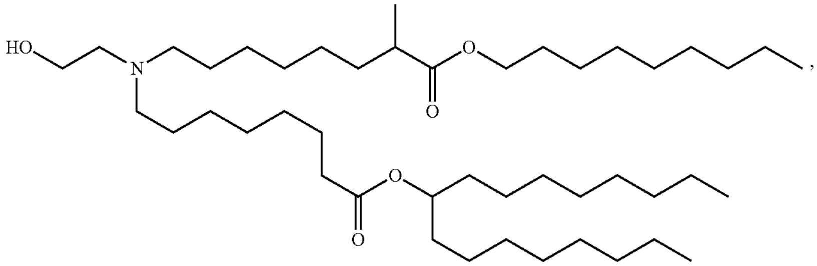
, -continued
(Compound 165)
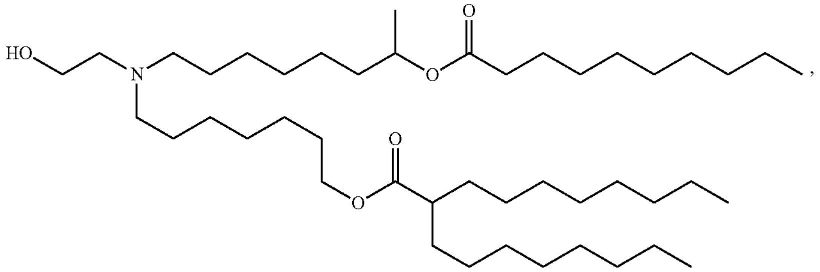
(Compound 166)
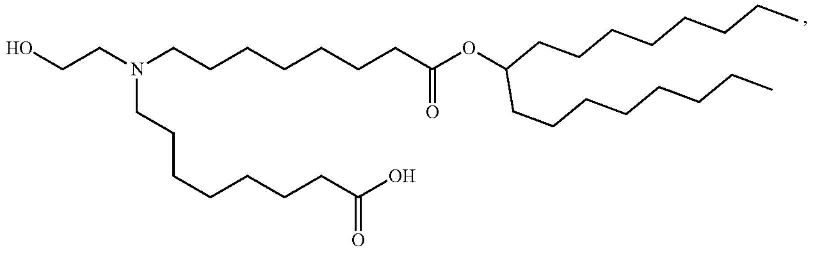
(Compound 167)
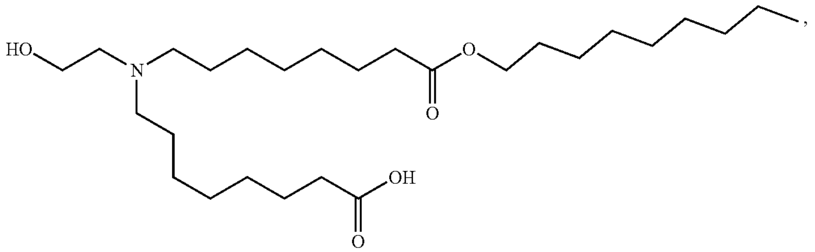
(Compound 168)
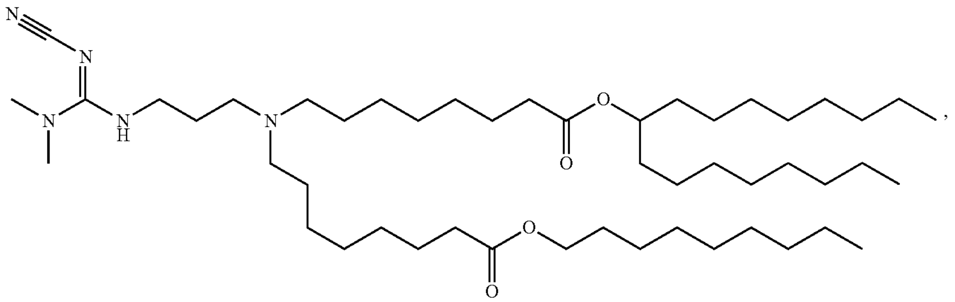
(Compound 169)
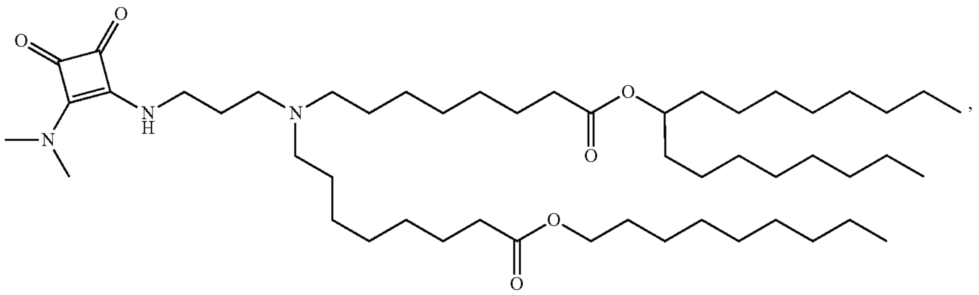

-continued
(Compound 170)
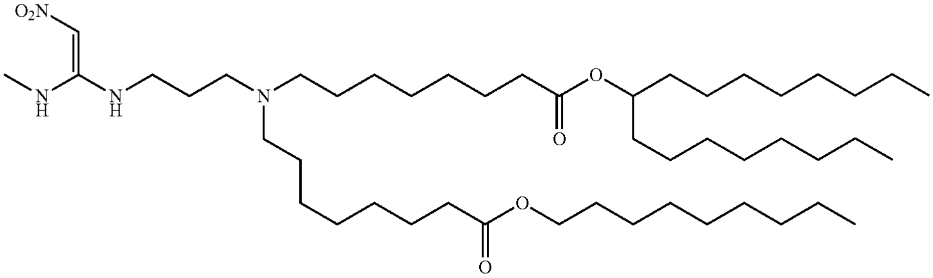
,
(Compound 171)
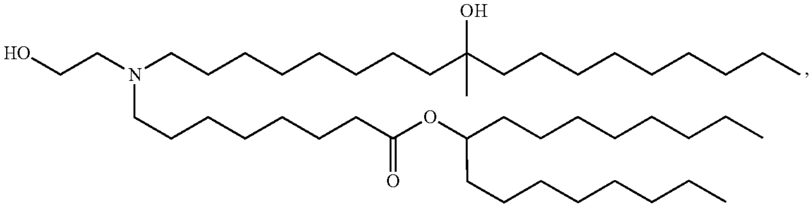
,
(Compound 172)
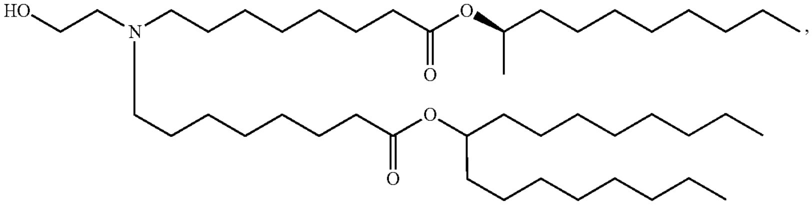
,
(Compound 173)
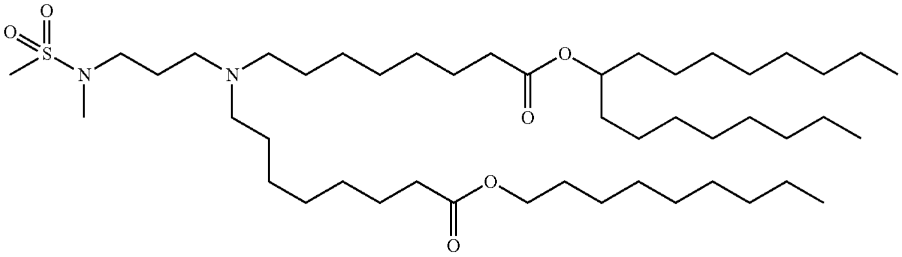
,
(Compound 174)
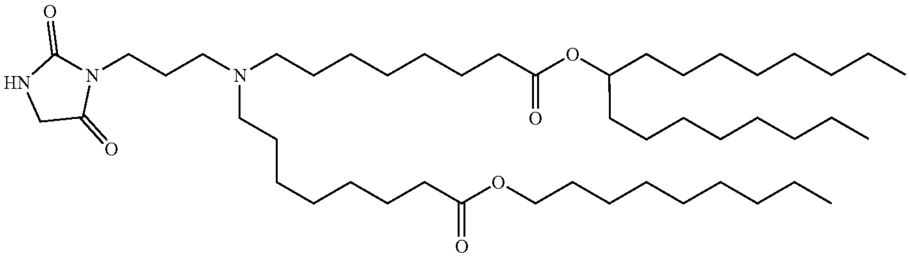
,
(Compound 175)
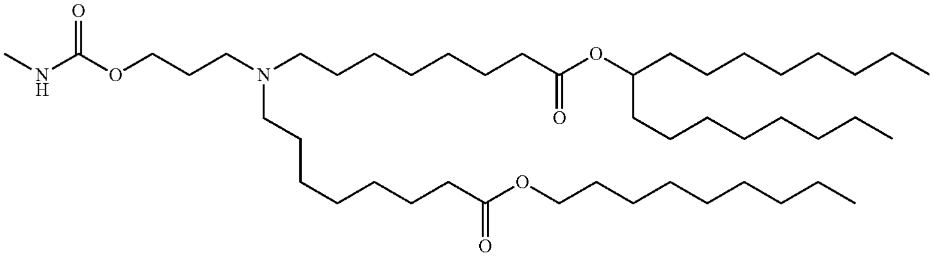
, -continued
(Compound 176)
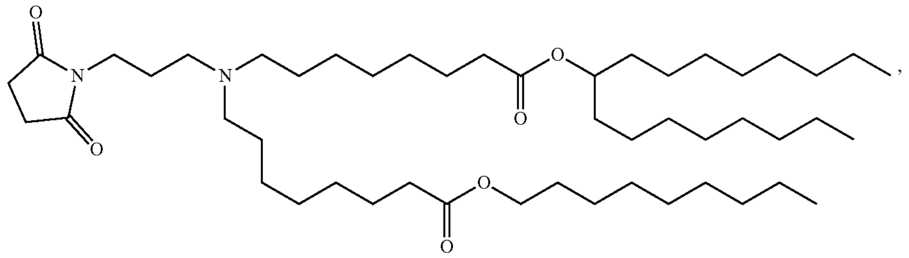
(Compound 177)
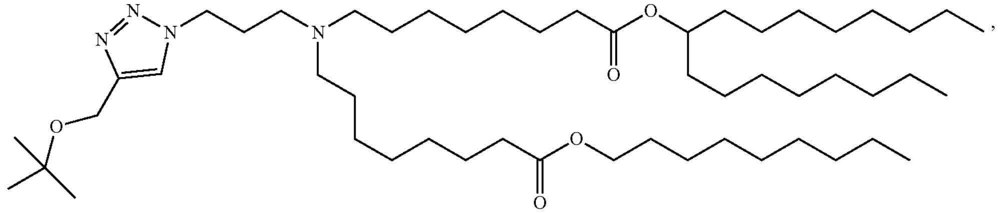
(Compound 178)
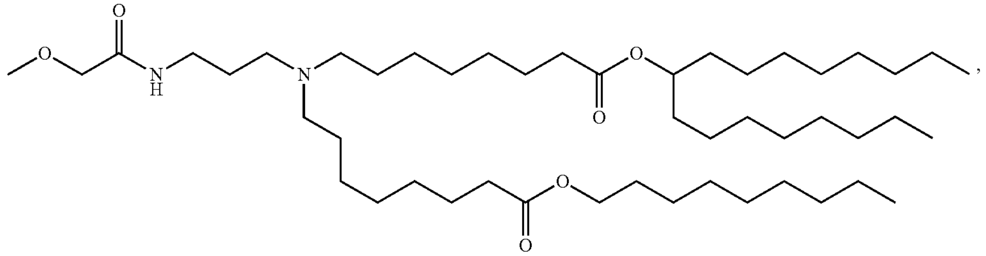
(Compound 179)
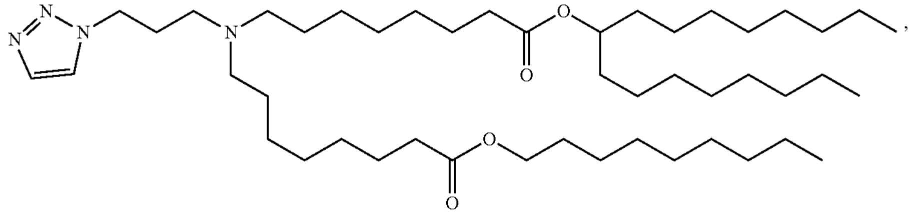
(Compound 180)
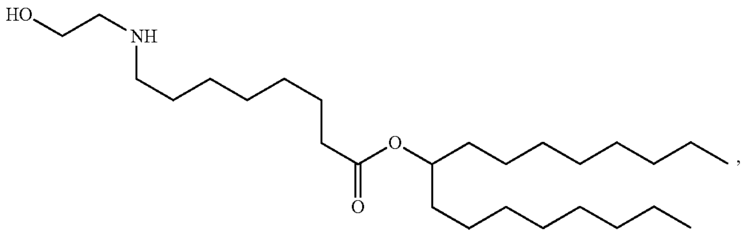
(Compound 181)
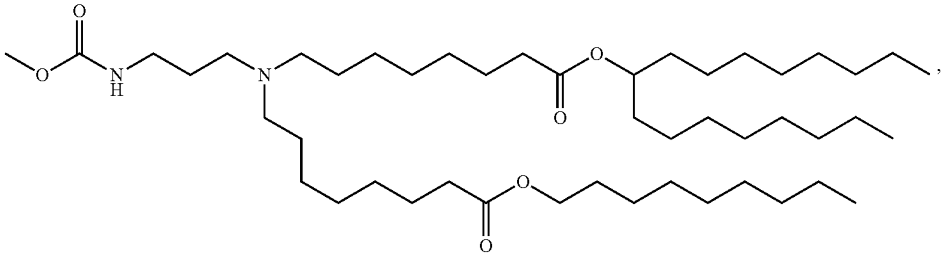

-continued
(Compound 182)
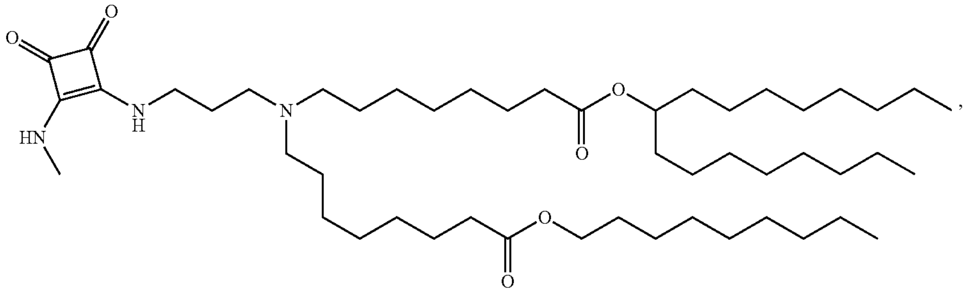
(Compound 183)
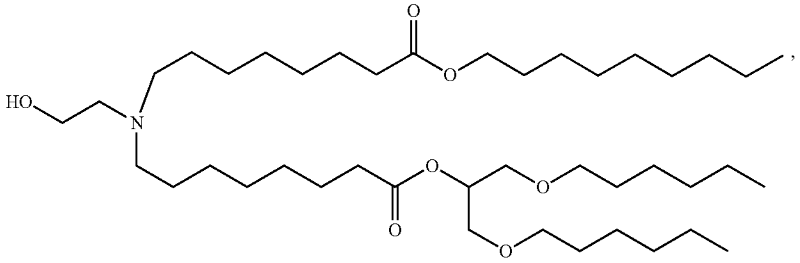
(Compound 184)
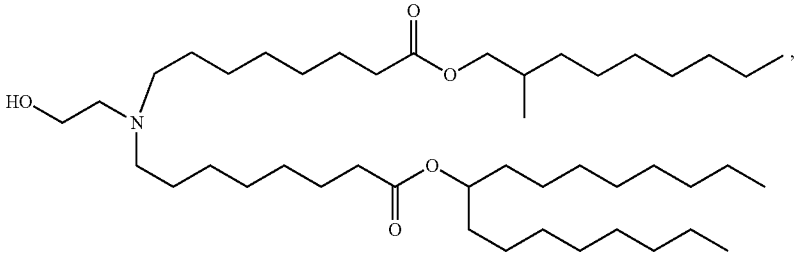
(Compound 185)
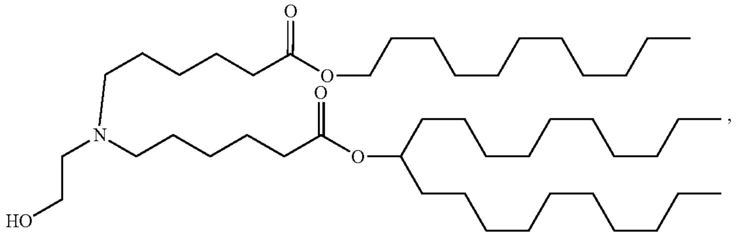
(Compound 186)
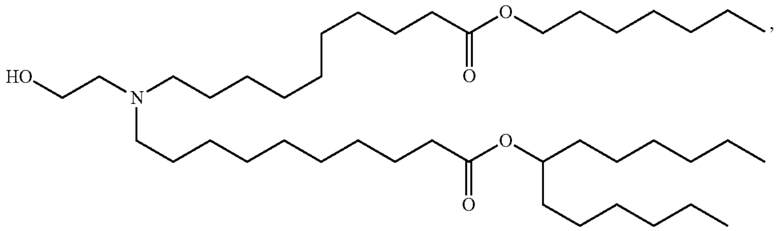
(Compound 187)
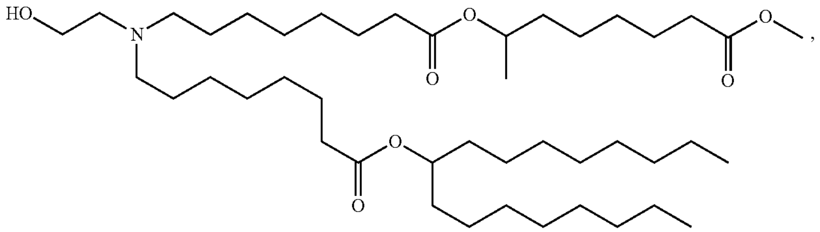

-continued
(Compound 188)
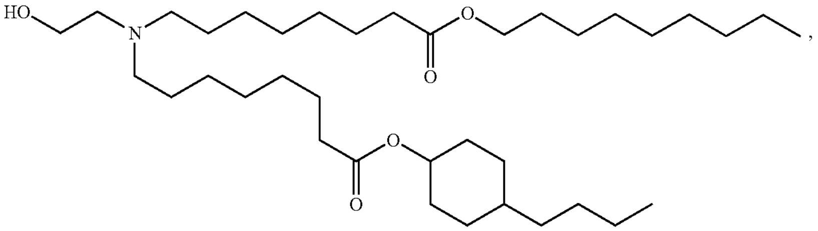
(Compound 189)
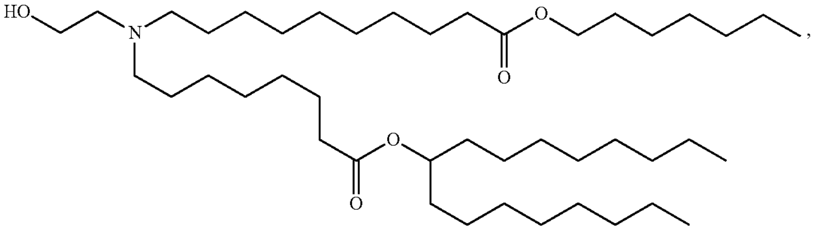
(Compound 190)
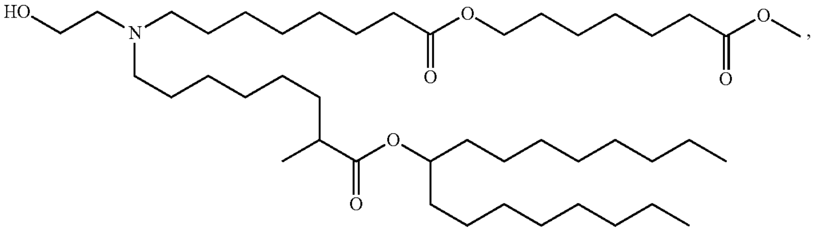
(Compound 191)
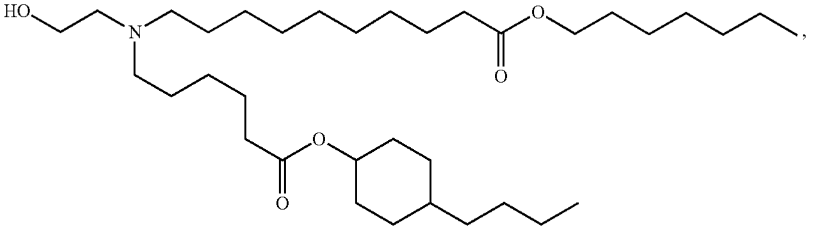
(Compound 192)
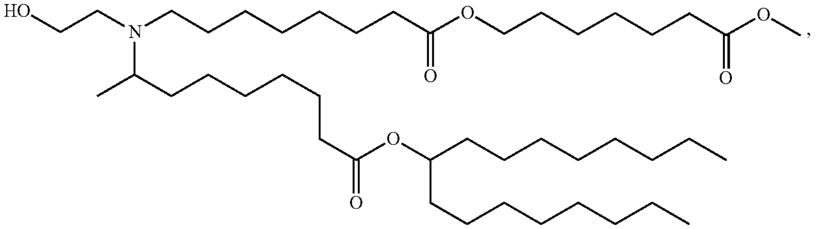
(Compound 193)
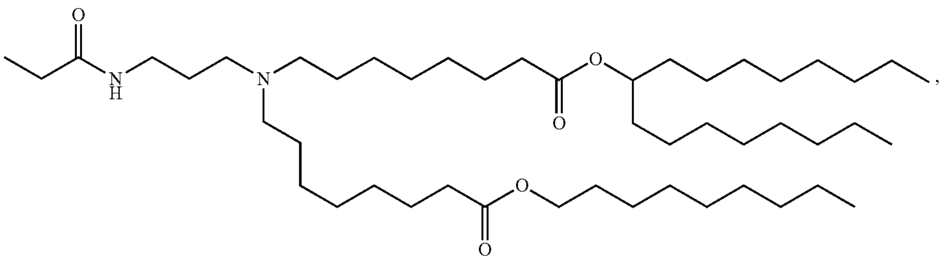

-continued
(Compound 194)
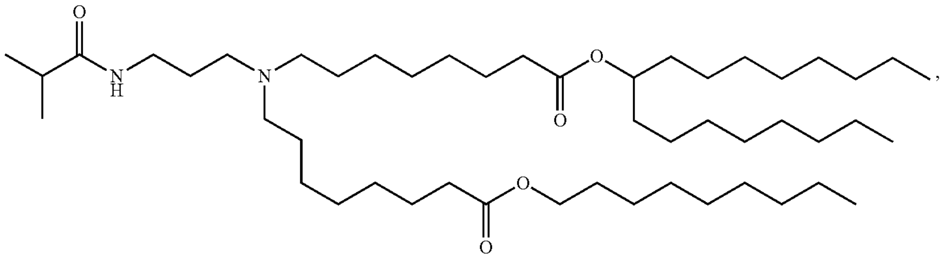
(Compound 195)
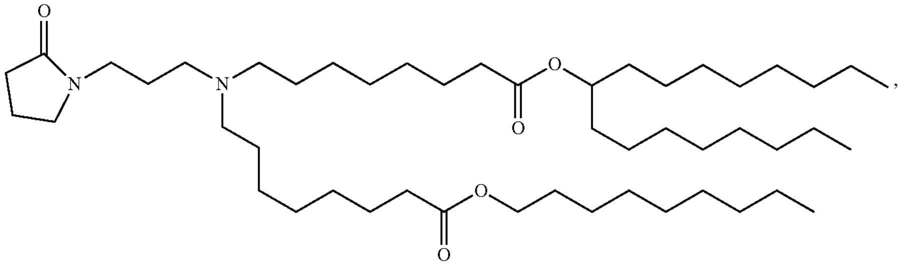
(Compound 196)
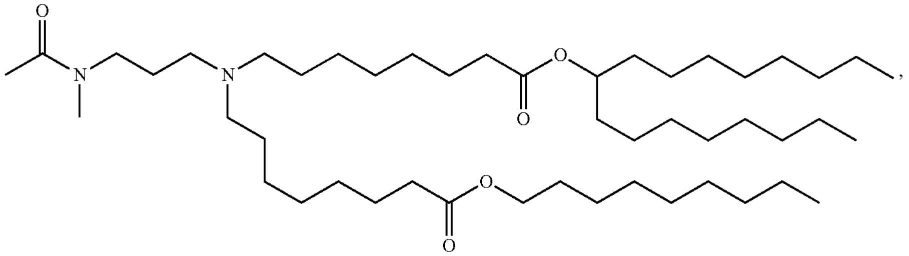
(Compound 197)
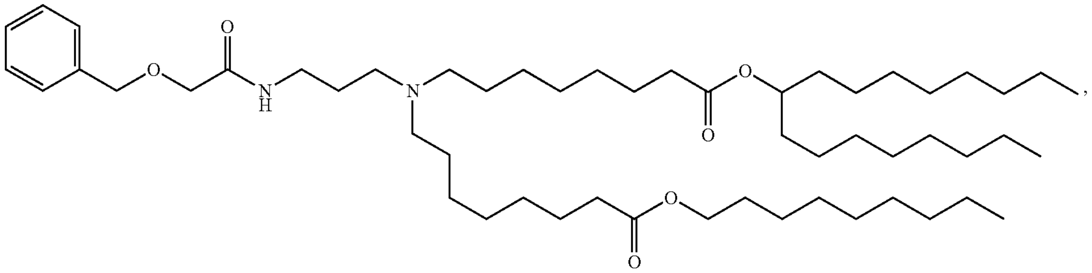
(Compound 198)
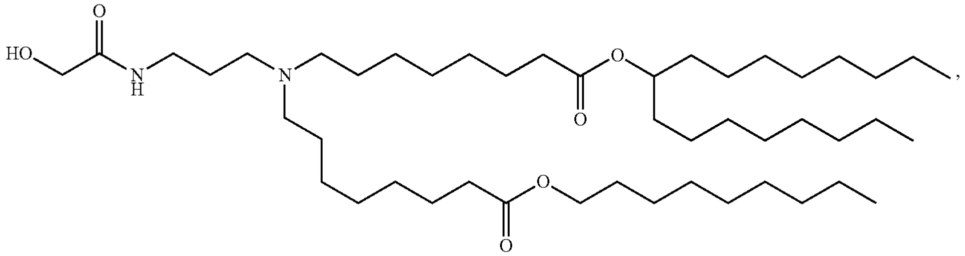
(Compound 199)
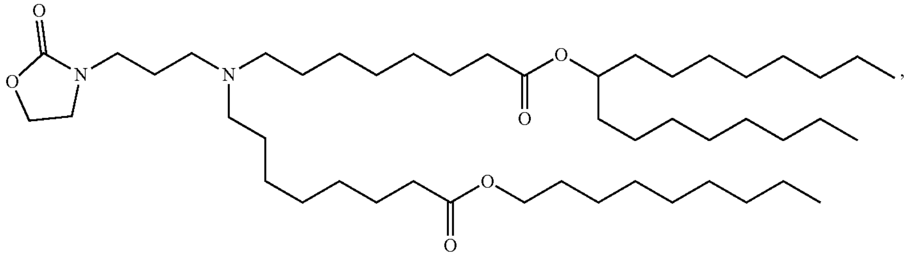

-continued
(Compound 200)
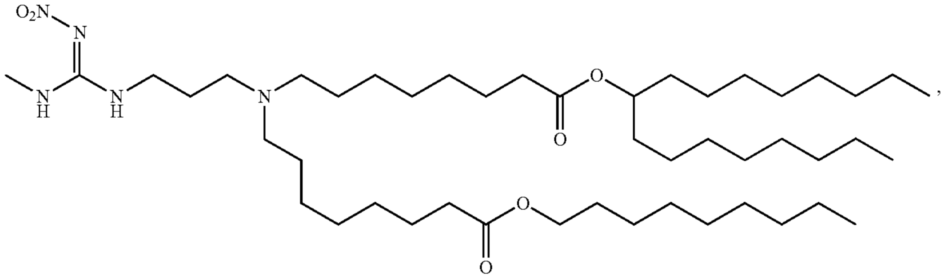
(Compound 201)
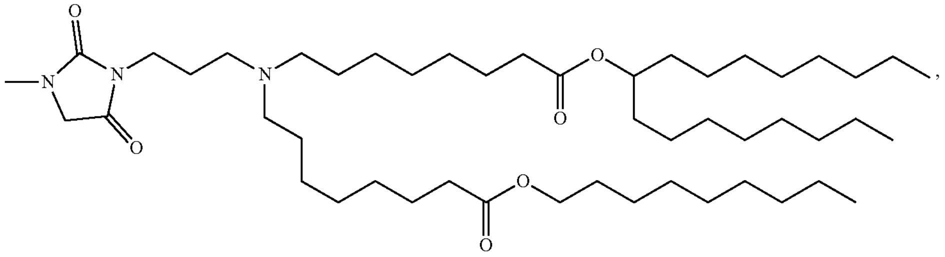
(Compound 202)
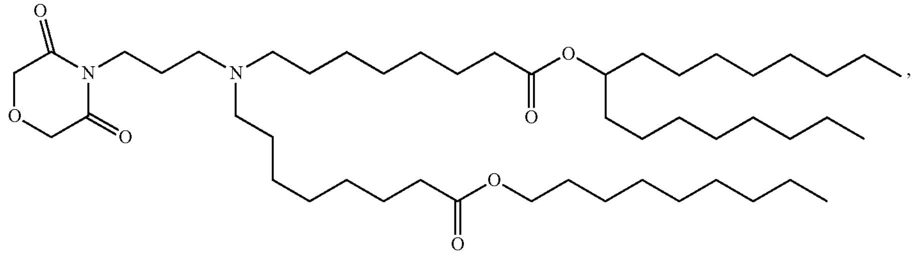
(Compound 203)
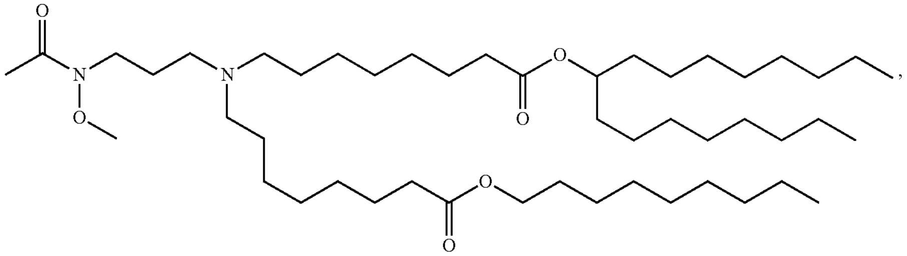
(Compound 204)
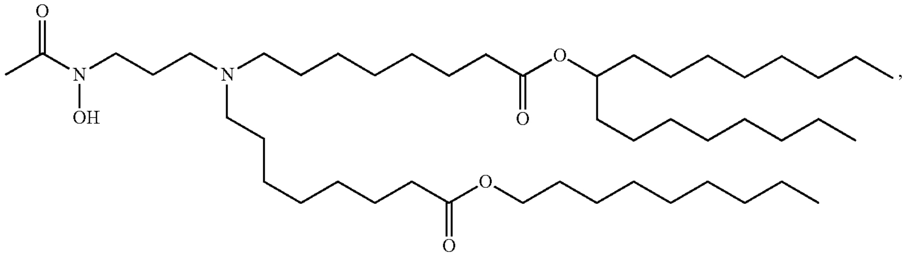
(Compound 205)
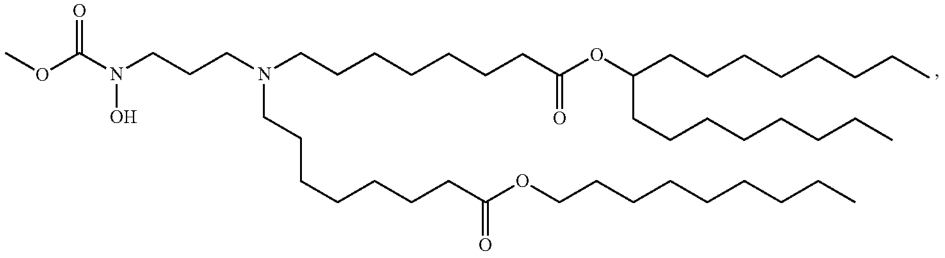

-continued
(Compound 206)
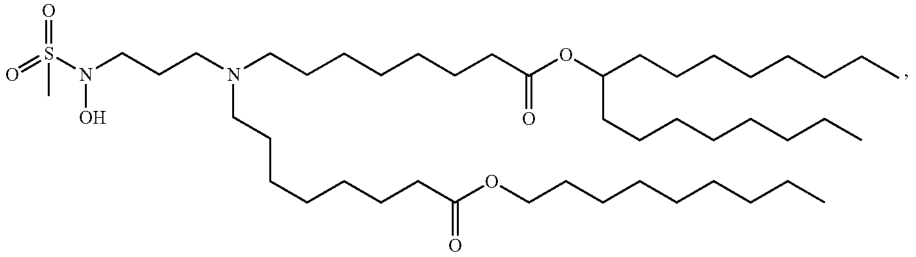
(Compound 207)
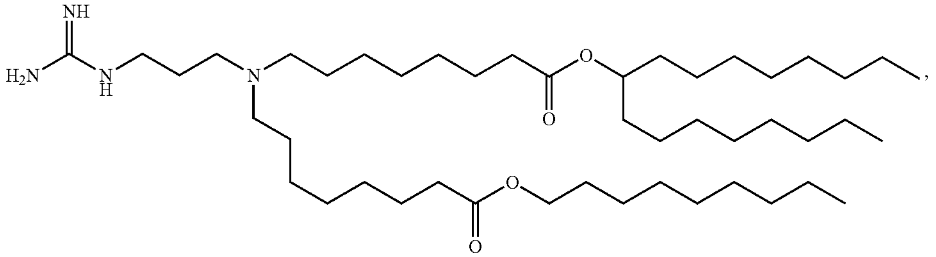
(Compound 208)
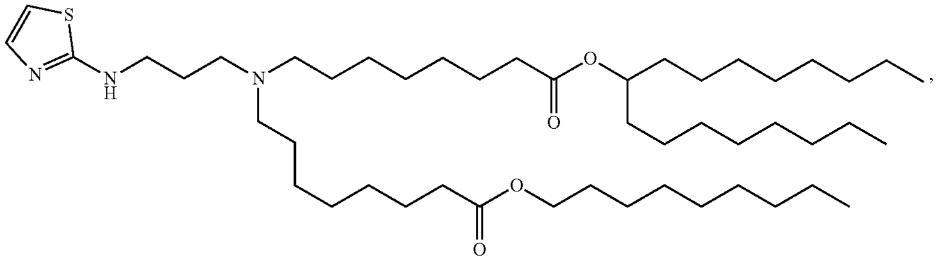
(Compound 209)
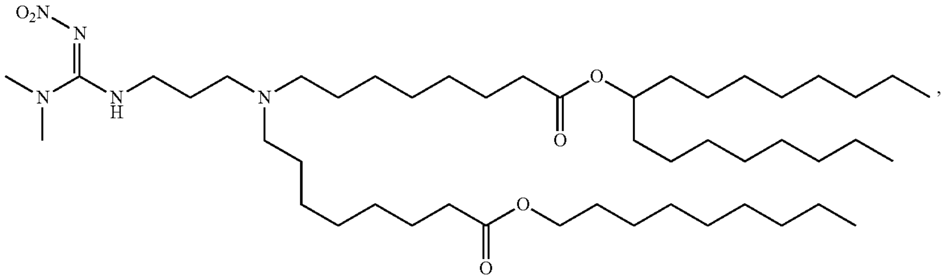
(Compound 210)
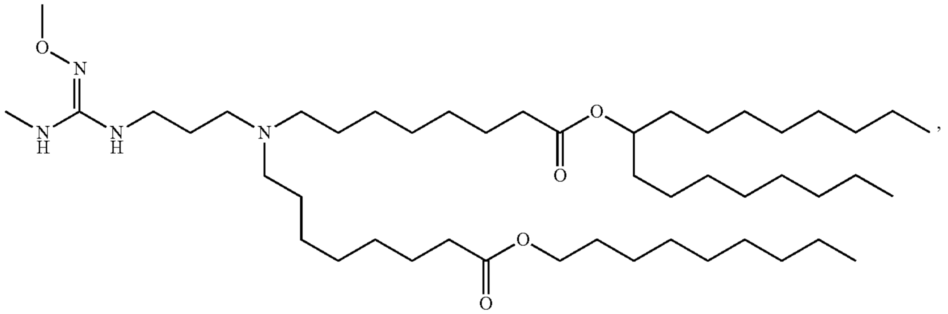

-continued
(Compound 211)
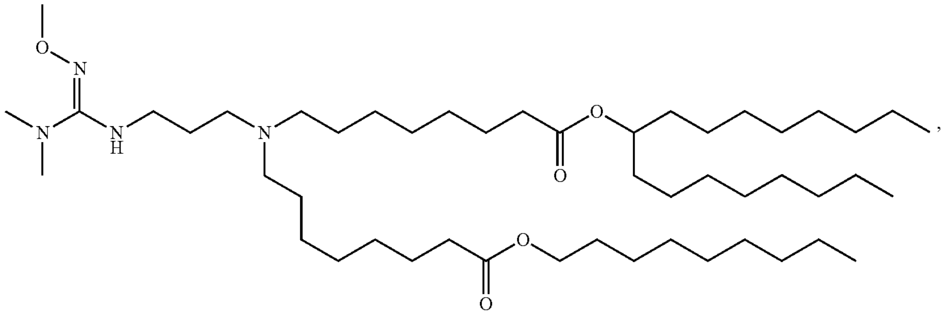
(Compound 212)
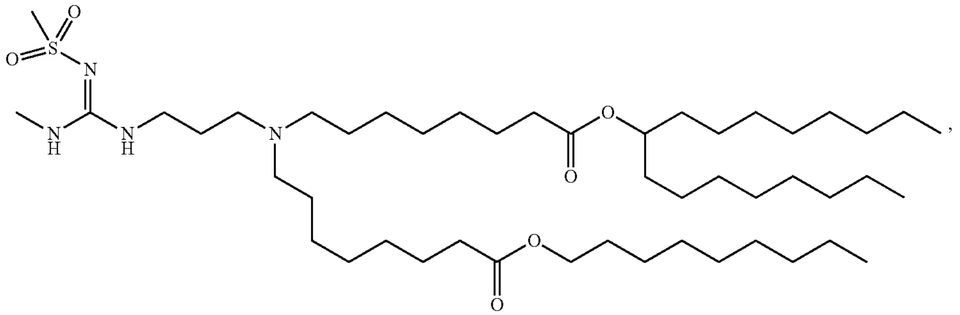
(Compound 213)
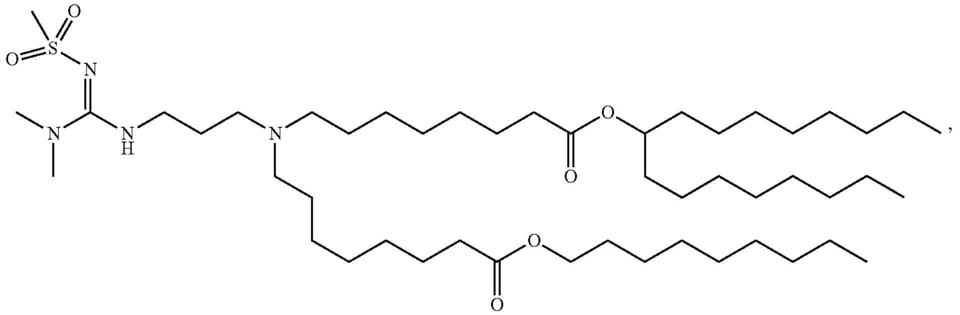
(Compound 214)
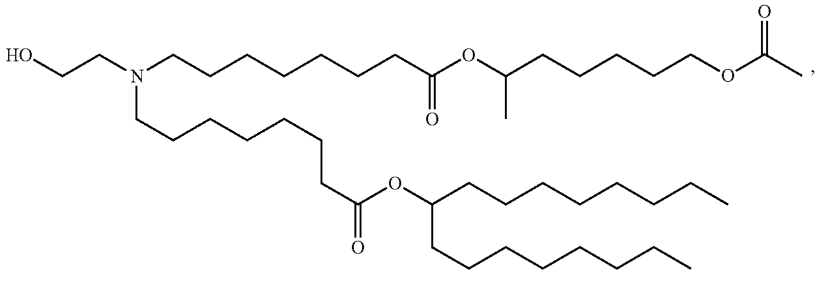
(Compound 215)
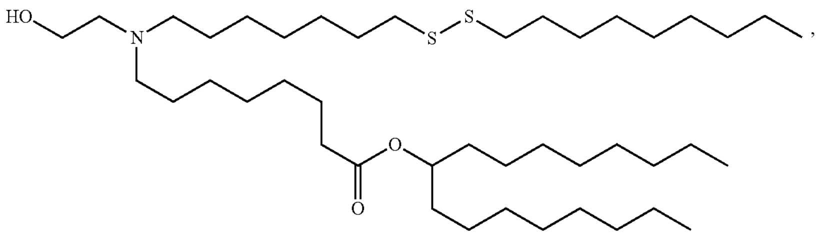

-continued
(Compound 216)
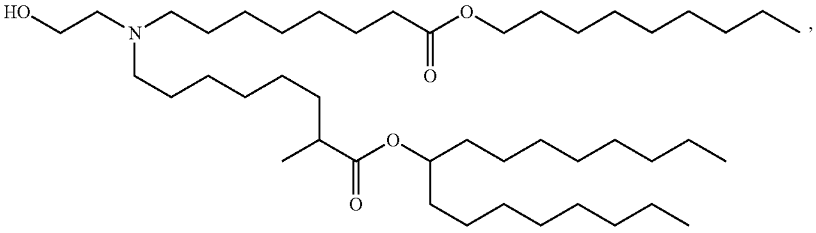
,
(Compound 217)
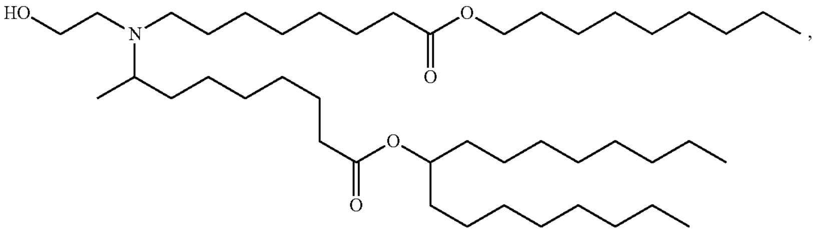
,
(Compound 218)
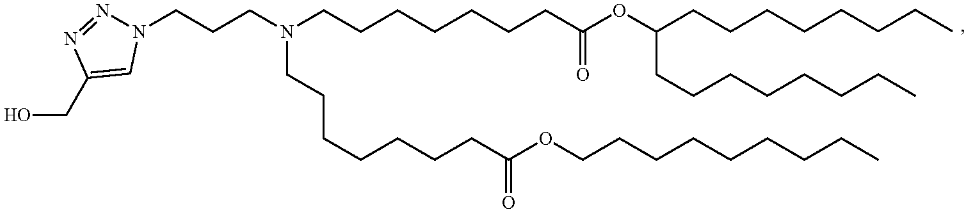
,
(Compound 219)
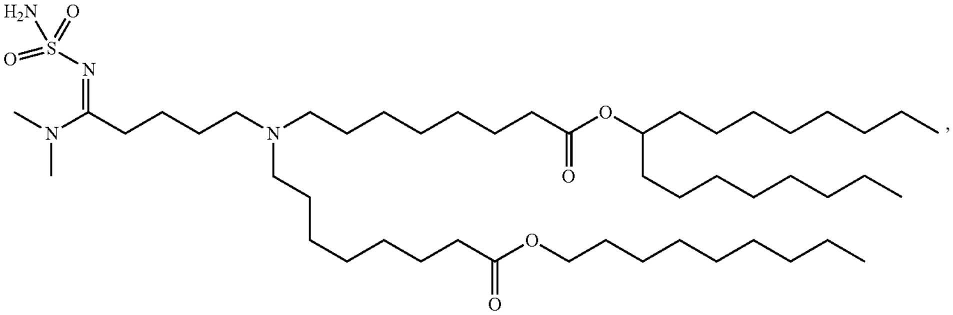
,
(Compound 220)
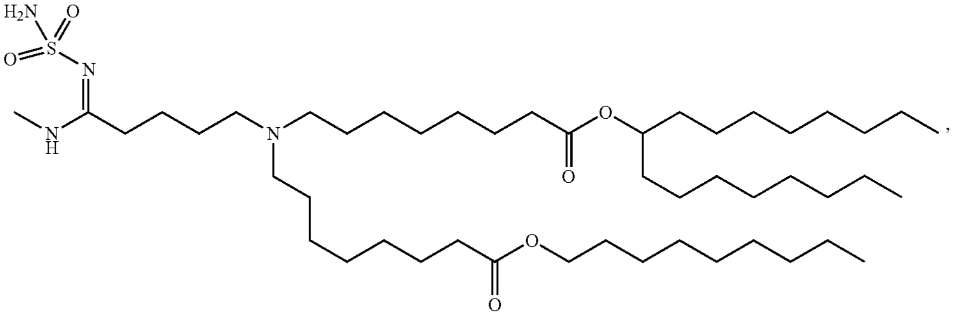
, -continued
(Compound 221)
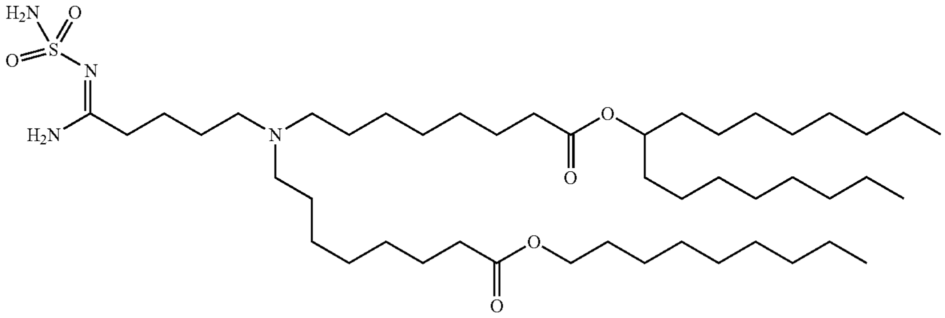
,
(Compound 222)
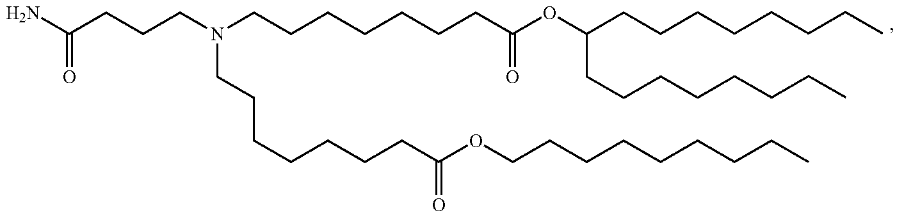
,
(Compound 223)
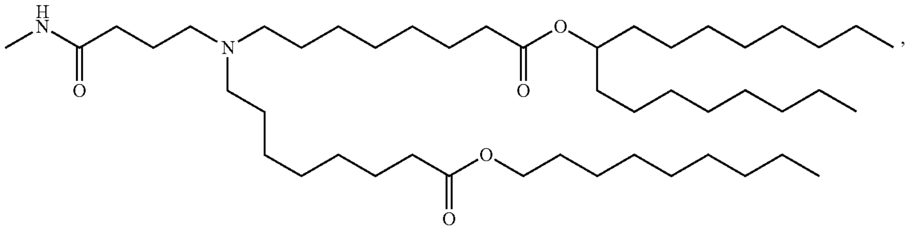
,
(Compound 224)
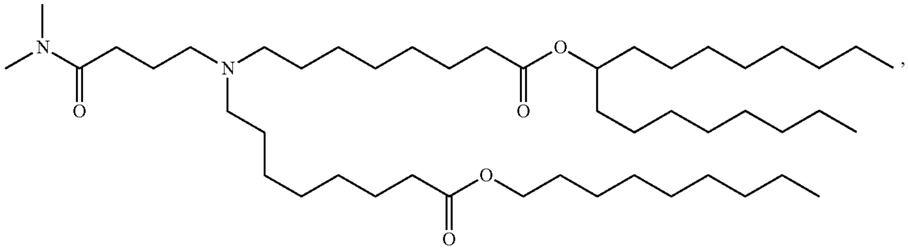
,
(Compound 225)
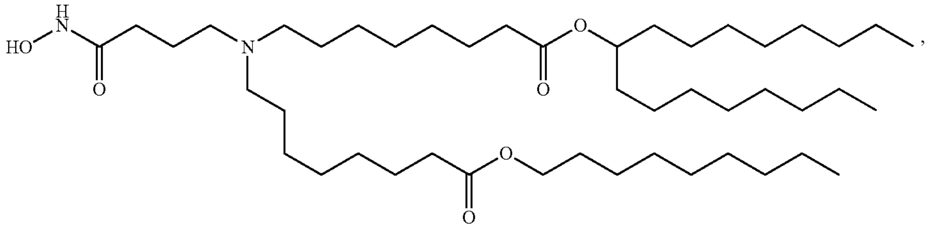
,
(Compound 226)
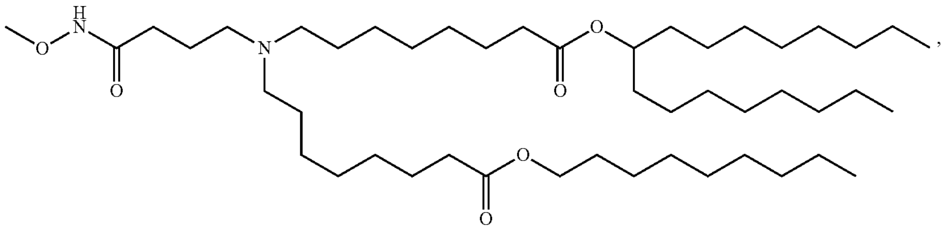
, -continued
(Compound 227)
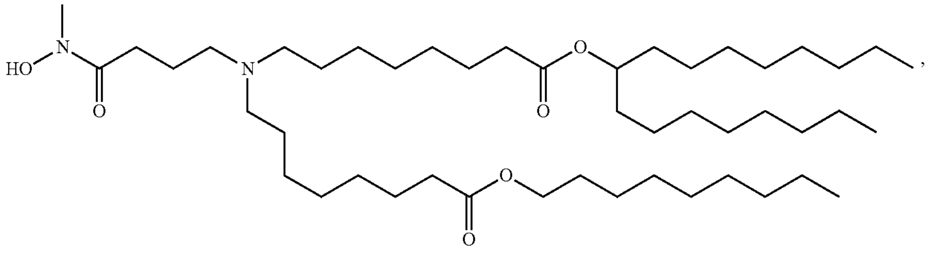
(Compound 228)
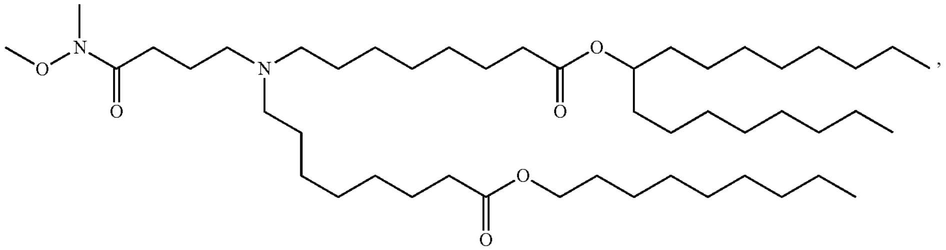
(Compound 229)
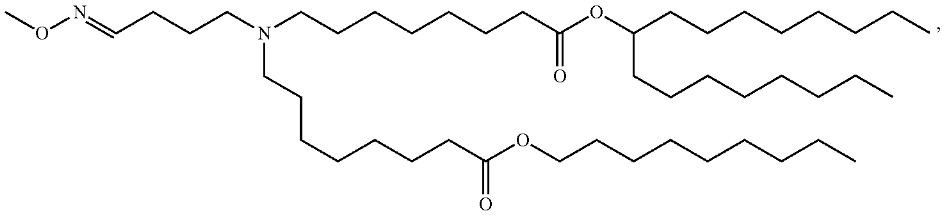
(Compound 230)
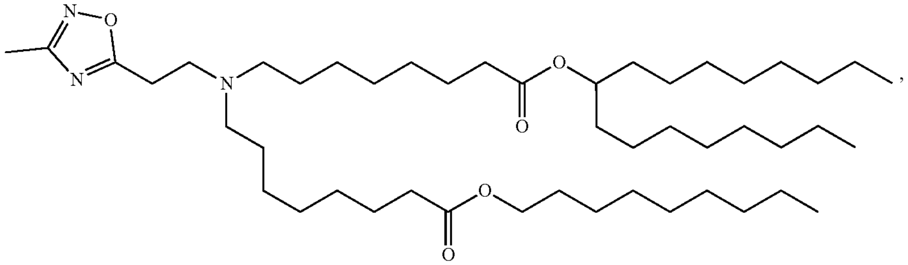
(Compound 231)
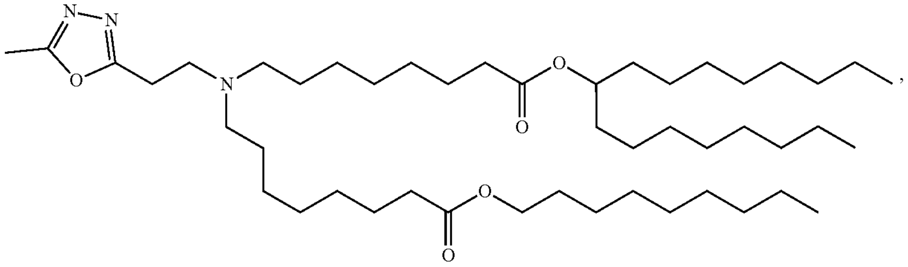
(Compound 232)
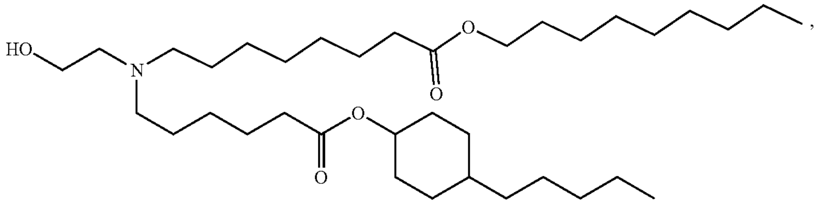
and salts and isomers thereof.

In some embodiments, a nanoparticle comprises the following compound:

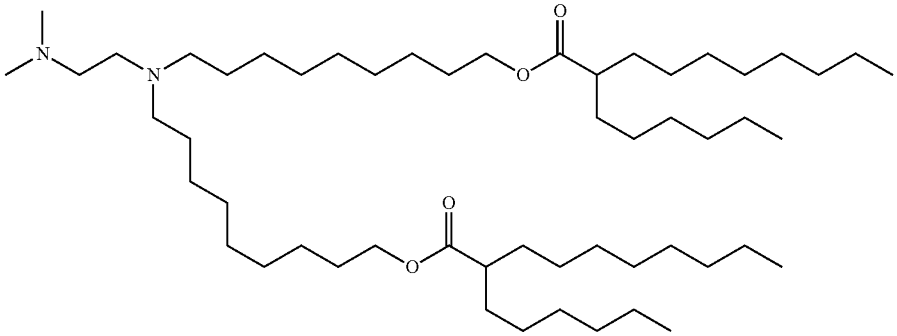

(Compound 233)

or salts and isomers thereof.

In some embodiments, the disclosure features a nanoparticle composition including a lipid component comprising a compound as described herein (e.g., a compound according to Formula (I), (IA), (II), (IIa), (IIb), (IIc), (IId) or (IIe)).

In some embodiments, the disclosure features a pharmaceutical composition comprising a nanoparticle composition according to the preceding embodiments and a pharmaceutically acceptable carrier. For example, the pharmaceutical composition is refrigerated or frozen for storage and/or shipment (e.g., being stored at a temperature of 4° C. or lower, such as a temperature between about −150° C. and about 0° C. or between about −80° C. and about −20° C. (e.g., about −5° C., −10° C., −15° C., −20° C., −25° C., −30° C., −40° C., −50° C., −60° C., −70° C., −80° C., −90° C., −130° C. or −150° C.). For example, the pharmaceutical composition is a solution that is refrigerated for storage and/or shipment at, for example, about −20° C., −30° C., −40° C., −50° C., −60° C., −70° C., or −80° C.

In some embodiments, the disclosure provides a method of delivering a therapeutic and/or prophylactic (e.g., RNA, such as mRNA) to a cell (e.g., a mammalian cell). This method includes the step of administering to a subject (e.g., a mammal, such as a human) a nanoparticle composition including (i) a lipid component including a phospholipid (such as a polyunsaturated lipid), a PEG lipid, a structural lipid, and a compound of Formula (I), (IA), (II), (IIa), (IIb), (IIc), (IId) or (IIe) and (ii) a therapeutic and/or prophylactic, in which administering involves contacting the cell with the nanoparticle composition, whereby the therapeutic and/or prophylactic is delivered to the cell.

In some embodiments, the disclosure provides a method of producing a polypeptide of interest in a cell (e.g., a mammalian cell). The method includes the step of contacting the cell with a nanoparticle composition including (i) a lipid component including a phospholipid (such as a polyunsaturated lipid), a PEG lipid, a structural lipid, and a compound of Formula (I), (IA), (II), (IIa), (IIb), (IIc), (IId) or (IIe) and (ii) an mRNA encoding the polypeptide of interest, whereby the mRNA is capable of being translated in the cell to produce the polypeptide.

In some embodiments, the disclosure provides a method of treating a disease or disorder in a mammal (e.g., a human) in need thereof. The method includes the step of administering to the mammal a therapeutically effective amount of a nanoparticle composition including (i) a lipid component including a phospholipid (such as a polyunsaturated lipid), a PEG lipid, a structural lipid, and a compound of Formula (I), (IA), (II), (IIa), (IIb), (IIc), (IId) or (IIe) and (ii) a therapeutic and/or prophylactic (e.g., an mRNA). In some embodiments, the disease or disorder is characterized by dysfunctional or aberrant protein or polypeptide activity. For example, the disease or disorder is selected from the group consisting of rare diseases, infectious diseases, cancer and proliferative diseases, genetic diseases (e.g., cystic fibrosis), autoimmune diseases, diabetes, neurodegenerative diseases, cardio- and reno-vascular diseases, and metabolic diseases.

In some embodiments, the disclosure provides a method of delivering (e.g., specifically delivering) a therapeutic and/or prophylactic to a mammalian organ (e.g., a liver, spleen, lung, or femur). This method includes the step of administering to a subject (e.g., a mammal) a nanoparticle composition including (i) a lipid component including a phospholipid, a PEG lipid, a structural lipid, and a compound of Formula (I), (IA), (II), (IIa), (IIb), (IIc), (IId) or (IIe) and (ii) a therapeutic and/or prophylactic (e.g., an mRNA), in which administering involves contacting the cell with the nanoparticle composition, whereby the therapeutic and/or prophylactic is delivered to the target organ (e.g., a liver, spleen, lung, or femur).

In some embodiments, the disclosure features a method for the enhanced delivery of a therapeutic and/or prophylactic (e.g., an mRNA) to a target tissue (e.g., a liver, spleen, lung, or femur). This method includes administering to a subject (e.g., a mammal) a nanoparticle composition, the composition including (i) a lipid component including a compound of Formula (I), (IA), (II), (IIa), (IIb), (IIc), (IId) or (IIe), a phospholipid, a structural lipid, and a PEG lipid; and (ii) a therapeutic and/or prophylactic, the administering including contacting the target tissue with the nanoparticle composition, whereby the therapeutic and/or prophylactic is delivered to the target tissue.

In some embodiments, the disclosure features a method of lowering immunogenicity comprising introducing the nanoparticle composition of the disclosure into cells, wherein the nanoparticle composition reduces the induction of the cellular immune response of the cells to the nanoparticle composition, as compared to the induction of the cellular immune response in cells induced by a reference composition which comprises a reference lipid instead of a compound of Formula (I), (IA), (II), (IIa), (IIb), (IIc), (IId) or (IIe). For example, the cellular immune response is an innate immune response, an adaptive immune response, or both.

The disclosure also includes methods of synthesizing a compound of Formula (I), (IA), (II), (IIa), (IIb), (IIc), (IId) or (IIe) and methods of making a nanoparticle composition including a lipid component comprising the compound of Formula (I), (IA), (II), (IIa), (IIb), (IIc), (IId) or (IIe).

Modes of Vaccine Administration

Respiratory virus RNA (e.g. mRNA) vaccines may be administered by any route which results in a therapeutically effective outcome. These include, but are not limited, to intradermal, intramuscular, and/or subcutaneous administration. The present disclosure provides methods comprising administering RNA (e.g., mRNA) vaccines to a subject in need thereof. The exact amount required will vary from subject to subject, depending on the species, age, and general condition of the subject, the severity of the disease, the particular composition, its mode of administration, its mode of activity, and the like. Respiratory virus RNA (e.g., mRNA) vaccines compositions are typically formulated in dosage unit form for ease of administration and uniformity of dosage. It will be understood, however, that the total daily usage of RNA (e.g., mRNA) vaccine compositions may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In some embodiments, respiratory virus RNA (e.g. mRNA) vaccines compositions may be administered at dosage levels sufficient to deliver 0.0001 mg/kg to 100 mg/kg, 0.001 mg/kg to 0.05 mg/kg, 0.005 mg/kg to 0.05 mg/kg, 0.001 mg/kg to 0.005 mg/kg, 0.05 mg/kg to 0.5 mg/kg, 0.01 mg/kg to 50 mg/kg, 0.1 mg/kg to 40 mg/kg, 0.5 mg/kg to 30 mg/kg, 0.01 mg/kg to 10 mg/kg, 0.1 mg/kg to 10 mg/kg, or 1 mg/kg to 25 mg/kg, of subject body weight per day, one or more times a day, per week, per month, etc. to obtain the desired therapeutic, diagnostic, prophylactic, or imaging effect (see, e.g., the range of unit doses described in International Publication No WO2013078199, the contents of which are herein incorporated by reference in their entirety). The desired dosage may be delivered three times a day, two times a day, once a day, every other day, every third day, every week, every two weeks, every three weeks, every four weeks, every 2 months, every three months, every 6 months, etc. In some embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used. In exemplary embodiments, respiratory virus RNA (e.g., mRNA) vaccines compositions may be administered at dosage levels sufficient to deliver 0.0005 mg/kg to 0.01 mg/kg, e.g., about 0.0005 mg/kg to about 0.0075 mg/kg, e.g., about 0.0005 mg/kg, about 0.001 mg/kg, about 0.002 mg/kg, about 0.003 mg/kg, about 0.004 mg/kg or about 0.005 mg/kg.

In some embodiments, respiratory virus RNA (e.g., mRNA) vaccine compositions may be administered once or twice (or more) at dosage levels sufficient to deliver 0.025 mg/kg to 0.250 mg/kg, 0.025 mg/kg to 0.500 mg/kg, 0.025 mg/kg to 0.750 mg/kg, or 0.025 mg/kg to 1.0 mg/kg.

In some embodiments, respiratory virus RNA (e.g., mRNA) vaccine compositions may be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.0100 mg, 0.025 mg, 0.050 mg, 0.075 mg, 0.100 mg, 0.125 mg, 0.150 mg, 0.175 mg, 0.200 mg, 0.225 mg, 0.250 mg, 0.275 mg, 0.300 mg, 0.325 mg, 0.350 mg, 0.375 mg, 0.400 mg, 0.425 mg, 0.450 mg, 0.475 mg, 0.500 mg, 0.525 mg, 0.550 mg, 0.575 mg, 0.600 mg, 0.625 mg, 0.650 mg, 0.675 mg, 0.700 mg, 0.725 mg, 0.750 mg, 0.775 mg, 0.800 mg, 0.825 mg, 0.850 mg, 0.875 mg, 0.900 mg, 0.925 mg, 0.950 mg, 0.975 mg, or 1.0 mg. Higher and lower dosages and frequency of administration are encompassed by the present disclosure. For example, a respiratory virus RNA (e.g., mRNA) vaccine composition may be administered three or four times.

In some embodiments, respiratory virus RNA (e.g., mRNA) vaccine compositions may be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.010 mg, 0.025 mg, 0.100 mg or 0.400 mg.

In some embodiments, the respiratory virus RNA (e.g., mRNA) vaccine for use in a method of vaccinating a subject is administered to the subject as a single dosage of between 10 μg/kg and 400 μg/kg of the nucleic acid vaccine (in an effective amount to vaccinate the subject). In some embodiments the RNA (e.g., mRNA) vaccine for use in a method of vaccinating a subject is administered to the subject as a single dosage of between 10 μg and 400 μg of the nucleic acid vaccine (in an effective amount to vaccinate the subject). In some embodiments, a respiratory virus RNA (e.g., mRNA) vaccine for use in a method of vaccinating a subject is administered to the subject as a single dosage of 25-1000 μg (e.g., a single dosage of mRNA encoding hMPV, PIV3, RSV, MeV and/or BetaCoV antigen). In some embodiments, a respiratory virus RNA (e.g., mRNA) vaccine is administered to the subject as a single dosage of 25, 50, 100, 150, 200, 250, 300, 350, 400, 450, 500, 550, 600, 650, 700, 750, 800, 850, 900, 950 or 1000 μg. For example, a respiratory virus RNA (e.g., mRNA) vaccine may be administered to a subject as a single dose of 25-100, 25-500, 50-100, 50-500, 50-1000, 100-500, 100-1000, 250-500, 250-1000, or 500-1000 μg. In some embodiments, a respiratory virus RNA (e.g., mRNA) vaccine for use in a method of vaccinating a subject is administered to the subject as two dosages, the combination of which equals 25-1000 μg of the respiratory virus RNA (e.g., mRNA) vaccine.

A respiratory virus RNA (e.g. mRNA) vaccine pharmaceutical composition described herein can be formulated into a dosage form described herein, such as an intranasal, intratracheal, or injectable (e.g., intravenous, intraocular, intravitreal, intramuscular, intradermal, intracardiac, intraperitoneal, and subcutaneous).

Respiratory Virus RNA (e.g., mRNA) Vaccine Formulations and Methods of Use

Some aspects of the present disclosure provide formulations of the respiratory virus RNA (e.g., mRNA) vaccine, wherein the RNA (e.g., mRNA) vaccine is formulated in an effective amount to produce an antigen specific immune response in a subject (e.g., production of antibodies specific to an hMPV, PIV3, RSV, MeV and/or BetaCoV antigenic polypeptide). "An effective amount" is a dose of an RNA (e.g., mRNA) vaccine effective to produce an antigen-specific immune response. Also provided herein are methods of inducing an antigen-specific immune response in a subject.

In some embodiments, the antigen-specific immune response is characterized by measuring an anti-hMPV, anti-PIV3, anti-RSV, anti-MeV and/or anti-BetaCoV antigenic polypeptide antibody titer produced in a subject administered a respiratory virus RNA (e.g., mRNA) vaccine as provided herein. An antibody titer is a measurement of the amount of antibodies within a subject, for example, antibodies that are specific to a particular antigen (e.g., an anti-hMPV, anti-PIV3, anti-RSV, anti-MeV and/or anti-BetaCoV antigenic polypeptide) or epitope of an antigen. Antibody titer is typically expressed as the inverse of the greatest dilution that provides a positive result. Enzyme-linked immunosorbent assay (ELISA) is a common assay for determining antibody titers, for example.

In some embodiments, an antibody titer is used to assess whether a subject has had an infection or to determine whether immunizations are required. In some embodiments, an antibody titer is used to determine the strength of an autoimmune response, to determine whether a booster immunization is needed, to determine whether a previous vaccine was effective, and to identify any recent or prior infections. In accordance with the present disclosure, an antibody titer may be used to determine the strength of an immune response induced in a subject by the respiratory virus RNA (e.g., mRNA) vaccine.

In some embodiments, an anti-antigenic polypeptide (e.g., an anti-hMPV, anti-PIV3, anti-RSV, anti-MeV and/or anti-BetaCoV antigenic polypeptide) antibody titer produced in a subject is increased by at least 1 log relative to a control. For example, anti-antigenic polypeptide antibody titer produced in a subject may be increased by at least 1.5, at least 2, at least 2.5, or at least 3 log relative to a control. In some embodiments, the anti-antigenic polypeptide antibody titer produced in the subject is increased by 1, 1.5, 2, 2.5 or 3 log relative to a control. In some embodiments, the anti-antigenic polypeptide antibody titer produced in the subject is increased by 1-3 log relative to a control. For example, the anti-antigenic polypeptide antibody titer produced in a subject may be increased by 1-1.5, 1-2, 1-2.5, 1-3, 1.5-2, 1.5-2.5, 1.5-3, 2-2.5, 2-3, or 2.5-3 log relative to a control.

In some embodiments, the anti-antigenic polypeptide (e.g., an anti-hMPV, anti-PIV3, anti-RSV, anti-MeV and/or anti-BetaCoV antigenic polypeptide) antibody titer produced in a subject is increased at least 2 times relative to a control. For example, the anti-antigenic polypeptide antibody titer produced in a subject may be increased at least 3 times, at least 4 times, at least 5 times, at least 6 times, at least 7 times, at least 8 times, at least 9 times, or at least 10 times relative to a control. In some embodiments, the anti-antigenic polypeptide antibody titer produced in the subject is increased 2, 3, 4, 5, 6, 7, 8, 9, or 10 times relative to a control. In some embodiments, the anti-antigenic polypeptide antibody titer produced in a subject is increased 2-10 times relative to a control. For example, the anti-antigenic polypeptide antibody titer produced in a subject may be increased 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, or 9-10 times relative to a control.

A control, in some embodiments, is the anti-antigenic polypeptide (e.g., an anti-hMPV, anti-PIV3, anti-RSV, anti-MeV and/or anti-BetaCoV antigenic polypeptide) antibody titer produced in a subject who has not been administered a respiratory virus RNA (e.g., mRNA) vaccine of the present disclosure. In some embodiments, a control is an anti-antigenic polypeptide (e.g., an anti-hMPV, anti-PIV3, anti-RSV, anti-MeV and/or anti-BetaCoV antigenic polypeptide) antibody titer produced in a subject who has been administered a live attenuated hMPV, PIV3, RSV, MeV and/or BetaCoV vaccine. An attenuated vaccine is a vaccine produced by reducing the virulence of a viable (live). An attenuated virus is altered in a manner that renders it harmless or less virulent relative to live, unmodified virus. In some embodiments, a control is an anti-antigenic polypeptide (e.g., an anti-hMPV, anti-PIV3, anti-RSV, anti-MeV and/or anti-BetaCoV antigenic polypeptide) antibody titer produced in a subject administered inactivated hMPV, PIV3, RSV, MeV and/or BetaCoV vaccine. In some embodiments, a control is an anti-antigenic polypeptide (e.g., an anti-hMPV, anti-PIV3, anti-RSV, anti-MeV and/or anti-BetaCoV antigenic polypeptide) antibody titer produced in a subject administered a recombinant or purified hMPV, PIV3, RSV, MeV and/or BetaCoV protein vaccine. Recombinant protein vaccines typically include protein antigens that either have been produced in a heterologous expression system (e.g., bacteria or yeast) or purified from large amounts of the pathogenic organism. In some embodiments, a control is an anti-antigenic polypeptide (e.g., an anti-hMPV, anti-PIV3, anti-RSV, anti-MeV and/or anti-BetaCoV antigenic polypeptide) antibody titer produced in a subject who has been administered an hMPV, PIV3, RSV, MeV and/or BetaCoV virus-like particle (VLP) vaccine. For example, an hMPV VLP vaccine used as a control may be a hMPV VLPs, comprising (or consisting of) viral matrix (M) and fusion (F) proteins, generated by expressing viral proteins in suspension-adapted human embryonic kidney epithelial (293-F) cells (see, e.g., Cox R G et al., *J Virol.* 2014 June; 88(11): 6368-6379, the contents of which are herein incorporated by reference).

In some embodiments, an effective amount of a respiratory virus RNA (e.g., mRNA) vaccine is a dose that is reduced compared to the standard of care dose of a recombinant hMPV, PIV3, RSV, MeV and/or BetaCoV protein vaccine. A "standard of care," as provided herein, refers to a medical or psychological treatment guideline and can be general or specific. "Standard of care" specifies appropriate treatment based on scientific evidence and collaboration between medical professionals involved in the treatment of a given condition. It is the diagnostic and treatment process that a physician/clinician should follow for a certain type of patient, illness or clinical circumstance. A "standard of care dose," as provided herein, refers to the dose of a recombinant or purified hMPV, PIV3, RSV, MeV and/or BetaCoV protein vaccine, or a live attenuated or inactivated hMPV, PIV3, RSV, MeV and/or BetaCoV vaccine, that a physician/clinician or other medical professional would administer to a subject to treat or prevent hMPV, PIV3, RSV, MeV and/or BetaCoV, or a hMPV-, PIV3-, RSV-, MeV- and/or BetaCoV-related condition, while following the standard of care guideline for treating or preventing hMPV, PIV3, RSV, MeV and/or BetaCoV, or a hMPV-, PIV3-, RSV-, MeV- and/or BetaCoV-related condition.

In some embodiments, the anti-antigenic polypeptide (e.g., an anti-hMPV, anti-PIV3, anti-RSV, anti-MeV and/or anti-BetaCoV antigenic polypeptide) antibody titer produced in a subject administered an effective amount of a respiratory virus RNA (e.g., mRNA) vaccine is equivalent to an anti-antigenic polypeptide (e.g., an anti-hMPV, anti-PIV3, anti-RSV, anti-MeV and/or anti-BetaCoV antigenic polypeptide) antibody titer produced in a control subject administered a standard of care dose of a recombinant or purified hMPV, PIV3, RSV, MeV and/or BetaCoV protein vaccine or a live attenuated or inactivated hMPV, PIV3, RSV, MeV and/or BetaCoV vaccine.

In some embodiments, an effective amount of a respiratory virus RNA (e.g., mRNA) vaccine is a dose equivalent to an at least 2-fold reduction in a standard of care dose of a recombinant or purified hMPV, PIV3, RSV, MeV and/or BetaCoV protein vaccine. For example, an effective amount of a respiratory virus RNA (e.g., mRNA) vaccine may be a dose equivalent to an at least 3-fold, at least 4-fold, at least 5-fold, at least 6-fold, at least 7-fold, at least 8-fold, at least 9-fold, or at least 10-fold reduction in a standard of care dose of a recombinant or purified hMPV, PIV3, RSV, MeV and/or BetaCoV protein vaccine. In some embodiments, an effective amount of a respiratory virus RNA (e.g., mRNA) vaccine is a dose equivalent to an at least at least 100-fold, at least 500-fold, or at least 1000-fold reduction in a standard of care dose of a recombinant or purified hMPV, PIV3, RSV, MeV and/or BetaCoV protein vaccine. In some embodiments, an effective amount of a respiratory virus RNA (e.g., mRNA) vaccine is a dose equivalent to a 2-, 3-, 4-, 5-, 6-, 7-, 8-, 9-, 10-, 20-, 50-, 100-, 250-, 500-, or 1000-fold reduction in a standard of care dose of a recombinant or purified hMPV, PIV3, RSV, MeV and/or BetaCoV protein vaccine. In some embodiments, the anti-antigenic polypeptide antibody titer produced in a subject administered an effective amount of a respiratory virus RNA (e.g., mRNA) vaccine is equivalent to an anti-antigenic polypeptide antibody titer produced in a control subject administered the standard of care dose of a recombinant or protein hMPV, PIV3, RSV, MeV and/or BetaCoV protein vaccine or a live attenuated or inactivated hMPV, PIV3, RSV, MeV and/or BetaCoV vaccine. In some embodiments, an effective amount of a respiratory virus RNA (e.g., mRNA) vaccine is a dose equivalent to a 2-fold to 1000-fold (e.g., 2-fold to 100-fold, 10-fold to 1000-fold) reduction in the standard of care dose of a recombinant or purified hMPV, PIV3, RSV, MeV and/or BetaCoV protein vaccine, wherein the anti-antigenic polypeptide antibody titer produced in the subject is equivalent to an anti-antigenic polypeptide antibody titer produced in a control subject administered the standard of care dose of a recombinant or purified hMPV, PIV3, RSV, MeV and/or BetaCoV protein vaccine or a live attenuated or inactivated hMPV, PIV3, RSV, MeV and/or BetaCoV vaccine.

In some embodiments, the effective amount of a respiratory virus RNA (e.g., mRNA) vaccine is a dose equivalent to a 2 to 1000-, 2 to 900-, 2 to 800-, 2 to 700-, 2 to 600-, 2 to 500-, 2 to 400-, 2 to 300-, 2 to 200-, 2 to 100-, 2 to 90-, 2 to 80-, 2 to 70-, 2 to 60-, 2 to 50-, 2 to 40-, 2 to 30-, 2 to 20-, 2 to 10-, 2 to 9-, 2 to 8-, 2 to 7-, 2 to 6-, 2 to 5-, 2 to 4-, 2 to 3-, 3 to 1000-, 3 to 900-, 3 to 800-, 3 to 700-, 3 to 600-, 3 to 500-, 3 to 400-, 3 to 3 to 00-, 3 to 200-, 3 to 100-, 3 to 90-, 3 to 80-, 3 to 70-, 3 to 60-, 3 to 50-, 3 to 40-, 3 to 30-, 3 to 20-, 3 to 10-, 3 to 9-, 3 to 8-, 3 to 7-, 3 to 6-, 3 to 5-, 3 to 4-, 4 to 1000-, 4 to 900-, 4 to 800-, 4 to 700-, 4 to 600-, 4 to 500-, 4 to 400-, 4 to 4 to 00-, 4 to 200-, 4 to 100-, 4 to 90-, 4 to 80-, 4 to 70-, 4 to 60-, 4 to 50-, 4 to 40-, 4 to 30-, 4 to 20-, 4 to 10-, 4 to 9-, 4 to 8-, 4 to 7-, 4 to 6-, 4 to 5-, 4 to 4-, 5 to 1000-, 5 to 900-, 5 to 800-, 5 to 700-, 5 to 600-, 5 to 500-, 5 to 400-, 5 to 300-, 5 to 200-, 5 to 100-, 5 to 90-, 5 to 80-, 5 to 70-, 5 to 60-, 5 to 50-, 5 to 40-, 5 to 30-, 5 to 20-, 5 to 10-, 5 to 9-, 5 to 8-, 5 to 7-, 5 to 6-, 6 to 1000-, 6 to 900-, 6 to 800-, 6 to 700-, 6 to 600-, 6 to 500-, 6 to 400-, 6 to 300-, 6 to 200-, 6 to 100-, 6 to 90-, 6 to 80-, 6 to 70-, 6 to 60-, 6 to 50-, 6 to 40-, 6 to 30-, 6 to 20-, 6 to 10-, 6 to 9-, 6 to 8-, 6 to 7-, 7 to 1000-, 7 to 900-, 7 to 800-, 7 to 700-, 7 to 600-, 7 to 500-, 7 to 400-, 7 to 300-, 7 to 200-, 7 to 100-, 7 to 90-, 7 to 80-, 7 to 70-, 7 to 60-, 7 to 50-, 7 to 40-, 7 to 30-, 7 to 20-, 7 to 10-, 7 to 9-, 7 to 8-, 8 to 1000-, 8 to 900-, 8 to 800-, 8 to 700-, 8 to 600-, 8 to 500-, 8 to 400-, 8 to 300-, 8 to 200-, 8 to 100-, 8 to 90-, 8 to 80-, 8 to 70-, 8 to 60-, 8 to 50-, 8 to 40-, 8 to 30-, 8 to 20-, 8 to 10-, 8 to 9-, 9 to 1000-, 9 to 900-, 9 to 800-, 9 to 700-, 9 to 600-, 9 to 500-, 9 to 400-, 9 to 300-, 9 to 200-, 9 to 100-, 9 to 90-, 9 to 80-, 9 to 70-, 9 to 60-, 9 to 50-, 9 to 40-, 9 to 30-, 9 to 20-, 9 to 10-, 10 to 1000-, 10 to 900-, 10 to 800-, 10 to 700-, 10 to 600-, 10 to 500-, 10 to 400-, 10 to 300-, 10 to 200-, 10 to 100-, 10 to 90-, 10 to 80-, 10 to 70-, 10 to 60-, 10 to 50-, 10 to 40-, 10 to 30-, 10 to 20-, 20 to 1000-, 20 to 900-, 20 to 800-, 20 to 700-, 20 to 600-, 20 to 500-, 20 to 400-, 20 to 300-, 20 to 200-, 20 to 100-, 20 to 90-, 20 to 80-, 20 to 70-, 20 to 60-, 20 to 50-, 20 to 40-, 20 to 30-, 30 to 1000-, 30 to 900-, 30 to 800-, 30 to 700-, 30 to 600-, 30 to 500-, 30 to 400-, 30 to 300-, 30 to 200-, 30 to 100-, 30 to 90-, 30 to 80-, 30 to 70-, 30 to 60-, 30 to 50-, 30 to 40-, 40 to 1000-, 40 to 900-, 40 to 800-, 40 to 700-, 40 to 600-, 40 to 500-, 40 to 400-, 40 to 300-, 40 to 200-, 40 to 100-, 40 to 90-, 40 to 80-, 40 to 70-, 40 to 60-, 40 to 50-, 50 to 1000-, 50 to 900-, 50 to 800-, 50 to 700-, 50 to 600-, 50 to 500-, 50 to 400-, 50 to 300-, 50 to 200-, 50 to 100-, 50 to 90-, 50 to 80-, 50 to 70-, 50 to 60-, 60 to 1000-, 60 to 900-, 60 to 800-, 60 to 700-, 60 to 600-, 60 to 500-, 60 to 400-, 60 to 300-, 60 to 200-, 60 to 100-, 60 to 90-, 60 to 80-, 60 to 70-, 70 to 1000-, 70 to 900-, 70 to 800-, 70 to 700-, 70 to 600-, 70 to 500-, 70 to 400-, 70 to 300-, 70 to 200-, 70 to 100-, 70 to 90-, 70 to 80-, 80 to 1000-, 80 to 900-, 80 to 800-, 80 to 700-, 80 to 600-, 80 to 500-, 80 to 400-, 80 to 300-, 80 to 200-, 80 to 100-, 80 to 90-, 90 to 1000-, 90 to 900-, 90 to 800-, 90 to 700-, 90 to 600-, 90 to 500-, 90 to 400-, 90 to 300-, 90 to 200-, 90 to 100-, 100 to 1000-, 100 to 900-, 100 to 800-, 100 to 700-, 100 to 600-, 100 to 500-, 100 to 400-, 100 to 300-, 100 to 200-, 200 to 1000-, 200 to 900-, 200 to 800-, 200 to 700-, 200 to 600-, 200 to 500-, 200 to 400-, 200 to 300-, 300 to 1000-, 300 to 900-, 300 to 800-, 300 to 700-, 300 to 600-, 300 to 500-, 300 to 400-, 400 to 1000-, 400 to 900-, 400 to 800-, 400 to 700-, 400 to 600-, 400 to 500-, 500 to 1000-, 500 to 900-, 500 to 800-, 500 to 700-, 500 to 600-, 600 to 1000-, 600 to 900-, 600 to 800-, 600 to 700-, 700 to 1000-, 700 to 900-, 700 to 800-, 800 to 1000-, 800 to 900-, or 900 to 1000-fold reduction in the standard of care dose of a recombinant hMPV, PIV3, RSV, MeV and/or BetaCoV protein vaccine. In some embodiments, the anti-antigenic polypeptide antibody titer produced in the subject is equivalent to an anti-antigenic polypeptide antibody titer produced in a control subject administered the standard of care dose of a recombinant or purified hMPV, PIV3, RSV, MeV and/or BetaCoV protein vaccine or a live attenuated or inactivated hMPV, PIV3, RSV, MeV and/or BetaCoV vaccine. In some embodiments, the effective amount is a dose equivalent to (or equivalent to an at least) 2-, 3-, 4-, 5-, 6-, 7-, 8-, 9-, 10-, 20-, 30-, 40-, 50-, 60-, 70-, 80-, 90-, 100-, 110-, 120-, 130-, 140-, 150-, 160-, 170-, 1280-, 190-, 200-, 210-, 220-, 230-, 240-, 250-, 260-, 270-, 280-, 290-, 300-, 310-, 320-, 330-, 340-, 350-, 360-, 370-, 380-, 390-, 400-, 410-, 420-, 430-, 440-, 450-, 4360-, 470-, 480-, 490-, 500-, 510-, 520-, 530-, 540-, 550-, 560-, 5760-, 580-, 590-, 600-, 610-, 620-, 630-, 640-, 650-, 660-, 670-, 680-, 690-, 700-, 710-, 720-, 730-, 740-, 750-, 760-, 770-, 780-, 790-, 800-, 810-, 820-, 830-, 840-, 850-, 860-, 870-, 880-, 890-, 900-, 910-, 920-, 930-, 940-, 950-, 960-, 970-, 980-, 990-, or 1000-fold reduction in the standard of care dose of a recombinant hMPV, PIV3, RSV, MeV and/or BetaCoV protein vaccine. In some embodiments, an anti-antigenic polypeptide antibody titer produced in the subject is equivalent to an anti-antigenic polypeptide antibody titer produced in a control subject administered the standard of care dose of a recombinant or purified hMPV, PIV3, RSV, MeV and/or BetaCoV protein vaccine or a live attenuated or inactivated hMPV, PIV3, RSV, MeV and/or BetaCoV vaccine.

In some embodiments, the effective amount of a respiratory virus RNA (e.g., mRNA) vaccine is a total dose of 50-1000 μg. In some embodiments, the effective amount of a respiratory virus RNA (e.g., mRNA) vaccine is a total dose of 50-1000, 50-900, 50-800, 50-700, 50-600, 50-500, 50-400, 50-300, 50-200, 50-100, 50-90, 50-80, 50-70, 50-60, 60-1000, 60-900, 60-800, 60-700, 60-600, 60-500, 60-400, 60-300, 60-200, 60-100, 60-90, 60-80, 60-70, 70-1000, 70-900, 70-800, 70-700, 70-600, 70-500, 70-400, 70-300, 70-200, 70-100, 70-90, 70-80, 80-1000, 80-900, 80-800, 80-700, 80-600, 80-500, 80-400, 80-300, 80-200, 80-100, 80-90, 90-1000, 90-900, 90-800, 90-700, 90-600, 90-500, 90-400, 90-300, 90-200, 90-100, 100-1000, 100-900, 100-800, 100-700, 100-600, 100-500, 100-400, 100-300, 100-200, 200-1000, 200-900, 200-800, 200-700, 200-600, 200-500, 200-400, 200-300, 300-1000, 300-900, 300-800, 300-700, 300-600, 300-500, 300-400, 400-1000, 400-900, 400-800, 400-700, 400-600, 400-500, 500-1000, 500-900, 500-800, 500-700, 500-600, 600-1000, 600-900, 600-900, 600-700, 700-1000, 700-900, 700-800, 800-1000, 800-900, or 900-1000 μg. In some embodiments, the effective amount of a respiratory virus RNA (e.g., mRNA) vaccine is a total dose of 50, 100, 150, 200, 250, 300, 350, 400, 450, 500, 550, 600, 650, 700, 750, 800, 850, 900, 950 or 1000 μg. In some embodiments, the effective amount is a dose of 25-500 μg administered to the subject a total of two times. In some embodiments, the effective amount of a respiratory virus RNA (e.g., mRNA) vaccine is a dose of 25-500, 25-400, 25-300, 25-200, 25-100, 25-50, 50-500, 50-400, 50-300, 50-200, 50-100, 100-500, 100-400, 100-300, 100-200, 150-500, 150-400, 150-300, 150-200, 200-500, 200-400, 200-300, 250-500, 250-400, 250-300, 300-500, 300-400, 350-500, 350-400, 400-500 or 450-500 μg administered to the subject a total of two times. In some embodiments, the effective amount of a respiratory virus RNA (e.g., mRNA) vaccine is a total dose of 25, 50, 100, 150, 200, 250, 300, 350, 400, 450, or 500 μg administered to the subject a total of two times.

Examples of Additional Embodiments of the Disclosure

Additional embodiments of the present disclosure are encompassed by the following numbered paragraphs:

1. A respiratory virus vaccine, comprising: at least one ribonucleic acid (RNA) polynucleotide having an open reading frame encoding at least one, at least two, at least three, at least four or at least five antigenic polypeptides selected from human metapneumovirus (hMPV) antigenic polypeptides or immunogenic fragments thereof, human parainfluenza virus type 3 (PIV3) antigenic polypeptides or immunogenic fragments thereof, respiratory syncytial virus (RSV) antigenic polypeptides or immunogenic fragments thereof, measles virus (MeV) antigenic polypeptides or immunogenic fragments thereof, and betacoronavirus (BetaCoV) antigenic polypeptides or immunogenic fragments thereof.

2. The respiratory virus vaccine of paragraph 1, comprising:

at least one RNA polynucleotide having an open reading frame encoding a hMPV antigenic polypeptide or an immunogenic fragment thereof and a PIV3 antigenic polypeptide or an immunogenic fragment thereof; or at least two RNA polynucleotides, one having an open reading frame encoding a hMPV antigenic polypeptide or an immunogenic fragment thereof and one having an open reading frame encoding a PIV3 antigenic polypeptide or an immunogenic fragment thereof.

3. The respiratory virus vaccine of paragraph 2, wherein the hMPV antigenic polypeptide comprises an amino acid sequence identified by any one of SEQ ID NO: 5-8 or an amino acid sequence having at least 90% or 95% identity to an amino acid sequence identified by any one of SEQ ID NO: 5-8, and/or wherein the PIV3 antigenic polypeptide comprises an amino acid sequence identified by any one of SEQ ID NO: 12-13 or an amino acid sequence having at least 90% or 95% identity to an amino acid sequence identified by any one of SEQ ID NO: 12-13.

4. The respiratory virus vaccine of paragraph 1, comprising:

at least one RNA polynucleotide having an open reading frame encoding a hMPV antigenic polypeptide or an immunogenic fragment thereof and a RSV antigenic polypeptide or an immunogenic fragment thereof; or at least two RNA polynucleotides, one having an open reading frame encoding a hMPV antigenic polypeptide or an immunogenic fragment thereof and one having an open reading frame encoding a RSV antigenic polypeptide or an immunogenic fragment thereof.

5. The respiratory virus vaccine of paragraph 4, wherein the hMPV antigenic polypeptide comprises an amino acid sequence identified by any one of SEQ ID NO: 5-8 or an amino acid sequence having at least 90% or 95% identity to an amino acid sequence identified by any one of SEQ ID NO: 5-8.

6. The respiratory virus vaccine of paragraph 1, comprising:

at least one RNA polynucleotide having an open reading frame encoding a hMPV antigenic polypeptide or an immunogenic fragment thereof and MeV antigenic polypeptide or an immunogenic fragment thereof; or at least two RNA polynucleotides, one having an open reading frame encoding a hMPV antigenic polypeptide or an immunogenic fragment thereof and one having an open reading frame encoding a MeV antigenic polypeptide or an immunogenic fragment thereof.

7. The respiratory virus vaccine of paragraph 6, wherein the hMPV antigenic polypeptide comprises an amino acid sequence identified by any one of SEQ ID NO: 5-8 or an amino acid sequence having at least 90% or 95% identity to an amino acid sequence identified by any one of SEQ ID NO: 5-8, and/or wherein the MeV antigenic polypeptide comprises an amino acid sequence identified by any one of SEQ ID NO: 47-50 or an amino acid sequence having at least 90% or 95% identity to an amino acid sequence identified by any one of SEQ ID NO: 47-50.

8. The respiratory virus vaccine of paragraph 1, comprising:

at least one RNA polynucleotide having an open reading frame encoding a hMPV antigenic polypeptide or an immunogenic fragment thereof and a BetaCoV antigenic polypeptide or an immunogenic fragment thereof; or at least two RNA polynucleotides, one having an open reading frame encoding a hMPV antigenic polypeptide or an immunogenic fragment thereof and one having an open reading frame encoding a BetaCoV antigenic polypeptide or an immunogenic fragment thereof.

9. The respiratory virus vaccine of paragraph 8, wherein the hMPV antigenic polypeptide comprises an amino acid sequence identified by any one of SEQ ID NO: 5-8 or an amino acid sequence having at least 90% or 95% identity to an amino acid sequence identified by any one of SEQ ID NO: 5-8, and/or wherein the BetaCoV antigenic polypeptide comprises an amino acid sequence identified by any one of SEQ ID NO: 24-34 or an amino acid sequence having at least 90% or 95% identity to an amino acid sequence identified by any one of SEQ ID NO: 24-34.

10. The respiratory virus vaccine of paragraph 1, comprising:

at least one RNA polynucleotide having an open reading frame encoding a PIV3 antigenic polypeptide or an immunogenic fragment thereof and a RSV antigenic polypeptide or an immunogenic fragment thereof; or at least two RNA polynucleotides, one having an open reading frame encoding a PIV3 antigenic polypeptide or an immunogenic fragment thereof and one having an open reading frame encoding a RSV antigenic polypeptide or an immunogenic fragment thereof.

11. The respiratory virus vaccine of paragraph 10, wherein the PIV3 antigenic polypeptide comprises an amino acid sequence identified by any one of SEQ ID NO: 12-13 or an amino acid sequence having at least 90% or 95% identity to an amino acid sequence identified by any one of SEQ ID NO: 12-13.

12. The respiratory virus vaccine of paragraph 1, comprising:

at least one RNA polynucleotide having an open reading frame encoding a PIV3 antigenic polypeptide or an immunogenic fragment thereof and a MeV antigenic polypeptide or an immunogenic fragment thereof; or at least two RNA polynucleotides, one having an open reading frame encoding a PIV3 antigenic polypeptide or an immunogenic fragment thereof and one having an open reading frame encoding a MeV antigenic polypeptide or an immunogenic fragment thereof.

13. The respiratory virus vaccine of paragraph 12, wherein the PIV3 antigenic polypeptide comprises an amino acid sequence identified by any one of SEQ ID NO: 12-13 or an amino acid sequence having at least 90% or 95% identity to an amino acid sequence identified by any one of SEQ ID NO: 12-13, and/or wherein the MeV antigenic polypeptide comprises an amino acid sequence identified by any one of SEQ ID NO: 47-50 or an amino acid sequence having at least 90% or 95% identity to an amino acid sequence identified by any one of SEQ ID NO: 47-50.

14. The respiratory virus vaccine of paragraph 1, comprising:

at least one RNA polynucleotide having an open reading frame encoding a PIV3 antigenic polypeptide or an immunogenic fragment thereof and a BetaCoV antigenic polypeptide or an immunogenic fragment thereof; or at least two RNA polynucleotides, one having an open reading frame encoding a PIV3 antigenic polypeptide or an immunogenic fragment thereof and one having an open reading frame encoding a BetaCoV antigenic polypeptide or an immunogenic fragment thereof.

15. The respiratory virus vaccine of paragraph 14, wherein the PIV3 antigenic polypeptide comprises an amino acid sequence identified by any one of SEQ ID NO: 12-13 or an amino acid sequence having at least 90% or 95% identity to an amino acid sequence identified by any one of SEQ ID NO: 12-13, and/or wherein the BetaCoV antigenic polypeptide comprises an amino acid sequence identified by any one of SEQ ID NO: 24-34 or an amino acid sequence having at least 90% or 95% identity to an amino acid sequence identified by any one of SEQ ID NO: 24-34.

16. The respiratory virus vaccine of paragraph 1, comprising:

at least one RNA polynucleotide having an open reading frame encoding a RSV antigenic polypeptide or an immunogenic fragment thereof and a MeV antigenic polypeptide or an immunogenic fragment thereof; or at least two RNA polynucleotides, one having an open reading frame encoding a RSV antigenic polypeptide or an immunogenic fragment thereof and one having an open reading frame encoding a MeV antigenic polypeptide or an immunogenic fragment thereof.

17. The respiratory virus vaccine of paragraph 16, wherein the MeV antigenic polypeptide comprises an amino acid sequence identified by any one of SEQ ID NO: 47-50 or an amino acid sequence having at least 90% or 95% identity to an amino acid sequence identified by any one of SEQ ID NO: 47-50.

18. The respiratory virus vaccine of paragraph 1, comprising:

at least one RNA polynucleotide having an open reading frame encoding a RSV antigenic polypeptide or an immunogenic fragment thereof and a BetaCoV antigenic polypeptide or an immunogenic fragment thereof; or at least two RNA polynucleotides, one having an open reading frame encoding a RSV antigenic polypeptide or an immunogenic fragment thereof and one having an open reading frame encoding a BetaCoV antigenic polypeptide or an immunogenic fragment thereof.

19. The respiratory virus vaccine of paragraph 18, wherein the BetaCoV antigenic polypeptide comprises an amino acid sequence identified by any one of SEQ ID NO: 24-34 or an amino acid sequence having at least 90% or 95% identity to an amino acid sequence identified by any one of SEQ ID NO: 24-34.

20. The respiratory virus vaccine of paragraph 1, comprising:

at least one RNA polynucleotide having an open reading frame encoding a MeV antigenic polypeptide or an immunogenic fragment thereof and a BetaCoV antigenic polypeptide or an immunogenic fragment thereof; or at least two RNA polynucleotides, one having an open reading frame encoding a MeV antigenic polypeptide or an immunogenic fragment thereof and one having an open reading frame encoding a BetaCoV antigenic polypeptide or an immunogenic fragment thereof.

21. The respiratory virus vaccine of paragraph 20, wherein the MeV antigenic polypeptide comprises an amino acid sequence identified by any one of SEQ ID NO: 47-50 or an amino acid sequence having at least 90% or 95% identity to an amino acid sequence identified by any one of SEQ ID NO: 47-50, and/or wherein the BetaCoV antigenic polypeptide comprises an amino acid sequence identified by any one of SEQ ID NO: 24-34 or an amino acid sequence having at least 90% or 95% identity to an amino acid sequence identified by any one of SEQ ID NO: 24-34.

22. The respiratory virus vaccine of paragraph 1, comprising:

at least one RNA polynucleotide having an open reading frame encoding a hMPV antigenic polypeptide or an immunogenic fragment thereof, a PIV3 antigenic polypeptide or an immunogenic fragment thereof, and a RSV antigenic polypeptide or an immunogenic fragment thereof; or at least two or three RNA polynucleotides, one having an open reading frame encoding a hMPV antigenic polypeptide or an immunogenic fragment thereof, one having an open reading frame encoding a PIV3 antigenic polypeptide or an immunogenic fragment thereof, and one having an open reading frame encoding a RSV antigenic polypeptide or an immunogenic fragment thereof.

23. The respiratory virus vaccine of paragraph 22, wherein the hMPV antigenic polypeptide comprises an amino acid sequence identified by any one of SEQ ID NO: 5-8 or an amino acid sequence having at least 90% or 95% identity to an amino acid sequence identified by any one of SEQ ID NO: 5-8, and/or wherein the PIV3 antigenic polypeptide comprises an amino acid sequence identified by any one of SEQ ID NO: 12-13 or an amino acid sequence having at least 90% or 95% identity to an amino acid sequence identified by any one of SEQ ID NO: 12-13.

24. The respiratory virus vaccine of paragraph 1, comprising:

at least one RNA polynucleotide having an open reading frame encoding a hMPV antigenic polypeptide or an immunogenic fragment thereof, a PIV3 antigenic polypeptide or an immunogenic fragment thereof, and a MeV antigenic polypeptide or an immunogenic fragment thereof; or at least two or three RNA polynucleotides, one having an open reading frame encoding a hMPV antigenic polypeptide or an immunogenic fragment thereof, one having an open reading frame encoding a PIV3 antigenic polypeptide or an immunogenic fragment thereof, and one having an open reading frame encoding a MeV antigenic polypeptide or an immunogenic fragment thereof.

25. The respiratory virus vaccine of paragraph 24, wherein the hMPV antigenic polypeptide comprises an amino acid sequence identified by any one of SEQ ID NO: 5-8 or an amino acid sequence having at least 90% or 95% identity to an amino acid sequence identified by any one of SEQ ID NO: 5-8, wherein the PIV3 antigenic polypeptide comprises an amino acid sequence identified by any one of SEQ ID NO: 12-13 or an amino acid sequence having at least 90% or 95% identity to an amino acid sequence identified by any one of SEQ ID NO: 12-13, and/or wherein the MeV antigenic polypeptide comprises an amino acid sequence identified by any one of SEQ ID NO: 47-50 or an amino acid sequence having at least 90% or 95% identity to an amino acid sequence identified by any one of SEQ ID NO: 47-50.

26. The respiratory virus vaccine of paragraph 1, comprising:

at least one RNA polynucleotide having an open reading frame encoding a hMPV antigenic polypeptide or an immunogenic fragment thereof, a PIV3 antigenic polypeptide or an immunogenic fragment thereof, and a BetaCoV antigenic polypeptide or an immunogenic fragment thereof; or at least two or three RNA polynucleotides, one having an open reading frame encoding a hMPV antigenic polypeptide or an immunogenic fragment thereof, one having an open reading frame encoding a PIV3 antigenic polypeptide or an immunogenic fragment thereof, and one having an open reading frame encoding a BetaCoV antigenic polypeptide or an immunogenic fragment thereof.

27. The respiratory virus vaccine of paragraph 26, wherein the hMPV antigenic polypeptide comprises an amino acid sequence identified by any one of SEQ ID NO: 5-8 or an amino acid sequence having at least 90% or 95% identity to an amino acid sequence identified by any one of SEQ ID NO: 5-8, wherein the PIV3 antigenic polypeptide comprises an amino acid sequence identified by any one of SEQ ID NO: 12-13 or an amino acid sequence having at least 90% or 95% identity to an amino acid sequence identified by any one of SEQ ID NO: 12-13 and/or wherein the BetaCoV antigenic polypeptide comprises an amino acid sequence identified by any one of SEQ ID NO: 23-34 or an amino acid sequence having at least 90% or 95% identity to an amino acid sequence identified by any one of SEQ ID NO: 23-34.

28. The respiratory virus vaccine of paragraph 1, comprising:

at least one RNA polynucleotide having an open reading frame encoding a hMPV antigenic polypeptide or an immunogenic fragment thereof, a RSV antigenic polypeptide or an immunogenic fragment thereof, and a MeV antigenic polypeptide or an immunogenic fragment thereof; or at least two or three RNA polynucleotides, one having an open reading frame encoding a hMPV antigenic polypeptide or an immunogenic fragment thereof, one having an open reading frame encoding a RSV antigenic polypeptide or an immunogenic fragment thereof, and one having an open reading frame encoding a MeV antigenic polypeptide or an immunogenic fragment thereof.

29. The respiratory virus vaccine of paragraph 28, wherein the hMPV antigenic polypeptide comprises an amino acid sequence identified by any one of SEQ ID NO: 5-8 or an amino acid sequence having at least 90% or 95% identity to an amino acid sequence identified by any one of SEQ ID NO: 5-8, and/or wherein the MeV antigenic polypeptide comprises an amino acid sequence identified by any one of SEQ ID NO: 47-50 or an amino acid sequence having at least 90% or 95% identity to an amino acid sequence identified by any one of SEQ ID NO: 47-50.

30. The respiratory virus vaccine of paragraph 1, comprising:

at least one RNA polynucleotide having an open reading frame encoding a hMPV antigenic polypeptide or an immunogenic fragment thereof, a RSV antigenic polypeptide or an immunogenic fragment thereof, and a BetaCoV antigenic polypeptide or an immunogenic fragment thereof; or at least two or three RNA polynucleotides, one having an open reading frame encoding a hMPV antigenic polypeptide or an immunogenic fragment thereof, one having an open reading frame encoding a RSV antigenic polypeptide or an immunogenic fragment thereof, and one having an open reading frame encoding a BetaCoV antigenic polypeptide or an immunogenic fragment thereof.

31. The respiratory virus vaccine of paragraph 30, wherein the hMPV antigenic polypeptide comprises an amino acid sequence identified by any one of SEQ ID NO: 5-8 or an amino acid sequence having at least 90% or 95% identity to an amino acid sequence identified by any one of SEQ ID NO: 5-8, and/or wherein the BetaCoV antigenic polypeptide comprises an amino acid sequence identified by any one of SEQ ID NO: 23-34 or an amino acid sequence having at least 90% or 95% identity to an amino acid sequence identified by any one of SEQ ID NO: 23-34.

32. The respiratory virus vaccine of paragraph 1, comprising:

at least one RNA polynucleotide having an open reading frame encoding a hMPV antigenic polypeptide or an immunogenic fragment thereof, a MeV antigenic polypeptide or an immunogenic fragment thereof, and a BetaCoV antigenic polypeptide or an immunogenic fragment thereof; or at least two or three RNA polynucleotides, one having an open reading frame encoding a hMPV antigenic polypeptide or an immunogenic fragment thereof, one having an open reading frame encoding a MeV antigenic polypeptide or an immunogenic fragment thereof, and one having an open reading frame encoding a BetaCoV antigenic polypeptide or an immunogenic fragment thereof.

33. The respiratory virus vaccine of paragraph 32, wherein the hMPV antigenic polypeptide comprises an amino acid sequence identified by any one of SEQ ID NO: 5-8 or an amino acid sequence having at least 90% or 95% identity to an amino acid sequence identified by any one of SEQ ID NO: 5-8, wherein the MeV antigenic polypeptide comprises an amino acid sequence identified by any one of SEQ ID NO: 47-50 or an amino acid sequence having at least 90% or 95% identity to an amino acid sequence identified by any one of SEQ ID NO: 47-50, and/or wherein the BetaCoV antigenic polypeptide comprises an amino acid sequence identified by any one of SEQ ID NO: 23-34 or an amino acid sequence having at least 90% or 95% identity to an amino acid sequence identified by any one of SEQ ID NO: 23-34.

34. The respiratory virus vaccine of paragraph 1, comprising:

at least one RNA polynucleotide having an open reading frame encoding a PIV3 antigenic polypeptide or an immunogenic fragment thereof, a RSV antigenic polypeptide or an immunogenic fragment thereof, and a MeV antigenic polypeptide or an immunogenic fragment thereof; or at least two or three RNA polynucleotides, one having an open reading frame encoding a PIV3 antigenic polypeptide or an immunogenic fragment thereof, one having an open reading frame encoding a RSV antigenic polypeptide or an immunogenic fragment thereof, and one having an open reading frame encoding a MeV antigenic polypeptide or an immunogenic fragment thereof.

35. The respiratory virus vaccine of paragraph 34, wherein the PIV3 antigenic polypeptide comprises an amino acid sequence identified by any one of SEQ ID NO: 12-13 or an amino acid sequence having at least 90% or 95% identity to an amino acid sequence identified by any one of SEQ ID NO: 12-13, and/or wherein the MeV antigenic polypeptide comprises an amino acid sequence identified by any one of SEQ ID NO: 47-50 or an amino acid sequence having at least 90% or 95% identity to an amino acid sequence identified by any one of SEQ ID NO: 47-50.

36. The respiratory virus vaccine of paragraph 1, comprising:

at least one RNA polynucleotide having an open reading frame encoding a PIV3 antigenic polypeptide or an immunogenic fragment thereof, a RSV antigenic polypeptide or an immunogenic fragment thereof, and a BetaCoV antigenic polypeptide or an immunogenic fragment thereof; or at least two or three RNA polynucleotides, one having an open reading frame encoding a PIV3 antigenic polypeptide or an immunogenic fragment thereof, one having an open reading frame encoding a RSV antigenic polypeptide or an immunogenic fragment thereof, and one having an open reading frame encoding a BetaCoV antigenic polypeptide or an immunogenic fragment thereof.

37. The respiratory virus vaccine of paragraph 36, wherein the PIV3 antigenic polypeptide comprises an amino acid sequence identified by any one of SEQ ID NO: 12-13 or an amino acid sequence having at least 90% or 95% identity to an amino acid sequence identified by any one of SEQ ID NO: 12-13, and/or wherein the BetaCoV antigenic polypeptide comprises an amino acid sequence identified by any one of SEQ ID NO: 23-34 or an amino acid sequence having at least 90% or 95% identity to an amino acid sequence identified by any one of SEQ ID NO: 23-34.

38. The respiratory virus vaccine of paragraph 1, comprising:

at least one RNA polynucleotide having an open reading frame encoding a RSV antigenic polypeptide or an immunogenic fragment thereof, a MeV antigenic polypeptide or an immunogenic fragment thereof, and a BetaCoV antigenic polypeptide or an immunogenic fragment thereof; or at least two or three RNA polynucleotides, one having an open reading frame encoding a RSV antigenic polypeptide or an immunogenic fragment thereof, one having an open reading frame encoding a MeV antigenic polypeptide or an immunogenic fragment thereof, and one having an open reading frame encoding a BetaCoV antigenic polypeptide or an immunogenic fragment thereof.

39. The respiratory virus vaccine of paragraph 38, wherein the MeV antigenic polypeptide comprises an amino acid sequence identified by any one of SEQ ID NO: 47-50 or an amino acid sequence having at least 90% or 95% identity to an amino acid sequence identified by any one of SEQ ID NO: 47-50, and/or wherein the BetaCoV antigenic polypeptide comprises an amino acid sequence identified by any one of SEQ ID NO: 23-34 or an amino acid sequence having at least 90% or 95% identity to an amino acid sequence identified by any one of SEQ ID NO: 23-34.

40. The respiratory virus vaccine of paragraph 1, comprising:

at least one RNA polynucleotide having an open reading frame encoding a PIV3 antigenic polypeptide or an immunogenic fragment thereof, a MeV antigenic polypeptide or an immunogenic fragment thereof, and a BetaCoV antigenic polypeptide or an immunogenic fragment thereof; or at least two or three RNA polynucleotides, one having an open reading frame encoding a PIV3 antigenic polypeptide or an immunogenic fragment thereof, one having an open reading frame encoding a MeV antigenic polypeptide or an immunogenic fragment thereof, and one having an open reading frame encoding a BetaCoV antigenic polypeptide or an immunogenic fragment thereof.

41. The respiratory virus vaccine of paragraph 40, wherein the PIV3 antigenic polypeptide comprises an amino acid sequence identified by any one of SEQ ID NO: 12-13 or an amino acid sequence having at least 90% or 95% identity to an amino acid sequence identified by any one of SEQ ID NO: 12-13, wherein the MeV antigenic polypeptide comprises an amino acid sequence identified by any one of SEQ ID NO: 47-50 or an amino acid sequence having at least 90% or 95% identity to an amino acid sequence identified by any one of SEQ ID NO: 47-50, and/or wherein the BetaCoV antigenic polypeptide comprises an amino acid sequence identified by any one of SEQ ID NO: 23-34 or an amino acid sequence having at least 90% or 95% identity to an amino acid sequence identified by any one of SEQ ID NO: 23-34.

42. The respiratory virus vaccine of paragraph 1, comprising:

at least one RNA polynucleotide having an open reading frame encoding a hMPV antigenic polypeptide or an immunogenic fragment thereof, a PIV3 antigenic polypeptide or an immunogenic fragment thereof, a RSV antigenic polypeptide or an immunogenic fragment thereof, and a MeV antigenic polypeptide or an immunogenic fragment thereof; or at least two, three or four RNA polynucleotides, one having an open reading frame encoding a hMPV antigenic polypeptide or an immunogenic fragment thereof, one having an open reading frame encoding a PIV3 antigenic polypeptide or an immunogenic fragment thereof, one having an open reading frame encoding a RSV antigenic polypeptide or an immunogenic fragment thereof, and one having an open reading frame encoding a MeV antigenic polypeptide or an immunogenic fragment thereof.

43. The respiratory virus vaccine of paragraph 42, wherein the hMPV antigenic polypeptide comprises an amino acid sequence identified by any one of SEQ ID NO: 5-8 or an amino acid sequence having at least 90% or 95% identity to an amino acid sequence identified by any one of SEQ ID NO: 5-8, wherein the PIV3 antigenic polypeptide comprises an amino acid sequence identified by any one of SEQ ID NO: 12-13 or an amino acid sequence having at least 90% or 95% identity to an amino acid sequence identified by any one of SEQ ID NO: 12-13, and/or wherein the MeV antigenic polypeptide comprises an amino acid sequence identified by any one of SEQ ID NO: 47-50 or an amino acid sequence having at least 90% or 95% identity to an amino acid sequence identified by any one of SEQ ID NO: 47-50.

44. The respiratory virus vaccine of paragraph 1, comprising:

at least one RNA polynucleotide having an open reading frame encoding a hMPV antigenic polypeptide or an immunogenic fragment thereof, a PIV3 antigenic polypeptide or an immunogenic fragment thereof, a RSV antigenic polypeptide or an immunogenic fragment thereof, and a BetaCoV antigenic polypeptide or an immunogenic fragment thereof; or at least two, three or four RNA polynucleotides, one having an open reading frame encoding a hMPV antigenic polypeptide or an immunogenic fragment thereof, one having an open reading frame encoding a PIV3 antigenic polypeptide or an immunogenic fragment thereof, one having an open reading frame encoding a RSV antigenic polypeptide or an immunogenic fragment thereof, and one having an open reading frame encoding a BetaCoV antigenic polypeptide or an immunogenic fragment thereof.

45. The respiratory virus vaccine of paragraph 44, wherein the hMPV antigenic polypeptide comprises an amino acid sequence identified by any one of SEQ ID NO: 5-8 or an amino acid sequence having at least 90% or 95% identity to an amino acid sequence identified by any one of SEQ ID NO: 5-8, wherein the PIV3 antigenic polypeptide comprises an amino acid sequence identified by any one of SEQ ID NO: 12-13 or an amino acid sequence having at least 90% or 95% identity to an amino acid sequence identified by any one of SEQ ID NO: 12-13, and/or wherein the BetaCoV antigenic polypeptide comprises an amino acid sequence identified by any one of SEQ ID NO: 24-34 or an amino acid sequence having at least 90% or 95% identity to an amino acid sequence identified by any one of SEQ ID NO: 24-34.

46. The respiratory virus vaccine of paragraph 1, comprising:

at least one RNA polynucleotide having an open reading frame encoding a hMPV antigenic polypeptide or an immunogenic fragment thereof, a PIV3 antigenic polypeptide or an immunogenic fragment thereof, a MeV antigenic polypeptide or an immunogenic fragment thereof, and a BetaCoV antigenic polypeptide or an immunogenic fragment thereof; or at least two, three or four RNA polynucleotides, one having an open reading frame encoding a hMPV antigenic polypeptide or an immunogenic fragment thereof, one having an open reading frame encoding a PIV3 antigenic polypeptide or an immunogenic fragment thereof, one having an open reading frame encoding a MeV antigenic polypeptide or an immunogenic fragment thereof, and one having an open reading frame encoding a BetaCoV antigenic polypeptide or an immunogenic fragment thereof.

47. The respiratory virus vaccine of paragraph 46, wherein the hMPV antigenic polypeptide comprises an amino acid sequence identified by any one of SEQ ID NO: 5-8 or an amino acid sequence having at least 90% or 95% identity to an amino acid sequence identified by any one of SEQ ID NO: 5-8, wherein the PIV3 antigenic polypeptide comprises an amino acid sequence identified by any one of SEQ ID NO: 12-13 or an amino acid sequence having at least 90% or 95% identity to an amino acid sequence identified by any one of SEQ ID NO: 12-13, wherein the MeV antigenic polypeptide comprises an amino acid sequence identified by any one of SEQ ID NO: 47-50 or an amino acid sequence having at least 90% or 95% identity to an amino acid sequence identified by any one of SEQ ID NO: 47-50, and/or wherein the BetaCoV antigenic polypeptide comprises an amino acid sequence identified by any one of SEQ ID NO: 24-34 or an amino acid sequence having at least 90% or 95% identity to an amino acid sequence identified by any one of SEQ ID NO: 24-34.

48. The respiratory virus vaccine of paragraph 1, comprising:

at least one RNA polynucleotide having an open reading frame encoding a hMPV antigenic polypeptide or an immunogenic fragment thereof, a RSV antigenic polypeptide or an immunogenic fragment thereof, a MeV antigenic polypeptide or an immunogenic fragment thereof, and a BetaCoV antigenic polypeptide or an immunogenic fragment thereof; or at least two, three or four RNA polynucleotides, one having an open reading frame encoding a hMPV antigenic polypeptide or an immunogenic fragment thereof, one having an open reading frame encoding a RSV antigenic polypeptide or an immunogenic fragment thereof, one having an open reading frame encoding a MeV antigenic polypeptide or an immunogenic fragment thereof, and one having an open reading frame encoding a BetaCoV antigenic polypeptide or an immunogenic fragment thereof.

49. The respiratory virus vaccine of paragraph 48, wherein the hMPV antigenic polypeptide comprises an amino acid sequence identified by any one of SEQ ID NO: 5-8 or an amino acid sequence having at least 90% or 95% identity to an amino acid sequence identified by any one of SEQ ID NO: 5-8, wherein the MeV antigenic polypeptide comprises an amino acid sequence identified by any one of SEQ ID NO: 47-50 or an amino acid sequence having at least 90% or 95% identity to an amino acid sequence identified by any one of SEQ ID NO: 47-50, and/or wherein the BetaCoV antigenic polypeptide comprises an amino acid sequence identified by any one of SEQ ID NO: 24-34 or an amino acid sequence having at least 90% or 95% identity to an amino acid sequence identified by any one of SEQ ID NO: 24-34.

50. The respiratory virus vaccine of paragraph 1, comprising:

at least one RNA polynucleotide having an open reading frame encoding a PIV3 antigenic polypeptide or an immunogenic fragment thereof, a RSV antigenic polypeptide or an immunogenic fragment thereof, a MeV antigenic polypeptide or an immunogenic fragment thereof, and a BetaCoV antigenic polypeptide or an immunogenic fragment thereof; or at least two, three or four RNA polynucleotides, one having an open reading frame encoding a PIV3 antigenic polypeptide or an immunogenic fragment thereof, one having an open reading frame encoding a RSV antigenic polypeptide or an immunogenic fragment thereof, one having an open reading frame encoding a MeV antigenic polypeptide or an immunogenic fragment thereof, and one having an open reading frame encoding a BetaCoV antigenic polypeptide or an immunogenic fragment thereof.

51. The respiratory virus vaccine of paragraph 50, wherein the PIV3 antigenic polypeptide comprises an amino acid sequence identified by any one of SEQ ID NO: 12-13 or an amino acid sequence having at least 90% or 95% identity to an amino acid sequence identified by any one of SEQ ID NO: 12-13, wherein the MeV antigenic polypeptide comprises an amino acid sequence identified by any one of SEQ ID NO: 47-50 or an amino acid sequence having at least 90% or 95% identity to an amino acid sequence identified by any one of SEQ ID NO: 47-50, and/or wherein the BetaCoV antigenic polypeptide comprises an amino acid sequence identified by any one of SEQ ID NO: 24-34 or an amino acid sequence having at least 90% or 95% identity to an amino acid sequence identified by any one of SEQ ID NO: 24-34.

52. The respiratory virus vaccine of paragraph 1, comprising:

at least one RNA polynucleotide having an open reading frame encoding a hMPV antigenic polypeptide or an immunogenic fragment thereof, a PIV3 antigenic polypeptide or an immunogenic fragment thereof, a RSV antigenic polypeptide or an immunogenic fragment thereof, a MeV antigenic polypeptide or an immunogenic fragment thereof, and a BetaCoV antigenic polypeptide or an immunogenic fragment thereof; or at least two, three, four or five RNA polynucleotides, one having an open reading frame encoding a hMPV antigenic polypeptide or an immunogenic fragment thereof, one having an open reading frame encoding a PIV3 antigenic polypeptide or an immunogenic fragment thereof, one having an open reading frame encoding a RSV antigenic polypeptide or an immunogenic fragment thereof, one having an open reading frame encoding a MeV antigenic polypeptide or an immunogenic fragment thereof, and one having an open reading frame encoding a BetaCoV antigenic polypeptide or an immunogenic fragment thereof.

53. The respiratory virus vaccine of paragraph 52, wherein the hMPV antigenic polypeptide comprises an amino acid sequence identified by any one of SEQ ID NO: 5-8 or an amino acid sequence having at least 90% or 95% identity to an amino acid sequence identified by any one of SEQ ID NO: 5-8, wherein the PIV3 antigenic polypeptide comprises an amino acid sequence identified by any one of SEQ ID NO: 12-13 or an amino acid sequence having at least 90% or 95% identity to an amino acid sequence identified by any one of SEQ ID NO: 12-13, wherein the MeV antigenic polypeptide comprises an amino acid sequence identified by any one of SEQ ID NO: 47-50 or an amino acid sequence having at least 90% or 95% identity to an amino acid sequence identified by any one of SEQ ID NO: 47-50, and/or wherein the BetaCoV antigenic polypeptide comprises an amino acid sequence identified by any one of SEQ ID NO: 24-34 or an amino acid sequence having at least 90% or 95% identity to an amino acid sequence identified by any one of SEQ ID NO: 24-34.

54. The vaccine of any one of paragraphs 1-53, wherein at least one RNA polynucleotide has less than 80% identity to wild-type mRNA sequence.

55. The vaccine of any one of paragraphs 1-53, wherein at least one RNA polynucleotide has at least 80% identity to wild-type mRNA sequence, but does not include wild-type mRNA sequence.

56. The vaccine of any one of paragraphs 1-55, wherein at least one antigenic polypeptide has membrane fusion activity, attaches to cell receptors, causes fusion of viral and cellular membranes, and/or is responsible for binding of the virus to a cell being infected.

57. The vaccine of any one of paragraphs 1-56, wherein at least one RNA polynucleotide comprises at least one chemical modification.

58. The vaccine of paragraph 57, wherein the chemical modification is selected from pseudouridine, N1-methylpseudouridine, N1-ethylpseudouridine, 2-thiouridine, 4'-thiouridine, 5-methylcytosine, 5-methyluridine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine and 2'-O-methyl uridine.

59. The vaccine of paragraph 57 or 58, wherein the chemical modification is in the 5-position of the uracil.

60. The vaccine of any one of paragraphs 57-59, wherein the chemical modification is a N1-methylpseudouridine or N1-ethylpseudouridine.

61. The vaccine of any one of paragraphs 57-60, wherein at least 80%, at least 90% or 100% of the uracil in the open reading frame have a chemical modification.

62. The vaccine of any one of paragraphs 1-61, wherein at least one RNA polynucleotide further encodes at least one 5' terminal cap, optionally wherein the 5' terminal cap is 7mG(5')ppp(5')NlmpNp.

63. The vaccine of any one of paragraphs 1-62, wherein at least one antigenic polypeptide or immunogenic fragment thereof is fused to a signal peptide selected from: a HuIgGk signal peptide (METPAQLLFLLLLWLPDTTG; SEQ ID NO: 15); IgE heavy chain epsilon-1 signal peptide (MDWTWILFLVAAATRVHS; SEQ ID NO: 16); Japanese encephalitis PRM signal sequence (MLGSNSGQRVVFTILLLLVAPAYS; SEQ ID NO: 17), VSVg protein signal sequence (MKCLLYLAFLFIGVNCA; SEQ ID NO: 18) and Japanese encephalitis JEV signal sequence (MWLVSLAIVTACAGA; SEQ ID NO:19).

64. The vaccine of paragraph 63, wherein the signal peptide is fused to the N-terminus or the C-terminus of at least one antigenic polypeptide.

65. The vaccine of any one of paragraphs 1-64, wherein the antigenic polypeptide or immunogenic fragment thereof comprises a mutated N-linked glycosylation site.

66. The vaccine of any one of paragraphs 1-65 formulated in a nanoparticle, optionally a a lipid nanoparticle.

67. The vaccine of paragraph 66, wherein the lipid nanoparticle comprises a cationic lipid, a PEG-modified lipid, a sterol and a non-cationic lipid; optionally wherein the lipid nanoparticle carrier comprises a molar ratio of about 20-60% cationic lipid, 0.5-15% PEG-modified lipid, 25-55% sterol, and 25% non-cationic lipid; optionally wherein the cationic lipid is an ionizable cationic lipid and the non-cationic lipid is a neutral lipid, and the sterol is a cholesterol; and optionally wherein the cationic lipid is selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319). Formula (II)

68. The vaccine of paragraph 66 or 67, wherein the nanoparticle (e.g., lipid nanoparticle) comprises a compound of Formula (I) and/or Formula (II), optionally Compound 3, 18, 20, 25, 26, 29, 30, 60, 108-112, or 122.

69. The vaccine of any one of paragraphs 1-68 further comprising an adjuvant, optionally a flagellin protein or peptide that optionally comprises an amino acid sequence identified by any one of SEQ ID NO: 54-56.

70. The vaccine of any one of paragraphs 1-69, wherein the open reading frame is codon-optimized.

71. The vaccine of any one of paragraphs 1-70 formulated in an effective amount to produce an antigen-specific immune response.

72. A method of inducing an immune response in a subject, the method comprising administering to the subject the vaccine of any one of paragraphs 1-71 in an amount effective to produce an antigen-specific immune response in the subject.

73. The method of paragraph 72, wherein the subject is administered a single dose of the vaccine, or wherein the subject is administered a first dose and then a booster dose of the vaccine.

74. The method of paragraph 72 or 73, wherein the vaccine is administered to the subject by intradermal injection or intramuscular injection.

75. The method of any one of paragraphs 72-74, wherein an anti-antigenic polypeptide antibody titer produced in the subject is increased by at least 1 log relative to a control, and/or wherein the anti-antigenic polypeptide antibody titer produced in the subject is increased at least 2 times relative to a control.

76. The method of any one of paragraphs 72-75, wherein the control is an anti-antigenic polypeptide antibody titer produced in a subject who has not been administered a vaccine against the virus, and/or wherein the control is an anti-antigenic polypeptide antibody titer produced in a subject who has been administered a live attenuated vaccine or an inactivated vaccine against the virus, and/or, wherein the control is an anti-antigenic polypeptide antibody titer produced in a subject who has been administered a recombinant protein vaccine or purified protein vaccine against the virus, and/or wherein the control is an anti-antigenic polypeptide antibody titer produced in a subject who has been administered a VLP vaccine against the virus.

77. The method of any one of paragraphs 72-76, wherein the effective amount is a dose equivalent to an at least 2-fold reduction in the standard of care dose of a recombinant protein vaccine or a purified protein vaccine against the virus, and wherein an anti-antigenic polypeptide antibody titer produced in the subject is equivalent to an anti-antigenic polypeptide antibody titer produced in a control subject administered the standard of care dose of a recombinant protein vaccine or a purified protein vaccine against the virus, respectively; and/or wherein the effective amount is a dose equivalent to an at least 2-fold reduction in the standard of care dose of a live attenuated vaccine or an inactivated vaccine against the virus, and wherein an anti-antigenic polypeptide antibody titer produced in the subject is equivalent to an anti-antigenic polypeptide antibody titer produced in a control subject administered the standard of care dose of a live attenuated vaccine or an inactivated vaccine against the virus, respectively; and/or wherein the effective amount is a dose equivalent to an at least 2-fold reduction in the standard of care dose of a VLP vaccine against the virus, and wherein an anti-antigenic polypeptide antibody titer produced in the subject is equivalent to an anti-antigenic polypeptide antibody titer produced in a control subject administered the standard of care dose of a VLP vaccine against the virus.

78. The method of any one of paragraphs 72-77, wherein the effective amount is a total dose of 50 μg-1000 μg, optionally wherein the effective amount is a dose of 25 μg, 100 μg, 400 μg, or 500 μg administered to the subject a total of two times.

79. The method of any one of paragraphs 72-78, wherein the efficacy of the vaccine against the virus is greater than 65%; and/or wherein the vaccine immunizes the subject against the virus for up to 2 years or wherein the vaccine immunizes the subject against the virus for more than 2 years.

80. The method of any one of paragraphs 72-79, wherein the subject has an age of about 5 years old or younger or wherein the subject has an age of about 60 years old or older; and/or wherein the subject has a chronic pulmonary disease; and/or the subject has been exposed to the virus, wherein the subject is infected with the virus, or wherein the subject is at risk of infection by the virus; and/or wherein the subject is immunocompromised.

81. The respiratory virus vaccine of any one of paragraphs 1-71, comprising at least one (e.g., at least two, at least three, at least four, or at least five) RNA polynucleotide having an open reading frame encoding at least one (e.g., at least two, at least three, at least four, or at least five) antigenic polypeptide selected from hMPV antigenic polypeptides (SEQ ID NO: 5-8), PIV3 antigenic polypeptides (SEQ ID NO: 12-13), RSV antigenic polypeptides, MeV antigenic polypeptides (SEQ ID NO: 47-50) and BetaCoV antigenic polypeptides (e.g., MERS-CoV, SARS-CoV, HCoV-OC43, HCoV-229E, HCoV-NL63, HCoV-NL, HCoV-NH or HCoV-HKU1; (SEQ ID NO: 24-34)), formulated in a cationic lipid nanoparticle (a) having a molar ratio of about 20-60% cationic lipid, about 5-25% non-cationic lipid, about 25-55% sterol, and about 0.5-15% PEG-modified lipid, and/or (b) comprising a compound of Formula (I) and/or Formula (II), wherein the at least one (e.g., at least two, at least three, at least four, or at least five) RNA polynucleotide comprises at least one chemical modification.

82. The respiratory virus vaccine of any one of paragraphs 1-71, comprising at least one (e.g., at least two, at least three, at least four, or at least five) RNA polynucleotide having an open reading frame encoding at least one (e.g., at least two, at least three, at least four, or at least five) antigenic polypeptide selected from hMPV antigenic polypeptides (SEQ ID NO: 5-8), PIV3 antigenic polypeptides (SEQ ID NO: 12-13), RSV antigenic polypeptides, MeV antigenic polypeptides (SEQ ID NO: 47-50) and BetaCoV antigenic polypeptides (e.g., MERS-CoV, SARS-CoV, HCoV-OC43, HCoV-229E, HCoV-NL63, HCoV-NL, HCoV-NH or HCoV-HKU1; (SEQ ID NO: 24-34)), formulated in a cationic lipid nanoparticle (a) having a molar ratio of about 20-60% cationic lipid, about 5-25% non-cationic lipid, about 25-55% sterol, and about 0.5-15% PEG-modified lipid, and/or (b) comprising at least one (e.g., at least 1, 2, 3, 4, 5, 6, 7, 8, 9, 10, 11, 12, 13, or 14) Compound selected from Compounds 3, 18, 20, 25, 26, 29, 30, 60, 108-112 and 122.

83. The respiratory virus vaccine of paragraphs 81 or 82, wherein the at least one antigenic polypeptide is selected from hMPV antigentic polypeptides (e.g., SEQ ID NO: 5-8).

84. The respiratory virus vaccine of any one of paragraphs 81-83, wherein the at least one antigenic polypeptide is selected from PIV3 antigentic polypeptides (e.g., SEQ ID NO: 12-13).

85. The respiratory virus vaccine of any one of paragraphs 81-84, wherein the at least one antigenic polypeptide is selected from RSV antigentic polypeptides.

86. The respiratory virus vaccine of any one of paragraphs 81-85, wherein the at least one antigenic polypeptide is selected from MeV antigentic polypeptides (e.g., SEQ ID NO: 47-50).

87. The respiratory virus vaccine of any one of paragraphs 81-86, wherein the at least one antigenic polypeptide is selected from BetaCoV antigentic polypeptides (e.g., SEQ ID NO: 24-34).

88. The respiratory virus vaccine of paragraph 87, wherein the BetaCoV antigentic polypeptides are MERS antigentic polypeptides.

89. The respiratory virus vaccine of paragraph 87, wherein the BetaCoV antigentic polypeptides are SARS antigentic polypeptides.

90. The respiratory virus vaccine of any one of paragraphs 81-89, wherein the at least one (e.g., at least two, at least three, at least four, or at least five) RNA polynucleotide comprises at least one chemical modification (e.g., selected from pseudouridine, N1-methylpseudouridine, N1-ethylpseudouridine, 2-thiouridine, 4'-thiouridine, 5-methylcytosine, 5-methyluridine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine and 2'-O-methyl uridine).

91. A respiratory virus vaccine, comprising:

at least one messenger ribonucleic acid (mRNA) polynucleotide having a 5' terminal cap, an open reading frame encoding at least one respiratory virus antigenic polypeptide, and a 3' polyA tail.

92. The vaccine of paragraph 91, wherein the at least one mRNA polynucleotide comprises a sequence identified by any one of SEQ ID NO: 57-80.

93. The vaccine of paragraph 91 or 92, wherein the 5' terminal cap is or comprises 7mG(5')ppp(5')NlmpNp.

94. The vaccine of any one of paragraphs 91-93, wherein 100% of the uracil in the open reading frame is modified to include N1-methyl pseudouridine at the 5-position of the uracil.

95. The vaccine of any one of paragraphs 91-94, wherein the vaccine is formulated in a lipid nanoparticle comprising: DLin-MC3-DMA; cholesterol; 1,2-Distearoyl-sn-glycero-3-phosphocholine (DSPC); and polyethylene glycol (PEG) 2000-DMG.

96. The vaccine of paragraph 95, wherein the lipid nanoparticle further comprises trisodium citrate buffer, sucrose and water.

97. A respiratory syncytial virus (RSV) vaccine, comprising:

at least one messenger ribonucleic acid (mRNA) polynucleotide having a 5' terminal cap 7mG(5')ppp(5')NlmpNp, a sequence identified by any one of SEQ ID NO: 57-80 and a 3' polyA tail, formulated in a lipid nanoparticle comprising DLin-MC3-DMA, cholesterol, 1,2-Distearoyl-sn-glycero-3-phosphocholine (DSPC), and polyethylene glycol (PEG) 2000-DMG, wherein the uracil nucleotides of the sequence identified by any one of SEQ ID NO: 57-80 are modified to include N1-methyl pseudouridine at the 5-position of the uracil nucleotide.

This disclosure is not limited in its application to the details of construction and the arrangement of components set forth in the following description or illustrated in the drawings. The disclosure is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

EXAMPLES

Example 1: Manufacture of Polynucleotides

According to the present disclosure, the manufacture of polynucleotides and/or parts or regions thereof may be accomplished utilizing the methods taught in International Publication WO2014/152027, entitled "Manufacturing Methods for Production of RNA Transcripts," the contents of which is incorporated herein by reference in its entirety.

Purification methods may include those taught in International Publication WO2014/152030 and International Publication WO2014/152031, each of which is incorporated herein by reference in its entirety.

Detection and characterization methods of the polynucleotides may be performed as taught in International Publication WO2014/144039, which is incorporated herein by reference in its entirety.

Characterization of the polynucleotides of the disclosure may be accomplished using polynucleotide mapping, reverse transcriptase sequencing, charge distribution analysis, detection of RNA impurities, or any combination of two or more of the foregoing. "Characterizing" comprises determining the RNA transcript sequence, determining the purity of the RNA transcript, or determining the charge heterogeneity of the RNA transcript, for example. Such methods are taught in, for example, International Publication WO2014/144711 and International Publication WO2014/144767, the content of each of which is incorporated herein by reference in its entirety.

Example 2: Chimeric Polynucleotide Synthesis

According to the present disclosure, two regions or parts of a chimeric polynucleotide may be joined or ligated using triphosphate chemistry. A first region or part of 100 nucleotides or less is chemically synthesized with a 5' monophosphate and terminal 3'desOH or blocked OH, for example. If the region is longer than 80 nucleotides, it may be synthesized as two strands for ligation.

If the first region or part is synthesized as a non-positionally modified region or part using in vitro transcription (IVT), conversion the 5'monophosphate with subsequent capping of the 3' terminus may follow.

Monophosphate protecting groups may be selected from any of those known in the art.

The second region or part of the chimeric polynucleotide may be synthesized using either chemical synthesis or IVT methods. IVT methods may include an RNA polymerase that can utilize a primer with a modified cap. Alternatively, a cap of up to 130 nucleotides may be chemically synthesized and coupled to the IVT region or part.

For ligation methods, ligation with DNA T4 ligase, followed by treatment with DNase should readily avoid concatenation.

The entire chimeric polynucleotide need not be manufactured with a phosphate-sugar backbone. If one of the regions or parts encodes a polypeptide, then such region or part may comprise a phosphate-sugar backbone.

Ligation is then performed using any known click chemistry, orthoclick chemistry, solulink, or other bioconjugate chemistries known to those in the art.

Synthetic Route

The chimeric polynucleotide may be made using a series of starting segments. Such segments include:

(a) a capped and protected 5' segment comprising a normal 3'OH (SEG. 1)

(b) a 5' triphosphate segment, which may include the coding region of a polypeptide and a normal 3'OH (SEG. 2)

(c) a 5' monophosphate segment for the 3' end of the chimeric polynucleotide (e.g., the tail) comprising cordycepin or no 3'OH (SEG. 3)

After synthesis (chemical or IVT), segment 3 (SEG. 3) may be treated with cordycepin and then with pyrophosphatase to create the 5' monophosphate.

Segment 2 (SEG. 2) may then be ligated to SEG. 3 using RNA ligase. The ligated polynucleotide is then purified and treated with pyrophosphatase to cleave the diphosphate. The treated SEG.2-SEG. 3 construct may then be purified and SEG. 1 is ligated to the 5' terminus. A further purification step of the chimeric polynucleotide may be performed.

Where the chimeric polynucleotide encodes a polypeptide, the ligated or joined segments may be represented as: 5'UTR (SEG. 1), open reading frame or ORF (SEG. 2) and 3'UTR+PolyA (SEG. 3).

The yields of each step may be as much as 90-95%.

Example 3: PCR for cDNA Production

PCR procedures for the preparation of cDNA may be performed using 2×KAPA HIFI™ HotStart ReadyMix by Kapa Biosystems (Woburn, Mass.). This system includes 2×KAPA ReadyMix 12.5 μl; Forward Primer (10 μM) 0.75 μl; Reverse Primer (10 μM) 0.75 μl; Template cDNA 100 ng; and $dH_2O$ diluted to 25.0 μl. The reaction conditions may be at 95° C. for 5 min. The reaction may be performed for 25 cycles of 98° C. for 20 sec, then 58° C. for 15 sec, then 72° C. for 45 sec, then 72° C. for 5 min, then 4° C. to termination.

The reaction may be cleaned up using Invitrogen's PURELINK™ PCR Micro Kit (Carlsbad, Calif.) per manufacturer's instructions (up to 5 μg). Larger reactions may require a cleanup using a product with a larger capacity. Following the cleanup, the cDNA may be quantified using the NANODROP™ and analyzed by agarose gel electrophoresis to confirm that the cDNA is the expected size. The cDNA may then be submitted for sequencing analysis before proceeding to the in vitro transcription reaction.

Example 4: In Vitro Transcription (IVT)

The in vitro transcription reaction generates RNA polynucleotides. Such polynucleotides may comprise a region or part of the polynucleotides of the disclosure, including chemically modified RNA (e.g., mRNA) polynucleotides. The chemically modified RNA polynucleotides can be uniformly modified polynucleotides. The in vitro transcription reaction utilizes a custom mix of nucleotide triphosphates (NTPs). The NTPs may comprise chemically modified NTPs, or a mix of natural and chemically modified NTPs, or natural NTPs.

A typical in vitro transcription reaction includes the following:

| | | |
|---|---|---|
| 1) | Template cDNA | 1.0 μg |
| 2) | 10x transcription buffer (400 mM Tris-HCl pH 8.0, 190 mM $MgCl_2$, 50 mM DTT, 10 mM Spermidine) | 2.0 μl |
| 3) | Custom NTPs (25 mM each) | 0.2 μl |
| 4) | RNase Inhibitor | 20 U |
| 5) | T7 RNA polymerase | 3000 U |
| 6) | $dH_20$ | up to 20.0 μl. and |
| 7) | Incubation at 37° C. for 3 hr-5 hrs. | |

The crude IVT mix may be stored at 4° C. overnight for cleanup the next day. 1 U of RNase-free DNase may then be used to digest the original template. After 15 minutes of incubation at 37° C., the mRNA may be purified using Ambion's MEGACLEAR™ Kit (Austin, Tex.) following the manufacturer's instructions. This kit can purify up to 500 μg of RNA. Following the cleanup, the RNA polynucleotide may be quantified using the NanoDrop and analyzed by agarose gel electrophoresis to confirm the RNA polynucleotide is the proper size and that no degradation of the RNA has occurred.

Example 5: Enzymatic Capping

Capping of a RNA polynucleotide is performed as follows where the mixture includes: IVT RNA 60 μg-180 μg and $dH_2O$ up to 72 μl. The mixture is incubated at 65° C. for 5 minutes to denature RNA, and then is transferred immediately to ice.

The protocol then involves the mixing of 10× Capping Buffer (0.5 M Tris-HCl (pH 8.0), 60 mM KCl, 12.5 mM $MgCl_2$) (10.0 μl); 20 mM GTP (5.0 μl); 20 mM S-Adenosyl Methionine (2.5 μl); RNase Inhibitor (100 U); 2'-O-Methyltransferase (400U); Vaccinia capping enzyme (Guanylyl transferase) (40 U); $dH_2O$ (Up to 28 μl); and incubation at 37° C. for 30 minutes for 60 μg RNA or up to 2 hours for 180 μg of RNA.

The RNA polynucleotide may then be purified using Ambion's MEGACLEAR™ Kit (Austin, Tex.) following the manufacturer's instructions. Following the cleanup, the RNA may be quantified using the NANODROP™ (ThermoFisher, Waltham, Mass.) and analyzed by agarose gel electrophoresis to confirm the RNA polynucleotide is the proper size and that no degradation of the RNA has occurred. The RNA polynucleotide product may also be sequenced by running a reverse-transcription-PCR to generate the cDNA for sequencing.

Example 6: PolyA Tailing Reaction

Without a poly-T in the cDNA, a poly-A tailing reaction must be performed before cleaning the final product. This is done by mixing capped IVT RNA (100 μl); RNase Inhibitor (20 U); 10× Tailing Buffer (0.5 M Tris-HCl (pH 8.0), 2.5 M NaCl, 100 mM $MgCl_2$) (12.0 μl); 20 mM ATP (6.0 μl); Poly-A Polymerase (20 U); $dH_2O$ up to 123.5 μl and incubation at 37° C. for 30 min. If the poly-A tail is already in the transcript, then the tailing reaction may be skipped and proceed directly to cleanup with Ambion's MEGACLEAR™ kit (Austin, Tex.) (up to 500 μg). Poly-A Polymerase may be a recombinant enzyme expressed in yeast.

It should be understood that the processivity or integrity of the polyA tailing reaction may not always result in an exact size polyA tail. Hence, polyA tails of approximately between 40-200 nucleotides, e.g., about 40, 50, 60, 70, 80, 90, 91, 92, 93, 94, 95, 96, 97, 98, 99, 100, 101, 102, 103, 104, 105, 106, 107, 108, 109, 110, 150-165, 155, 156, 157, 158, 159, 160, 161, 162, 163, 164 or 165 are within the scope of the present disclosure.

Example 7: Natural 5' Caps and 5' Cap Analogues

5'-capping of polynucleotides may be completed concomitantly during the in vitro-transcription reaction using the following chemical RNA cap analogs to generate the 5'-guanosine cap structure according to manufacturer protocols: 3'-O-Me-m7G(5')ppp(5') G [the ARCA cap]; G(5')

ppp(5')A; G(5')ppp(5')G; m7G(5')ppp(5')A; m7G(5')ppp (5')G (New England BioLabs, Ipswich, Mass.). 5'-capping of modified RNA may be completed post-transcriptionally using a Vaccinia Virus Capping Enzyme to generate the "Cap 0" structure: m7G(5')ppp(5')G (New England BioLabs, Ipswich, Mass.). Cap 1 structure may be generated using both Vaccinia Virus Capping Enzyme and a 2'-O methyl-transferase to generate: m7G(5')ppp(5')G-2'-O-methyl. Cap 2 structure may be generated from the Cap 1 structure followed by the 2'-O-methylation of the 5'-antepenultimate nucleotide using a 2'-O methyl-transferase. Cap 3 structure may be generated from the Cap 2 structure followed by the 2'-O-methylation of the 5'-preantepenultimate nucleotide using a 2'-O methyl-transferase. Enzymes are preferably derived from a recombinant source.

When transfected into mammalian cells, the modified mRNAs have a stability of between 12-18 hours or more than 18 hours, e.g., 24, 36, 48, 60, 72 or greater than 72 hours.

Example 8: Capping Assays

Protein Expression Assay

Polynucleotides (e.g., mRNA) encoding a polypeptide, containing any of the caps taught herein, can be transfected into cells at equal concentrations. The amount of protein secreted into the culture medium can be assayed by ELISA at 6, 12, 24 and/or 36 hours post-transfection. Synthetic polynucleotides that secrete higher levels of protein into the medium correspond to a synthetic polynucleotide with a higher translationally-competent cap structure.

Purity Analysis Synthesis

RNA (e.g., mRNA) polynucleotides encoding a polypeptide, containing any of the caps taught herein can be compared for purity using denaturing Agarose-Urea gel electrophoresis or HPLC analysis. RNA polynucleotides with a single, consolidated band by electrophoresis correspond to the higher purity product compared to polynucleotides with multiple bands or streaking bands. Chemically modified RNA polynucleotides with a single HPLC peak also correspond to a higher purity product. The capping reaction with a higher efficiency provides a more pure polynucleotide population.

Cytokine Analysis

RNA (e.g., mRNA) polynucleotides encoding a polypeptide, containing any of the caps taught herein can be transfected into cells at multiple concentrations. The amount of pro-inflammatory cytokines, such as TNF-alpha and IFN-beta, secreted into the culture medium can be assayed by ELISA at 6, 12, 24 and/or 36 hours post-transfection. RNA polynucleotides resulting in the secretion of higher levels of pro-inflammatory cytokines into the medium correspond to a polynucleotides containing an immune-activating cap structure.

Capping Reaction Efficiency

RNA (e.g., mRNA) polynucleotides encoding a polypeptide, containing any of the caps taught herein can be analyzed for capping reaction efficiency by LC-MS after nuclease treatment. Nuclease treatment of capped polynucleotides yield a mixture of free nucleotides and the capped 5'-5-triphosphate cap structure detectable by LC-MS. The amount of capped product on the LC-MS spectra can be expressed as a percent of total polynucleotide from the reaction and correspond to capping reaction efficiency. The cap structure with a higher capping reaction efficiency has a higher amount of capped product by LC-MS.

Example 9: Agarose Gel Electrophoresis of Modified RNA or RT PCR Products

Individual RNA polynucleotides (200-400 ng in a 20 μl volume) or reverse transcribed PCR products (200-400 ng) may be loaded into a well on a non-denaturing 1.2% Agarose E-Gel (Invitrogen, Carlsbad, Calif.) and run for 12-15 minutes, according to the manufacturer protocol.

Example 10: Nanodrop Modified RNA Quantification and UV Spectral Data

Chemically modified RNA polynucleotides in TE buffer (1 μl) are used for Nanodrop UV absorbance readings to quantitate the yield of each polynucleotide from an chemical synthesis or in vitro transcription reaction.

Example 11: Formulation of Modified mRNA Using Lipidoids

RNA (e.g., mRNA) polynucleotides may be formulated for in vitro experiments by mixing the polynucleotides with the lipidoid at a set ratio prior to addition to cells. In vivo formulation may require the addition of extra ingredients to facilitate circulation throughout the body. To test the ability of these lipidoids to form particles suitable for in vivo work, a standard formulation process used for siRNA-lipidoid formulations may be used as a starting point. After formation of the particle, polynucleotide is added and allowed to integrate with the complex. The encapsulation efficiency is determined using a standard dye exclusion assays.

Example 12: Immunogenicity Study

The instant study is designed to test the immunogenicity in mice of candidate hMPV vaccines comprising a mRNA polynucleotide encoding Fusion (F) glycoprotein, major surface glycoprotein G, or a combination thereof, obtained from hMPV.

Mice are immunized intravenously (IV), intramuscularly (IM), or intradermally (ID) with candidate vaccines. Candidate vaccines are chemically modified or unmodified. A total of four immunizations are given at 3-week intervals (i.e., at weeks 0, 3, 6, and 9), and sera are collected after each immunization until weeks 33-51. Serum antibody titers against Fusion (F) glycoprotein or major surface glycoprotein (G) protein are determined by ELISA. Sera collected from each mouse during weeks 10-16 are pooled, and total IgG purified. Purified antibodies are used for immunoelectron microscopy, antibody-affinity testing, and in vitro protection assays.

Example 13: hMPV Rodent Challenge

The instant study is designed to test the efficacy in cotton rats of candidate hMPV vaccines against a lethal challenge using an hMPV vaccine comprising mRNA encoding Fusion (F) glycoprotein, major surface glycoprotein G, or a combination of both antigens obtained from hMPV. Cotton rats are challenged with a lethal dose of the hMPV.

Animals are immunized intravenously (IV), intramuscularly (IM), or intradermally (ID) at week 0 and week 3 with candidate hMPV vaccines with and without adjuvant. Candidate vaccines are chemically modified or unmodified. The animals are then challenged with a lethal dose of hMPV on week 7 via IV, IM or ID. Endpoint is day 13 post infection, death or euthanasia. Animals displaying severe illness as determined by >30% weight loss, extreme lethargy or paralysis are euthanized. Body temperature and weight are assessed and recorded daily.

In experiments where a lipid nanoparticle (LNP) formulation is used, the formulation may include a cationic lipid, non-cationic lipid, PEG lipid and structural lipid in the ratios 50:10:1.5:38.5. The cationic lipid is DLin-KC2-DMA (50 mol %) or DLin-MC3-DMA (50 mol %), the non-cationic lipid is DSPC (10 mol %), the PEG lipid is PEG-DOMG (1.5 mol %) and the structural lipid is cholesterol (38.5 mol %), for example.

Example 14: Immunogenicity of hMPV mRNA Vaccine in BALB/c Mice

Figure 2B:
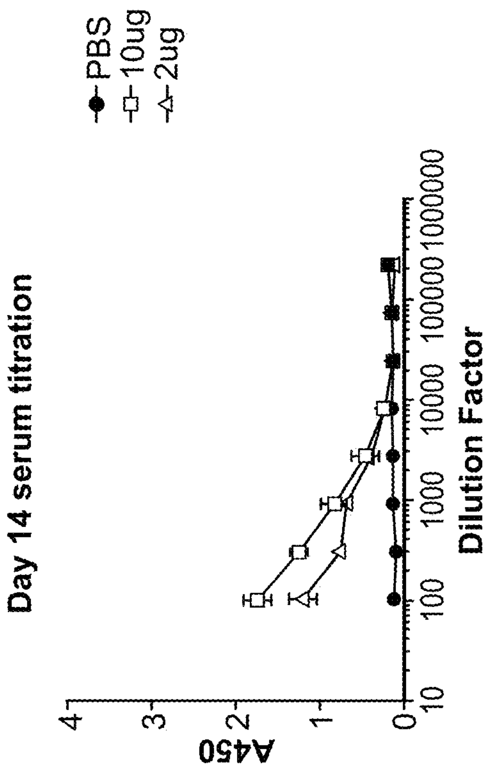
FIGS. 2A-2C are graphs showing the levels of anti-hMPV fusion protein-specific antibodies in the serum of mice immunized with hMPV mRNA vaccines on day 0 (FIG. 2A), day 14 (FIG. 2B) and day 35 (FIG. 2C) post immunization. The mice were immunized with a single dose (2 μg or 10 μg) on day 0 and were given a boost dose (2 μg or 10 μg) on day 21, hMPV fusion protein-specific antibodies were detected at up to 1:10000 dilution of serum on day 35 for both doses.
Figure 2A:
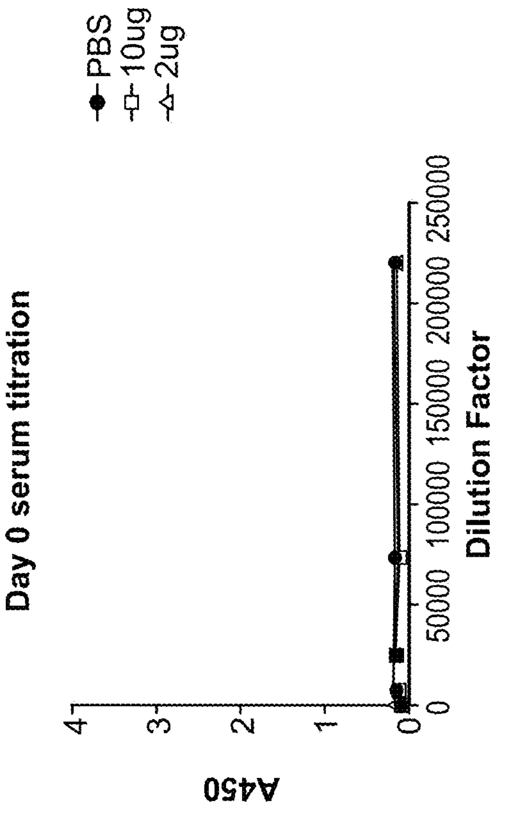
Figure 2C:
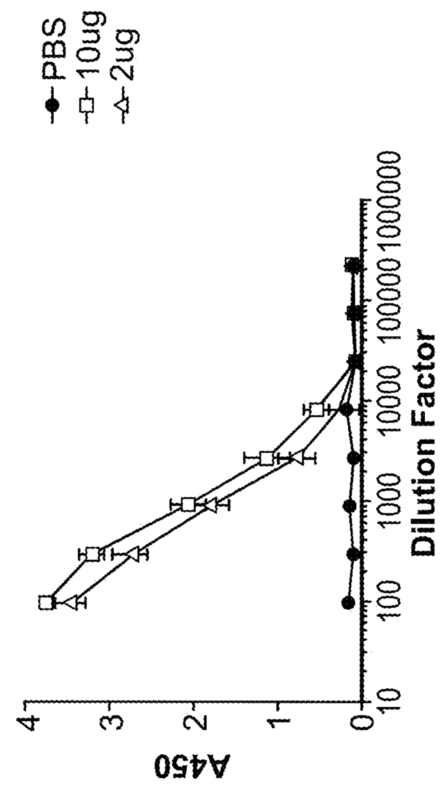

The instant study was designed to test the immunogenicity in BALB/c mice of hMPV vaccines comprising an mRNA polynucleotide encoding the hMPV Fusion (F) glycoprotein. The mRNA polynucleotide encodes the full-length fusion protein and comprises the wild-type nucleotide sequence obtained from the hMPV A2a strain. Mice were divided into 3 groups (n=8 for each group) and immunized intramuscularly (IM) with PBS, a 10 μg dose of mRNA vaccines encoding hMPV fusion protein, or a 2 μg dose of mRNA vaccines encoding hMPV fusion protein. A total of two immunizations were given at 3-week intervals (i.e., at weeks 0, and 3 weeks), and sera were collected after each immunization according to the schedule described in Table 1. Serum antibody titers against hMPV fusion glycoprotein were determined by ELISA and antibodies were detected in the sera collected on day 14 onward. Both vaccine doses tested induced comparable levels of immune response in mice (FIGS. 2A-2C).

Figures 3A, 3B, 3C:
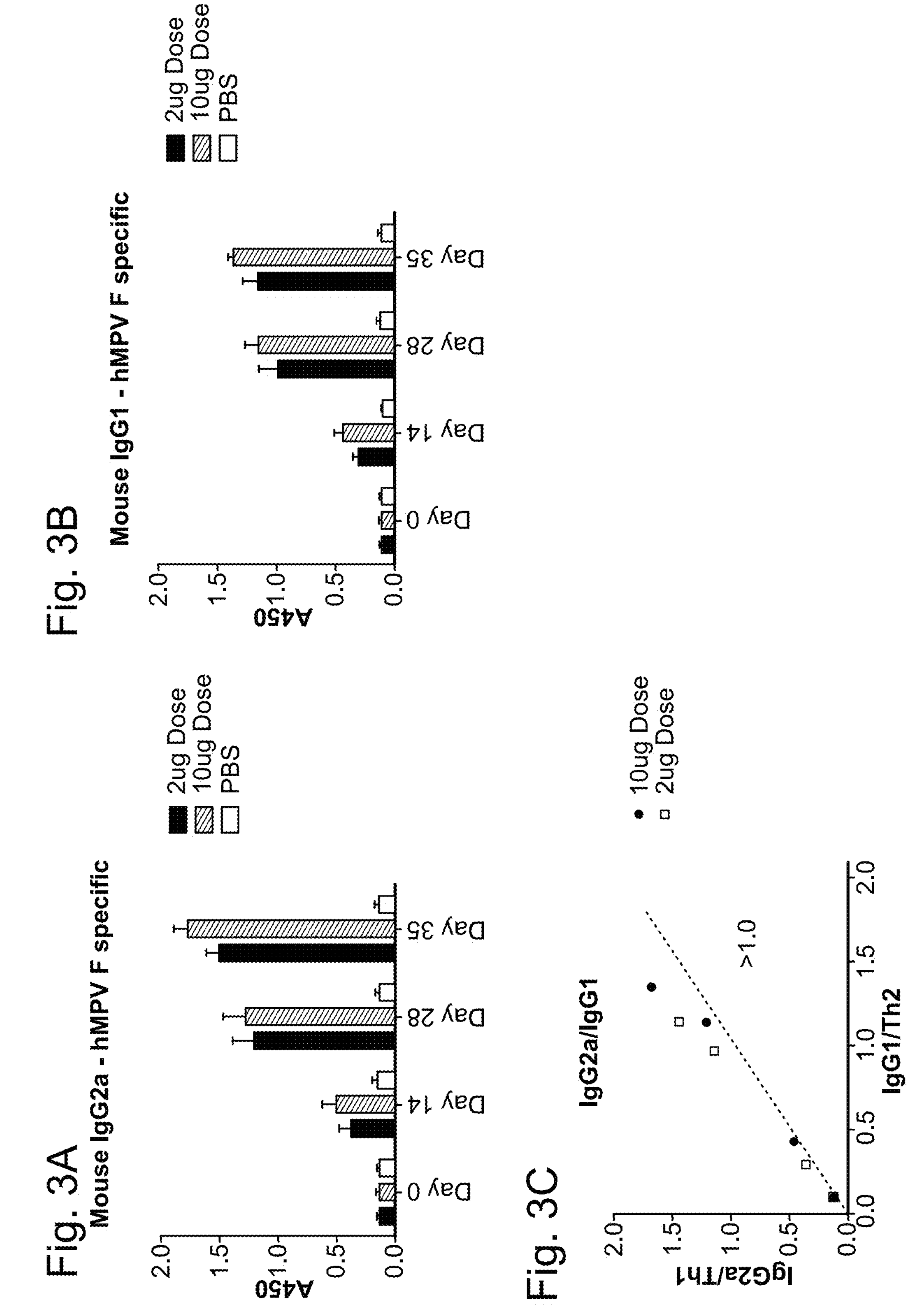
FIGS. 3A-3C are graphs showing the result of IgG isotyping in the serum of mice immunized with hMPV mRNA vaccines. The levels of hMPV fusion protein-specific IgG2a (FIG. 3A) and IgG1 (FIG. 3B) antibodies in the serum are measured by ELISA.

Additionally, mice sera were used for IgG isotyping (FIGS. 3A-3C). Both hMPV fusion protein-specific IgG1 and IgG2a were detected in mice sera. hMPV fusion protein mRNA vaccine also induced Th1 and Th2 cytokine responses, with a Th1 bias.

Figure 4:
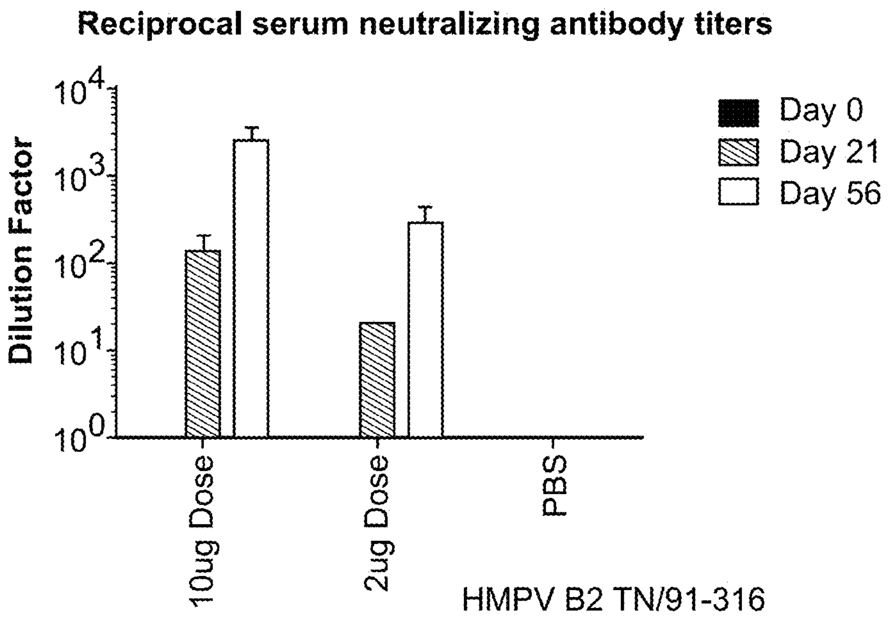
FIG. 4 is a graph showing in vitro neutralization of a hMPV B2 strain (TN/91-316) using the sera of mice immunized with a mRNA vaccine encoding hMPV fusion protein. Mouse serum obtained from mice receiving a 10 μg or a 2 μg dose contained hMPV-neutralizing antibodies.

Sera from mice immunized with either 10 μg or 2 μg doses of the hMPV fusion protein mRNA vaccine contain neutralizing antibodies. The ability of these antibodies to neutralize hMPV B2 strain was also tested. The antibody-containing sera successfully neutralized the hMPV B2 virus (FIG. 4).

Example 15: T-Cell Stimulation

The instant study was designed to test T-cell stimulation in the splenocytes of mice immunized with mRNA vaccines encoding hMPV fusion protein, as described herein. Immunization of BALB/c mice was performed as described in Example 14. The splenocytes for each group were pooled and split into two parts. One part of splenocytes from each group of mice was stimulated with hMPV-free media, Concanavalin A or a hMPV fusion protein peptide pool comprising 15-mers (15 amino acids long); while the other part of splenocytes from each group of mice was stimulated with hMPV-free media, Concanavalin A or inactivated hMPV virus. Secreted mouse cytokines were measured using the Meso Scale Discovery (MSD) assay.

Figures 5A, 5B, 5C:
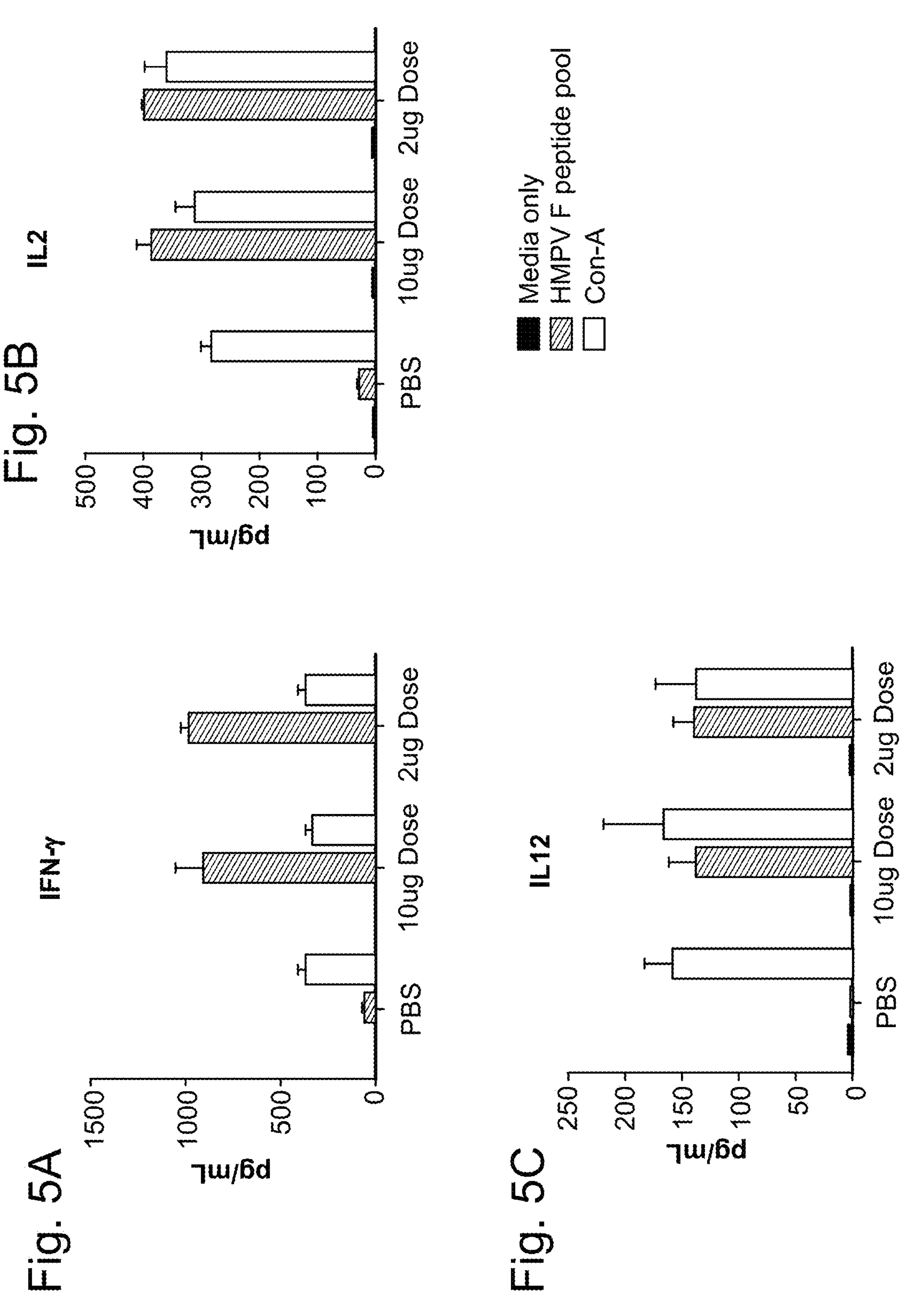
FIGS. 5A-5C are graphs showing a Th1 cytokine response induced by a hMPV fusion peptide pool (15-mers-5O (overlap)) in splenocytes isolated from mice immunized with the hMPV mRNA vaccines. Virus-free media was used as a negative control and Concanavalin A (ConA, a positive control for splenocyte stimulation) was included. The cytokines tested included IFN-γ (FIG. 5A), IL-2 (FIG. 5B) and IL12 (FIG. 5C).
Figures 6A, 6B, 6C, 6D, 6E:
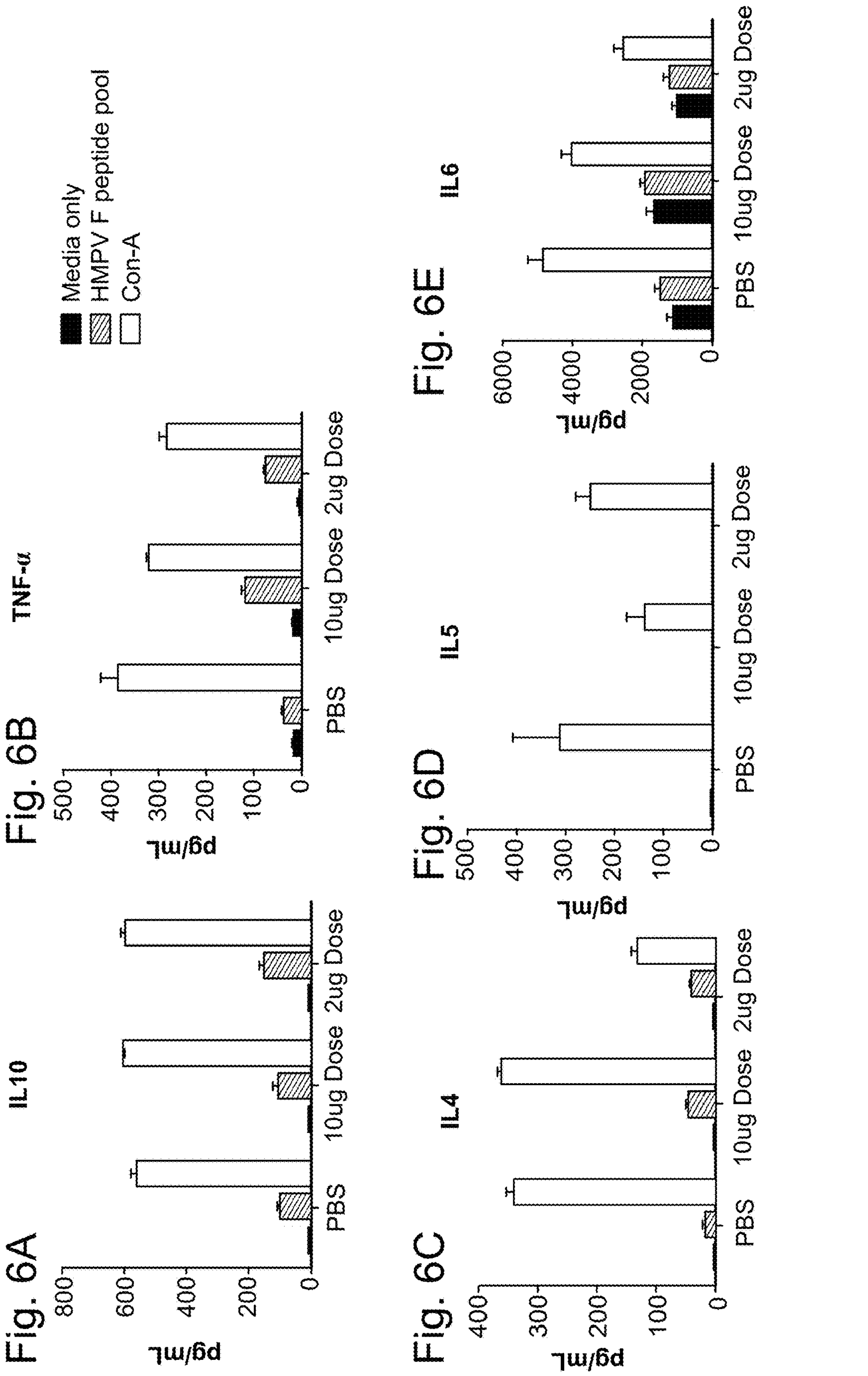
FIGS. 6A-6E are graphs showing the Th2 cytokine response induced by a hMPV fusion peptide pool (15-mers-50) in splenocytes isolated from mice immunized with the hMPV mRNA vaccines. Virus-free media was used as a negative control and Concanavalin A was also included. The cytokines tested included IL-10 (FIG. 6A), TNF-α (FIG. 6B), IL4 (FIG. 6C), IL-5 (FIG. 6D) and IL-6 (FIG. 6E).

Cytokines specific to Th1 or Th2 responses were measured. For Th1 response, IFN-γ, IL2 and IL12 were detected from splenocytes stimulated with the hMPV fusion protein peptide pool at a level comparable to that of Concanavalin A (FIGS. 5A-5C). For a Th2 response, the hMPV fusion protein peptide pool induced the secretion of detectable IL10, TNF-α, IL4 and IL, but not IL5, while Concanavalin A stimulated the secretion of all the above-mentioned Th2 cytokines (FIGS. 6A-6E) at a much higher level.

Figure 7B:
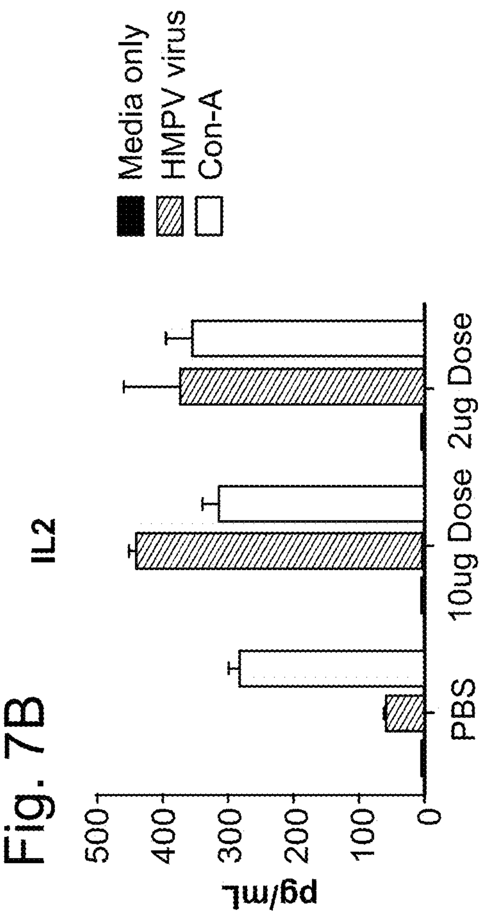
FIGS. 7A-7C are graphs showing the Th1 response induced by inactivated hMPV virus in splenocytes isolated from mice immunized with hMPV mRNA vaccines. Virus-free media was used as a negative control and Concanavalin A was included. The cytokines tested included IFN-γ (FIG. 7A), IL-2 (FIG. 7B) and IL12 (FIG. 7C).
Figure 7A:
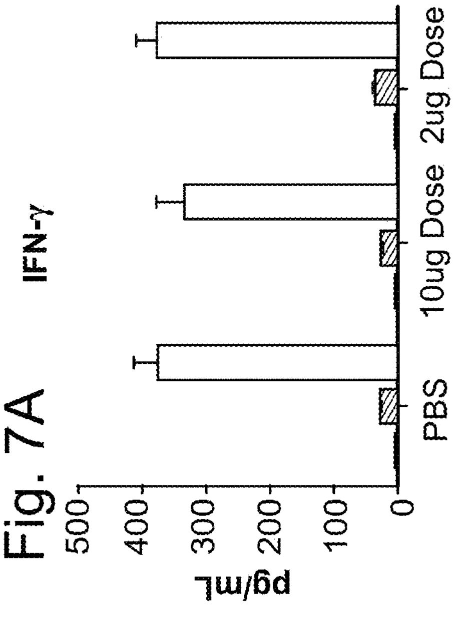
Figure 7C:
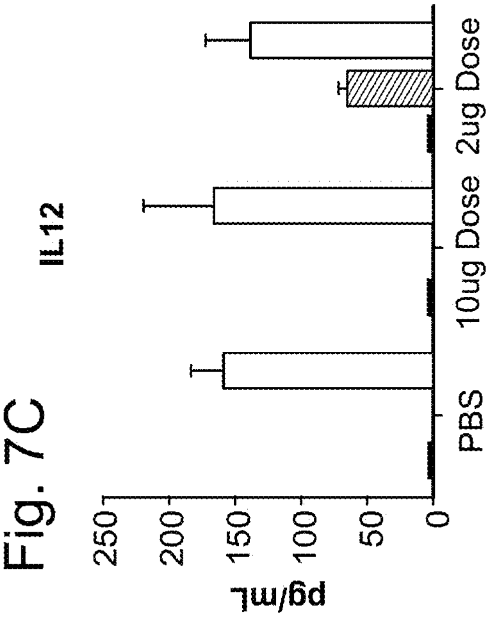
Figures 8A, 8B, 8C, 8D, 8E:
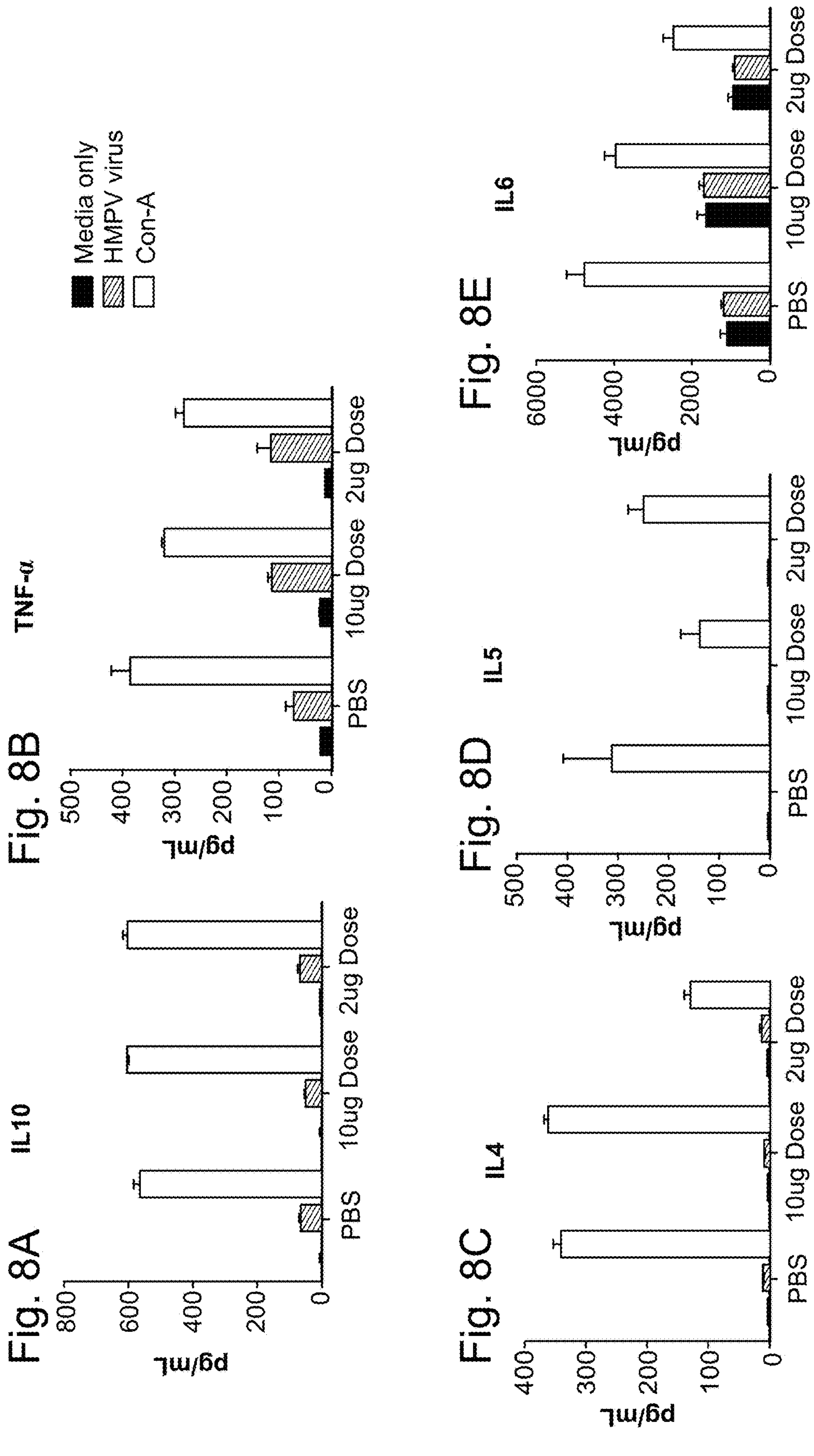
FIGS. 8A-8E are graphs showing the Th2 response induced by inactivated hMPV virus in splenocytes isolated from mice immunized with the hMPV mRNA vaccines. Virus-free media was used as a negative control and Concanavalin A was included. The cytokines tested include IL-10 (FIG. 8A), TNF-α (FIG. 8B), IL4 (FIG. 8C), IL-5 (FIG. 8D) and IL-6 (FIG. 8E).

In contrast, inactivated hMPV virus only induced the secretion of IL2 in the Th1 response comparable to that of Concanavalin A (FIGS. 7A-7C). For the Th2 response, the inactivated hMPV virus induced the secretion of detectable IL10, TNF-α, IL4 and IL6, but not IL5, while Concanavalin A stimulated the secretion of all the above-mentioned Th2 cytokines (FIGS. 8A-8E) at a much higher level.

Example 16: hMPV Rodent Challenge in Cotton Rats Immunized with mRNA Vaccine Encoding hMPV Fusion Protein The instant study was designed to test the efficacy in cotton rats of hMPV vaccines against a lethal challenge. mRNA vaccines encoding hMPV fusion protein were used. The mRNA polynucleotide encodes a full-length fusion protein and comprises the wild-type nucleotide sequence obtained from the hMPV A2a strain.

Figure 9A:
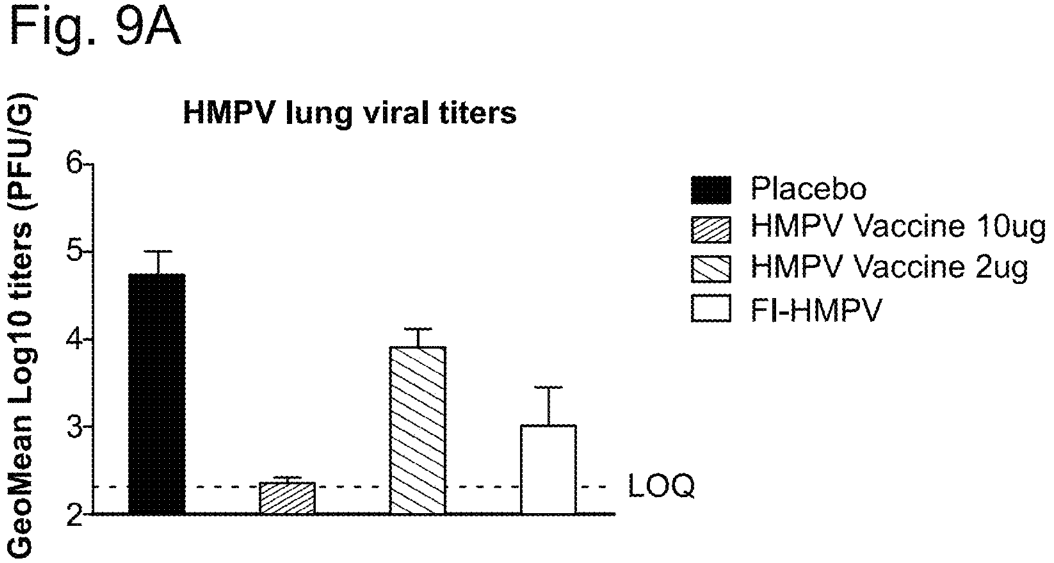
FIGS. 9A-9B are graphs showing the results of cotton rat challenge experiments. Two different doses of the hMPV mRNA vaccines were used (2 μg or 10 μg doses) to immunize the cotton rats before challenge. The hMPV mRNA vaccines reduced the viral titer in the lung and nose of the cotton rat, with the 10 μg dose being more effective in reducing viral titer. Use of a 10 μg dose resulted in 100% protection in the lung and a ~2 log reduction in nose viral titer. Use of a 2 μg dose resulted in a 1 log reduction in lung vital titer and no reduction in nose viral titer. The vaccine was administered on Day 0, and a boost was administered on Day 21.
Figure 9B:
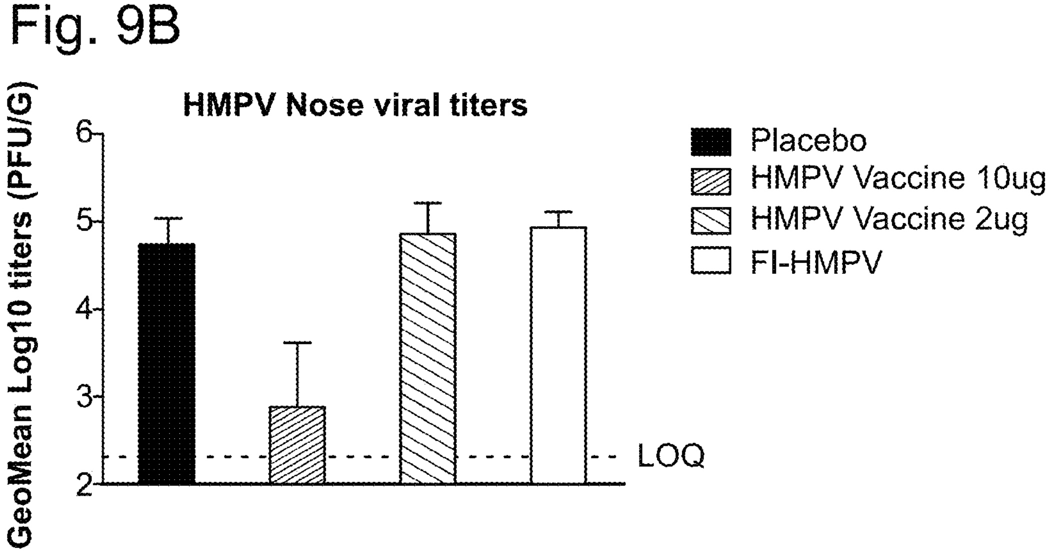

Cotton rats were immunized intramuscularly (IM) at week 0 and week 3 with the mRNA vaccines encoding hMPV fusion protein with either 2 μg or 10 μg doses for each immunization. The animals were then challenged with a lethal dose of hMPV in week 7 post initial immunization via IV, IM or ID. The endpoint was day 13 post infection, death or euthanasia. Viral titers in the noses and lungs of the cotton rats were measured. The results (FIGS. 9A and 9B) show that a 10 μg dose of mRNA vaccine protected the cotton mice 100% in the lung and drastically reduced the viral titer in the nose after challenge (~2 log reduction). Moreover, a 2 μg dose of mRNA vaccine showed a 1 log reduction in lung viral titer in the cotton mice challenged.

Figure 10:
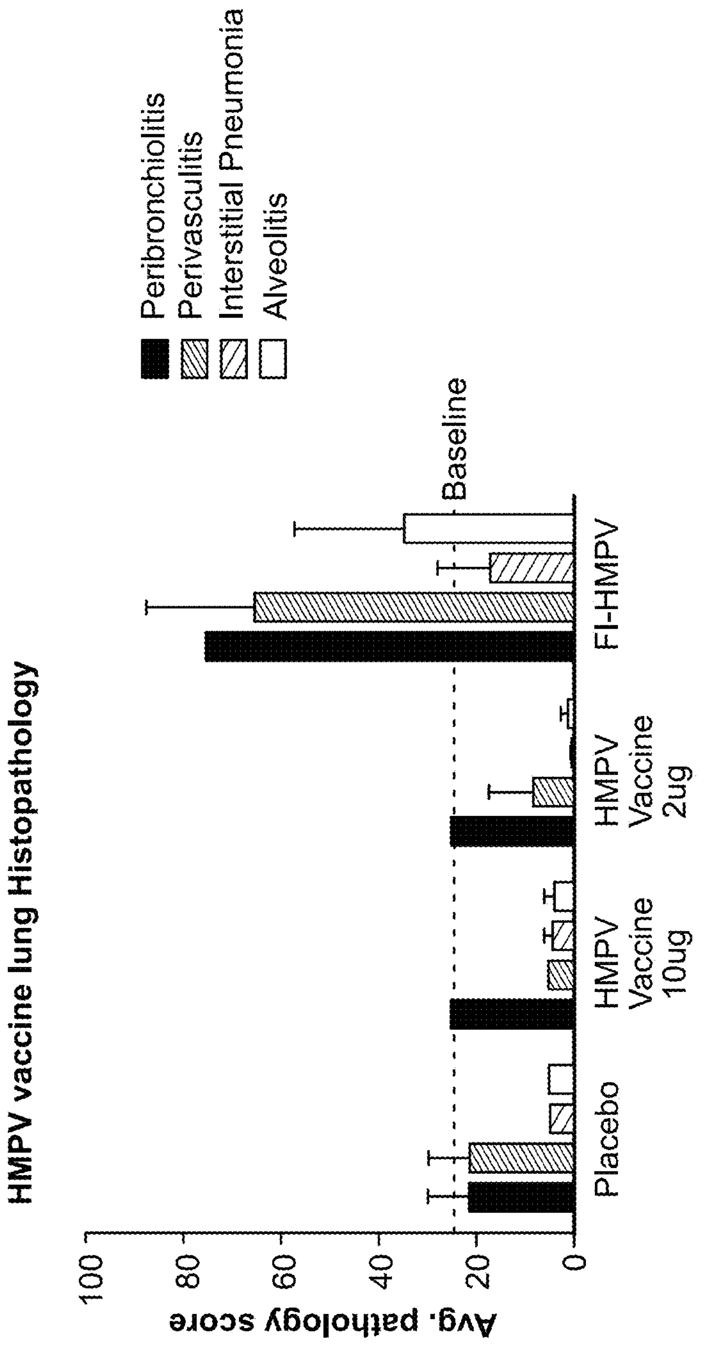
FIG. 10 is a graph showing the lung histopathology of cotton rats that received hMPV mRNA vaccines. Pathology associated with vaccine-enhanced disease was not observed in immunized groups.

Further, the histopathology of the lungs of the cotton mice immunized and challenged showed no pathology associated with vaccine-enhanced disease (FIG. 10).

Example 17: Immunogenicity Study

The instant study is designed to test the immunogenicity in mice of candidate PIV3 vaccines comprising a mRNA polynucleotide encoding hemagglutinin-neuraminidase or fusion protein (F or F0) obtained from PIV3.

Mice are immunized intravenously (IV), intramuscularly (IM), or intradermally (ID) with candidate vaccines. Candidate vaccines are chemically modified or unmodified. A total of four immunizations are given at 3-week intervals (i.e., at weeks 0, 3, 6, and 9), and sera are collected after each immunization until weeks 33-51. Serum antibody titers against hemagglutinin-neuraminidase or fusion protein (F or F0) are determined by ELISA. Sera collected from each mouse during weeks 10-16 are, optionally, pooled, and total IgGs are purified. Purified antibodies are used for immunoelectron microscopy, antibody-affinity testing, and in vitro protection assays.

Example 18: PIV3 Rodent Challenge

The instant study is designed to test the efficacy in cotton rats of candidate PIV3 vaccines against a lethal challenge using a PIV3 vaccine comprising mRNA encoding hemagglutinin-neuraminidase or fusion protein (F or F0) obtained from PIV3. Cotton rats are challenged with a lethal dose of the PIV3.

Animals are immunized intravenously (IV), intramuscularly (IM), or intradermally (ID) at week 0 and week 3 with candidate PIV3 vaccines with and without adjuvant. Candidate vaccines are chemically modified or unmodified. The animals are then challenged with a lethal dose of PIV3 on week 7 via IV, IM or ID. Endpoint is day 13 post infection, death or euthanasia. Animals displaying severe illness as determined by >30% weight loss, extreme lethargy or paralysis are euthanized. Body temperature and weight are assessed and recorded daily.

In experiments where a lipid nanoparticle (LNP) formulation is used, the formulation may include a cationic lipid, non-cationic lipid, PEG lipid and structural lipid in the ratios 50:10:1.5:38.5. The cationic lipid is DLin-KC2-DMA (50 mol %) or DLin-MC3-DMA (50 mol %), the non-cationic lipid is DSPC (10 mol %), the PEG lipid is PEG-DOMG (1.5 mol %) and the structural lipid is cholesterol (38.5 mol %), for example.

Example 19: hMPV/PIV Cotton Rat Challenge

The instant study was designed to test the efficacy in cotton rats of candidate hMPV mRNA vaccines, PIV3 mRNA vaccines, or hMPV/PIV combination mRNA vaccines against a lethal challenge using PIV3 strain or hMPV/A2 strain. The study design is shown in Table 9.

Cotton rats of 10-12 weeks old were divided into 12 groups (n=5), and each group was vaccinated with mRNA vaccines indicated in Table 9. The PIV3 vaccine comprises mRNA encoding hemagglutinin-neuraminidase or fusion protein (F or F0) obtained from PIV3. The hMPV mRNA vaccine encodes the full-length hMPV fusion protein. The hMPV/PIV combination mRNA vaccine is a mixture of the PIV3 vaccine and hMPV vaccine at a 1:1 ratio.

Cotton rats were immunized intramuscularly (IM) at week 0 and week 3 with candidate vaccines with the doses indicated in Table 9. Cotton rats immunized with hMPV mRNA vaccines or hMPV/PIV combination mRNA vaccines were challenged with a lethal dose of hMPV/A2 strain on week 7 via IM. Cotton rats immunized with PIV mRNA vaccines or hMPV/PIV combination mRNA vaccines were challenged with a lethal dose of PIV3 strain on week 7 via IM.

The endpoint was day 13 post infection, death or euthanasia. Animals displaying severe illness as determined by >30% weight loss, extreme lethargy or paralysis were euthanized. Body temperature and weight were assessed and recorded daily.

Figure 11:
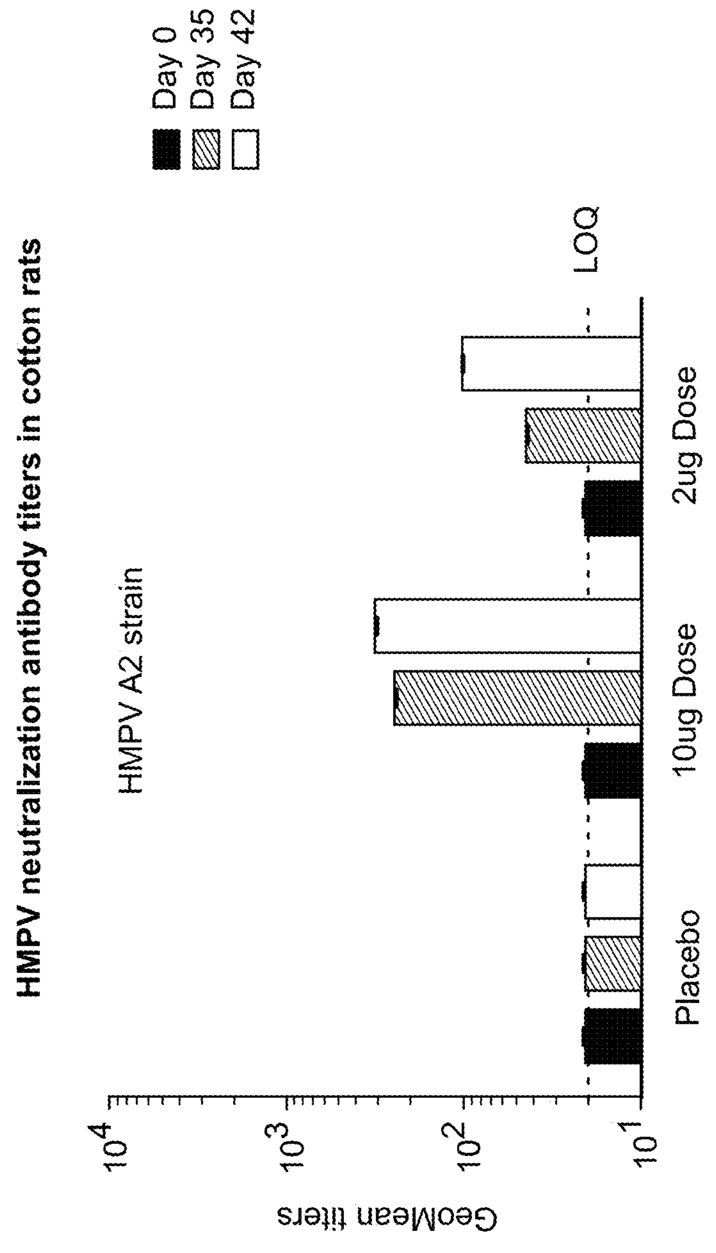
FIG. 11 is a graph showing hMPV neutralization antibody titers in cotton rats that received hMPV mRNA vaccines (2 μg or 10 μg doses) on days 35 and 42 post immunization.
Figure 12:
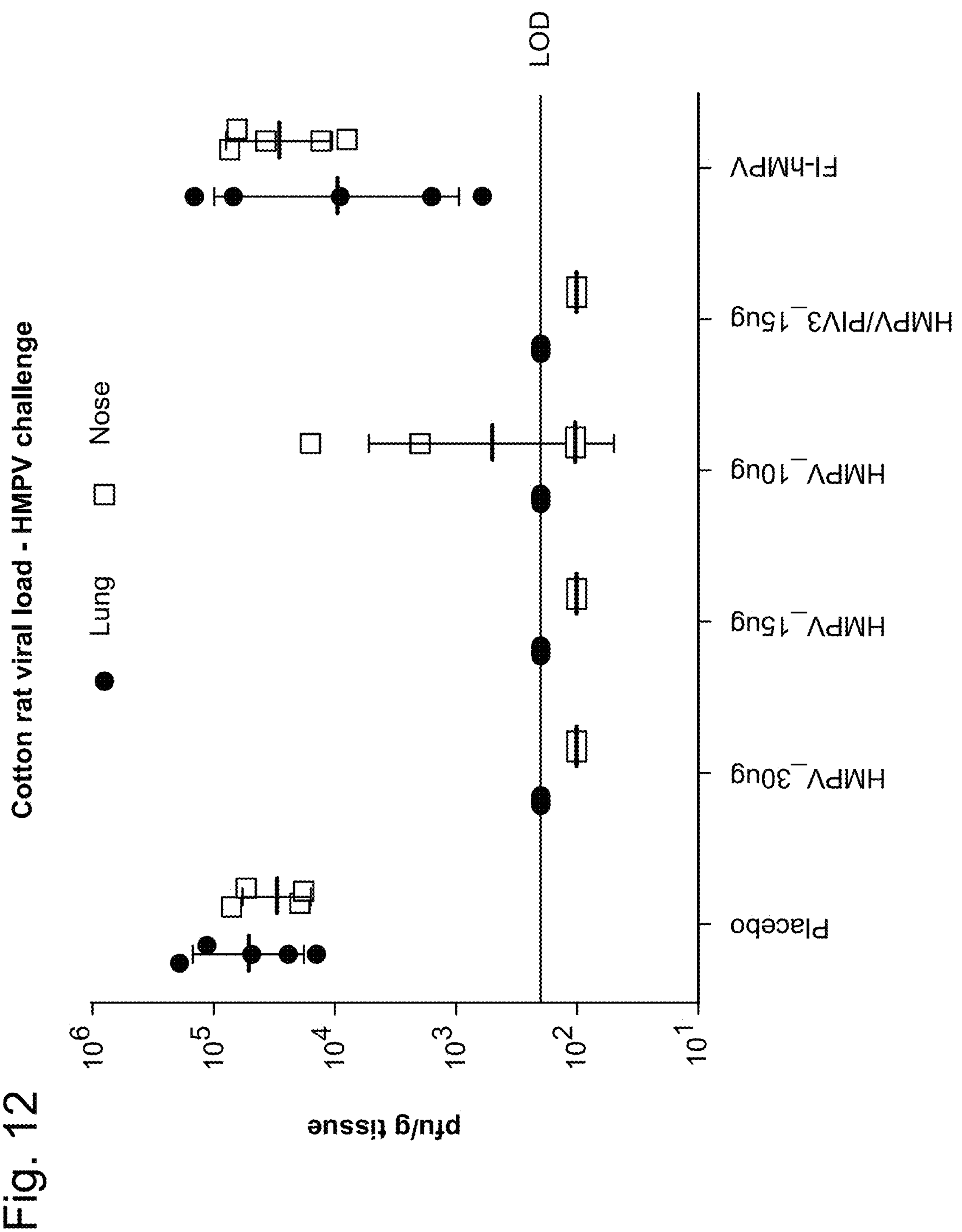
FIG. 12 is a graph showing the lung and nose viral load in cotton rats challenged with a hMPV/A2 strain after immunization with the indicated mRNA vaccines (hMPV mRNA vaccine or hMPV/PIV mRNA combination vaccine). Vaccinated cotton rats showed reduced lung and nose viral loads after challenge, compared to control.
Figure 13:
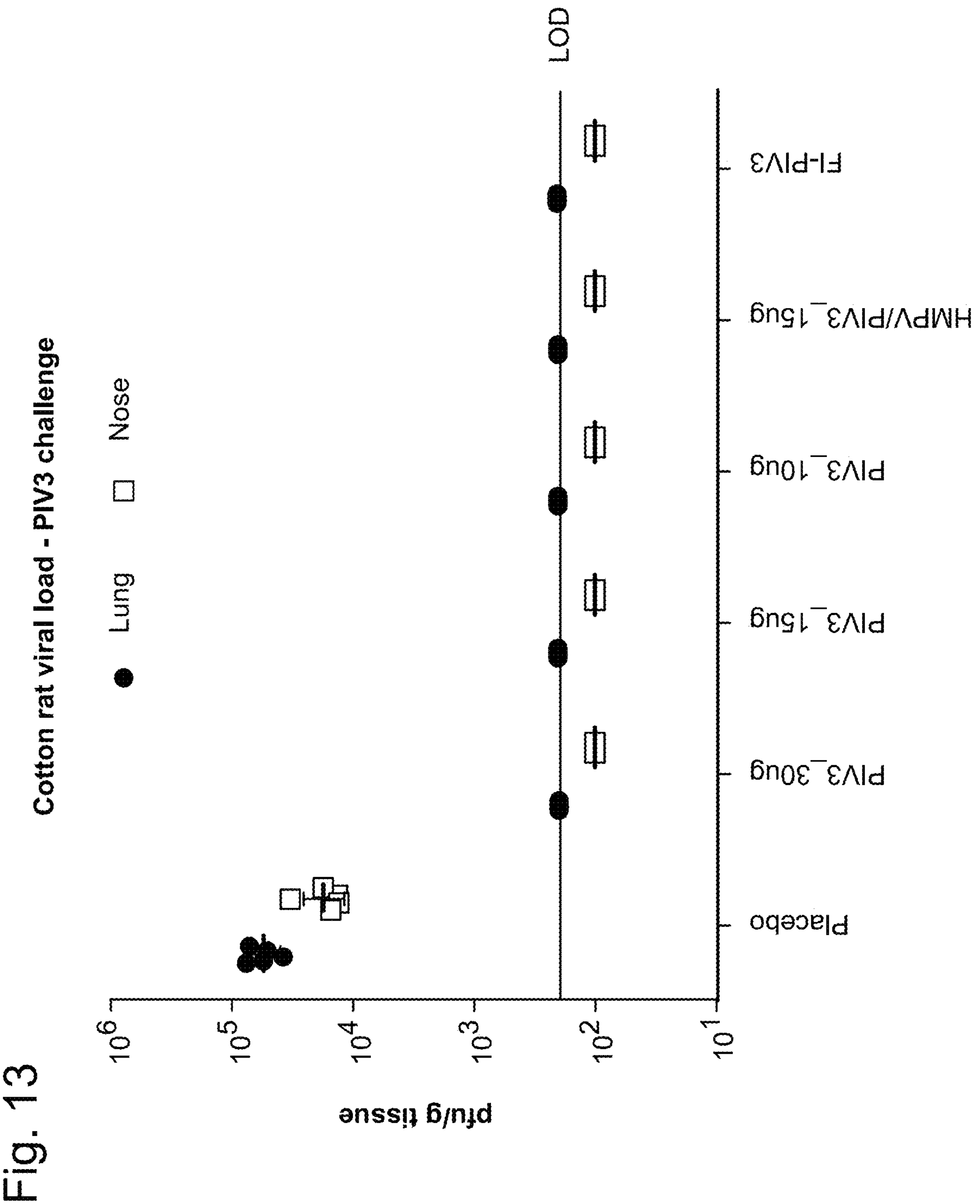
FIG. 13 is a graph showing the lung and nose viral load in cotton rats challenged with PIV3 strain after immunization with indicated mRNA vaccines (PIV mRNA vaccine or hMPV/PIV combination vaccine). Vaccinated cotton rats showed reduced lung and nose viral loads after challenge, compared to control.
Figure 14:
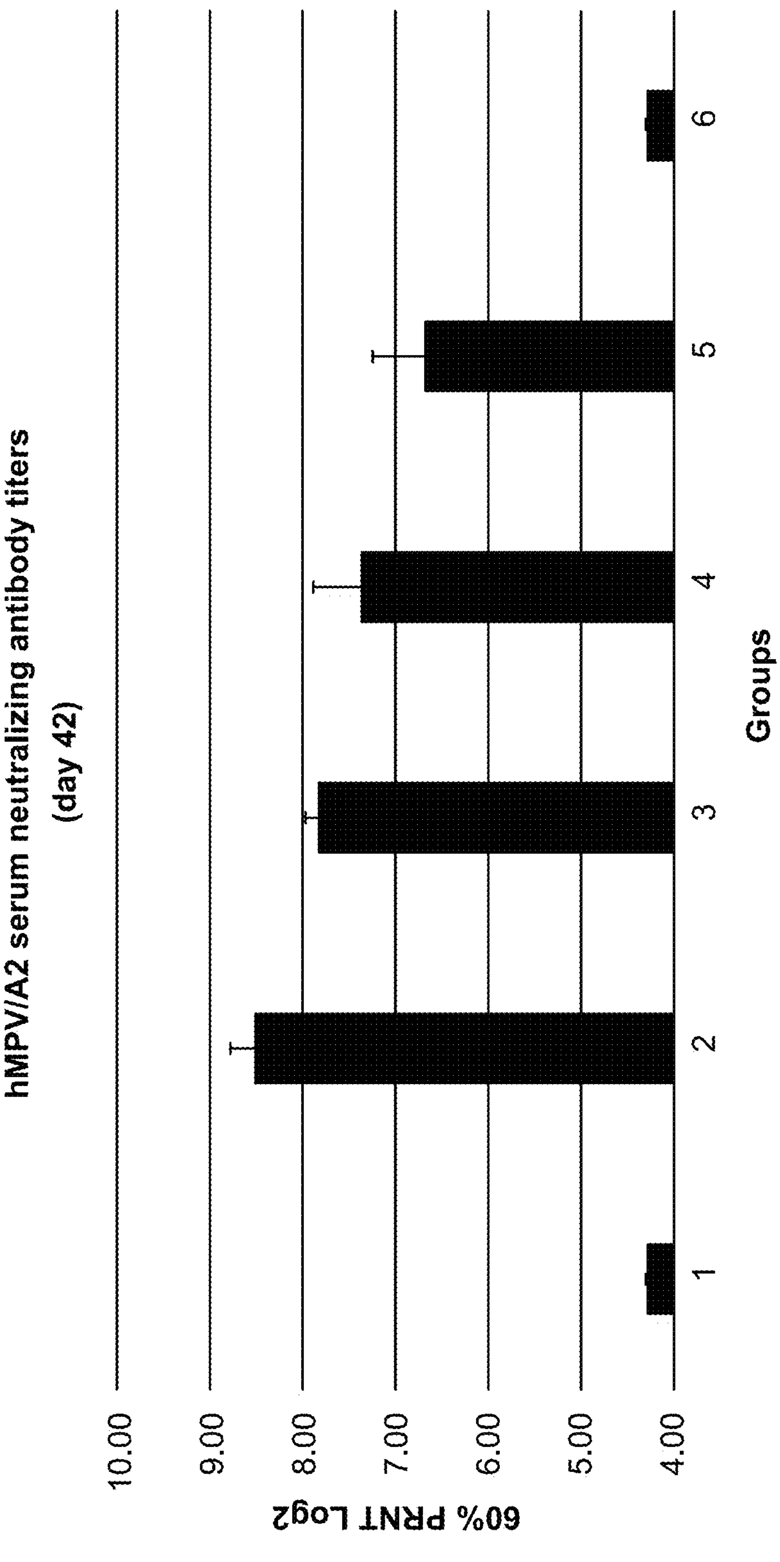
FIG. 14 is a graph showing hMPV neutralizing antibody titers in cotton rats that received different dosages of hMPV mRNA vaccines or hMPV/PIV combination mRNA vaccines on day 42 post immunization. The dosages of the vaccine are indicated in Table 9.
Figure 15:
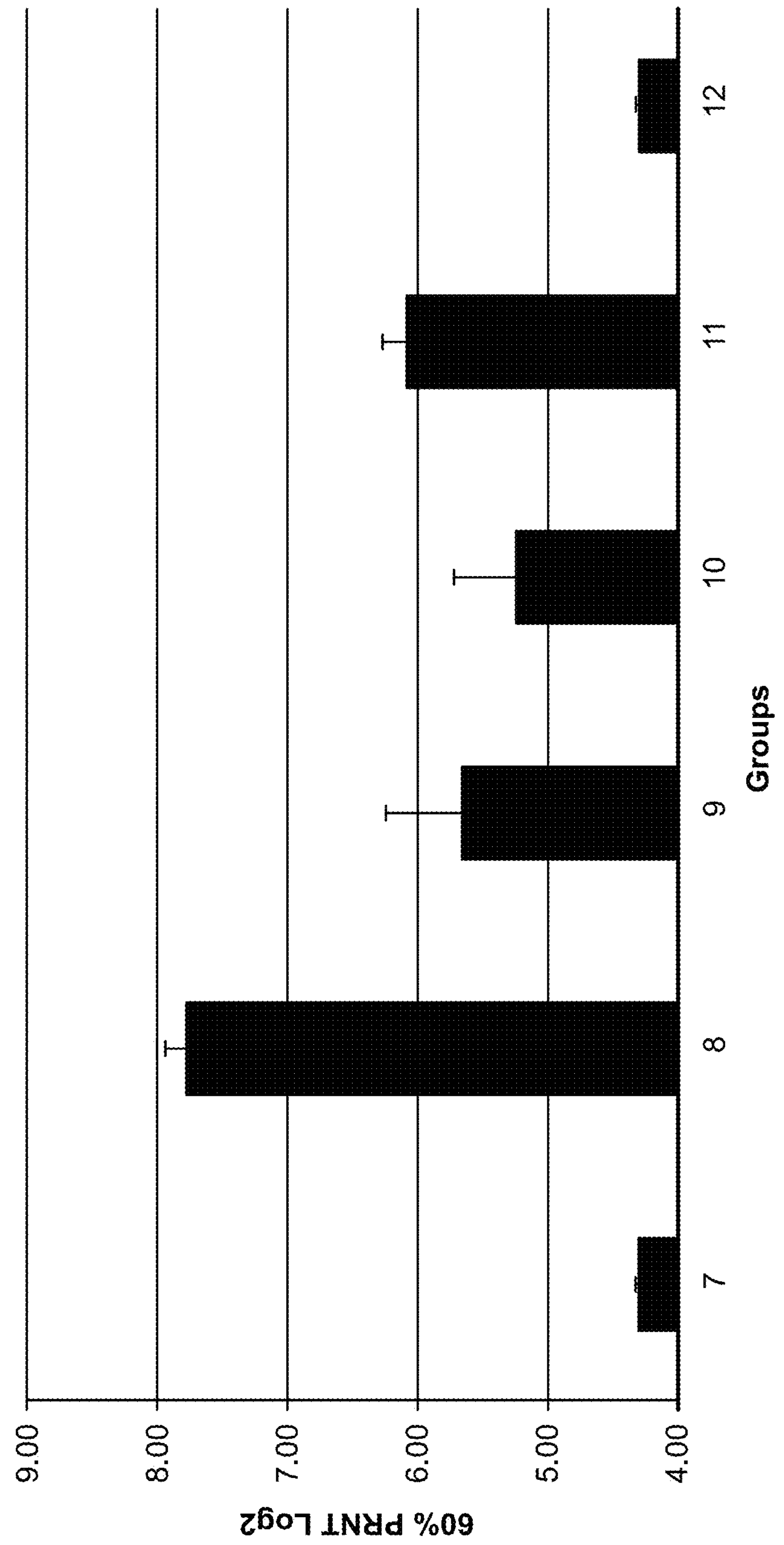
FIG. 15 is a graph showing PIV3 neutralizing antibody titers in cotton rats that received different dosages of PIV mRNA vaccines or hMPV/PIV combination mRNA vaccines on day 42 post immunization. The dosages of the vaccine are indicated in Table 9.
Figure 16:
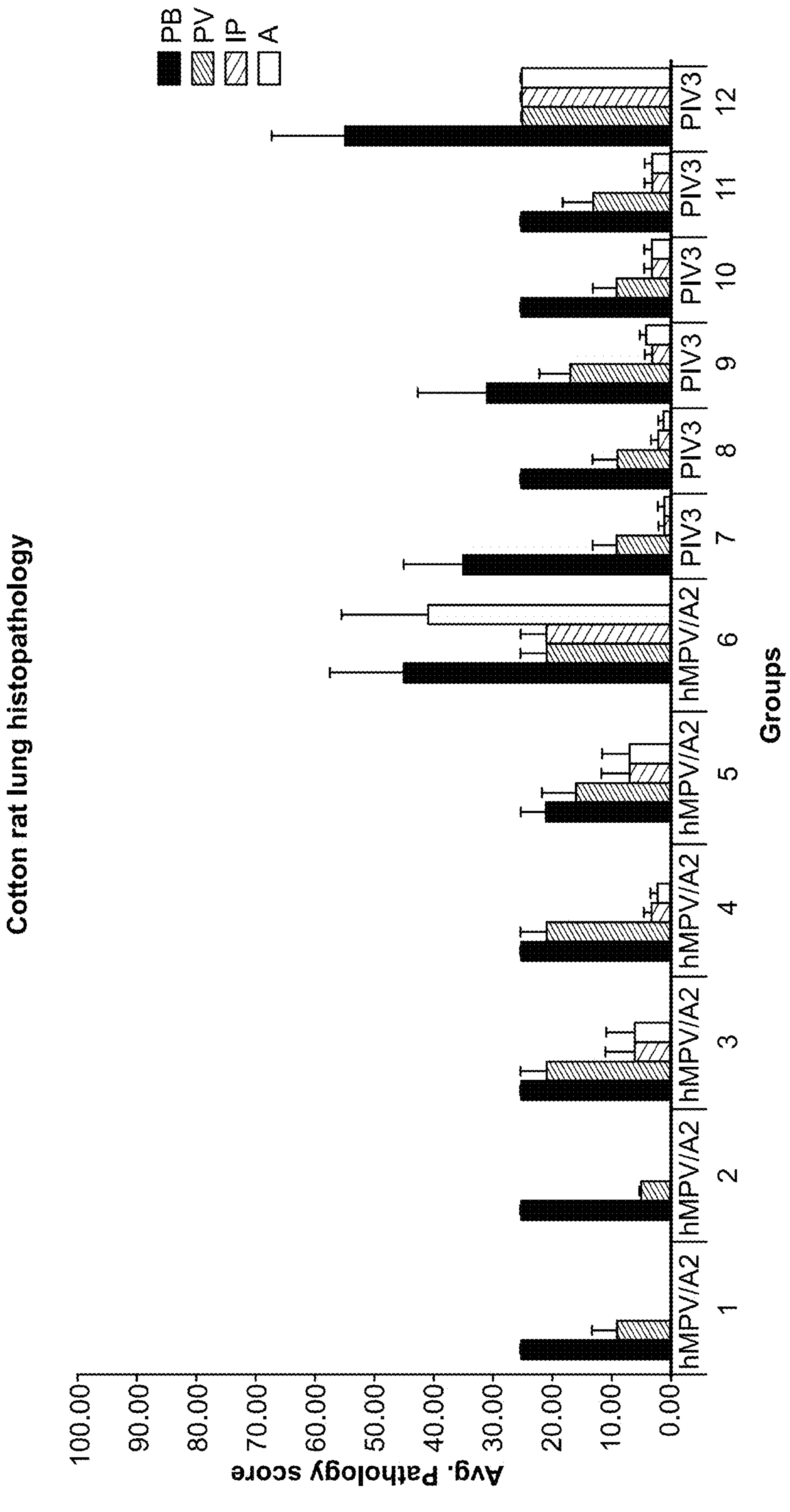
FIG. 16 is a graph showing the lung histopathology score of cotton rats immunized with hMPV mRNA vaccines, PIV mRNA vaccines or hMPV/PIV combination mRNA vaccines as indicated in Table 9. Low occurrence of alevolitis and interstitial pneumonia was observed, indicating no antibody-dependent enhancement (ADE) of hMPV associated diseases.

Lung and nose hMPV/A2 (FIG. 12) or PIV3 (FIG. 13) viral titers were assessed. Lung histopathology of the immunized and challenged cotton rat immunized and challenged were assessed to determine pathology associated with vaccine enhance disease. Neutralization antibody titers in the serum of immunized cotton rats on day 0 and 42 post immunization were assessed (FIG. 11).

hMPV/A2 (FIG. 14) or PIV3 (FIG. 15) neutralizing antibody titers in the serum samples of the immunized cotton rat 42 days post immunization were measured. All mRNA vaccines tested induced strong neutralizing antibodies cotton rats. Lung histopathology of the immunized cotton rats were also evaluated (FIG. 16). Low occurrence of alevolitis and interstitial pneumonia was observed, indicating no antibody-dependent enhancement (ADE) of hMPV or PIV associated diseases.

Example 20: Betacoronavirus Immunogenicity Study

The instant study is designed to test the immunogenicity in rabbits of candidate betacoronavirus (e.g., MERS-CoV, SARS-CoV, HCoV-OC43, HCoV-229E, HCoV-NL63, HCoV-NL, HCoV-NH or HCoV-HKU1 or a combination thereof) vaccines comprising a mRNA polynucleotide encoding the spike (S) protein, the S1 subunit (S1) of the spike protein, or the S2 subunit (S2) of the spike protein obtained from a betacoronavirus (e.g., MERS-CoV, SARS-CoV, HCoV-OC43, HCoV-229E, HCoV-NL63, HCoV-NL, HCoV-NH or HCoV-HKU1).

Rabbits are vaccinated on week 0 and 3 via intravenous (IV), intramuscular (IM), or intradermal (ID) routes. One group remains unvaccinated and one is administered inactivated betacoronavirus. Serum is collected from each rabbit on weeks 1, 3 (pre-dose) and 5. Individual bleeds are tested for anti-S, anti-S1 or anti-S2 activity via a virus neutralization assay from all three time points, and pooled samples from week 5 only are tested by Western blot using inactivated betacoronavirus (e.g., inactivated MERS-CoV, SARS-CoV, HCoV-OC43, HCoV-229E, HCoV-NL63, HCoV-NL, HCoV-NH or HCoV-HKU1).

In experiments where a lipid nanoparticle (LNP) formulation is used, the formulation may include a cationic lipid, non-cationic lipid, PEG lipid and structural lipid in the ratios 50:10:1.5:38.5. The cationic lipid is DLin-KC2-DMA (50 mol %) or DLin-MC3-DMA (50 mol %), the non-cationic lipid is DSPC (10 mol %), the PEG lipid is PEG-DOMG (1.5 mol %) and the structural lipid is cholesterol (38.5 mol %), for example.

Example 21: Betacoronavirus Challenge

The instant study is designed to test the efficacy in rabbits of candidate betacoronavirus (e.g., MERS-CoV, SARS-CoV, HCoV-OC43, HCoV-HKU1 or a combination thereof) vaccines against a lethal challenge using a betacoronavirus (e.g., MERS-CoV, SARS-CoV, HCoV-OC43, HCoV-HKU1 or a combination thereof) vaccine comprising mRNA encoding the spike (S) protein, the S1 subunit (S1) of the spike protein, or the S2 subunit (S2) of the spike protein obtained from betacoronavirus (e.g., MERS-CoV, SARS-CoV, HCoV-OC43, HCoV-229E, HCoV-NL63, HCoV-NL, HCoV-NH or HCoV-HKU1). Rabbits are challenged with a lethal dose (10×LD90; ~100 plaque-forming units; PFU) of betacoronavirus (e.g., MERS-CoV, SARS-CoV, HCoV-OC43, HCoV-229E, HCoV-NL63, HCoV-NL, HCoV-NH or HCoV-HKU1).

The animals used are 6-8 week old female rabbits in groups of 10. Rabbits are vaccinated on weeks 0 and 3 via an IM, ID or IV route of administration. Candidate vaccines are chemically modified or unmodified. Rabbit serum is tested for microneutralization (see Example 14). Rabbits are then challenged with ~1 LD90 of betacoronavirus (e.g., MERS-CoV, SARS-CoV, HCoV-OC43, HCoV-229E, HCoV-NL63, HCoV-NL, HCoV-NH or HCoV-HKU1) on week 7 via an IN, IM, ID or IV route of administration. Endpoint is day 13 post infection, death or euthanasia. Animals displaying severe illness as determined by >30% weight loss, extreme lethargy or paralysis are euthanized. Body temperature and weight are assessed and recorded daily.

Example 22: Microneutralization Assay

Nine serial 2-fold dilutions (1:50-1:12,800) of rabbit serum are made in 50 μl virus growth medium (VGM) with trypsin in 96 well microtiter plates. Fifty microliters of virus containing ~50 pfu of betacoronavirus (e.g., MERS-CoV, SARS-CoV, HCoV-OC43, HCoV-229E, HCoV-NL63, HCoV-NL, HCoV-NH or HCoV-HKU1) is added to the serum dilutions and allowed to incubate for 60 minutes at room temperature (RT). Positive control wells of virus without sera and negative control wells without virus or sera are included in triplicate on each plate. While the serum-virus mixtures incubate, a single cell suspension of Madin-Darby Canine-Kidney cells are prepared by trypsinizing (Gibco 0.5% bovine pancrease trypsin in EDTA) a confluent monolayer and suspended cells are transferred to a 50 ml centrifuge tube, topped with sterile PBS and gently mixed. The cells are then pelleted at 200 g for 5 minutes, supernatant aspirated and cells resuspended in PBS. This procedure is repeated once and the cells are resuspended at a concentration of $3\times10^5$/ml in VGM with porcine trypsin. Then, 100 µl of cells are added to the serum-virus mixtures and the plates incubated at 35° C. in $CO_2$ for 5 days. The plates are fixed with 80% acetone in phosphate buffered saline (PBS) for 15 minutes at RT, air dried and then blocked for 30 minutes containing PBS with 0.5% gelatin and 2% FCS. An antibody to the S proteins, 51 protein or S2 protein is diluted in PBS with 0.5% gelatin/2% FCS/0.5% Tween 20 and incubated at RT for 2 hours. Wells are washed and horseradish peroxidase-conjugated goat anti-mouse IgG added, followed by another 2 hour incubation. After washing, 0-phenylenediamine dihydrochloride is added and the neutralization titer is defined as the titer of serum that reduced color development by 50% compared to the positive control wells.

Example 23: MERS CoV Vaccine Immunogenicity Study in Mice

The instant study was designed to test the immunogenicity in mice of candidate MERS-CoV vaccines comprising a mRNA polynucleotide encoding the full-length Spike (S) protein, or the S2 subunit (S2) of the Spike protein obtained from MERS-CoV.

Mice were vaccinated with a 10 µg dose of MERS-CoV mRNA vaccine encoding either the full-length MERS-CoV Spike (S) protein, or the S2 subunit (S2) of the Spike protein on days 0 and 21. Sera were collected from each mice on days 0, 21, 42, and 56. Individual bleeds were tested for anti-S, anti-S2 activity via a virus neutralization assay from all four time points.

Figure 17:
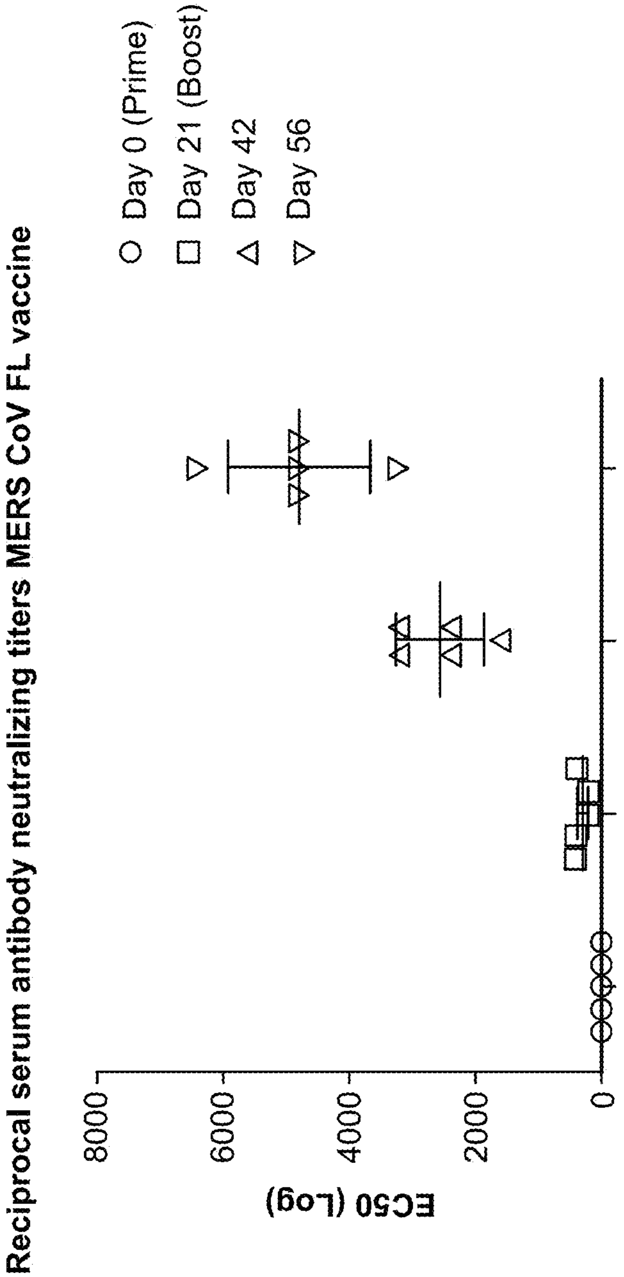
FIG. 17 is a graph showing the reciprocal MERS-CoV neutralizing antibody titers in mice immunized with betacoronavirus mRNA vaccine encoding the MERS-CoV full-length Spike protein, on days 0, 21, 42, and 56 post immunization.
Figure 18:
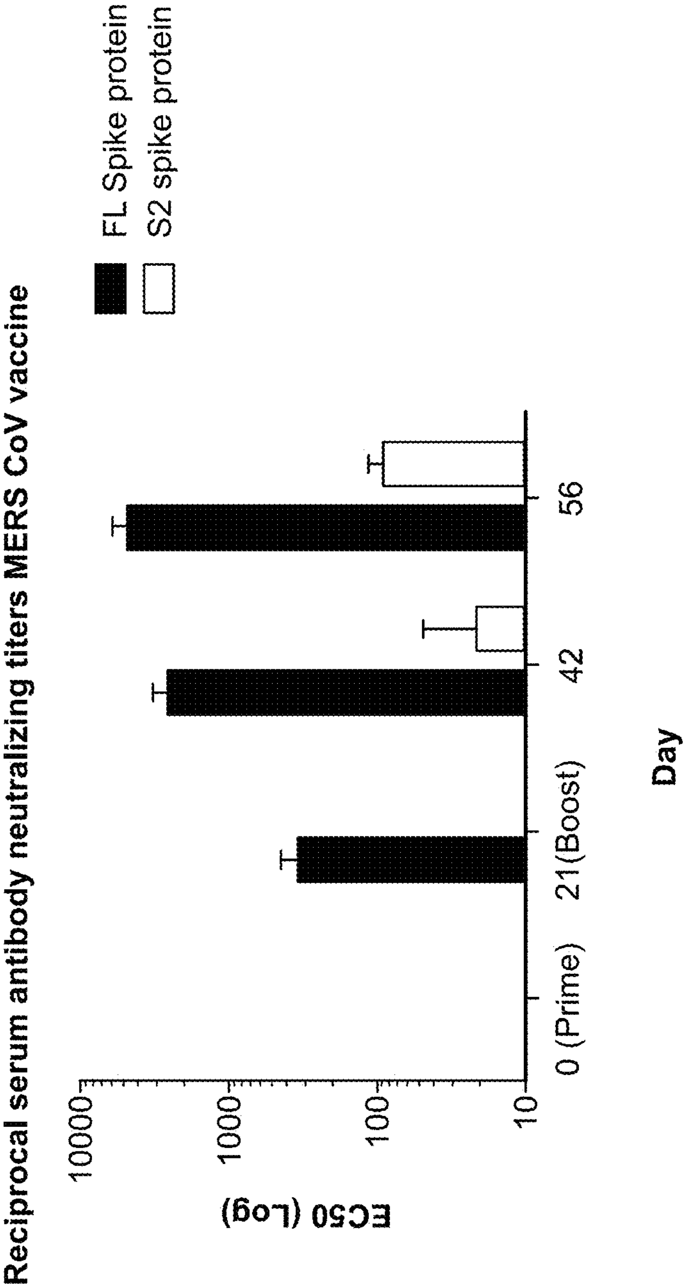
FIG. 18 is a graph showing the reciprocal MERS-CoV neutralizing antibody titers in mice immunized with betacoronavirus mRNA vaccine encoding either the MERS-CoV full-length Spike protein, or the S2 subunit of the Spike protein. The full length spike protein induced a stronger immune response compared to the S2 subunit alone.

As shown in FIG. 17, the MERS-CoV vaccine encoding the full-length S protein induced strong immune response after the boost dose on day 21. Further, full-length S protein vaccine generated much higher neutralizing antibody titers as compared to S2 alone (FIG. 18).

Example 24: MERS CoV Vaccine Immunogenicity Study in New Zealand White Rabbits The instant study was designed to test the immunogenicity of candidate MERS-CoV mRNA vaccines encoding the full-length Spike (S) protein. The New Zealand white rabbits used in this study weighed about 4-5 kg. The rabbits were divided into three groups (Group 1a, Group 1b, and Group 2, n=8). Rabbits in Group 1a were immunized intramuscularly (IM) with one 20 µg dose of the MERS-CoV mRNA vaccine encoding the full-length Spike protein on day 0. Rabbits in Group 1b were immunized intramuscularly (IM) with one 20 µg dose of the MERS-CoV mRNA vaccine encoding the full-length Spike protein on day 0, and again on day 21 (booster dose). Group 2 received placebo (PBS). The immunized rabbits were then challenged and samples were collected 4 days after challenge. The viral loads in the lungs, bronchoalveolar lavage (Bal), nose, and throat of the rabbits were determined, e.g., via quantitative PCR. Replicating virus in the lung tissues of the rabbits were also detected. Lung histopathology were evaluated and the neutralizing antibody titers in serum samples of the rabbits were determined.

Figure 19A:
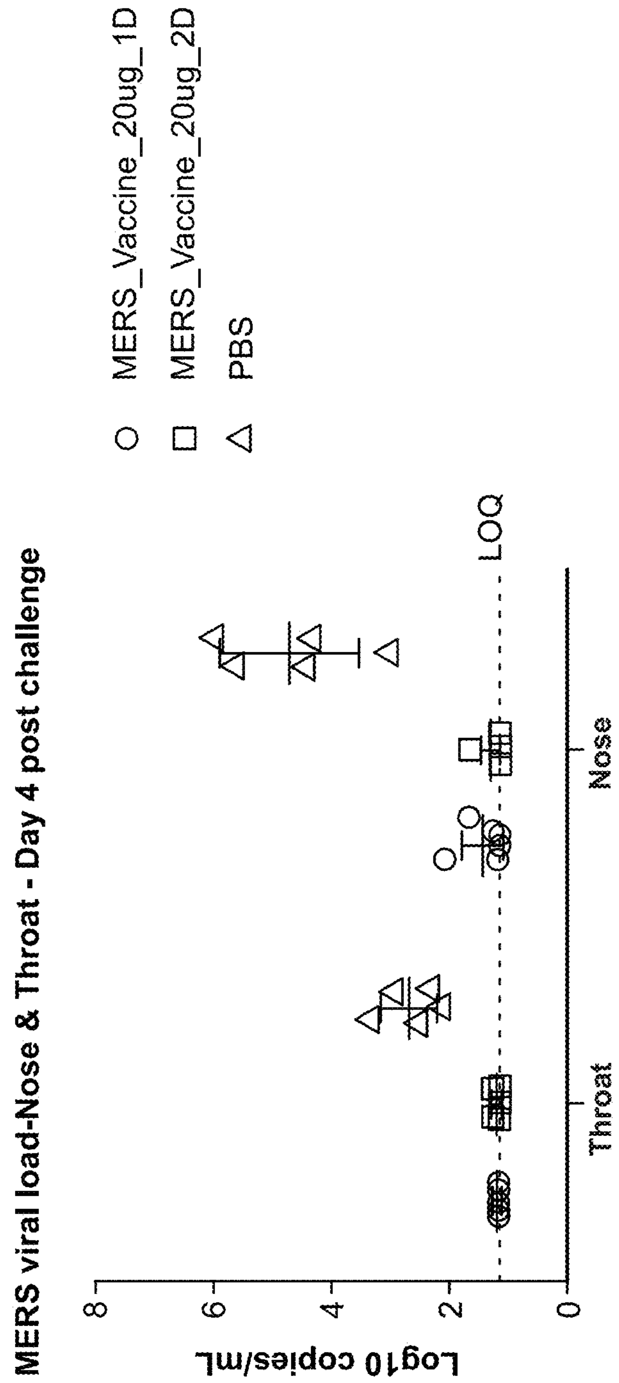
FIGS. 19A-19C are graphs showing the viral load in the nose and throat, the bronchoalveolar lavage (BAL), or the lungs of New Zealand white rabbits 4 days post challenge with MERS-CoV. The New Zealand white rabbits were immunized with one 20 μg-dose (on day 0) or two 20
Figure 19B:
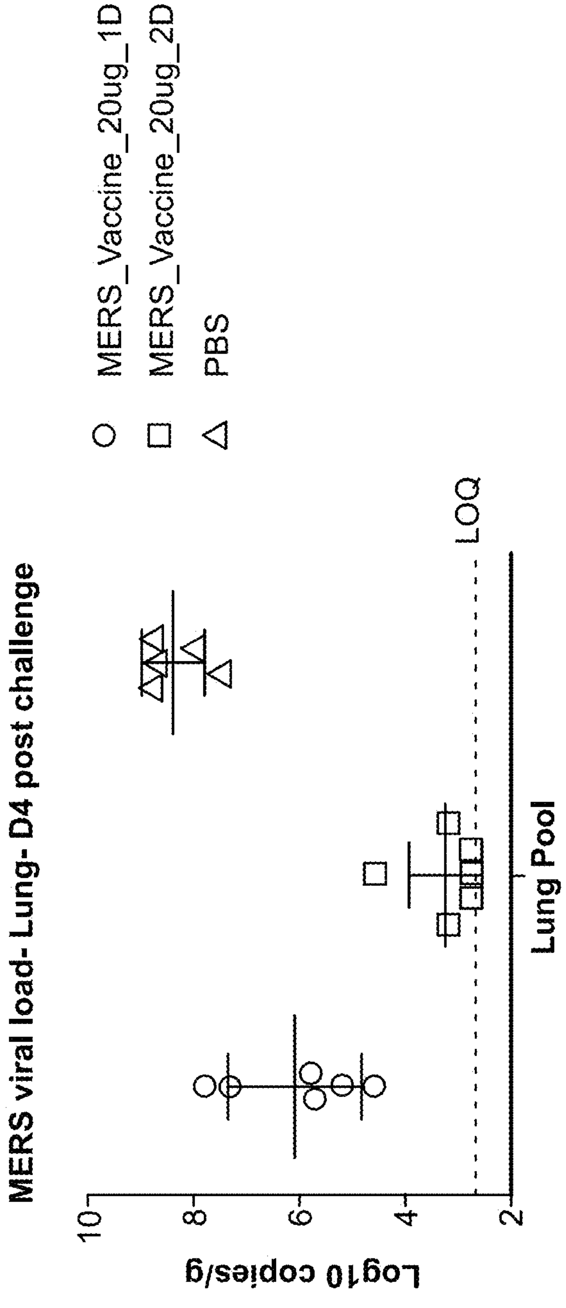
Figure 19C:
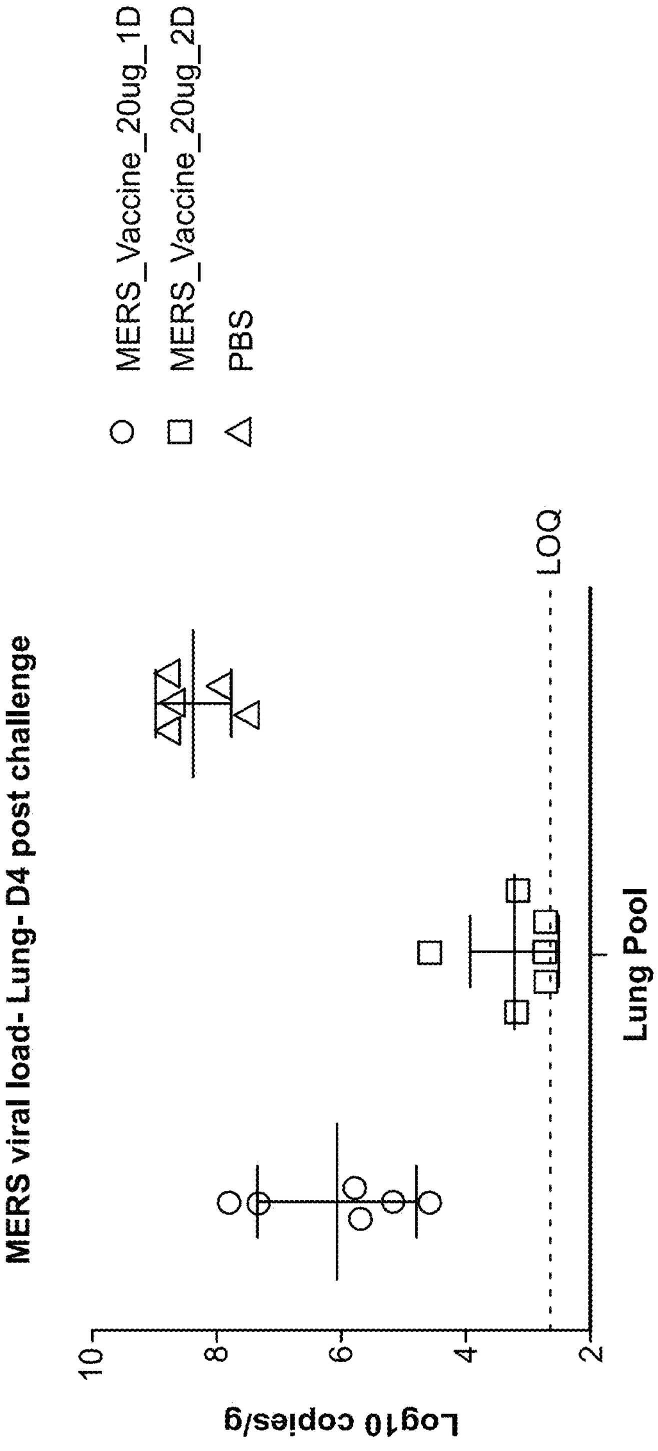

Two 20 µg doses of MERS-CoV mRNA vaccine resulted in a 3 log reduction of viral load in the nose and led to complete protection in the throat of the New Zealand white rabbits (FIG. 19A). Two 20 µg doses of MERS-CoV mRNA vaccine also resulted in a 4 log reduction of viral load in the BAL of the New Zealand white rabbits (FIG. 19B). One 20 µg dose of MERS-CoV mRNA vaccine resulted in a 2 log reduction of viral load, while two 20 µg doses of MERS-CoV mRNA vaccine resulted in an over 4 log reduction of viral load in the lungs of the New Zealand white rabbits (FIG. 19C).

Figure 20A:
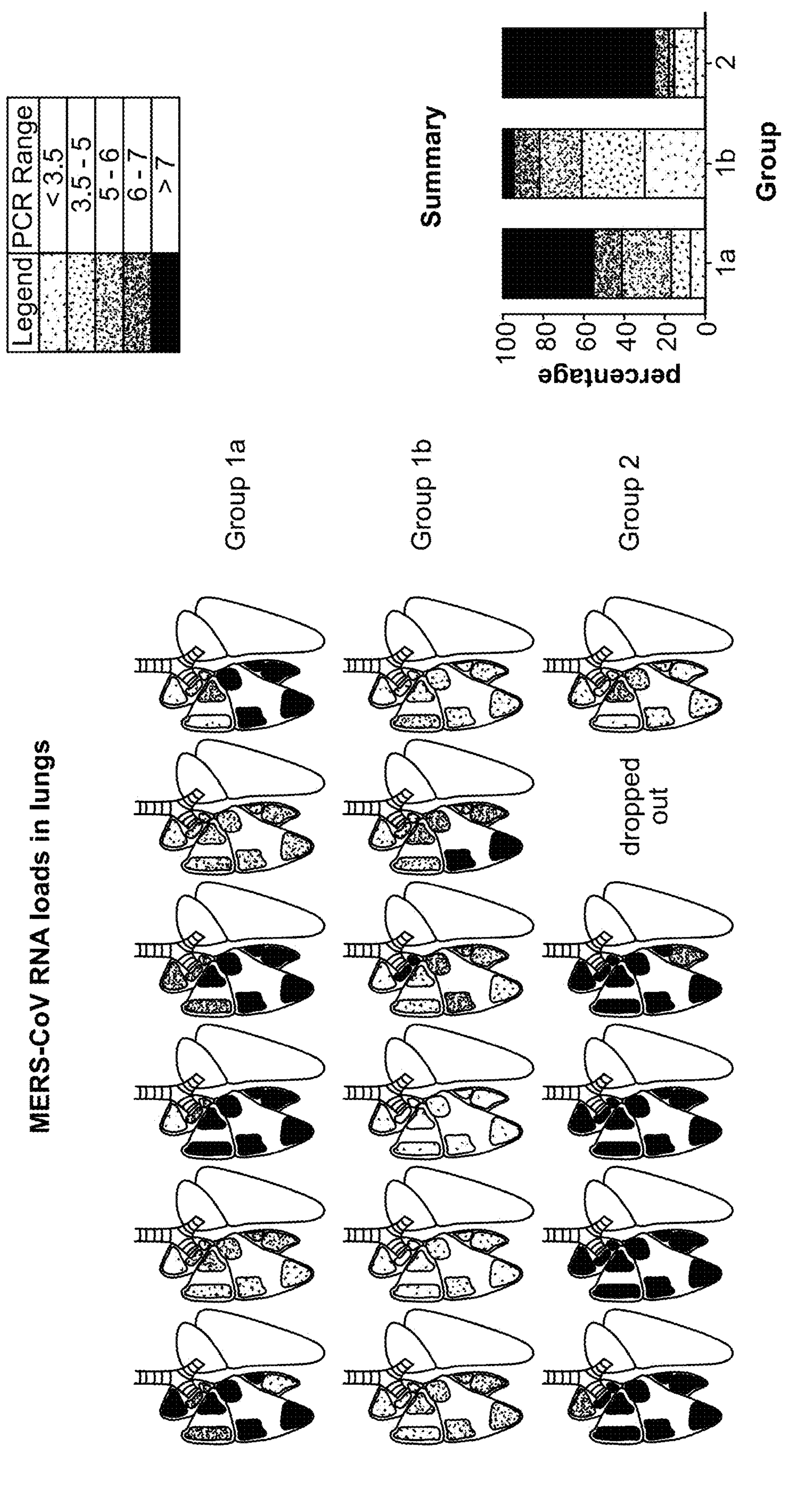
FIGS. 20A-20B are images and graphs showing viral load or replicating virus detected by PCR in the lungs of New Zealand white rabbits 4 days post challenge with MERS-CoV. The New Zealand white rabbits were immunized with a single 20 µg dose (on day 0, Group 1a) of MERS-CoV mRNA vaccine encoding the full-length Spike protein, two 20 µg doses (on day 0 and 21, Group 1b) of MERS-CoV mRNA vaccine encoding the full-length Spike protein, or placebo (Group 2) before challenge.
Figure 20B:
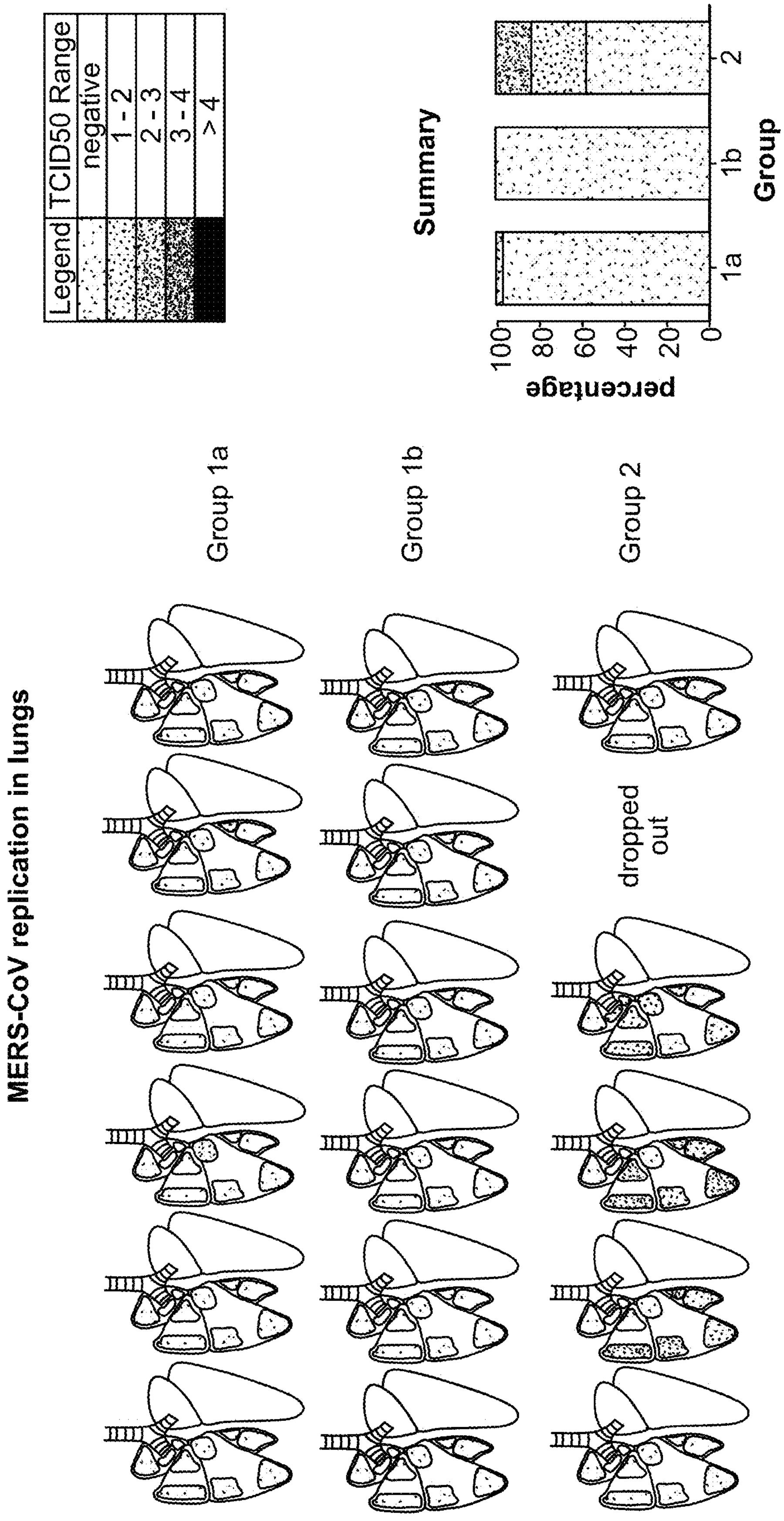

Quantitative PCR results show that two 20 µg doses of MERS-CoV mRNA vaccine reduced over 99% (2 log) of viruses in the lungs of New Zealand white rabbits (FIG. 20A). No replicating virus were detected in the lungs (FIG. 20B).

Figure 21:
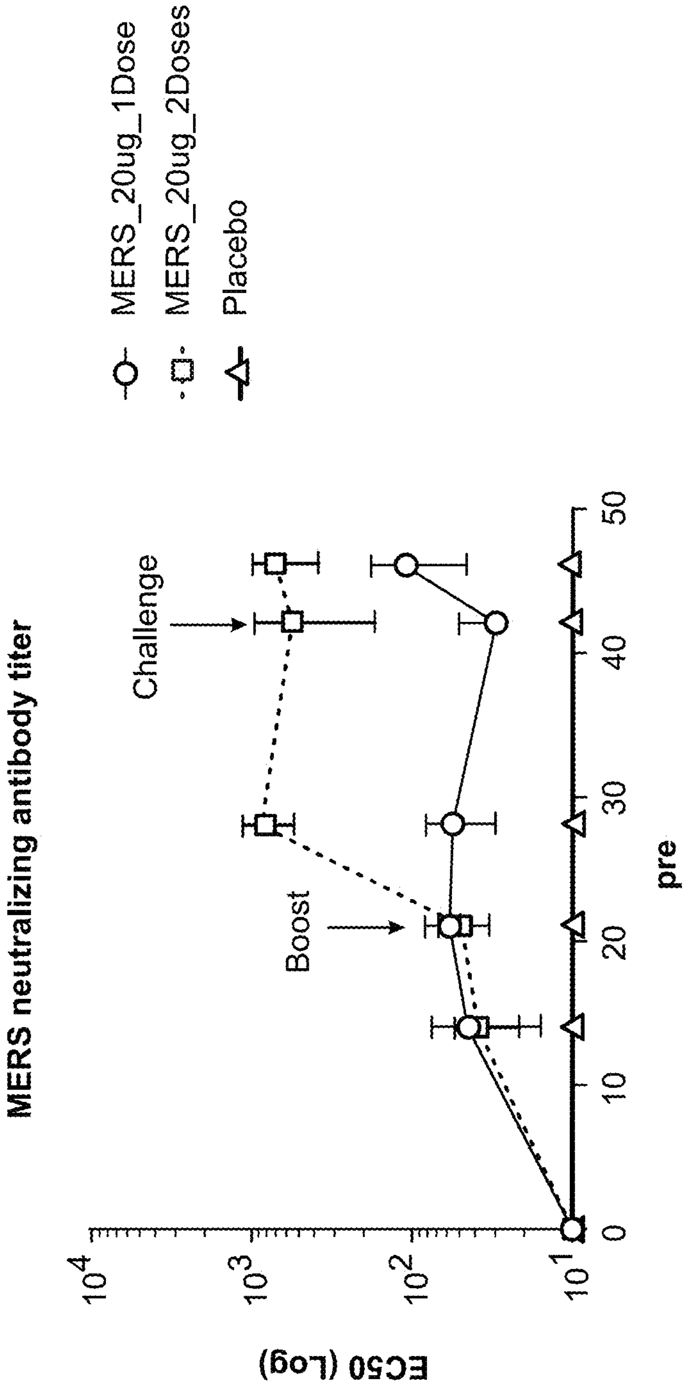
FIG. 21 is a graph showing the MERS-CoV neutralizing antibody titers in New Zealand white rabbits immunized with MERS-CoV mRNA vaccine encoding the full-length Spike protein. Immunization of the in New Zealand white rabbits were carried out as described in FIGS. 21A-21C. The results show that two doses of 20 µg MERS-CoV mRNA vaccine induced a significant amount of neutralizing antibodies against MERS-CoV ($EC_{50}$ between 500-1000). The MERS-CoV mRNA vaccine induced antibody titer is 3-5 fold better than any other vaccines tested in the same model.

Further, as shown in FIG. 21, two 20 µg doses of MERS-CoV mRNA vaccine induced significant amount of neutralizing antibodies against MERS-CoV ($EC_{50}$ between 500-1000). The MERS-CoV mRNA vaccine induced antibody titer is 3-5 fold better than any other vaccines tested in the same model.

Example 25: Immunogenicity Study

The instant study is designed to test the immunogenicity in mice of candidate MeV vaccines comprising a mRNA polynucleotide encoding MeV hemagglutinin (HA) protein, MeV Fusion (F) protein or a combination of both.

Mice are immunized intravenously (IV), intramuscularly (IM), or intradermally (ID) with candidate vaccines. Up to three immunizations are given at 3-week intervals (i.e., at weeks 0, 3, 6, and 9), and sera are collected after each immunization until weeks 33-51. Serum antibody titers against MeV HA protein or MeV F protein are determined by ELISA.

Example 26: MeV Rodent Challenge

The instant study is designed to test the efficacy in transgenic mice of candidate MeV vaccines against a lethal challenge using a MeV vaccine comprising mRNA encoding MeV HA protein or MeV F protein. The transgenic mice express human receptor CD46 or signaling lymphocyte activation molecule (SLAM) (also referred to as CD150). Humans are the only natural host for MeV infection, thus transgenic lines are required for this study. CD46 is a complement regulatory protein that protects host tissue from complement deposition by binding to complement components C3b and C4b. Its expression on murine fibroblast and lymphoid cell lines renders these otherwise refractory cells permissive for MeV infection, and the expression of CD46 on primate cells parallels the clinical tropism of MeV infection in humans and nonhuman primates (Rall G F et al. *PNAS USA* 1997; 94(9):4659-63). SLAM is a type 1 membrane glycoprotein belonging to the immunoglobulin superfamily. It is expressed on the surface of activated lymphocytes, macrophages, and dendritic cells and is thought to play an important role in lymphocyte signaling. SLAM is a receptor for both wild-type and vaccine MeV strains (Sellin C I et al. *J Virol.* 2006; 80(13):6420-29).

CD46 or SLAM/CD150 transgenic mice are challenged with a lethal dose of the MeV. Animals are immunized intravenously (IV), intramuscularly (IM), or intradermally (ID) at week 0 and week 3 with candidate MeV vaccines with and without adjuvant. The animals are then challenged with a lethal dose of MeV on week 7 via IV, IM or ID. Endpoint is day 13 post infection, death or euthanasia. Animals displaying severe illness as determined by >30% weight loss, extreme lethargy or paralysis are euthanized. Body temperature and weight are assessed and recorded daily.

In experiments where a lipid nanoparticle (LNP) formulation is used, the formulation may include a cationic lipid, non-cationic lipid, PEG lipid and structural lipid in the ratios 50:10:1.5:38.5. The cationic lipid is DLin-KC2-DMA (50 mol %), the non-cationic lipid is DSPC (10 mol %), the PEG lipid is PEG-DOMG (1.5 mol %) and the structural lipid is cholesterol (38.5 mol %), for example.

TABLE 1

| hMPV Immunogenicity studies bleeding schedule | | | | | | | | | | |
|---|---|---|---|---|---|---|---|---|---|---|
| | Animal groups | | Day | | | | | | | |
| | (n = 8) | vaccine | −2 | 0 | 7 | 14 | 21 | 28 | 35 | 56 |
| Placebo | Group 1 (n = 8) | PBS (IM) | Pre-Bleed | Prime | Bleeds | Bleeds | Bleeds/Boost | Bleeds | Bleeds | Harvest Spleens/Terminal Bleeds |
| 10 µg Dose | Group 2 (n = 8) | 10 µg (IM) | | | | | | | | |
| 2 µg Dose | Group 3 (n = 8) | 2 µg (IM) | | | | | | | | |

Total n = 24

Each of the sequences described herein encompasses a chemically modified sequence or an unmodified sequence which includes no nucleotide modifications.

TABLE 2

| Description | Sequence | SEQ ID NO: |
|---|---|---|
| | hMPV Nucleic Acid Sequences | |
| gi\|122891979\|gb\|EF051124.1\| Human metapneumovirus isolate TN/92-4 fusion protein gene, complete genome | ATGAGCTGGAAGGTGGTGATTATCTTCAGCCTGCTGATTACACCTCAACACGGCCTGAAGGAGAGCTACCTGGAAGAGAGCTGCTCCACCATCACCGAGGGCTACCTGAGCGTGCTGCGGACCGGCTGGTACACCAACGTGTTCACCCTGGAGGTGGGCGACGTGGAGAACCTGACCTGCAGCGACGGCCCTAGCCTGATCAAGACCGAGCTGGACCTGACCAAGAGCGCTCTGAGAGAGCTGAAGACCGTGTCCGCCGACCAGCTGGCCAGAGAGGAACAGATCGAGAACCCTCGGCAGAGCAGATTCGTGCTGGGCGCCATCGCTCTGGGAGTCGCCGCTGCCGCTGCAGTGACAGCTGGAGTGGCCATTGCTAAGACCATCAGACTGGAAAGCGAGGTGACAGCCATCAACAATGCCCTGAAGAAGACCAACGAGGCCGTGAGCACCCTGGGCAATGGAGTGAGAGTGCTGGCCACAGCCGTGCGGGAGCTGAAGGACTTCGTGAGCAAGAACCTGACCAGAGCCATCAACAAGAACAAGTGCGACATCGATGACCTGAAGATGGCCGTGAGCTTCTCCCAGTTCAACAGACGGTTCCTGAACGTGGTGAGACAGTTCTCCGACAACGCTGGAATCACACCTGCCATTAGCCTGGACCTGATGACCGACGCCGAGCTGGCTAGAGCCGTGCCCAACATGCCCACCAGCGCTGGCCAGATCAAGCTGATGCTGGAGAACAGAGCCATGGTGCGGAGAAAGGGCTTCGGCATCCTGATTGGGGTGTATGGAAGCTCCGTGATCTACATGGTGCAGCTGCCCATCTTCGGCGTGATCGACACACCCTGCTGGATCGTGAAGGCCGCTCCTAGCTGCTCCGAGAAGAAAGGAAACTATGCCTGTCTGCTGAGAGAGGACCAGGGCTGGTACTGCCAGAACGCCGGAAGCACAGTGTACTATCCCAACGAGAAGGACTGCGAGACCAGAGGCGACCACGTGTTCTGCGACACCGCTGCCGGAATCAACGTGGCCGAGCAGAGCAAGGAGTGCAACATCAACATCAGCACAACCAACTACCCCTGCAAGGTGAGCACCGGACGGCACCCCATCAGCATGGTGGCTCTGAGCCCTCTGGGCGCTCTGGTGGCCTGCTATAAGGGCGTGTCCTGTAGCATCGGCAGCAATCGGGTGGGCATCATCAAGCAGCTGAACAAGGGATGCTCCTACATCACCAACCAGGACGCCGACACCGTGACCATCGACAACACCGTGTACCAGCTGAGCAAGGTGGAGGGCGAGCAGCACGTGATCAAGGGCAGACCCGTGAGCTCCAGCTTCGACCCCATCAAGTTCCCTGAGGACCAGTTCAACGTGGCCCTGGACCAGGTGTTTGAGAACATCGAGAACAGCCAGGCCCTGGTGGACCAGAGCAACAGAATCCTGTCCAGCGCTGAGAAGGGCAACACCGGCTTCATCATTGTGATCATTCTGATCGCCGTGCTGGGCAGCTCCATGATCCTGGTGAGCATCTTCATCATTATCAAGAAGACCAAGAAACCCACCGGAGCCCCTCCTGAGCTGAGCGGCGTGACCAACAATGGCTTCATTCCCCACAACTGA | 1 |
| gb\|AY525843.1\|:3065-4684 Human metapneumovirus isolate NL/1/99, complete genome | ATGTCTTGGAAAGTGATGATCATCATTTCGTTACTCATAACACCCCAGCACGGGCTAAAGGAGAGTTATTTGGAAGAATCATGTAGTACTATAACTGAGGGATACCTCAGTGTTTTAAGAACAGGCTGGTACACTAATGTCTTCACATTAGAAGTTGGTGATGTTGAAAATCTTACATGTACTGATGGACCTAGCTTAATCAAAACAGAACTTGATCTAACAAAAAGTGCTTTAAGGGAACTCAAAACAGTCTCTGCTGATCAGTTGGCGAGAGAGG | 2 |

TABLE 2-continued

| Description | Sequence | SEQ ID NO: |
|---|---|---|
| | AGCAAATTGAAAATCCCAGACAATCAAGATTTGTCTTAG GTGCGATAGCTCTCGGAGTTGCTACAGCAGCAGCAGTCA CAGCAGGCATTGCAATAGCCAAAACCATAAGGCTTGAGA GTGAGGTGAATGCAATTAAAGGTGCTCTCAAACAAACTA ATGAAGCAGTATCCACATTAGGGAATGGTGTGCGGGTCC TAGCCACTGCAGTGAGAGAGCTAAAAGAATTTGTGAGCA AAAACCTGACTAGTGCAATCAACAGGAACAAATGTGACA TTGCTGATCTGAAGATGGCTGTCAGCTTCAGTCAATTCAA CAGAAGATTTCTAAATGTTGTGCGGCAGTTTTCAGACAAT GCAGGGATAACACCAGCAATATCATTGGACCTGATGACT GATGCTGAGTTGGCCAGAGCTGTATCATACATGCCAACA TCTGCAGGGCAGATAAAACTGATGTTGGAGAACCGCGCA ATGGTAAGGAGAAAAGGATTTGGAATCCTGATAGGGGTC TACGGAAGCTCTGTGATTTACATGGTTCAATTGCCGATCT TTGGTGTCATAGATACACCTTGTTGGATCATCAAGGCAGC TCCCTCTTGCTCAGAAAAAAACGGGAATTATGCTTGCCTC CTAAGAGAGGATCAAGGGTGGTATTGTAAAAATGCAGGA TCTACTGTTTACTACCCAAATGAAAAAGACTGCGAAACA AGAGGTGATCATGTTTTTTGTGACACAGCAGCAGGGATC AATGTTGCTGAGCAATCAAGAGAATGCAACATCAACATA TCTACTACCAACTACCCATGCAAAGTCAGCACAGGAAGA CACCCTATAAGCATGGTTGCACTATCACCTCTCGGTGCTT TGGTGGCTTGCTATAAAGGGGTAAGCTGCTCGATTGGCA GCAATTGGGT TGGAATCATCAAACAATTACCCAAAGGCTGCTCATACAT AACCAACCAGGATGCAGACACTGTAACAATTGACAATAC CGTGTATCAACTAAGCAAAGTTGAAGGTGAACAGCATGT AATAAAAGGGAGACCAGTTTCAAGCAGTTTTGATCCAAT CAAGTTTCCTGAGGATCAGTTCAATGTTGCGCTTGATCAA GTCTTCGAAAGCATTGAGAACAGTCAGGCACTAGTGGAC CAGTCAAACAAAATTCTAAACAGTGCAGAAAAAGGAAA CACTGGTTTCATTATCGTAGTAATTTTGGTTGCTGTTCTTG GTCTAACCATGATTTCAGTGAGCATCATCATCATAATCAA GAAAACAAGGAAGCCCACAGGAGCACCTCCAGAGCTGA ATGGTGTCACCAACGGCGGTTTCATACCACATAGTTA | |
| gb\|KJ627414.1\|:3015-4634 Human metapneumovirus strain hMPV/*Homo sapiens*/PER/CFI0497/2010/B, complete genome | ATGTCTTGGAAAGTGATGATTATCATTTCGTTACTCATAA CACCTCAGCATGGACTAAAAGAAAGTTATTTAGAAGAAT CATGTAGTACTATAACTGAAGGATATCTCAGTGTTTTAAG AACAGGTTGGTACACCAATGTCTTTACATTAGAAGTTGGT GATGTTGAAAATCTTACATGTACTGATGGACCTAGCTTAA TCAAAACAGAACTTGACCTAACCAAAAGTGCTTTAAGAG AACTCAAAACAGTTTCTGCTGATCAGTTAGCGAGAGAAG AACAAATTGAAAATCCCAGACAATCAAGGTTTGTCCTAG GTGCAATAGCTCTTGGAGTTGCCACAGCAGCAGCAGTCA CAGCAGGCATTGCAATAGCCAAAACTATAAGGCTTGAGA GTGAAGTGAATGCAATCAAAGGTGCTCTCAAAACAACCA ATGAGGCAGTATCAACACTAGGAAATGGAGTGCGGGTCC TAGCCACTGCAGTAAGAGAGCTGAAAGAATTTGTGAGCA AAAACCTGACTAGTGCGATCAACAAGAACAAGTGTGACA TTGCTGATTTGAAGATGGCTGTCAGCTTCAGTCAGTTCAA CAGAAGATTCCTAAATGTTGTGCGGCAGTTTTCAGACAAT GCAGGGATAACACCAGCAATATCATTGGACCTGATGAAT GATGCTGAGCTGGCCAGAGCTGTATCATACATGCCAACA TCTGCAGGACAGATAAAACTAATGTTAGAGAACCGTGCA ATGGTGAGGAGAAAAGGATTTGGAATCTTGATAGGGGTC TACGGAAGCTCTGTGATTTACATGGTCCAGCTGCCGATCT TTGGTGTCATAAATACACCTTGTTGGATAATCAAGGCAGC TCCCTCTTGTTCAGAAAAAGATGGAAATTATGCTTGCCTC CTAAGAGAGGATCAAGGGTGGTATTGTAAAAATGCAGGA TCCACTGTTTACTACCCAAATGAAAAAGACTGCGAAACA AGAGGTGATCATGTTTTTTGTGACACAGCAGCAGGGATC AATGTTGCTGAGCAATCAAGAGAATGCAACATCAACATA TCTACCACCAACTACCCATGCAAAGTCAGCACAGGAAGA CACCCTATCAGCATGGTTGCACTATCACCTCTCGGTGCTT TGGTAGCTTGCTACAAAGGGGTTAGCTGCTCGACTGGCA GTAATCAGGTTGGAATAATCAAACAACTACCTAAAGGCT GCTCATACATAACTAACCAGGACGCAGACACTGTAACAA TTGACAACACTGTGTATCAACTAAGCAAAGTTGAGGGTG AACAGCATGTAATAAAAGGGAGACCAGTTTCAAGCAGTT TTGATCCAATCAGGTTTCCTGAGGATCAGTTCAATGTTGC GCTTGATCAAGTCTTTGAAAGCATTGAAAACAGTCAAGC ACTAGTGGACCAGTCAAACAAAATTCTGAACAGTGCAGA AAAAGGAAACACTGGT TTCATTATTGTAATAATTTTGATTGCTGTTCTTGGGTTAAC CATGATTTCAGTGAGCATCATCATCATAATCAAAAAAAC | 3 |

TABLE 2-continued

| Description | Sequence | SEQ ID NO: |
|---|---|---|
| | AAGGAAGCCCACAGGGGCACCTCCGGAGCTGAATGGTGT TACCAACGGCGGTTTCATACCGCATAGTTAG | |
| gb\|KJ723483.1\|:5586-7310 Human respiratory syncytial virus strain RSV A/*Homo sapiens*/USA/84I-215A-01/1984, complete genome | ATGGAGTTGCCAATCCTCAAAACAAATGCAATTACCACA ATCCTTGCTGCAGTCACACTCTGTTTCGCTTCCAGTCAAA ACATCACTGAAGAATTTTATCAATCAACATGCAGTGCAG TTAGCAAAGGCTATCTTAGTGCTCTAAGAACTGGTTGGTA TACTAGTGTTATAACTATAGAATTAAGTAATATCAAGGA AAATAAGTGTAATGGAACAGATGCTAAGGTAAAATTGAT AAAACAAGAATTAGATAAATATAAAAATGCTGTAACAGA ATTGCAGTTGCTCATGCAAAGCACACCAGCAGCCAACAA TCGAGCCAGAAGAGAACTACCAAGGTTTATGAATTATAC ACTCAATAATACCAAAAATACCAATGTAACATTAAGCAA GAAAAGGAAAAGAAGATTTCTTGGCTTTTTGTTAGGTGTT GGATCTGCAATCGCCAGTGGCATTGCTGTATCTAAGGTCC TGCACCTAGAAGGGGAAGTGAACAAAATCAAAAGTGCTC TACTATCCACAAACAAGGCTGTAGTCAGCTTATCAAATG GAGTTAGTGTCTTAACCAGCAAAGTGTTAGACCTCAAAA ACTATATAGATAAACAGTTGTTACCTATTGTGAACAAGC AAAGCTGCAGCATATCAAACATTGAAACTGTGATAGAGT TCCAACAAAAGAACAACAGACTACTAGAGATTACCAGGG AATTTAGTGTTAATGCAGGTGTAACTACACCTGTAAGCAC TTATATGTTAACTAATAGTGAATTATTATCATTAATCAAT GATATGCCTATAACAAATGATCAGAAAAAGTTAATGTCC AACAATGTTCAAATAGTTAGACAGCAAAGTTACTCTATC ATGTCCATAATAAAGGAGGAAGTCTTAGCATATGTAGTA CAATTACCACTATATGGTGTAATAGATACACCCTGTTGGA AACTGCACACATCCCCTCTATGTACAACCAACACAAAGG AAGGGTCCAACATCTGCTTAACAAGAACCGACAGAGGAT GGTATTGTGACAATGCAGGATCAGTATCTTTCTTCCCACA AGCTGAAACATGTAAAGTTCAATCGAATCGGGTATTTTGT GACACAATGAACAGTTTAACATTACCAAGTGAAGTAAAT CTCTGCAACATTGACATATTCAACCCCAAATATGATTGCA AAATTATGACTTCAAAAACAGATGTAAGCAGCTCCGTTA TCACATCTCTAGGAGCCATTGTGTCATGCTATGGCAAAAC TAAATGTACAGCATCCAATAAAAATCGTGGGATCATAAA GACATTTTCTAACGGGTGTGATTATGTATCAAATAAGGG GGTGGATACTGTGTCTGTAGGTAATACATTATATTATGTA AATAAGCAAGAAGGCAAAAGTCTCTATGTAAAAGGTGAA CCAATAATAAATTTCTATGACCCATTAGTGTTCCCCTCTG ATGAATTTGATGCATCAATATCTCAAGTCAATGAGAAGA TTAACCAGAGCCTAGCATTTATTCGTAAATCCGATGAATT ATTACATAATGTAAATGCTGGTAAATCCACCACAAATAT CATGATAACTACTATAATTATAGTGATTATAGTAATATTG TTATCATTAATTGCAGTTGGACTGCTCCTATACTGCAAGG CCAGAAGCACACCAGTCACACTAAGTAAGGATCAACTGA GTGGTATAAATAATATTGCATTTAGTAACTGA | 4 |

hMPV mRNA Sequences

| Description | Sequence | SEQ ID NO: |
|---|---|---|
| gi\|122891979\|gb\|EF051124.1\| Human metapneumovirus isolate TN/92-4 fusion protein gene, complete genome | AUGAGCUGGAAGGUGGUGAUUAUCUUCAGCCUGCUGAU UACACCUCAACACGGCCUGAAGGAGAGCUACCUGGAAG AGAGCUGCUCCACCAUCACCGAGGGCUACCUGAGCGUG CUGCGGACCGGCUGGUACACCAACGUGUUCACCCUGGA GGUGGGCGACGUGGAGAACCUGACCUGCAGCGACGGCC CUAGCCUGAUCAAGACCGAGCUGGACCUGACCAAGAGC GCUCUGAGAGAGCUGAAGACCGUGUCCGCCGACCAGCU GGCCAGAGAGGAACAGAUCGAGAACCCUCGGCAGAGCA GAUUCGUGCUGGGCGCCAUCGCUCUGGGAGUCGCCGCU GCCGCUGCAGUGACAGCUGGAGUGGCCAUUGCUAAGAC CAUCAGACUGGAAAGCGAGGUGACAGCCAUCAACAAUG CCCUGAAGAAGACCAACGAGGCCGUGAGCACCCUGGGC AAUGGAGUGAGAGUGCUGGCCACAGCCGUGCGGGAGCU GAAGGACUUCGUGAGCAAGAACCUGACCAGAGCCAUCA ACAAGAACAAGUGCGACAUCGAUGACCUGAAGAUGGCC GUGAGCUUCUCCCAGUUCAACAGACGGUUCCUGAACGU GGUGAGACAGUUCUCCGACAACGCUGGAAUCACACCUG CCAUUAGCCUGGACCUGAUGACCGACGCCGAGCUGGCU AGAGCCGUGCCCAACAUGCCCACCAGCGCUGGCCAGAU CAAGCUGAUGCUGGAGAACAGAGCCAUGGUGCGGAGAA AGGGCUUCGGCAUCCUGAUUGGGGUGUAUGGAAGCUCC GUGAUCUACAUGGUGCAGCUGCCCAUCUUCGGCGUGAU CGACACACCCUGCUGGAUCGUGAAGGCCGCUCCUAGCU GCUCCGAGAAGAAAGGAAACUAUGCCUGUCUGCUGAGA GAGGACCAGGGCUGGUACUGCCAGAACGCCGGAAGCAC AGUGUACUAUCCCAACGAGAAGGACUGCGAGACCAGAG | 57 |

TABLE 2-continued

| Description | Sequence | SEQ ID NO: |
|---|---|---|
| | GCGACCACGUGUUCUGCGACACCGCUGCCGGAAUCAAC GUGGCCGAGCAGAGCAAGGAGUGCAACAUCAACAUCAG CACAACCAACUACCCCUGCAAGGUGAGCACCGGACGGC ACCCCAUCAGCAUGGUGGCUCUGAGCCCUCUGGGCGCU CUGGUGGCCUGCUAUAAGGGCGUGUCCUGUAGCAUCGG CAGCAAUCGGGUGGGCAUCAUCAAGCAGCUGAACAAGG GAUGCUCCUACAUCACCAACCAGGACGCCGACACCGUG ACCAUCGACAACACCGUGUACCAGCUGAGCAAGGUGGA GGGCGAGCAGCACGUGAUCAAGGGCAGACCCGUGAGCU CCAGCUUCGACCCCAUCAAGUUCCCUGAGGACCAGUUC AACGUGGCCCUGGACCAGGUGUUUGAGAACAUCGAGAA CAGCCAGGCCCUGGUGGACCAGAGCAACAGAAUCCUGU CCAGCGCUGAGAAGGGCAACACCGGCUUCAUCAUUGUG AUCAUUCUGAUCGCCGUGCUGGGCAGCUCCAUGAUCCU GGUGAGCAUCUUCAUCAUUAUCAAGAAGACCAAGAAAC CCACCGGAGCCCCUCCUGAGCUGAGCGGCGUGACCAAC AAUGGCUUCAUUCCCCACAACUGA | |
| gb\|AY525843.1\|:3065-4684 Human metapneumovirus isolate NL/1/99, complete genome | AUGUCUUGGAAAGUGAUGAUCAUCAUUUCGUUACUCAU AACACCCCAGCACGGGCUAAAGGAGAGUUAUUUGGAAG AAUCAUGUAGUACUAUAACUGAGGGAUACCUCAGUGUU UUAAGAACAGGCUGGUACACUAAUGUCUUCACAUUAGA AGUUGGUGAUGUUGAAAAUCUUACAUGUACUGAUGGA CCUAGCUUAAUCAAAACAGAACUUGAUCUAACAAAAAG UGCUUUAAGGGAACUCAAAACAGUCUCUGCUGAUCAGU UGGCGAGAGAGGAGCAAAUUGAAAAUCCCAGACAAUCA AGAUUUGUCUUAGGUGCGAUAGCUCUCGGAGUUGCUAC AGCAGCAGCAGUCACAGCAGGCAUUGCAAUAGCCAAAA CCAUAAGGCUUGAGAGUGAGGUGAAUGCAAUUAAAGG UGCUCUCAAACAAACUAAUGAAGCAGUAUCCACAUUAG GGAAUGGUGUGCGGGUCCUAGCCACUGCAGUGAGAGAG CUAAAAGAAUUUGUGAGCAAAAACCUGACUAGUGCAAU CAACAGGAACAAAUGUGACAUUGCUGAUCUGAAGAUGG CUGUCAGCUUCAGUCAAUUCAACAGAAGAUUUCUAAAU GUUGUGCGGCAGUUUUCAGACAAUGCAGGGAUAACACC AGCAAUAUCAUUGGACCUGAUGACUGAUGCUGAGUUGG CCAGAGCUGUAUCAUACAUGCCAACAUCUGCAGGGCAG AUAAAACUGAUGUUGGAGAACCGCGCAAUGGUAAGGAG AAAAGGAUUUGGAAUCCUGAUAGGGGUCUACGGAAGCU CUGUGAUUUACAUGGUUCAAUUGCCGAUCUUUGGUGUC AUAGAUACACCUUGUUGGAUCAUCAAGGCAGCUCCCUC UUGCUCAGAAAAAAACGGGAAUUAUGCUUGCCUCCUAA UACUGUUUACUACCCAAAUGAAAAAGACUGCGAAACAA GAGGUGAUCAUGUUUUUUGUGACACAGCAGCAGGGAUC AAUGUUGCUGAGCAAUCAAGAGAAUGCAACAUCAACAU AUCUACUACCAACUACCCAUGCAAAGUCAGCACAGGAA GACACCCUAUAAGCAUGGUUGCACUAUCACCUCUCGGU GCUUUGGUGGCUUGCUAUAAAGGGGUAAGCUGCUCGAU UGGCAGCAAUUGGGU UGGAAUCAUCAAACAAUUACCCAAAGGCUGCUCAUACA UAACCAACCAGGAUGCAGACACUGUAACAAUUGACAAU ACCGUGUAUCAACUAAGCAAAGUUGAAGGUGAACAGCA UGUAAUAAAAGGGAGACCAGUUUCAAGCAGUUUUGAUC CAAUCAAGUUUCCUGAGGAUCAGUUCAAUGUUGCGCUU GAUCAAGUCUUCGAAAGCAUUGAGAACAGUCAGGCACU AGUGGACCAGUCAAACAAAAUUCUAAACAGUGCAGAAA AAGGAAACACUGGUUUCAUUAUCGUAGUAAUUUUGGU UGCUGUUCUUGGUCUAACCAUGAUUUCAGUGAGCAUCA UCAUCAUAAUCAAGAAAACAAGGAAGCCCACAGGAGCA CCUCCAGAGCUGAAUGGUGUCACCAACGGCGGUUUCAU ACCACAUAGUUAG | 58 |
| gb\|KJ627414.1\|:3015-4634 Human metapneumovirus strain hMPV/*Homo sapiens*/PER/CFI0497/2010/B, complete genome | AUGUCUUGGAAAGUGAUGAUUAUCAUUUCGUUACUCAU AACACCUCAGCAUGGACUAAAAGAAAGUUAUUUAGAAG AAUCAUGUAGUACUAUAACUGAAGGAUAUCUCAGUGUU UUAAGAACAGGUUGGUACACCAAUGUCUUUACAUUAGA AGUUGGUGAUGUUGAAAAUCUUACAUGUACUGAUGGA CCUAGCUUAAUCAAAACAGAACUUGACCUAACCAAAAG UGCUUUAAGAGAACUCAAAACAGUUUCUGCUGAUCAGU UAGCGAGAGAAGAACAAAUUGAAAAUCCCAGACAAUCA AGGUUUGUCCUAGGUGCAAUAGCUCUUGGAGUUGCCAC AGCAGCAGCAGUCACAGCAGGCAUUGCAAUAGCCAAAA CUAUAAGGCUUGAGAGUGAAGUGAAUGCAAUCAAAGG UGCUCUCAAAACAACCAAUGAGGCAGUAUCAACACUAG GAAAUGGAGUGCGGGUCCUAGCCACUGCAGUAAGAGAG CUGAAAGAAUUUGUGAGCAAAAACCUGACUAGUGCGAU | 59 |

TABLE 2-continued

| Description | Sequence | SEQ ID NO: |
|---|---|---|
| | CAACAAGAACAAGUGUGACAUUGCUGAUUUGAAGAUGG<br>CUGUCAGCUUCAGUCAGUUCAACAGAAGAUUCCUAAAU<br>GUUGUGCGGCAGUUUUCAGACAAUGCAGGGAUAACACC<br>AGCAAUAUCAUUGGACCUGAUGAAUGAUGCUGAGCUGG<br>CCAGAGCUGUAUCAUACAUGCCAACAUCUGCAGGACAG<br>AUAAAACUAAUGUUAGAGAACCGUGCAAUGGUGAGGA<br>GAAAAGGAUUUGGAAUCUUGAUAGGGGUCUACGGAAG<br>CUCUGUGAUUUACAUGGUCCAGCUGCCGAUCUUUGGUG<br>UCAUAAAUACACCUUGUUGGAUAAUCAAGGCAGCUCCC<br>UCUUGUUCAGAAAAAGAUGGAAAUUAUGCUUGCCUCCU<br>AAGAGAGGAUCAAGGGUGGUAUUGUAAAAAUGCAGGA<br>UCCACUGUUUACUACCCAAAUGAAAAAGACUGCGAAAC<br>AAGAGGUGAUCAUGUUUUUUGUGACACAGCAGCAGGGA<br>UCAAUGUUGCUGAGCAAUCAAGAGAAUGCAACAUCAAC<br>AUAUCUACCACCAACUACCCAUGCAAAGUCAGCACAGG<br>AAGACACCCUAUCAGCAUGGUUGCACUAUCACCUCUCG<br>GUGCUUUGGUAGCUUGCUACAAAGGGGUUAGCUGCUCG<br>ACUGGCAGUAAUCAGGUUGGAAUAAUCAAACAACUACC<br>UAAAGGCUGCUCAUACAUAACUAACCAGGACGCAGACA<br>CUGUAACAAUUGACAACACUGUGUAUCAACUAAGCAAA<br>GUUGAGGGUGAACAGCAUGUAAUAAAAGGGAGACCAG<br>UUUCAAGCAGUUUUGAUCCAAUCAGGUUUCCUGAGGAU<br>CAGUUCAAUGUUGCGCUUGAUCAAGUCUUUGAAAGCAU<br>UGAAAACAGUCAAGCACUAGUGGACCAGUCAAACAAAA<br>UUCUGAACAGUGCAGAAAAAGGAAACACUGGU<br>UUCAUUAUUGUAAUAAUUUUGAUUGCUGUUCUUGGGU<br>UAACCAUGAUUUCAGUGAGCAUCAUCAUCAUAAUCAAA<br>AAAACAAGGAAGCCCACAGGGGCACCUCCGGAGCUGAA<br>UGGUGUUACCAACGGCGGUUUCAUACCGCAUAGUUAG | |
| gb\|KJ723483.1\|:5586-7310 Human respiratory syncytial virus strain RSV A/*Homo sapiens*/USA/84I-215A-01/1984, complete genome | AUGGAGUUGCCAAUCCUCAAAACAAAUGCAAUUACCAC<br>AAUCCUUGCUGCAGUCACACUCUGUUUCGCUUCCAGUC<br>AAAACAUCACUGAAGAAUUUUAUCAAUCAACAUGCAGU<br>GCAGUUAGCAAAGGCUAUCUUAGUGCUCUAAGAACUGG<br>UUGGUAUACUAGUGUUAUAACUAUAGAAUUAAGUAAU<br>AUCAAGGAAAAUAAGUGUAAUGGAACAGAUGCUAAGG<br>UAAAAUUGAUAAAACAAGAAUUAGAUAAAUAUAAAAA<br>UGCUGUAACAGAAUUGCAGUUGCUCAUGCAAAGCACAC<br>CAGCAGCCAACAAUCGAGCCAGAAGAGAACUACCAAGG<br>UUUAUGAAUUAUACACUCAAUAAUACCAAAAAUACCAA<br>UGUAACAUUAAGCAAGAAAAGGAAAAGAAGAUUUCUU<br>GGCUUUUUGUUAGGUGUUGGAUCUGCAAUCGCCAGUGG<br>CAUUGCUGUAUCUAAGGUCCUGCACCUAGAAGGGGAAG<br>UGAACAAAAUCAAAAGUGCUCUACUAUCCACAAACAAG<br>GCUGUAGUCAGCUUAUCAAAUGGAGUUAGUGUCUUAAC<br>CAGCAAAGUGUUAGACCUCAAAAACUAUAUAGAUAAAC<br>AGUUGUUACCUAUUGUGAACAAGCAAAGCUGCAGCAUA<br>UCAAACAUUGAAACUGUGAUAGAGUUCCAACAAAAGAA<br>CAACAGACUACUAGAGAUUACCAGGGAAUUUAGUGUUA<br>AUGCAGGUGUAACUACACCUGUAAGCACUUAUAUGUUA<br>ACUAAUAGUGAAUUAUUAUCAUUAAUCAAUGAUAUGCC<br>UAUAACAAAUGAUCAGAAAAAGUUAAUGUCCAACAAUG<br>UUCAAAUAGUUAGACAGCAAAGUUACUCUAUCAUGUCC<br>AUAAUAAAGGAGGAAGUCUUAGCAUAUGUAGUACAAU<br>UACCACUAUAUGGUGUAAUAGAUACACCCUGUUGGAAA<br>CUGCACACAUCCCCUCUAUGUACAACCAACACAAAGGA<br>AGGGUCCAACAUCUGCUUAACAAGAACCGACAGAGGAU<br>GGUAUUGUGACAAUGCAGGAUCAGUAUCUUUCUUCCCA<br>CAAGCUGAAACAUGUAAAGUUCAAUCGAAUCGGGUAUU<br>UUGUGACACAAUGAACAGUUUAACAUUACCAAGUGAAG<br>UAAAUCUCUGCAACAUUGACAUAUUCAACCCCAAAUAU<br>GAUUGCAAAAUUAUGACUUCAAAAACAGAUGUAAGCAG<br>CUCCGUUAUCACAUCUCUAGGAGCCAUUGUGUCAUGCU<br>AUGGCAAAACUAAAUGUACAGCAUCCAAUAAAAAUCGU<br>GGGAUCAUAAAGACAUUUUCUAACGGGUGUGAUUAUG<br>UAUCAAAUAAGGGGGUGGAUACUGUGUCUGUAGGUAA<br>UACAUUAUAUUAUGUAAAUAAGCAAGAAGGCAAAAGU<br>CUCUAUGUAAAAGGUGAACCAAUAAUAAAUUUCUAUGA<br>CCCAUUAGUGUUCCCCUCUGAUGAAUUUGAUGCAUCAA<br>UAUCUCAAGUCAAUGAGAAGAUUAACCAGAGCCUAGCA<br>UUUAUUCGUAAAUCCGAUGAAUUAUUACAUAAUGUAA<br>AUGCUGGUAAAUCCACCACAAAUAUCAUGAUAACUACU | 60 |

TABLE 2-continued

<table>
<tr><th>Description</th><th>Sequence</th><th>SEQ ID NO:</th></tr>
<tr><td></td><td>AUAAUUAUAGUGAUUAUAGUAAUAUUGUUAUCAUUAA<br>UUGCAGUUGGACUGCUCCUAUACUGCAAGGCCAGAAGC<br>ACACCAGUCACACUAAGUAAGGAUCAACUGAGUGGUAU<br>AAAUAAUAUUGCAUUUAGUAACUGA</td><td></td></tr>
</table>

TABLE 3

<table>
<tr><th colspan="3">hMPV Amino Acid Sequences</th></tr>
<tr><th>Description</th><th>Sequence</th><th>SEQ ID NO:</th></tr>
<tr><td>gi|122891979|gb|E<br>F051124.1| Human<br>metapneumovirus<br>isolate TN/92-4<br>fusion protein gene,<br>complete cds</td><td>MSWKVVIIFSLLITPQHGLKESYLEESCSTITEGYLSVLRTGW<br>YTNVFTLEVGDVENLTCSDGPSLIKTELDLTKSALRELKTVS<br>ADQLAREEQIENPRQSRFVLGAIALGVAAAAAVTAGVAIAK<br>TIRLESEVTAINNALKKTNEAVSTLGNGVRVLATAVRELKD<br>FVSKNLTRAINKNKCDIDDLKMAVSFSQFNRRFLNVVRQFS<br>DNAGITPAISLDLMTDAELARAVPNMPTSAGQIKLMLENRA<br>MVRRKGFGILIGVYGSSVIYMVQLPIFGVIDTPCWIVKAAPS<br>CSEKKGNYACLLREDQGWYCQNAGSTVYYPNEKDCETRG<br>DHVFCDTAAGINVAEQSKECNINISTTNYPCKVSTGRHPISM<br>VALSPLGALVACYKGVSCSIGSNRVGIIKQLNKGCSYITNQD<br>ADTVTIDNTVYQLSKVEGEQHVIKGRPVSSSFDPIKFPEDQF<br>NVALDQVFENIENSQALVDQSNRILSSAEKGNTGFIIVIILIAV<br>LGSSMILVSIFIIIKKTKKPTGAPPELSGVTNNGFIPHN</td><td>5</td></tr>
<tr><td>gb|AY525843.1|:30<br>65-4684 Human<br>metapneumovirus<br>isolate NL/1/99,<br>complete cds</td><td>MSWKVMIIISLLITPQHGLKESYLEESCSTITEGYLSVLRTGW<br>YTNVFTLEVGDVENLTCTDGPSLIKTELDLTKSALRELKTVS<br>ADQLAREEQIENPRQSRFVLGAIALGVATAAAVTAGIAIAKT<br>IRLESEVNAIKGALKQTNEAVSTLGNGVRVLATAVRELKEF<br>VSKNLTSAINRNKCDIADLKMAVSFSQFNRRFLNVVRQFSD<br>NAGITPAISLDLMTDAELARAVSYMPTSAGQIKLMLENRAM<br>VRRKGFGILIGVYGSSVIYMVQLPIFGVIDTPCWIIKAAPSCS<br>EKNGNYACLLREDQGWYCKNAGSTVYYPNEKDCETRGDH<br>VFCDTAAGINVAEQSRECNINISTTNYPCKVSTGRHPISMVA<br>LSPLGALVACYKGVSCSIGSNWVGIIKQLPKGCSYITNQDAD<br>TVTIDNTVYQLSKVEGEQHVIKGRPVSSSFDPIKFPEDQFNV<br>ALDQVFESIENSQALVDQSNKILNSAEKGNTGFIIVVILVAVL<br>GLTMISVSIIIIIKKTRKPTGAPPELNGVTNGGFIPHS</td><td>6</td></tr>
<tr><td>gb|KJ627414.1|:30<br>15-4634 Human<br>metapneumovirus<br>strain hMPV/Homo<br>sapiens/PER/CFI04<br>97/2010/B,<br>complete cds</td><td>MSWKVMIIISLLITPQHGLKESYLEESCSTITEGYLSVLRTGW<br>YTNVFTLEVGDVENLTCTDGPSLIKTELDLTKSALRELKTVS<br>ADQLAREEQIENPRQSRFVLGAIALGVATAAAVTAGIAIAKT<br>IRLESEVNAIKGALKTTNEAVSTLGNGVRVLATAVRELKEF<br>VSKNLTSAINKNKCDIADLKMAVSFSQFNRRFLNVVRQFSD<br>NAGITPAISLDLMNDAELARAVSYMPTSAGQIKLMLENRAM<br>VRRKGFGILIGVYGSSVIYMVQLPIFGVINTPCWIIKAAPSCS<br>EKDGNYACLLREDQGWYCKNAGSTVYYPNEKDCETRGDH<br>VFCDTAAGINVAEQSRECNINISTTNYPCKVSTGRHPISMVA<br>LSPLGALVACYKGVSCSTGSNQVGIIKQLPKGCSYITNQDAD<br>TVTIDNTVYQLSKVEGEQHVIKGRPVSSSFDPIRFPEDQFNV<br>ALDQVFESIENSQALVDQSNKILNSAEKGNTGFIIVIILIAVLG<br>LTMISVSIIIIIKKTRKPTGAPPELNGVTNGGFIPHS</td><td>7</td></tr>
<tr><td>gb|KJ723483.1|:55<br>86-7310 Human<br>respiratory<br>syncytial virus<br>strain RSV A/Homo<br>sapiens/USA/84I-<br>215A-01/1984,<br>complete cds</td><td>MELPILKTNAITTILAAVTLCFASSQNITEEFYQSTCSAVSKG<br>YLSALRTGWYTSVITIELSNIKENKCNGTDAKVKLIKQELDK<br>YKNAVTELQLLMQSTPAANNRARRELPRFMNYTLNNTKNT<br>NVTLSKKRKRRFLGFLLGVGSAIASGIAVSKVLHLEGEVNKI<br>KSALLSTNKAVVSLSNGVSVLTSKVLDLKNYIDKQLLPIVN<br>KQSCSISNIETVIEFQQKNNRLLEITREFSVNAGVTTPVSTYM<br>LTNSELLSLINDMPITNDQKKLMSNNVQIVRQQSYSIMSIIKE<br>EVLAYVVQLPLYGVIDTPCWKLHTSPLCTTNTKEGSNICLTR<br>TDRGWYCDNAGSVSFFPQAETCKVQSNRVFCDTMNSLTLP<br>SEVNLCNIDIFNPKYDCKIMTSKTDVSSSVITSLGAIVSCYGK<br>TKCTASNKNRGIIKTFSNGCDYVSNKGVDTVSVGNTLYYVN<br>KQEGKSLYVKGEPIINFYDPLVFPSDEFDASISQVNEKINQSL<br>AFIRKSDELLHNVNAGKSTTNIMITTIIIVIIVILLSLIAVGLLL<br>YCKARSTPVTLSKDQLSGINNIAFSN</td><td>8</td></tr>
</table>

TABLE 4 hMPV NCBI Accession Numbers (Amino Acid Sequences)

| Virus | GenBank Accession |
|---|---|
| F [Human metapneumovirus] [Human metapneumovirus] | AEK26895.1 |
| fusion glycoprotein [Human metapneumovirus] | ACJ53565.1 |
| fusion glycoprotein [Human metapneumovirus] | ACJ53566.1 |
| fusion glycoprotein [Human metapneumovirus] | ACJ53569.1 |
| fusion protein [Human metapneumovirus] | AEZ52347.1 |
| fusion glycoprotein [Human metapneumovirus] | ACJ53574.1 |
| fusion glycoprotein [Human metapneumovirus] | AHV79473.1 |
| fusion glycoprotein [Human metapneumovirus] | ACJ53570.1 |
| fusion glycoprotein [Human metapneumovirus] | ACJ53567.1 |
| fusion protein [Human metapneumovirus] | AAS22125.1 |
| fusion glycoprotein [Human metapneumovirus] | AHV79795.1 |
| fusion glycoprotein [Human metapneumovirus] | AHV79455.1 |
| fusion glycoprotein [Human metapneumovirus] | ACJ53568.1 |
| fusion protein [Human metapneumovirus] | AAS22109.1 |
| fusion glycoprotein [Human metapneumovirus] | AGU68417.1 |
| fusion glycoprotein [Human metapneumovirus] | AGJ74228.1 |
| fusion glycoprotein [Human metapneumovirus] | ACJ53575.1 |
| fusion protein [Human metapneumovirus] | AAU25820.1 |
| fusion glycoprotein [Human metapneumovirus] | AGU68377.1 |
| fusion glycoprotein [Human metapneumovirus] | AGU68371.1 |
| fusion glycoprotein [Human metapneumovirus] | AGJ74087.1 |
| fusion glycoprotein [Human metapneumovirus] | ACJ53560.1 |
| fusion glycoprotein [Human metapneumovirus] | AHV79858.1 |
| fusion glycoprotein [Human metapneumovirus] | ACJ53577.1 |
| fusion protein [Human metapneumovirus] | AAS22085.1 |
| fusion protein [Human metapneumovirus] | AEZ52348.1 |
| fusion glycoprotein [Human metapneumovirus] | AGJ74044.1 |
| fusion glycoprotein [Human metapneumovirus] | ACJ53563.1 |
| fusion glycoprotein precursor [Human metapneumovirus] | YP_012608.1 |
| fusion glycoprotein [Human metapneumovirus] | AGJ74053.1 |
| fusion protein [Human metapneumovirus] | BAM37562.1 |
| fusion glycoprotein [Human metapneumovirus] | ACJ53561.1 |
| fusion glycoprotein [Human metapneumovirus] | AGU68387.1 |
| fusion [Human metapneumovirus] | AGL74060.1 |
| fusion glycoprotein precursor [Human metapneumovirus] | AAV88364.1 |
| fusion protein [Human metapneumovirus] | AAN52910.1 |
| fusion protein [Human metapneumovirus] | AAN52915.1 |
| fusion protein [Human metapneumovirus] | BAM37564.1 |
| fusion glycoprotein precursor [Human metapneumovirus] | BAH59618.1 |
| fusion protein [Human metapneumovirus] | AAQ90144.1 |
| fusion glycoprotein [Human metapneumovirus] | AHV79446.1 |
| fusion protein [Human metapneumovirus] | AEL87260.1 |
| fusion glycoprotein [Human metapneumovirus] | AHV79867.1 |
| fusion protein [Human metapneumovirus] | ABQ66027.2 |
| fusion glycoprotein [Human metapneumovirus] | ACJ53621.1 |
| fusion protein [Human metapneumovirus] | AAN52911.1 |
| fusion glycoprotein [Human metapneumovirus] | AHV79536.1 |
| fusion glycoprotein [Human metapneumovirus] | AGU68411.1 |
| fusion protein [Human metapneumovirus] | AEZ52346.1 |
| fusion protein [Human metapneumovirus] | AAN52913.1 |
| fusion protein [Human metapneumovirus] | AAN52908.1 |
| fusion glycoprotein [Human metapneumovirus] | ACJ53553.1 |
| fusion glycoprotein [Human metapneumovirus] | AIY25727.1 |
| fusion protein [Human metapneumovirus] | ABM67072.1 |
| fusion protein [Human metapneumovirus] | AEZ52361.1 |
| fusion protein [Human metapneumovirus] | AAS22093.1 |
| fusion glycoprotein [Human metapneumovirus] | AGH27049.1 |
| fusion protein [Human metapneumovirus] | AAK62968.2 |
| fusion glycoprotein [Human metapneumovirus] | ACJ53556.1 |
| fusion glycoprotein [Human metapneumovirus] | ACJ53620.1 |
| fusion protein [Human metapneumovirus] | ABQ58820.1 |
| F [Human metapneumovirus] [Human metapneumovirus] | AEK26886.1 |
| fusion glycoprotein [Human metapneumovirus] | ACJ53619.1 |
| fusion glycoprotein [Human metapneumovirus] | ACJ53555.1 |
| fusion [Human metapneumovirus] | AGL74057.1 |
| fusion protein [Human metapneumovirus] | ABD27850.1 |
| fusion protein [Human metapneumovirus] | AEZ52349.1 |
| fusion protein [Human metapneumovirus] | ABD27848.1 |
| fusion protein [Human metapneumovirus] | ABD27846.1 |
| fusion protein [Human metapneumovirus] | ABQ66021.1 |
| fusion protein [Human metapneumovirus] | AFM57710.1 |
| fusion protein [Human metapneumovirus] | AFM57709.1 |
| fusion protein [Human metapneumovirus] | ABH05968.1 |
| fusion protein [Human metapneumovirus] | AEZ52350.1 |
| fusion protein [Human metapneumovirus] | AFM57712.1 |
| fusion protein [Human metapneumovirus] | AEZ52364.1 |

TABLE 4-continued hMPV NCBI Accession Numbers (Amino Acid Sequences)

| Virus | GenBank Accession |
|---|---|
| fusion protein [Human metapneumovirus] | AAN52912.1 |
| fusion protein [Human metapneumovirus] | AEZ52363.1 |
| fusion [Human metapneumovirus] | AGL74059.1 |
| fusion glycoprotein [Human metapneumovirus] | ACJ53583.1 |
| fusion protein [Human metapneumovirus] | AEZ52356.1 |
| fusion protein [Human metapneumovirus] | AEZ52353.1 |
| fusion glycoprotein [Human metapneumovirus] | ACJ53581.1 |
| fusion glycoprotein [Human metapneumovirus] | ACJ53578.1 |
| fusion protein [Human metapneumovirus] | AAS22117.1 |
| fusion protein [Human metapneumovirus] | BAN75965.1 |
| fusion protein [Human metapneumovirus] | AGF92105.1 |
| fusion protein [Human metapneumovirus] | AAS22077.1 |
| fusion protein [Human metapneumovirus] | AAN52909.1 |
| fusion glycoprotein [Human metapneumovirus] | ACJ53586.1 |
| fusion protein [Human metapneumovirus] | AAQ90145.1 |
| fusion glycoprotein [Human metapneumovirus] | AGT75042.1 |
| fusion [Human metapneumovirus] | AGL74058.1 |
| fusion protein [Human metapneumovirus] | AEL87263.1 |
| fusion glycoprotein [Human metapneumovirus] | AGH27057.1 |
| fusion glycoprotein [Human metapneumovirus] | AHV79491.1 |
| F [Human metapneumovirus] [Human metapneumovirus] | AEK26906.1 |
| fusion glycoprotein [Human metapneumovirus] | ACJ53580.1 |
| fusion protein [Human metapneumovirus] | AEZ52354.1 |
| fusion protein [Human metapneumovirus] | AAN52914.1 |
| G [Human metapneumovirus] [Human metapneumovirus] | AEK26901.1 |
| glycoprotein [Human metapneumovirus] | AFI56738.1 |
| glycoprotein [Human metapneumovirus] | AFI56739.1 |
| glycoprotein [Human metapneumovirus] | AFI56745.1 |
| G protein [Human metapneumovirus] | AAQ62718.1 |
| G protein [Human metapneumovirus] | AAQ62719.1 |
| attachment glycoprotein G [Human metapneumovirus] | AGH27104.1 |
| G protein [Human metapneumovirus] | AAQ62729.1 |
| G protein [Human metapneumovirus] | AAQ62728.1 |
| glycoprotein [Human metapneumovirus] | AFI56753.1 |
| glycoprotein [Human metapneumovirus] | AFI56746.1 |
| glycoprotein [Human metapneumovirus] | AFI56750.1 |
| glycoprotein [Human metapneumovirus] | AFI56747.1 |
| G protein [Human metapneumovirus] | AAQ62721.1 |
| glycoprotein [Human metapneumovirus] | AAT46573.1 |
| glycoprotein [Human metapneumovirus] | AFI56748.1 |
| glycoprotein [Human metapneumovirus] | AFI56736.1 |
| glycoprotein [Human metapneumovirus] | AFI56749.1 |
| attachment glycoprotein G [Human metapneumovirus] | AGH27131.1 |
| attachment glycoprotein G [Human metapneumovirus] | AHV79558.1 |
| glycoprotein [Human metapneumovirus] | AFI56740.1 |
| glycoprotein [Human metapneumovirus] | AFI56741.1 |
| glycoprotein [Human metapneumovirus] | AFI56744.1 |
| attachment glycoprotein G [Human metapneumovirus] | AHV79790.1 |
| attachment glycoprotein G [Human metapneumovirus] | AGH27122.1 |
| attachment glycoprotein G [Human metapneumovirus] | AHV79763.1 |
| attachment glycoprotein G [Human metapneumovirus] | AGZ48849.1 |
| glycoprotein [Human metapneumovirus] | AFI56743.1 |
| attachment glycoprotein G [Human metapneumovirus] | AHV79450.1 |
| glycoprotein [Human metapneumovirus] | AFI56751.1 |
| attachment glycoprotein [Human metapneumovirus] | AAS48482.1 |
| attachment glycoprotein G [Human metapneumovirus] | AHV79889.1 |
| attachment surface glycoprotein [Human metapneumovirus] | AGW43050.1 |
| glycoprotein [Human metapneumovirus] | AFI56754.1 |
| attachment glycoprotein G [Human metapneumovirus] | AHV79601.1 |
| glycoprotein [Human metapneumovirus] | AFI56752.1 |
| attachment glycoprotein G [Human metapneumovirus] | AHV79871.1 |
| G protein [Human metapneumovirus] | AEZ68099.1 |
| attachment glycoprotein G [Human metapneumovirus] | AHV79817.1 |
| attachment glycoprotein G [Human metapneumovirus] | AHV79943.1 |
| attachment glycoprotein G [Human metapneumovirus] | BAN75968.1 |
| attachment surface glycoprotein [Human metapneumovirus] | AGW43045.1 |
| attachment glycoprotein G [Human metapneumovirus] | AHV79628.1 |
| attachment glycoprotein [Human metapneumovirus] | AFK49783.1 |
| G protein [Human metapneumovirus] | AAQ62723.1 |
| attachment glycoprotein [Human metapneumovirus] | ABD27839.1 |
| attachment surface glycoprotein [Human metapneumovirus] | AGW43046.1 |
| G protein [Human metapneumovirus] | AAQ62717.1 |
| glycoprotein [Human metapneumovirus] | AFI56742.1 |
| attachment protein [Human metapneumovirus] | ABQ44522.1 |
| glycoprotein [Human metapneumovirus] | AFI56735.1 |
| attachment surface glycoprotein [Human metapneumovirus] | AGW43065.1 |

TABLE 4-continued

| hMPV NCBI Accession Numbers (Amino Acid Sequences) | |
|---|---|
| Virus | GenBank Accession |
| G protein [Human metapneumovirus] | AAQ62724.1 |
| attachment surface glycoprotein [Human metapneumovirus] | AGW43075.1 |
| attachment surface glycoprotein [Human metapneumovirus] | AGW43062.1 |
| glycoprotein [Human metapneumovirus] | AAT46579.1 |
| attachment surface glycoprotein [Human metapneumovirus] | AGW43064.1 |
| attachment surface glycoprotein [Human metapneumovirus] | AGW43054.1 |
| attachment surface glycoprotein [Human metapneumovirus] | AGW43042.1 |
| attachment surface glycoprotein [Human metapneumovirus] | AGW43078.1 |
| attachment surface glycoprotein [Human metapneumovirus] | AGW43067.1 |
| G protein [Human metapneumovirus] | AAQ62722.1 |
| attachment surface glycoprotein [Human metapneumovirus] | AGW43063.1 |
| glycoprotein [Human metapneumovirus] | AAT46571.1 |
| glycoprotein [Human metapneumovirus] | AAT46578.1 |
| attachment glycoprotein G [Human metapneumovirus] | AGJ74232.1 |
| glycoprotein [Human metapneumovirus] | AAT46580.1 |
| glycoprotein [Human metapneumovirus] | AAT46574.1 |
| attachment surface glycoprotein [Human metapneumovirus] | AGW43061.1 |
| attachment glycoprotein [Human metapneumovirus] | AFK49791.1 |
| attachment surface glycoprotein [Human metapneumovirus] | AGW43047.1 |
| glycoprotein [Human metapneumovirus] | ABC26386.1 |
| attachment glycoprotein [Human metapneumovirus] | AAS48466.1 |
| attachment surface glycoprotein [Human metapneumovirus] | AGW43048.1 |
| attachment glycoprotein G [Human metapneumovirus] | AGH27140.1 |
| attachment surface glycoprotein [Human metapneumovirus] | AGW43049.1 |
| attachment glycoprotein G [Human metapneumovirus] | AGJ74082.1 |
| attachment glycoprotein G [Human metapneumovirus] | AHV79442.1 |
| attachment glycoprotein G [Human metapneumovirus] | AGJ74091.1 |
| attachment glycoprotein G [Human metapneumovirus] | AHV79477.1 |
| attachment surface glycoprotein [Human metapneumovirus] | AGW43056.1 |
| attachment protein [Human metapneumovirus] | ABQ44523.1 |
| attachment glycoprotein G [Human metapneumovirus] | BAH59622.1 |
| attachment surface glycoprotein [Human metapneumovirus] | AGW43070.1 |
| glycoprotein [Human metapneumovirus] | AAT46585.1 |
| attachment glycoprotein G [Human metapneumovirus] | AGU68409.1 |
| attachment glycoprotein G [Human metapneumovirus] | AGJ74223.1 |
| attachment glycoprotein [Human metapneumovirus] | AAS22129.1 |
| attachment glycoprotein G [Human metapneumovirus] | AGJ74048.1 |
| G protein [Human metapneumovirus] | AAQ62725.1 |
| glycoprotein [Human metapneumovirus] | ABC26384.1 |
| attachment protein [Human metapneumovirus] | ABQ44525.1 |
| attachment glycoprotein G [Human metapneumovirus] | YP_012612.1 |
| attachment surface glycoprotein [Human metapneumovirus] | AGW43071.1 |
| attachment glycoprotein G [Human metapneumovirus] | AGJ74162.1 |
| attachment glycoprotein G [Human metapneumovirus] | AGH27095.1 |
| attachment glycoprotein G [Human metapneumovirus] | AHV79531.1 |
| G protein [Human metapneumovirus] | AAQ62726.1 |
| attachment glycoprotein [Human metapneumovirus] | AAS48465.1 |
| attachment surface glycoprotein [Human metapneumovirus] | AGW43058.1 |
| P [Human metapneumovirus] [Human metapneumovirus] | AEK26894.1 |
| phosphoprotein [Human metapneumovirus] | AHV79631.1 |
| phosphoprotein [Human metapneumovirus] | AHV79901.1 |
| phosphoprotein [Human metapneumovirus] | AHV79570.1 |
| phosphoprotein [Human metapneumovirus] | AGJ74076.1 |
| phosphoprotein [Human metapneumovirus] | AAS22123.1 |
| phosphoprotein [Human metapneumovirus] | ABB16895.1 |
| phosphoprotein [Human metapneumovirus] | AHV79579.1 |
| phosphoprotein [Human metapneumovirus] | AGJ74244.1 |
| phosphoprotein [Human metapneumovirus] | AHV79856.1 |
| phosphoprotein [Human metapneumovirus] | ACJ70113.1 |
| phosphoprotein [Human metapneumovirus] | AGZ48843.1 |
| phosphoprotein [Human metapneumovirus] | AHV79498.1 |
| phosphoprotein [Human metapneumovirus] | AHV79480.1 |
| phosphoprotein [Human metapneumovirus] | ABQ43382.1 |
| phosphoprotein [Human metapneumovirus] | AAS22107.1 |
| phosphoprotein [Human metapneumovirus] | ABB16898.1 |
| phosphoprotein [Human metapneumovirus] | AGH27134.1 |
| phosphoprotein [Human metapneumovirus] | ABB16899.1 |
| phosphoprotein [Human metapneumovirus] | AGH27098.1 |
| phosphoprotein [Human metapneumovirus] | AAN52866.1 |
| phosphoprotein [Human metapneumovirus] | AAS22083.1 |
| phosphoprotein [Human metapneumovirus] | YP_012606.1 |
| phosphoprotein [Human metapneumovirus] | AHV79973.1 |
| phosphoprotein [Human metapneumovirus] | AHV79462.1 |
| phosphoprotein [Human metapneumovirus] | AGJ74042.1 |
| phosphoprotein [Human metapneumovirus] | AAV88362.1 |
| P [Human metapneumovirus] [Human metapneumovirus] | AIL23591.1 |

TABLE 4-continued

| hMPV NCBI Accession Numbers (Amino Acid Sequences) | |
|---|---|
| Virus | GenBank Accession |
| phosphoprotein [Human metapneumovirus] | AHV79453.1 |
| phosphoprotein [Human metapneumovirus] | AGJ74261.1 |
| phosphoprotein [Human metapneumovirus] | AGH27116.1 |
| phosphoprotein [Human metapneumovirus] | ABB16444.1 |
| phosphoprotein [Human metapneumovirus] | ABB16445.1 |
| phosphoprotein [Human metapneumovirus] | AHV79507.1 |
| phosphoprotein [Human metapneumovirus] | BAH59616.1 |
| phosphoprotein [Human metapneumovirus] | ABB16443.1 |
| phosphoprotein [Human metapneumovirus] | ABQ43388.1 |
| phosphoprotein [Human metapneumovirus] | ABQ43389.1 |
| phosphoprotein [Human metapneumovirus] | ABQ43395.1 |
| phosphoprotein [Human metapneumovirus] | ABQ43385.1 |
| phosphoprotein [Human metapneumovirus] | AAP84042.1 |
| phosphoprotein [Human metapneumovirus] | AAN52868.1 |
| phosphoprotein [Human metapneumovirus] | AAP84041.1 |
| phosphoprotein [Human metapneumovirus] | AGH27080.1 |
| phosphoprotein [Human metapneumovirus] | ABQ43387.1 |
| phosphoprotein [Human metapneumovirus] | AAS22099.1 |
| phosphoprotein [Human metapneumovirus] | ABB16896.1 |
| phosphoprotein [Human metapneumovirus] | AGJ74094.1 |
| phosphoprotein [Human metapneumovirus] | AEZ68089.1 |
| phosphoprotein [Human metapneumovirus] | ABK97002.1 |
| phosphoprotein [Human metapneumovirus] | AAP13486.1 |
| phosphoprotein [Human metapneumovirus] | AHV79444.1 |
| phosphoprotein [Human metapneumovirus] | AHV79865.1 |
| phosphoprotein [Human metapneumovirus] | AGJ74226.1 |
| phosphoprotein [Human metapneumovirus] | ABQ43383.1 |
| phosphoprotein [Human metapneumovirus] | AAN52863.1 |
| phosphoprotein [Human metapneumovirus] | AHV79775.1 |
| phosphoprotein [Human metapneumovirus] | AEZ68094.1 |
| phosphoprotein [Human metapneumovirus] | AHV79883.1 |
| phosphoprotein [Human metapneumovirus] | AEZ68092.1 |
| phosphoprotein [Human metapneumovirus] | ABQ43390.1 |
| phosphoprotein [Human metapneumovirus] | ABQ43386.1 |
| phosphoprotein [Human metapneumovirus] | ABQ43391.1 |
| phosphoprotein [Human metapneumovirus] | ACS16062.1 |
| phosphoprotein [Human metapneumovirus] | AEZ68090.1 |
| phosphoprotein [Human metapneumovirus] | AAK62967.1 |
| phosphoprotein [Human metapneumovirus] | AEZ68093.1 |
| phosphoprotein [Human metapneumovirus] | AEZ68088.1 |
| phosphoprotein [Human metapneumovirus] | ABQ43392.1 |
| phosphoprotein [Human metapneumovirus] | ABQ43393.1 |
| phosphoprotein [Human metapneumovirus] | ABQ43384.1 |
| phosphoprotein [Human metapneumovirus] | ABQ43394.1 |
| phosphoprotein [Human metapneumovirus] | ABK96999.1 |
| phosphoprotein [Human metapneumovirus] | AHV79489.1 |
| phosphoprotein [Human metapneumovirus] | AGJ74235.1 |
| phosphoprotein [Human metapneumovirus] | AAS22075.1 |
| phosphoprotein [Human metapneumovirus] | AAS22115.1 |
| phosphoprotein [Human metapneumovirus] | AII17601.1 |
| phosphoprotein [Human metapneumovirus] | ABK97000.1 |
| phosphoprotein [Human metapneumovirus] | AHV79561.1 |
| phosphoprotein [Human metapneumovirus] | AGT75040.1 |
| phosphoprotein [Human metapneumovirus] | AAN52864.1 |
| phosphoprotein [Human metapneumovirus] | ABK97001.1 |
| phosphoprotein [Human metapneumovirus] | AGT74979.1 |
| phosphoprotein [Human metapneumovirus] | AHV79955.1 |
| phosphoprotein [Human metapneumovirus] | AGH27055.1 |
| phosphoprotein [Human metapneumovirus] | AAV88361.1 |
| phosphoprotein [Human metapneumovirus] | ABQ43397.1 |
| phosphoprotein [Human metapneumovirus] | AGJ74173.1 |
| P [Human metapneumovirus] [Human metapneumovirus] | AEK26904.1 |
| phosphoprotein [Human metapneumovirus] | ACJ70104.1 |
| phosphoprotein [Human metapneumovirus] | ABK97003.1 |
| phosphoprotein [Human metapneumovirus] | AGT74955.1 |
| phosphoprotein [Human metapneumovirus] | AAN52856.1 |
| phosphoprotein [Human metapneumovirus] | AAN52862.1 |
| phosphoprotein [Human metapneumovirus] | AGJ74138.1 |
| phosphoprotein [Human metapneumovirus] | AHV79613.1 |
| phosphoprotein [Human metapneumovirus] | AGJ74060.1 |
| phosphoprotein [Human metapneumovirus] | AAQ67684.1 |
| phosphoprotein [Human metapneumovirus] | AEA02278.1 |
| N [Human metapneumovirus] [Human metapneumovirus] | AEK26899.1 |
| nucleoprotein [Human metapneumovirus] | ACS16061.1 |
| nucleoprotein [Human metapneumovirus] | AAS88425.1 |
| nucleoprotein [Human metapneumovirus] | YP_012605.1 |

TABLE 4-continued

| hMPV NCBI Accession Numbers (Amino Acid Sequences) | |
|---|---|
| Virus | GenBank Accession |
| nucleoprotein [Human metapneumovirus] | AHV79882.1 |
| nucleoprotein [Human metapneumovirus] | AHV79774.1 |
| nucleocapsid protein [Human metapneumovirus] | AAN52886.1 |
| nucleoprotein [Human metapneumovirus] | AAS22082.1 |
| nucleoprotein [Human metapneumovirus] | AHV79864.1 |
| nucleoprotein [Human metapneumovirus] | AHV79828.1 |
| nucleoprotein [Human metapneumovirus] | AGJ74084.1 |
| nucleocapsid protein [Human metapneumovirus] | AAN52888.1 |
| N [Human metapneumovirus] [Human metapneumovirus] | AIL23590.1 |
| nucleoprotein [Human metapneumovirus] | AAK62966.1 |
| nucleoprotein [Human metapneumovirus] | AHV79972.1 |
| nucleoprotein [Human metapneumovirus] | AHV79470.1 |
| nucleoprotein [Human metapneumovirus] | AHV79452.1 |
| nucleoprotein [Human metapneumovirus] | AGJ74243.1 |
| nucleoprotein [Human metapneumovirus] | AHV79533.1 |
| nucleoprotein [Human metapneumovirus] | AGJ74181.1 |
| nucleoprotein [Human metapneumovirus] | AHV79497.1 |
| nucleoprotein [Human metapneumovirus] | AHV79702.1 |
| nucleoprotein [Human metapneumovirus] | AHV79648.1 |
| nucleoprotein [Human metapneumovirus] | AHV79435.1 |
| putative nucleoprotein [Human metapneumovirus] | AGJ74260.1 |
| nucleocapsid protein [Human metapneumovirus] | AAN52887.1 |
| nucleoprotein [Human metapneumovirus] | AGU68386.1 |
| nucleocapsid protein [Human metapneumovirus] | AAN52899.1 |
| nucleoprotein [Human metapneumovirus] | AAR17673.1 |
| nucleocapsid protein [Human metapneumovirus] | AAN52898.1 |
| nucleoprotein [Human metapneumovirus] | AEA02277.1 |
| nucleoprotein [Human metapneumovirus] | AHV79612.1 |
| nucleoprotein [Human metapneumovirus] | AGU68416.1 |
| nucleoprotein [Human metapneumovirus] | AGU68408.1 |
| nucleoprotein [Human metapneumovirus] | AGU68370.1 |
| nucleoprotein [Human metapneumovirus] | AAQ67683.1 |
| nucleoprotein [Human metapneumovirus] | AGJ74137.1 |
| nucleoprotein [Human metapneumovirus] | AGU68344.1 |
| nucleocapsid protein [Human metapneumovirus] | ABK96997.1 |
| nucleoprotein [Human metapneumovirus] | AGU68413.1 |
| nucleocapsid protein [Human metapneumovirus] | AAN52891.1 |
| nucleoprotein [Human metapneumovirus] | AGU68360.1 |
| nucleoprotein [Human metapneumovirus] | AGU68353.1 |
| nucleocapsid protein [Human metapneumovirus] | ABK96996.1 |
| nucleoprotein [Human metapneumovirus] | AAR17666.1 |
| N [Human metapneumovirus] [Human metapneumovirus] | AEK26903.1 |
| nucleoprotein [Human metapneumovirus] | AGT75039.1 |
| nucleoprotein [Human metapneumovirus] | AGU68410.1 |
| nucleoprotein [Human metapneumovirus] | AAS22074.1 |
| nucleoprotein [Human metapneumovirus] | AHV79560.1 |
| nucleoprotein [Human metapneumovirus] | AGT74978.1 |
| nucleoprotein [Human metapneumovirus] | AGJ74128.1 |
| nucleoprotein [Human metapneumovirus] | AAR17663.1 |
| nucleoprotein [Human metapneumovirus] | AAR17662.1 |
| nucleoprotein [Human metapneumovirus] | AAR17664.1 |
| nucleoprotein [Human metapneumovirus] | AAR17657.1 |
| nucleoprotein [Human metapneumovirus] | AAR17659.1 |
| nucleoprotein [Human metapneumovirus] | AAR17661.1 |
| nucleoprotein [Human metapneumovirus] | AGU68352.1 |
| nucleoprotein [Human metapneumovirus] | AGU68373.1 |
| nucleoprotein [Human metapneumovirus] | AGU68376.1 |
| nucleoprotein [Human metapneumovirus] | AGU68342.1 |
| nucleoprotein [Human metapneumovirus] | AGU68365.1 |
| nucleoprotein [Human metapneumovirus] | AGU68363.1 |
| nucleoprotein [Human metapneumovirus] | AGU68398.1 |
| nucleoprotein [Human metapneumovirus] | AGU68348.1 |
| nucleoprotein [Human metapneumovirus] | AGU68354.1 |
| nucleoprotein [Human metapneumovirus] | AGU68391.1 |
| nucleoprotein [Human metapneumovirus] | AGU68389.1 |
| nucleoprotein [Human metapneumovirus] | AGU68399.1 |
| nucleoprotein [Human metapneumovirus] | AGU68337.1 |
| nucleoprotein [Human metapneumovirus] | AAR17660.1 |
| nucleoprotein [Human metapneumovirus] | AAR17667.1 |
| nucleoprotein [Human metapneumovirus] | AGU68402.1 |
| nucleoprotein [Avian metapneumovirus type C] | CDN30025.1 |
| nucleoprotein [Avian metapneumovirus] | AGZ87947.1 |
| Nucleoprotein [Avian metapneumovirus type C] | CAL25113.1 |
| nucleocapsid protein [Avian metapneumovirus] | ABO42286.1 |
| nucleocapsid protein [Avian metapneumovirus] | AAK38430.1 |
| nucleocapsid protein [Avian metapneumovirus] | AAK54155.1 |

TABLE 4-continued

| hMPV NCBI Accession Numbers (Amino Acid Sequences) | |
|---|---|
| Virus | GenBank Accession |
| nucleocapsid protein [Avian metapneumovirus] | AAK38426.1 |
| nucleocapsid protein [Avian metapneumovirus] | AAK38425.1 |
| nucleocapsid protein [Avian metapneumovirus] | AAK38424.1 |
| nucleocapsid protein [Avian metapneumovirus] | AAF05909.1 |
| nucleocapsid protein [Avian metapneumovirus] | AAK38435.1 |
| nucleocapsid protein [Avian metapneumovirus] | AAK38428.1 |
| nucleoprotein [Human metapneumovirus] | AAR17669.1 |
| nucleocapsid protein [Avian metapneumovirus] | AAK38429.1 |
| nucleocapsid protein [Avian metapneumovirus] | AAK38427.1 |
| nucleocapsid protein [Avian metapneumovirus] | AAK38423.1 |
| nucleocapsid protein [Avian metapneumovirus] | AAK38434.1 |
| nucleoprotein [Human metapneumovirus] | AGU68338.1 |
| nucleoprotein [Avian metapneumovirus] | YP_443837.1 |
| nucleoprotein [Human metapneumovirus] | AGU68384.1 |
| nucleocapsid protein [Avian metapneumovirus] | AAK38431.1 |
| nucleoprotein [Human metapneumovirus] | AGU68405.1 |
| nucleoprotein [Human metapneumovirus] | AGU68382.1 |
| nucleoprotein [Human metapneumovirus] | AGU68395.1 |
| nucleocapsid [Human metapneumovirus] | AAL35389.3 |
| nucleoprotein [Human metapneumovirus] | AEZ68064.1 |

TABLE 5

| Description | Sequence | SEQ ID NO: |
|---|---|---|
| | PIV3 Nucleic Acid Sequences | |
| >gb\|KJ672601.1\|:4990-6609 Human parainfluenza virus 3 strain HPIV3/*Homo sapiens*/PER/FLA4815/2008[fusion glycoprotein F0] | ATGCCAATTTCAATACTGTTAATTATTACAACCATGATC ATGGCATCACACTGCCAAATAGACATCACAAAACTACA GCATGTAGGTGTATTGGTCAACAGTCCCAAAGGGATGA AGATATCACAAAACTTCGAAACAAGATATCTAATCCTGA GTCTCATACCAAAAATAGAAGATTCTAACTCTTGTGGTG ACCAACAGATCAAGCAATACAAGAGGTTATTGGATAGA CTGATCATTCCTTTATATGATGGACTAAGATTACAGAAG GATGTGATAGTGACTAATCAAGAATCCAATGAAAACAC TGATCCCAGAACAGAACGATTCTTTGGAGGGGTAATTGG AACTATTGCTCTAGGAGTAGCAACCTCAGCACAAATTAC AGCAGCAGTTGCTCTGGTTGAAGCCAAGCAGGCAAGAT CAGACATTGAAAAACTCAAGGAAGCAATCAGGGACACA AATAAAGCAGTGCAGTCAGTTCAGAGCTCTGTAGGAAA TTTGATAGTAGCAATTAAATCAGTCCAGGATTATGTCAA CAAAGAAATCGTGCCATCGATTGCGAGACTAGGTTGTG AAGCAGCAGGACTTCAGTTAGGGATTGCATTAACACAG CATTACTCAGAATTAACAAATATATTTGGTGATAACATA GGATCGTTACAAGAAAAAGGAATAAAATTACAAGGTAT AGCATCATTATACCGTACAAATATCACAGAAATATTCAC AACATCAACAGTTGACAAATATGATATTTATGATCTATT ATTTACAGAATCAATAAAGGTGAGAGTTATAGATGTTGA TTTGAATGATTACTCAATAACCCTCCAAGTCAGACTCCC TTTATTGACCAGACTGCTGAACACTCAAATCTACAAAGT AGATTCCATATCATACAATATCCAAAATAGAGAATGGTA TATCCCTCTTCCCAGCCATATCATGACGAAAGGGGCATT TCTAGGTGGAGCAGATGTCAAAGAATGCATAGAAGCAT TCAGCAGTTATATATGCCCTTCTGATCCAGGATTTGTACT AAACCATGAAATGGAGAGCTGTCTATCAGGAAACATAT CCCAATGTCCAAGAACCACAGTCACATCAGACATAGTTC CTAGGTATGCATTTGTCAATGGAGGAGTGGTTGCGAATT GTATAACAACTACATGTACATGCAATGGTATCGGTAATA GAATCAACCAACCACCTGATCAAGGAGTCAAAATTATA ACACATAAAGAATGTAATACAATAGGTATCAACGGAAT GCTATTCAACACAAACAAAGAAGGAACTCTTGCATTCTA CACACCAGACGACATAACATTAAACAATTCTGTTGCACT TGATCCGATTGACATATCAATCGAGCTCAACAAGGCCAA ATCAGATCTTGAGGAATCAAAAGAATGGATAAGAAGGT CAAATCAAAAGCTAGATTCTATTGGAAGTTGGCATCAAT CTAGCACTACAATCATAGTTATTTTGATAATGATGATTA TATTGTTTATAATTAATATAACAATAATTACAATTGCAA TTAAGTATTACAGAATTCAAAAGAGAAATCGAGTGGAT CAAAATGATAAGCCGTATGTATTAACAAACAAG | 9 |

TABLE 5-continued

| Description | Sequence | SEQ ID NO: |
|---|---|---|
| gi\|612507167\|gb\|AHX22430.1\| hemagglutinin-neuraminidase [Human parainfluenza virus 3] | ATGGAATACTGGAAGCACACCAACCACGGAAAGGATGC<br>TGGTAATGAGCTGGAGACATCCACAGCCACTCATGGCA<br>ACAAGCTCACCAACAAGATAACATATATATTGTGGACG<br>ATAACCCTGGTGTTATTATCAATAGTCTTCATCATAGTG<br>CTAACTAATTCCATCAAAAGTGAAAAGGCCCGCGAATC<br>ATTGCTACAAGACATAAATAATGAGTTTATGGAAGTTAC<br>AGAAAAGATCCAAGTGGCATCGGATAATACTAATGATC<br>TAATACAGTCAGGAGTGAATACAAGGCTTCTTACAATTC<br>AGAGTCATGTCCAGAATTATATACCAATATCATTGACAC<br>AACAAATATCGGATCTTAGGAAATTCATTAGTGAAATTA<br>CAATTAGAAATGATAATCAAGAAGTGCCACCACAAAGA<br>ATAACACATGATGTGGGTATAAAACCTTTAAATCCAGAT<br>GATTTCTGGAGATGCACGTCTGGTCTTCCATCTTTGATG<br>AAAACTCCAAAAATAAGATTAATGCCGGGACCAGGATT<br>ATTAGCTATGCCAACGACTGTTGATGGCTGTGTCAGAAC<br>CCCGTCCTTAGTGATAAATGATCTGATTTATGCTTACAC<br>CTCAAATCTAATTACTCGAGGTTGCCAGGATATAGGGAA<br>ATCATATCAAGTATTACAGATAGGGATAATAACTGTAAA<br>CTCAGACTTGGTACCTGACTTAAATCCTAGGATCTCTCA<br>TACCTTCAACATAAATGACAATAGAAAGTCATGTTCTCT<br>AGCACTCCTAAATACAGATGTATATCAACTGTGTTCAAC<br>CCCAAAAGTTGATGAAAGATCAGATTATGCATCATCAG<br>GCATAGAAGATATTGTACTTGATATTGTCAATTATGATG<br>GCTCAATCTCGACAACAAGATTTAAGAATAATAATATAA<br>GTTTTGATCAACCATATGCGGCATTATACCCATCTGTTG<br>GACCAGGGATATACTACAAAGGCAAAATAATATTTCTC<br>GGGTATGGAGGTCTTGAACATCCAATAAATGAGAATGC<br>AATCTGCAACACAACTGGGTGTCCTGGGAAAACACAGA<br>GAGACTGTAATCAAGCATCTCATAGTCCATGGTTTTCAG<br>ATAGAAGGATGGTCAACTCTATAATTGTTGTTGACAAGG<br>GCTTGAACTCAGTTCCAAAATTGAAGGTATGGACGATAT<br>CTATGAGACAAAATTACTGGGGGTCAGAAGGAAGATTA<br>CTTCTACTAGGTAACAAGATCTACATATACACAAGATCT<br>ACAAGTTGGCACAGCAAGTTACAATTAGGAATAATTGA<br>CATTACTGACTACAGTGATATAAGGATAAAATGGACAT<br>GGCATAATGTGCTATCAAGACCAGGAAACAATGAATGT<br>CCATGGGGACATTCATGTCCGGATGGATGTATAACGGG<br>AGTATATACCGATGCATATCCACTCAATCCCACAGGAAG<br>CATTGTATCATCTGTCATATTGGACTCACAAAAATCGAG<br>AGTCAACCCAGTCATAACTTACTCAACAGCAACCGAAA<br>GGGTAAACGAGCTGGCTATCCGAAACAAAACACTCTCA<br>GCTGGGTACACAACAACAAGCTGCATTACACACTATAA<br>CAAAGGGTATTGTTTTCATATAGTAGAAATAAATCATAA<br>AAGCTTAAACACATTTCAACCCATGTTGTTCAAAACAGA<br>GATTCCAAAAAGCTGCAGT | 10 |
| HPIV3_HN_Codon Optimized | ATGGAATACTGGAAGCACACCAACCACGGCAAGGACGC<br>CGGCAACGAGCTGGAAACCAGCACAGCCACACACGGCA<br>ACAAGCTGACCAACAAGATCACCTACATCCTGTGGACC<br>ATCACCCTGGTGCTGCTGAGCATCGTGTTCATCATCGTG<br>CTGACCAATAGCATCAAGAGCGAGAAGGCCAGAGAGAG<br>CCTGCTGCAGGACATCAACAACGAGTTCATGGAAGTGA<br>CCGAGAAGATCCAGGTGGCCAGCGACAACACCAACGAC<br>CTGATCCAGAGCGGCGTGAACACCCGGCTGCTGACCATC<br>CAGAGCCACGTGCAGAACTACATCCCCATCAGCCTGACC<br>CAGCAGATCAGCGACCTGCGGAAGTTCATCAGCGAGAT<br>CACCATCCGGAACGACAACCAGGAAGTGCCCCCCCAGA<br>GAATCACCCACGACGTGGGCATCAAGCCCCTGAACCCC<br>GACGATTTCTGGCGGTGTACAAGCGGCCTGCCCAGCCTG<br>ATGAAGACCCCCAAGATCCGGCTGATGCCTGGCCCTGG<br>ACTGCTGGCCATGCCTACCACAGTGGATGGCTGTGTGCG<br>GACCCCCAGCCTCGTGATCAACGATCTGATCTACGCCTA<br>CACCAGCAACCTGATCACCCGGGGCTGCCAGGATATCG<br>GCAAGAGCTACCAGGTGCTGCAGATCGGCATCATCACC<br>GTGAACTCCGACCTGGTGCCCGACCTGAACCCTCGGATC<br>AGCCACACCTTCAACATCAACGACAACAGAAAGAGCTG<br>CAGCCTGGCTCTGCTGAACACCGACGTGTACCAGCTGTG<br>CAGCACCCCCAAGGTGGACGAGAGAAGCGACTACGCCA<br>GCAGCGGCATCGAGGATATCGTGCTGGACATCGTGAAC<br>TACGACGGCAGCATCAGCACCACCCGGTTCAAGAACAA<br>CAACATCAGCTTCGACCAGCCCTACGCCGCCCTGTACCC<br>TTCTGTGGGCCCTGGCATCTACTACAAGGGCAAGATCAT<br>CTTCCTGGGCTACGGCGGCCTGGAACACCCCATCAACGA<br>GAACGCCATCTGCAACACCACCGGCTGCCCTGGCAAGA<br>CCCAGAGAGACTGCAATCAGGCCAGCCACAGCCCCTGG | 11 |

TABLE 5-continued

| Description | Sequence | SEQ ID NO: |
|---|---|---|
| | TTCAGCGACCGCAGAATGGTCAACTCTATCATCGTGGTG<br>GACAAGGGCCTGAACAGCGTGCCCAAGCTGAAAGTGTG<br>GACAATCAGCATGCGCCAGAACTACTGGGGCAGCGAGG<br>GCAGACTTCTGCTGCTGGGAAACAAGATCTACATCTACA<br>CCCGGTCCACCAGCTGGCACAGCAAACTGCAGCTGGGA<br>ATCATCGACATCACCGACTACAGCGACATCCGGATCAA<br>GTGGACCTGGCACAACGTGCTGAGCAGACCCGGCAACA<br>ATGAGTGCCCTTGGGGCCACAGCTGCCCCGATGGATGTA<br>TCACCGGCGTGTACACCGACGCCTACCCCCTGAATCCTA<br>CCGGCTCCATCGTGTCCAGCGTGATCCTGGACAGCCAGA<br>AAAGCAGAGTGAACCCCGTGATCACATACAGCACCGCC<br>ACCGAGAGAGTGAACGAACTGGCCATCAGAAACAAGAC<br>CCTGAGCGCCGGCTACACCACCACAAGCTGCATCACAC<br>ACTACAACAAGGGCTACTGCTTCCACATCGTGGAAATCA<br>ACCACAAGTCCCTGAACACCTTCCAGCCCATGCTGTTCA<br>AGACCGAGATCCCCAAGAGCTGCTCC | |
| HPIV3_F_Codon Optimized | ATGCCCATCAGCATCCTGCTGATCATCACCACAATGATC<br>ATGGCCAGCCACTGCCAGATCGACATCACCAAGCTGCA<br>GCACGTGGGCGTGCTCGTGAACAGCCCCAAGGGCATGA<br>AGATCAGCCAGAACTTCGAGACACGCTACCTGATCCTGA<br>GCCTGATCCCCAAGATCGAGGACAGCAACAGCTGCGGC<br>GACCAGCAGATCAAGCAGTACAAGCGGCTGCTGGACAG<br>ACTGATCATCCCCCTGTACGACGGCCTGCGGCTGCAGAA<br>AGACGTGATCGTGACCAACCAGGAAAGCAACGAGAACA<br>CCGACCCCCGGACCGAGAGATTCTTCGGCGGCGTGATCG<br>GCACAATCGCCCTGGGAGTGGCCACAAGCGCCCAGATT<br>ACAGCCGCTGTGGCCCTGGTGGAAGCCAAGCAGGCCAG<br>AAGCGACATCGAGAAGCTGAAAGAGGCCATCCGGGACA<br>CCAACAAGGCCGTGCAGAGCGTGCAGTCCAGCGTGGGC<br>AATCTGATCGTGGCCATCAAGTCCGTGCAGGACTACGTG<br>AACAAAGAAATCGTGCCCTCTATCGCCCGGCTGGGCTGT<br>GAAGCTGCCGGACTGCAGCTGGGCATTGCCCTGACACA<br>GCACTACAGCGAGCTGACCAACATCTTCGGCGACAACA<br>TCGGCAGCCTGCAGGAAAAGGGCATTAAGCTGCAGGGA<br>ATCGCCAGCCTGTACCGCACCAACATCACCGAGATCTTC<br>ACCACCAGCACCGTGGATAAGTACGACATCTACGACCT<br>GCTGTTCACCGAGAGCATCAAAGTGCGCGTGATCGACGT<br>GGACCTGAACGACTACAGCATCACCCTGCAAGTGCGGC<br>TGCCCCTGCTGACCAGACTGCTGAACACCCAGATCTACA<br>AGGTGGACAGCATCTCCTACAACATCCAGAACCGCGAG<br>TGGTACATCCCTCTGCCCAGCCACATTATGACCAAGGGC<br>GCCTTTCTGGGCGGAGCCGACGTGAAAGAGTGCATCGA<br>GGCCTTCAGCAGCTACATCTGCCCCAGCGACCCTGGCTT<br>CGTGCTGAACCACGAGATGGAAAGCTGCCTGAGCGGCA<br>ACATCAGCCAGTGCCCCAGAACCACCGTGACCTCCGAC<br>ATCGTGCCCAGATACGCCTTCGTGAATGGCGGCGTGGTG<br>GCCAACTGCATCACCACCACCTGTACCTGCAACGGCATC<br>GGCAACCGGATCAACCAGCCTCCCGATCAGGGCGTGAA<br>GATTATCACCCACAAAGAGTGTAACACCATCGGCATCA<br>ACGGCATGCTGTTCAATACCAACAAAGAGGGCACCCTG<br>GCCTTCTACACCCCCGACGATATCACCCTGAACAACTCC<br>GTGGCTCTGGACCCCATCGACATCTCCATCGAGCTGAAC<br>AAGGCCAAGAGCGACCTGGAAGAGTCCAAAGAGTGGAT<br>CCGGCGGAGCAACCAGAAGCTGGACTCTATCGGCAGCT<br>GGCACCAGAGCAGCACCACCATCATCGTGATCCTGATTA<br>TGATGATTATCCTGTTCATCATCAACATTACCATCATCAC<br>TATCGCCATTAAGTACTACCGGATCCAGAAACGGAACC<br>GGGTGGACCAGAATGACAAGCCCTACGTGCTGACAAAC<br>AAG | 12 |
| | PIV3 mRNA Sequences | |
| >gb\|KJ672601.1\|:4990-6609 Human parainfluenza virus 3 strain HPIV3/*Homo sapiens*/PER/FLA4815/2008[fusion glycoprotein F0] | AUGCCAAUUUCAAUACUGUUAAUUAUUACAACCAUGA<br>UCAUGGCAUCACACUGCCAAAUAGACAUCACAAAACU<br>ACAGCAUGUAGGUGUAUUGGUCAACAGUCCCAAAGGG<br>AUGAAGAUAUCACAAAACUUCGAAACAAGAUAUCUAA<br>UCCUGAGUCUCAUACCAAAAAUAGAAGAUUCUAACUC<br>UUGUGGUGACCAACAGAUCAAGCAAUACAAGAGGUUA<br>UUGGAUAGACUGAUCAUUCCUUUAUAUGAUGGACUAA<br>GAUUACAGAAGGAUGUGAUAGUGACUAAUCAAGAAUC<br>CAAUGAAAACACUGAUCCCAGAACAGAACGAUUCUUU<br>GGAGGGGUAAUUGGAACUAUUGCUCUAGGAGUAGCAA<br>CCUCAGCACAAAUUACAGCAGCAGUUGCUCUGGUUGA<br>AGCCAAGCAGGCAAGAUCAGACAUUGAAAAACUCAAG<br>GAAGCAAUCAGGGACACAAAUAAAGCAGUGCAGUCAG | 61 |

TABLE 5-continued

| Description | Sequence | SEQ ID NO: |
|---|---|---|
| | UUCAGAGCUCUGUAGGAAAUUUGAUAGUAGCAAUUAA AUCAGUCCAGGAUUAUGUCAACAAAGAAAUCGUGCCA UCGAUUGCGAGACUAGGUUGUGAAGCAGCAGGACUUC AGUUAGGGAUUGCAUUAACACAGCAUUACUCAGAAUU AACAAAUAUAUUUGGUGAUAACAUAGGAUCGUUACAA GAAAAAGGAAUAAAAUUACAAGGUAUAGCAUCAUUAU ACCGUACAAAUAUCACAGAAAUAUUCACAACAUCAAC AGUUGACAAAUAUGAUAUUUAUGAUCUAUUAUUUACA GAAUCAAUAAAGGUGAGAGUUAUAGAUGUUGAUUUGA AUGAUUACUCAAUAACCCUCCAAGUCAGACUCCCUUU AUUGACCAGACUGCUGAACACUCAAAUCUACAAAGUA GAUUCCAUAUCAUACAAUAUCCAAAAUAGAGAAUGGU AUAUCCCUCUUCCCAGCCAUAUCAUGACGAAAGGGGC AUUUCUAGGUGGAGCAGAUGUCAAAGAAUGCAUAGAA GCAUUCAGCAGUUAUAUAUGCCCUUCUGAUCCAGGAU UUGUACUAAACCAUGAAAUGGAGAGCUGUCUAUCAGG AAACAUAUCCCAAUGUCCAAGAACCACAGUCACAUCA GACAUAGUUCCUAGGUAUGCAUUUGUCAAUGGAGGAG UGGUUGCGAAUUGUAUAACAACUACAUGUACAUGCAA UGGUAUCGGUAAUAGAAUCAACCAACCACCUGAUCAA GGAGUCAAAAUUAUAACACAUAAAGAAUGUAAUACAA UAGGUAUCAACGGAAUGCUAUUCAACACAAACAAAGA AGGAACUCUUGCAUUCUACACACCAGACGACAUAACA UUAAACAAUUCUGUUGCACUUGAUCCGAUUGACAUAU CAAUCGAGCUCAACAAGGCCAAAUCAGAUCUUGAGGA AUCAAAAGAAUGGAUAAGAAGGUCAAAUCAAAAGCUA GAUUCUAUUGGAAGUUGGCAUCAAUCUAGCACUACAA UCAUAGUUAUUUUGAUAAUGAUGAUUAUAUUGUUUAU AAUUAAUAUAACAAUAAUUACAAUUGCAAUUAAGUAU UACAGAAUUCAAAAGAGAAAUCGAGUGGAUCAAAAUG AUAAGCCGUAUGUAUUAACAAACAAG | |
| gi\|612507167\|gb\|AHX22430.1\| hemagglutinin-neuraminidase [Human parainfluenza virus 3] | AUGGAAUACUGGAAGCACACCAACCACGGAAAGGAUG CUGGUAAUGAGCUGGAGACAUCCACAGCCACUCAUGG CAACAAGCUCACCAACAAGAUAACAUAUAUAUUGUGG ACGAUAACCCUGGUGUUAUUAUCAAUAGUCUUCAUCA UAGUGCUAACUAAUUCCAUCAAAAGUGAAAAGGCCCG CGAAUCAUUGCUACAAGACAUAAAUAAUGAGUUUAUG GAAGUUACAGAAAAGAUCCAAGUGGCAUCGGAUAAUA CUAAUGAUCUAAUACAGUCAGGAGUGAAUACAAGGCU UCUUACAAUUCAGAGUCAUGUCCAGAAUUAUAUACCA AUAUCAUUGACACAACAAAUAUCGGAUCUUAGGAAAU UCAUUAGUGAAAUUACAAUUAGAAAUGAUAAUCAAGA AGUGCCACCACAAAGAAUAACACAUGAUGUGGGUAUA AAACCUUUAAAUCCAGAUGAUUUCUGGAGAUGCACGU CUGGUCUUCCAUCUUUGAUGAAAACUCCAAAAAUAAG AUUAAUGCCGGGACCAGGAUUAUUAGCUAUGCCAACG ACUGUUGAUGGCUGUGUCAGAACCCCGUCCUUAGUGA UAAAUGAUCUGAUUUAUGCUUACACCUCAAAUCUAAU UACUCGAGGUUGCCAGGAUAUAGGGAAAUCAUAUCAA GUAUUACAGAUAGGGAUAAUAACUGUAAACUCAGACU UGGUACCUGACUUAAAUCCUAGGAUCUCUCAUACCUU CAACAUAAAUGACAAUAGAAAGUCAUGUUCUCUAGCA CUCCUAAAUACAGAUGUAUAUCAACUGUGUUCAACCC CAAAAGUUGAUGAAAGAUCAGAUUAUGCAUCAUCAGG CAUAGAAGAUAUUGUACUUGAUAUUGUCAAUUAUGAU GGCUCAAUCUCGACAACAAGAUUUAAGAAUAAUAAUA UAAGUUUUGAUCAACCAUAUGCGGCAUUAUACCCAUC UGUUGGACCAGGGAUAUACUACAAAGGCAAAAUAAUA UUUCUCGGGUAUGGAGGUCUUGAACAUCCAAUAAAUG AGAAUGCAAUCUGCAACACAACUGGGUGUCCUGGGAA AACACAGAGAGACUGUAAUCAAGCAUCUCAUAGUCCA UGGUUUUCAGAUAGAAGGAUGGUCAACUCUAUAAUUG UUGUUGACAAGGGCUUGAACUCAGUUCCAAAAUUGAA GGUAUGGACGAUAUCUAUGAGACAAAAUUACUGGGGG UCAGAAGGAAGAUUACUUCUACUAGGUAACAAGAUCU ACAUAUACACAAGAUCUACAAGUUGGCACAGCAAGUU ACAAUUAGGAAUAAUUGACAUUACUGACUACAGUGAU AUAAGGAUAAAAUGGACAUGGCAUAAUGUGCUAUCAA GACCAGGAAACAAUGAAUGUCCAUGGGGACAUUCAUG UCCGGAUGGAUGUAUAACGGGAGUAUAUACCGAUGCA UAUCCACUCAAUCCCACAGGAAGCAUUGUAUCAUCUG UCAUAUUGGACUCACAAAAAUCGAGAGUCAACCCAGU CAUAACUUACUCAACAGCAACCGAAAGGGUAAACGAG CUGGCUAUCCGAAACAAAACACUCUCAGCUGGUACA CAACAACAAGCUGCAUUACACACUAUAACAAAGGGUA | 62 |

TABLE 5-continued

| Description | Sequence | SEQ ID NO: |
|---|---|---|
| | UUGUUUUCAUAUAGUAGAAAUAAAUCAUAAAAGCUUA AACACAUUUCAACCCAUGUUGUUCAAAACAGAGAUUC CAAAAAGCUGCAGU | |
| HPIV3_HN_Codon Optimized | AUGGAAUACUGGAAGCACACCAACCACGGCAAGGACG CCGGCAACGAGCUGGAAACCAGCACAGCCACACACGGC AACAAGCUGACCAACAAGAUCACCUACAUCCUGUGGA CCAUCACCCUGGUGCUGCUGAGCAUCGUGUUCAUCAUC GUGCUGACCAAUAGCAUCAAGAGCGAGAAGGCCAGAG AGAGCCUGCUGCAGGACAUCAACAACGAGUUCAUGGA AGUGACCGAGAAGAUCCAGGUGGCCAGCGACAACACC AACGACCUGAUCCAGAGCGGCGUGAACACCCGGCUGCU GACCAUCCAGAGCCACGUGCAGAACUACAUCCCCAUCA GCCUGACCCAGCAGAUCAGCGACCUGCGGAAGUUCAUC AGCGAGAUCACCAUCCGGAACGACAACCAGGAAGUGC CCCCCCAGAGAAUCACCCACGACGUGGGCAUCAAGCCC CUGAACCCCGACGAUUUCUGGCGGUGUACAAGCGGCC UGCCCAGCCUGAUGAAGACCCCCAAGAUCCGGCUGAUG CCUGGCCCUGGACUGCUGGCCAUGCCUACCACAGUGGA UGGCUGUGUGCGGACCCCCAGCCUCGUGAUCAACGAUC UGAUCUACGCCUACACCAGCAACCUGAUCACCCGGGGC UGCCAGGAUAUCGGCAAGAGCUACCAGGUGCUGCAGA UCGGCAUCAUCACCGUGAACUCCGACCUGGUGCCCGAC CUGAACCCUCGGAUCAGCCACACCUUCAACAUCAACGA CAACAGAAAGAGCUGCAGCCUGGCUCUGCUGAACACC GACGUGUACCAGCUGUGCAGCACCCCCAAGGUGGACG AGAGAAGCGACUACGCCAGCAGCGGCAUCGAGGAUAU CGUGCUGGACAUCGUGAACUACGACGGCAGCAUCAGC ACCACCCGGUUCAAGAACAACAACAUCAGCUUCGACCA GCCCUACGCCGCCCUGUACCCUUCUGUGGGCCCUGGCA UCUACUACAAGGGCAAGAUCAUCUUCCUGGGCUACGG CGGCCUGGAACACCCCAUCAACGAGAACGCCAUCUGCA ACACCACCGGCUGCCCUGGCAAGACCCAGAGAGACUGC AAUCAGGCCAGCCACAGCCCCUGGUUCAGCGACCGCAG AAUGGUCAACUCUAUCAUCGUGGUGGACAAGGGCCUG AACAGCGUGCCCAAGCUGAAAGUGUGGACAAUCAGCA UGCGCCAGAACUACUGGGGCAGCGAGGGCAGACUUCU GCUGCUGGGAAACAAGAUCUACAUCUACACCCGGUCC ACCAGCUGGCACAGCAAACUGCAGCUGGGAAUCAUCG ACAUCACCGACUACAGCGACAUCCGGAUCAAGUGGACC UGGCACAACGUGCUGAGCAGACCCGGCAACAAUGAGU GCCCUUGGGGCCACAGCUGCCCCGAUGGAUGUAUCACC GGCGUGUACACCGACGCCUACCCCCUGAAUCCUACCGG CUCCAUCGUGUCCAGCGUGAUCCUGGACAGCCAGAAA AGCAGAGUGAACCCCGUGAUCACAUACAGCACCGCCAC CGAGAGAGUGAACGAACUGGCCAUCAGAAACAAGACC CUGAGCGCCGGCUACACCACCACAAGCUGCAUCACACA CUACAACAAGGGCUACUGCUUCCACAUCGUGGAAAUC AACCACAAGUCCCUGAACACCUUCCAGCCCAUGCUGUU CAAGACCGAGAUCCCCAAGAGCUGCUCC | 63 |
| HPIV3_F_Codon Optimized mRNA sequence | AUGCCCAUCAGCAUCCUGCUGAUCAUCACCACAAUGAU CAUGGCCAGCCACUGCCAGAUCGACAUCACCAAGCUGC AGCACGUGGGCGUGCUCGUGAACAGCCCCAAGGGCAU GAAGAUCAGCCAGAACUUCGAGACACGCUACCUGAUC CUGAGCCUGAUCCCCAAGAUCGAGGACAGCAACAGCU GCGGCGACCAGCAGAUCAAGCAGUACAAGCGGCUGCU GGACAGACUGAUCAUCCCCCUGUACGACGGCCUGCGGC UGCAGAAAGACGUGAUCGUGACCAACCAGGAAAGCAA CGAGAACACCGACCCCCGGACCGAGAGAUUCUUCGGCG GCGUGAUCGGCACAAUCGCCCUGGGAGUGGCCACAAG CGCCCAGAUUACAGCCGCUGUGGCCCUGGUGGAAGCCA AGCAGGCCAGAAGCGACAUCGAGAAGCUGAAAGAGGC CAUCCGGGACACCAACAAGGCCGUGCAGAGCGUGCAG UCCAGCGUGGGCAAUCUGAUCGUGGCCAUCAAGUCCG UGCAGGACUACGUGAACAAAGAAAUCGUGCCCUCUAU CGCCCGGCUGGGCUGUGAAGCUGCCGGACUGCAGCUG GGCAUUGCCCUGACACAGCACUACAGCGAGCUGACCAA CAUCUUCGGCGACAACAUCGGCAGCCUGCAGGAAAAG GGCAUUAAGCUGCAGGGAAUCGCCAGCCUGUACCGCA CCAACAUCACCGAGAUCUUCACCACCAGCACCGUGGAU AAGUACGACAUCUACGACCUGCUGUUCACCGAGAGCA UCAAAGUGCGCGUGAUCGACGUGGACCUGAACGACUA CAGCAUCACCCUGCAAGUGCGGCUGCCCCUGCUGACCA GACUGCUGAACACCCAGAUCUACAAGGUGGACAGCAU CUCCUACAACAUCCAGAACCGCGAGUGGUACAUCCCUC | 64 |

TABLE 5-continued

| Description | Sequence | SEQ ID NO: |
|---|---|---|
| | UGCCCAGCCACAUUAUGACCAAGGGCGCCUUUCUGGGC GGAGCCGACGUGAAAGAGUGCAUCGAGGCCUUCAGCA GCUACAUCUGCCCCAGCGACCCUGGCUUCGUGCUGAAC CACGAGAUGGAAAGCUGCCUGAGCGGCAACAUCAGCC AGUGCCCCAGAACCACCGUGACCUCCGACAUCGUGCCC AGAUACGCCUUCGUGAAUGGCGGCGUGGUGGCCAACU GCAUCACCACCACCUGUACCUGCAACGGCAUCGGCAAC CGGAUCAACCAGCCUCCCGAUCAGGGCGUGAAGAUUA UCACCCACAAAGAGUGUAACACCAUCGGCAUCAACGGC AUGCUGUUCAAUACCAACAAAGAGGGCACCCUGGCCU UCUACACCCCCGACGAUAUCACCCUGAACAACUCCGUG GCUCUGGACCCCAUCGACAUCUCCAUCGAGCUGAACAA GGCCAAGAGCGACCUGGAAGAGUCCAAAGAGUGGAUC CGGCGGAGCAACCAGAAGCUGGACUCUAUCGGCAGCU GGCACCAGAGCAGCACCACCAUCAUCGUGAUCCUGAUU AUGAUGAUUAUCCUGUUCAUCAUCAACAUUACCAUCA UCACUAUCGCCAUUAAGUACUACCGGAUCCAGAAACG GAACCGGGUGGACCAGAAUGACAAGCCCUACGUGCUG ACAAACAAG | |

TABLE 6

PIV3 Amino Acid Sequences

| Description | Sequence | SEQ ID NO: |
|---|---|---|
| >gi\|612507166\|gb\|AHX22429.1\| fusion glycoprotein F0 [Human parainfluenza virus 3] | MPISILLIITTMIMASHCQIDITKLQHVGVLVNSPKGMKISQ NFETRYLILSLIPKIEDSNSCGDQQIKQYKRLLDRLIIPLYDG LRLQKDVIVTNQESNENTDPRTERFFGGVIGTIALGVATSA QITAAVALVEAKQARSDIEKLKEAIRDTNKAVQSVQSSVG NLIVAIKSVQDYVNKEIVPSIARLGCEAAGLQLGIALTQHYS ELTNIFGDNIGSLQEKGIKLQGIASLYRTNITEIFTTSTVDKY DIYDLLFTESIKVRVIDVDLNDYSITLQVRLPLLTRLLNTQIY KVDSISYNIQNREWYIPLPSHIMTKGAFLGGADVKECIEAFS SYICPSDPGFVLNHEMESCLSGNISQCPRTTVTSDIVPRYAF VNGGVVANCITTTCTCNGIGNRINQPPDQGVKIITHKECNTI GINGMLFNTNKEGTLAFYTPDDITLNNSVALDPIDISIELNK AKSDLEESKEWIRRSNQKLDSIGSWHQSSTTIIVILIMMIILFI INITIITIAIKYYRIQKRNRVDQNDKPYVLTNK | 13 |
| gi\|612507167\|gb\|AHX22430.1\| hemagglutinin-neuraminidase [Human parainfluenza virus 3] | MEYWKHTNHGKDAGNELETSTATHGNKLTNKITYILWTIT LVLLSIVFIIVLTNSIKSEKARESLLQDINNEFMEVTEKIQVA SDNTNDLIQSGVNTRLLTIQSHVQNYIPISLTQQISDLRKFIS EITIRNDNQEVPPQRITHDVGIKPLNPDDFWRCTSGLPSLMK TPKIRLMPGPGLLAMPTTVDGCVRTPSLVINDLIYAYTSNLI TRGCQDIGKSYQVLQIGIITVNSDLVPDLNPRISHTFNINDN RKSCSLALLNTDVYQLCSTPKVDERSDYASSGIEDIVLDIV NYDGSISTTRFKNNNISFDQPYAALYPSVGPGIYYKGKIIFL GYGGLEHPINENAICNTTGCPGKTQRDCNQASHSPWFSDR RMVNSIIVVDKGLNSVPKLKVWTISMRQNYWGSEGRLLLL GNKIYIYTRSTSWHSKLQLGIIDITDYSDIRIKWTWHNVLSR PGNNECPWGHSCPDGCITGVYTDAYPLNPTGSIVSSVILDS QKSRVNPVITYSTATERVNELAIRNKTLSAGYTTTSCITHY NKGYCFHIVEINHKSLNTFQPMLFKTEIPKSCS | 14 |

TABLE 7

| PIV3 NCBI Accession Numbers (Nucleic Acid and Amino Acid Sequences) | |
|---|---|
| Description | GenBank Accession |
| Fusion glycoprotein F0 [Human parainfluenza virus 3] HPIV3/*Homo sapiens*/PER/FLA4815/2008 | KJ672601.1\|: 4990-6609 AHX22429 (Fusion protein) |
| hemagglutinin-neuraminidase [Human parainfluenza virus 3] HPIV3/*Homo sapiens*/PER/FLA4815/2008 | KJ672601.1\|: 6724-8442 AHX22430 (HN protein) |
| Recombinant PIV3/PIV1 virus fusion glycoprotein (F) and hemagglutinin (HN) genes, complete cds; and RNA dependent RNA polymerase (L) gene, partial cds. | AF016281 AAC23947 (hemagglutinin) |
| Recombinant PIV3/PIV1 virus fusion glycoprotein (F) and hemagglutinin (HN) genes, complete cds; and RNA dependent RNA polymerase (L) gene, partial cds. | AF016281 AAC23947 (fusion protein) |
| hemagglutinin-neuraminidase [Human parainfluenza virus 3] | BAO32044.1 |
| hemagglutinin-neuraminidase [Human parainfluenza virus 3] | BAO32051.1 |
| C protein [Human parainfluenza virus 3] | NP_599251.1 |
| C protein [Human parainfluenza virus 3] | ABZ85670.1 |
| C protein [Human parainfluenza virus 3] | AGT75164.1 |
| C protein [Human parainfluenza virus 3] | AAB48686.1 |
| C protein [Human parainfluenza virus 3] | AHX22115.1 |
| C protein [Human parainfluenza virus 3] | AGW51066.1 |
| C protein [Human parainfluenza virus 3] | AGW51162.1 |
| C protein [Human parainfluenza virus 3] | AGT75252.1 |
| C protein [Human parainfluenza virus 3] | AGT75188.1 |
| C protein [Human parainfluenza virus 3] | AGW51218.1 |
| C protein [Human parainfluenza virus 3] | AGW51074.1 |
| C protein [Human parainfluenza virus 3] | AGT75323.1 |
| C protein [Human parainfluenza virus 3] | AGT75307.1 |
| C protein [Human parainfluenza virus 3] | AHX22131.1 |
| C protein [Human parainfluenza virus 3] | AGW51243.1 |
| C protein [Human parainfluenza virus 3] | AGT75180.1 |
| C protein [Human parainfluenza virus 3] | AGT75212.1 |
| C protein [Human parainfluenza virus 3] | AGW51186.1 |
| C protein [Human parainfluenza virus 3] | AHX22075.1 |
| C protein [Human parainfluenza virus 3] | AHX22163.1 |
| C protein [Human parainfluenza virus 3] | AGT75196.1 |
| C protein [Human parainfluenza virus 3] | AHX22491.1 |
| C protein [Human parainfluenza virus 3] | AHX22139.1 |
| C protein [Human parainfluenza virus 3] | AGW51138.1 |
| C protein [Human parainfluenza virus 3] | AGW51114.1 |
| C protein [Human parainfluenza virus 3] | AGT75220.1 |
| C protein [Human parainfluenza virus 3] | AHX22251.1 |
| RecName: Full = Protein C; AltName: Full = VP18 protein | P06165.1 |
| C protein [Human parainfluenza virus 3] | AHX22187.1 |
| C protein [Human parainfluenza virus 3] | AGT75228.1 |
| C protein [Human parainfluenza virus 3] | AHX22179.1 |
| C protein [Human parainfluenza virus 3] | AHX22427.1 |
| C protein [Human parainfluenza virus 3] | AGW51210.1 |
| nonstructural protein C [Human parainfluenza virus 3] | BAA00922.1 |
| C protein [Human parainfluenza virus 3] | AHX22315.1 |
| C protein [Human parainfluenza virus 3] | AGW51259.1 |
| C protein [Human parainfluenza virus 3] | AHX22435.1 |
| C protein [Human parainfluenza virus 3] | AHX22123.1 |
| C protein [Human parainfluenza virus 3] | AHX22299.1 |
| C protein [Human parainfluenza virus 3] | AGW51267.1 |
| unnamed protein product [Human parainfluenza virus 3] | CAA28430.1 |
| C protein [Human parainfluenza virus 3] | AGW51178.1 |
| C protein [Human parainfluenza virus 3] | AHX22411.1 |
| RecName: Full = Protein C | P06164.1 |
| phosphoprotein [Human parainfluenza virus 3] | NP_067149.1 |
| phosphoprotein [Human parainfluenza virus 3] | AAB48685.1 |
| phosphoprotein [Human parainfluenza virus 3] | AHX22498.1 |
| phosphoprotein [Human parainfluenza virus 3] | AHX22490.1 |
| phosphoprotein [Human parainfluenza virus 3] | AGT75259.1 |
| phosphoprotein [Human parainfluenza virus 3] | AGW51137.1 |
| phosphoprotein [Human parainfluenza virus 3] | AGW51145.1 |
| phosphoprotein [Human parainfluenza virus 3] | AGT75298.1 |
| phosphoprotein [Human parainfluenza virus 3] | AGW51113.1 |
| phosphoprotein [Human parainfluenza virus 3] | AGT75203.1 |
| phosphoprotein [Human parainfluenza virus 3] | AGT75163.1 |
| phosphoprotein [Human parainfluenza virus 3] | AHX22506.1 |
| phosphoprotein [Human parainfluenza virus 3] | AGW51129.1 |
| phosphoprotein [Human parainfluenza virus 3] | AHX22194.1 |
| phosphoprotein [Human parainfluenza virus 3] | AGT75211.1 |
| phosphoprotein [Human parainfluenza virus 3] | AHX22258.1 |

TABLE 7-continued

PIV3 NCBI Accession Numbers (Nucleic Acid and Amino Acid Sequences)

| Description | GenBank Accession |
|---|---|
| phosphoprotein [Human parainfluenza virus 3] | AGW51121.1 |
| phosphoprotein [Human parainfluenza virus 3] | AGT75282.1 |
| phosphoprotein [Human parainfluenza virus 3] | AHX22146.1 |
| phosphoprotein [Human parainfluenza virus 3] | AHX22138.1 |
| phosphoprotein [Human parainfluenza virus 3] | AHX22322.1 |
| phosphoprotein [Human parainfluenza virus 3] | AHX22370.1 |
| phosphoprotein [Human parainfluenza virus 3] | AHX22098.1 |
| phosphoprotein [Human parainfluenza virus 3] | AHX22130.1 |
| phosphoprotein [Human parainfluenza virus 3] | AHX22418.1 |
| phosphoprotein [Human parainfluenza virus 3] | AHX22114.1 |
| phosphoprotein [Human parainfluenza virus 3] | AHX22410.1 |
| phosphoprotein [Human parainfluenza virus 3] | AGT75306.1 |
| phosphoprotein [Human parainfluenza virus 3] | AHX22170.1 |
| phosphoprotein [Human parainfluenza virus 3] | AHX22266.1 |
| phosphoprotein [Human parainfluenza virus 3] | AHX22090.1 |
| phosphoprotein [Human parainfluenza virus 3] | AGT75195.1 |
| phosphoprotein [Human parainfluenza virus 3] | AHX22226.1 |
| phosphoprotein [Human parainfluenza virus 3] | AHX22178.1 |
| phosphoprotein [Human parainfluenza virus 3] | AHX22122.1 |
| phosphoprotein [Human parainfluenza virus 3] | AHX22186.1 |
| phosphoprotein [Human parainfluenza virus 3] | AHX22066.1 |
| phosphoprotein [Human parainfluenza virus 3] | AHX22522.1 |
| phosphoprotein [Human parainfluenza virus 3] | AGW51225.1 |
| phosphoprotein [Human parainfluenza virus 3] | BAN29032.1 |
| phosphoprotein [Human parainfluenza virus 3] | ABZ85669.1 |
| phosphoprotein [Human parainfluenza virus 3] | AHX22426.1 |
| phosphoprotein [Human parainfluenza virus 3] | AHX22058.1 |
| phosphoprotein [Simian Agent 10] | ADR00400.1 |
| phosphoprotein [Human parainfluenza virus 3] | AHX22250.1 |
| phosphoprotein [Human parainfluenza virus 3] | AHX22434.1 |
| phosphoprotein [Human parainfluenza virus 3] | AHX22298.1 |
| phosphoprotein [Human parainfluenza virus 3] | AHX22442.1 |
| phosphoprotein [Human parainfluenza virus 3] | AHX22074.1 |
| phosphoprotein [Human parainfluenza virus 3] | AGW51153.1 |
| phosphoprotein [Human parainfluenza virus 3] | AGW51241.1 |
| phosphoprotein [Human parainfluenza virus 3] | AHX22210.1 |
| phosphoprotein [Human parainfluenza virus 3] | AGW51105.1 |
| phosphoprotein [Human parainfluenza virus 3] | AGT75251.1 |
| phosphoprotein [Human parainfluenza virus 3] | AHX22362.1 |
| phosphoprotein [Human parainfluenza virus 3] | AHX22474.1 |
| phosphoprotein [Human parainfluenza virus 3] | AGW51217.1 |
| phosphoprotein [Human parainfluenza virus 3] | AIG60038.1 |
| phosphoprotein [Human parainfluenza virus 3] | AHX22378.1 |
| phosphoprotein [Human parainfluenza virus 3] | AGW51057.1 |
| phosphoprotein [Human parainfluenza virus 3] | AGT75187.1 |
| phosphoprotein [Human parainfluenza virus 3] | AGW51233.1 |
| phosphoprotein [Human parainfluenza virus 3] | AHX22482.1 |
| phosphoprotein [Human parainfluenza virus 3] | AGW51161.1 |
| phosphoprotein [Human parainfluenza virus 3] | AHX22306.1 |
| phosphoprotein [Human parainfluenza virus 3] | AHX22162.1 |
| phosphoprotein [Human parainfluenza virus 3] | ACJ70087.1 |
| phosphoprotein [Human parainfluenza virus 3] | AHX22466.1 |
| phosphoprotein [Human parainfluenza virus 3] | AHX22346.1 |
| phosphoprotein [Human parainfluenza virus 3] | AGW51089.1 |
| phosphoprotein [Human parainfluenza virus 3] | AGW51073.1 |
| phosphoprotein [Human parainfluenza virus 3] | AGW51185.1 |
| phosphoprotein [Human parainfluenza virus 3] | AGW51065.1 |
| phosphoprotein [Human parainfluenza virus 3] | ABY47603.1 |
| phosphoprotein [Human parainfluenza virus 3] | AGW51049.1 |
| phosphoprotein [Human parainfluenza virus 3] | AHX22330.1 |
| phosphoprotein [Human parainfluenza virus 3] | AGW51250.1 |
| phosphoprotein [Human parainfluenza virus 3] | AGT75227.1 |
| phosphoprotein [Human parainfluenza virus 3] | AGW51282.1 |
| phosphoprotein [Human parainfluenza virus 3] | AGW51209.1 |
| phosphoprotein [Human parainfluenza virus 3] | AGW51193.1 |
| phosphoprotein [Human parainfluenza virus 3] | AGT75322.1 |
| phosphoprotein [Human parainfluenza virus 3] | AGT75219.1 |
| phosphoprotein [Human parainfluenza virus 3] | AGW51258.1 |
| phosphoprotein [Human parainfluenza virus 3] | AGW51041.1 |
| phosphoprotein [Human parainfluenza virus 3] | ACD99698.1 |
| phosphoprotein [Human parainfluenza virus 3] | AGW51266.1 |
| phosphoprotein [Human parainfluenza virus 3] | AGT75179.1 |
| phosphoprotein [Human parainfluenza virus 3] | AHX22282.1 |
| phosphoprotein [Human parainfluenza virus 3] | AGW51169.1 |
| phosphoprotein [Human parainfluenza virus 3] | AGW51274.1 |
| phosphoprotein [Human parainfluenza virus 3] | AGW51201.1 |

TABLE 7-continued

PIV3 NCBI Accession Numbers (Nucleic Acid and Amino Acid Sequences)

| Description | GenBank Accession |
|---|---|
| phosphoprotein [Human parainfluenza virus 3] | AGW51177.1 |
| RecName: Full = Phosphoprotein; Short = Protein P | P06162.1 |
| P protein [Human parainfluenza virus 3] | AAA66818.1 |
| phosphoprotein [Human parainfluenza virus 3] | AAA46866.1 |
| phosphoprotein [Human parainfluenza virus 3] | BAA00031.1 |
| polymerase-associated nucleocapsid phosphoprotein (version 2) - parainfluenza virus type 3 [Human parainfluenza virus 3] | RRNZP5 |
| phosphoprotein [Human parainfluenza virus 3] | AGT75171.1 |
| phosphoprotein [Human parainfluenza virus 3] | BAA00921.1 |
| D protein [Human parainfluenza virus 3] | NP_599250.1 |
| D protein [Human parainfluenza virus 3] | AHX22377.1 |
| D protein [Human parainfluenza virus 3] | AHX22121.1 |
| D protein [Human parainfluenza virus 3] | AGT75297.1 |
| D protein [Human parainfluenza virus 3] | AGW51136.1 |
| D protein [Human parainfluenza virus 3] | AGW51242.1 |
| D protein [Human parainfluenza virus 3] | AGW51112.1 |
| D protein [Human parainfluenza virus 3] | AHX22497.1 |
| D protein [Human parainfluenza virus 3] | AHX22145.1 |
| D protein [Human parainfluenza virus 3] | AGT75202.1 |
| D protein [Human parainfluenza virus 3] | AHX22385.1 |
| D protein [Human parainfluenza virus 3] | AGW51216.1 |
| D protein [Human parainfluenza virus 3] | AGT75281.1 |
| D protein [Human parainfluenza virus 3] | AGT75194.1 |
| D protein [Human parainfluenza virus 3] | AHX22521.1 |
| D protein [Human parainfluenza virus 3] | AGW51120.1 |
| D protein [Human parainfluenza virus 3] | AGT75313.1 |
| D protein [Human parainfluenza virus 3] | AHX22249.1 |
| D protein [Human parainfluenza virus 3] | AHX22097.1 |
| D protein [Human parainfluenza virus 3] | AGW51144.1 |
| D protein [Human parainfluenza virus 3] | AHX22089.1 |
| D protein [Human parainfluenza virus 3] | AHX22225.1 |
| D protein [Human parainfluenza virus 3] | AHX22137.1 |
| D protein [Human parainfluenza virus 3] | AHX22065.1 |
| D protein [Human parainfluenza virus 3] | AGW51224.1 |
| D protein [Human parainfluenza virus 3] | AGT75210.1 |
| D protein [Human parainfluenza virus 3] | AHX22393.1 |
| D protein [Human parainfluenza virus 3] | AGT75258.1 |
| D protein [Human parainfluenza virus 3] | AHX22345.1 |
| D protein [Human parainfluenza virus 3] | AGT75250.1 |
| D protein [Human parainfluenza virus 3] | AHX22113.1 |
| D protein [Human parainfluenza virus 3] | AGW51232.1 |
| D protein [Human parainfluenza virus 3] | AHX22057.1 |
| D protein [Human parainfluenza virus 3] | AHX22209.1 |
| D protein [Human parainfluenza virus 3] | AGW51056.1 |
| D protein [Human parainfluenza virus 3] | AHX22161.1 |
| D protein [Simian Agent 10] | ADR00402.1 |
| D protein [Human parainfluenza virus 3] | AHX22361.1 |
| D protein [Human parainfluenza virus 3] | AGW51281.1 |
| D protein [Human parainfluenza virus 3] | AGW51184.1 |
| D protein [Human parainfluenza virus 3] | AGW51160.1 |
| D protein [Human parainfluenza virus 3] | AHX22465.1 |
| D protein [Human parainfluenza virus 3] | AHX22329.1 |
| D protein [Human parainfluenza virus 3] | AGW51064.1 |
| D protein [Human parainfluenza virus 3] | AGW51040.1 |
| D protein [Human parainfluenza virus 3] | AGT75226.1 |
| D protein [Human parainfluenza virus 3] | AHX22425.1 |
| D protein [Human parainfluenza virus 3] | AHX22305.1 |
| D protein [Human parainfluenza virus 3] | AGW51249.1 |
| D protein [Human parainfluenza virus 3] | AHX22481.1 |
| D protein [Human parainfluenza virus 3] | AHX22281.1 |
| D protein [Human parainfluenza virus 3] | AGW51048.1 |
| D protein [Human parainfluenza virus 3] | AHX22297.1 |
| D protein [Human parainfluenza virus 3] | AGW51088.1 |
| D protein [Human parainfluenza virus 3] | AGT75305.1 |
| D protein [Human parainfluenza virus 3] | AHX22185.1 |
| D protein [Human parainfluenza virus 3] | AGW51104.1 |
| D protein [Human parainfluenza virus 3] | AHX22081.1 |
| D protein [Human parainfluenza virus 3] | AGW51192.1 |
| D protein [Human parainfluenza virus 3] | AHX22489.1 |
| D protein [Human parainfluenza virus 3] | AHX22441.1 |
| D protein [Human parainfluenza virus 3] | AHX22409.1 |
| D protein [Human parainfluenza virus 3] | AHX22369.1 |
| D protein [Human parainfluenza virus 3] | AHX22321.1 |
| D protein [Human parainfluenza virus 3] | AHX22073.1 |
| D protein [Human parainfluenza virus 3] | AGW51152.1 |

TABLE 7-continued

| PIV3 NCBI Accession Numbers (Nucleic Acid and Amino Acid Sequences) | |
|---|---|
| Description | GenBank Accession |
| D protein [Human parainfluenza virus 3] | AGW51072.1 |
| D protein [Human parainfluenza virus 3] | AGT75321.1 |
| D protein [Human parainfluenza virus 3] | AHX22257.1 |
| D protein [Human parainfluenza virus 3] | AHX22129.1 |
| D protein [Human parainfluenza virus 3] | AHX22417.1 |
| D protein [Human parainfluenza virus 3] | AGT75218.1 |
| D protein [Human parainfluenza virus 3] | AHX22265.1 |
| D protein [Human parainfluenza virus 3] | AGT75178.1 |
| D protein [Human parainfluenza virus 3] | AHX22433.1 |
| D protein [Human parainfluenza virus 3] | AGW51273.1 |
| D protein [Human parainfluenza virus 3] | AGW51208.1 |
| D protein [Human parainfluenza virus 3] | AGT75170.1 |
| D protein [Human parainfluenza virus 3] | AGT75162.1 |
| D protein [Human parainfluenza virus 3] | AGW51257.1 |
| D protein [Human parainfluenza virus 3] | AGW51200.1 |
| D protein [Human parainfluenza virus 3] | AGW51176.1 |
| D protein [Human parainfluenza virus 3] | AGT75186.1 |
| D protein [Human parainfluenza virus 3] | AGW51265.1 |
| D protein [Human parainfluenza virus 3] | AGW51168.1 |

TABLE 8

| Signal Peptides | | |
|---|---|---|
| Description | Sequence | SEQ ID NO: |
| $HuIgG_k$ signal peptide | METPAQLLFLLLLWLPDTTG | 15 |
| IgE heavy chain epsilon -1 signal peptide | MDWTWILFLVAAATRVHS | 16 |
| Japanese encephalitis PRM signal sequence | MLGSNSGQRVVFTILLLLVAPAYS | 17 |
| VSVg protein signal sequence | MKCLLYLAFLFIGVNCA | 18 |
| Japanese encephalitis JEV signal sequence | MWLVSLAIVTACAGA | 19 |

TABLE 9

| hMPV/PIV Cotton Rat Challenge Study Design | | | | | |
|---|---|---|---|---|---|
| Group | n | Test Article | [conc]/μg | Route | Challenge |
| 1 | 5 | Placebo | n/a | IM | hMPV/A2 |
| 2 | 5 | hMPV vaccine mRNA | 30 | IM | hMPV/A2 |
| 3 | 5 | hMPV vaccine mRNA | 15 | IM | hMPV/A2 |
| 4 | 5 | hMPV vaccine mRNA | 10 | IM | hMPV/A2 |
| 5 | 5 | hMPV/PIV3 vaccine mRNA (15/15) | 30 | IM | hMPV/A2 |
| 6 | 5 | FI-hMPV | n/a | IM | hMPV/A2 |
| 7 | 5 | Placebo | n/a | IM | PIV3 |
| 8 | 5 | PIV3 vaccine mRNA | 30 | IM | PIV3 |
| 9 | 5 | PIV3 vaccine mRNA | 15 | IM | PIV3 |
| 10 | 5 | PIV3 vaccine mRNA | 10 | IM | PIV3 |
| 11 | 5 | hMPV/PIV3 vaccine mRNA (15/15) | 30 | IM | PIV3 |
| 12 | 5 | FI-PIV3 | n/a | IM | PIV3 |

TABLE 10

| Betacoronavirus Nucleic Acid Sequence | | |
|---|---|---|
| Strain | Nucleic Acid Sequence | SEQ ID NO: |
| gb\|KJ156934.1\|:21405-25466 Middle East respiratory syndrome coronavirus isolate Riyadh_14_2013, spike protein (nucleotide) | ATGATACACTCAGTGTTTCTACTGATGTTCTTGTTAACACC TACAGAAAGTTACGTTGATGTAGGGCCAGATTCTGTTAAG TCTGCTTGTATTGAGGTTGATATACAACAGACCTTCTTTGA TAAAACTTGGCCTAGGCCAATTGATGTTTCTAAGGCTGAC GGTATTATATACCCTCAAGGCCGTACATATTCTAACATAA CTATCACTTATCAAGGTCTTTTTCCCTATCAGGGAGACCAT GGTGATATGTATGTTTACTCTGCAGGACATGCTACAGGCA CAACTCCACAAAAGTTGTTTGTAGCTAACTATTCTCAGGA CGTCAAACAGTTTGCTAATGGGTTTGTCGTCCGTATAGGA GCAGCTGCCAATTCCACTGGCACTGTTATTATTAGCCCATC TACCAGCGCTACTATACGAAAAATTTACCCTGCTTTTATGC TGGGTTCTTCAGTTGGTAATTTCTCAGATGGTAAAATGGG CCGCTTCTTCAATCATACTCTAGTTCTTTTGCCCGATGGAT GTGGCACTTTACTTAGAGCTTTTTATTGTATTCTAGAGCCT CGCTCTGGAAATCATTGTCCTGCTGGCAATTCCTATACTTC TTTTGCCACTTATCACACTCCTGCAACAGATTGTTCTGATG GCAATTACAATCGTAATGCCAGTCTGAACTCTTTTAAGGA GTATTTTAATTTACGTAACTGCACCTTTATGTACACTTATA ACATTACCGAAGATGAGATTTTAGAGTGGTTTGGCATTAC | 20 |

TABLE 10-continued

| Betacoronavirus Nucleic Acid Sequence | | |
|---|---|---|
| Strain | Nucleic Acid Sequence | SEQ ID NO: |
| | ACAAACTGCTCAAGGTGTTCACCTCTTCTCATCTCGGTATG | |
| | TTGATTTGTACGGCGGCAATATGTTTCAATTTGCCACCTTG | |
| | CCTGTTTATGATACTATTAAGTATTATTCTATCATTCCTCA | |
| | CAGTATTCGTTCTATCCAAAGTGATAGAAAAGCTTGGGCT | |
| | GCCTTCTACGTATATAAACTTCAACCGTTAACTTTCCTGTT | |
| | GGATTTTTCTGTTGATGGTTATATACGCAGAGCTATAGACT | |
| | GTGGTTTTAATGATTTGTCACAACTCCACTGCTCATATGAA | |
| | TCCTTCGATGTTGAATCTGGAGTTTATTCAGTTTCGTCTTT | |
| | CGAAGCAAAACCTTCTGGCTCAGTTGTGGAACAGGCTGAA | |
| | GGTGTTGAATGTGATTTTTCACCTCTTCTGTCTGGCACACC | |
| | TCCTCAGGTTTATAATTTCAAGCGTTTGGTTTTTACCAATT | |
| | GCAATTATAATCTTACCAAATTGCTTTCACTTTTTTCTGTG | |
| | AATGATTTTACTTGTAGTCAAATATCTCCAGCAGCAATTGC | |
| | TAGCAACTGTTATTCTTCACTGATTTTGGATTATTTTTCAT | |
| | ACCCACTTAGTATGAAATCCGATCTCAGTGTTAGTTCTGCT | |
| | GGTCCAATATCCCAGTTTAATTATAAACAGTCCTTTTCTAA | |
| | TCCCACATGTTTGATCTTAGCGACTGTTCCTCATAACCTTA | |
| | CTACTATTACTAAGCCTCTTAAGTACAGCTATATTAACAA | |
| | GTGCTCTCGTCTTCTTTCTGATGATCGTACTGAAGTACCTC | |
| | AGTTAGTGAACGCTAATCAATACTCACCCTGTGTATCCATT | |
| | GTCCCATCCACTGTGTGGGAAGACGGTGATTATTATAGGA | |
| | AACAACTATCTCCACTTGAAGGTGGTGGCTGGCTTGTTGC | |
| | TAGTGGCTCAACTGTTGCCATGACTGAGCAATTACAGATG | |
| | GGCTTTGGTATTACAGTTCAATATGGTACAGACACCAATA | |
| | GTGTTTGCCCCAAGCTTGAATTTGCTAATGACACAAAAAT | |
| | TGCCTCTCAATTAGGCAATTGCGTGGAATATTCCCTCTATG | |
| | GTGTTTCGGGCCGTGGTGTTTTTCAGAATTGCACAGCTGTA | |
| | GGTGTTCGACAGCAGCGCTTTGTTTATGATGCGTACCAGA | |
| | ATTTAGTTGGCTATTATTCTGATGATGGCAACTACTACTGT | |
| | CTGCGTGCTTGTGTTAGTGTTCCTGTTTCTGTCATCTATGA | |
| | TAAAGAAACTAAAACCCACGCTACTCTATTTGGTAGTGTT | |
| | GCATGTGAACACATTTCTTCTACCATGTCTCAATACTCCCG | |
| | TTCTACGCGATCAATGCTTAAACGGCGAGATTCTACATAT | |
| | GGCCCCCTTCAGACACCTGTTGGTTGTGTCCTAGGACTTGT | |
| | TAATTCCTCTTTGTTCGTAGAGGACTGCAAGTTGCCTCTCG | |
| | GTCAATCTCTCTGTGCTCTTCCTGACACACCTAGTACTCTC | |
| | ACACCTCGCAGTGTGCGCTCTGTGCCAGGTGAAATGCGCT | |
| | TGGCATCCATTGCTTTTAATCATCCCATTCAGGTTGATCAA | |
| | CTTAATAGTAGTTATTTTAAATTAAGTATACCCACTAATTT | |
| | TTCCTTTGGTGTGACTCAGGAGTACATTCAGACAACCATTC | |
| | AGAAAGTTACTGTTGATTGTAAACAGTACGTTTGCAATGG | |
| | TTTCCAGAAGTGTGAGCAATTACTGCGCGAGTATGGCCAG | |
| | TTTTGTTCCAAAATAAACCAGGCTCTCCATGGTGCCAATTT | |
| | ACGCCAGGATGATTCTGTACGTAATTTGTTTGCGAGCGTG | |
| | AAAAGCTCTCAATCATCTCCTATCATACCAGGTTTTGGAG | |
| | GTGACTTTAATTTGACACTTCTAGAACCTGTTTCTATATCT | |
| | ACTGGCAGTCGTAGTGCACGTAGTGCTATTGAGGATTTGC | |
| | TATTTGACAAAGTCACTATAGCTGATCCTGGTTATATGCA | |
| | AGGTTACGATGATTGTATGCAGCAAGGTCCAGCATCAGCT | |
| | CGTGATCTTATTTGTGCTCAATATGTGGCTGGTTATAAAGT | |
| | ATTACCTCCTCTTATGGATGTTAATATGGAAGCCGCGTATA | |
| | CTTCATCTTTGCTTGGCAGCATAGCAGGTGTTGGCTGGACT | |
| | GCTGGCTTATCCTCCTTTGCTGCTATTCCATTTGCACAGAG | |
| | TATYTTTTATAGGTTAAACGGTGTTGGCATTACTCAACAG | |
| | GTTCTTTCAGAGAACCAAAAGCTTATTGCCAATAAGTTTA | |
| | ATCAGGCTCTGGGAGCTATGCAAACAGGCTTCACTACAAC | |
| | TAATGAAGCTTTTCGGAAGGTTCAGGATGCTGTGAACAAC | |
| | AATGCACAGGCTCTATCCAAATTAGCTAGCGAGCTATCTA | |
| | ATACTTTTGGTGCTATTTCCGCCTCTATTGGAGACATCATA | |
| | CAACGTCTTGATGTTCTCGAACAGGACGCCCAAATAGACA | |
| | GACTTATTAATGGCCGTTTGACAACACTAAATGCTTTTGTT | |
| | GCACAGCAGCTTGTTCGTTCCGAATCAGCTGCTCTTTCCGC | |
| | TCAATTGGCTAAAGATAAAGTCAATGAGTGTGTCAAGGCA | |
| | CAATCCAAGCGTTCTGGATTTTGCGGTCAAGGCACACATA | |
| | TAGTGTCCTTTGTTGTAAATGCCCCTAATGGCCTTTACTTT | |
| | ATGCATGTTGGTTATTACCCTAGCAACCACATTGAGGTTGT | |
| | TTCTGCTTATGGTCTTTGCGATGCAGCTAACCCTACTAATT | |
| | GTATAGCCCCTGTTAATGGCTACTTTATTAAAACTAATAAC | |
| | ACTAGGATTGTTGATGAGTGGTCATATACTGGCTCGTCCTT | |
| | CTATGCACCTGAGCCCATCACCTCTCTTAATACTAAGTATG | |
| | TTGCACCACAGGTGACATACCAAAACATTTCTACTAACCT | |
| | CCCTCCTCCTCTTCTCGGCAATTCCACCGGGATTGACTTCC | |
| | AAGATGAGTTGGATGAGTTTTTCAAAAATGTTAGCACCAG | |
| | TATACCTAATTTTGGTTCTCTAACACAGATTAATACTACAT | |
| | TACTCGATCTTACCTACGAGATGTTGTCTCTTCAACAAGTT | |

TABLE 10-continued

| Betacoronavirus Nucleic Acid Sequence | | |
|---|---|---|
| Strain | Nucleic Acid Sequence | SEQ ID NO: |
| | GTTAAAGCCCTTAATGAGTCTTACATAGACCTTAAAGAGC<br>TTGGCAATTATACTTATTACAACAAATGGCCGTGGTACAT<br>TTGGCTTGGTTTCATTGCTGGGCTTGTTGCCTTAGCTCTAT<br>GCGTCTTCTTCATACTGTGCTGCACTGGTTGTGGCACAAAC<br>TGTATGGGAAAACTTAAGTGTAATCGTTGTTGTGATAGAT<br>ACGAGGAATACGACCTCGAGCCGCATAAGGTTCATGTTCA<br>CTAA | |
| MERS S FL SPIKE 2cEMC/2012 (XBaI change (T to G)) (nucleotide) | ATGATACACTCAGTGTTTCTACTGATGTTCTTGTTAACACC<br>TACAGAAAGTTACGTTGATGTAGGGCCAGATTCTGTTAAG<br>TCTGCTTGTATTGAGGTTGATATACAACAGACTTTCTTTGA<br>TAAAACTTGGCCTAGGCCAATTGATGTTTCTAAGGCTGAC<br>GGTATTATATACCCTCAAGGCCGTACATATTCTAACATAA<br>CTATCACTTATCAAGGTCTTTTTCCCTATCAGGGAGACCAT<br>GGTGATATGTATGTTTACTCTGCAGGACATGCTACAGGCA<br>CAACTCCACAAAAGTTGTTTGTAGCTAACTATTCTCAGGA<br>CGTCAAACAGTTTGCTAATGGGTTTGTCGTCCGTATAGGA<br>GCAGCTGCCAATTCCACTGGCACTGTTATTATTAGCCCATC<br>TACCAGCGCTACTATACGAAAAATTTACCCTGCTTTTATGC<br>TGGGTTCTTCAGTTGGTAATTTCTCAGATGGTAAAATGGG<br>CCGCTTCTTCAATCATACTCTAGTTCTTTTGCCCGATGGAT<br>GTGGCACTTTACTTAGAGCTTTTTATTGTATTCTGGAGCCT<br>CGCTCTGGAAATCATTGTCCTGCTGGCAATTCCTATACTTC<br>TTTTGCCACTTATCACACTCCTGCAACAGATTGTTCTGATG<br>GCAATTACAATCGTAATGCCAGTCTGAACTCTTTTAAGGA<br>GTATTTTAATTTACGTAACTGCACCTTTATGTACACTTATA<br>ACATTACCGAAGATGAGATTTTAGAGTGGTTTGGCATTAC<br>ACAAACTGCTCAAGGTGTTCACCTCTTCTCATCTCGGTATG<br>TTGATTTGTACGGCGGCAATATGTTTCAATTTGCCACCTTG<br>CCTGTTTATGATACTATTAAGTATTATTCTATCATTCCTCA<br>CAGTATTCGTTCTATCCAAAGTGATAGAAAAGCTTGGGCT<br>GCCTTCTACGTATATAAACTTCAACCGTTAACTTTCCTGTT<br>GGATTTTTCTGTTGATGGTTATATACGCAGAGCTATAGACT<br>GTGGTTTTAATGATTTGTCACAACTCCACTGCTCATATGAA<br>TCCTTCGATGTTGAATCTGGAGTTTATTCAGTTTCGTCTTT<br>CGAAGCAAAACCTTCTGGCTCAGTTGTGGAACAGGCTGAA<br>GGTGTTGAATGTGATTTTTCACCTCTTCTGTCTGGCACACC<br>TCCTCAGGTTTATAATTTCAAGCGTTTGGTTTTTACCAATT<br>GCAATTATAATCTTACCAAATTGCTTTCACTTTTTTCTGTG<br>AATGATTTTACTTGTAGTCAAATATCTCCAGCAGCAATTGC<br>TAGCAACTGTTATTCTTCACTGATTTTGGATTACTTTTCAT<br>ACCCACTTAGTATGAAATCCGATCTCAGTGTTAGTTCTGCT<br>GGTCCAATATCCCAGTTTAATTATAAACAGTCCTTTTCTAA<br>TCCCACATGTTTGATTTTAGCGACTGTTCCTCATAACCTTA<br>CTACTATTACTAAGCCTCTTAAGTACAGCTATATTAACAA<br>GTGCTCTCGTCTTCTTTCTGATGATCGTACTGAAGTACCTC<br>AGTTAGTGAACGCTAATCAATACTCACCCTGTGTATCCATT<br>GTCCCATCCACTGTGTGGGAAGACGGTGATTATTATAGGA<br>AACAACTATCTCCACTTGAAGGTGGTGGCTGGCTTGTTGC<br>TAGTGGCTCAACTGTTGCCATGACTGAGCAATTACAGATG<br>GGCTTTGGTATTACAGTTCAATATGGTACAGACACCAATA<br>GTGTTTGCCCCAAGCTTGAATTTGCTAATGACACAAAAAT<br>TGCCTCTCAATTAGGCAATTGCGTGGAATATTCCCTCTATG<br>GTGTTTCGGGCCGTGGTGTTTTTCAGAATTGCACAGCTGTA<br>GGTGTTCGACAGCAGCGCTTTGTTTATGATGCGTACCAGA<br>ATTTAGTTGGCTATTATTCTGATGATGGCAACTACTACTGT<br>TTGCGTGCTTGTGTTAGTGTTCCTGTTTCTGTCATCTATGAT<br>AAAGAAACTAAAACCCACGCTACTCTATTTGGTAGTGTTG<br>CATGTGAACACATTTCTTCTACCATGTCTCAATACTCCCGT<br>TCTACGCGATCAATGCTTAAACGGCGAGATTCTACATATG<br>GCCCCCTTCAGACACCTGTTGGTTGTGTCCTAGGACTTGTT<br>AATTCCTCTTTGTTCGTAGAGGACTGCAAGTTGCCTCTTGG<br>TCAATCTCTCTGTGCTCTTCCTGACACACCTAGTACTCTCA<br>CACCTCGCAGTGTGCGCTCTGTTCCAGGTGAAATGCGCTT<br>GGCATCCATTGCTTTTAATCATCCTATTCAGGTTGATCAAC<br>TTAATAGTAGTTATTTTAAATTAAGTATACCCACTAATTTT<br>TCCTTTGGTGTGACTCAGGAGTACATTCAGACAACCATTC<br>AGAAAGTTACTGTTGATTGTAAACAGTACGTTTGCAATGG<br>TTTCCAGAAGTGTGAGCAATTACTGCGCGAGTATGGCCAG<br>TTTTGTTCCAAAATAAACCAGGCTCTCCATGGTGCCAATTT<br>ACGCCAGGATGATTCTGTACGTAATTTGTTTGCGAGCGTG<br>AAAAGCTCTCAATCATCTCCTATCATACCAGGTTTTGGAG<br>GTGACTTTAATTTGACACTTCTGGAACCTGTTTCTATATCT<br>ACTGGCAGTCGTAGTGCACGTAGTGCTATTGAGGATTTGC<br>TATTTGACAAAGTCACTATAGCTGATCCTGGTTATATGCA | 21 |

TABLE 10-continued

| Betacoronavirus Nucleic Acid Sequence | | |
|---|---|---|
| Strain | Nucleic Acid Sequence | SEQ ID NO: |
| | AGGTTACGATGATTGCATGCAGCAAGGTCCAGCATCAGCT<br>CGTGATCTTATTTGTGCTCAATATGTGGCTGGTTACAAAGT<br>ATTACCTCCTCTTATGGATGTTAATATGGAAGCCGCGTATA<br>CTTCATCTTTGCTTGGCAGCATAGCAGGTGTTGGCTGGACT<br>GCTGGCTTATCCTCCTTTGCTGCTATTCCATTTGCACAGAG<br>TATCTTTTATAGGTTAAACGGTGTTGGCATTACTCAACAGG<br>TTCTTTCAGAGAACCAAAAGCTTATTGCCAATAAGTTTAA<br>TCAGGCTCTGGGAGCTATGCAAACAGGCTTCACTACAACT<br>AATGAAGCTTTTCAGAAGGTTCAGGATGCTGTGAACAACA<br>ATGCACAGGCTCTATCCAAATTAGCTAGCGAGCTATCTAA<br>TACTTTTGGTGCTATTTCCGCCTCTATTGGAGACATCATAC<br>AACGTCTTGATGTTCTCGAACAGGACGCCCAAATAGACAG<br>ACTTATTAATGGCCGTTTGACAACACTAAATGCTTTTGTTG<br>CACAGCAGCTTGTTCGTTCCGAATCAGCTGCTCTTTCCGCT<br>CAATTGGCTAAAGATAAAGTCAATGAGTGTGTCAAGGCAC<br>AATCCAAGCGTTCTGGATTTTGCGGTCAAGGCACACATAT<br>AGTGTCCTTTGTTGTAAATGCCCCTAATGGCCTTTACTTCA<br>TGCATGTTGGTTATTACCCTAGCAACCACATTGAGGTTGTT<br>TCTGCTTATGGTCTTTGCGATGCAGCTAACCCTACTAATTG<br>TATAGCCCCTGTTAATGGCTACTTTATTAAAACTAATAACA<br>CTAGGATTGTTGATGAGTGGTCATATACTGGCTCGTCCTTC<br>TATGCACCTGAGCCCATTACCTCCCTTAATACTAAGTATGT<br>TGCACCACAGGTGACATACCAAAACATTTCTACTAACCTC<br>CCTCCTCCTCTTCTCGGCAATTCCACCGGGATTGACTTCCA<br>AGATGAGTTGGATGAGTTTTTCAAAAATGTTAGCACCAGT<br>ATACCTAATTTTGGTTCCCTAACACAGATTAATACTACATT<br>ACTCGATCTTACCTACGAGATGTTGTCTCTTCAACAAGTTG<br>TTAAAGCCCTTAATGAGTCTTACATAGACCTTAAAGAGCT<br>TGGCAATTATACTTATTACAACAAATGGCCGTGGTACATT<br>TGGCTTGGTTTCATTGCTGGGCTTGTTGCCTTAGCTCTATG<br>CGTCTTCTTCATACTGTGCTGCACTGGTTGTGGCACAAACT<br>GTATGGGAAAACTTAAGTGTAATCGTTGTTGTGATAGATA<br>CGAGGAATACGACCTCGAGCCGCATAAGGTTCATGTTCAC<br>TAA | |
| Novel_MERS_S2_<br>subunit_trimeric<br>vaccine<br>(nucleotide) | ATGATCCACTCCGTGTTCCTCCTCATGTTCCTGTTGACCCC<br>CACTGAGTCAGACTGCAAGCTCCCGCTGGGACAGTCCCTG<br>TGTGCGCTGCCTGACACTCCTAGCACTCTGACCCCACGCTC<br>CGTGCGGTCGGTGCCTGGCGAAATGCGGCTGGCCTCCATC<br>GCCTTCAATCACCCAATCCAAGTGGATCAGCTGAATAGCT<br>CGTATTTCAAGCTGTCCATCCCCACGAACTTCTCGTTCGGG<br>GTCACCCAGGAGTACATCCAGACCACAATTCAGAAGGTCA<br>CCGTCGATTGCAAGCAATACGTGTGCAACGGCTTCCAGAA<br>GTGCGAGCAGCTGCTGAGAGAATACGGGCAGTTTTGCAGC<br>AAGATCAACCAGGCGCTGCATGGAGCTAACTTGCGCCAGG<br>ACGACTCCGTGCGCAACCTCTTTGCCTCTGTGAAGTCATCC<br>CAGTCCTCCCCAATCATCCCGGGATTCGGAGGGGACTTCA<br>ACCTGACCCTCCTGGAGCCCGTGTCGATCAGCACCGGTAG<br>CAGATCGGCGCGCTCAGCCATTGAAGATCTTCTGTTCGAC<br>AAGGTCACCATCGCCGATCCGGGCTACATGCAGGGATACG<br>ACGACTGTATGCAGCAGGGACCAGCCTCCGCGAGGGACCT<br>CATCTGCGCGCAATACGTGGCCGGGTACAAAGTGCTGCCT<br>CCTCTGATGGATGTGAACATGGAGGCCGCTTATACTTCGT<br>CCCTGCTCGGCTCTATCGCCGGCGTGGGGTGGACCGCCGG<br>CCTGTCCTCCTTCGCCGCTATCCCCTTTGCACAATCCATTT<br>TCTACCGGCTCAACGGCGTGGGCATTACTCAACAAGTCCT<br>GTCGGAGAACCAGAAGTTGATCGCAAACAAGTTCAATCA<br>GGCCCTGGGGGCCATGCAGACTGGATTCACTACGACTAAC<br>GAAGCGTTCCAGAAGGTCCAGGACGCTGTGAACAACAAC<br>GCCCAGGCGCTCTCAAAGCTGGCCTCCGAACTCAGCAACA<br>CCTTCGGAGCCATCAGCGCATCGATCGGTGACATAATTCA<br>GCGGCTGGACGTGCTGGAGCAGGACGCCCAGATCGACCG<br>CCTCATCAACGGACGGCTGACCACCTTGAATGCCTTCGTG<br>GCACAACAGCTGGTCCGGAGCGAATCAGCGGCACTTTCCG<br>CCCAACTCGCCAAGGACAAAGTCAACGAATGCGTGAAGG<br>CCCAGTCCAAGAGGTCCGGTTTCTGCGGTCAAGGAACCCA<br>TATTGTGTCCTTCGTCGTGAACGCGCCCAACGGTCTGTACT<br>TTATGCACGTCGGCTACTACCCGAGCAATCATATCGAAGT<br>GGTGTCCGCCTACGGCCTGTGCGATGCCGCTAACCCCACT<br>AACTGTATTGCCCCTGTGAACGGATATTTTATTAAGACCA<br>ACAACACCCGCATTGTGGACGAATGGTCATACACCGGTTC<br>GTCCTTCTACGCGCCCGAGCCCATCACTTCACTGAACACC<br>AAATACGTGGCTCCGCAAGTGACCTACCAGAACATCTCCA<br>CCAATTTGCCGCCGCCGCTGCTCGGAAACAGCACCGGAAT<br>TGATTTCCAAGATGAACTGGACGAATTCTTCAAGAACGTG | 22 |

TABLE 10-continued

Betacoronavirus Nucleic Acid Sequence

| Strain | Nucleic Acid Sequence | SEQ ID NO: |
|---|---|---|
| | TCCACTTCCATTCCCAACTTCGGAAGCCTGACACAGATCA<br>ACACCACCCTTCTCGACCTGACCTACGAGATGCTGAGCCT<br>TCAACAAGTGGTCAAGGCCCTGAACGAGAGCTACATCGAC<br>CTGAAGGAGCTGGGCAACTATACCTACTACAACAAGTGGC<br>CGGACAAGATTGAGGAGATTCTGTCGAAAATCTACCACAT<br>TGAAAACGAGATCGCCAGAATCAAGAAGCTTATCGGCGA<br>AGCC | |
| MERS_S0_Full-length Spike protein (nucleotide, codon optimized) | ATGGAAACCCCTGCCCAGCTGCTGTTCCTGCTGCTGCTGTG<br>GCTGCCTGATACCACCGGCAGCTATGTGGACGTGGGCCCC<br>GATAGCGTGAAGTCCGCCTGTATCGAAGTGGACATCCAGC<br>AGACCTTTTTCGACAAGACCTGGCCCAGACCCATCGACGT<br>GTCCAAGGCCGACGGCATCATCTATCCACAAGGCCGGACC<br>TACAGCAACATCACCATTACCTACCAGGGCCTGTTCCCAT<br>ATCAAGGCGACCACGGCGATATGTACGTGTACTCTGCCGG<br>CCACGCCACCGGCACCACACCCCAGAAACTGTTCGTGGCC<br>AACTACAGCCAGGACGTGAAGCAGTTCGCCAACGGCTTCG<br>TCGTGCGGATTGGCGCCGCTGCCAATAGCACCGGCACAGT<br>GATCATCAGCCCCAGCACCAGCGCCACCATCCGGAAGATC<br>TACCCCGCCTTCATGCTGGGCAGCTCCGTGGGCAATTTCA<br>GCGACGGCAAGATGGGCCGGTTCTTCAACCACACCCTGGT<br>GCTGCTGCCCGATGGCTGTGGCACACTGCTGAGAGCCTTC<br>TACTGCATCCTGGAACCCAGAAGCGGCAACCACTGCCCTG<br>CCGGCAATAGCTACACCAGCTTCGCCACCTACCACACACC<br>CGCCACCGATTGCTCCGACGGCAACTACAACCGGAACGCC<br>AGCCTGAACAGCTTCAAAGAGTACTTCAACCTGCGGAACT<br>GCACCTTCATGTACACCTACAATATCACCGAGGACGAGAT<br>CCTGGAATGGTTCGGCATCACCCAGACCGCCCAGGGCGTG<br>CACCTGTTCAGCAGCAGATACGTGGACCTGTACGGCGGCA<br>ACATGTTCCAGTTTGCCACCCTGCCCGTGTACGACACCATC<br>AAGTACTACAGCATCATCCCCCACAGCATCCGGTCCATCC<br>AGAGCGACAGAAAAGCCTGGGCCGCCTTCTACGTGTACAA<br>GCTGCAGCCCCTGACCTTCCTGCTGGACTTCAGCGTGGAC<br>GGCTACATCAGACGGGCCATCGACTGCGGCTTCAACGACC<br>TGAGCCAGCTGCACTGCTCCTACGAGAGCTTCGACGTGGA<br>AAGCGGCGTGTACAGCGTGTCCAGCTTCGAGGCCAAGCCT<br>AGCGGCAGCGTGGTGGAACAGGCTGAGGGCGTGGAATGC<br>GACTTCAGCCCTCTGCTGAGCGGCACCCCTCCCCAGGTGT<br>ACAACTTCAAGCGGCTGGTGTTCACCAACTGCAATTACAA<br>CCTGACCAAGCTGCTGAGCCTGTTCTCCGTGAACGACTTC<br>ACCTGTAGCCAGATCAGCCCTGCCGCCATTGCCAGCAACT<br>GCTACAGCAGCCTGATCCTGGACTACTTCAGCTACCCCCT<br>GAGCATGAAGTCCGATCTGAGCGTGTCCTCCGCCGGACCC<br>ATCAGCCAGTTCAACTACAAGCAGAGCTTCAGCAACCCTA<br>CCTGCCTGATTCTGGCCACCGTGCCCCACAATCTGACCAC<br>CATCACCAAGCCCCTGAAGTACAGCTACATCAACAAGTGC<br>AGCAGACTGCTGTCCGACGACCGGACCGAAGTGCCCCAGC<br>TCGTGAACGCCAACCAGTACAGCCCCTGCGTGTCCATCGT<br>GCCCAGCACCGTGTGGGAGGACGGCGACTACTACAGAAA<br>GCAGCTGAGCCCCCTGGAAGGCGGCGGATGGCTGGTGGCT<br>TCTGGAAGCACAGTGGCCATGACCGAGCAGCTGCAGATG<br>GGCTTTGGCATCACCGTGCAGTACGGCACCGACACCAACA<br>GCGTGTGCCCCAAGCTGGAATTCGCCAATGACACCAAGAT<br>CGCCAGCCAGCTGGGAAACTGCGTGGAATACTCCCTGTAT<br>GGCGTGTCCGGACGGGGCGTGTTCCAGAATTGCACAGCAG<br>TGGGAGTGCGGCAGCAGAGATTCGTGTACGATGCCTACCA<br>GAACCTCGTGGGCTACTACAGCGACGACGGCAATTACTAC<br>TGCCTGCGGGCCTGTGTGTCCGTGCCCGTGTCCGTGATCTA<br>CGACAAAGAGACAAAGACCCACGCCACACTGTTCGGCTCC<br>GTGGCCTGCGAGCACATCAGCTCCACCATGAGCCAGTACT<br>CCCGCTCCACCCGGTCCATGCTGAAGCGGAGAGATAGCAC<br>CTACGGCCCCCTGCAGACACCTGTGGGATGTGTGCTGGGC<br>CTCGTGAACAGCTCCCTGTTTGTGGAAGATTGCAAGCTGC<br>CCCTGGGCCAGAGCCTGTGTGCCCTGCCAGATACCCCTAG<br>CACCCTGACCCCTAGAAGCGTGCGCTCTGTGCCCGGCGAA<br>ATGCGGCTGGCCTCTATCGCCTTCAATCACCCCATCCAGGT<br>GGACCAGCTGAACTCCAGCTACTTCAAGCTGAGCATCCCC<br>ACCAACTTCAGCTTCGGCGTGACCCAGGAGTACATCCAGA<br>CCACAATCCAGAAAGTGACCGTGGACTGCAAGCAGTACGT<br>GTGCAACGGCTTTCAGAAGTGCGAACAGCTGCTGCGCGAG<br>TACGGCCAGTTCTGCAGCAAGATCAACCAGGCCCTGCACG<br>GCGCCAACCTGAGACAGGATGACAGCGTGCGGAACCTGTT<br>CGCCAGCGTGAAAAGCAGCCAGTCCAGCCCCATCATCCCT<br>GGCTTCGGCGGCGACTTTAACCTGACCCTGCTGGAACCTG<br>TGTCCATCAGCACCGGCTCCAGAAGCGCCAGATCCGCCAT | 23 |

TABLE 10-continued

| Strain | Nucleic Acid Sequence | SEQ ID NO: |
|---|---|---|
| | **Betacoronavirus Nucleic Acid Sequence** | |
| | CGAGGACCTGCTGTTCGACAAAGTGACCATTGCCGACCCC<br>GGCTACATGCAGGGCTACGACGATTGCATGCAGCAGGGCC<br>CAGCCAGCGCCAGGGATCTGATCTGTGCCCAGTATGTGGC<br>CGGCTACAAGGTGCTGCCCCCCCTGATGGACGTGAACATG<br>GAAGCCGCCTACACCTCCAGCCTGCTGGGCTCTATTGCTG<br>GCGTGGGATGGACAGCCGGCCTGTCTAGCTTTGCCGCCAT<br>CCCTTTCGCCCAGAGCATCTTCTACCGGCTGAACGGCGTG<br>GGCATCACACAACAGGTGCTGAGCGAGAACCAGAAGCTG<br>ATCGCCAACAAGTTTAACCAGGCACTGGGCGCCATGCAGA<br>CCGGCTTCACCACCACCAACGAGGCCTTCAGAAAGGTGCA<br>GGACGCCGTGAACAACAACGCCCAGGCTCTGAGCAAGCT<br>GGCCTCCGAGCTGAGCAATACCTTCGGCGCCATCAGCGCC<br>TCCATCGGCGACATCATCCAGCGGCTGGACGTGCTGGAAC<br>AGGACGCCCAGATCGACCGGCTGATCAACGGCAGACTGA<br>CCACCCTGAACGCCTTCGTGGCACAGCAGCTCGTGCGGAG<br>CGAATCTGCCGCTCTGTCTGCTCAGCTGGCCAAGGACAAA<br>GTGAACGAGTGCGTGAAGGCCCAGTCCAAGCGGAGCGGC<br>TTTTGTGGCCAGGGCACCCACATCGTGTCCTTCGTCGTGAA<br>TGCCCCCAACGGCCTGTACTTTATGCACGTGGGCTATTACC<br>CCAGCAACCACATCGAGGTGGTGTCCGCCTATGGCCTGTG<br>CGACGCCGCCAATCCTACCAACTGTATCGCCCCCGTGAAC<br>GGCTACTTCATCAAGACCAACAACACCCGGATCGTGGACG<br>AGTGGTCCTACACAGGCAGCAGCTTCTACGCCCCCGAGCC<br>CATCACCTCCCTGAACACCAAATACGTGGCCCCCCAAGTG<br>ACATACCAGAACATCTCCACCAACCTGCCCCCTCCACTGC<br>TGGGAAATTCCACCGGCATCGACTTCCAGGACGAGCTGGA<br>CGAGTTCTTCAAGAACGTGTCCACCTCCATCCCCAACTTCG<br>GCAGCCTGACCCAGATCAACACCACTCTGCTGGACCTGAC<br>CTACGAGATGCTGTCCCTGCAACAGGTCGTGAAAGCCCTG<br>AACGAGAGCTACATCGACCTGAAAGAGCTGGGGAACTAC<br>ACCTACTACAACAAGTGGCCTTGGTACATTTGGCTGGGCT<br>TTATCGCCGGCCTGGTGGCCCTGGCCCTGTGCGTGTTCTTC<br>ATCCTGTGCTGCACCGGCTGCGGCACCAATTGCATGGGCA<br>AGCTGAAATGCAACCGGTGCTGCGACAGATACGAGGAAT<br>ACGACCTGGAACCTCACAAAGTGCATGTGCAC | |
| | **Betacoronavirus mRNA Sequences** | |
| gb\|KJ156934.1\|:21 405-25466 Middle East respiratory syndrome coronavirus isolate Riyadh_14_2013, spike protein (nucleotide) | AUGAUACACUCAGUGUUUCUACUGAUGUUCUUGUUAAC<br>ACCUACAGAAAGUUACGUUGAUGUAGGGCCAGAUUCUG<br>UUAAGUCUGCUUGUAUUGAGGUUGAUAUACAACAGACC<br>UUCUUUGAUAAAACUUGGCCUAGGCCAAUUGAUGUUUC<br>UAAGGCUGACGGUAUUAUAUACCCUCAAGGCCGUACAU<br>AUUCUAACAUAACUAUCACUUAUCAAGGUCUUUUUCCCU<br>AUCAGGGAGACCAUGGUGAUAUGUAUGUUUACUCUGCA<br>GGACAUGCUACAGGCACAACUCCACAAAAGUUGUUUGU<br>AGCUAACUAUUCUCAGGACGUCAAACAGUUUGCUAAUG<br>GGUUUGUCGUCCGUAUAGGAGCAGCUGCCAAUUCCACUG<br>GCACUGUUAUUAUUAGCCCAUCUACCAGCGCUACUAUAC<br>GAAAAAUUUACCCUGCUUUUAUGCUGGGUUCUUCAGUU<br>GGUAAUUUCUCAGAUGGUAAAAUGGGCCGCUUCUUCAA<br>UCAUACUCUAGUUCUUUUGCCCGAUGGAUGUGGCACUU<br>UACUUAGAGCUUUUUAUUGUAUUCUAGAGCCUCGCUCU<br>GGAAAUCAUUGUCCUGCUGGCAAUUCCUAUACUUCUUU<br>UGCCACUUAUCACACUCCUGCAACAGAUUGUUCUGAUGG<br>CAAUUACAAUCGUAAUGCCAGUCUGAACUCUUUUAAGG<br>AGUAUUUUAAUUUACGUAACUGCACCUUUAUGUACACU<br>UAUAACAUUACCGAAGAUGAGAUUUUAGAGUGGUUUGG<br>CAUUACACAAACUGCUCAAGGUGUUCACCUCUUCUCAUC<br>UCGGUAUGUUGAUUUGUACGGCGGCAAUAUGUUUCAAU<br>UUGCCACCUUGCCUGUUUAUGAUACUAUUAAGUAUUAU<br>UCUAUCAUUCCUCACAGUAUUCGUUCUAUCCAAAGUGAU<br>AGAAAAGCUUGGGCUGCCUUCUACGUAUAUAAACUUCA<br>ACCGUUAACUUUCCUGUUGGAUUUUUCUGUUGAUGGUU<br>AUAUACGCAGAGCUAUAGACUGUGGUUUUAAUGAUUUG<br>UCACAACUCCACUGCUCAUAUGAAUCCUUCGAUGUUGAA<br>UCUGGAGUUUAUUCAGUUUCGUCUUUCGAAGCAAAACC<br>UUCUGGCUCAGUUGUGGAACAGGCUGAAGGUGUUGAAU<br>GUGAUUUUUCACCUCUUCUGUCUGGCACACCUCCUCAGG<br>UUUAUAAUUUCAAGCGUUUGGUUUUUACCAAUUGCAAU<br>UAUAAUCUUACCAAAUUGCUUUCACUUUUUUCUGUGAA<br>UGAUUUUACUUGUAGUCAAAUAUCUCCAGCAGCAAUUG<br>CUAGCAACUGUUAUUCUUCACUGAUUUUGGAUUAUUUU<br>UCAUACCCACUUAGUAUGAAAUCCGAUCUCAGUGUUAG<br>UUCUGCUGGUCCAAUAUCCCAGUUUAAUUAUAAACAGU | 65 |

TABLE 10-continued

Betacoronavirus Nucleic Acid Sequence

| Strain | Nucleic Acid Sequence | SEQ ID NO: |
|---|---|---|
| | CCUUUUCUAAUCCCACAUGUUUGAUCUUAGCGACUGUUC<br>CUCAUAACCUUACUACUAUUACUAAGCCUCUUAAGUACA<br>GCUAUAUUAACAAGUGCUCUCGUCUUCUUUCUGAUGAU<br>CGUACUGAAGUACCUCAGUUAGUGAACGCUAAUCAAUA<br>CUCACCCUGUGUAUCCAUUGUCCCAUCCACUGUGUGGGA<br>AGACGGUGAUUAUUAUAGGAAACAACUAUCUCCACUUG<br>AAGGUGGUGGCUGGCUUGUUGCUAGUGGCUCAACUGUU<br>GCCAUGACUGAGCAAUUACAGAUGGGCUUUGGUAUUAC<br>AGUUCAAUAUGGUACAGACACCAAUAGUGUUUGCCCCA<br>AGCUUGAAUUUGCUAAUGACACAAAAAUUGCCUCUCAA<br>UUAGGCAAUUGCGUGGAAUAUUCCCUCUAUGGUGUUUC<br>GGGCCGUGGUGUUUUUCAGAAUUGCACAGCUGUAGGUG<br>UUCGACAGCAGCGCUUUGUUUAUGAUGCGUACCAGAAU<br>UUAGUUGGCUAUUAUUCUGAUGAUGGCAACUACUACUG<br>UCUGCGUGCUUGUGUUAGUGUUCCUGUUUCUGUCAUCU<br>AUGAUAAAGAAACUAAAACCCACGCUACUCUAUUUGGU<br>AGUGUUGCAUGUGAACACAUUUCUUCUACCAUGUCUCA<br>AUACUCCCGUUCUACGCGAUCAAUGCUUAAACGGCGAGA<br>UUCUACAUAUGGCCCCCUUCAGACACCUGUUGGUUGUGU<br>CCUAGGACUUGUUAAUUCCUCUUUGUUCGUAGAGGACU<br>GCAAGUUGCCUCUCGGUCAAUCUCUCUGUGCUCUUCCUG<br>ACACACCUAGUACUCUCACACCUCGCAGUGUGCGCUCUG<br>UGCCAGGUGAAAUGCGCUUGGCAUCCAUUGCUUUUAAU<br>CAUCCCAUUCAGGUUGAUCAACUUAAUAGUAGUUAUUU<br>UAAAUUAAGUAUACCCACUAAUUUUUCCUUUGGUGUGA<br>CUCAGGAGUACAUUCAGACAACCAUUCAGAAAGUUACU<br>GUUGAUUGUAAACAGUACGUUUGCAAUGGUUUCCAGAA<br>GUGUGAGCAAUUACUGCGCGAGUAUGGCCAGUUUUGUU<br>CCAAAAUAAACCAGGCUCUCCAUGGUGCCAAUUUACGCC<br>AGGAUGAUUCUGUACGUAAUUUGUUUGCGAGCGUGAAA<br>AGCUCUCAAUCAUCUCCUAUCAUACCAGGUUUUGGAGGU<br>GACUUUAAUUUGACACUUCUAGAACCUGUUUCUAUAUC<br>UACUGGCAGUCGUAGUGCACGUAGUGCUAUUGAGGAUU<br>UGCUAUUUGACAAAGUCACUAUAGCUGAUCCUGGUUAU<br>AUGCAAGGUUACGAUGAUUGUAUGCAGCAAGGUCCAGC<br>AUCAGCUCGUGAUCUUAUUUGUGCUCAAUAUGUGGCUG<br>GUUAUAAAGUAUUACCUCCUCUUAUGGAUGUUAAUAUG<br>GAAGCCGCGUAUACUUCAUCUUUGCUUGGCAGCAUAGCA<br>GGUGUUGGCUGGACUGCUGGCUUAUCCUCCUUUGCUGCU<br>AUUCCAUUUGCACAGAGUAUYUUUUAUAGGUUAAACGG<br>UGUUGGCAUUACUCAACAGGUUCUUUCAGAGAACCAAA<br>AGCUUAUUGCCAAUAAGUUUAAUCAGGCUCUGGGAGCU<br>AUGCAAACAGGCUUCACUACAACUAAUGAAGCUUUUCG<br>GAAGGUUCAGGAUGCUGUGAACAACAAUGCACAGGCUC<br>UAUCCAAAUUAGCUAGCGAGCUAUCUAAUACUUUUGGU<br>GCUAUUUCCGCCUCUAUUGGAGACAUCAUACAACGUCUU<br>GAUGUUCUCGAACAGGACGCCCAAAUAGACAGACUUAU<br>UAAUGGCCGUUUGACAACACUAAAUGCUUUUGUUGCAC<br>AGCAGCUUGUUCGUUCCGAAUCAGCUGCUCUUUCCGCUC<br>AAUUGGCUAAAGAUAAAGUCAAUGAGUGUGUCAAGGCA<br>CAAUCCAAGCGUUCUGGAUUUUGCGGUCAAGGCACACAU<br>AUAGUGUCCUUUGUUGUAAAUGCCCCUAAUGGCCUUUA<br>CUUUAUGCAUGUUGGUUAUUACCCUAGCAACCACAUUG<br>AGGUUGUUUCUGCUUAUGGUCUUUGCGAUGCAGCUAAC<br>CCUACUAAUUGUAUAGCCCCUGUUAAUGGCUACUUUAU<br>UAAAACUAAUAACACUAGGAUUGUUGAUGAGUGGUCAU<br>AUACUGGCUCGUCCUUCUAUGCACCUGAGCCCAUCACCU<br>CUCUUAAUACUAAGUAUGUUGCACCACAGGUGACAUACC<br>AAAACAUUUCUACUAACCUCCCUCCUCCUCUUCUCGGCA<br>AUUCCACCGGGAUUGACUUCCAAGAUGAGUUGGAUGAG<br>UUUUUCAAAAAUGUUAGCACCAGUAUACCUAAUUUUGG<br>UUCUCUAACACAGAUUAAUACUACAUUACUCGAUCUUAC<br>CUACGAGAUGUUGUCUCUUCAACAAGUUGUUAAAGCCC<br>UUAAUGAGUCUUACAUAGACCUUAAAGAGCUUGGCAAU<br>UAUACUUAUUACAACAAAUGGCCGUGGUACAUUUGGCU<br>UGGUUUCAUUGCUGGGCUUGUUGCCUUAGCUCUAUGCG<br>UCUUCUUCAUACUGUGCUGCACUGGUUGUGGCACAAACU<br>GUAUGGGAAAACUUAAGUGUAAUCGUUGUUGUGAUAGA<br>UACGAGGAAUACGACCUCGAGCCGCAUAAGGUUCAUGU<br>UCACUAA | |

TABLE 10-continued

| Betacoronavirus Nucleic Acid Sequence | | |
|---|---|---|
| Strain | Nucleic Acid Sequence | SEQ ID NO: |
| MERS S FL SPIKE 2cEMC/2012 (XBaI change (U to G)) (nucleotide) | AUGAUACACUCAGUGUUUCUACUGAUGUUCUUGUUAAC<br>ACCUACAGAAAGUUACGUUGAUGUAGGGCCAGAUUCUG<br>UUAAGUCUGCUUGUAUUGAGGUUGAUAUACAACAGACU<br>UUCUUUGAUAAAACUUGGCCUAGGCCAAUUGAUGUUUC<br>UAAGGCUGACGGUAUUAUAUACCCUCAAGGCCGUACAU<br>AUUCUAACAUAACUAUCACUUAUCAAGGUCUUUUUCCCU<br>AUCAGGGAGACCAUGGUGAUAUGUAUGUUUACUCUGCA<br>GGACAUGCUACAGGCACAACUCCACAAAAGUUGUUUGU<br>AGCUAACUAUUCUCAGGACGUCAAACAGUUUGCUAAUG<br>GGUUUGUCGUCCGUAUAGGAGCAGCUGCCAAUUCCACUG<br>GCACUGUUAUUAUUAGCCCAUCUACCAGCGCUACUAUAC<br>GAAAAAUUUACCCUGCUUUUAUGCUGGGUUCUUCAGUU<br>GGUAAUUUCUCAGAUGGUAAAAUGGGCCGCUUCUUCAA<br>UCAUACUCUAGUUCUUUUGCCCGAUGGAUGUGGCACUU<br>UACUUAGAGCUUUUUAUUGUAUUCUGGAGCCUCGCUCU<br>GGAAAUCAUUGUCCUGCUGGCAAUUCCUAUACUUCUUU<br>UGCCACUUAUCACACUCCUGCAACAGAUUGUUCUGAUGG<br>CAAUUACAAUCGUAAUGCCAGUCUGAACUCUUUUAAGG<br>AGUAUUUUAAUUUACGUAACUGCACCUUUAUGUACACU<br>UAUAACAUUACCGAAGAUGAGAUUUUAGAGUGGUUUGG<br>CAUUACACAAACUGCUCAAGGUGUUCACCUCUUCUCAUC<br>UCGGUAUGUUGAUUUGUACGGCGGCAAUAUGUUUCAAU<br>UUGCCACCUUGCCUGUUUAUGAUACUAUUAAGUAUUAU<br>UCUAUCAUUCCUCACAGUAUUCGUUCUAUCCAAAGUGAU<br>AGAAAAGCUUGGGCUGCCUUCUACGUAUAUAAACUUCA<br>ACCGUUAACUUUCCUGUUGGAUUUUUCUGUUGAUGGUU<br>AUAUACGCAGAGCUAUAGACUGUGGUUUUAAUGAUUUG<br>UCACAACUCCACUGCUCAUAUGAAUCCUUCGAUGUUGAA<br>UCUGGAGUUUAUUCAGUUUCGUCUUUCGAAGCAAAACC<br>UUCUGGCUCAGUUGUGGAACAGGCUGAAGGUGUUGAAU<br>GUGAUUUUUCACCUCUUCUGUCUGGCACACCUCCUCAGG<br>UUUAUAAUUUCAAGCGUUUGGUUUUUACCAAUUGCAAU<br>UAUAAUCUUACCAAAUUGCUUUCACUUUUUUCUGUGAA<br>UGAUUUUACUUGUAGUCAAAUAUCUCCAGCAGCAAUUG<br>CUAGCAACUGUUAUUCUUCACUGAUUUUGGAUUACUUU<br>UCAUACCCACUUAGUAUGAAAUCCGAUCUCAGUGUUAG<br>UUCUGCUGGUCCAAUAUCCCAGUUUAAUUAUAAACAGU<br>CCUUUUCUAAUCCCACAUGUUUGAUUUUAGCGACUGUUC<br>CUCAUAACCUUACUACUAUUACUAAGCCUCUUAAGUACA<br>GCUAUAUUAACAAGUGCUCUCGUCUUCUUUCUGAUGAU<br>CGUACUGAAGUACCUCAGUUAGUGAACGCUAAUCAAUA<br>CUCACCCUGUGUAUCCAUUGUCCCAUCCACUGUGUGGGA<br>AGACGGUGAUUAUUAUAGGAAACAACUAUCUCCACUUG<br>AAGGUGGUGGCUGGCUUGUUGCUAGUGGCUCAACUGUU<br>GCCAUGACUGAGCAAUUACAGAUGGGCUUUGGUAUUAC<br>AGUUCAAUAUGGUACAGACACCAAUAGUGUUUGCCCCA<br>AGCUUGAAUUUGCUAAUGACACAAAAAUUGCCUCUCAA<br>UUAGGCAAUUGCGUGGAAUAUUCCCUCUAUGGUGUUUC<br>GGGCCGUGGUGUUUUUCAGAAUUGCACAGCUGUAGGUG<br>UUCGACAGCAGCGCUUUGUUUAUGAUGCGUACCAGAAU<br>UUAGUUGGCUAUUAUUCUGAUGAUGGCAACUACUACUG<br>UUUGCGUGCUUGUGUUAGUGUUCCUGUUUCUGUCAUCU<br>AUGAUAAAGAAACUAAAACCCACGCUACUCUAUUUGGU<br>AGUGUUGCAUGUGAACACAUUUCUUCUACCAUGUCUCA<br>AUACUCCCGUUCUACGCGAUCAAUGCUUAAACGGCGAGA<br>UUCUACAUAUGGCCCCCUUCAGACACCUGUUGGUUGUGU<br>CCUAGGACUUGUUAAUUCCUCUUUGUUCGUAGAGGACU<br>GCAAGUUGCCUCUUGGUCAAUCUCUCUGUGCUCUUCCUG<br>ACACACCUAGUACUCUCACACCUCGCAGUGUGCGCUCUG<br>UUCCAGGUGAAAUGCGCUUGGCAUCCAUUGCUUUUAAU<br>CAUCCUAUUCAGGUUGAUCAACUUAAUAGUAGUUAUUU<br>UAAAUUAAGUAUACCCACUAAUUUUUCCUUUGGUGUGA<br>CUCAGGAGUACAUUCAGACAACCAUUCAGAAAGUUACU<br>GUUGAUUGUAAACAGUACGUUUGCAAUGGUUUCCAGAA<br>GUGUGAGCAAUUACUGCGCGAGUAUGGCCAGUUUUGUU<br>CCAAAAUAAACCAGGCUCUCCAUGGUGCCAAUUUACGCC<br>AGGAUGAUUCUGUACGUAAUUUGUUUGCGAGCGUGAAA<br>AGCUCUCAAUCAUCUCCUAUCAUACCAGGUUUUGGAGGU<br>GACUUUAAUUUGACACUUCUGGAACCUGUUUCUAUAUC<br>UACUGGCAGUCGUAGUGCACGUAGUGCUAUUGAGGAUU<br>UGCUAUUUGACAAAGUCACUAUAGCUGAUCCUGGUUAU<br>AUGCAAGGUUACGAUGAUUGCAUGCAGCAAGGUCCAGC<br>AUCAGCUCGUGAUCUUAUUUGUGCUCAAUAUGUGGCUG<br>GUUACAAAGUAUUACCUCCUCUUAUGGAUGUUAAUAUG | 66 |

TABLE 10-continued

| Betacoronavirus Nucleic Acid Sequence | | |
|---|---|---|
| Strain | Nucleic Acid Sequence | SEQ ID NO: |
| | GAAGCCGCGUAUACUUCAUCUUUGCUUGGCAGCAUAGCA GGUGUUGGCUGGACUGCUGGCUUAUCCUCCUUUGCUGCU AUUCCAUUUGCACAGAGUAUCUUUUAUAGGUUAAACGG UGUUGGCAUUACUCAACAGGUUCUUUCAGAGAACCAAA AGCUUAUUGCCAAUAAGUUUAAUCAGGCUCUGGGAGCU AUGCAAACAGGCUUCACUACAACUAAUGAAGCUUUUCA GAAGGUUCAGGAUGCUGUGAACAACAAUGCACAGGCUC UAUCCAAAUUAGCUAGCGAGCUAUCUAAUACUUUUGGU GCUAUUUCCGCCUCUAUUGGAGACAUCAUACAACGUCUU GAUGUUCUCGAACAGGACGCCCAAAUAGACAGACUUAU UAAUGGCCGUUUGACAACACUAAAUGCUUUUGUUGCAC AGCAGCUUGUUCGUUCCGAAUCAGCUGCUCUUUCCGCUC AAUUGGCUAAAGAUAAAGUCAAUGAGUGUGUCAAGGCA CAAUCCAAGCGUUCUGGAUUUUGCGGUCAAGGCACACAU AUAGUGUCCUUUGUUGUAAAUGCCCCUAAUGGCCUUUA CUUCAUGCAUGUUGGUUAUUACCCUAGCAACCACAUUGA GGUUGUUUCUGCUUAUGGUCUUUGCGAUGCAGCUAACC CUACUAAUUGUAUAGCCCCUGUUAAUGGCUACUUUAUU AAAACUAAUAACACUAGGAUUGUUGAUGAGUGGUCAUA UACUGGCUCGUCCUUCUAUGCACCUGAGCCCAUUACCUC CCUUAAUACUAAGUAUGUUGCACCACAGGUGACAUACCA AAACAUUUCUACUAACCUCCCUCCUCCCUCUUCUCGGCAA UUCCACCGGGAUUGACUUCCAAGAUGAGUUGGAUGAGU UUUUCAAAAAUGUUAGCACCAGUAUACCUAAUUUUGGU UCCCUAACACAGAUUAAUACUACAUUACUCGAUCUUACC UACGAGAUGUUGUCUCUUCAACAAGUUGUUAAAGCCCU UAAUGAGUCUUACAUAGACCUUAAAGAGCUUGGCAAUU AUACUUAUUACAACAAAUGGCCGUGGUACAUUUGGCUU GGUUUCAUUGCUGGGCUUGUUGCCUUAGCUCUAUGCGU CUUCUUCAUACUGUGCUGCACUGGUUGUGGCACAAACUG UAUGGGAAAACUUAAGUGUAAUCGUUGUUGUGAUAGAU ACGAGGAAUACGACCUCGAGCCGCAUAAGGUUCAUGUUC ACUAA | |
| Novel_MERS_S2_ subunit_trimeric vaccine (nucleotide) | AUGAUCCACUCCGUGUUCCUCCUCAUGUUCCUGUUGACC CCCACUGAGUCAGACUGCAAGCUCCCGCUGGGACAGUCC CUGUGUGCGCUGCCUGACACUCCUAGCACUCUGACCCCA CGCUCCGUGCGGUCGGUGCCUGGCGAAAUGCGGCUGGCC UCCAUCGCCUUCAAUCACCCAAUCCAAGUGGAUCAGCUG AAUAGCUCGUAUUUCAAGCUGUCCAUCCCCACGAACUUC UCGUUCGGGGUCACCCAGGAGUACAUCCAGACCACAAUU CAGAAGGUCACCGUCGAUUGCAAGCAAUACGUGUGCAAC GGCUUCCAGAAGUGCGAGCAGCUGCUGAGAGAAUACGG GCAGUUUUGCAGCAAGAUCAACCAGGCGCUGCAUGGAGC UAACUUGCGCCAGGACGACUCCGUGCGCAACCUCUUUGC CUCUGUGAAGUCAUCCCAGUCCUCCCCAAUCAUCCCGGG AUUCGGAGGGGACUUCAACCUGACCCUCCUGGAGCCCGU GUCGAUCAGCACCGGUAGCAGAUCGGCGCGCUCAGCCAU UGAAGAUCUUCUGUUCGACAAGGUCACCAUCGCCGAUCC GGGCUACAUGCAGGAUACGACGACUGUAUGCAGCAGG GACCAGCCUCCGCGAGGGACCUCAUCUGCGCGCAAUACG UGGCCGGGUACAAAGUGCUGCCUCCUCUGAUGGAUGUG AACAUGGAGGCCGCUUAUACUUCGUCCCUGCUCGGCUCU AUCGCCGGCGUGGGGUGGACCGCCGGCCUGUCCUCCUUC GCCGCUAUCCCCUUUGCACAAUCCAUUUUCUACCGGCUC AACGGCGUGGGCAUUACUCAACAAGUCCUGUCGGAGAAC CAGAAGUUGAUCGCAAACAAGUUCAAUCAGGCCCUGGG GGCCAUGCAGACUGGAUUCACUACGACUAACGAAGCGUU CCAGAAGGUCCAGGACGCUGUGAACAACAACGCCCAGGC GCUCUCAAAGCUGGCCUCCGAACUCAGCAACACCUUCGG AGCCAUCAGCGCAUCGAUCGGUGACAUAAUUCAGCGGCU GGACGUGCUGGAGCAGGACGCCCAGAUCGACCGCCUCAU CAACGGACGGCUGACCACCUUGAAUGCCUUCGUGGCACA ACAGCUGGUCCGGAGCGAAUCAGCGGCACUUUCCGCCCA ACUCGCCAAGGACAAAGUCAACGAAUGCGUGAAGGCCCA GUCCAAGAGGUCCGGUUUCUGCGGUCAAGGAACCCAUAU UGUGUCCUUCGUCGUGAACGCGCCCAACGGUCUGUACUU UAUGCACGUCGGCUACUACCCGAGCAAUCAUAUCGAAGU GGUGUCCGCCUACGGCCUGUGCGAUGCCGCUAACCCCAC UAACUGUAUUGCCCCUGUGAACGGAUAUUUUAUUAAGA CCAACAACACCCGCAUUGUGGACGAAUGGUCAUACACCG GUUCGUCCUUCUACGCGCCCGAGCCCAUCACUUCACUGA ACACCAAAUACGUGGCUCCGCAAGUGACCUACCAGAACA UCUCCACCAAUUUGCCGCCGCCGCUGCUCGGAAACAGCA CCGGAAUUGAUUUCCAAGAUGAACUGGACGAAUUCUUC | 67 |

TABLE 10-continued

| Betacoronavirus Nucleic Acid Sequence | | |
|---|---|---|
| Strain | Nucleic Acid Sequence | SEQ ID NO: |
| | AAGAACGUGUCCACUUCCAUUCCCAACUUCGGAAGCCUG ACACAGAUCAACACCACCCUUCUCGACCUGACCUACGAG AUGCUGAGCCUUCAACAAGUGGUCAAGGCCCUGAACGAG AGCUACAUCGACCUGAAGGAGCUGGGCAACUAUACCUAC UACAACAAGUGGCCGGACAAGAUUGAGGAGAUUCUGUC GAAAAUCUACCACAUUGAAAACGAGAUCGCCAGAAUCA AGAAGCUUAUCGGCGAAGCC | |
| MERS_S0_Full-length Spike protein (nucleotide, codon optimized) | AUGGAAACCCCUGCCCAGCUGCUGUUCCUGCUGCUGCUG UGGCUGCCUGAUACCACCGGCAGCUAUGUGGACGUGGGC CCCGAUAGCGUGAAGUCCGCCUGUAUCGAAGUGGACAUC CAGCAGACCUUUUUCGACAAGACCUGGCCCAGACCCAUC GACGUGUCCAAGGCCGACGGCAUCAUCUAUCCACAAGGC CGGACCUACAGCAACAUCACCAUUACCUACCAGGGCCUG UUCCCAUAUCAAGGCGACCACGGCGAUAUGUACGUGUAC UCUGCCGGCCACGCCACCGGCACCACACCCCAGAAACUG UUCGUGGCCAACUACAGCCAGGACGUGAAGCAGUUCGCC AACGGCUUCGUCGUGCGGAUUGGCGCCGCUGCCAAUAGC ACCGGCACAGUGAUCAUCAGCCCCAGCACCAGCGCCACC AUCCGGAAGAUCUACCCCGCCUUCAUGCUGGGCAGCUCC GUGGGCAAUUUCAGCGACGGCAAGAUGGGCCGGUUCUU CAACCACACCCUGGUGCUGCUGCCCGAUGGCUGUGGCAC ACUGCUGAGAGCCUUCUACUGCAUCCUGGAACCCAGAAG CGGCAACCACUGCCCUGCCGGCAAUAGCUACACCAGCUU CGCCACCUACCACACACCCGCCACCGAUUGCUCCGACGG CAACUACAACCGGAACGCCAGCCUGAACAGCUUCAAAGA GUACUUCAACCUGCGGAACUGCACCUUCAUGUACACCUA CAAUAUCACCGAGGACGAGAUCCUGGAAUGGUUCGGCA UCACCCAGACCGCCCAGGGCGUGCACCUGUUCAGCAGCA GAUACGUGGACCUGUACGGCGGCAACAUGUUCCAGUUU GCCACCCUGCCCGUGUACGACACCAUCAAGUACUACAGC AUCAUCCCCCACAGCAUCCGGUCCAUCCAGAGCGACAGA AAAGCCUGGGCCGCCUUCUACGUGUACAAGCUGCAGCCC CUGACCUUCCUGCUGGACUUCAGCGUGGACGGCUACAUC AGACGGGCCAUCGACUGCGGCUUCAACGACCUGAGCCAG CUGCACUGCUCCUACGAGAGCUUCGACGUGGAAAGCGGC GUGUACAGCGUGUCCAGCUUCGAGGCCAAGCCUAGCGGC AGCGUGGUGGAACAGGCUGAGGGCGUGGAAUGCGACUU CAGCCCUCUGCUGAGCGGCACCCCUCCCCAGGUGUACAA CUUCAAGCGGCUGGUGUUCACCAACUGCAAUUACAACCU GACCAAGCUGCUGAGCCUGUUCUCCGUGAACGACUUCAC CUGUAGCCAGAUCAGCCCUGCCGCCAUUGCCAGCAACUG CUACAGCAGCCUGAUCCUGGACUACUUCAGCUACCCCCU GAGCAUGAAGUCCGAUCUGAGCGUGUCCUCCGCCGGACC CAUCAGCCAGUUCAACUACAAGCAGAGCUUCAGCAACCC UACCUGCCUGAUUCUGGCCACCGUGCCCCACAAUCUGAC CACCAUCACCAAGCCCCUGAAGUACAGCUACAUCAACAA GUGCAGCAGACUGCUGUCCGACGACCGGACCGAAGUGCC CCAGCUCGUGAACGCCAACCAGUACAGCCCCUGCGUGUC CAUCGUGCCCAGCACCGUGUGGGAGGACGGCGACUACUA CAGAAAGCAGCUGAGCCCCCUGGAAGGCGGCGGAUGGCU GGUGGCUUCUGGAAGCACAGUGGCCAUGACCGAGCAGCU GCAGAUGGGCUUUGGCAUCACCGUGCAGUACGGCACCGA CACCAACAGCGUGUGCCCCAAGCUGGAAUUCGCCAAUGA CACCAAGAUCGCCAGCCAGCUGGGAAACUGCGUGGAAUA CUCCCUGUAUGGCGUGUCCGGACGGGGCGUGUUCCAGAA UUGCACAGCAGUGGGAGUGCGGCAGCAGAGAUUCGUGU ACGAUGCCUACCAGAACCUCGUGGGCUACUACAGCGACG ACGGCAAUUACUACUGCCUGCGGGCCUGUGUGUCCGUGC CCGUGUCCGUGAUCUACGACAAAGAGACAAAGACCCACG CCACACUGUUCGGCUCCGUGGCCUGCGAGCACAUCAGCU CCACCAUGAGCCAGUACUCCCGCUCCACCCGGUCCAUGC UGAAGCGGAGAGAUAGCACCUACGGCCCCCUGCAGACAC CUGUGGGAUGUGUGCUGGGCCUCGUGAACAGCUCCCUGU UUGUGGAAGAUUGCAAGCUGCCCCUGGGCCAGAGCCUGU GUGCCCUGCCAGAUACCCCUAGCACCCUGACCCCUAGAA GCGUGCGCUCUGUGCCCGGCGAAAUGCGGCUGGCCUCUA UCGCCUUCAAUCACCCCAUCCAGGUGGACCAGCUGAACU CCAGCUACUUCAAGCUGAGCAUCCCCACCAACUUCAGCU UCGGCGUGACCCAGGAGUACAUCCAGACCACAAUCCAGA AAGUGACCGUGGACUGCAAGCAGUACGUGUGCAACGGC UUUCAGAAGUGCGAACAGCUGCUGCGCGAGUACGGCCAG UUCUGCAGCAAGAUCAACCAGGCCCUGCACGGCGCCAAC CUGAGACAGGAUGACAGCGUGCGGAACCUGUUCGCCAGC GUGAAAAGCAGCCAGUCCAGCCCCAUCAUCCCUGGCUUC | 68 |

TABLE 10-continued

| Betacoronavirus Nucleic Acid Sequence | | |
|---|---|---|
| Strain | Nucleic Acid Sequence | SEQ ID NO: |
| | GGCGGCGACUUUAACCUGACCCUGCUGGAACCUGUGUCC<br>AUCAGCACCGGCUCCAGAAGCGCCAGAUCCGCCAUCGAG<br>GACCUGCUGUUCGACAAAGUGACCAUUGCCGACCCCGGC<br>UACAUGCAGGGCUACGACGAUUGCAUGCAGCAGGGCCCA<br>GCCAGCGCCAGGGAUCUGAUCUGUGCCCAGUAUGUGGCC<br>GGCUACAAGGUGCUGCCCCCCCUGAUGGACGUGAACAUG<br>GAAGCCGCCUACACCUCCAGCCUGCUGGGCUCUAUUGCU<br>GGCGUGGGAUGGACAGCCGGCCUGUCUAGCUUUGCCGCC<br>AUCCCUUUCGCCCAGAGCAUCUUCUACCGGCUGAACGGC<br>GUGGGCAUCACACAACAGGUGCUGAGCGAGAACCAGAA<br>GCUGAUCGCCAACAAGUUUAACCAGGCACUGGGCGCCAU<br>GCAGACCGGCUUCACCACCACCAACGAGGCCUUCAGAAA<br>GGUGCAGGACGCCGUGAACAACAACGCCCAGGCUCUGAG<br>CAAGCUGGCCUCCGAGCUGAGCAAUACCUUCGGCGCCAU<br>CAGCGCCUCCAUCGGCGACAUCAUCCAGCGGCUGGACGU<br>GCUGGAACAGGACGCCCAGAUCGACCGGCUGAUCAACGG<br>CAGACUGACCACCCUGAACGCCUUCGUGGCACAGCAGCU<br>CGUGCGGAGCGAAUCUGCCGCUCUGUCUGCUCAGCUGGC<br>CAAGGACAAAGUGAACGAGUGCGUGAAGGCCCAGUCCA<br>AGCGGAGCGGCUUUUGUGGCCAGGGCACCCACAUCGUGU<br>CCUUCGUCGUGAAUGCCCCCAACGGCCUGUACUUUAUGC<br>ACGUGGGCUAUUACCCCAGCAACCACAUCGAGGUGGUGU<br>CCGCCUAUGGCCUGUGCGACGCCGCCAAUCCUACCAACU<br>GUAUCGCCCCCGUGAACGGCUACUUCAUCAAGACCAACA<br>ACACCCGGAUCGUGGACGAGUGGUCCUACACAGGCAGCA<br>GCUUCUACGCCCCCGAGCCCAUCACCUCCCUGAACACCA<br>AAUACGUGGCCCCCCAAGUGACAUACCAGAACAUCUCCA<br>CCAACCUGCCCCCUCCACUGCUGGGAAAUUCCACCGGCA<br>UCGACUUCCAGGACGAGCUGGACGAGUUCUUCAAGAACG<br>UGUCCACCUCCAUCCCCAACUUCGGCAGCCUGACCCAGA<br>UCAACACCACUCUGCUGGACCUGACCUACGAGAUGCUGU<br>CCCUGCAACAGGUCGUGAAAGCCCUGAACGAGAGCUACA<br>UCGACCUGAAAGAGCUGGGGAACUACACCUACUACAACA<br>AGUGGCCUUGGUACAUUUGGCUGGGCUUUAUCGCCGGCC<br>UGGUGGCCCUGGCCCUGUGCGUGUUCUUCAUCCUGUGCU<br>GCACCGGCUGCGGCACCAAUUGCAUGGGCAAGCUGAAAU<br>GCAACCGGUGCUGCGACAGAUACGAGGAAUACGACCUGG<br>AACCUCACAAAGUGCAUGUGCAC | |

TABLE 11

| Betacoronavirus Amino Acid Sequences | | |
|---|---|---|
| Strain | Amino Acid Sequence | SEQ ID NO: |
| gb\|KJ156934.1\|:21405-25466 Middle East respiratory syndrome coronavirus isolate Riyadh_14_2013, spike protein (amino acid) | MIHSVFLLMFLLTPTESYVDVGPDSVKSACIEVDIQQTFFDKT<br>WPRPIDVSKADGIIYPQGRTYSNITITYQGLFPYQGDHGDMY<br>VYSAGHATGTTpQKLFVANYSQDVKQFANGFVVRIGAAANS<br>TGTVIISPSTSATIRKIYPAFMLGSSVGNFSDGKMGRFFNHTL<br>VLLPDGCGTLLRAFYCILEPRSGNHCPAGNSYTSFATYHTPA<br>TDCSDGNYNRNASLNSFKEYFNLRNCTFMYTYNITEDEILEW<br>FGITQTAQGVHLFSSRYVDLYGGNMFQFATLPVYDTIKYYSII<br>PHSIRSIQSDRKAWAAFYVYKLQPLTFLLDFSVDGYIRRAIDC<br>GFNDLSQLHCSYESFDVESGVYSVSSFEAKPSGSVVEQAEGV<br>ECDFSPLLSGTPPQVYNFKRLVFTNCNYNLTKLLSLFSVNDFt<br>CSQISPAAIASNCYSSLILDYFSYPLSMKSDLSVSSAGPISQFN<br>YKQSFSNPTCLILATVPHNLTTITKPLKYSYINKCSRLLSDDRT<br>EVPQLVNANQYSPCVSIVPSTVWEDGDYYRKQLSPLEGGGW<br>LVASGSTVAMTEQLQMGFGITVQYGTDTNSVCPKLEFANDT<br>KIASQLGNCVEYSLYGVSGRGVFQNCTAVGVRQQRFVYDA<br>YQNLVGYYSDDGNYYCLRACVSVPVSVIYDKETKTHATLFG<br>SVACEHISSTMSQYSRSTRSMLKRRDSTYGPLQTPVGCVLGL<br>VNSSLFVEDCKLPLGQSLCALPDTPSTLTPRSVRSVPGEMRLA<br>SIAFNHPIQVDQLNSSYFKLSIPTNFSFGVTQEYIQTTIQKVTV<br>DCKQYVCNGFQKCEQLLREYGQFCSKINqALHGANLRQDDS<br>VRNLFASVKSSQSSPIIPGFGGDFNLTLLEPVSISTGSRSARSAI<br>EDLLFDKVTIADPGYMQGYDDCMQQGPASARDLICAQYVA<br>GYKVLPPLMDVNMEAAYTSSLLGSIAGVGWTAGLSSFAAIPF<br>AQSIFYRLNGVGITQQVLSENQKLIANKFNQALGAMQTGFTT<br>TNEAFrKVQDAVNNNAQALSKLASELSNTFGAISASIGDIIQR<br>LDVLEQDAQIDRLINGRLTTLNAFVAQQLVRSESAALSAQLA | 24 |

TABLE 11-continued

| Betacoronavirus Amino Acid Sequences | | |
|---|---|---|
| Strain | Amino Acid Sequence | SEQ ID NO: |
| | KDKVNECVKAQSKRSGFCGQGTHIVSFVVNAPNGLYFMHV GYYPSNHIEVVSAYGLCDAANPTNCIAPVNGYFIKTNNTRIV DEWSYTGSSFYAPEPITSLNTKYVAPQVTYQNISTNLPPPLLG NSTGIDFQDELDEFFKNVSTSIPNFGSLTQINTTLLDLTYEMLS LQQVVKALNESYIDLKELGNYTYYNKWPWYIWLGFIAGLVA LALCVFFILCCTGCGTNCMGKLKCNRCCDRYEEYDLEPHKV HVH | |
| MERS S FL SPIKE 2cEMC/2012 (XBaI change (T to G)) (amino acid) | MIHSVFLLMFLLTPTESYVDVGPDSVKSACIEVDIQQTFFDKT WPRPIDVSKADGIIYPQGRTYSNITITYQGLFPYQGDHGDMY VYSAGHATGTTPQKLFVANYSQDVKQFANGFVVRIGAAANS TGTVIISPSTSATIRKIYPAFMLGSSVGNFSDGKMGRFFNHTL VLLPDGCGTLLRAFYCILEPRSGNHCPAGNSYTSFATYHTPA TDCSDGNYNRNASLNSFKEYFNLRNCTFMYTYNITEDEILEW FGITQTAQGVHLFSSRYVDLYGGNMFQFATLPVYDTIKYYSII PHSIRSIQSDRKAWAAFYVYKLQPLTFLLDFSVDGYIRRAIDC GFNDLSQLHCSYESFDVESGVYSVSSFEAKPSGSVVEQAEGV ECDFSPLLSGTPPQVYNFKRLVFTNCNYNLTKLLSLFSVNDFT CSQISPAAIASNCYSSLILDYFSYPLSMKSDLSVSSAGPISQFN YKQSFSNPTCLILATVPHNLTTITKPLKYSYINKCSRLLSDDRT EVPQLVNANQYSPCVSIVPSTVWEDGDYYRKQLSPLEGGGW LVASGSTVAMTEQLQMGFGITVQYGTDTNSVCPKLEFANDT KIASQLGNCVEYSLYGVSGRGVFQNCTAVGVRQQRFVYDA YQNLVGYYSDDGNYYCLRACVSVPVSVIYDKETKTHATLFG SVACEHISSTMSQYSRSTRSMLKRRDSTYGPLQTPVGCVLGL VNSSLFVEDCKLPLGQSLCALPDTPSTLTPRSVRSVPGEMRLA SIAFNHPIQVDQLNSSYFKLSIPTNFSFGVTQEYIQTTIQKVTV DCKQYVCNGFQKCEQLLREYGQFCSKINQALHGANLRQDDS VRNLFASVKSSQSSPIIPGFGGDFNLTLLEPVSISTGSRSARSAI EDLLFDKVTIADPGYMQGYDDCMQQGPASARDLICAQYVA GYKVLPPLMDVNMEAAYTSSLLGSIAGVGWTAGLSSFAAIPF AQSIFYRLNGVGITQQVLSENQKLIANKFNQALGAMQTGFTT TNEAFQKVQDAVNNNAQALSKLASELSNTFGAISASIGDIIQR LDVLEQDAQIDRLINGRLTTLNAFVAQQLVRSESAALSAQLA KDKVNECVKAQSKRSGFCGQGTHIVSFVVNAPNGLYFMHV GYYPSNHIEVVSAYGLCDAANPTNCIAPVNGYFIKTNNTRIV DEWSYTGSSFYAPEPITSLNTKYVAPQVTYQNISTNLPPPLLG NSTGIDFQDELDEFFKNVSTSIPNFGSLTQINTTLLDLTYEMLS LQQVVKALNESYIDLKELGNYTYYNKWPWYIWLGFIAGLVA LALCVFFILCCTGCGTNCMGKLKCNRCCDRYEEYDLEPHKV HVH | 25 |
| Novel_MERS_S2_ subunit_trimeric vaccine (amino acid) | MIHSVFLLMFLLTPTESDCKLPLGQSLCALPDTPSTLTPRSVR SVPGEMRLASIAFNHPIQVDQLNSSYFKLSIPTNFSFGVTQEYI QTTIQKVTVDCKQYVCNGFQKCEQLLREYGQFCSKINQALH GANLRQDDSVRNLFASVKSSQSSPIIPGFGGDFNLTLLEPVSIS TGSRSARSAIEDLLFDKVTIADPGYMQGYDDCMQQGPASAR DLICAQYVAGYKVLPPLMDVNMEAAYTSSLLGSIAGVGWTA GLSSFAAIPFAQSIFYRLNGVGITQQVLSENQKLIANKFNQAL GAMQTGFTTTNEAFQKVQDAVNNNAQALSKLASELSNTFG AISASIGDIIQRLDVLEQDAQIDRLINGRLTTLNAFVAQQLVRS ESAALSAQLAKDKVNECVKAQSKRSGFCGQGTHIVSFVVNA PNGLYFMHVGYYPSNHIEVVSAYGLCDAANPTNCIAPVNGY FIKTNNTRIVDEWSYTGSSFYAPEPITSLNTKYVAPQVTYQNI STNLPPPLLGNSTGIDFQDELDEFFKNVSTSIPNFGSLTQINTTL LDLTYEMLSLQQVVKALNESYIDLKELGNYTYYNKWPDKIE EILSKIYHIENEIARIKKLIGEA | 26 |
| Isolate A1-Hasa_1_2013 (NCBI accession #AGN70962) | MIHSVFLLMFLLTPTESYVDVGPDSVKSACIEVDIQQTFFDKT WPRPIDVSKADGIIYPQGRTYSNITITYQGLFPYQGDHGDMY VYSAGHATGTTPQKLFVANYSQDVKQFANGFVVRIGAAANS TGTVIISPSTSATIRKIYPAFMLGSSVGNFSDGKMGRFFNHTL VLLPDGCGTLLRAFYCILEPRSGNHCPAGNSYTSFATYHTPA TDCSDGNYNRNASLNSFKEYFNLRNCTFMYTYNITEDEILEW FGITQTAQGVHLFSSRYVDLYGGNMFQFATLPVYDTIKYYSII PHSIRSIQSDRKAWAAFYVYKLQPLTFLLDFSVDGYIRRAIDC GFNDLSQLHCSYESFDVESGVYSVSSFEAKPSGSVVEQAEGV ECDFSPLLSGTPPQVYNFKRLVFTNCNYNLTKLLSLFSVNDFT CSQISPAAIASNCYSSLILDYFSYPLSMKSDLSVSSAGPISQFN YKQSFSNPTCLILATVPHNLTTITKPLKYSYINKCSRLLSDDRT EVPQLVNANQYSPCVSIVPSTVWEDGDYYRKQLSPLEGGGW LVASGSTVAMTEQLQMGFGITVQYGTDTNSVCPKLEFANDT KIASQLGNCVEYSLYGVSGRGVFQNCTAVGVRQQRFVYDA YQNLVGYYSDDGNYYCLRACVSVPVSVIYDKETKTHATLFG SVACEHISSTMSQYSRSTRSMLKRRDSTYGPLQTPVGCVLGL | 27 |

TABLE 11-continued

| Betacoronavirus Amino Acid Sequences | | |
|---|---|---|
| Strain | Amino Acid Sequence | SEQ ID NO: |
| | VNSSLFVEDCKLPLGQSLCALPDTPSTLTPRSVRSVPGEMRLA SIAFNHPIQVDQLNSSYFKLSIPTNFSFGVTQEYIQTTIQKVTV DCKQYVCNGFQKCEQLLREYGQFCSKINQALHGANLRQDDS VRNLFASVKSSQSSPIIPGFGGDFNLTLLEPVSISTGSRSARSAI EDLLFDKVTIADPGYMQGYDDCMQQGPASARDLICAQYVA GYKVLPPLMDVNMEAAYTSSLLGSIAGVGWTAGLSSFAAIPF AQSIFYRLNGVGITQQVLSENQKLIANKFNQALGAMQTGFTT TNEAFRKVQDAVNNNAQALSKLASELSNTFGAISASIGDIIQR LDVLEQDAQIDRLINGRLTTLNAFVAQQLVRSESAALSAQLA KDKVNECVKAQSKRSGFCGQGTHIVSFVVNAPNGLYFMHV GYYPSNHIEVVSAYGLCDAANPTNCIAPVNGYFIKTNNTRIV DEWSYTGSSFYAPEPITSLNTKYVAPHVTYQNISTNLPPPLLG NSTGIDFQDELDEFFKNVSTSIPNFGSLTQINTTLLDLTYEMLS LQQVVKALNESYIDLKELGNYTYYNKWPWYIWLGFIAGLVA LALCVFFILCCTGCGTNCMGKLKCNRCCDRYEEYDLEPHKV HVH | |
| Middle East respiratory syndrome coronavirus S protein UniProtKB-R9UQ53 | MIHSVFLLMFLLTPTESYVDVGPDSVKSACIEVDIQQTFFDKT WPRPIDVSKADGIIYPQGRTYSNITITYQGLFPYQGDHGDMY VYSAGHATGTTPQKLFVANYSQDVKQFANGFVVRIGAAANS TGTVIISPSTSATIRKIYPAFMLGSSVGNFSDGKMGRFFNHTL VLLPDGCGTLLRAFYCILEPRSGNHCPAGNSYTSFATYHTPA TDCSDGNYNRNASLNSFKEYFNLRNCTFMYTYNITEDEILEW FGITQTAQGVHLFSSRYVDLYGGNMFQFATLPVYDTIKYYSII PHSIRSIQSDRKAWAAFYVYKLQPLTFLLDFSVDGYIRRAIDC GFNDLSQLHCSYESFDVESGVYSVSSFEAKPSGSVVEQAEGV ECDFSPLLSGTPPQVYNFKRLVFTNCNYNLTKLLSLFSVNDFT CSQISPAAIASNCYSSLILDYFSYPLSMKSDLSVSSAGPISQFN YKQSFSNPTCLILATVPHNLTTITKPLKYSYINKCSRLLSDDRT EVPQLVNANQYSPCVSIVPSTVWEDGDYYRKQLSPLEGGGW LVASGSTVAMTEQLQMGFGITVQYGTDTNSVCPKLEFANDT KIASQLGNCVEYSLYGVSGRGVFQNCTAVGVRQQRFVYDA YQNLVGYYSDDGNYYCLRACVSVPVSVIYDKETKTHATLFG SVACEHISSTMSQYSRSTRSMLKRRDSTYGPLQTPVGCVLGL VNSSLFVEDCKLPLGQSLCALPDTPSTLTPRSVRSVPGEMRLA SIAFNHPIQVDQLNSSYFKLSIPTNFSFGVTQEYIQTTIQKVTV DCKQYVCNGFQKCEQLLREYGQFCSKINQALHGANLRQDDS VRNLFASVKSSQSSPIIPGFGGDFNLTLLEPVSISTGSRSARSAI EDLLFDKVTIADPGYMQGYDDCMQQGPASARDLICAQYVA GYKVLPPLMDVNMEAAYTSSLLGSIAGVGWTAGLSSFAAIPF AQSIFYRLNGVGITQQVLSENQKLIANKFNQALGAMQTGFTT TNEAFRKVQDAVNNNAQALSKLASELSNTFGAISASIGDIIQR LDVLEQDAQIDRLINGRLTTLNAFVAQQLVRSESAALSAQLA KDKVNECVKAQSKRSGFCGQGTHIVSFVVNAPNGLYFMHV GYYPSNHIEVVSAYGLCDAANPTNCIAPVNGYFIKTNNTRIV DEWSYTGSSFYAPEPITSLNTKYVAPHVTYQNISTNLPPPLLG NSTGIDFQDELDEFFKNVSTSIPNFGSLTQINTTLLDLTYEMLS LQQVVKALNESYIDLKELGNYTYYNKWPWYIWLGFIAGLVA LALCVFFILCCTGCGTNCMGKLKCNRCCDRYEEYDLEPHKV HVH | 28 |
| Human SARS coronavirus (SARS-CoV) (Severe acute respiratory syndrome coronavirus) Spike glycoprotein UniProtKB-P59594 | MFIFLLFLTLTSGSDLDRCTTFDDVQAPNYTQHTSSMRGVYY PDEIFRSDTLYLTQDLFLPFYSNVTGFHTINHTFGNPVIPFKDG IYFAATEKSNVVRGWVFGSTMNNKSQSVIIINNSTNVVIRAC NFELCDNPFFAVSKPMGTQTHTMIFDNAFNCTFEYISDAFSLD VSEKSGNFKHLREFVFKNKDGFLYVYKGYQPIDVVRDLPSGF NTLKPIFKLPLGINITNFRAILTAFSPAQDIWGTSAAAYFVGYL KPTTFMLKYDENGTITDAVDCSQNPLAELKCSVKSFEIDKGI YQTSNFRVVPSGDVVRFPNITNLCPFGEVFNATKFPSVYAWE RKKISNCVADYSVLYNSTFFSTFKCYGVSATKLNDLCFSNVY ADSFVVKGDDVRQIAPGQTGVIADYNYKLPDDFMGCVLAW NTRNIDATSTGNYNYKYRYLRHGKLRPFERDISNVPFSPDGK PCTPPALNCYWPLNDYGFYTTTGIGYQPYRVVVLSFELLNAP ATVCGPKLSTDLIKNQCVNFNFNGLTGTGVLTPSSKRFQPFQ QFGRDVSDFTDSVRDPKTSEILDISPCSFGGVSVITPGTNASSE VAVLYQDVNCTDVSTAIHADQLTPAWRIYSTGNNVFQTQAG CLIGAEHVDTSYECDIPIGAGICASYHTVSLLRSTSQKSIVAYT MSLGADSSIAYSNNTIAIPTNFSISITTEVMPVSMAKTSVDCN MYICGDSTECANLLLQYGSFCTQLNRALSGIAAEQDRNTREV FAQVKQMYKTPTLKYFGGFNFSQILPDPLKPTKRSFIEDLLFN KVTLADAGFMKQYGECLGDINARDLICAQKFNGLTVLPPLL TDDMIAAYTAALVSGTATAGWTFGAGAALQIPFAMQMAYR FNGIGVTQNVLYENQKQIANQFNKAISQIQESLTTTSTALGKL QDVVNQNAQALNTLVKQLSSNFGAISSVLNDILSRLDKVEAE VQIDRLITGRLQSLQTYVTQQLIRAAEIRASANLAATKMSEC | 29 |

TABLE 11-continued

| Betacoronavirus Amino Acid Sequences | | |
|---|---|---|
| Strain | Amino Acid Sequence | SEQ ID NO: |
| | VLGQSKRVDFCGKGYHLMSFPQAAPHGVVFLHVTYVPSQER NFTTAPAICHEGKAYFPREGVFVFNGTSWFITQRNFFSPQIITT DNTFVSGNCDVVIGIINNTVYDPLQPELDSFKEELDKYFKNH TSPDVDLGDISGINASVVNIQKEIDRLNEVAKNLNESLIDLQE LGKYEQYIKWPWYVWLGFIAGLIAIVMVTILLCCMTSCCSCL KGACSCGSCCKFDEDDSEPVLKGVKLHYT | |
| Human coronavirus OC43 (HCoV-OC43) Spike glycoprotein UniProtKB-P36334 | MFLILLISLPTAFAVIGDLKCTSDNINDKDTGPPPISTDTVDVT NGLGTYYVLDRVYLNTTLFLNGYYPTSGSTYRNMALKGSVL LSRLWFKPPFLSDFINGIFAKVKNTKVIKDRVMYSEFPAITIGS TFVNTSYSVVVQPRTINSTQDGDNKLQGLLEVSVCQYNMCE YPQTICHPNLGNHRKELWHLDTGVVSCLYKRNFTYDVNAD YLYFHFYQEGGTFYAYFTDTGVVTKFLFNVYLGMALSHYYV MPLTCNSKLTLEYWVTPLTSRQYLLAFNQDGIIFNAEDCMSD FMSEIKCKTQSIAPPTGVYELNGYTVQPIADVYRRKPNLPNC NIEAWLNDKSVPSPLNWERKTFSNCNFNMSSLMSFIQADSFT CNNIDAAKIYGMCFSSITIDKFAIPNGRKVDLQLGNLGYLQSF NYRIDTTATSCQLYYNLPAANVSVSRFNPSTWNKRFGFIEDS VFKPRPAGVLTNHDVVYAQHCFKAPKNFCPCKLNGSCVGSG PGKNNGIGTCPAGTNYLTCDNLCTPDPITFTGTYKCPQTKSL VGIGEHCSGLAVKSDYCGGNSCTCRPQAFLGWSADSCLQGD KCNIFANFILHDVNSGLTCSTDLQKANTDIILGVCVNYDLYGI LGQGIFVEVNATYYNSWQNLLYDSNGNLYGFRDYIINRTFMI RSCYSGRVSAAFHANSSEPALLFRNIKCNYVFNNSLTRQLQPI NYFDSYLGCVVNAYNSTAISVQTCDLTVGSGYCVDYSKNRR SRGAITTGYRFTNFEPFTVNSVNDSLEPVGGLYEIQIPSEFTIG NMVEFIQTSSPKVTIDCAAFVCGDYAACKSQLVEYGSFCDNI NAILTEVNELLDTTQLQVANSLMNGVTLSTKLKDGVNFNVD DINFSPVLGCLGSECSKASSRSAIEDLLFDKVKLSDVGFVEAY NNCTGGAEIRDLICVQSYKGIKVLPPLLSENQISGYTLAATSA SLFPPWTAAAGVPFYLNVQYRINGLGVTMDVLSQNQKLIAN AFNNALYAIQEGFDATNSALVKIQAVVNANAEALNNLLQQL SNRFGAISASLQEILSRLDALEAEAQIDRLINGRLTALNAYVS QQLSDSTLVKFSAAQAMEKVNECVKSQSSRINFCGNGNHIIS LVQNAPYGLYFIHFSYVPTKYVTARVSPGLCIAGDRGIAPKS GYFVNVNNTWMYTGSGYYYPEPITENNVVVMSTCAVNYTK APYVMLNTSIPNLPDFKEELDQWFKNQTSVAPDLSLDYINVT FLDLQVEMNRLQEAIKVLNQSYINLKDIGTYEYYVKWPWYV WLLICLAGVAMLVLLFFICCCTGCGTSCFKKCGGCCDDYTG YQELVIKTSHDD | 30 |
| Human coronavirus HKU1 (isolate N5) (HCoV-HKU1) Spike glycoprotein UniProtKB-Q0ZME7 | MFLIIFILPTTLAVIGDFNCTNSFINDYNKTIPRISEDVVDVSLG LGTYYVLNRVYLNTTLLFTGYFPKSGANFRDLALKGSIYLST LWYKPPFLSDFNNGIFSKVKNTKLYVNNTLYSEFSTIVIGSVF VNTSYTIVVQPHNGILEITACQYTMCEYPHTVCKSKGSIRNES WHIDSSEPLCLFKKNFTYNVSADWLYFHFYQERGVFYAYYA DVGMPTTFLFSLYLGTILSHYYVMPLTCNAISSNTDNETLEY WVTPLSRRQYLLNFDEHGVITNAVDCSSSFLSEIQCKTQSFAP NTGVYDLSGFTVKPVATVYRRIPNLPDCDIDNWLNNVSVPSP LNWERRIFSNCNFNLSTLLRLVHVDSFSCNNLDKSKIFGSCFN SITVDKFAIPNRRRDDLQLGSSGFLQSSNYKIDISSSSCQLYYS LPLVNVTINNFNPSSWNRRYGFGSFNLSSYDVVYSDHCFSVN SDFCPCADPSVVNSCAKSKPPSAICPAGTKYRHCDLDTTLYV KNWCRCSCLPDPISTYSPNTCPQKKVVVGIGEHCPGLGINEE KCGTQLNHSSCFCSPDAFLGWSFDSCISNNRCNIFSNFIFNGIN SGTTCSNDLLYSNTEISTGVCVNYDLYGITGQGIFKEVSAAY YNNWQNLLYDSNGNIIGFKDFLTNKTYTILPCYSGRVSAAFY QNSSSPALLYRNLKCSYVLNNISFISQPFYFDSYLGCVLNAVN LTSYSVSSCDLRMGSGFCIDYALPSSRRKRRGISSPYRFVTFEP FNVSFVNDSVETVGGLFEIQIPTNFTIAGHEEFIQTSSPKVTIDC SAFVCSNYAACHDLLSEYGTFCDNINSILNEVNDLLDITQLQV ANALMQGVTLSSNLNTNLHSDVDNIDFKSLLGCLGSQCGSSS RSLLEDLLFNKVKLSDVGFVEAYNNCTGGSEIRDLLCVQSFN GIKVLPPILSETQISGYTTAATVAAMFPPWSAAAGVPFSLNVQ YRINGLGVTMDVLNKNQKLIANAFNKALLSIQNGFTATNSAL AKIQSVVNANAQALNSLLQQLFNKFGAISSSLQEILSRLDNLE AQVQIDRLINGRLTALNAYVSQQLSDITLIKAGASRAIEKVNE CVKSQSPRINFCGNGNHILSLVQNAPYGLLFIHFSYKPTSFKT VLVSPGLCLSGDRGIAPKQGYFIKQNDSWMFTGSSYYYPEPIS DKNVVFMNSCSVNFTKAPFIYLNNSIPNLSDFEAELSLWFKN HTSIAPNLTFNSHINATFLDLYYEMNVIQESIKSLNSSFINLKEI GTYEMYVKWPWYIWLLIVILFIIFLMILFFICCCTGCGSACFSK CHNCCDEYGGHNDFVIKASHDD | 31 |

TABLE 11-continued

| Betacoronavirus Amino Acid Sequences | | |
|---|---|---|
| Strain | Amino Acid Sequence | SEQ ID NO: |
| Novel_SARS_S2 | MFIFLLFLTLTSGSDLDRALSGIAAEQDRNTREVFAQVKQMY<br>KTPTLKYFGGFNFSQILPDPLKPTKRSFIEDLLFNKVTLADAG<br>FMKQYGECLGDINARDLICAQKFNGLTVLPPLLTDDMIAAYT<br>AALVSGTATAGWTFGAGAALQIPFAMQMAYRFNGIGVTQN<br>VLYENQKQIANQFNKAISQIQESLTTTSTALGKLQDVVNQNA<br>QALNTLVKQLSSNFGAISSVLNDILSRLDKVEAEVQIDRLITG<br>RLQSLQTYVTQQLIRAAEIRASANLAATKMSECVLGQSKRV<br>DFCGKGYHLMSFPQAAPHGVVFLHVTYVPSQERNFTTAPAIC<br>HEGKAYFPREGVFVFNGTSWFITQRNFFSPQIITTDNTFVSGN<br>CDVVIGIINNTVYDPLQPELDSFKEELDKYFKNHTSPDVDLG<br>DISGINASVVNIQKEIDRLNEVAKNLNESLIDLQELGKYEQYI<br>KWPWYVWLGFIAGLIAIVMVTILLCCMTSCCSCLKGACSCGS<br>CCKFDEDDSEPVLKGVKLHYT | 32 |
| Novel_MERS_S2 | MIHSVFLLMFLLTPTESDCKLPLGQSLCALPDTPSTLTPRSVR<br>SVPGEMRLASIAFNHPIQVDQLNSSYFKLSIPTNFSFGVTQEYI<br>QTTIQKVTVDCKQYVCNGFQKCEQLLREYGQFCSKINQALH<br>GANLRQDDSVRNLFASVKSSQSSPIIPGFGGDFNLTLLEPVSIS<br>TGSRSARSAIEDLLFDKVTIADPGYMQGYDDCMQQGPASAR<br>DLICAQYVAGYKVLPPLMDVNMEAAYTSSLLGSIAGVGWTA<br>GLSSFAAIPFAQSIFYRLNGVGITQQVLSENQKLIANKFNQAL<br>GAMQTGFTTTNEAFQKVQDAVNNNAQALSKLASELSNTFG<br>AISASIGDIIQRLDVLEQDAQIDRLINGRLTTLNAFVAQQLVRS<br>ESAALSAQLAKDKVNECVKAQSKRSGFCGQGTHIVSFVVNA<br>PNGLYFMHVGYYPSNHIEVVSAYGLCDAANPTNCIAPVNGY<br>FIKTNNTRIVDEWSYTGSSFYAPEPITSLNTKYVAPQVTYQNI<br>STNLPPPLLGNSTGIDFQDELDEFFKNVSTSIPNFGSLTQINTTL<br>LDLTYEMLSLQQVVKALNESYIDLKELGNYTYYNKWP | 33 |
| Novel_Trimeric_ SARS_S2 | MFIFLLFLTLTSGSDLDRALSGIAAEQDRNTREVFAQVKQMY<br>KTPTLKYFGGFNFSQILPDPLKPTKRSFIEDLLFNKVTLADAG<br>FMKQYGECLGDINARDLICAQKFNGLTVLPPLLTDDMIAAYT<br>AALVSGTATAGWTFGAGAALQIPFAMQMAYRFNGIGVTQN<br>VLYENQKQIANQFNKAISQIQESLTTTSTALGKLQDVVNQNA<br>QALNTLVKQLSSNFGAISSVLNDILSRLDKVEAEVQIDRLITG<br>RLQSLQTYVTQQLIRAAEIRASANLAATKMSECVLGQSKRV<br>DFCGKGYHLMSFPQAAPHGVVFLHVTYVPSQERNFTTAPAIC<br>HEGKAYFPREGVFVFNGTSWFITQRNFFSPQIITTDNTFVSGN<br>CDVVIGIINNTVYDPLQPELDSFKEELDKYFKNHTSPDVDLG<br>DISGINASVVNIQKEIDRLNEVAKNLNESLIDLQELGKYEQYI<br>KWPWYVWLGFIAGLIAIVMVTILLCCMTSCCSCLKGACSCGS<br>CCKFDEDDSEPVLKGVKLHYT | 34 |

TABLE 12

| Full-length Spike Glycoprotein Amino Acid Sequences (*Homo sapiens* strains) | | | | |
|---|---|---|---|---|
| GenBank Accession | Country | Collection Date | Release Date | Virus Name |
| AFY13307 | United Kingdom | 2012 Sep. 11 | 2012 Dec. 5 | Betacoronavirus England 1, complete genome |
| AFS88936 | | 2012 Jun. 13 | 2012 Sep. 27 | Human betacoronavirus 2c EMC/2012, complete genome |
| AGG22542 | United Kingdom | 2012 Sep. 19 | 2013 Feb. 27 | Human betacoronavirus 2c England-Qatar/2012, complete genome |
| AHY21469 | Jordan | 2012 | 2014 May 4 | Human betacoronavirus 2c Jordan-N3/2012 isolate MG167, complete genome |
| AGH58717 | Jordan | 2012 April | 2013 Mar. 25 | Human betacoronavirus 2c Jordan-N3/2012, complete genome |
| AGV08444 | Saudi Arabia | 2013 May 7 | 2013 Sep. 17 | Middle East respiratory syndrome coronavirus isolate Al-Hasa_12_2013, complete genome |
| AGV08546 | Saudi Arabia | 2013 May 11 | 2013 Sep. 17 | Middle East respiratory syndrome coronavirus isolate Al-Hasa_15_2013, complete genome |
| AGV08535 | Saudi Arabia | 2013 May 12 | 2013 Sep. 17 | Middle East respiratory syndrome coronavirus isolate Al-Hasa_16_2013, complete genome |

TABLE 12-continued

| Full-length Spike Glycoprotein Amino Acid Sequences (*Homo sapiens* strains) | | | | |
|---|---|---|---|---|
| GenBank Accession | Country | Collection Date | Release Date | Virus Name |
| AGV08558 | Saudi Arabia | 2013 May 15 | 2013 Sep. 17 | Middle East respiratory syndrome coronavirus isolate Al-Hasa_17_2013, complete genome |
| AGV08573 | Saudi Arabia | 2013 May 23 | 2013 Sep. 17 | Middle East respiratory syndrome coronavirus isolate Al-Hasa_18_2013, complete genome |
| AGV08480 | Saudi Arabia | 2013 May 23 | 2013 Sep. 17 | Middle East respiratory syndrome coronavirus isolate Al-Hasa_19_2013, complete genome |
| AGN70962 | Saudi Arabia | 2013 May 9 | 2013 Jun. 10 | Middle East respiratory syndrome coronavirus isolate Al-Hasa_1_2013, complete genome |
| AGV08492 | Saudi Arabia | 2013 May 30 | 2013 Sep. 17 | Middle East respiratory syndrome coronavirus isolate Al-Hasa_21_2013, complete genome |
| AHI48517 | Saudi Arabia | 2013 May 2 | 2014 Feb. 6 | Middle East respiratory syndrome coronavirus isolate Al-Hasa_25_2013, complete genome |
| AGN70951 | Saudi Arabia | 2013 Apr. 21 | 2013 Jun. 10 | Middle East respiratory syndrome coronavirus isolate Al-Hasa_2_2013, complete genome |
| AGN70973 | Saudi Arabia | 2013 Apr. 22 | 2013 Jun. 10 | Middle East respiratory syndrome coronavirus isolate Al-Hasa_3_2013, complete genome |
| AGN70929 | Saudi Arabia | 2013 May 1 | 2013 Jun. 10 | Middle East respiratory syndrome coronavirus isolate Al-Hasa_4_2013, complete genome |
| AGV08408 | Saudi Arabia | 2012 Jun. 19 | 2013 Sep. 17 | Middle East respiratory syndrome coronavirus isolate Bisha_1_2012, complete genome |
| AGV08467 | Saudi Arabia | 2013 May 13 | 2013 Sep. 17 | Middle East respiratory syndrome coronavirus isolate Buraidah_1_2013, complete genome |
| AID50418 | United Kingdom | 2013 Feb. 10 | 2014 Jun. 18 | Middle East respiratory syndrome coronavirus isolate England/2/2013, complete genome |
| AJD81451 | United Kingdom | 2013 Feb. 10 | 2015 Jan. 18 | Middle East respiratory syndrome coronavirus isolate England/3/2013, complete genome |
| AJD81440 | United Kingdom | 2013 Feb. 13 | 2015 Jan. 18 | Middle East respiratory syndrome coronavirus isolate England/4/2013, complete genome |
| AHB33326 | France | 2013 May 7 | 2013 Dec. 7 | Middle East respiratory syndrome coronavirus isolate FRA/UAE, complete genome |
| AIZ48760 | USA | 2014 June | 2014 Dec. 14 | Middle East respiratory syndrome coronavirus isolate Florida/USA-2_Saudi Arabia_2014, complete genome |
| AGV08455 | Saudi Arabia | 2013 Jun. 4 | 2013 Sep. 17 | Middle East respiratory syndrome coronavirus isolate Hafr-Al-Batin_1_2013, complete genome |
| AHI48561 | Saudi Arabia | 2013 Aug. 5 | 2014 Feb. 6 | Middle East respiratory syndrome coronavirus isolate Hafr-Al-Batin_2_2013, complete genome |
| AHI48539 | Saudi Arabia | 2013 Aug. 28 | 2014 Feb. 6 | Middle East respiratory syndrome coronavirus isolate Hafr-Al-Batin_6_2013, complete genome |
| AIZ74417 | France | 2013 Apr. 26 | 2015 Mar. 10 | Middle East respiratory syndrome coronavirus isolate Hu-France (UAE) - FRA1_1627-2013_BAL_Sanger, complete genome |
| AIZ74433 | France | 2013 May 7 | 2015 Mar. 10 | Middle East respiratory syndrome coronavirus isolate Hu-France - FRA2_130569-2013_IS_HTS, complete genome |
| AIZ74439 | France | 2013 May 7 | 2015 Mar. 10 | Middle East respiratory syndrome coronavirus isolate Hu-France - FRA2_130569-2013_InSpu_Sanger, complete genome |
| AIZ74450 | France | 2013 May 7 | 2015 Mar. 10 | Middle East respiratory syndrome coronavirus isolate Hu-France - FRA2_130569-2013_Isolate_Sanger, complete genome |

TABLE 12-continued

Full-length Spike Glycoprotein Amino Acid Sequences (*Homo sapiens* strains)

| GenBank Accession | Country | Collection Date | Release Date | Virus Name |
|---|---|---|---|---|
| AKK52602 | Saudi Arabia | 2015 Feb. 10 | 2015 Jun. 8 | Middle East respiratory syndrome coronavirus isolate Hu/Riyadh_KSA_2959_2015, complete genome |
| AKK52612 | Saudi Arabia | 2015 Mar. 1 | 2015 Jun. 8 | Middle East respiratory syndrome coronavirus isolate Hu/Riyadh_KSA_4050_2015, complete genome |
| AHN10812 | Saudi Arabia | 2013 Nov. 6 | 2014 Mar. 24 | Middle East respiratory syndrome coronavirus isolate Jeddah_1_2013, complete genome |
| AID55071 | Saudi Arabia | 2014 Apr. 21 | 2014 Nov. 12 | Middle East respiratory syndrome coronavirus isolate Jeddah_C10306/KSA/2014-04-20, complete genome |
| AID55066 | Saudi Arabia | 2014 | 2014 Nov. 12 | Middle East respiratory syndrome coronavirus isolate Jeddah_C7149/KSA/2014-04-05, complete genome |
| AID55067 | Saudi Arabia | 2014 | 2014 Nov. 12 | Middle East respiratory syndrome coronavirus isolate Jeddah_C7569/KSA/2014-04-03, complete genome |
| AID55068 | Saudi Arabia | 2014 Apr. 7 | 2014 Nov. 12 | Middle East respiratory syndrome coronavirus isolate Jeddah_C7770/KSA/2014-04-07, complete genome |
| AID55069 | Saudi Arabia | 2014 Apr. 12 | 2014 Nov. 12 | Middle East respiratory syndrome coronavirus isolate Jeddah_C8826/KSA/2014-04-12, complete genome |
| AID55070 | Saudi Arabia | 2014 Apr. 14 | 2014 Nov. 12 | Middle East respiratory syndrome coronavirus isolate Jeddah_C9055/KSA/2014-04-14, complete genome |
| AHE78108 | Saudi Arabia | 2013 Nov. 5 | 2014 May 1 | Middle East respiratory syndrome coronavirus isolate MERS-CoV-Jeddah-human-1, complete genome |
| AKL59401 | South Korea | 2015 May 20 | 2015 Jun. 9 | Middle East respiratory syndrome coronavirus isolate MERS-CoV/KOR/KNIH/002_05_2015, complete genome |
| ALD51904 | Thailand | 2015 Jun. 17 | 2015 Jul. 7 | Middle East respiratory syndrome coronavirus isolate MERS-CoV/THA/CU/17_06_2015, complete genome |
| AID55072 | Saudi Arabia | 2014 Apr. 15 | 2014 Nov. 12 | Middle East respiratory syndrome coronavirus isolate Makkah_C9355/KSA/Makkah/2014-04-15, complete genome |
| AHC74088 | Qatar | 2013 Oct. 13 | 2013 Dec. 23 | Middle East respiratory syndrome coronavirus isolate Qatar3, complete genome |
| AHC74098 | Qatar | 2013 Oct. 17 | 2013 Dec. 23 | Middle East respiratory syndrome coronavirus isolate Qatar4, complete genome |
| AHI48572 | Saudi Arabia | 2013 Aug. 15 | 2014 Feb. 6 | Middle East respiratory syndrome coronavirus isolate Riyadh_14_2013, complete genome |
| AGV08379 | Saudi Arabia | 2012 Oct. 23 | 2013 Sep. 17 | Middle East respiratory syndrome coronavirus isolate Riyadh_1_2012, complete genome |
| AID55073 | Saudi Arabia | 2014 Apr. 22 | 2014 Nov. 12 | Middle East respiratory syndrome coronavirus isolate Riyadh_2014KSA_683/KSA/2014, complete genome |
| AGV08584 | Saudi Arabia | 2012 Oct. 30 | 2013 Sep. 17 | Middle East respiratory syndrome coronavirus isolate Riyadh_2_2012, complete genome |
| AGV08390 | Saudi Arabia | 2013 Feb. 5 | 2013 Sep. 17 | Middle East respiratory syndrome coronavirus isolate Riyadh_3_2013, complete genome |
| AHI48605 | Saudi Arabia | 2013 Mar. 1 | 2014 Feb. 6 | Middle East respiratory syndrome coronavirus isolate Riyadh_4_2013, complete genome |

TABLE 12-continued

Full-length Spike Glycoprotein Amino Acid Sequences (*Homo sapiens* strains)

| GenBank Accession | Country | Collection Date | Release Date | Virus Name |
|---|---|---|---|---|
| AHI48583 | Saudi Arabia | 2013 Jul. 2 | 2014 Feb. 6 | Middle East respiratory syndrome coronavirus isolate Riyadh_5_2013, complete genome |
| AHI48528 | Saudi Arabia | 2013 Jul. 17 | 2014 Feb. 6 | Middle East respiratory syndrome coronavirus isolate Riyadh_9_2013, complete genome |
| AHI48594 | Saudi Arabia | 2013 Jun. 12 | 2014 Feb. 6 | Middle East respiratory syndrome coronavirus isolate Taif_1_2013, complete genome |
| AHI48550 | Saudi Arabia | 2013 Jun. 12 | 2014 Feb. 6 | Middle East respiratory syndrome coronavirus isolate Wadi-Ad-Dawasir_1_2013, complete genome |
| AIY60558 | United Arab Emirates | 2014 Mar. 7 | 2014 Dec. 6 | Middle East respiratory syndrome coronavirus strain Abu Dhabi/Gayathi_UAE_2_2014, complete genome |
| AIY60538 | United Arab Emirates | 2014 Apr. 10 | 2014 Dec. 6 | Middle East respiratory syndrome coronavirus strain Abu Dhabi_UAE_16_2014, complete genome |
| AIY60528 | United Arab Emirates | 2014 Apr. 10 | 2014 Dec. 6 | Middle East respiratory syndrome coronavirus strain Abu Dhabi_UAE_18_2014, complete genome |
| AIY60588 | United Arab Emirates | 2014 Apr. 13 | 2014 Dec. 6 | Middle East respiratory syndrome coronavirus strain Abu Dhabi_UAE_26_2014, complete genome |
| AIY60548 | United Arab Emirates | 2014 Apr. 19 | 2014 Dec. 6 | Middle East respiratory syndrome coronavirus strain Abu Dhabi_UAE_30_2014, complete genome |
| AIY60568 | United Arab Emirates | 2014 Apr. 17 | 2014 Dec. 6 | Middle East respiratory syndrome coronavirus strain Abu Dhabi_UAE_33_2014, complete genome |
| AIY60518 | United Arab Emirates | 2014 Apr. 7 | 2014 Dec. 6 | Middle East respiratory syndrome coronavirus strain Abu Dhabi_UAE_8_2014, complete genome |
| AIY60578 | United Arab Emirates | 2013 Nov. 15 | 2014 Dec. 6 | Middle East respiratory syndrome coronavirus strain Abu Dhabi_UAE_9_2013, complete genome |
| AKJ80137 | China | 2015 May 27 | 2015 Jun. 5 | Middle East respiratory syndrome coronavirus strain ChinaGD01, complete genome |
| AHZ64057 | USA | 2014 May 10 | 2014 May 14 | Middle East respiratory syndrome coronavirus strain Florida/USA-2_Saudi Arabia_2014, complete genome |
| AKM76229 | Oman | 2013 Oct. 28 | 2015 Jun. 23 | Middle East respiratory syndrome coronavirus strain Hu/Oman_2285_2013, complete genome |
| AKM76239 | Oman | 2013 Dec. 28 | 2015 Jun. 23 | Middle East respiratory syndrome coronavirus strain Hu/Oman_2874_2013, complete genome |
| AKI29284 | Saudi Arabia | 2015 Jan. 6 | 2015 May 27 | Middle East respiratory syndrome coronavirus strain Hu/Riyadh-KSA-2049/2015, complete genome |
| AKI29265 | Saudi Arabia | 2015 Jan. 21 | 2015 May 27 | Middle East respiratory syndrome coronavirus strain Hu/Riyadh-KSA-2343/2015, complete genome |
| AKI29255 | Saudi Arabia | 2015 Jan. 21 | 2015 May 27 | Middle East respiratory syndrome coronavirus strain Hu/Riyadh-KSA-2345/2015, complete genome |
| AKI29275 | Saudi Arabia | 2015 Jan. 26 | 2015 May 27 | Middle East respiratory syndrome coronavirus strain Hu/Riyadh-KSA-2466/2015, complete genome |
| AKK52582 | Saudi Arabia | 2015 Feb. 10 | 2015 Jun. 8 | Middle East respiratory syndrome coronavirus strain Hu/Riyadh_KSA_2959_2015, complete genome |

TABLE 12-continued

| Full-length Spike Glycoprotein Amino Acid Sequences (*Homo sapiens* strains) | | | | |
|---|---|---|---|---|
| GenBank Accession | Country | Collection Date | Release Date | Virus Name |
| AKK52592 | Saudi Arabia | 2015 Mar. 1 | 2015 Jun. 8 | Middle East respiratory syndrome coronavirus strain Hu/Riyadh_KSA_4050_2015, complete genome |
| AHZ58501 | USA | 2014 Apr. 30 | 2014 May 13 | Middle East respiratory syndrome coronavirus strain Indiana/USA-1_Saudi Arabia_2014, complete genome |
| AGN52936 | United Arab Emirates | 2013 | 2013 Jun. 10 | Middle East respiratory syndrome coronavirus, complete genome |

TABLE 13

| MeV Nucleic Acid Sequences | | |
|---|---|---|
| Description | Sequence | SEQ ID NO: |
| GC_F_MEASLES_ B3.1 Sequence, NT (5' UTR, ORF, 3' UTR) Sequence Length: 1864 | TCAAGCTTTTGGACCCTCGTACAGAAGCTAATACGACT CACTATAGGGAAATAAGAGAGAAAAGAAGAGTAAGAA GAAATATAAGAGCCACCATGGGTCTCAAGGTGAACGTC TCTGCCGTATTCATGGCAGTACTGTTAACTCTCCAAACA CCCGCCGGTCAAATTCATTGGGGCAATCTCTCTAAGAT AGGGGTAGTAGGAATAGGAAGTGCAAGCTACAAAGTT ATGACTCGTTCCAGCCATCAATCATTAGTCATAAAATT AATGCCCAATATAACTCTCCTCAATAACTGCACGAGGG TAGAGATTGCAGAATACAGGAGACTACTAAGAACAGTT TTGGAACCAATTAGGGATGCACTTAATGCAATGACCCA GAACATAAGGCCGGTTCAGAGCGTAGCTTCAAGTAGGA GACACAAGAGATTTGCGGGAGTAGTCCTGGCAGGTGCG GCCCTAGGTGTTGCCACAGCTGCTCAGATAACAGCCGG CATTGCACTTCACCGGTCCATGCTGAACTCTCAGGCCAT CGACAATCTGAGAGCGAGCCTGGAAACTACTAATCAGG CAATTGAGGCAATCAGACAAGCAGGGCAGGAGATGAT ATTGGCTGTTCAGGGTGTCCAAGACTACATCAATAATG AGCTGATACCGTCTATGAACCAGCTATCTTGTGATCTA ATCGGTCAGAAGCTCGGGCTCAAATTGCTTAGATACTA TACAGAAATCCTGTCATTATTTGGCCCCAGCCTACGGG ACCCCATATCTGCGGAGATATCTATCCAGGCTTTGAGTT ATGCACTTGGAGGAGATATCAATAAGGTGTTAGAAAAG CTCGGATACAGTGGAGGCGATTTACTAGGCATCTTAGA GAGCAGAGGAATAAAGGCTCGGATAACTCACGTCGAC ACAGAGTCCTACTTCATAGTCCTCAGTATAGCCTATCCG ACGCTGTCCGAGATTAAGGGGGTGATTGTCCACCGGCT AGAGGGGGTCTCGTACAACATAGGCTCTCAAGAGTGGT ATACCACTGTGCCCAAGTATGTTGCAACCCAAGGGTAC CTTATCTCGAATTTTGATGAGTCATCATGTACTTTCATG CCAGAGGGGACTGTGTGCAGCCAAAATGCCTTGTACCC GATGAGTCCTCTGCTCCAAGAATGCCTCCGGGGGTCCA CCAAGTCCTGTGCTCGTACACTCGTATCCGGGTCTTTTG GGAACCGGTTCATTTTATCACAAGGGAACCTAATAGCC AATTGTGCATCAATTCTTTGTAAGTGTTACACAACAGGT ACGATTATTAATCAAGACCCTGACAAGATCCTAACATA CATTGCTGCCGATCGCTGCCCGGTAGTCGAGGTGAACG GCGTGACCATCCAAGTCGGGAGCAGGAGGTATCCAGA CGCTGTGTACTTGCACAGAATTGACCTCGGTCCTCCCAT ATCATTGGAGAGGTTGGACGTAGGGACAAATCTGGGG AATGCAATTGCCAAATTGGAGGATGCCAAGGAATTGTT GGAATCATCGGACCAGATATTGAGAAGTATGAAAGGTT TATCGAGCACTAGCATAGTCTACATCCTGATTGCAGTG TGTCTTGGAGGGTTGATAGGGATCCCCACTTTAATATGT TGCTGCAGGGGGCGTTGTAACAAAAAGGGAGAACAAG TTGGTATGTCAAGACCAGGCCTAAAGCCTGACCTTACA GGAACATCAAAATCCTATGTAAGATCGCTTTGATGATA ATAGGCTGGAGCCTCGGTGGCCAAGCTTCTTGCCCCTT GGGCCTCCCCCCAGCCCCTCCTCCCCTTCCTGCACCCGT ACCCCCGTGGTCTTTGAATAAAGTCTGAGTGGGCGGC | 35 |
| GC_F_MEASLES_ B3.1 ORF Sequence, NT | ATGGGTCTCAAGGTGAACGTCTCTGCCGTATTCATGGC AGTACTGTTAACTCTCCAAACACCCGCCGGTCAAATTC ATTGGGGCAATCTCTCTAAGATAGGGGTAGTAGGAATA | 36 |

TABLE 13-continued

| MeV Nucleic Acid Sequences | | |
|---|---|---|
| Description | Sequence | SEQ ID NO: |
| | GGAAGTGCAAGCTACAAAGTTATGACTCGTTCCAGCCA TCAATCATTAGTCATAAAATTAATGCCCAATATAACTCT CCTCAATAACTGCACGAGGGTAGAGATTGCAGAATACA GGAGACTACTAAGAACAGTTTTGGAACCAATTAGGGAT GCACTTAATGCAATGACCCAGAACATAAGGCCGGTTCA GAGCGTAGCTTCAAGTAGGAGACACAAGAGATTTGCG GGAGTAGTCCTGGCAGGTGCGGCCCTAGGTGTTGCCAC AGCTGCTCAGATAACAGCCGGCATTGCACTTCACCGGT CCATGCTGAACTCTCAGGCCATCGACAATCTGAGAGCG AGCCTGGAAACTACTAATCAGGCAATTGAGGCAATCAG ACAAGCAGGGCAGGAGATGATATTGGCTGTTCAGGGTG TCCAAGACTACATCAATAATGAGCTGATACCGTCTATG AACCAGCTATCTTGTGATCTAATCGGTCAGAAGCTCGG GCTCAAATTGCTTAGATACTATACAGAAATCCTGTCATT ATTTGGCCCCAGCCTACGGGACCCCATATCTGCGGAGA TATCTATCCAGGCTTTGAGTTATGCACTTGGAGGAGAT ATCAATAAGGTGTTAGAAAAGCTCGGATACAGTGGAG GCGATTTACTAGGCATCTTAGAGAGCAGAGGAATAAAG GCTCGGATAACTCACGTCGACACAGAGTCCTACTTCAT AGTCCTCAGTATAGCCTATCCGACGCTGTCCGAGATTA AGGGGGTGATTGTCCACCGGCTAGAGGGGGTCTCGTAC AACATAGGCTCTCAAGAGTGGTATACCACTGTGCCCAA GTATGTTGCAACCCAAGGGTACCTTATCTCGAATTTTGA TGAGTCATCATGTACTTTCATGCCAGAGGGGACTGTGT GCAGCCAAAATGCCTTGTACCCGATGAGTCCTCTGCTC CAAGAATGCCTCCGGGGGTCCACCAAGTCCTGTGCTCG TACACTCGTATCCGGGTCTTTTGGGAACCGGTTCATTTT ATCACAAGGGAACCTAATAGCCAATTGTGCATCAATTC TTTGTAAGTGTTACACAACAGGTACGATTATTAATCAA GACCCTGACAAGATCCTAACATACATTGCTGCCGATCG CTGCCCGGTAGTCGAGGTGAACGGCGTGACCATCCAAG TCGGGAGCAGGAGGTATCCAGACGCTGTGTACTTGCAC AGAATTGACCTCGGTCCTCCCATATCATTGGAGAGGTT GGACGTAGGGACAAATCTGGGGAATGCAATTGCCAAA TTGGAGGATGCCAAGGAATTGTTGGAATCATCGGACCA GATATTGAGAAGTATGAAAGGTTTATCGAGCACTAGCA TAGTCTACATCCTGATTGCAGTGTGTCTTGGAGGGTTGA TAGGGATCCCCACTTTAATATGTTGCTGCAGGGGGCGT TGTAACAAAAAGGGAGAACAAGTTGGTATGTCAAGAC CAGGCCTAAAGCCTGACCTTACAGGAACATCAAAATCC TATGTAAGATCGCTTTGA | |
| GC_F_MEASLES_ B3.1 mRNA Sequence (assumes T100 tail) mRNA Sequence Length: 1925 | G*GGGAAATAAGAGAGAAAAGAAGAGTAAGAAGAAAT ATAAGAGCCACCATGGGTCTCAAGGTGAACGTCTCTGC CGTATTCATGGCAGTACTGTTAACTCTCCAAACACCCG CCGGTCAAATTCATTGGGGCAATCTCTCTAAGATAGGG GTAGTAGGAATAGGAAGTGCAAGCTACAAAGTTATGA CTCGTTCCAGCCATCAATCATTAGTCATAAAATTAATGC CCAATATAACTCTCCTCAATAACTGCACGAGGGTAGAG ATTGCAGAATACAGGAGACTACTAAGAACAGTTTTGGA ACCAATTAGGGATGCACTTAATGCAATGACCCAGAACA TAAGGCCGGTTCAGAGCGTAGCTTCAAGTAGGAGACAC AAGAGATTTGCGGGAGTAGTCCTGGCAGGTGCGGCCCT AGGTGTTGCCACAGCTGCTCAGATAACAGCCGGCATTG CACTTCACCGGTCCATGCTGAACTCTCAGGCCATCGAC AATCTGAGAGCGAGCCTGGAAACTACTAATCAGGCAAT TGAGGCAATCAGACAAGCAGGGCAGGAGATGATATTG GCTGTTCAGGGTGTCCAAGACTACATCAATAATGAGCT GATACCGTCTATGAACCAGCTATCTTGTGATCTAATCG GTCAGAAGCTCGGGCTCAAATTGCTTAGATACTATACA GAAATCCTGTCATTATTTGGCCCCAGCCTACGGGACCC CATATCTGCGGAGATATCTATCCAGGCTTTGAGTTATGC ACTTGGAGGAGATATCAATAAGGTGTTAGAAAAGCTCG GATACAGTGGAGGCGATTTACTAGGCATCTTAGAGAGC AGAGGAATAAAGGCTCGGATAACTCACGTCGACACAG AGTCCTACTTCATAGTCCTCAGTATAGCCTATCCGACGC TGTCCGAGATTAAGGGGGTGATTGTCCACCGGCTAGAG GGGGTCTCGTACAACATAGGCTCTCAAGAGTGGTATAC CACTGTGCCCAAGTATGTTGCAACCCAAGGGTACCTTA TCTCGAATTTTGATGAGTCATCATGTACTTTCATGCCAG AGGGGACTGTGTGCAGCCAAAATGCCTTGTACCCGATG AGTCCTCTGCTCCAAGAATGCCTCCGGGGGTCCACCAA GTCCTGTGCTCGTACACTCGTATCCGGGTCTTTTGGGAA CCGGTTCATTTTATCACAAGGGAACCTAATAGCCAATT GTGCATCAATTCTTTGTAAGTGTTACACAACAGGTACG | 37 |

TABLE 13-continued

MeV Nucleic Acid Sequences

| Description | Sequence | SEQ ID NO: |
|---|---|---|
| | ATTATTAATCAAGACCCTGACAAGATCCTAACATACAT TGCTGCCGATCGCTGCCCGGTAGTCGAGGTGAACGGCG TGACCATCCAAGTCGGGAGCAGGAGGTATCCAGACGCT GTGTACTTGCACAGAATTGACCTCGGTCCTCCCATATCA TTGGAGAGGTTGGACGTAGGGACAAATCTGGGGAATG CAATTGCCAAATTGGAGGATGCCAAGGAATTGTTGGAA TCATCGGACCAGATATTGAGAAGTATGAAAGGTTTATC GAGCACTAGCATAGTCTACATCCTGATTGCAGTGTGTC TTGGAGGGTTGATAGGGATCCCCACTTTAATATGTTGCT GCAGGGGGCGTTGTAACAAAAAGGGAGAACAAGTTGG TATGTCAAGACCAGGCCTAAAGCCTGACCTTACAGGAA CATCAAAATCCTATGTAAGATCGCTTTGATGATAATAG GCTGGAGCCTCGGTGGCCAAGCTTCTTGCCCCTTGGGC CTCCCCCCAGCCCCTCCTCCCCTTCCTGCACCCGTACCC CCGTGGTCTTTGAATAAAGTCTGAGTGGGCGGCAAAAA AAAAAAAAAAAAAAAAAAAAAAAAAAAAAAAAAAAA AAAAAAAAAAAAAAAAAAAAAAAAAAAAAAAAAAAA AAAAAAAAAAAAAAAAAAAAAAAATCTAG | |
| GC_F_MEASLES_ D8 Sequence, NT (5' UTR, ORF, 3' UTR) Sequence Length: 1864 | TCAAGCTTTTGGACCCTCGTACAGAAGCTAATACGACT CACTATAGGGAAATAAGAGAGAAAAGAAGAGTAAGAA GAAATATAAGAGCCACCATGGGTCTCAAGGTGAACGTC TCTGTCATATTCATGGCAGTACTGTTAACTCTTCAAACA CCCACCGGTCAAATCCATTGGGGCAATCTCTCTAAGAT AGGGGTGGTAGGGGTAGGAAGTGCAAGCTACAAAGTT ATGACTCGTTCCAGCCATCAATCATTAGTCATAAAGTT AATGCCCAATATAACTCTCCTCAACAATTGCACGAGGG TAGGGATTGCAGAATACAGGAGACTACTGAGAACAGTT CTGGAACCAATTAGAGATGCACTTAATGCAATGACCCA GAATATAAGACCGGTTCAGAGTGTAGCTTCAAGTAGGA GACACAAGAGATTTGCGGGAGTTGTCCTGGCAGGTGCG GCCCTAGGCGTTGCCACAGCTGCTCAAATAACAGCCGG TATTGCACTTCACCAGTCCATGCTGAACTCTCAAGCCAT CGACAATCTGAGAGCGAGCCTAGAAACTACTAATCAGG CAATTGAGGCAATCAGACAAGCAGGGCAGGAGATGAT ATTGGCTGTTCAGGGTGTCCAAGACTACATCAATAATG AGCTGATACCGTCTATGAATCAACTATCTTGTGATTTAA TCGGCCAGAAGCTAGGGCTCAAATTGCTCAGATACTAT ACAGAAATCCTGTCATTATTTGGCCCCAGCTTACGGGA CCCCATATCTGCGGAGATATCTATCCAGGCTTTGAGCT ATGCGCTTGGAGGAGATATCAATAAGGTGTTGGAAAAG CTCGGATACAGTGGAGGTGATCTACTGGGCATCTTAGA GAGCAGAGGAATAAAGGCCCGGATAACTCACGTCGAC ACAGAGTCCTACTTCATTGTACTCAGTATAGCCTATCCG ACGCTATCCGAGATTAAGGGGGTGATTGTCCACCGGCT AGAGGGGGTCTCGTACAACATAGGCTCTCAAGAGTGGT ATACCACTGTGCCCAAGTATGTTGCAACCCAAGGGTAC CTTATCTCGAATTTTGATGAGTCATCATGCACTTTCATG CCAGAGGGGACTGTGTGCAGCCAGAATGCCTTGTACCC GATGAGTCCTCTGCTCCAAGAATGCCTCCGGGGGTCCA CTAAGTCCTGTGCTCGTACACTCGTATCCGGGTCTTTCG GGAACCGGTTCATTTTATCACAGGGGAACCTAATAGCC AATTGTGCATCAATCCTTTGCAAGTGTTACACAACAGG AACAATCATTAATCAAGACCCTGACAAGATCCTAACAT ACATTGCTGCCGATCACTGCCCGGTGGTCGAGGTGAAT GGCGTGACCATCCAAGTCGGGAGCAGGAGGTATCCGG ACGCTGTGTACTTGCACAGGATTGACCTCGGTCCTCCC ATATCTTTGGAGAGGTTGGACGTAGGGACAAATCTGGG GAATGCAATTGCTAAGTTGGAGGATGCCAAGGAATTGT TGGAGTCATCGGACCAGATATTGAGGAGTATGAAAGGT TTATCGAGCACTAGTATAGTTTACATCCTGATTGCAGTG TGTCTTGGAGGATTGATAGGGATCCCCGCTTTAATATGT TGCTGCAGGGGGCGTTGTAACAAGAAGGGAGAACAAG TTGGTATGTCAAGACCAGGCCTAAAGCCTGATCTTACA GGAACATCAAAATCCTATGTAAGGTCACTCTGATGATA ATAGGCTGGAGCCTCGGTGGCCAAGCTTCTTGCCCCTT GGGCCTCCCCCCAGCCCCTCCTCCCCTTCCTGCACCCGT ACCCCCGTGGTCTTTGAATAAAGTCTGAGTGGGCGGC | 38 |
| GC_F_MEASLES_ D8 ORF Sequence, NT | ATGGGTCTCAAGGTGAACGTCTCTGTCATATTCATGGC AGTACTGTTAACTCTTCAAACACCCACCGGTCAAATCC ATTGGGGCAATCTCTCTAAGATAGGGGTGGTAGGGGTA GGAAGTGCAAGCTACAAAGTTATGACTCGTTCCAGCCA TCAATCATTAGTCATAAAGTTAATGCCCAATATAACTCT CCTCAACAATTGCACGAGGGTAGGGATTGCAGAATACA | 39 |

TABLE 13-continued

MeV Nucleic Acid Sequences

| Description | Sequence | SEQ ID NO: |
|---|---|---|
| | GGAGACTACTGAGAACAGTTCTGGAACCAATTAGAGAT GCACTTAATGCAATGACCCAGAATATAAGACCGGTTCA GAGTGTAGCTTCAAGTAGGAGACACAAGAGATTTGCGG GAGTTGTCCTGGCAGGTGCGGCCCTAGGCGTTGCCACA GCTGCTCAAATAACAGCCGGTATTGCACTTCACCAGTC CATGCTGAACTCTCAAGCCATCGACAATCTGAGAGCGA GCCTAGAAACTACTAATCAGGCAATTGAGGCAATCAGA CAAGCAGGGCAGGAGATGATATTGGCTGTTCAGGGTGT CCAAGACTACATCAATAATGAGCTGATACCGTCTATGA ATCAACTATCTTGTGATTTAATCGGCCAGAAGCTAGGG CTCAAATTGCTCAGATACTATACAGAAATCCTGTCATT ATTTGGCCCCAGCTTACGGGACCCCATATCTGCGGAGA TATCTATCCAGGCTTTGAGCTATGCGCTTGGAGGAGAT ATCAATAAGGTGTTGGAAAAGCTCGGATACAGTGGAG GTGATCTACTGGGCATCTTAGAGAGCAGAGGAATAAAG GCCCGGATAACTCACGTCGACACAGAGTCCTACTTCAT TGTACTCAGTATAGCCTATCCGACGCTATCCGAGATTA AGGGGGTGATTGTCCACCGGCTAGAGGGGGTCTCGTAC AACATAGGCTCTCAAGAGTGGTATACCACTGTGCCCAA GTATGTTGCAACCCAAGGGTACCTTATCTCGAATTTTGA TGAGTCATCATGCACTTTCATGCCAGAGGGGACTGTGT GCAGCCAGAATGCCTTGTACCCGATGAGTCCTCTGCTC CAAGAATGCCTCCGGGGGTCCACTAAGTCCTGTGCTCG TACACTCGTATCCGGGTCTTTCGGGAACCGGTTCATTTT ATCACAGGGGAACCTAATAGCCAATTGTGCATCAATCC TTTGCAAGTGTTACACAACAGGAACAATCATTAATCAA GACCCTGACAAGATCCTAACATACATTGCTGCCGATCA CTGCCCGGTGGTCGAGGTGAATGGCGTGACCATCCAAG TCGGGAGCAGGAGGTATCCGGACGCTGTGTACTTGCAC AGGATTGACCTCGGTCCTCCCATATCTTTGGAGAGGTT GGACGTAGGGACAAATCTGGGGAATGCAATTGCTAAGT TGGAGGATGCCAAGGAATTGTTGGAGTCATCGGACCAG ATATTGAGGAGTATGAAAGGTTTATCGAGCACTAGTAT AGTTTACATCCTGATTGCAGTGTGTCTTGGAGGATTGAT AGGGATCCCCGCTTTAATATGTTGCTGCAGGGGGCGTT GTAACAAGAAGGGAGAACAAGTTGGTATGTCAAGACC AGGCCTAAAGCCTGATCTTACAGGAACATCAAAATCCT ATGTAAGGTCACTCTGA | |
| GC_F_MEASLES_ D8 mRNA Sequence (assumes T100 tail) Sequence Length: 1925 | G*GGGAAATAAGAGAGAAAAGAAGAGTAAGAAGAAAT ATAAGAGCCACCATGGGTCTCAAGGTGAACGTCTCTGT CATATTCATGGCAGTACTGTTAACTCTTCAAACACCCAC CGGTCAAATCCATTGGGGCAATCTCTCTAAGATAGGGG TGGTAGGGGTAGGAAGTGCAAGCTACAAAGTTATGACT CGTTCCAGCCATCAATCATTAGTCATAAAGTTAATGCC CAATATAACTCTCCTCAACAATTGCACGAGGGTAGGGA TTGCAGAATACAGGAGACTACTGAGAACAGTTCTGGAA CCAATTAGAGATGCACTTAATGCAATGACCCAGAATAT AAGACCGGTTCAGAGTGTAGCTTCAAGTAGGAGACACA AGAGATTTGCGGGAGTTGTCCTGGCAGGTGCGGCCCTA GGCGTTGCCACAGCTGCTCAAATAACAGCCGGTATTGC ACTTCACCAGTCCATGCTGAACTCTCAAGCCATCGACA ATCTGAGAGCGAGCCTAGAAACTACTAATCAGGCAATT GAGGCAATCAGACAAGCAGGGCAGGAGATGATATTGG CTGTTCAGGGTGTCCAAGACTACATCAATAATGAGCTG ATACCGTCTATGAATCAACTATCTTGTGATTTAATCGGC CAGAAGCTAGGGCTCAAATTGCTCAGATACTATACAGA AATCCTGTCATTATTTGGCCCCAGCTTACGGGACCCCAT ATCTGCGGAGATATCTATCCAGGCTTTGAGCTATGCGC TTGGAGGAGATATCAATAAGGTGTTGGAAAAGCTCGGA TACAGTGGAGGTGATCTACTGGGCATCTTAGAGAGCAG AGGAATAAAGGCCCGGATAACTCACGTCGACACAGAG TCCTACTTCATTGTACTCAGTATAGCCTATCCGACGCTA TCCGAGATTAAGGGGGTGATTGTCCACCGGCTAGAGGG GGTCTCGTACAACATAGGCTCTCAAGAGTGGTATACCA CTGTGCCCAAGTATGTTGCAACCCAAGGGTACCTTATC TCGAATTTTGATGAGTCATCATGCACTTTCATGCCAGAG GGGACTGTGTGCAGCCAGAATGCCTTGTACCCGATGAG TCCTCTGCTCCAAGAATGCCTCCGGGGGTCCACTAAGT CCTGTGCTCGTACACTCGTATCCGGGTCTTTCGGGAACC GGTTCATTTTATCACAGGGGAACCTAATAGCCAATTGT GCATCAATCCTTTGCAAGTGTTACACAACAGGAACAAT CATTAATCAAGACCCTGACAAGATCCTAACATACATTG CTGCCGATCACTGCCCGGTGGTCGAGGTGAATGGCGTG ACCATCCAAGTCGGGAGCAGGAGGTATCCGGACGCTGT | 40 |

TABLE 13-continued

MeV Nucleic Acid Sequences

| Description | Sequence | SEQ ID NO: |
|---|---|---|
| | GTACTTGCACAGGATTGACCTCGGTCCTCCCATATCTTT GGAGAGGTTGGACGTAGGGACAAATCTGGGGAATGCA ATTGCTAAGTTGGAGGATGCCAAGGAATTGTTGGAGTC ATCGGACCAGATATTGAGGAGTATGAAAGGTTTATCGA GCACTAGTATAGTTTACATCCTGATTGCAGTGTGTCTTG GAGGATTGATAGGGATCCCCGCTTTAATATGTTGCTGC AGGGGGCGTTGTAACAAGAAGGGAGAACAAGTTGGTA TGTCAAGACCAGGCCTAAAGCCTGATCTTACAGGAACA TCAAAATCCTATGTAAGGTCACTCTGATGATAATAGGC TGGAGCCTCGGTGGCCAAGCTTCTTGCCCCTTGGGCCTC CCCCCAGCCCCTCCTCCCCTTCCTGCACCCGTACCCCCG TGGTCTTTGAATAAAGTCTGAGTGGGCGGCAAAAAAAA AAAAAAAAAAAAAAAAAAAAAAAAAAAAAAAAAAAAA AAAAAAAAAAAAAAAAAAAAAAAAAAAAAAAAAAAAA AAAAAAAAAAAAAAAAAAAATCTAG | |
| GC_H_MEASLES_ B3 Sequence, NT (5' UTR, ORF, 3' UTR) Sequence Length: 2065 | TCAAGCTTTTGGACCCTCGTACAGAAGCTAATACGACT CACTATAGGGAAATAAGAGAGAAAAGAAGAGTAAGAA GAAATATAAGAGCCACCATGTCACCGCAACGAGACCG GATAAATGCCTTCTACAAAGATAACCCTTATCCCAAGG GAAGTAGGATAGTTATTAACAGAGAACATCTTATGATT GACAGACCCTATGTTCTGCTGGCTGTTCTGTTCGTCATG TTTCTGAGCTTGATCGGATTGCTGGCAATTGCAGGCATT AGACTTCATCGGGCAGCCATCTACACCGCGGAGATCCA TAAAAGCCTCAGTACCAATCTGGATGTGACTAACTCCA TCGAGCATCAGGTCAAGGACGTGCTGACACCACTCTTT AAAATCATCGGGGATGAAGTGGGCCTGAGAACACCTC AGAGATTCACTGACCTAGTGAAATTCATCTCGGACAAG ATTAAATTCCTTAATCCGGATAGGGAGTACGACTTCAG AGATCTCACTTGGTGCATCAACCCGCCAGAGAGGATCA AACTAGATTATGATCAATACTGTGCAGATGTGGCTGCT GAAGAGCTCATGAATGCATTGGTGAACTCAACTCTACT GGAGACCAGAACAACCACTCAGTTCCTAGCTGTCTCAA AGGGAAACTGCTCAGGGCCCACTACAATCAGAGGTCA ATTCTCAAACATGTCGCTGTCCTTGTTGGACTTGTACTT AGGTCGAGGTTACAATGTGTCATCTATAGTCACTATGA CATCCCAGGGAATGTATGGGGGAACCTACCTAGTTGAA AAGCCTAATCTGAACAGCAAAGGGTCAGAGTTGTCACA ACTGAGCATGTACCGAGTGTTTGAAGTAGGTGTGATCA GAAACCCGGGTTTGGGGGCTCCGGTGTTCCATATGACA AACTATTTTGAGCAACCAGTCAGTAATGGTCTCGGCAA CTGTATGGTGGCTTTGGGGGAGCTCAAACTCGCAGCCC TTTGTCACGGGGACGATTCTATCATAATTCCCTATCAGG GATCAGGGAAAGGTGTCAGCTTCCAGCTCGTCAAGCTG GGTGTCTGGAAATCCCCAACCGACATGCAATCCTGGGT CCCCTTATCAACGGATGATCCAGTGGTAGACAGGCTTT ACCTCTCATCTCACAGAGGTGTCATCGCTGACAATCAA GCAAAATGGGCTGTCCCGACAACACGAACAGATGACA AGTTGCGAATGGAGACATGCTTCCAGCAGGCGTGTAAA GGTAAAATCCAAGCACTCTGCGAGAATCCCGAGTGGGT ACCATTGAAGGATAACAGGATTCCTTCATACGGGGTCC TGTCTGTTGATCTGAGTCTGACGGTTGAGCTTAAAATCA AAATTGCTTCGGGATTCGGGCCATTGATCACACACGGC TCAGGGATGGACCTATACAAATCCAACTGCAACAATGT GTATTGGCTGACTATTCCGCCAATGAGAAATCTAGCCT TAGGCGTAATCAACACATTGGAGTGGATACCGAGATTC AAGGTTAGTCCCAACCTCTTCACTGTCCCAATTAAGGA AGCAGGCGAAGACTGCCATGCCCCAACATACCTACCTG CGGAGGTGGACGGTGATGTCAAACTCAGTTCCAACCTG GTGATTCTACCTGGTCAAGATCTCCAATATGTTTTGGCA ACCTACGATACCTCCAGGGTTGAGCATGCTGTGGTTTA TTACGTTTACAGCCCAAGCCGCTCATTTTCTTACTTTTA TCCTTTTAGGTTGCCTATAAAGGGGGTCCCAATCGAAC TACAAGTGGAATGCTTCACATGGGATCAAAAACTCTGG TGCCGTCACTTCTGTGTGCTTGCGGACTCAGAATCCGGT GGACTTATCACTCACTCTGGGATGGTGGGCATGGGAGT CAGCTGCACAGCTACCCGGGAAGATGGAACCAATCGC AGATAATGATAATAGGCTGGAGCCTCGGTGGCCAAGCT TCTTGCCCCTTGGGCCTCCCCCCAGCCCCTCCTCCCCTT CCTGCACCCGTACCCCCGTGGTCTTTGAATAAAGTCTG AGTGGGCGGC | 41 |
| GC_H_MEASLES_ B3 ORF Sequence, NT | ATGTCACCGCAACGAGACCGGATAAATGCCTTCTACAA AGATAACCCTTATCCCAAGGGAAGTAGGATAGTTATTA ACAGAGAACATCTTATGATTGACAGACCCTATGTTCTG | 42 |

TABLE 13-continued

MeV Nucleic Acid Sequences

| Description | Sequence | SEQ ID NO: |
|---|---|---|
| | CTGGCTGTTCTGTTCGTCATGTTTCTGAGCTTGATCGGA TTGCTGGCAATTGCAGGCATTAGACTTCATCGGGCAGC CATCTACACCGCGGAGATCCATAAAAGCCTCAGTACCA ATCTGGATGTGACTAACTCCATCGAGCATCAGGTCAAG GACGTGCTGACACCACTCTTTAAAATCATCGGGGATGA AGTGGGCCTGAGAACACCTCAGAGATTCACTGACCTAG TGAAATTCATCTCGGACAAGATTAAATTCCTTAATCCG GATAGGGAGTACGACTTCAGAGATCTCACTTGGTGCAT CAACCCGCCAGAGAGGATCAAACTAGATTATGATCAAT ACTGTGCAGATGTGGCTGCTGAAGAGCTCATGAATGCA TTGGTGAACTCAACTCTACTGGAGACCAGAACAACCAC TCAGTTCCTAGCTGTCTCAAAGGGAAACTGCTCAGGGC CCACTACAATCAGAGGTCAATTCTCAAACATGTCGCTG TCCTTGTTGGACTTGTACTTAGGTCGAGGTTACAATGTG TCATCTATAGTCACTATGACATCCCAGGGAATGTATGG GGGAACCTACCTAGTTGAAAAGCCTAATCTGAACAGCA AAGGGTCAGAGTTGTCACAACTGAGCATGTACCGAGTG TTTGAAGTAGGTGTGATCAGAAACCCGGGTTTGGGGGC TCCGGTGTTCCATATGACAAACTATTTTGAGCAACCAG TCAGTAATGGTCTCGGCAACTGTATGGTGGCTTTGGGG GAGCTCAAACTCGCAGCCCTTTGTCACGGGGACGATTC TATCATAATTCCCTATCAGGGATCAGGGAAAGGTGTCA GCTTCCAGCTCGTCAAGCTGGGTGTCTGGAAATCCCCA ACCGACATGCAATCCTGGGTCCCCTTATCAACGGATGA TCCAGTGGTAGACAGGCTTTACCTCTCATCTCACAGAG GTGTCATCGCTGACAATCAAGCAAAATGGGCTGTCCCG ACAACACGAACAGATGACAAGTTGCGAATGGAGACAT GCTTCCAGCAGGCGTGTAAAGGTAAAATCCAAGCACTC TGCGAGAATCCCGAGTGGGTACCATTGAAGGATAACAG GATTCCTTCATACGGGGTCCTGTCTGTTGATCTGAGTCT GACGGTTGAGCTTAAAATCAAAATTGCTTCGGGATTCG GGCCATTGATCACACACGGCTCAGGGATGGACCTATAC AAATCCAACTGCAACAATGTGTATTGGCTGACTATTCC GCCAATGAGAAATCTAGCCTTAGGCGTAATCAACACAT TGGAGTGGATACCGAGATTCAAGGTTAGTCCCAACCTC TTCACTGTCCCAATTAAGGAAGCAGGCGAAGACTGCCA TGCCCCAACATACCTACCTGCGGAGGTGGACGGTGATG TCAAACTCAGTTCCAACCTGGTGATTCTACCTGGTCAA GATCTCCAATATGTTTTGGCAACCTACGATACCTCCAG GGTTGAGCATGCTGTGGTTTATTACGTTTACAGCCCAA GCCGCTCATTTTCTTACTTTTATCCTTTTAGGTTGCCTAT AAAGGGGGTCCCAATCGAACTACAAGTGGAATGCTTCA CATGGGATCAAAAACTCTGGTGCCGTCACTTCTGTGTG CTTGCGGACTCAGAATCCGGTGGACTTATCACTCACTCT GGGATGGTGGGCATGGGAGTCAGCTGCACAGCTACCCG GGAAGATGGAACCAATCGCAGATAA | |
| GC_H_MEASLES_ B3 mRNA Sequence (assumes T100 tail) Sequence Length: 2126 | G*GGGAAATAAGAGAGAAAAGAAGAGTAAGAAGAAAT ATAAGAGCCACCATGTCACCGCAACGAGACCGGATAA ATGCCTTCTACAAAGATAACCCTTATCCCAAGGGAAGT AGGATAGTTATTAACAGAGAACATCTTATGATTGACAG ACCCTATGTTCTGCTGGCTGTTCTGTTCGTCATGTTTCT GAGCTTGATCGGATTGCTGGCAATTGCAGGCATTAGAC TTCATCGGGCAGCCATCTACACCGCGGAGATCCATAAA AGCCTCAGTACCAATCTGGATGTGACTAACTCCATCGA GCATCAGGTCAAGGACGTGCTGACACCACTCTTTAAAA TCATCGGGGATGAAGTGGGCCTGAGAACACCTCAGAG ATTCACTGACCTAGTGAAATTCATCTCGGACAAGATTA AATTCCTTAATCCGGATAGGGAGTACGACTTCAGAGAT CTCACTTGGTGCATCAACCCGCCAGAGAGGATCAAACT AGATTATGATCAATACTGTGCAGATGTGGCTGCTGAAG AGCTCATGAATGCATTGGTGAACTCAACTCTACTGGAG ACCAGAACAACCACTCAGTTCCTAGCTGTCTCAAAGGG AAACTGCTCAGGGCCCACTACAATCAGAGGTCAATTCT CAAACATGTCGCTGTCCTTGTTGGACTTGTACTTAGGTC GAGGTTACAATGTGTCATCTATAGTCACTATGACATCC CAGGGAATGTATGGGGGAACCTACCTAGTTGAAAAGCC TAATCTGAACAGCAAAGGGTCAGAGTTGTCACAACTGA GCATGTACCGAGTGTTTGAAGTAGGTGTGATCAGAAAC CCGGGTTTGGGGGCTCCGGTGTTCCATATGACAAACTA TTTTGAGCAACCAGTCAGTAATGGTCTCGGCAACTGTA TGGTGGCTTTGGGGGAGCTCAAACTCGCAGCCCTTTGT CACGGGGACGATTCTATCATAATTCCCTATCAGGGATC AGGGAAAGGTGTCAGCTTCCAGCTCGTCAAGCTGGGTG TCTGGAAATCCCCAACCGACATGCAATCCTGGGTCCCC | 43 |

TABLE 13-continued

MeV Nucleic Acid Sequences

| Description | Sequence | SEQ ID NO: |
|---|---|---|
| | TTATCAACGGATGATCCAGTGGTAGACAGGCTTTACCT<br>CTCATCTCACAGAGGTGTCATCGCTGACAATCAAGCAA<br>AATGGGCTGTCCCGACAACACGAACAGATGACAAGTTG<br>CGAATGGAGACATGCTTCCAGCAGGCGTGTAAAGGTAA<br>AATCCAAGCACTCTGCGAGAATCCCGAGTGGGTACCAT<br>TGAAGGATAACAGGATTCCTTCATACGGGGTCCTGTCT<br>GTTGATCTGAGTCTGACGGTTGAGCTTAAAATCAAAAT<br>TGCTTCGGGATTCGGGCCATTGATCACACACGGCTCAG<br>GGATGGACCTATACAAATCCAACTGCAACAATGTGTAT<br>TGGCTGACTATTCCGCCAATGAGAAATCTAGCCTTAGG<br>CGTAATCAACACATTGGAGTGGATACCGAGATTCAAGG<br>TTAGTCCCAACCTCTTCACTGTCCCAATTAAGGAAGCA<br>GGCGAAGACTGCCATGCCCCAACATACCTACCTGCGGA<br>GGTGGACGGTGATGTCAAACTCAGTTCCAACCTGGTGA<br>TTCTACCTGGTCAAGATCTCCAATATGTTTTGGCAACCT<br>ACGATACCTCCAGGGTTGAGCATGCTGTGGTTTATTAC<br>GTTTACAGCCCAAGCCGCTCATTTTCTTACTTTTATCCT<br>TTTAGGTTGCCTATAAAGGGGGTCCCAATCGAACTACA<br>AGTGGAATGCTTCACATGGGATCAAAAACTCTGGTGCC<br>GTCACTTCTGTGTGCTTGCGGACTCAGAATCCGGTGGA<br>CTTATCACTCACTCTGGGATGGTGGGCATGGGAGTCAG<br>CTGCACAGCTACCCGGGAAGATGGAACCAATCGCAGAT<br>AATGATAATAGGCTGGAGCCTCGGTGGCCAAGCTTCTT<br>GCCCCTTGGGCCTCCCCCCAGCCCCTCCTCCCCTTCCTG<br>CACCCGTACCCCCGTGGTCTTTGAATAAAGTCTGAGTG<br>GGCGGCAAAAAAAAAAAAAAAAAAAAAAAAAAAAAAAA<br>AAAAAAAAAAAAAAAAAAAAAAAAAAAAAAAAAAAAAA<br>AAAAAAAAAAAAAAAAAAAAAAAAAAAAAAAAAAATC<br>TAG | |
| GC_H_MEASLES_<br>D8<br>Sequence, NT (5'<br>UTR, ORF, 3'<br>UTR)<br>Sequence Length:<br>2065 | TCAAGCTTTTGGACCCTCGTACAGAAGCTAATACGACT<br>CACTATAGGGAAATAAGAGAGAAAAGAAGAGTAAGAA<br>GAAATATAAGAGCCACCATGTCACCACAACGAGACCG<br>GATAAATGCCTTCTACAAAGACAACCCCCATCCTAAGG<br>GAAGTAGGATAGTTATTAACAGAGAACATCTTATGATT<br>GATAGACCTTATGTTTTGCTGGCTGTTCTATTCGTCATG<br>TTTCTGAGCTTGATCGGGTTGCTAGCCATTGCAGGCATT<br>AGACTTCATCGGGCAGCCATCTACACCGCAGAGATCCA<br>TAAAAGCCTCAGCACCAATCTGGATGTAACTAACTCAA<br>TCGAGCATCAGGTTAAGGACGTGCTGACACCACTCTTC<br>AAGATCATCGGTGATGAAGTGGGCTTGAGGACACCTCA<br>GAGATTCACTGACCTAGTGAAGTTCATCTCTGACAAGA<br>TTAAATTCCTTAATCCGGACAGGGAATACGACTTCAGA<br>GATCTCACTTGGTGTATCAACCCGCCAGAGAGAATCAA<br>ATTGGATTATGATCAATACTGTGCAGATGTGGCTGCTG<br>AAGAACTCATGAATGCATTGGTGAACTCAACTCTACTG<br>GAGACCAGGGCAACCAATCAGTTCCTAGCTGTCTCAAA<br>GGGAAACTGCTCAGGGCCCACTACAATCAGAGGCCAAT<br>TCTCAAACATGTCGCTGTCCCTGTTGGACTTGTATTTAA<br>GTCGAGGTTACAATGTGTCATCTATAGTCACTATGACA<br>TCCCAGGGAATGTACGGGGGAACTTACCTAGTGGAAAA<br>GCCTAATCTGAGCAGCAAAGGGTCAGAGTTGTCACAAC<br>TGAGCATGCACCGAGTGTTTGAAGTAGGTGTTATCAGA<br>AATCCGGGTTTGGGGGCTCCGGTATTCCATATGACAAA<br>CTATCTTGAGCAACCAGTCAGTAATGATTTCAGCAACT<br>GCATGGTGGCTTTGGGGGAGCTCAAGTTCGCAGCCCTC<br>TGTCACAGGGAAGATTCTATCACAATTCCCTATCAGGG<br>ATCAGGGAAAGGTGTCAGCTTCCAGCTTGTCAAGCTAG<br>GTGTCTGGAAATCCCCAACCGACATGCAATCCTGGGTC<br>CCCCTATCAACGGATGATCCAGTGATAGACAGGCTTTA<br>CCTCTCATCTCACAGAGGCGTTATCGCTGACAATCAAG<br>CAAAATGGGCTGTCCCGACAACACGGACAGATGACAA<br>GTTGCGAATGGAGACATGCTTCCAGCAGGCGTGTAAGG<br>GTAAAATCCAAGCACTTTGCGAGAATCCCGAGTGGACA<br>CCATTGAAGGATAACAGGATTCCTTCATACGGGGTCTT<br>GTCTGTTGATCTGAGTCTGACAGTTGAGCTTAAAATCA<br>AAATTGTTTCAGGATTCGGGCCATTGATCACACACGGT<br>TCAGGGATGGACCTATACAAATCCAACCACAACAATAT<br>GTATTGGCTGACTATCCCGCCAATGAAGAACCTGGCCT<br>TAGGTGTAATCAACACATTGGAGTGGATACCGAGATTC<br>AAGGTTAGTCCCAACCTCTTCACTGTTCCAATTAAGGA<br>AGCAGGCGAGGACTGCCATGCCCCAACATACCTACCTG<br>CGGAGGTGGATGGTGATGTCAAACTCAGTTCCAATCTG<br>GTGATTCTACCTGGTCAAGATCTCCAATATGTTCTGGCA<br>ACCTACGATACTTCCAGAGTTGAACATGCTGTAGTTTAT | 44 |

TABLE 13-continued

MeV Nucleic Acid Sequences

| Description | Sequence | SEQ ID NO: |
|---|---|---|
| | TACGTTTACAGCCCAAGCCGCTCATTTTCTTACTTTTAT CCTTTTAGGTTGCCTGTAAGGGGGGTCCCCATTGAATTA CAAGTGGAATGCTTCACATGGGACCAAAAACTCTGGTG CCGTCACTTCTGTGTGCTTGCGGACTCAGAATCTGGTGG ACATATCACTCACTCTGGGATGGTGGGCATGGGAGTCA GCTGCACAGCCACTCGGGAAGATGGAACCAGCCGCAG ATAGTGATAATAGGCTGGAGCCTCGGTGGCCAAGCTTC TTGCCCCTTGGGCCTCCCCCCAGCCCCTCCTCCCCTTCC TGCACCCGTACCCCCGTGGTCTTTGAATAAAGTCTGAG TGGGCGGC | |
| GC_H_MEASLES_ D8 ORF Sequence, NT | ATGTCACCACAACGAGACCGGATAAATGCCTTCTACAA AGACAACCCCCATCCTAAGGGAAGTAGGATAGTTATTA ACAGAGAACATCTTATGATTGATAGACCTTATGTTTTGC TGGCTGTTCTATTCGTCATGTTTCTGAGCTTGATCGGGT TGCTAGCCATTGCAGGCATTAGACTTCATCGGGCAGCC ATCTACACCGCAGAGATCCATAAAAGCCTCAGCACCAA TCTGGATGTAACTAACTCAATCGAGCATCAGGTTAAGG ACGTGCTGACACCACTCTTCAAGATCATCGGTGATGAA GTGGGCTTGAGGACACCTCAGAGATTCACTGACCTAGT GAAGTTCATCTCTGACAAGATTAAATTCCTTAATCCGG ACAGGGAATACGACTTCAGAGATCTCACTTGGTGTATC AACCCGCCAGAGAGAATCAAATTGGATTATGATCAATA CTGTGCAGATGTGGCTGCTGAAGAACTCATGAATGCAT TGGTGAACTCAACTCTACTGGAGACCAGGGCAACCAAT CAGTTCCTAGCTGTCTCAAAGGGAAACTGCTCAGGGCC CACTACAATCAGAGGCCAATTCTCAAACATGTCGCTGT CCCTGTTGGACTTGTATTTAAGTCGAGGTTACAATGTGT CATCTATAGTCACTATGACATCCCAGGGAATGTACGGG GGAACTTACCTAGTGGAAAAGCCTAATCTGAGCAGCAA AGGGTCAGAGTTGTCACAACTGAGCATGCACCGAGTGT TTGAAGTAGGTGTTATCAGAAATCCGGGTTTGGGGGCT CCGGTATTCCATATGACAAACTATCTTGAGCAACCAGT CAGTAATGATTTCAGCAACTGCATGGTGGCTTTGGGGG AGCTCAAGTTCGCAGCCCTCTGTCACAGGGAAGATTCT ATCACAATTCCCTATCAGGGATCAGGGAAAGGTGTCAG CTTCCAGCTTGTCAAGCTAGGTGTCTGGAAATCCCCAA CCGACATGCAATCCTGGGTCCCCCTATCAACGGATGAT CCAGTGATAGACAGGCTTTACCTCTCATCTCACAGAGG CGTTATCGCTGACAATCAAGCAAAATGGGCTGTCCCGA CAACACGGACAGATGACAAGTTGCGAATGGAGACATG CTTCCAGCAGGCGTGTAAGGGTAAAATCCAAGCACTTT GCGAGAATCCCGAGTGGACACCATTGAAGGATAACAG GATTCCTTCATACGGGGTCTTGTCTGTTGATCTGAGTCT GACAGTTGAGCTTAAAATCAAAATTGTTTCAGGATTCG GGCCATTGATCACACACGGTTCAGGGATGGACCTATAC AAATCCAACCACAACAATATGTATTGGCTGACTATCCC GCCAATGAAGAACCTGGCCTTAGGTGTAATCAACACAT TGGAGTGGATACCGAGATTCAAGGTTAGTCCCAACCTC TTCACTGTTCCAATTAAGGAAGCAGGCGAGGACTGCCA TGCCCCAACATACCTACCTGCGGAGGTGGATGGTGATG TCAAACTCAGTTCCAATCTGGTGATTCTACCTGGTCAAG ATCTCCAATATGTTCTGGCAACCTACGATACTTCCAGA GTTGAACATGCTGTAGTTTATTACGTTTACAGCCCAAGC CGCTCATTTTCTTACTTTTATCCTTTTAGGTTGCCTGTAA GGGGGGTCCCCATTGAATTACAAGTGGAATGCTTCACA TGGGACCAAAAACTCTGGTGCCGTCACTTCTGTGTGCTT GCGGACTCAGAATCTGGTGGACATATCACTCACTCTGG GATGGTGGGCATGGGAGTCAGCTGCACAGCCACTCGGG AAGATGGAACCAGCCGCAGATAG | 45 |
| GC_H_MEASLES_ D8 mRNA Sequence (assumes T100 tail) Sequence Length: 2126 | G*GGGAAATAAGAGAGAAAAGAAGAGTAAGAAGAAAT ATAAGAGCCACCATGTCACCACAACGAGACCGGATAA ATGCCTTCTACAAAGACAACCCCCATCCTAAGGGAAGT AGGATAGTTATTAACAGAGAACATCTTATGATTGATAG ACCTTATGTTTTGCTGGCTGTTCTATTCGTCATGTTTCTG AGCTTGATCGGGTTGCTAGCCATTGCAGGCATTAGACT TCATCGGGCAGCCATCTACACCGCAGAGATCCATAAAA GCCTCAGCACCAATCTGGATGTAACTAACTCAATCGAG CATCAGGTTAAGGACGTGCTGACACCACTCTTCAAGAT CATCGGTGATGAAGTGGGCTTGAGGACACCTCAGAGAT TCACTGACCTAGTGAAGTTCATCTCTGACAAGATTAAA TTCCTTAATCCGGACAGGGAATACGACTTCAGAGATCT CACTTGGTGTATCAACCCGCCAGAGAGAATCAAATTGG ATTATGATCAATACTGTGCAGATGTGGCTGCTGAAGAA | 46 |

TABLE 13-continued

| Description | Sequence | SEQ ID NO: |
|---|---|---|
| MeV Nucleic Acid Sequences | | |
| | CTCATGAATGCATTGGTGAACTCAACTCTACTGGAGAC CAGGGCAACCAATCAGTTCCTAGCTGTCTCAAAGGGAA ACTGCTCAGGGCCCACTACAATCAGAGGCCAATTCTCA AACATGTCGCTGTCCCTGTTGGACTTGTATTTAAGTCGA GGTTACAATGTGTCATCTATAGTCACTATGACATCCCA GGGAATGTACGGGGGAACTTACCTAGTGGAAAAGCCT AATCTGAGCAGCAAAGGGTCAGAGTTGTCACAACTGAG CATGCACCGAGTGTTTGAAGTAGGTGTTATCAGAAATC CGGGTTTGGGGGCTCCGGTATTCCATATGACAAACTAT CTTGAGCAACCAGTCAGTAATGATTTCAGCAACTGCAT GGTGGCTTTGGGGGAGCTCAAGTTCGCAGCCCTCTGTC ACAGGGAAGATTCTATCACAATTCCCTATCAGGGATCA GGGAAAGGTGTCAGCTTCCAGCTTGTCAAGCTAGGTGT CTGGAAATCCCCAACCGACATGCAATCCTGGGTCCCCC TATCAACGGATGATCCAGTGATAGACAGGCTTTACCTC TCATCTCACAGAGGCGTTATCGCTGACAATCAAGCAAA ATGGGCTGTCCCGACAACACGGACAGATGACAAGTTGC GAATGGAGACATGCTTCCAGCAGGCGTGTAAGGGTAA AATCCAAGCACTTTGCGAGAATCCCGAGTGGACACCAT TGAAGGATAACAGGATTCCTTCATACGGGGTCTTGTCT GTTGATCTGAGTCTGACAGTTGAGCTTAAAATCAAAAT TGTTTCAGGATTCGGGCCATTGATCACACACGGTTCAG GGATGGACCTATACAAATCCAACCACAACAATATGTAT TGGCTGACTATCCCGCCAATGAAGAACCTGGCCTTAGG TGTAATCAACACATTGGAGTGGATACCGAGATTCAAGG TTAGTCCCAACCTCTTCACTGTTCCAATTAAGGAAGCA GGCGAGGACTGCCATGCCCCAACATACCTACCTGCGGA GGTGGATGGTGATGTCAAACTCAGTTCCAATCTGGTGA TTCTACCTGGTCAAGATCTCCAATATGTTCTGGCAACCT ACGATACTTCCAGAGTTGAACATGCTGTAGTTTATTAC GTTTACAGCCCAAGCCGCTCATTTTCTTACTTTTATCCT TTTAGGTTGCCTGTAAGGGGGGTCCCCATTGAATTACA AGTGGAATGCTTCACATGGGACCAAAAACTCTGGTGCC GTCACTTCTGTGTGCTTGCGGACTCAGAATCTGGTGGA CATATCACTCACTCTGGGATGGTGGGCATGGGAGTCAG CTGCACAGCCACTCGGGAAGATGGAACCAGCCGCAGA TAGTGATAATAGGCTGGAGCCTCGGTGGCCAAGCTTCT TGCCCCTTGGGCCTCCCCCCAGCCCCTCCTCCCCTTCCT GCACCCGTACCCCCGTGGTCTTTGAATAAAGTCTGAGT GGGCGGCAAAAAAAAAAAAAAAAAAAAAAAAAAAAAA AAAAAAAAAAAAAAAAAAAAAAAAAAAAAAAAAAAAA AAAAAAAAAAAAAAAAAAAAAAAAAAAAAAAAAAAAT CTAG | |
| MeV mRNA Sequences | | |
| GC_F_MEASLES_ B3.1 Sequence, NT (5' UTR, ORF, 3' UTR) Sequence Length: 1864 | UCAAGCUUUUGGACCCUCGUACAGAAGCUAAUACGAC UCACUAUAGGGAAAUAAGAGAGAAAAGAAGAGUAAG AAGAAAUAUAAGAGCCACCAUGGGUCUCAAGGUGAA CGUCUCUGCCGUAUUCAUGGCAGUACUGUUAACUCUC CAAACACCCGCCGGUCAAAUUCAUUGGGGCAAUCUCU CUAAGAUAGGGGUAGUAGGAAUAGGAAGUGCAAGCU ACAAAGUUAUGACUCGUUCCAGCCAUCAAUCAUUAGU CAUAAAAUUAAUGCCCAAUAUAACUCUCCUCAAUAAC UGCACGAGGGUAGAGAUUGCAGAAUACAGGAGACUA CUAAGAACAGUUUUGGAACCAAUUAGGGAUGCACUU AAUGCAAUGACCCAGAACAUAAGGCCGGUUCAGAGCG UAGCUUCAAGUAGGAGACACAAGAGAUUUGCGGGAG UAGUCCUGGCAGGUGCGGCCCUAGGUGUUGCCACAGC UGCUCAGAUAACAGCCGGCAUUGCACUUCACCGGUCC AUGCUGAACUCUCAGGCCAUCGACAAUCUGAGAGCGA GCCUGGAAACUACUAAUCAGGCAAUUGAGGCAAUCAG ACAAGCAGGGCAGGAGAUGAUAUUGGCUGUUCAGGG UGUCCAAGACUACAUCAAUAAUGAGCUGAUACCGUCU AUGAACCAGCUAUCUUGUGAUCUAAUCGGUCAGAAGC UCGGGCUCAAAUUGCUUAGAUACUAUACAGAAAUCCU GUCAUUAUUUGGCCCCAGCCUACGGGACCCCAUAUCU GCGGAGAUAUCUAUCCAGGCUUUGAGUUAUGCACUU GGAGGAGAUAUCAAUAAGGUGUUAGAAAAGCUCGGA UACAGUGGAGGCGAUUUACUAGGCAUCUUAGAGAGC AGAGGAAUAAAGGCUCGGAUAACUCACGUCGACACAG AGUCCUACUUCAUAGUCCUCAGUAUAGCCUAUCCGAC GCUGUCCGAGAUUAAGGGGGUGAUUGUCCACCGGCUA GAGGGGGUCUCGUACAACAUAGGCUCUCAAGAGUGG UAUACCACUGUGCCCAAGUAUGUUGCAACCCAAGGGU | 69 |

TABLE 13-continued

| MeV Nucleic Acid Sequences | | |
|---|---|---|
| Description | Sequence | SEQ ID NO: |
| | ACCUUAUCUCGAAUUUUGAUGAGUCAUCAUGUACUU UCAUGCCAGAGGGGACUGUGUGCAGCCAAAAUGCCUU GUACCCGAUGAGUCCUCUGCUCCAAGAAUGCCUCCGG GGGUCCACCAAGUCCUGUGCUCGUACACUCGUAUCCG GGUCUUUUGGGAACCGGUUCAUUUUAUCACAAGGGA ACCUAAUAGCCAAUUGUGCAUCAAUUCUUUGUAAGU GUUACACAACAGGUACGAUUAUUAAUCAAGACCCUGA CAAGAUCCUAACAUACAUUGCUGCCGAUCGCUGCCCG GUAGUCGAGGUGAACGGCGUGACCAUCCAAGUCGGGA GCAGGAGGUAUCCAGACGCUGUGUACUUGCACAGAAU UGACCUCGGUCCUCCCAUAUCAUUGGAGAGGUUGGAC GUAGGGACAAAUCUGGGGAAUGCAAUUGCCAAAUUG GAGGAUGCCAAGGAAUUGUUGGAAUCAUCGGACCAG AUAUUGAGAAGUAUGAAAGGUUUAUCGAGCACUAGC AUAGUCUACAUCCUGAUUGCAGUGUGUCUUGGAGGG UUGAUAGGGAUCCCCACUUUAAUAUGUUGCUGCAGG GGGCGUUGUAACAAAAAGGGAGAACAAGUUGGUAUG UCAAGACCAGGCCUAAAGCCUGACCUUACAGGAACAU CAAAAUCCUAUGUAAGAUCGCUUUGAUGAUAAUAGG CUGGAGCCUCGGUGGCCAAGCUUCUUGCCCCUUGGGC CUCCCCCCAGCCCCUCCUCCCCUUCCUGCACCCGUACC CCCGUGGUCUUUGAAUAAAGUCUGAGUGGGCGGC | |
| GC_F_MEASLES_ B3.1 ORF Sequence, NT | AUGGGUCUCAAGGUGAACGUCUCUGCCGUAUUCAUGG CAGUACUGUUAACUCUCCAAACACCCGCCGGUCAAAU UCAUUGGGGCAAUCUCUCUAAGAUAGGGGUAGUAGG AAUAGGAAGUGCAAGCUACAAAGUUAUGACUCGUUC CAGCCAUCAAUCAUUAGUCAUAAAAUUAAUGCCCAAU AUAACUCUCCUCAAUAACUGCACGAGGGUAGAGAUUG CAGAAUACAGGAGACUACUAAGAACAGUUUUGGAAC CAAUUAGGGAUGCACUUAAUGCAAUGACCCAGAACAU AAGGCCGGUUCAGAGCGUAGCUUCAAGUAGGAGACAC AAGAGAUUUGCGGGAGUAGUCCUGGCAGGUGCGGCCC UAGGUGUUGCCACAGCUGCUCAGAUAACAGCCGGCAU UGCACUUCACCGGUCCAUGCUGAACUCUCAGGCCAUC GACAAUCUGAGAGCGAGCCUGGAAACUACUAAUCAGG CAAUUGAGGCAAUCAGACAAGCAGGGCAGGAGAUGA UAUUGGCUGUUCAGGGUGUCCAAGACUACAUCAAUA AUGAGCUGAUACCGUCUAUGAACCAGCUAUCUUGUGA UCUAAUCGGUCAGAAGCUCGGGCUCAAAUUGCUUAGA UACUAUACAGAAAUCCUGUCAUUAUUUGGCCCCAGCC UACGGGACCCCAUAUCUGCGGAGAUAUCUAUCCAGGC UUUGAGUUAUGCACUUGGAGGAGAUAUCAAUAAGGU GUUAGAAAAGCUCGGAUACAGUGGAGGCGAUUUACU AGGCAUCUUAGAGAGCAGAGGAAUAAAGGCUCGGAU AACUCACGUCGACACAGAGUCCUACUUCAUAGUCCUC AGUAUAGCCUAUCCGACGCUGUCCGAGAUUAAGGGGG UGAUUGUCCACCGGCUAGAGGGGGUCUCGUACAACAU AGGCUCUCAAGAGUGGUAUACCACUGUGCCCAAGUAU GUUGCAACCCAAGGGUACCUUAUCUCGAAUUUUGAUG AGUCAUCAUGUACUUUCAUGCCAGAGGGGACUGUGU GCAGCCAAAAUGCCUUGUACCCGAUGAGUCCUCUGCU CCAAGAAUGCCUCCGGGGGUCCACCAAGUCCUGUGCU CGUACACUCGUAUCCGGGUCUUUUGGGAACCGGUUCA UUUUAUCACAAGGGAACCUAAUAGCCAAUUGUGCAUC AAUUCUUUGUAAGUGUUACACAACAGGUACGAUUAU UAAUCAAGACCCUGACAAGAUCCUAACAUACAUUGCU GCCGAUCGCUGCCCGGUAGUCGAGGUGAACGGCGUGA CCAUCCAAGUCGGGAGCAGGAGGUAUCCAGACGCUGU GUACUUGCACAGAAUUGACCUCGGUCCUCCCAUAUCA UUGGAGAGGUUGGACGUAGGGACAAAUCUGGGGAAU GCAAUUGCCAAAUUGGAGGAUGCCAAGGAAUUGUUG GAAUCAUCGGACCAGAUAUUGAGAAGUAUGAAAGGU UUAUCGAGCACUAGCAUAGUCUACAUCCUGAUUGCAG UGUGUCUUGGAGGGUUGAUAGGGAUCCCCACUUUAA UAUGUUGCUGCAGGGGGCGUUGUAACAAAAAGGGAG AACAAGUUGGUAUGUCAAGACCAGGCCUAAAGCCUGA CCUUACAGGAACAUCAAAAUCCUAUGUAAGAUCGCUU UGA | 70 |
| GC_F_MEASLES_ B3.1 mRNA Sequence (assumes T100 tail) | G*GGGAAAUAAGAGAGAAAAGAAGAGUAAGAAGAAA UAUAAGAGCCACCAUGGGUCUCAAGGUGAACGUCUCU GCCGUAUUCAUGGCAGUACUGUUAACUCUCCAAACAC CCGCCGGUCAAAUUCAUUGGGGCAAUCUCUCUAAGAU AGGGGUAGUAGGAAUAGGAAGUGCAAGCUACAAAGU | 71 |

TABLE 13-continued

| MeV Nucleic Acid Sequences | | |
|---|---|---|
| Description | Sequence | SEQ ID NO: |
| mRNA Sequence Length: 1925 | UAUGACUCGUUCCAGCCAUCAAUCAUUAGUCAUAAAA UUAAUGCCCAAUAUAACUCUCCUCAAUAACUGCACGA GGGUAGAGAUUGCAGAAUACAGGAGACUACUAAGAA CAGUUUUGGAACCAAUUAGGGAUGCACUUAAUGCAA UGACCCAGAACAUAAGGCCGGUUCAGAGCGUAGCUUC AAGUAGGAGACACAAGAGAUUUGCGGGAGUAGUCCU GGCAGGUGCGGCCCUAGGUGUUGCCACAGCUGCUCAG AUAACAGCCGGCAUUGCACUUCACCGGUCCAUGCUGA ACUCUCAGGCCAUCGACAAUCUGAGAGCGAGCCUGGA AACUACUAAUCAGGCAAUUGAGGCAAUCAGACAAGCA GGGCAGGAGAUGAUAUUGGCUGUUCAGGGUGUCCAA GACUACAUCAAUAAUGAGCUGAUACCGUCUAUGAACC AGCUAUCUUGUGAUCUAAUCGGUCAGAAGCUCGGGCU CAAAUUGCUUAGAUACUAUACAGAAAUCCUGUCAUU AUUUGGCCCCAGCCUACGGGACCCCAUAUCUGCGGAG AUAUCUAUCCAGGCUUUGAGUUAUGCACUUGGAGGA GAUAUCAAUAAGGUGUUAGAAAAGCUCGGAUACAGU GGAGGCGAUUUACUAGGCAUCUUAGAGAGCAGAGGA AUAAAGGCUCGGAUAACUCACGUCGACACAGAGUCCU ACUUCAUAGUCCUCAGUAUAGCCUAUCCGACGCUGUC CGAGAUUAAGGGGGUGAUUGUCCACCGGCUAGAGGG GGUCUCGUACAACAUAGGCUCUCAAGAGUGGUAUACC ACUGUGCCCAAGUAUGUUGCAACCCAAGGGUACCUUA UCUCGAAUUUUGAUGAGUCAUCAUGUACUUUCAUGCC AGAGGGGACUGUGUGCAGCCAAAAUGCCUUGUACCCG AUGAGUCCUCUGCUCCAAGAAUGCCUCCGGGGGUCCA CCAAGUCCUGUGCUCGUACACUCGUAUCCGGGUCUUU UGGGAACCGGUUCAUUUUAUCACAAGGGAACCUAAU AGCCAAUUGUGCAUCAAUUCUUUGUAAGUGUUACAC AACAGGUACGAUUAUUAAUCAAGACCCUGACAAGAUC CUAACAUACAUUGCUGCCGAUCGCUGCCCGGUAGUCG AGGUGAACGGCGUGACCAUCCAAGUCGGGAGCAGGAG GUAUCCAGACGCUGUGUACUUGCACAGAAUUGACCUC GGUCCUCCCAUAUCAUUGGAGAGGUUGGACGUAGGG ACAAAUCUGGGGAAUGCAAUUGCCAAAUUGGAGGAU GCCAAGGAAUUGUUGGAAUCAUCGGACCAGAUAUUG AGAAGUAUGAAAGGUUUAUCGAGCACUAGCAUAGUC UACAUCCUGAUUGCAGUGUGUCUUGGAGGGUUGAUA GGGAUCCCCACUUUAAUAUGUUGCUGCAGGGGGCGUU GUAACAAAAAGGGAGAACAAGUUGGUAUGUCAAGAC CAGGCCUAAAGCCUGACCUUACAGGAACAUCAAAAUC CUAUGUAAGAUCGCUUUGAUGAUAAUAGGCUGGAGC CUCGGUGGCCAAGCUUCUUGCCCCUUGGGCCUCCCCC CAGCCCCUCCUCCCCUUCCUGCACCCGUACCCCCGUGG UCUUUGAAUAAAGUCUGAGUGGGCGGCAAAAAAAAA AAAAAAAAAAAAAAAAAAAAAAAAAAAAAAAAAAAA AAAAAAAAAAAAAAAAAAAAAAAAAAAAAAAAAAAA AAAAAAAAAAAAAAAAAAAUCUAG | |
| GC_F_MEASLES_ D8 Sequence, NT (5' UTR, ORF, 3' UTR) Sequence Length: 1864 | UCAAGCUUUUGGACCCUCGUACAGAAGCUAAUACGAC UCACUAUAGGGAAAUAAGAGAGAAAAGAAGAGUAAG AAGAAAUAUAAGAGCCACCAUGGGUCUCAAGGUGAA CGUCUCUGUCAUAUUCAUGGCAGUACUGUUAACUCUU CAAACACCCACCGGUCAAAUCCAUUGGGGCAAUCUCU CUAAGAUAGGGGUGGUAGGGGUAGGAAGUGCAAGCU ACAAAGUUAUGACUCGUUCCAGCCAUCAAUCAUUAGU CAUAAAGUUAAUGCCCAAUAUAACUCUCCUCAACAAU UGCACGAGGGUAGGGAUUGCAGAAUACAGGAGACUA CUGAGAACAGUUCUGGAACCAAUUAGAGAUGCACUU AAUGCAAUGACCCAGAAUAUAAGACCGGUUCAGAGU GUAGCUUCAAGUAGGAGACACAAGAGAUUUGCGGGA GUUGUCCUGGCAGGUGCGGCCCUAGGCGUUGCCACAG CUGCUCAAAUAACAGCCGGUAUUGCACUUCACCAGUC CAUGCUGAACUCUCAAGCCAUCGACAAUCUGAGAGCG AGCCUAGAAACUACUAAUCAGGCAAUUGAGGCAAUCA GACAAGCAGGGCAGGAGAUGAUAUUGGCUGUUCAGG GUGUCCAAGACUACAUCAAUAAUGAGCUGAUACCGUC UAUGAAUCAACUAUCUUGUGAUUUAAUCGGCCAGAA GCUAGGGCUCAAAUUGCUCAGAUACUAUACAGAAAUC CUGUCAUUAUUUGGCCCCAGCUUACGGGACCCCAUAU CUGCGGAGAUAUCUAUCCAGGCUUUGAGCUAUGCGCU UGGAGGAGAUAUCAAUAAGGUGUUGGAAAAGCUCGG AUACAGUGGAGGUGAUCUACUGGGCAUCUUAGAGAG CAGAGGAAUAAAGGCCCGGAUAACUCACGUCGACACA GAGUCCUACUUCAUUGUACUCAGUAUAGCCUAUCCGA | 72 |

TABLE 13-continued

MeV Nucleic Acid Sequences

| Description | Sequence | SEQ ID NO: |
|---|---|---|
| | CGCUAUCCGAGAUUAAGGGGGUGAUUGUCCACCGGCU AGAGGGGGUCUCGUACAACAUAGGCUCUCAAGAGUG GUAUACCACUGUGCCCAAGUAUGUUGCAACCCAAGGG UACCUUAUCUCGAAUUUUGAUGAGUCAUCAUGCACUU UCAUGCCAGAGGGGACUGUGUGCAGCCAGAAUGCCUU GUACCCGAUGAGUCCUCUGCUCCAAGAAUGCCUCCGG GGGUCCACUAAGUCCUGUGCUCGUACACUCGUAUCCG GGUCUUUCGGGAACCGGUUCAUUUUAUCACAGGGGA ACCUAAUAGCCAAUUGUGCAUCAAUCCUUUGCAAGUG UUACACAACAGGAACAAUCAUUAAUCAAGACCCUGAC AAGAUCCUAACAUACAUUGCUGCCGAUCACUGCCCGG UGGUCGAGGUGAAUGGCGUGACCAUCCAAGUCGGGA GCAGGAGGUAUCCGGACGCUGUGUACUUGCACAGGAU UGACCUCGGUCCUCCCAUAUCUUUGGAGAGGUUGGAC GUAGGGACAAAUCUGGGGAAUGCAAUUGCUAAGUUG GAGGAUGCCAAGGAAUUGUUGGAGUCAUCGGACCAG AUAUUGAGGAGUAUGAAAGGUUUAUCGAGCACUAGU AUAGUUUACAUCCUGAUUGCAGUGUGUCUUGGAGGA UUGAUAGGGAUCCCCGCUUUAAUAUGUUGCUGCAGG GGGCGUUGUAACAAGAAGGGAGAACAAGUUGGUAUG UCAAGACCAGGCCUAAAGCCUGAUCUUACAGGAACAU CAAAAUCCUAUGUAAGGUCACUCUGAUGAUAAUAGG CUGGAGCCUCGGUGGCCAAGCUUCUUGCCCCUUGGGC CUCCCCCCAGCCCCUCCUCCCCUUCCUGCACCCGUACC CCCGUGGUCUUUGAAUAAAGUCUGAGUGGGCGGC | |
| GC_F_MEASLES_ D8 ORF Sequence, NT | AUGGGUCUCAAGGUGAACGUCUCUGUCAUAUUCAUG GCAGUACUGUUAACUCUUCAAACACCCACCGGUCAAA UCCAUUGGGGCAAUCUCUCUAAGAUAGGGGUGGUAG GGGUAGGAAGUGCAAGCUACAAAGUUAUGACUCGUU CCAGCCAUCAAUCAUUAGUCAUAAAGUUAAUGCCCAA UAUAACUCUCCUCAACAAUUGCACGAGGGUAGGGAUU GCAGAAUACAGGAGACUACUGAGAACAGUUCUGGAA CCAAUUAGAGAUGCACUUAAUGCAAUGACCCAGAAUA UAAGACCGGUUCAGAGUGUAGCUUCAAGUAGGAGAC ACAAGAGAUUUGCGGGAGUUGUCCUGGCAGGUGCGG CCCUAGGCGUUGCCACAGCUGCUCAAAUAACAGCCGG UAUUGCACUUCACCAGUCCAUGCUGAACUCUCAAGCC AUCGACAAUCUGAGAGCGAGCCUAGAAACUACUAAUC AGGCAAUUGAGGCAAUCAGACAAGCAGGGCAGGAGA UGAUAUUGGCUGUUCAGGGUGUCCAAGACUACAUCA AUAAUGAGCUGAUACCGUCUAUGAAUCAACUAUCUU GUGAUUUAAUCGGCCAGAAGCUAGGGCUCAAAUUGC UCAGAUACUAUACAGAAAUCCUGUCAUUAUUUGGCCC CAGCUUACGGGACCCCAUAUCUGCGGAGAUAUCUAUC CAGGCUUUGAGCUAUGCGCUUGGAGGAGAUAUCAAU AAGGUGUUGGAAAAGCUCGGAUACAGUGGAGGUGAU CUACUGGGCAUCUUAGAGAGCAGAGGAAUAAAGGCCC GGAUAACUCACGUCGACACAGAGUCCUACUUCAUUGU ACUCAGUAUAGCCUAUCCGACGCUAUCCGAGAUUAAG GGGGUGAUUGUCCACCGGCUAGAGGGGGUCUCGUACA ACAUAGGCUCUCAAGAGUGGUAUACCACUGUGCCCAA GUAUGUUGCAACCCAAGGGUACCUUAUCUCGAAUUUU GAUGAGUCAUCAUGCACUUUCAUGCCAGAGGGGACUG UGUGCAGCCAGAAUGCCUUGUACCCGAUGAGUCCUCU GCUCCAAGAAUGCCUCCGGGGGUCCACUAAGUCCUGU GCUCGUACACUCGUAUCCGGGUCUUUCGGGAACCGGU UCAUUUUAUCACAGGGGAACCUAAUAGCCAAUUGUGC AUCAAUCCUUUGCAAGUGUUACACAACAGGAACAAUC AUUAAUCAAGACCCUGACAAGAUCCUAACAUACAUUG CUGCCGAUCACUGCCCGGUGGUCGAGGUGAAUGGCGU GACCAUCCAAGUCGGGAGCAGGAGGUAUCCGGACGCU GUGUACUUGCACAGGAUUGACCUCGGUCCUCCCAUAU CUUUGGAGAGGUUGGACGUAGGGACAAAUCUGGGGA AUGCAAUUGCUAAGUUGGAGGAUGCCAAGGAAUUGU UGGAGUCAUCGGACCAGAUAUUGAGGAGUAUGAAAG GUUUAUCGAGCACUAGUAUAGUUUACAUCCUGAUUG CAGUGUGUCUUGGAGGAUUGAUAGGGAUCCCCGCUU UAAUAUGUUGCUGCAGGGGGCGUUGUAACAAGAAGG GAGAACAAGUUGGUAUGUCAAGACCAGGCCUAAAGCC UGAUCUUACAGGAACAUCAAAAUCCUAUGUAAGGUC ACUCUGA | 73 |
| GC_F_MEASLES_ D8 | G*GGGAAAUAAGAGAGAAAAGAAGAGUAAGAAGAAA UAUAAGAGCCACCAUGGGUCUCAAGGUGAACGUCUCU | 74 |

TABLE 13-continued

MeV Nucleic Acid Sequences

| Description | Sequence | SEQ ID NO: |
|---|---|---|
| mRNA Sequence (assumes T100 tail) Sequence Length: 1925 | GUCAUAUUCAUGGCAGUACUGUUAACUCUUCAAACAC CCACCGGUCAAAUCCAUUGGGGCAAUCUCUCUAAGAU AGGGGUGGUAGGGGUAGGAAGUGCAAGCUACAAAGU UAUGACUCGUUCCAGCCAUCAAUCAUUAGUCAUAAAG UUAAUGCCCAAUAUAACUCUCCUCAACAAUUGCACGA GGGUAGGGAUUGCAGAAUACAGGAGACUACUGAGAA CAGUUCUGGAACCAAUUAGAGAUGCACUUAAUGCAA UGACCCAGAAUAUAAGACCGGUUCAGAGUGUAGCUUC AAGUAGGAGACACAAGAGAUUUGCGGGAGUUGUCCU GGCAGGUGCGGCCCUAGGCGUUGCCACAGCUGCUCAA AUAACAGCCGGUAUUGCACUUCACCAGUCCAUGCUGA ACUCUCAAGCCAUCGACAAUCUGAGAGCGAGCCUAGA AACUACUAAUCAGGCAAUUGAGGCAAUCAGACAAGCA GGGCAGGAGAUGAUAUUGGCUGUUCAGGGUGUCCAA GACUACAUCAAUAAUGAGCUGAUACCGUCUAUGAAUC AACUAUCUUGUGAUUUAAUCGGCCAGAAGCUAGGGC UCAAAUUGCUCAGAUACUAUACAGAAAUCCUGUCAUU AUUUGGCCCCAGCUUACGGGACCCCAUAUCUGCGGAG AUAUCUAUCCAGGCUUUGAGCUAUGCGCUUGGAGGA GAUAUCAAUAAGGUGUUGGAAAAGCUCGGAUACAGU GGAGGUGAUCUACUGGGCAUCUUAGAGAGCAGAGGA AUAAAGGCCCGGAUAACUCACGUCGACACAGAGUCCU ACUUCAUUGUACUCAGUAUAGCCUAUCCGACGCUAUC CGAGAUUAAGGGGGUGAUUGUCCACCGGCUAGAGGG GGUCUCGUACAACAUAGGCUCUCAAGAGUGGUAUACC ACUGUGCCCAAGUAUGUUGCAACCCAAGGGUACCUUA UCUCGAAUUUUGAUGAGUCAUCAUGCACUUUCAUGCC AGAGGGGACUGUGUGCAGCCAGAAUGCCUUGUACCCG AUGAGUCCUCUGCUCCAAGAAUGCCUCCGGGGGUCCA CUAAGUCCUGUGCUCGUACACUCGUAUCCGGGUCUUU CGGGAACCGGUUCAUUUUAUCACAGGGGAACCUAAUA GCCAAUUGUGCAUCAAUCCUUUGCAAGUGUUACACAA CAGGAACAAUCAUUAAUCAAGACCCUGACAAGAUCCU AACAUACAUUGCUGCCGAUCACUGCCCGGUGGUCGAG GUGAAUGGCGUGACCAUCCAAGUCGGGAGCAGGAGG UAUCCGGACGCUGUGUACUUGCACAGGAUUGACCUCG GUCCUCCCAUAUCUUUGGAGAGGUUGGACGUAGGGAC AAAUCUGGGGAAUGCAAUUGCUAAGUUGGAGGAUGC CAAGGAAUUGUUGGAGUCAUCGGACCAGAUAUUGAG GAGUAUGAAAGGUUUAUCGAGCACUAGUAUAGUUUA CAUCCUGAUUGCAGUGUGUCUUGGAGGAUUGAUAGG GAUCCCCGCUUUAAUAUGUUGCUGCAGGGGGCGUUGU AACAAGAAGGGAGAACAAGUUGGUAUGUCAAGACCA GGCCUAAAGCCUGAUCUUACAGGAACAUCAAAAUCCU AUGUAAGGUCACUCUGAUGAUAAUAGGCUGGAGCCU CGGUGGCCAAGCUUCUUGCCCCUUGGGCCUCCCCCCA GCCCCUCCUCCCCUUCCUGCACCCGUACCCCCGUGGUC UUUGAAUAAAGUCUGAGUGGGCGGCAAAAAAAAAAA AAAAAAAAAAAAAAAAAAAAAAAAAAAAAAAAAAAA AAAAAAAAAAAAAAAAAAAAAAAAAAAAAAAAAAAA AAAAAAAAAAAAAAAAAUCUAG | |
| GC_H_MEASLES_B3 Sequence, NT (5' UTR, ORF, 3' UTR) Sequence Length: 2065 | UCAAGCUUUUGGACCCUCGUACAGAAGCUAAUACGAC UCACUAUAGGGAAAUAAGAGAGAAAAGAAGAGUAAG AAGAAAUAUAAGAGCCACCAUGUCACCGCAACGAGAC CGGAUAAAUGCCUUCUACAAAGAUAACCCUUAUCCCA AGGGAAGUAGGAUAGUUAUUAACAGAGAACAUCUUA UGAUUGACAGACCCUAUGUUCUGCUGGCUGUUCUGUU CGUCAUGUUUCUGAGCUUGAUCGGAUUGCUGGCAAU UGCAGGCAUUAGACUUCAUCGGGCAGCCAUCUACACC GCGGAGAUCCAUAAAAGCCUCAGUACCAAUCUGGAUG UGACUAACUCCAUCGAGCAUCAGGUCAAGGACGUGCU GACACCACUCUUUAAAAUCAUCGGGGAUGAAGUGGGC CUGAGAACACCUCAGAGAUUCACUGACCUAGUGAAAU UCAUCUCGGACAAGAUUAAAUUCCUUAAUCCGGAUAG GGAGUACGACUUCAGAGAUCUCACUUGGUGCAUCAAC CCGCCAGAGAGGAUCAAACUAGAUUAUGAUCAAUACU GUGCAGAUGUGGCUGCUGAAGAGCUCAUGAAUGCAU UGGUGAACUCAACUCUACUGGAGACCAGAACAACCAC UCAGUUCCUAGCUGUCUCAAAGGGAAACUGCUCAGGG CCCACUACAAUCAGAGGUCAAUUCUCAAACAUGUCGC UGUCCUUGUUGGACUUGUACUUAGGUCGAGGUUACA AUGUGUCAUCUAUAGUCACUAUGACAUCCCAGGGAAU GUAUGGGGGAACCUACCUAGUUGAAAAGCCUAAUCU GAACAGCAAAGGGUCAGAGUUGUCACAACUGAGCAU | 75 |

TABLE 13-continued

MeV Nucleic Acid Sequences

| Description | Sequence | SEQ ID NO: |
|---|---|---|
| | GUACCGAGUGUUUGAAGUAGGUGUGAUCAGAAACCC GGGUUUGGGGGCUCCGGUGUUCCAUAUGACAAACUA UUUUGAGCAACCAGUCAGUAAUGGUCUCGGCAACUGU AUGGUGGCUUUGGGGGAGCUCAAACUCGCAGCCCUUU GUCACGGGGACGAUUCUAUCAUAAUUCCCUAUCAGGG AUCAGGGAAAGGUGUCAGCUUCCAGCUCGUCAAGCUG GGUGUCUGGAAAUCCCCAACCGACAUGCAAUCCUGGG UCCCCUUAUCAACGGAUGAUCCAGUGGUAGACAGGCU UUACCUCUCAUCUCACAGAGGUGUCAUCGCUGACAAU CAAGCAAAAUGGGCUGUCCCGACAACACGAACAGAUG ACAAGUUGCGAAUGGAGACAUGCUUCCAGCAGGCGUG UAAAGGUAAAAUCCAAGCACUCUGCGAGAAUCCCGAG UGGGUACCAUUGAAGGAUAACAGGAUUCCUUCAUAC GGGGUCCUGUCUGUUGAUCUGAGUCUGACGGUUGAG CUUAAAAUCAAAAUUGCUUCGGGAUUCGGGCCAUUG AUCACACACGGCUCAGGGAUGGACCUAUACAAAUCCA ACUGCAACAAUGUGUAUUGGCUGACUAUUCCGCCAAU GAGAAAUCUAGCCUUAGGCGUAAUCAACACAUUGGA GUGGAUACCGAGAUUCAAGGUUAGUCCCAACCUCUUC ACUGUCCCAAUUAAGGAAGCAGGCGAAGACUGCCAUG CCCCAACAUACCUACCUGCGGAGGUGGACGGUGAUGU CAAACUCAGUUCCAACCUGGUGAUUCUACCUGGUCAA GAUCUCCAAUAUGUUUUGGCAACCUACGAUACCUCCA GGGUUGAGCAUGCUGUGGUUUAUUACGUUUACAGCC CAAGCCGCUCAUUUUCUUACUUUUAUCCUUUUAGGUU GCCUAUAAAGGGGGUCCCAAUCGAACUACAAGUGGAA UGCUUCACAUGGGAUCAAAAACUCUGGUGCCGUCACU UCUGUGUGCUUGCGGACUCAGAAUCCGGUGGACUUAU CACUCACUCUGGGAUGGUGGGCAUGGGAGUCAGCUGC ACAGCUACCCGGGAAGAUGGAACCAAUCGCAGAUAAU GAUAAUAGGCUGGAGCCUCGGUGGCCAAGCUUCUUGC CCCUUGGGCCUCCCCCCAGCCCCUCCUCCCCUUCCUGC ACCCGUACCCCCGUGGUCUUUGAAUAAAGUCUGAGUG GGCGGC | |
| GC_H_MEASLES_ B3 ORF Sequence, NT | AUGUCACCGCAACGAGACCGGAUAAAUGCCUUCUACA AAGAUAACCCUUAUCCCAAGGGAAGUAGGAUAGUUA UUAACAGAGAACAUCUUAUGAUUGACAGACCCUAUG UUCUGCUGGCUGUUCUGUUCGUCAUGUUUCUGAGCUU GAUCGGAUUGCUGGCAAUUGCAGGCAUUAGACUUCA UCGGGCAGCCAUCUACACCGCGGAGAUCCAUAAAAGC CUCAGUACCAAUCUGGAUGUGACUAACUCCAUCGAGC AUCAGGUCAAGGACGUGCUGACACCACUCUUUAAAAU CAUCGGGGAUGAAGUGGGCCUGAGAACACCUCAGAGA UUCACUGACCUAGUGAAAUUCAUCUCGGACAAGAUUA AAUUCCUUAAUCCGGAUAGGGAGUACGACUUCAGAG AUCUCACUUGGUGCAUCAACCCGCCAGAGAGGAUCAA ACUAGAUUAUGAUCAAUACUGUGCAGAUGUGGCUGC UGAAGAGCUCAUGAAUGCAUUGGUGAACUCAACUCU ACUGGAGACCAGAACAACCACUCAGUUCCUAGCUGUC UCAAAGGGAAACUGCUCAGGGCCCACUACAAUCAGAG GUCAAUUCUCAAACAUGUCGCUGUCCUUGUUGGACUU GUACUUAGGUCGAGGUUACAAUGUGUCAUCUAUAGU CACUAUGACAUCCCAGGGAAUGUAUGGGGGAACCUAC CUAGUUGAAAAGCCUAAUCUGAACAGCAAAGGGUCA GAGUUGUCACAACUGAGCAUGUACCGAGUGUUUGAA GUAGGUGUGAUCAGAAACCCGGGUUUGGGGGCUCCG GUGUUCCAUAUGACAAACUAUUUUGAGCAACCAGUCA GUAAUGGUCUCGGCAACUGUAUGGUGGCUUUGGGGG AGCUCAAACUCGCAGCCCUUUGUCACGGGGACGAUUC UAUCAUAAUUCCCUAUCAGGGAUCAGGGAAAGGUGU CAGCUUCCAGCUCGUCAAGCUGGGUGUCUGGAAAUCC CCAACCGACAUGCAAUCCUGGGUCCCCUUAUCAACGG AUGAUCCAGUGGUAGACAGGCUUUACCUCUCAUCUCA CAGAGGUGUCAUCGCUGACAAUCAAGCAAAAUGGGCU GUCCCGACAACACGAACAGAUGACAAGUUGCGAAUGG AGACAUGCUUCCAGCAGGCGUGUAAAGGUAAAAUCCA AGCACUCUGCGAGAAUCCCGAGUGGGUACCAUUGAAG GAUAACAGGAUUCCUUCAUACGGGGUCCUGUCUGUUG AUCUGAGUCUGACGGUUGAGCUUAAAAUCAAAAUUG CUUCGGGAUUCGGGCCAUUGAUCACACACGGCUCAGG GAUGGACCUAUACAAAUCCAACUGCAACAAUGUGUAU UGGCUGACUAUUCCGCCAAUGAGAAAUCUAGCCUUAG GCGUAAUCAACACAUUGGAGUGGAUACCGAGAUUCA AGGUUAGUCCCAACCUCUUCACUGUCCCAAUUAAGGA | 76 |

TABLE 13-continued

| MeV Nucleic Acid Sequences | | |
|---|---|---|
| Description | Sequence | SEQ ID NO: |
| | AGCAGGCGAAGACUGCCAUGCCCCAACAUACCUACCU GCGGAGGUGGACGGUGAUGUCAAACUCAGUUCCAACC UGGUGAUUCUACCUGGUCAAGAUCUCCAAUAUGUUU UGGCAACCUACGAUACCUCCAGGGUUGAGCAUGCUGU GGUUUAUUACGUUUACAGCCCAAGCCGCUCAUUUUCU UACUUUUAUCCUUUUAGGUUGCCUAUAAAGGGGGUC CCAAUCGAACUACAAGUGGAAUGCUUCACAUGGGAUC AAAAACUCUGGUGCCGUCACUUCUGUGUGCUUGCGGA CUCAGAAUCCGGUGGACUUAUCACUCACUCUGGGAUG GUGGGCAUGGGAGUCAGCUGCACAGCUACCCGGGAAG AUGGAACCAAUCGCAGAUAA | |
| GC_H_MEASLES_ B3 mRNA Sequence (assumes T100 Tail) Sequence Length: 2126 | G*GGGAAAUAAGAGAGAAAAGAAGAGUAAGAAGAAA UAUAAGAGCCACCAUGUCACCGCAACGAGACCGGAUA AAUGCCUUCUACAAAGAUAACCCUUAUCCCAAGGGAA GUAGGAUAGUUAUUAACAGAGAACAUCUUAUGAUUG ACAGACCCUAUGUUCUGCUGGCUGUUCUGUUCGUCAU GUUUCUGAGCUUGAUCGGAUUGCUGGCAAUUGCAGG CAUUAGACUUCAUCGGGCAGCCAUCUACACCGCGGAG AUCCAUAAAAGCCUCAGUACCAAUCUGGAUGUGACUA ACUCCAUCGAGCAUCAGGUCAAGGACGUGCUGACACC ACUCUUUAAAAUCAUCGGGGAUGAAGUGGGCCUGAG AACACCUCAGAGAUUCACUGACCUAGUGAAAUUCAUC UCGGACAAGAUUAAAUUCCUUAAUCCGGAUAGGGAG UACGACUUCAGAGAUCUCACUUGGUGCAUCAACCCGC CAGAGAGGAUCAAACUAGAUUAUGAUCAAUACUGUG CAGAUGUGGCUGCUGAAGAGCUCAUGAAUGCAUUGG UGAACUCAACUCUACUGGAGACCAGAACAACCACUCA GUUCCUAGCUGUCUCAAAGGGAAACUGCUCAGGGCCC ACUACAAUCAGAGGUCAAUUCUCAAACAUGUCGCUGU CCUUGUUGGACUUGUACUUAGGUCGAGGUUACAAUG UGUCAUCUAUAGUCACUAUGACAUCCCAGGGAAUGUA UGGGGGAACCUACCUAGUUGAAAAGCCUAAUCUGAAC AGCAAAGGGUCAGAGUUGUCACAACUGAGCAUGUACC GAGUGUUUGAAGUAGGUGUGAUCAGAAACCCGGGUU UGGGGGCUCCGGUGUUCCAUAUGACAAACUAUUUUG AGCAACCAGUCAGUAAUGGUCUCGGCAACUGUAUGGU GGCUUUGGGGGAGCUCAAACUCGCAGCCCUUUGUCAC GGGGACGAUUCUAUCAUAAUUCCCUAUCAGGGAUCAG GGAAAGGUGUCAGCUUCCAGCUCGUCAAGCUGGGUGU CUGGAAAUCCCCAACCGACAUGCAAUCCUGGGUCCCC UUAUCAACGGAUGAUCCAGUGGUAGACAGGCUUUACC UCUCAUCUCACAGAGGUGUCAUCGCUGACAAUCAAGC AAAAUGGGCUGUCCCGACAACACGAACAGAUGACAAG UUGCGAAUGGAGACAUGCUUCCAGCAGGCGUGUAAA GGUAAAAUCCAAGCACUCUGCGAGAAUCCCGAGUGGG UACCAUUGAAGGAUAACAGGAUUCCUUCAUACGGGG UCCUGUCUGUUGAUCUGAGUCUGACGGUUGAGCUUA AAAUCAAAAUUGCUUCGGGAUUCGGGCCAUUGAUCAC ACACGGCUCAGGGAUGGACCUAUACAAAUCCAACUGC AACAAUGUGUAUUGGCUGACUAUUCCGCCAAUGAGA AAUCUAGCCUUAGGCGUAAUCAACACAUUGGAGUGG AUACCGAGAUUCAAGGUUAGUCCCAACCUCUUCACUG UCCCAAUUAAGGAAGCAGGCGAAGACUGCCAUGCCCC AACAUACCUACCUGCGGAGGUGGACGGUGAUGUCAAA CUCAGUUCCAACCUGGUGAUUCUACCUGGUCAAGAUC UCCAAUAUGUUUUGGCAACCUACGAUACCUCCAGGGU UGAGCAUGCUGUGGUUUAUUACGUUUACAGCCCAAGC CGCUCAUUUUCUUACUUUUAUCCUUUUAGGUUGCCUA UAAAGGGGGUCCCAAUCGAACUACAAGUGGAAUGCU UCACAUGGGAUCAAAAACUCUGGUGCCGUCACUUCUG UGUGCUUGCGGACUCAGAAUCCGGUGGACUUAUCACU CACUCUGGGAUGGUGGGCAUGGGAGUCAGCUGCACAG CUACCCGGGAAGAUGGAACCAAUCGCAGAUAAUGAUA AUAGGCUGGAGCCUCGGUGGCCAAGCUUCUUGCCCCU UGGGCCUCCCCCCAGCCCCUCCUCCCCUUCCUGCACCC GUACCCCCGUGGUCUUUGAAUAAAGUCUGAGUGGGCG GCAAAAAAAAAAAAAAAAAAAAAAAAAAAAAAAAAAA AAAAAAAAAAAAAAAAAAAAAAAAAAAAAAAAAAAA AAAAAAAAAAAAAAAAAAAAAAAAAAAAAAAUCUAG | 77 |
| GC_H_MEASLES_ D8 Sequence, NT (5' UTR, ORF, 3' | UCAAGCUUUUGGACCCUCGUACAGAAGCUAAUACGAC UCACUAUAGGGAAAUAAGAGAGAAAAGAAGAGUAAG AAGAAAUAUAAGAGCCACCAUGUCACCACAACGAGAC CGGAUAAAUGCCUUCUACAAAGACAACCCCCAUCCUA | 78 |

TABLE 13-continued

| MeV Nucleic Acid Sequences | | |
|---|---|---|
| Description | Sequence | SEQ ID NO: |
| UTR) Sequence Length: 2065 | AGGGAAGUAGGAUAGUUAUUAACAGAGAACAUCUUA UGAUUGAUAGACCUUAUGUUUUGCUGGCUGUUCUAU UCGUCAUGUUUCUGAGCUUGAUCGGGUUGCUAGCCAU UGCAGGCAUUAGACUUCAUCGGGCAGCCAUCUACACC GCAGAGAUCCAUAAAAGCCUCAGCACCAAUCUGGAUG UAACUAACUCAAUCGAGCAUCAGGUUAAGGACGUGCU GACACCACUCUUCAAGAUCAUCGGUGAUGAAGUGGGC UUGAGGACACCUCAGAGAUUCACUGACCUAGUGAAGU UCAUCUCUGACAAGAUUAAAUUCCUUAAUCCGGACAG GGAAUACGACUUCAGAGAUCUCACUUGGUGUAUCAAC CCGCCAGAGAGAAUCAAAUUGGAUUAUGAUCAAUAC UGUGCAGAUGUGGCUGCUGAAGAACUCAUGAAUGCA UUGGUGAACUCAACUCUACUGGAGACCAGGGCAACCA AUCAGUUCCUAGCUGUCUCAAAGGGAAACUGCUCAGG GCCCACUACAAUCAGAGGCCAAUUCUCAAACAUGUCG CUGUCCCUGUUGGACUUGUAUUUAAGUCGAGGUUAC AAUGUGUCAUCUAUAGUCACUAUGACAUCCCAGGGAA UGUACGGGGGAACUUACCUAGUGGAAAAGCCUAAUC UGAGCAGCAAAGGGUCAGAGUUGUCACAACUGAGCA UGCACCGAGUGUUUGAAGUAGGUGUUAUCAGAAAUC CGGGUUUGGGGGCUCCGGUAUUCCAUAUGACAAACUA UCUUGAGCAACCAGUCAGUAAUGAUUUCAGCAACUGC AUGGUGGCUUUGGGGGAGCUCAAGUUCGCAGCCCUCU GUCACAGGGAAGAUUCUAUCACAAUUCCCUAUCAGGG AUCAGGGAAAGGUGUCAGCUUCCAGCUUGUCAAGCUA GGUGUCUGGAAAUCCCCAACCGACAUGCAAUCCUGGG UCCCCCUAUCAACGGAUGAUCCAGUGAUAGACAGGCU UUACCUCUCAUCUCACAGAGGCGUUAUCGCUGACAAU CAAGCAAAAUGGGCUGUCCCGACAACACGGACAGAUG ACAAGUUGCGAAUGGAGACAUGCUUCCAGCAGGCGUG UAAGGGUAAAAUCCAAGCACUUUGCGAGAAUCCCGAG UGGACACCAUUGAAGGAUAACAGGAUUCCUUCAUACG GGGUCUUGUCUGUUGAUCUGAGUCUGACAGUUGAGC UUAAAAUCAAAAUUGUUUCAGGAUUCGGGCCAUUGA UCACACACGGUUCAGGGAUGGACCUAUACAAAUCCAA CCACAACAAUAUGUAUUGGCUGACUAUCCCGCCAAUG AAGAACCUGGCCUUAGGUGUAAUCAACACAUUGGAG UGGAUACCGAGAUUCAAGGUUAGUCCCAACCUCUUCA CUGUUCCAAUUAAGGAAGCAGGCGAGGACUGCCAUGC CCCAACAUACCUACCUGCGGAGGUGGAUGGUGAUGUC AAACUCAGUUCCAAUCUGGUGAUUCUACCUGGUCAAG AUCUCCAAUAUGUUCUGGCAACCUACGAUACUUCCAG AGUUGAACAUGCUGUAGUUUAUUACGUUUACAGCCC AAGCCGCUCAUUUUCUUACUUUUAUCCUUUUAGGUUG CCUGUAAGGGGGGUCCCCAUUGAAUUACAAGUGGAA UGCUUCACAUGGGACCAAAAACUCUGGUGCCGUCACU UCUGUGUGCUUGCGGACUCAGAAUCUGGUGGACAUA UCACUCACUCUGGGAUGGUGGGCAUGGGAGUCAGCUG CACAGCCACUCGGGAAGAUGGAACCAGCCGCAGAUAG UGAUAAUAGGCUGGAGCCUCGGUGGCCAAGCUUCUUG CCCCUUGGGCCUCCCCCCAGCCCCUCCUCCCCUUCCUG CACCCGUACCCCCGUGGUCUUUGAAUAAAGUCUGAGU GGGCGGC | |
| GC_H_MEASLES_ D8 ORF Sequence, NT | AUGUCACCACAACGAGACCGGAUAAAUGCCUUCUACA AAGACAACCCCCAUCCUAAGGGAAGUAGGAUAGUUAU UAACAGAGAACAUCUUAUGAUUGAUAGACCUUAUGU UUUGCUGGCUGUUCUAUUCGUCAUGUUUCUGAGCUU GAUCGGGUUGCUAGCCAUUGCAGGCAUUAGACUUCAU CGGGCAGCCAUCUACACCGCAGAGAUCCAUAAAAGCC UCAGCACCAAUCUGGAUGUAACUAACUCAAUCGAGCA UCAGGUUAAGGACGUGCUGACACCACUCUUCAAGAUC AUCGGUGAUGAAGUGGGCUUGAGGACACCUCAGAGA UUCACUGACCUAGUGAAGUUCAUCUCUGACAAGAUUA AAUUCCUUAAUCCGGACAGGGAAUACGACUUCAGAGA UCUCACUUGGUGUAUCAACCCGCCAGAGAGAAUCAAA UUGGAUUAUGAUCAAUACUGUGCAGAUGUGGCUGCU GAAGAACUCAUGAAUGCAUUGGUGAACUCAACUCUAC UGGAGACCAGGGCAACCAAUCAGUUCCUAGCUGUCUC AAAGGGAAACUGCUCAGGGCCCACUACAAUCAGAGGC CAAUUCUCAAACAUGUCGCUGUCCCUGUUGGACUUGU AUUUAAGUCGAGGUUACAAUGUGUCAUCUAUAGUCA CUAUGACAUCCCAGGGAAUGUACGGGGGAACUUACCU AGUGGAAAAGCCUAAUCUGAGCAGCAAAGGGUCAGA GUUGUCACAACUGAGCAUGCACCGAGUGUUUGAAGU | 79 |

TABLE 13-continued

MeV Nucleic Acid Sequences

| Description | Sequence | SEQ ID NO: |
|---|---|---|
| | AGGUGUUAUCAGAAAUCCGGGUUUGGGGGCUCCGGU AUUCCAUAUGACAAACUAUCUUGAGCAACCAGUCAGU AAUGAUUUCAGCAACUGCAUGGUGGCUUUGGGGGAG CUCAAGUUCGCAGCCCUCUGUCACAGGGAAGAUUCUA UCACAAUUCCCUAUCAGGGAUCAGGGAAAGGUGUCAG CUUCCAGCUUGUCAAGCUAGGUGUCUGGAAAUCCCCA ACCGACAUGCAAUCCUGGGUCCCCCUAUCAACGGAUG AUCCAGUGAUAGACAGGCUUUACCUCUCAUCUCACAG AGGCGUUAUCGCUGACAAUCAAGCAAAAUGGGCUGUC CCGACAACACGGACAGAUGACAAGUUGCGAAUGGAGA CAUGCUUCCAGCAGGCGUGUAAGGGUAAAAUCCAAGC ACUUUGCGAGAAUCCCGAGUGGACACCAUUGAAGGAU AACAGGAUUCCUUCAUACGGGGUCUUGUCUGUUGAUC UGAGUCUGACAGUUGAGCUUAAAAUCAAAAUUGUUU CAGGAUUCGGGCCAUUGAUCACACACGGUUCAGGGAU GGACCUAUACAAAUCCAACCACAACAAUAUGUAUUGG CUGACUAUCCCGCCAAUGAAGAACCUGGCCUUAGGUG UAAUCAACACAUUGGAGUGGAUACCGAGAUUCAAGG UUAGUCCCAACCUCUUCACUGUUCCAAUUAAGGAAGC AGGCGAGGACUGCCAUGCCCCAACAUACCUACCUGCG GAGGUGGAUGGUGAUGUCAAACUCAGUUCCAAUCUG GUGAUUCUACCUGGUCAAGAUCUCCAAUAUGUUCUGG CAACCUACGAUACUUCCAGAGUUGAACAUGCUGUAGU UUAUUACGUUUACAGCCCAAGCCGCUCAUUUUCUUAC UUUUAUCCUUUUAGGUUGCCUGUAAGGGGGGUCCCCA UUGAAUUACAAGUGGAAUGCUUCACAUGGGACCAAA AACUCUGGUGCCGUCACUUCUGUGUGCUUGCGGACUC AGAAUCUGGUGGACAUAUCACUCACUCUGGGAUGGU GGGCAUGGGAGUCAGCUGCACAGCCACUCGGGAAGAU GGAACCAGCCGCAGAUAG | |
| GC_H_MEASLES_ D8 mRNA Sequence (assumes T100 tail) Sequence Length: 2126 | G*GGGAAAUAAGAGAGAAAAGAAGAGUAAGAAGAAA UAUAAGAGCCACCAUGUCACCACAACGAGACCGGAUA AAUGCCUUCUACAAAGACAACCCCCAUCCUAAGGGAA GUAGGAUAGUUAUUAACAGAGAACAUCUUAUGAUUG AUAGACCUUAUGUUUUGCUGGCUGUUCUAUUCGUCA UGUUUCUGAGCUUGAUCGGGUUGCUAGCCAUUGCAG GCAUUAGACUUCAUCGGGCAGCCAUCUACACCGCAGA GAUCCAUAAAAGCCUCAGCACCAAUCUGGAUGUAACU AACUCAAUCGAGCAUCAGGUUAAGGACGUGCUGACAC CACUCUUCAAGAUCAUCGGUGAUGAAGUGGGCUUGA GGACACCUCAGAGAUUCACUGACCUAGUGAAGUUCAU CUCUGACAAGAUUAAAUUCCUUAAUCCGGACAGGGAA UACGACUUCAGAGAUCUCACUUGGUGUAUCAACCCGC CAGAGAGAAUCAAAUUGGAUUAUGAUCAAUACUGUG CAGAUGUGGCUGCUGAAGAACUCAUGAAUGCAUUGG UGAACUCAACUCUACUGGAGACCAGGGCAACCAAUCA GUUCCUAGCUGUCUCAAAGGGAAACUGCUCAGGGCCC ACUACAAUCAGAGGCCAAUUCUCAAACAUGUCGCUGU CCCUGUUGGACUUGUAUUUAAGUCGAGGUUACAAUG UGUCAUCUAUAGUCACUAUGACAUCCCAGGGAAUGUA CGGGGGAACUUACCUAGUGGAAAAGCCUAAUCUGAGC AGCAAAGGGUCAGAGUUGUCACAACUGAGCAUGCACC GAGUGUUUGAAGUAGGUGUUAUCAGAAAUCCGGGUU UGGGGGCUCCGGUAUUCCAUAUGACAAACUAUCUUGA GCAACCAGUCAGUAAUGAUUUCAGCAACUGCAUGGUG GCUUUGGGGGAGCUCAAGUUCGCAGCCCUCUGUCACA GGGAAGAUUCUAUCACAAUUCCCUAUCAGGGAUCAGG GAAAGGUGUCAGCUUCCAGCUUGUCAAGCUAGGUGUC UGGAAAUCCCCAACCGACAUGCAAUCCUGGGUCCCCC UAUCAACGGAUGAUCCAGUGAUAGACAGGCUUUACCU CUCAUCUCACAGAGGCGUUAUCGCUGACAAUCAAGCA AAAUGGGCUGUCCCGACAACACGGACAGAUGACAAGU UGCGAAUGGAGACAUGCUUCCAGCAGGCGUGUAAGG GUAAAAUCCAAGCACUUUGCGAGAAUCCCGAGUGGAC ACCAUUGAAGGAUAACAGGAUUCCUUCAUACGGGGUC UUGUCUGUUGAUCUGAGUCUGACAGUUGAGCUUAAA AUCAAAAUUGUUUCAGGAUUCGGGCCAUUGAUCACAC ACGGUUCAGGGAUGGACCUAUACAAAUCCAACCACAA CAAUAUGUAUUGGCUGACUAUCCCGCCAAUGAAGAAC CUGGCCUUAGGUGUAAUCAACACAUUGGAGUGGAUA CCGAGAUUCAAGGUUAGUCCCAACCUCUUCACUGUUC CAAUUAAGGAAGCAGGCGAGGACUGCCAUGCCCCAAC AUACCUACCUGCGGAGGUGGAUGGUGAUGUCAAACUC AGUUCCAAUCUGGUGAUUCUACCUGGUCAAGAUCUCC | 80 |

TABLE 13-continued

| MeV Nucleic Acid Sequences | | |
|---|---|---|
| Description | Sequence | SEQ ID NO: |
| | AAUAUGUUCUGGCAACCUACGAUACUUCCAGAGUUGA ACAUGCUGUAGUUUAUUACGUUUACAGCCCAAGCCGC UCAUUUUCUUACUUUUAUCCUUUUAGGUUGCCUGUA AGGGGGGUCCCCAUUGAAUUACAAGUGGAAUGCUUC ACAUGGGACCAAAAACUCUGGUGCCGUCACUUCUGUG UGCUUGCGGACUCAGAAUCUGGUGGACAUAUCACUCA CUCUGGGAUGGUGGGCAUGGGAGUCAGCUGCACAGCC ACUCGGGAAGAUGGAACCAGCCGCAGAUAGUGAUAA UAGGCUGGAGCCUCGGUGGCCAAGCUUCUUGCCCCUU GGGCCUCCCCCCAGCCCCUCCUCCCCUUCCUGCACCCG UACCCCCGUGGUCUUUGAAUAAAGUCUGAGUGGGCGG CAAAAAAAAAAAAAAAAAAAAAAAAAAAAAAAAAAA AAAAAAAAAAAAAAAAAAAAAAAAAAAAAAAAAAAA AAAAAAAAAAAAAAAAAAAAAAAAAAAAAAAUCUAG | |

TABLE 14

| MeV Amino Acid Sequences | | |
|---|---|---|
| Description | Sequence | SEQ ID NO: |
| GC_F_MEASLES_ B3.1 ORF Sequence, AA | MGLKVNVSAVFMAVLLTLQTPAGQIHWGNLSKIGVV GIGSASYKVMTRSSHQSLVIKLMPNITLLNNCTRVEIA EYRRLLRTVLEPIRDALNAMTQNIRPVQSVASSRRHK RFAGVVLAGAALGVATAAQITAGIALHRSMLNSQAID NLRASLETTNQAIEAIRQAGQEMILAVQGVQDYINNE LIPSMNQLSCDLIGQKLGLKLLRYYTEILSLFGPSLRDP ISAEISIQALSYALGGDINKVLEKLGYSGGDLLGILESR GIKARITHVDTESYFIVLSIAYPTLSEIKGVIVHRLEGVS YNIGSQEWYTTVPKYVATQGYLISNFDESSCTFMPEG TVCSQNALYPMSPLLQECLRGSTKSCARTLVSGSFGN RFILSQGNLIANCASILCKCYTTGTIINQDPDKILTYIAA DRCPVVEVNGVTIQVGSRRYPDAVYLHRIDLGPPISLE RLDVGTNLGNAIAKLEDAKELLESSDQILRSMKGLSST SIVYILIAVCLGGLIGIPTLICCCRGRCNKKGEQVGMSR PGLKPDLTGTSKSYVRSL* | 47 |
| GC_F_MEASLES_D8 ORF Sequence, AA | MGLKVNVSVIFMAVLLTLQTPTGQIHWGNLSKIGVVG VGSASYKVMTRSSHQSLVIKLMPNITLLNNCTRVGIAE YRRLLRTVLEPIRDALNAMTQNIRPVQSVASSRRHKR FAGVVLAGAALGVATAAQITAGIALHQSMLNSQAIDN LRASLETTNQAIEAIRQAGQEMILAVQGVQDYINNELI PSMNQLSCDLIGQKLGLKLLRYYTEILSLFGPSLRDPIS AEISIQALSYALGGDINKVLEKLGYSGGDLLGILESRGI KARITHVDTESYFIVLSIAYPTLSEIKGVIVHRLEGVSY NIGSQEWYTTVPKYVATQGYLISNFDESSCTFMPEGT VCSQNALYPMSPLLQECLRGSTKSCARTLVSGSFGNR FILSQGNLIANCASILCKCYTTGTIINQDPDKILTYIAAD HCPVVEVNGVTIQVGSRRYPDAVYLHRIDLGPPISLER LDVGTNLGNAIAKLEDAKELLESSDQILRSMKGLSSTS IVYILIAVCLGGLIGIPALICCCRGRCNKKGEQVGMSRP GLKPDLTGTSKSYVRSL* | 48 |
| GC_H_MEASLES_B3 ORF Sequence, AA | MSPQRDRINAFYKDNPYPKGSRIVINREHLMIDRPYVL LAVLFVMFLSLIGLLAIAGIRLHRAAIYTAEIHKSLSTN LDVTNSIEHQVKDVLTPLFKIIGDEVGLRTPQRFTDLV KFISDKIKFLNPDREYDFRDLTWCINPPERIKLDYDQY CADVAAEELMNALVNSTLLETRTTTQFLAVSKGNCS GPTTIRGQFSNMSLSLLDLYLGRGYNVSSIVTMTSQG MYGGTYLVEKPNLNSKGSELSQLSMYRVFEVGVIRNP GLGAPVFHMTNYFEQPVSNGLGNCMVALGELKLAAL CHGDDSIIIPYQGSGKGVSFQLVKLGVWKSPTDMQSW VPLSTDDPVVDRLYLSSHRGVIADNQAKWAVPTTRT DDKLRMETCFQQACKGKIQALCENPEWVPLKDNRIPS YGVLSVDLSLTVELKIKIASGFGPLITHGSGMDLYKSN CNNVYWLTIPPMRNLALGVINTLEWIPRFKVSPNLFTV PIKEAGEDCHAPTYLPAEVDGDVKLSSNLVILPGQDL QYVLATYDTSRVEHAVVYYVYSPSRSFSYFYPFRLPIK GVPIELQVECFTWDQKLWCRHFCVLADSESGGLITHS GMVGMGVSCTATREDGTNRR* | 49 |

TABLE 14-continued

| MeV Amino Acid Sequences | | |
|---|---|---|
| Description | Sequence | SEQ ID NO: |
| GC_H_MEASLES_D8 ORF Sequence, AA | MSPQRDRINAFYKDNPHPKGSRIVINREHLMIDRPYVL LAVLFVMFLSLIGLLAIAGIRLHRAAIYTAEIHKSLSTN LDVTNSIEHQVKDVLTPLFKIIGDEVGLRTPQRFTDLV KFISDKIKFLNPDREYDFRDLTWCINPPERIKLDYDQY CADVAAEELMNALVNSTLLETRATNQFLAVSKGNCS GPTTIRGQFSNMSLSLLDLYLSRGYNVSSIVTMTSQGM YGGTYLVEKPNLSSKGSELSQLSMHRVFEVGVIRNPG LGAPVFHMTNYLEQPVSNDFSNCMVALGELKFAALC HREDSITIPYQGSGKGVSFQLVKLGVWKSPTDMQSW VPLSTDDPVIDRLYLSSHRGVIADNQAKWAVPTTRTD DKLRMETCFQQACKGKIQALCENPEWTPLKDNRIPSY GVLSVDLSLTVELKIKIVSGFGPLITHGSGMDLYKSNH NNMYWLTIPPMKNLALGVINTLEWIPRFKVSPNLFTV PIKEAGEDCHAPTYLPAEVDGDVKLSSNLVILPGQDL QYVLATYDTSRVEHAVVYYVYSPSRSFSYFYPFRLPV RGVPIELQVECFTWDQKLWCRHFCVLADSESGGHITH SGMVGMGVSCTATREDGTSRR* | 50 |

TABLE 15

| MeV NCBI Accession Numbers (Amino Acid Sequences) | | |
|---|---|---|
| Type | Virus Name | GenBank Accession |
| hemagglutinin | hemagglutinin [Measles virus strain Moraten] | AAF85673.1 |
| hemagglutinin | hemagglutinin [Measles virus strain Rubeovax] | AAF85689.1 |
| hemagglutinin | hemagglutinin [Measles virus] | AAF89824.1 |
| hemagglutinin | hemagglutinin protein [Measles virus] | CAA91369.1 |
| hemagglutinin | hemagglutinin [Measles virus] | BAJ23068.1 |
| hemagglutinin | hemagglutinin protein [Measles virus] | BAB39848.1 |
| hemagglutinin | hemagglutinin [Measles virus] | AAA50551.1 |
| hemagglutinin | RecName: Full = Hemagglutinin glycoprotein | P08362.1 |
| hemagglutinin | hemagglutinin [Measles virus] | AAB63802.1 |
| hemagglutinin | hemagglutinin [Measles virus] | AAA56650.1 |
| hemagglutinin | hemagglutinin [Measles virus] | AAA56642.1 |
| hemagglutinin | hemagglutinin [Measles virus] | AAA74936.1 |
| hemagglutinin | hemagglutinin protein [Measles virus] | BAH56665.1 |
| hemagglutinin | hemagglutinin [Measles virus] | ACC86105.1 |
| hemagglutinin | hemagglutinin [Measles virus strain Edmonston-Zagreb] | AAF85697.1 |
| hemagglutinin | hemagglutinin [Measles virus] | AAR89413.1 |
| hemagglutinin | hemagglutinin [Measles virus] | AAA56653.1 |
| hemagglutinin | RecName: Full = Hemagglutinin glycoprotein | P35971.1 |
| hemagglutinin | Hemagglutinin [Measles virus] | CAB94916.1 |
| hemagglutinin | hemagglutinin [Measles virus] | AAC03036.1 |
| hemagglutinin | hemagglutinin [Measles virus] | AAF85681.1 |
| hemagglutinin | Hemagglutinin [Measles virus] | CAB94927.1 |
| hemagglutinin | Hemagglutinin [Measles virus] | CAB94925.1 |
| hemagglutinin | hemagglutinin protein [Measles virus] | BAB39835.1 |
| hemagglutinin | Hemagglutinin [Measles virus] | CAB94931.1 |
| hemagglutinin | hemagglutinin [Measles virus genotype A] | AFO84712.1 |
| hemagglutinin | hemagglutinin [Measles virus] | AAA56639.1 |
| hemagglutinin | Hemagglutinin [Measles virus] | CAB94926.1 |
| hemagglutinin | hemagglutinin protein [Measles virus] | BAB39836.1 |
| hemagglutinin | Hemagglutinin [Measles virus] | CAB94929.1 |
| hemagglutinin | RecName: Full = Hemagglutinin glycoprotein | P06830.1 |
| hemagglutinin | Hemagglutinin [Measles virus] | CAB94928.1 |
| hemagglutinin | hemagglutinin protein [Measles virus] | BAB39837.1 |
| hemagglutinin | hemagglutinin [Measles virus] | AAA74935.1 |
| hemagglutinin | hemagglutinin protein [Measles virus] | CAB43780.1 |
| hemagglutinin | hemagglutinin [Measles virus] | BAA09952.1 |
| hemagglutinin | hemagglutinin protein [Measles virus] | CAB43815.1 |
| hemagglutinin | hemagglutinin [Measles virus] | AAF28390.1 |
| hemagglutinin | Hemagglutinin [Measles virus] | CAB94923.1 |
| hemagglutinin | hemagglutinin protein [Measles virus] | CAB43785.1 |
| hemagglutinin | hemagglutinin [Measles virus] | ABD34001.1 |
| hemagglutinin | hemagglutinin protein [Measles virus] | CAB43782.1 |
| hemagglutinin | hemagglutinin protein [Measles virus] | CAB43781.1 |
| hemagglutinin | hemagglutinin [Measles virus] | BAH22353.1 |
| hemagglutinin | hemagglutinin [Measles virus] | AAC35878.2 |
| hemagglutinin | hemagglutinin protein [Measles virus] | AAL86996.1 |
| hemagglutinin | hemagglutinin [Measles virus] | CAA76066.2 |
| hemagglutinin | hemagglutinin [Measles virus] | AAA46428.1 |

TABLE 15-continued

| MeV NCBI Accession Numbers (Amino Acid Sequences) | | |
|---|---|---|
| Type | Virus Name | GenBank Accession |
| hemagglutinin | hemagglutinin protein [Measles virus] | CAB43803.1 |
| hemagglutinin | Hemagglutinin [Measles virus] | CAB94918.1 |
| hemagglutinin | hemagglutinin [Measles virus] | AAF72162.1 |
| hemagglutinin | hemagglutinin [Measles virus] | AAM70154.1 |
| hemagglutinin | hemagglutinin protein [Measles virus] | CAB43776.1 |
| hemagglutinin | hemagglutinin [Measles virus genotype D4] | ACT78395.1 |
| hemagglutinin | hemagglutinin [Measles virus genotype D7] | AAL02030.1 |
| hemagglutinin | hemagglutinin protein [Measles virus] | CAB43789.1 |
| hemagglutinin | hemagglutinin protein [Measles virus] | CAB43774.1 |
| hemagglutinin | Hemagglutinin [Measles virus] | CAB94920.1 |
| hemagglutinin | Hemagglutinin [Measles virus] | CAB94922.1 |
| hemagglutinin | hemagglutinin [Measles virus] | ABB59491.1 |
| hemagglutinin | hemagglutinin protein [Measles virus] | BAB39843.1 |
| hemagglutinin | hemagglutinin protein [Measles virus] | CAB43804.1 |
| hemagglutinin | hemagglutinin [Measles virus] | AAX52048.1 |
| hemagglutinin | Hemagglutinin [Measles virus] | CAB94930.1 |
| hemagglutinin | hemagglutinin [Measles virus] | AAA74526.1 |
| hemagglutinin | hemagglutinin protein [Measles virus] | CAB43814.1 |
| hemagglutinin | hemagglutinin [Measles virus] | ABB59493.1 |
| hemagglutinin | hemagglutinin [Measles virus genotype D4] | AAL02019.1 |
| hemagglutinin | Hemagglutinin [Measles virus] | CAB94919.1 |
| hemagglutinin | hemagglutinin protein [Measles virus] | AAL86997.1 |
| hemagglutinin | hemagglutinin [Measles virus genotype C2] | AAL02017.1 |
| hemagglutinin | hemagglutinin protein [Measles virus] | CAB43769.1 |
| hemagglutinin | hemagglutinin protein [Measles virus] | CAB43808.1 |
| hemagglutinin | hemagglutinin [Measles virus] | BAO97032.1 |
| hemagglutinin | hemagglutinin protein [Measles virus] | CAB43805.1 |
| hemagglutinin | hemagglutinin protein [Measles virus] | CAB43777.1 |
| hemagglutinin | hemagglutinin [Measles virus] | AAL67793.1 |
| hemagglutinin | hemagglutinin [Measles virus] | AAF89816.1 |
| hemagglutinin | hemagglutinin [Measles virus genotype D4] | AAL02020.1 |
| hemagglutinin | hemagglutinin protein [Measles virus] | CAB43786.1 |
| hemagglutinin | hemagglutinin protein [Measles virus strain MVi/New Jersey.USA/45.05] | AEP40452.1 |
| hemagglutinin | hemagglutinin [Measles virus] | AAA74531.1 |
| hemagglutinin | hemagglutinin [Measles virus] | AAB63800.1 |
| hemagglutinin | hemagglutinin [Measles virus] | AAO21711.1 |
| hemagglutinin | hemagglutinin [Measles virus genotype D8] | ALE27189.1 |
| hemagglutinin | hemagglutinin protein [Measles virus] | CAB43810.1 |
| hemagglutinin | hemagglutinin [Measles virus] | AAF89817.1 |
| hemagglutinin | hemagglutinin [Measles virus genotype D6] | AAL02022.1 |
| hemagglutinin | hemagglutinin protein [Measles virus] | CAB43800.1 |
| hemagglutinin | hemagglutinin protein [Measles virus genotype B3] | AGA17219.1 |
| hemagglutinin | hemagglutinin protein [Measles virus] | CAB43770.1 |
| hemagglutinin | hemagglutinin protein [Measles virus strain MVi/Texas.USA/4.07] | AEP40444.1 |
| hemagglutinin | hemagglutinin [Measles virus] | AAX52047.1 |
| hemagglutinin | hemagglutinin [Measles virus] | AAB63794.1 |
| hemagglutinin | hemagglutinin [Measles virus] | AAB63796.1 |
| hemagglutinin | hemagglutinin [Measles virus] | AAA74528.1 |
| hemagglutinin | hemagglutinin [Measles virus] | AAB63774.1 |
| hemagglutinin | hemagglutinin [Measles virus] | AAB63795.1 |
| hemagglutinin | hemagglutinin [Measles virus] | AAA74519.1 |
| hemagglutinin | hemagglutinin protein [Measles virus] | CAB43778.1 |
| fusion protein | fusion protein [Measles virus strain Moraten] | AAF85672.1 |
| fasion protein | fusion protein [Measles virus] | AAA56645.1 |
| fusion protein | fusion protein [Measles virus strain Rubeovax] | AAF85688.1 |
| fusion protein | fusion protein [Measles virus] | AAF85680.1 |
| fusion protein | fusion protein [Measles virus] | AEF30359.1 |
| fusion protein | fusion protein [Measles virus] | BAA09957.1 |
| fusion protein | fusion protein [Measles virus] | AAV84957.1 |
| fusion protein | fusion protein [Measles virus MeV-eGFP__Edm-tag] | AII16636.1 |
| fusion protein | fusion protein [Measles virus] | ABY58018.1 |
| fusion protein | fusion protein [Measles virus] | BAA19838.1 |
| fusion protein | fusion protein [Measles virus] | AAA56641.1 |
| fusion protein | F protein [Measles virus] | ABK40529.1 |
| fusion protein | fusion protein [Measles virus] | AAA56652.1 |
| fusion protein | fusion protein [Measles virus] | ABY58017.1 |
| fusion protein | fusion protein [Measles virus] | ABB71645.1 |
| fusion protein | fusion protein [Measles virus] | NP__056922.1 |
| fusion protein | fusion protein [Measles virus strain AIK-C] | AAF85664.1 |
| fusion protein | fusion protein [Measles virus] | BAB60865.1 |
| fusion protein | fusion protein [Measles virus] | BAA09950.1 |
| fusion protein | fusion protein [Measles virus strain MVi/New York.USA/26.09/3] | AEP40403.1 |
| fusion protein | fusion protein [Measles virus] | AAA74934.1 |

TABLE 15-continued

| MeV NCBI Accession Numbers (Amino Acid Sequences) | | |
|---|---|---|
| Type | Virus Name | GenBank Accession |
| fusion protein | fusion protein [Measles virus] | CAB38075.1 |
| fusion protein | fusion protein [Measles virus strain MVi/Texas.USA/4.07] | AEP40443.1 |
| fusion protein | fusion protein [Measles virus] | AAF02695.1 |
| fusion protein | fusion protein [Measles virus] | AAF02696.1 |
| fusion protein | fusion protein [Measles virus] | AAT99301.1 |
| fusion protein | fusion protein [Measles virus] | ABB71661.1 |
| fusion protein | fusion protein [Measles virus] | BAK08874.1 |
| fusion protein | fusion protein [Measles virus] | AAF02697.1 |
| fusion protein | fusion protein [Measles virus genotype D4] | AFY12704.1 |
| fusion protein | fusion protein [Measles virus strain MVi/California.USA/16.03] | AEP40467.1 |
| fusion protein | fusion protein [Measles virus genotype D8] | AHN07989.1 |
| fusion protein | fusion protein [Measles virus] | AAA46421.1 |
| fusion protein | fusion protein [Measles virus] | AAA56638.1 |
| fusion protein | fusion protein [Measles virus strain MVi/Virginia.USA/15.09] | AEP40419.1 |
| fusion protein | fusion protein [Measles virus genotype D8] | ALE27200.1 |
| fusion protein | fusion protein [Measles virus genotype D8] | AFY12695.1 |
| fusion protein | fusion protein [Measles virus genotype D8] | ALE27248.1 |
| fusion protein | fusion protein [Measles virus genotype D8] | ALE27224.1 |
| fusion protein | fusion protein [Measles virus] | AAT99300.1 |
| fusion protein | fusion protein [Measles virus] | BAH96592.1 |
| fusion protein | fusion protein [Measles virus strain MVi/California.USA/8.04] | AEP40459.1 |
| fusion protein | fusion protein [Measles virus genotype D8] | AIG94081.1 |
| fusion protein | fusion protein [Measles virus] | BAA09951.1 |
| fusion protein | fusion protein [Measles virus genotype D8] | ALE27194.1 |
| fusion protein | fusion protein [Measles virus] | BAA33871.1 |
| fusion protein | fusion protein [Measles virus strain MVi/Washington.USA/18.08/1] | AEP40427.1 |
| fusion protein | fusion protein [Measles virus] | ABY21182.1 |
| fusion protein | fusion protein [Measles virus genotype D8] | ALE27284.1 |
| fusion protein | fusion protein [Measles virus] | ACA09725.1 |
| fusion protein | fusion protein [Measles virus genotype D8] | ALE27314.1 |
| fusion protein | fusion protein [Measles virus genotype G3] | AFY12712.1 |
| fusion protein | fusion protein [Measles virus genotype D8] | ALE27368.1 |
| fusion protein | RecName: Full = Fusion glycoprotein F0; Contains: RecName: Full = Fusion glycoprotein F2; Contains: RecName: Full = Fusion glycoprotein F1; Flags: Precursor | P35973.1 |
| fusion protein | fusion protein [Measles virus genotype H1] | AIG53713.1 |
| | unnamed protein product [Measles virus] | CAA34588.1 |
| fusion protein | fusion protein [Measles virus] | CAA76888.1 |
| fusion protein | fusion protein [Measles virus genotype B3.1] | AIY55563.1 |
| fusion protein | fusion protein [Measles virus] | ADO17330.1 |
| fusion protein | fusion protein [Measles virus genotype H1] | AIG53703.1 |
| fusion protein | fusion protein [Measles virus genotype B3] | AGA17208.1 |
| fusion protein | fusion protein [Measles virus] | AAL29688.1 |
| fusion protein | fusion protein [Measles virus genotype H1] | AIG53706.1 |
| fusion protein | fusion protein [Measles virus genotype H1] | AIG53701.1 |
| fusion protein | fusion protein [Measles virus genotype B3] | ALE27092.1 |
| fusion protein | fusion protein [Measles virus genotype H1] | AIG53714.1 |
| fusion protein | fusion protein [Measles virus genotype H1] | AIG53694.1 |
| fusion protein | fusion protein [Measles virus genotype H1] | AIG53668.1 |
| fusion protein | fusion protein [Measles virus] | ACC86094.1 |
| fusion protein | fusion protein [Measles virus genotype H1] | AIG53670.1 |
| fusion protein | fusion protein [Measles virus genotype H1] | AIG53707.1 |
| fusion protein | fusion protein [Measles virus genotype B3] | AGA17216.1 |
| fusion protein | fusion protein [Measles virus genotype H1] | AIG53671.1 |
| fusion protein | fusion protein [Measles virus strain MVi/New Jersey.USA/45.05] | AEP40451.1 |
| fusion protein | fusion protein [Measles virus genotype H1] | AIG53684.1 |
| fusion protein | fusion protein [Measles virus genotype H1] | AIG53688.1 |
| fusion protein | fusion protein [Measles virus genotype B3] | AGA17214.1 |
| fusion protein | fusion protein [Measles virus genotype H1] | AIG53683.1 |
| fusion protein | fusion protein [Measles virus genotype H1] | AIG53667.1 |
| fusion protein | fusion protein [Measles virus genotype H1] | AIG53686.1 |
| fusion protein | fusion protein [Measles virus genotype H1] | AIG53685.1 |
| fusion protein | fusion protein [Measles virus genotype H1] | AIG53681.1 |
| | unnamed protein product [Measles virus] | CAA34589.1 |
| fusion protein | fusion protein [Measles virus genotype H1] | AIG53678.1 |
| fusion protein | fusion protein [Measles virus genotype H1] | AIG53710.1 |
| fusion protein | fusion protein [Measles virus genotype H1] | AIG53669.1 |
| fusion protein | fusion protein [Measles virus genotype H1] | AIG53664.1 |
| fusion protein | fusion protein [Measles virus] | AAA50547.1 |
| fusion protein | fusion protein [Measles virus genotype H1] | AIG53679.1 |

TABLE 15-continued

MeV NCBI Accession Numbers (Amino Acid Sequences)

| Type | Virus Name | GenBank Accession |
|---|---|---|
| fusion protein | fusion protein [Measles virus genotype H1] | AIG53709.1 |
| fusion protein | fusion protein [Measles virus genotype H1] | AIG53672.1 |
| fusion protein | fusion protein [Measles virus genotype H1] | AIG53697.1 |
| fusion protein | fusion protein [Measles virus genotype H1] | AIG53689.1 |
| fusion protein | fusion protein [Measles virus genotype H1] | AIG53676.1 |
| fusion protein | fusion protein [Measles virus genotype H1] | AIG53675.1 |
| fusion protein | fusion protein [Measles virus genotype H1] | AIG53663.1 |
| fusion protein | fusion protein [Measles virus] | BAA19841.1 |
| fusion protein | fusion protein [Measles virus] | AAF02701.1 |
| fusion protein | fusion protein [Measles virus genotype H1] | AIG53680.1 |
| fusion protein | fusion protein [Measles virus genotype H1] | AIG53674.1 |
| C protein | C protein [Measles virus strain Moraten] | AAF85670.1 |
| C protein | RecName: Full = Protein C | P03424.1 |
| C protein | C protein [Measles virus] | ACN54404.1 |
| C protein | C protein [Measles virus] | ACN54412.1 |
| C protein | RecName: Full = Protein C | P35977.1 |
| C protein | C protein [Measles virus] | AAF85678.1 |
| C protein | C protein [Measles virus] | ABD33998.1 |
| C protein | unnamed protein product [Measles virus] | CAA34586.1 |
| C protein | C protein [Measles virus] | BAJ51786.1 |
| C protein | C protein [Measles virus] | BAA33869.1 |
| C protein | virulence factor [Measles virus] | ABO69700.1 |
| C protein | C protein [Measles virus] | NP_056920.1 |
| C protein | C protein [Measles virus] | ADO17333.1 |
| C protein | C protein [Measles virus] | ACC86082.1 |
| C protein | C protein [Measles virus] | BAA33875.1 |
| C protein | C protein [Measles virus] | ABY21189.1 |
| C protein | C protein [Measles virus] | BAE98296.1 |
| C protein | C protein [Measles virus] | ADU17782.1 |
| C protein | C protein [Measles virus strain MVi/Virginia.USA/15.09] | AEP40417.1 |
| C protein | C protein [Measles virus] | ADU17814.1 |
| C protein | C protein [Measles virus] | ADU17798.1 |
| C protein | C protein [Measles virus genotype D4] | AFY12700.1 |
| C protein | C protein [Measles virus] | ADU17784.1 |
| C protein | C protein [Measles virus strain MVi/California.USA/16.03] | AEP40465.1 |
| C protein | C protein [Measles virus] | ABB71643.1 |
| C protein | C protein [Measles virus] | AEI91027.1 |
| C protein | C protein [Measles virus] | ADU17874.1 |
| C protein | C protein [Measles virus] | ADU17903.1 |
| C protein | C protein [Measles virus] | CAA34579.1 |
| C protein | C protein [Measles virus] | ADU17790.1 |
| C protein | C protein [Measles virus] | ADU17800.1 |
| C protein | C protein [Measles virus] | ABB71667.1 |
| C protein | unnamed protein product [Measles virus] | CAA34572.1 |
| C protein | C protein [Measles virus strain MVi/Arizona.USA/11.08/2] | AEP40433.1 |
| C protein | C protein [Measles virus] | ADU17830.1 |
| C protein | C protein [Measles virus] | ADU17947.1 |
| C protein | C protein [Measles virus] | ADU17818.1 |
| C protein | C protein [Measles virus strain MVi/New Jersey.USA/45.05] | AEP40449.1 |
| C protein | C protein [Measles virus strain MVi/Texas.USA/4.07] | AEP40441.1 |
| C protein | C protein [Measles virus] | ADU17864.1 |
| C protein | C protein [Measles virus] | ADU17838.1 |
| C protein | C protein [Measles virus] | ADU17881.1 |
| C protein | C protein [Measles virus strain MVi/Washington.USA/18.08/1] | AEP40425.1 |
| C protein | C protein [Measles virus] | ADU17927.1 |
| C protein | C protein [Measles virus] | ADU17953.1 |
| C protein | C protein [Measles virus] | ADU17889.1 |
| C protein | C protein [Measles virus] | ADU17963.1 |
| C protein | C protein [Measles virus] | ADU17893.1 |
| C protein | C protein [Measles virus] | ADU17820.1 |
| C protein | C protein [Measles virus] | ABB71651.1 |
| C protein | C protein [Measles virus] | ADU17786.1 |
| C protein | C protein [Measles virus] | ADU17862.1 |
| C protein | C protein [Measles virus] | ADU17923.1 |
| C protein | C protein [Measles virus] | ADU17959.1 |
| C protein | C protein [Measles virus] | ADU17951.1 |
| C protein | C protein [Measles virus] | ADU17916.1 |
| C protein | C protein [Measles virus] | ADU17957.1 |
| C protein | C protein [Measles virus] | ADU17925.1 |
| C protein | C protein [Measles virus] | ADU17901.1 |

TABLE 15-continued

MeV NCBI Accession Numbers (Amino Acid Sequences)

| Type | Virus Name | GenBank Accession |
|---|---|---|
| C protein | C protein [Measles virus] | ADU17887.1 |
| C protein | C protein [Measles virus] | ADU17832.1 |
| C protein | C protein [Measles virus] | ADU17891.1 |
| C protein | C protein [Measles virus] | ADU17961.1 |
| C protein | C protein [Measles virus] | ADU17872.1 |
| C protein | C protein [Measles virus] | ADU17929.1 |
| C protein | C protein [Measles virus] | ADU17908.1 |
| C protein | C protein [Measles virus] | ADU17910.1 |
| C protein | C protein [Measles virus] | ADU17921.1 |
| C protein | C protein [Measles virus] | ADU17824.1 |
| C protein | C protein [Measles virus strain MVi/Pennsylvania.USA/20.09] | AEP40473.1 |
| C protein | C protein [Measles virus] | ADU17828.1 |
| C protein | C protein [Measles virus] | ADU17812.1 |
| C protein | C protein [Measles virus genotype D8] | AFY12692.1 |
| C protein | nonstructural C protein [Measles virus] | ABA59559.1 |
| C protein | RecName: Full = Protein C | Q00794.1 |
| C protein | nonstructural C protein [Measles virus] | ADO17934.1 |
| C protein | nonstructural C protein [Measles virus] | ACJ66773.1 |
| C protein | C protein [Measles virus genotype G3] | AFY12708.1 |
| C protein | RecName: Full = Protein C | P26035.1 |
| C protein | C protein [Measles virus] | BAA84128.1 |
| nucleoprotein | RecName: Full = Nucleoprotein; AltName: Full = Nucleocapsid protein; Short = NP; Short = Protein N | Q77M43.1 |
| nucleoprotein | nucleocapsid protein [Measles virus strain Rubeovax] | AAF85683.1 |
| nucleoprotein | RecName: Full = Nucleoprotein; AltName: Full = Nucleocapsid protein; Short = NP; Short = Protein N | Q89933.1 |
| nucleoprotein | nucleocapsid protein [Measles virus strain AIK-C] | AAF85659.1 |
| nucleoprotein | nucleoprotein [Measles virus] | ABI54102.1 |
| nucleoprotein | nucleoprotein [Measles virus] | AAA56643.1 |
| nucleoprotein | nucleoprotein [Measles virus] | AAC03050.1 |
| nucleoprotein | nucleoprotein [Measles virus] | AAA18990.1 |
| nucleoprotein | nucleoprotein [Measles virus] | AAA56640.1 |
| nucleoprotein | RecName: Full = Nucleoprotein; AltName: Full = Nucleocapsid protein; Short = NP; Short = Protein N | P35972.1 |
| nucleoprotein | RecName: Full=Nucleoprotein; AltName: Full = Nucleocapsid protein; Short = NP; Short = Protein N | P10050.1 |
| nucleoprotein | N protein [Measles virus] | BAB60956.1 |
| nucleoprotein | RecName: Full = Nucleoprotein; AltName: Full = Nucleocapsid protein; Short = NP; Short = Protein N | B1AAA7.1 |
| nucleoprotein | nucleoprotein [Measles virus] | AAA18991.1 |
| nucleoprotein | nucleoprotein [Measles virus] | CAB46894.1 |
| nucleoprotein | nucleoprotein [Measles virus] | CAB46871.1 |
| nucleoprotein | nucleoprotein [Measles virus] | CAB46872.1 |
| nucleoprotein | nucleoprotein [Measles virus] | ABU49606.1 |
| nucleoprotein | nucleocapsid protein [Measles virus] | AAA75494.1 |
| nucleoprotein | nucleoprotein [Measles virus] | CAB46883.1 |
| nucleoprotein | nucleoprotein [Measles virus] | CAB46892.1 |
| nucleoprotein | unnamed protein product [Measles virus] | CAA34584.1 |
| nucleoprotein | nucleoprotein [Measles virus] | AAA18997.1 |
| nucleoprotein | nucleoprotein [Measles virus] | CAB46863.1 |
| nucleoprotein | nucleoprotein [Measles virus] | AEF30352.1 |
| nucleoprotein | nucleoprotein [Measles virus] | ABI54103.1 |
| nucleoprotein | nucleocapsid protein [Measles virus] | AAA46433.1 |
| nucleoprotein | nucleoprotein [Measles virus] | CAB46902.1 |
| nucleoprotein | nucleoprotein [Measles virus] | CAB46873.1 |
| nucleoprotein | nucleoprotein [Measles virus] | CAB46906.1 |
| nucleoprotein | nucleoprotein [Measles virus] | AAA74547.1 |
| nucleoprotein | nucleoprotein [Measles virus] | AAA74537.1 |
| nucleoprotein | nucleoprotein [Measles virus] | CAB46862.1 |
| nucleoprotein | nucleocapsid protein [Measles virus] | BAA09961.1 |
| nucleoprotein | nucleoprotein [Measles virus] | AAO15875.1 |
| nucleoprotein | nucleoprotein [Measles virus] | AAO15871.1 |
| nucleoprotein | nucleoprotein [Measles virus] | CAB46882.1 |
| nucleoprotein | nucleoprotein [Measles virus] | CAB60124.1 |
| nucleoprotein | nucleoprotein [Measles virus] | ABI54104.1 |
| nucleoprotein | nucleoprotein [Measles virus] | CAB46869.1 |
| nucleoprotein | nucleoprotein [Measles virus] | CAB46880.1 |
| nucleoprotein | nucleoprotein [Measles virus] | AAA74541.1 |
| nucleoprotein | nucleocapsid protein [Measles virus strain MVi/New Jersey.USA/45.05] | AEP40446.1 |

TABLE 15-continued

| MeV NCBI Accession Numbers (Amino Acid Sequences) | | |
|---|---|---|
| Type | Virus Name | GenBank Accession |
| nucleoprotein | nucleoprotein [Measles virus] | ABI54110.1 |
| nucleoprotein | nucleoprotein [Measles virus] | CAB46903.1 |
| nucleoprotein | nucleoprotein [Measles virus] | CAB46899.1 |
| nucleoprotein | nucleoprotein [Measles virus] | CAB46901.1 |
| nucleoprotein | nucleocapsid protein [Measles virus] | ABB71640.1 |
| nucleoprotein | nucleoprotein [Measles virus] | CAB60113.1 |
| nucleoprotein | nucleoprotein [Measles virus] | CAB60114.1 |
| nucleoprotein | nucleoprotein [Measles virus] | CAB60116.1 |
| nucleoprotein | nucleoprotein [Measles virus] | CAB46895.1 |
| nucleoprotein | nucleoprotein [Measles virus] | CAB60121.1 |
| nucleoprotein | nucleoprotein [Measles virus] | ABI54111.1 |
| nucleoprotein | nucleoprotein [Measles virus] | CAB46889.1 |
| nucleoprotein | nucleoprotein [Measles virus] | CAB46898.1 |
| nucleoprotein | nucleoprotein [Measles virus genotype B3] | ALE27083.1 |
| nucleoprotein | nucleoprotein [Measles virus] | CAB60118.1 |
| nucleoprotein | nucleocapsid protein [Measles virus] | CAA34570.1 |
| nucleoprotein | nucleoprotein [Measles virus] | AAC29443.1 |
| nucleoprotein | nucleocapsid protein [Measles virus strain MVi/Washington.USA/18.08/1] | AEP40422.1 |
| nucleoprotein | nucleoprotein [Measles virus] | AAO15872.1 |
| nucleoprotein | nucleoprotein [Measles virus] | CAB46874.1 |
| nucleoprotein | nucleoprotein [Measles virus] | AAA74550.1 |
| nucleoprotein | nucleocapsid protein [Measles virus] | ABB71648.1 |
| nucleoprotein | nucleoprotein [Measles virus] | CAB46900.1 |
| nucleoprotein | nucleoprotein [Measles virus] | BAH22440.1 |
| nucleoprotein | nucleocapsid protein [Measles virus] | AAA46432.1 |
| nucleoprotein | nucleocapsid protein [Measles virus] | BAA33867.1 |
| nucleoprotein | nucleoprotein [Measles virus] | AAA74539.1 |
| nucleoprotein | nucleoprotein [Measles virus] | CAB60115.1 |
| nucleoprotein | nucleoprotein [Measles virus] | CAB60123.1 |
| nucleoprotein | nucleocapsid protein [Measles virus] | ABB71664.1 |
| nucleoprotein | nucleoprotein [Measles virus] | CAB60125.1 |
| nucleoprotein | nucleoprotein [Measles virus] | AAA74546.1 |
| nucleoprotein | nucleoprotein [Measles virus] | CAB46886.1 |
| nucleoprotein | nucleoprotein [Measles virus] | BAH22350.1 |
| nucleoprotein | nucleoprotein [Measles virus] | CAB46867.1 |
| nucleoprotein | nucleocapsid protein [Measles virus] | BAA09954.1 |
| nucleoprotein | nucleoprotein [Measles virus] | AAO15873.1 |
| nucleoprotein | nucleocapsid protein [Measles virus] | AEP95735.1 |
| nucleoprotein | nucleoprotein [Measles virus] | AAL37726.1 |
| nucleoprotein | nucleoprotein [Measles virus] | AAA74549.1 |
| nucleoprotein | RecName: Full = Nucleoprotein; AltName: Full = Nucleocapsid protein; Short = NP; Short = Protein N | P26030.1 |
| nucleoprotein | nucleoprotein [Measles virus ETH55/99] | AAK07777.1 |
| nucleoprotein | nucleoprotein [Measles virus genotype B3] | AGA17238.1 |
| nucleoprotein | nucleoprotein [Measles virus] | AEF30351.1 |
| nucleoprotein | nucleoprotein [Measles virus genotype B3] | AGA17242.1 |
| nucleoprotein | nucleoprotein [Measles virus ETH54/98] | AAK07776.1 |
| nucleoprotein | nucleoprotein [Measles virus] | AAA74548.1 |
| nucleoprotein | nucleoprotein [Measles virus] | AAA19221.1 |
| nucleoprotein | nucleoprotein [Measles virus] | AAC03039.1 |
| nucleoprotein | nucleoprotein [Measles virus] | AAA19223.1 |
| nucleoprotein | nucleoprotein [Measles virus genotype B3] | AGA17241.1 |
| nucleoprotein | nucleoprotein [Measles virus] | CAB60122.1 |
| nucleoprotein | nucleoprotein [Measles virus] | CAC34599.1 |
| nucleoprotein | nucleoprotein [Measles virus] | AAC03042.1 |
| nucleoprotein | nucleoprotein [Measles virus] | CAC34604.1 |
| nucleoprotein | nucleoprotein [Measles virus] | AAA74544.1 |
| nucleoprotein | nucleocapsid protein [Measles virus] | NP_056918.1 |
| V Protein | RecName: Full = Non-structural protein V | Q9IC37.1 |
| V Protein | RecName: Full = Non-structural protein V | Q9EMA9.1 |
| V Protein | V protein [Measles virus] | ACN54411.1 |
| V Protein | V protein [Measles virus] | ACN54403.1 |
| V Protein | V protein [Measles virus] | AEP95742.1 |
| V Protein | V protein [Measles virus strain MVi/Virginia.USA/15.09] | AEP40416.1 |
| V Protein | V protein [Measles virus] | ADU17801.1 |
| V Protein | V protein [Measles virus] | ADU17849.1 |
| V Protein | V protein [Measles virus] | ABB71642.1 |
| V Protein | V protein [Measles virus genotype D8] | AFY12693.1 |
| V Protein | V protein [Measles virus] | YP_003873249.2 |
| V Protein | V protein [Measles virus strain MVi/Arizona.USA/11.08/2] | AEP40432.1 |
| V Protein | RecName: Full = Non-structural protein V | P26036.1 |

TABLE 15-continued

| MeV NCBI Accession Numbers (Amino Acid Sequences) | | |
|---|---|---|
| Type | Virus Name | GenBank Accession |
| V Protein | V protein [Measles virus strain MVi/California.USA/16.03] | AEP40464.1 |
| V Protein | V protein [Measles virus strain MVi/California.USA/8.04] | AEP40456.1 |
| V Protein | V protein [Measles virus] | ABY21188.1 |
| V Protein | V protein [Measles virus strain MVi/Washington.USA/18.08/1] | AEP40424.1 |
| V Protein | V protein [Measles virus] | BAH96581.1 |
| V Protein | V protein [Measles virus] | ABB71666.1 |
| V Protein | RecName: Full = Non-structural protein V | P60168.1 |
| V Protein | V protein [Measles virus] | BAH96589.1 |
| V Protein | V protein [Measles virus] | ADU17954.1 |
| V Protein | V protein [Measles virus strain MVi/New York.USA/26.09/3] | AEP40400.1 |
| V Protein | V protein [Measles virus] | ABY21196.1 |
| V Protein | virulence factor [Measles virus] | ABO69701.1 |
| V Protein | V protein [Measles virus] | ABB71650.1 |
| V Protein | V protein [Measles virus] | ACC86086.1 |
| V Protein | V protein [Measles virus genotype D4] | AFY12702.1 |
| V Protein | V protein [Measles virus strain MVi/New Jersey.USA/45.05] | AEP40448.1 |
| V Protein | V protein [Measles virus] | BAE98295.1 |
| V Protein | V protein [Measles virus] | ACC86083.1 |
| V Protein | V protein [Measles virus] | ACU5139.1 |
| V Protein | V protein [Measles virus] | ADO17334.1 |
| V Protein | V protein [Measles virus] | ADU17930.1 |
| V Protein | V protein [Measles virus genotype G3] | AFY12710.1 |
| V Protein | V protein [Measles virus strain MVi/Pennsylvania.USA/20.09] | AEP40472.1 |
| V Protein | phosphoprotein [Measles virus] | ADU17839.1 |
| V Protein | V protein [Measles virus] | ADU17894.1 |
| V Protein | V protein [Measles virus] | ACN50010.1 |
| V Protein | V protein [Measles virus] | ADU17892.1 |
| | unnamed protein product [Measles virus] | CAA34585.1 |
| V Protein | V protein [Measles virus] | ABD33997.1 |

TABLE 16

| Flagellin Nucleic Acid Sequences | | |
|---|---|---|
| Name | Sequence | SEQ ID NO: |
| NT (5' UTR, ORF, 3' UTR) | TCAAGCTTTTGGACCCTCGTACAGAAGCTAATACGACTCACTAT AGGGAAATAAGAGAGAAAAGAAGAGTAAGAAGAAATATAAG AGCCACCATGGCACAAGTCATTAATACAAACAGCCTGTCGCTG TTGACCCAGAATAACCTGAACAAATCCCAGTCCGCACTGGGCA CTGCTATCGAGCGTTTGTCTTCCGGTCTGCGTATCAACAGCGCG AAAGACGATGCGGCAGGACAGGCGATTGCTAACCGTTTTACCG CGAACATCAAAGGTCTGACTCAGGCTTCCCGTAACGCTAACGA CGGTATCTCCATTGCGCAGACCACTGAAGGCGCGCTGAACGAA ATCAACAACAACCTGCAGCGTGTGCGTGAACTGGCGGTTCAGT CTGCGAATGGTACTAACTCCCAGTCTGACCTCGACTCCATCCAG GCTGAAATCACCCAGCGCCTGAACGAAATCGACCGTGTATCCG GCCAGACTCAGTTCAACGGCGTGAAAGTCCTGGCGCAGGACAA CACCCTGACCATCCAGGTTGGTGCCAACGACGGTGAAACTATC GATATTGATTTAAAAGAAATCAGCTCTAAAACACTGGGACTTG ATAAGCTTAATGTCCAAGATGCCTACACCCCGAAAGAAACTGC TGTAACCGTTGATAAAACTACCTATAAAAATGGTACAGATCCT ATTACAGCCCAGAGCAATACTGATATCCAAACTGCAATTGGCG GTGGTGCAACGGGGGTTACTGGGGCTGATATCAAATTTAAAGA TGGTCAATACTATTTAGATGTTAAAGGCGGTGCTTCTGCTGGTG TTTATAAAGCCACTTATGATGAAACTACAAAGAAAGTTAATAT TGATACGACTGATAAAACTCCGTTGGCAACTGCGGAAGCTACA GCTATTCGGGGAACGGCCACTATAACCCACAACCAAATTGCTG AAGTAACAAAAGAGGGTGTTGATACGACCACAGTTGCGGCTCA ACTTGCTGCAGCAGGGGTTACTGGCGCCGATAAGGACAATACT AGCCTTGTAAAACTATCGTTTGAGGATAAAAACGGTAAGGTTA TTGATGGTGGCTATGCAGTGAAAATGGGCGACGATTTCTATGC CGCTACATATGATGAGAAAACAGGTGCAATTACTGCTAAAACC ACTACTTATACAGATGGTACTGGCGTTGCTCAAACTGGAGCTGT GAAATTTGGTGGCGCAAATGGTAAATCTGAAGTTGTTACTGCT ACCGATGGTAAGACTTACTTAGCAAGCGACCTTGACAAACATA | 51 |

TABLE 16-continued

| Name | Sequence | SEQ ID NO: |
| --- | --- | --- |
| | ACTTCAGAACAGGCGGTGAGCTTAAAGAGGTTAATACAGATAA<br>GACTGAAAACCCACTGCAGAAAATTGATGCTGCCTTGGCACAG<br>GTTGATACACTTCGTTCTGACCTGGGTGCGGTTCAGAACCGTTT<br>CAACTCCGCTATCACCAACCTGGGCAATACCGTAAATAACCTG<br>TCTTCTGCCCGTAGCCGTATCGAAGATTCCGACTACGCAACCGA<br>AGTCTCCAACATGTCTCGCGCGCAGATTCTGCAGCAGGCCGGT<br>ACCTCCGTTCTGGCGCAGGCGAACCAGGTTCCGCAAAACGTCC<br>TCTCTTTACTGCGTTGATAATAGGCTGGAGCCTCGGTGGCCATG<br>CTTCTTGCCCCTTGGGCCTCCCCCCAGCCCCTCCTCCCCTTCCTG<br>CACCCGTACCCCCGTGGTCTTTGAATAAAGTCTGAGTGGGCGG<br>C | |
| ORF Sequence, NT | ATGGCACAAGTCATTAATACAAACAGCCTGTCGCTGTTGACCC<br>AGAATAACCTGAACAAATCCCAGTCCGCACTGGGCACTGCTAT<br>CGAGCGTTTGTCTTCCGGTCTGCGTATCAACAGCGCGAAAGAC<br>GATGCGGCAGGACAGGCGATTGCTAACCGTTTTACCGCGAACA<br>TCAAAGGTCTGACTCAGGCTTCCCGTAACGCTAACGACGGTAT<br>CTCCATTGCGCAGACCACTGAAGGCGCGCTGAACGAAATCAAC<br>AACAACCTGCAGCGTGTGCGTGAACTGGCGGTTCAGTCTGCGA<br>ATGGTACTAACTCCCAGTCTGACCTCGACTCCATCCAGGCTGAA<br>ATCACCCAGCGCCTGAACGAAATCGACCGTGTATCCGGCCAGA<br>CTCAGTTCAACGGCGTGAAAGTCCTGGCGCAGGACAACACCCT<br>GACCATCCAGGTTGGTGCCAACGACGGTGAAACTATCGATATT<br>GATTTAAAAGAAATCAGCTCTAAAACACTGGGACTTGATAAGC<br>TTAATGTCCAAGATGCCTACACCCCGAAAGAAACTGCTGTAAC<br>CGTTGATAAAACTACCTATAAAAATGGTACAGATCCTATTACA<br>GCCCAGAGCAATACTGATATCCAAACTGCAATTGGCGGTGGTG<br>CAACGGGGGTTACTGGGGCTGATATCAAATTTAAAGATGGTCA<br>ATACTATTTAGATGTTAAAGGCGGTGCTTCTGCTGGTGTTTATA<br>AAGCCACTTATGATGAAACTACAAAGAAAGTTAATATTGATAC<br>GACTGATAAAACTCCGTTGGCAACTGCGGAAGCTACAGCTATT<br>CGGGGAACGGCCACTATAACCCACAACCAAATTGCTGAAGTAA<br>CAAAAGAGGGTGTTGATACGACCACAGTTGCGGCTCAACTTGC<br>TGCAGCAGGGGTTACTGGCGCCGATAAGGACAATACTAGCCTT<br>GTAAAACTATCGTTTGAGGATAAAAACGGTAAGGTTATTGATG<br>GTGGCTATGCAGTGAAAATGGGCGACGATTTCTATGCCGCTAC<br>ATATGATGAGAAAACAGGTGCAATTACTGCTAAAACCACTACT<br>TATACAGATGGTACTGGCGTTGCTCAAACTGGAGCTGTGAAAT<br>TTGGTGGCGCAAATGGTAAATCTGAAGTTGTTACTGCTACCGAT<br>GGTAAGACTTACTTAGCAAGCGACCTTGACAAACATAACTTCA<br>GAACAGGCGGTGAGCTTAAAGAGGTTAATACAGATAAGACTG<br>AAAACCCACTGCAGAAAATTGATGCTGCCTTGGCACAGGTTGA<br>TACACTTCGTTCTGACCTGGGTGCGGTTCAGAACCGTTTCAACT<br>CCGCTATCACCAACCTGGGCAATACCGTAAATAACCTGTCTTCT<br>GCCCGTAGCCGTATCGAAGATTCCGACTACGCAACCGAAGTCT<br>CCAACATGTCTCGCGCGCAGATTCTGCAGCAGGCCGGTACCTC<br>CGTTCTGGCGCAGGCGAACCAGGTTCCGCAAAACGTCCTCTCTT<br>TACTGCGT | 52 |
| mRNA Sequence (assumes T100 tail) | G*GGGAAAUAAGAGAGAAAAGAAGAGUAAGAAGAAAUAUAA<br>GAGCCACCAUGGCACAAGUCAUUAAUACAAACAGCCUGUCGC<br>UGUUGACCCAGAAUAACCUGAACAAAUCCCAGUCCGCACUGG<br>GCACUGCUAUCGAGCGUUUGUCUUCCGGUCUGCGUAUCAACA<br>GCGCGAAAGACGAUGCGGCAGGACAGGCGAUUGCUAACCGUU<br>UUACCGCGAACAUCAAAGGUCUGACUCAGGCUUCCCGUAACG<br>CUAACGACGGUAUCUCCAUUGCGCAGACCACUGAAGGCGCGC<br>UGAACGAAAUCAACAACAACCUGCAGCGUGUGCGUGAACUGG<br>CGGUUCAGUCUGCGAAUGGUACUAACUCCCAGUCUGACCUCG<br>ACUCCAUCCAGGCUGAAAUCACCCAGCGCCUGAACGAAAUCG<br>ACCGUGUAUCCGGCCAGACUCAGUUCAACGGCGUGAAAGUCC<br>UGGCGCAGGACAACACCCUGACCAUCCAGGUUGGUGCCAACG<br>ACGGUGAAACUAUCGAUAUUGAUUUAAAAGAAAUCAGCUCU<br>AAAACACUGGGACUUGAUAAGCUUAAUGUCCAAGAUGCCUAC<br>ACCCCGAAAGAAACUGCUGUAACCGUUGAUAAAACUACCUAU<br>AAAAAUGGUACAGAUCCUAUUACAGCCCAGAGCAAUACUGAU<br>AUCCAAACUGCAAUUGGCGGUGGUGCAACGGGGGUUACUGG<br>GGCUGAUAUCAAAUUUAAAGAUGGUCAAUACUAUUUAGAUG<br>UUAAAGGCGGUGCUUCUGCUGGUGUUUAUAAAGCCACUUAU<br>GAUGAAACUACAAAGAAAGUUAAUAUUGAUACGACUGAUAA<br>AACUCCGUUGGCAACUGCGGAAGCUACAGCUAUUCGGGGAAC<br>GGCCACUAUAACCCACAACCAAAUUGCUGAAGUAACAAAAGA<br>GGGUGUUGAUACGACCACAGUUGCGGCUCAACUUGCUGCAGC<br>AGGGGUUACUGGCGCCGAUAAGGACAAUACUAGCCUUGUAA<br>AACUAUCGUUUGAGGAUAAAAACGGUAAGGUUAUUGAUGGU<br>GGCUAUGCAGUGAAAAUGGGCGACGAUUUCUAUGCCGCUACA | 53 |

TABLE 16-continued

Flagellin Nucleic Acid Sequences

| Name | Sequence | SEQ ID NO: |
|---|---|---|
| | UAUGAUGAGAAAACAGGUGCAAUUACUGCUAAAACCACUAC<br>UUAUACAGAUGGUACUGGCGUUGCUCAAACUGGAGCUGUGA<br>AAUUUGGUGGCGCAAAUGGUAAAUCUGAAGUUGUUACUGCU<br>ACCGAUGGUAAGACUUACUUAGCAAGCGACCUUGACAAACAU<br>AACUUCAGAACAGGCGGUGAGCUUAAAGAGGUUAAUACAGA<br>UAAGACUGAAAACCCACUGCAGAAAAUUGAUGCUGCCUUGGC<br>ACAGGUUGAUACACUUCGUUCUGACCUGGGUGCGGUUCAGAA<br>CCGUUUCAACUCCGCUAUCACCAACCUGGGCAAUACCGUAAA<br>UAACCUGUCUUCUGCCCGUAGCCGUAUCGAAGAUUCCGACUA<br>CGCAACCGAAGUCUCCAACAUGUCUCGCGCGCAGAUUCUGCA<br>GCAGGCCGGUACCUCCGUUCUGGCGCAGGCGAACCAGGUUCC<br>GCAAAACGUCCUCUCUUUACUGCGUUGAUAAUAGGCUGGAGC<br>CUCGGUGGCCAUGCUUCUUGCCCCUUGGGCCUCCCCCCAGCC<br>CCUCCUCCCCUUCCUGCACCCGUACCCCCGUGGUCUUUGAAU<br>AAAGUCUGAGUGGGCGGCAAAAAAAAAAAAAAAAAAAAAAAA<br>AAAAAAAAAAAAAAAAAAAAAAAAAAAAAAAAAAAAAAAAAA<br>AAAAAAAAAAAAAAAAAAAAAAAAAAAAAAAAAAAAAUCUAG | |

Flagellin mRNA Sequences

| Name | Sequence | SEQ ID NO: |
|---|---|---|
| NT (5' UTR, ORF, 3' UTR) | UCAAGCUUUUGGACCCUCGUACAGAAGCUAAUACGACUCACU<br>AUAGGGAAAUAAGAGAGAAAAGAAGAGUAAGAAGAAAUAUA<br>AGAGCCACCAUGGCACAAGUCAUUAAUACAAACAGCCUGUCG<br>CUGUUGACCCAGAAUAACCUGAACAAAUCCCAGUCCGCACUG<br>GGCACUGCUAUCGAGCGUUUGUCUUCCGGUCUGCGUAUCAAC<br>AGCGCGAAAGACGAUGCGGCAGGACAGGCGAUUGCUAACCGU<br>UUUACCGCGAACAUCAAAGGUCUGACUCAGGCUUCCCGUAAC<br>GCUAACGACGGUAUCUCCAUUGCGCAGACCACUGAAGGCGCG<br>CUGAACGAAAUCAACAACAACCUGCAGCGUGUGCGUGAACUG<br>GCGGUUCAGUCUGCGAAUGGUACUAACUCCCAGUCUGACCUC<br>GACUCCAUCCAGGCUGAAAUCACCCAGCGCCUGAACGAAAUC<br>GACCGUGUAUCCGGCCAGACUCAGUUCAACGGCGUGAAAGUC<br>CUGGCGCAGGACAACACCCUGACCAUCCAGGUUGGUGCCAAC<br>GACGGUGAAACUAUCGAUAUUGAUUUAAAAGAAAUCAGCUC<br>UAAAACACUGGGACUUGAUAAGCUUAAUGUCCAAGAUGCCU<br>ACACCCCGAAAGAAACUGCUGUAACCGUUGAUAAAACUACCU<br>AUAAAAAUGGUACAGAUCCUAUUACAGCCCAGAGCAAUACUG<br>AUAUCCAAACUGCAAUUGGCGGUGGUGCAACGGGGGUUACU<br>GGGGCUGAUAUCAAAUUUAAAGAUGGUCAAUACUAUUUAGA<br>UGUUAAAGGCGGUGCUUCUGCUGGUGUUUAUAAAGCCACUU<br>AUGAUGAAACUACAAAGAAAGUUAAUAUUGAUACGACUGAU<br>AAAACUCCGUUGGCAACUGCGGAAGCUACAGCUAUUCGGGGA<br>ACGGCCACUAUAACCCACAACCAAAUUGCUGAAGUAACAAAA<br>GAGGGUGUUGAUACGACCACAGUUGCGGCUCAACUUGCUGCA<br>GCAGGGGUUACUGGCGCCGAUAAGGACAAUACUAGCCUUGUA<br>AAACUAUCGUUUGAGGAUAAAAACGGUAAGGUUAUUGAUGG<br>UGGCUAUGCAGUGAAAAUGGGCGACGAUUUCUAUGCCGCUAC<br>AUAUGAUGAGAAAACAGGUGCAAUUACUGCUAAAACCACUA<br>CUUAUACAGAUGGUACUGGCGUUGCUCAAACUGGAGCUGUG<br>AAAUUUGGUGGCGCAAAUGGUAAAUCUGAAGUUGUUACUGC<br>UACCGAUGGUAAGACUUACUUAGCAAGCGACCUUGACAAACA<br>UAACUUCAGAACAGGCGGUGAGCUUAAAGAGGUUAAUACAG<br>AUAAGACUGAAAACCCACUGCAGAAAAUUGAUGCUGCCUUGG<br>CACAGGUUGAUACACUUCGUUCUGACCUGGGUGCGGUUCAGA<br>ACCGUUUCAACUCCGCUAUCACCAACCUGGGCAAUACCGUAA<br>AUAACCUGUCUUCUGCCCGUAGCCGUAUCGAAGAUUCCGACU<br>ACGCAACCGAAGUCUCCAACAUGUCUCGCGCGCAGAUUCUGC<br>AGCAGGCCGGUACCUCCGUUCUGGCGCAGGCGAACCAGGUUC<br>CGCAAAACGUCCUCUCUUUACUGCGUUGAUAAUAGGCUGGAG<br>CCUCGGUGGCCAUGCUUCUUGCCCCUUGGGCCUCCCCCCAGC<br>CCCUCCUCCCCUUCCUGCACCCGUACCCCCGUGGUCUUUGAA<br>UAAAGUCUGAGUGGGCGGC | 81 |
| ORF Sequence, NT | AUGGCACAAGUCAUUAAUACAAACAGCCUGUCGCUGUUGACC<br>CAGAAUAACCUGAACAAAUCCCAGUCCGCACUGGGCACUGCU<br>AUCGAGCGUUUGUCUUCCGGUCUGCGUAUCAACAGCGCGAAA<br>GACGAUGCGGCAGGACAGGCGAUUGCUAACCGUUUUACCGCG<br>AACAUCAAAGGUCUGACUCAGGCUUCCCGUAACGCUAACGAC<br>GGUAUCUCCAUUGCGCAGACCACUGAAGGCGCGCUGAACGAA<br>AUCAACAACAACCUGCAGCGUGUGCGUGAACUGGCGGUUCAG<br>UCUGCGAAUGGUACUAACUCCCAGUCUGACCUCGACUCCAUC<br>CAGGCUGAAAUCACCCAGCGCCUGAACGAAAUCGACCGUGUA<br>UCCGGCCAGACUCAGUUCAACGGCGUGAAAGUCCUGGCGCAG<br>GACAACACCCUGACCAUCCAGGUUGGUGCCAACGACGGUGAA<br>ACUAUCGAUAUUGAUUUAAAAGAAAUCAGCUCUAAAACACU | 82 |

TABLE 16-continued

| Flagellin Nucleic Acid Sequences | | |
|---|---|---|
| Name | Sequence | SEQ ID NO: |
| | GGGACUUGAUAAGCUUAAUGUCCAAGAUGCCUACACCCCGAA AGAAACUGCUGUAACCGUUGAUAAAACUACCUAUAAAAAUG GUACAGAUCCUAUUACAGCCCAGAGCAAUACUGAUAUCCAAA CUGCAAUUGGCGGUGGUGCAACGGGGGUUACUGGGGCUGAU AUCAAAUUUAAAGAUGGUCAAUACUAUUUAGAUGUUAAAGG CGGUGCUUCUGCUGGUGUUUAUAAAGCCACUUAUGAUGAAA CUACAAAGAAAGUUAAUAUUGAUACGACUGAUAAAACUCCG UUGGCAACUGCGGAAGCUACAGCUAUUCGGGGAACGGCCACU AUAACCCACAACCAAAUUGCUGAAGUAACAAAAGAGGGUGU UGAUACGACCACAGUUGCGGCUCAACUUGCUGCAGCAGGGGU UACUGGCGCCGAUAAGGACAAUACUAGCCUUGUAAAACUAUC GUUUGAGGAUAAAAACGGUAAGGUUAUUGAUGGUGGCUAUG CAGUGAAAAUGGGCGACGAUUUCUAUGCCGCUACAUAUGAU GAGAAAACAGGUGCAAUUACUGCUAAAACCACUACUUAUACA GAUGGUACUGGCGUUGCUCAAACUGGAGCUGUGAAAUUUGG UGGCGCAAAUGGUAAAUCUGAAGUUGUUACUGCUACCGAUG GUAAGACUUACUUAGCAAGCGACCUUGACAAACAUAACUUCA GAACAGGCGGUGAGCUUAAAGAGGUUAAUACAGAUAAGACU GAAAACCCACUGCAGAAAAUUGAUGCUGCCUUGGCACAGGUU GAUACACUUCGUUCUGACCUGGGUGCGGUUCAGAACCGUUUC AACUCCGCUAUCACCAACCUGGGCAAUACCGUAAAUAACCUG UCUUCUGCCCGUAGCCGUAUCGAAGAUUCCGACUACGCAACC GAAGUCUCCAACAUGUCUCGCGCGCAGAUUCUGCAGCAGGCC GGUACCUCCGUUCUGGCGCAGGCGAACCAGGUUCCGCAAAAC GUCCUCUCUUUACUGCGU | |
| mRNA Sequence (assumes T100 tail) | G*GGGAAAUAAGAGAGAAAAGAAGAGUAAGAAGAAAUAUAA GAGCCACCAUGGCACAAGUCAUUAAUACAAACAGCCUGUCGC UGUUGACCCAGAAUAACCUGAACAAAUCCCAGUCCGCACUGG GCACUGCUAUCGAGCGUUUGUCUUCCGGUCUGCGUAUCAACA GCGCGAAAGACGAUGCGGCAGGACAGGCGAUUGCUAACCGUU UUACCGCGAACAUCAAAGGUCUGACUCAGGCUUCCCGUAACG CUAACGACGGUAUCUCCAUUGCGCAGACCACUGAAGGCGCGC UGAACGAAAUCAACAACAACCUGCAGCGUGUGCGUGAACUGG CGGUUCAGUCUGCGAAUGGUACUAACUCCCAGUCUGACCUCG ACUCCAUCCAGGCUGAAAUCACCCAGCGCCUGAACGAAAUCG ACCGUGUAUCCGGCCAGACUCAGUUCAACGGCGUGAAAGUCC UGGCGCAGGACAACACCCUGACCAUCCAGGUUGGUGCCAACG ACGGUGAAACUAUCGAUAUUGAUUUAAAAGAAAUCAGCUCU AAAACACUGGGACUUGAUAAGCUUAAUGUCCAAGAUGCCUAC ACCCCGAAAGAAACUGCUGUAACCGUUGAUAAAACUACCUAU AAAAAUGGUACAGAUCCUAUUACAGCCCAGAGCAAUACUGAU AUCCAAACUGCAAUUGGCGGUGGUGCAACGGGGGUUACUGG GGCUGAUAUCAAAUUUAAAGAUGGUCAAUACUAUUUAGAUG UUAAAGGCGGUGCUUCUGCUGGUGUUUAUAAAGCCACUUAU GAUGAAACUACAAAGAAAGUUAAUAUUGAUACGACUGAUAA AACUCCGUUGGCAACUGCGGAAGCUACAGCUAUUCGGGGAAC GGCCACUAUAACCCACAACCAAAUUGCUGAAGUAACAAAAGA GGGUGUUGAUACGACCACAGUUGCGGCUCAACUUGCUGCAGC AGGGGUUACUGGCGCCGAUAAGGACAAUACUAGCCUUGUAA AACUAUCGUUUGAGGAUAAAAACGGUAAGGUUAUUGAUGGU GGCUAUGCAGUGAAAAUGGGCGACGAUUUCUAUGCCGCUACA UAUGAUGAGAAAACAGGUGCAAUUACUGCUAAAACCACUAC UUAUACAGAUGGUACUGGCGUUGCUCAAACUGGAGCUGUGA AAUUUGGUGGCGCAAAUGGUAAAUCUGAAGUUGUUACUGCU ACCGAUGGUAAGACUUACUUAGCAAGCGACCUUGACAAACAU AACUUCAGAACAGGCGGUGAGCUUAAAGAGGUUAAUACAGA UAAGACUGAAAACCCACUGCAGAAAAUUGAUGCUGCCUUGGC ACAGGUUGAUACACUUCGUUCUGACCUGGGUGCGGUUCAGAA CCGUUUCAACUCCGCUAUCACCAACCUGGGCAAUACCGUAAA UAACCUGUCUUCUGCCCGUAGCCGUAUCGAAGAUUCCGACUA CGCAACCGAAGUCUCCAACAUGUCUCGCGCGCAGAUUCUGCA GCAGGCCGGUACCUCCGUUCUGGCGCAGGCGAACCAGGUUCC GCAAAACGUCCUCUCUUUACUGCGUUGAUAAUAGGCUGGAGC CUCGGUGGCCAUGCUUCUUGCCCCUUGGGCCUCCCCCCAGCC CCUCCUCCCCUUCCUGCACCCGUACCCCCGUGGUCUUUGAAU AAAGUCUGAGUGGGCGGCAAAAAAAAAAAAAAAAAAAAAAA AAAAAAAAAAAAAAAAAAAAAAAAAAAAAAAAAAAAAAAA AAAAAAAAAAAAAAAAAAAAAAAAAAAAAAAAAAAUCUAG | 83 |

TABLE 17

| Flagellin Amino Acid Sequences | | |
|---|---|---|
| Name | Sequence | SEQ ID NO: |
| ORF Sequence, AA | MAQVINTNSLSLLTQNNLNKSQSALGTAIERLSSGLRINSAKDDAA GQAIANRFTANIKGLTQASRNANDGISIAQTTEGALNEINNNLQRV RELAVQSANGTNSQSDLDSIQAEITQRLNEIDRVSGQTQFNGVKVL AQDNTLTIQVGANDGETIDIDLKEISSKTLGLDKLNVQDAYTPKET AVTVDKTTYKNGTDPITAQSNTDIQTAIGGGATGVTGADIKFKDG QYYLDVKGGASAGVYKATYDETTKKVNIDTTDKTPLATAEATAI RGTATITHNQIAEVTKEGVDTTTVAAQLAAAGVTGADKDNTSLV KLSFEDKNGKVIDGGYAVKMGDDFYAATYDEKTGAITAKTTTYT DGTGVAQTGAVKFGGANGKSEVVTATDGKTYLASDLDKHNFRT GGELKEVNTDKTENPLQKIDAALAQVDTLRSDLGAVQNRFNSAIT NLGNTVNNLSSARSRIEDSDYATEVSNMSRAQILQQAGTSVLAQA NQVPQNVLSLLR | 54 |
| Flagellin-GS linker-circumspor-ozoite protein (CSP) | MAQVINTNSLSLLTQNNLNKSQSALGTAIERLSSGLRINSAKDDAA GQAIANRFTANIKGLTQASRNANDGISIAQTTEGALNEINNNLQRV RELAVQSANSTNSQSDLDSIQAEITQRLNEIDRVSGQTQFNGVKVL AQDNTLTIQVGANDGETIDIDLKQINSQTLGLDTLNVQQKYKVSD TAATVTGYADTTIALDNSTFKASATGLGGTDQKIDGDLKFDDTTG KYYAKVTVTGGTGKDGYYEVSVDKTNGEVTLAGGATSPLTGGLP ATATEDVKNVQVANADLTEAKAALTAAGVTGTASVVKMSYTDN NGKTIDGGLAVKVGDDYYSATQNKDGSISINTTKYTADDGTSKTA LNKLGGADGKTEVVSIGGKTYAASKAEGHNFKAQPDLAEAAATT TENPLQKIDAALAQVDTLRSDLGAVQNRFNSAITNLGNTVNNLTS ARSRIEDSDYATEVSNMSRAQILQQAGTSVLAQANQVPQNVLSLL RGGGGSGGGGSMMAPDPNANPNANPNANPNANPNANPNANPNA NPNANPNANPNANPNANPNANPNANPNANPNANPNANPNANPN ANPNANPNKNNQGNGQGHNMPNDPNRNVDENANANNAVKNNN NEEPSDKHIEQYLKKIKNSISTEWSPCSVTCGNGIQVRIKPGSANKP KDELDYENDIEKKICKMEKCSSVFNVVNS | 55 |
| Flagellin-RPVT linker-circumspor-ozoite protein (CSP) | MMAPDPNANPNANPNANPNANPNANPNANPNANPNANPNANPN ANPNANPNANPNANPNANPNANPNANPNANPNANPNANPNKNN QGNGQGHNMPNDPNRNVDENANANNAVKNNNNEEPSDKHIEQY LKKIKNSISTEWSPCSVTCGNGIQVRIKPGSANKPKDELDYENDIEK KICKMEKCSSVFNVVNSRPVTMAQVINTNSLSLLTQNNLNKSQSA LGTAIERLSSGLRINSAKDDAAGQAIANRFTANIKGLTQASRNAND GISIAQTTEGALNEINNNLQRVRELAVQSANSTNSQSDLDSIQAEIT QRLNEIDRVSGQTQFNGVKVLAQDNTLTIQVGANDGETIDIDLKQI NSQTLGLDTLNVQQKYKVSDTAATVTGYADTTIALDNSTFKASAT GLGGTDQKIDGDLKFDDTTGKYYAKVTVTGGTGKDGYYEVSVD KTNGEVTLAGGATSPLTGGLPATATEDVKNVQVANADLTEAKAA LTAAGVTGTASVVKMSYTDNNGKTIDGGLAVKVGDDYYSATQN KDGSISINTTKYTADDGTSKTALNKLGGADGKTEVVSIGGKTYAA SKAEGHNFKAQPDLAEAAATTTENPLQKIDAALAQVDTLRSDLG AVQNRFNSAITNLGNTVNNLTSARSRIEDSDYATEVSNMSRAQILQ QAGTSVLAQANQVPQNVLSLLR | 56 |

TABLE 18

| Human Metapneumovirus Mutant Amino Acid Sequences | | |
|---|---|---|
| Strain | Sequence | SEQ ID NO: |
| HMPV_SC_ DSCAV1_4MMV | MSWKVVIIFSLLITPQHGLKESYLEESCSTITEGYLSVLRTGWYTNVFTLEVG DVENLTCSDGPSLIKTELDLTKSALRELKTVSADQLAREEQIENPGSGSFVLG AIALGVAAAAAVTAGVAICKTIRLESEVTAINNALKKTNEAVSTLGNGVRV LAFAVRELKDFVSKNLTRALNKNKCDIDDLKMAVSFSQFNRRFLNVVRQFS DNAGITPAISLDLMTDAELARAVPNMPTSAGQIKLMLENRAMVRRKGFGIL CGVYGSSVIYMVQLPIFGVIDTPCWIVKAAPSCSEKKGNYACLLREDQGWY CQNAGSTVYYPNEKDCETRGDHVFCDTAAGINVAEQSKECNINISTTNYPC KVSTGRHPISMVALSPLGALVACYKGVSCSIGSNRVGIIKQLNKGCSYITNQ DADTVTIDNTVYQLSKVEGEQHVIKGRPVSSSFDPIKFPEDQFNVALDQVFE NIENSQALVDQSNRILSSAEKGNTGFIIVIILIAVLGSSMILVSIFIIIKKTKKPTG APPELSGVTNNGFIPHN | 85 |
| HMPV_SC_ DSTRIC_4MMV | MSWKVVIIFSLLITPQHGLKESYLEESCSTITEGYLSVLRTGWYTNVFTLEVG DVENLTCSDGPSLIKTELDLTKSALRELKTVSADQLAREEQIENPGSGSFVLG AIALGVAAAAAVTAGVAICKTIRLESEVTAINNALKKTNEAVSTLGNGVRV LATAVRELKDFVSKNLTRAINKNKCDIDDLKMAVSFSQFNRRFLNVVRQFS DNAGITPAISLDLMTDAELARAVPNMPTSAGQIKLMLENRAMVRRKGFGIL CGVYGSSVIYMVQLPIFGVIDTPCWIVKAAPSCSEKKGNYACLLREDQGWY | 86 |

TABLE 18-continued

Human Metapneumovirus Mutant Amino Acid Sequences

| Strain | Sequence | SEQ ID NO: |
|---|---|---|
| | CQNAGSTVYYPNEKDCETRGDHVFCDTAAGINVAEQSKECNINISTTNYPC<br>KVSTGRHPISMVALSPLGALVACYKGVSCSIGSNRVGIIKQLNKGCSYITNQ<br>DADTVTIDNTVYQLSKVEGEQHVIKGRPVSSSFDPIKFPEHQWHVALDQVFE<br>NIENSQALVDQSNRILSSAEKGNTGFIIVIILIAVLGSSMILVSIFIIIKKTKKPTG<br>APPELSGVTNNGFIPHN | |
| HMPV_SC_<br>DM_Krarup_<br>T74LD185P | MSWKVVIIFSLLITPQHGLKESYLEESCSTITEGYLSVLRTGWYTNVFTLEVG<br>DVENLTCSDGPSLIKTELDLLKSALRELKTVSADQLAREEQIENPGSGSFVLG<br>AIALGVAAAAAVTAGVAIAKTIRLESEVTAINNALKKTNEAVSTLGNGVRV<br>LATAVRELKDFVSKNLTRAINKNKCDIPDLKMAVSFSQFNRRFLNVVRQFS<br>DNAGITPAISLDLMTDAELARAVPNMPTSAGQIKLMLENRAMVRRKGFGILI<br>GVYGSSVIYMVQLPIFGVIDTPCWIVKAAPSCSEKKGNYACLLREDQGWYC<br>QNAGSTVYYPNEKDCETRGDHVFCDTAAGINVAEQSKECNINISTTNYPCK<br>VSTGRHPISMVALSPLGALVACYKGVSCSIGSNRVGIIKQLNKGCSYITNQD<br>ADTVTIDNTVYQLSKVEGEQHVIKGRPVSSSFDPIKFPEDQFQVALDQVFENI<br>ENSQALVDQSNRILSSAEKGNTGFIIVIILIAVLGSSMILVSIFIIIKKTKKPTGA<br>PPELSGVTNNGFIPHN | 87 |
| HMPV_SC_<br>TM_Krarup_<br>T74LD185PD454N | MSWKVVIIFSLLITPQHGLKESYLEESCSTITEGYLSVLRTGWYTNVFTLEVG<br>DVENLTCSDGPSLIKTELDLLKSALRELKTVSADQLAREEQIENPGSGSFVLG<br>AIALGVAAAAAVTAGVAIAKTIRLESEVTAINNALKKTNEAVSTLGNGVRV<br>LATAVRELKDFVSKNLTRAINKNKCDIPDLKMAVSFSQFNRRFLNVVRQFS<br>DNAGITPAISLDLMTDAELARAVPNMPTSAGQIKLMLENRAMVRRKGFGILI<br>GVYGSSVIYMVQLPIFGVIDTPCWIVKAAPSCSEKKGNYACLLREDQGWYC<br>QNAGSTVYYPNEKDCETRGDHVFCDTAAGINVAEQSKECNINISTTNYPCK<br>VSTGRHPISMVALSPLGALVACYKGVSCSIGSNRVGIIKQLNKGCSYITNQD<br>ADTVTIDNTVYQLSKVEGEQHVIKGRPVSSSFDPIKFPENQFQVALDQVFENI<br>ENSQALVDQSNRILSSAEKGNTGFIIVIILIAVLGSSMILVSIFIIIKKTKKPTGA<br>PPELSGVTNNGFIPHN | 88 |
| HMPV_SC_<br>4M_Krarup_<br>T74LS170LD185P | MSWKVVIIFSLLITPQHGLKESYLEESCSTITEGYLSVLRTGWYTNVFTLEVG<br>DVENLTCSDGPSLIKTELDLLKSALRELKTVSADQLAREEQIENPGSGSFVLG<br>AIALGVAAAAAVTAGVAIAKTIRLESEVTAINNALKKTNEAVSTLGNGVRV<br>LATAVRELKDFVLKNLTRAINKNKCDIPDLKMAVSFSQFNRRFLNVVRQFS<br>DNAGITPAISLDLMTDAELARAVPNMPTSAGQIKLMLENRAMVRRKGFGILI<br>GVYGSSVIYMVQLPIFGVIDTPCWIVKAAPSCSEKKGNYACLLREDQGWYC<br>QNAGSTVYYPNEKDCETRGDHVFCDTAAGINVAEQSKECNINISTTNYPCK<br>VSTGRHPISMVALSPLGALVACYKGVSCSIGSNRVGIIKQLNKGCSYITNQD<br>ADTVTIDNTVYQLSKVEGEQHVIKGRPVSSSFDPIKFPEDQFQVALDQVFENI<br>ENSQALVDQSNRILSSAEKGNTGFIIVIILIAVLGSSMILVSIFIIIKKTKKPTGA<br>PPELSGVTNNGFIPHN | 89 |
| HMPV_SC_<br>5M_Krarup_<br>T74L5170LD185PD454N | MSWKVVIIFSLLITPQHGLKESYLEESCSTITEGYLSVLRTGWYTNVFTLEVG<br>DVENLTCSDGPSLIKTELDLLKSALRELKTVSADQLAREEQIENPGSGSFVLG<br>AIALGVAAAAAVTAGVAIAKTIRLESEVTAINNALKKTNEAVSTLGNGVRV<br>LATAVRELKDFVLKNLTRAINKNKCDIPDLKMAVSFSQFNRRFLNVVRQFS<br>DNAGITPAISLDLMTDAELARAVPNMPTSAGQIKLMLENRAMVRRKGFGILI<br>GVYGSSVIYMVQLPIFGVIDTPCWIVKAAPSCSEKKGNYACLLREDQGWYC<br>QNAGSTVYYPNEKDCETRGDHVFCDTAAGINVAEQSKECNINISTTNYPCK<br>VSTGRHPISMVALSPLGALVACYKGVSCSIGSNRVGIIKQLNKGCSYITNQD<br>ADTVTIDNTVYQLSKVEGEQHVIKGRPVSSSFDPIKFPENQFQVALDQVFENI<br>ENSQALVDQSNRILSSAEKGNTGFIIVIILIAVLGSSMILVSIFIIIKKTKKPTGA<br>PPELSGVTNNGFIPHN | 90 |
| HMPV_SC_<br>DM_Krarup_<br>E51PT74L | MSWKVVIIFSLLITPQHGLKESYLEESCSTITEGYLSVLRTGWYTNVFTLPVG<br>DVENLTCSDGPSLIKTELDLLKSALRELKTVSADQLAREEQIENPGSGSFVLG<br>AIALGVAAAAAVTAGVAIAKTIRLESEVTAINNALKKTNEAVSTLGNGVRV<br>LATAVRELKDFVSKNLTRAINKNKCDIDDLKMAVSFSQFNRRFLNVVRQFS<br>DNAGITPAISLDLMTDAELARAVPNMPTSAGQIKLMLENRAMVRRKGFGILI<br>GVYGSSVIYMVQLPIFGVIDTPCWIVKAAPSCSEKKGNYACLLREDQGWYC<br>QNAGSTVYYPNEKDCETRGDHVFCDTAAGINVAEQSKECNINISTTNYPCK<br>VSTGRHPISMVALSPLGALVACYKGVSCSIGSNRVGIIKQLNKGCSYITNQD<br>ADTVTIDNTVYQLSKVEGEQHVIKGRPVSSSFDPIKFPEDQFQVALDQVFENI<br>ENSQALVDQSNRILSSAEKGNTGFIIVIILIAVLGSSMILVSIFIIIKKTKKPTGA<br>PPELSGVTNNGFIPHN | 91 |
| HMPV_SC_<br>TM_Krarup_<br>E51PT74LD454N | MSWKVVIIFSLLITPQHGLKESYLEESCSTITEGYLSVLRTGWYTNVFTLPVG<br>DVENLTCSDGPSLIKTELDLLKSALRELKTVSADQLAREEQIENPGSGSFVLG<br>AIALGVAAAAAVTAGVAIAKTIRLESEVTAINNALKKTNEAVSTLGNGVRV<br>LATAVRELKDFVSKNLTRAINKNKCDIDDLKMAVSFSQFNRRFLNVVRQFS<br>DNAGITPAISLDLMTDAELARAVPNMPTSAGQIKLMLENRAMVRRKGFGILI<br>GVYGSSVIYMVQLPIFGVIDTPCWIVKAAPSCSEKKGNYACLLREDQGWYC<br>QNAGSTVYYPNEKDCETRGDHVFCDTAAGINVAEQSKECNINISTTNYPCK<br>VSTGRHPISMVALSPLGALVACYKGVSCSIGSNRVGIIKQLNKGCSYITNQD<br>ADTVTIDNTVYQLSKVEGEQHVIKGRPVSSSFDPIKFPENQFQVALDQVFENI | 92 |

TABLE 18-continued

Human Metapneumovirus Mutant Amino Acid Sequences

| Strain | Sequence | SEQ ID NO: |
|---|---|---|
| | ENSQALVDQSNRILSSAEKGNTGFIIVIILIAVLGSSMILVSIFIIIKKTKKPTGA PPELSGVTNNGFIPHN | |
| HMPV_SC_ StabilizeAlpha T74L | MSWKVVIIFSLLITPQHGLKESYLEESCSTITEGYLSVLRTGWYTNVFTLEVG DVENLTCSDGPSLIKTELDLLKSALRELKTVSADQLAREEQIENPGSGSFVLG AIALGVAAAAAVTAGVAIAKTIRLESEVTAINNALKKTNEAVSTLGNGVRV LATAVRELKDFVSKNLTRAINKNKCDIDDLKMAVSFSQFNRRFLNVVRQFS DNAGITPAISLDLMTDAELARAVPNMPTSAGQIKLMLENRAMVRRKGFGILI GVYGSSVIYMVQLPIFGVIDTPCWIVKAAPSCSEKKGNYACLLREDQGWYC QNAGSTVYYPNEKDCETRGDHVFCDTAAGINVAEQSKECNINISTTNYPCK VSTGRHPISMVALSPLGALVACYKGVSCSIGSNRVGIIKQLNKGCSYITNQD ADTVTIDNTVYQLSKVEGEQHVIKGRPVSSSFDPIKFPEDQFQVALDQVFENI ENSQALVDQSNRILSSAEKGNTGFIIVIILIAVLGSSMILVSIFIIIKKTKKPTGA PPELSGVTNNGFIPHN | 93 |
| HMPV_SC_ StabilizeAlpha_ V55L | MSWKVVIIFSLLITPQHGLKESYLEESCSTITEGYLSVLRTGWYTNVFTLEVG DLENLTCSDGPSLIKTELDLTKSALRELKTVSADQLAREEQIENPGSGSFVLG AIALGVAAAAAVTAGVAIAKTIRLESEVTAINNALKKTNEAVSTLGNGVRV LATAVRELKDFVSKNLTRAINKNKCDIDDLKMAVSFSQFNRRFLNVVRQFS DNAGITPAISLDLMTDAELARAVPNMPTSAGQIKLMLENRAMVRRKGFGILI GVYGSSVIYMVQLPIFGVIDTPCWIVKAAPSCSEKKGNYACLLREDQGWYC QNAGSTVYYPNEKDCETRGDHVFCDTAAGINVAEQSKECNINISTTNYPCK VSTGRHPISMVALSPLGALVACYKGVSCSIGSNRVGIIKQLNKGCSYITNQD ADTVTIDNTVYQLSKVEGEQHVIKGRPVSSSFDPIKFPEDQFQVALDQVFENI ENSQALVDQSNRILSSAEKGNTGFIIVIILIAVLGSSMILVSIFIIIKKTKKPTGA PPELSGVTNNGFIPHN | 94 |
| HMPV_SC_ StabilizeAlpha_ S170L | MSWKVVIIFSLLITPQHGLKESYLEESCSTITEGYLSVLRTGWYTNVFTLEVG DVENLTCSDGPSLIKTELDLTKSALRELKTVSADQLAREEQIENPGSGSFVLG AIALGVAAAAAVTAGVAIAKTIRLESEVTAINNALKKTNEAVSTLGNGVRV LATAVRELKDFVLKNLTRAINKNKCDIDDLKMAVSFSQFNRRFLNVVRQFS DNAGITPAISLDLMTDAELARAVPNMPTSAGQIKLMLENRAMVRRKGFGILI GVYGSSVIYMVQLPIFGVIDTPCWIVKAAPSCSEKKGNYACLLREDQGWYC QNAGSTVYYPNEKDCETRGDHVFCDTAAGINVAEQSKECNINISTTNYPCK VSTGRHPISMVALSPLGALVACYKGVSCSIGSNRVGIIKQLNKGCSYITNQD ADTVTIDNTVYQLSKVEGEQHVIKGRPVSSSFDPIKFPEDQFQVALDQVFENI ENSQALVDQSNRILSSAEKGNTGFIIVIILIAVLGSSMILVSIFIIIKKTKKPTGA PPELSGVTNNGFIPHN | 95 |
| HMPV_SC_ StabilizeAlpha_ T174W | MSWKVVIIFSLLITPQHGLKESYLEESCSTITEGYLSVLRTGWYTNVFTLEVG DVENLTCSDGPSLIKTELDLTKSALRELKTVSADQLAREEQIENPGSGSFVLG AIALGVAAAAAVTAGVAIAKTIRLESEVTAINNALKKTNEAVSTLGNGVRV LATAVRELKDFVSKNLWRAINKNKCDIDDLKMAVSFSQFNRRFLNVVRQFS DNAGITPAISLDLMTDAELARAVPNMPTSAGQIKLMLENRAMVRRKGFGILI GVYGSSVIYMVQLPIFGVIDTPCWIVKAAPSCSEKKGNYACLLREDQGWYC QNAGSTVYYPNEKDCETRGDHVFCDTAAGINVAEQSKECNINISTTNYPCK VSTGRHPISMVALSPLGALVACYKGVSCSIGSNRVGIIKQLNKGCSYITNQD ADTVTIDNTVYQLSKVEGEQHVIKGRPVSSSFDPIKFPEDQFQVALDQVFENI ENSQALVDQSNRILSSAEKGNTGFIIVIILIAVLGSSMILVSIFIIIKKTKKPTGA PPELSGVTNNGFIPHN | 96 |
| HMPV_SC_4M_ Stabilize Alpha_ V55LT74L5170LT174W | MSWKVVIIFSLLITPQHGLKESYLEESCSTITEGYLSVLRTGWYTNVFTLEVG DLENLTCSDGPSLIKTELDLLKSALRELKTVSADQLAREEQIENPGSGSFVLG AIALGVAAAAAVTAGVAIAKTIRLESEVTAINNALKKTNEAVSTLGNGVRV LATAVRELKDFVLKNLWRAINKNKCDIDDLKMAVSFSQFNRRFLNVVRQFS DNAGITPAISLDLMTDAELARAVPNMPTSAGQIKLMLENRAMVRRKGFGILI GVYGSSVIYMVQLPIFGVIDTPCWIVKAAPSCSEKKGNYACLLREDQGWYC QNAGSTVYYPNEKDCETRGDHVFCDTAAGINVAEQSKECNINISTTNYPCK VSTGRHPISMVALSPLGALVACYKGVSCSIGSNRVGIIKQLNKGCSYITNQD ADTVTIDNTVYQLSKVEGEQHVIKGRPVSSSFDPIKFPEDQFQVALDQVFENI ENSQALVDQSNRILSSAEKGNTGFIIVIILIAVLGSSMILVSIFIIIKKTKKPTGA PPELSGVTNNGFIPHN | 97 |
| HMPV_ ProlineStab_ E51P | MSWKVVIIFSLLITPQHGLKESYLEESCSTITEGYLSVLRTGWYTNVFTLPVG DVENLTCSDGPSLIKTELDLTKSALRELKTVSADQLAREEQIENPGSGSFVLG AIALGVAAAAAVTAGVAIAKTIRLESEVTAINNALKKTNEAVSTLGNGVRV LATAVRELKDFVSKNLTRAINKNKCDIDDLKMAVSFSQFNRRFLNVVRQFS DNAGITPAISLDLMTDAELARAVPNMPTSAGQIKLMLENRAMVRRKGFGILI GVYGSSVIYMVQLPIFGVIDTPCWIVKAAPSCSEKKGNYACLLREDQGWYC QNAGSTVYYPNEKDCETRGDHVFCDTAAGINVAEQSKECNINISTTNYPCK VSTGRHPISMVALSPLGALVACYKGVSCSIGSNRVGIIKQLNKGCSYITNQD ADTVTIDNTVYQLSKVEGEQHVIKGRPVSSSFDPIKFPEDQFQVALDQVFENI ENSQALVDQSNRILSSAEKGNTGFIIVIILIAVLGSSMILVSIFIIIKKTKKPTGA PPELSGVTNNGFIPHN | 98 |

TABLE 18-continued

Human Metapneumovirus Mutant Amino Acid Sequences

| Strain | Sequence | SEQ ID NO: |
|---|---|---|
| HMPV_ ProlineStab_ D185P | MSWKVVIIFSLLITPQHGLKESYLEESCSTITEGYLSVLRTGWYTNVFTLEVG DVENLTCSDGPSLIKTELDLTKSALRELKTVSADQLAREEQIENPGSGSFVLG AIALGVAAAAAVTAGVAIAKTIRLESEVTAINNALKKTNEAVSTLGNGVRV LATAVRELKDFVSKNLTRAINKNKCDIPDLKMAVSFSQFNRRFLNVVRQFS DNAGITPAISLDLMTDAELARAVPNMPTSAGQIKLMLENRAMVRRKGFGILI GVYGSSVIYMVQLPIFGVIDTPCWIVKAAPSCSEKKGNYACLLREDQGWYC QNAGSTVYYPNEKDCETRGDHVFCDTAAGINVAEQSKECNINISTTNYPCK VSTGRHPISMVALSPLGALVACYKGVSCSIGSNRVGIIKQLNKGCSYITNQD ADTVTIDNTVYQLSKVEGEQHVIKGRPVSSSFDPIKFPEDQFQVALDQVFENI ENSQALVDQSNRILSSAEKGNTGFIIVIILIAVLGSSMILVSIFIIIKKTKKPTGA PPELSGVTNNGFIPHN | 99 |
| HMPV_ ProlineStab_ D183P | MSWKVVIIFSLLITPQHGLKESYLEESCSTITEGYLSVLRTGWYTNVFTLEVG DVENLTCSDGPSLIKTELDLTKSALRELKTVSADQLAREEQIENPGSGSFVLG AIALGVAAAAAVTAGVAIAKTIRLESEVTAINNALKKTNEAVSTLGNGVRV LATAVRELKDFVSKNLTRAINKNKCPIDDLKMAVSFSQFNRRFLNVVRQFS DNAGITPAISLDLMTDAELARAVPNMPTSAGQIKLMLENRAMVRRKGFGILI GVYGSSVIYMVQLPIFGVIDTPCWIVKAAPSCSEKKGNYACLLREDQGWYC QNAGSTVYYPNEKDCETRGDHVFCDTAAGINVAEQSKECNINISTTNYPCK VSTGRHPISMVALSPLGALVACYKGVSCSIGSNRVGIIKQLNKGCSYITNQD ADTVTIDNTVYQLSKVEGEQHVIKGRPVSSSFDPIKFPEDQFQVALDQVFENI ENSQALVDQSNRILSSAEKGNTGFIIVIILIAVLGSSMILVSIFIIIKKTKKPTGA PPELSGVTNNGFIPHN | 100 |
| HMPV_ ProlineStab_ E131P | MSWKVVIIFSLLITPQHGLKESYLEESCSTITEGYLSVLRTGWYTNVFTLEVG DVENLTCSDGPSLIKTELDLTKSALRELKTVSADQLAREEQIENPGSGSFVLG AIALGVAAAAAVTAGVAIAKTIRLPSEVTAINNALKKTNEAVSTLGNGVRV LATAVRELKDFVSKNLTRAINKNKCDIDDLKMAVSFSQFNRRFLNVVRQFS DNAGITPAISLDLMTDAELARAVPNMPTSAGQIKLMLENRAMVRRKGFGILI GVYGSSVIYMVQLPIFGVIDTPCWIVKAAPSCSEKKGNYACLLREDQGWYC QNAGSTVYYPNEKDCETRGDHVFCDTAAGINVAEQSKECNINISTTNYPCK VSTGRHPISMVALSPLGALVACYKGVSCSIGSNRVGIIKQLNKGCSYITNQD ADTVTIDNTVYQLSKVEGEQHVIKGRPVSSSFDPIKFPEDQFQVALDQVFENI ENSQALVDQSNRILSSAEKGNTGFIIVIILIAVLGSSMILVSIFIIIKKTKKPTGA PPELSGVTNNGFIPHN | 101 |
| HMPV_ ProlineStab_ D447P | MSWKVVIIFSLLITPQHGLKESYLEESCSTITEGYLSVLRTGWYTNVFTLEVG DVENLTCSDGPSLIKTELDLTKSALRELKTVSADQLAREEQIENPGSGSFVLG AIALGVAAAAAVTAGVAIAKTIRLESEVTAINNALKKTNEAVSTLGNGVRV LATAVRELKDFVSKNLTRAINKNKCDIDDLKMAVSFSQFNRRFLNVVRQFS DNAGITPAISLDLMTDAELARAVPNMPTSAGQIKLMLENRAMVRRKGFGILI GVYGSSVIYMVQLPIFGVIDTPCWIVKAAPSCSEKKGNYACLLREDQGWYC QNAGSTVYYPNEKDCETRGDHVFCDTAAGINVAEQSKECNINISTTNYPCK VSTGRHPISMVALSPLGALVACYKGVSCSIGSNRVGIIKQLNKGCSYITNQD ADTVTIDNTVYQLSKVEGEQHVIKGRPVSSSFPPIKFPEDQFQVALDQVFENI ENSQALVDQSNRILSSAEKGNTGFIIVIILIAVLGSSMILVSIFIIIKKTKKPTGA PPELSGVTNNGFIPHN | 102 |
| HMPV_ TrimerRepulsion D454N | MSWKVVIIFSLLITPQHGLKESYLEESCSTITEGYLSVLRTGWYTNVFTLEVG DVENLTCSDGPSLIKTELDLTKSALRELKTVSADQLAREEQIENPGSGSFVLG AIALGVAAAAAVTAGVAIAKTIRLESEVTAINNALKKTNEAVSTLGNGVRV LATAVRELKDFVSKNLTRAINKNKCDIDDLKMAVSFSQFNRRFLNVVRQFS DNAGITPAISLDLMTDAELARAVPNMPTSAGQIKLMLENRAMVRRKGFGILI GVYGSSVIYMVQLPIFGVIDTPCWIVKAAPSCSEKKGNYACLLREDQGWYC QNAGSTVYYPNEKDCETRGDHVFCDTAAGINVAEQSKECNINISTTNYPCK VSTGRHPISMVALSPLGALVACYKGVSCSIGSNRVGIIKQLNKGCSYITNQD ADTVTIDNTVYQLSKVEGEQHVIKGRPVSSSFDPIKFPENQFQVALDQVFENI ENSQALVDQSNRILSSAEKGNTGFIIVIILIAVLGSSMILVSIFIIIKKTKKPTGA PPELSGVTNNGFIPHN | 103 |
| HMPV_ TrimerRepulsion E453N | MSWKVVIIFSLLITPQHGLKESYLEESCSTITEGYLSVLRTGWYTNVFTLEVG DVENLTCSDGPSLIKTELDLTKSALRELKTVSADQLAREEQIENPGSGSFVLG AIALGVAAAAAVTAGVAIAKTIRLESEVTAINNALKKTNEAVSTLGNGVRV LATAVRELKDFVSKNLTRAINKNKCDIDDLKMAVSFSQFNRRFLNVVRQFS DNAGITPAISLDLMTDAELARAVPNMPTSAGQIKLMLENRAMVRRKGFGILI GVYGSSVIYMVQLPIFGVIDTPCWIVKAAPSCSEKKGNYACLLREDQGWYC QNAGSTVYYPNEKDCETRGDHVFCDTAAGINVAEQSKECNINISTTNYPCK VSTGRHPISMVALSPLGALVACYKGVSCSIGSNRVGIIKQLNKGCSYITNQD ADTVTIDNTVYQLSKVEGEQHVIKGRPVSSSFDPIKFPQDQFQVALDQVFENI ENSQALVDQSNRILSSAEKGNTGFIIVIILIAVLGSSMILVSIFIIIKKTKKPTGA PPELSGVTNNGFIPHN | 104 |
| HMPV_ Stabilize AlphaF196W | MSWKVVIIFSLLITPQHGLKESYLEESCSTITEGYLSVLRTGWYTNVFTLEVG DVENLTCSDGPSLIKTELDLTKSALRELKTVSADQLAREEQIENPGSGSFVLG AIALGVAAAAAVTAGVAIAKTIRLESEVTAINNALKKTNEAVSTLGNGVRV | 105 |

TABLE 18-continued

Human Metapneumovirus Mutant Amino Acid Sequences

| Strain | Sequence | SEQ ID NO: |
|---|---|---|
| | LATAVRELKDFVSKNLTRAINKNKCDIDDLKMAVSFSQWNRRFLNVVRQFS DNAGITPAISLDLMTDAELARAVPNMPTSAGQIKLMLENRAMVRRKGFGILI GVYGSSVIYMVQLPIFGVIDTPCWIVKAAPSCSEKKGNYACLLREDQGWYC QNAGSTVYYPNEKDCETRGDHVFCDTAAGINVAEQSKECNINISTTNYPCK VSTGRHPISMVALSPLGALVACYKGVSCSIGSNRVGIIKQLNKGCSYITNQD ADTVTIDNTVYQLSKVEGEQHVIKGRPVSSSFDPIKFPEDQFQVALDQVFENI ENSQALVDQSNRILSSAEKGNTGFIIVIILIAVLGSSMILVSIFIIIKKTKKPTGA PPELSGVTNNGFIPHN | |

TABLE 19

Human Metapneumovirus Mutant Nucleic Acid Sequences

| Strain | Nucleic Acid Sequence | SEQ ID NO: |
|---|---|---|
| HMPV_SC_ DSCAV1_4MMV | ATGAGCTGGAAGGTGGTCATCATCTTCAGCCTGCTGATCA CACCTCAGCACGGCCTGAAAGAGAGCTACCTGGAAGAGT CCTGCAGCACCATCACAGAGGGCTACCTGTCTGTGCTGAG AACCGGCTGGTACACCAACGTGTTCACACTGGAAGTGGGC GACGTCGAGAATCTGACATGCTCTGATGGCCCTAGCCTGA TCAAGACCGAGCTGGATCTGACCAAGAGCGCCCTGAGAG AACTCAAGACCGTGTCTGCCGATCAGCTGGCCAGAGAGGA ACAGATCGAGAATCCTGGCAGCGGCAGCTTTGTGCTGGGA GCCATTGCTCTTGGAGTGGCTGCTGCTGCAGCTGTTACAG CAGGCGTGGCCATCTGCAAGACCATCAGACTGGAAAGCG AAGTGACCGCCATCAACAACGCCCTGAAGAAGACAAACG AGGCCGTCAGCACACTCGGCAATGGCGTTAGAGTGCTGGC CTTTGCCGTGCGCGAGCTGAAGGACTTCGTGTCCAAGAAC CTGACACGGGCCCTGAACAAGAACAAGTGCGACATCGAC GACCTGAAGATGGCCGTGTCCTTTAGCCAGTTCAACCGGC GGTTTCTGAACGTCGTGCGGCAGTTTAGCGACAACGCCGG AATCACACCAGCCATCAGCCTGGACCTGATGACAGATGCT GAGCTGGCTAGAGCCGTGCCTAACATGCCTACATCTGCCG GCCAGATCAAGCTGATGCTCGAGAATAGAGCCATGGTCCG ACGGAAAGGCTTCGGCATTCTGTGTGGCGTGTACGGCAGC AGCGTGATCTATATGGTGCAGCTGCCTATCTTCGGCGTGA TCGACACACCCTGCTGGATTGTGAAGGCCGCTCCTAGCTG TAGCGAGAAGAAGGGCAATTACGCCTGCCTGCTGAGAGA GGACCAAGGCTGGTATTGTCAGAACGCCGGCAGCACCGTG TACTACCCTAACGAGAAGGACTGCGAGACAAGAGGCGAC CACGTGTTCTGTGATACCGCCGCTGGAATCAATGTGGCCG AGCAGAGCAAAGAGTGCAACATCAACATCAGCACCACCA ACTATCCCTGCAAGGTGTCCACCGGCAGGCACCCTATTTC TATGGTGGCTCTGTCTCCTCTGGGAGCCCTGGTGGCTTGTT ATAAGGGCGTGTCCTGTAGCATCGGCAGCAACAGAGTGG GCATCATCAAGCAGCTGAACAAGGGCTGCAGCTACATCAC CAACCAGGACGCCGATACCGTGACCATCGACAACACCGTG TATCAGCTGAGCAAGGTGGAAGGCGAACAGCACGTGATC AAGGGCAGACCTGTGTCCAGCAGCTTCGACCCTATCAAGT TCCCTGAGGATCAGTTCAACGTGGCCCTGGACCAGGTGTT CGAGAACATCGAGAATTCCCAGGCTCTGGTGGACCAGTCC AACAGAATCCTGTCTAGCGCCGAGAAGGGAAACACCGGC TTCATCATCGTGATCATCCTGATCGCCGTGCTGGGCAGCTC CATGATCCTGGTGTCCATCTTCATCATTATCAAGAAGACC AAGAAGCCCACCGGCGCTCCTCCAGAACTGAGCGGAGTG ACCAACAATGGCTTCATCCCTCACAAC | 106 |
| HMPV_SC_ DSTRIC_4MMV | ATGAGCTGGAAGGTGGTCATCATCTTCAGCCTGCTGATCA CACCTCAGCACGGCCTGAAAGAGAGCTACCTGGAAGAGT CCTGCAGCACCATCACAGAGGGCTACCTGTCTGTGCTGAG AACCGGCTGGTACACCAACGTGTTCACACTGGAAGTGGGC GACGTCGAGAATCTGACATGCTCTGATGGCCCTAGCCTGA TCAAGACCGAGCTGGATCTGACCAAGAGCGCCCTGAGAG AACTCAAGACCGTGTCTGCCGATCAGCTGGCCAGAGAGGA ACAGATCGAGAATCCTGGCAGCGGCAGCTTTGTGCTGGGA GCCATTGCTCTTGGAGTGGCTGCTGCTGCAGCTGTTACAG CAGGCGTGGCCATCTGCAAGACCATCAGACTGGAAAGCG AAGTGACCGCCATCAACAACGCCCTGAAGAAGACAAACG AGGCCGTCAGCACACTCGGCAATGGCGTTAGAGTGCTGGC CACAGCCGTGCGCGAGCTGAAGGACTTCGTGTCCAAGAAC CTGACACGGGCCATTAACAAGAACAAGTGCGACATCGAC | 107 |

TABLE 19-continued

Human Metapneumovirus Mutant Nucleic Acid Sequences

| Strain | Nucleic Acid Sequence | SEQ ID NO: |
|---|---|---|
| | GACCTGAAGATGGCCGTGTCCTTTAGCCAGTTCAACCGGC<br>GGTTTCTGAACGTCGTGCGGCAGTTTAGCGACAACGCCGG<br>AATCACACCAGCCATCAGCCTGGACCTGATGACAGATGCT<br>GAGCTGGCTAGAGCCGTGCCTAACATGCCTACATCTGCCG<br>GCCAGATCAAGCTGATGCTCGAGAATAGAGCCATGGTCCG<br>ACGGAAAGGCTTCGGCATTCTGTGTGGCGTGTACGGCAGC<br>AGCGTGATCTATATGGTGCAGCTGCCTATCTTCGGCGTGA<br>TCGACACACCCTGCTGGATTGTGAAGGCCGCTCCTAGCTG<br>TAGCGAGAAGAAGGGCAATTACGCCTGCCTGCTGAGAGA<br>GGACCAAGGCTGGTATTGTCAGAACGCCGGCAGCACCGTG<br>TACTACCCTAACGAGAAGGACTGCGAGACAAGAGGCGAC<br>CACGTGTTCTGTGATACCGCCGCTGGAATCAATGTGGCCG<br>AGCAGAGCAAAGAGTGCAACATCAACATCAGCACCACCA<br>ACTATCCCTGCAAGGTGTCCACCGGCAGGCACCCTATTTC<br>TATGGTGGCTCTGTCTCCTCTGGGAGCCCTGGTGGCTTGTT<br>ATAAGGGCGTGTCCTGTAGCATCGGCAGCAACAGAGTGG<br>GCATCATCAAGCAGCTGAACAAGGGCTGCAGCTACATCAC<br>CAACCAGGACGCCGATACCGTGACCATCGACAACACCGTG<br>TATCAGCTGAGCAAGGTGGAAGGCGAACAGCACGTGATC<br>AAGGGCAGACCTGTGTCCAGCAGCTTCGACCCTATCAAGT<br>TCCCTGAGCACCAGTGGCATGTGGCCCTGGACCAGGTGTT<br>CGAGAACATCGAGAATTCCCAGGCTCTGGTGGACCAGTCC<br>AACAGAATCCTGTCTAGCGCCGAGAAGGGAAACACCGGC<br>TTCATCATCGTGATCATCCTGATCGCCGTGCTGGGCAGCTC<br>CATGATCCTGGTGTCCATCTTCATCATTATCAAGAAGACC<br>AAGAAGCCCACCGGCGCTCCTCCAGAACTGAGCGGAGTG<br>ACCAACAATGGCTTCATCCCTCACAAC | |
| HMPV_SC_DM_<br>Krarup_<br>T74LD185P | ATGAGCTGGAAGGTGGTCATCATCTTCAGCCTGCTGATCA<br>CACCTCAGCACGGCCTGAAAGAGAGCTACCTGGAAGAGT<br>CCTGCAGCACCATCACAGAGGGCTACCTGTCTGTGCTGAG<br>AACCGGCTGGTACACCAACGTGTTCACACTGGAAGTGGGC<br>GACGTCGAGAATCTGACATGCTCTGATGGCCCTAGCCTGA<br>TCAAGACCGAGCTGGATCTGCTCAAGAGCGCCCTGAGAGA<br>ACTCAAGACCGTGTCTGCCGATCAGCTGGCCAGAGAGGAA<br>CAGATCGAGAATCCTGGCAGCGGCAGCTTTGTGCTGGGAG<br>CCATTGCTCTTGGAGTGGCTGCTGCTGCAGCTGTTACAGC<br>AGGCGTGGCCATCGCTAAGACCATCAGACTGGAAAGCGA<br>AGTGACCGCCATCAACAACGCCCTGAAGAAGACAAACGA<br>GGCCGTCAGCACACTCGGCAATGGCGTTAGAGTGCTGGCC<br>ACAGCCGTGCGCGAGCTGAAGGACTTCGTGTCCAAGAACC<br>TGACACGGGCCATTAACAAGAACAAGTGCGACATCCCTGA<br>CCTGAAGATGGCCGTGTCCTTTAGCCAGTTCAACCGGCGG<br>TTTCTGAACGTCGTGCGGCAGTTTAGCGACAACGCCGGAA<br>TCACACCAGCCATCAGCCTGGACCTGATGACAGATGCTGA<br>GCTGGCTAGAGCCGTGCCTAACATGCCTACATCTGCCGGC<br>CAGATCAAGCTGATGCTCGAGAATAGAGCCATGGTCCGAC<br>GGAAAGGCTTCGGCATTCTGATTGGCGTGTACGGCAGCAG<br>CGTGATCTATATGGTGCAGCTGCCTATCTTCGGCGTGATCG<br>ACACACCCTGCTGGATTGTGAAGGCCGCTCCTAGCTGTAG<br>CGAGAAGAAGGGCAATTACGCCTGCCTGCTGAGAGAGGA<br>CCAAGGCTGGTATTGTCAGAACGCCGGCAGCACCGTGTAC<br>TACCCTAACGAGAAGGACTGCGAGACAAGAGGCGACCAC<br>GTGTTCTGTGATACCGCCGCTGGAATCAATGTGGCCGAGC<br>AGAGCAAAGAGTGCAACATCAACATCAGCACCACCAACT<br>ATCCCTGCAAGGTGTCCACCGGCAGGCACCCTATTTCTAT<br>GGTGGCTCTGTCTCCTCTGGGAGCCCTGGTGGCTTGTTATA<br>AGGGCGTGTCCTGTAGCATCGGCAGCAACAGAGTGGGCAT<br>CATCAAGCAGCTGAACAAGGGCTGCAGCTACATCACCAAC<br>CAGGACGCCGATACCGTGACCATCGACAACACCGTGTATC<br>AGCTGAGCAAGGTGGAAGGCGAACAGCACGTGATCAAGG<br>GCAGACCTGTGTCCAGCAGCTTCGACCCTATCAAGTTCCC<br>TGAGGATCAGTTCCAGGTGGCCCTGGACCAGGTGTTCGAG<br>AACATCGAGAATTCCCAGGCTCTGGTGGACCAGTCCAACA<br>GAATCCTGTCTAGCGCCGAGAAGGGAAACACCGGCTTCAT<br>CATCGTGATCATCCTGATCGCCGTGCTGGGCAGCTCCATG<br>ATCCTGGTGTCCATCTTCATCATTATCAAGAAGACCAAGA<br>AGCCCACCGGCGCTCCTCCAGAACTGAGCGGAGTGACCAA<br>CAATGGCTTCATCCCTCACAAC | 108 |
| HMPV_SC_TM_<br>Krarup_<br>T74LD185PD454N | ATGAGCTGGAAGGTGGTCATCATCTTCAGCCTGCTGATCA<br>CACCTCAGCACGGCCTGAAAGAGAGCTACCTGGAAGAGT<br>CCTGCAGCACCATCACAGAGGGCTACCTGTCTGTGCTGAG<br>AACCGGCTGGTACACCAACGTGTTCACACTGGAAGTGGGC<br>GACGTCGAGAATCTGACATGCTCTGATGGCCCTAGCCTGA | 109 |

TABLE 19-continued

| Human Metapneumovirus Mutant Nucleic Acid Sequences | | |
|---|---|---|
| Strain | Nucleic Acid Sequence | SEQ ID NO: |
| | TCAAGACCGAGCTGGATCTGCTCAAGAGCGCCCTGAGAGA<br>ACTCAAGACCGTGTCTGCCGATCAGCTGGCCAGAGAGGAA<br>CAGATCGAGAATCCTGGCAGCGGCAGCTTTGTGCTGGGAG<br>CCATTGCTCTTGGAGTGGCTGCTGCTGCAGCTGTTACAGC<br>AGGCGTGGCCATCGCTAAGACCATCAGACTGGAAAGCGA<br>AGTGACCGCCATCAACAACGCCCTGAAGAAGACAAACGA<br>GGCCGTCAGCACACTCGGCAATGGCGTTAGAGTGCTGGCC<br>ACAGCCGTGCGCGAGCTGAAGGACTTCGTGTCCAAGAACC<br>TGACACGGGCCATTAACAAGAACAAGTGCGACATCCCTGA<br>CCTGAAGATGGCCGTGTCCTTTAGCCAGTTCAACCGGCGG<br>TTTCTGAACGTCGTGCGGCAGTTTAGCGACAACGCCGGAA<br>TCACACCAGCCATCAGCCTGGACCTGATGACAGATGCTGA<br>GCTGGCTAGAGCCGTGCCTAACATGCCTACATCTGCCGGC<br>CAGATCAAGCTGATGCTCGAGAATAGAGCCATGGTCCGAC<br>GGAAAGGCTTCGGCATTCTGATTGGCGTGTACGGCAGCAG<br>CGTGATCTATATGGTGCAGCTGCCTATCTTCGGCGTGATCG<br>ACACACCCTGCTGGATTGTGAAGGCCGCTCCTAGCTGTAG<br>CGAGAAGAAGGGCAATTACGCCTGCCTGCTGAGAGAGGA<br>CCAAGGCTGGTATTGTCAGAACGCCGGCAGCACCGTGTAC<br>TACCCTAACGAGAAGGACTGCGAGACAAGAGGCGACCAC<br>GTGTTCTGTGATACCGCCGCTGGAATCAATGTGGCCGAGC<br>AGAGCAAAGAGTGCAACATCAACATCAGCACCACCAACT<br>ATCCCTGCAAGGTGTCCACCGGCAGGCACCCTATTTCTAT<br>GGTGGCTCTGTCTCCTCTGGGAGCCCTGGTGGCTTGTTATA<br>AGGGCGTGTCCTGTAGCATCGGCAGCAACAGAGTGGGCAT<br>CATCAAGCAGCTGAACAAGGGCTGCAGCTACATCACCAAC<br>CAGGACGCCGATACCGTGACCATCGACAACACCGTGTATC<br>AGCTGAGCAAGGTGGAAGGCGAACAGCACGTGATCAAGG<br>GCAGACCTGTGTCCAGCAGCTTCGACCCTATCAAGTTCCC<br>TGAGAACCAGTTCCAGGTGGCCCTGGACCAGGTGTTCGAG<br>AACATCGAGAATTCCCAGGCTCTGGTGGACCAGTCCAACA<br>GAATCCTGTCTAGCGCCGAGAAGGGAAACACCGGCTTCAT<br>CATCGTGATCATCCTGATCGCCGTGCTGGGCAGCTCCATG<br>ATCCTGGTGTCCATCTTCATCATTATCAAGAAGACCAAGA<br>AGCCCACCGGCGCTCCTCCAGAACTGAGCGGAGTGACCAA<br>CAATGGCTTCATCCCTCACAAC | |
| HMPV_SC_4M_<br>Krarup_<br>T74L5170LD185P | ATGAGCTGGAAGGTGGTCATCATCTTCAGCCTGCTGATCA<br>CACCTCAGCACGGCCTGAAAGAGAGCTACCTGGAAGAGT<br>CCTGCAGCACCATCACAGAGGGCTACCTGTCTGTGCTGAG<br>AACCGGCTGGTACACCAACGTGTTCACACTGGAAGTGGGC<br>GACGTCGAGAATCTGACATGCTCTGATGGCCCTAGCCTGA<br>TCAAGACCGAGCTGGATCTGCTCAAGAGCGCCCTGAGAGA<br>ACTCAAGACCGTGTCTGCCGATCAGCTGGCCAGAGAGGAA<br>CAGATCGAGAATCCTGGCAGCGGCAGCTTTGTGCTGGGAG<br>CCATTGCTCTTGGAGTGGCTGCTGCTGCAGCTGTTACAGC<br>AGGCGTGGCCATCGCTAAGACCATCAGACTGGAAAGCGA<br>AGTGACCGCCATCAACAACGCCCTGAAGAAGACAAACGA<br>GGCCGTCAGCACACTCGGCAATGGCGTTAGAGTGCTGGCC<br>ACAGCCGTGCGCGAGCTGAAGGACTTCGTGCTTAAGAACC<br>TGACACGGGCCATTAACAAGAACAAGTGCGACATCCCTGA<br>CCTGAAGATGGCCGTGTCCTTTAGCCAGTTCAACCGGCGG<br>TTTCTGAACGTCGTGCGGCAGTTTAGCGACAACGCCGGAA<br>TCACACCAGCCATCAGCCTGGACCTGATGACAGATGCTGA<br>GCTGGCTAGAGCCGTGCCTAACATGCCTACATCTGCCGGC<br>CAGATCAAGCTGATGCTCGAGAATAGAGCCATGGTCCGAC<br>GGAAAGGCTTCGGCATTCTGATTGGCGTGTACGGCAGCAG<br>CGTGATCTATATGGTGCAGCTGCCTATCTTCGGCGTGATCG<br>ACACACCCTGCTGGATTGTGAAGGCCGCTCCTAGCTGTAG<br>CGAGAAGAAGGGCAATTACGCCTGCCTGCTGAGAGAGGA<br>CCAAGGCTGGTATTGTCAGAACGCCGGCAGCACCGTGTAC<br>TACCCTAACGAGAAGGACTGCGAGACAAGAGGCGACCAC<br>GTGTTCTGTGATACCGCCGCTGGAATCAATGTGGCCGAGC<br>AGAGCAAAGAGTGCAACATCAACATCAGCACCACCAACT<br>ATCCCTGCAAGGTGTCCACCGGCAGGCACCCTATTTCTAT<br>GGTGGCTCTGTCTCCTCTGGGAGCCCTGGTGGCTTGTTATA<br>AGGGCGTGTCCTGTAGCATCGGCAGCAACAGAGTGGGCAT<br>CATCAAGCAGCTGAACAAGGGCTGCAGCTACATCACCAAC<br>CAGGACGCCGATACCGTGACCATCGACAACACCGTGTATC<br>AGCTGAGCAAGGTGGAAGGCGAACAGCACGTGATCAAGG<br>GCAGACCTGTGTCCAGCAGCTTCGACCCTATCAAGTTCCC<br>TGAGGATCAGTTCCAGGTGGCCCTGGACCAGGTGTTCGAG<br>AACATCGAGAATTCCCAGGCTCTGGTGGACCAGTCCAACA<br>GAATCCTGTCTAGCGCCGAGAAGGGAAACACCGGCTTCAT<br>CATCGTGATCATCCTGATCGCCGTGCTGGGCAGCTCCATG | 110 |

TABLE 19-continued

| Human Metapneumovirus Mutant Nucleic Acid Sequences | | |
|---|---|---|
| Strain | Nucleic Acid Sequence | SEQ ID NO: |
| | ATCCTGGTGTCCATCTTCATCATTATCAAGAAGACCAAGA AGCCCACCGGCGCTCCTCCAGAACTGAGCGGAGTGACCAA CAATGGCTTCATCCCTCACAAC | |
| HMPV_SC_5M_ Krarup_ T74LS170LD185PD454N | ATGAGCTGGAAGGTGGTCATCATCTTCAGCCTGCTGATCA CACCTCAGCACGGCCTGAAAGAGAGCTACCTGGAAGAGT CCTGCAGCACCATCACAGAGGGCTACCTGTCTGTGCTGAG AACCGGCTGGTACACCAACGTGTTCACACTGGAAGTGGGC GACGTCGAGAATCTGACATGCTCTGATGGCCCTAGCCTGA TCAAGACCGAGCTGGATCTGCTCAAGAGCGCCCTGAGAGA ACTCAAGACCGTGTCTGCCGATCAGCTGGCCAGAGAGGAA CAGATCGAGAATCCTGGCAGCGGCAGCTTTGTGCTGGGAG CCATTGCTCTTGGAGTGGCTGCTGCTGCAGCTGTTACAGC AGGCGTGGCCATCGCTAAGACCATCAGACTGGAAAGCGA AGTGACCGCCATCAACAACGCCCTGAAGAAGACAAACGA GGCCGTCAGCACACTCGGCAATGGCGTTAGAGTGCTGGCC ACAGCCGTGCGCGAGCTGAAGGACTTCGTGCTTAAGAACC TGACACGGGCCATTAACAAGAACAAGTGCGACATCCCTGA CCTGAAGATGGCCGTGTCCTTTAGCCAGTTCAACCGGCGG TTTCTGAACGTCGTGCGGCAGTTTAGCGACAACGCCGGAA TCACACCAGCCATCAGCCTGGACCTGATGACAGATGCTGA GCTGGCTAGAGCCGTGCCTAACATGCCTACATCTGCCGGC CAGATCAAGCTGATGCTCGAGAATAGAGCCATGGTCCGAC GGAAAGGCTTCGGCATTCTGATTGGCGTGTACGGCAGCAG CGTGATCTATATGGTGCAGCTGCCTATCTTCGGCGTGATCG ACACACCCTGCTGGATTGTGAAGGCCGCTCCTAGCTGTAG CGAGAAGAAGGGCAATTACGCCTGCCTGCTGAGAGAGGA CCAAGGCTGGTATTGTCAGAACGCCGGCAGCACCGTGTAC TACCCTAACGAGAAGGACTGCGAGACAAGAGGCGACCAC GTGTTCTGTGATACCGCCGCTGGAATCAATGTGGCCGAGC AGAGCAAAGAGTGCAACATCAACATCAGCACCACCAACT ATCCCTGCAAGGTGTCCACCGGCAGGCACCCTATTTCTAT GGTGGCTCTGTCTCCTCTGGGAGCCCTGGTGGCTTGTTATA AGGGCGTGTCCTGTAGCATCGGCAGCAACAGAGTGGGCAT CATCAAGCAGCTGAACAAGGGCTGCAGCTACATCACCAAC CAGGACGCCGATACCGTGACCATCGACAACACCGTGTATC AGCTGAGCAAGGTGGAAGGCGAACAGCACGTGATCAAGG GCAGACCTGTGTCCAGCAGCTTCGACCCTATCAAGTTCCC TGAGAACCAGTTCCAGGTGGCCCTGGACCAGGTGTTCGAG AACATCGAGAATTCCCAGGCTCTGGTGGACCAGTCCAACA GAATCCTGTCTAGCGCCGAGAAGGGAAACACCGGCTTCAT CATCGTGATCATCCTGATCGCCGTGCTGGGCAGCTCCATG ATCCTGGTGTCCATCTTCATCATTATCAAGAAGACCAAGA AGCCCACCGGCGCTCCTCCAGAACTGAGCGGAGTGACCAA CAATGGCTTCATCCCTCACAAC | 111 |
| HMPV_SC_DM_ Krarup_E51PT74L | ATGAGCTGGAAGGTGGTCATCATCTTCAGCCTGCTGATCA CACCTCAGCACGGCCTGAAAGAGAGCTACCTGGAAGAGT CCTGCAGCACCATCACAGAGGGCTACCTGTCTGTGCTGAG AACCGGCTGGTACACCAACGTGTTCACACTGCCTGTGGGC GACGTCGAGAATCTGACATGCTCTGATGGCCCTAGCCTGA TCAAGACCGAGCTGGATCTGCTCAAGAGCGCCCTGAGAGA ACTCAAGACCGTGTCTGCCGATCAGCTGGCCAGAGAGGAA CAGATCGAGAATCCTGGCAGCGGCAGCTTTGTGCTGGGAG CCATTGCTCTTGGAGTGGCTGCTGCTGCAGCTGTTACAGC AGGCGTGGCCATCGCTAAGACCATCAGACTGGAAAGCGA AGTGACCGCCATCAACAACGCCCTGAAGAAGACAAACGA GGCCGTCAGCACACTCGGCAATGGCGTTAGAGTGCTGGCC ACAGCCGTGCGCGAGCTGAAGGACTTCGTGTCCAAGAACC TGACACGGGCCATTAACAAGAACAAGTGCGACATCGACG ACCTGAAGATGGCCGTGTCCTTTAGCCAGTTCAACCGGCG GTTTCTGAACGTCGTGCGGCAGTTTAGCGACAACGCCGGA ATCACACCAGCCATCAGCCTGGACCTGATGACAGATGCTG AGCTGGCTAGAGCCGTGCCTAACATGCCTACATCTGCCGG CCAGATCAAGCTGATGCTCGAGAATAGAGCCATGGTCCGA CGGAAAGGCTTCGGCATTCTGATTGGCGTGTACGGCAGCA GCGTGATCTATATGGTGCAGCTGCCTATCTTCGGCGTGATC GACACACCCTGCTGGATTGTGAAGGCCGCTCCTAGCTGTA GCGAGAAGAAGGGCAATTACGCCTGCCTGCTGAGAGAGG ACCAAGGCTGGTATTGTCAGAACGCCGGCAGCACCGTGTA CTACCCTAACGAGAAGGACTGCGAGACAAGAGGCGACCA CGTGTTCTGTGATACCGCCGCTGGAATCAATGTGGCCGAG CAGAGCAAAGAGTGCAACATCAACATCAGCACCACCAAC TATCCCTGCAAGGTGTCCACCGGCAGGCACCCTATTTCTAT GGTGGCTCTGTCTCCTCTGGGAGCCCTGGTGGCTTGTTATA | 112 |

TABLE 19-continued

Human Metapneumovirus Mutant Nucleic Acid Sequences

| Strain | Nucleic Acid Sequence | SEQ ID NO: |
|---|---|---|
| | AGGGCGTGTCCTGTAGCATCGGCAGCAACAGAGTGGGCAT CATCAAGCAGCTGAACAAGGGCTGCAGCTACATCACCAAC CAGGACGCCGATACCGTGACCATCGACAACACCGTGTATC AGCTGAGCAAGGTGGAAGGCGAACAGCACGTGATCAAGG GCAGACCTGTGTCCAGCAGCTTCGACCCTATCAAGTTCCC TGAGGATCAGTTCCAGGTGGCCCTGGACCAGGTGTTCGAG AACATCGAGAATTCCCAGGCTCTGGTGGACCAGTCCAACA GAATCCTGTCTAGCGCCGAGAAGGGAAACACCGGCTTCAT CATCGTGATCATCCTGATCGCCGTGCTGGGCAGCTCCATG ATCCTGGTGTCCATCTTCATCATTATCAAGAAGACCAAGA AGCCCACCGGCGCTCCTCCAGAACTGAGCGGAGTGACCAA CAATGGCTTCATCCCTCACAAC | |
| HMPV_SC_TM_ Krarup_ E51PT74LD454N | ATGAGCTGGAAGGTGGTCATCATCTTCAGCCTGCTGATCA CACCTCAGCACGGCCTGAAAGAGAGCTACCTGGAAGAGT CCTGCAGCACCATCACAGAGGGCTACCTGTCTGTGCTGAG AACCGGCTGGTACACCAACGTGTTCACACTGCCTGTGGGC GACGTCGAGAATCTGACATGCTCTGATGGCCCTAGCCTGA TCAAGACCGAGCTGGATCTGCTCAAGAGCGCCCTGAGAGA ACTCAAGACCGTGTCTGCCGATCAGCTGGCCAGAGAGGAA CAGATCGAGAATCCTGGCAGCGGCAGCTTTGTGCTGGGAG CCATTGCTCTTGGAGTGGCTGCTGCTGCAGCTGTTACAGC AGGCGTGGCCATCGCTAAGACCATCAGACTGGAAAGCGA AGTGACCGCCATCAACAACGCCCTGAAGAAGACAAACGA GGCCGTCAGCACACTCGGCAATGGCGTTAGAGTGCTGGCC ACAGCCGTGCGCGAGCTGAAGGACTTCGTGTCCAAGAACC TGACACGGGCCATTAACAAGAACAAGTGCGACATCGACG ACCTGAAGATGGCCGTGTCCTTTAGCCAGTTCAACCGGCG GTTTCTGAACGTCGTGCGGCAGTTTAGCGACAACGCCGGA ATCACACCAGCCATCAGCCTGGACCTGATGACAGATGCTG AGCTGGCTAGAGCCGTGCCTAACATGCCTACATCTGCCGG CCAGATCAAGCTGATGCTCGAGAATAGAGCCATGGTCCGA CGGAAAGGCTTCGGCATTCTGATTGGCGTGTACGGCAGCA GCGTGATCTATATGGTGCAGCTGCCTATCTTCGGCGTGATC GACACACCCTGCTGGATTGTGAAGGCCGCTCCTAGCTGTA GCGAGAAGAAGGGCAATTACGCCTGCCTGCTGAGAGAGG ACCAAGGCTGGTATTGTCAGAACGCCGGCAGCACCGTGTA CTACCCTAACGAGAAGGACTGCGAGACAAGAGGCGACCA CGTGTTCTGTGATACCGCCGCTGGAATCAATGTGGCCGAG CAGAGCAAAGAGTGCAACATCAACATCAGCACCACCAAC TATCCCTGCAAGGTGTCCACCGGCAGGCACCCTATTTCTAT GGTGGCTCTGTCTCCTCTGGGAGCCCTGGTGGCTTGTTATA AGGGCGTGTCCTGTAGCATCGGCAGCAACAGAGTGGGCAT CATCAAGCAGCTGAACAAGGGCTGCAGCTACATCACCAAC CAGGACGCCGATACCGTGACCATCGACAACACCGTGTATC AGCTGAGCAAGGTGGAAGGCGAACAGCACGTGATCAAGG GCAGACCTGTGTCCAGCAGCTTCGACCCTATCAAGTTCCC TGAGAACCAGTTCCAGGTGGCCCTGGACCAGGTGTTCGAG AACATCGAGAATTCCCAGGCTCTGGTGGACCAGTCCAACA GAATCCTGTCTAGCGCCGAGAAGGGAAACACCGGCTTCAT CATCGTGATCATCCTGATCGCCGTGCTGGGCAGCTCCATG ATCCTGGTGTCCATCTTCATCATTATCAAGAAGACCAAGA AGCCCACCGGCGCTCCTCCAGAACTGAGCGGAGTGACCAA CAATGGCTTCATCCCTCACAAC | 113 |
| HMPV_SC_ StabilizeAlpha_ T74L | ATGAGCTGGAAGGTGGTCATCATCTTCAGCCTGCTGATCA CACCTCAGCACGGCCTGAAAGAGAGCTACCTGGAAGAGT CCTGCAGCACCATCACAGAGGGCTACCTGTCTGTGCTGAG AACCGGCTGGTACACCAACGTGTTCACACTGGAAGTGGGC GACGTCGAGAATCTGACATGCTCTGATGGCCCTAGCCTGA TCAAGACCGAGCTGGATCTGCTCAAGAGCGCCCTGAGAGA ACTCAAGACCGTGTCTGCCGATCAGCTGGCCAGAGAGGAA CAGATCGAGAATCCTGGCAGCGGCAGCTTTGTGCTGGGAG CCATTGCTCTTGGAGTGGCTGCTGCTGCAGCTGTTACAGC AGGCGTGGCCATCGCTAAGACCATCAGACTGGAAAGCGA AGTGACCGCCATCAACAACGCCCTGAAGAAGACAAACGA GGCCGTCAGCACACTCGGCAATGGCGTTAGAGTGCTGGCC ACAGCCGTGCGCGAGCTGAAGGACTTCGTGTCCAAGAACC TGACACGGGCCATTAACAAGAACAAGTGCGACATCGACG ACCTGAAGATGGCCGTGTCCTTTAGCCAGTTCAACCGGCG GTTTCTGAACGTCGTGCGGCAGTTTAGCGACAACGCCGGA ATCACACCAGCCATCAGCCTGGACCTGATGACAGATGCTG AGCTGGCTAGAGCCGTGCCTAACATGCCTACATCTGCCGG CCAGATCAAGCTGATGCTCGAGAATAGAGCCATGGTCCGA CGGAAAGGCTTCGGCATTCTGATTGGCGTGTACGGCAGCA | 114 |

TABLE 19-continued

Human Metapneumovirus Mutant Nucleic Acid Sequences

| Strain | Nucleic Acid Sequence | SEQ ID NO: |
|---|---|---|
| | GCGTGATCTATATGGTGCAGCTGCCTATCTTCGGCGTGATC<br>GACACACCCTGCTGGATTGTGAAGGCCGCTCCTAGCTGTA<br>GCGAGAAGAAGGGCAATTACGCCTGCCTGCTGAGAGAGG<br>ACCAAGGCTGGTATTGTCAGAACGCCGGCAGCACCGTGTA<br>CTACCCTAACGAGAAGGACTGCGAGACAAGAGGCGACCA<br>CGTGTTCTGTGATACCGCCGCTGGAATCAATGTGGCCGAG<br>CAGAGCAAAGAGTGCAACATCAACATCAGCACCACCAAC<br>TATCCCTGCAAGGTGTCCACCGGCAGGCACCCTATTTCTAT<br>GGTGGCTCTGTCTCCTCTGGGAGCCCTGGTGGCTTGTTATA<br>AGGGCGTGTCCTGTAGCATCGGCAGCAACAGAGTGGGCAT<br>CATCAAGCAGCTGAACAAGGGCTGCAGCTACATCACCAAC<br>CAGGACGCCGATACCGTGACCATCGACAACACCGTGTATC<br>AGCTGAGCAAGGTGGAAGGCGAACAGCACGTGATCAAGG<br>GCAGACCTGTGTCCAGCAGCTTCGACCCTATCAAGTTCCC<br>TGAGGATCAGTTCCAGGTGGCCCTGGACCAGGTGTTCGAG<br>AACATCGAGAATTCCCAGGCTCTGGTGGACCAGTCCAACA<br>GAATCCTGTCTAGCGCCGAGAAGGGAAACACCGGCTTCAT<br>CATCGTGATCATCCTGATCGCCGTGCTGGGCAGCTCCATG<br>ATCCTGGTGTCCATCTTCATCATTATCAAGAAGACCAAGA<br>AGCCCACCGGCGCTCCTCCAGAACTGAGCGGAGTGACCAA<br>CAATGGCTTCATCCCTCACAAC | |
| HMPV_SC_<br>StabilizeAlpha_<br>V55L | ATGAGCTGGAAGGTGGTCATCATCTTCAGCCTGCTGATCA<br>CACCTCAGCACGGCCTGAAAGAGAGCTACCTGGAAGAGT<br>CCTGCAGCACCATCACAGAGGGCTACCTGTCTGTGCTGAG<br>AACCGGCTGGTACACCAACGTGTTCACACTGGAAGTGGGC<br>GACCTCGAGAATCTGACATGCTCTGATGGCCCTAGCCTGA<br>TCAAGACCGAGCTGGATCTGACCAAGAGCGCCCTGAGAG<br>AACTCAAGACCGTGTCTGCCGATCAGCTGGCCAGAGAGGA<br>ACAGATCGAGAATCCTGGCAGCGGCAGCTTTGTGCTGGGA<br>GCCATTGCTCTTGGAGTGGCTGCTGCTGCAGCTGTTACAG<br>CAGGCGTGGCCATCGCTAAGACCATCAGACTGGAAAGCG<br>AAGTGACCGCCATCAACAACGCCCTGAAGAAGACAAACG<br>AGGCCGTCAGCACACTCGGCAATGGCGTTAGAGTGCTGGC<br>CACAGCCGTGCGCGAGCTGAAGGACTTCGTGTCCAAGAAC<br>CTGACACGGGCCATTAACAAGAACAAGTGCGACATCGAC<br>GACCTGAAGATGGCCGTGTCCTTTAGCCAGTTCAACCGGC<br>GGTTTCTGAACGTCGTGCGGCAGTTTAGCGACAACGCCGG<br>AATCACACCAGCCATCAGCCTGGACCTGATGACAGATGCT<br>GAGCTGGCTAGAGCCGTGCCTAACATGCCTACATCTGCCG<br>GCCAGATCAAGCTGATGCTCGAGAATAGAGCCATGGTCCG<br>ACGGAAAGGCTTCGGCATTCTGATTGGCGTGTACGGCAGC<br>AGCGTGATCTATATGGTGCAGCTGCCTATCTTCGGCGTGA<br>TCGACACACCCTGCTGGATTGTGAAGGCCGCTCCTAGCTG<br>TAGCGAGAAGAAGGGCAATTACGCCTGCCTGCTGAGAGA<br>GGACCAAGGCTGGTATTGTCAGAACGCCGGCAGCACCGTG<br>TACTACCCTAACGAGAAGGACTGCGAGACAAGAGGCGAC<br>CACGTGTTCTGTGATACCGCCGCTGGAATCAATGTGGCCG<br>AGCAGAGCAAAGAGTGCAACATCAACATCAGCACCACCA<br>ACTATCCCTGCAAGGTGTCCACCGGCAGGCACCCTATTTC<br>TATGGTGGCTCTGTCTCCTCTGGGAGCCCTGGTGGCTTGTT<br>ATAAGGGCGTGTCCTGTAGCATCGGCAGCAACAGAGTGG<br>GCATCATCAAGCAGCTGAACAAGGGCTGCAGCTACATCAC<br>CAACCAGGACGCCGATACCGTGACCATCGACAACACCGTG<br>TATCAGCTGAGCAAGGTGGAAGGCGAACAGCACGTGATC<br>AAGGGCAGACCTGTGTCCAGCAGCTTCGACCCTATCAAGT<br>TCCCTGAGGATCAGTTCCAGGTGGCCCTGGACCAGGTGTT<br>CGAGAACATCGAGAATTCCCAGGCTCTGGTGGACCAGTCC<br>AACAGAATCCTGTCTAGCGCCGAGAAGGGAAACACCGGC<br>TTCATCATCGTGATCATCCTGATCGCCGTGCTGGGCAGCTC<br>CATGATCCTGGTGTCCATCTTCATCATTATCAAGAAGACC<br>AAGAAGCCCACCGGCGCTCCTCCAGAACTGAGCGGAGTG<br>ACCAACAATGGCTTCATCCCTCACAAC | 115 |
| HMPV_SC_<br>StabilizeAlpha_<br>S170L | ATGAGCTGGAAGGTGGTCATCATCTTCAGCCTGCTGATCA<br>CACCTCAGCACGGCCTGAAAGAGAGCTACCTGGAAGAGT<br>CCTGCAGCACCATCACAGAGGGCTACCTGTCTGTGCTGAG<br>AACCGGCTGGTACACCAACGTGTTCACACTGGAAGTGGGC<br>GACGTCGAGAATCTGACATGCTCTGATGGCCCTAGCCTGA<br>TCAAGACCGAGCTGGATCTGACCAAGAGCGCCCTGAGAG<br>AACTCAAGACCGTGTCTGCCGATCAGCTGGCCAGAGAGGA<br>ACAGATCGAGAATCCTGGCAGCGGCAGCTTTGTGCTGGGA<br>GCCATTGCTCTTGGAGTGGCTGCTGCTGCAGCTGTTACAG<br>CAGGCGTGGCCATCGCTAAGACCATCAGACTGGAAAGCG<br>AAGTGACCGCCATCAACAACGCCCTGAAGAAGACAAACG | 116 |

TABLE 19-continued

| Human Metapneumovirus Mutant Nucleic Acid Sequences | | |
|---|---|---|
| Strain | Nucleic Acid Sequence | SEQ ID NO: |
| | AGGCCGTCAGCACACTCGGCAATGGCGTTAGAGTGCTGGC CACAGCCGTGCGCGAGCTGAAGGACTTCGTGCTTAAGAAC CTGACACGGGCCATTAACAAGAACAAGTGCGACATCGAC GACCTGAAGATGGCCGTGTCCTTTAGCCAGTTCAACCGGC GGTTTCTGAACGTCGTGCGGCAGTTTAGCGACAACGCCGG AATCACACCAGCCATCAGCCTGGACCTGATGACAGATGCT GAGCTGGCTAGAGCCGTGCCTAACATGCCTACATCTGCCG GCCAGATCAAGCTGATGCTCGAGAATAGAGCCATGGTCCG ACGGAAAGGCTTCGGCATTCTGATTGGCGTGTACGGCAGC AGCGTGATCTATATGGTGCAGCTGCCTATCTTCGGCGTGA TCGACACACCCTGCTGGATTGTGAAGGCCGCTCCTAGCTG TAGCGAGAAGAAGGGCAATTACGCCTGCCTGCTGAGAGA GGACCAAGGCTGGTATTGTCAGAACGCCGGCAGCACCGTG TACTACCCTAACGAGAAGGACTGCGAGACAAGAGGCGAC CACGTGTTCTGTGATACCGCCGCTGGAATCAATGTGGCCG AGCAGAGCAAAGAGTGCAACATCAACATCAGCACCACCA ACTATCCCTGCAAGGTGTCCACCGGCAGGCACCCTATTTC TATGGTGGCTCTGTCTCCTCTGGGAGCCCTGGTGGCTTGTT ATAAGGGCGTGTCCTGTAGCATCGGCAGCAACAGAGTGG GCATCATCAAGCAGCTGAACAAGGGCTGCAGCTACATCAC CAACCAGGACGCCGATACCGTGACCATCGACAACACCGTG TATCAGCTGAGCAAGGTGGAAGGCGAACAGCACGTGATC AAGGGCAGACCTGTGTCCAGCAGCTTCGACCCTATCAAGT TCCCTGAGGATCAGTTCCAGGTGGCCCTGGACCAGGTGTT CGAGAACATCGAGAATTCCCAGGCTCTGGTGGACCAGTCC AACAGAATCCTGTCTAGCGCCGAGAAGGGAAACACCGGC TTCATCATCGTGATCATCCTGATCGCCGTGCTGGGCAGCTC CATGATCCTGGTGTCCATCTTCATCATTATCAAGAAGACC AAGAAGCCCACCGGCGCTCCTCCAGAACTGAGCGGAGTG ACCAACAATGGCTTCATCCCTCACAAC | |
| HMPV_SC_ StabilizeAlpha_ T174W | ATGAGCTGGAAGGTGGTCATCATCTTCAGCCTGCTGATCA CACCTCAGCACGGCCTGAAAGAGAGCTACCTGGAAGAGT CCTGCAGCACCATCACAGAGGGCTACCTGTCTGTGCTGAG AACCGGCTGGTACACCAACGTGTTCACACTGGAAGTGGGC GACGTCGAGAATCTGACATGCTCTGATGGCCCTAGCCTGA TCAAGACCGAGCTGGATCTGACCAAGAGCGCCCTGAGAG AACTCAAGACCGTGTCTGCCGATCAGCTGGCCAGAGAGGA ACAGATCGAGAATCCTGGCAGCGGCAGCTTTGTGCTGGGA GCCATTGCTCTTGGAGTGGCTGCTGCTGCAGCTGTTACAG CAGGCGTGGCCATCGCTAAGACCATCAGACTGGAAAGCG AAGTGACCGCCATCAACAACGCCCTGAAGAAGACAAACG AGGCCGTCAGCACACTCGGCAATGGCGTTAGAGTGCTGGC CACAGCCGTGCGCGAGCTGAAGGACTTCGTGTCCAAGAAC CTGTGGCGGGCCATTAACAAGAACAAGTGCGACATCGAC GACCTGAAGATGGCCGTGTCCTTTAGCCAGTTCAACCGGC GGTTTCTGAACGTCGTGCGGCAGTTTAGCGACAACGCCGG AATCACACCAGCCATCAGCCTGGACCTGATGACAGATGCT GAGCTGGCTAGAGCCGTGCCTAACATGCCTACATCTGCCG GCCAGATCAAGCTGATGCTCGAGAATAGAGCCATGGTCCG ACGGAAAGGCTTCGGCATTCTGATTGGCGTGTACGGCAGC AGCGTGATCTATATGGTGCAGCTGCCTATCTTCGGCGTGA TCGACACACCCTGCTGGATTGTGAAGGCCGCTCCTAGCTG TAGCGAGAAGAAGGGCAATTACGCCTGCCTGCTGAGAGA GGACCAAGGCTGGTATTGTCAGAACGCCGGCAGCACCGTG TACTACCCTAACGAGAAGGACTGCGAGACAAGAGGCGAC CACGTGTTCTGTGATACCGCCGCTGGAATCAATGTGGCCG AGCAGAGCAAAGAGTGCAACATCAACATCAGCACCACCA ACTATCCCTGCAAGGTGTCCACCGGCAGGCACCCTATTTC TATGGTGGCTCTGTCTCCTCTGGGAGCCCTGGTGGCTTGTT ATAAGGGCGTGTCCTGTAGCATCGGCAGCAACAGAGTGG GCATCATCAAGCAGCTGAACAAGGGCTGCAGCTACATCAC CAACCAGGACGCCGATACCGTGACCATCGACAACACCGTG TATCAGCTGAGCAAGGTGGAAGGCGAACAGCACGTGATC AAGGGCAGACCTGTGTCCAGCAGCTTCGACCCTATCAAGT TCCCTGAGGATCAGTTCCAGGTGGCCCTGGACCAGGTGTT CGAGAACATCGAGAATTCCCAGGCTCTGGTGGACCAGTCC AACAGAATCCTGTCTAGCGCCGAGAAGGGAAACACCGGC TTCATCATCGTGATCATCCTGATCGCCGTGCTGGGCAGCTC CATGATCCTGGTGTCCATCTTCATCATTATCAAGAAGACC AAGAAGCCCACCGGCGCTCCTCCAGAACTGAGCGGAGTG ACCAACAATGGCTTCATCCCTCACAAC | 117 |
| HMPV_SC_4M_ StabilizeAlpha_ | ATGAGCTGGAAGGTGGTCATCATCTTCAGCCTGCTGATCA CACCTCAGCACGGCCTGAAAGAGAGCTACCTGGAAGAGT | 118 |

TABLE 19-continued

Human Metapneumovirus Mutant Nucleic Acid Sequences

| Strain | Nucleic Acid Sequence | SEQ ID NO: |
|---|---|---|
| V55LT74L5170LT174W | CCTGCAGCACCATCACAGAGGGCTACCTGTCTGTGCTGAG<br>AACCGGCTGGTACACCAACGTGTTCACACTGGAAGTGGGC<br>GACCTCGAGAATCTGACATGCTCTGATGGCCCTAGCCTGA<br>TCAAGACCGAGCTGGATCTGCTCAAGAGCGCCCTGAGAGA<br>ACTCAAGACCGTGTCTGCCGATCAGCTGGCCAGAGAGGAA<br>CAGATCGAGAATCCTGGCAGCGGCAGCTTTGTGCTGGGAG<br>CCATTGCTCTTGGAGTGGCTGCTGCTGCAGCTGTTACAGC<br>AGGCGTGGCCATCGCTAAGACCATCAGACTGGAAAGCGA<br>AGTGACCGCCATCAACAACGCCCTGAAGAAGACAAACGA<br>GGCCGTCAGCACACTCGGCAATGGCGTTAGAGTGCTGGCC<br>ACAGCCGTGCGCGAGCTGAAGGACTTCGTGCTTAAGAACC<br>TGTGGCGGGCCATTAACAAGAACAAGTGCGACATCGACG<br>ACCTGAAGATGGCCGTGTCCTTTAGCCAGTTCAACCGGCG<br>GTTTCTGAACGTCGTGCGGCAGTTTAGCGACAACGCCGGA<br>ATCACACCAGCCATCAGCCTGGACCTGATGACAGATGCTG<br>AGCTGGCTAGAGCCGTGCCTAACATGCCTACATCTGCCGG<br>CCAGATCAAGCTGATGCTCGAGAATAGAGCCATGGTCCGA<br>CGGAAAGGCTTCGGCATTCTGATTGGCGTGTACGGCAGCA<br>GCGTGATCTATATGGTGCAGCTGCCTATCTTCGGCGTGATC<br>GACACACCCTGCTGGATTGTGAAGGCCGCTCCTAGCTGTA<br>GCGAGAAGAAGGGCAATTACGCCTGCCTGCTGAGAGAGG<br>ACCAAGGCTGGTATTGTCAGAACGCCGGCAGCACCGTGTA<br>CTACCCTAACGAGAAGGACTGCGAGACAAGAGGCGACCA<br>CGTGTTCTGTGATACCGCCGCTGGAATCAATGTGGCCGAG<br>CAGAGCAAAGAGTGCAACATCAACATCAGCACCACCAAC<br>TATCCCTGCAAGGTGTCCACCGGCAGGCACCCTATTTCTAT<br>GGTGGCTCTGTCTCCTCTGGGAGCCCTGGTGGCTTGTTATA<br>AGGGCGTGTCCTGTAGCATCGGCAGCAACAGAGTGGGCAT<br>CATCAAGCAGCTGAACAAGGGCTGCAGCTACATCACCAAC<br>CAGGACGCCGATACCGTGACCATCGACAACACCGTGTATC<br>AGCTGAGCAAGGTGGAAGGCGAACAGCACGTGATCAAGG<br>GCAGACCTGTGTCCAGCAGCTTCGACCCTATCAAGTTCCC<br>TGAGGATCAGTTCCAGGTGGCCCTGGACCAGGTGTTCGAG<br>AACATCGAGAATTCCCAGGCTCTGGTGGACCAGTCCAACA<br>GAATCCTGTCTAGCGCCGAGAAGGGAAACACCGGCTTCAT<br>CATCGTGATCATCCTGATCGCCGTGCTGGGCAGCTCCATG<br>ATCCTGGTGTCCATCTTCATCATTATCAAGAAGACCAAGA<br>AGCCCACCGGCGCTCCTCCAGAACTGAGCGGAGTGACCAA<br>CAATGGCTTCATCCCTCACAAC | |
| HMPV_Proline<br>Stab_E51P | ATGAGCTGGAAGGTGGTCATCATCTTCAGCCTGCTGATCA<br>CACCTCAGCACGGCCTGAAAGAGAGCTACCTGGAAGAGT<br>CCTGCAGCACCATCACAGAGGGCTACCTGTCTGTGCTGAG<br>AACCGGCTGGTACACCAACGTGTTCACACTGCCTGTGGGC<br>GACGTCGAGAATCTGACATGCTCTGATGGCCCTAGCCTGA<br>TCAAGACCGAGCTGGATCTGACCAAGAGCGCCCTGAGAG<br>AACTCAAGACCGTGTCTGCCGATCAGCTGGCCAGAGAGGA<br>ACAGATCGAGAATCCTGGCAGCGGCAGCTTTGTGCTGGGA<br>GCCATTGCTCTTGGAGTGGCTGCTGCTGCAGCTGTTACAG<br>CAGGCGTGGCCATCGCTAAGACCATCAGACTGGAAAGCG<br>AAGTGACCGCCATCAACAACGCCCTGAAGAAGACAAACG<br>AGGCCGTCAGCACACTCGGCAATGGCGTTAGAGTGCTGGC<br>CACAGCCGTGCGCGAGCTGAAGGACTTCGTGTCCAAGAAC<br>CTGACACGGGCCATTAACAAGAACAAGTGCGACATCGAC<br>GACCTGAAGATGGCCGTGTCCTTTAGCCAGTTCAACCGGC<br>GGTTTCTGAACGTCGTGCGGCAGTTTAGCGACAACGCCGG<br>AATCACACCAGCCATCAGCCTGGACCTGATGACAGATGCT<br>GAGCTGGCTAGAGCCGTGCCTAACATGCCTACATCTGCCG<br>GCCAGATCAAGCTGATGCTCGAGAATAGAGCCATGGTCCG<br>ACGGAAAGGCTTCGGCATTCTGATTGGCGTGTACGGCAGC<br>AGCGTGATCTATATGGTGCAGCTGCCTATCTTCGGCGTGA<br>TCGACACACCCTGCTGGATTGTGAAGGCCGCTCCTAGCTG<br>TAGCGAGAAGAAGGGCAATTACGCCTGCCTGCTGAGAGA<br>GGACCAAGGCTGGTATTGTCAGAACGCCGGCAGCACCGTG<br>TACTACCCTAACGAGAAGGACTGCGAGACAAGAGGCGAC<br>CACGTGTTCTGTGATACCGCCGCTGGAATCAATGTGGCCG<br>AGCAGAGCAAAGAGTGCAACATCAACATCAGCACCACCA<br>ACTATCCCTGCAAGGTGTCCACCGGCAGGCACCCTATTTC<br>TATGGTGGCTCTGTCTCCTCTGGGAGCCCTGGTGGCTTGTT<br>ATAAGGGCGTGTCCTGTAGCATCGGCAGCAACAGAGTGG<br>GCATCATCAAGCAGCTGAACAAGGGCTGCAGCTACATCAC<br>CAACCAGGACGCCGATACCGTGACCATCGACAACACCGTG<br>TATCAGCTGAGCAAGGTGGAAGGCGAACAGCACGTGATC<br>AAGGGCAGACCTGTGTCCAGCAGCTTCGACCCTATCAAGT<br>TCCCTGAGGATCAGTTCCAGGTGGCCCTGGACCAGGTGTT | 119 |

TABLE 19-continued

Human Metapneumovirus Mutant Nucleic Acid Sequences

| Strain | Nucleic Acid Sequence | SEQ ID NO: |
|---|---|---|
| | CGAGAACATCGAGAATTCCCAGGCTCTGGTGGACCAGTCC<br>AACAGAATCCTGTCTAGCGCCGAGAAGGGAAACACCGGC<br>TTCATCATCGTGATCATCCTGATCGCCGTGCTGGGCAGCTC<br>CATGATCCTGGTGTCCATCTTCATCATTATCAAGAAGACC<br>AAGAAGCCCACCGGCGCTCCTCCAGAACTGAGCGGAGTG<br>ACCAACAATGGCTTCATCCCTCACAAC | |
| HMPV_Proline<br>Stab_D185P | ATGAGCTGGAAGGTGGTCATCATCTTCAGCCTGCTGATCA<br>CACCTCAGCACGGCCTGAAAGAGAGCTACCTGGAAGAGT<br>CCTGCAGCACCATCACAGAGGGCTACCTGTCTGTGCTGAG<br>AACCGGCTGGTACACCAACGTGTTCACACTGGAAGTGGGC<br>GACGTCGAGAATCTGACATGCTCTGATGGCCCTAGCCTGA<br>TCAAGACCGAGCTGGATCTGACCAAGAGCGCCCTGAGAG<br>AACTCAAGACCGTGTCTGCCGATCAGCTGGCCAGAGAGGA<br>ACAGATCGAGAATCCTGGCAGCGGCAGCTTTGTGCTGGGA<br>GCCATTGCTCTTGGAGTGGCTGCTGCTGCAGCTGTTACAG<br>CAGGCGTGGCCATCGCTAAGACCATCAGACTGGAAAGCG<br>AAGTGACCGCCATCAACAACGCCCTGAAGAAGACAAACG<br>AGGCCGTCAGCACACTCGGCAATGGCGTTAGAGTGCTGGC<br>CACAGCCGTGCGCGAGCTGAAGGACTTCGTGTCCAAGAAC<br>CTGACACGGGCCATTAACAAGAACAAGTGCGACATCCCTG<br>ACCTGAAGATGGCCGTGTCCTTTAGCCAGTTCAACCGGCG<br>GTTTCTGAACGTCGTGCGGCAGTTTAGCGACAACGCCGGA<br>ATCACACCAGCCATCAGCCTGGACCTGATGACAGATGCTG<br>AGCTGGCTAGAGCCGTGCCTAACATGCCTACATCTGCCGG<br>CCAGATCAAGCTGATGCTCGAGAATAGAGCCATGGTCCGA<br>CGGAAAGGCTTCGGCATTCTGATTGGCGTGTACGGCAGCA<br>GCGTGATCTATATGGTGCAGCTGCCTATCTTCGGCGTGATC<br>GACACACCCTGCTGGATTGTGAAGGCCGCTCCTAGCTGTA<br>GCGAGAAGAAGGGCAATTACGCCTGCCTGCTGAGAGAGG<br>ACCAAGGCTGGTATTGTCAGAACGCCGGCAGCACCGTGTA<br>CTACCCTAACGAGAAGGACTGCGAGACAAGAGGCGACCA<br>CGTGTTCTGTGATACCGCCGCTGGAATCAATGTGGCCGAG<br>CAGAGCAAAGAGTGCAACATCAACATCAGCACCACCAAC<br>TATCCCTGCAAGGTGTCCACCGGCAGGCACCCTATTTCTAT<br>GGTGGCTCTGTCTCCTCTGGGAGCCCTGGTGGCTTGTTATA<br>AGGGCGTGTCCTGTAGCATCGGCAGCAACAGAGTGGGCAT<br>CATCAAGCAGCTGAACAAGGGCTGCAGCTACATCACCAAC<br>CAGGACGCCGATACCGTGACCATCGACAACACCGTGTATC<br>AGCTGAGCAAGGTGGAAGGCGAACAGCACGTGATCAAGG<br>GCAGACCTGTGTCCAGCAGCTTCGACCCTATCAAGTTCCC<br>TGAGGATCAGTTCCAGGTGGCCCTGGACCAGGTGTTCGAG<br>AACATCGAGAATTCCCAGGCTCTGGTGGACCAGTCCAACA<br>GAATCCTGTCTAGCGCCGAGAAGGGAAACACCGGCTTCAT<br>CATCGTGATCATCCTGATCGCCGTGCTGGGCAGCTCCATG<br>ATCCTGGTGTCCATCTTCATCATTATCAAGAAGACCAAGA<br>AGCCCACCGGCGCTCCTCCAGAACTGAGCGGAGTGACCAA<br>CAATGGCTTCATCCCTCACAAC | 120 |
| HMPV_Proline<br>Stab_D183P | ATGAGCTGGAAGGTGGTCATCATCTTCAGCCTGCTGATCA<br>CACCTCAGCACGGCCTGAAAGAGAGCTACCTGGAAGAGT<br>CCTGCAGCACCATCACAGAGGGCTACCTGTCTGTGCTGAG<br>AACCGGCTGGTACACCAACGTGTTCACACTGGAAGTGGGC<br>GACGTCGAGAATCTGACATGCTCTGATGGCCCTAGCCTGA<br>TCAAGACCGAGCTGGATCTGACCAAGAGCGCCCTGAGAG<br>AACTCAAGACCGTGTCTGCCGATCAGCTGGCCAGAGAGGA<br>ACAGATCGAGAATCCTGGCAGCGGCAGCTTTGTGCTGGGA<br>GCCATTGCTCTTGGAGTGGCTGCTGCTGCAGCTGTTACAG<br>CAGGCGTGGCCATCGCTAAGACCATCAGACTGGAAAGCG<br>AAGTGACCGCCATCAACAACGCCCTGAAGAAGACAAACG<br>AGGCCGTCAGCACACTCGGCAATGGCGTTAGAGTGCTGGC<br>CACAGCCGTGCGCGAGCTGAAGGACTTCGTGTCCAAGAAC<br>CTGACACGGGCCATTAACAAGAACAAGTGCCCTATCGACG<br>ACCTGAAGATGGCCGTGTCCTTTAGCCAGTTCAACCGGCG<br>GTTTCTGAACGTCGTGCGGCAGTTTAGCGACAACGCCGGA<br>ATCACACCAGCCATCAGCCTGGACCTGATGACAGATGCTG<br>AGCTGGCTAGAGCCGTGCCTAACATGCCTACATCTGCCGG<br>CCAGATCAAGCTGATGCTCGAGAATAGAGCCATGGTCCGA<br>CGGAAAGGCTTCGGCATTCTGATTGGCGTGTACGGCAGCA<br>GCGTGATCTATATGGTGCAGCTGCCTATCTTCGGCGTGATC<br>GACACACCCTGCTGGATTGTGAAGGCCGCTCCTAGCTGTA<br>GCGAGAAGAAGGGCAATTACGCCTGCCTGCTGAGAGAGG<br>ACCAAGGCTGGTATTGTCAGAACGCCGGCAGCACCGTGTA<br>CTACCCTAACGAGAAGGACTGCGAGACAAGAGGCGACCA<br>CGTGTTCTGTGATACCGCCGCTGGAATCAATGTGGCCGAG | 121 |

TABLE 19-continued

Human Metapneumovirus Mutant Nucleic Acid Sequences

| Strain | Nucleic Acid Sequence | SEQ ID NO: |
|---|---|---|
| | CAGAGCAAAGAGTGCAACATCAACATCAGCACCACCAAC<br>TATCCCTGCAAGGTGTCCACCGGCAGGCACCCTATTTCTAT<br>GGTGGCTCTGTCTCCTCTGGGAGCCCTGGTGGCTTGTTATA<br>AGGGCGTGTCCTGTAGCATCGGCAGCAACAGAGTGGGCAT<br>CATCAAGCAGCTGAACAAGGGCTGCAGCTACATCACCAAC<br>CAGGACGCCGATACCGTGACCATCGACAACACCGTGTATC<br>AGCTGAGCAAGGTGGAAGGCGAACAGCACGTGATCAAGG<br>GCAGACCTGTGTCCAGCAGCTTCGACCCTATCAAGTTCCC<br>TGAGGATCAGTTCCAGGTGGCCCTGGACCAGGTGTTCGAG<br>AACATCGAGAATTCCCAGGCTCTGGTGGACCAGTCCAACA<br>GAATCCTGTCTAGCGCCGAGAAGGGAAACACCGGCTTCAT<br>CATCGTGATCATCCTGATCGCCGTGCTGGGCAGCTCCATG<br>ATCCTGGTGTCCATCTTCATCATTATCAAGAAGACCAAGA<br>AGCCCACCGGCGCTCCTCCAGAACTGAGCGGAGTGACCAA<br>CAATGGCTTCATCCCTCACAAC | |
| HMPV_Proline Stab_E131P | ATGAGCTGGAAGGTGGTCATCATCTTCAGCCTGCTGATCA<br>CACCTCAGCACGGCCTGAAAGAGAGCTACCTGGAAGAGT<br>CCTGCAGCACCATCACAGAGGGCTACCTGTCTGTGCTGAG<br>AACCGGCTGGTACACCAACGTGTTCACACTGGAAGTGGGC<br>GACGTCGAGAATCTGACATGCTCTGATGGCCCTAGCCTGA<br>TCAAGACCGAGCTGGATCTGACCAAGAGCGCCCTGAGAG<br>AACTCAAGACCGTGTCTGCCGATCAGCTGGCCAGAGAGGA<br>ACAGATCGAGAATCCTGGCAGCGGCAGCTTTGTGCTGGGA<br>GCCATTGCTCTTGGAGTGGCTGCTGCTGCAGCTGTTACAG<br>CAGGCGTGGCCATCGCTAAGACCATCAGACTGCCTAGCGA<br>AGTGACCGCCATCAACAACGCCCTGAAGAAGACAAACGA<br>GGCCGTCAGCACACTCGGCAATGGCGTTAGAGTGCTGGCC<br>ACAGCCGTGCGCGAGCTGAAGGACTTCGTGTCCAAGAACC<br>TGACACGGGCCATTAACAAGAACAAGTGCGACATCGACG<br>ACCTGAAGATGGCCGTGTCCTTTAGCCAGTTCAACCGGCG<br>GTTTCTGAACGTCGTGCGGCAGTTTAGCGACAACGCCGGA<br>ATCACACCAGCCATCAGCCTGGACCTGATGACAGATGCTG<br>AGCTGGCTAGAGCCGTGCCTAACATGCCTACATCTGCCGG<br>CCAGATCAAGCTGATGCTCGAGAATAGAGCCATGGTCCGA<br>CGGAAAGGCTTCGGCATTCTGATTGGCGTGTACGGCAGCA<br>GCGTGATCTATATGGTGCAGCTGCCTATCTTCGGCGTGATC<br>GACACACCCTGCTGGATTGTGAAGGCCGCTCCTAGCTGTA<br>GCGAGAAGAAGGGCAATTACGCCTGCCTGCTGAGAGAGG<br>ACCAAGGCTGGTATTGTCAGAACGCCGGCAGCACCGTGTA<br>CTACCCTAACGAGAAGGACTGCGAGACAAGAGGCGACCA<br>CGTGTTCTGTGATACCGCCGCTGGAATCAATGTGGCCGAG<br>CAGAGCAAAGAGTGCAACATCAACATCAGCACCACCAAC<br>TATCCCTGCAAGGTGTCCACCGGCAGGCACCCTATTTCTAT<br>GGTGGCTCTGTCTCCTCTGGGAGCCCTGGTGGCTTGTTATA<br>AGGGCGTGTCCTGTAGCATCGGCAGCAACAGAGTGGGCAT<br>CATCAAGCAGCTGAACAAGGGCTGCAGCTACATCACCAAC<br>CAGGACGCCGATACCGTGACCATCGACAACACCGTGTATC<br>AGCTGAGCAAGGTGGAAGGCGAACAGCACGTGATCAAGG<br>GCAGACCTGTGTCCAGCAGCTTCGACCCTATCAAGTTCCC<br>TGAGGATCAGTTCCAGGTGGCCCTGGACCAGGTGTTCGAG<br>AACATCGAGAATTCCCAGGCTCTGGTGGACCAGTCCAACA<br>GAATCCTGTCTAGCGCCGAGAAGGGAAACACCGGCTTCAT<br>CATCGTGATCATCCTGATCGCCGTGCTGGGCAGCTCCATG<br>ATCCTGGTGTCCATCTTCATCATTATCAAGAAGACCAAGA<br>AGCCCACCGGCGCTCCTCCAGAACTGAGCGGAGTGACCAA<br>CAATGGCTTCATCCCTCACAAC | 122 |
| HMPV_Proline Stab_D447P | ATGAGCTGGAAGGTGGTCATCATCTTCAGCCTGCTGATCA<br>CACCTCAGCACGGCCTGAAAGAGAGCTACCTGGAAGAGT<br>CCTGCAGCACCATCACAGAGGGCTACCTGTCTGTGCTGAG<br>AACCGGCTGGTACACCAACGTGTTCACACTGGAAGTGGGC<br>GACGTCGAGAATCTGACATGCTCTGATGGCCCTAGCCTGA<br>TCAAGACCGAGCTGGATCTGACCAAGAGCGCCCTGAGAG<br>AACTCAAGACCGTGTCTGCCGATCAGCTGGCCAGAGAGGA<br>ACAGATCGAGAATCCTGGCAGCGGCAGCTTTGTGCTGGGA<br>GCCATTGCTCTTGGAGTGGCTGCTGCTGCAGCTGTTACAG<br>CAGGCGTGGCCATCGCTAAGACCATCAGACTGGAAAGCG<br>AAGTGACCGCCATCAACAACGCCCTGAAGAAGACAAACG<br>AGGCCGTCAGCACACTCGGCAATGGCGTTAGAGTGCTGGC<br>CACAGCCGTGCGCGAGCTGAAGGACTTCGTGTCCAAGAAC<br>CTGACACGGGCCATTAACAAGAACAAGTGCGACATCGAC<br>GACCTGAAGATGGCCGTGTCCTTTAGCCAGTTCAACCGGC<br>GGTTTCTGAACGTCGTGCGGCAGTTTAGCGACAACGCCGG<br>AATCACACCAGCCATCAGCCTGGACCTGATGACAGATGCT | 123 |

TABLE 19-continued

Human Metapneumovirus Mutant Nucleic Acid Sequences

| Strain | Nucleic Acid Sequence | SEQ ID NO: |
|---|---|---|
| | GAGCTGGCTAGAGCCGTGCCTAACATGCCTACATCTGCCG GCCAGATCAAGCTGATGCTCGAGAATAGAGCCATGGTCCG ACGGAAAGGCTTCGGCATTCTGATTGGCGTGTACGGCAGC AGCGTGATCTATATGGTGCAGCTGCCTATCTTCGGCGTGA TCGACACACCCTGCTGGATTGTGAAGGCCGCTCCTAGCTG TAGCGAGAAGAAGGGCAATTACGCCTGCCTGCTGAGAGA GGACCAAGGCTGGTATTGTCAGAACGCCGGCAGCACCGTG TACTACCCTAACGAGAAGGACTGCGAGACAAGAGGCGAC CACGTGTTCTGTGATACCGCCGCTGGAATCAATGTGGCCG AGCAGAGCAAAGAGTGCAACATCAACATCAGCACCACCA ACTATCCCTGCAAGGTGTCCACCGGCAGGCACCCTATTTC TATGGTGGCTCTGTCTCCTCTGGGAGCCCTGGTGGCTTGTT ATAAGGGCGTGTCCTGTAGCATCGGCAGCAACAGAGTGG GCATCATCAAGCAGCTGAACAAGGGCTGCAGCTACATCAC CAACCAGGACGCCGATACCGTGACCATCGACAACACCGTG TATCAGCTGAGCAAGGTGGAAGGCGAACAGCACGTGATC AAGGGCAGACCTGTGTCCAGCAGCTTCCCACCTATCAAGT TCCCTGAGGATCAGTTCCAGGTGGCCCTGGACCAGGTGTT CGAGAACATCGAGAATTCCCAGGCTCTGGTGGACCAGTCC AACAGAATCCTGTCTAGCGCCGAGAAGGGAAACACCGGC TTCATCATCGTGATCATCCTGATCGCCGTGCTGGGCAGCTC CATGATCCTGGTGTCCATCTTCATCATTATCAAGAAGACC AAGAAGCCCACCGGCGCTCCTCCAGAACTGAGCGGAGTG ACCAACAATGGCTTCATCCCTCACAAC | |
| HMPV_Trimer RepulsionD454N | ATGAGCTGGAAGGTGGTCATCATCTTCAGCCTGCTGATCA CACCTCAGCACGGCCTGAAAGAGAGCTACCTGGAAGAGT CCTGCAGCACCATCACAGAGGGCTACCTGTCTGTGCTGAG AACCGGCTGGTACACCAACGTGTTCACACTGGAAGTGGGC GACGTCGAGAATCTGACATGCTCTGATGGCCCTAGCCTGA TCAAGACCGAGCTGGATCTGACCAAGAGCGCCCTGAGAG AACTCAAGACCGTGTCTGCCGATCAGCTGGCCAGAGAGGA ACAGATCGAGAATCCTGGCAGCGGCAGCTTTGTGCTGGGA GCCATTGCTCTTGGAGTGGCTGCTGCTGCAGCTGTTACAG CAGGCGTGGCCATCGCTAAGACCATCAGACTGGAAAGCG AAGTGACCGCCATCAACAACGCCCTGAAGAAGACAAACG AGGCCGTCAGCACACTCGGCAATGGCGTTAGAGTGCTGGC CACAGCCGTGCGCGAGCTGAAGGACTTCGTGTCCAAGAAC CTGACACGGGCCATTAACAAGAACAAGTGCGACATCGAC GACCTGAAGATGGCCGTGTCCTTTAGCCAGTTCAACCGGC GGTTTCTGAACGTCGTGCGGCAGTTTAGCGACAACGCCGG AATCACACCAGCCATCAGCCTGGACCTGATGACAGATGCT GAGCTGGCTAGAGCCGTGCCTAACATGCCTACATCTGCCG GCCAGATCAAGCTGATGCTCGAGAATAGAGCCATGGTCCG ACGGAAAGGCTTCGGCATTCTGATTGGCGTGTACGGCAGC AGCGTGATCTATATGGTGCAGCTGCCTATCTTCGGCGTGA TCGACACACCCTGCTGGATTGTGAAGGCCGCTCCTAGCTG TAGCGAGAAGAAGGGCAATTACGCCTGCCTGCTGAGAGA GGACCAAGGCTGGTATTGTCAGAACGCCGGCAGCACCGTG TACTACCCTAACGAGAAGGACTGCGAGACAAGAGGCGAC CACGTGTTCTGTGATACCGCCGCTGGAATCAATGTGGCCG AGCAGAGCAAAGAGTGCAACATCAACATCAGCACCACCA ACTATCCCTGCAAGGTGTCCACCGGCAGGCACCCTATTTC TATGGTGGCTCTGTCTCCTCTGGGAGCCCTGGTGGCTTGTT ATAAGGGCGTGTCCTGTAGCATCGGCAGCAACAGAGTGG GCATCATCAAGCAGCTGAACAAGGGCTGCAGCTACATCAC CAACCAGGACGCCGATACCGTGACCATCGACAACACCGTG TATCAGCTGAGCAAGGTGGAAGGCGAACAGCACGTGATC AAGGGCAGACCTGTGTCCAGCAGCTTCGACCCTATCAAGT TCCCTGAGAACCAGTTCCAGGTGGCCCTGGACCAGGTGTT CGAGAACATCGAGAATTCCCAGGCTCTGGTGGACCAGTCC AACAGAATCCTGTCTAGCGCCGAGAAGGGAAACACCGGC TTCATCATCGTGATCATCCTGATCGCCGTGCTGGGCAGCTC CATGATCCTGGTGTCCATCTTCATCATTATCAAGAAGACC AAGAAGCCCACCGGCGCTCCTCCAGAACTGAGCGGAGTG ACCAACAATGGCTTCATCCCTCACAAC | 124 |
| HMPV_Trimer RepulsionE453N | ATGAGCTGGAAGGTGGTCATCATCTTCAGCCTGCTGATCA CACCTCAGCACGGCCTGAAAGAGAGCTACCTGGAAGAGT CCTGCAGCACCATCACAGAGGGCTACCTGTCTGTGCTGAG AACCGGCTGGTACACCAACGTGTTCACACTGGAAGTGGGC GACGTCGAGAATCTGACATGCTCTGATGGCCCTAGCCTGA TCAAGACCGAGCTGGATCTGACCAAGAGCGCCCTGAGAG AACTCAAGACCGTGTCTGCCGATCAGCTGGCCAGAGAGGA ACAGATCGAGAATCCTGGCAGCGGCAGCTTTGTGCTGGGA | 125 |

TABLE 19-continued

| Human Metapneumovirus Mutant Nucleic Acid Sequences | | |
|---|---|---|
| Strain | Nucleic Acid Sequence | SEQ ID NO: |
| | GCCATTGCTCTTGGAGTGGCTGCTGCTGCAGCTGTTACAG CAGGCGTGGCCATCGCTAAGACCATCAGACTGGAAAGCG AAGTGACCGCCATCAACAACGCCCTGAAGAAGACAAACG AGGCCGTCAGCACACTCGGCAATGGCGTTAGAGTGCTGGC CACAGCCGTGCGCGAGCTGAAGGACTTCGTGTCCAAGAAC CTGACACGGGCCATTAACAAGAACAAGTGCGACATCGAC GACCTGAAGATGGCCGTGTCCTTTAGCCAGTTCAACCGGC GGTTTCTGAACGTCGTGCGGCAGTTTAGCGACAACGCCGG AATCACACCAGCCATCAGCCTGGACCTGATGACAGATGCT GAGCTGGCTAGAGCCGTGCCTAACATGCCTACATCTGCCG GCCAGATCAAGCTGATGCTCGAGAATAGAGCCATGGTCCG ACGGAAAGGCTTCGGCATTCTGATTGGCGTGTACGGCAGC AGCGTGATCTATATGGTGCAGCTGCCTATCTTCGGCGTGA TCGACACACCCTGCTGGATTGTGAAGGCCGCTCCTAGCTG TAGCGAGAAGAAGGGCAATTACGCCTGCCTGCTGAGAGA GGACCAAGGCTGGTATTGTCAGAACGCCGGCAGCACCGTG TACTACCCTAACGAGAAGGACTGCGAGACAAGAGGCGAC CACGTGTTCTGTGATACCGCCGCTGGAATCAATGTGGCCG AGCAGAGCAAAGAGTGCAACATCAACATCAGCACCACCA ACTATCCCTGCAAGGTGTCCACCGGCAGGCACCCTATTTC TATGGTGGCTCTGTCTCCTCTGGGAGCCCTGGTGGCTTGTT ATAAGGGCGTGTCCTGTAGCATCGGCAGCAACAGAGTGG GCATCATCAAGCAGCTGAACAAGGGCTGCAGCTACATCAC CAACCAGGACGCCGATACCGTGACCATCGACAACACCGTG TATCAGCTGAGCAAGGTGGAAGGCGAACAGCACGTGATC AAGGGCAGACCTGTGTCCAGCAGCTTCGACCCTATCAAGT TCCCTCAGGATCAGTTCCAGGTGGCCCTGGACCAGGTGTT CGAGAACATCGAGAATTCCCAGGCTCTGGTGGACCAGTCC AACAGAATCCTGTCTAGCGCCGAGAAGGGAAACACCGGC TTCATCATCGTGATCATCCTGATCGCCGTGCTGGGCAGCTC CATGATCCTGGTGTCCATCTTCATCATTATCAAGAAGACC AAGAAGCCCACCGGCGCTCCTCCAGAACTGAGCGGAGTG ACCAACAATGGCTTCATCCCTCACAAC | |
| HMPV_Stabilize AlphaF196W | ATGAGCTGGAAGGTGGTCATCATCTTCAGCCTGCTGATCA CACCTCAGCACGGCCTGAAAGAGAGCTACCTGGAAGAGT CCTGCAGCACCATCACAGAGGGCTACCTGTCTGTGCTGAG AACCGGCTGGTACACCAACGTGTTCACACTGGAAGTGGGC GACGTCGAGAATCTGACATGCTCTGATGGCCCTAGCCTGA TCAAGACCGAGCTGGATCTGACCAAGAGCGCCCTGAGAG AACTCAAGACCGTGTCTGCCGATCAGCTGGCCAGAGAGGA ACAGATCGAGAATCCTGGCAGCGGCAGCTTTGTGCTGGGA GCCATTGCTCTTGGAGTGGCTGCTGCTGCAGCTGTTACAG CAGGCGTGGCCATCGCTAAGACCATCAGACTGGAAAGCG AAGTGACCGCCATCAACAACGCCCTGAAGAAGACAAACG AGGCCGTCAGCACACTCGGCAATGGCGTTAGAGTGCTGGC CACAGCCGTGCGCGAGCTGAAGGACTTCGTGTCCAAGAAC CTGACACGGGCCATTAACAAGAACAAGTGCGACATCGAC GACCTGAAGATGGCCGTGTCCTTTAGCCAGTGGAACCGGC GGTTTCTGAACGTCGTGCGGCAGTTTAGCGACAACGCCGG AATCACACCAGCCATCAGCCTGGACCTGATGACAGATGCT GAGCTGGCTAGAGCCGTGCCTAACATGCCTACATCTGCCG GCCAGATCAAGCTGATGCTCGAGAATAGAGCCATGGTCCG ACGGAAAGGCTTCGGCATTCTGATTGGCGTGTACGGCAGC AGCGTGATCTATATGGTGCAGCTGCCTATCTTCGGCGTGA TCGACACACCCTGCTGGATTGTGAAGGCCGCTCCTAGCTG TAGCGAGAAGAAGGGCAATTACGCCTGCCTGCTGAGAGA GGACCAAGGCTGGTATTGTCAGAACGCCGGCAGCACCGTG TACTACCCTAACGAGAAGGACTGCGAGACAAGAGGCGAC CACGTGTTCTGTGATACCGCCGCTGGAATCAATGTGGCCG AGCAGAGCAAAGAGTGCAACATCAACATCAGCACCACCA ACTATCCCTGCAAGGTGTCCACCGGCAGGCACCCTATTTC TATGGTGGCTCTGTCTCCTCTGGGAGCCCTGGTGGCTTGTT ATAAGGGCGTGTCCTGTAGCATCGGCAGCAACAGAGTGG GCATCATCAAGCAGCTGAACAAGGGCTGCAGCTACATCAC CAACCAGGACGCCGATACCGTGACCATCGACAACACCGTG TATCAGCTGAGCAAGGTGGAAGGCGAACAGCACGTGATC AAGGGCAGACCTGTGTCCAGCAGCTTCGACCCTATCAAGT TCCCTGAGGATCAGTTCCAGGTGGCCCTGGACCAGGTGTT CGAGAACATCGAGAATTCCCAGGCTCTGGTGGACCAGTCC AACAGAATCCTGTCTAGCGCCGAGAAGGGAAACACCGGC TTCATCATCGTGATCATCCTGATCGCCGTGCTGGGCAGCTC | 126 |

TABLE 19-continued

| Strain | Nucleic Acid Sequence | SEQ ID NO: |
|---|---|---|
| **Human Metapneumovirus Mutant Nucleic Acid Sequences** | | |
| | CATGATCCTGGTGTCCATCTTCATCATTATCAAGAAGACC AAGAAGCCCACCGGCGCTCCTCCAGAACTGAGCGGAGTG ACCAACAATGGCTTCATCCCTCACAAC | |
| **Human Metapneumovirus mRNA Sequences** | | |
| HMPV_SC_ DSCAV1_4MMV | AUGAGCUGGAAGGUGGUCAUCAUCUUCAGCCUGCUGAU CACACCUCAGCACGGCCUGAAAGAGAGCUACCUGGAAGA GUCCUGCAGCACCAUCACAGAGGGCUACCUGUCUGUGCU GAGAACCGGCUGGUACACCAACGUGUUCACACUGGAAGU GGGCGACGUCGAGAAUCUGACAUGCUCUGAUGGCCCUAG CCUGAUCAAGACCGAGCUGGAUCUGACCAAGAGCGCCCU GAGAGAACUCAAGACCGUGUCUGCCGAUCAGCUGGCCAG AGAGGAACAGAUCGAGAAUCCUGGCAGCGGCAGCUUUG UGCUGGGAGCCAUUGCUCUUGGAGUGGCUGCUGCUGCA GCUGUUACAGCAGGCGUGGCCAUCUGCAAGACCAUCAGA CUGGAAAGCGAAGUGACCGCCAUCAACAACGCCCUGAAG AAGACAAACGAGGCCGUCAGCACACUCGGCAAUGGCGUU AGAGUGCUGGCCUUUGCCGUGCGCGAGCUGAAGGACUUC GUGUCCAAGAACCUGACACGGGCCCUGAACAAGAACAAG UGCGACAUCGACGACCUGAAGAUGGCCGUGUCCUUUAGC CAGUUCAACCGGCGGUUUCUGAACGUCGUGCGGCAGUUU AGCGACAACGCCGGAAUCACACCAGCCAUCAGCCUGGAC CUGAUGACAGAUGCUGAGCUGGCUAGAGCCGUGCCUAAC AUGCCUACAUCUGCCGGCCAGAUCAAGCUGAUGCUCGAG AAUAGAGCCAUGGUCCGACGGAAAGGCUUCGGCAUUCU GUGUGGCGUGUACGGCAGCAGCGUGAUCUAUAUGGUGC AGCUGCCUAUCUUCGGCGUGAUCGACACACCCUGCUGGA UUGUGAAGGCCGCUCCUAGCUGUAGCGAGAAGAAGGGC AAUUACGCCUGCCUGCUGAGAGAGGACCAAGGCUGGUA UUGUCAGAACGCCGGCAGCACCGUGUACUACCCUAACGA GAAGGACUGCGAGACAAGAGGCGACCACGUGUUCUGUG AUACCGCCGCUGGAAUCAAUGUGGCCGAGCAGAGCAAAG AGUGCAACAUCAACAUCAGCACCACCAACUAUCCCUGCA AGGUGUCCACCGGCAGGCACCCUAUUUCUAUGGUGGCUC UGUCUCCUCUGGGAGCCCUGGUGGCUUGUUAUAAGGGC GUGUCCUGUAGCAUCGGCAGCAACAGAGUGGGCAUCAUC AAGCAGCUGAACAAGGGCUGCAGCUACAUCACCAACCAG GACGCCGAUACCGUGACCAUCGACAACACCGUGUAUCAG CUGAGCAAGGUGGAAGGCGAACAGCACGUGAUCAAGGG CAGACCUGUGUCCAGCAGCUUCGACCCUAUCAAGUUCCC UGAGGAUCAGUUCAACGUGGCCCUGGACCAGGUGUUCG AGAACAUCGAGAAUUCCCAGGCUCUGGUGGACCAGUCCA ACAGAAUCCUGUCUAGCGCCGAGAAGGGAAACACCGGCU UCAUCAUCGUGAUCAUCCUGAUCGCCGUGCUGGGCAGCU CCAUGAUCCUGGUGUCCAUCUUCAUCAUUAUCAAGAAGA CCAAGAAGCCCACCGGCGCUCCUCCAGAACUGAGCGGAG UGACCAACAAUGGCUUCAUCCCUCACAAC | 127 |
| HMPV_SC_ DSURIC_4MMV | AUGAGCUGGAAGGUGGUCAUCAUCUUCAGCCUGCUGAU CACACCUCAGCACGGCCUGAAAGAGAGCUACCUGGAAGA GUCCUGCAGCACCAUCACAGAGGGCUACCUGUCUGUGCU GAGAACCGGCUGGUACACCAACGUGUUCACACUGGAAGU GGGCGACGUCGAGAAUCUGACAUGCUCUGAUGGCCCUAG CCUGAUCAAGACCGAGCUGGAUCUGACCAAGAGCGCCCU GAGAGAACUCAAGACCGUGUCUGCCGAUCAGCUGGCCAG AGAGGAACAGAUCGAGAAUCCUGGCAGCGGCAGCUUUG UGCUGGGAGCCAUUGCUCUUGGAGUGGCUGCUGCUGCA GCUGUUACAGCAGGCGUGGCCAUCUGCAAGACCAUCAGA CUGGAAAGCGAAGUGACCGCCAUCAACAACGCCCUGAAG AAGACAAACGAGGCCGUCAGCACACUCGGCAAUGGCGUU AGAGUGCUGGCCACAGCCGUGCGCGAGCUGAAGGACUUC GUGUCCAAGAACCUGACACGGGCCAUUAACAAGAACAAG UGCGACAUCGACGACCUGAAGAUGGCCGUGUCCUUUAGC CAGUUCAACCGGCGGUUUCUGAACGUCGUGCGGCAGUUU AGCGACAACGCCGGAAUCACACCAGCCAUCAGCCUGGAC CUGAUGACAGAUGCUGAGCUGGCUAGAGCCGUGCCUAAC AUGCCUACAUCUGCCGGCCAGAUCAAGCUGAUGCUCGAG AAUAGAGCCAUGGUCCGACGGAAAGGCUUCGGCAUUCU GUGUGGCGUGUACGGCAGCAGCGUGAUCUAUAUGGUGC AGCUGCCUAUCUUCGGCGUGAUCGACACACCCUGCUGGA UUGUGAAGGCCGCUCCUAGCUGUAGCGAGAAGAAGGGC AAUUACGCCUGCCUGCUGAGAGAGGACCAAGGCUGGUA UUGUCAGAACGCCGGCAGCACCGUGUACUACCCUAACGA GAAGGACUGCGAGACAAGAGGCGACCACGUGUUCUGUG | 128 |

TABLE 19-continued

| Human Metapneumovirus Mutant Nucleic Acid Sequences | | |
|---|---|---|
| Strain | Nucleic Acid Sequence | SEQ ID NO: |
| | AUACCGCCGCUGGAAUCAAUGUGGCCGAGCAGAGCAAAG AGUGCAACAUCAACAUCAGCACCACCAACUAUCCCUGCA AGGUGUCCACCGGCAGGCACCCUAUUUCUAUGGUGGCUC UGUCUCCUCUGGGAGCCCUGGUGGCUUGUUAUAAGGGC GUGUCCUGUAGCAUCGGCAGCAACAGAGUGGGCAUCAUC AAGCAGCUGAACAAGGGCUGCAGCUACAUCACCAACCAG GACGCCGAUACCGUGACCAUCGACAACACCGUGUAUCAG CUGAGCAAGGUGGAAGGCGAACAGCACGUGAUCAAGGG CAGACCUGUGUCCAGCAGCUUCGACCCUAUCAAGUUCCC UGAGCACCAGUGGCAUGUGGCCCUGGACCAGGUGUUCGA GAACAUCGAGAAUUCCCAGGCUCUGGUGGACCAGUCCAA CAGAAUCCUGUCUAGCGCCGAGAAGGGAAACACCGGCUU CAUCAUCGUGAUCAUCCUGAUCGCCGUGCUGGGCAGCUC CAUGAUCCUGGUGUCCAUCUUCAUCAUUAUCAAGAAGAC CAAGAAGCCCACCGGCGCUCCUCCAGAACUGAGCGGAGU GACCAACAAUGGCUUCAUCCCUCACAAC | |
| HMPV_SC_DM_ Krarup_U74LD185P | AUGAGCUGGAAGGUGGUCAUCAUCUUCAGCCUGCUGAU CACACCUCAGCACGGCCUGAAAGAGAGCUACCUGGAAGA GUCCUGCAGCACCAUCACAGAGGGCUACCUGUCUGUGCU GAGAACCGGCUGGUACACCAACGUGUUCACACUGGAAGU GGGCGACGUCGAGAAUCUGACAUGCUCUGAUGGCCCUAG CCUGAUCAAGACCGAGCUGGAUCUGCUCAAGAGCGCCCU GAGAGAACUCAAGACCGUGUCUGCCGAUCAGCUGGCCAG AGAGGAACAGAUCGAGAAUCCUGGCAGCGGCAGCUUUG UGCUGGGAGCCAUUGCUCUUGGAGUGGCUGCUGCUGCA GCUGUUACAGCAGGCGUGGCCAUCGCUAAGACCAUCAGA CUGGAAAGCGAAGUGACCGCCAUCAACAACGCCCUGAAG AAGACAAACGAGGCCGUCAGCACACUCGGCAAUGGCGUU AGAGUGCUGGCCACAGCCGUGCGCGAGCUGAAGGACUUC GUGUCCAAGAACCUGACACGGGCCAUUAACAAGAACAAG UGCGACAUCCCUGACCUGAAGAUGGCCGUGUCCUUUAGC CAGUUCAACCGGCGGUUUCUGAACGUCGUGCGGCAGUUU AGCGACAACGCCGGAAUCACACCAGCCAUCAGCCUGGAC CUGAUGACAGAUGCUGAGCUGGCUAGAGCCGUGCCUAAC AUGCCUACAUCUGCCGGCCAGAUCAAGCUGAUGCUCGAG AAUAGAGCCAUGGUCCGACGGAAAGGCUUCGGCAUUCU GAUUGGCGUGUACGGCAGCAGCGUGAUCUAUAUGGUGC AGCUGCCUAUCUUCGGCGUGAUCGACACACCCUGCUGGA UUGUGAAGGCCGCUCCUAGCUGUAGCGAGAAGAAGGGC AAUUACGCCUGCCUGCUGAGAGAGGACCAAGGCUGGUA UUGUCAGAACGCCGGCAGCACCGUGUACUACCCUAACGA GAAGGACUGCGAGACAAGAGGCGACCACGUGUUCUGUG AUACCGCCGCUGGAAUCAAUGUGGCCGAGCAGAGCAAAG AGUGCAACAUCAACAUCAGCACCACCAACUAUCCCUGCA AGGUGUCCACCGGCAGGCACCCUAUUUCUAUGGUGGCUC UGUCUCCUCUGGGAGCCCUGGUGGCUUGUUAUAAGGGC GUGUCCUGUAGCAUCGGCAGCAACAGAGUGGGCAUCAUC AAGCAGCUGAACAAGGGCUGCAGCUACAUCACCAACCAG GACGCCGAUACCGUGACCAUCGACAACACCGUGUAUCAG CUGAGCAAGGUGGAAGGCGAACAGCACGUGAUCAAGGG CAGACCUGUGUCCAGCAGCUUCGACCCUAUCAAGUUCCC UGAGGAUCAGUUCCAGGUGGCCCUGGACCAGGUGUUCG AGAACAUCGAGAAUUCCCAGGCUCUGGUGGACCAGUCCA ACAGAAUCCUGUCUAGCGCCGAGAAGGGAAACACCGGCU UCAUCAUCGUGAUCAUCCUGAUCGCCGUGCUGGGCAGCU CCAUGAUCCUGGUGUCCAUCUUCAUCAUUAUCAAGAAGA CCAAGAAGCCCACCGGCGCUCCUCCAGAACUGAGCGGAG UGACCAACAAUGGCUUCAUCCCUCACAAC | 129 |
| HMPV_SC_UM_ Krarup_ U74LD185PD454N | AUGAGCUGGAAGGUGGUCAUCAUCUUCAGCCUGCUGAU CACACCUCAGCACGGCCUGAAAGAGAGCUACCUGGAAGA GUCCUGCAGCACCAUCACAGAGGGCUACCUGUCUGUGCU GAGAACCGGCUGGUACACCAACGUGUUCACACUGGAAGU GGGCGACGUCGAGAAUCUGACAUGCUCUGAUGGCCCUAG CCUGAUCAAGACCGAGCUGGAUCUGCUCAAGAGCGCCCU GAGAGAACUCAAGACCGUGUCUGCCGAUCAGCUGGCCAG AGAGGAACAGAUCGAGAAUCCUGGCAGCGGCAGCUUUG UGCUGGGAGCCAUUGCUCUUGGAGUGGCUGCUGCUGCA GCUGUUACAGCAGGCGUGGCCAUCGCUAAGACCAUCAGA CUGGAAAGCGAAGUGACCGCCAUCAACAACGCCCUGAAG AAGACAAACGAGGCCGUCAGCACACUCGGCAAUGGCGUU AGAGUGCUGGCCACAGCCGUGCGCGAGCUGAAGGACUUC GUGUCCAAGAACCUGACACGGGCCAUUAACAAGAACAAG UGCGACAUCCCUGACCUGAAGAUGGCCGUGUCCUUUAGC | 130 |

TABLE 19-continued

| Human Metapneumovirus Mutant Nucleic Acid Sequences | | |
|---|---|---|
| Strain | Nucleic Acid Sequence | SEQ ID NO: |
| | CAGUUCAACCGGCGGUUUCUGAACGUCGUGCGGCAGUUU<br>AGCGACAACGCCGGAAUCACACCAGCCAUCAGCCUGGAC<br>CUGAUGACAGAUGCUGAGCUGGCUAGAGCCGUGCCUAAC<br>AUGCCUACAUCUGCCGGCCAGAUCAAGCUGAUGCUCGAG<br>AAUAGAGCCAUGGUCCGACGGAAAGGCUUCGGCAUUCU<br>GAUUGGCGUGUACGGCAGCAGCGUGAUCUAUAUGGUGC<br>AGCUGCCUAUCUUCGGCGUGAUCGACACACCCUGCUGGA<br>UUGUGAAGGCCGCUCCUAGCUGUAGCGAGAAGAAGGGC<br>AAUUACGCCUGCCUGCUGAGAGAGGACCAAGGCUGGUA<br>UUGUCAGAACGCCGGCAGCACCGUGUACUACCCUAACGA<br>GAAGGACUGCGAGACAAGAGGCGACCACGUGUUCUGUG<br>AUACCGCCGCUGGAAUCAAUGUGGCCGAGCAGAGCAAAG<br>AGUGCAACAUCAACAUCAGCACCACCAACUAUCCCUGCA<br>AGGUGUCCACCGGCAGGCACCCUAUUUCUAUGGUGGCUC<br>UGUCUCCUCUGGGAGCCCUGGUGGCUUGUUAUAAGGGC<br>GUGUCCUGUAGCAUCGGCAGCAACAGAGUGGGCAUCAUC<br>AAGCAGCUGAACAAGGGCUGCAGCUACAUCACCAACCAG<br>GACGCCGAUACCGUGACCAUCGACAACACCGUGUAUCAG<br>CUGAGCAAGGUGGAAGGCGAACAGCACGUGAUCAAGGG<br>CAGACCUGUGUCCAGCAGCUUCGACCCUAUCAAGUUCCC<br>UGAGAACCAGUUCCAGGUGGCCCUGGACCAGGUGUUCGA<br>GAACAUCGAGAAUUCCCAGGCUCUGGUGGACCAGUCCAA<br>CAGAAUCCUGUCUAGCGCCGAGAAGGGAAACACCGGCUU<br>CAUCAUCGUGAUCAUCCUGAUCGCCGUGCUGGGCAGCUC<br>CAUGAUCCUGGUGUCCAUCUUCAUCAUUAUCAAGAAGAC<br>CAAGAAGCCCACCGGCGCUCCUCCAGAACUGAGCGGAGU<br>GACCAACAAUGGCUUCAUCCCUCACAAC | |
| HMPV_SC_4M_<br>Krarup_<br>U74L5170LD185P | AUGAGCUGGAAGGUGGUCAUCAUCUUCAGCCUGCUGAU<br>CACACCUCAGCACGGCCUGAAAGAGAGCUACCUGGAAGA<br>GUCCUGCAGCACCAUCACAGAGGGCUACCUGUCUGUGCU<br>GAGAACCGGCUGGUACACCAACGUGUUCACACUGGAAGU<br>GGGCGACGUCGAGAAUCUGACAUGCUCUGAUGGCCCUAG<br>CCUGAUCAAGACCGAGCUGGAUCUGCUCAAGAGCGCCCU<br>GAGAGAACUCAAGACCGUGUCUGCCGAUCAGCUGGCCAG<br>AGAGGAACAGAUCGAGAAUCCUGGCAGCGGCAGCUUUG<br>UGCUGGGAGCCAUUGCUCUUGGAGUGGCUGCUGCUGCA<br>GCUGUUACAGCAGGCGUGGCCAUCGCUAAGACCAUCAGA<br>CUGGAAAGCGAAGUGACCGCCAUCAACAACGCCCUGAAG<br>AAGACAAACGAGGCCGUCAGCACACUCGGCAAUGGCGUU<br>AGAGUGCUGGCCACAGCCGUGCGCGAGCUGAAGGACUUC<br>GUGCUUAAGAACCUGACACGGGCCAUUAACAAGAACAA<br>GUGCGACAUCCCUGACCUGAAGAUGGCCGUGUCCUUUAG<br>CCAGUUCAACCGGCGGUUUCUGAACGUCGUGCGGCAGUU<br>UAGCGACAACGCCGGAAUCACACCAGCCAUCAGCCUGGA<br>CCUGAUGACAGAUGCUGAGCUGGCUAGAGCCGUGCCUAA<br>CAUGCCUACAUCUGCCGGCCAGAUCAAGCUGAUGCUCGA<br>GAAUAGAGCCAUGGUCCGACGGAAAGGCUUCGGCAUUC<br>UGAUUGGCGUGUACGGCAGCAGCGUGAUCUAUAUGGUG<br>CAGCUGCCUAUCUUCGGCGUGAUCGACACACCCUGCUGG<br>AUUGUGAAGGCCGCUCCUAGCUGUAGCGAGAAGAAGGG<br>CAAUUACGCCUGCCUGCUGAGAGAGGACCAAGGCUGGUA<br>UUGUCAGAACGCCGGCAGCACCGUGUACUACCCUAACGA<br>GAAGGACUGCGAGACAAGAGGCGACCACGUGUUCUGUG<br>AUACCGCCGCUGGAAUCAAUGUGGCCGAGCAGAGCAAAG<br>AGUGCAACAUCAACAUCAGCACCACCAACUAUCCCUGCA<br>AGGUGUCCACCGGCAGGCACCCUAUUUCUAUGGUGGCUC<br>UGUCUCCUCUGGGAGCCCUGGUGGCUUGUUAUAAGGGC<br>GUGUCCUGUAGCAUCGGCAGCAACAGAGUGGGCAUCAUC<br>AAGCAGCUGAACAAGGGCUGCAGCUACAUCACCAACCAG<br>GACGCCGAUACCGUGACCAUCGACAACACCGUGUAUCAG<br>CUGAGCAAGGUGGAAGGCGAACAGCACGUGAUCAAGGG<br>CAGACCUGUGUCCAGCAGCUUCGACCCUAUCAAGUUCCC<br>UGAGGAUCAGUUCCAGGUGGCCCUGGACCAGGUGUUCG<br>AGAACAUCGAGAAUUCCCAGGCUCUGGUGGACCAGUCCA<br>ACAGAAUCCUGUCUAGCGCCGAGAAGGGAAACACCGGCU<br>UCAUCAUCGUGAUCAUCCUGAUCGCCGUGCUGGGCAGCU<br>CCAUGAUCCUGGUGUCCAUCUUCAUCAUUAUCAAGAAGA<br>CCAAGAAGCCCACCGGCGCUCCUCCAGAACUGAGCGGAG<br>UGACCAACAAUGGCUUCAUCCCUCACAAC | 131 |
| HMPV_SC_5M_<br>Krarup_<br>U74LS170LD185PD454N | AUGAGCUGGAAGGUGGUCAUCAUCUUCAGCCUGCUGAU<br>CACACCUCAGCACGGCCUGAAAGAGAGCUACCUGGAAGA<br>GUCCUGCAGCACCAUCACAGAGGGCUACCUGUCUGUGCU<br>GAGAACCGGCUGGUACACCAACGUGUUCACACUGGAAGU | 132 |

TABLE 19-continued

Human Metapneumovirus Mutant Nucleic Acid Sequences

| Strain | Nucleic Acid Sequence | SEQ ID NO: |
| --- | --- | --- |
| | GGGCGACGUCGAGAAUCUGACAUGCUCUGAUGGCCCUAG<br>CCUGAUCAAGACCGAGCUGGAUCUGCUCAAGAGCGCCCU<br>GAGAGAACUCAAGACCGUGUCUGCCGAUCAGCUGGCCAG<br>AGAGGAACAGAUCGAGAAUCCUGGCAGCGGCAGCUUUG<br>UGCUGGGAGCCAUUGCUCUUGGAGUGGCUGCUGCUGCA<br>GCUGUUACAGCAGGCGUGGCCAUCGCUAAGACCAUCAGA<br>CUGGAAAGCGAAGUGACCGCCAUCAACAACGCCCUGAAG<br>AAGACAAACGAGGCCGUCAGCACACUCGGCAAUGGCGUU<br>AGAGUGCUGGCCACAGCCGUGCGCGAGCUGAAGGACUUC<br>GUGCUUAAGAACCUGACACGGGCCAUUAACAAGAACAA<br>GUGCGACAUCCCUGACCUGAAGAUGGCCGUGUCCUUUAG<br>CCAGUUCAACCGGCGGUUUCUGAACGUCGUGCGGCAGUU<br>UAGCGACAACGCCGGAAUCACACCAGCCAUCAGCCUGGA<br>CCUGAUGACAGAUGCUGAGCUGGCUAGAGCCGUGCCUAA<br>CAUGCCUACAUCUGCCGGCCAGAUCAAGCUGAUGCUCGA<br>GAAUAGAGCCAUGGUCCGACGGAAAGGCUUCGGCAUUC<br>UGAUUGGCGUGUACGGCAGCAGCGUGAUCUAUAUGGUG<br>CAGCUGCCUAUCUUCGGCGUGAUCGACACACCCUGCUGG<br>AUUGUGAAGGCCGCUCCUAGCUGUAGCGAGAAGAAGGG<br>CAAUUACGCCUGCCUGCUGAGAGAGGACCAAGGCUGGUA<br>UUGUCAGAACGCCGGCAGCACCGUGUACUACCCUAACGA<br>GAAGGACUGCGAGACAAGAGGCGACCACGUGUUCUGUG<br>AUACCGCCGCUGGAAUCAAUGUGGCCGAGCAGAGCAAAG<br>AGUGCAACAUCAACAUCAGCACCACCAACUAUCCCUGCA<br>AGGUGUCCACCGGCAGGCACCCUAUUUCUAUGGUGGCUC<br>UGUCUCCUCUGGGAGCCCUGGUGGCUUGUUAUAAGGGC<br>GUGUCCUGUAGCAUCGGCAGCAACAGAGUGGGCAUCAUC<br>AAGCAGCUGAACAAGGGCUGCAGCUACAUCACCAACCAG<br>GACGCCGAUACCGUGACCAUCGACAACACCGUGUAUCAG<br>CUGAGCAAGGUGGAAGGCGAACAGCACGUGAUCAAGGG<br>CAGACCUGUGUCCAGCAGCUUCGACCCUAUCAAGUUCCC<br>UGAGAACCAGUUCCAGGUGGCCCUGGACCAGGUGUUCGA<br>GAACAUCGAGAAUUCCCAGGCUCUGGUGGACCAGUCCAA<br>CAGAAUCCUGUCUAGCGCCGAGAAGGGAAACACCGGCUU<br>CAUCAUCGUGAUCAUCCUGAUCGCCGUGCUGGGCAGCUC<br>CAUGAUCCUGGUGUCCAUCUUCAUCAUUAUCAAGAAGAC<br>CAAGAAGCCCACCGGCGCUCCUCCAGAACUGAGCGGAGU<br>GACCAACAAUGGCUUCAUCCCUCACAAC | |
| HMPV_SC_DM_<br>Krarup_E51PU74L | AUGAGCUGGAAGGUGGUCAUCAUCUUCAGCCUGCUGAU<br>CACACCUCAGCACGGCCUGAAAGAGAGCUACCUGGAAGA<br>GUCCUGCAGCACCAUCACAGAGGGCUACCUGUCUGUGCU<br>GAGAACCGGCUGGUACACCAACGUGUUCACACUGCCUGU<br>GGGCGACGUCGAGAAUCUGACAUGCUCUGAUGGCCCUAG<br>CCUGAUCAAGACCGAGCUGGAUCUGCUCAAGAGCGCCCU<br>GAGAGAACUCAAGACCGUGUCUGCCGAUCAGCUGGCCAG<br>AGAGGAACAGAUCGAGAAUCCUGGCAGCGGCAGCUUUG<br>UGCUGGGAGCCAUUGCUCUUGGAGUGGCUGCUGCUGCA<br>GCUGUUACAGCAGGCGUGGCCAUCGCUAAGACCAUCAGA<br>CUGGAAAGCGAAGUGACCGCCAUCAACAACGCCCUGAAG<br>AAGACAAACGAGGCCGUCAGCACACUCGGCAAUGGCGUU<br>AGAGUGCUGGCCACAGCCGUGCGCGAGCUGAAGGACUUC<br>GUGUCCAAGAACCUGACACGGGCCAUUAACAAGAACAAG<br>UGCGACAUCGACGACCUGAAGAUGGCCGUGUCCUUUAGC<br>CAGUUCAACCGGCGGUUUCUGAACGUCGUGCGGCAGUUU<br>AGCGACAACGCCGGAAUCACACCAGCCAUCAGCCUGGAC<br>CUGAUGACAGAUGCUGAGCUGGCUAGAGCCGUGCCUAAC<br>AUGCCUACAUCUGCCGGCCAGAUCAAGCUGAUGCUCGAG<br>AAUAGAGCCAUGGUCCGACGGAAAGGCUUCGGCAUUCU<br>GAUUGGCGUGUACGGCAGCAGCGUGAUCUAUAUGGUGC<br>AGCUGCCUAUCUUCGGCGUGAUCGACACACCCUGCUGGA<br>UUGUGAAGGCCGCUCCUAGCUGUAGCGAGAAGAAGGGC<br>AAUUACGCCUGCCUGCUGAGAGAGGACCAAGGCUGGUA<br>UUGUCAGAACGCCGGCAGCACCGUGUACUACCCUAACGA<br>GAAGGACUGCGAGACAAGAGGCGACCACGUGUUCUGUG<br>AUACCGCCGCUGGAAUCAAUGUGGCCGAGCAGAGCAAAG<br>AGUGCAACAUCAACAUCAGCACCACCAACUAUCCCUGCA<br>AGGUGUCCACCGGCAGGCACCCUAUUUCUAUGGUGGCUC<br>UGUCUCCUCUGGGAGCCCUGGUGGCUUGUUAUAAGGGC<br>GUGUCCUGUAGCAUCGGCAGCAACAGAGUGGGCAUCAUC<br>AAGCAGCUGAACAAGGGCUGCAGCUACAUCACCAACCAG<br>GACGCCGAUACCGUGACCAUCGACAACACCGUGUAUCAG<br>CUGAGCAAGGUGGAAGGCGAACAGCACGUGAUCAAGGG<br>CAGACCUGUGUCCAGCAGCUUCGACCCUAUCAAGUUCCC<br>UGAGGAUCAGUUCCAGGUGGCCCUGGACCAGGUGUUCG | 133 |

TABLE 19-continued

| Human Metapneumovirus Mutant Nucleic Acid Sequences | | |
|---|---|---|
| Strain | Nucleic Acid Sequence | SEQ ID NO: |
| | AGAACAUCGAGAAUUCCCAGGCUCUGGUGGACCAGUCCA ACAGAAUCCUGUCUAGCGCCGAGAAGGGAAACACCGGCU UCAUCAUCGUGAUCAUCCUGAUCGCCGUGCUGGGCAGCU CCAUGAUCCUGGUGUCCAUCUUCAUCAUUAUCAAGAAGA CCAAGAAGCCCACCGGCGCUCCUCCAGAACUGAGCGGAG UGACCAACAAUGGCUUCAUCCCUCACAAC | |
| HMPV_SC_UM_ Krarup_ E51PU74LD454N | AUGAGCUGGAAGGUGGUCAUCAUCUUCAGCCUGCUGAU CACACCUCAGCACGGCCUGAAAGAGAGCUACCUGGAAGA GUCCUGCAGCACCAUCACAGAGGGCUACCUGUCUGUGCU GAGAACCGGCUGGUACACCAACGUGUUCACACUGCCUGU GGGCGACGUCGAGAAUCUGACAUGCUCUGAUGGCCCUAG CCUGAUCAAGACCGAGCUGGAUCUGCUCAAGAGCGCCCU GAGAGAACUCAAGACCGUGUCUGCCGAUCAGCUGGCCAG AGAGGAACAGAUCGAGAAUCCUGGCAGCGGCAGCUUUG UGCUGGGAGCCAUUGCUCUUGGAGUGGCUGCUGCUGCA GCUGUUACAGCAGGCGUGGCCAUCGCUAAGACCAUCAGA CUGGAAAGCGAAGUGACCGCCAUCAACAACGCCCUGAAG AAGACAAACGAGGCCGUCAGCACACUCGGCAAUGGCGUU AGAGUGCUGGCCACAGCCGUGCGCGAGCUGAAGGACUUC GUGUCCAAGAACCUGACACGGGCCAUUAACAAGAACAAG UGCGACAUCGACGACCUGAAGAUGGCCGUGUCCUUUAGC CAGUUCAACCGGCGGUUUCUGAACGUCGUGCGGCAGUUU AGCGACAACGCCGGAAUCACACCAGCCAUCAGCCUGGAC CUGAUGACAGAUGCUGAGCUGGCUAGAGCCGUGCCUAAC AUGCCUACAUCUGCCGGCCAGAUCAAGCUGAUGCUCGAG AAUAGAGCCAUGGUCCGACGGAAAGGCUUCGGCAUUCU GAUUGGCGUGUACGGCAGCAGCGUGAUCUAUAUGGUGC AGCUGCCUAUCUUCGGCGUGAUCGACACACCCUGCUGGA UUGUGAAGGCCGCUCCUAGCUGUAGCGAGAAGAAGGGC AAUUACGCCUGCCUGCUGAGAGAGGACCAAGGCUGGUA UUGUCAGAACGCCGGCAGCACCGUGUACUACCCUAACGA GAAGGACUGCGAGACAAGAGGCGACCACGUGUUCUGUG AUACCGCCGCUGGAAUCAAUGUGGCCGAGCAGAGCAAAG AGUGCAACAUCAACAUCAGCACCACCAACUAUCCCUGCA AGGUGUCCACCGGCAGGCACCCUAUUUCUAUGGUGGCUC UGUCUCCUCUGGGAGCCCUGGUGGCUUGUUAUAAGGGC GUGUCCUGUAGCAUCGGCAGCAACAGAGUGGGCAUCAUC AAGCAGCUGAACAAGGGCUGCAGCUACAUCACCAACCAG GACGCCGAUACCGUGACCAUCGACAACACCGUGUAUCAG CUGAGCAAGGUGGAAGGCGAACAGCACGUGAUCAAGGG CAGACCUGUGUCCAGCAGCUUCGACCCUAUCAAGUUCCC UGAGAACCAGUUCCAGGUGGCCCUGGACCAGGUGUUCGA GAACAUCGAGAAUUCCCAGGCUCUGGUGGACCAGUCCAA CAGAAUCCUGUCUAGCGCCGAGAAGGGAAACACCGGCUU CAUCAUCGUGAUCAUCCUGAUCGCCGUGCUGGGCAGCUC CAUGAUCCUGGUGUCCAUCUUCAUCAUUAUCAAGAAGAC CAAGAAGCCCACCGGCGCUCCUCCAGAACUGAGCGGAGU GACCAACAAUGGCUUCAUCCCUCACAAC | 134 |
| HMPV_SC_ SUabilizeAlpha_ U74L | AUGAGCUGGAAGGUGGUCAUCAUCUUCAGCCUGCUGAU CACACCUCAGCACGGCCUGAAAGAGAGCUACCUGGAAGA GUCCUGCAGCACCAUCACAGAGGGCUACCUGUCUGUGCU GAGAACCGGCUGGUACACCAACGUGUUCACACUGGAAGU GGGCGACGUCGAGAAUCUGACAUGCUCUGAUGGCCCUAG CCUGAUCAAGACCGAGCUGGAUCUGCUCAAGAGCGCCCU GAGAGAACUCAAGACCGUGUCUGCCGAUCAGCUGGCCAG AGAGGAACAGAUCGAGAAUCCUGGCAGCGGCAGCUUUG UGCUGGGAGCCAUUGCUCUUGGAGUGGCUGCUGCUGCA GCUGUUACAGCAGGCGUGGCCAUCGCUAAGACCAUCAGA CUGGAAAGCGAAGUGACCGCCAUCAACAACGCCCUGAAG AAGACAAACGAGGCCGUCAGCACACUCGGCAAUGGCGUU AGAGUGCUGGCCACAGCCGUGCGCGAGCUGAAGGACUUC GUGUCCAAGAACCUGACACGGGCCAUUAACAAGAACAAG UGCGACAUCGACGACCUGAAGAUGGCCGUGUCCUUUAGC CAGUUCAACCGGCGGUUUCUGAACGUCGUGCGGCAGUUU AGCGACAACGCCGGAAUCACACCAGCCAUCAGCCUGGAC CUGAUGACAGAUGCUGAGCUGGCUAGAGCCGUGCCUAAC AUGCCUACAUCUGCCGGCCAGAUCAAGCUGAUGCUCGAG AAUAGAGCCAUGGUCCGACGGAAAGGCUUCGGCAUUCU GAUUGGCGUGUACGGCAGCAGCGUGAUCUAUAUGGUGC AGCUGCCUAUCUUCGGCGUGAUCGACACACCCUGCUGGA UUGUGAAGGCCGCUCCUAGCUGUAGCGAGAAGAAGGGC AAUUACGCCUGCCUGCUGAGAGAGGACCAAGGCUGGUA UUGUCAGAACGCCGGCAGCACCGUGUACUACCCUAACGA | 135 |

TABLE 19-continued

Human Metapneumovirus Mutant Nucleic Acid Sequences

| Strain | Nucleic Acid Sequence | SEQ ID NO: |
|---|---|---|
| | GAAGGACUGCGAGACAAGAGGCGACCACGUGUUCUGUG<br>AUACCGCCGCUGGAAUCAAUGUGGCCGAGCAGAGCAAAG<br>AGUGCAACAUCAACAUCAGCACCACCAACUAUCCCUGCA<br>AGGUGUCCACCGGCAGGCACCCUAUUUCUAUGGUGGCUC<br>UGUCUCCUCUGGGAGCCCUGGUGGCUUGUUAUAAGGGC<br>GUGUCCUGUAGCAUCGGCAGCAACAGAGUGGGCAUCAUC<br>AAGCAGCUGAACAAGGGCUGCAGCUACAUCACCAACCAG<br>GACGCCGAUACCGUGACCAUCGACAACACCGUGUAUCAG<br>CUGAGCAAGGUGGAAGGCGAACAGCACGUGAUCAAGGG<br>CAGACCUGUGUCCAGCAGCUUCGACCCUAUCAAGUUCCC<br>UGAGGAUCAGUUCCAGGUGGCCCUGGACCAGGUGUUCG<br>AGAACAUCGAGAAUUCCCAGGCUCUGGUGGACCAGUCCA<br>ACAGAAUCCUGUCUAGCGCCGAGAAGGGAAACACCGGCU<br>UCAUCAUCGUGAUCAUCCUGAUCGCCGUGCUGGGCAGCU<br>CCAUGAUCCUGGUGUCCAUCUUCAUCAUUAUCAAGAAGA<br>CCAAGAAGCCCACCGGCGCUCCUCCAGAACUGAGCGGAG<br>UGACCAACAAUGGCUUCAUCCCUCACAAC | |
| HMPV_SC_<br>SUabilizeAlpha_<br>V55L | AUGAGCUGGAAGGUGGUCAUCAUCUUCAGCCUGCUGAU<br>CACACCUCAGCACGGCCUGAAAGAGAGCUACCUGGAAGA<br>GUCCUGCAGCACCAUCACAGAGGGCUACCUGUCUGUGCU<br>GAGAACCGGCUGGUACACCAACGUGUUCACACUGGAAGU<br>GGGCGACCUCGAGAAUCUGACAUGCUCUGAUGGCCCUAG<br>CCUGAUCAAGACCGAGCUGGAUCUGACCAAGAGCGCCCU<br>GAGAGAACUCAAGACCGUGUCUGCCGAUCAGCUGGCCAG<br>AGAGGAACAGAUCGAGAAUCCUGGCAGCGGCAGCUUUG<br>UGCUGGGAGCCAUUGCUCUUGGAGUGGCUGCUGCUGCA<br>GCUGUUACAGCAGGCGUGGCCAUCGCUAAGACCAUCAGA<br>CUGGAAAGCGAAGUGACCGCCAUCAACAACGCCCUGAAG<br>AAGACAAACGAGGCCGUCAGCACACUCGGCAAUGGCGUU<br>AGAGUGCUGGCCACAGCCGUGCGCGAGCUGAAGGACUUC<br>GUGUCCAAGAACCUGACACGGGCCAUUAACAAGAACAAG<br>UGCGACAUCGACGACCUGAAGAUGGCCGUGUCCUUUAGC<br>CAGUUCAACCGGCGGUUUCUGAACGUCGUGCGGCAGUUU<br>AGCGACAACGCCGGAAUCACACCAGCCAUCAGCCUGGAC<br>CUGAUGACAGAUGCUGAGCUGGCUAGAGCCGUGCCUAAC<br>AUGCCUACAUCUGCCGGCCAGAUCAAGCUGAUGCUCGAG<br>AAUAGAGCCAUGGUCCGACGGAAAGGCUUCGGCAUUCU<br>GAUUGGCGUGUACGGCAGCAGCGUGAUCUAUAUGGUGC<br>AGCUGCCUAUCUUCGGCGUGAUCGACACACCCUGCUGGA<br>UUGUGAAGGCCGCUCCUAGCUGUAGCGAGAAGAAGGGC<br>AAUUACGCCUGCCUGCUGAGAGAGGACCAAGGCUGGUA<br>UUGUCAGAACGCCGGCAGCACCGUGUACUACCCUAACGA<br>GAAGGACUGCGAGACAAGAGGCGACCACGUGUUCUGUG<br>AUACCGCCGCUGGAAUCAAUGUGGCCGAGCAGAGCAAAG<br>AGUGCAACAUCAACAUCAGCACCACCAACUAUCCCUGCA<br>AGGUGUCCACCGGCAGGCACCCUAUUUCUAUGGUGGCUC<br>UGUCUCCUCUGGGAGCCCUGGUGGCUUGUUAUAAGGGC<br>GUGUCCUGUAGCAUCGGCAGCAACAGAGUGGGCAUCAUC<br>AAGCAGCUGAACAAGGGCUGCAGCUACAUCACCAACCAG<br>GACGCCGAUACCGUGACCAUCGACAACACCGUGUAUCAG<br>CUGAGCAAGGUGGAAGGCGAACAGCACGUGAUCAAGGG<br>CAGACCUGUGUCCAGCAGCUUCGACCCUAUCAAGUUCCC<br>UGAGGAUCAGUUCCAGGUGGCCCUGGACCAGGUGUUCG<br>AGAACAUCGAGAAUUCCCAGGCUCUGGUGGACCAGUCCA<br>ACAGAAUCCUGUCUAGCGCCGAGAAGGGAAACACCGGCU<br>UCAUCAUCGUGAUCAUCCUGAUCGCCGUGCUGGGCAGCU<br>CCAUGAUCCUGGUGUCCAUCUUCAUCAUUAUCAAGAAGA<br>CCAAGAAGCCCACCGGCGCUCCUCCAGAACUGAGCGGAG<br>UGACCAACAAUGGCUUCAUCCCUCACAAC | 136 |
| HMPV_SC_<br>SUabilizeAlpha_<br>S170L | AUGAGCUGGAAGGUGGUCAUCAUCUUCAGCCUGCUGAU<br>CACACCUCAGCACGGCCUGAAAGAGAGCUACCUGGAAGA<br>GUCCUGCAGCACCAUCACAGAGGGCUACCUGUCUGUGCU<br>GAGAACCGGCUGGUACACCAACGUGUUCACACUGGAAGU<br>GGGCGACGUCGAGAAUCUGACAUGCUCUGAUGGCCCUAG<br>CCUGAUCAAGACCGAGCUGGAUCUGACCAAGAGCGCCCU<br>GAGAGAACUCAAGACCGUGUCUGCCGAUCAGCUGGCCAG<br>AGAGGAACAGAUCGAGAAUCCUGGCAGCGGCAGCUUUG<br>UGCUGGGAGCCAUUGCUCUUGGAGUGGCUGCUGCUGCA<br>GCUGUUACAGCAGGCGUGGCCAUCGCUAAGACCAUCAGA<br>CUGGAAAGCGAAGUGACCGCCAUCAACAACGCCCUGAAG<br>AAGACAAACGAGGCCGUCAGCACACUCGGCAAUGGCGUU<br>AGAGUGCUGGCCACAGCCGUGCGCGAGCUGAAGGACUUC<br>GUGCUUAAGAACCUGACACGGGCCAUUAACAAGAACAA | 137 |

TABLE 19-continued

Human Metapneumovirus Mutant Nucleic Acid Sequences

| Strain | Nucleic Acid Sequence | SEQ ID NO: |
|---|---|---|
| | GUGCGACAUCGACGACCUGAAGAUGGCCGUGUCCUUUAG<br>CCAGUUCAACCGGCGGUUUCUGAACGUCGUGCGGCAGUU<br>UAGCGACAACGCCGGAAUCACACCAGCCAUCAGCCUGGA<br>CCUGAUGACAGAUGCUGAGCUGGCUAGAGCCGUGCCUAA<br>CAUGCCUACAUCUGCCGGCCAGAUCAAGCUGAUGCUCGA<br>GAAUAGAGCCAUGGUCCGACGGAAAGGCUUCGGCAUUC<br>UGAUUGGCGUGUACGGCAGCAGCGUGAUCUAUAUGGUG<br>CAGCUGCCUAUCUUCGGCGUGAUCGACACACCCUGCUGG<br>AUUGUGAAGGCCGCUCCUAGCUGUAGCGAGAAGAAGGG<br>CAAUUACGCCUGCCUGCUGAGAGAGGACCAAGGCUGGUA<br>UUGUCAGAACGCCGGCAGCACCGUGUACUACCCUAACGA<br>GAAGGACUGCGAGACAAGAGGCGACCACGUGUUCUGUG<br>AUACCGCCGCUGGAAUCAAUGUGGCCGAGCAGAGCAAAG<br>AGUGCAACAUCAACAUCAGCACCACCAACUAUCCCUGCA<br>AGGUGUCCACCGGCAGGCACCCUAUUUCUAUGGUGGCUC<br>UGUCUCCUCUGGGAGCCCUGGUGGCUUGUUAUAAGGGC<br>GUGUCCUGUAGCAUCGGCAGCAACAGAGUGGGCAUCAUC<br>AAGCAGCUGAACAAGGGCUGCAGCUACAUCACCAACCAG<br>GACGCCGAUACCGUGACCAUCGACAACACCGUGUAUCAG<br>CUGAGCAAGGUGGAAGGCGAACAGCACGUGAUCAAGGG<br>CAGACCUGUGUCCAGCAGCUUCGACCCUAUCAAGUUCCC<br>UGAGGAUCAGUUCCAGGUGGCCCUGGACCAGGUGUUCG<br>AGAACAUCGAGAAUUCCCAGGCUCUGGUGGACCAGUCCA<br>ACAGAAUCCUGUCUAGCGCCGAGAAGGGAAACACCGGCU<br>UCAUCAUCGUGAUCAUCCUGAUCGCCGUGCUGGGCAGCU<br>CCAUGAUCCUGGUGUCCAUCUUCAUCAUUAUCAAGAAGA<br>CCAAGAAGCCCACCGGCGCUCCUCCAGAACUGAGCGGAG<br>UGACCAACAAUGGCUUCAUCCCUCACAAC | |
| HMPV_SC_<br>SUabilizeAlpha_<br>U174W | AUGAGCUGGAAGGUGGUCAUCAUCUUCAGCCUGCUGAU<br>CACACCUCAGCACGGCCUGAAAGAGAGCUACCUGGAAGA<br>GUCCUGCAGCACCAUCACAGAGGGCUACCUGUCUGUGCU<br>GAGAACCGGCUGGUACACCAACGUGUUCACACUGGAAGU<br>GGGCGACGUCGAGAAUCUGACAUGCUCUGAUGGCCCUAG<br>CCUGAUCAAGACCGAGCUGGAUCUGACCAAGAGCGCCCU<br>GAGAGAACUCAAGACCGUGUCUGCCGAUCAGCUGGCCAG<br>AGAGGAACAGAUCGAGAAUCCUGGCAGCGGCAGCUUUG<br>UGCUGGGAGCCAUUGCUCUUGGAGUGGCUGCUGCUGCA<br>GCUGUUACAGCAGGCGUGGCCAUCGCUAAGACCAUCAGA<br>CUGGAAAGCGAAGUGACCGCCAUCAACAACGCCCUGAAG<br>AAGACAAACGAGGCCGUCAGCACACUCGGCAAUGGCGUU<br>AGAGUGCUGGCCACAGCCGUGCGCGAGCUGAAGGACUUC<br>GUGUCCAAGAACCUGUGGCGGGCCAUUAACAAGAACAA<br>GUGCGACAUCGACGACCUGAAGAUGGCCGUGUCCUUUAG<br>CCAGUUCAACCGGCGGUUUCUGAACGUCGUGCGGCAGUU<br>UAGCGACAACGCCGGAAUCACACCAGCCAUCAGCCUGGA<br>CCUGAUGACAGAUGCUGAGCUGGCUAGAGCCGUGCCUAA<br>CAUGCCUACAUCUGCCGGCCAGAUCAAGCUGAUGCUCGA<br>GAAUAGAGCCAUGGUCCGACGGAAAGGCUUCGGCAUUC<br>UGAUUGGCGUGUACGGCAGCAGCGUGAUCUAUAUGGUG<br>CAGCUGCCUAUCUUCGGCGUGAUCGACACACCCUGCUGG<br>AUUGUGAAGGCCGCUCCUAGCUGUAGCGAGAAGAAGGG<br>CAAUUACGCCUGCCUGCUGAGAGAGGACCAAGGCUGGUA<br>UUGUCAGAACGCCGGCAGCACCGUGUACUACCCUAACGA<br>GAAGGACUGCGAGACAAGAGGCGACCACGUGUUCUGUG<br>AUACCGCCGCUGGAAUCAAUGUGGCCGAGCAGAGCAAAG<br>AGUGCAACAUCAACAUCAGCACCACCAACUAUCCCUGCA<br>AGGUGUCCACCGGCAGGCACCCUAUUUCUAUGGUGGCUC<br>UGUCUCCUCUGGGAGCCCUGGUGGCUUGUUAUAAGGGC<br>GUGUCCUGUAGCAUCGGCAGCAACAGAGUGGGCAUCAUC<br>AAGCAGCUGAACAAGGGCUGCAGCUACAUCACCAACCAG<br>GACGCCGAUACCGUGACCAUCGACAACACCGUGUAUCAG<br>CUGAGCAAGGUGGAAGGCGAACAGCACGUGAUCAAGGG<br>CAGACCUGUGUCCAGCAGCUUCGACCCUAUCAAGUUCCC<br>UGAGGAUCAGUUCCAGGUGGCCCUGGACCAGGUGUUCG<br>AGAACAUCGAGAAUUCCCAGGCUCUGGUGGACCAGUCCA<br>ACAGAAUCCUGUCUAGCGCCGAGAAGGGAAACACCGGCU<br>UCAUCAUCGUGAUCAUCCUGAUCGCCGUGCUGGGCAGCU<br>CCAUGAUCCUGGUGUCCAUCUUCAUCAUUAUCAAGAAGA<br>CCAAGAAGCCCACCGGCGCUCCUCCAGAACUGAGCGGAG<br>UGACCAACAAUGGCUUCAUCCCUCACAAC | 138 |
| HMPV_SC_4M_<br>SUabilizeAlpha_<br>V55LU74L5170LU174W | AUGAGCUGGAAGGUGGUCAUCAUCUUCAGCCUGCUGAU<br>CACACCUCAGCACGGCCUGAAAGAGAGCUACCUGGAAGA<br>GUCCUGCAGCACCAUCACAGAGGGCUACCUGUCUGUGCU | 139 |

TABLE 19-continued

Human Metapneumovirus Mutant Nucleic Acid Sequences

| Strain | Nucleic Acid Sequence | SEQ ID NO: |
|---|---|---|
| | GAGAACCGGCUGGUACACCAACGUGUUCACACUGGAAGU<br>GGGCGACCUCGAGAAUCUGACAUGCUCUGAUGGCCCUAG<br>CCUGAUCAAGACCGAGCUGGAUCUGCUCAAGAGCGCCCU<br>GAGAGAACUCAAGACCGUGUCUGCCGAUCAGCUGGCCAG<br>AGAGGAACAGAUCGAGAAUCCUGGCAGCGGCAGCUUUG<br>UGCUGGGAGCCAUUGCUCUUGGAGUGGCUGCUGCUGCA<br>GCUGUUACAGCAGGCGUGGCCAUCGCUAAGACCAUCAGA<br>CUGGAAAGCGAAGUGACCGCCAUCAACAACGCCCUGAAG<br>AAGACAAACGAGGCCGUCAGCACACUCGGCAAUGGCGUU<br>AGAGUGCUGGCCACAGCCGUGCGCGAGCUGAAGGACUUC<br>GUGCUUAAGAACCUGUGGCGGGCCAUUAACAAGAACAA<br>GUGCGACAUCGACGACCUGAAGAUGGCCGUGUCCUUUAG<br>CCAGUUCAACCGGCGGUUUCUGAACGUCGUGCGGCAGUU<br>UAGCGACAACGCCGGAAUCACACCAGCCAUCAGCCUGGA<br>CCUGAUGACAGAUGCUGAGCUGGCUAGAGCCGUGCCUAA<br>CAUGCCUACAUCUGCCGGCCAGAUCAAGCUGAUGCUCGA<br>GAAUAGAGCCAUGGUCCGACGGAAAGGCUUCGGCAUUC<br>UGAUUGGCGUGUACGGCAGCAGCGUGAUCUAUAUGGUG<br>CAGCUGCCUAUCUUCGGCGUGAUCGACACACCCUGCUGG<br>AUUGUGAAGGCCGCUCCUAGCUGUAGCGAGAAGAAGGG<br>CAAUUACGCCUGCCUGCUGAGAGAGGACCAAGGCUGGUA<br>UUGUCAGAACGCCGGCAGCACCGUGUACUACCCUAACGA<br>GAAGGACUGCGAGACAAGAGGCGACCACGUGUUCUGUG<br>AUACCGCCGCUGGAAUCAAUGUGGCCGAGCAGAGCAAAG<br>AGUGCAACAUCAACAUCAGCACCACCAACUAUCCCUGCA<br>AGGUGUCCACCGGCAGGCACCCUAUUUCUAUGGUGGCUC<br>UGUCUCCUCUGGGAGCCCUGGUGGCUUGUUAUAAGGGC<br>GUGUCCUGUAGCAUCGGCAGCAACAGAGUGGGCAUCAUC<br>AAGCAGCUGAACAAGGGCUGCAGCUACAUCACCAACCAG<br>GACGCCGAUACCGUGACCAUCGACAACACCGUGUAUCAG<br>CUGAGCAAGGUGGAAGGCGAACAGCACGUGAUCAAGGG<br>CAGACCUGUGUCCAGCAGCUUCGACCCUAUCAAGUUCCC<br>UGAGGAUCAGUUCCAGGUGGCCCUGGACCAGGUGUUCG<br>AGAACAUCGAGAAUUCCCAGGCUCUGGUGGACCAGUCCA<br>ACAGAAUCCUGUCUAGCGCCGAGAAGGGAAACACCGGCU<br>UCAUCAUCGUGAUCAUCCUGAUCGCCGUGCUGGGCAGCU<br>CCAUGAUCCUGGUGUCCAUCUUCAUCAUUAUCAAGAAGA<br>CCAAGAAGCCCACCGGCGCUCCUCCAGAACUGAGCGGAG<br>UGACCAACAAUGGCUUCAUCCCUCACAAC | |
| HMPV_Proline<br>SUab_E51P | AUGAGCUGGAAGGUGGUCAUCAUCUUCAGCCUGCUGAU<br>CACACCUCAGCACGGCCUGAAAGAGAGCUACCUGGAAGA<br>GUCCUGCAGCACCAUCACAGAGGGCUACCUGUCUGUGCU<br>GAGAACCGGCUGGUACACCAACGUGUUCACACUGGAAGU<br>GGGCGACGUCGAGAAUCUGACAUGCUCUGAUGGCCCUAG<br>CCUGAUCAAGACCGAGCUGGAUCUGACCAAGAGCGCCCU<br>GAGAGAACUCAAGACCGUGUCUGCCGAUCAGCUGGCCAG<br>AGAGGAACAGAUCGAGAAUCCUGGCAGCGGCAGCUUUG<br>UGCUGGGAGCCAUUGCUCUUGGAGUGGCUGCUGCUGCA<br>GCUGUUACAGCAGGCGUGGCCAUCGCUAAGACCAUCAGA<br>CUGGAAAGCGAAGUGACCGCCAUCAACAACGCCCUGAAG<br>AAGACAAACGAGGCCGUCAGCACACUCGGCAAUGGCGUU<br>AGAGUGCUGGCCACAGCCGUGCGCGAGCUGAAGGACUUC<br>GUGUCCAAGAACCUGACACGGGCCAUUAACAAGAACAAG<br>UGCGACAUCGACGACCUGAAGAUGGCCGUGUCCUUUAGC<br>CAGUUCAACCGGCGGUUUCUGAACGUCGUGCGGCAGUUU<br>AGCGACAACGCCGGAAUCACACCAGCCAUCAGCCUGGAC<br>CUGAUGACAGAUGCUGAGCUGGCUAGAGCCGUGCCUAAC<br>AUGCCUACAUCUGCCGGCCAGAUCAAGCUGAUGCUCGAG<br>AAUAGAGCCAUGGUCCGACGGAAAGGCUUCGGCAUUCU<br>GAUUGGCGUGUACGGCAGCAGCGUGAUCUAUAUGGUGC<br>AGCUGCCUAUCUUCGGCGUGAUCGACACACCCUGCUGGA<br>UUGUGAAGGCCGCUCCUAGCUGUAGCGAGAAGAAGGGC<br>AAUUACGCCUGCCUGCUGAGAGAGGACCAAGGCUGGUA<br>UUGUCAGAACGCCGGCAGCACCGUGUACUACCCUAACGA<br>GAAGGACUGCGAGACAAGAGGCGACCACGUGUUCUGUG<br>AUACCGCCGCUGGAAUCAAUGUGGCCGAGCAGAGCAAAG<br>AGUGCAACAUCAACAUCAGCACCACCAACUAUCCCUGCA<br>AGGUGUCCACCGGCAGGCACCCUAUUUCUAUGGUGGCUC<br>UGUCUCCUCUGGGAGCCCUGGUGGCUUGUUAUAAGGGC<br>GUGUCCUGUAGCAUCGGCAGCAACAGAGUGGGCAUCAUC<br>AAGCAGCUGAACAAGGGCUGCAGCUACAUCACCAACCAG<br>GACGCCGAUACCGUGACCAUCGACAACACCGUGUAUCAG<br>CUGAGCAAGGUGGAAGGCGAACAGCACGUGAUCAAGGG<br>CAGACCUGUGUCCAGCAGCUUCGACCCUAUCAAGUUCCC | 140 |

TABLE 19-continued

| Human Metapneumovirus Mutant Nucleic Acid Sequences | | |
|---|---|---|
| Strain | Nucleic Acid Sequence | SEQ ID NO: |
| | UGAGGAUCAGUUCCAGGUGGCCCUGGACCAGGUGUUCG AGAACAUCGAGAAUUCCCAGGCUCUGGUGGACCAGUCCA ACAGAAUCCUGUCUAGCGCCGAGAAGGGAAACACCGGCU UCAUCAUCGUGAUCAUCCUGAUCGCCGUGCUGGGCAGCU CCAUGAUCCUGGUGUCCAUCUUCAUCAUUAUCAAGAAGA CCAAGAAGCCCACCGGCGCUCCUCCAGAACUGAGCGGAG UGACCAACAAUGGCUUCAUCCCUCACAAC | |
| HMPV_Proline SUab_D185P | AUGAGCUGGAAGGUGGUCAUCAUCUUCAGCCUGCUGAU CACACCUCAGCACGGCCUGAAAGAGAGCUACCUGGAAGA GUCCUGCAGCACCAUCACAGAGGGCUACCUGUCUGUGCU GAGAACCGGCUGGUACACCAACGUGUUCACACUGGAAGU GGGCGACGUCGAGAAUCUGACAUGCUCUGAUGGCCCUAG CCUGAUCAAGACCGAGCUGGAUCUGACCAAGAGCGCCCU GAGAGAACUCAAGACCGUGUCUGCCGAUCAGCUGGCCAG AGAGGAACAGAUCGAGAAUCCUGGCAGCGGCAGCUUUG UGCUGGGAGCCAUUGCUCUUGGAGUGGCUGCUGCUGCA GCUGUUACAGCAGGCGUGGCCAUCGCUAAGACCAUCAGA CUGGAAAGCGAAGUGACCGCCAUCAACAACGCCCUGAAG AAGACAAACGAGGCCGUCAGCACACUCGGCAAUGGCGUU AGAGUGCUGGCCACAGCCGUGCGCGAGCUGAAGGACUUC GUGUCCAAGAACCUGACACGGGCCAUUAACAAGAACAAG UGCGACAUCCCUGACCUGAAGAUGGCCGUGUCCUUUAGC CAGUUCAACCGGCGGUUUCUGAACGUCGUGCGGCAGUUU AGCGACAACGCCGGAAUCACACCAGCCAUCAGCCUGGAC CUGAUGACAGAUGCUGAGCUGGCUAGAGCCGUGCCUAAC AUGCCUACAUCUGCCGGCCAGAUCAAGCUGAUGCUCGAG AAUAGAGCCAUGGUCCGACGGAAAGGCUUCGGCAUUCU GAUUGGCGUGUACGGCAGCAGCGUGAUCUAUAUGGUGC AGCUGCCUAUCUUCGGCGUGAUCGACACACCCUGCUGGA UUGUGAAGGCCGCUCCUAGCUGUAGCGAGAAGAAGGGC AAUUACGCCUGCCUGCUGAGAGAGGACCAAGGCUGGUA UUGUCAGAACGCCGGCAGCACCGUGUACUACCCUAACGA GAAGGACUGCGAGACAAGAGGCGACCACGUGUUCUGUG AUACCGCCGCUGGAAUCAAUGUGGCCGAGCAGAGCAAAG AGUGCAACAUCAACAUCAGCACCACCAACUAUCCCUGCA AGGUGUCCACCGGCAGGCACCCUAUUUCUAUGGUGGCUC UGUCUCCCUCUGGGAGCCCUGGUGGCUUGUUAUAAGGGC GUGUCCUGUAGCAUCGGCAGCAACAGAGUGGGCAUCAUC AAGCAGCUGAACAAGGGCUGCAGCUACAUCACCAACCAG GACGCCGAUACCGUGACCAUCGACAACACCGUGUAUCAG CUGAGCAAGGUGGAAGGCGAACAGCACGUGAUCAAGGG CAGACCUGUGUCCAGCAGCUUCGACCCUAUCAAGUUCCC UGAGGAUCAGUUCCAGGUGGCCCUGGACCAGGUGUUCG AGAACAUCGAGAAUUCCCAGGCUCUGGUGGACCAGUCCA ACAGAAUCCUGUCUAGCGCCGAGAAGGGAAACACCGGCU UCAUCAUCGUGAUCAUCCUGAUCGCCGUGCUGGGCAGCU CCAUGAUCCUGGUGUCCAUCUUCAUCAUUAUCAAGAAGA CCAAGAAGCCCACCGGCGCUCCUCCAGAACUGAGCGGAG UGACCAACAAUGGCUUCAUCCCUCACAAC | 141 |
| HMPV_Proline SUab_D183P | AUGAGCUGGAAGGUGGUCAUCAUCUUCAGCCUGCUGAU CACACCUCAGCACGGCCUGAAAGAGAGCUACCUGGAAGA GUCCUGCAGCACCAUCACAGAGGGCUACCUGUCUGUGCU GAGAACCGGCUGGUACACCAACGUGUUCACACUGGAAGU GGGCGACGUCGAGAAUCUGACAUGCUCUGAUGGCCCUAG CCUGAUCAAGACCGAGCUGGAUCUGACCAAGAGCGCCCU GAGAGAACUCAAGACCGUGUCUGCCGAUCAGCUGGCCAG AGAGGAACAGAUCGAGAAUCCUGGCAGCGGCAGCUUUG UGCUGGGAGCCAUUGCUCUUGGAGUGGCUGCUGCUGCA GCUGUUACAGCAGGCGUGGCCAUCGCUAAGACCAUCAGA CUGGAAAGCGAAGUGACCGCCAUCAACAACGCCCUGAAG AAGACAAACGAGGCCGUCAGCACACUCGGCAAUGGCGUU AGAGUGCUGGCCACAGCCGUGCGCGAGCUGAAGGACUUC GUGUCCAAGAACCUGACACGGGCCAUUAACAAGAACAAG UGCCCUAUCGACGACCUGAAGAUGGCCGUGUCCUUUAGC CAGUUCAACCGGCGGUUUCUGAACGUCGUGCGGCAGUUU AGCGACAACGCCGGAAUCACACCAGCCAUCAGCCUGGAC CUGAUGACAGAUGCUGAGCUGGCUAGAGCCGUGCCUAAC AUGCCUACAUCUGCCGGCCAGAUCAAGCUGAUGCUCGAG AAUAGAGCCAUGGUCCGACGGAAAGGCUUCGGCAUUCU GAUUGGCGUGUACGGCAGCAGCGUGAUCUAUAUGGUGC AGCUGCCUAUCUUCGGCGUGAUCGACACACCCUGCUGGA UUGUGAAGGCCGCUCCUAGCUGUAGCGAGAAGAAGGGC AAUUACGCCUGCCUGCUGAGAGAGGACCAAGGCUGGUA | 142 |

TABLE 19-continued

Human Metapneumovirus Mutant Nucleic Acid Sequences

| Strain | Nucleic Acid Sequence | SEQ ID NO: |
|---|---|---|
| | UUGUCAGAACGCCGGCAGCACCGUGUACUACCCUAACGA GAAGGACUGCGAGACAAGAGGCGACCACGUGUUCUGUG AUACCGCCGCUGGAAUCAAUGUGGCCGAGCAGAGCAAAG AGUGCAACAUCAACAUCAGCACCACCAACUAUCCCUGCA AGGUGUCCACCGGCAGGCACCCUAUUUCUAUGGUGGCUC UGUCUCCUCUGGGAGCCCUGGUGGCUUGUUAUAAGGGC GUGUCCUGUAGCAUCGGCAGCAACAGAGUGGGCAUCAUC AAGCAGCUGAACAAGGGCUGCAGCUACAUCACCAACCAG GACGCCGAUACCGUGACCAUCGACAACACCGUGUAUCAG CUGAGCAAGGUGGAAGGCGAACAGCACGUGAUCAAGGG CAGACCUGUGUCCAGCAGCUUCGACCCUAUCAAGUUCCC UGAGGAUCAGUUCCAGGUGGCCCUGGACCAGGUGUUCG AGAACAUCGAGAAUUCCCAGGCUCUGGUGGACCAGUCCA ACAGAAUCCUGUCUAGCGCCGAGAAGGGAAACACCGGCU UCAUCAUCGUGAUCAUCCUGAUCGCCGUGCUGGGCAGCU CCAUGAUCCUGGUGUCCAUCUUCAUCAUUAUCAAGAAGA CCAAGAAGCCCACCGGCGCUCCUCCAGAACUGAGCGGAG UGACCAACAAUGGCUUCAUCCCUCACAAC | |
| HMPV_Proline SUab_E131P | AUGAGCUGGAAGGUGGUCAUCAUCUUCAGCCUGCUGAU CACACCUCAGCACGGCCUGAAAGAGAGCUACCUGGAAGA GUCCUGCAGCACCAUCACAGAGGGCUACCUGUCUGUGCU GAGAACCGGCUGGUACACCAACGUGUUCACACUGGAAGU GGGCGACGUCGAGAAUCUGACAUGCUCUGAUGGCCCUAG CCUGAUCAAGACCGAGCUGGAUCUGACCAAGAGCGCCCU GAGAGAACUCAAGACCGUGUCUGCCGAUCAGCUGGCCAG AGAGGAACAGAUCGAGAAUCCUGGCAGCGGCAGCUUUG UGCUGGGAGCCAUUGCUCUUGGAGUGGCUGCUGCUGCA GCUGUUACAGCAGGCGUGGCCAUCGCUAAGACCAUCAGA CUGCCUAGCGAAGUGACCGCCAUCAACAACGCCCUGAAG AAGACAAACGAGGCCGUCAGCACACUCGGCAAUGGCGUU AGAGUGCUGGCCACAGCCGUGCGCGAGCUGAAGGACUUC GUGUCCAAGAACCUGACACGGGCCAUUAACAAGAACAAG UGCGACAUCGACGACCUGAAGAUGGCCGUGUCCUUUAGC CAGUUCAACCGGCGGUUUCUGAACGUCGUGCGGCAGUUU AGCGACAACGCCGGAAUCACACCAGCCAUCAGCCUGGAC CUGAUGACAGAUGCUGAGCUGGCUAGAGCCGUGCCUAAC AUGCCUACAUCUGCCGGCCAGAUCAAGCUGAUGCUCGAG AAUAGAGCCAUGGUCCGACGGAAAGGCUUCGGCAUUCU GAUUGGCGUGUACGGCAGCAGCGUGAUCUAUAUGGUGC AGCUGCCUAUCUUCGGCGUGAUCGACACACCCUGCUGGA UUGUGAAGGCCGCUCCUAGCUGUAGCGAGAAGAAGGGC AAUUACGCCUGCCUGCUGAGAGAGGACCAAGGCUGGUA UUGUCAGAACGCCGGCAGCACCGUGUACUACCCUAACGA GAAGGACUGCGAGACAAGAGGCGACCACGUGUUCUGUG AUACCGCCGCUGGAAUCAAUGUGGCCGAGCAGAGCAAAG AGUGCAACAUCAACAUCAGCACCACCAACUAUCCCUGCA AGGUGUCCACCGGCAGGCACCCUAUUUCUAUGGUGGCUC UGUCUCCUCUGGGAGCCCUGGUGGCUUGUUAUAAGGGC GUGUCCUGUAGCAUCGGCAGCAACAGAGUGGGCAUCAUC AAGCAGCUGAACAAGGGCUGCAGCUACAUCACCAACCAG GACGCCGAUACCGUGACCAUCGACAACACCGUGUAUCAG CUGAGCAAGGUGGAAGGCGAACAGCACGUGAUCAAGGG CAGACCUGUGUCCAGCAGCUUCGACCCUAUCAAGUUCCC UGAGGAUCAGUUCCAGGUGGCCCUGGACCAGGUGUUCG AGAACAUCGAGAAUUCCCAGGCUCUGGUGGACCAGUCCA ACAGAAUCCUGUCUAGCGCCGAGAAGGGAAACACCGGCU UCAUCAUCGUGAUCAUCCUGAUCGCCGUGCUGGGCAGCU CCAUGAUCCUGGUGUCCAUCUUCAUCAUUAUCAAGAAGA CCAAGAAGCCCACCGGCGCUCCUCCAGAACUGAGCGGAG UGACCAACAAUGGCUUCAUCCCUCACAAC | 143 |
| HMPV_Proline SUab_D447P | AUGAGCUGGAAGGUGGUCAUCAUCUUCAGCCUGCUGAU CACACCUCAGCACGGCCUGAAAGAGAGCUACCUGGAAGA GUCCUGCAGCACCAUCACAGAGGGCUACCUGUCUGUGCU GAGAACCGGCUGGUACACCAACGUGUUCACACUGGAAGU GGGCGACGUCGAGAAUCUGACAUGCUCUGAUGGCCCUAG CCUGAUCAAGACCGAGCUGGAUCUGACCAAGAGCGCCCU GAGAGAACUCAAGACCGUGUCUGCCGAUCAGCUGGCCAG AGAGGAACAGAUCGAGAAUCCUGGCAGCGGCAGCUUUG UGCUGGGAGCCAUUGCUCUUGGAGUGGCUGCUGCUGCA GCUGUUACAGCAGGCGUGGCCAUCGCUAAGACCAUCAGA CUGGAAAGCGAAGUGACCGCCAUCAACAACGCCCUGAAG AAGACAAACGAGGCCGUCAGCACACUCGGCAAUGGCGUU AGAGUGCUGGCCACAGCCGUGCGCGAGCUGAAGGACUUC | 144 |

TABLE 19-continued

Human Metapneumovirus Mutant Nucleic Acid Sequences

| Strain | Nucleic Acid Sequence | SEQ ID NO: |
|---|---|---|
| | GUGUCCAAGAACCUGACACGGGCCAUUAACAAGAACAAG UGCGACAUCGACGACCUGAAGAUGGCCGUGUCCUUUAGC CAGUUCAACCGGCGGUUUCUGAACGUCGUGCGGCAGUUU AGCGACAACGCCGGAAUCACACCAGCCAUCAGCCUGGAC CUGAUGACAGAUGCUGAGCUGGCUAGAGCCGUGCCUAAC AUGCCUACAUCUGCCGGCCAGAUCAAGCUGAUGCUCGAG AAUAGAGCCAUGGUCCGACGGAAAGGCUUCGGCAUUCU GAUUGGCGUGUACGGCAGCAGCGUGAUCUAUAUGGUGC AGCUGCCUAUCUUCGGCGUGAUCGACACACCCUGCUGGA UUGUGAAGGCCGCUCCUAGCUGUAGCGAGAAGAAGGGC AAUUACGCCUGCCUGCUGAGAGAGGACCAAGGCUGGUA UUGUCAGAACGCCGGCAGCACCGUGUACUACCCUAACGA GAAGGACUGCGAGACAAGAGGCGACCACGUGUUCUGUG AUACCGCCGCUGGAAUCAAUGUGGCCGAGCAGAGCAAAG AGUGCAACAUCAACAUCAGCACCACCAACUAUCCCUGCA AGGUGUCCACCGGCAGGCACCCUAUUUCUAUGGUGGCUC UGUCUCCUCUGGGAGCCCUGGUGGCUUGUUAUAAGGGC GUGUCCUGUAGCAUCGGCAGCAACAGAGUGGGCAUCAUC AAGCAGCUGAACAAGGGCUGCAGCUACAUCACCAACCAG GACGCCGAUACCGUGACCAUCGACAACACCGUGUAUCAG CUGAGCAAGGUGGAAGGCGAACAGCACGUGAUCAAGGG CAGACCUGUGUCCAGCAGCUUCCCACCUAUCAAGUUCCC UGAGGAUCAGUUCCAGGUGGCCCUGGACCAGGUGUUCG AGAACAUCGAGAAUUCCCAGGCUCUGGUGGACCAGUCCA ACAGAAUCCUGUCUAGCGCCGAGAAGGGAAACACCGGCU UCAUCAUCGUGAUCAUCCUGAUCGCCGUGCUGGGCAGCU CCAUGAUCCUGGUGUCCAUCUUCAUCAUUAUCAAGAAGA CCAAGAAGCCCACCGGCGCUCCUCCAGAACUGAGCGGAG UGACCAACAAUGGCUUCAUCCCUCACAAC | |
| HMPV_Urimer RepulsionD454N | AUGAGCUGGAAGGUGGUCAUCAUCUUCAGCCUGCUGAU CACACCUCAGCACGGCCUGAAAGAGAGCUACCUGGAAGA GUCCUGCAGCACCAUCACAGAGGGCUACCUGUCUGUGCU GAGAACCGGCUGGUACACCAACGUGUUCACACUGGAAGU GGGCGACGUCGAGAAUCUGACAUGCUCUGAUGGCCCUAG CCUGAUCAAGACCGAGCUGGAUCUGACCAAGAGCGCCCU GAGAGAACUCAAGACCGUGUCUGCCGAUCAGCUGGCCAG AGAGGAACAGAUCGAGAAUCCUGGCAGCGGCAGCUUUG UGCUGGGAGCCAUUGCUCUUGGAGUGGCUGCUGCUGCA GCUGUUACAGCAGGCGUGGCCAUCGCUAAGACCAUCAGA CUGGAAAGCGAAGUGACCGCCAUCAACAACGCCCUGAAG AAGACAAACGAGGCCGUCAGCACACUCGGCAAUGGCGUU AGAGUGCUGGCCACAGCCGUGCGCGAGCUGAAGGACUUC GUGUCCAAGAACCUGACACGGGCCAUUAACAAGAACAAG UGCGACAUCGACGACCUGAAGAUGGCCGUGUCCUUUAGC CAGUUCAACCGGCGGUUUCUGAACGUCGUGCGGCAGUUU AGCGACAACGCCGGAAUCACACCAGCCAUCAGCCUGGAC CUGAUGACAGAUGCUGAGCUGGCUAGAGCCGUGCCUAAC AUGCCUACAUCUGCCGGCCAGAUCAAGCUGAUGCUCGAG AAUAGAGCCAUGGUCCGACGGAAAGGCUUCGGCAUUCU GAUUGGCGUGUACGGCAGCAGCGUGAUCUAUAUGGUGC AGCUGCCUAUCUUCGGCGUGAUCGACACACCCUGCUGGA UUGUGAAGGCCGCUCCUAGCUGUAGCGAGAAGAAGGGC AAUUACGCCUGCCUGCUGAGAGAGGACCAAGGCUGGUA UUGUCAGAACGCCGGCAGCACCGUGUACUACCCUAACGA GAAGGACUGCGAGACAAGAGGCGACCACGUGUUCUGUG AUACCGCCGCUGGAAUCAAUGUGGCCGAGCAGAGCAAAG AGUGCAACAUCAACAUCAGCACCACCAACUAUCCCUGCA AGGUGUCCACCGGCAGGCACCCUAUUUCUAUGGUGGCUC UGUCUCCUCUGGGAGCCCUGGUGGCUUGUUAUAAGGGC GUGUCCUGUAGCAUCGGCAGCAACAGAGUGGGCAUCAUC AAGCAGCUGAACAAGGGCUGCAGCUACAUCACCAACCAG GACGCCGAUACCGUGACCAUCGACAACACCGUGUAUCAG CUGAGCAAGGUGGAAGGCGAACAGCACGUGAUCAAGGG CAGACCUGUGUCCAGCAGCUUCGACCCUAUCAAGUUCCC UGAGAACCAGUUCCAGGUGGCCCUGGACCAGGUGUUCGA GAACAUCGAGAAUUCCCAGGCUCUGGUGGACCAGUCCAA CAGAAUCCUGUCUAGCGCCGAGAAGGGAAACACCGGCUU CAUCAUCGUGAUCAUCCUGAUCGCCGUGCUGGGCAGCUC CAUGAUCCUGGUGUCCAUCUUCAUCAUUAUCAAGAAGAC CAAGAAGCCCACCGGCGCUCCUCCAGAACUGAGCGGAGU GACCAACAAUGGCUUCAUCCCUCACAAC | 145 |
| HMPV_Urimer RepulsionE453N | AUGAGCUGGAAGGUGGUCAUCAUCUUCAGCCUGCUGAU CACACCUCAGCACGGCCUGAAAGAGAGCUACCUGGAAGA | 146 |

TABLE 19-continued

Human Metapneumovirus Mutant Nucleic Acid Sequences

| Strain | Nucleic Acid Sequence | SEQ ID NO: |
|---|---|---|
| | GUCCUGCAGCACCAUCACAGAGGGCUACCUGUCUGUGCU GAGAACCGGCUGGUACACCAACGUGUUCACACUGGAAGU GGGCGACGUCGAGAAUCUGACAUGCUCUGAUGGCCCUAG CCUGAUCAAGACCGAGCUGGAUCUGACCAAGAGCGCCCU GAGAGAACUCAAGACCGUGUCUGCCGAUCAGCUGGCCAG AGAGGAACAGAUCGAGAAUCCUGGCAGCGGCAGCUUUG UGCUGGGAGCCAUUGCUCUUGGAGUGGCUGCUGCUGCA GCUGUUACAGCAGGCGUGGCCAUCGCUAAGACCAUCAGA CUGGAAAGCGAAGUGACCGCCAUCAACAACGCCCUGAAG AAGACAAACGAGGCCGUCAGCACACUCGGCAAUGGCGUU AGAGUGCUGGCCACAGCCGUGCGCGAGCUGAAGGACUUC GUGUCCAAGAACCUGACACGGGCCAUUAACAAGAACAAG UGCGACAUCGACGACCUGAAGAUGGCCGUGUCCUUUAGC CAGUUCAACCGGCGGUUUCUGAACGUCGUGCGGCAGUUU AGCGACAACGCCGGAAUCACACCAGCCAUCAGCCUGGAC CUGAUGACAGAUGCUGAGCUGGCUAGAGCCGUGCCUAAC AUGCCUACAUCUGCCGGCCAGAUCAAGCUGAUGCUCGAG AAUAGAGCCAUGGUCCGACGGAAAGGCUUCGGCAUUCU GAUUGGCGUGUACGGCAGCAGCGUGAUCUAUAUGGUGC AGCUGCCUAUCUUCGGCGUGAUCGACACACCCUGCUGGA UUGUGAAGGCCGCUCCUAGCUGUAGCGAGAAGAAGGGC AAUUACGCCUGCCUGCUGAGAGAGGACCAAGGCUGGUA UUGUCAGAACGCCGGCAGCACCGUGUACUACCCUAACGA GAAGGACUGCGAGACAAGAGGCGACCACGUGUUCUGUG AUACCGCCGCUGGAAUCAAUGUGGCCGAGCAGAGCAAAG AGUGCAACAUCAACAUCAGCACCACCAACUAUCCCUGCA AGGUGUCCACCGGCAGGCACCCUAUUUCUAUGGUGGCUC UGUCUCCUCUGGGAGCCCUGGUGGCUUGUUAUAAGGGC GUGUCCUGUAGCAUCGGCAGCAACAGAGUGGGCAUCAUC AAGCAGCUGAACAAGGGCUGCAGCUACAUCACCAACCAG GACGCCGAUACCGUGACCAUCGACAACACCGUGUAUCAG CUGAGCAAGGUGGAAGGCGAACAGCACGUGAUCAAGGG CAGACCUGUGUCCAGCAGCUUCGACCCUAUCAAGUUCCC UCAGGAUCAGUUCCAGGUGGCCCUGGACCAGGUGUUCGA GAACAUCGAGAAUUCCCAGGCUCUGGUGGACCAGUCCAA CAGAAUCCUGUCUAGCGCCGAGAAGGGAAACACCGGCUU CAUCAUCGUGAUCAUCCUGAUCGCCGUGCUGGGCAGCUC CAUGAUCCUGGUGUCCAUCUUCAUCAUUAUCAAGAAGAC CAAGAAGCCCACCGGCGCUCCUCCAGAACUGAGCGGAGU GACCAACAAUGGCUUCAUCCCUCACAAC | |
| HMPV_ SUabilizeAlpha F196W | AUGAGCUGGAAGGUGGUCAUCAUCUUCAGCCUGCUGAU CACACCUCAGCACGGCCUGAAAGAGAGCUACCUGGAAGA GUCCUGCAGCACCAUCACAGAGGGCUACCUGUCUGUGCU GAGAACCGGCUGGUACACCAACGUGUUCACACUGGAAGU GGGCGACGUCGAGAAUCUGACAUGCUCUGAUGGCCCUAG CCUGAUCAAGACCGAGCUGGAUCUGACCAAGAGCGCCCU GAGAGAACUCAAGACCGUGUCUGCCGAUCAGCUGGCCAG AGAGGAACAGAUCGAGAAUCCUGGCAGCGGCAGCUUUG UGCUGGGAGCCAUUGCUCUUGGAGUGGCUGCUGCUGCA GCUGUUACAGCAGGCGUGGCCAUCGCUAAGACCAUCAGA CUGGAAAGCGAAGUGACCGCCAUCAACAACGCCCUGAAG AAGACAAACGAGGCCGUCAGCACACUCGGCAAUGGCGUU AGAGUGCUGGCCACAGCCGUGCGCGAGCUGAAGGACUUC GUGUCCAAGAACCUGACACGGGCCAUUAACAAGAACAAG UGCGACAUCGACGACCUGAAGAUGGCCGUGUCCUUUAGC CAGUGGAACCGGCGGUUUCUGAACGUCGUGCGGCAGUU UAGCGACAACGCCGGAAUCACACCAGCCAUCAGCCUGGA CCUGAUGACAGAUGCUGAGCUGGCUAGAGCCGUGCCUAA CAUGCCUACAUCUGCCGGCCAGAUCAAGCUGAUGCUCGA GAAUAGAGCCAUGGUCCGACGGAAAGGCUUCGGCAUUC UGAUUGGCGUGUACGGCAGCAGCGUGAUCUAUAUGGUG CAGCUGCCUAUCUUCGGCGUGAUCGACACACCCUGCUGG AUUGUGAAGGCCGCUCCUAGCUGUAGCGAGAAGAAGGG CAAUUACGCCUGCCUGCUGAGAGAGGACCAAGGCUGGUA UUGUCAGAACGCCGGCAGCACCGUGUACUACCCUAACGA GAAGGACUGCGAGACAAGAGGCGACCACGUGUUCUGUG AUACCGCCGCUGGAAUCAAUGUGGCCGAGCAGAGCAAAG AGUGCAACAUCAACAUCAGCACCACCAACUAUCCCUGCA AGGUGUCCACCGGCAGGCACCCUAUUUCUAUGGUGGCUC UGUCUCCUCUGGGAGCCCUGGUGGCUUGUUAUAAGGGC GUGUCCUGUAGCAUCGGCAGCAACAGAGUGGGCAUCAUC AAGCAGCUGAACAAGGGCUGCAGCUACAUCACCAACCAG GACGCCGAUACCGUGACCAUCGACAACACCGUGUAUCAG CUGAGCAAGGUGGAAGGCGAACAGCACGUGAUCAAGGG | 147 |

TABLE 19-continued

| Human Metapneumovirus Mutant Nucleic Acid Sequences | | |
|---|---|---|
| Strain | Nucleic Acid Sequence | SEQ ID NO: |
| | CAGACCUGUGUCCAGCAGCUUCGACCCUAUCAAGUUCCC UGAGGAUCAGUUCCAGGUGGCCCUGGACCAGGUGUUCG AGAACAUCGAGAAUUCCCAGGCUCUGGUGGACCAGUCCA ACAGAAUCCUGUCUAGCGCCGAGAAGGGAAACACCGGCU UCAUCAUCGUGAUCAUCCUGAUCGCCGUGCUGGGCAGCU CCAUGAUCCUGGUGUCCAUCUUCAUCAUUAUCAAGAAGA CCAAGAAGCCCACCGGCGCUCCUCCAGAACUGAGCGGAG UGACCAACAAUGGCUUCAUCCCUCACAAC | |

EQUIVALENTS

Those skilled in the art will recognize, or be able to ascertain using no more than routine experimentation, many equivalents to the specific embodiments of the disclosure described herein. Such equivalents are intended to be encompassed by the following claims.

All references, including patent documents, disclosed herein are incorporated by reference in their entirety.

What is claimed is:

1. A human metapneumovirus (hMPV) vaccine, comprising: an isolated messenger ribonucleic acid (mRNA) polynucleotide comprising an open reading frame encoding an antigenic hMPV Fusion (F) protein formulated in a lipid nanoparticle that comprises a molar ratio of 20-60% ionizable cationic lipid, 5-25% non-cationic lipid, 25-55% sterol, and 0.5-15% PEG-modified lipid in an effective amount to induce a T cell response and a neutralizing antibody response against hMPV F protein in a subject administered at least one dose of the vaccine, wherein the isolated mRNA polynucleotide is not self-replicating mRNA.

2. A method of inducing an antigen-specific immune response in a subject, the method comprising administering to the subject the vaccine of claim 1 to produce an antigen-specific immune response in the subject.

3. The hMPV vaccine of claim 1, wherein the isolated mRNA polynucleotide further encodes a 5' terminal cap, 7mG(5')ppp(5')NlmpNp.

4. The hMPV vaccine of claim 1, wherein at least 80% of the uracil in the open reading frame comprises a chemical modification selected from N1-methyl-pseudouridine and N1-ethyl-pseudouridine.

5. The hMPV vaccine of claim 1, wherein the chemical modification is in the 5-position of the uracil.

6. The hMPV vaccine of claim 1, wherein the open reading frame encoding an antigenic hMPV F protein comprises a mRNA sequence that has at least 90% identity to the sequence set forth in SEQ ID NO: 57.

7. The hMPV vaccine of claim 6, wherein the open reading frame encoding an antigenic hMPV F protein comprises the sequence set forth as SEQ ID NO: 57.

8. The hMPV vaccine of claim 1, wherein the antigenic hMPV F protein comprises an amino acid sequence that has at least 90% identity to the amino acid sequence set forth as SEQ ID NO: 5.

9. The hMPV vaccine of claim 8, wherein the antigenic hMPV F protein comprises the amino acid sequence set forth as SEQ ID NO: 5.

10. The hMPV vaccine of claim 1, wherein the effective amount is a total dose of 25 μg-200 μg.

11. The hMPV vaccine of claim 1, wherein the isolated mRNA polynucleotide further comprises 5' terminal cap, a 5' UTR, a 3' UTR, and a polyA tail.

12. The hMPV vaccine of claim 11, wherein the open reading frame encoding an antigenic hMPV F protein comprises an mRNA sequence that has at least 90% identity to the sequence set forth in SEQ ID NO: 57.

13. The hMPV vaccine of claim 12, wherein the open reading frame encoding an antigenic hMPV F protein comprises the sequence set forth as SEQ ID NO: 57.

14. The hMPV vaccine of claim 1, wherein the efficacy of the vaccine in vaccinated subjects is at least 60%, relative to unvaccinated subjects, following a single dose of the vaccine.

15. The hMPV vaccine of claim 1, wherein a single dose of the vaccine administered to a subject is sufficient to produce detectable levels of hMPV F protein as measured in serum of a subject vaccinated with at least one dose of the vaccine at 1-72 hours post administration.

16. The hMPV vaccine of claim 1, wherein a single dose of the vaccine administered to a subject is sufficient to produce a 1,000-10,000 neutralization titer produced by neutralizing antibody against the antigenic hMPV F protein as measured in serum of a subject vaccinated with at least one dose of the vaccine at 1-72 hours post administration.

17. The hMPV vaccine of claim 16, wherein the 1,000-10,000 neutralization titer is produced in the absence of antibody-dependent enhancement (ADE) of a hMPV-associated disease.

18. The hMPV vaccine of claim 17, wherein the hMPV-associated disease is alevolitis interstitial pneumonia.

19. The hMPV vaccine of claim 1, wherein an anti-hMPV F protein antibody titer produced in a subject vaccinated with at least one dose of the vaccine is increased by at least 1 log relative to a control, wherein the control is an anti-hMPV F protein antibody titer produced in a subject who has not been administered a vaccine against hMPV.

20. The hMPV vaccine of claim 1, wherein an anti-hMPV F protein antibody titer produced in a subject vaccinated with at least one dose of the vaccine is increased at least 2 times relative to a control, wherein the control is an anti-hMPV F protein antibody titer produced in a subject who has not been administered a vaccine against hMPV.

21. The hMPV vaccine of claim 1, wherein the ionizable cationic lipid comprises the following compound:

(Compound 25)

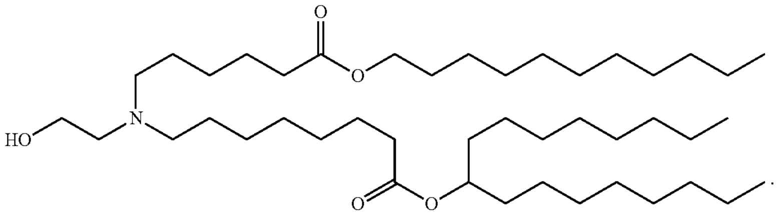

22. The hMPV vaccine of claim 1, wherein the noncationic lipid is DSPC (1,2-Distearoyl-sn-glycero-3-phosphocholine).

23. The hMPV vaccine of claim 1, wherein the PEG-modified lipid is DMG-PEG (1,2-dimyristoyl-racglycero-3-methoxypolyethylene glycol-2000).

24. The method of claim 1, wherein the lipid nanoparticle comprises 40-50% ionizable cationic lipid, 5-15% DSPC, 25-40% cholesterol, and 1-3.5% DMG-PEG.

25. The method of claim 24, wherein the lipid nanoparticle comprises 50% ionizable cationic lipid, 10% DSPC, 38.5% cholesterol, and 1.5% DMG-PEG.

* * * * *